(12) United States Patent
Nakano et al.

(10) Patent No.: US 10,763,441 B2
(45) Date of Patent: Sep. 1, 2020

(54) ORGANIC ELECTROLUMINESCENCE DEVICE AND ELECTRONIC APPARATUS PROVIDED WITH THE SAME

(71) Applicant: IDEMITSU KOSAN CO., LTD., Tokyo (JP)

(72) Inventors: Yuki Nakano, Sodegaura (JP); Taro Yamaki, Sodegaura (JP); Satomi Tasaki, Sodegaura (JP); Tomoki Kato, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 17 days.

(21) Appl. No.: 16/593,775

(22) Filed: Oct. 4, 2019

(65) Prior Publication Data

US 2020/0111968 A1 Apr. 9, 2020

(30) Foreign Application Priority Data

Oct. 9, 2018 (JP) ................................ 2018-191297
May 30, 2019 (JP) ................................ 2019-101674

(51) Int. Cl.
*H01L 51/00* (2006.01)
*H01L 51/50* (2006.01)
*H01L 51/52* (2006.01)

(52) U.S. Cl.
CPC ........ *H01L 51/0071* (2013.01); *H01L 51/008* (2013.01); *H01L 51/0052* (2013.01);
(Continued)

(58) Field of Classification Search
None
See application file for complete search history.

(56) References Cited

U.S. PATENT DOCUMENTS

2016/0351817 A1   12/2016   Kim et al.
2017/0125686 A1   5/2017   Heil et al.
(Continued)

FOREIGN PATENT DOCUMENTS

JP   2015-153911 A   8/2015
JP   2017-514807 A   6/2017
(Continued)

OTHER PUBLICATIONS

International Search Report dated Dec. 24, 2019 for corresponding Application No. PCT/JP2019/039918.

*Primary Examiner* — Nilufa Rahim
(74) *Attorney, Agent, or Firm* — Foley & Lardner LLP

(57) ABSTRACT

An organic electroluminescence device including a cathode, an anode, and an emitting layer disposed between the cathode and the anode, wherein the emitting layer includes a compound represented by the following formula (1) and one or more compounds selected from the group consisting (Continued)

of compounds represented by formulas (11), (21), (31), (41), (51), (61), (71) and (81). In the formula (1), at least one of $R_1$ to $R_8$ is a deuterium atom, and $Ar_2$ is a monovalent group represented by following formula (2), (3) or (4).

(1)

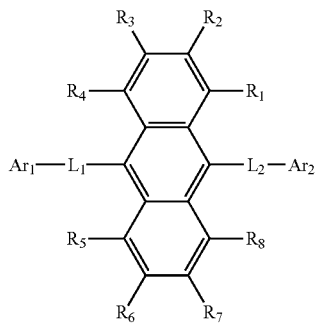

(2)

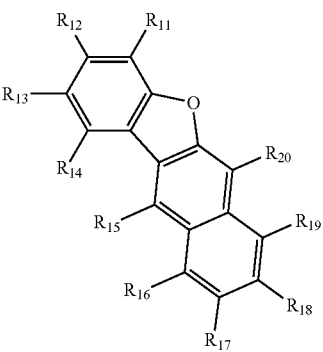

(3)

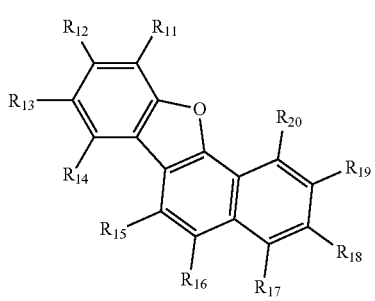

(4)

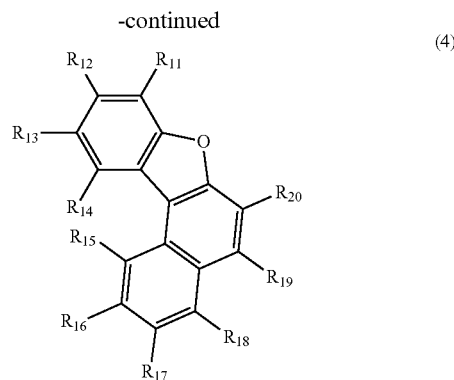

17 Claims, 1 Drawing Sheet

(52) U.S. Cl.
CPC ...... *H01L 51/0059* (2013.01); *H01L 51/5056* (2013.01); *H01L 51/5072* (2013.01); *H01L 51/5092* (2013.01); *H01L 51/5206* (2013.01)

(56) References Cited

U.S. PATENT DOCUMENTS

| | | | |
|---|---|---|---|
| 2017/0133600 A1 | 5/2017 | Pyo et al. | |
| 2017/0200899 A1 | 7/2017 | Kim et al. | |
| 2017/0324045 A1 | 11/2017 | Takahashi et al. | |
| 2018/0013071 A1 | 1/2018 | Cha et al. | |
| 2018/0094000 A1* | 4/2018 | Hatakeyama | C09K 11/06 |
| 2018/0198076 A1 | 7/2018 | Takahashi et al. | |
| 2018/0301629 A1 | 10/2018 | Hatakeyama et al. | |
| 2019/0027694 A1* | 1/2019 | Hatakeyama | H01L 51/5092 |
| 2019/0097142 A1 | 3/2019 | Takahashi et al. | |
| 2019/0181350 A1 | 6/2019 | Hatakeyama et al. | |
| 2019/0207112 A1 | 7/2019 | Hatakeyama et al. | |
| 2019/0305227 A1 | 10/2019 | Yoon et al. | |
| 2019/0341556 A1 | 11/2019 | Takahashi et al. | |
| 2019/0372023 A1* | 12/2019 | Hatakeyama | C07D 307/77 |
| 2019/0393420 A1 | 12/2019 | Takeda et al. | |

FOREIGN PATENT DOCUMENTS

| | | |
|---|---|---|
| JP | 2018-157209 A | 10/2018 |
| KR | 20160102881 A | 8/2016 |
| KR | 20160141361 | 12/2016 |
| KR | 20190056338 A | 5/2019 |
| KR | 20190122041 A | 10/2019 |
| WO | WO-2010/099534 A2 | 9/2010 |
| WO | WO-2016/152544 A1 | 9/2016 |
| WO | WO-2017/188111 A1 | 11/2017 |
| WO | WO-2018/151065 A1 | 8/2018 |
| WO | WO-2019/220283 A | 11/2019 |
| WO | WO-2020/022751 | 1/2020 |

\* cited by examiner

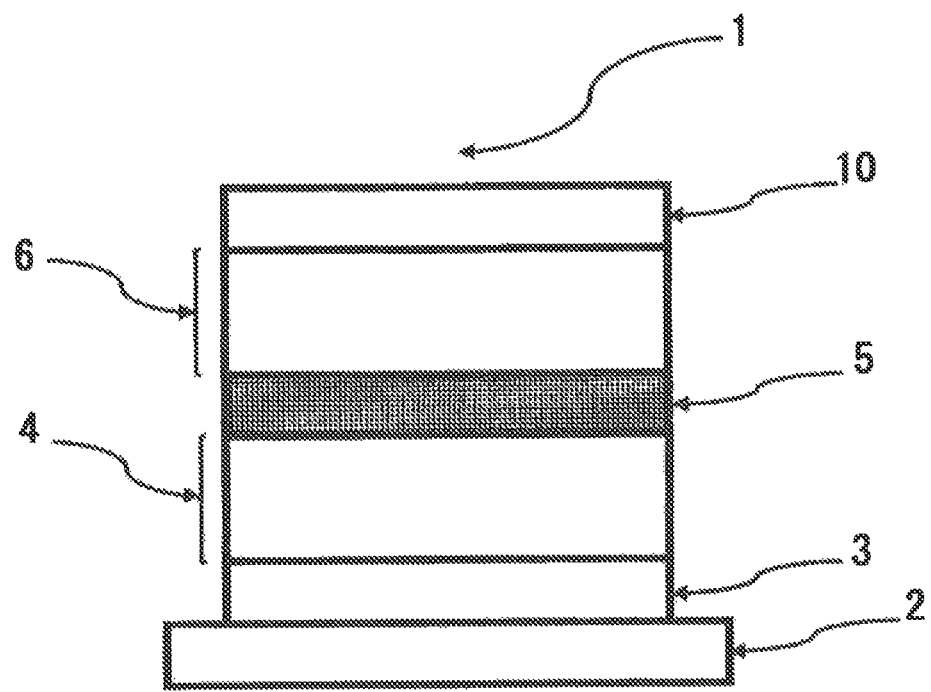

ORGANIC ELECTROLUMINESCENCE DEVICE AND ELECTRONIC APPARATUS PROVIDED WITH THE SAME

CROSS-REFERENCE TO RELATED APPLICATIONS

The present application claims priority to and the benefit of Japanese Patent Application Nos. 2018-191297, filed on Oct. 9, 2018, and 2019-101674, filed on May 30, 2019. The contents of these applications are hereby incorporated by reference in their entireties.

TECHNICAL FIELD

The invention relates to an organic electroluminescence device and an electronic apparatus provided with the organic electroluminescence device.

BACKGROUND ART

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

Although materials for an organic EL device are being improved gradually to increase the performances of the organic EL device (for example, Patent Documents 1 to 3), high performances are further offered. In particular, improvement in lifetime of an organic EL device is an important task relating to a lifetime of commercial products provided with the organic EL device, and thus a material enabling to realize a long-lifetime organic EL device is required.

RELATED ART DOCUMENTS

Patent Documents

Patent Document 1: WO2016/152544
Patent Document 2: WO2017/188111
Patent Document 3: Publication of US Patent Application No. 2017/324045

SUMMARY OF THE INVENTION

An object of the invention is to provide an organic EL device having a long lifetime, and to provide an electronic apparatus provided with the organic EL device.

As a result of extensive studies, the inventors have found that an organic EL device having a long lifetime can be obtained by using compounds having a specific structure in an emitting layer of the organic EL device in combination, and they have achieved the invention.

According to the invention, the following organic EL device and electric apparatus can be provided.
1. An organic electroluminescence device comprising:
   a cathode,
   an anode, and
   an emitting layer disposed between the cathode and the anode, wherein
   the emitting layer comprises a compound represented by the following formula (1) and one or more compounds selected from the group consisting of compounds represented by formulas (11), (21), (31), (41), (51), (61), (71) and (81):

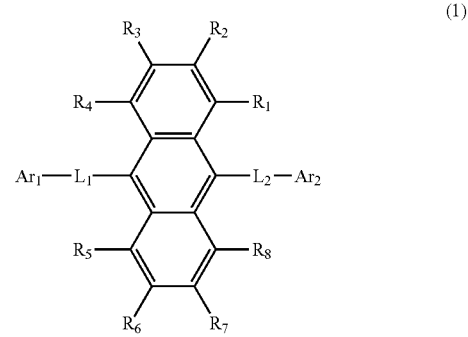

(1)

wherein in the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, $-Si(R_{9101})(R_{902})(R_{903})$, $-O-(R_{904})$, $-S-(R_{905})$,
$-N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms;
$Ar_1$ is
a substituted or unsubstituted aryl group having 6 to 50 ring carbon atoms, or
a substituted or unsubstituted monovalent heterocyclic group having 5 to 50 ring atoms;
$Ar_2$ is a monovalent group represented by the following formula (2), (3) or (4);

(2)

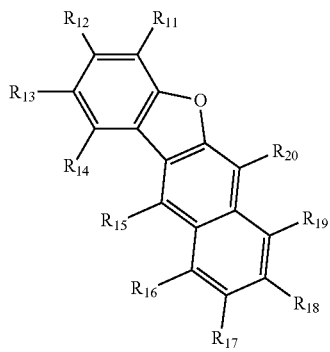

(3)

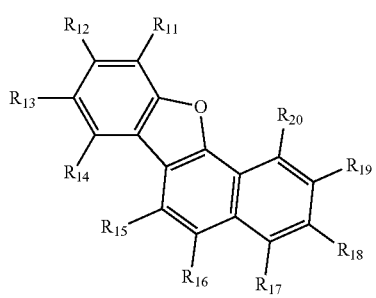

(4)

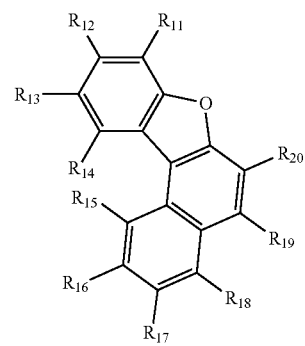

wherein in the formulas (2) to (4),
one or more pairs of two adjacent groups of $R_1$ to $R_{20}$ are bonded with each other to form a substituted or unsubstituted, saturated or unsaturated ring, or do not form a substituted or unsubstituted, saturated or unsaturated ring;

when one or more pairs of two adjacent groups of $R_{15}$ to $R_{20}$ are not bonded with each other and do not form a substituted or unsubstituted, saturated or unsaturated ring, one of $R_{11}$ to $R_{20}$ is a single bond bonding to $L_2$;

when one or more pairs of two adjacent groups of $R_{15}$ to $R_{20}$ are bonded with each other to form a substituted or unsubstituted, saturated or unsaturated ring, one of $R_{15}$ to $R_{20}$ which does not form a substituted or unsubstituted, saturated or unsaturated ring and $R_{11}$ to $R_{14}$ is a single bond bonding to $L_2$;

$R_{11}$ to $R_{20}$ that do not form the substituted or unsubstituted, saturated or unsaturated ring and that are not a single bond bonding to $L_2$ are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, —Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1);

(11)

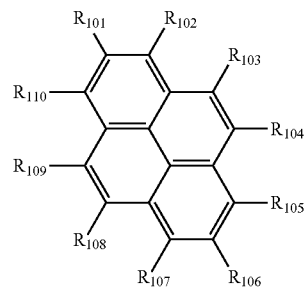

wherein, in the formula (11),
one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;
at least one of $R_{101}$ to $R_{110}$ is a monovalent group represented by the formula (12);
$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

(12)

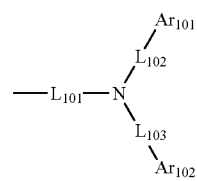

wherein, in the formula (12), $Ar_{101}$ and $Ar_{102}$ are independently
a substituted or unsubstituted aryl group having 6 to 50 ring carbon atoms, or
a substituted or unsubstituted monovalent heterocyclic group having 5 to 50 ring atoms;
$L_{101}$ to $L_{103}$ are independently
a single bonded,
a substituted or unsubstituted arylene group having 6 to 30 ring carbon atoms, or
a substituted or unsubstituted divalent heterocyclic group having 5 to 30 ring atoms;

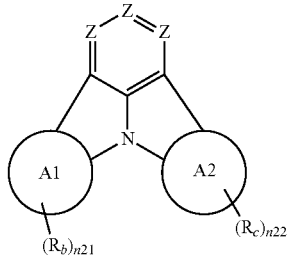

(21)

wherein, in the formula (21),
Zs are independently $CR_a$ or N;
A1 ring and A2 ring are independently a substituted or unsubstituted aromatic hydrocarbon ring having 6 to 50 ring carbon atoms, or a substituted or unsubstituted heterocyclic ring having 5 to 50 ring atoms;
when plural $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;
when plural $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;
when plural $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;
n21 and n22 are independently an integer of 0 to 4;
$R_a$ to $R_c$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

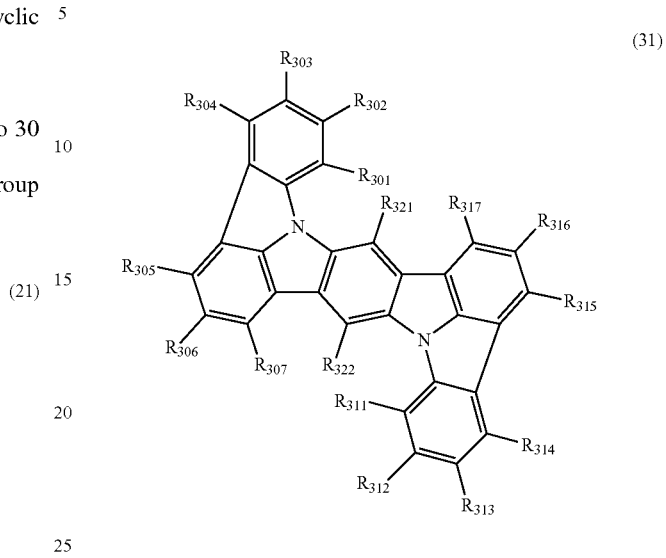

(31)

wherein, in the formula (31),
one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted saturated or unsaturated ring;
$R_{301}$ to $R_{307}$ and $R_{311}$ to $R_{317}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{321}$ and $R_{322}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

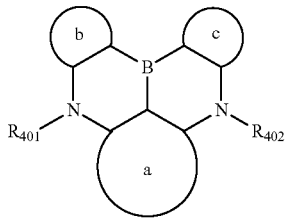

(41)

wherein, in the formula (41), a ring, b ring and c ring are independently a substituted or unsubstituted aromatic hydrocarbon ring having 6 to 50 ring carbon atoms, or a substituted or unsubstituted heterocyclic ring having 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

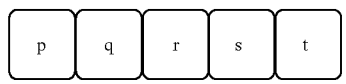

(51)

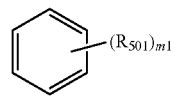

(52)

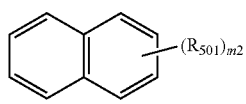

(53)

(54)

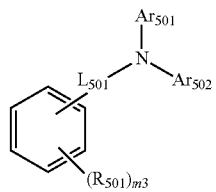

(55)

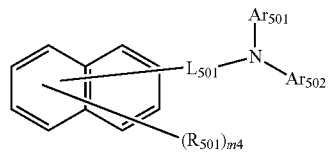

(56)

wherein, in the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when plural $R_{501}$s exist, adjacent plural $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

$Ar_{501}$ and $Ar_{502}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

$L_{501}$ is
a substituted or unsubstituted alkylene group having 1 to 50 carbon atoms,
a substituted or unsubstituted alkenylene group having 2 to 50 carbon atoms,
a substituted or unsubstituted alkynylene group having 2 to 50 carbon atoms,
a substituted or unsubstituted cycloalkylene group having 3 to 50 ring carbon atoms,
a substituted or unsubstituted arylene group having 6 to 50 ring carbon atoms, or
a substituted or unsubstituted divalent heterocyclic group having 5 to 50 ring atoms;
m1 is an integer of 0 to 2, m2 is an integer of 0 to 4, m3s are independently an integer of 0 to 3, and m4s are independently an integer of 0 to 5; when plural $R_{501}$s exist, the plural $R_{501}$s may be the same or different;

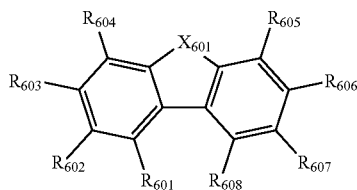

(61)

wherein, in the formula (61),
at least one pair of $R_{601}$ and $R_{602}$, $R_{602}$ and $R_{603}$, and $R_{603}$ and $R_{604}$ are bonded with each other to form a divalent group represented by the formula (62);
at least one pair of $R_{605}$ and $R_{606}$, $R_{606}$ and $R_{607}$, and $R_{607}$ and $R_{608}$ are bonded with each other to form a divalent group represented by formula (63);

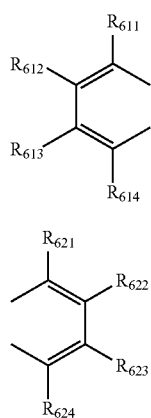

(63)

(64)

at least one of $R_{601}$ to $R_{604}$ that does not form the divalent group represented by the formula (62), and $R_{611}$ to $R_{614}$ is a monovalent group represented by the following formula (64);
at least one of $R_{605}$ to $R_{608}$ that do not form the divalent group represented by the formula (63), and $R_{621}$ to $R_{624}$ is a monovalent group represented by the following formula (64);
$X_{601}$ is an oxygen atom, a sulfur atom, or $NR_{609}$;
$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

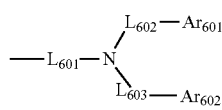

(64)

wherein, in the formula (64), $Ar_{601}$ and $Ar_{602}$ are independently
a substituted or unsubstituted aryl group having 6 to 50 ring carbon atoms, or
a substituted or unsubstituted monovalent heterocyclic group having 5 to 50 ring atoms;
$L_{601}$ to $L_{603}$ are independently
a single bonded,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups;

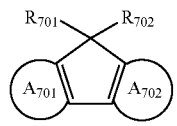

(71)

wherein, in the formula (71),
$A_{701}$ ring and $A_{702}$ ring are independently
a substituted or unsubstituted aromatic hydrocarbon ring having 6 to 50 ring carbon atoms, or
a substituted or unsubstituted heterocyclic ring having 5 to 50 ring atoms;
One or more rings selected from the group consisting of $A_{701}$ ring and $A_{702}$ ring are bonded to the bond * of the structure represented by the following formula (72);

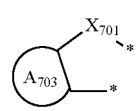

(72)

wherein, in the formula (72), $A_{703}$ rings are independently
a substituted or unsubstituted aromatic hydrocarbon ring having 6 to 50 ring carbon atoms, or
a substituted or unsubstituted heterocyclic ring having 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

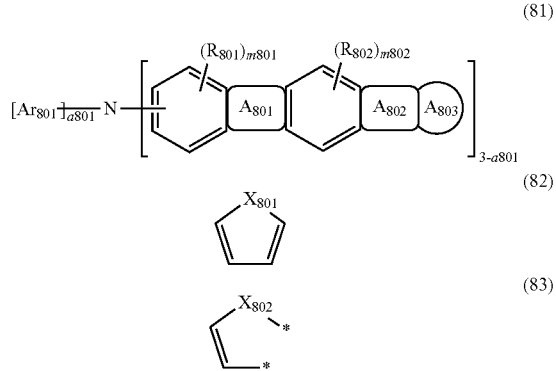

wherein, in the formula (81),
$A_{801}$ ring is a ring represented by the formula (82) which is fused to an adjacent ring at an arbitrary position;
$A_{802}$ ring is a ring represented by the formula (83) which is fused to an adjacent ring at an arbitrary position;
two bonds * bond to $A_{803}$ ring at an arbitrary position;
$X_{801}$ and $X_{802}$ are independently $C(R_{803})(R_{804})$, $Si(R_{805})(R_{806})$, an oxygen atom, or a sulfur atom;
$A_{803}$ ring is a substituted or unsubstituted aromatic hydrocarbon ring having 6 to 50 ring carbon atoms, or a substituted or unsubstituted heterocyclic ring having 5 to 50 ring atoms;
$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

m801 and m802 are independently an integer of 0 to 2; when these are 2, plural $R_{801}$s or $R_{802}$s may be the same or different;

a801 is an integer of 0 to 2; when a801 is 0 or 1, the structure in the parentheses indicated by "3-a801" may be the same or different from each other; when a801 is 2, $Ar_{801}$s may be the same or different from each other.

2. An electronic apparatus provided with the organic electroluminescence device according to the above 1.

According to the invention, an organic EL device having a long lifetime, and an electronic apparatus provided with the organic EL device can be provided.

BRIEF DESCRIPTION OF THE DRAWINGS

The FIGURE is a view showing a schematic configuration of one embodiment of the organic EL device of the invention.

MODE FOR CARRYING OUT THE INVENTION

Definition

In the present specification, a hydrogen atom means an atom including isotopes different in the number of neutrons, namely, a protium, a deuterium and a tritium.

In the present specification, to a bondable position in which a symbol such as "R", or "D" representing a deuterium atom is not specified in a chemical formula, a hydrogen atom, that is, a light hydrogen atom, a deuterium atom, or a tritium atom is bonded thereto.

In the present specification, a term "ring carbon atoms" represents the number of carbon atoms among atoms forming a subject ring itself of a compound having a structure in which atoms are bonded in a ring form (for example, a monocyclic compound, a fused ring compound, a crosslinked compound, a carbocyclic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenylfluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In the present specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In the present specification, a term "XX to YY carbon atoms" in an expression of "substituted or unsubstituted ZZ group having XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In the present specification, a term "XX to YY atoms" in an expression of "substituted or unsubstituted ZZ group having XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternatively, a term "substituted" in the case of "substituted or unsubstituted ZZ group" means that one or more hydrogen atoms in the ZZ group are substituted by a substituent. Similarly, a term "substituted" in the case of "BB group substituted by an AA group" means that one or more hydrogen atoms in the BB group are substituted by the AA group.

Hereinafter, the substituent described herein will be described.

The number of the ring carbon atoms of the "unsubstituted aryl group" described herein is 6 to 50, preferably 6 to 30, and more preferably 6 to 18, unless otherwise specified.

The number of the ring carbon atoms of the "unsubstituted heterocyclic group" described herein is 5 to 50, preferably 5 to 30, and more preferably 5 to 18, unless otherwise specified.

The number of the carbon atoms of the "unsubstituted alkyl group" described herein is 1 to 50, preferably 1 to 20, and more preferably 1 to 6, unless otherwise specified.

The number of the carbon atoms of the "unsubstituted alkenyl group" described herein is 2 to 50, preferably 2 to 20, and more preferably 2 to 6, unless otherwise specified.

The number of the carbon atoms of the "unsubstituted alkynyl group" described herein is 2 to 50, preferably 2 to 20, and more preferably 2 to 6, unless otherwise specified.

The number of the ring carbon atoms of the "unsubstituted cycloalkyl group" described herein is 3 to 50, preferably 3 to 20, and more preferably 3 to 6, unless otherwise specified.

The number of the ring carbon atoms of the "unsubstituted arylene group" described herein is 6 to 50, preferably 6 to 30, and more preferably 6 to 18, unless otherwise specified.

The number of the ring atoms of the "unsubstituted divalent heterocyclic group" described herein is 5 to 50, preferably 5 to 30, and more preferably 5 to 18, unless otherwise specified.

The number of the carbon atoms of the "unsubstituted alkylene group" described herein is 1 to 50, preferably 1 to 20, and more preferably 1 to 6, unless otherwise specified.

Specific examples (specific example group G1) of the "substituted or unsubstituted aryl group" described herein include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed herein are only one example, and the "substituted aryl group" described herein also includes a group in which a group in which "unsubstituted aryl group" has a substituent further has a substituent, and a group in which "substituted aryl group" further has a substituent, and the like.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group, a 9,9'-spirobifluorenyl group,
a benzofluorenyl group,
a dibenzofluorenyl group,
a fluoranethenyl group,
a benzofluoranethenyl group, and
a perylenyl group.

A substituted aryl group:
an o-tolyl group,
a m-tolyl group,
a p-tolyl group,
a p-xylyl group,
a m-xylyl group,
an o-xylyl group,
a p-isopropyl phenyl group,
a m-isopropyl phenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described herein is a ring group having at least one hetero atom in the ring atom. Specific examples of the hetero atom include a nitrogen atom, an oxygen atom, a sulfur atom, a silicon atom, a phosphorus atom and a boron atom.

The "heterocyclic group" described herein may be a monocyclic group, or a fused ring group.

The "heterocyclic group" described herein may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocylic group," and the substituted heterocyclic group refers to a case where the "substituted or unsubstituted heterocyclic group" is the "substituted heterocyclic group". Hereinafter, the case of merely "heterocyclic group" includes both the "unsubstituted heterocyclic group" and the "substituted heterocyclic group".

The "substituted heterocyclic group" refers to a case where the "unsubstituted heterocyclic group" has a substituent, and specific examples thereof include a group in which the "unsubstituted heterocyclic group" has a substituent, and a substituted heterocyclic group described below. It should be noted that examples of the "unsubstituted heterocyclic group" and examples of the "substituted heterocyclic group" listed herein are merely one example, and the "substituted heterocyclic group" described herein also includes a group in which "unsubstituted heterocyclic group" which has a substituent further has a substituent, and a group in which "substituted heterocyclic group" further has a substituent, and the like.

An unsubstituted heterocyclic group having a nitrogen atom:
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

An unsubstituted heterocyclic group having an oxygen atom:
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzooxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

An unsubstituted heterocyclic group having a sulfur atom;
a thienyl group,
a thiazolyl group,
an isothiazolyl group,
a thiadiazolyl group,
a benzothiophenyl group,
an isobenzothiophenyl group,
a dibenzothiophenyl group, a naphthobenzothiophenyl group,
a benzothiazolyl group,
a benzisothiazolyl group,
a phenothiazinyl group,
a dinaphthothiophenyl group,
an azadibenzothiophenyl group,
a diazadibenzothiophenyl group,
an azanaphthobenzothiophenyl group, and
a diazanaphthobenzothiophenyl group.

A substituted heterocyclic group having a nitrogen atom:
a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

A substituted heterocyclic group having an oxygen atom:
a phenyldibenzofuranyl group,
a methyldibenzofuranyl group,
a t-butyldibenzofuranyl group, and
a monovalent residue of spiro[9H-xanthene-9,9'-[9H]fluorene].

A substituted heterocyclic group having a sulfur atom:
a phenyldibenzothiophenyl group,
a methyldibenzothiophenyl group,
a t-butyldibenzothiophenyl group, and
a monovalent residue of spiro[9H-thioxantene-9,9'-[9H]fluorene].

A monovalent group derived from the following unsubstituted heterocyclic ring containing at least one of a nitrogen atom, an oxygen atom and a sulfur atom by removal of one hydrogen atom bonded to the ring atoms thereof, and a monovalent group in which a monovalent group derived from the following unsubstituted heterocyclic ring has a substituent by removal of one hydrogen atom bonded to the ring atoms thereof:

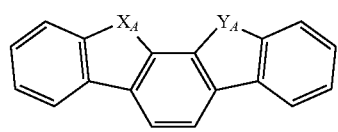

(XY-1)

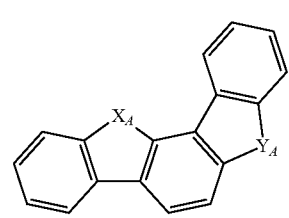

(XY-2)

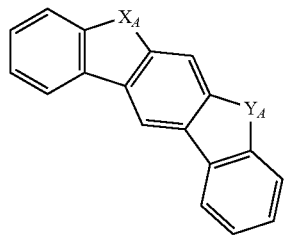

(XY-3)

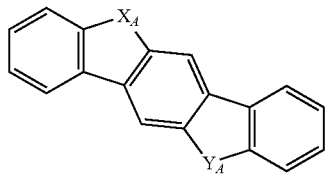

(XY-4)

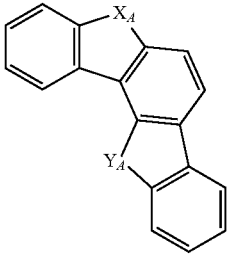

(XY-5)

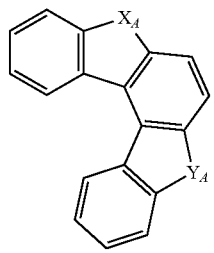

(XY-6)

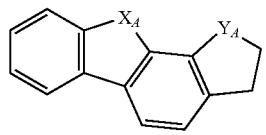

(XY-7)

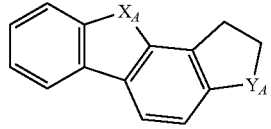

(XY-8)

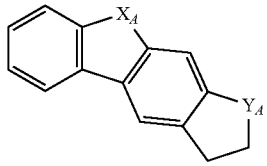

(XY-9)

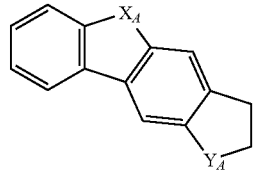

(XY-10)

(XY-11)

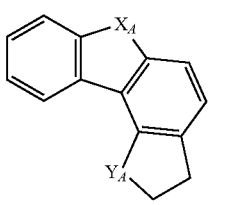

(XY-12)

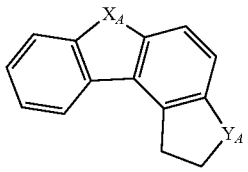

(XY-13)

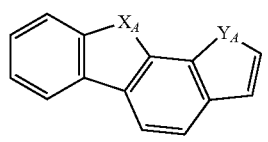

(XY-14)

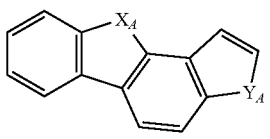

(XY-15)

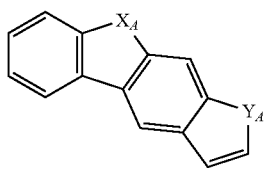

(XY-16)

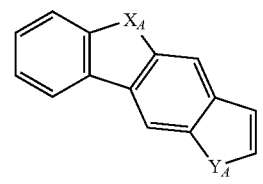

(XY-17)

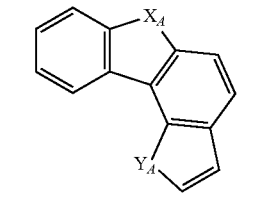

(XY-18)

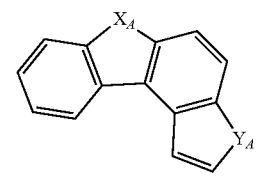

1.5 In the formulas (XY-1) to (XY-18), $X_A$ and $Y_A$ are independently an oxygen atom, a sulfur atom, NH or $CH_2$. However, at least one of $X_A$ and $Y_A$ is an oxygen atom, a sulfur atom or NH.

The heterocyclic ring represented by the formulas (XY-1) to (XY-18) becomes a monovalent heterocyclic group having a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or $CH_2$, and the hydrogen atom in the NH or $CH_2$ is replaced with a substituent.

Specific examples (specific example group G3) of the "substituted or unsubstituted alkyl group" include an unsubstituted alkyl group and a substituted alkyl group described below. (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed herein are merely one example, and the "substituted alkyl group" described herein also includes a group in which "unsubstituted alkyl group" has a substituent further has a substituent, a group in which "substituted alkyl group" further has a substituent, and the like.

An unsubstituted alkyl group:
a methyl group,
an ethyl group,
a n-propyl group,
an isopropyl group,
a n-butyl group,
an isobutyl group,
a s-butyl group, and
a t-butyl group.

A substituted alkyl group:
a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed herein are merely one example, and the "substituted alkenyl group" described herein also includes a group in which "unsubstituted alkenyl group" has a substituent further has a substituent, a group in which "substituted alkenyl group" further has a substituent, and the like.

An unsubstituted alkenyl group and a substituted alkenyl group:
a vinyl group,
an allyl group,
a 1-butenyl group,
a 2-butenyl group,
a 3-butenyl group,
a 1,3-butanedienyl group,
a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:
an ethynyl group.

Specific examples (specific example group G6) of the "substituted or unsubstituted cycloalkyl group" described herein include an unsubstituted cycloalkyl group and a substituted cycloalkyl group described below. (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a the substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed herein *are* merely one example, and the "substituted cycloalkyl group" described herein also includes a group in which "unsubstituted cycloalkyl group" has a substituent further has a substituent, a group in which "substituted cycloalkyl group" further has a substituent, and the like.

An unsubstituted aliphatic ring group:
a cyclopropyl group,
a cyclobutyl group,
a cyclopentyl group,
a cyclohexyl group,
a t-adamantyl group,
a 2-adamantyl group,
a 1-norbornyl group, and
a 2-norbornyl group.

A substituted cycloalkyl group:
a 4-methylcyclohexyl group.

Specific examples (specific example group G7) of the group represented by —Si($R_{901}$)($R_{902}$)($R_{903}$) described herein include
—Si(G1)(G1)(G1),
—Si(G1)(G2)(G2),
—Si(G1)(G1)(G2),
—Si(G2)(G2)(G2),
—Si(G3)(G3)(G3),
—Si(G5)(G5)(G5) and
—Si(G6)(G6)(G6).
In which,
G1 is the "aryl group" described in the specific example group G1.
G2 is the "heterocyclic group" described in the specific example group G2.
G3 is the "alkyl group" described in the specific example group G3.
G5 is the "alkynyl group" described in the specific example group G5.
G6 is the "cycloalkyl group" described in the specific example group G6.

Specific examples (specific example group G8) of the group represented by —O—($R_{904}$) described herein include
—O(G1),
—O(G2),
—O(G3) and
—O(G6).
In which,
G1 is the "aryl group" described in the specific example group G1.
G2 is the "heterocyclic group" described in the specific example group G2.
G3 is the "alkyl group" described in the specific example group G3.
G6 is the "cycloalkyl group" described in the specific example group G6.

Specific examples (specific example group G9) of the group represented by —S—($R_{905}$) described herein include
—S(G1),
—S(G2),
—S(G3) and
—S(G6).
In which,
G1 is the "aryl group" described in the specific example group G1.
G2 is the "heterocycle group" described in the specific example group G2.
G3 is the "alkyl group" described in the specific example group G3.
G6 is the "cycloalkyl group" described in the specific example group G6.

Specific examples (specific example group G10) of the group represented by —N($R_{905}$)($R_{907}$) described herein include
—N(G1)(G1),
—N(G2)(G2),
—N(G1)(G2).
—N(G3)(G3) and
—N(G6) (G6).
In which,
G1 is the "aryl group" described in the specific example group G1.
G2 is the "heterocycle group" described in the specific example group G2.
G3 is the "alkyl group" described in the specific example group G3.
G6 is the "cycloalkyl group" described in the specific example group G6.

Specific examples (specific example group G11) of the "halogen atom" described herein include a fluorine atom, a chlorine atom, a bromine atom and an iodine atom.

Specific examples of the "alkoxy group" described herein include a group represented by —O(G3), where G3 is the "alkyl group" described in the specific example group 1.0 G3. The number of carbon atoms of the "unsubstituted alkoxy group" are 1 to 50, preferably 1 to 30, and more preferably 1 to 18, unless otherwise specified.

Specific examples of the "alkylthio group" described herein include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described herein include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthio group" described herein include a group represented by —S(G1), where G1 is the "aryl group" described in the specific example group G1. The number of ring carbon atoms of the "unsubstituted arylthio group" are 6 to 50, preferably 6 to 30, and more preferably 6 to 18, unless otherwise specified.

Specific examples of the "aralkyl group" described herein include a group represented by -(G3)-(G1), where G3 is the "alkyl group" described in the specific example group G3, and G1 is the "aryl group" described in the specific example group G1. Accordingly, the "aralkyl group" is one embodiment of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a 1-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described herein is, unless otherwise specified, preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-diphenylfluorenyl group, or the like.

The substituted or unsubstituted heterocyclic group described herein is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazole-9-yl group, a phenylcarbazol-9-yl group, a phenyltriazinyl group, a biphenylyltriazinyl group, diphenyltriazinyl group, a phenyldibenzofuranyl group, a phenyldibenzothiophenyl group, an indrocarbazolyl group, a pyrazinyl group, a pyridazinyl group, a quinazolinyl group, a cinnolinyl group, a phthalazinyl group, a quinoxalinyl group, a pyrrolyl group, an indolyl group, a pyrrolo[3,2,1-jk]carbazolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, an indro[3,2,1-jk]carbazolyl group, a dibenzothiophenyl group, or the like.

The dibenzofuranyl group and the dibenzothiophenyl group as described above are specifically any group described below, unless otherwise specified.

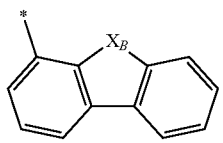

(XY-76)

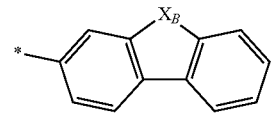

(XY-77)

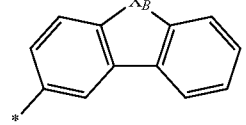

(XY-78)

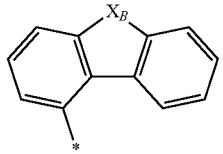

(XY-79)

In the formulas (XY-76) to (XY-79), $X_B$ is an oxygen atom or a sulfur atom.

The substituted or unsubstituted alkyl group described herein is, unless otherwise specified, preferably a methyl group, an ethyl group, a propyl group, an isopropyl group, a n-butyl group, an isobutyl group, a t-butyl group, or the like.

The "substituted or unsubstituted arylene group" descried herein refers to a group in which the above-described "aryl group" is converted into divalence, unless otherwise specified. Specific examples (specific example group G12) of the "substituted or unsubstituted arylene group" include a group in which the "aryl group" described in the specific example group G1 is converted into divalence. Namely, specific examples (specific example group G12) of the "substituted or unsubstituted arylene group" refer to a group derived from the "aryl group" described in specific example group G1 by removal of one hydrogen atom bonded to the ring carbon atoms thereof.

Specific examples (specific example group 013) of the "substituted or unsubstituted divalent heterocyclic group" include a group in which the "heterocyclic group" described in the specific example group G2 is converted into divalence. Namely, specific examples (specific example group 013) of the "substituted or unsubstituted divalent heterocyclic group" refer to a group derived from the "heterocyclic group" described in specific example group 02 by removal of one hydrogen atom bonded to the ring atoms thereof.

Specific examples (specific example group G14) of the "substituted or unsubstituted alkylene group" include a group in which the "alkyl group" described in the specific example group G3 is converted into divalence. Namely, specific examples (specific example group 014) of the "substituted or unsubstituted alkylene group" refer to a group derived from the "alkyl group" described in specific example group G3 by removal of one hydrogen atom bonded to the carbon atoms constituting the alkane structure thereof.

The substituted or unsubstituted arylene group described herein is any group described below, unless otherwise specified.

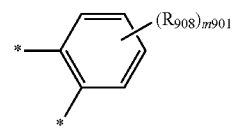
(XY-20)

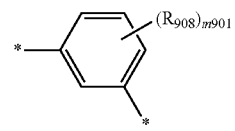
(XY-21)

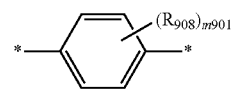
(XY-22)

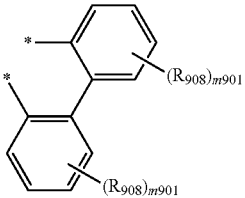
(XY-23)

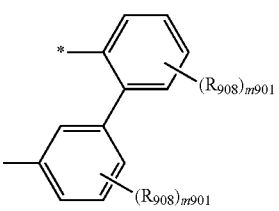
(XY-24)

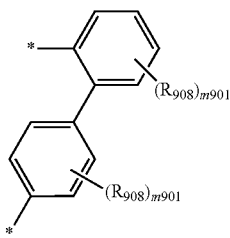
(XY-25)

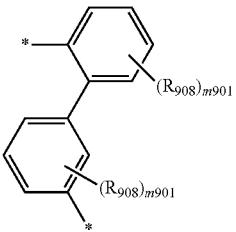
(XY-26)

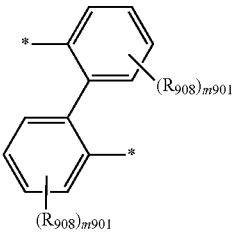
(XY-27)

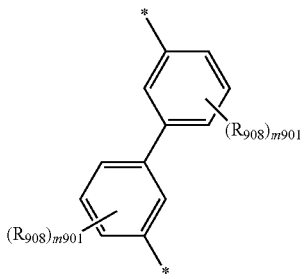
(XY-28)

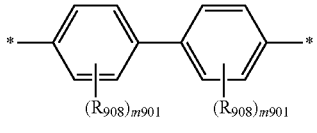
(XY-29)

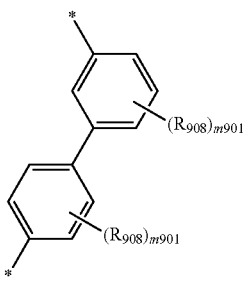
(XY-83)

In the formulas (XY-20) to (XY-29), (XY-83) and (XY-84), $R_{908}$ is a substituent.

Then, m901 is an integer of 0 to 4, and when m901 is 2 or more, a plurality of $R_{908}$ may be the same with or different from each other.

In the formulas (XY-30) to (XY-40), $R_{909}$ is independently a hydrogen atom or a substituent. Two of $R_{909}$ may be bonded with each other through a single bond to form a ring.

(XY-45)
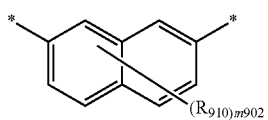
(XY-46)
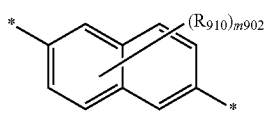
In the formulas (XY-41) to (XY-46), $R_{910}$ is a substituent.
Then, m902 is an integer of 0 to 6. When m902 is 2 or more, a plurality of $R_{910}$ may be the same with or different from each other.
The substituted or unsubstituted divalent heterocyclic group described herein is preferably any group described below, unless otherwise specified.
(XY-50)
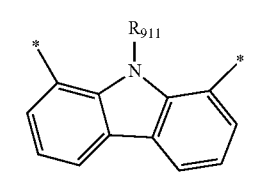
(XY-51)
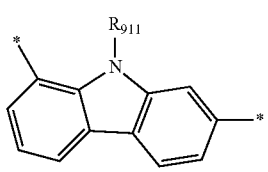
(XY-52)
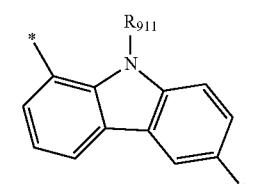
(XY-53)
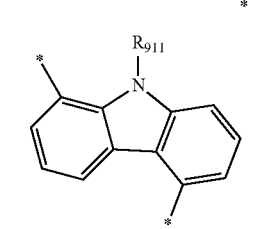
(XY-54)
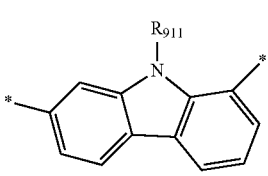
(XY-55)
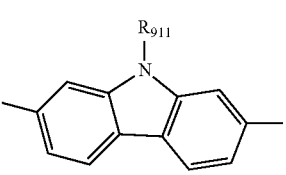
(XY-56)
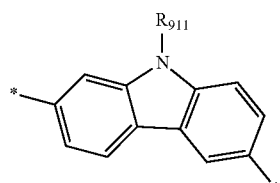
(XY-57)
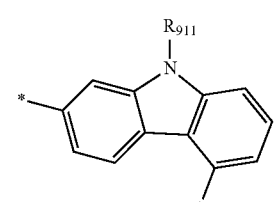
(XY-58)
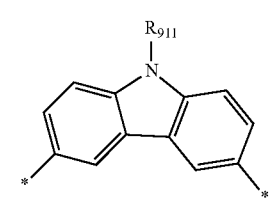
(XY-59)
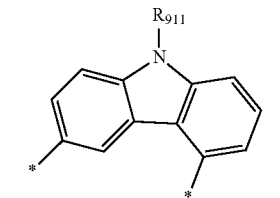
(XY-60)
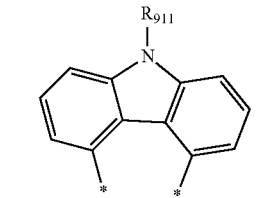
(XY-61)
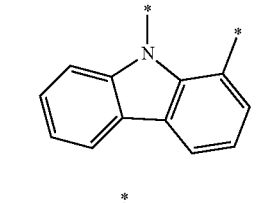
(XY-62)
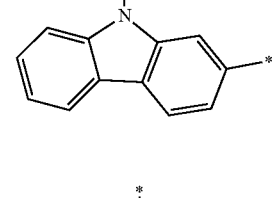
(XY-63)
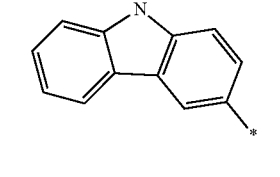

-continued (XY-64)

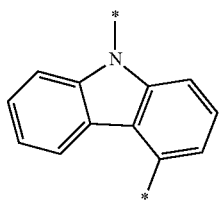

In the formulas (XY-50) to (XY-60), $R_{911}$ is a hydrogen atom or a substituent.

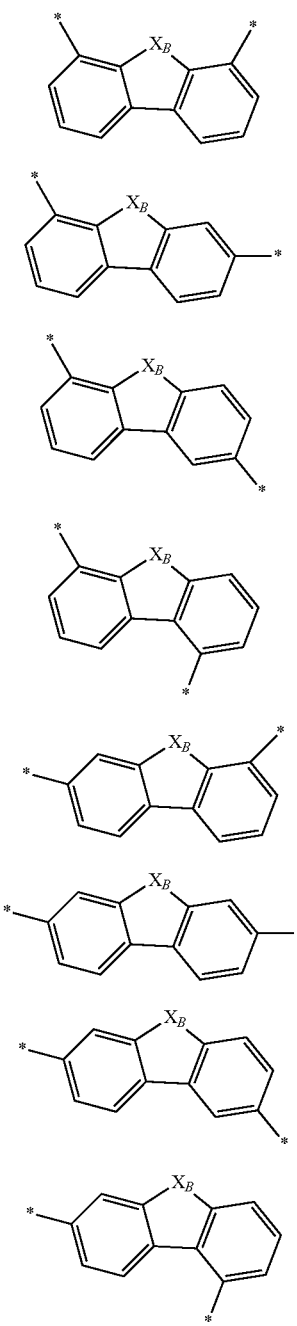

(XY-65)

(XY-66)

(XY-67)

(XY-68)

(XY-69)

(XY-70)

(XY-71)

(XY-72)

-continued

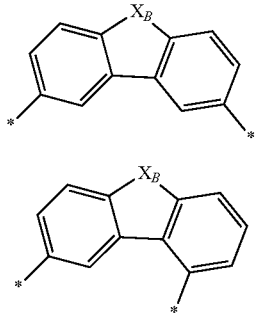

(XY-73)

(XY-74)

(XY-75)

In the formulas (XY-65) to (XY-75), $X_B$ is an oxygen atom or a sulfur atom.

Herein, a case where "one or more sets of two or more groups adjacent to each other are bonded with each other to form a substituted or unsubstituted and saturated or unsaturated ring" will be described by taking, as an example, a case of an anthracene compound represented by the following formula (XY-80) in which a mother skeleton is an anthracene ring.

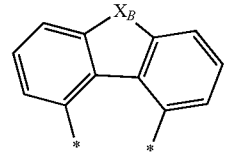

(XY-80)

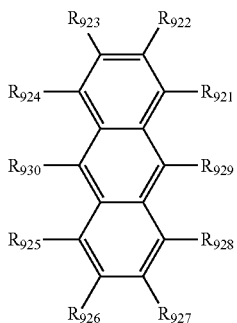

(XY-74)

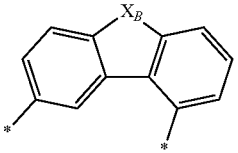

(XY-75)

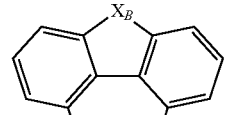

For example, two adjacent to each other into one set when "one or more sets of two or more groups adjacent to each other are bonded with each other to form the ring" among $R_{921}$ to $R_{930}$ include $R_{921}$ and $R_{922}$, $R_{922}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

The above-described "one or more sets" means that two or more sets of two groups adjacent to each other may simultaneously form the ring. For example, a case where $R_{921}$ and $R_{922}$ are bonded with each other to form a ring A, and simultaneously $R_{925}$ and $R_{926}$ are bonded with each other to form a ring B is represented by the following formula (XY-81).

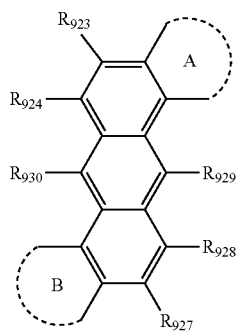

(XY-81)

A case where "two or more groups adjacent to each other" form a ring means that, for example, $R_{921}$ and $R_{922}$ are bonded with each other to form a ring A, and $R_{922}$ and $R_{923}$ are bonded with each other to form a ring C. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

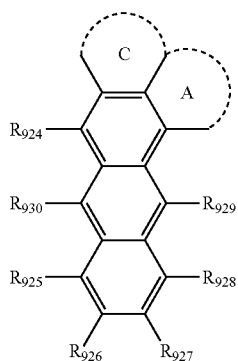

(XY-82)

The rings A to C formed in the formulas (XY-81) and (XY-82) are a saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{92}$ being bonded with each other, represented by the formula (XY-81), means a ring formed by a carbon atom of the anthracene skeleton bonded with $R_{921}$, a carbon atom of the anthracene skeleton bonded with $R_{922}$, and one or more arbitrary elements. Specific examples include, when the ring A is formed by $R_{921}$ and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into a benzene ring. Further, when a saturated ring is formed, the ring is formed into a cyclohexane ring.

Here, "arbitrary elements" are preferably a C element, a N element, an O element and a S element. In the arbitrary elements (for example, a case of the C element or the N element), the bond(s) that is(are) not involved in the formation of the ring may be terminated by a hydrogen atom, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

As specific examples of the aromatic hydrocarbon ring, a structure in which the aryl group described in specific example group G1 is terminated with a hydrogen atom may be mentioned.

As specific examples of the aromatic heterocyclic ring, a structure in which the aromatic heterocyclic group described in specific example group G2 is terminated with a hydrogen atom may be mentioned.

As specific examples of the aliphatic hydrocarbon ring, a structure in which the cycloalkyl group described in specific example group G6 is terminated with a hydrogen atom may be mentioned.

When the above-described "saturated or unsaturated ring" has a substituent, the substituent is an "arbitrary substituent" as described below, for example. When the above-mentioned "saturated or unsaturated ring" has a substituent, specific examples of the substituent refer to the substituents described in above-mentioned "the substituent described herein".

In one embodiment of the present specification, the substituent (hereinafter, referred to as an "arbitrary substituent" in several cases) in the case of the "substituted or unsubstituted" is a group selected from the group consisting of an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R_{901}$)($R_{902}$)($R_{903}$),
—O—($R_{904}$),
—S—($R_{905}$)
—N($R_{906}$)($R_{907}$)
wherein,
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms; and
when two or more of $R_{901}$ to $R_{907}$ exist, two or more of $R_{901}$ to $R_{907}$ may be the same with or different from each other,
a halogen atom, a cyano group, a nitro group,
an unsubstituted aryl group having 6 to 50 ring carbon atoms, and
an unsubstituted monovalent heterocyclic group having 5 to 50 ring atoms.

In one embodiment, the substituent in the case of "substituted or unsubstituted" is a group selected from the group consisting of an alkyl group having 1 to 50 carbon atoms,
an aryl group having 6 to 50 ring carbon atoms, and
a monovalent heterocyclic group having 5 to 50 ring atoms.

In one embodiment, the substituent in the case of "substituted or unsubstituted" is a group selected from the group consisting of
an alkyl group having 1 to 18 carbon atoms,
an aryl group having 6 to 18 ring carbon atoms, and
a monovalent heterocyclic group having 5 to 18 ring atoms.

Specific examples of each group of the arbitrary substituent described above are as described above.

Herein, unless otherwise specified, the saturated or unsaturated ring (preferably substituted or unsubstituted and saturated or unsaturated five-membered or six-membered ring, more preferably a benzene ring) may be formed by the arbitrary substituents adjacent to each other.

Herein, unless otherwise specified, the arbitrary substituent may further have the substituent. Specific examples of the substituent that the arbitrary substituent further has include to the ones same as the arbitrary substituent described above.

[Organic EL Device]

The organic EL device according to one aspect of the invention comprises a cathode, an anode and an emitting layer disposed between the cathode and the anode, and it is characterized in that the emitting layer comprises a compound represented by the following formula (1) and one or more compounds selected from the group consisting of compounds represented by formulas (11), (21), (31), (41), (51), (61), (71) and (81).

Each compound is described later.

The organic EL device according to one aspect of the invention exhibits high device performance by possessing the above-mentioned constitution. Specifically, it is possible to provide an organic EL device with longer life.

According to one aspect of the present invention, a method for improving a performance of an organic EL device can also be provided, the method is characterized in that the compound represented by the formula (1) and one or more compounds selected from the group consisting of the formulas (11) to (81) are used in combination in the emitting layer of the organic EL device. Specifically, the method can improve an organic EL device performance as compared with the case where a compound having the same structure as formula (1) except that only protium atoms are contained as hydrogen atoms (hereinafter also referred to as "protium compound") is used as a host material. The case where the protium compound is used means that a host material in an emitting layer consists essentially of the protium compound (the ratio of the protium compound to the sum of the protium compound and the compound represented by formula (1) is 90 mol % or more, 95 mol % or more, or 99 mol % or more).

That is, it is possible to increase a performance of an organic EL device by, instead of a protium compound or in addition to a protium compound, using a compound obtained by replacing at least one protium atoms on an anthracene skeleton of the protium compound with a deuterium atom (a compound represented by formula (1)) as a host material.

A schematic outline of the organic EL device of one aspect of the invention is explained by reference to the FIGURE.

The organic EL device 1 according to one aspect of the invention comprises substrate 2, anode 3, emitting layer 5, cathode 10, organic layer 4 disposed between the anode 3 and the emitting layer 5, and organic layer 6 disposed between the emitting layer 5 and the cathode 10.

The compound represented by the formula (1) and one or more compounds selected from a group consisting of compounds represented by the formula (11), (21), (31), (41), (51), (61), (71) and (81) are contained in emitting layer 5 disposed between the anode 3 and the cathode 10. Each compound contained in the emitting layer 5 may be used singly or in combination of two or more, (Compound Represented by Formula (1))

The compound represented by the formula (1) is explained below.

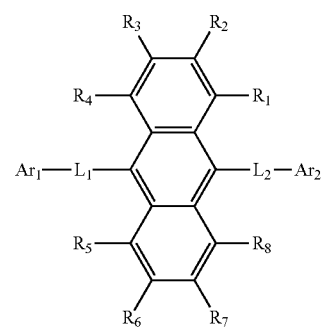

(1)

wherein in the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{301}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms;

Ar$_1$ is
a substituted or unsubstituted aryl group having 6 to 50 ring carbon atoms, or
a substituted or unsubstituted monovalent heterocyclic group having 5 to 50 ring atoms;

Ar$_2$ is a monovalent group represented by the following formula (2), (3) or (4);

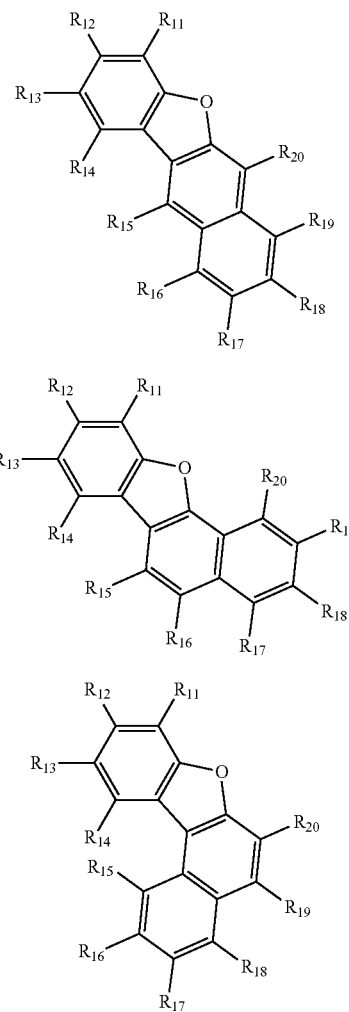

wherein in the formulas (2) to (4),
one or more pairs of two adjacent groups of R$_{15}$ to R$_{20}$ are bonded with each other to form a substituted or unsubstituted, saturated or unsaturated ring, or do not form a substituted or unsubstituted, saturated or unsaturated ring;

when one or more pairs of two adjacent groups of R$_{15}$ to R$_{20}$ are not bonded with each other and do not form a substituted or unsubstituted, saturated or unsaturated ring, one of R$_{11}$ to R$_{20}$ is a single bond bonding to L$_2$;

when one or more pairs of two adjacent groups of R$_{15}$ to R$_{20}$ are bonded with each other to form a substituted or unsubstituted, saturated or unsaturated ring, one of R$_{15}$ to R$_{20}$ which does not form a substituted or unsubstituted, saturated or unsaturated ring and R$_{11}$ to R$_{14}$ is a single bond bonding to L$_2$;

R$_{11}$ to R$_{20}$ that do not form the substituted or unsubstituted, saturated or unsaturated ring and that are not a single bond bonding to L$_2$ are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
R$_{901}$ to R$_{907}$ are as defined in the formula (1);

All of R$_1$ to R$_8$ may be deuterium atoms or a part of them (e.g., one, two or more of R$_1$ to R$_8$) may be deuterium atoms.

R$_1$ to R$_8$ that are not deuterium atoms are preferably hydrogen atoms (protium atoms).

In one embodiment, at least one hydrogen atom contained in one or more groups selected from a group consisting of L$_1$ and L$_2$ is a deuterium atom. In more detail, in one embodiment, one or more groups selected from the group consisting of L$_1$ and L$_2$ are an unsubstituted arylene group having 6 to 30 ring carbon atoms in which at least one hydrogen atom is a deuterium atom, or an unsubstituted divalent heterocyclic group having 5 to 30 ring atoms in which at least one hydrogen atom is a deuterium atom.

In one embodiment, L$_1$ and L$_2$ are independently a single bond, or a substituted or unsubstituted arylene group having 6 to 14 ring carbon atoms. It is preferable that at least one of L$_1$ and L$_2$ is a single bond.

In one embodiment, any one of R$_{11}$ to R$_{14}$ in formulas (2) to (4) is a single bond bonding to L$_2$.

In one embodiment, one or more pairs of two adjacent groups of R$_{15}$ to R$_{20}$ in formulas (2) to (4) are not bonded with each other and do not form a substituted or unsubstituted, saturated or unsaturated ring.

In one embodiment, among R$_{11}$ to R$_{20}$ in the formulas (2) to (4), those which are not a single bond bonding to L$_2$ and do not contribute to ring formation are preferably hydrogen atoms.

In one embodiment, among R$_{11}$ to R$_{20}$ in the formulas (2) to (4), at least one which is not a single bond bonding to L$_2$ and does not contribute to ring formation is a deuterium atom.

In one embodiment, at least one hydrogen atom contained in one or more Ar$_1$ is a deuterium atom. In more detail, in one embodiment, Ar$_1$ is an unsubstituted aryl group having 6 to 50 ring carbon atoms in which at least one hydrogen atom is a deuterium atom, or an unsubstituted monovalent heterocyclic group having 5 to 50 ring atoms in which at least one hydrogen atom is a deuterium atom.

Existence of a deuterium atom in the compound is confirmed by Mass Spectrometry or $^1$H-NMR Spectrometry. The bonding position of a deuterium atom in the compound is identified by $^1$H-NMR Spectrometry. In concrete terms, it is confirmed as follows.

If it is identified that, by Mass Spectrometry, a molecular weight of a target compound is greater by "one" than a molecular weight of a corresponding compound in which all hydrogen atoms are protium atoms, it is confirmed that one deuterium atom exists in the target compound. Further, the number of deuterium atoms in a molecule can be confirmed by an integration value obtained by $^1$H-NMR analysis on the target compound, since no signal is observed by performing $^1$H-NMR analysis on a deuterium atom. The bonding position of a deuterium can be identified by performing $^1$H-NMR analysis on the target compound and assigning signals.

In the organic EL device according to one aspect of the invention, the content ratio of the protium compound to the total of the compound represented by formula (1) and the protium compound in the emitting layer is preferably 99 mol % or less. The content ratio of the protium compound is confirmed by Mass Spectrometry.

In one embodiment, the emitting layer of the organic EL device according to one aspect of the invention includes the compound represented by the formula (1) and a protium compound, and the content ratio of the former to the total thereof is 30 mol % or more, 50 mol % or more, 70 mol % or more, 90 mol % or more, 95 mol % or more, 99 mol % or more, or 100 mol %.

$Ar_1$ is preferably a substituted or unsubstituted aryl group having 6 to 50 ring carbon atoms, more preferably selected from groups represented by the following formulas (a1) to (a4).

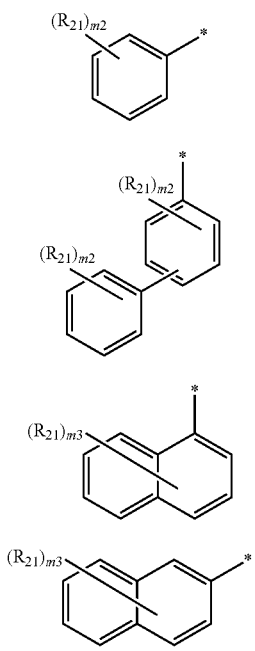

(a1)

(a2)

(a3)

(a4)

wherein in the formulas (a1) to (a4),
* is a single bond bonding to $L_1$;
$R_{21}$ is
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
m1 is an integer of 0 to 4;
m2 is an integer of 0 to 5;
m3 is an integer of 0 to 7;
when each of m1 to m3 is 2 or more, the plural $R_{21}$s may be the same or different; and when each of m1 to m3 is 2 or more, adjacent plural $R_{21}$s are bonded with each other to form a substituted or unsubstituted, saturated or unsaturated ring, or do not form a substituted or unsubstituted, saturated or unsaturated ring.

Preferably, $L_1$ and $L_2$ are independently a single bond, or a substituted or unsubstituted arylene group having 6 to 14 ring carbon atoms. It is preferable that at least one of $L_1$ and $L_2$ is a single bond.

In one embodiment, the compound represented by the formula (1) is a compound represented by any one of following formulas (1-1) to (1-3).

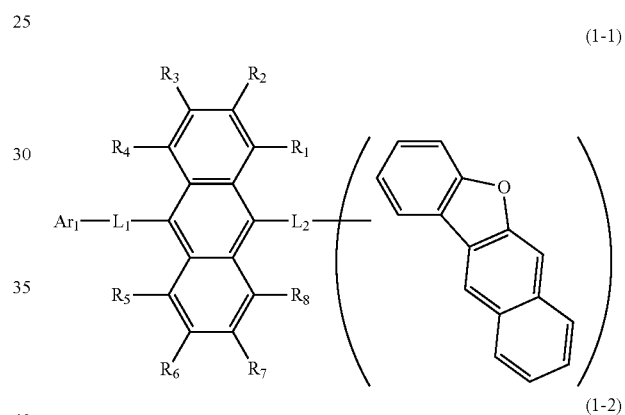

(1-1)

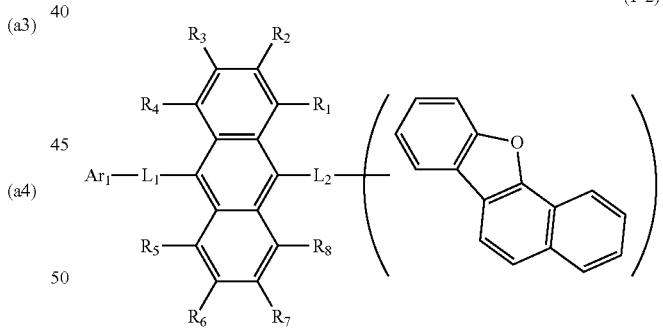

(1-2)

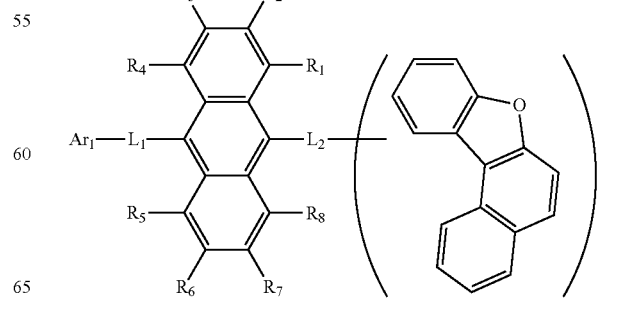

(1-3)

wherein in the formulas (1-1) to (1-3), $R_1$ to $R_3$, $Ar_1$, $L_1$ and $L_2$ are as defined in the formula (1).

In one embodiment, the compound represented by the formula (1) is a compound represented by any one of following formulas (1-11) to (1-13).

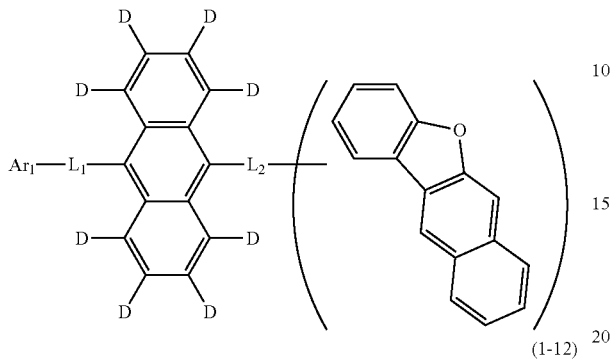

(1-11)

(1-12)

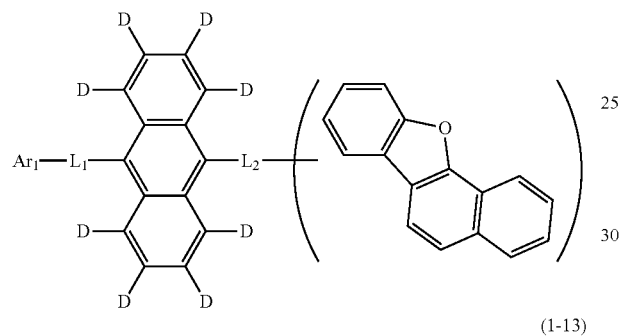

(1-13)

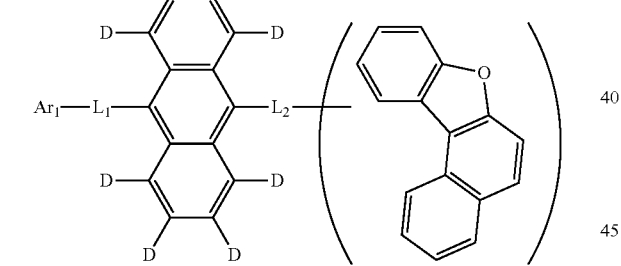

wherein in the formulas (1-11) to (1-13), $Ar_1$, $L_1$ and $L_2$ are as defined in the formula (1).

In one embodiment, the compound represented by the formula (1) is represented by the following formula (1A):

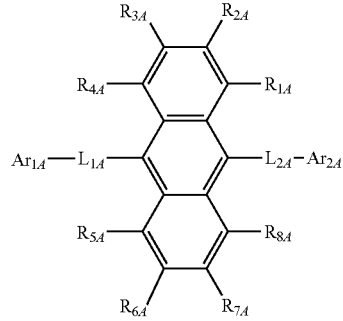

(1A)

wherein in the formula (1A), $R_{1A}$ to $R_{8A}$ are independently a hydrogen atom, and at least one of $R_{1A}$ to $R_{8A}$ is a deuterium atom;

$L_{1A}$ and $L_{2A}$ are independently a single bond, an unsubstituted phenylene group, or an unsubstituted naphthylene group;

$Ar_{1A}$ is a substituted or unsubstituted phenyl group or a substituted or unsubstituted naphthyl group, and the substituent for $Ar_{1A}$ is a phenyl group;

$Ar_{2A}$ is a monovalent group represented by the following formula (2A), (3A) or (4A):

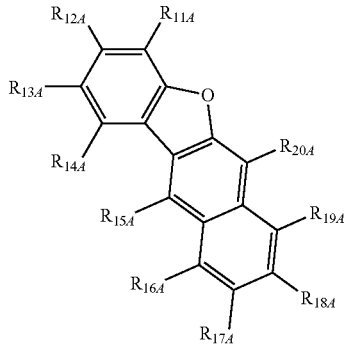

(2A)

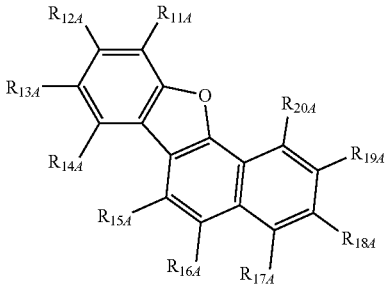

(3A)

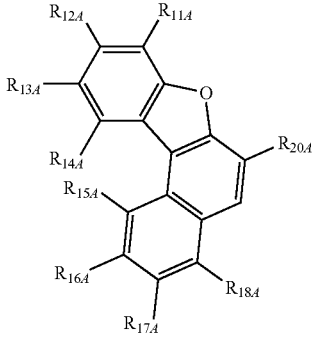

(4A)

wherein in the formulas (2A) to (4A), any one of $R_{13A}$ to $R_{14A}$ is a single bond bonding to $L_{2A}$; and $R_{11A}$, $R_{12A}$, $R_{15A}$ to $R_{20A}$, as well as $R_{13A}$ to $R_{14A}$ that are not a single bond bonding to $L_{2A}$ are independently a hydrogen atom or an unsubstituted aryl group including 6 to 50 ring carbon atoms.

In one embodiment, in the formula (1A), at least two of $R_{1A}$ to $R_{8A}$ are deuterium atoms.

In one embodiment, in the formula (1A), $R_{1A}$ to $R_{8A}$ are all deuterium atoms.

In one embodiment, in the formula (1A), at least one hydrogen atom contained in $Ar_{1A}$ is a deuterium atom.

In one embodiment, in the formula (1A), $R_{11A}$, $R_{12A}$, $R_{15A}$ to $R_{20A}$, as well as $R_{13A}$ to $R_{14A}$ that are not a single bond bonding to $L_{2A}$ are hydrogen atoms.

In one embodiment, in the formula (1A), at least one of $R_{11A}$, $R_{12A}$, $R_{15A}$ t $R_{20A}$, as well as $R_{13A}$ to $R_{14A}$ that are not a single bond bonding to $L_{2A}$ is a deuterium atoms.

The compound represented by the formula (1) can be synthesized in accordance with the synthesis process described in Examples by using publicly known alternative reactions or materials corresponding to a target compound.

Examples of the compound represented by formula (1) include the following compounds. In the following example compounds, D represents a deuterium atom.

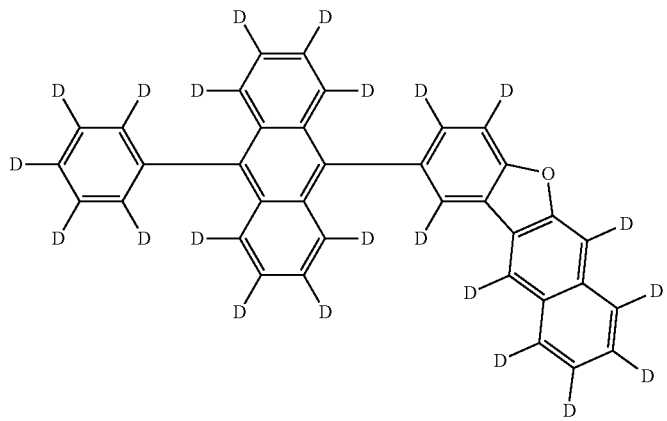

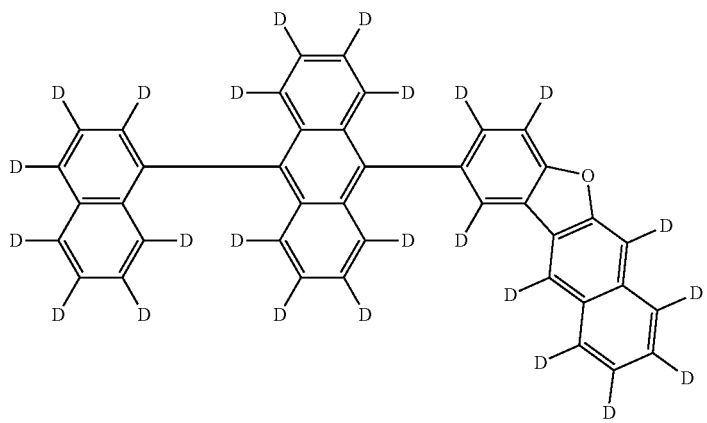

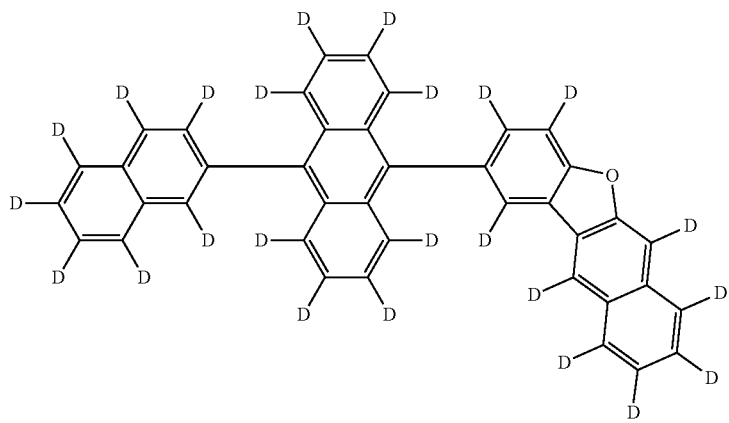

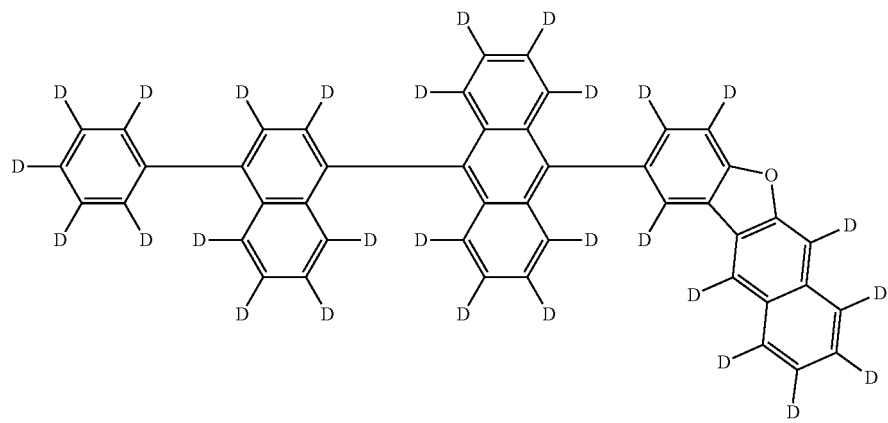
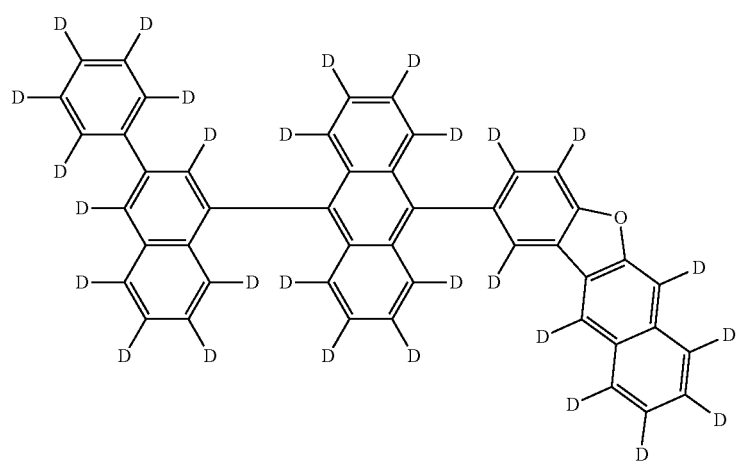
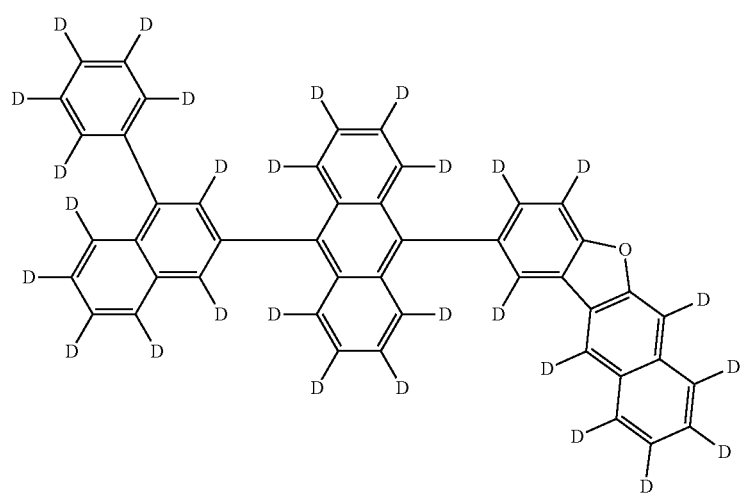

-continued
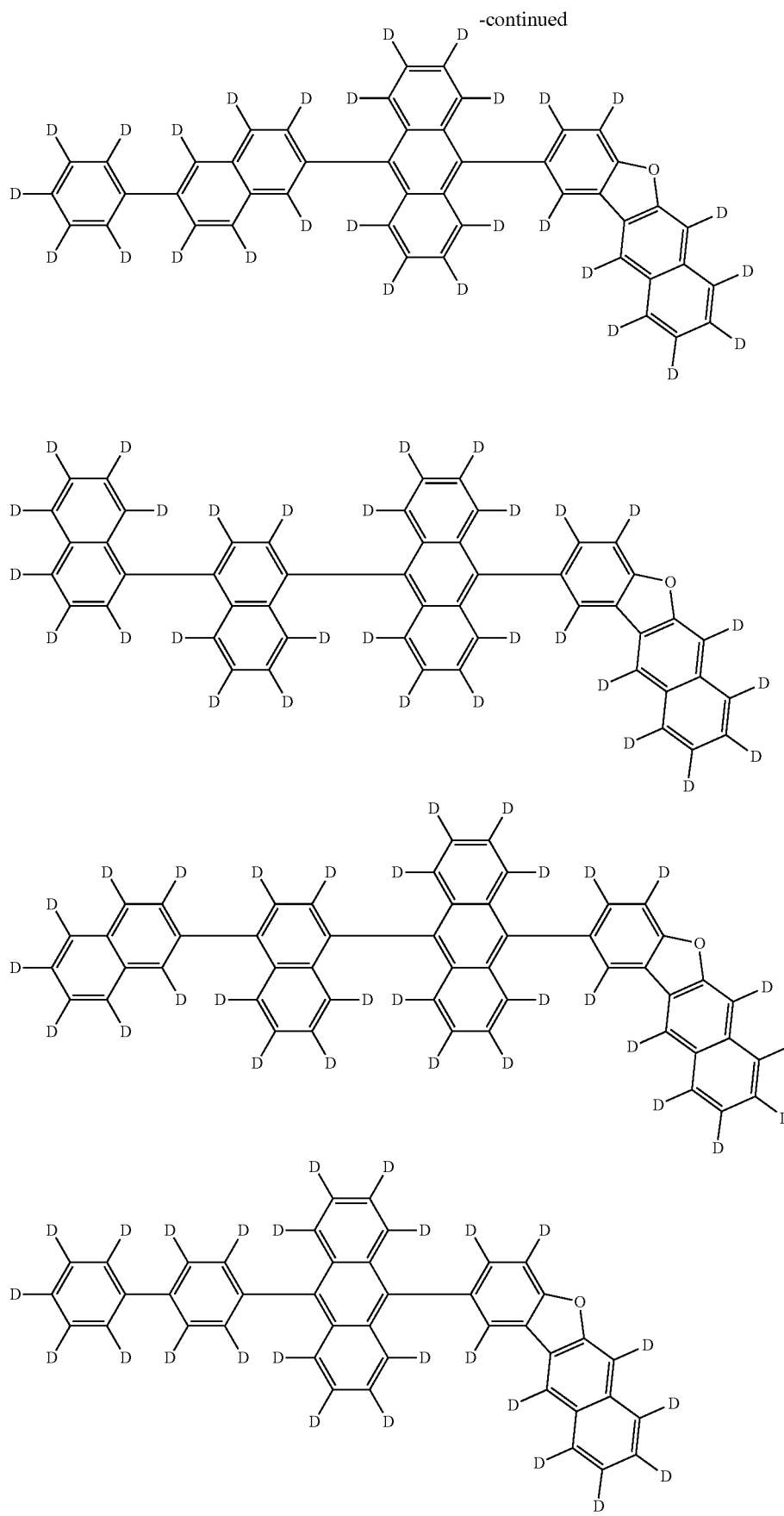

-continued
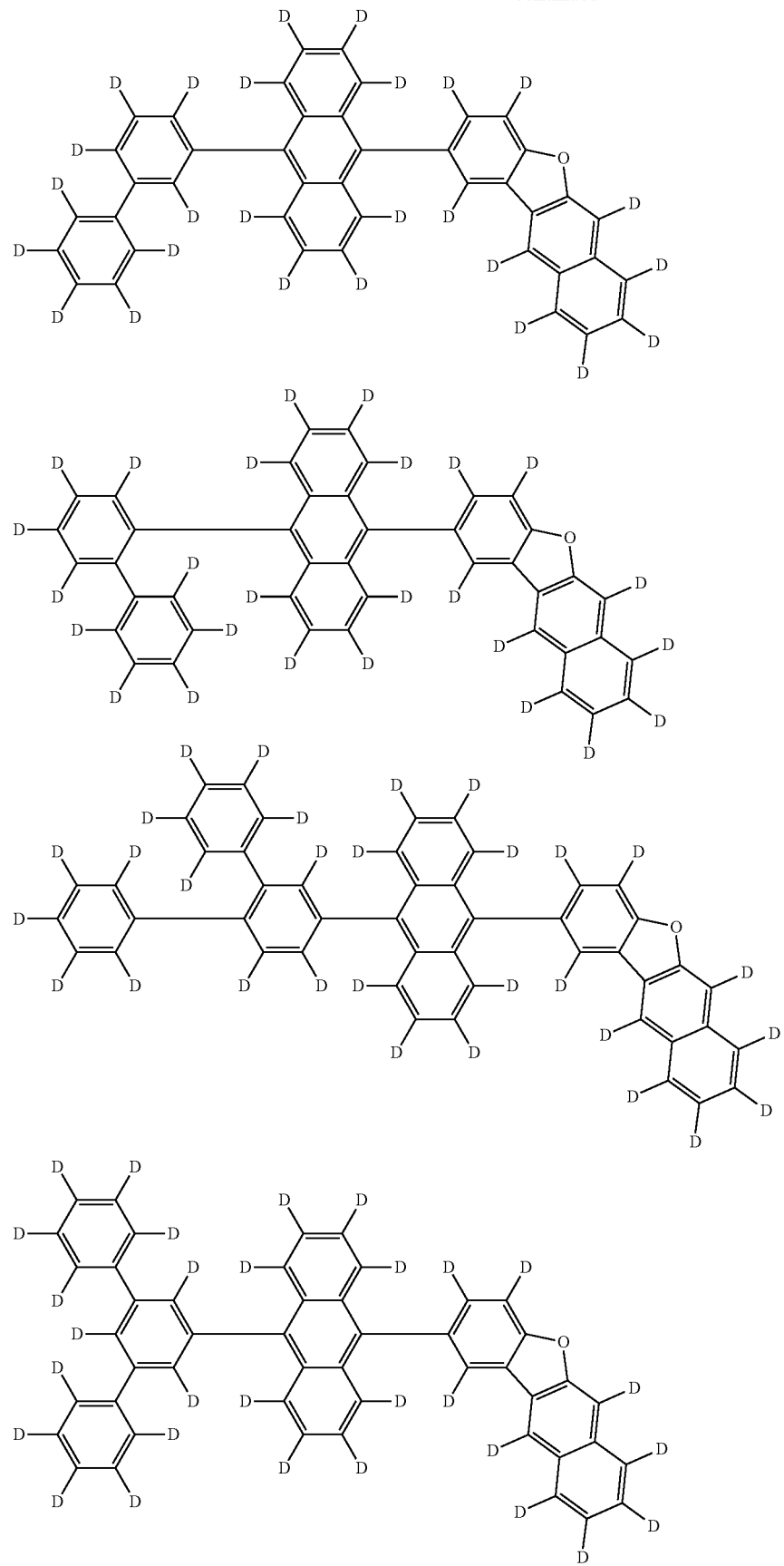

-continued
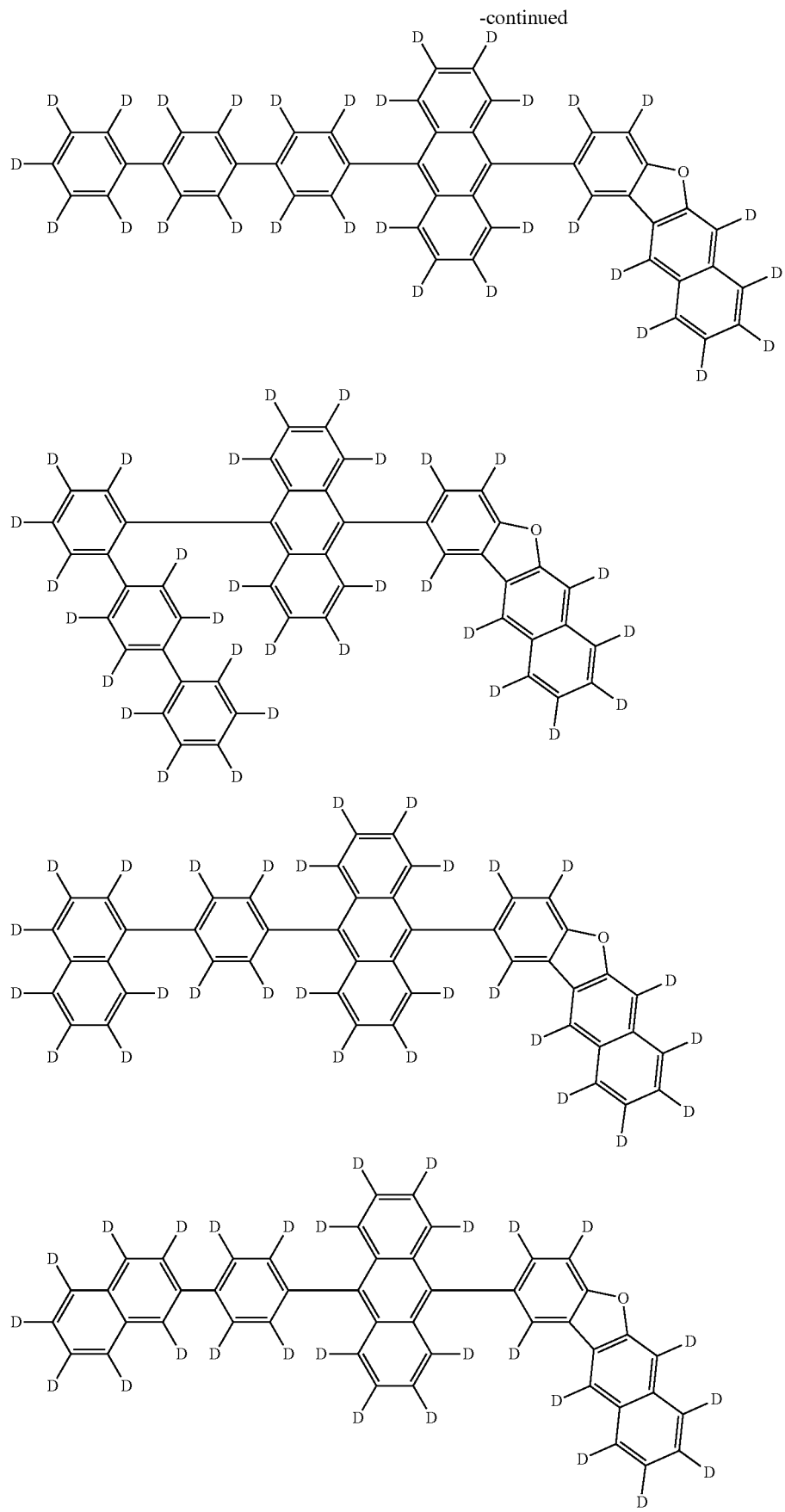

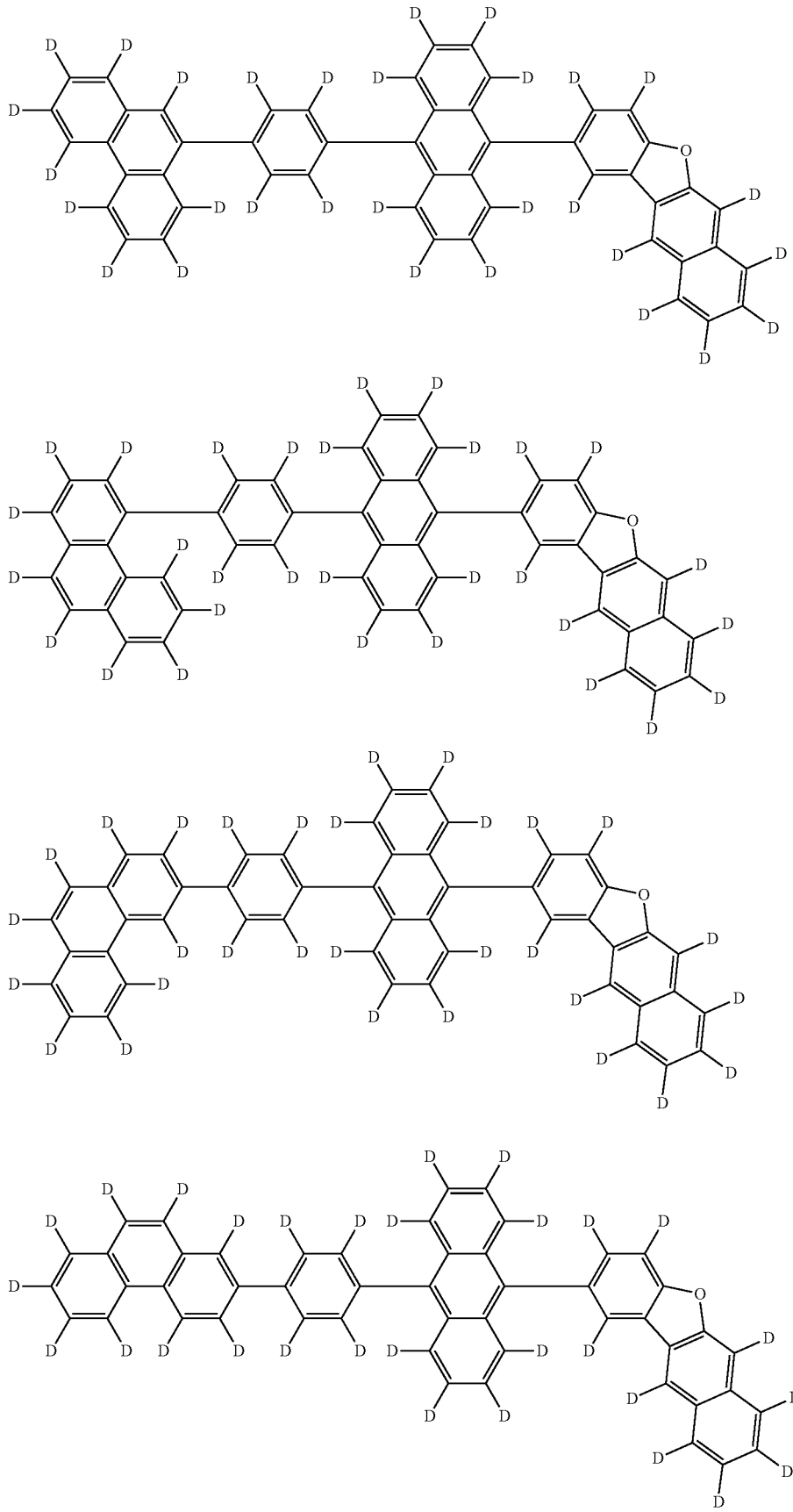

-continued
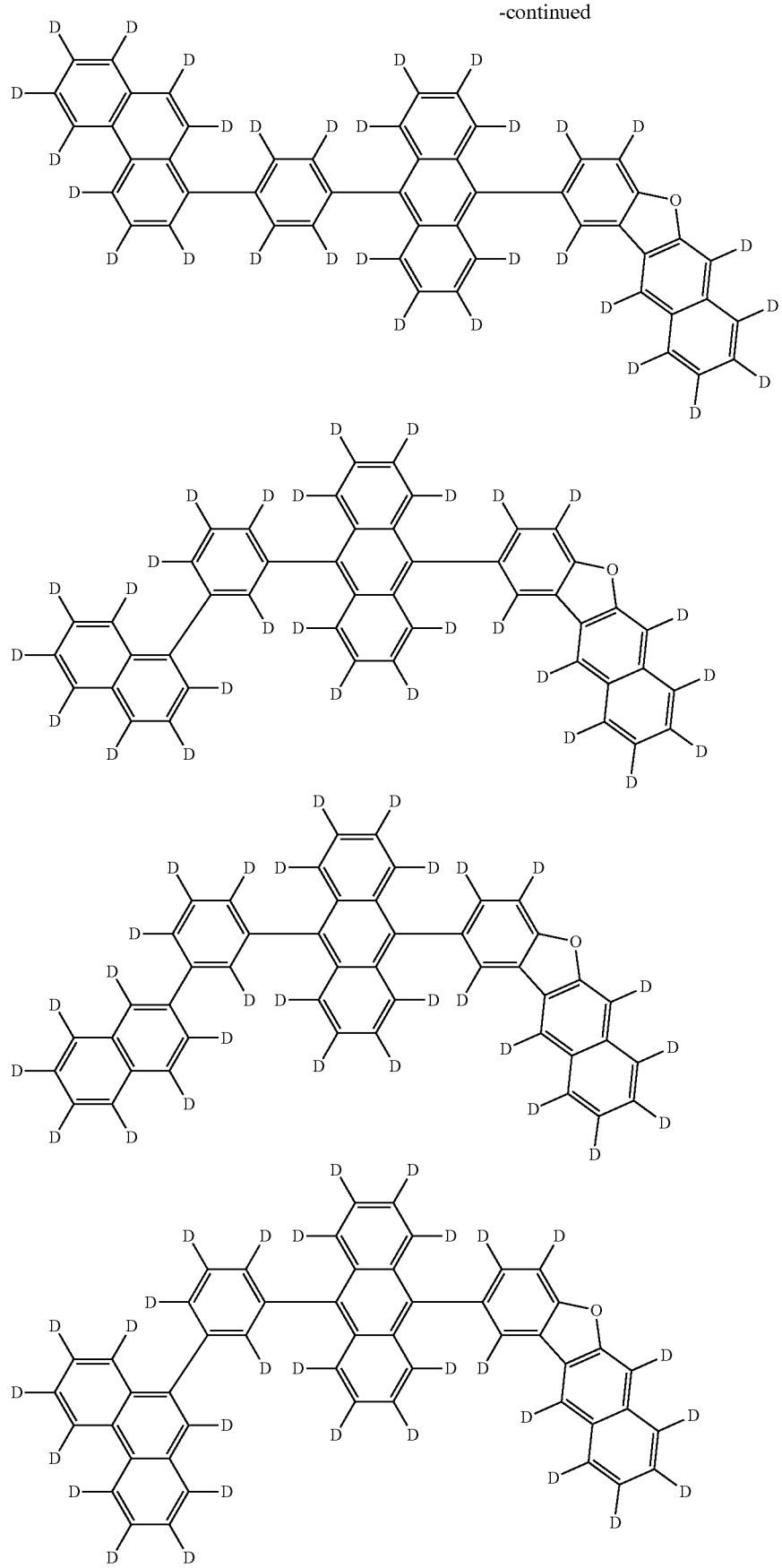

-continued
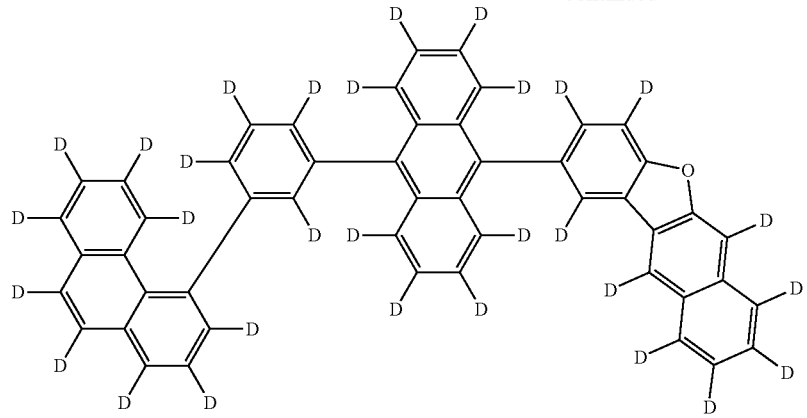
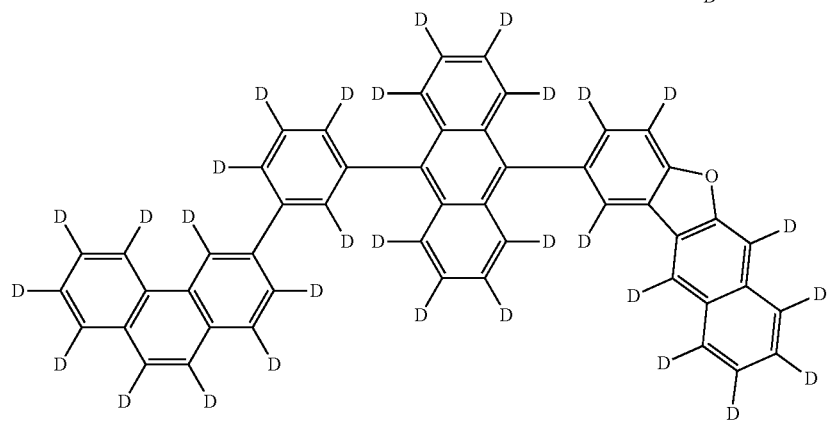
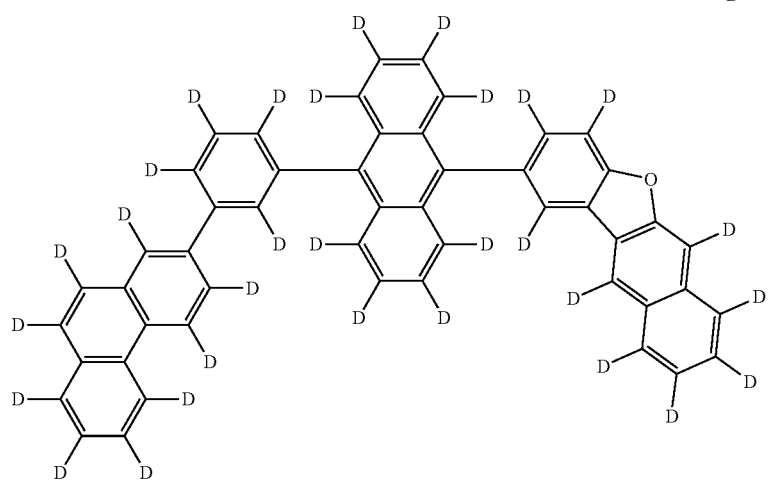
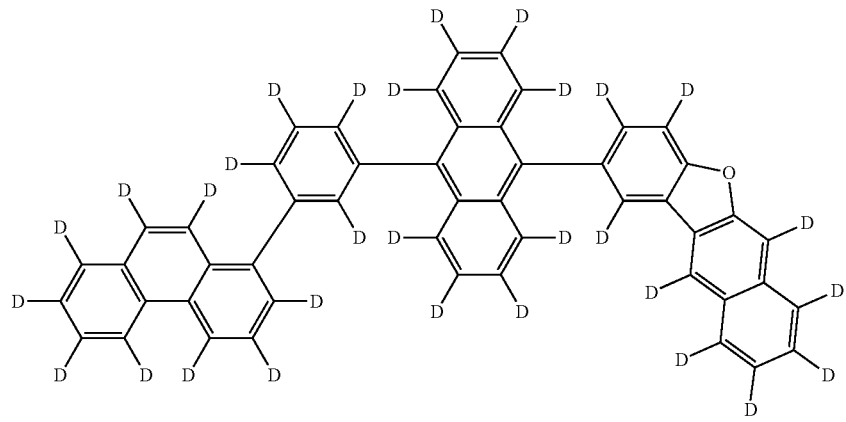

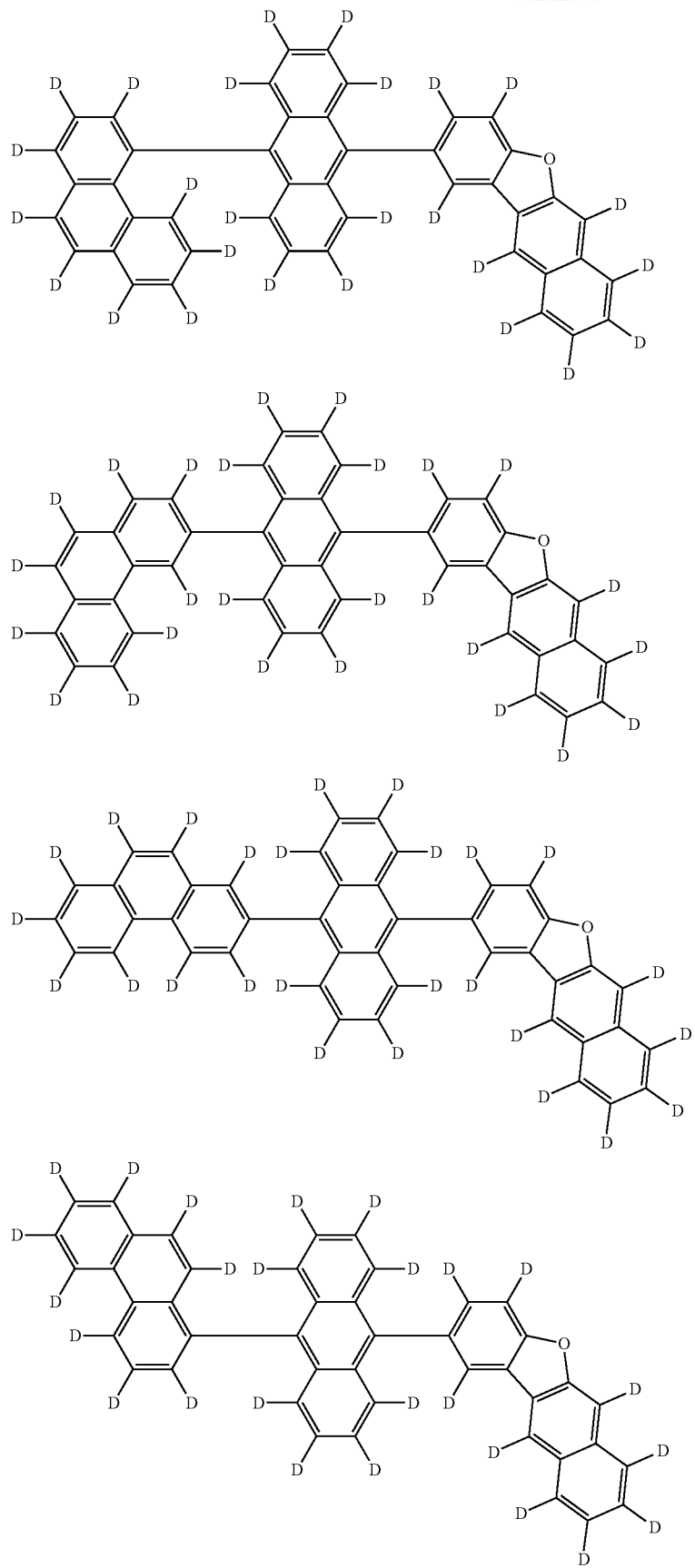

-continued
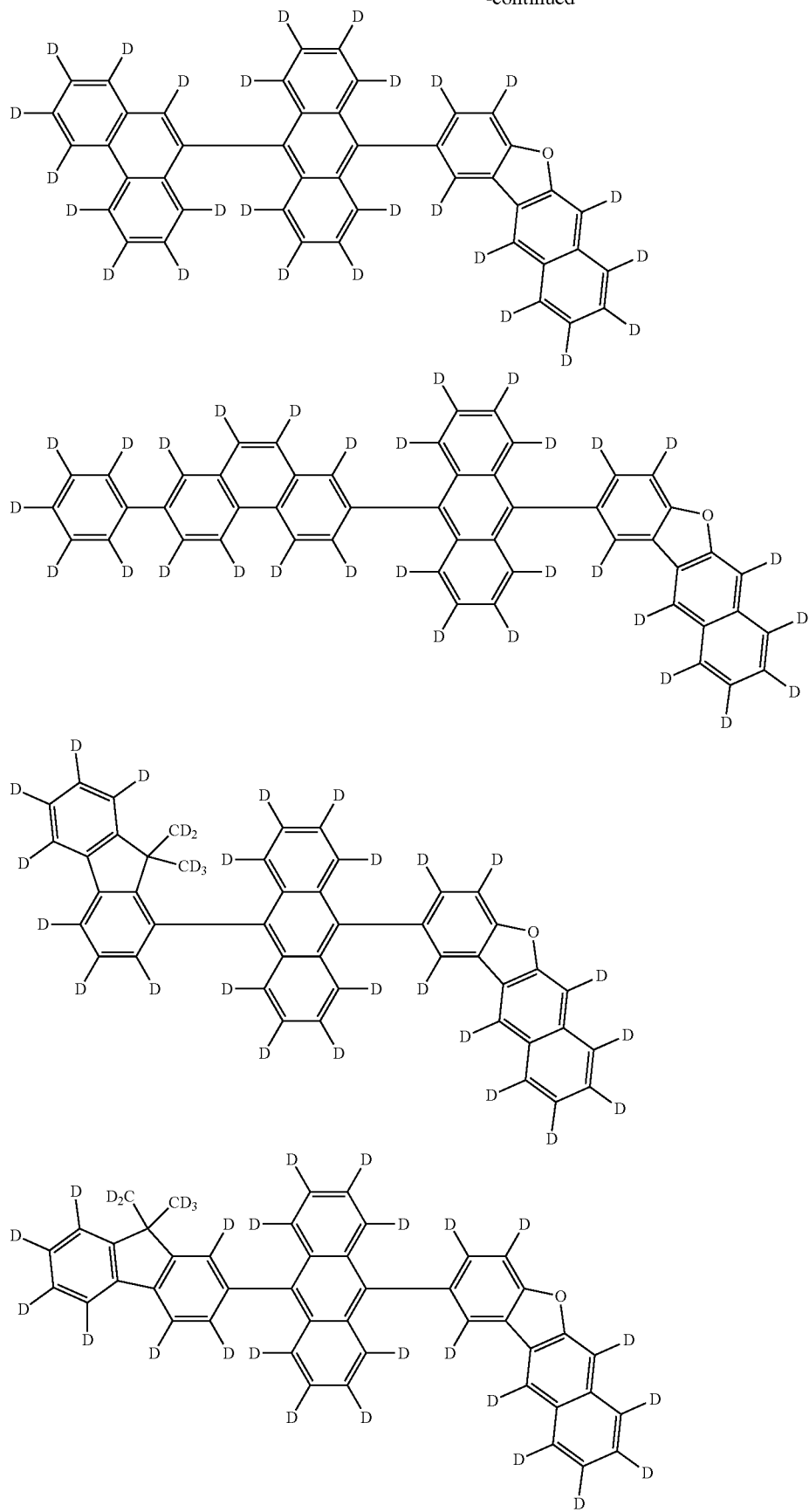

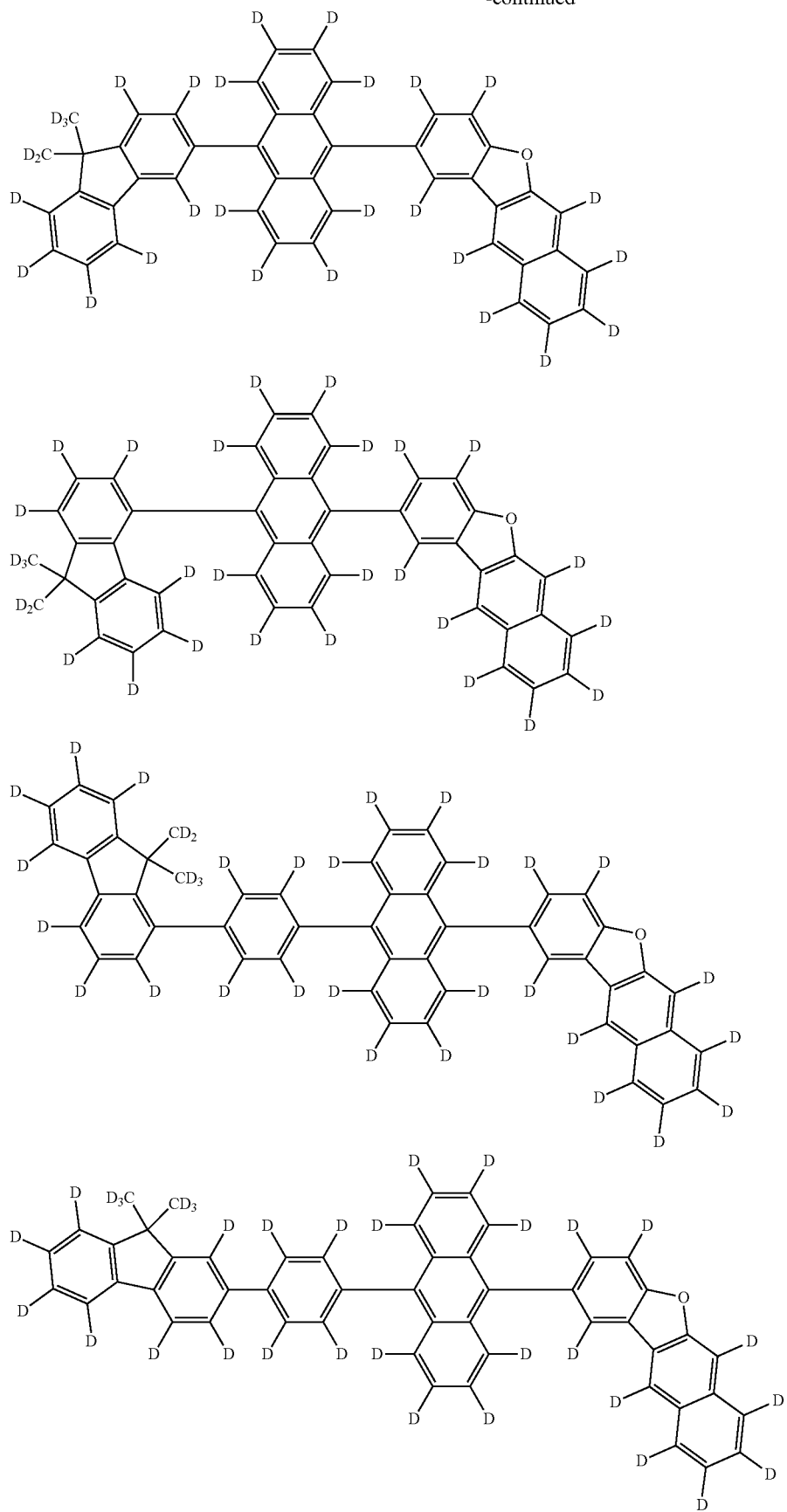

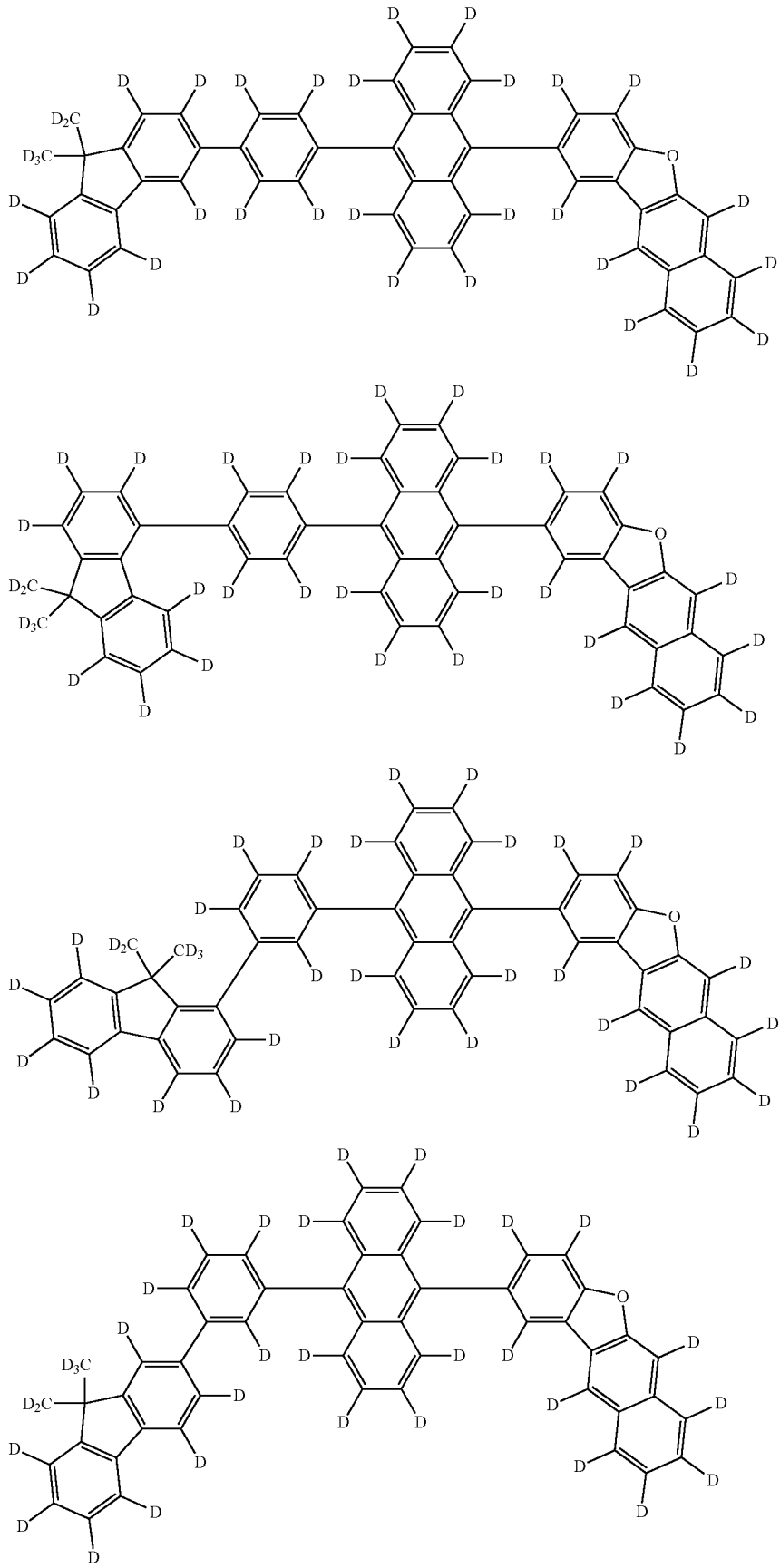

-continued
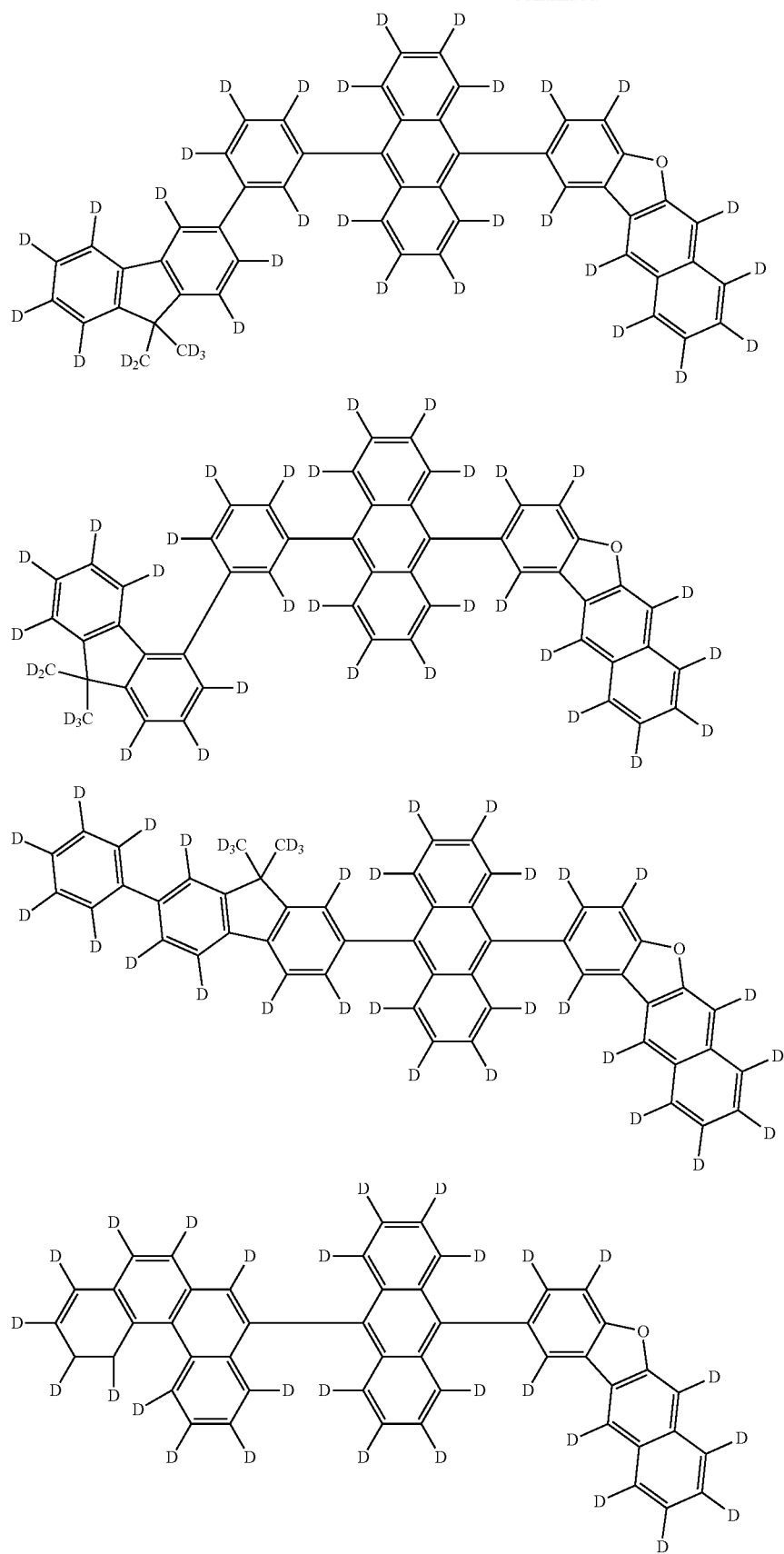

-continued
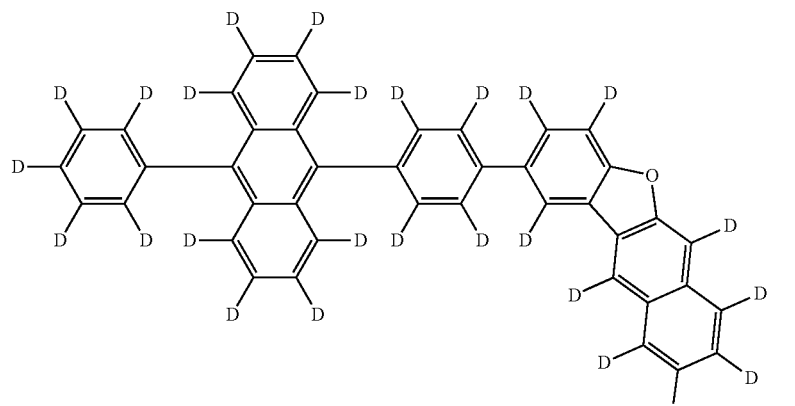
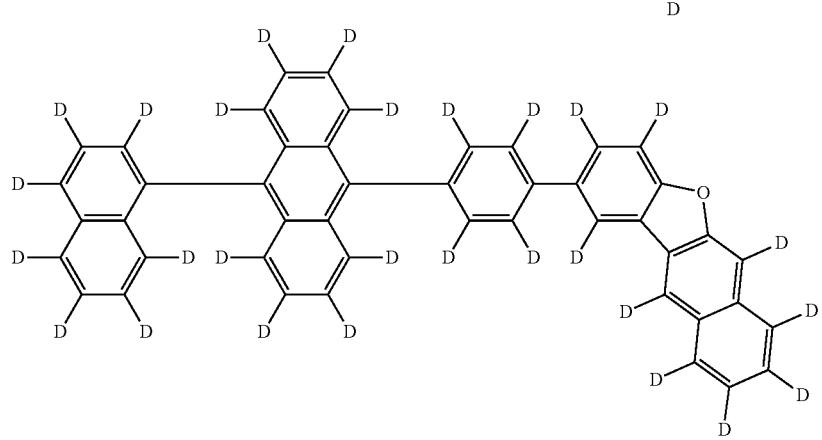
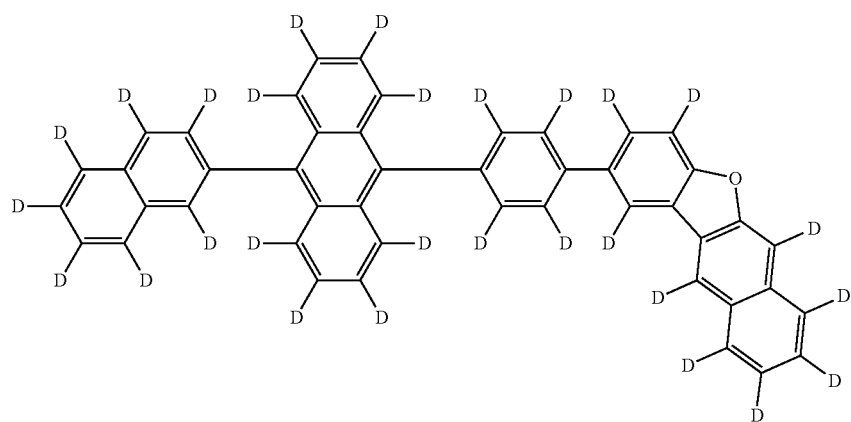
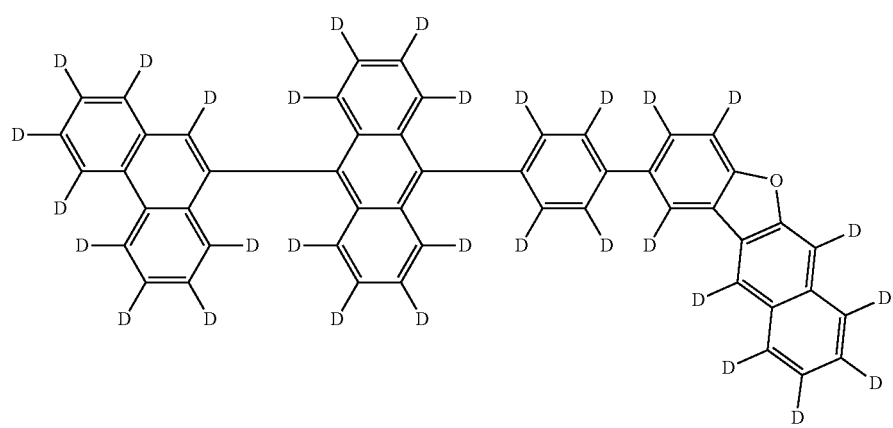

-continued
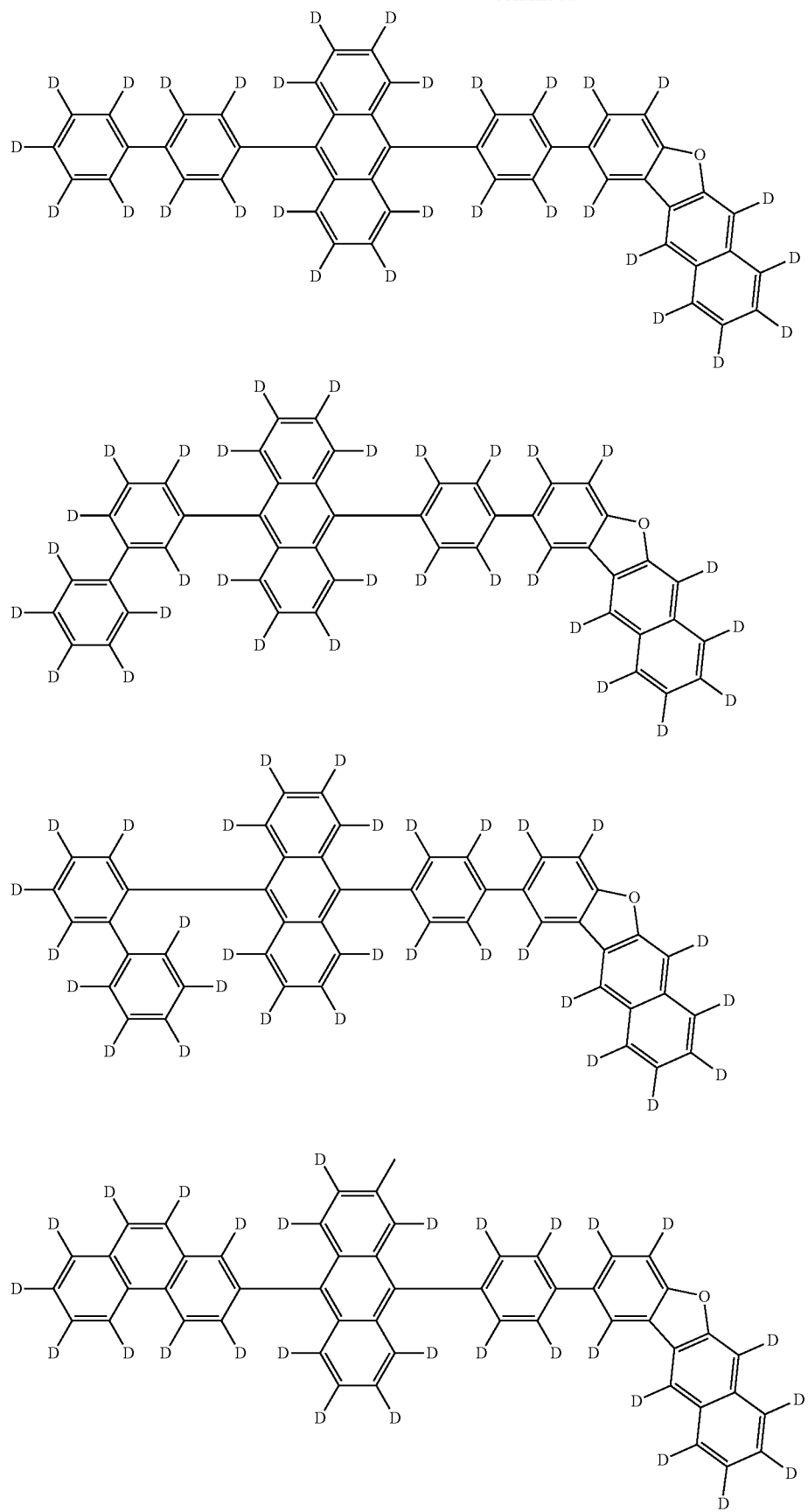

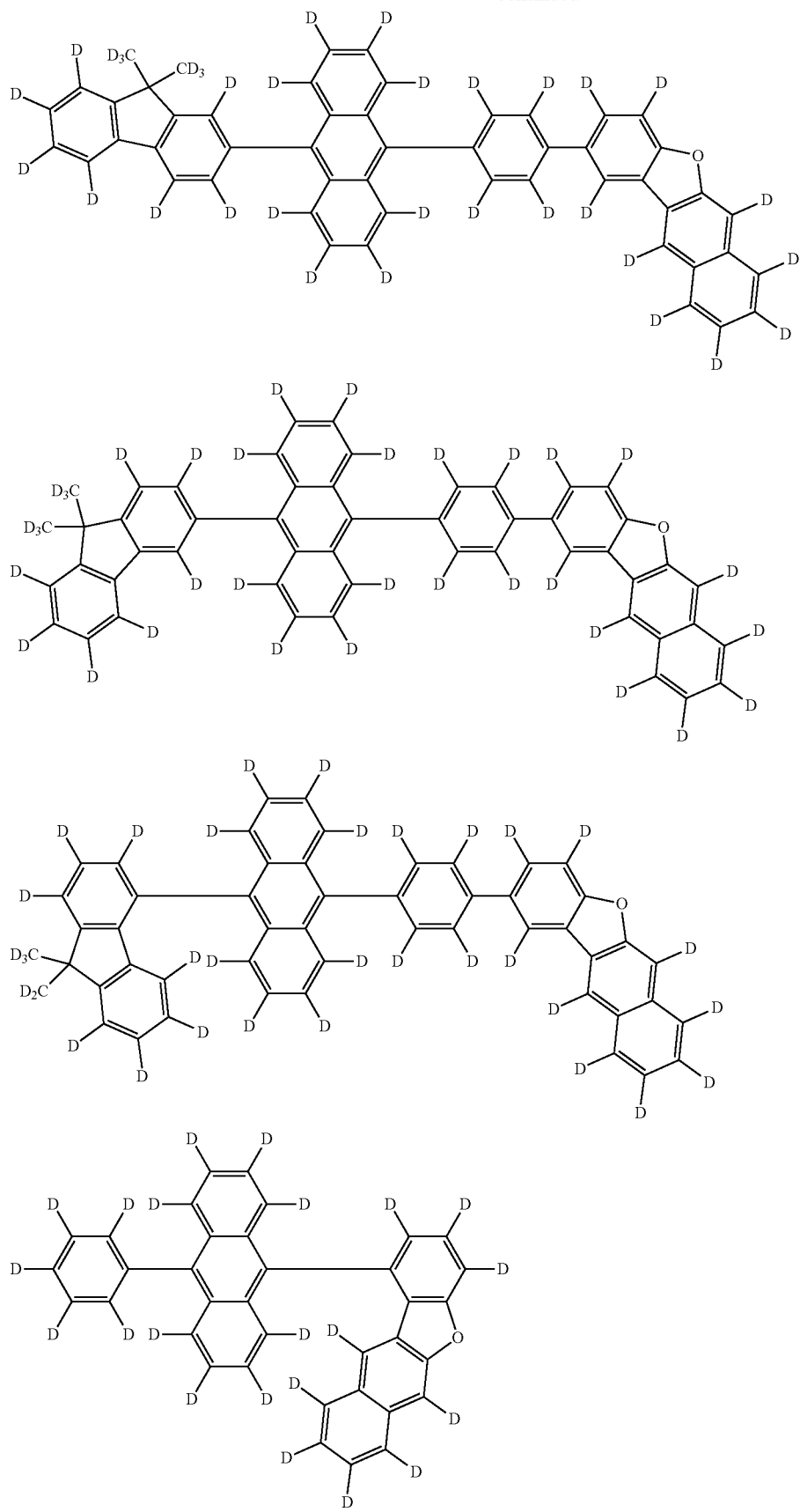

-continued
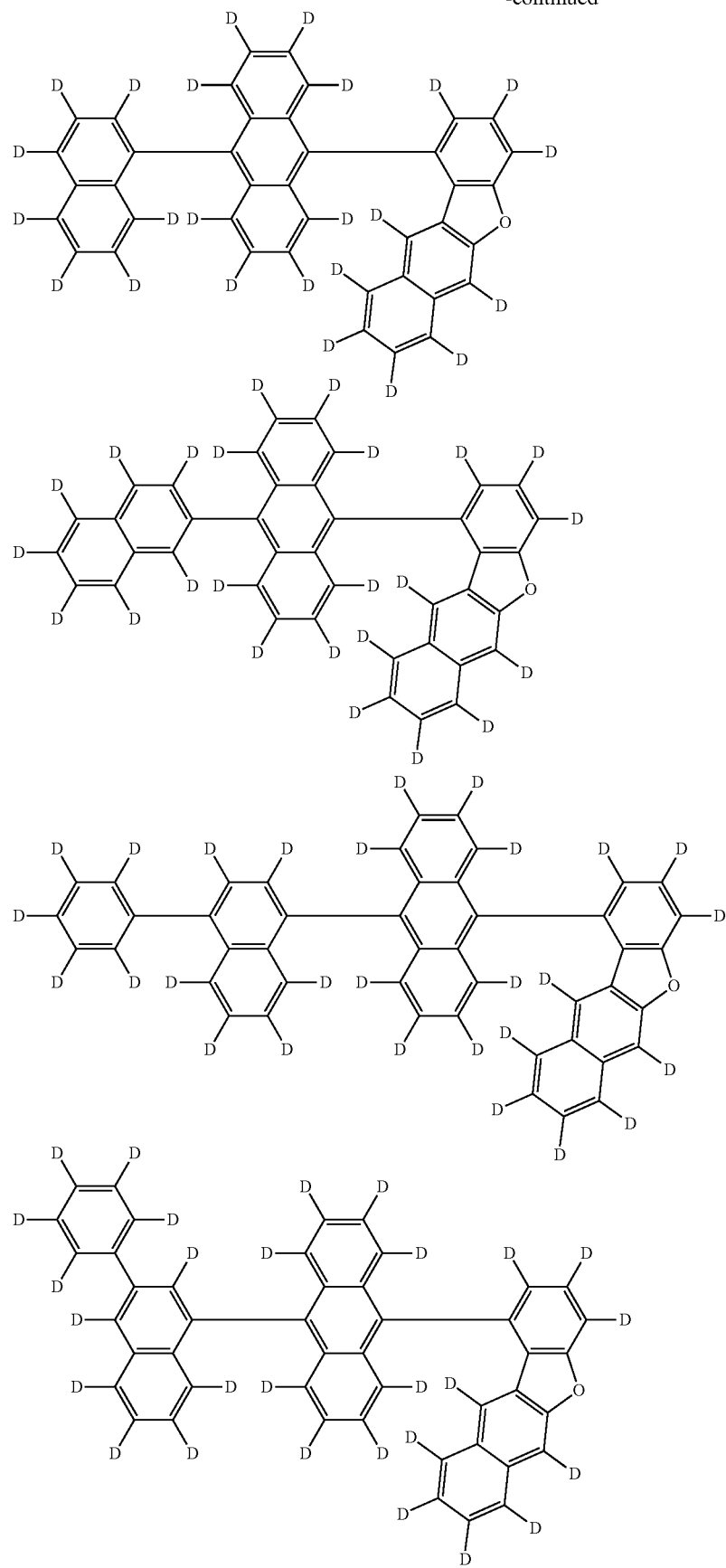

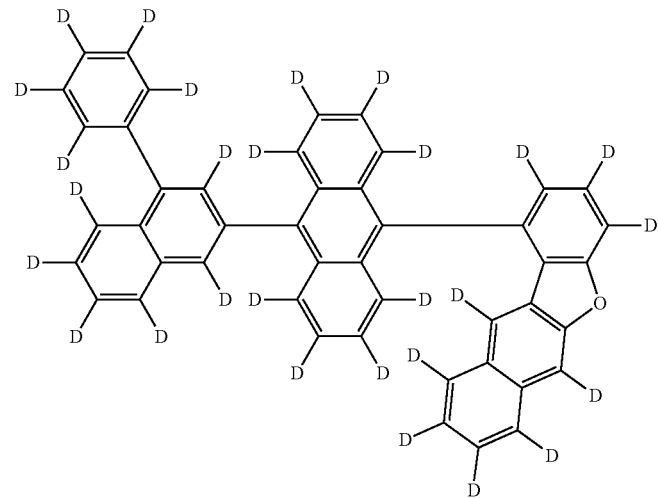
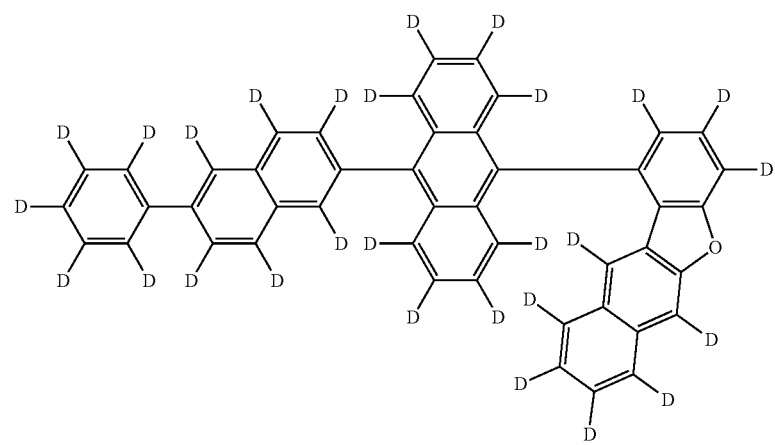
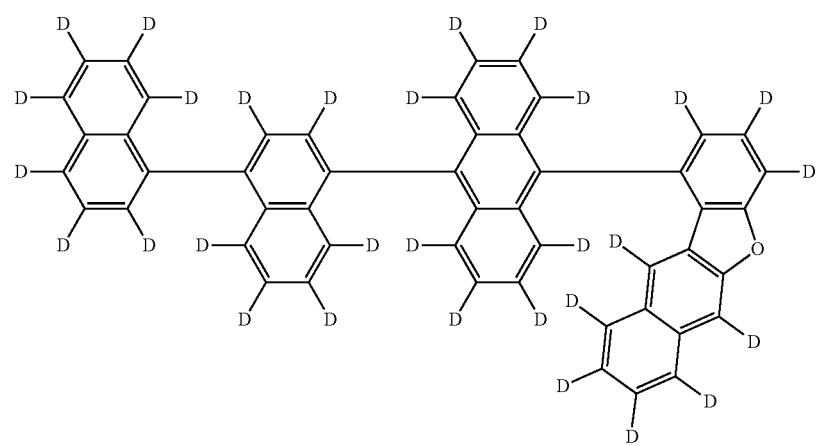

-continued
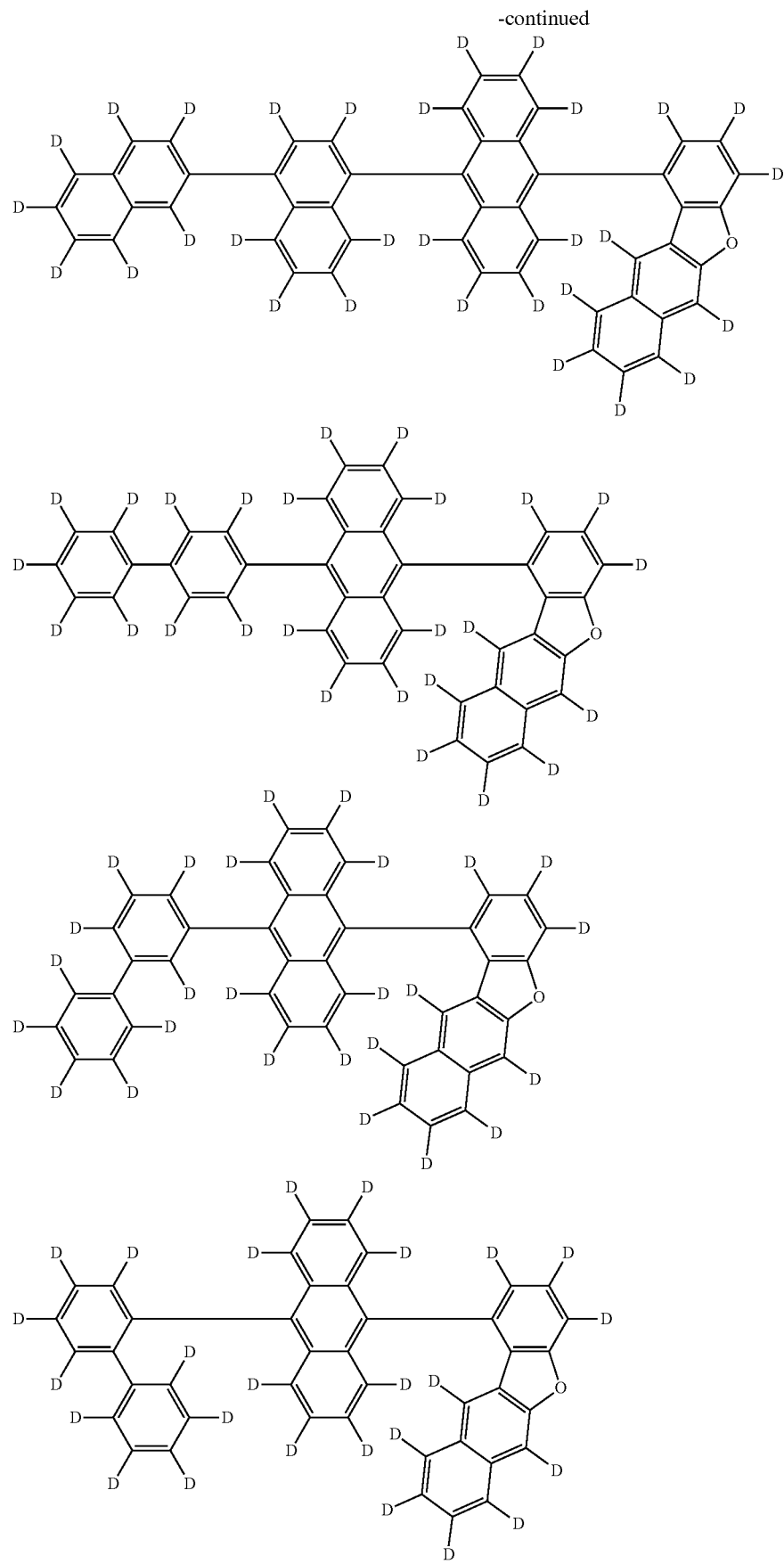

-continued
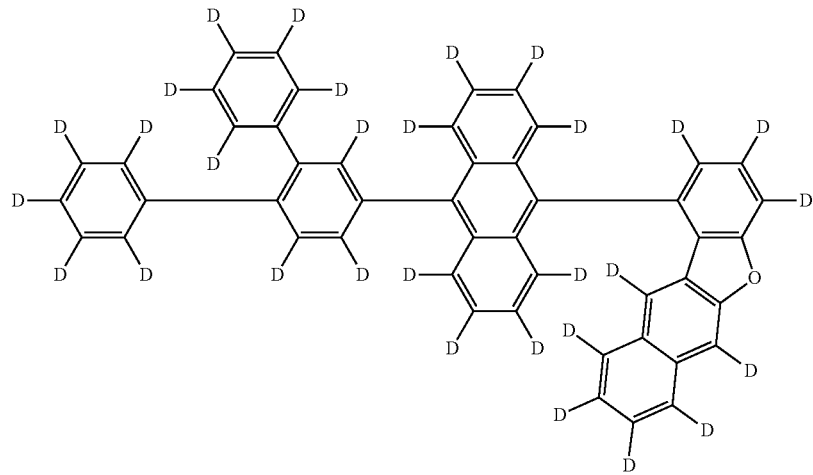
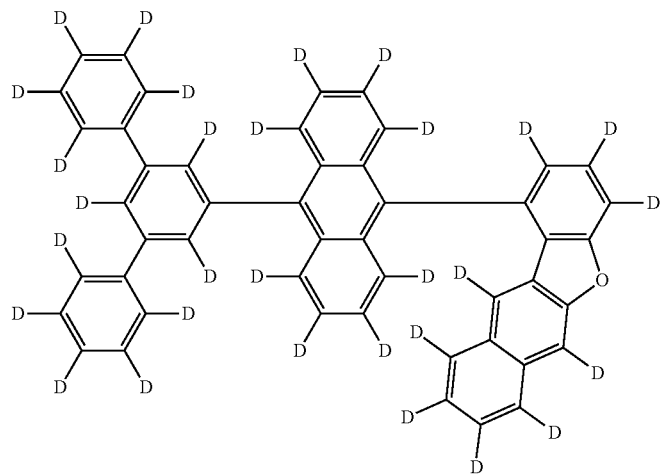
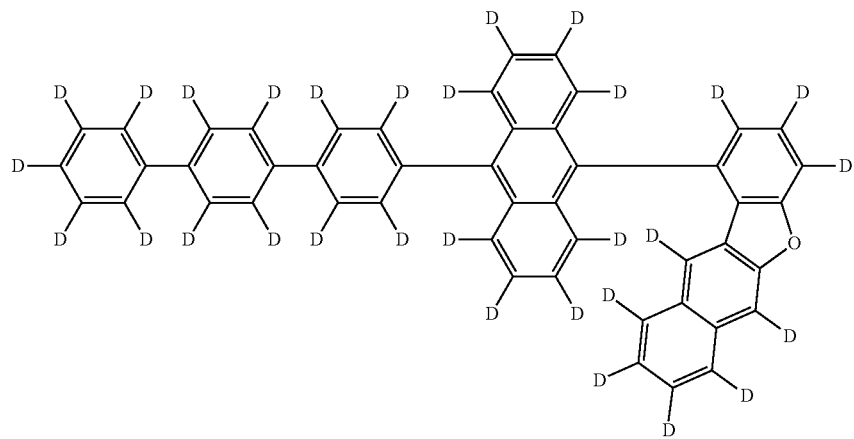

-continued
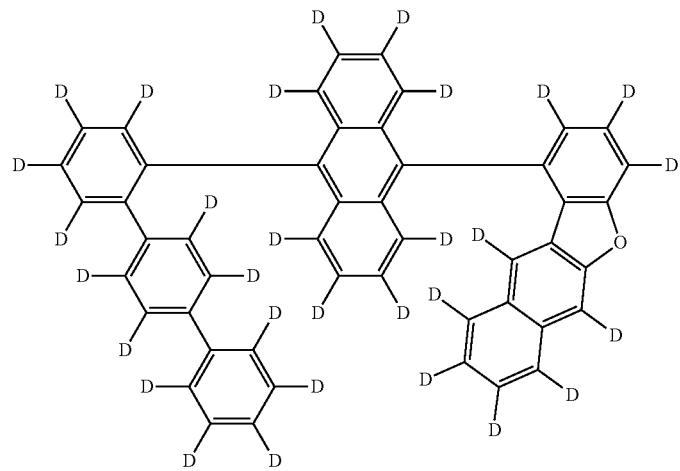
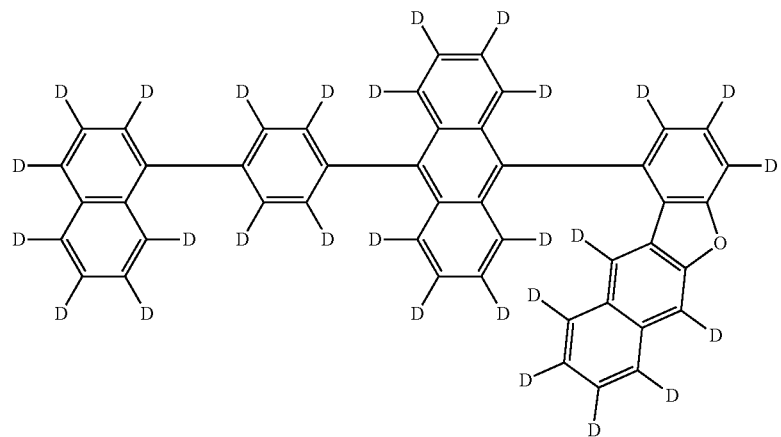
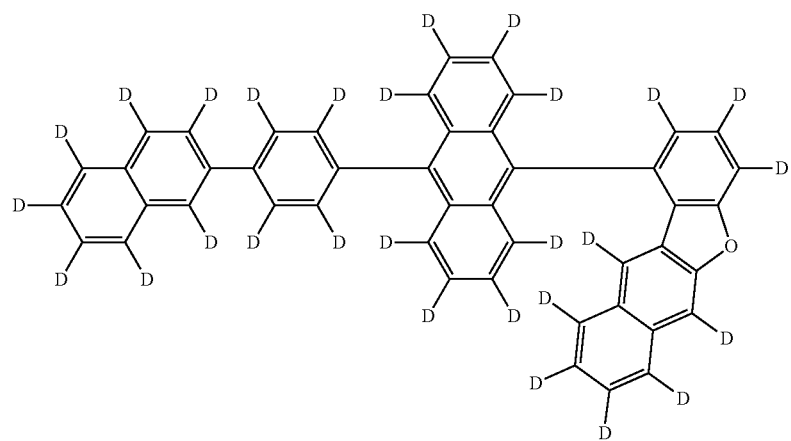

-continued
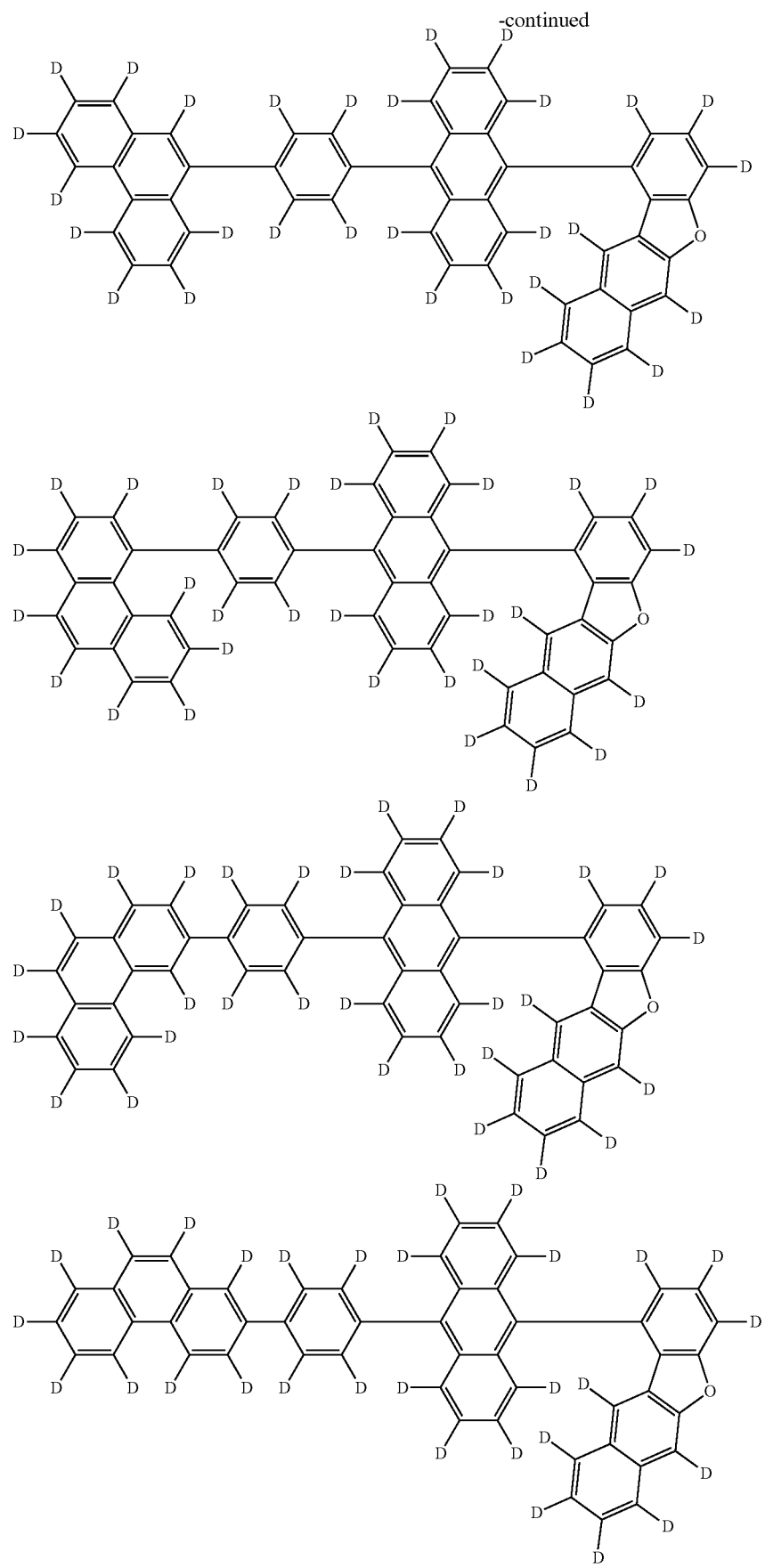

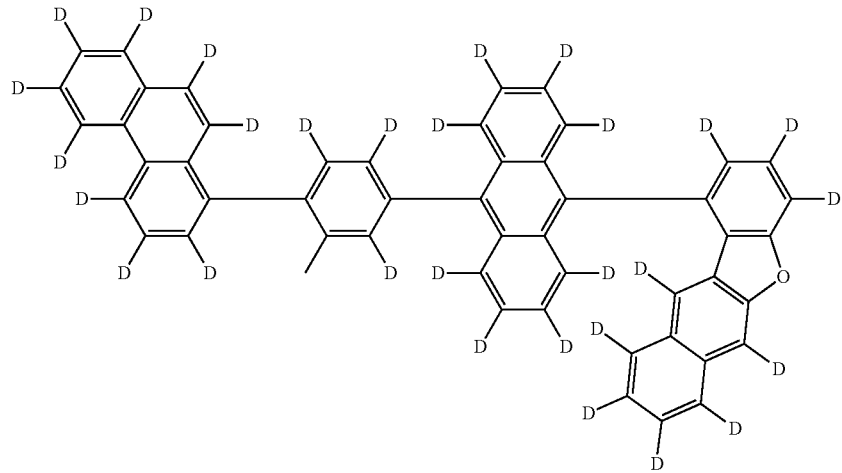
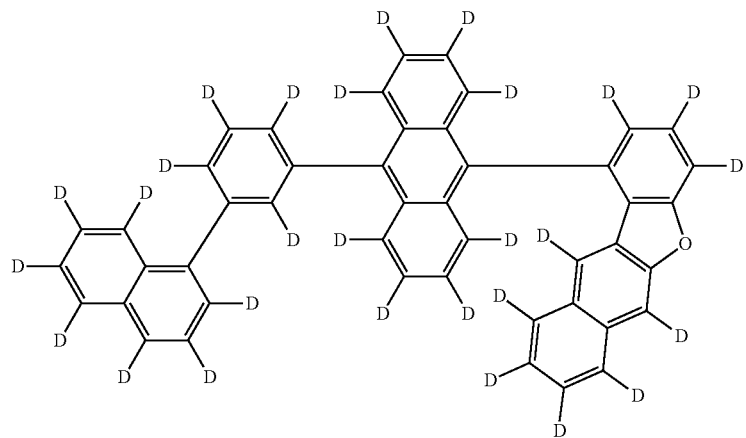
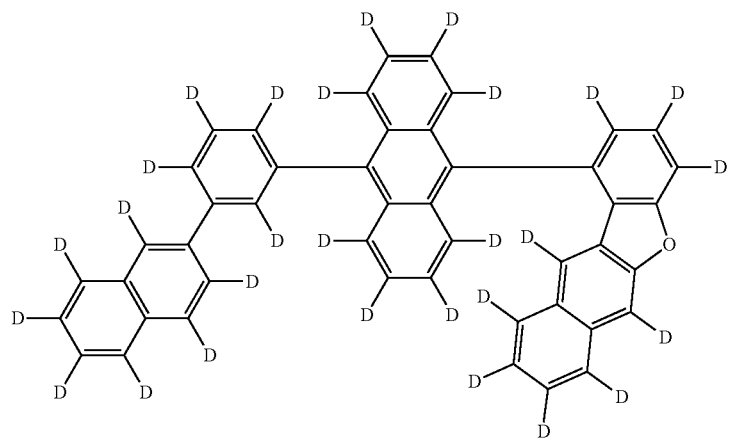

-continued
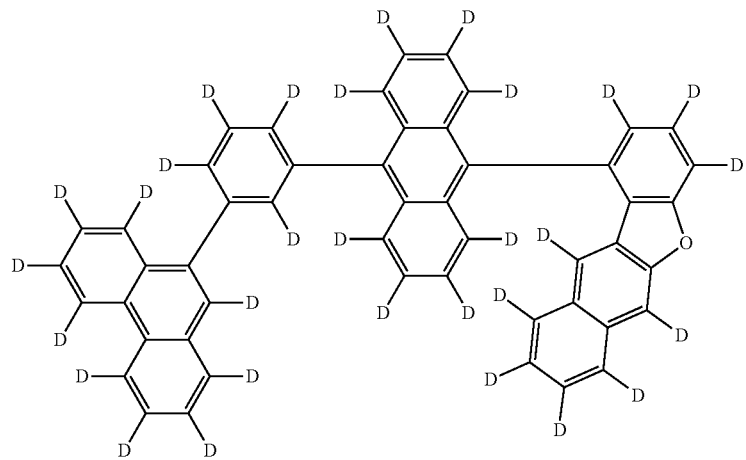
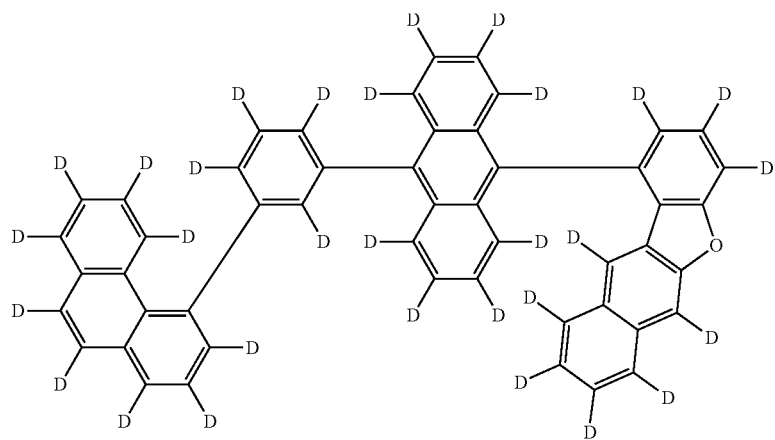
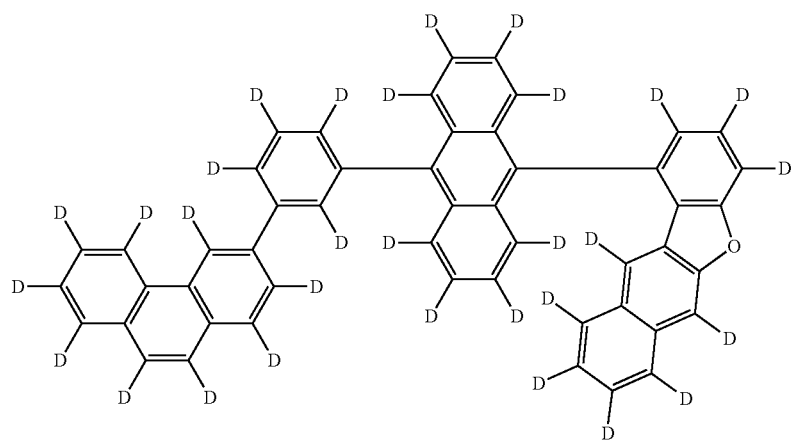

-continued
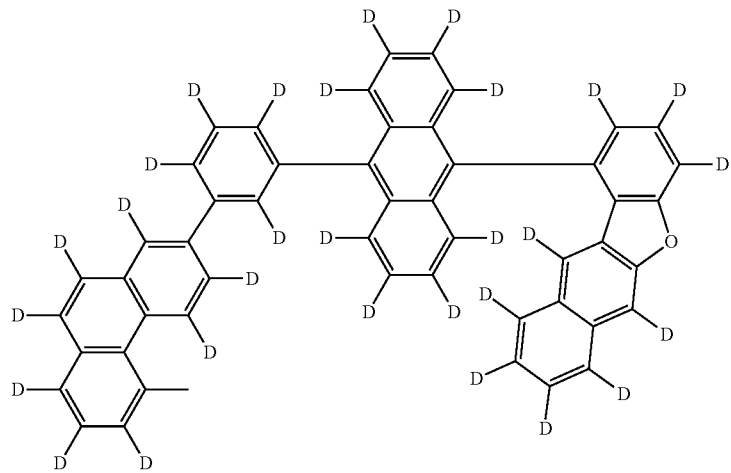
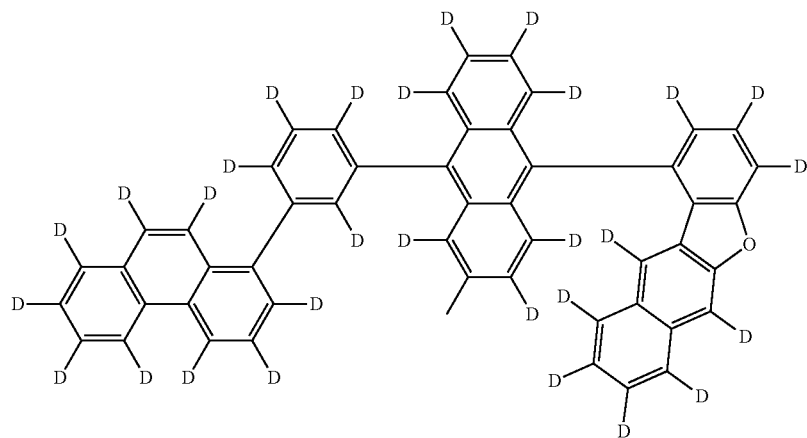
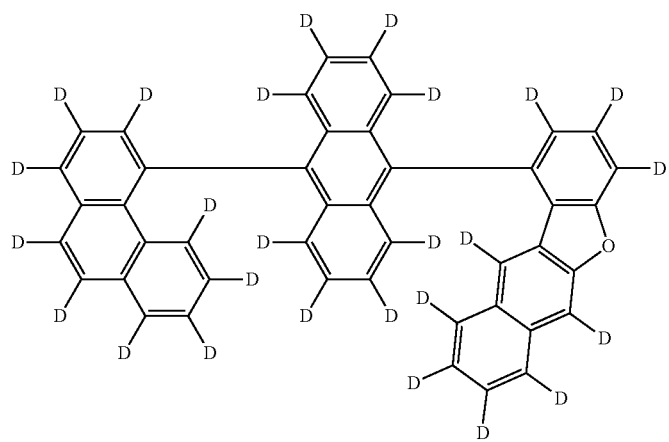

-continued
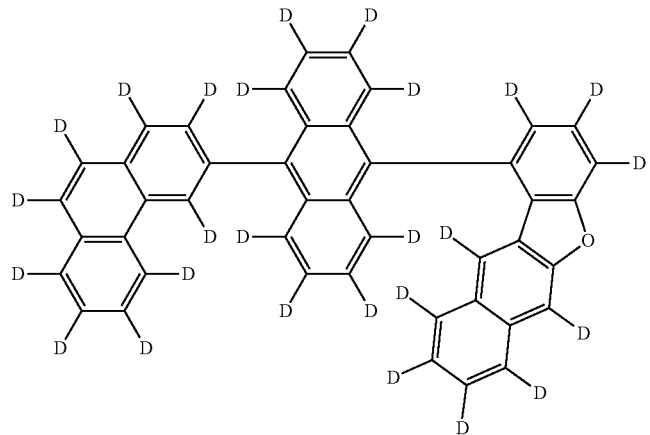
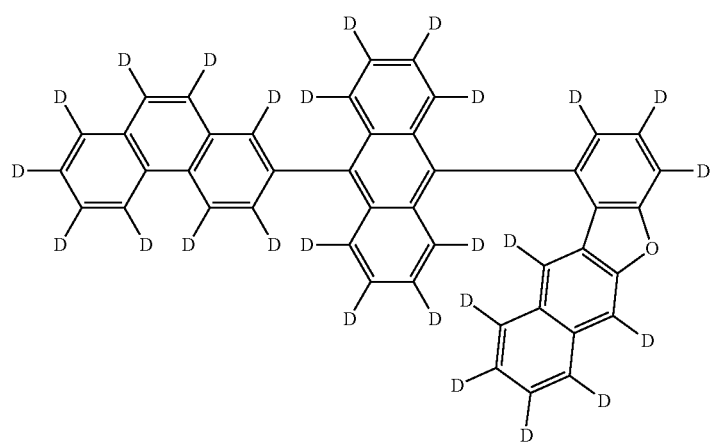
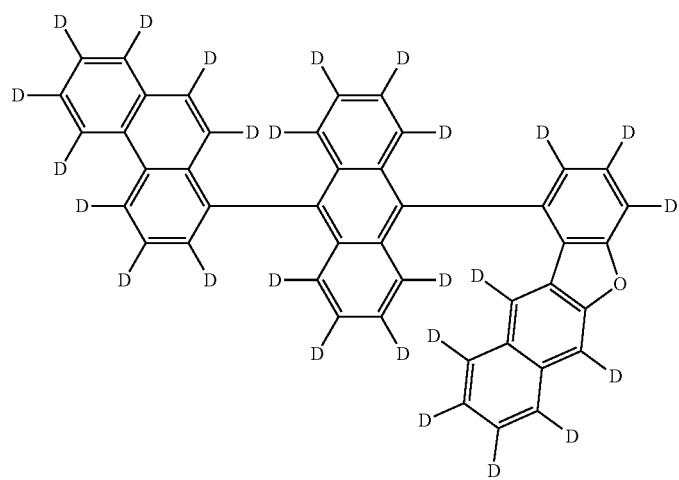

-continued
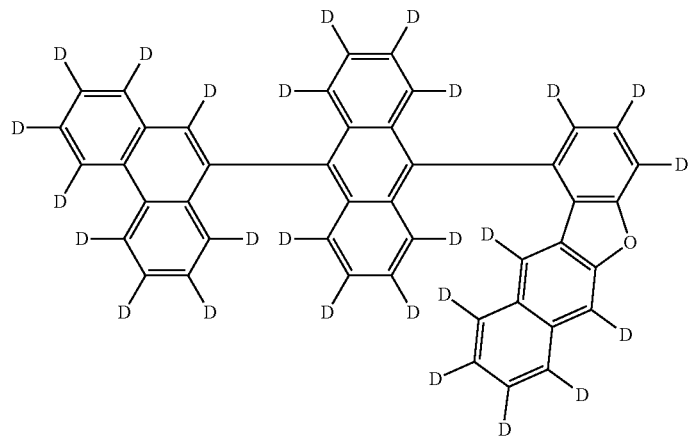
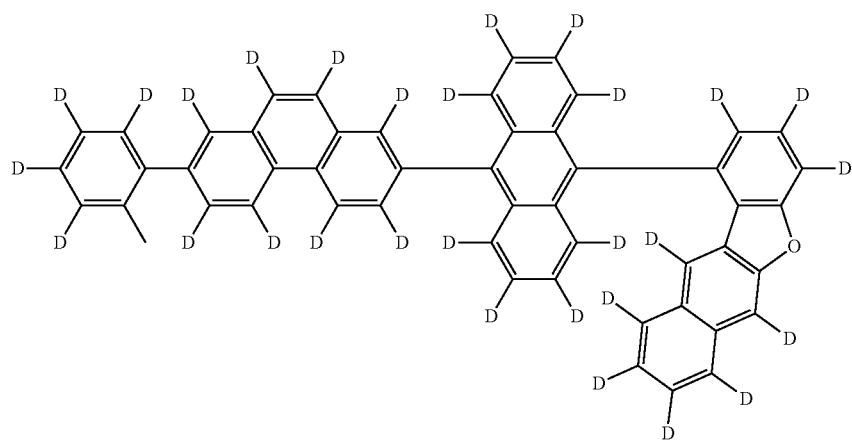
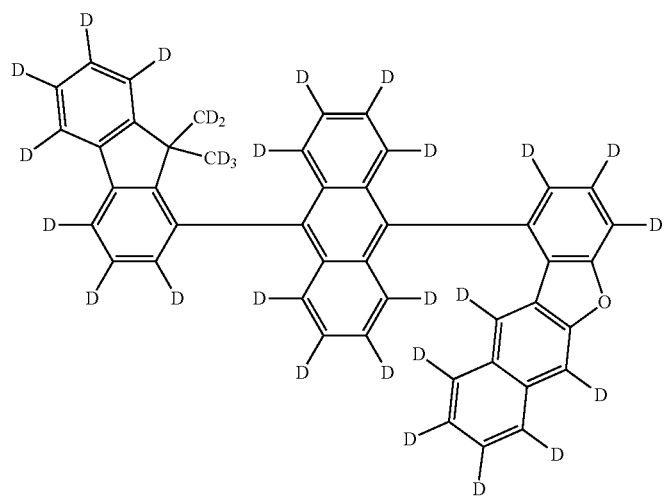

-continued
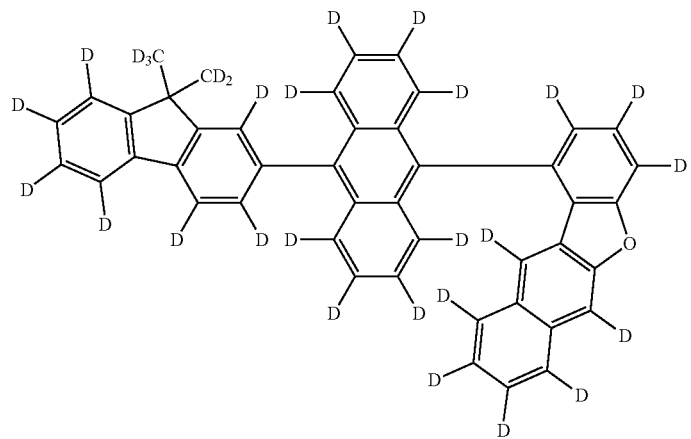
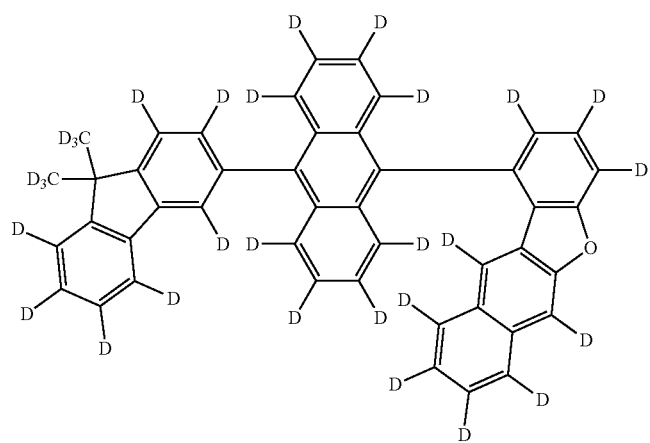
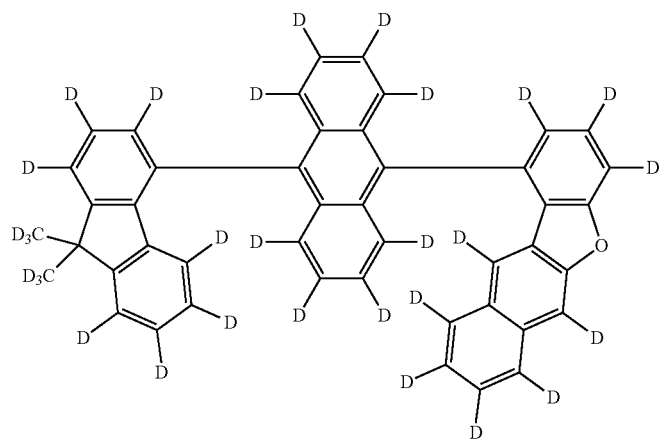

-continued
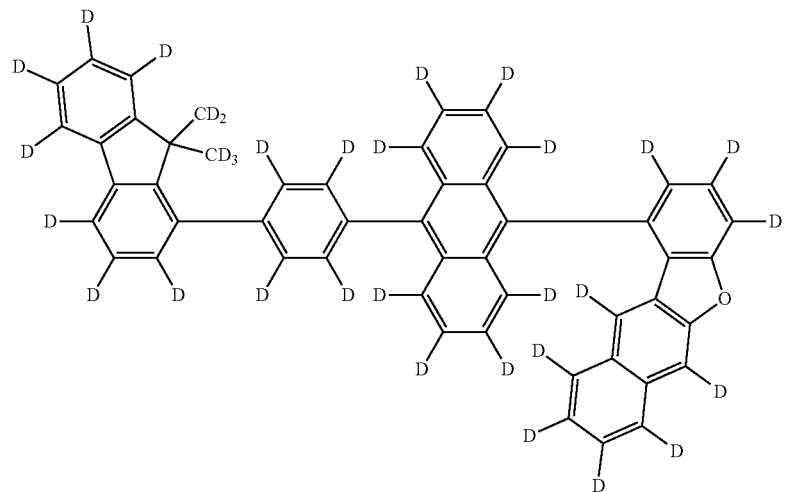
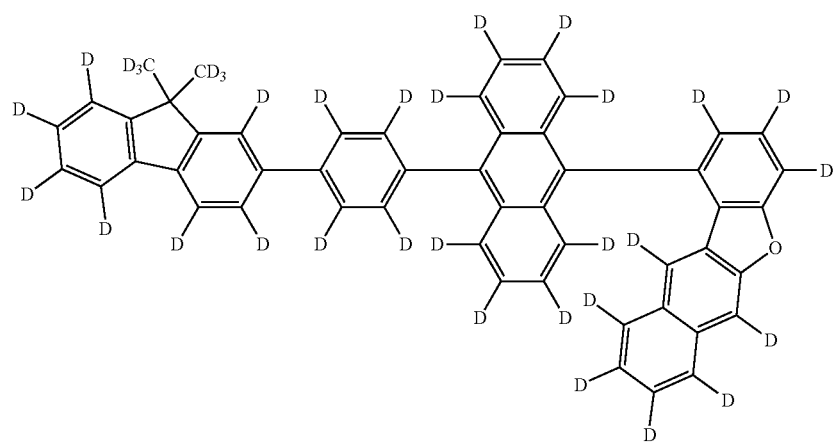
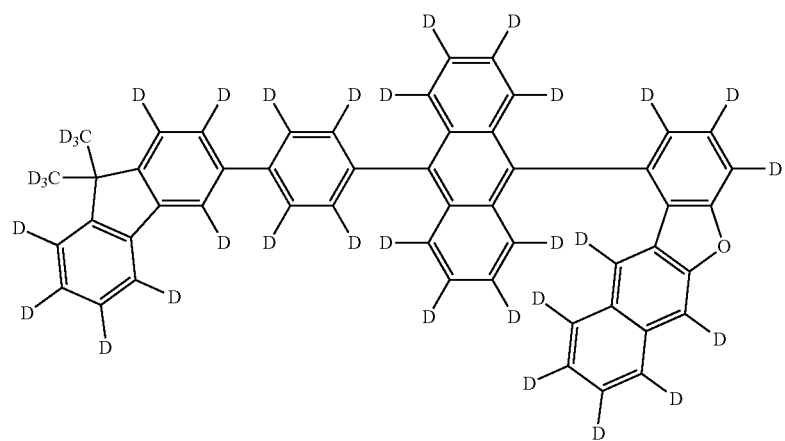

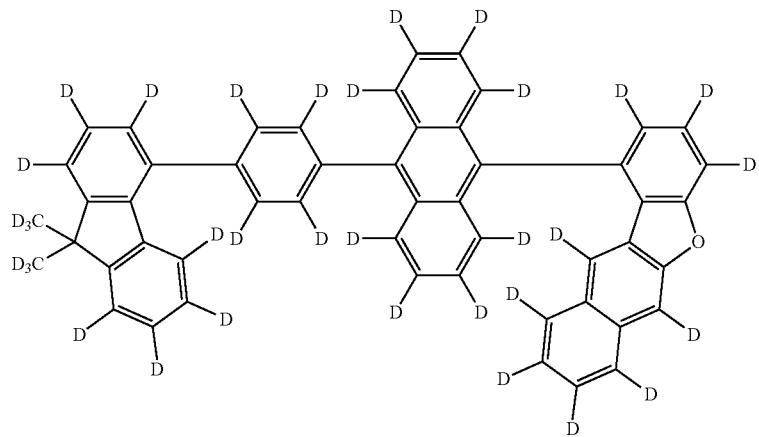
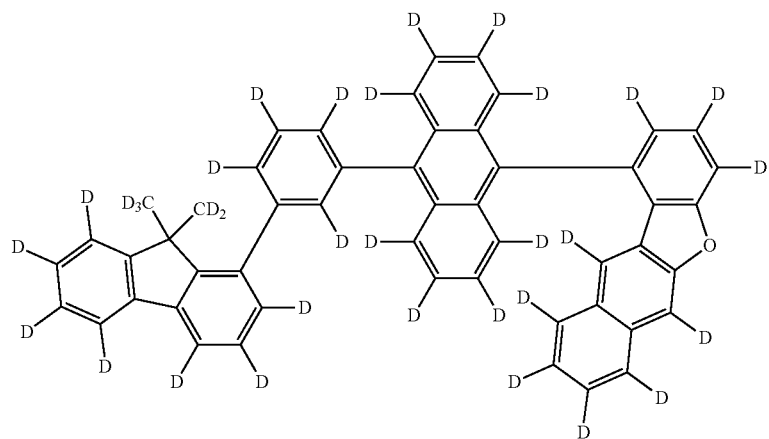
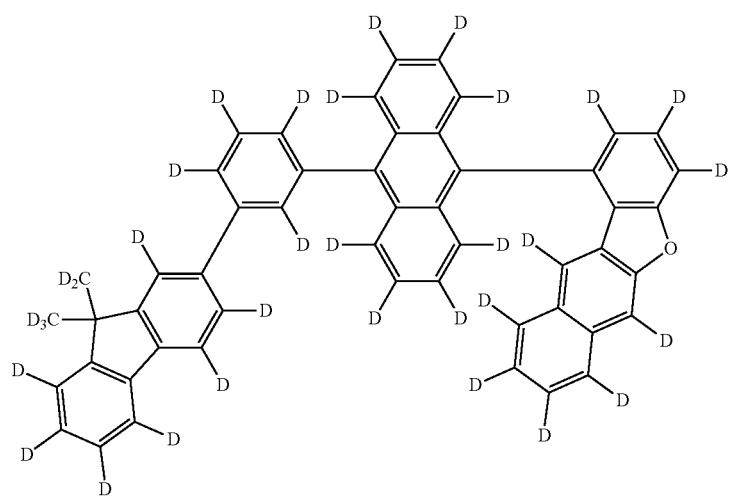

-continued
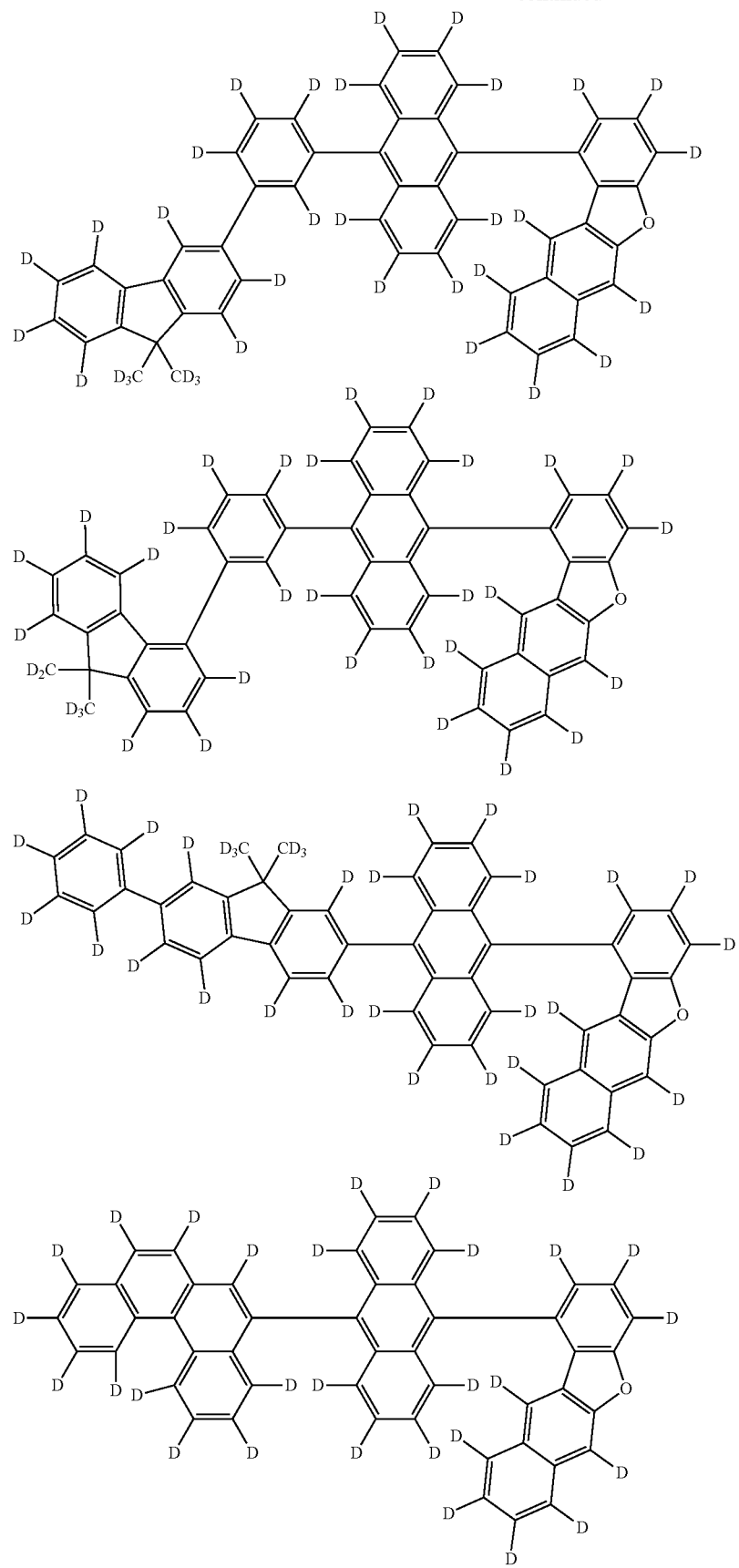

-continued
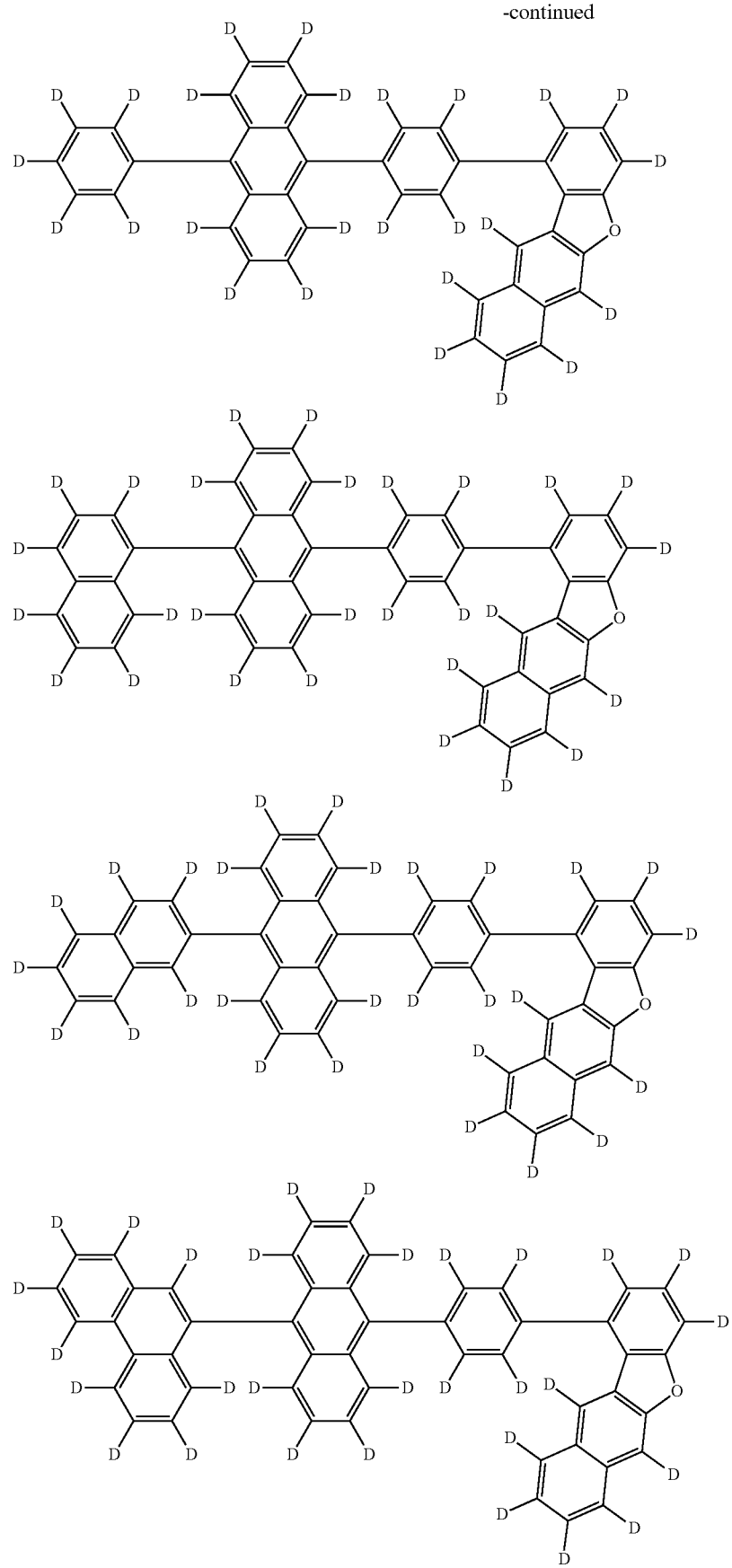

-continued
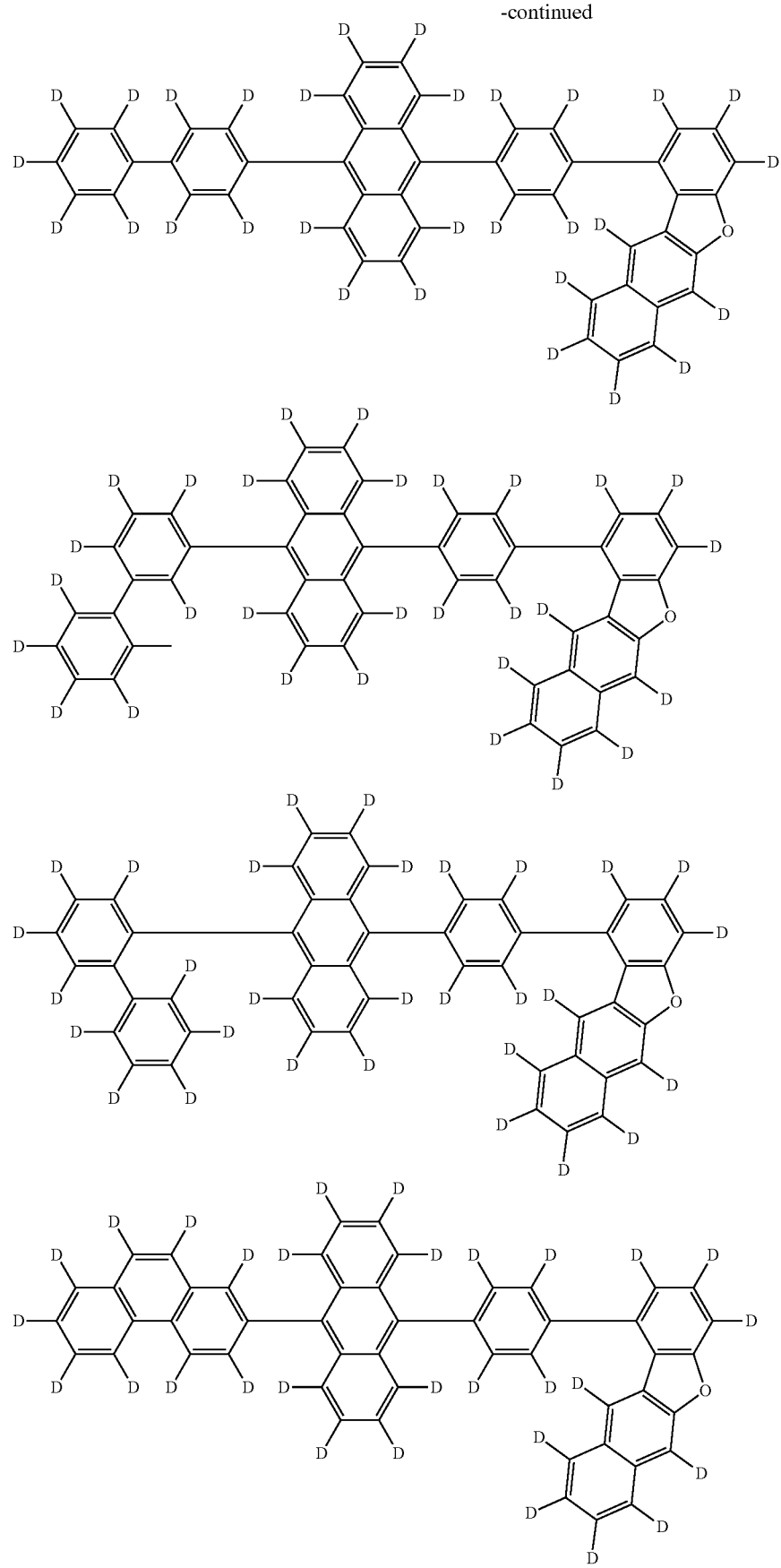

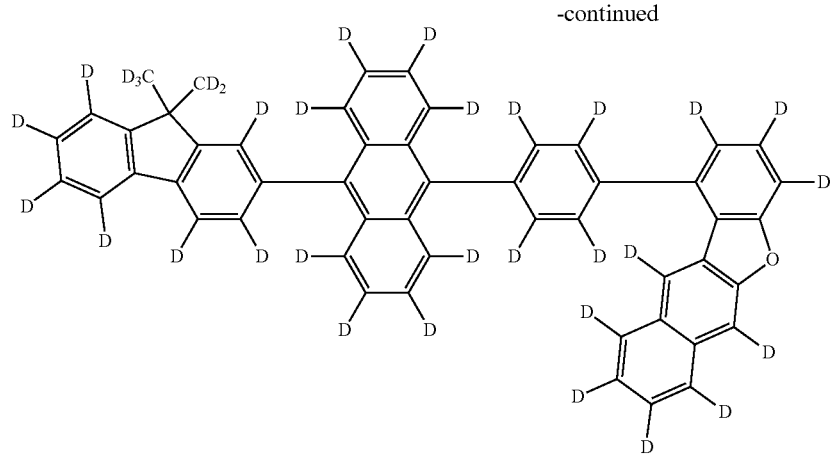
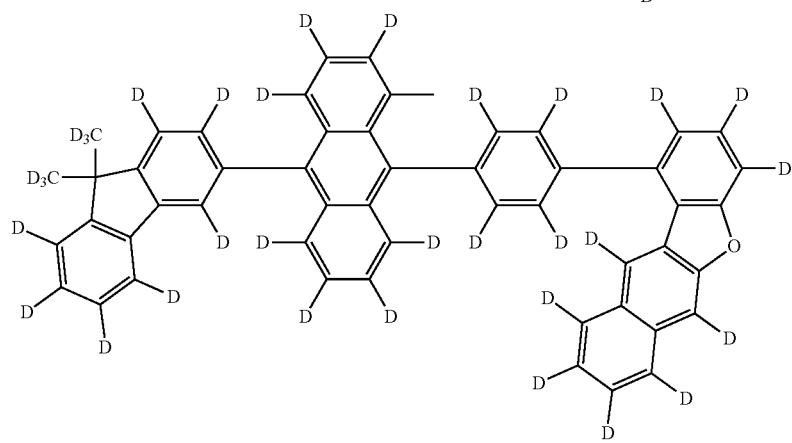
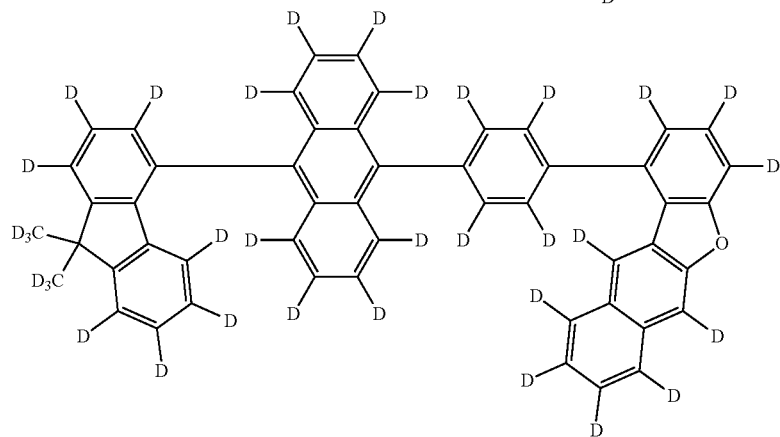
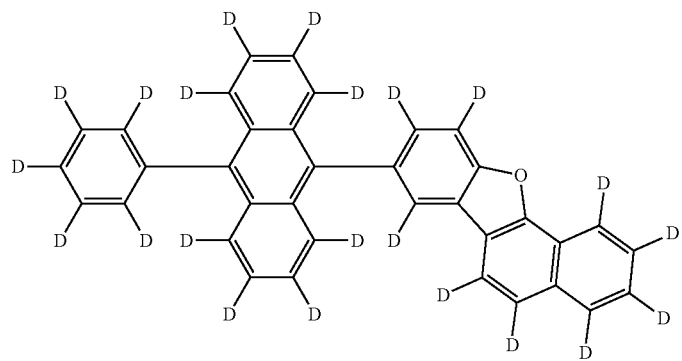

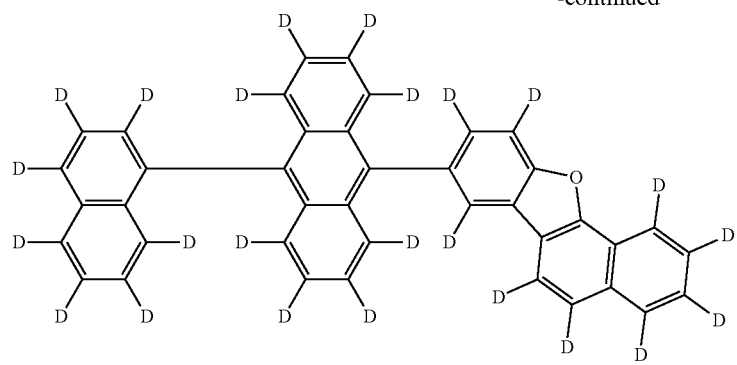
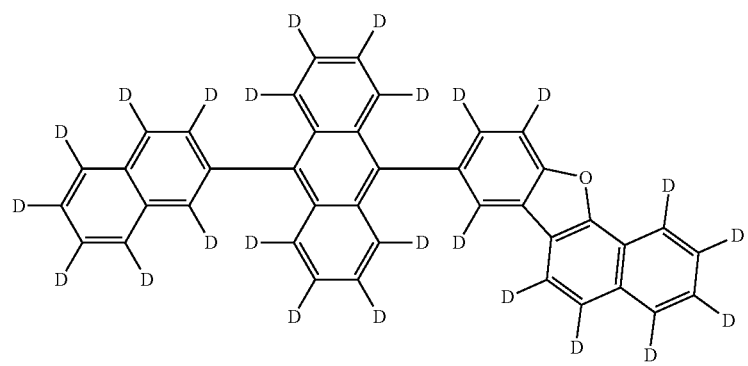
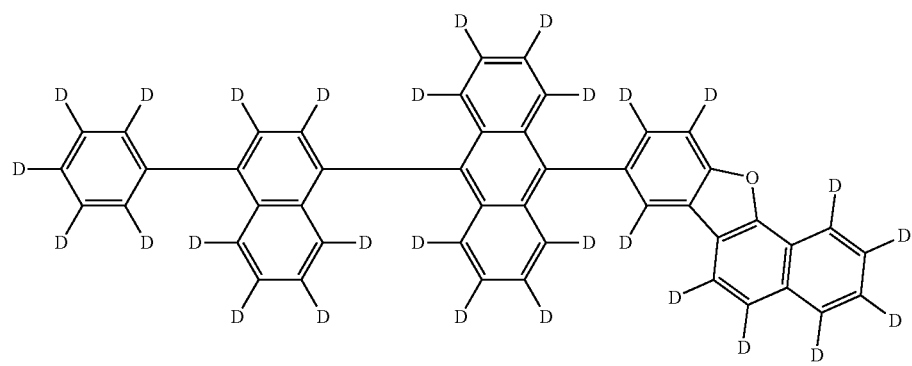
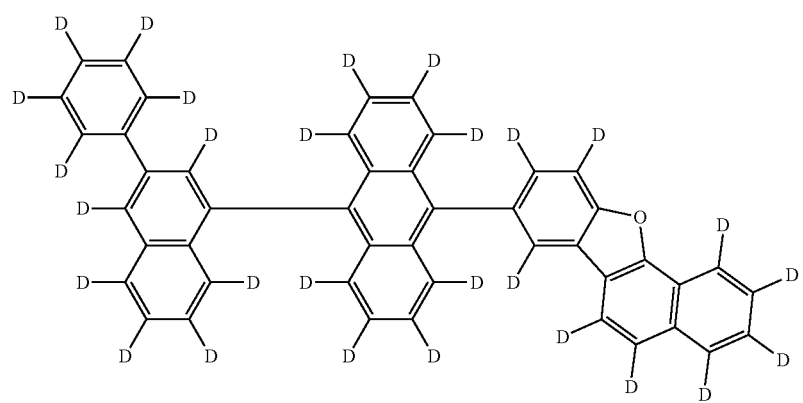

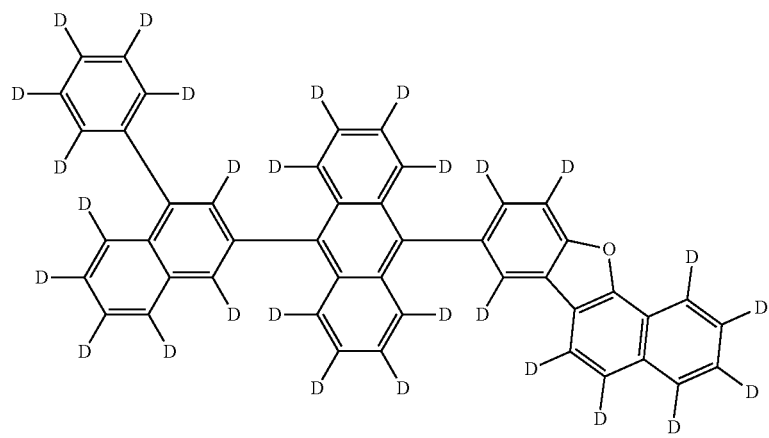
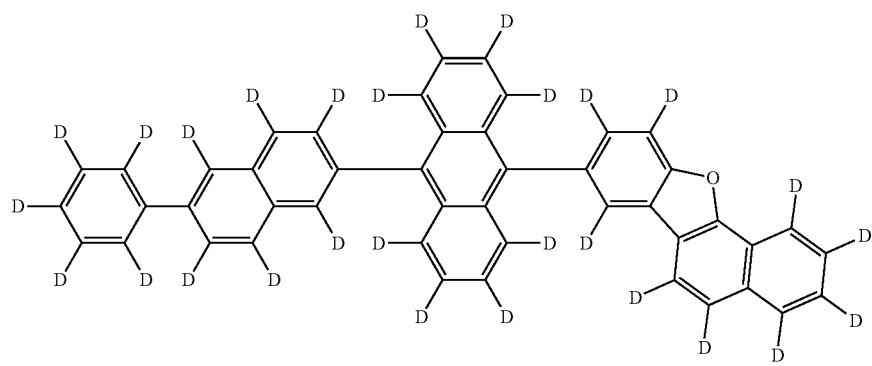
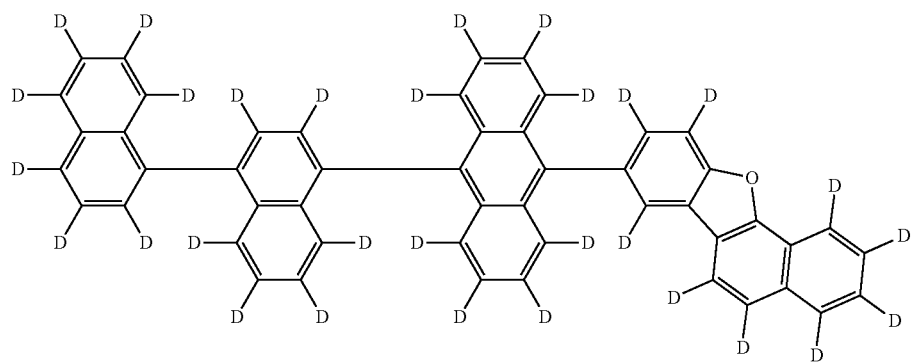
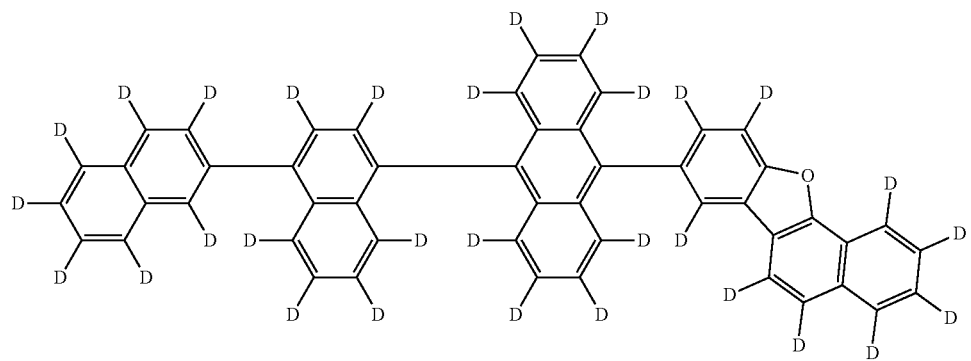

-continued
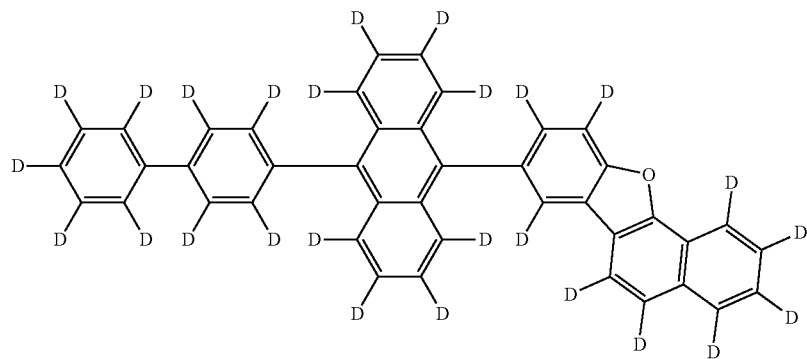
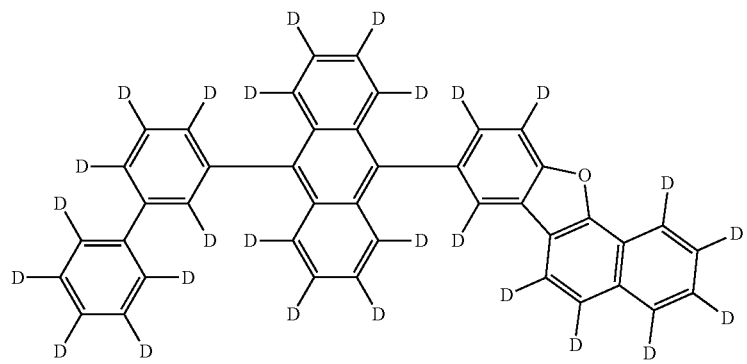
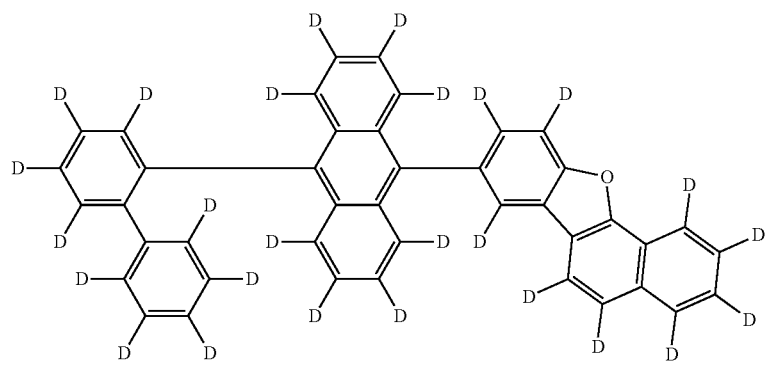
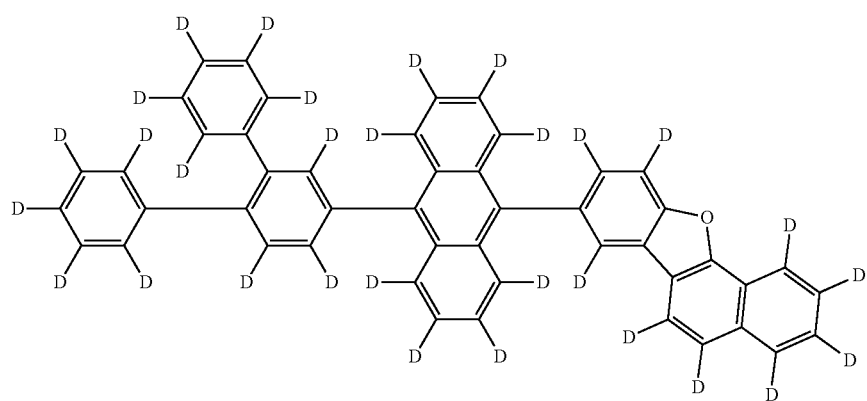

-continued
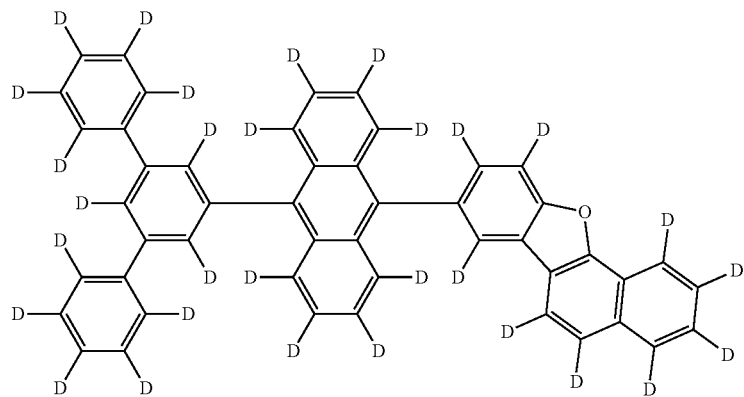
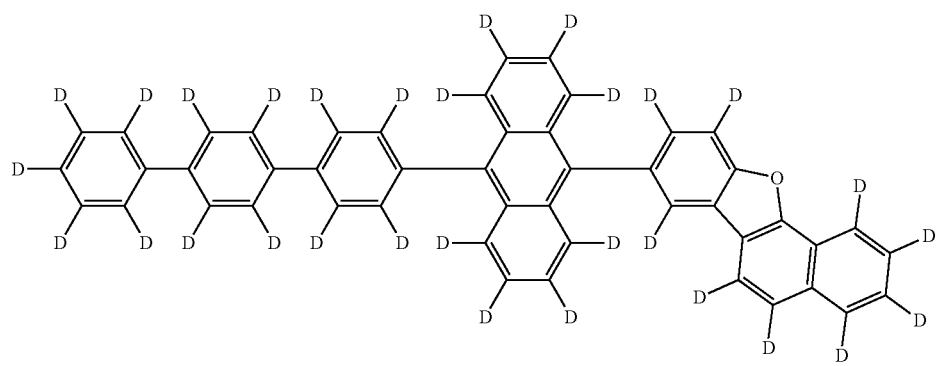
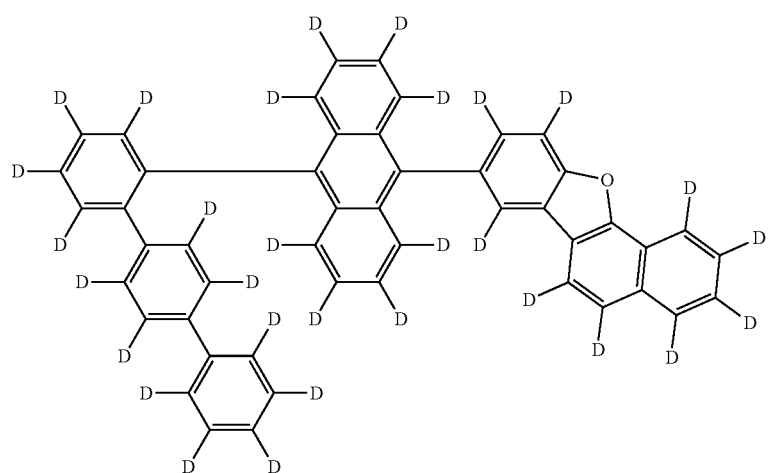
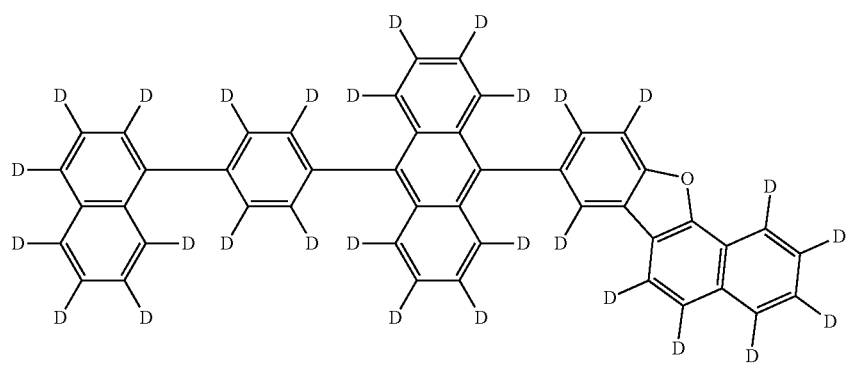

-continued
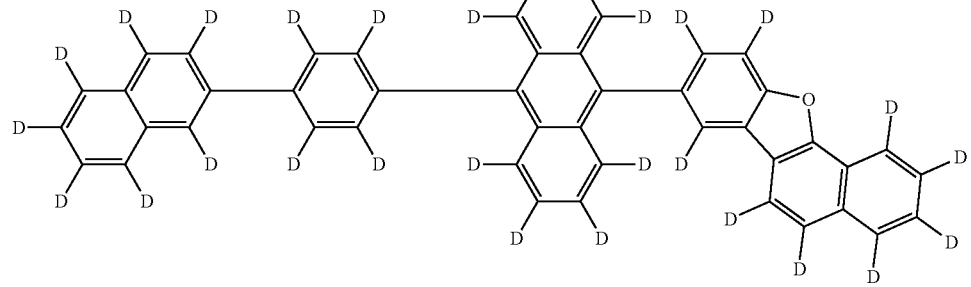
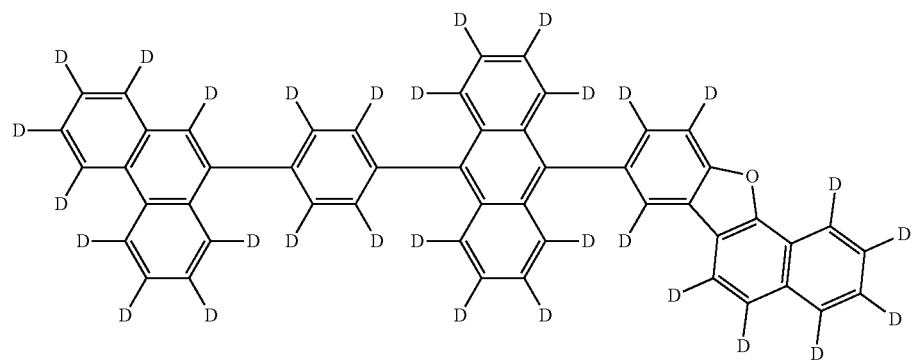
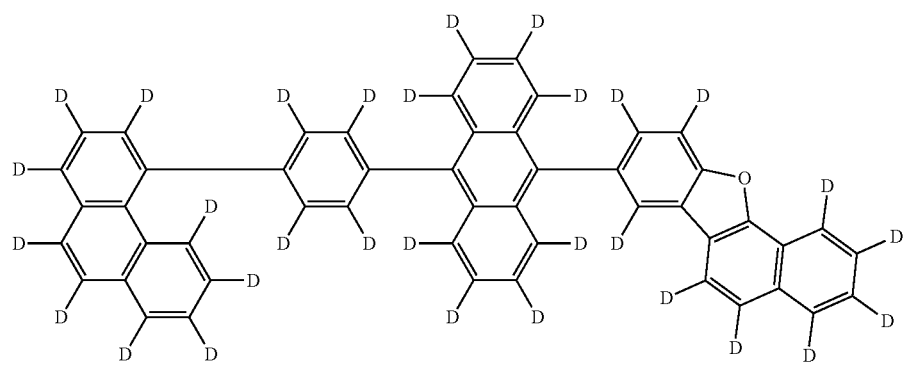
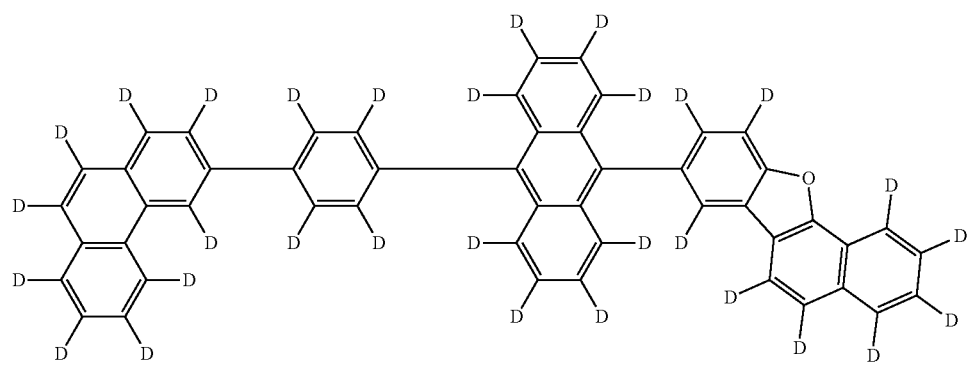

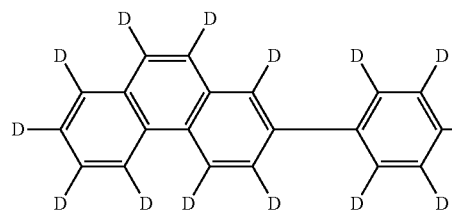
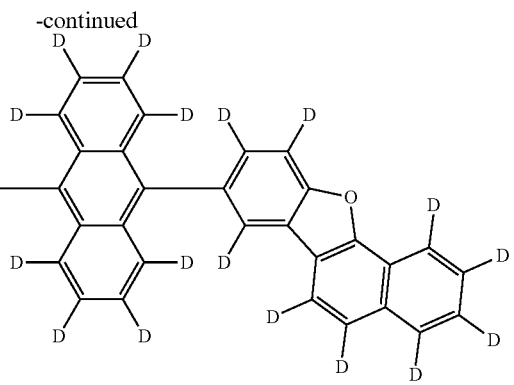
-continued
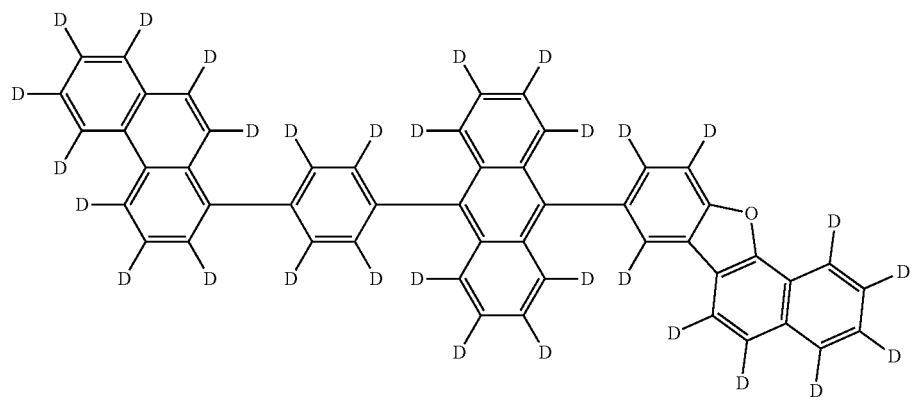
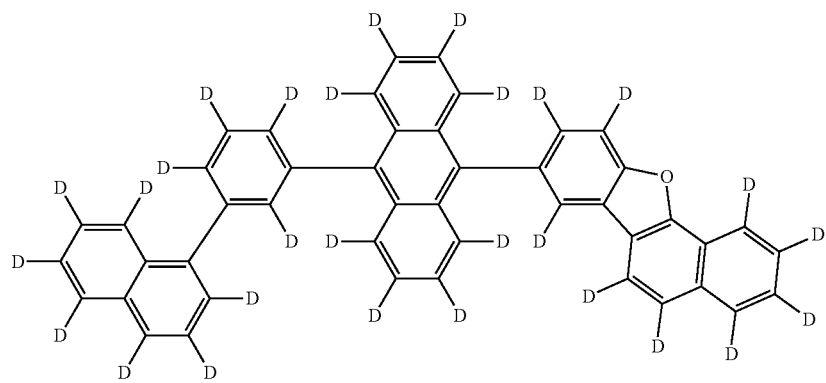
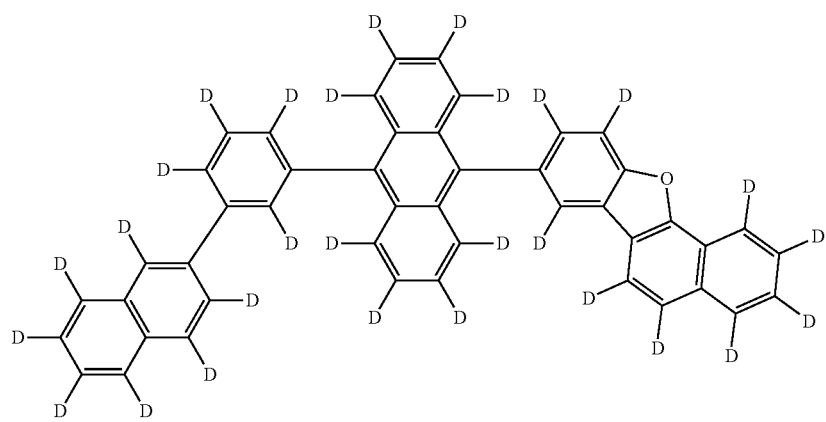

-continued
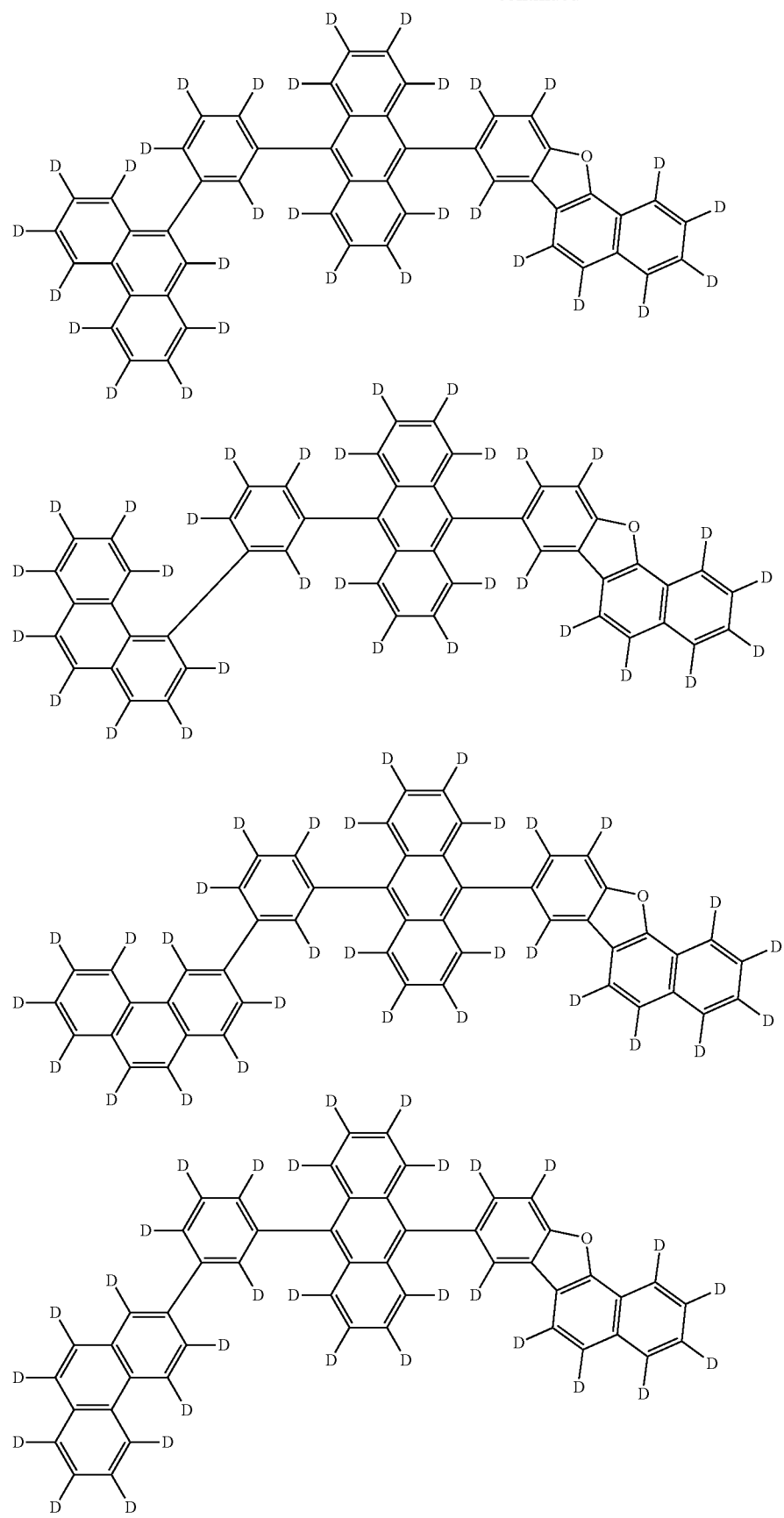

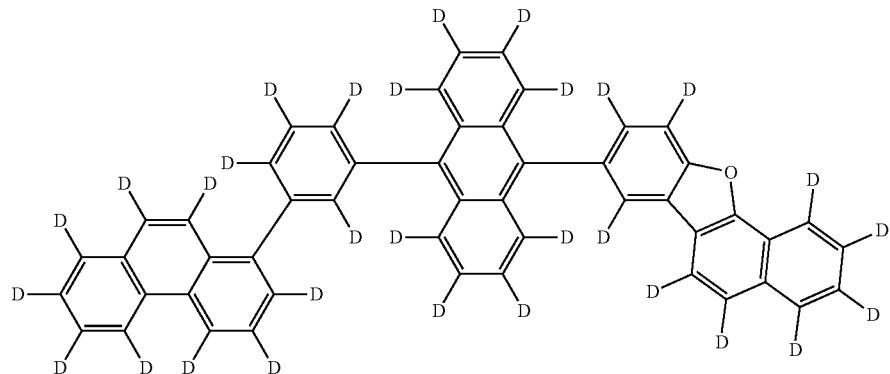
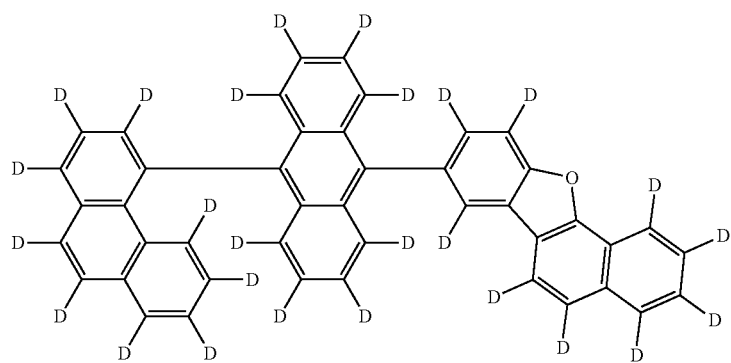
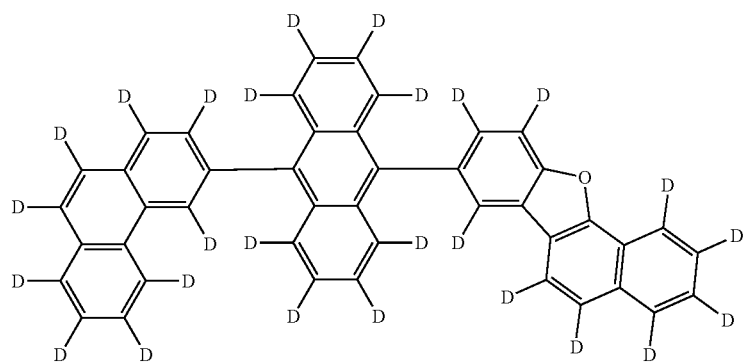
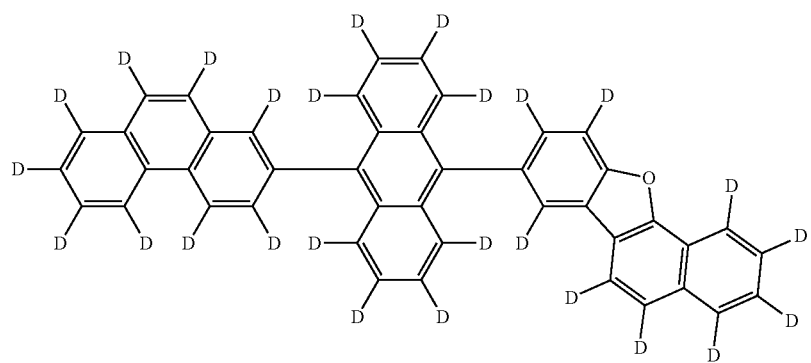

-continued
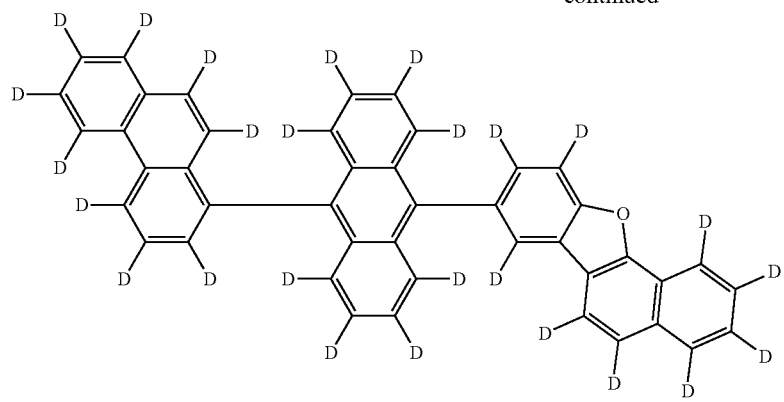
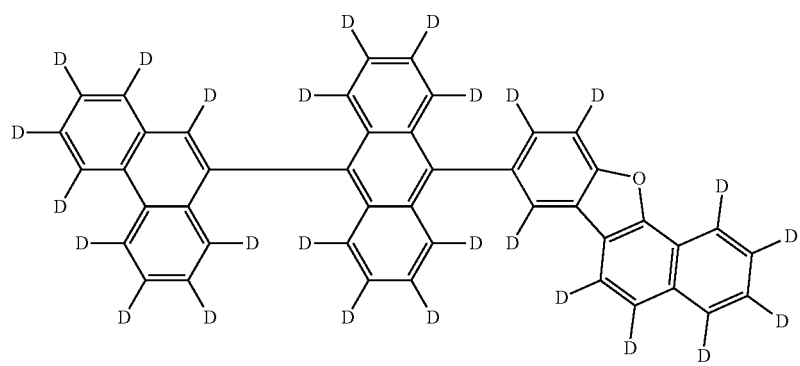
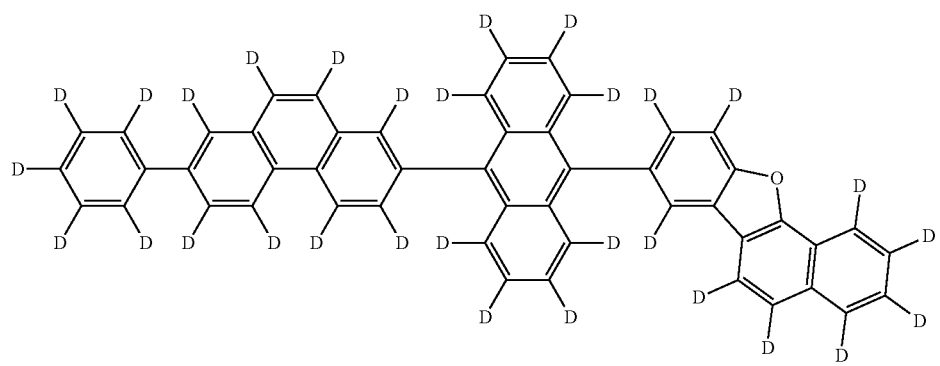
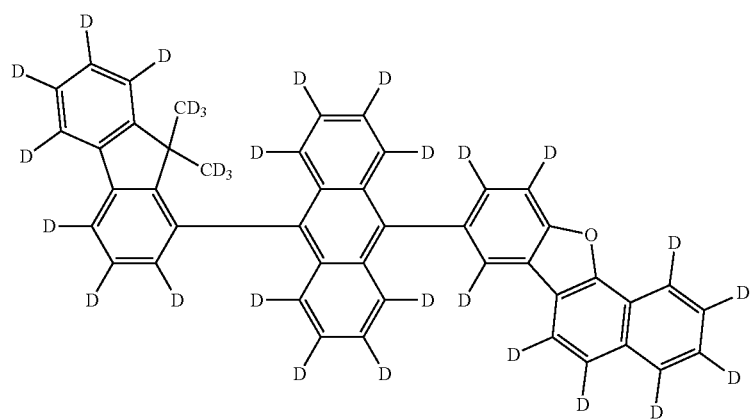

-continued
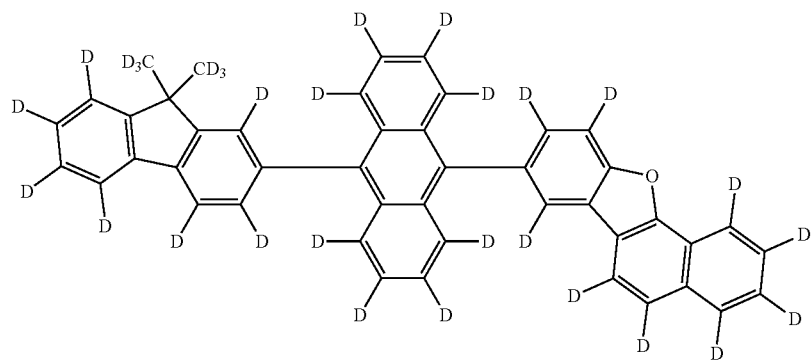
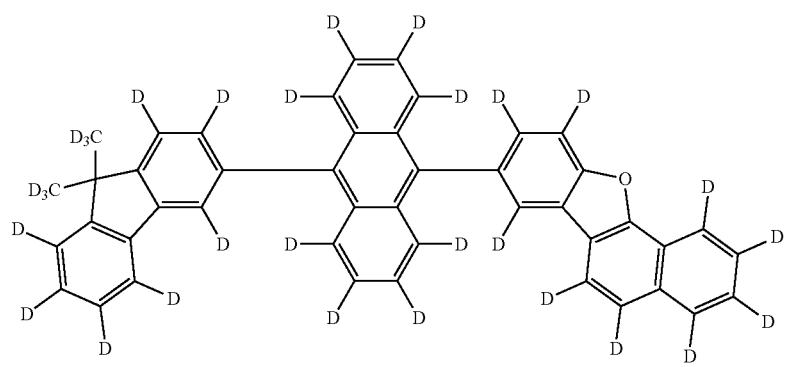
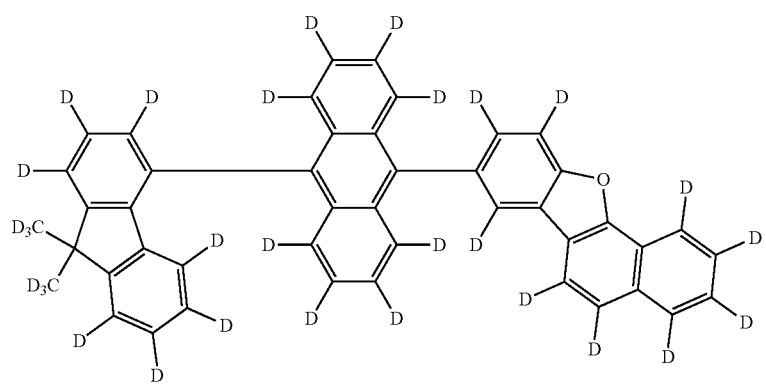
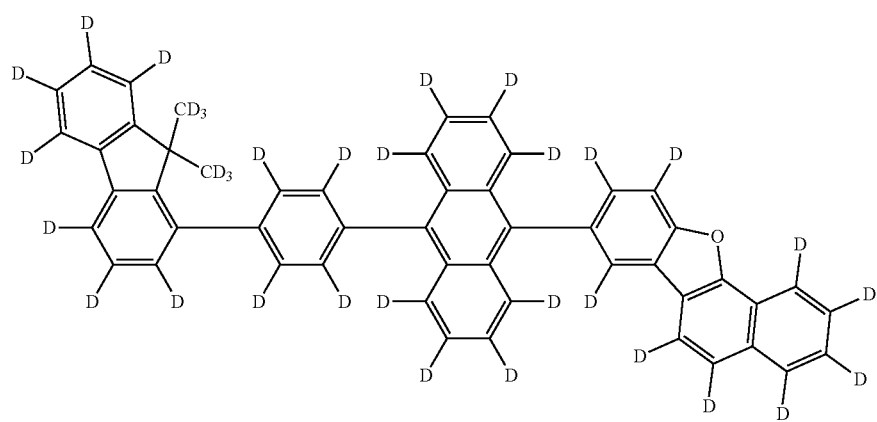

-continued
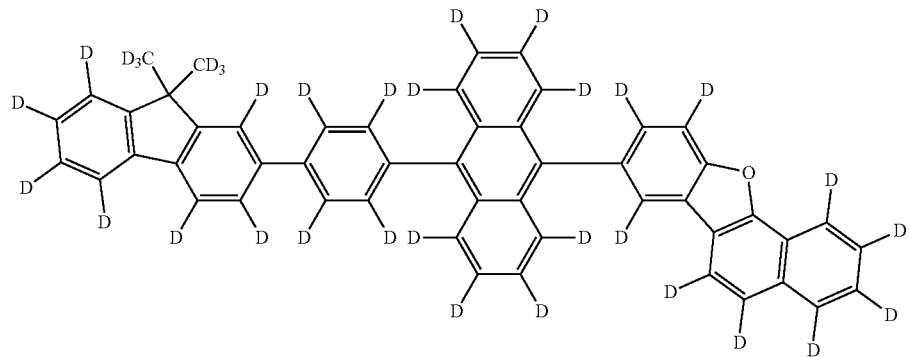
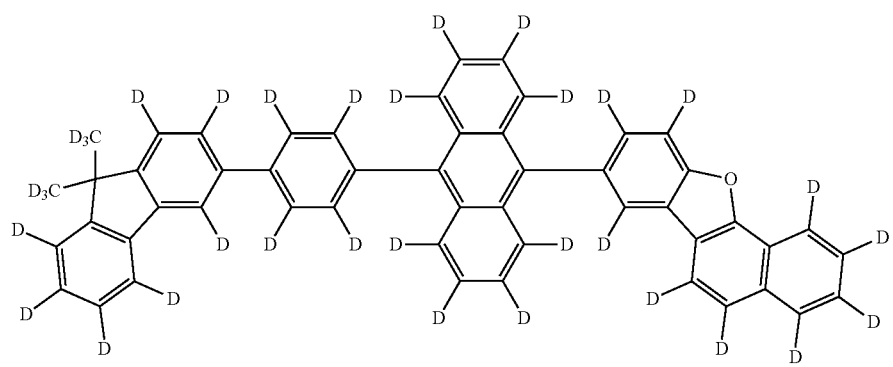
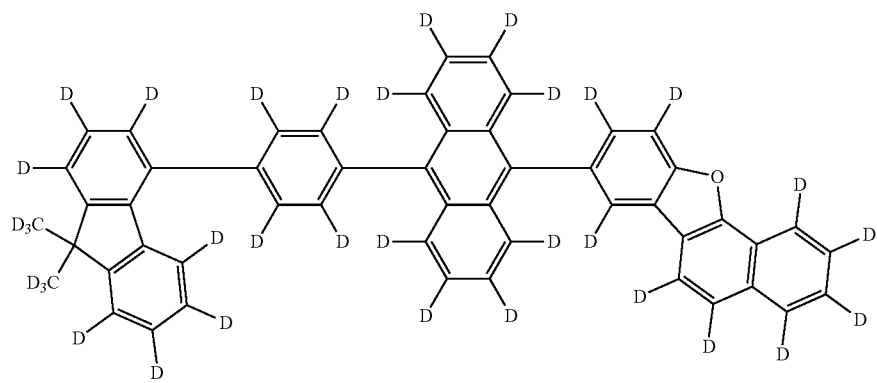
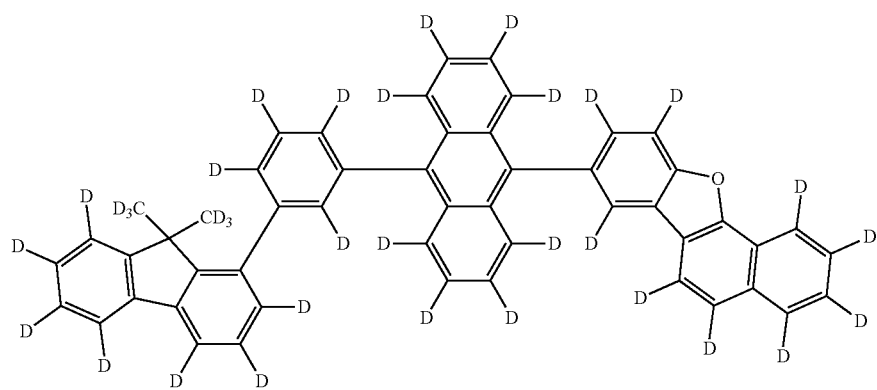

-continued
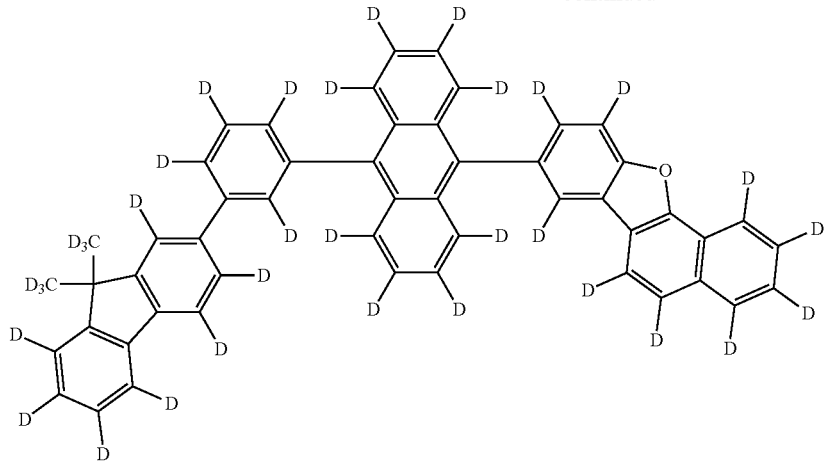
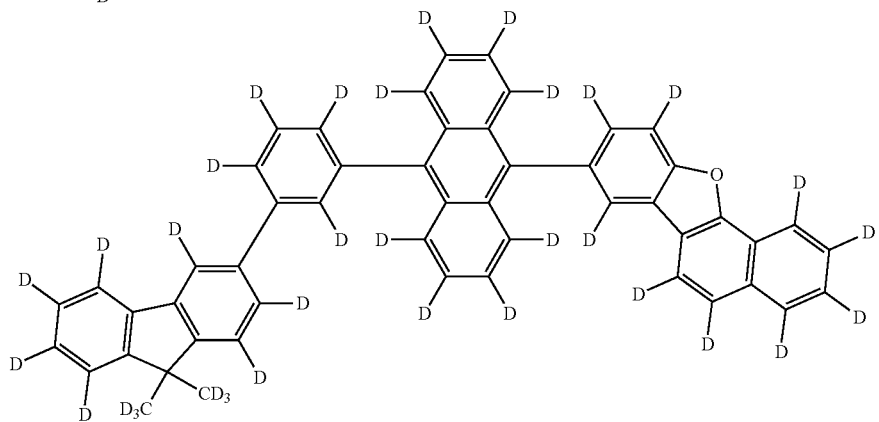
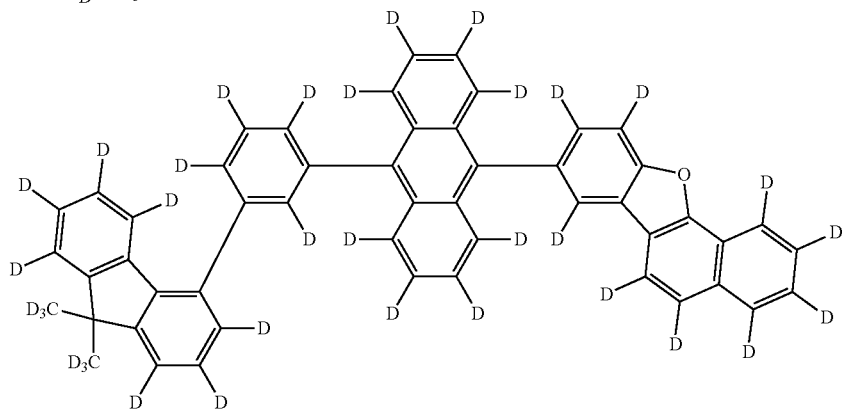
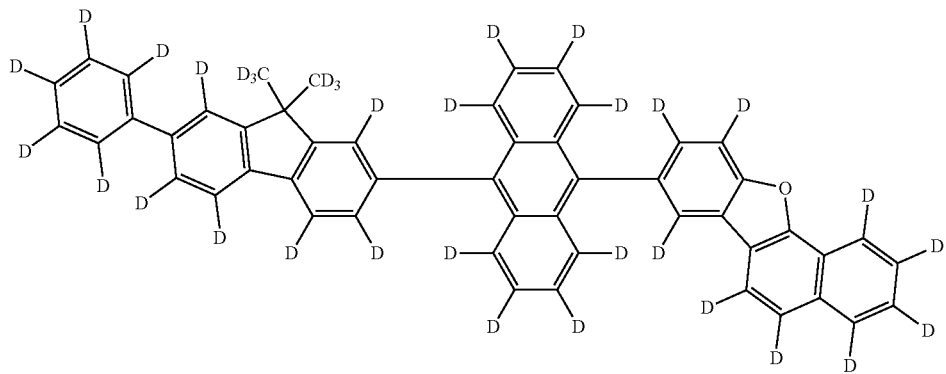

-continued
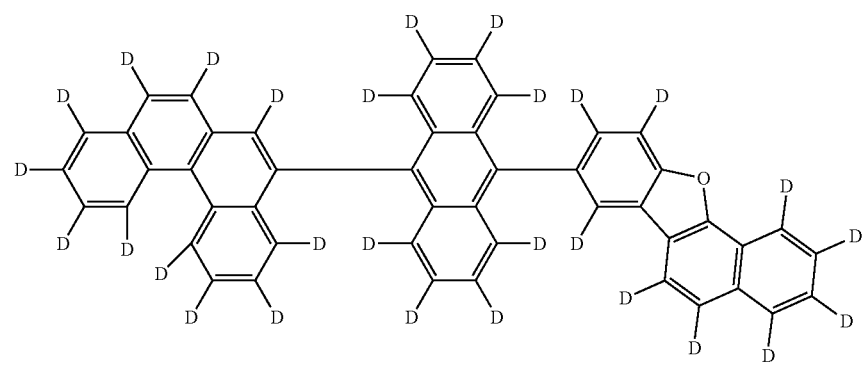
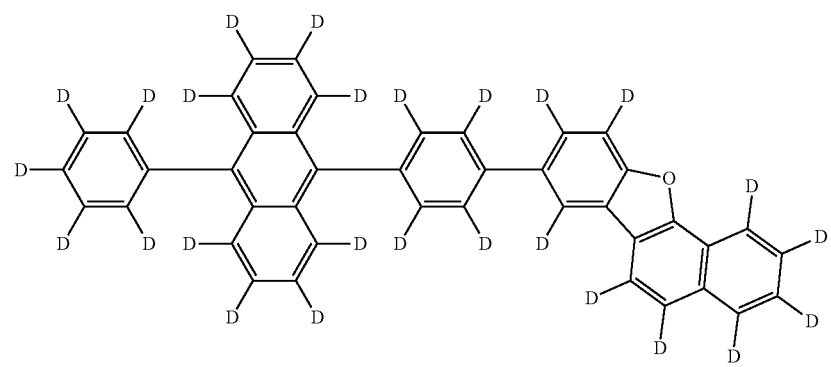
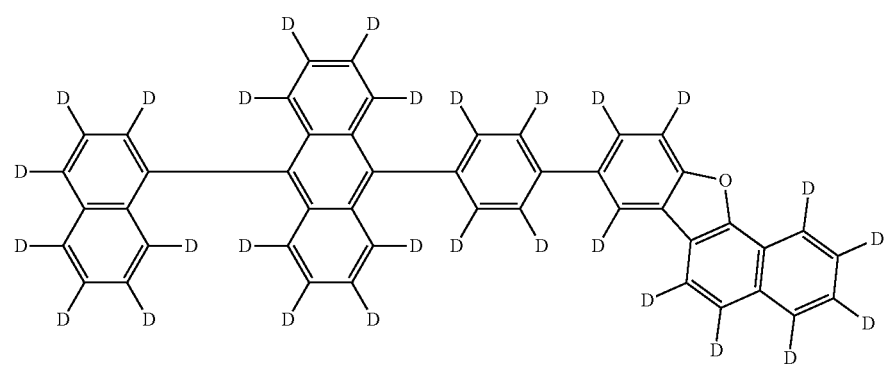
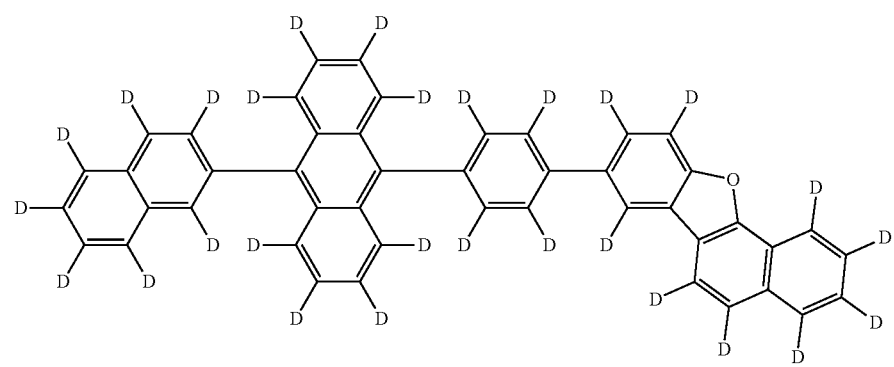

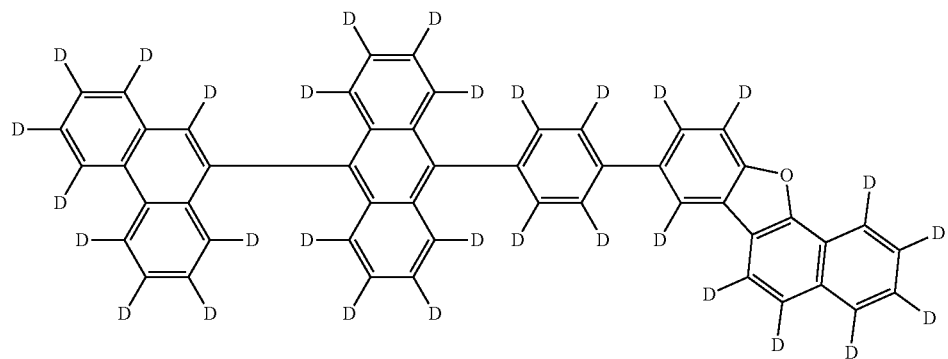
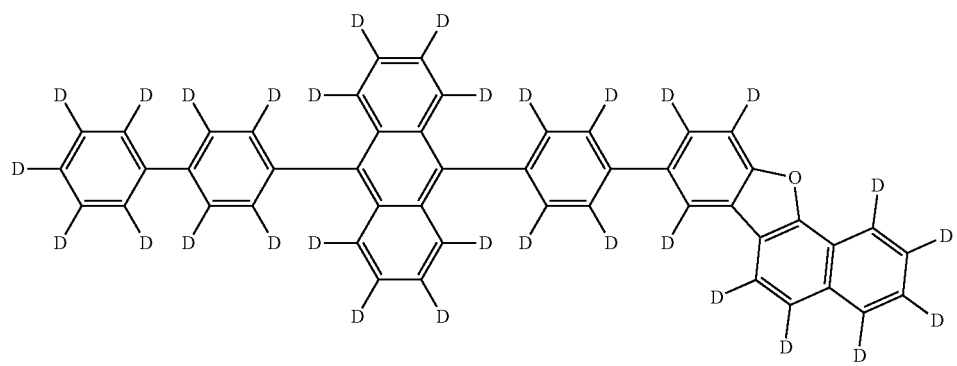
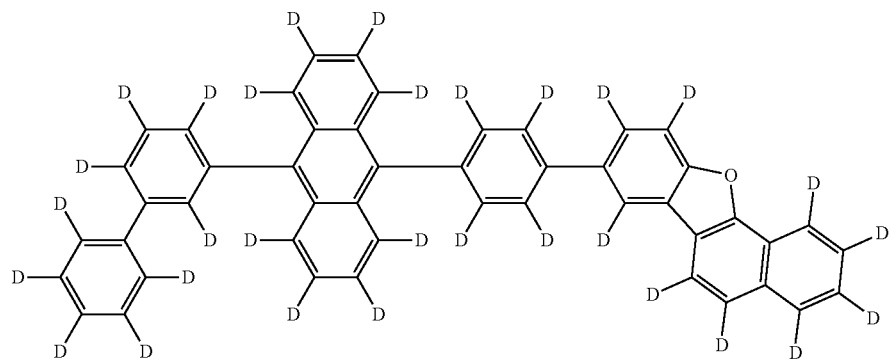
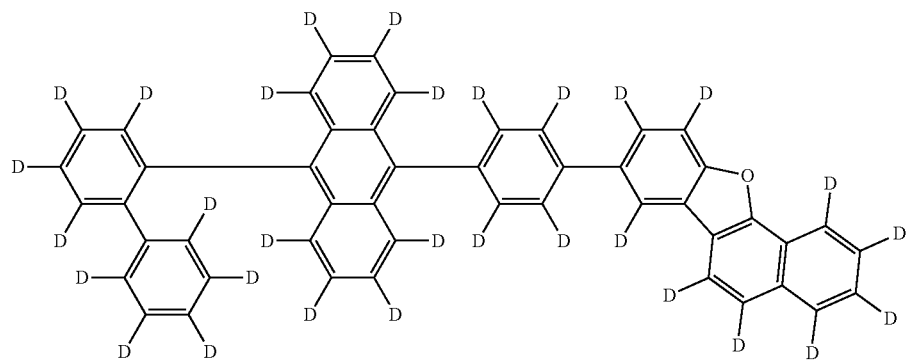

-continued
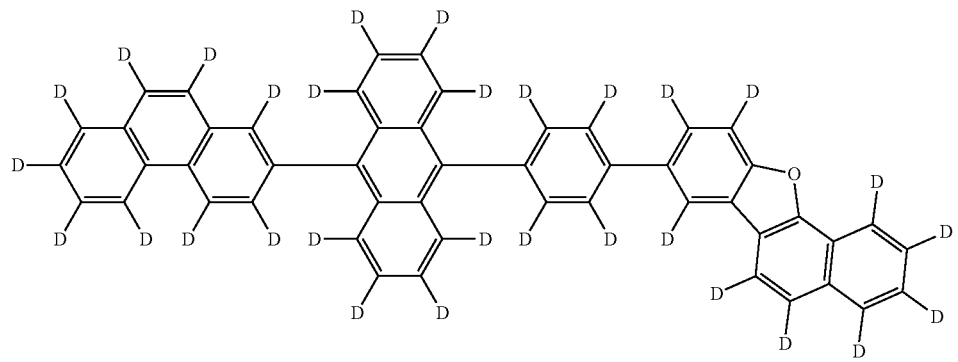
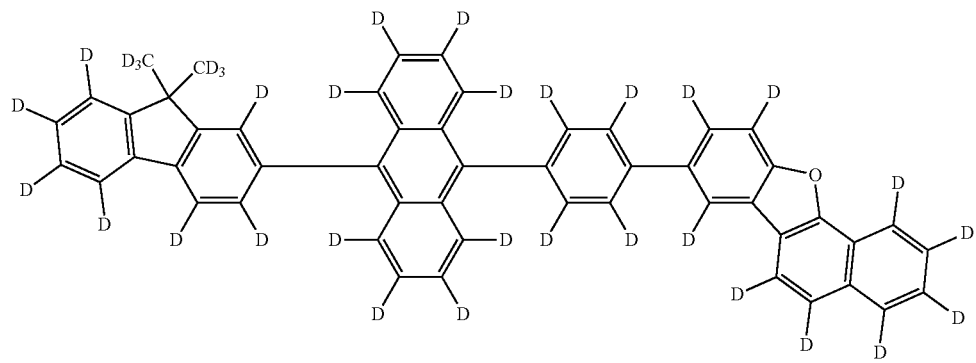
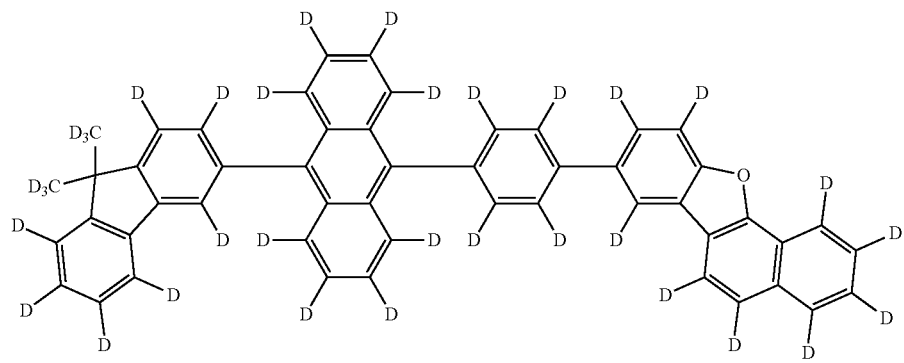
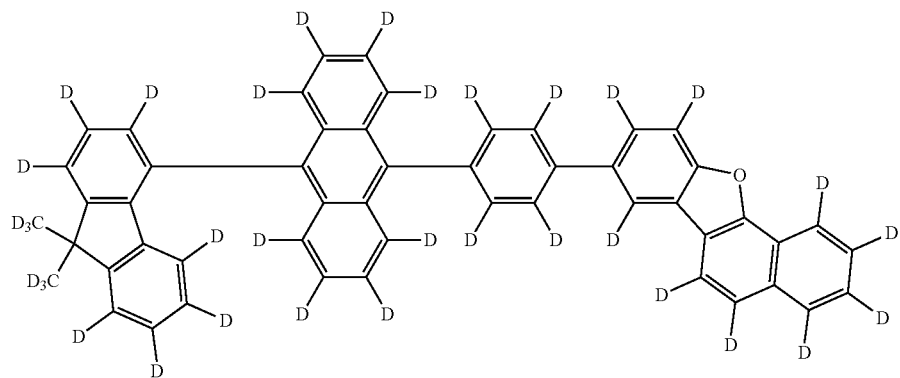

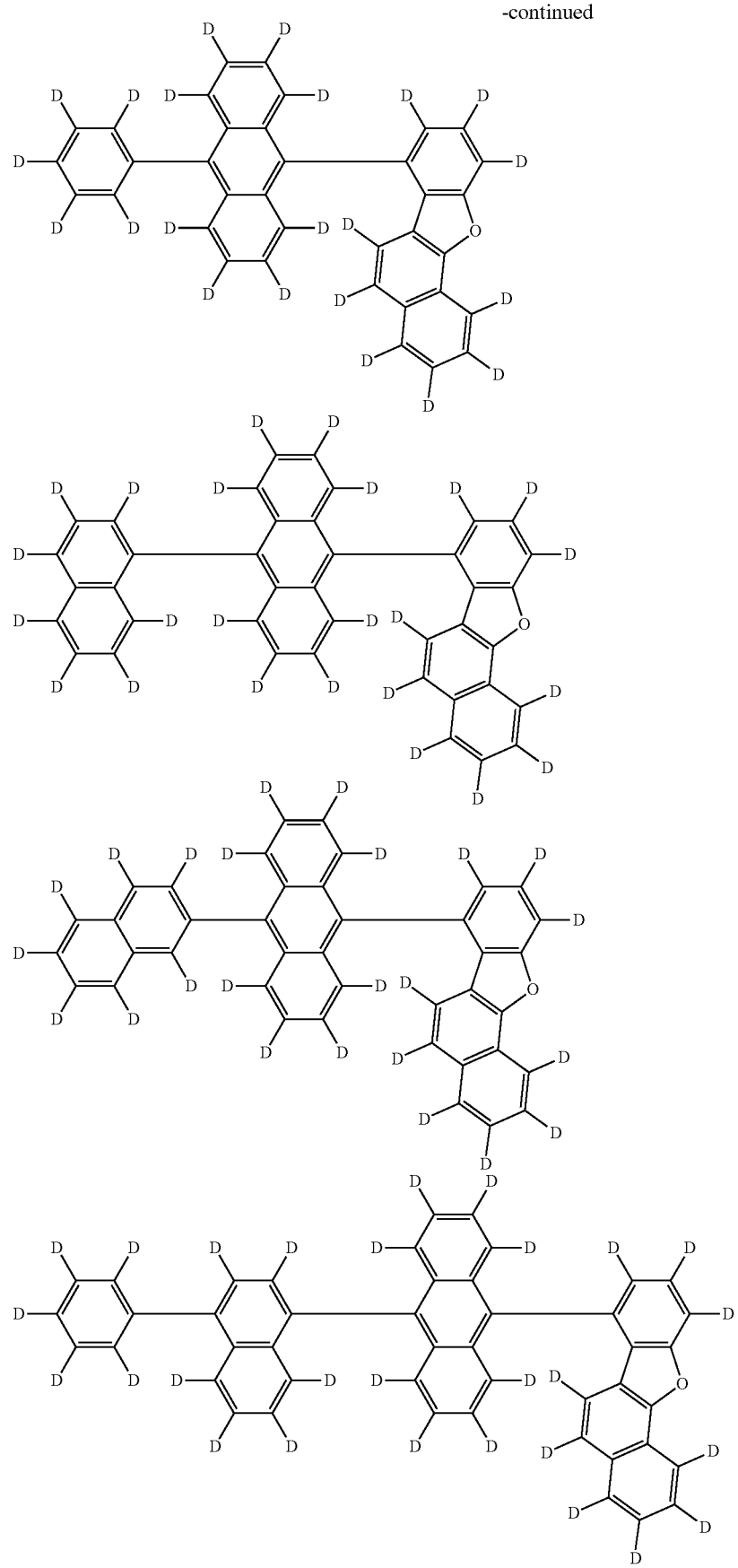

-continued
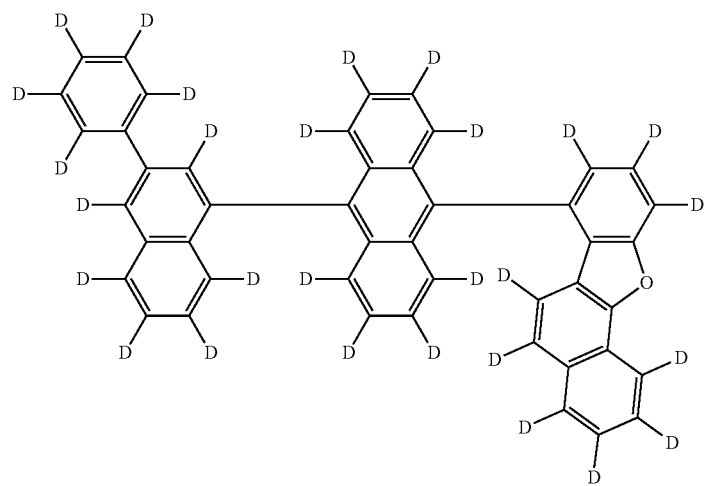
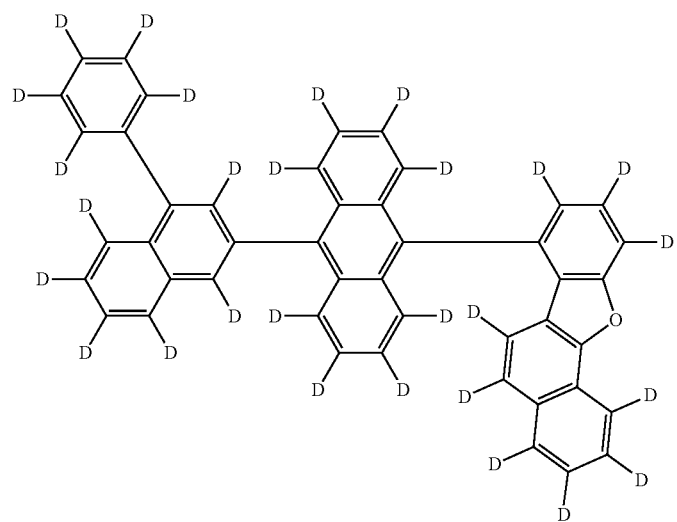
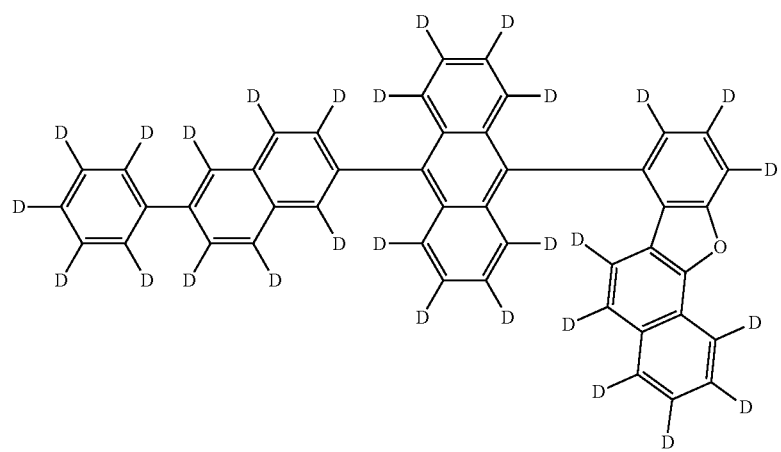

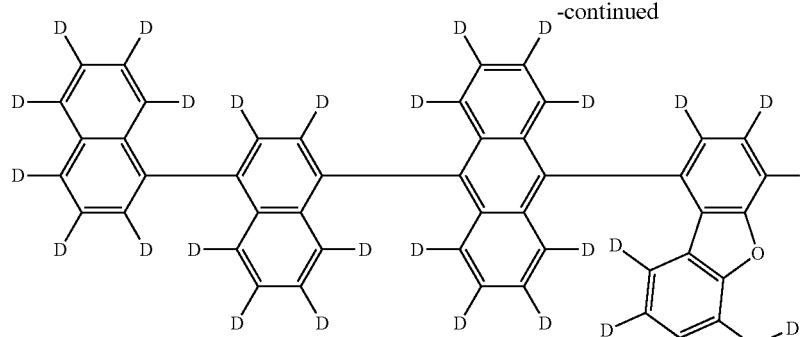
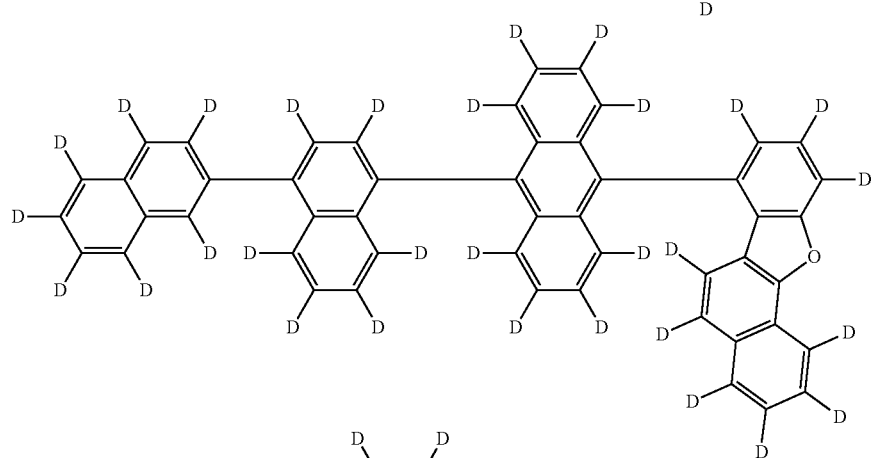
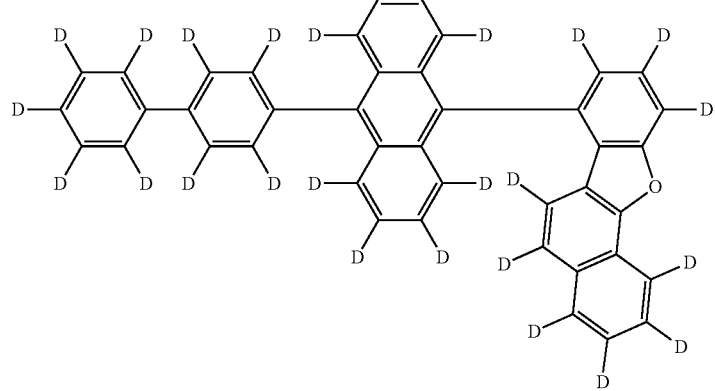
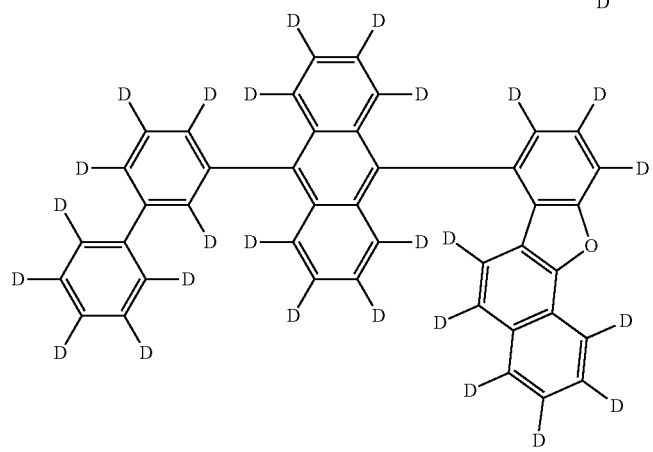

-continued
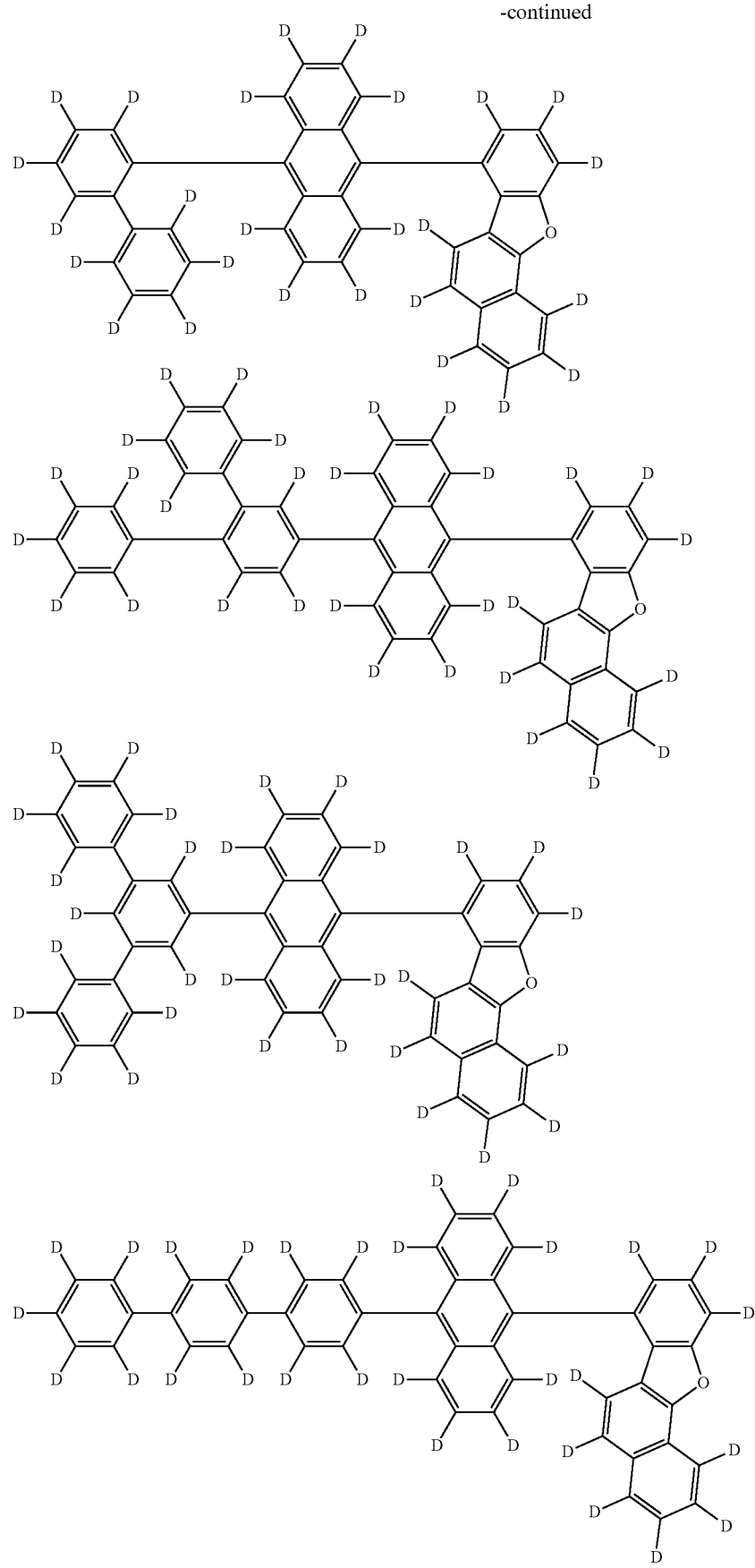

-continued
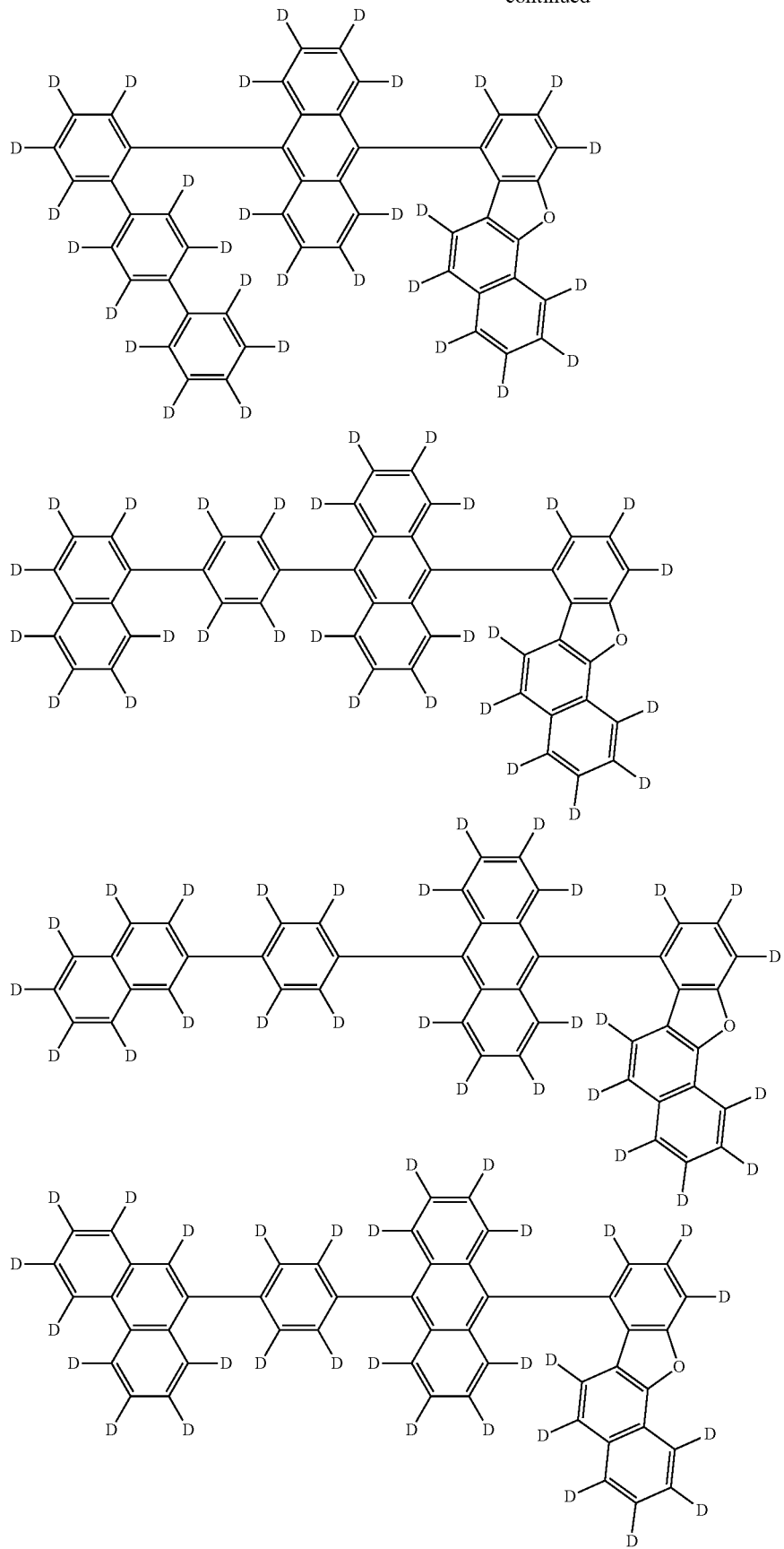

-continued
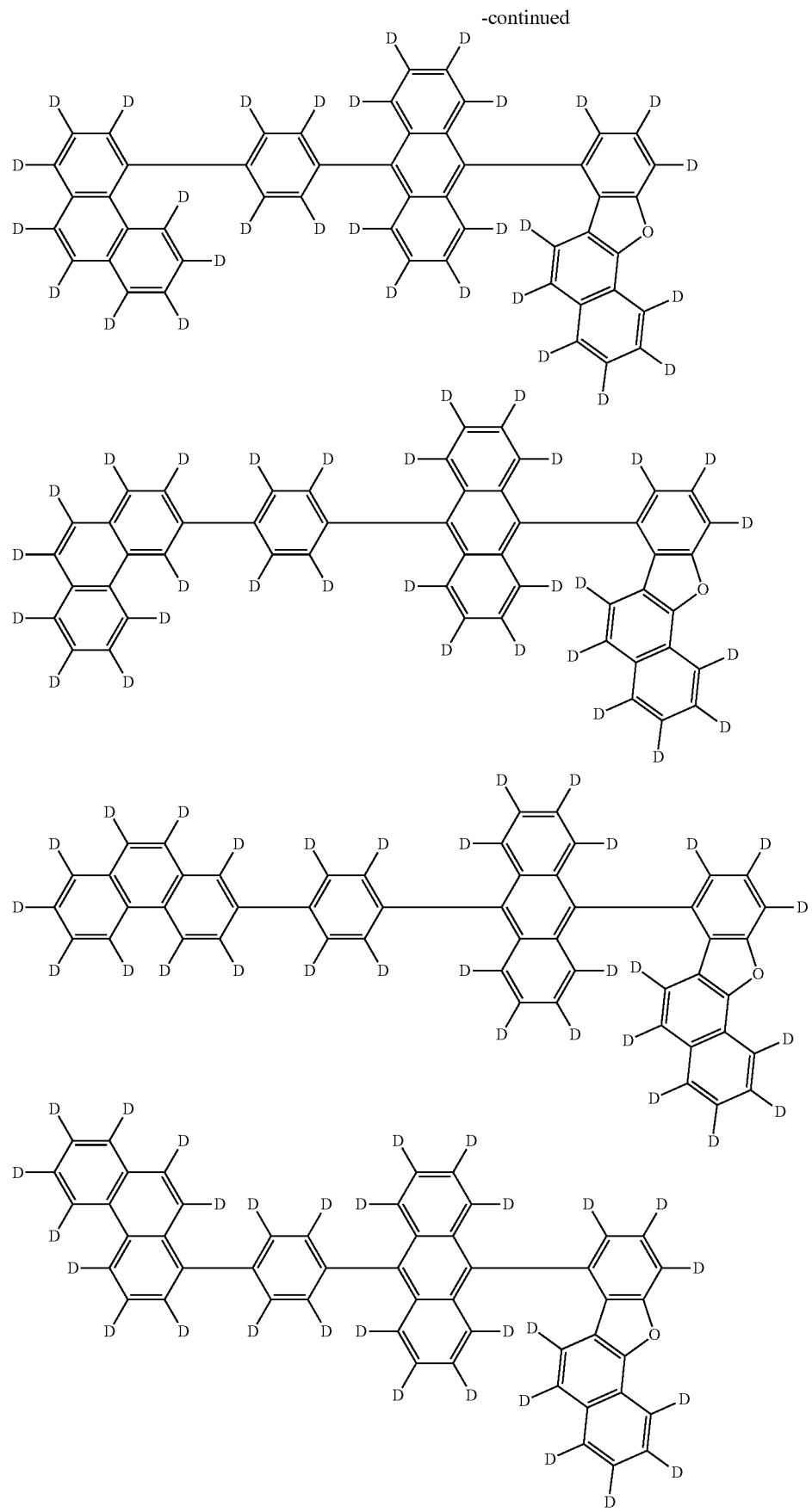

-continued
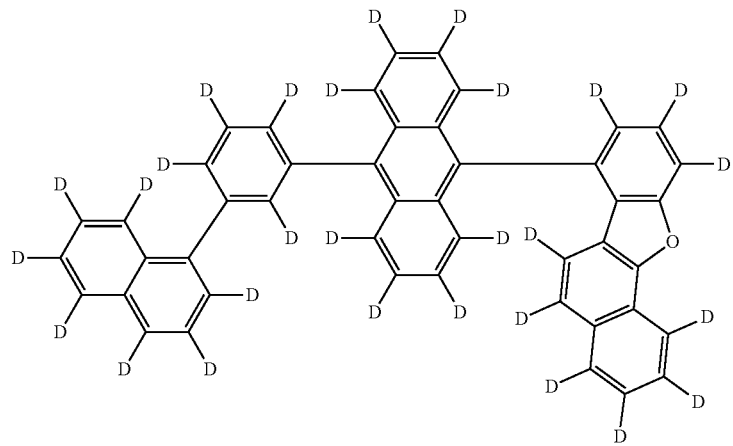
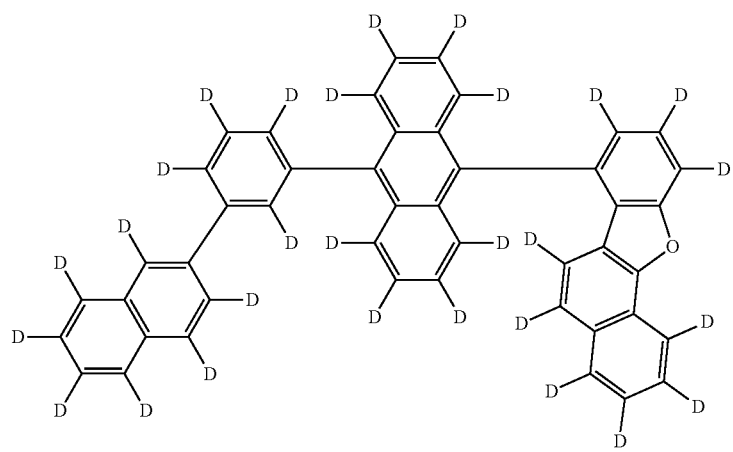
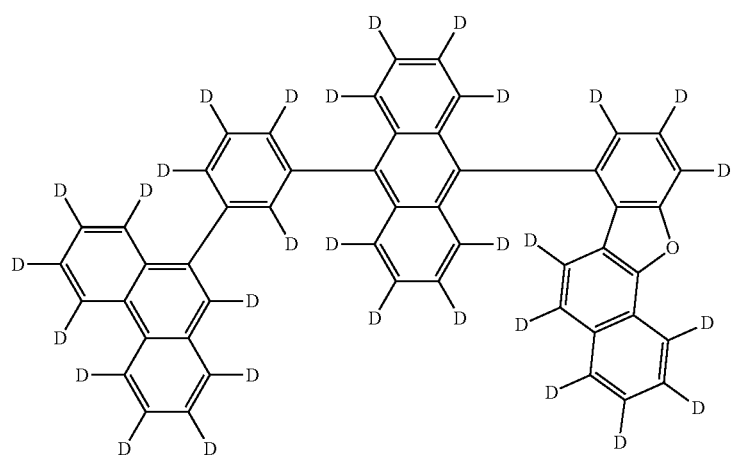

-continued
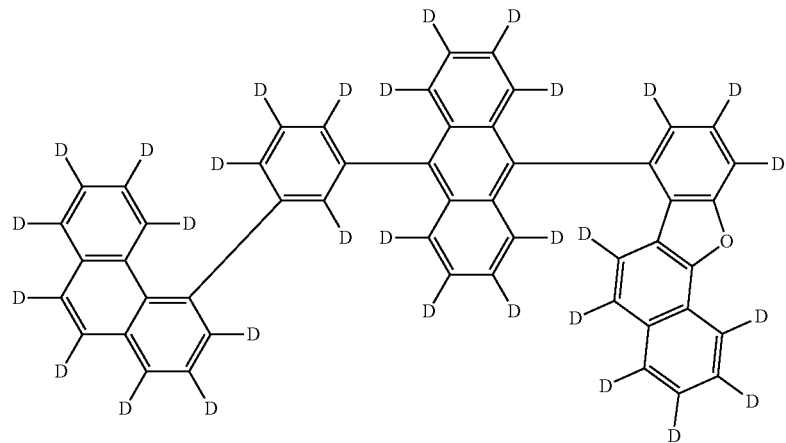
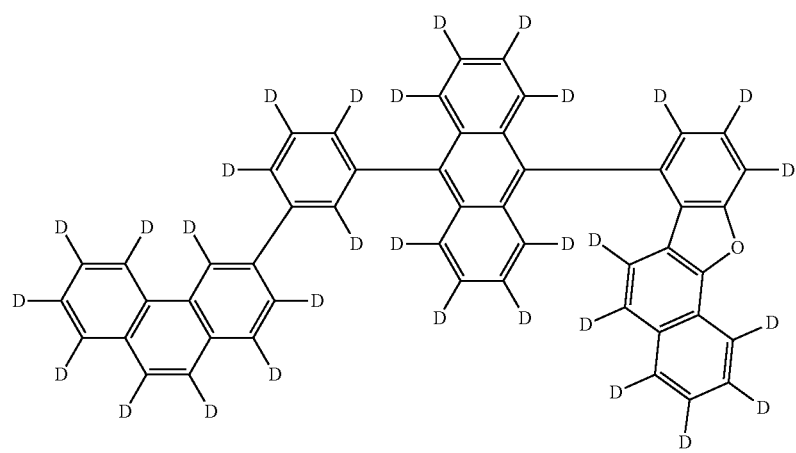
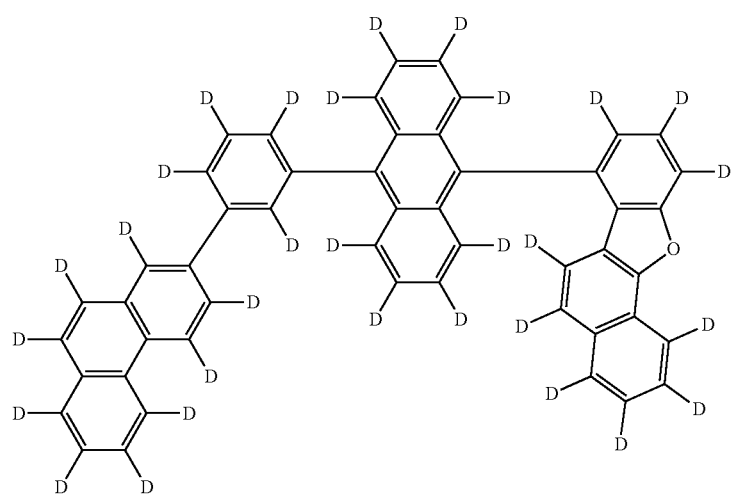

-continued
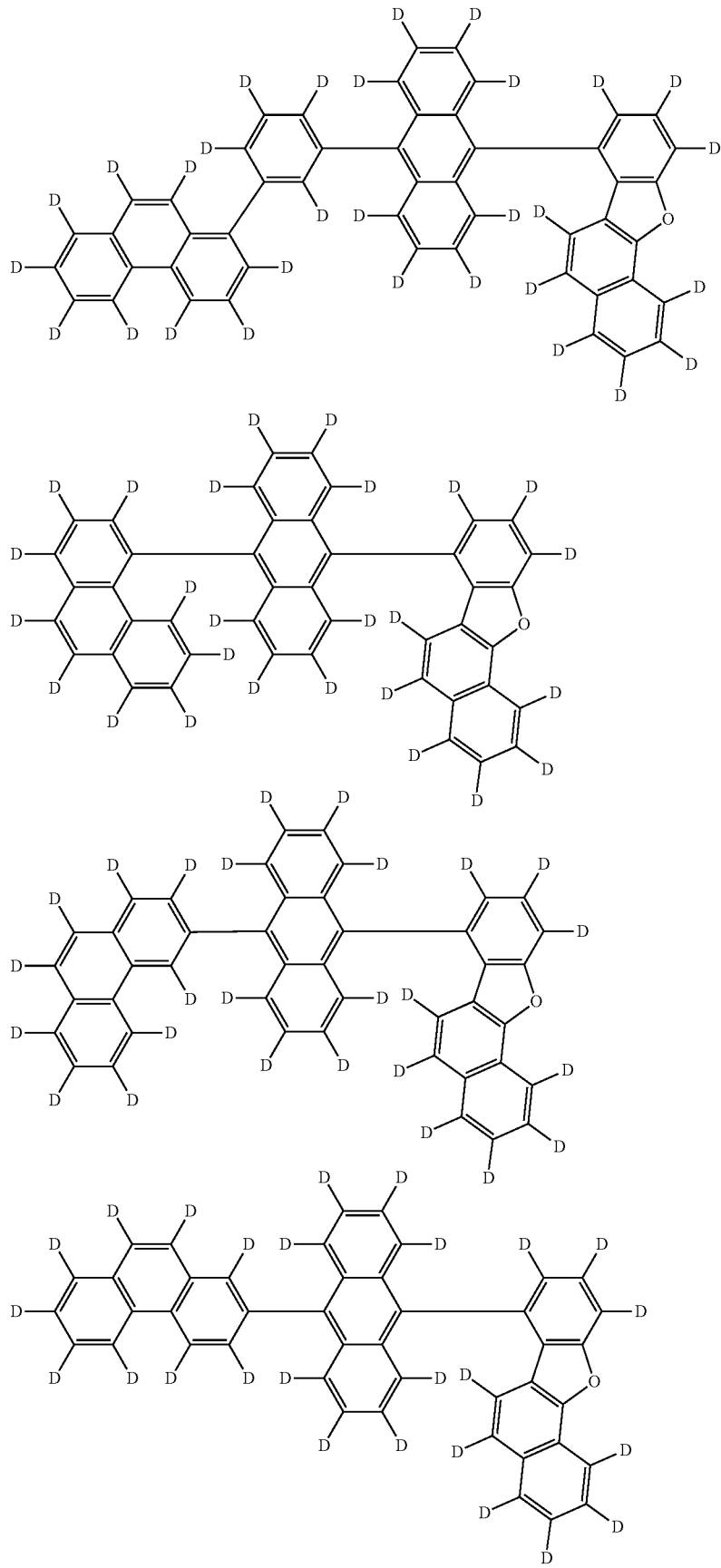

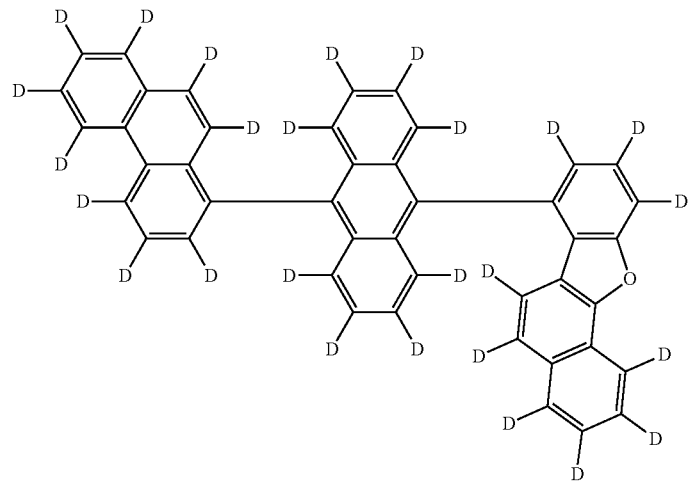

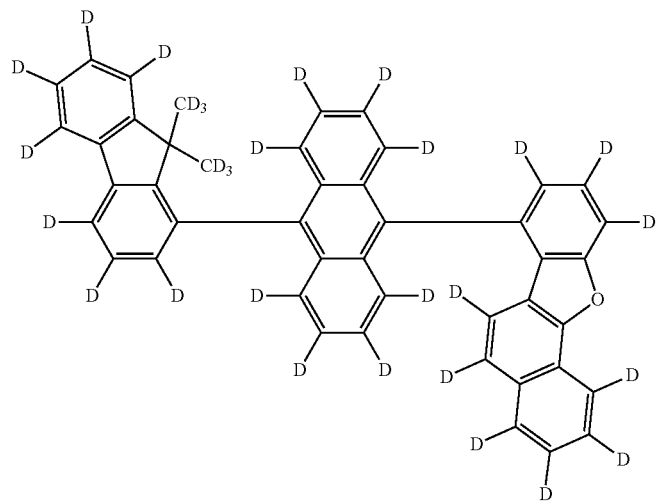
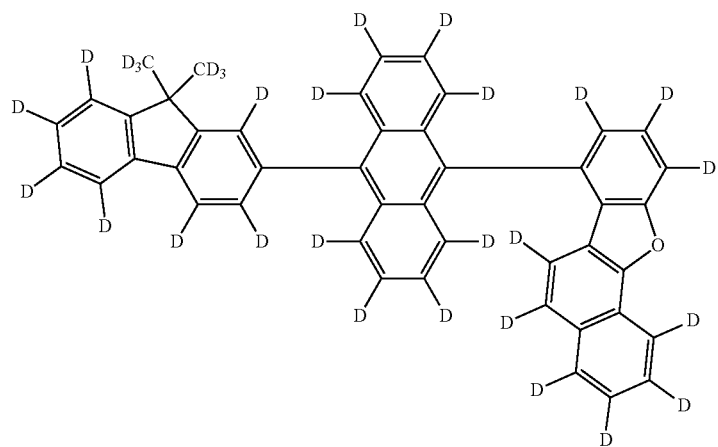
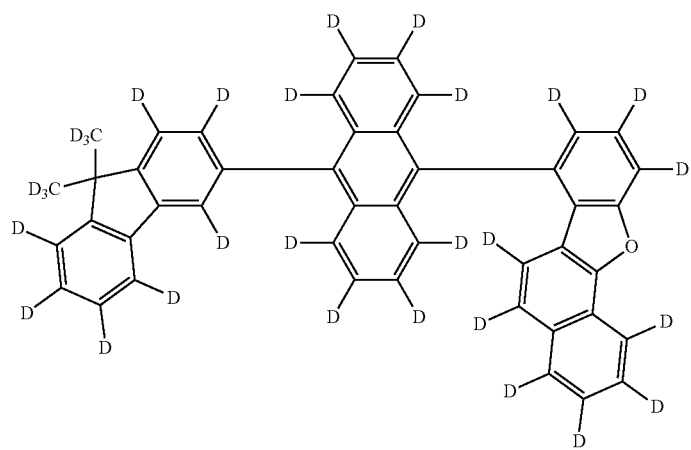

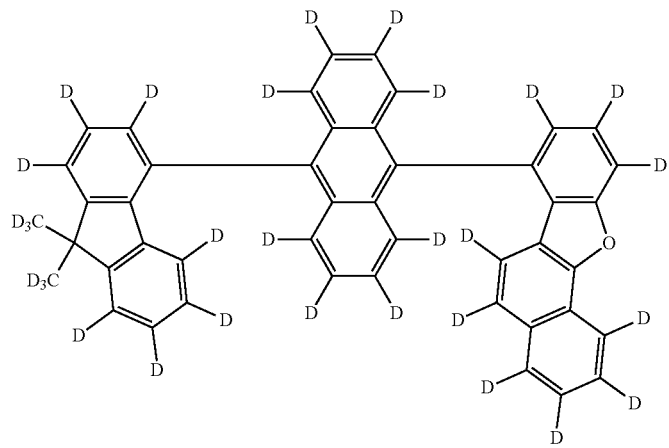
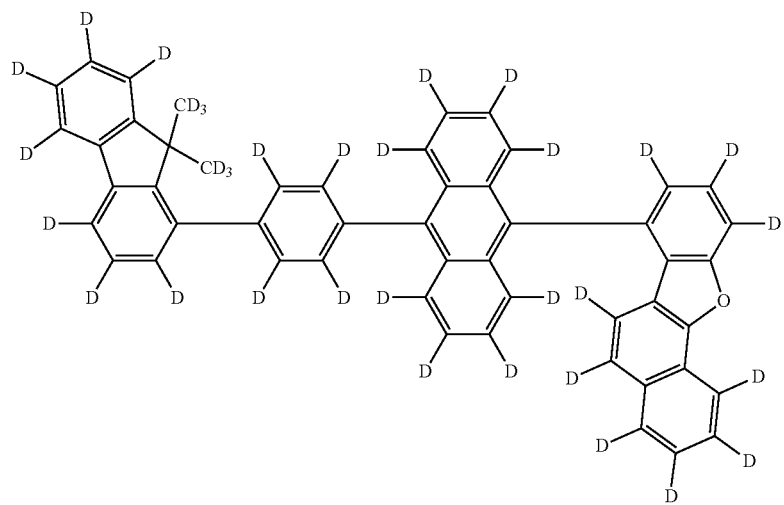
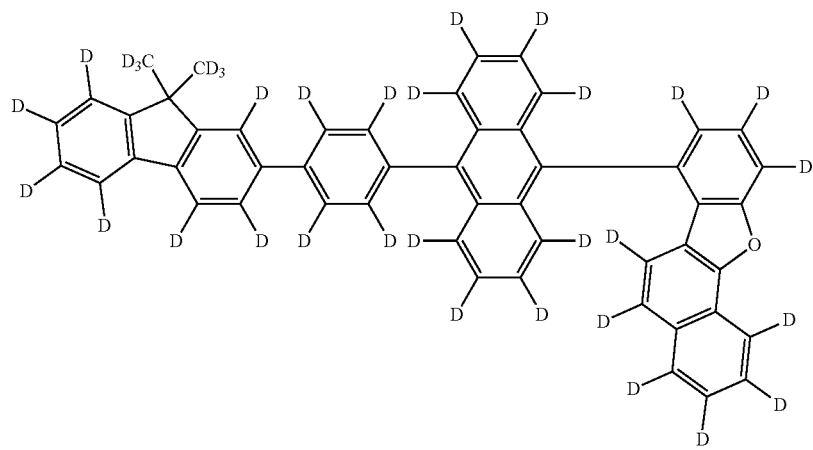

-continued
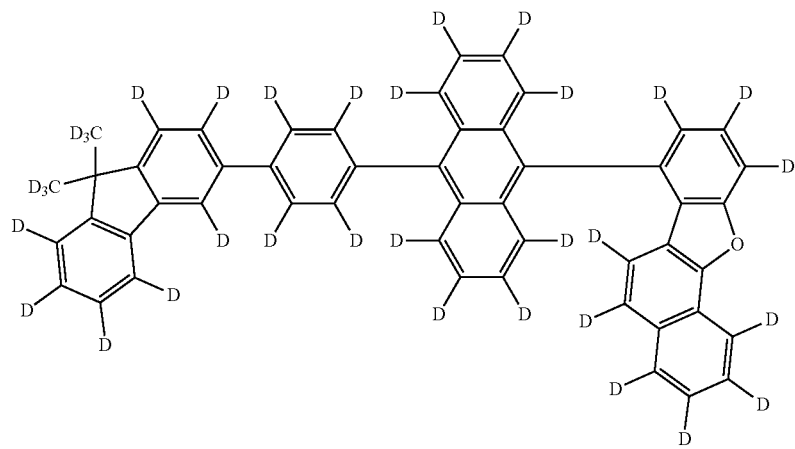
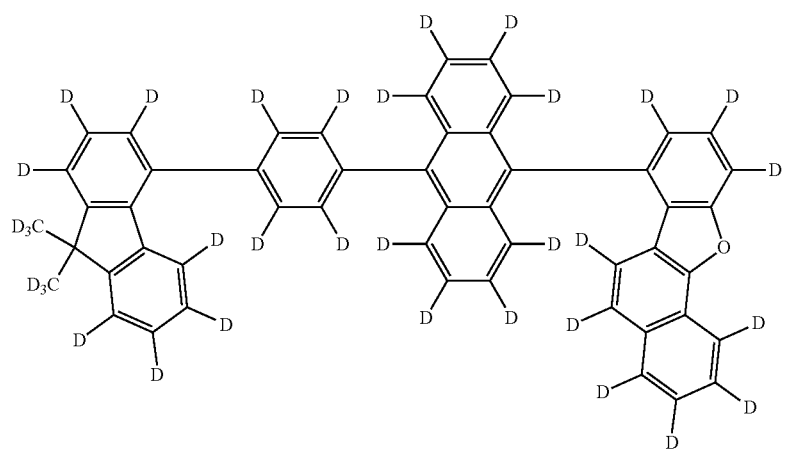
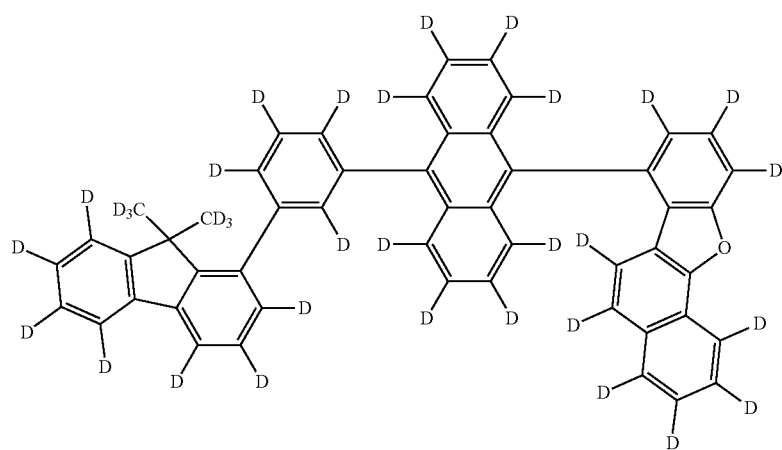

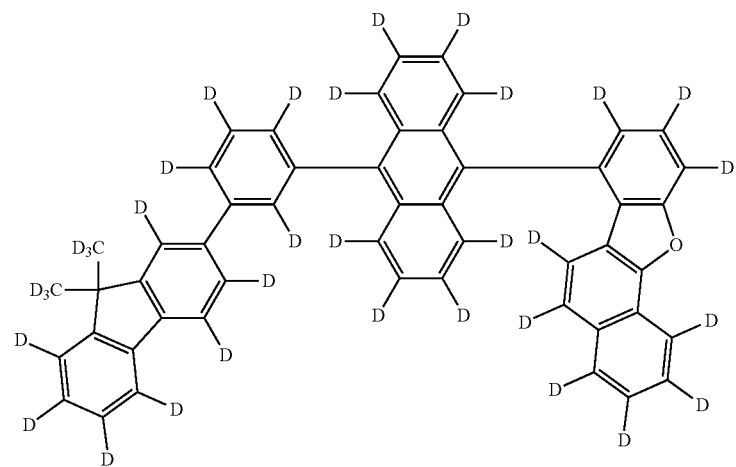
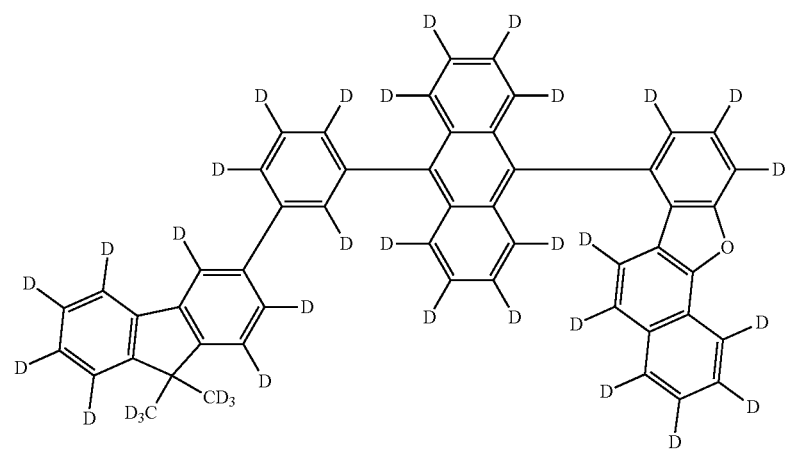
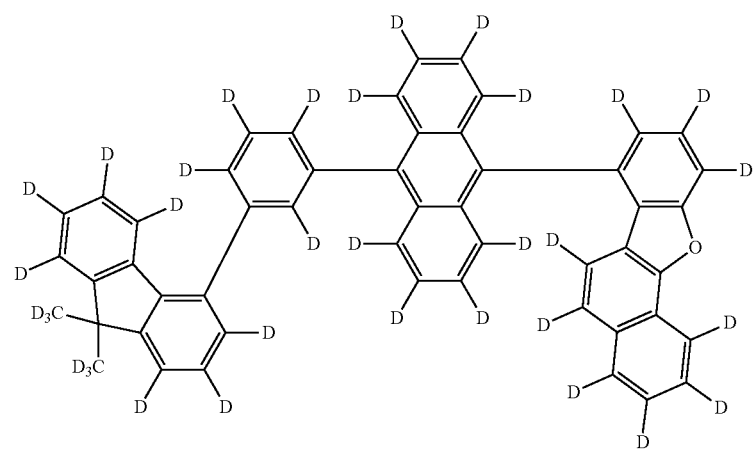

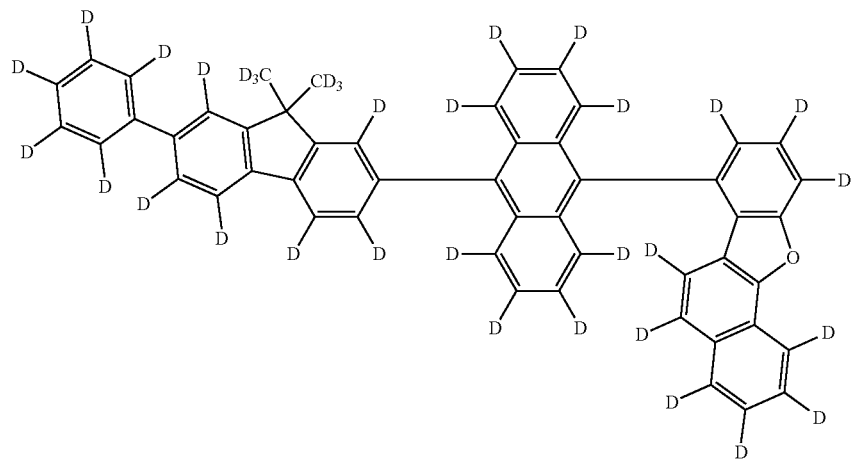
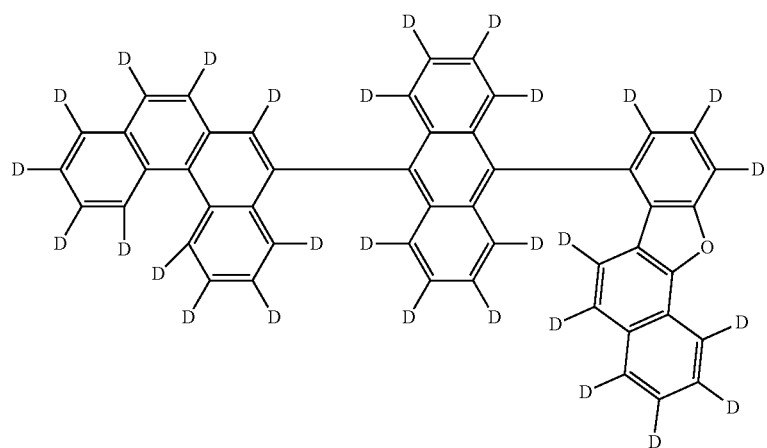
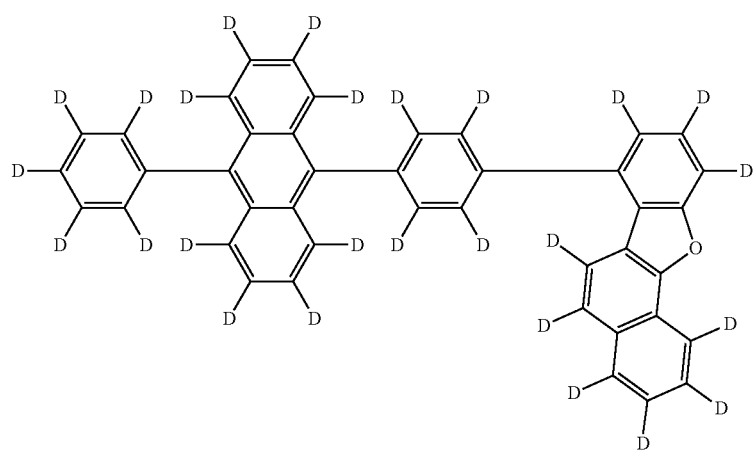

-continued
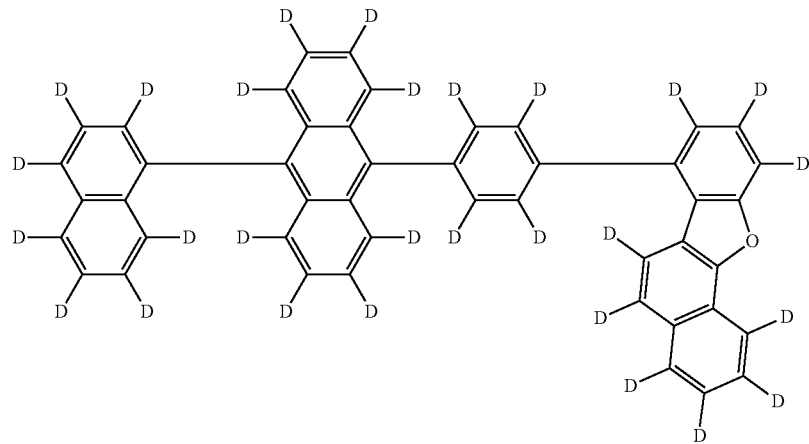
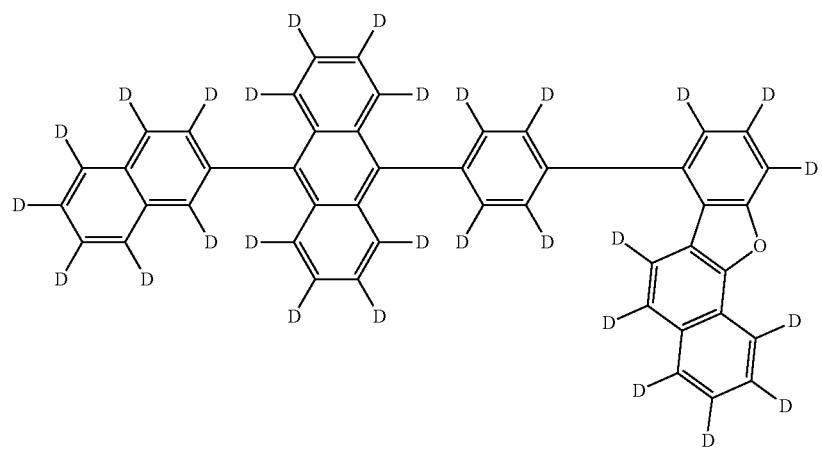
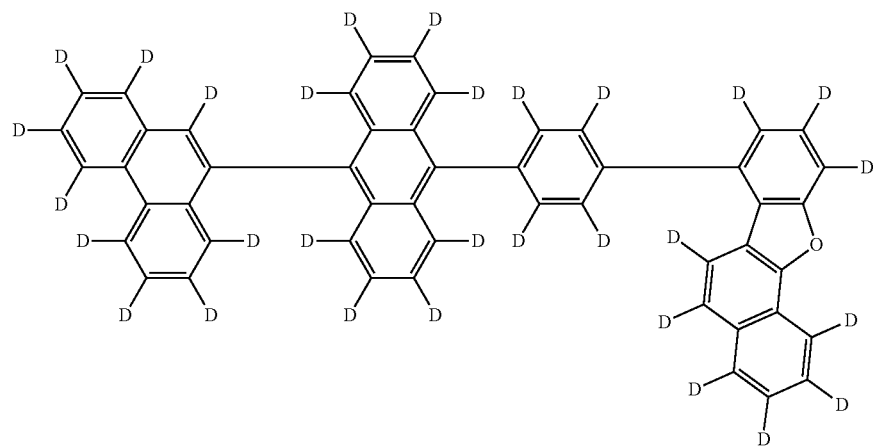

-continued
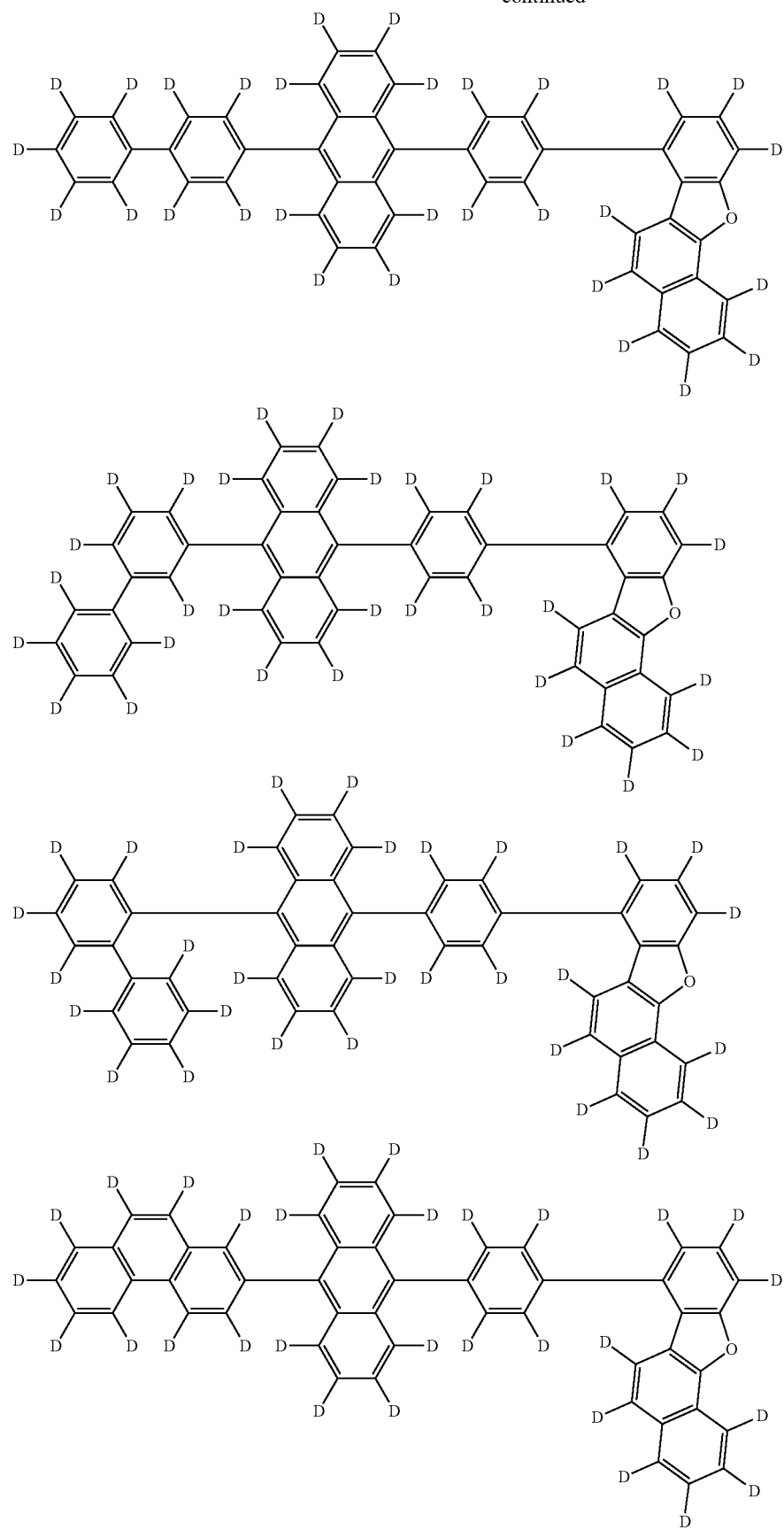

-continued
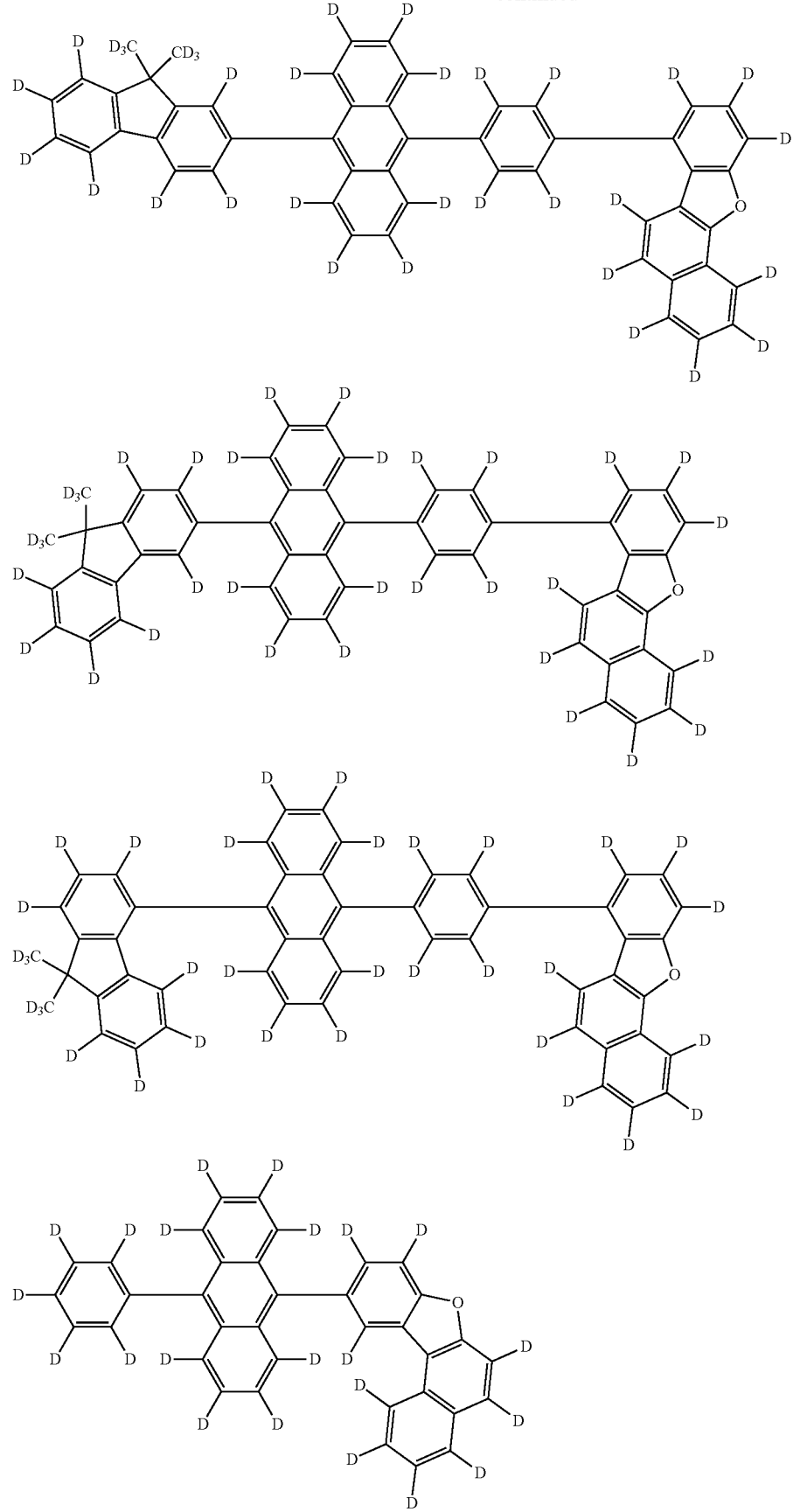

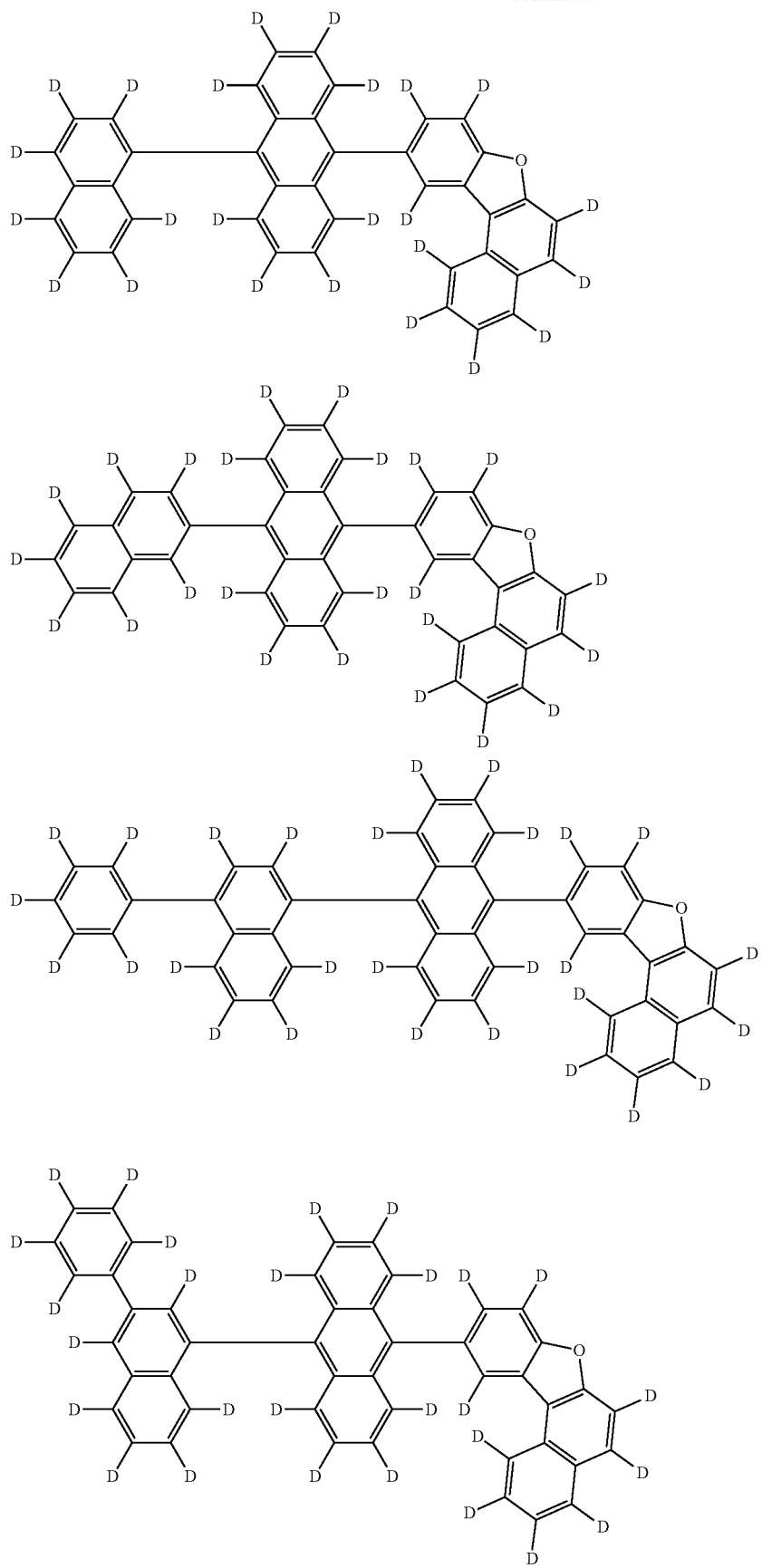

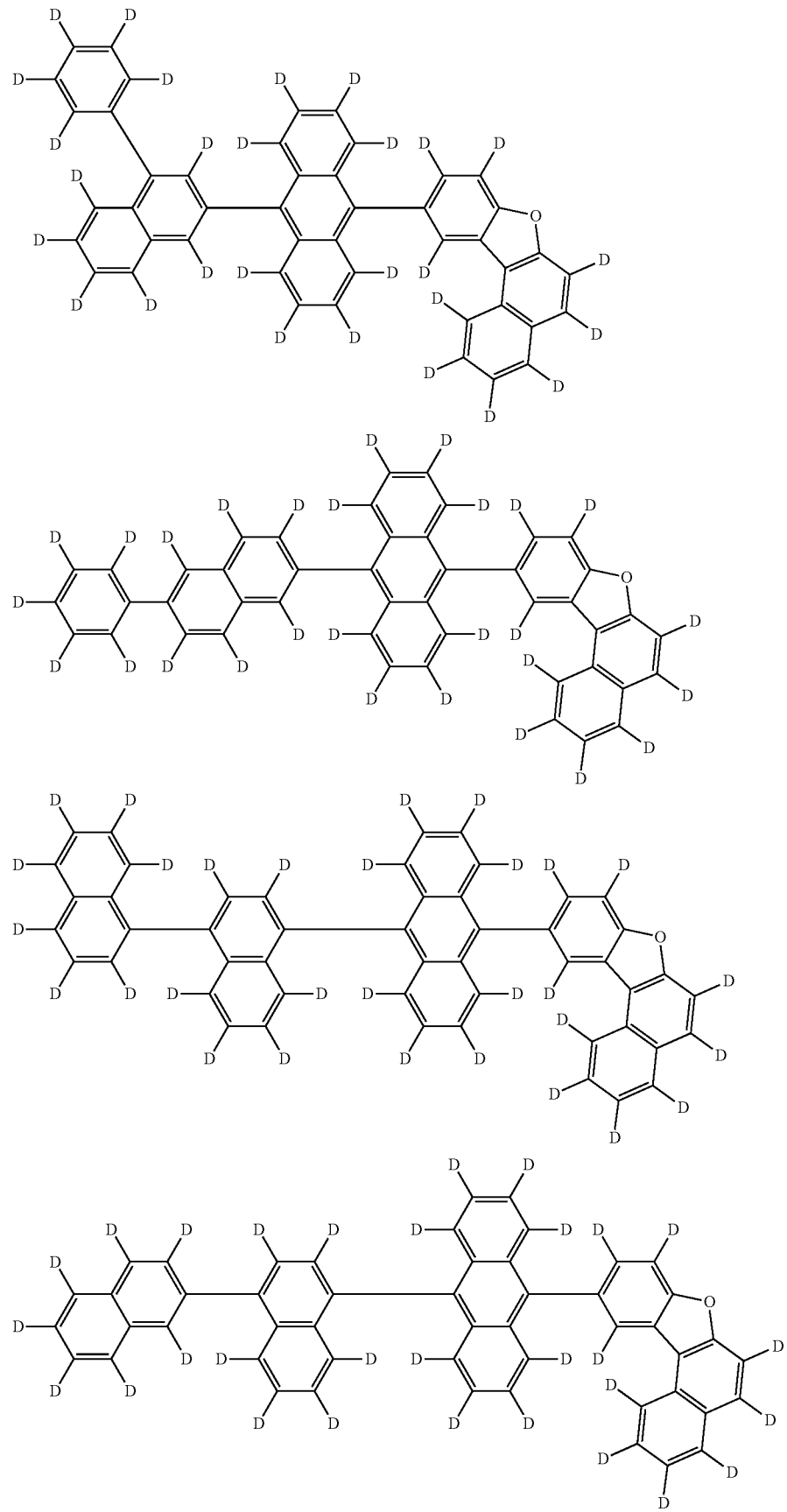

-continued
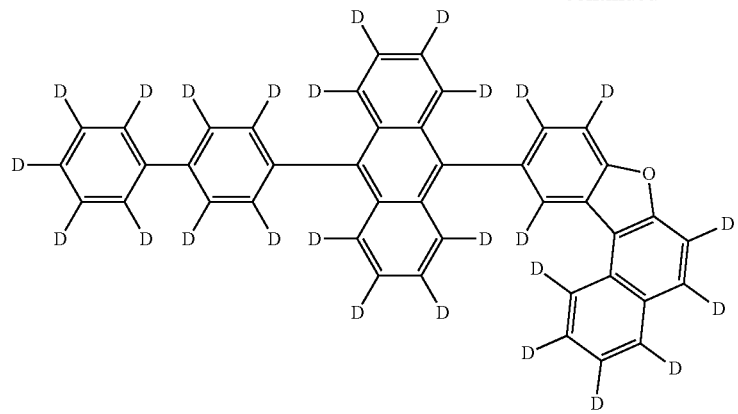
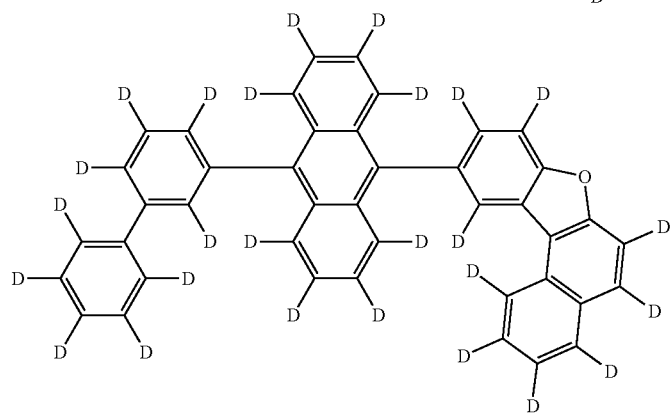
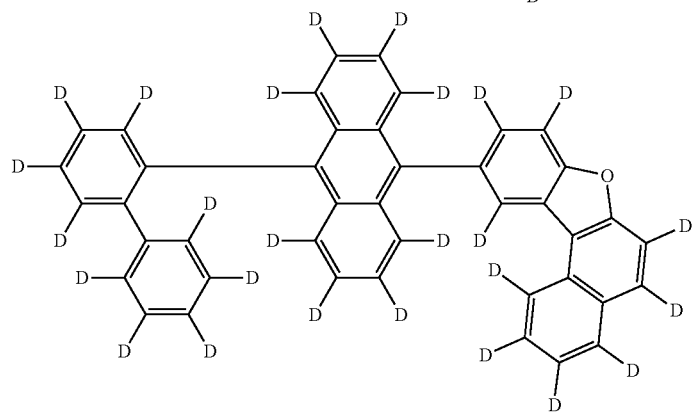
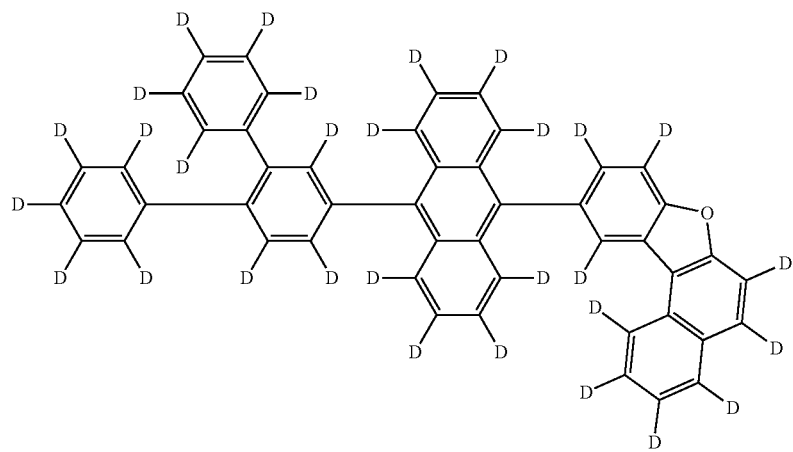

-continued
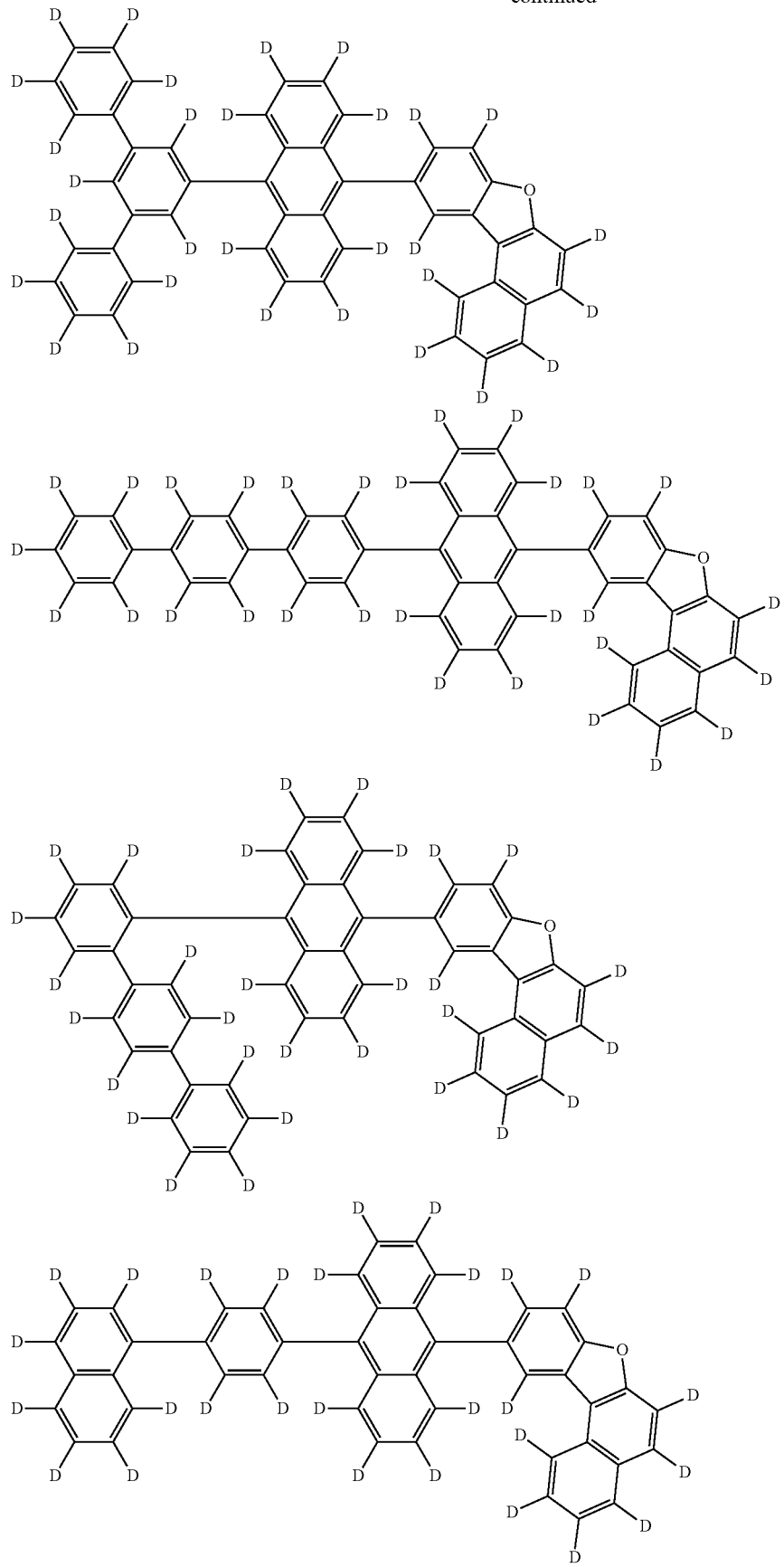

-continued
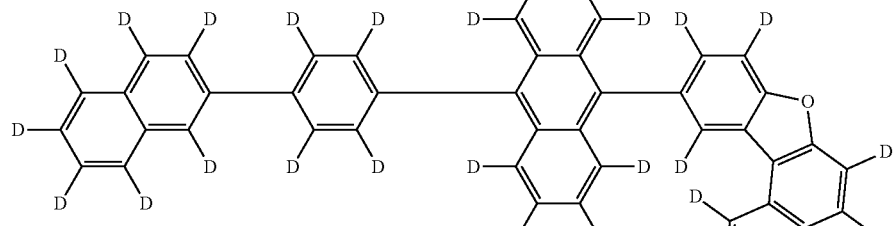
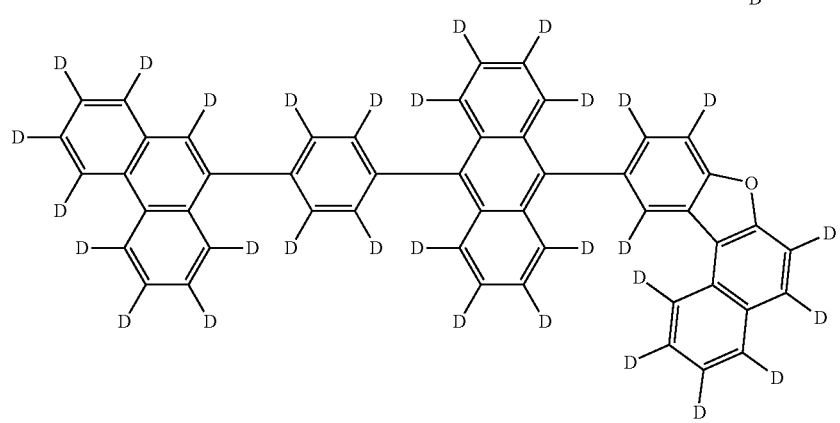
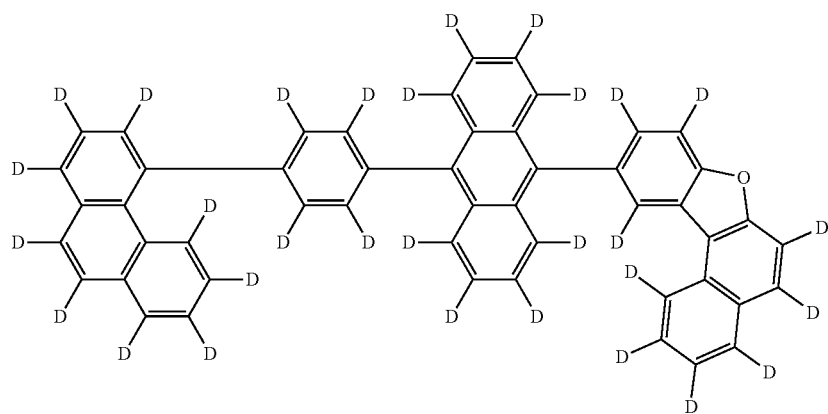
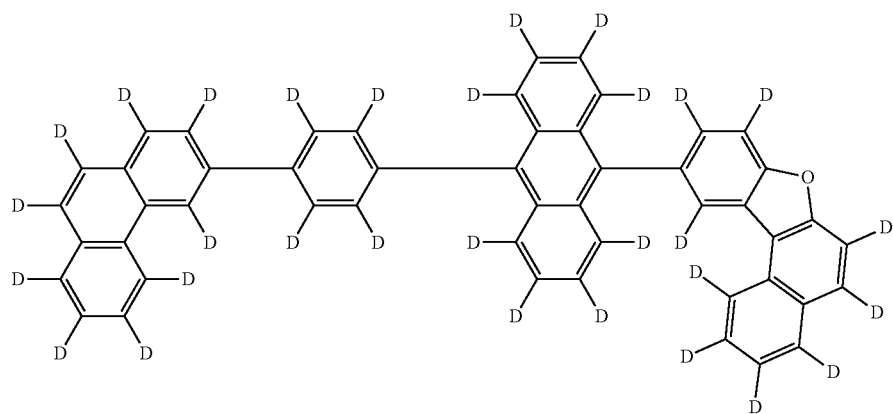

-continued
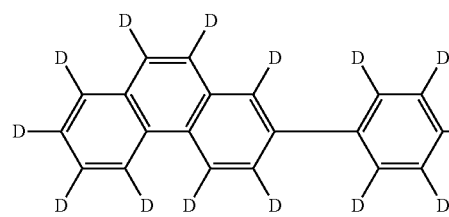
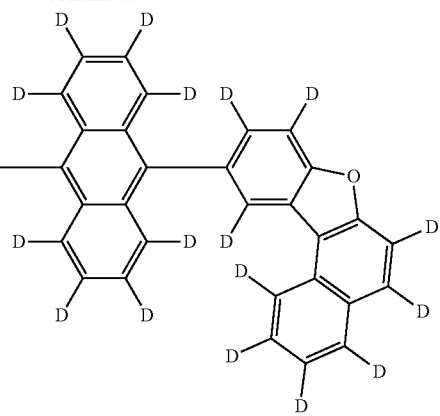
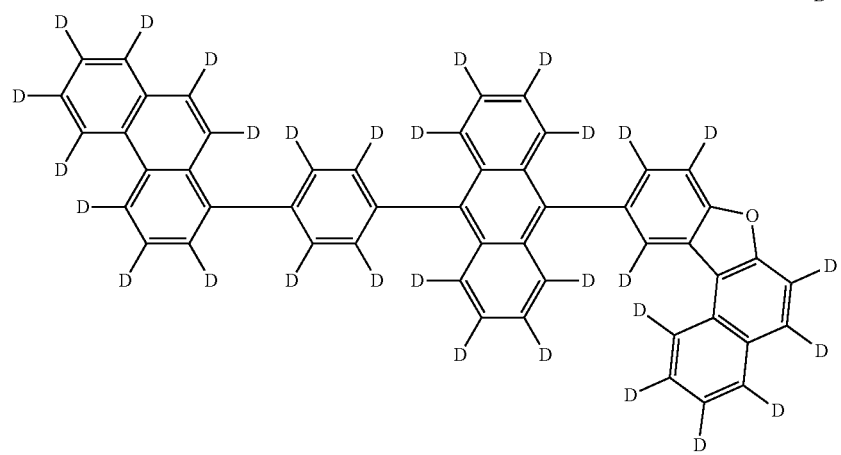
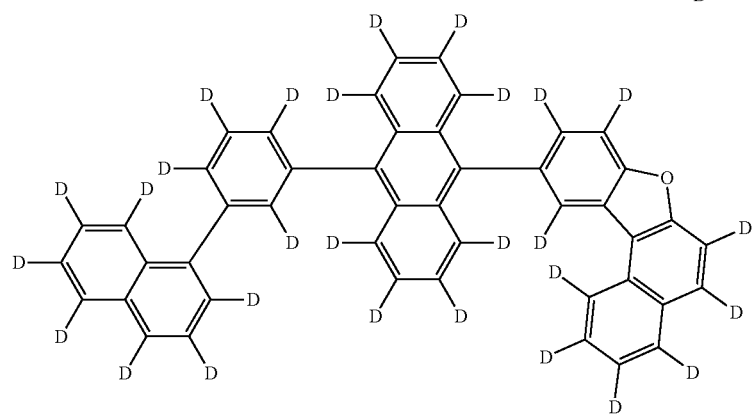
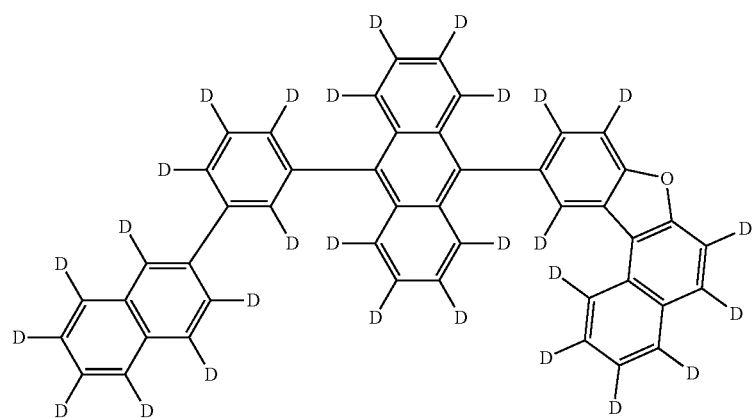

-continued
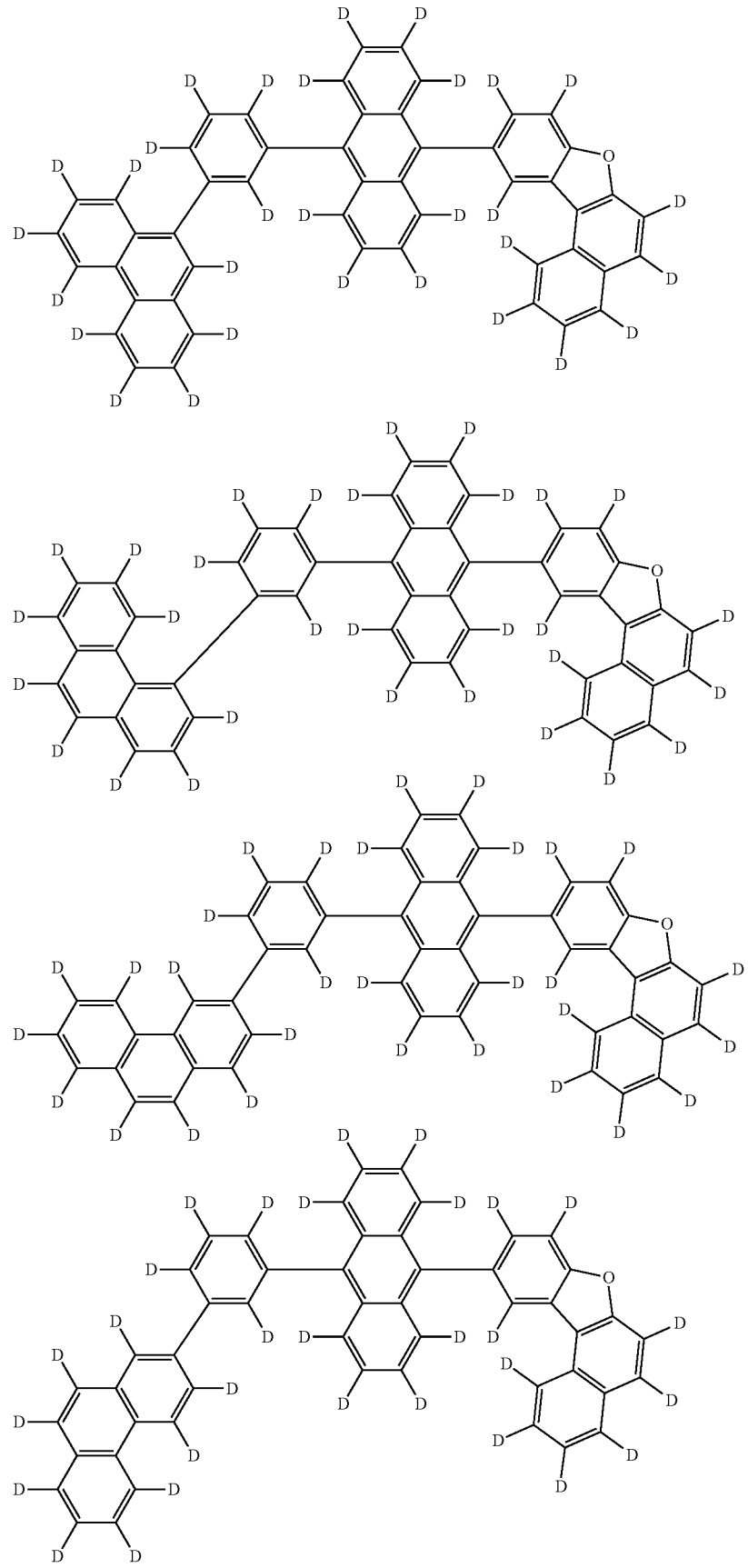

-continued
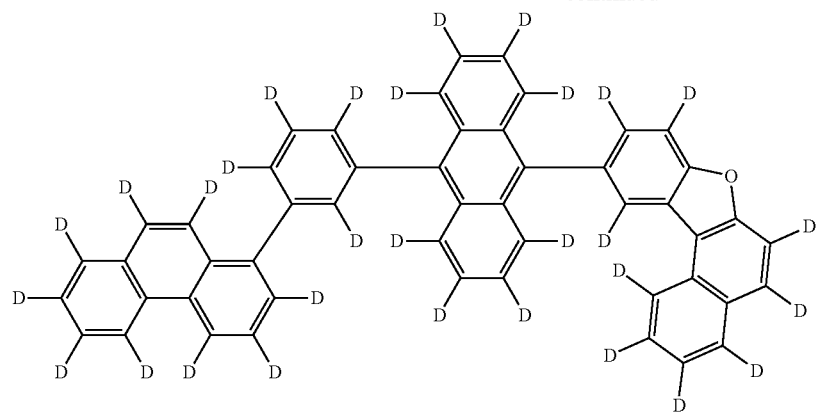
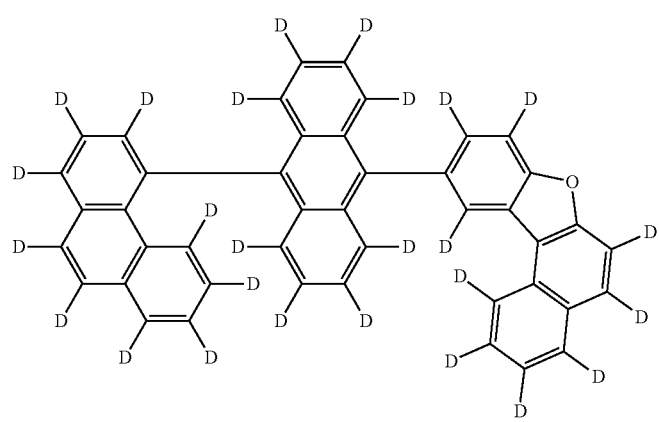
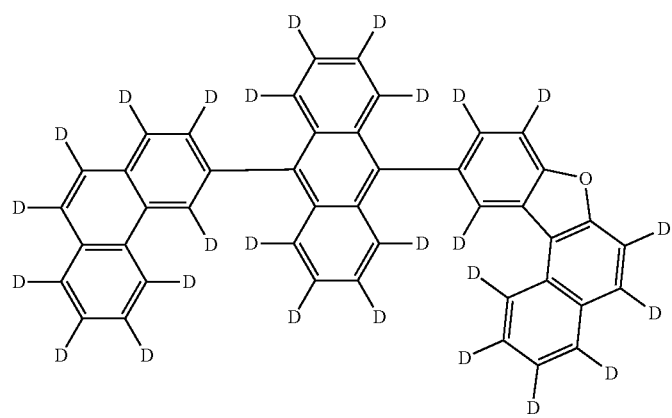
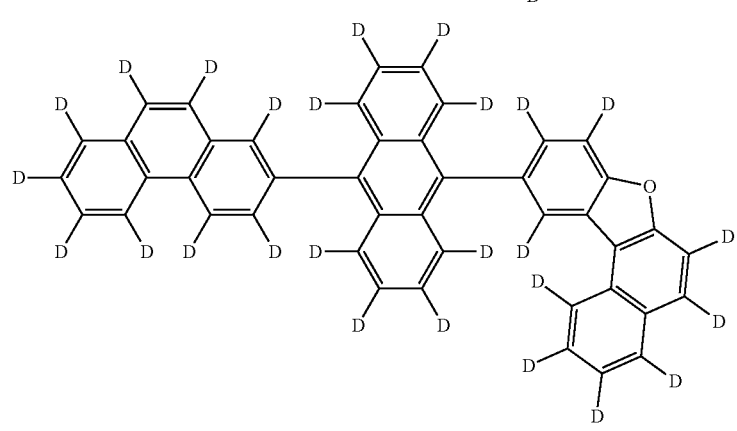

-continued
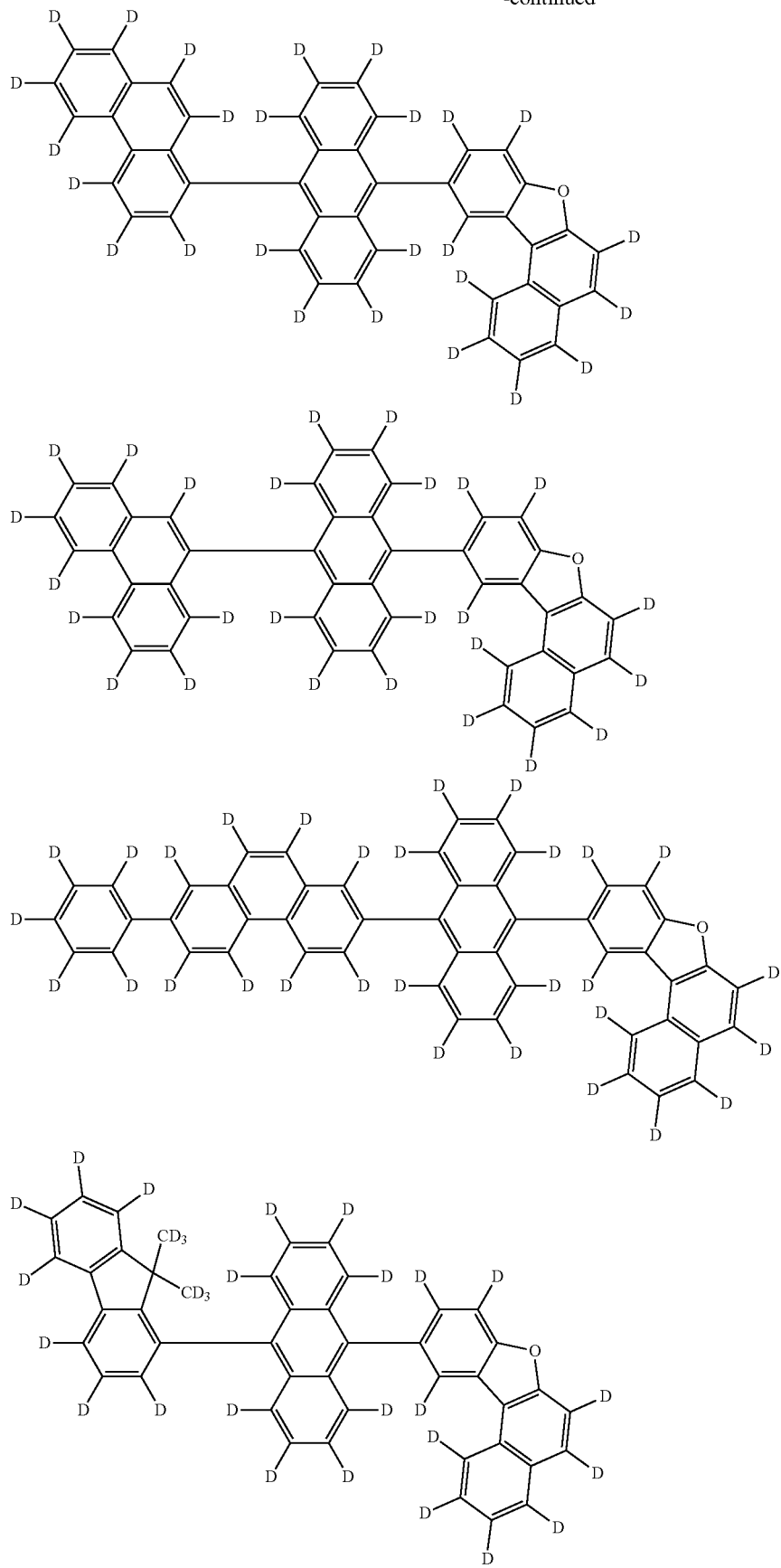

-continued
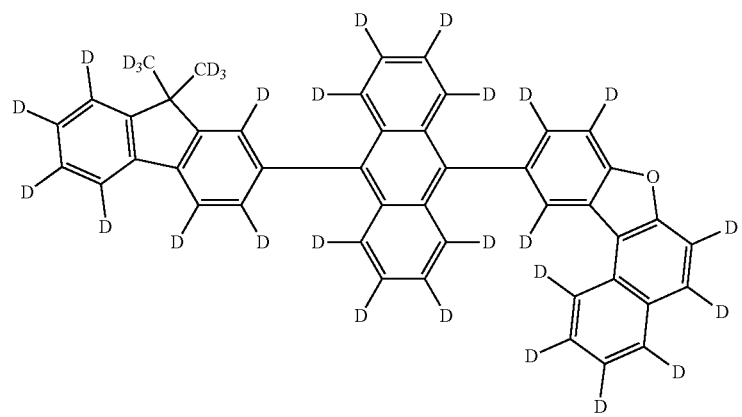
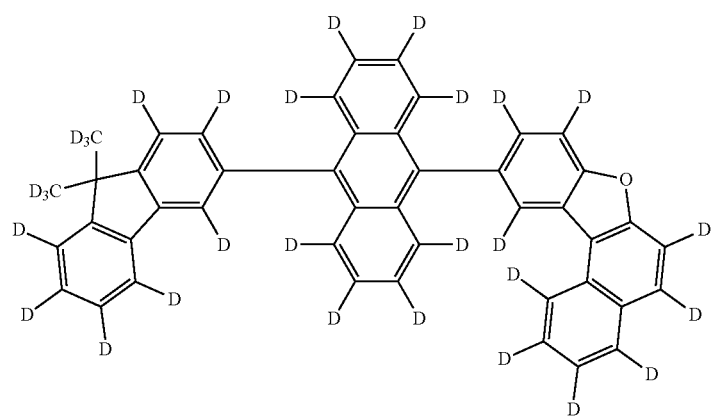
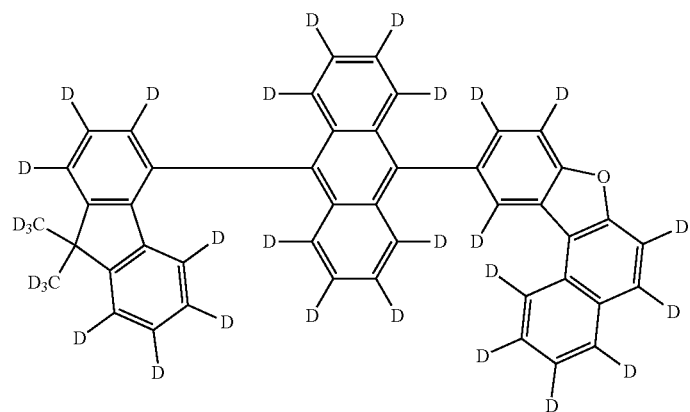
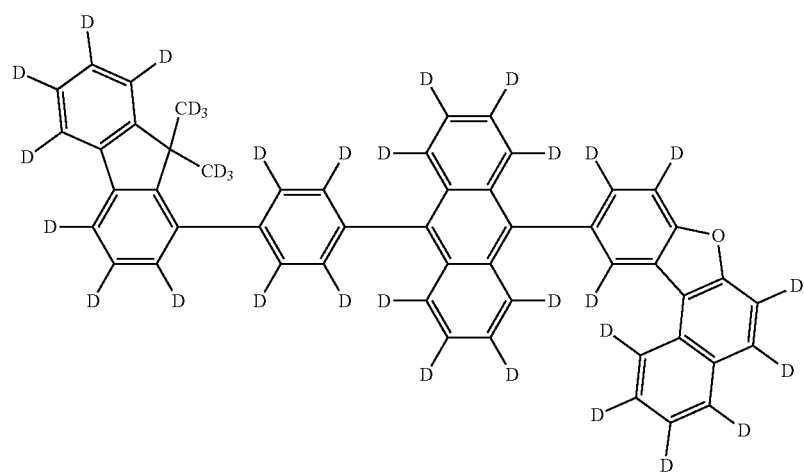

-continued
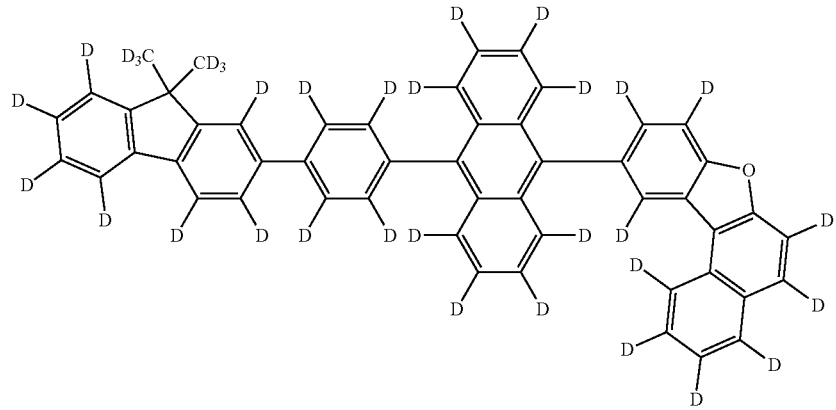
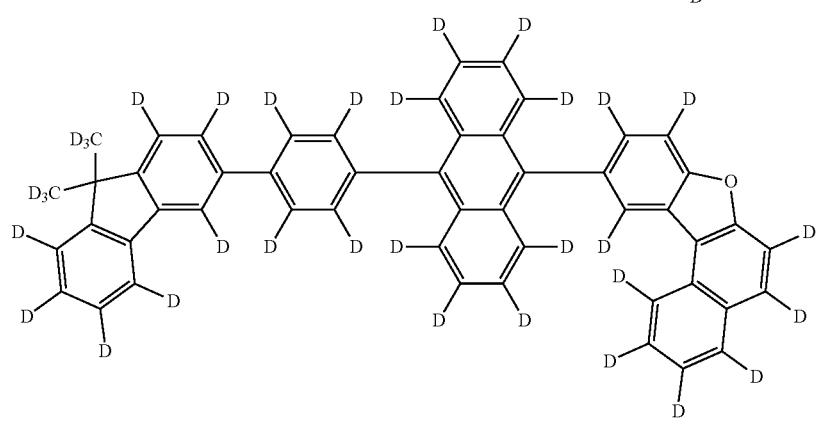
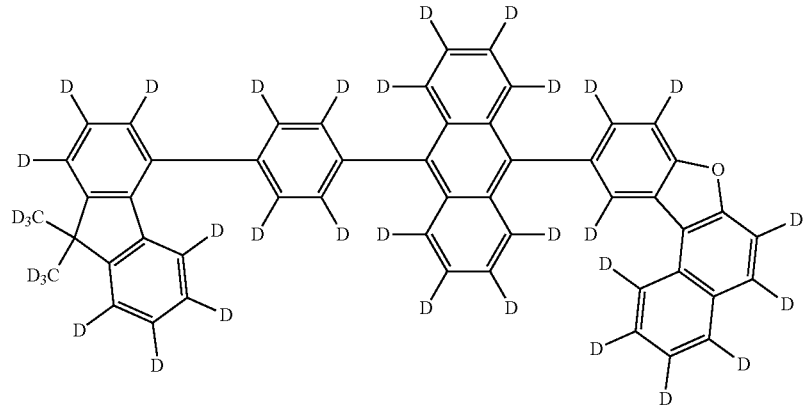
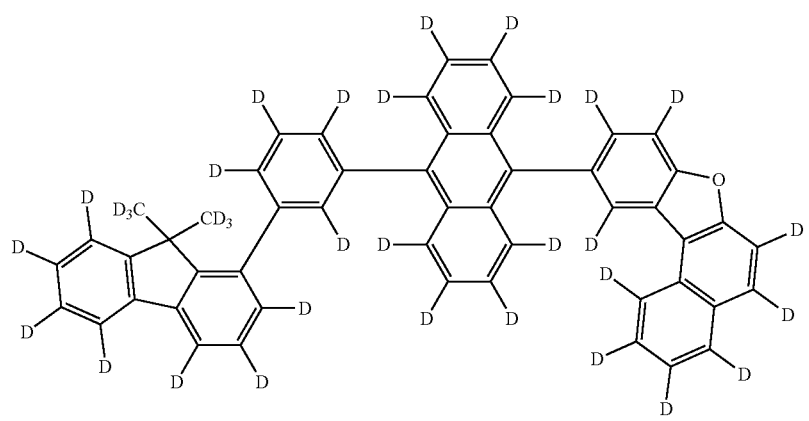

-continued
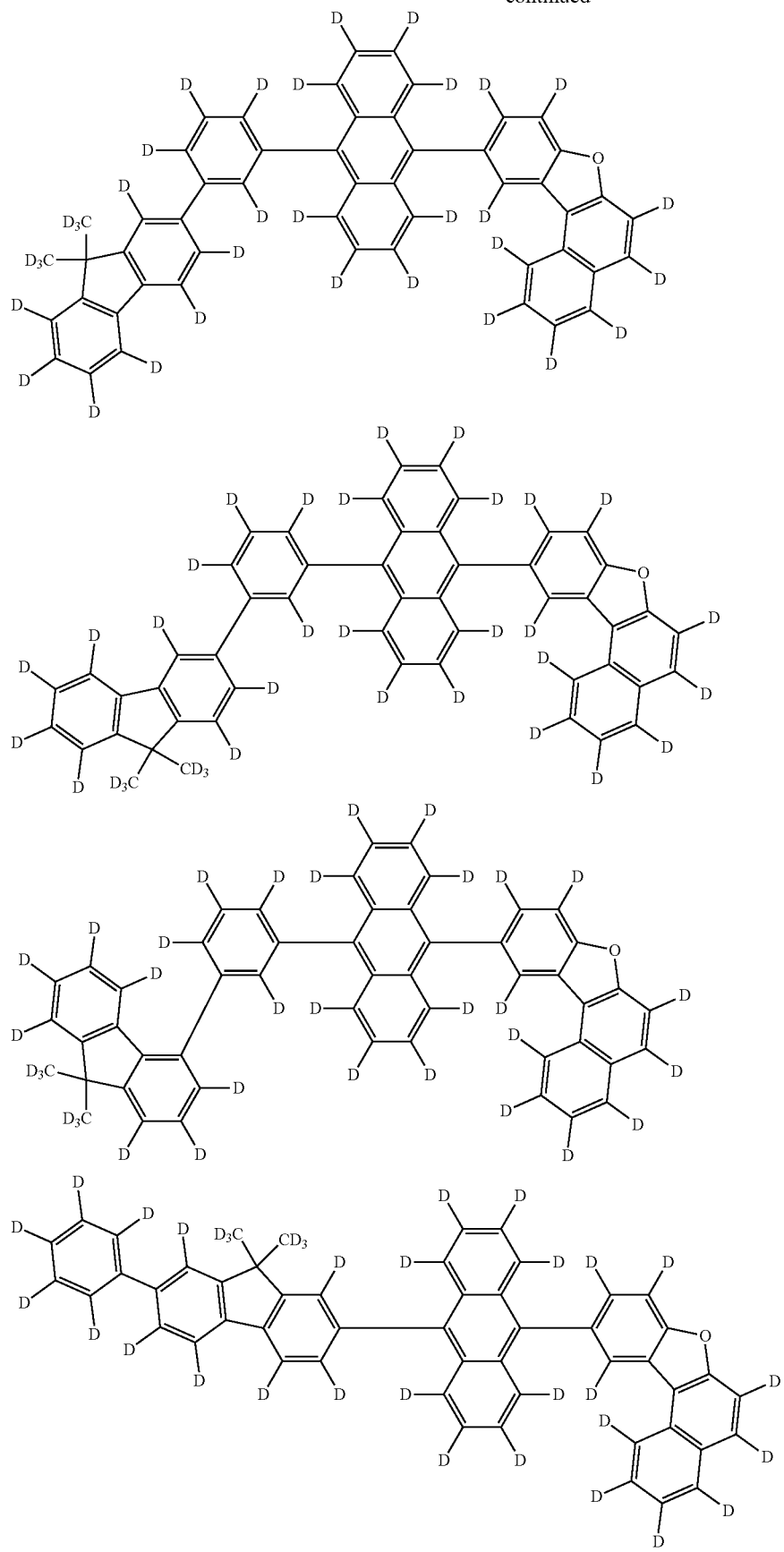

-continued
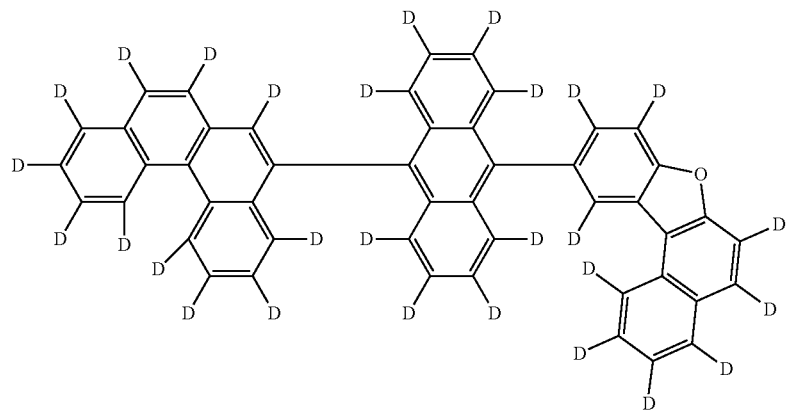
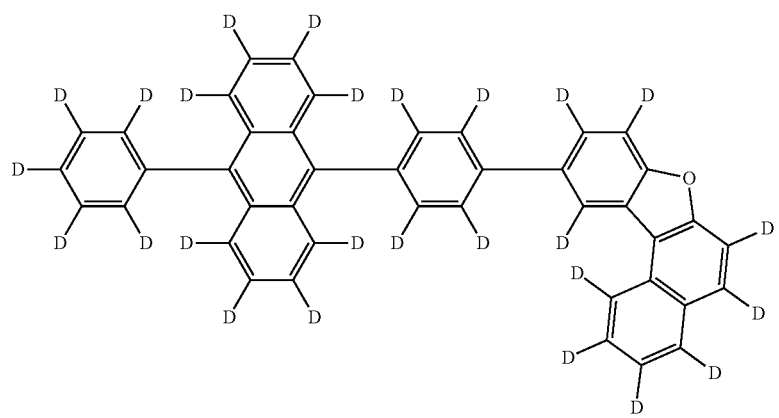
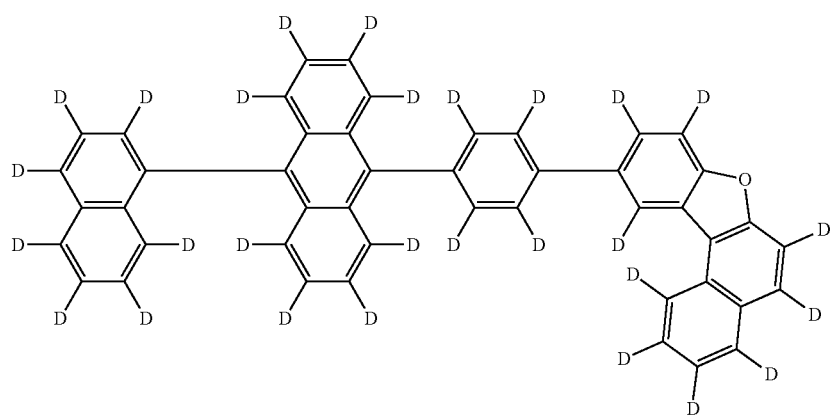
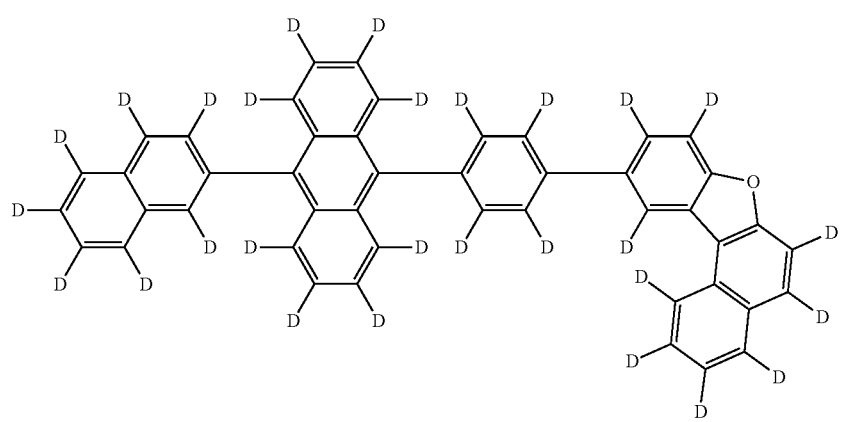

-continued
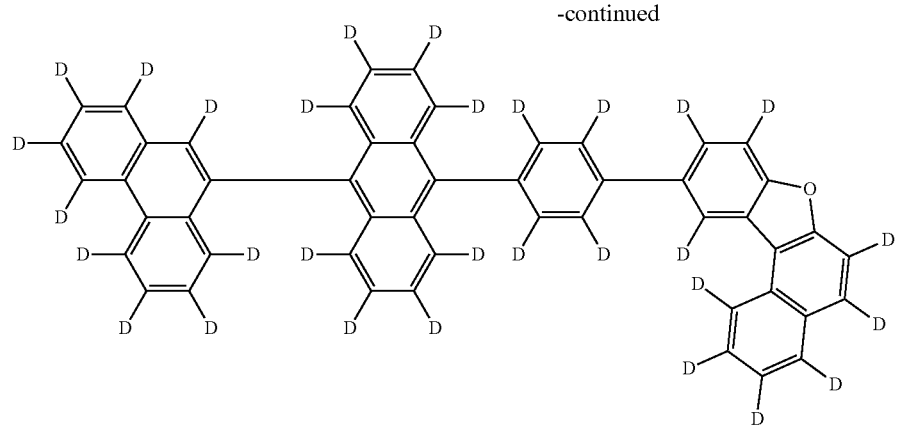
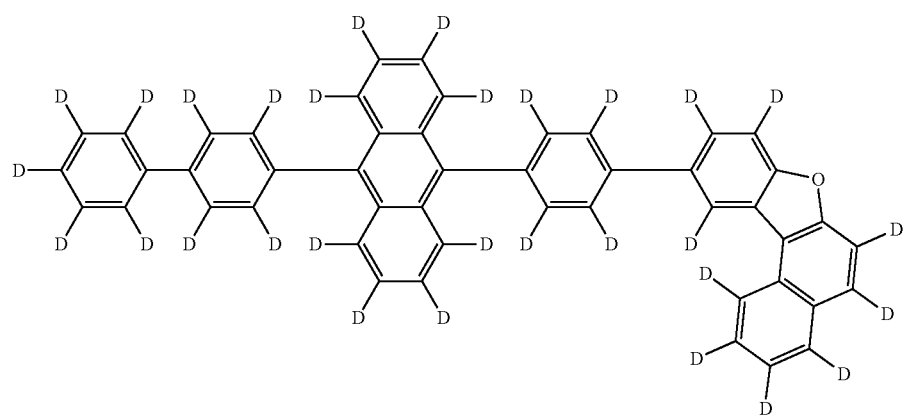
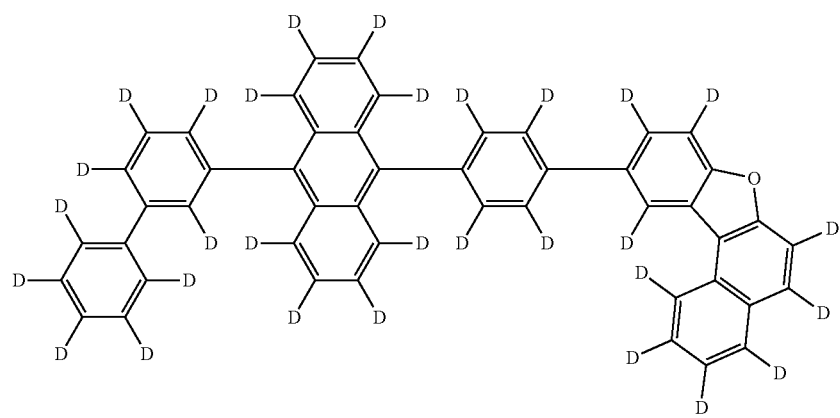
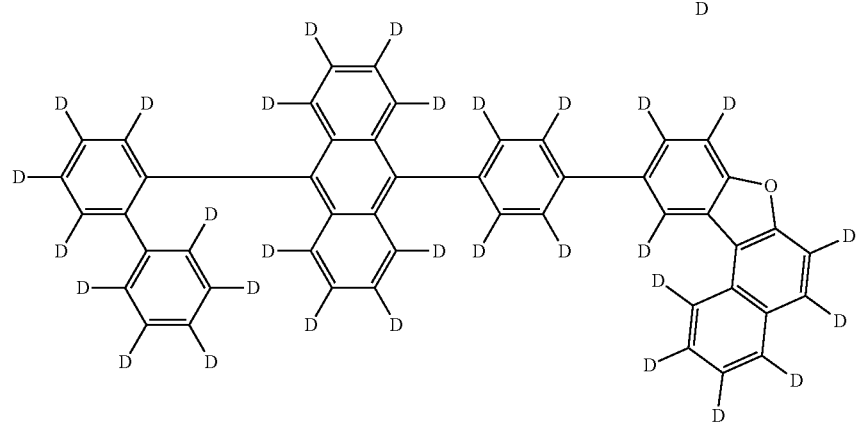

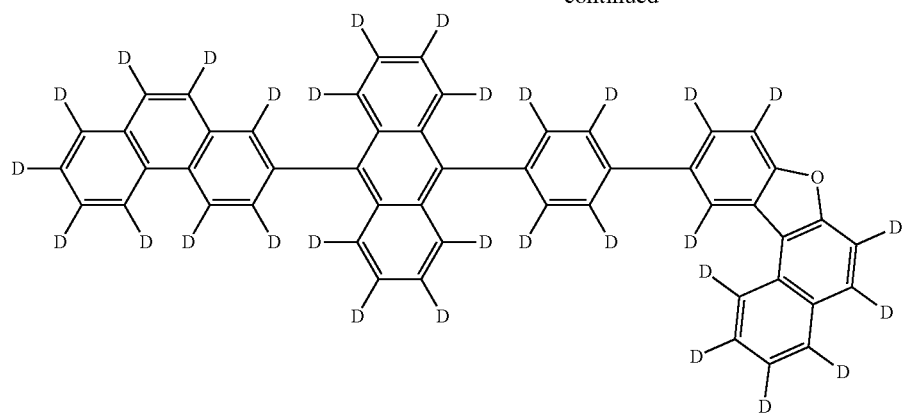
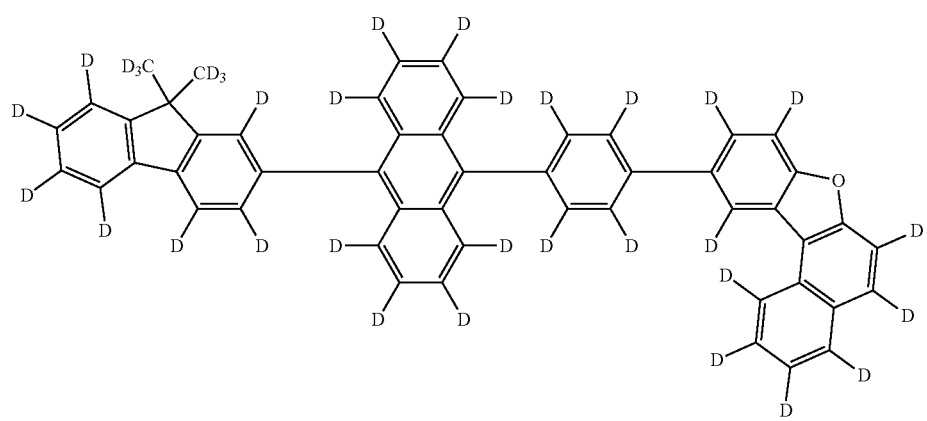
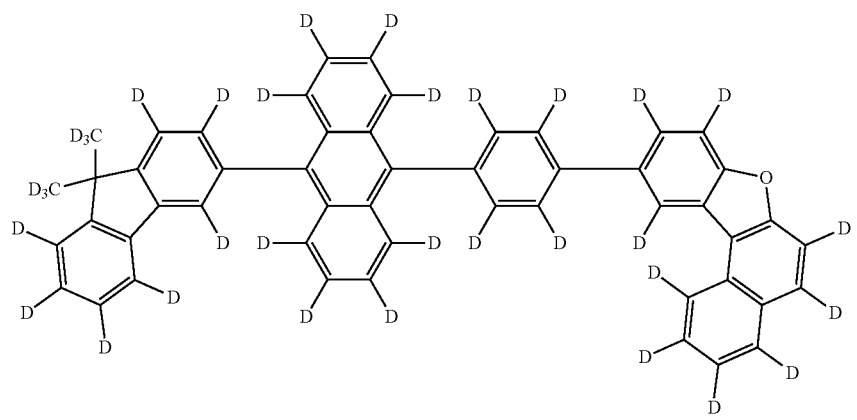
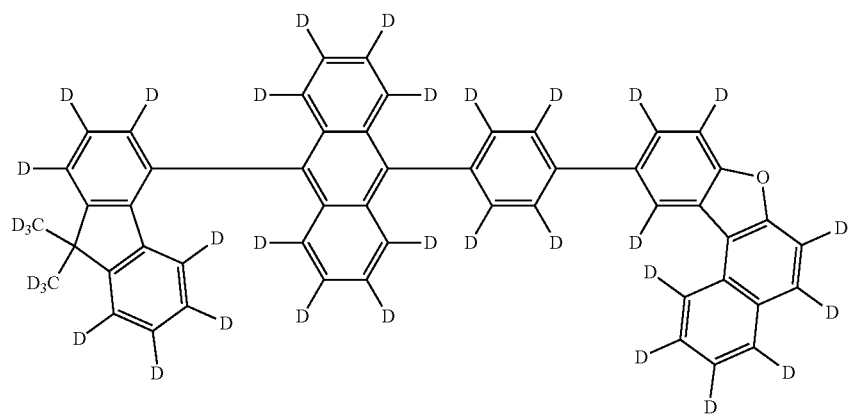

207
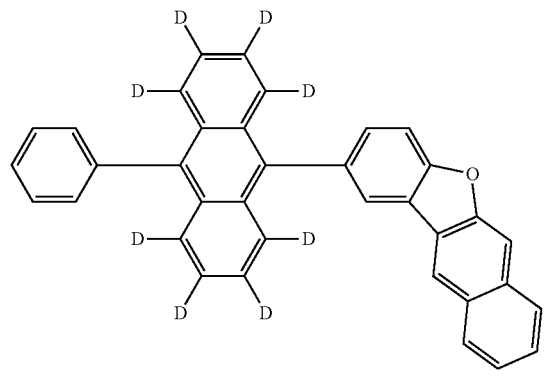
208
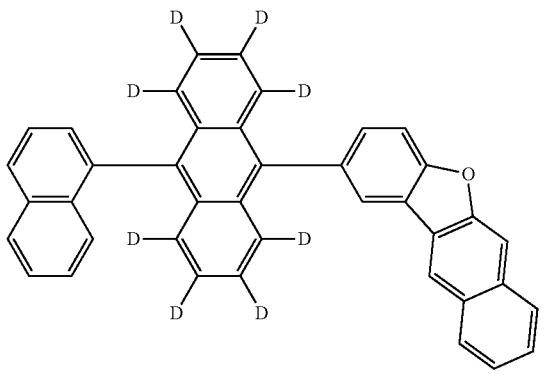
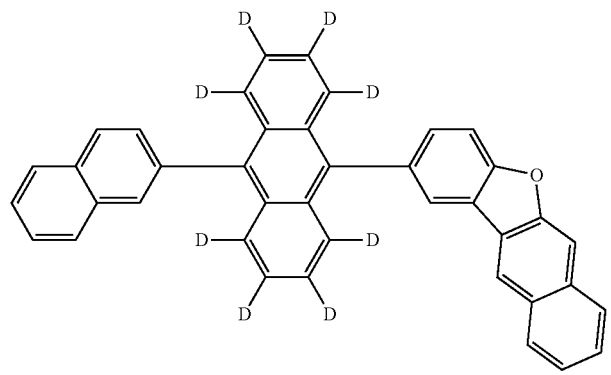
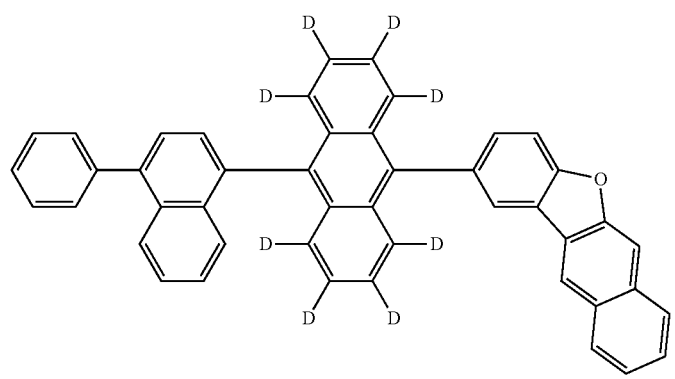
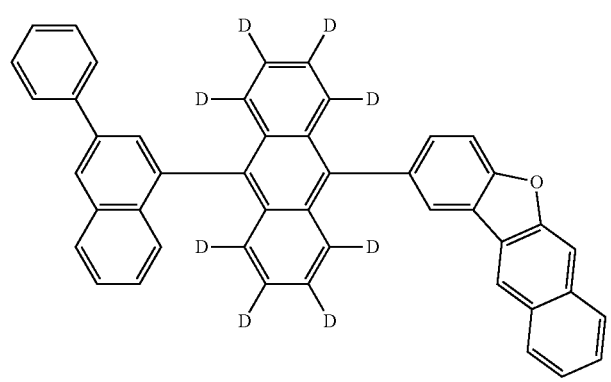

-continued
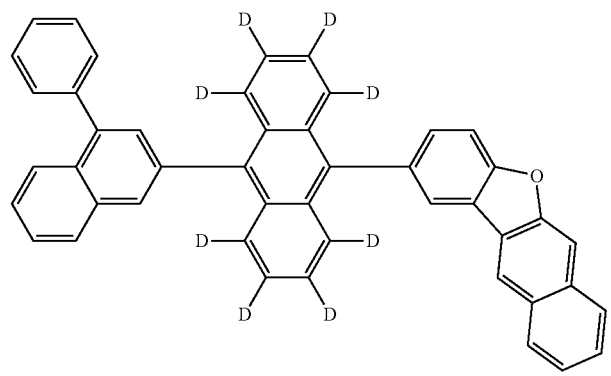
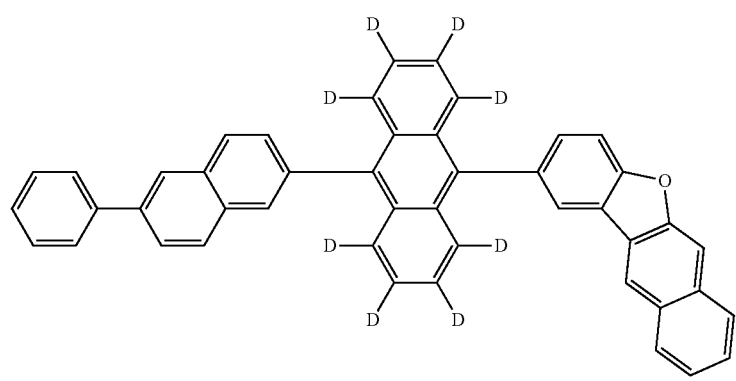
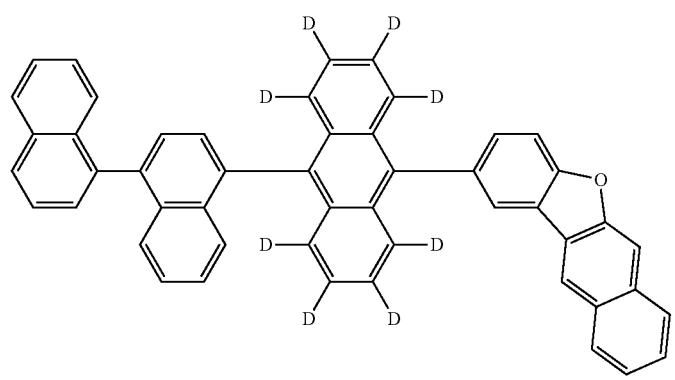
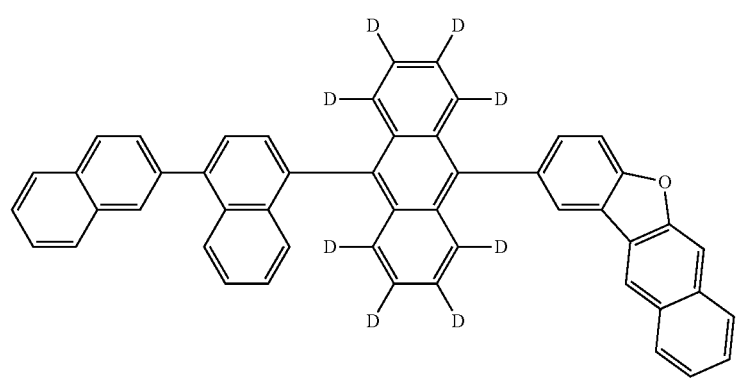

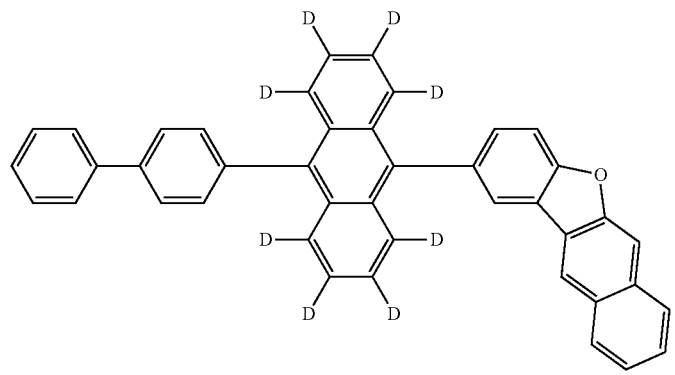
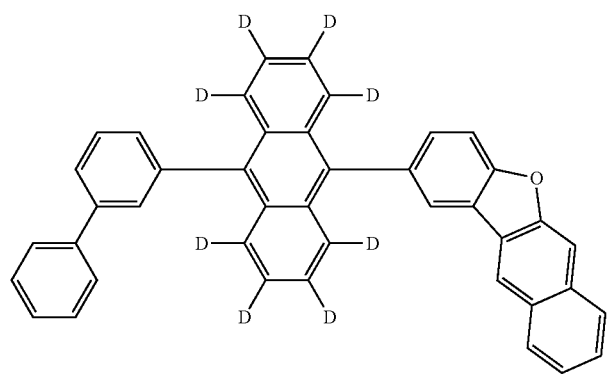
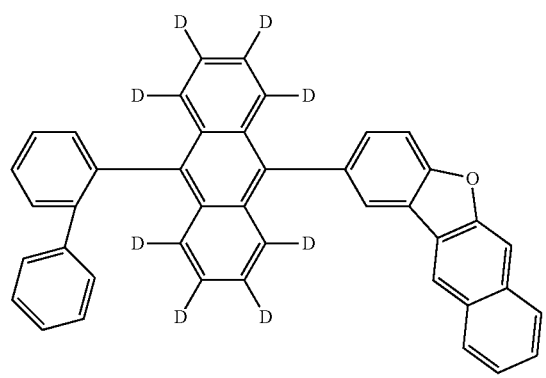
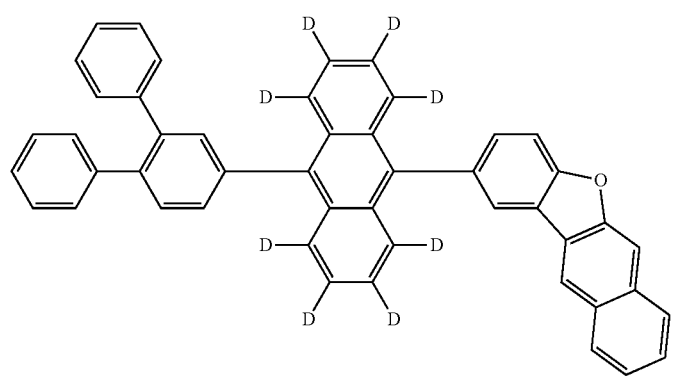

-continued
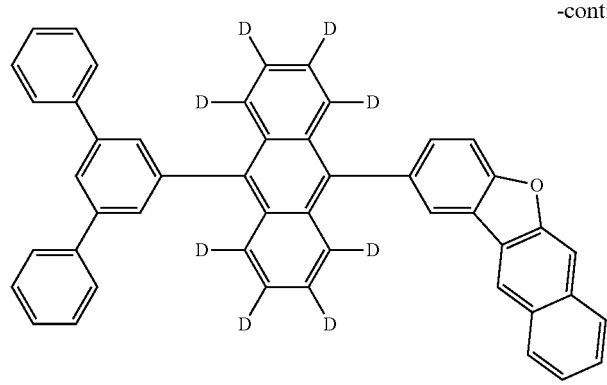
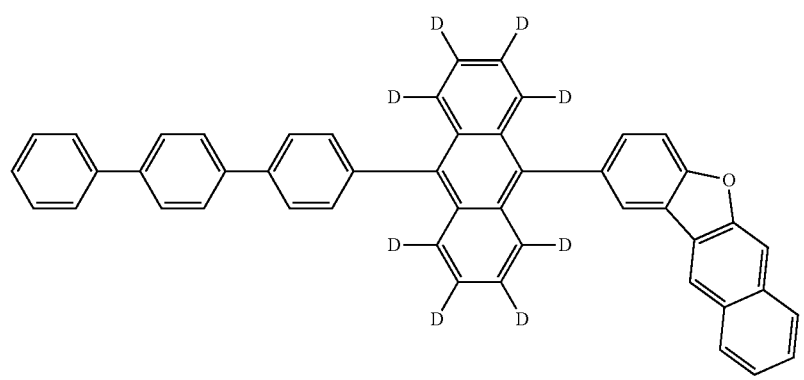
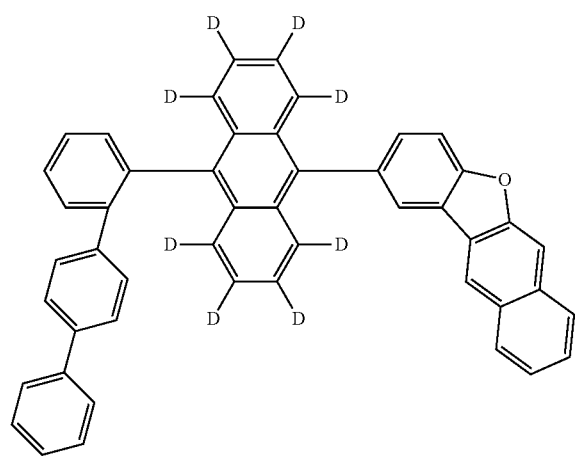
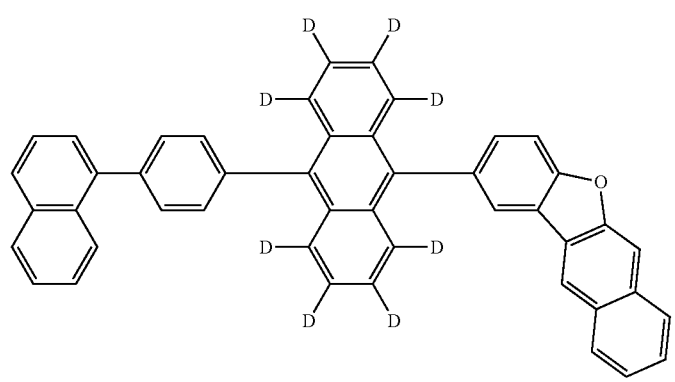

-continued
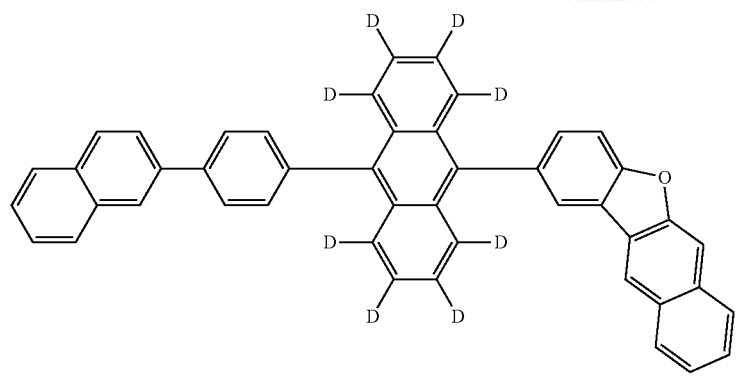
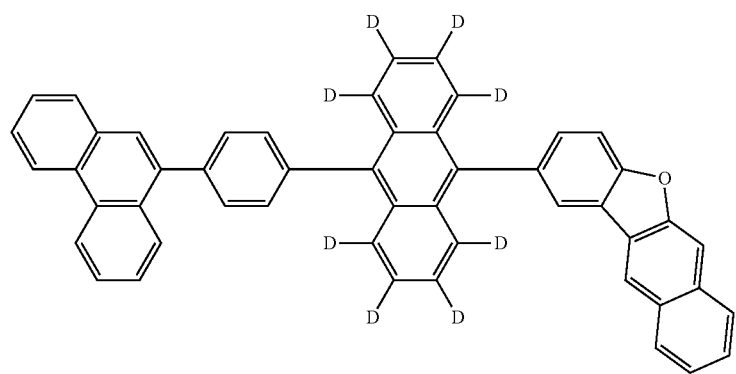
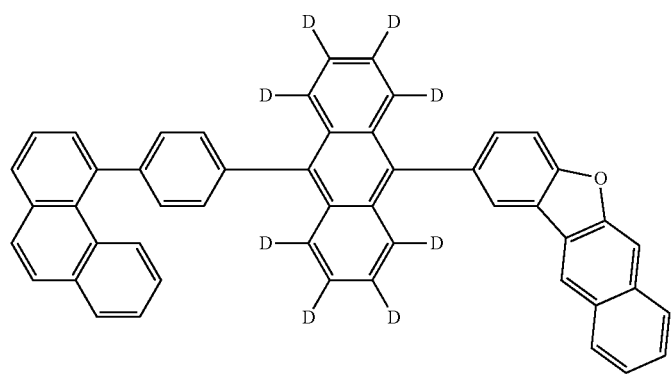
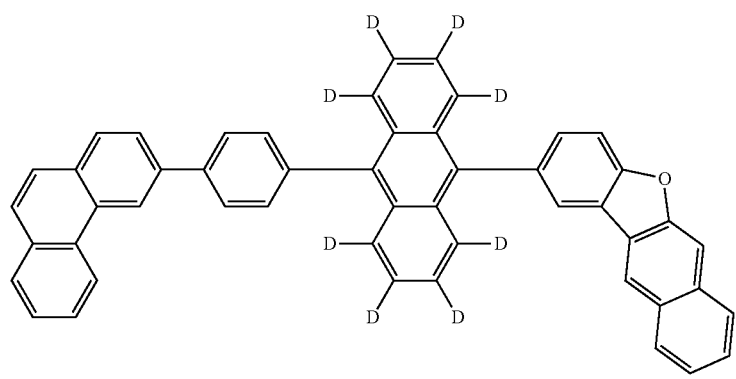

-continued
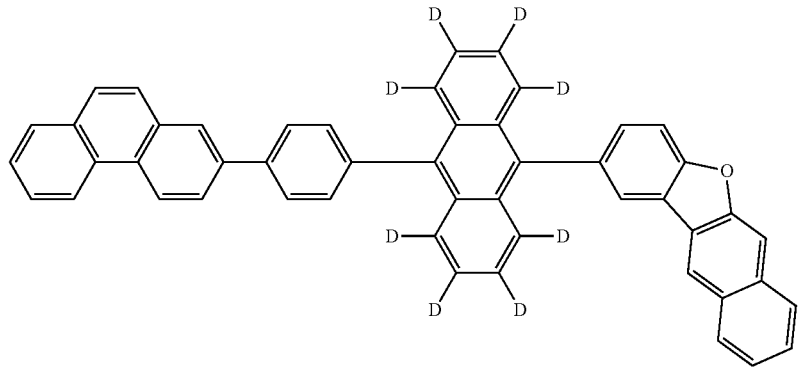
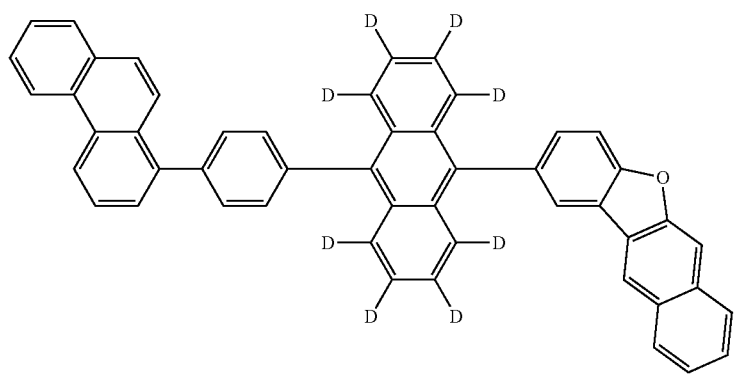
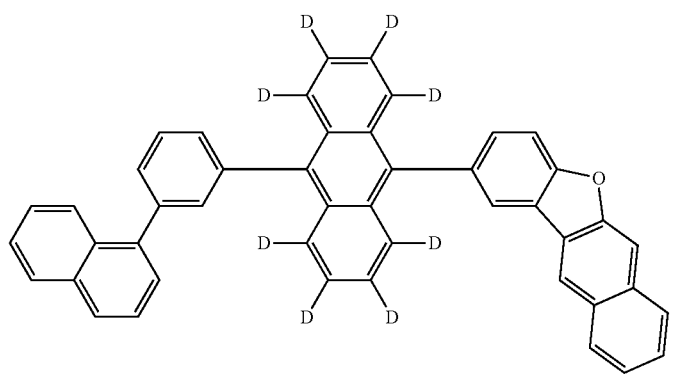
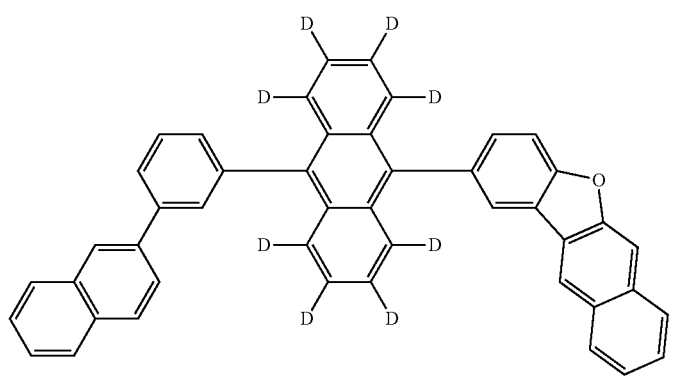

-continued
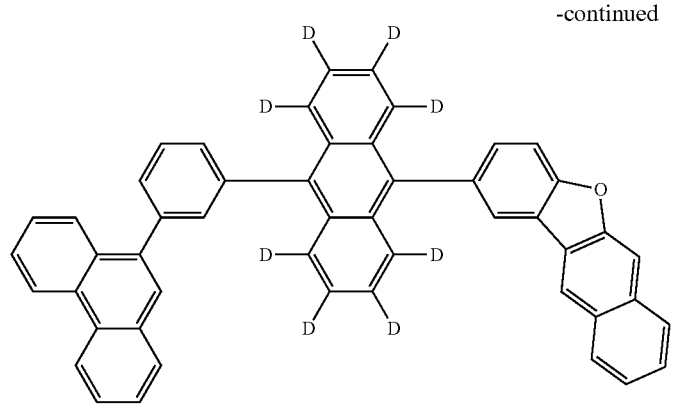
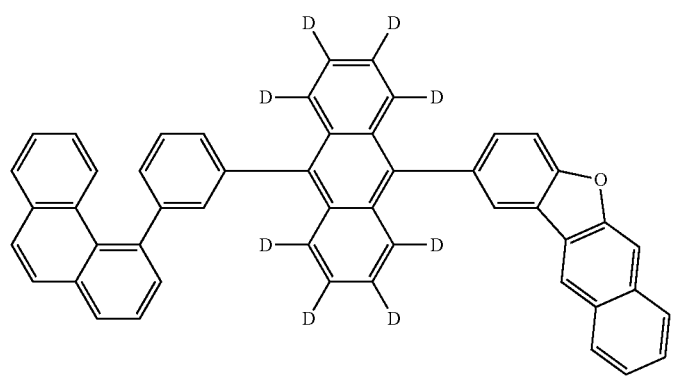
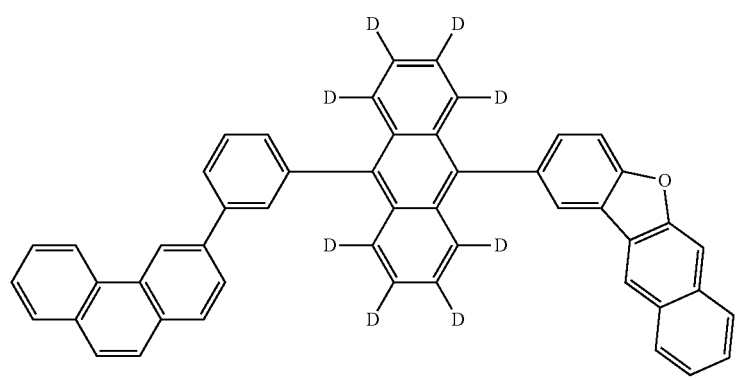
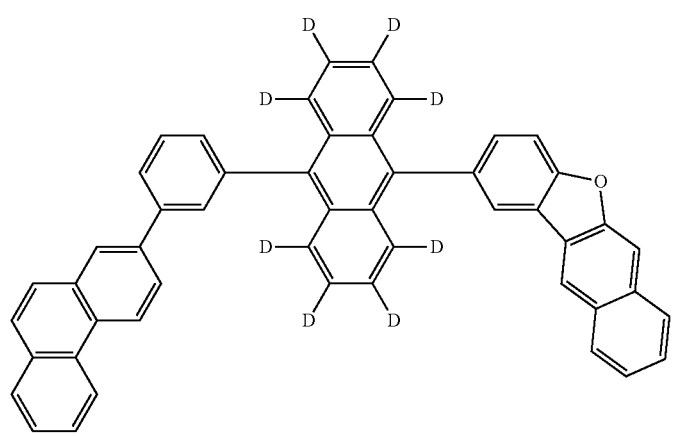

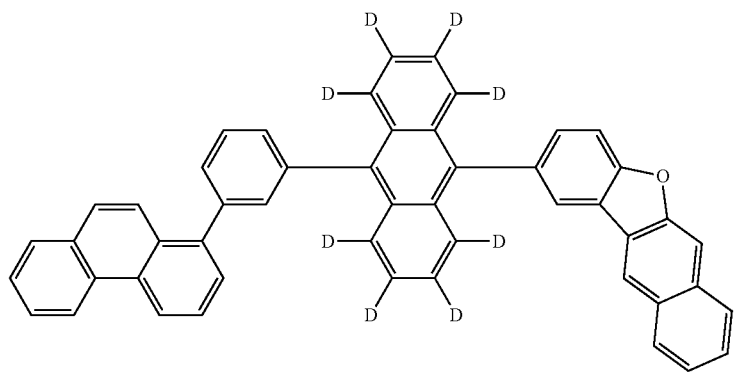
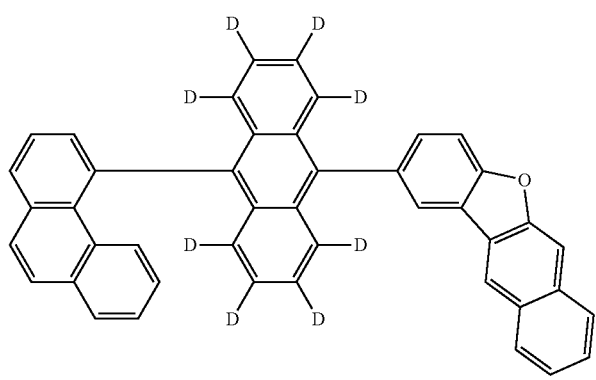
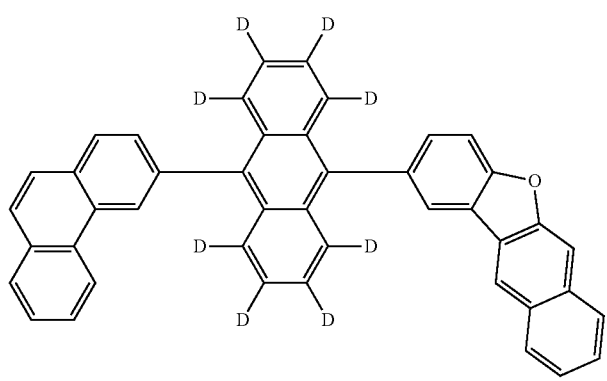
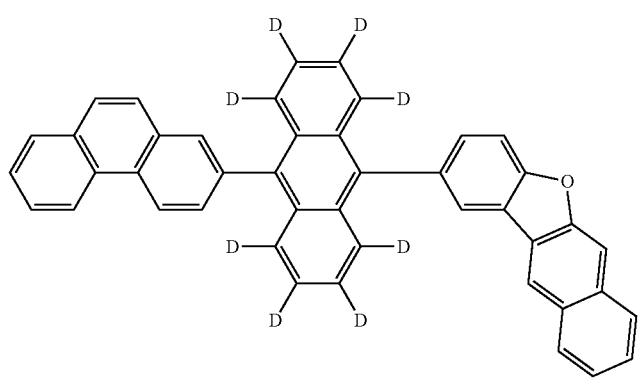

223
-continued
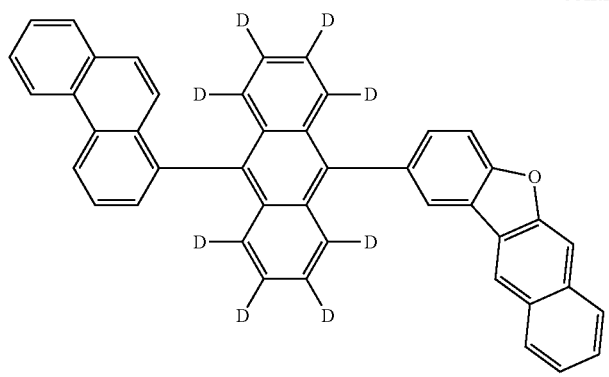
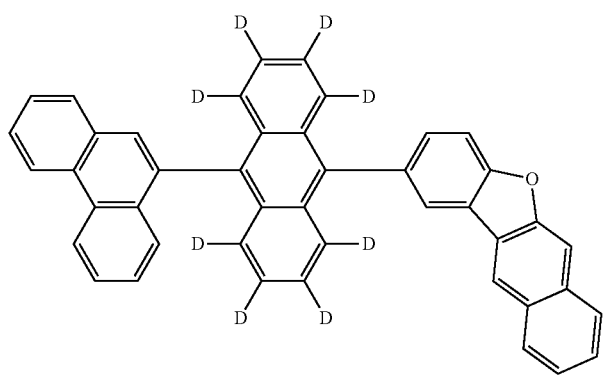
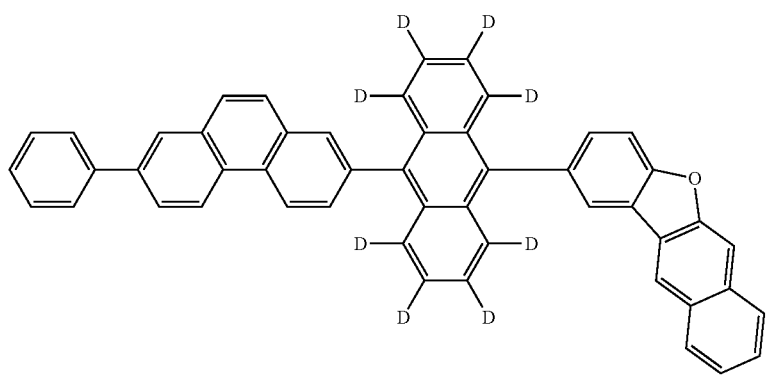
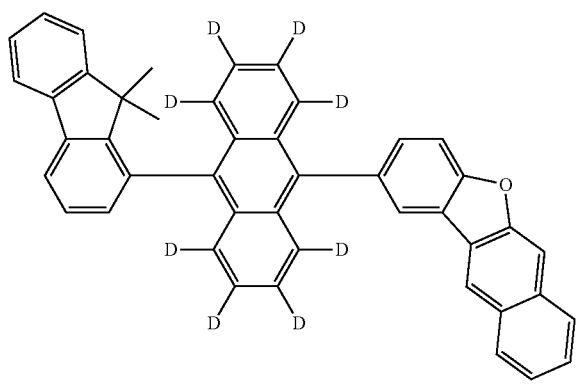
224

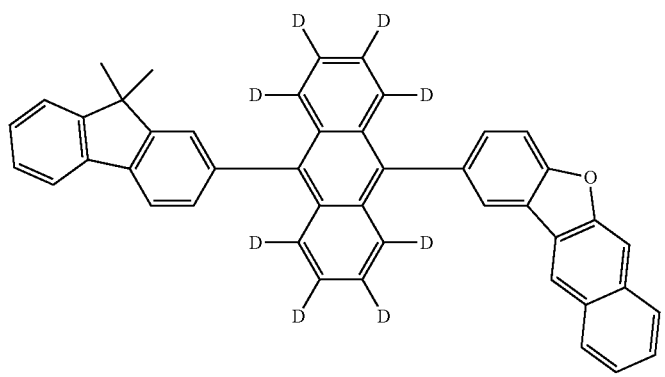
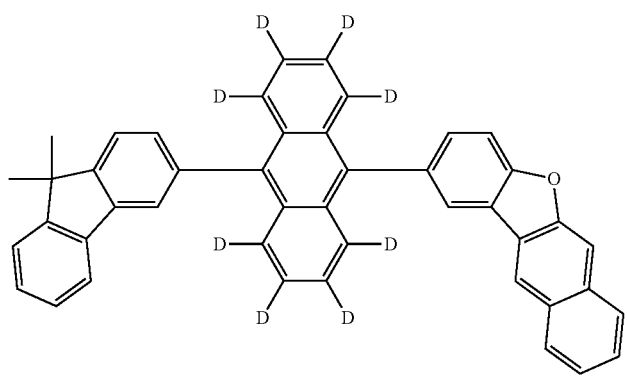
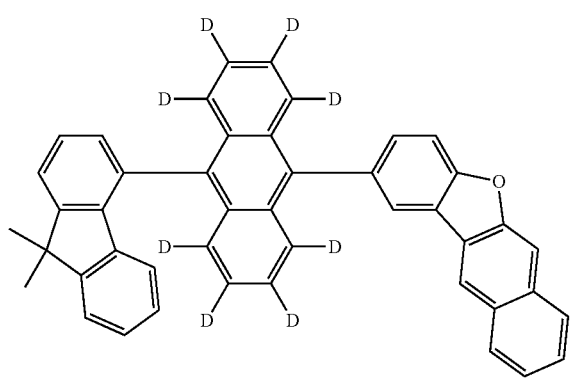
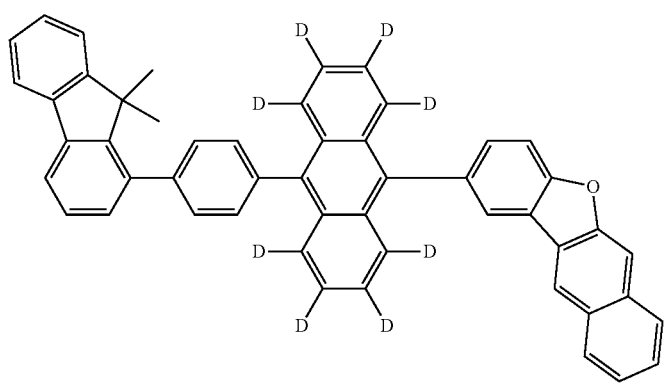

-continued
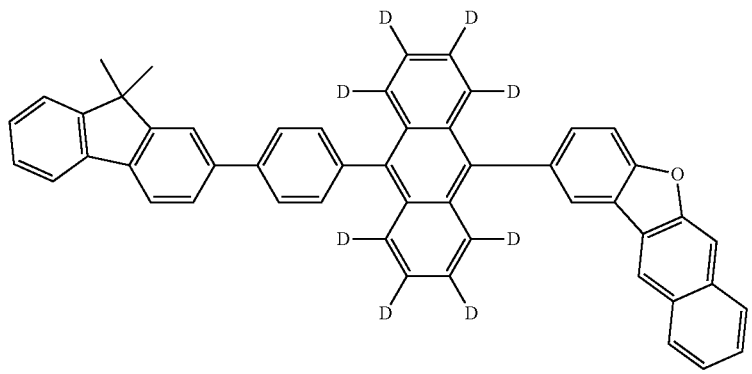
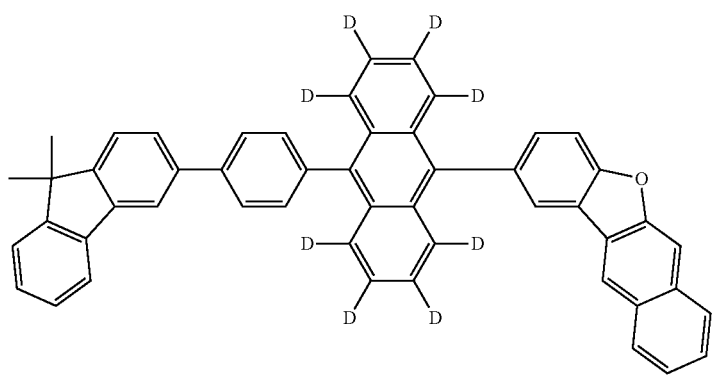
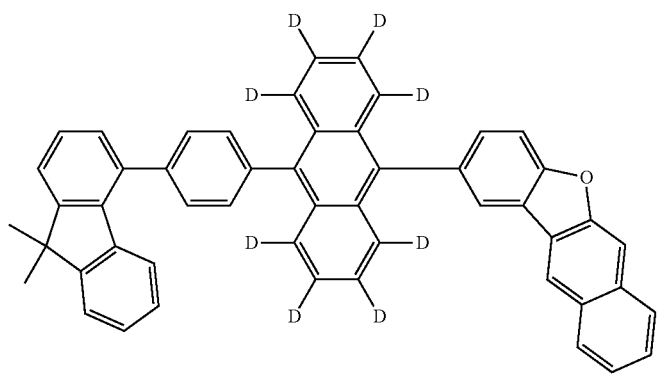
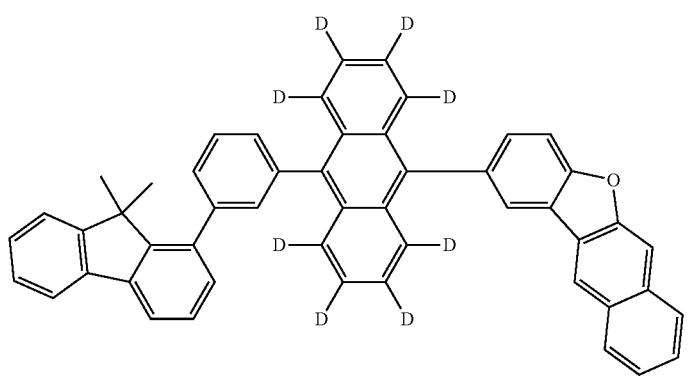

-continued
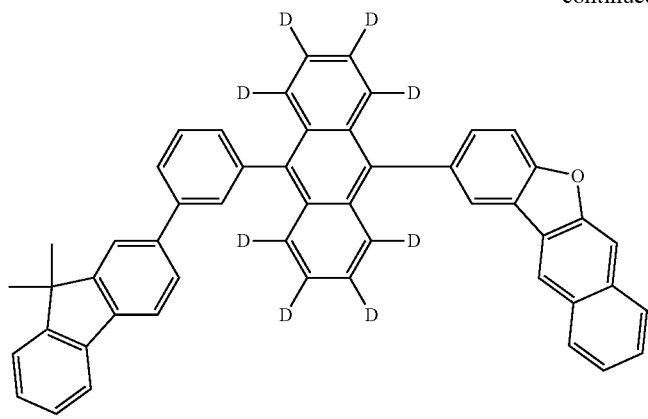
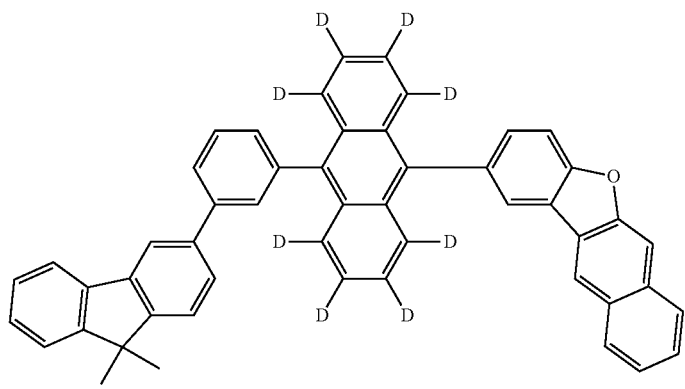
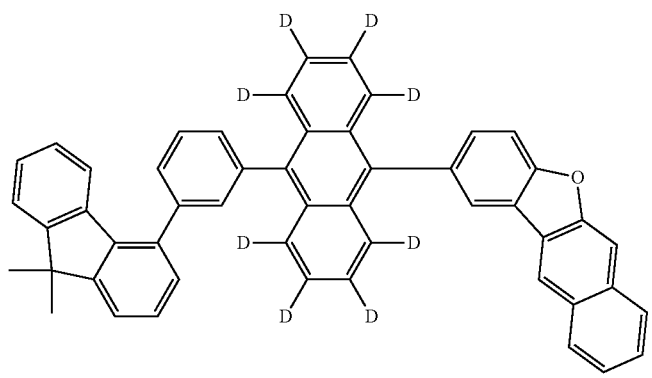
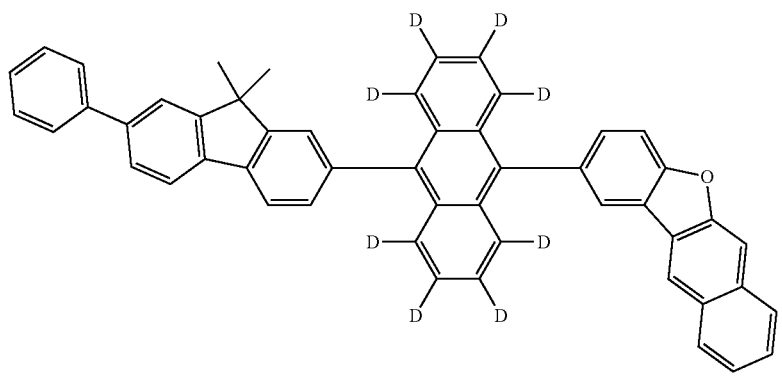

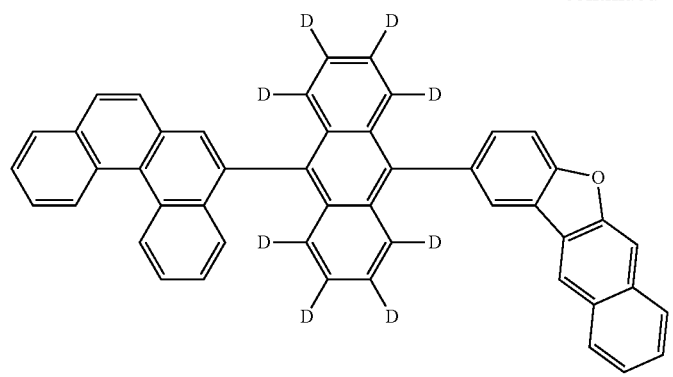

-continued
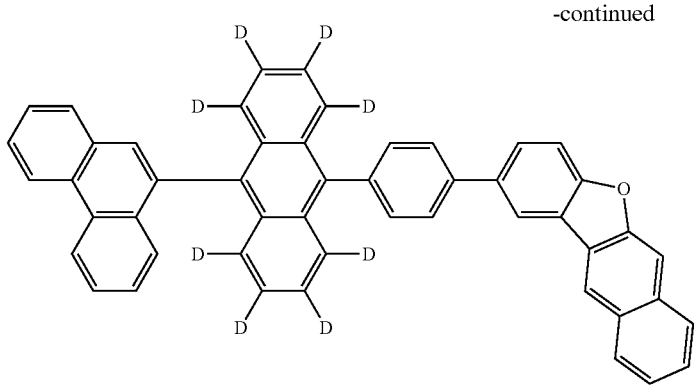
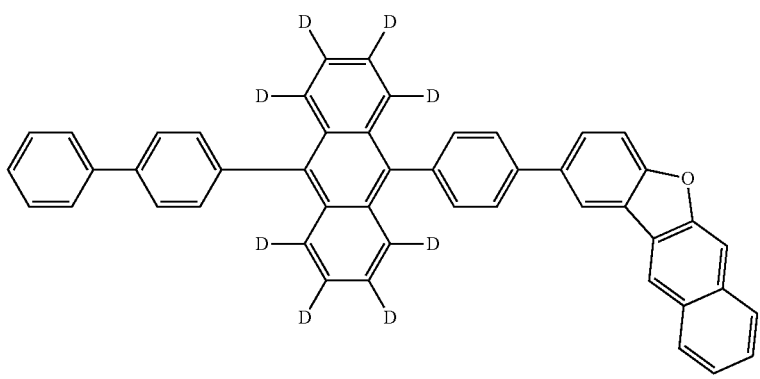
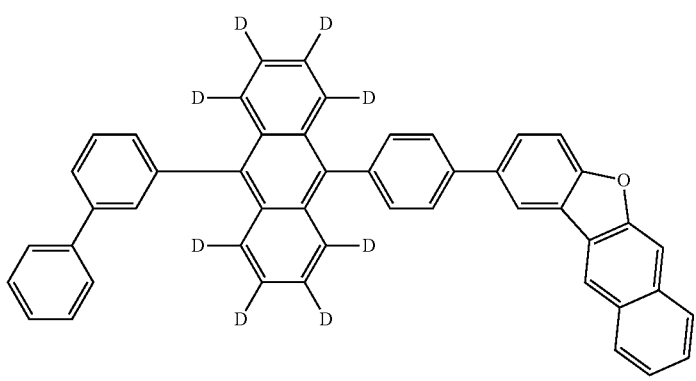
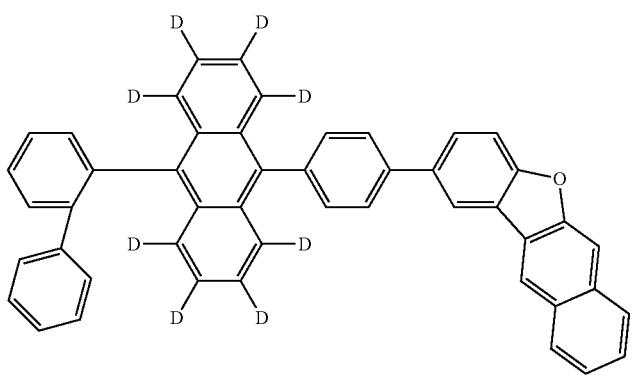

-continued
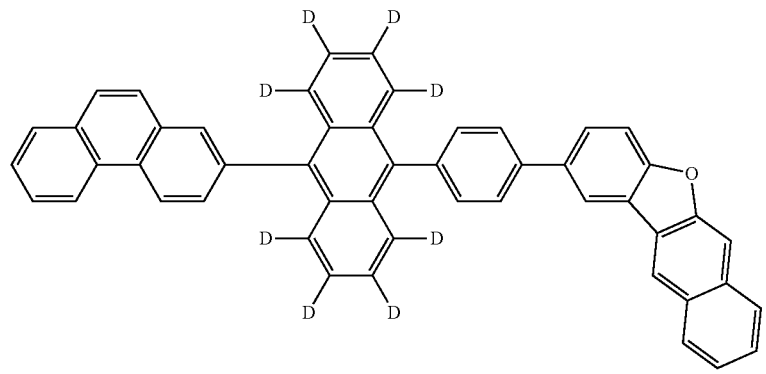
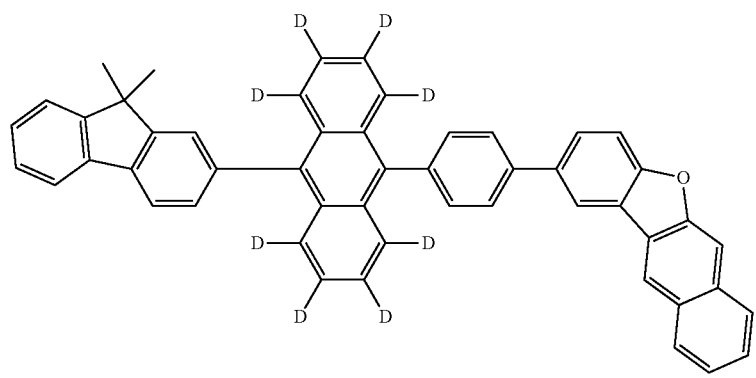
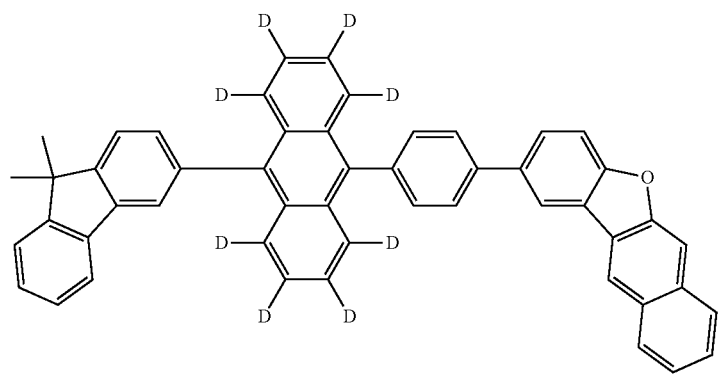
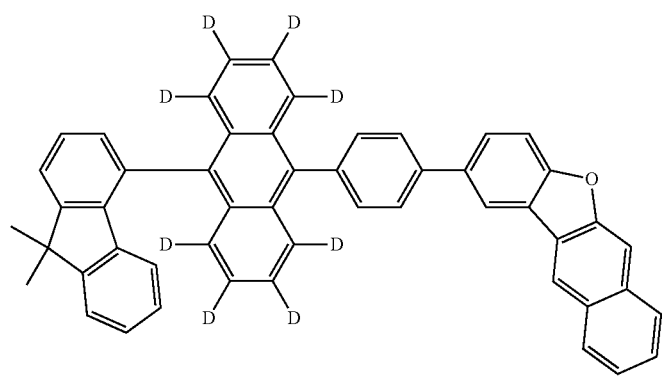

-continued
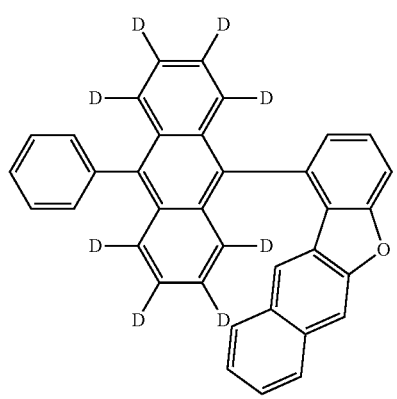
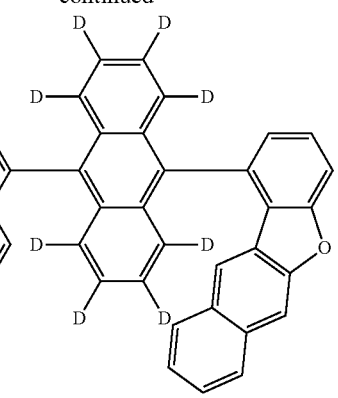
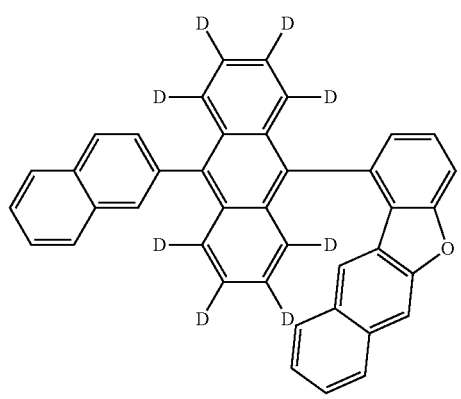
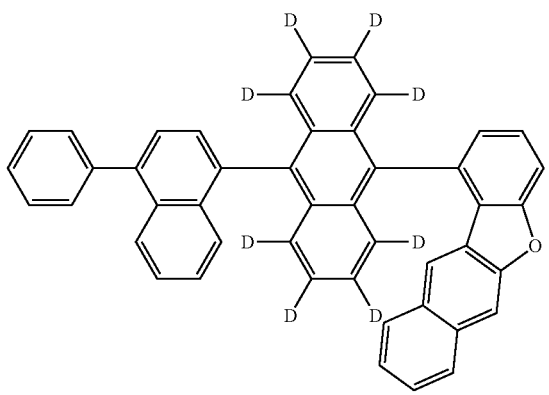
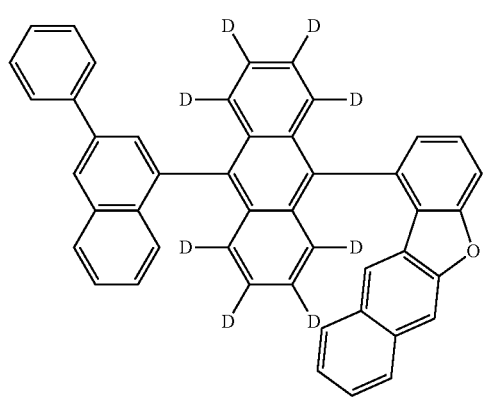
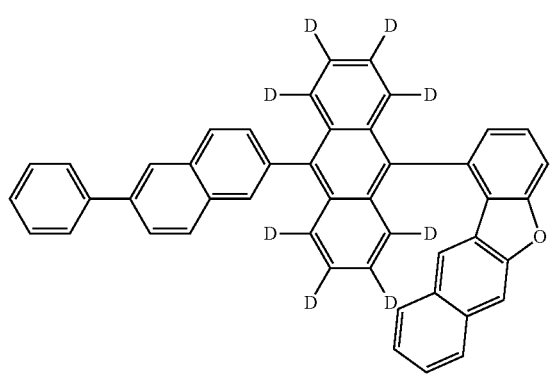

-continued
| 239 | 240 |
|---|---|
| 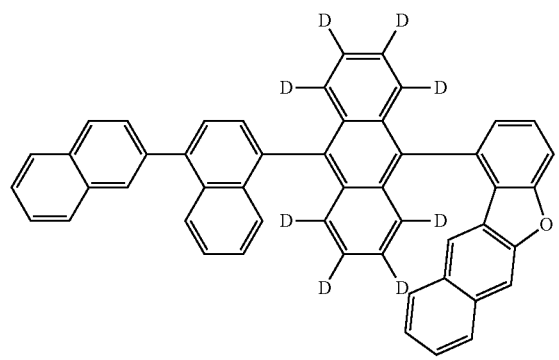 | 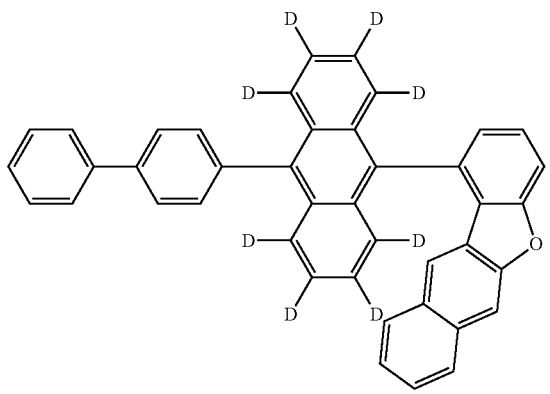 |
| 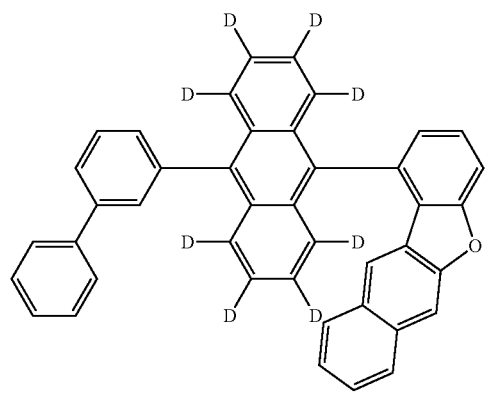 | 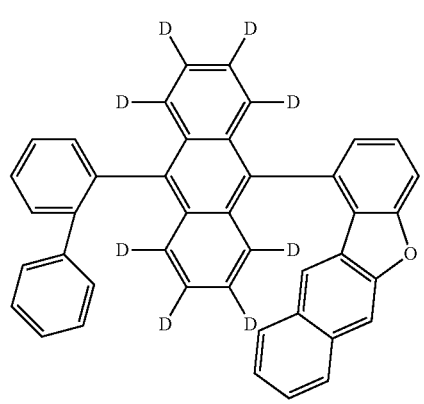 |
| 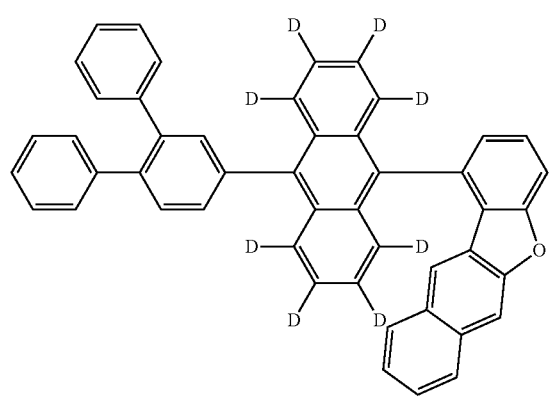 | 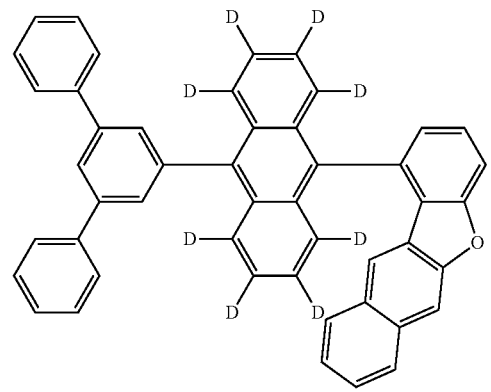 |
| 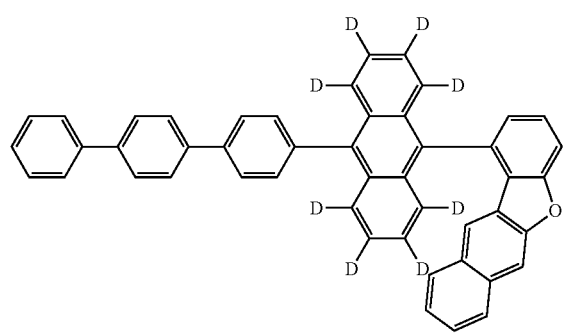 | 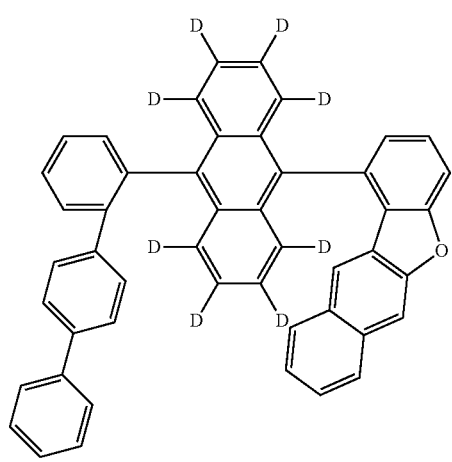 |

241 242
-continued
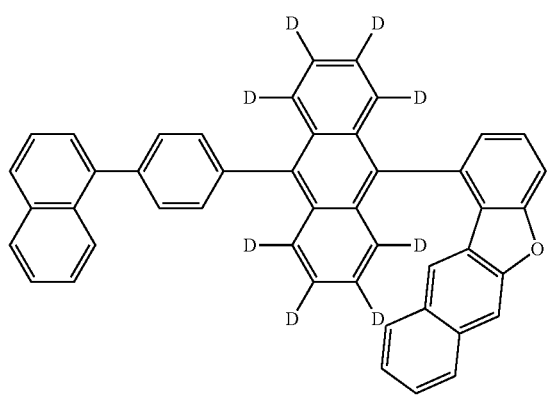
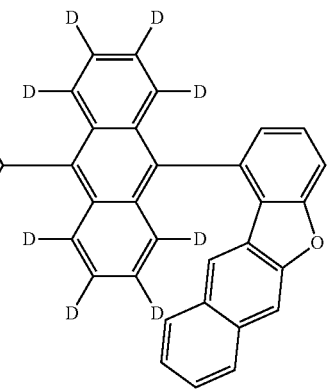
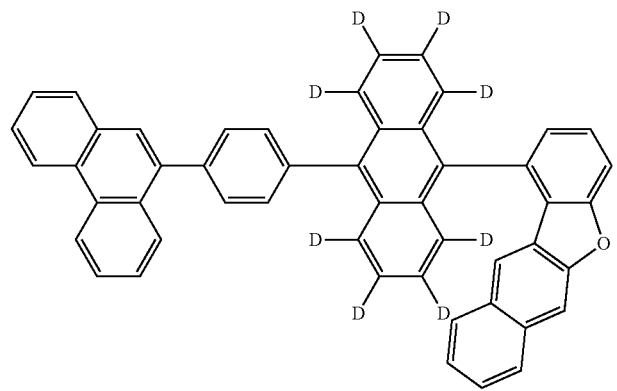
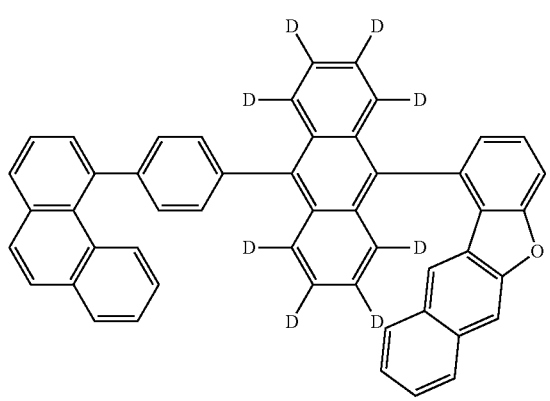
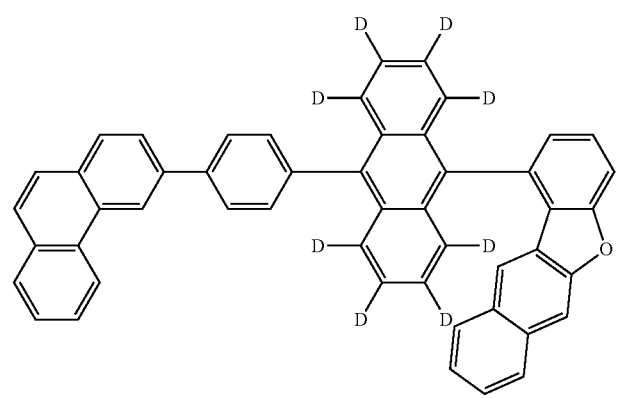
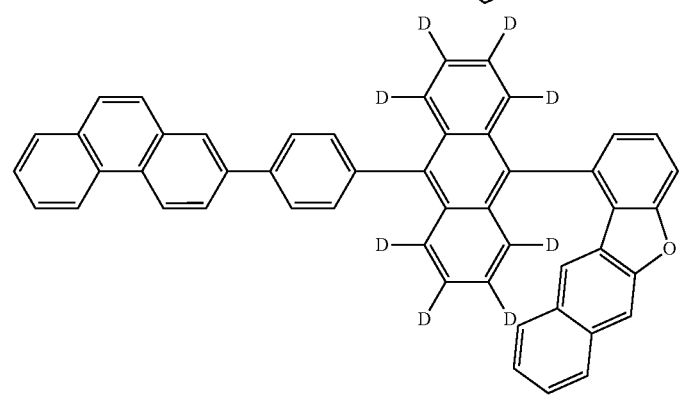

-continued
243 244
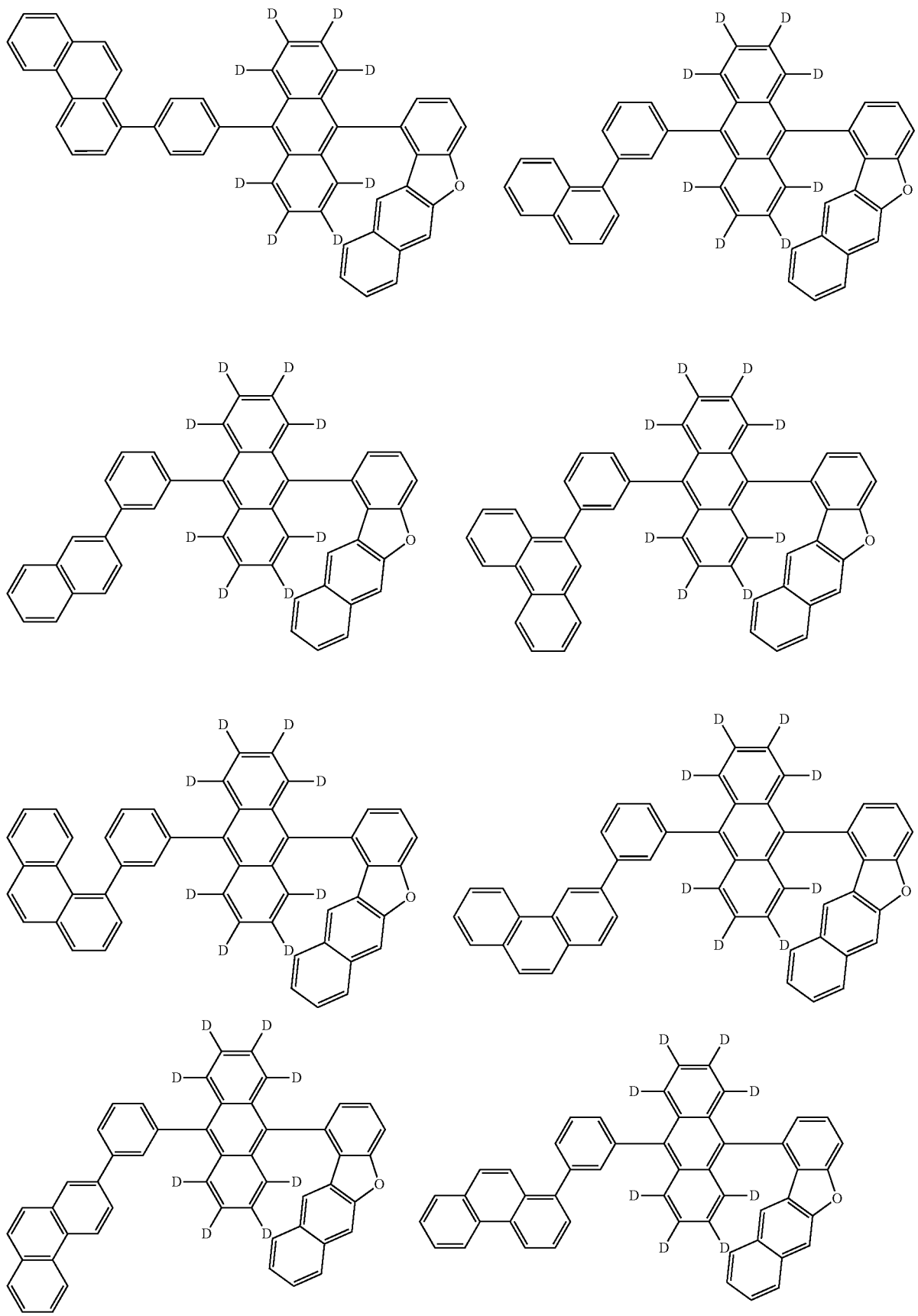

245
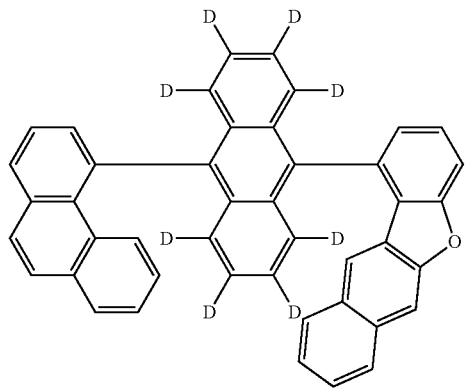
246
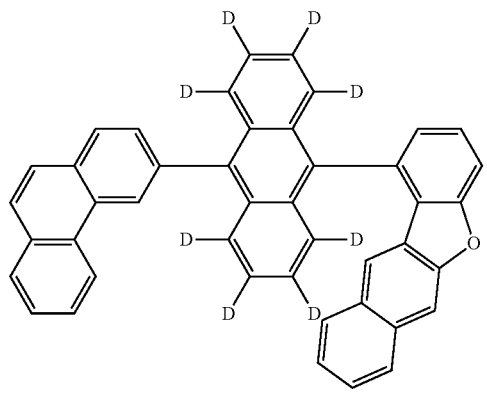
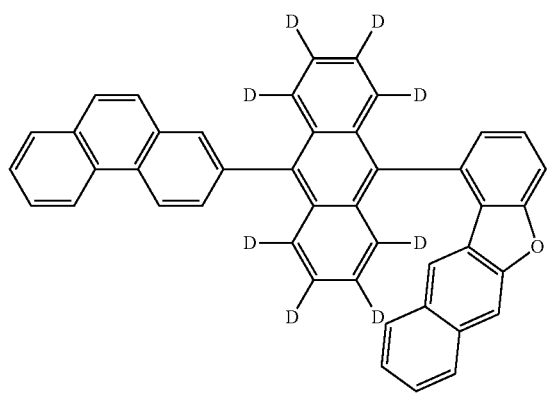
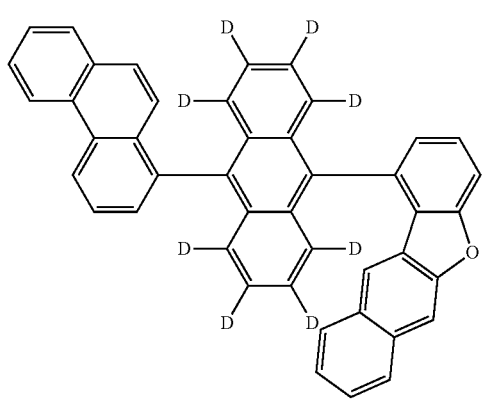
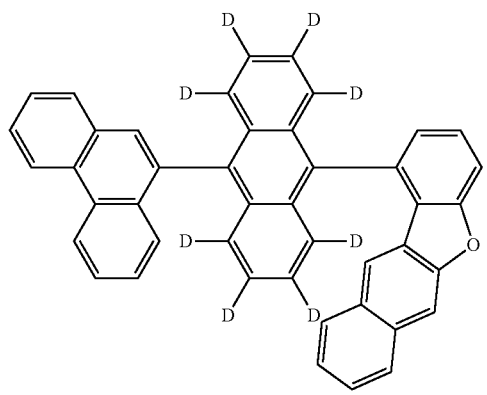
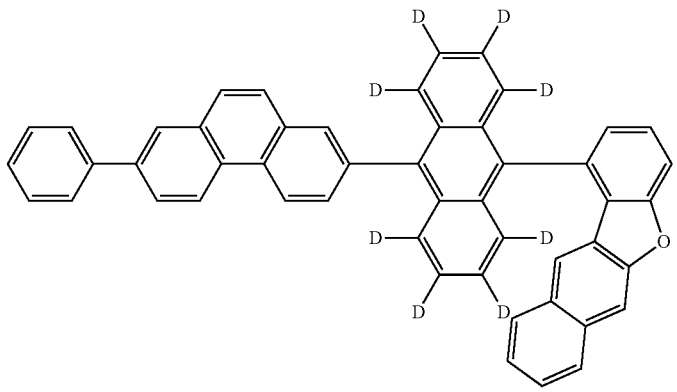
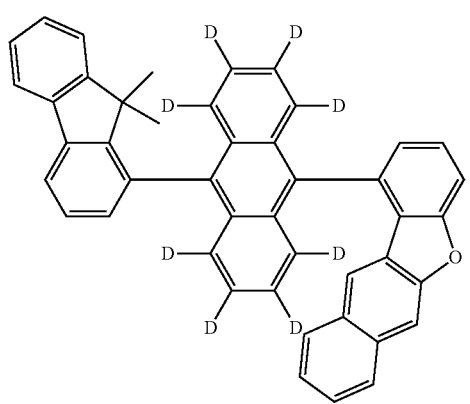
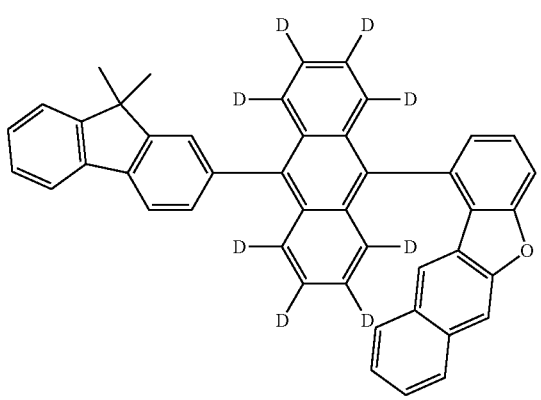

247
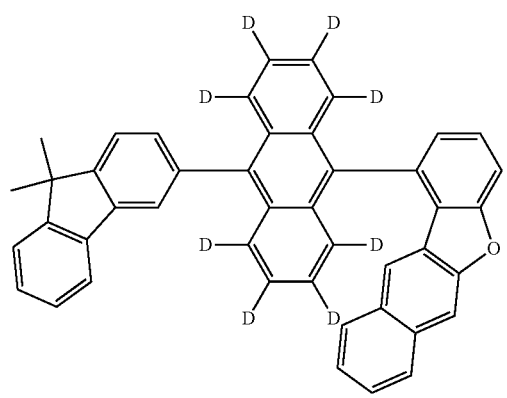
248
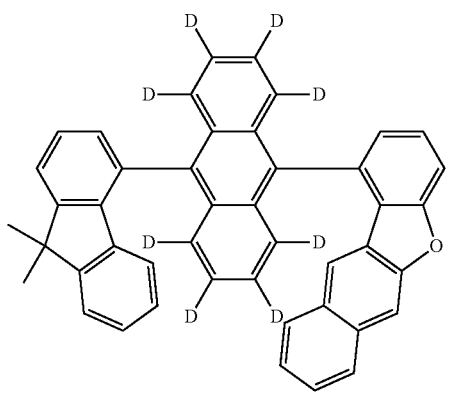
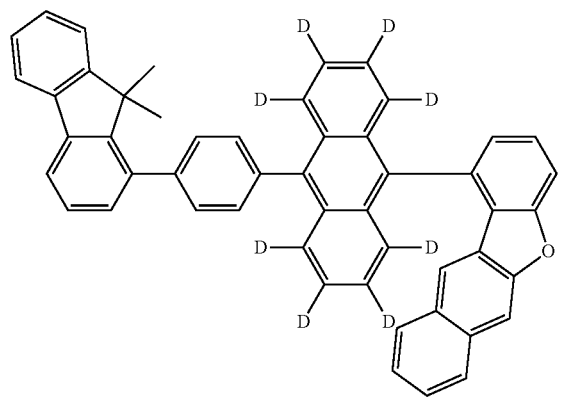
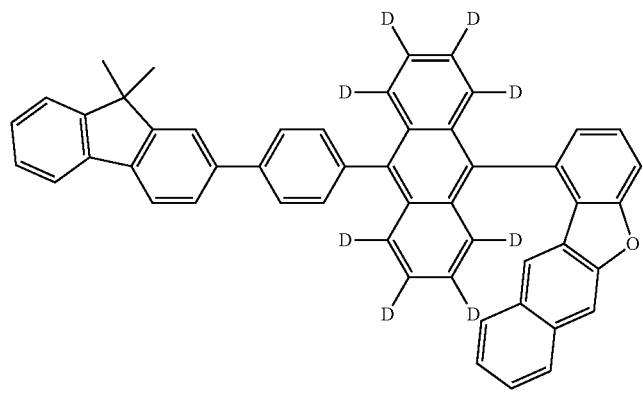
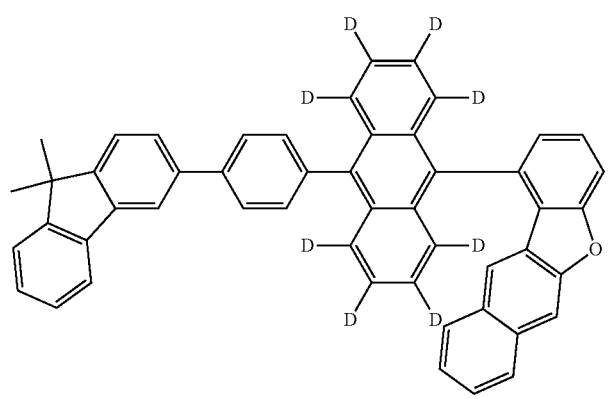
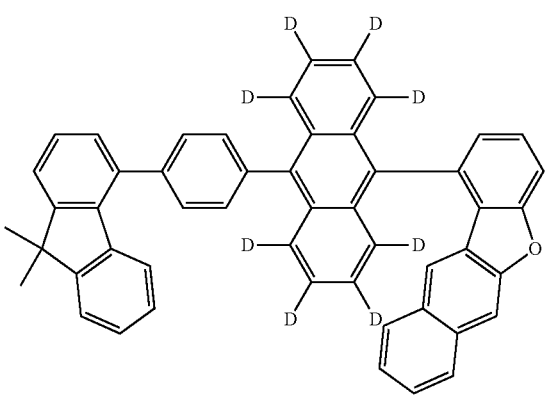

-continued
| 249 | 250 |
|---|---|
| 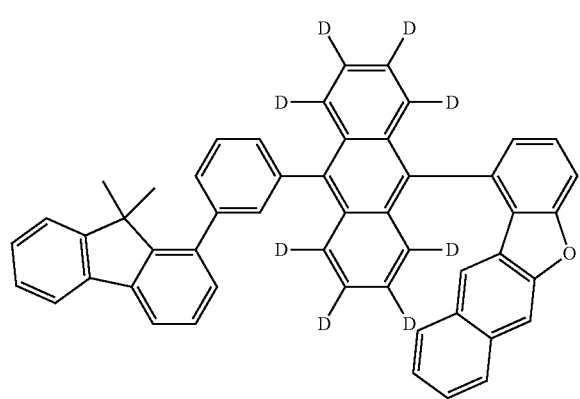 | 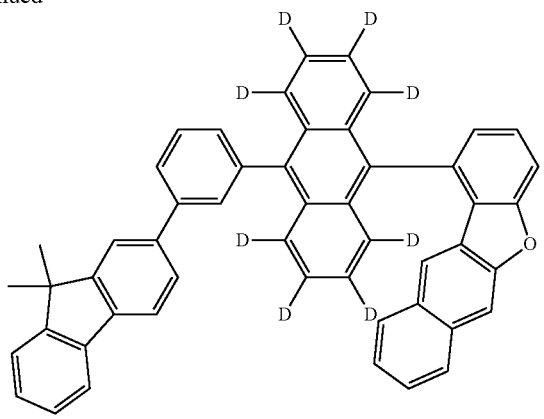 |
| 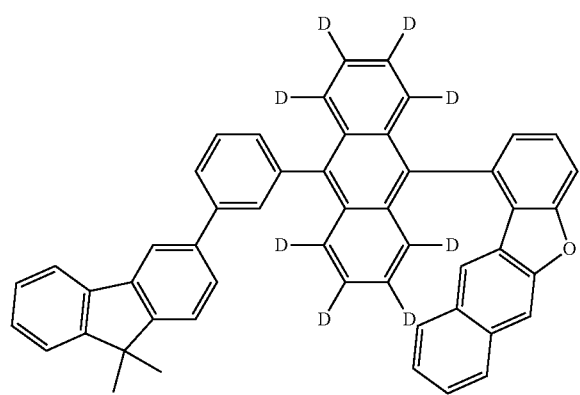 | 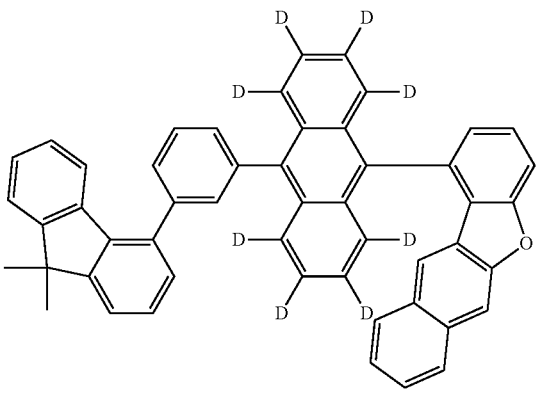 |
| 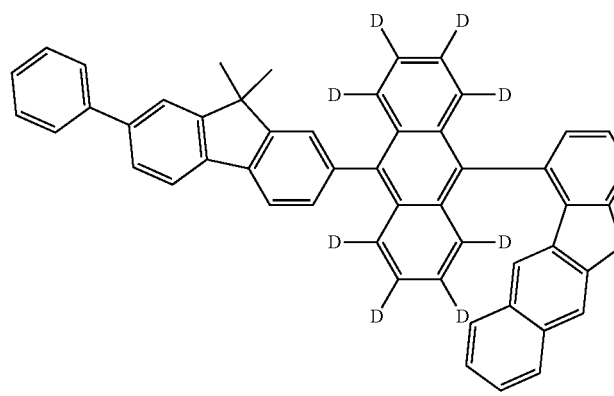 | 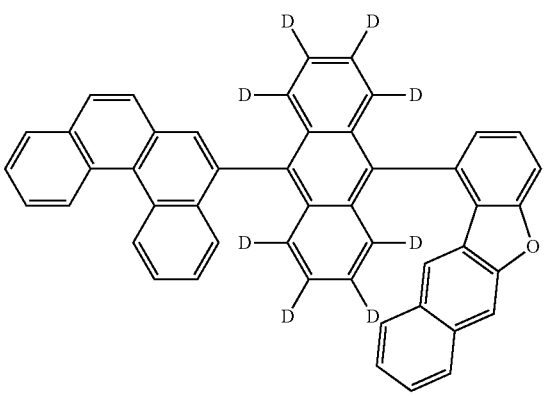 |
| 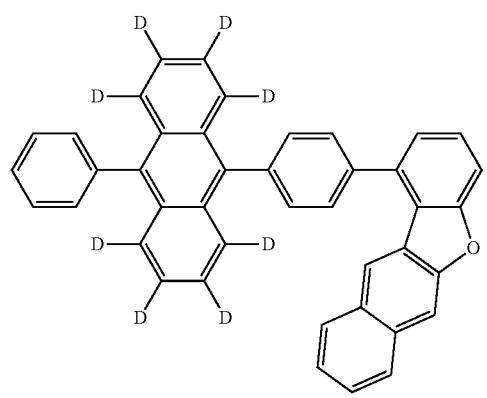 | 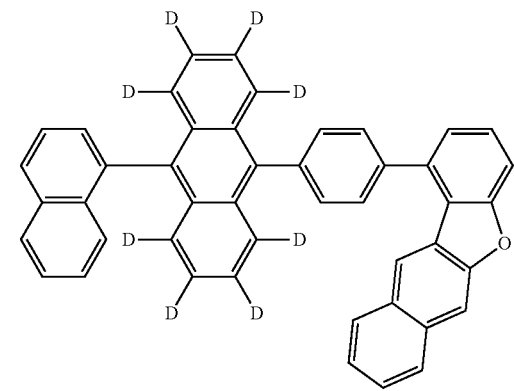 |

-continued
251
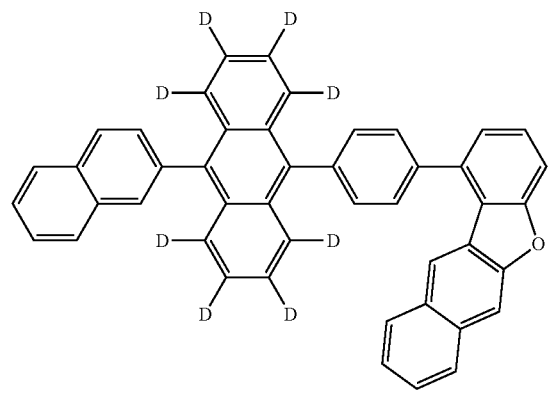
252
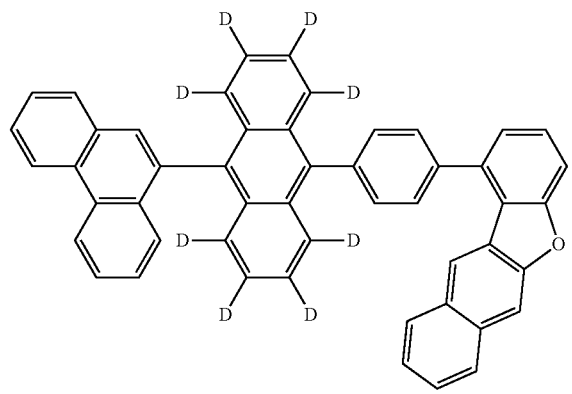
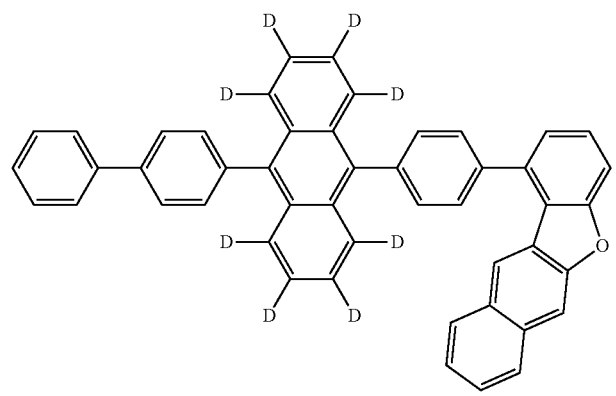
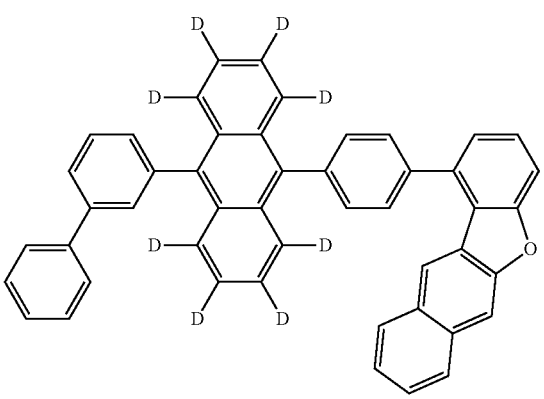
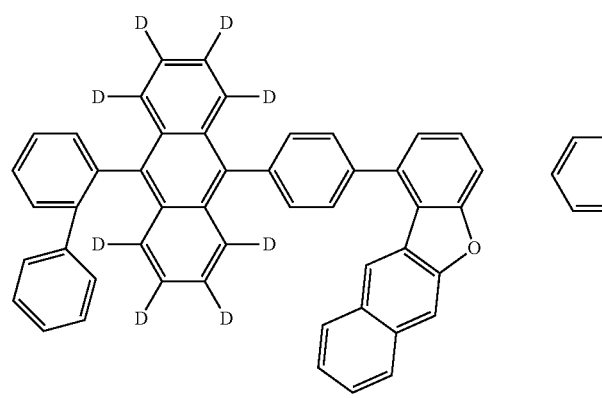
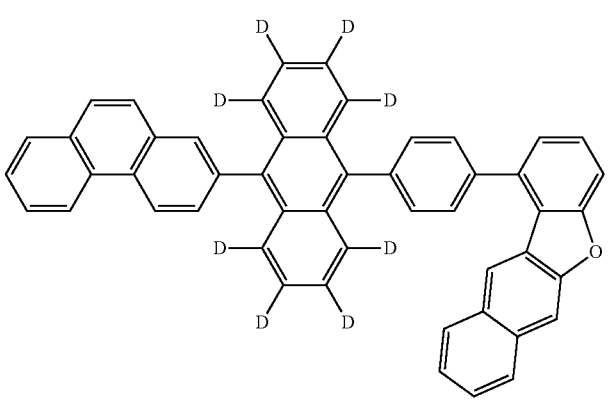
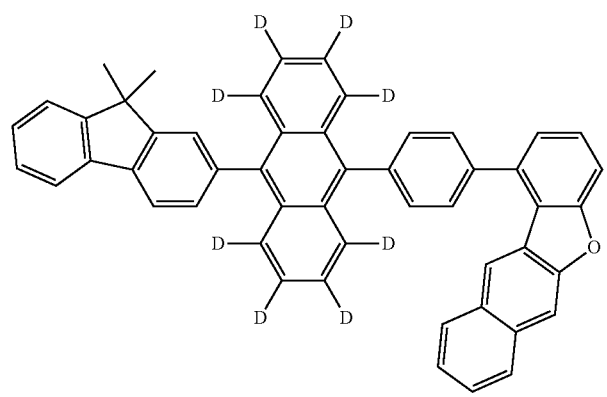

253 254
-continued
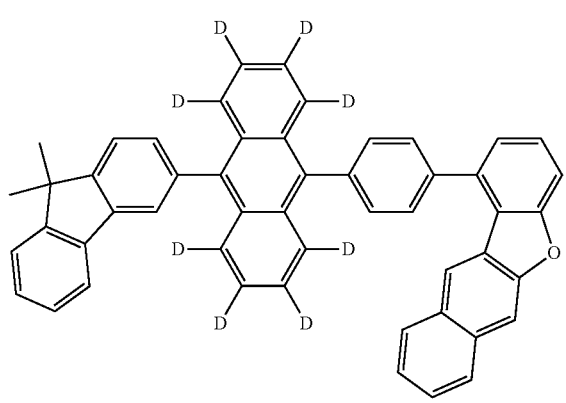
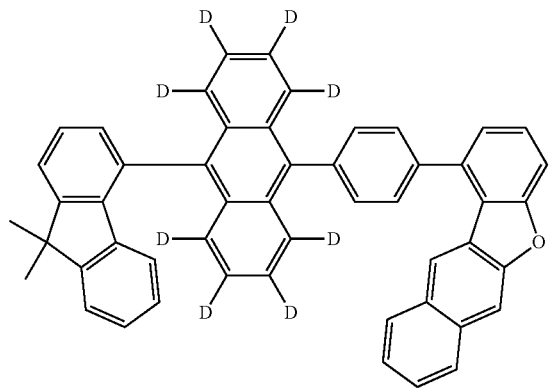
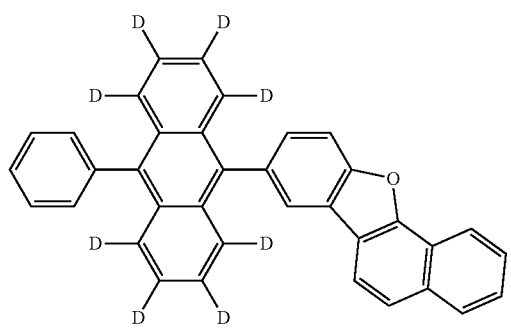
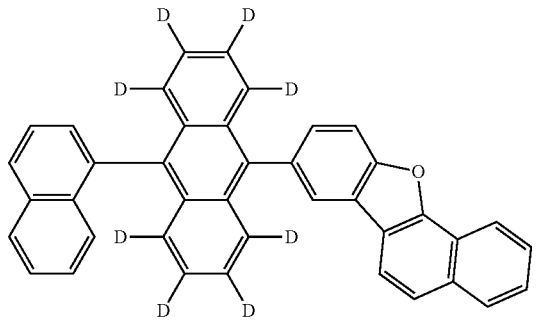
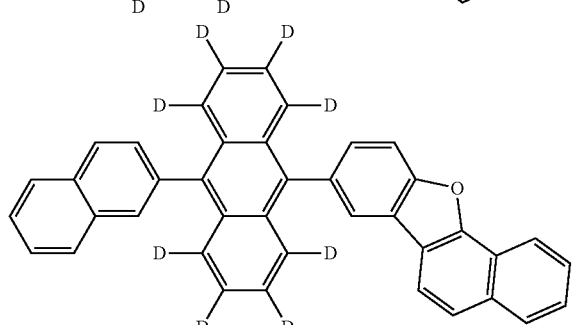
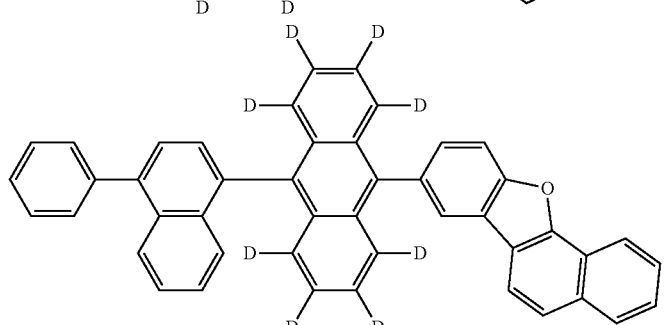
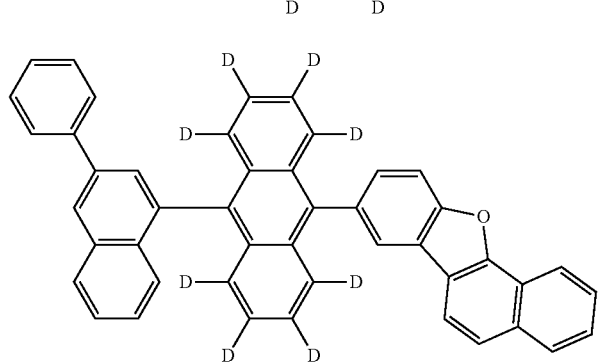
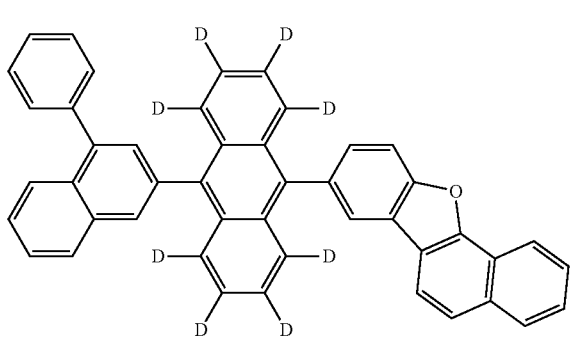

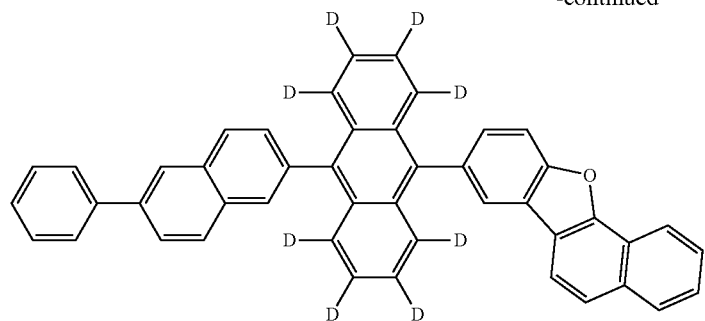
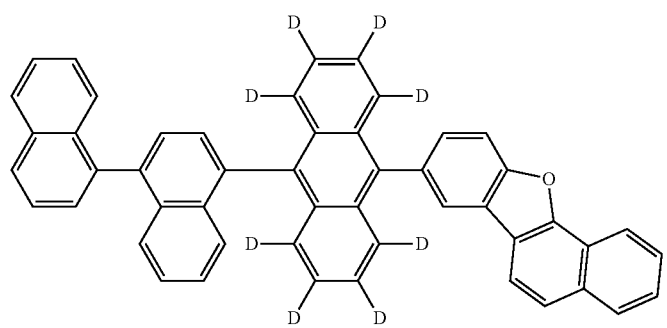
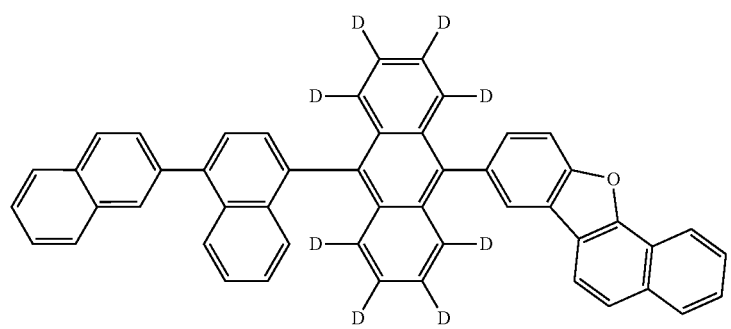
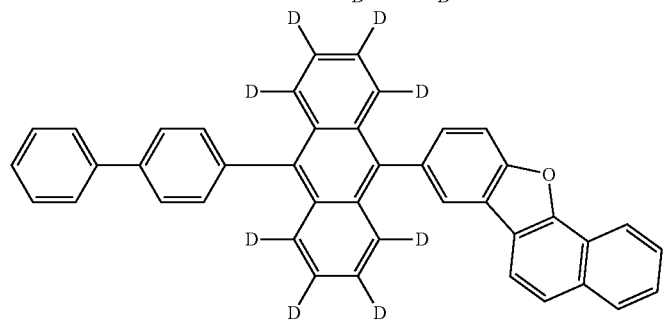
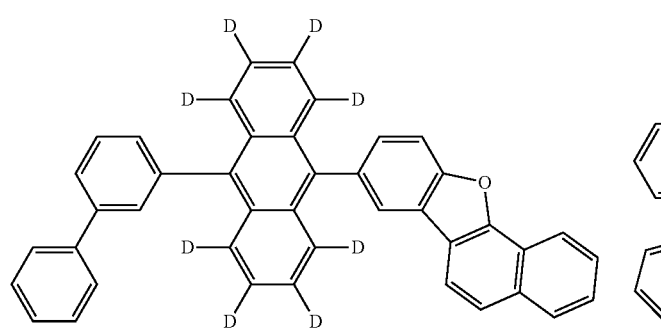
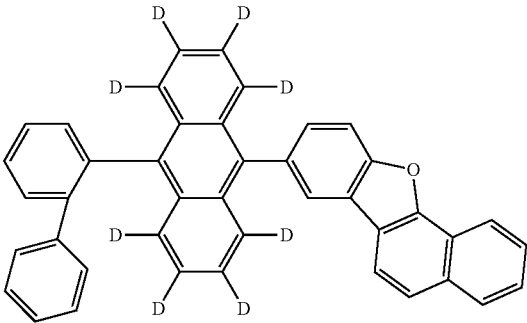

-continued
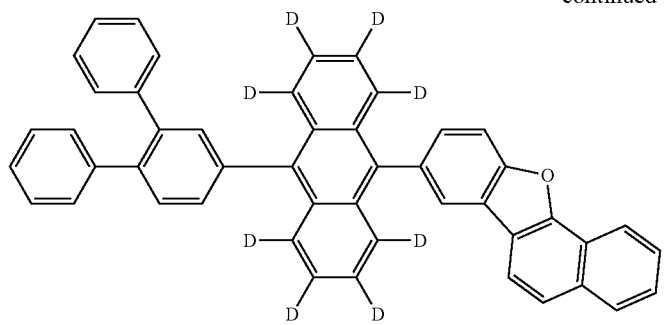
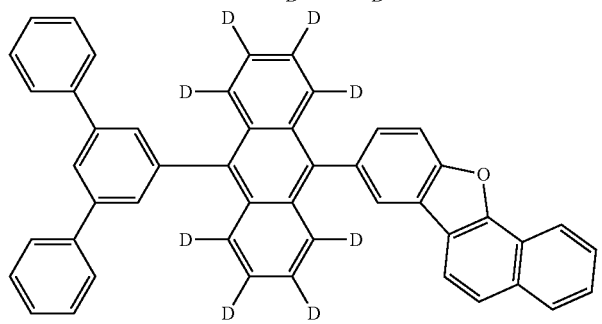
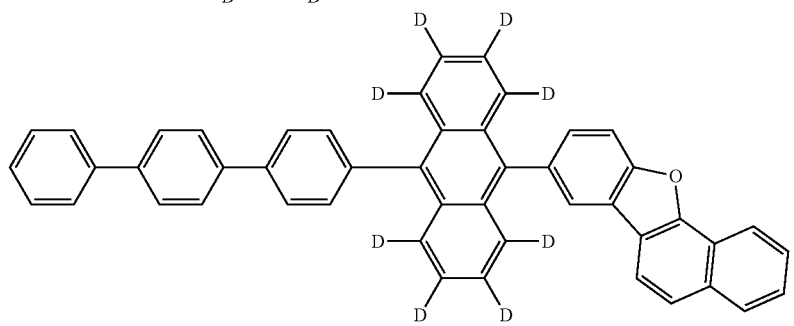
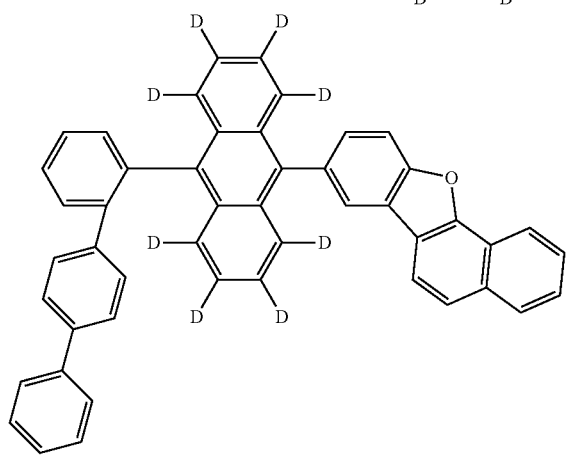
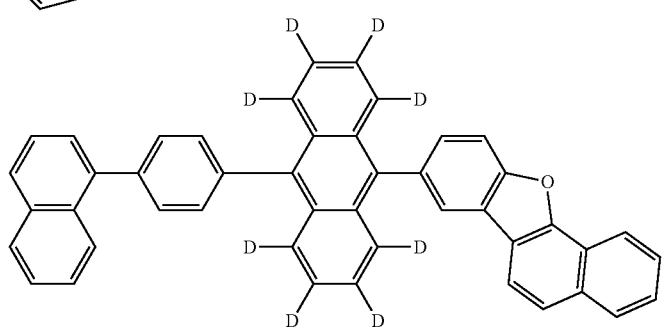

-continued
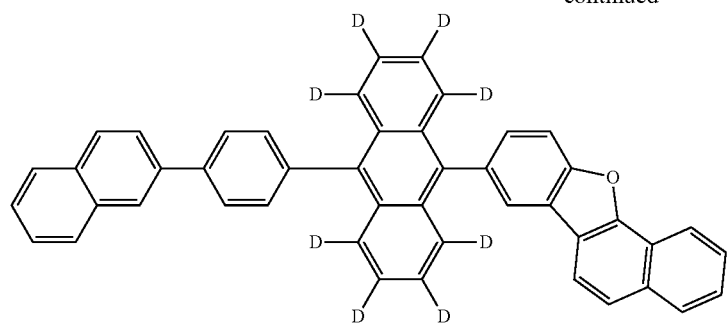

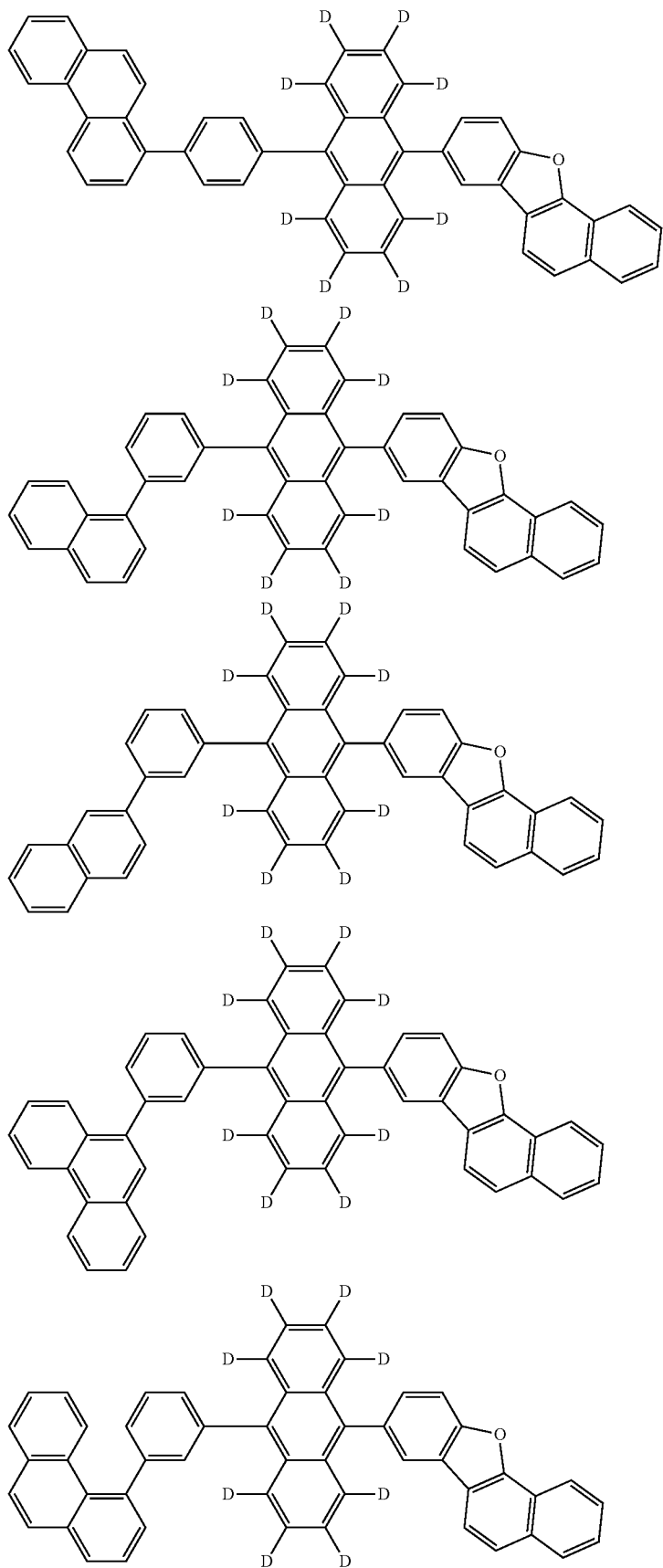

-continued
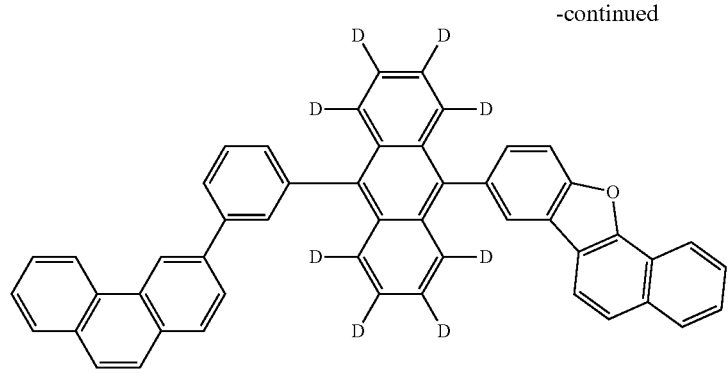
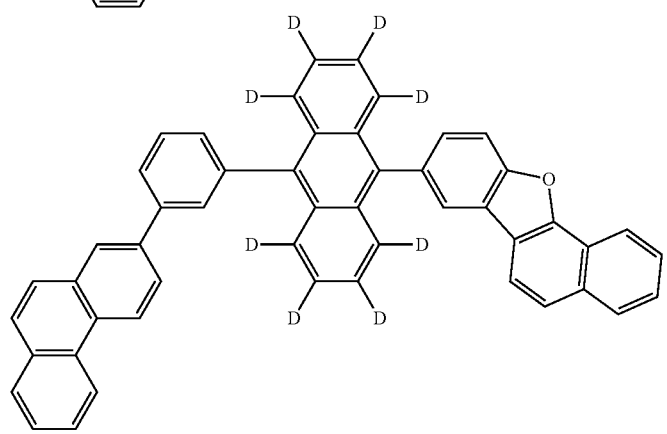
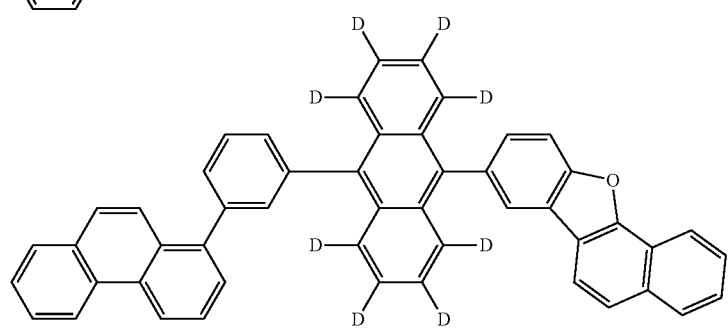
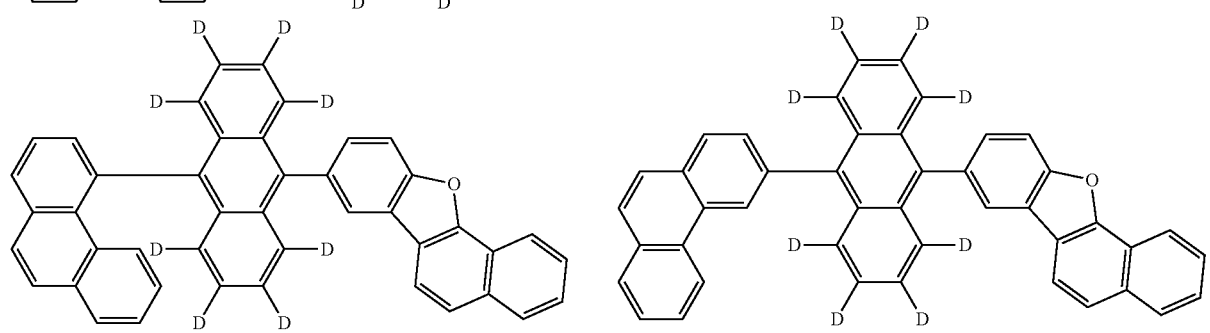
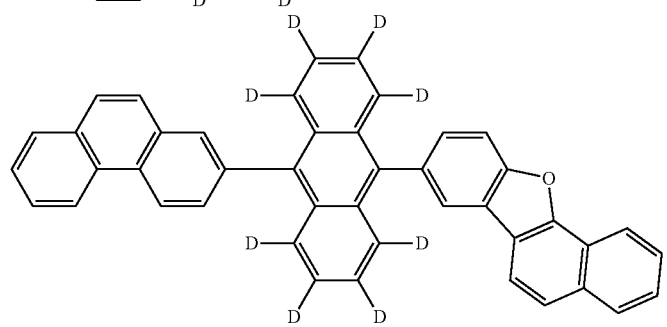

265
266
-continued
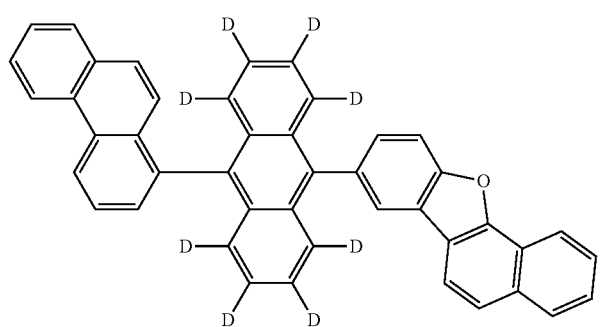
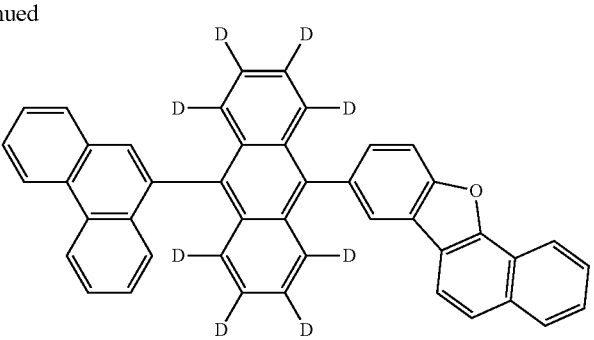
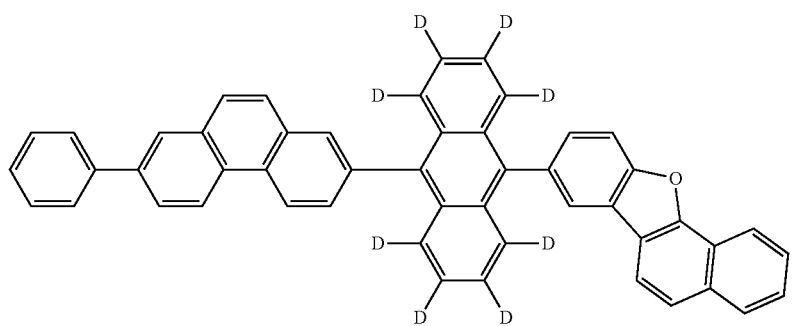
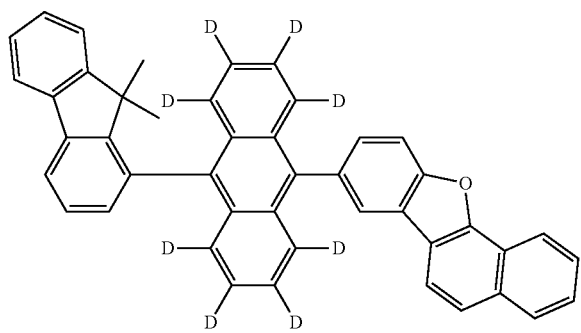
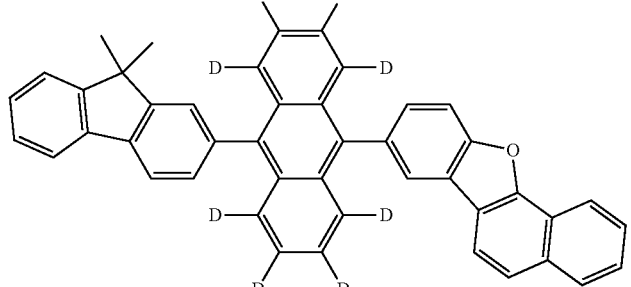
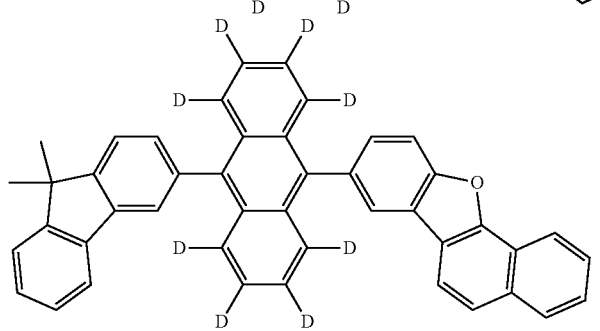

-continued
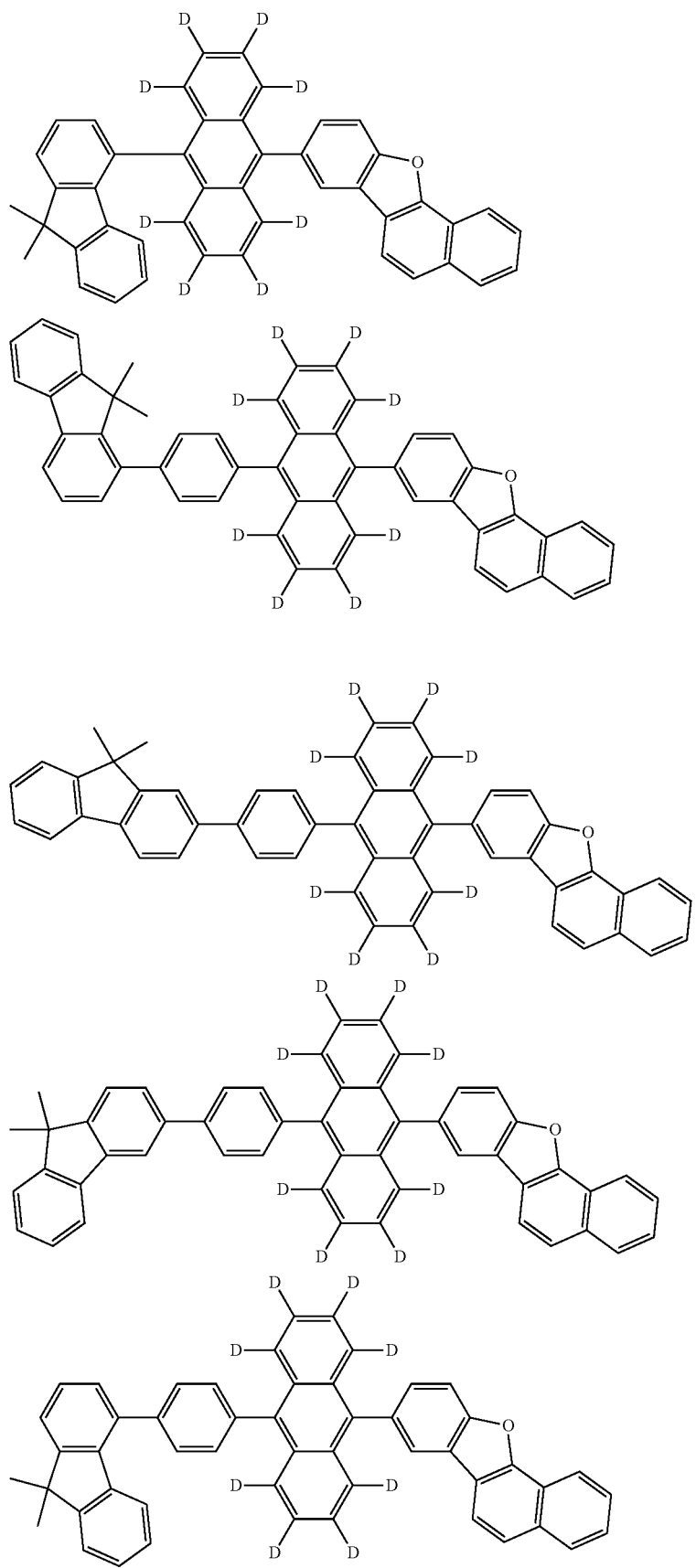

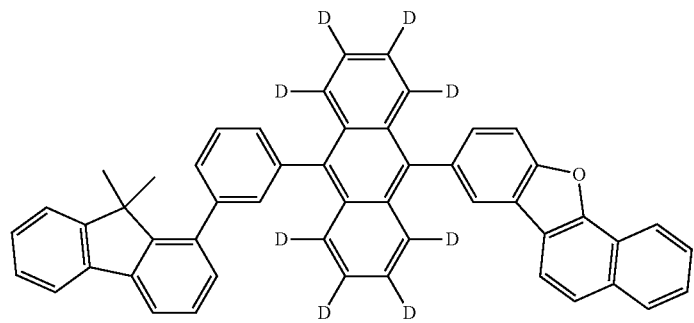
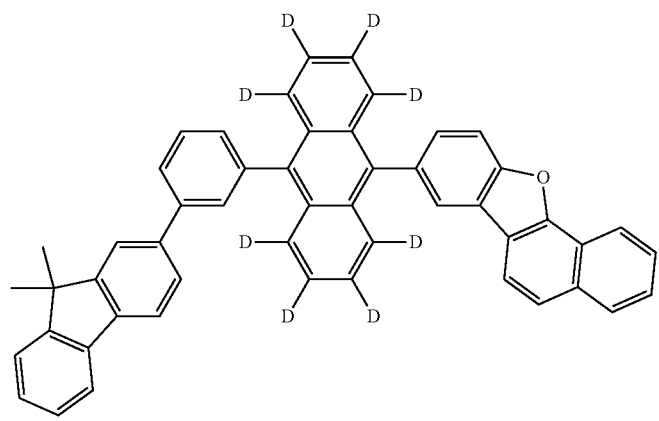
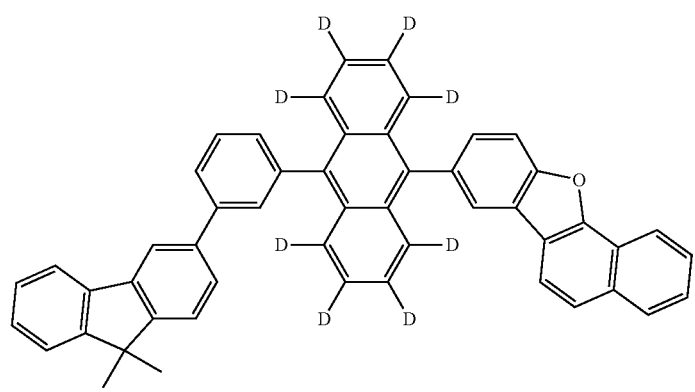
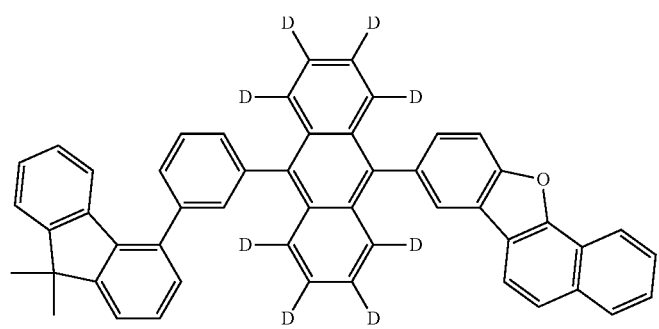

-continued
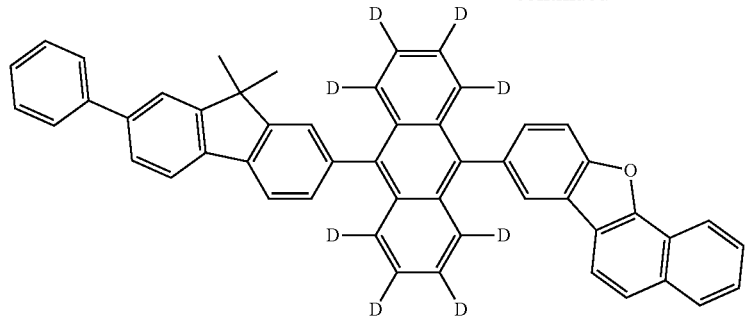
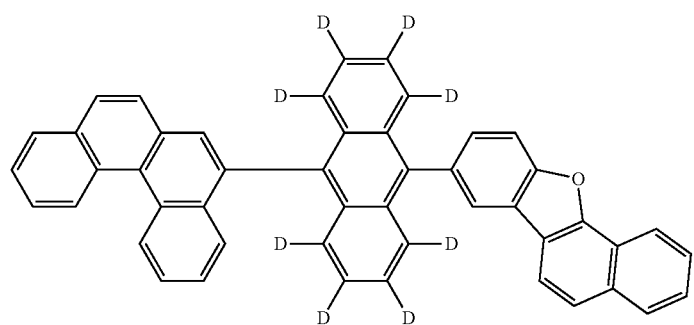
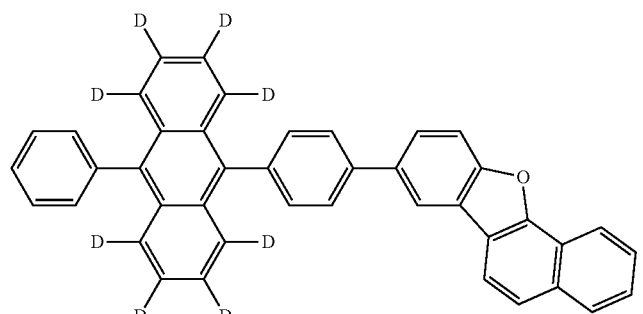
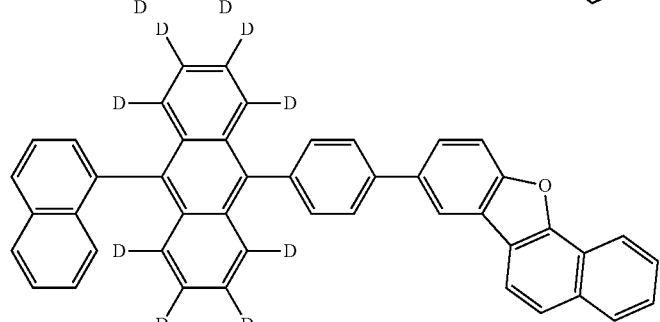
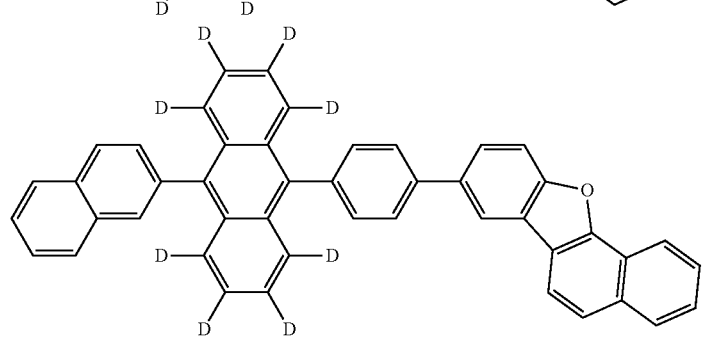

-continued
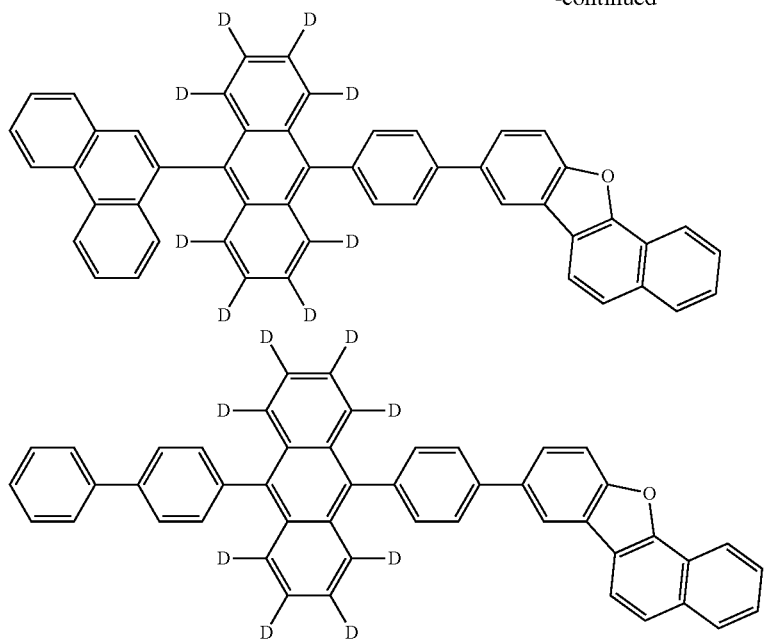
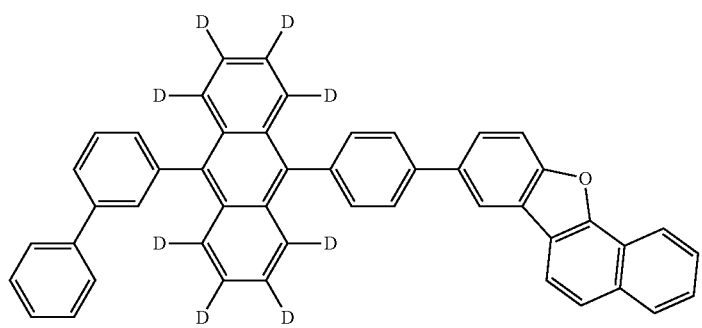
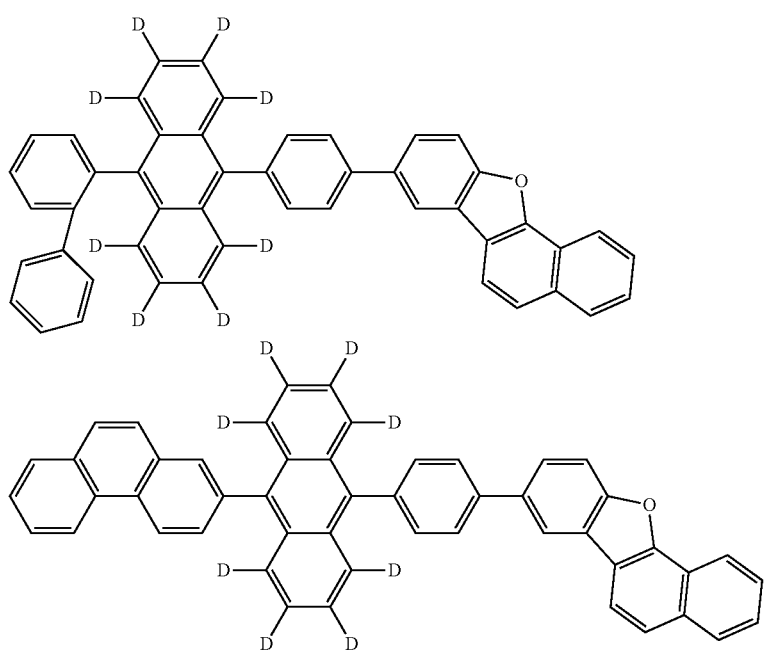

-continued
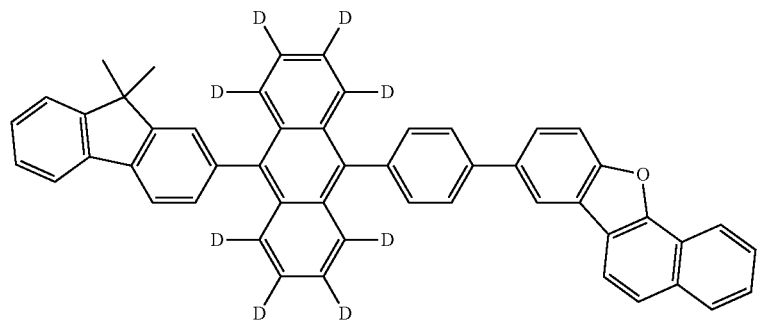
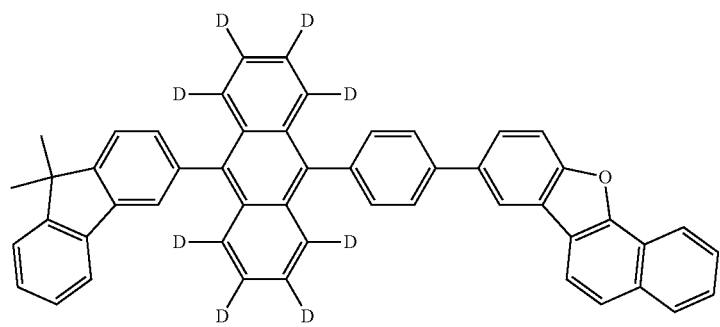
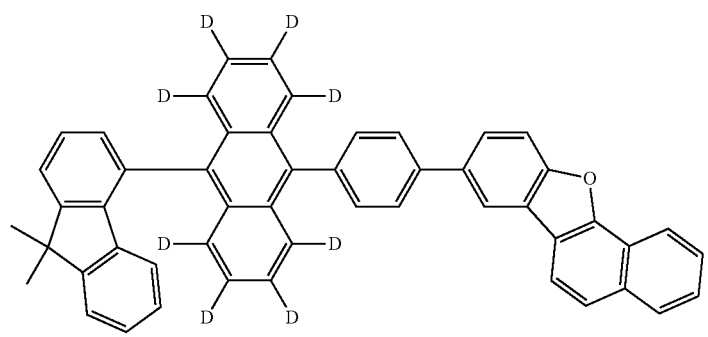
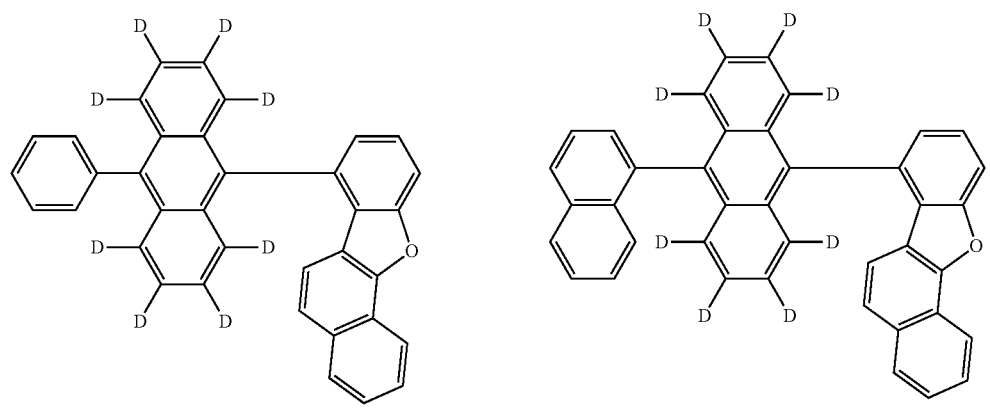

277
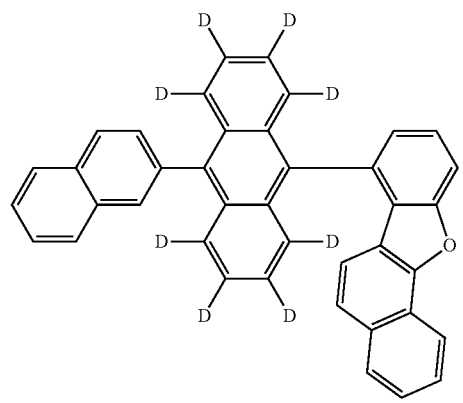
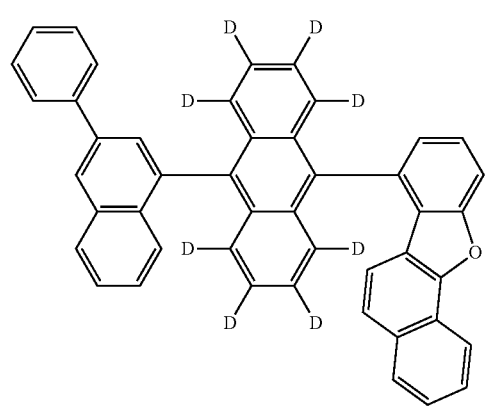
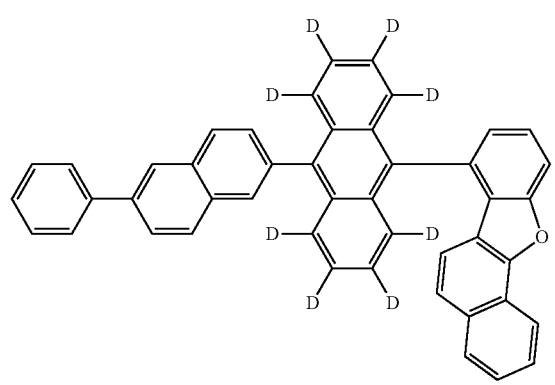
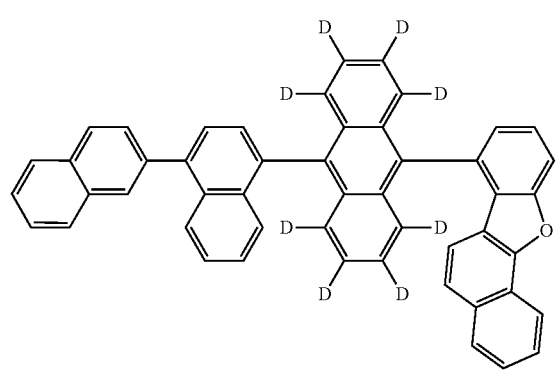
278
-continued
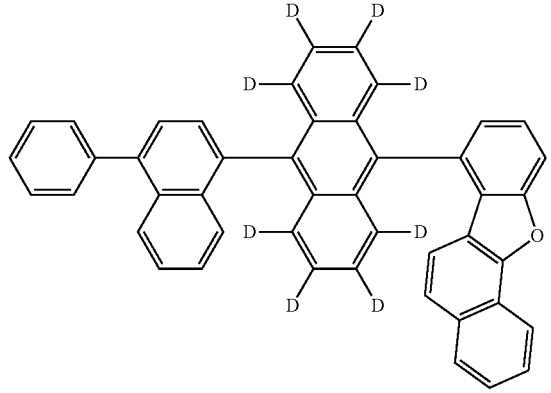
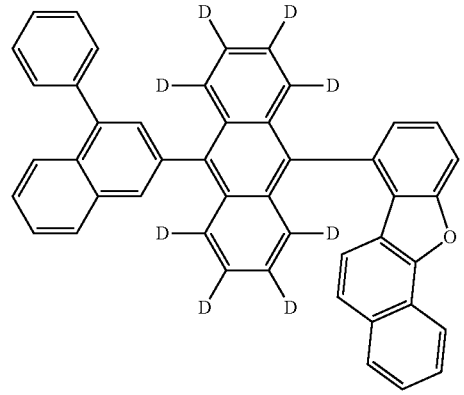
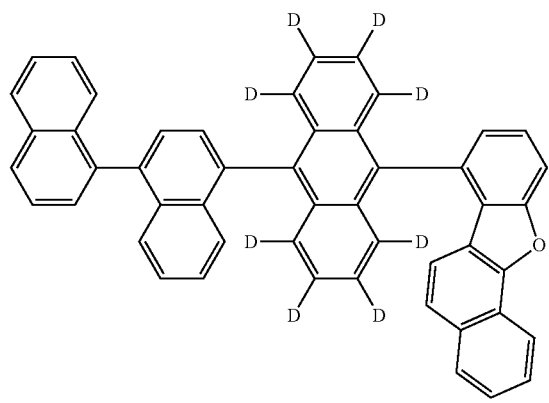
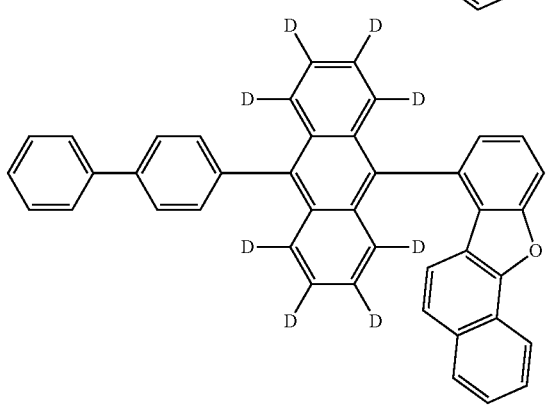

-continued
279
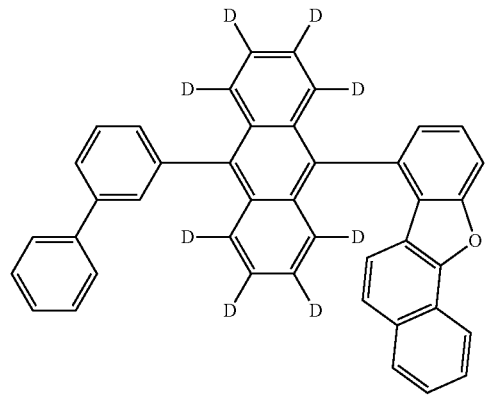
280
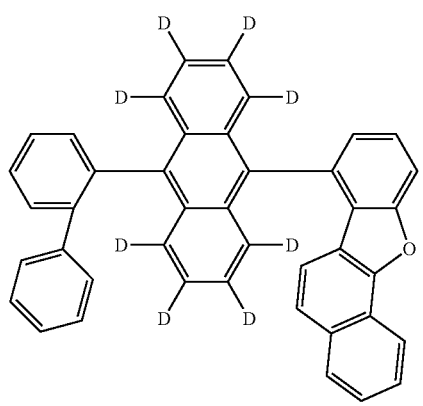
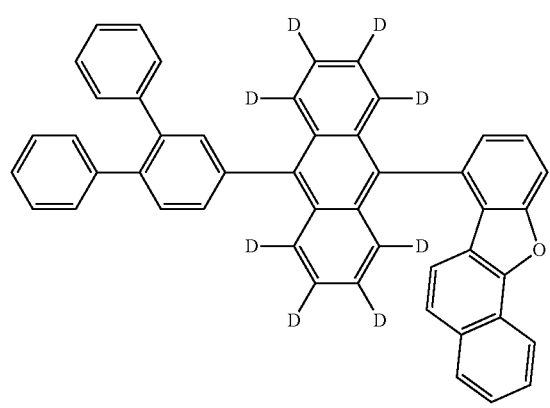
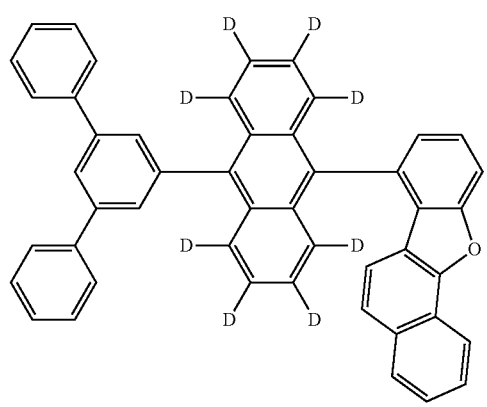
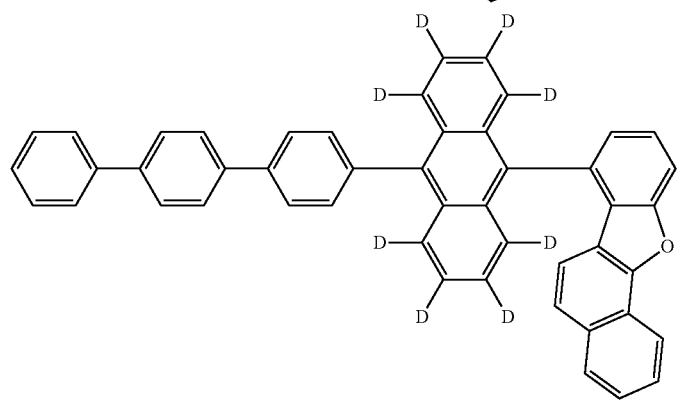
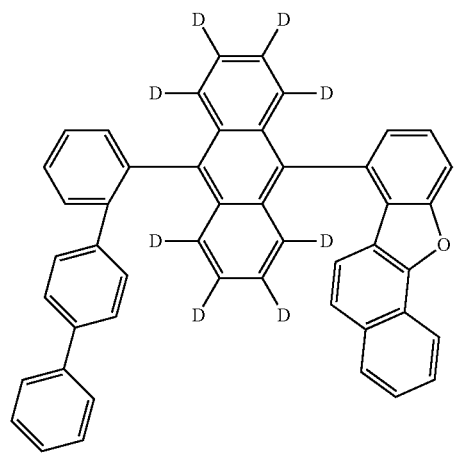

-continued
281
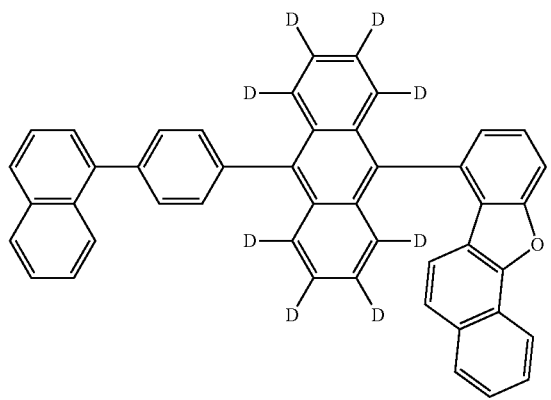
282
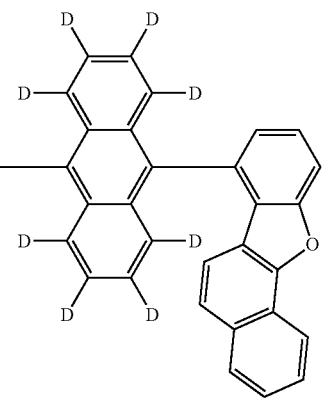
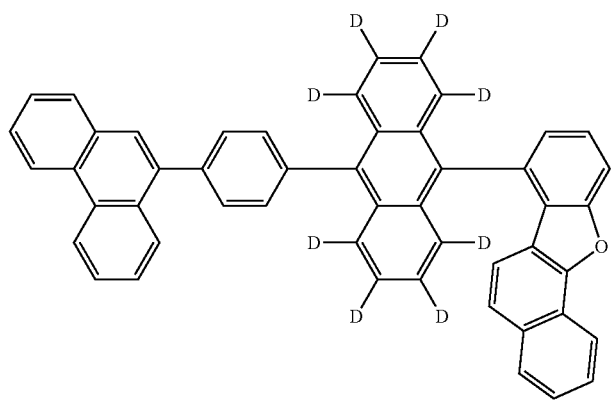
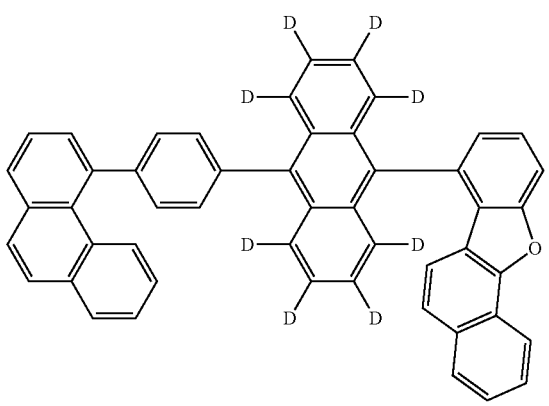
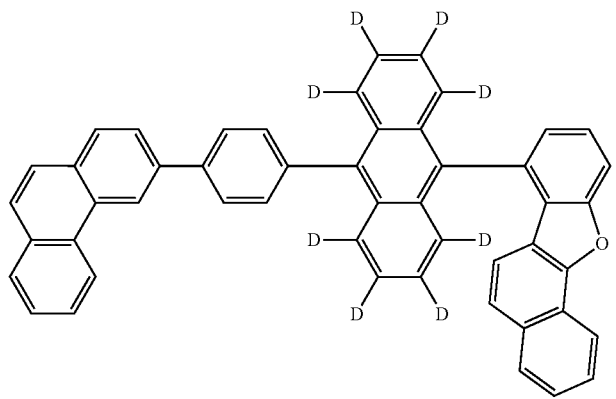
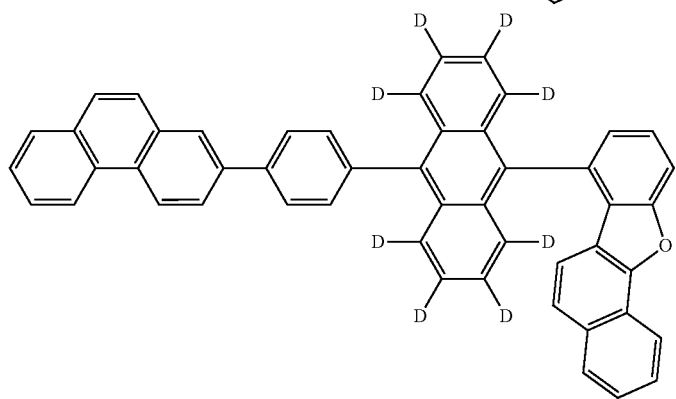

-continued
283
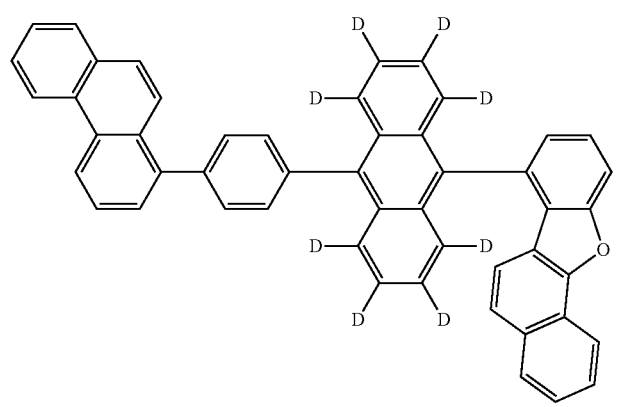
284
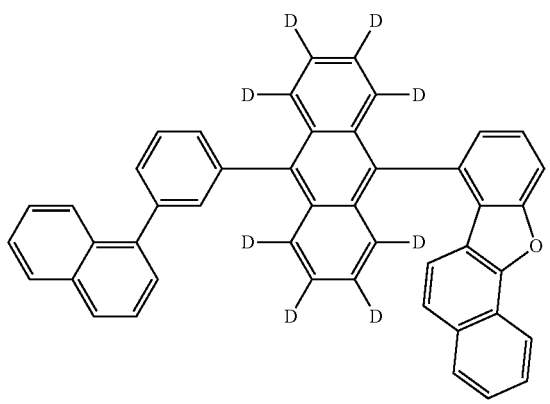
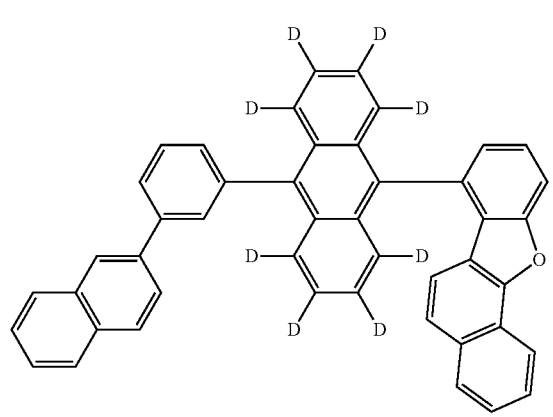
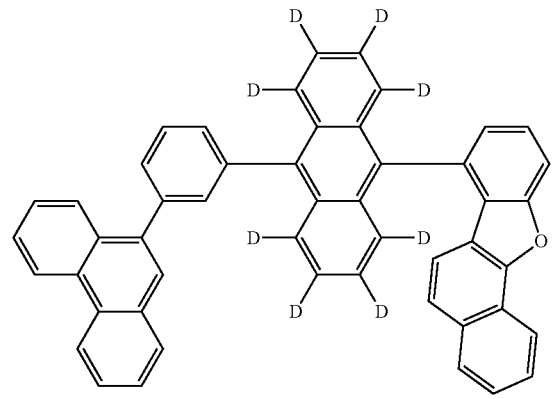
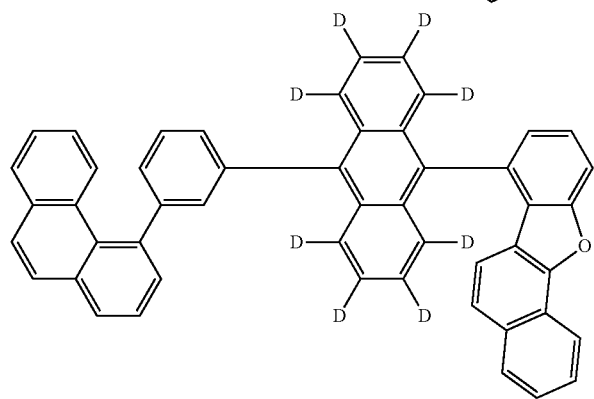
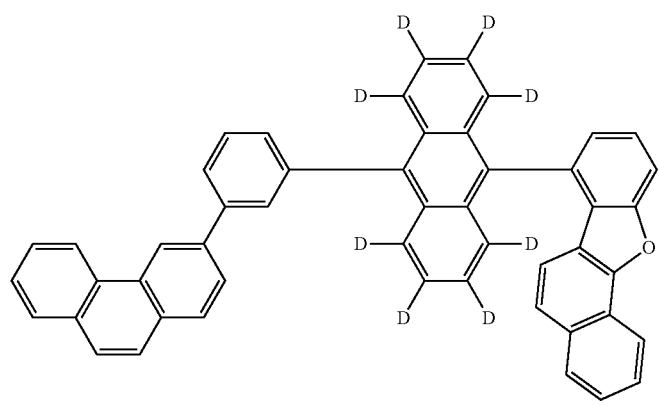

-continued
285
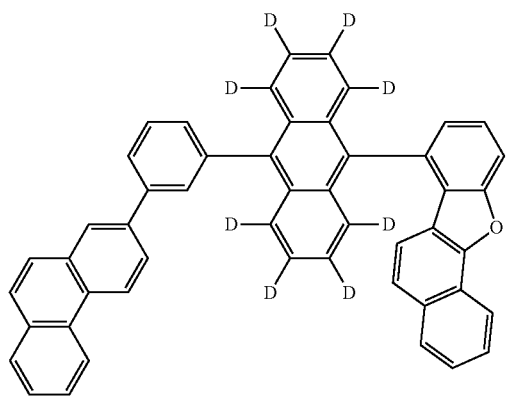
286
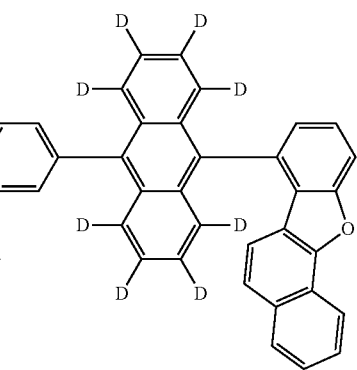
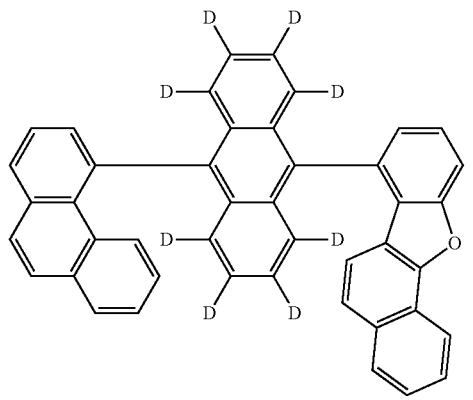
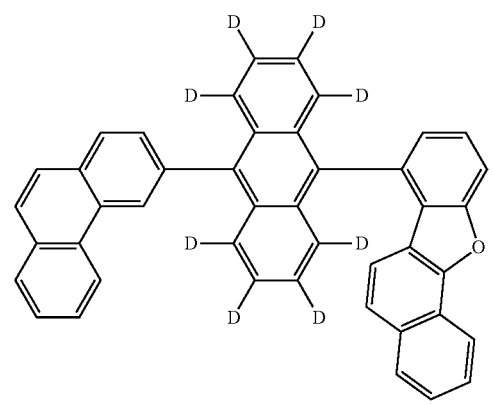
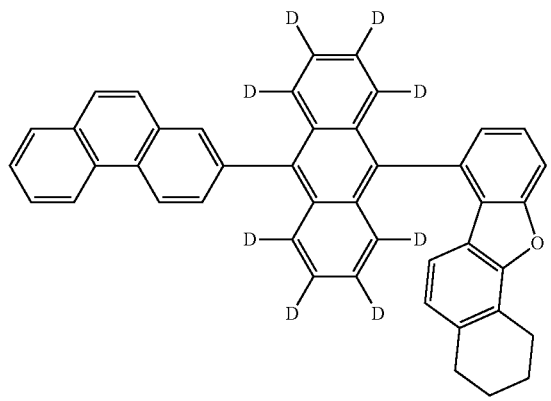
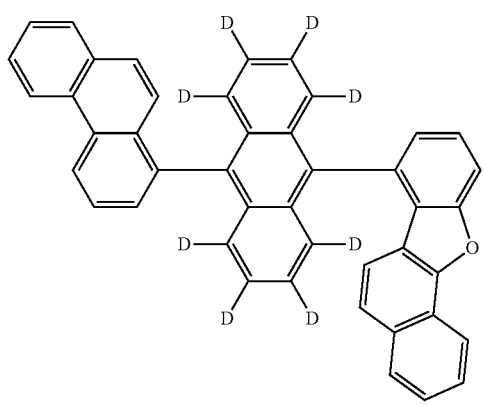
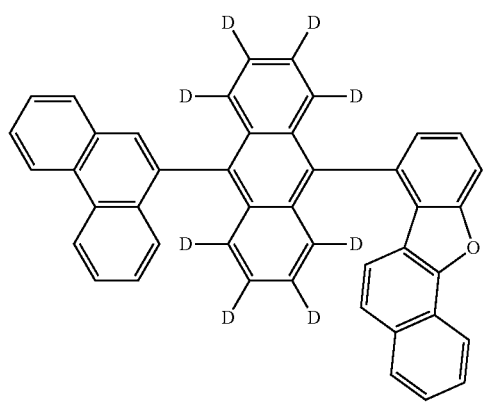
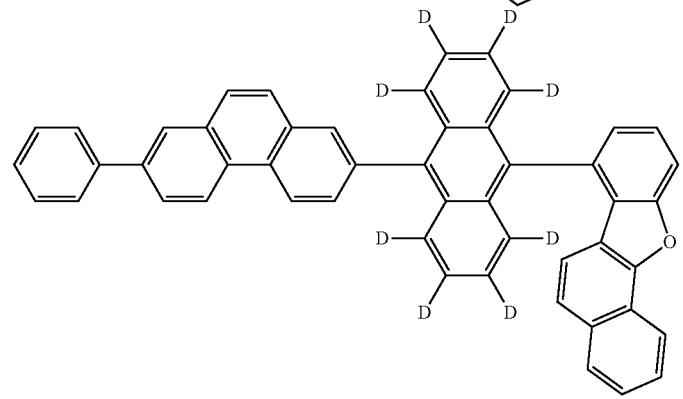

-continued
287
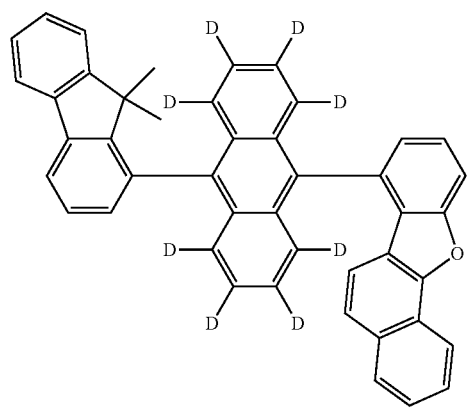
288
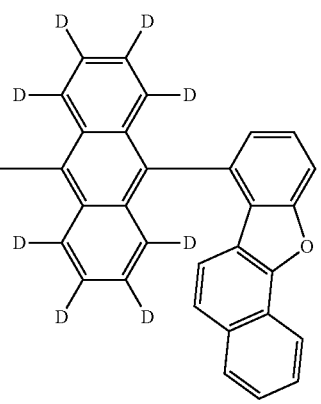
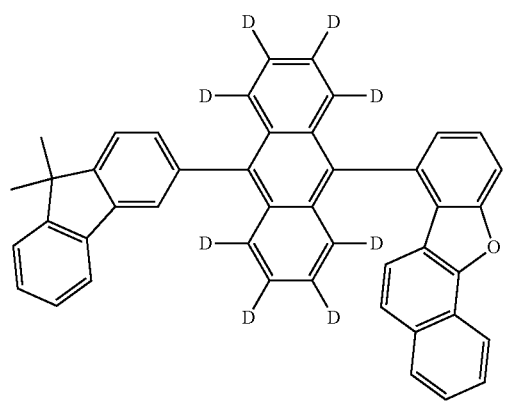
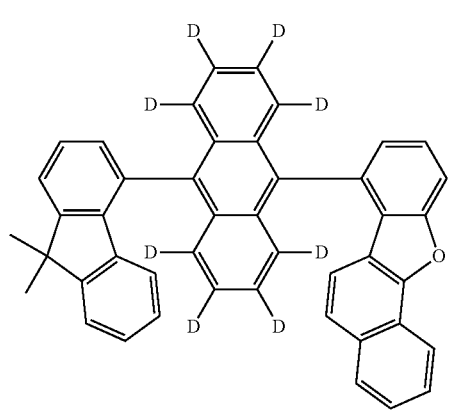
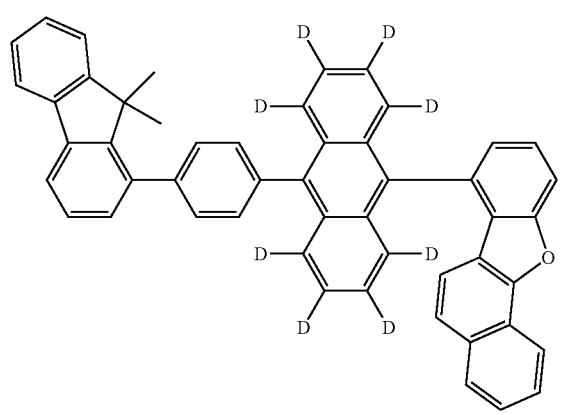
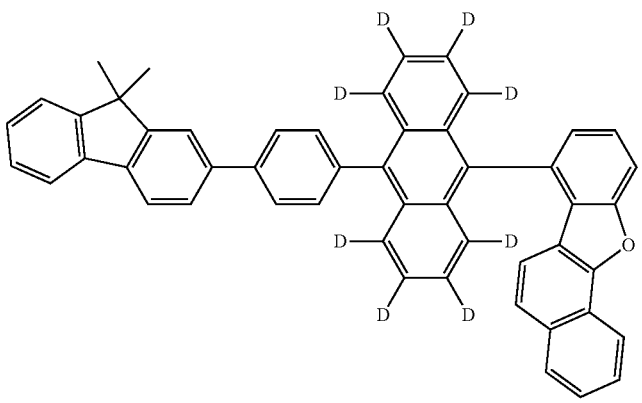
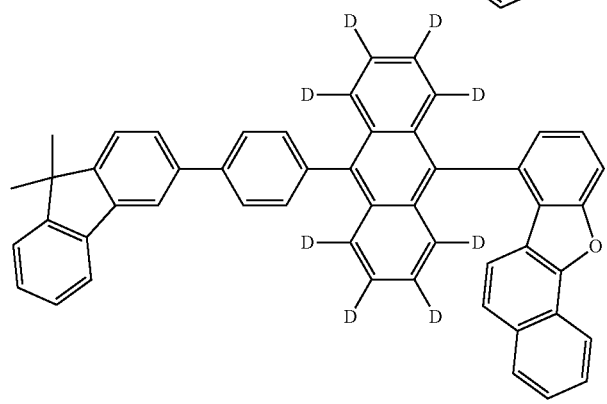

-continued
289 290
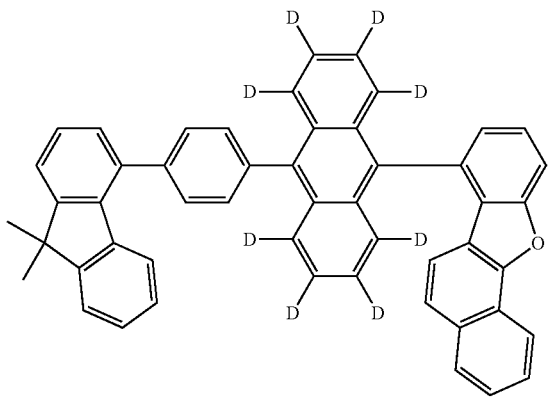
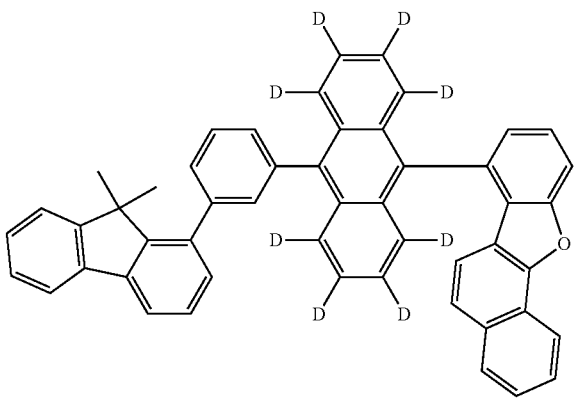
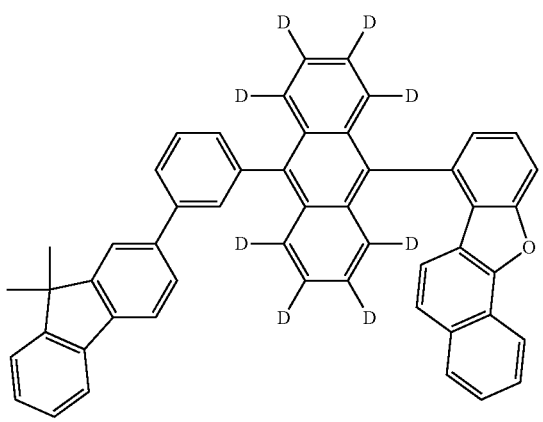
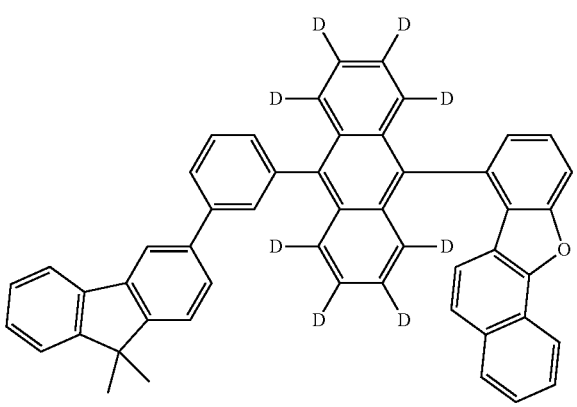
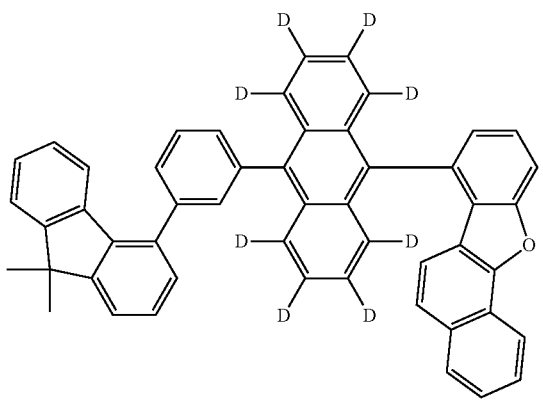
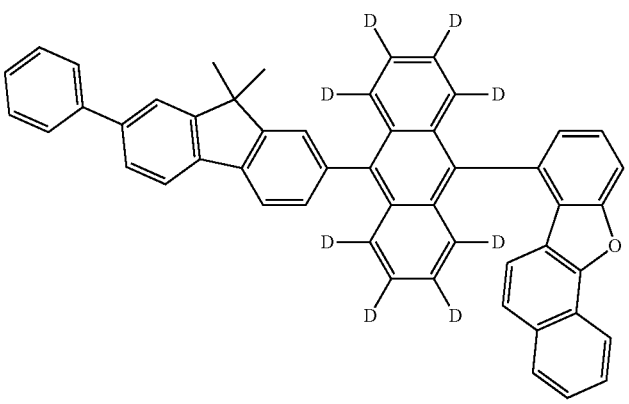
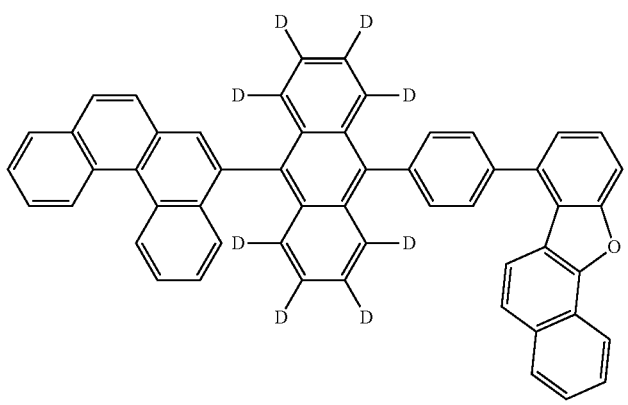
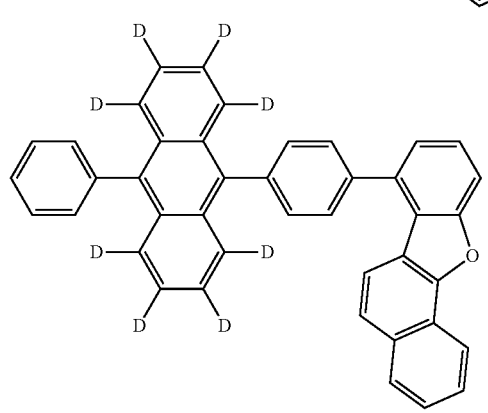

291
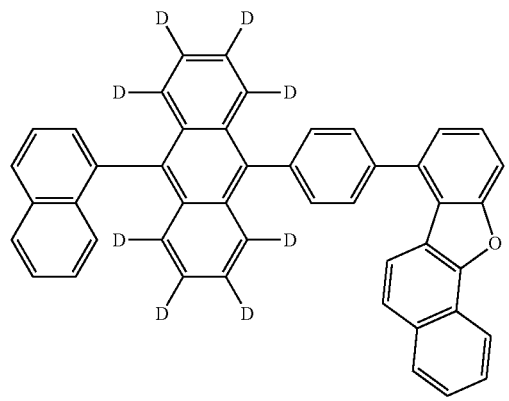
292
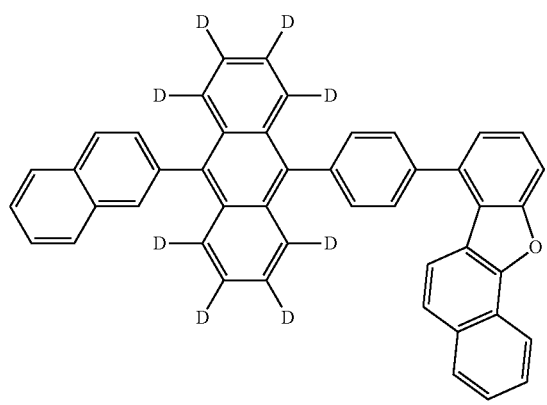
-continued
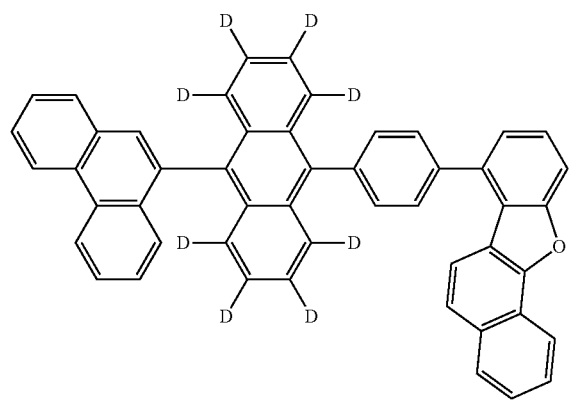
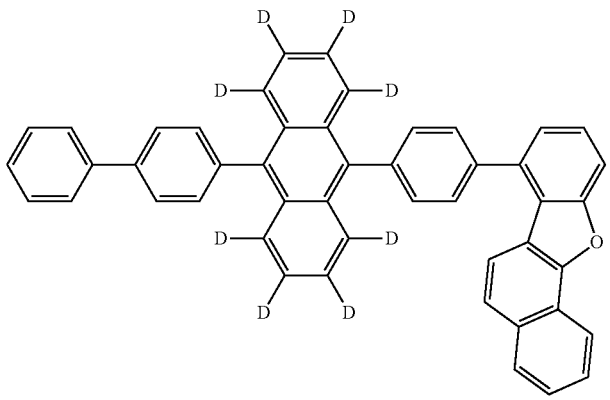
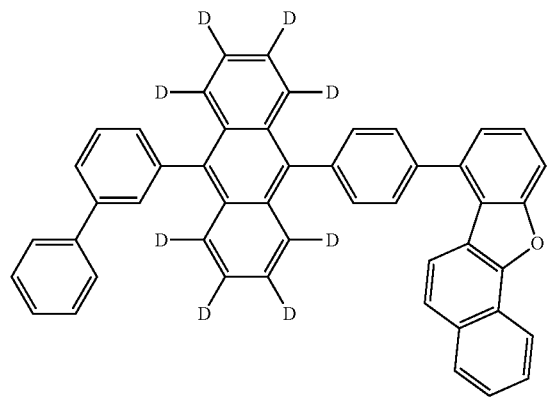
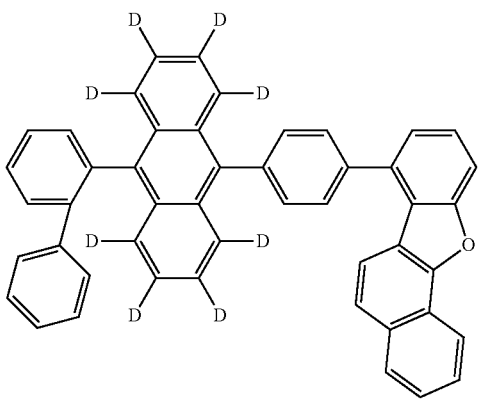
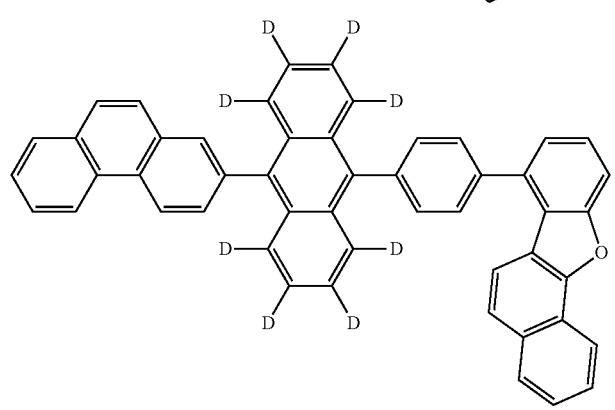

293 294
-continued
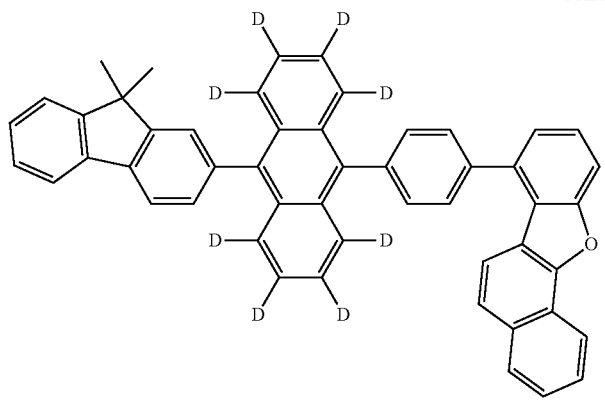
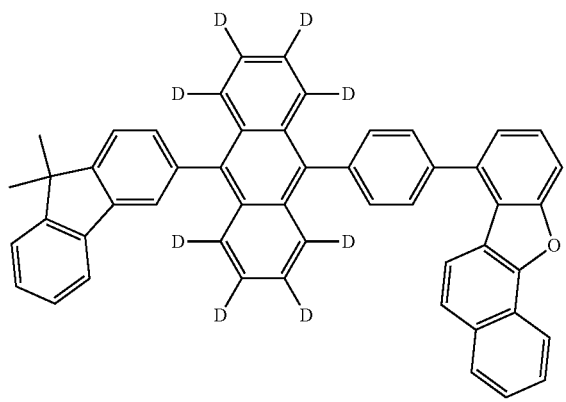 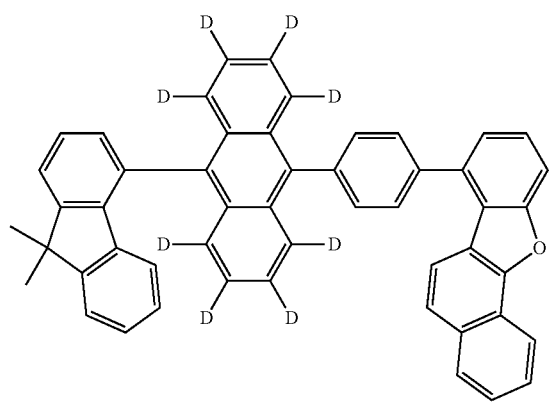
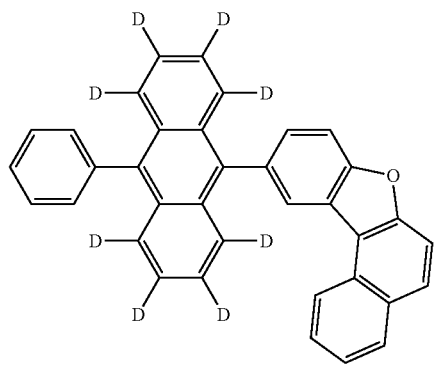 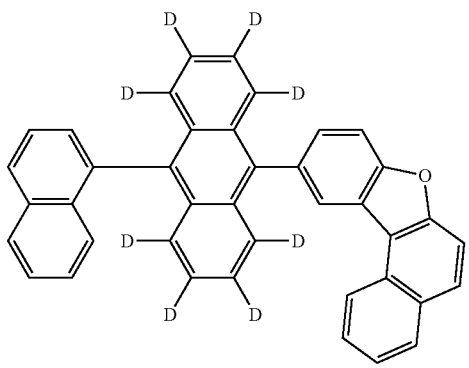
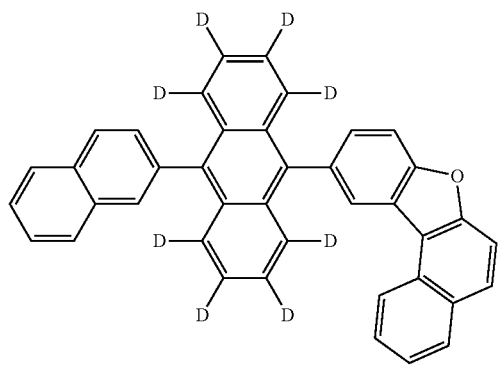 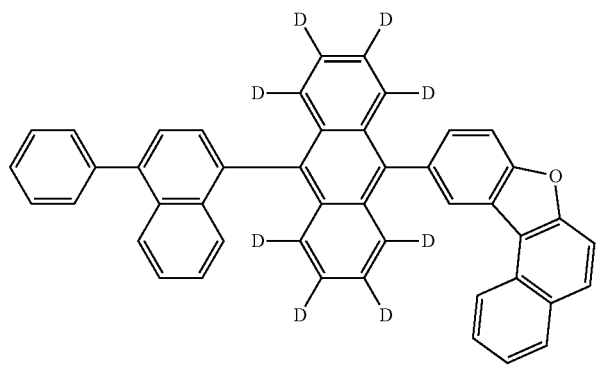

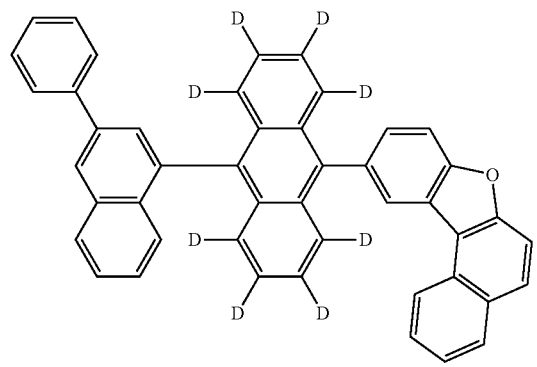
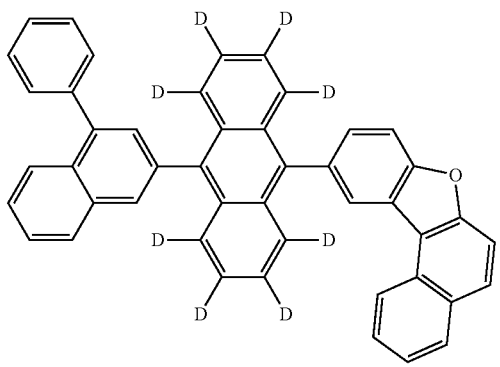
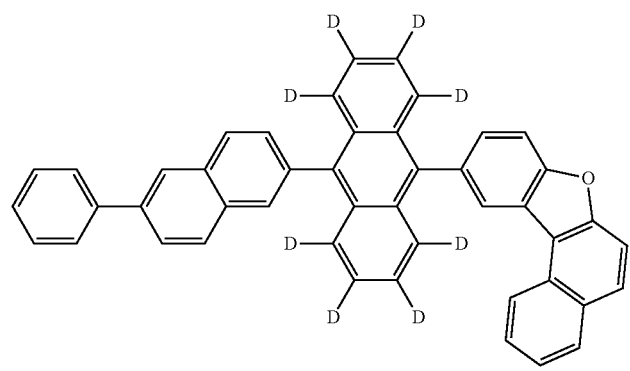
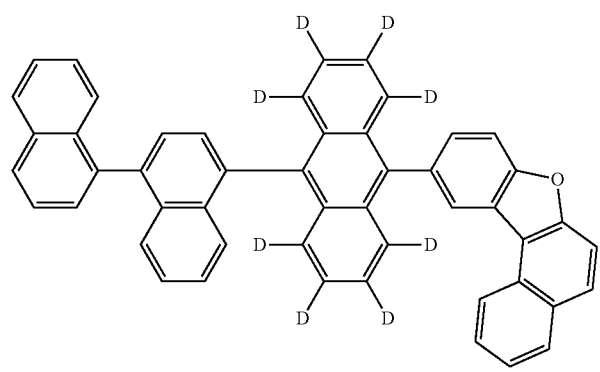
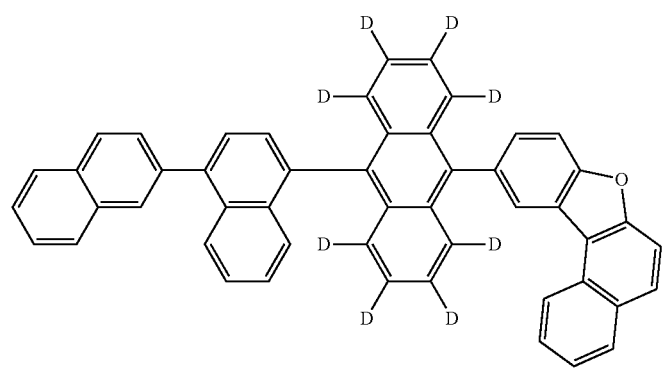

297 298
-continued
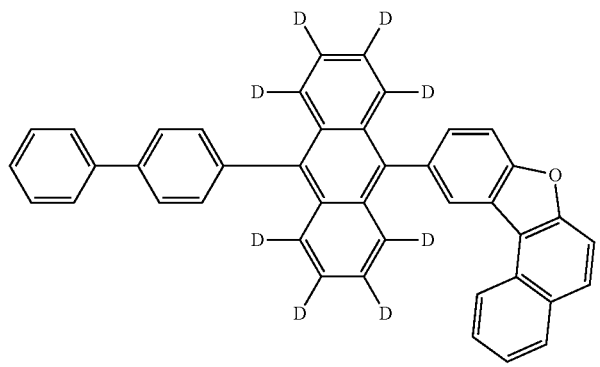
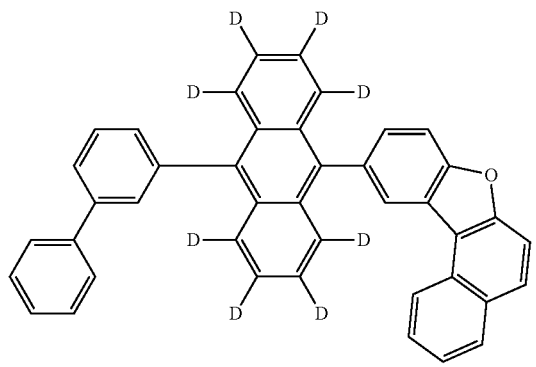
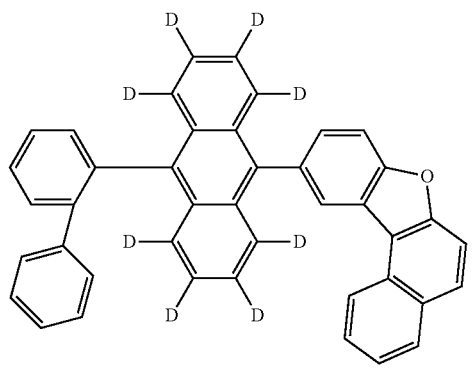
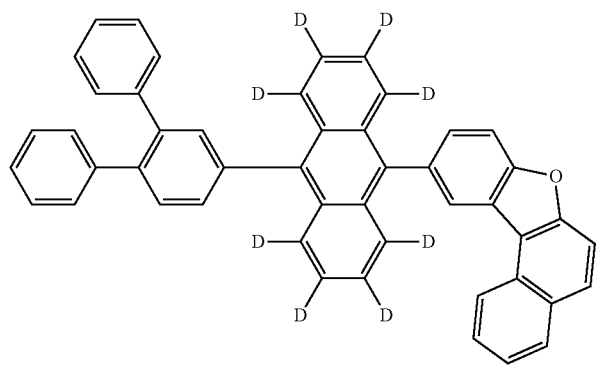
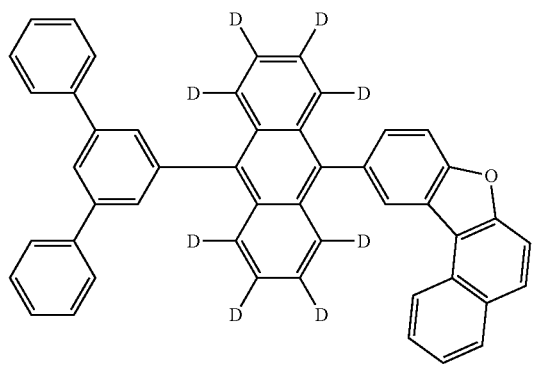
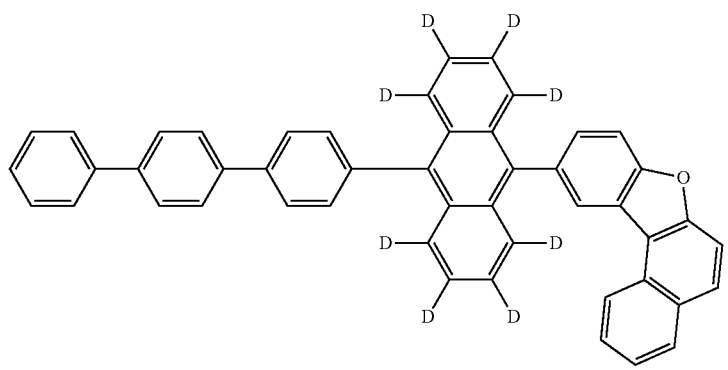

299 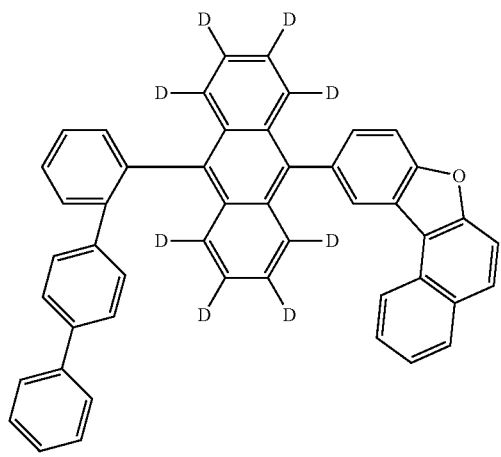
300 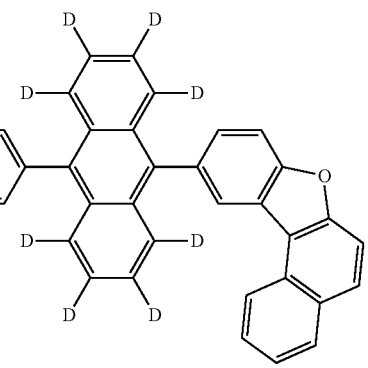
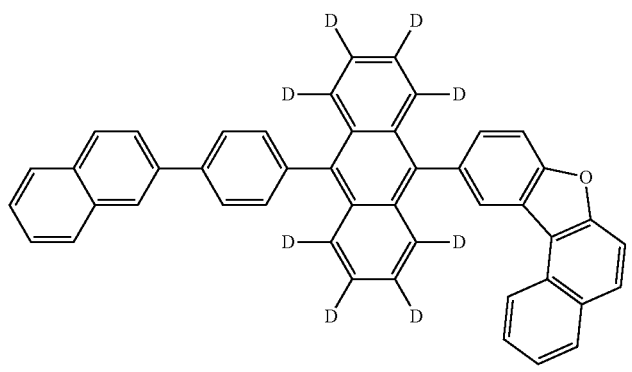
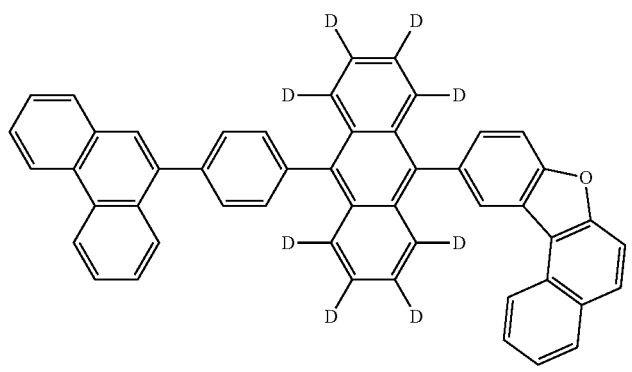
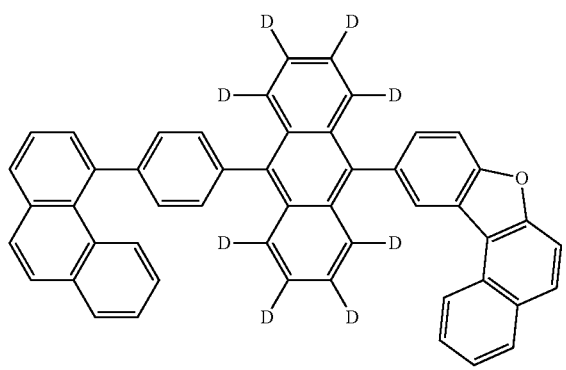

-continued
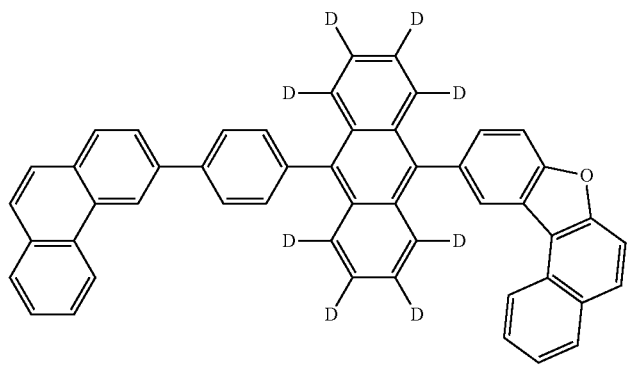
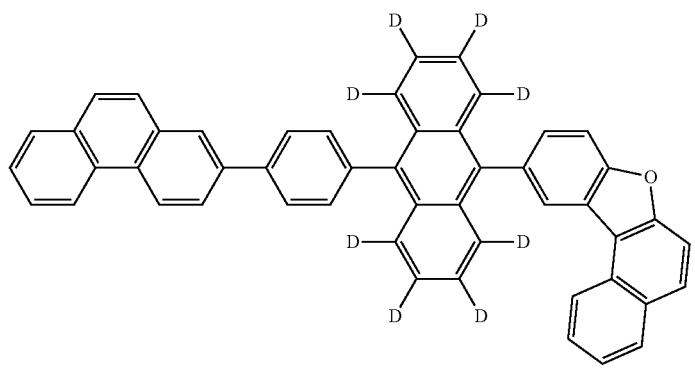
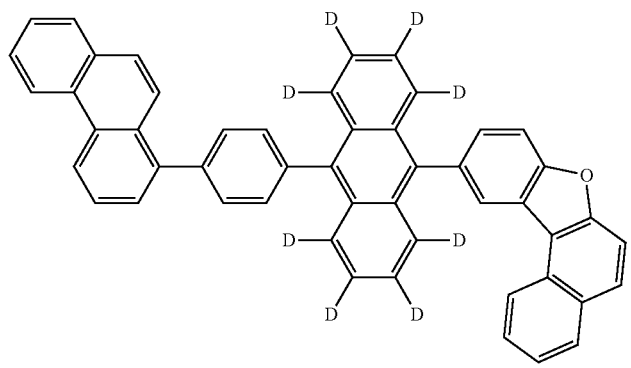
301
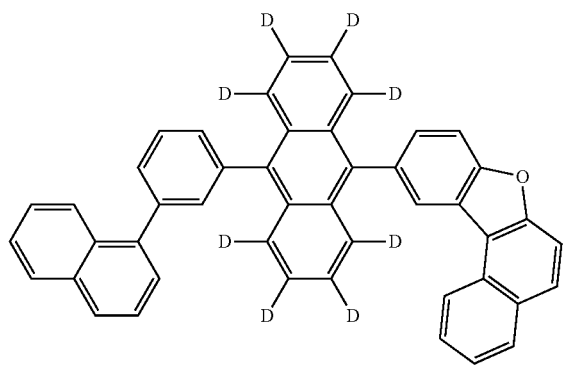
302
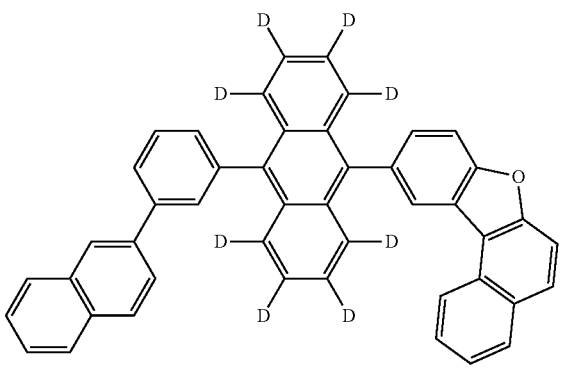

-continued
303
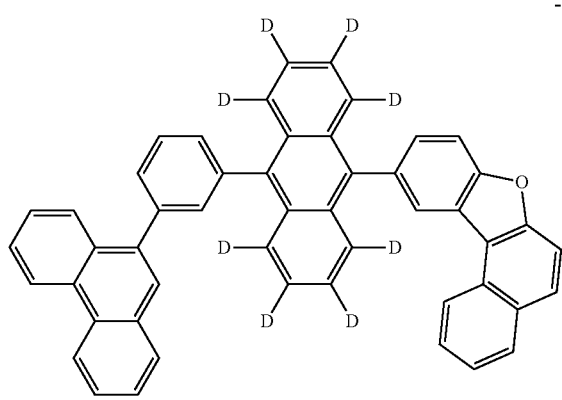
304
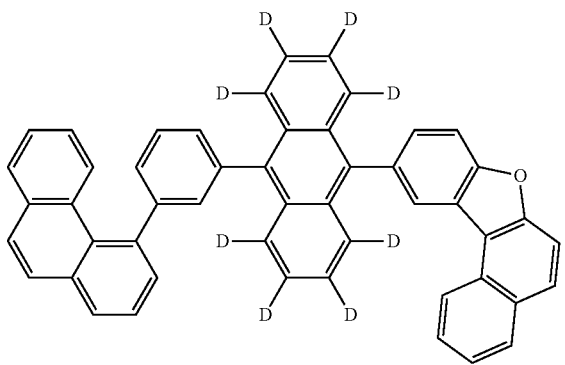
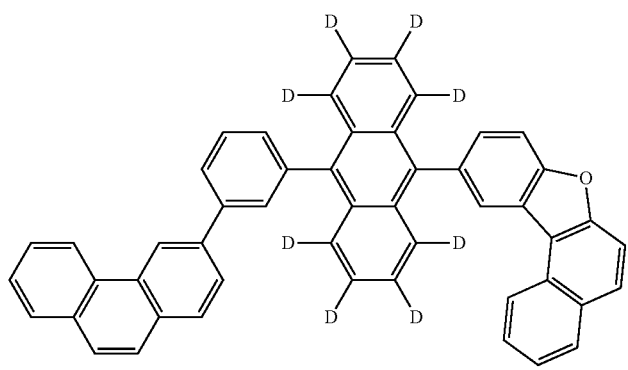
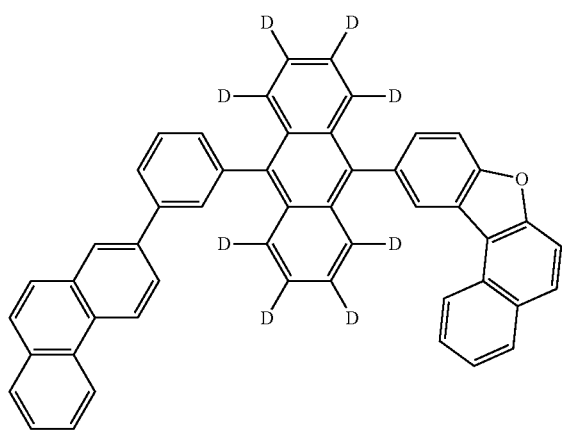
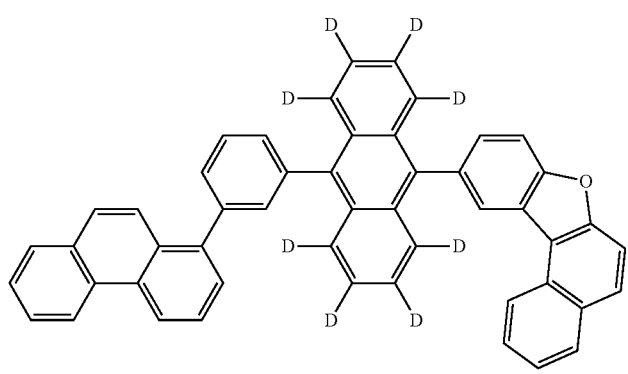
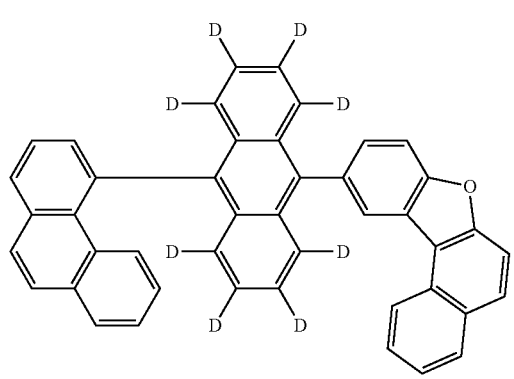

305
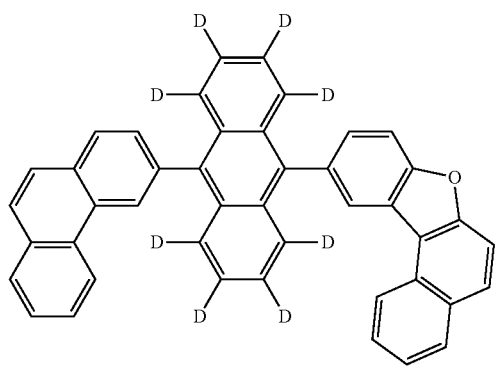
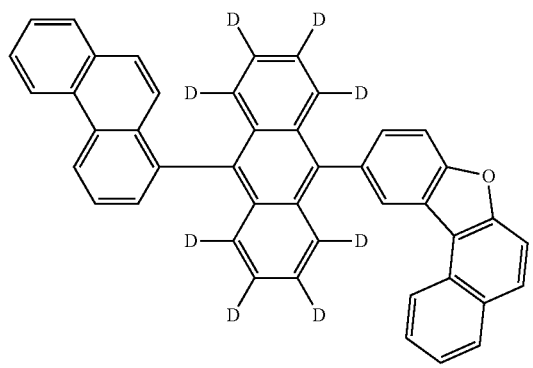
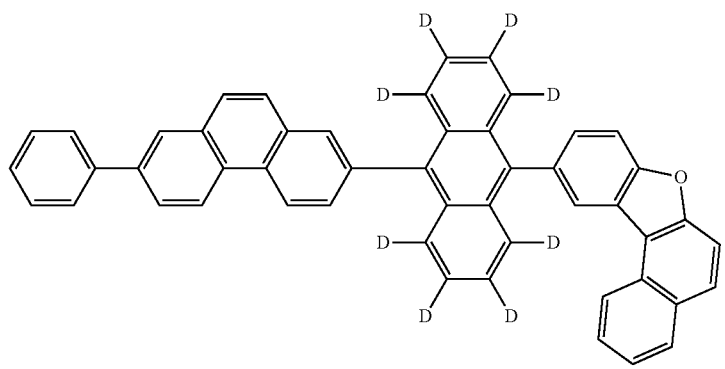
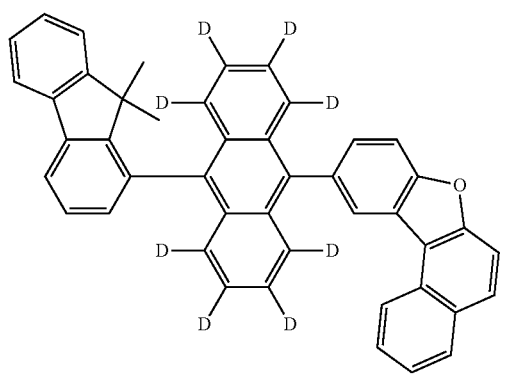
306
-continued
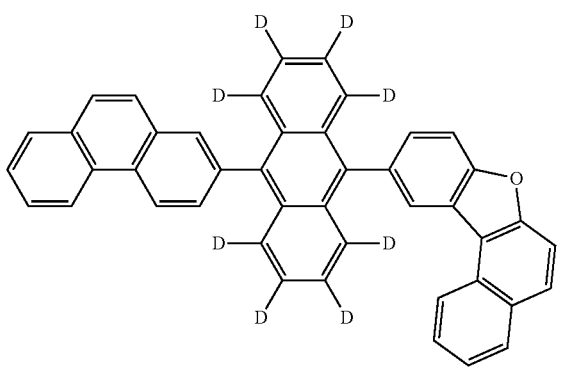
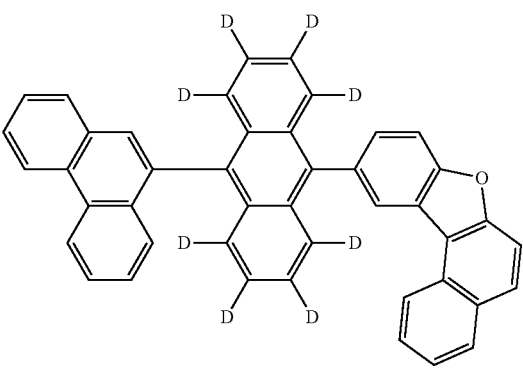
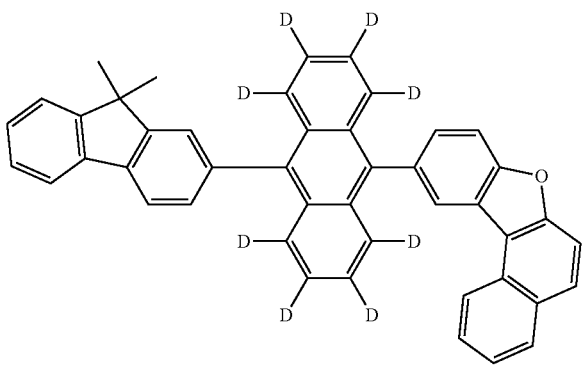

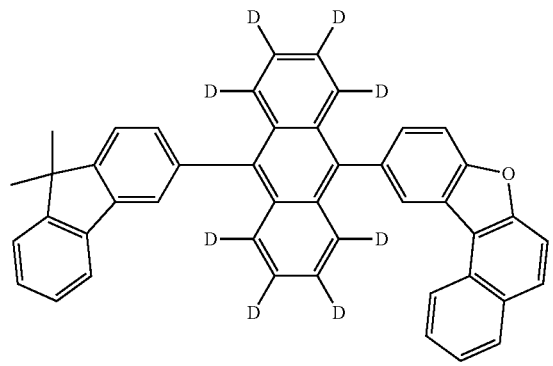
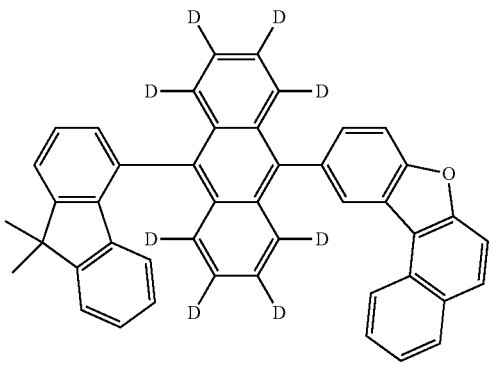
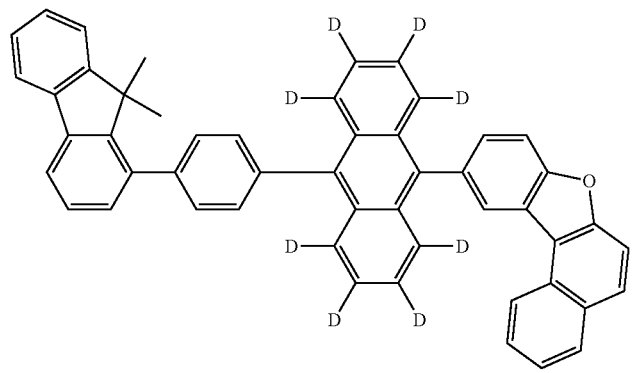
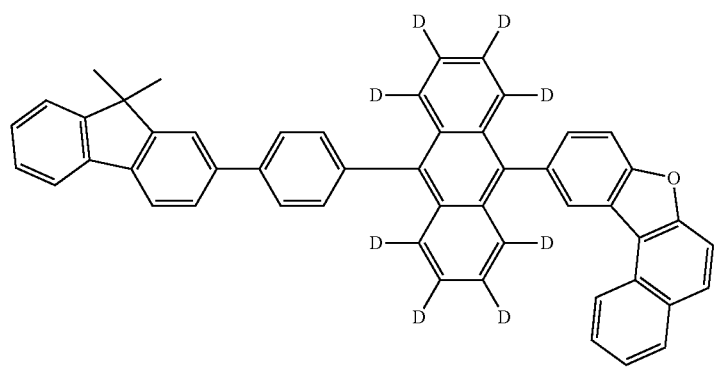
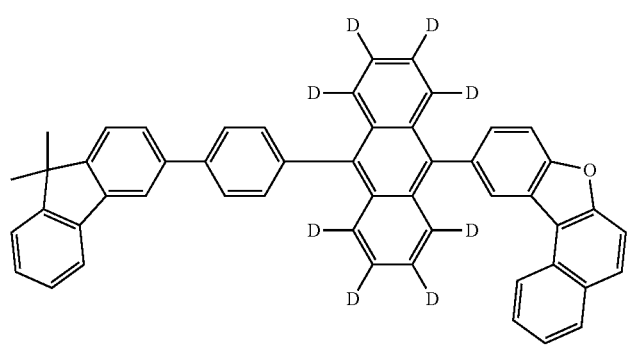

-continued
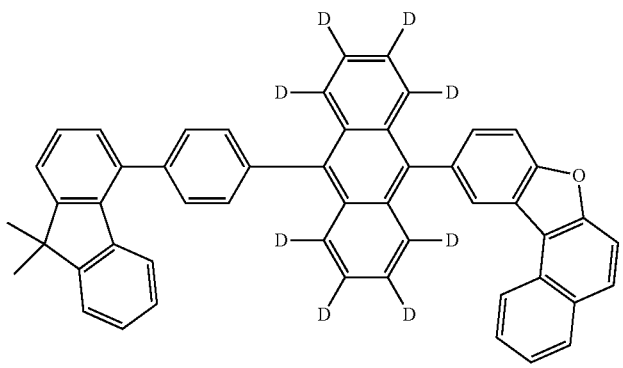
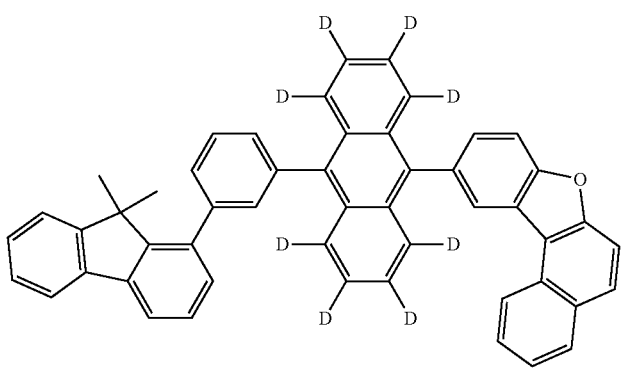
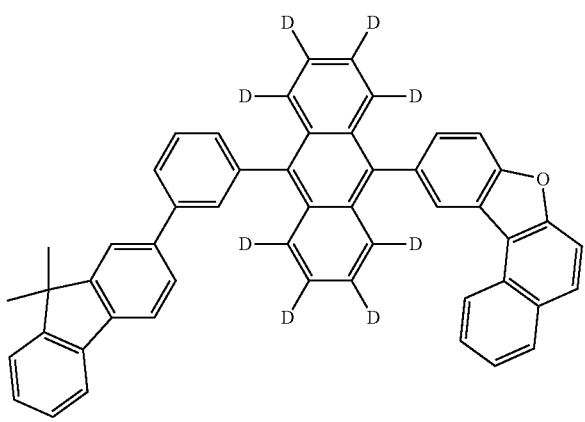
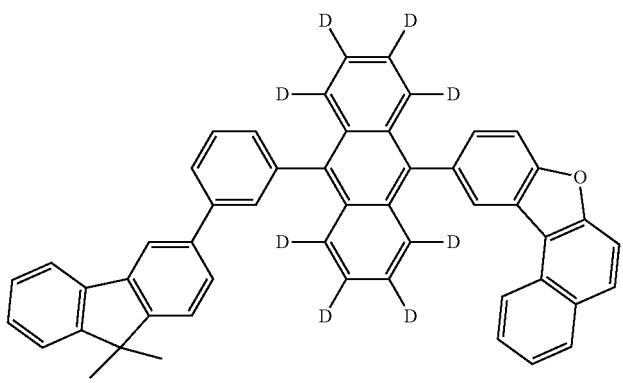

-continued
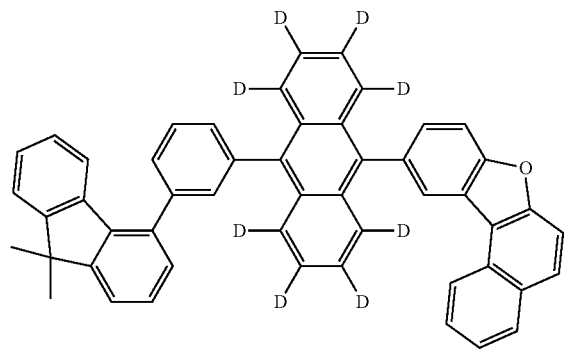
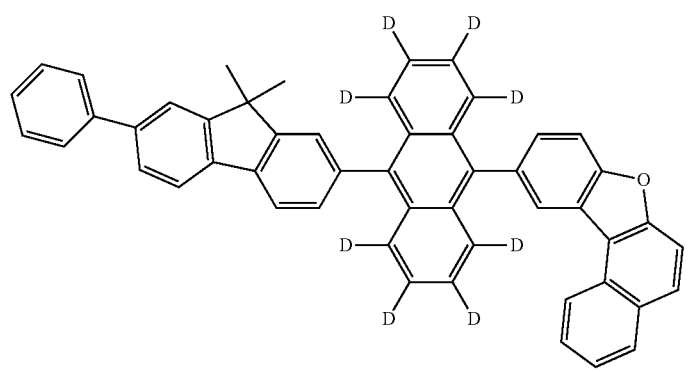
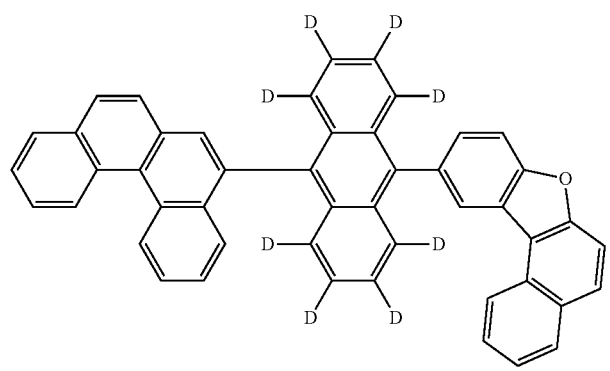
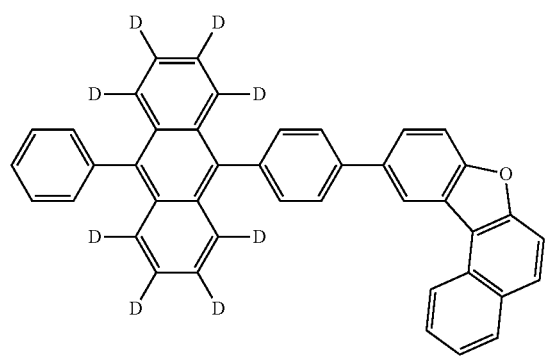
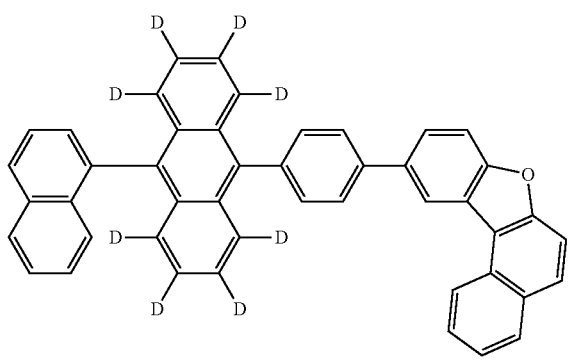

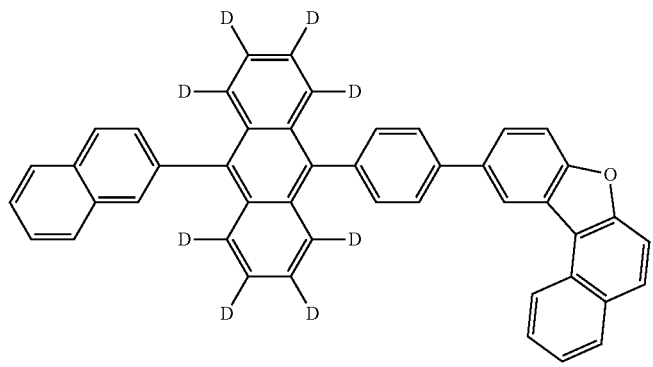
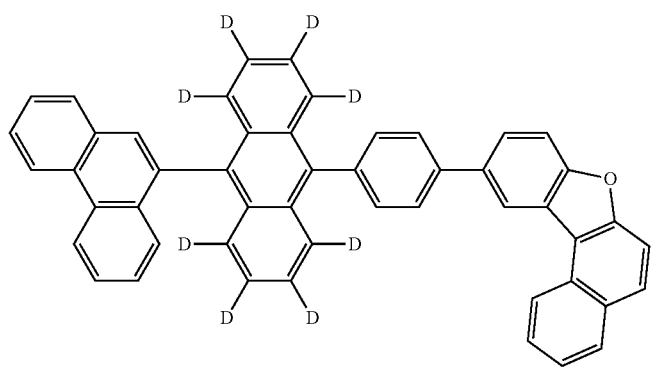
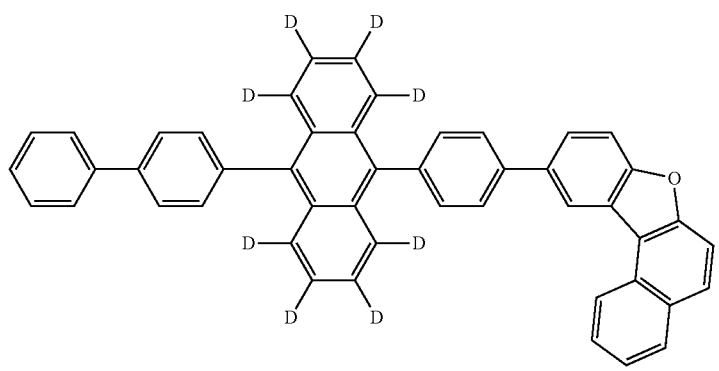
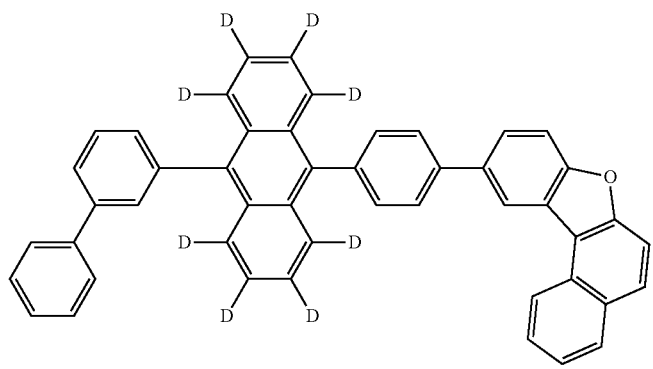

-continued
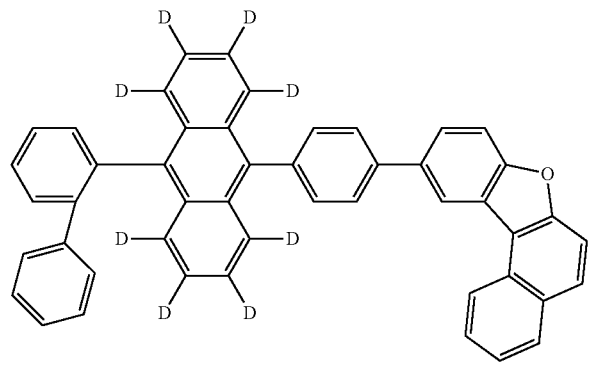
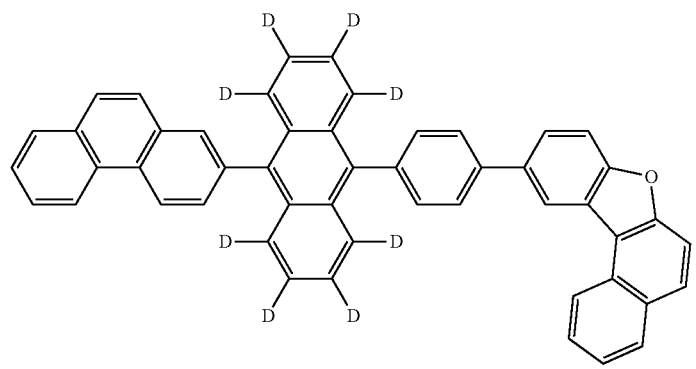
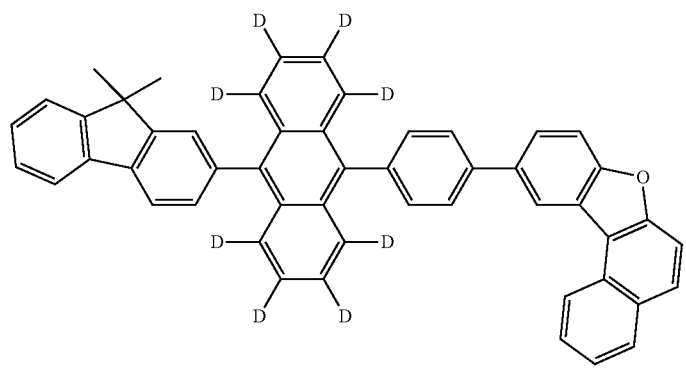
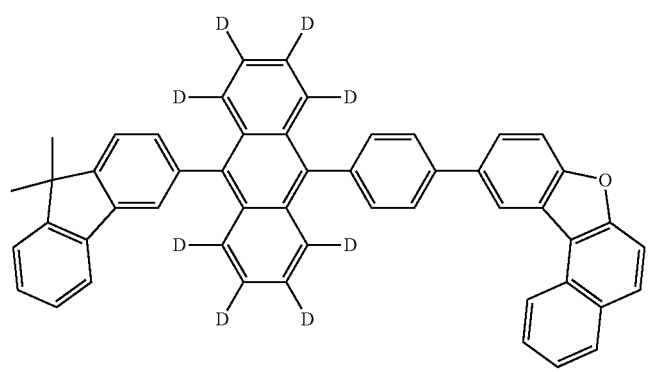

-continued
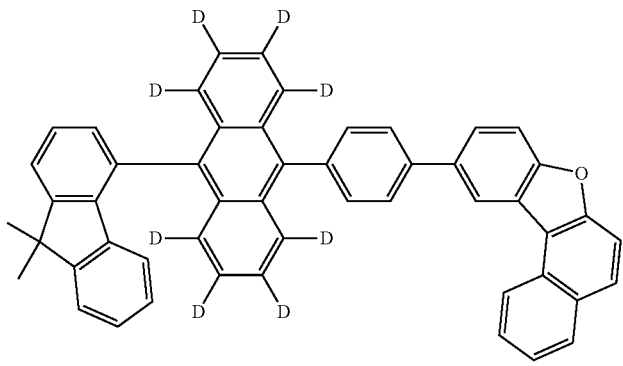
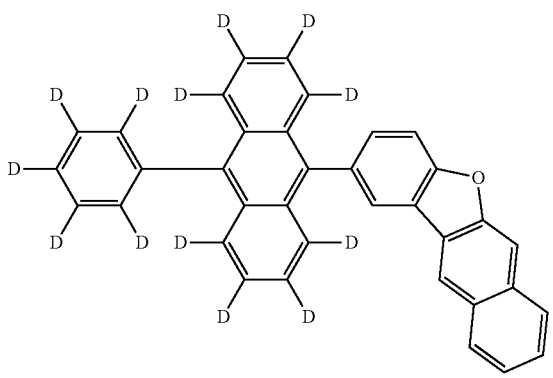
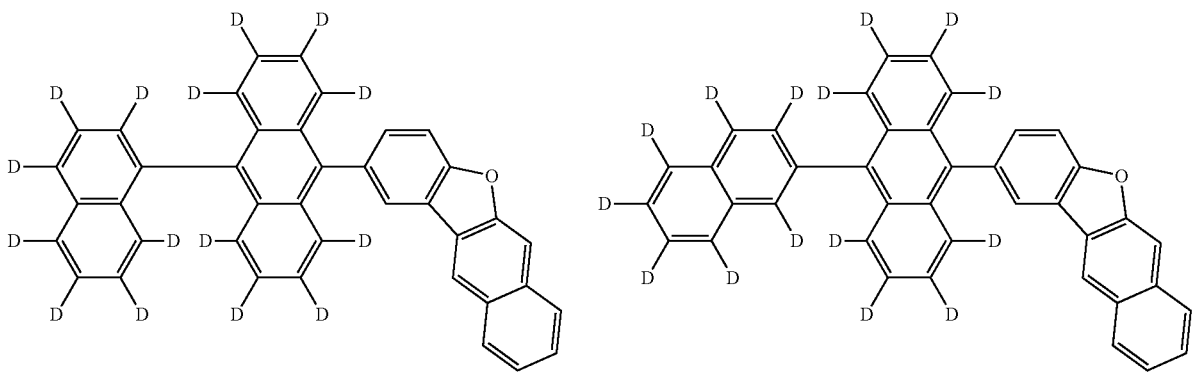
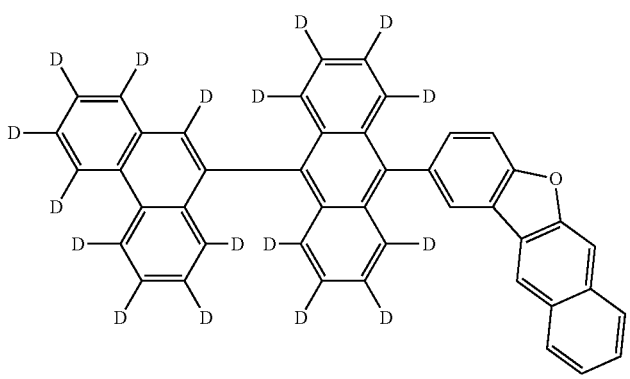

-continued
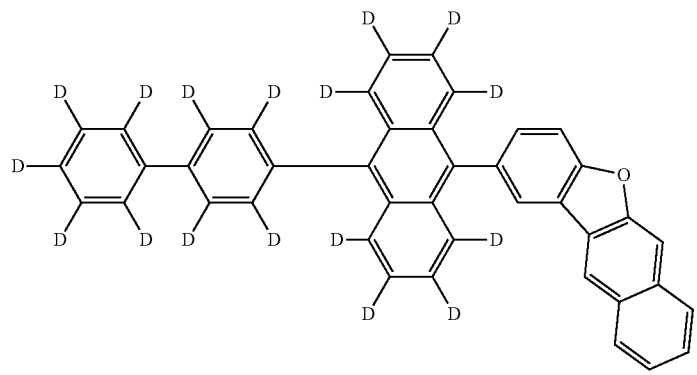
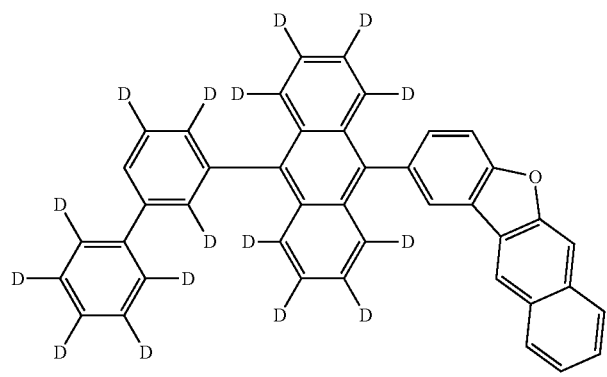
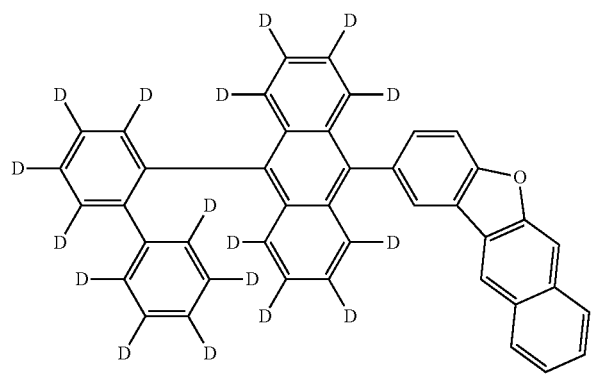
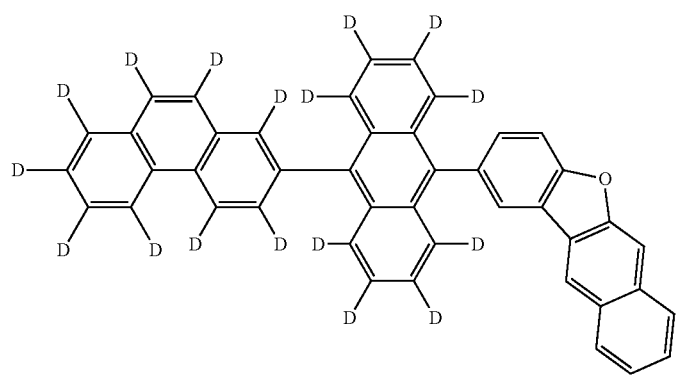

321
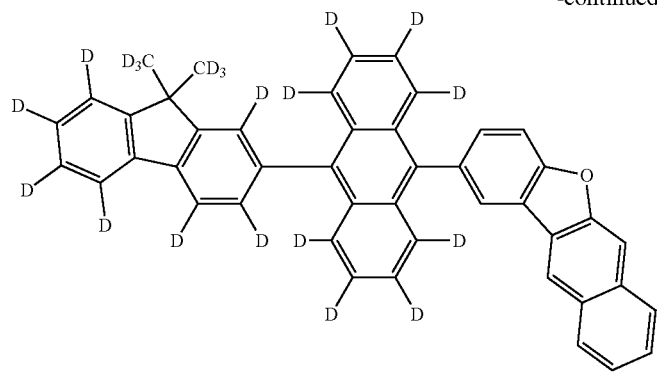
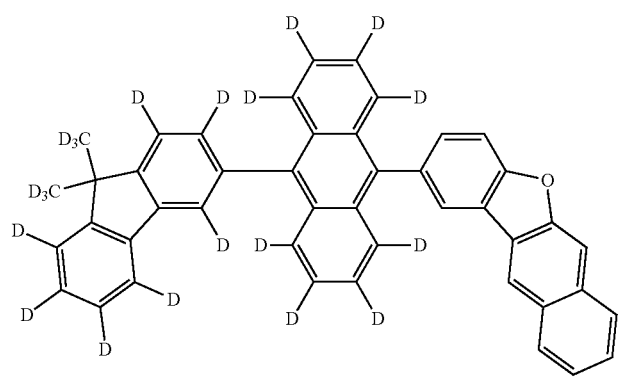
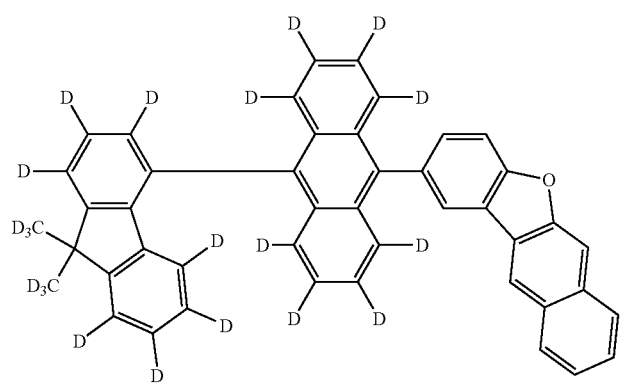
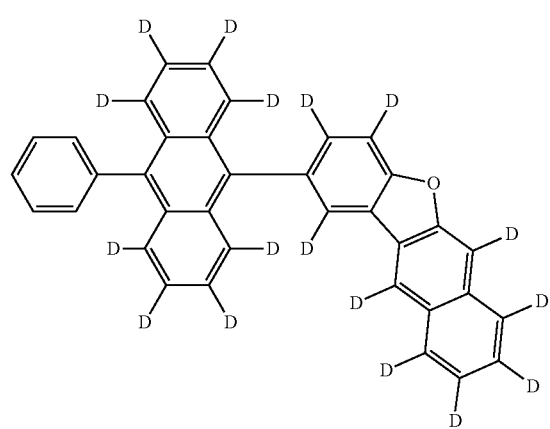
322
-continued
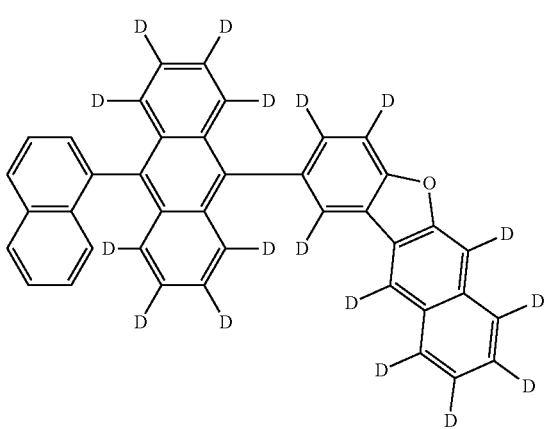

-continued
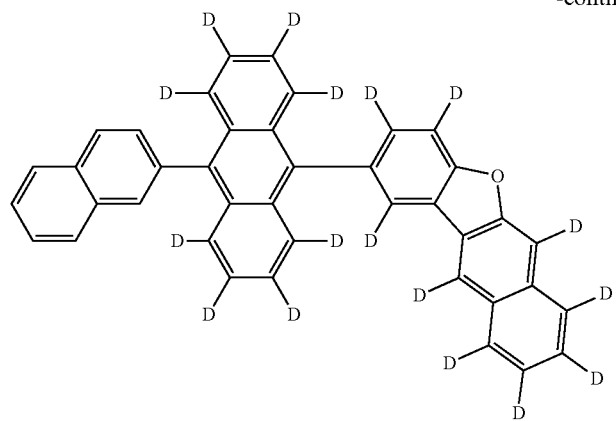
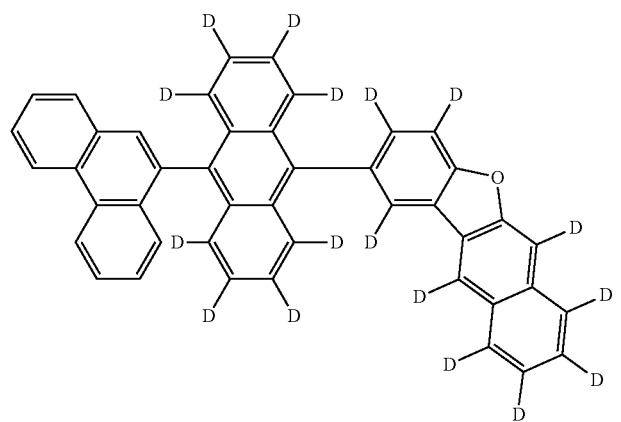
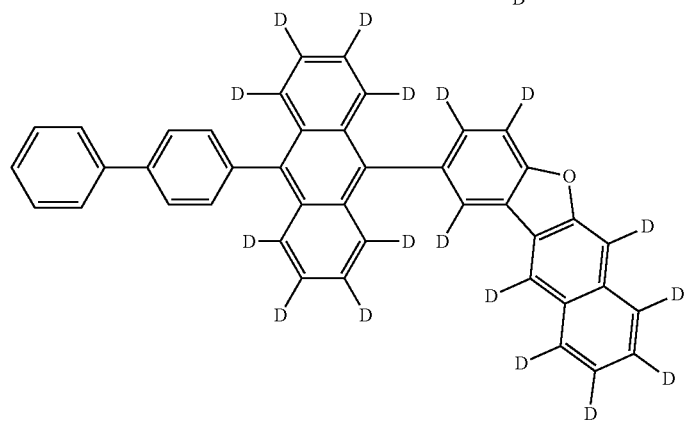
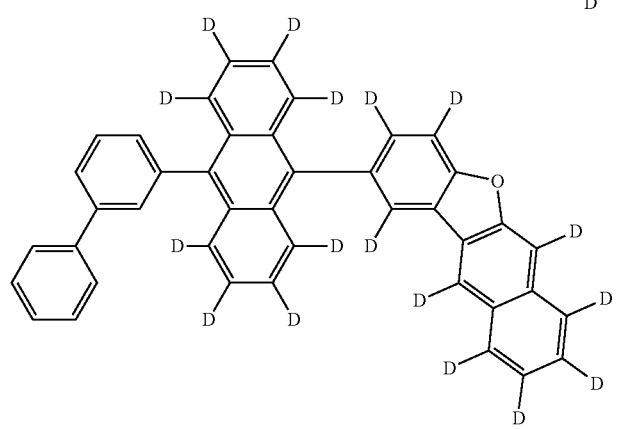

-continued
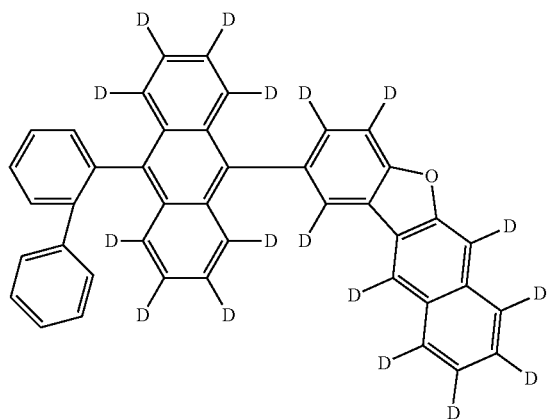
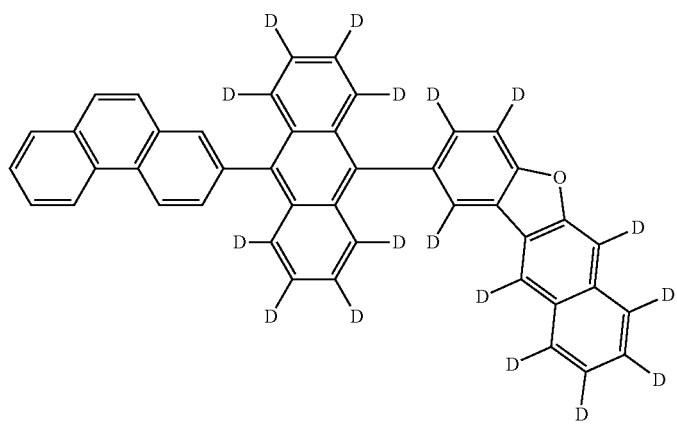
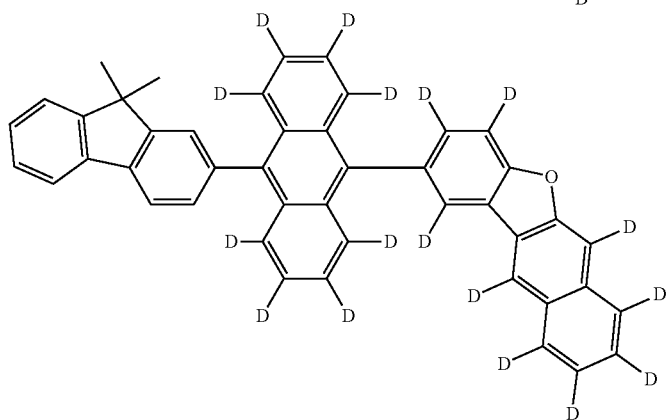
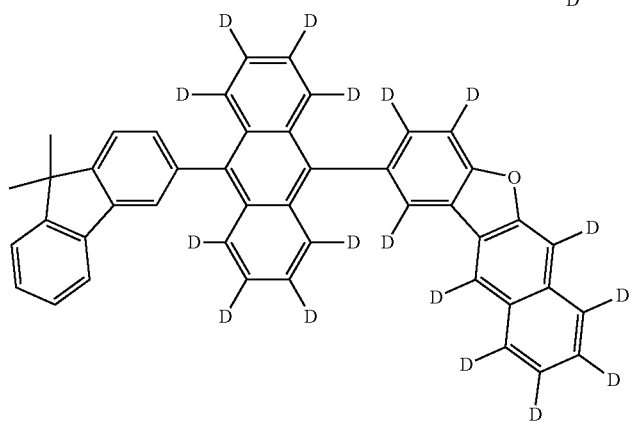

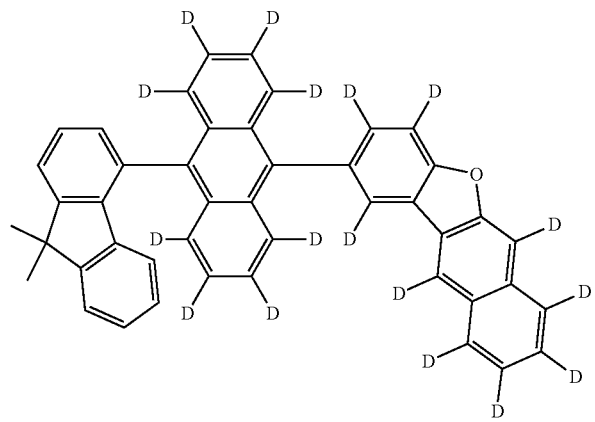 [SMILES: [2H]c1c(-c2c3c([2H])c([2H])c([2H])c([2H])c3c(-c3cccc4c3-c3ccccc3C4(C)C)c3c([2H])c([2H])c([2H])c([2H])c23)c([2H])c2c(oc3c([2H])c4c([2H])c([2H])c([2H])c([2H])c4c([2H])c32)c1[2H]]
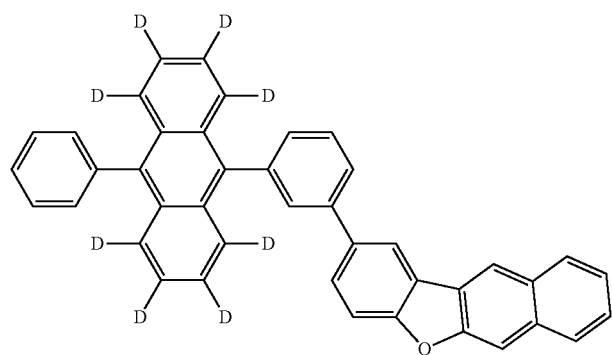
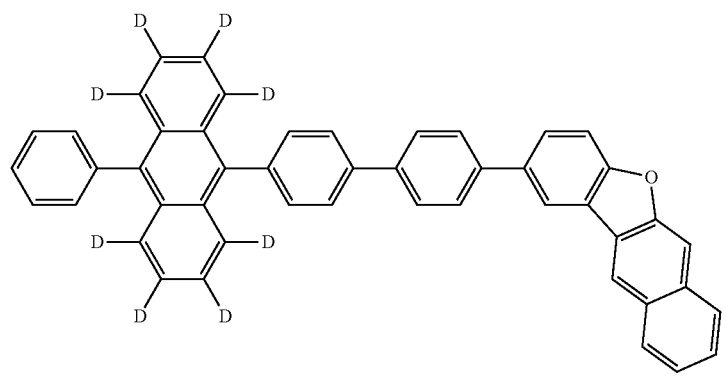
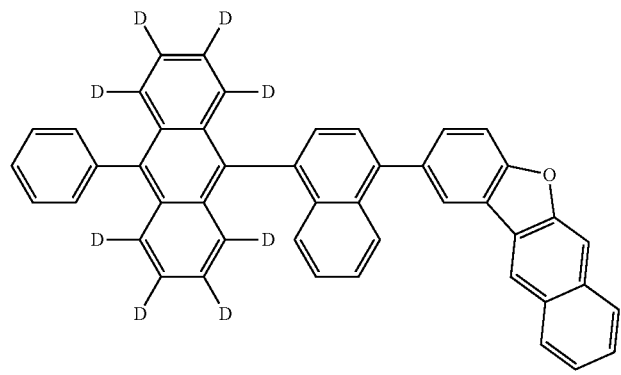

-continued
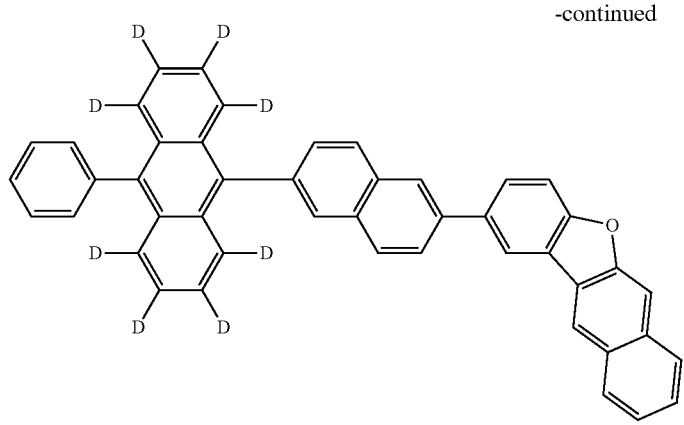
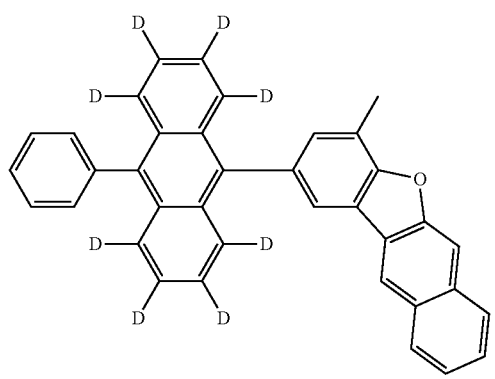
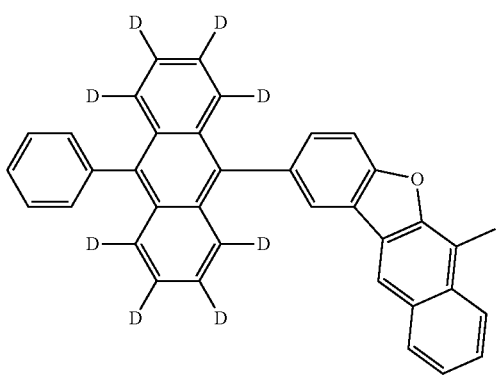
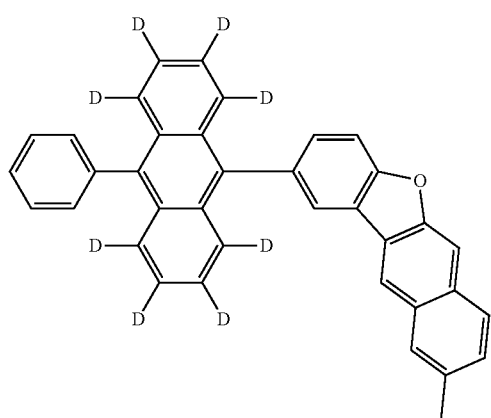
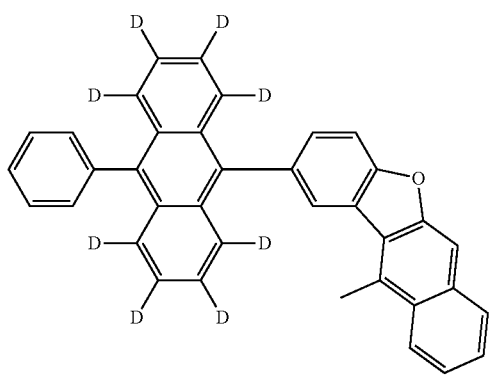
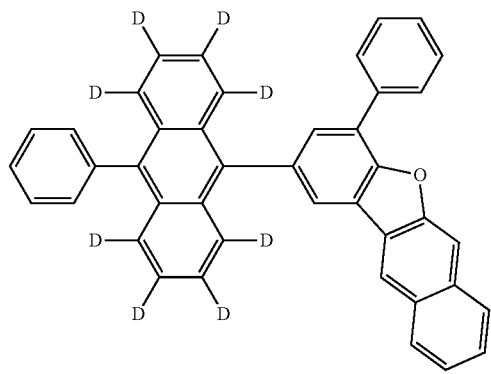
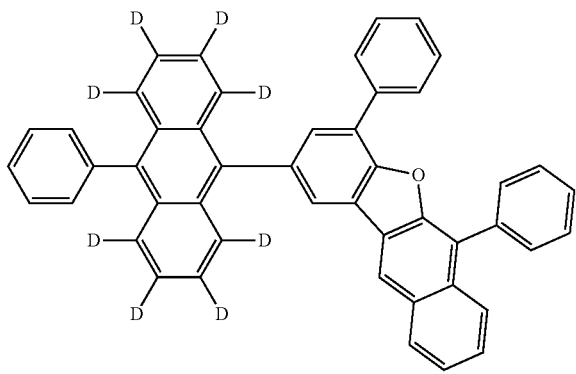

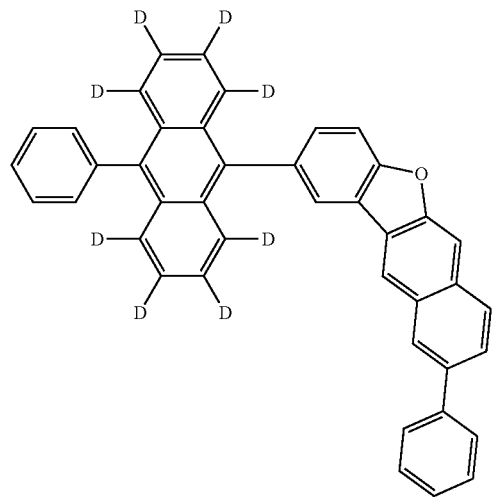
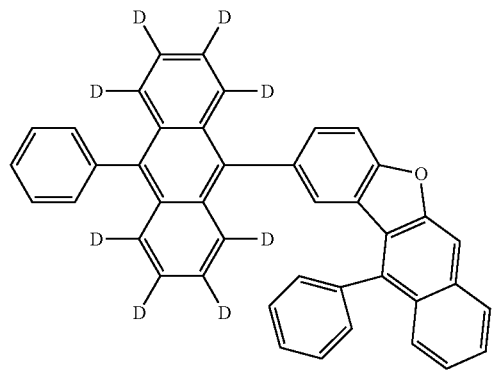
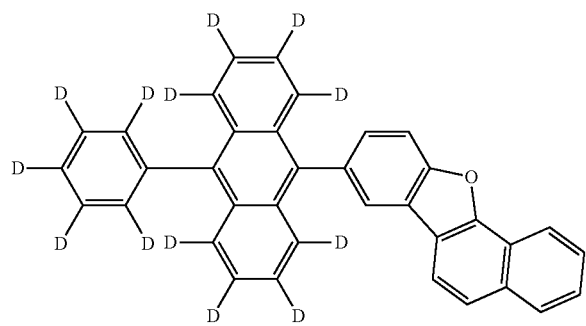
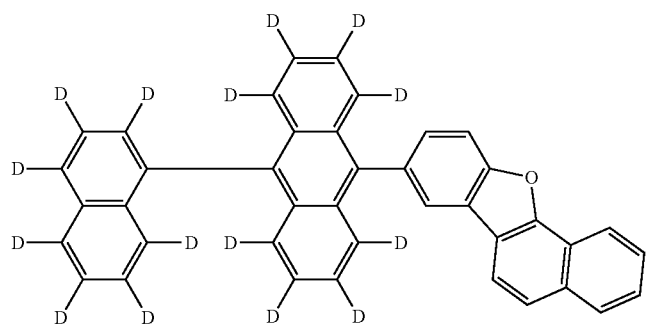
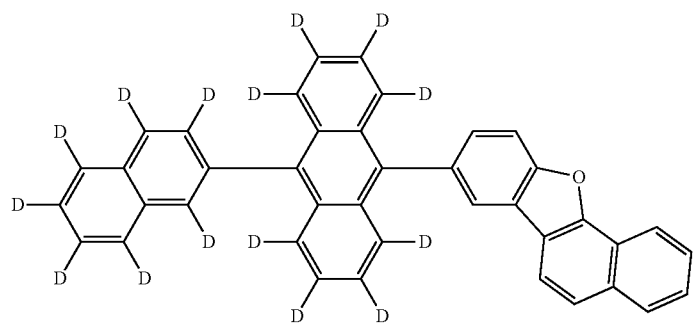

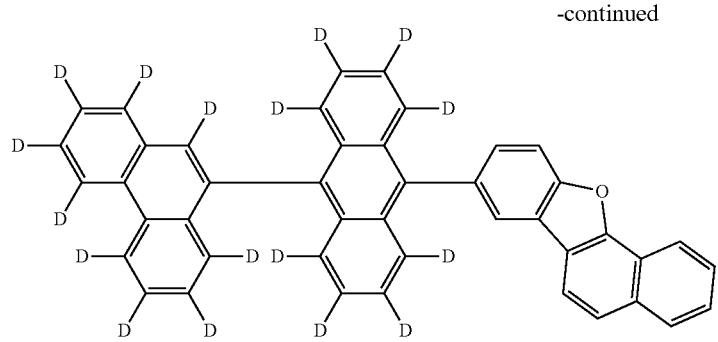
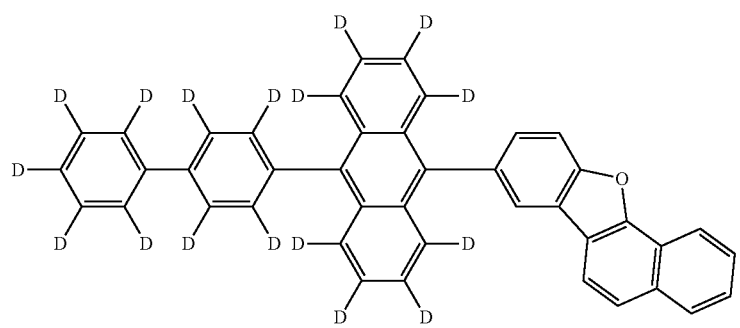
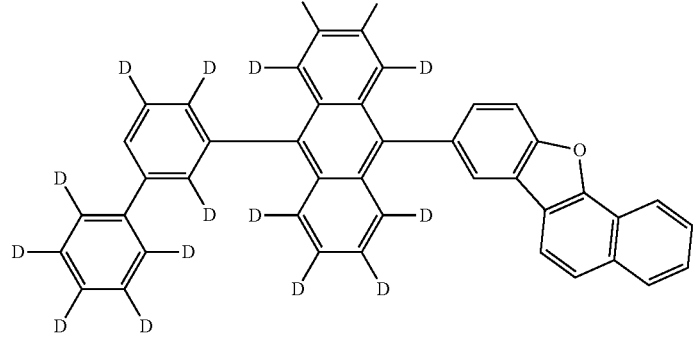
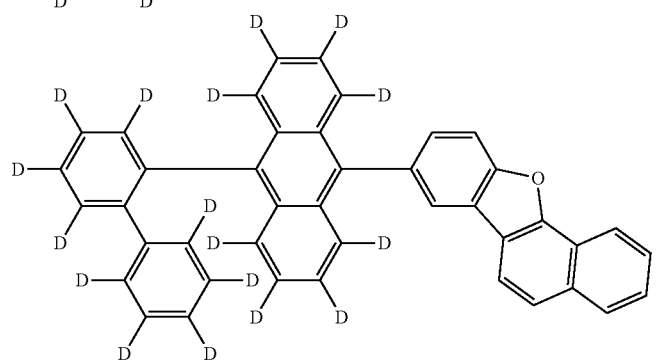
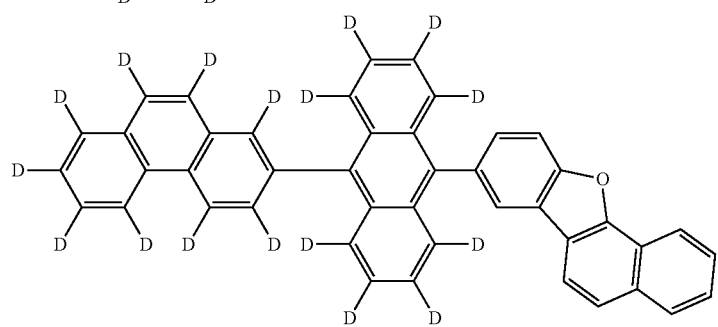

-continued
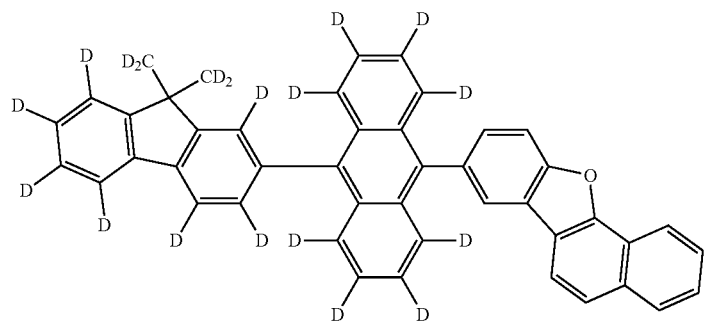
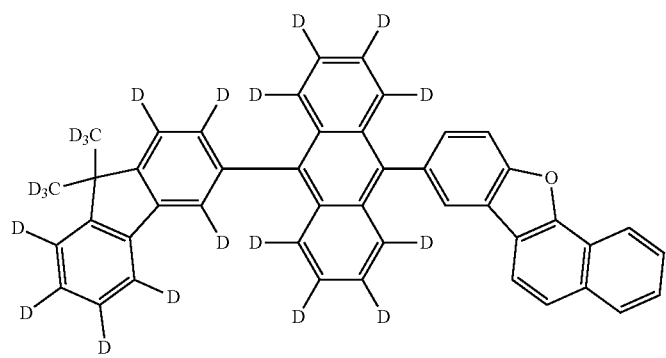
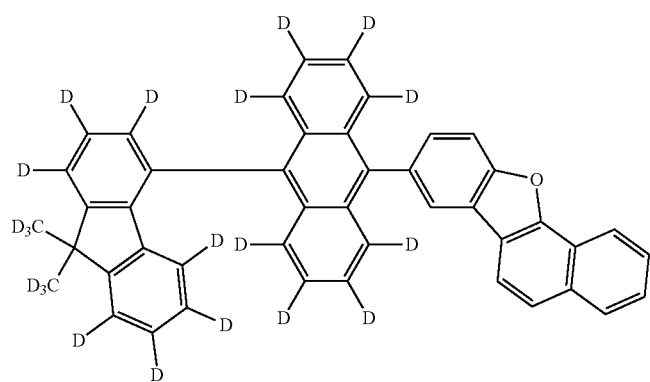
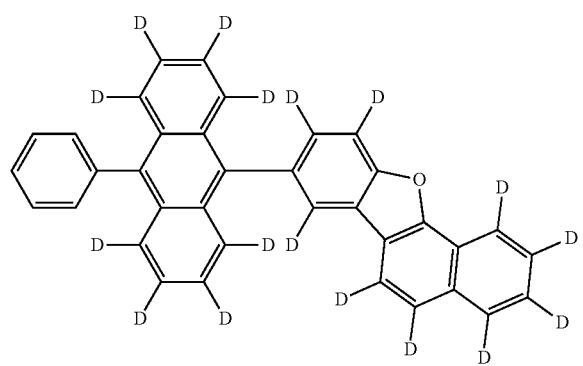

-continued
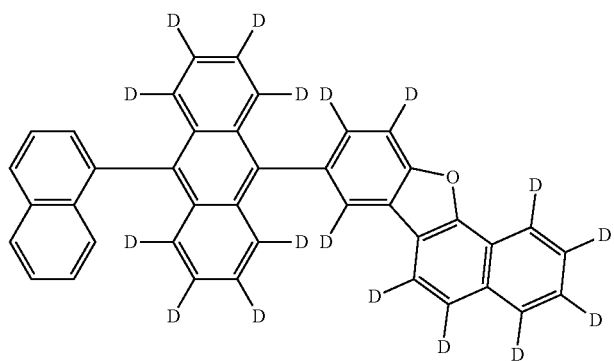
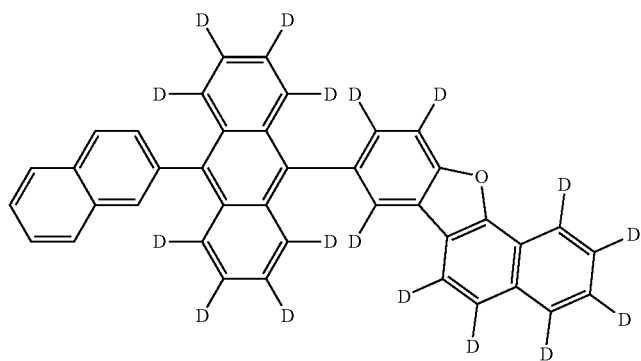
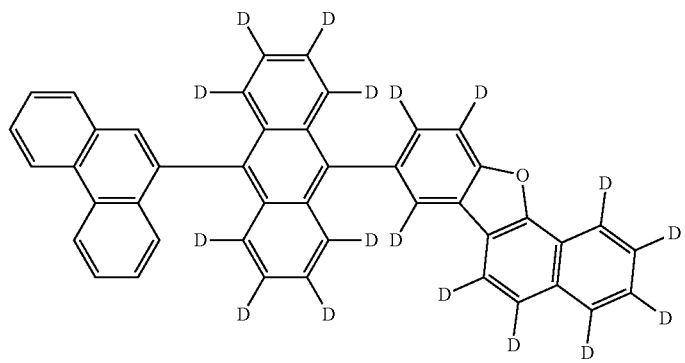
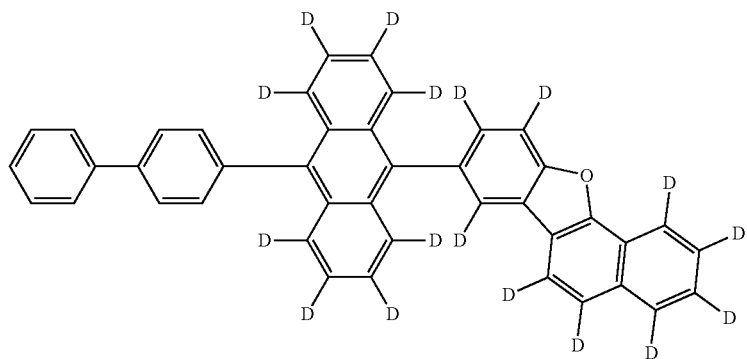

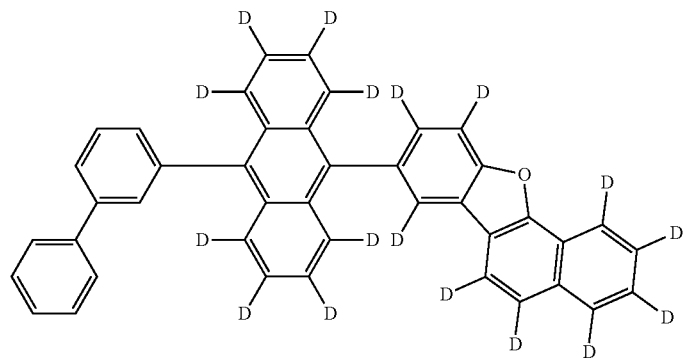
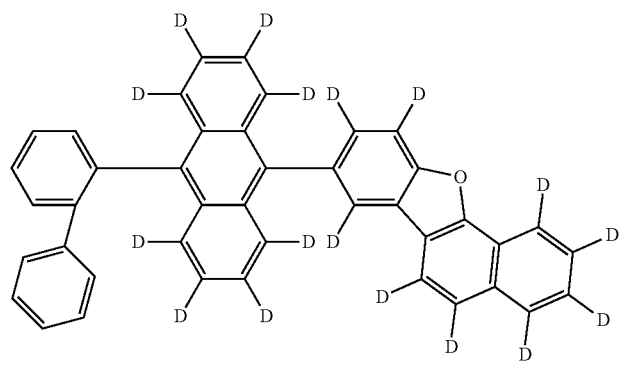
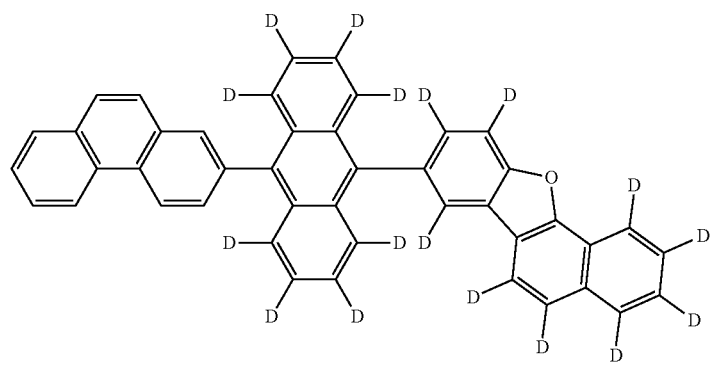
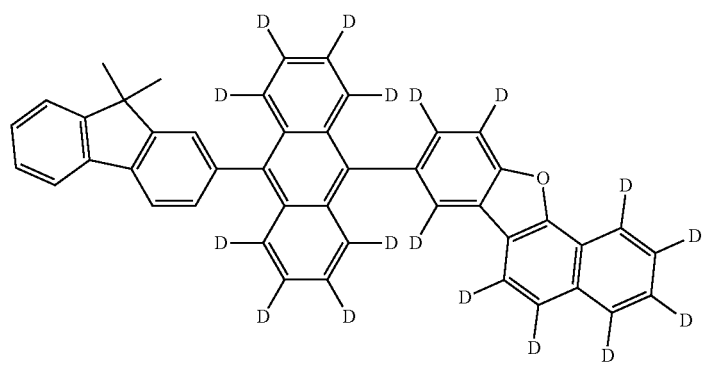

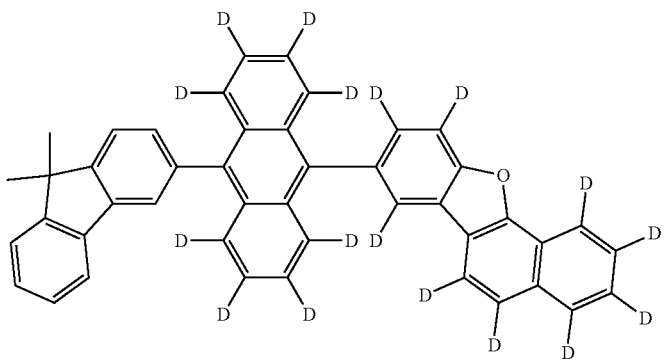
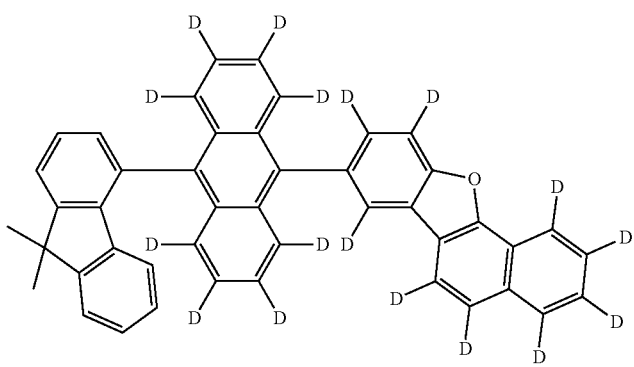
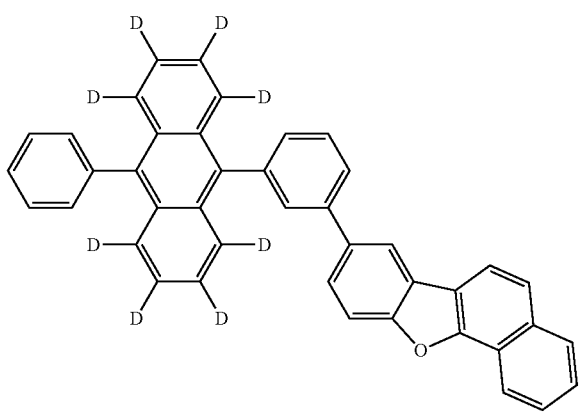
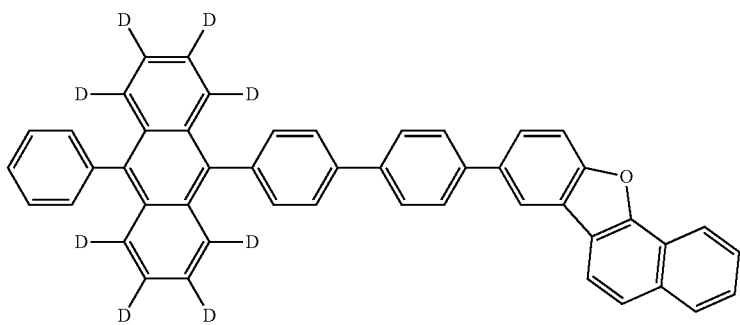

-continued
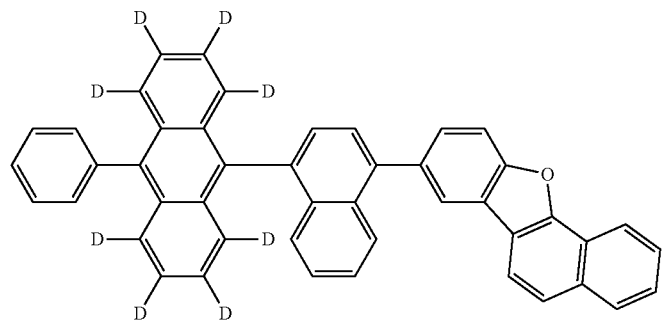
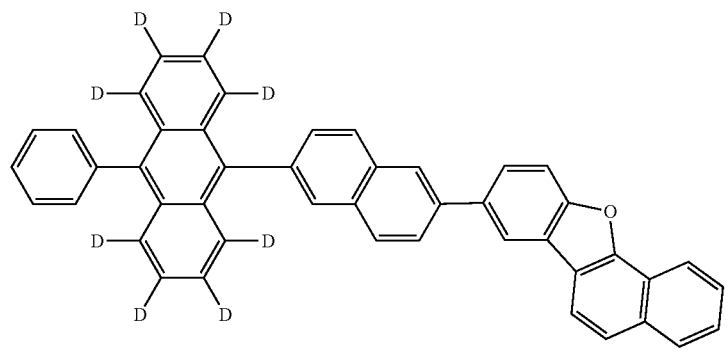
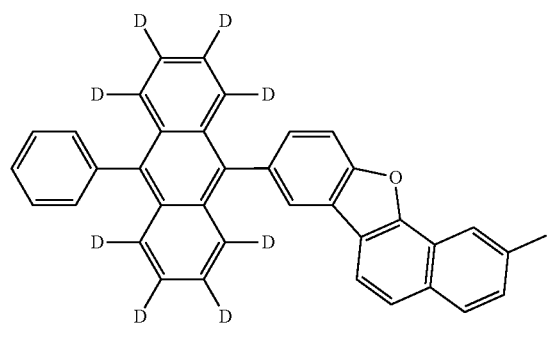
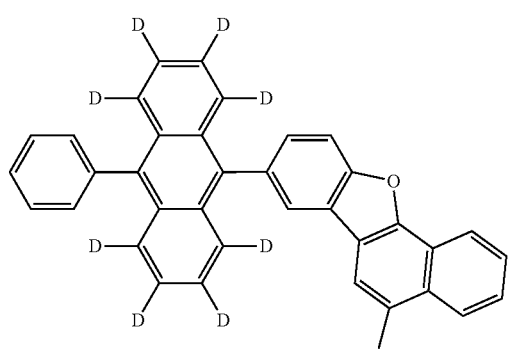
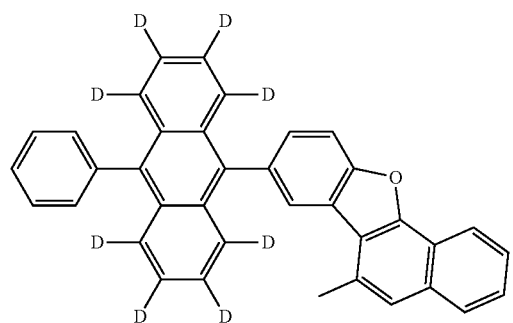
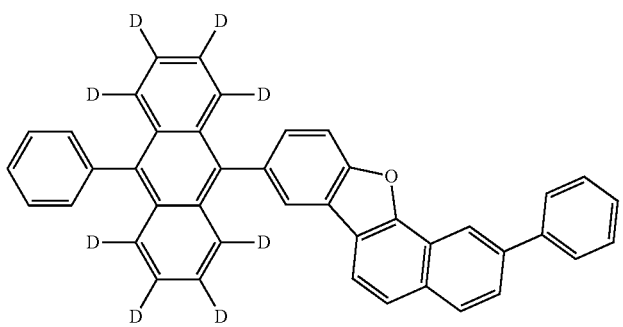

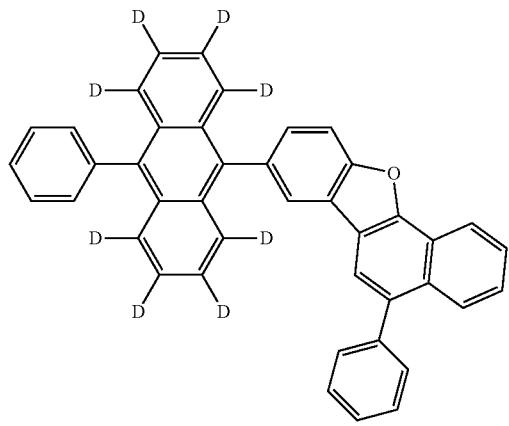
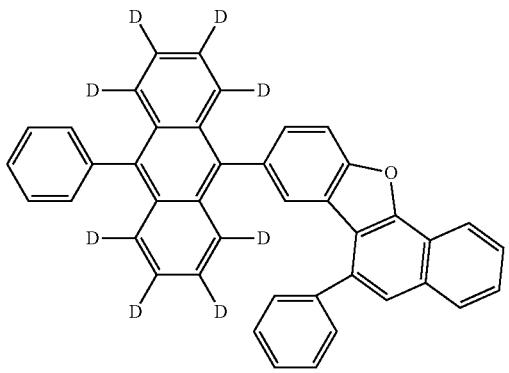
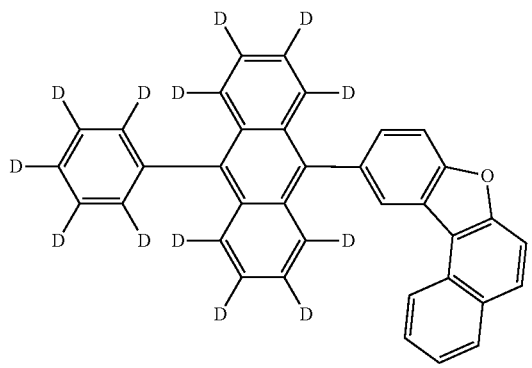
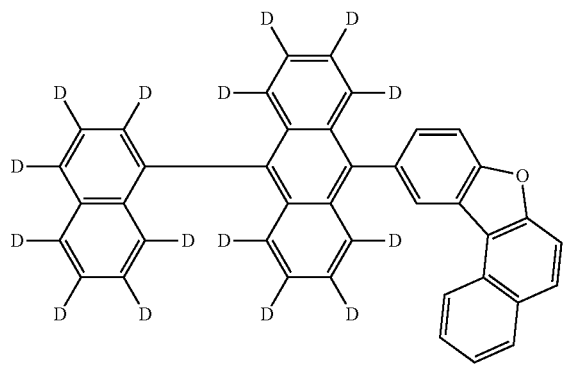
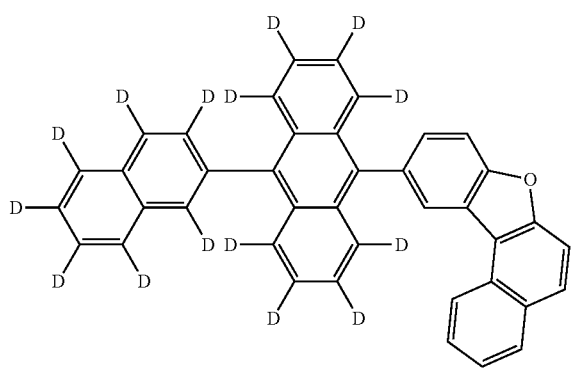
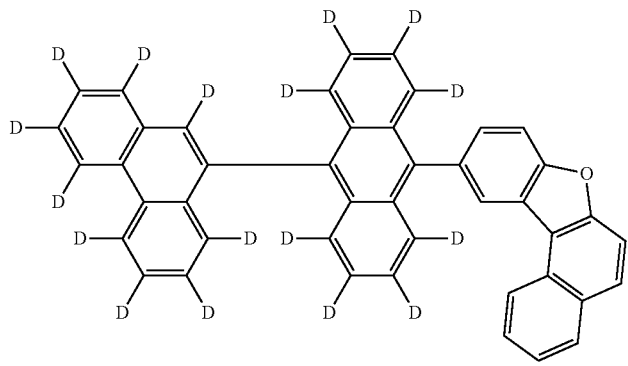

-continued
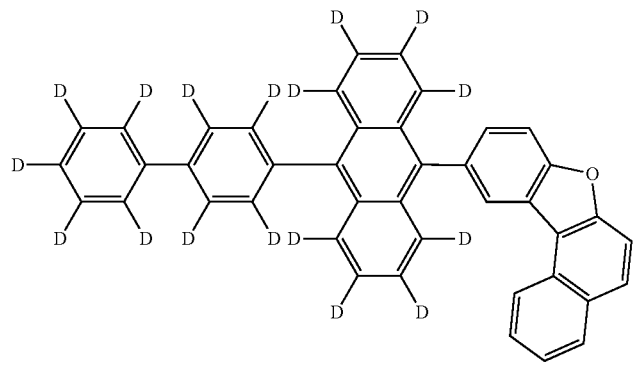
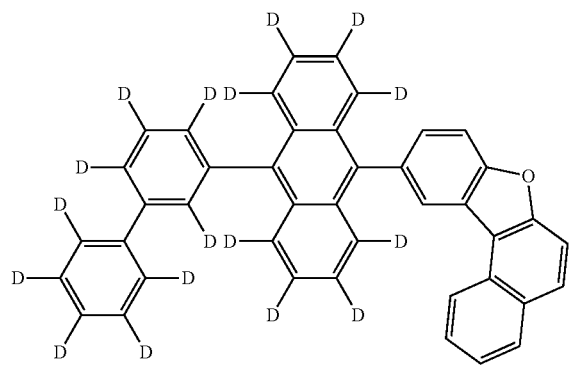
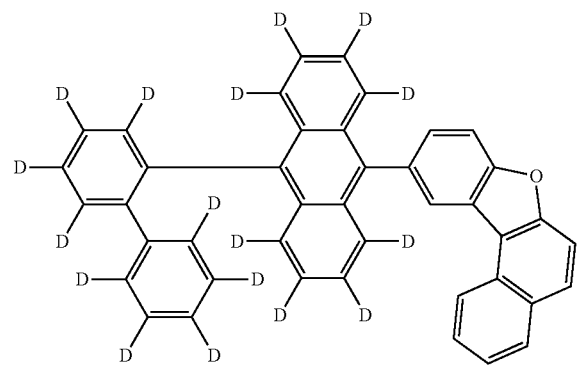
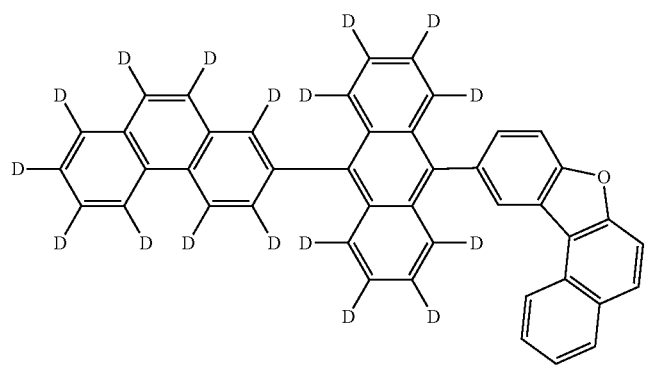
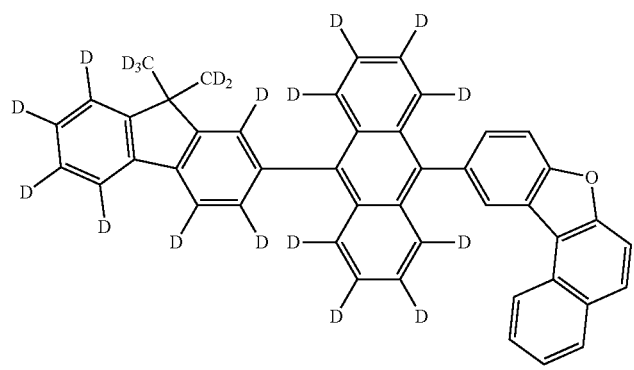

349
-continued
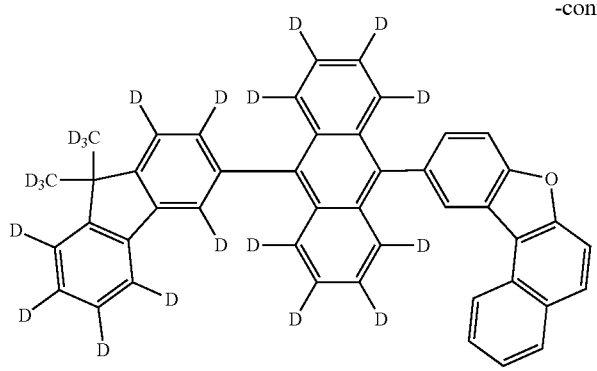
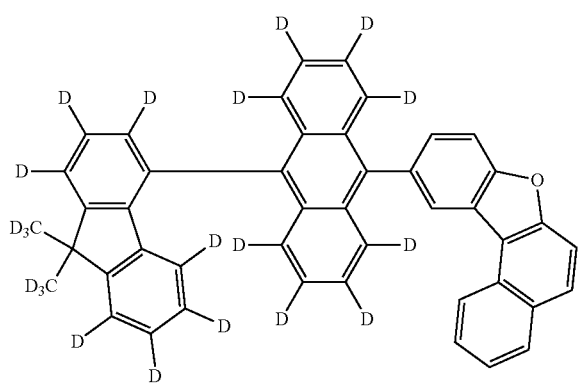
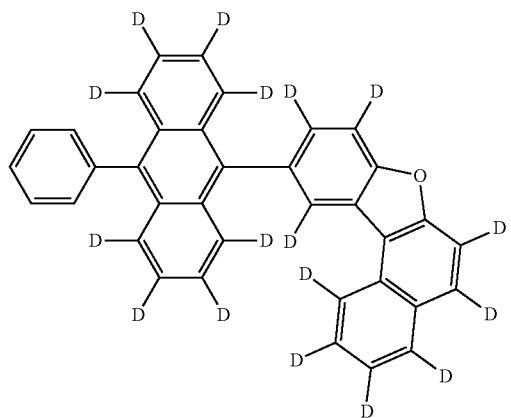
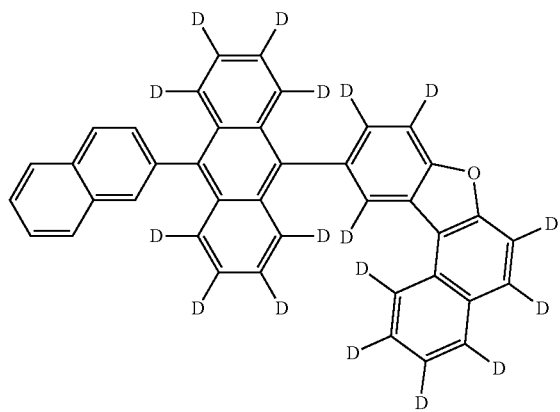
350
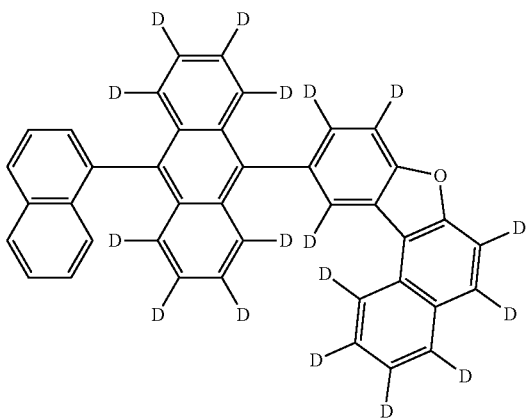
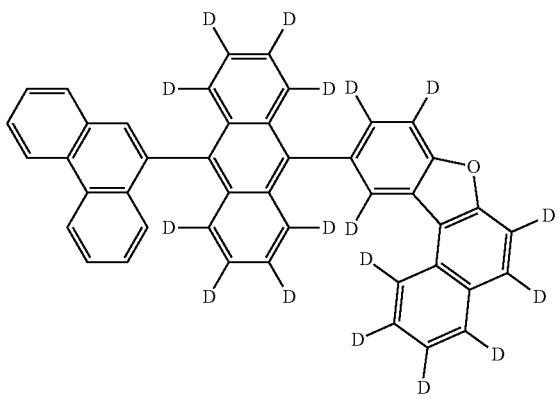

-continued
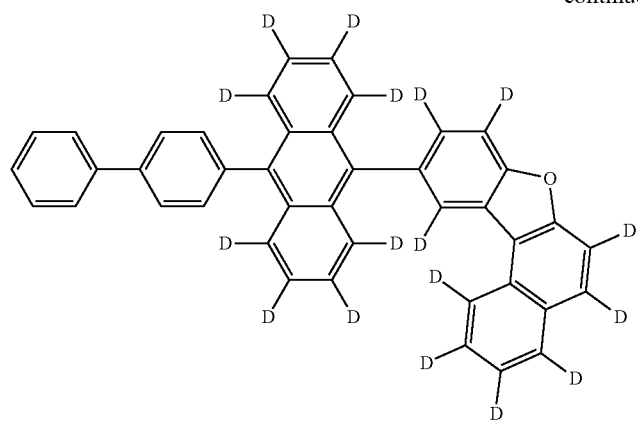
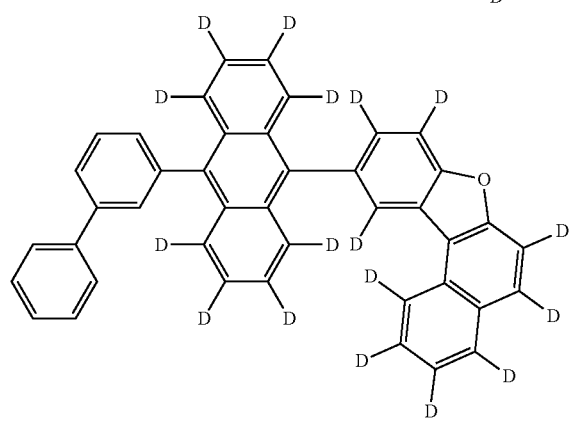
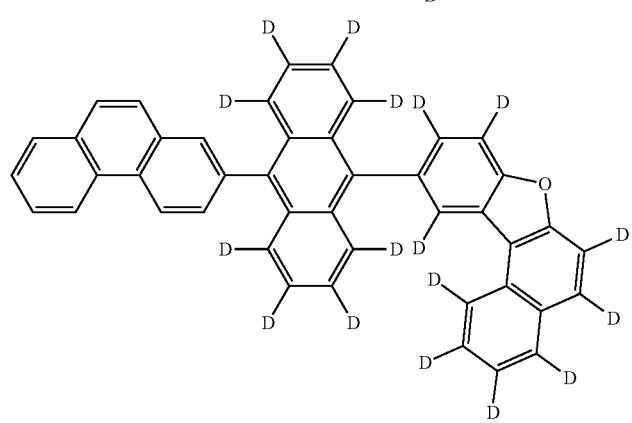
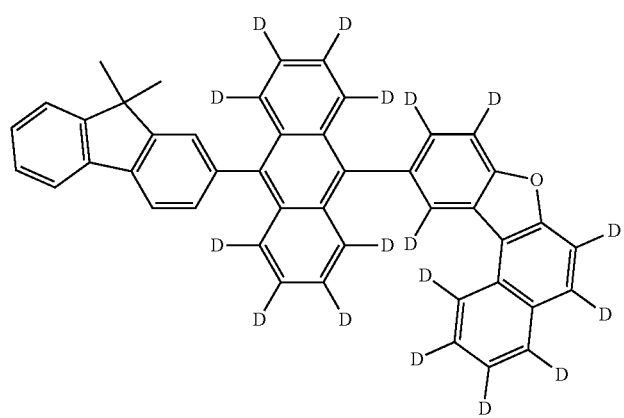

353 354
-continued
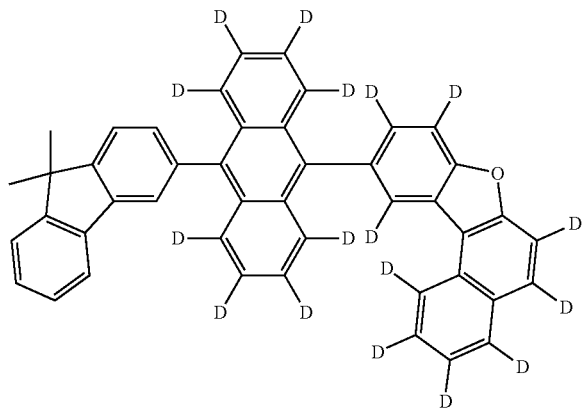
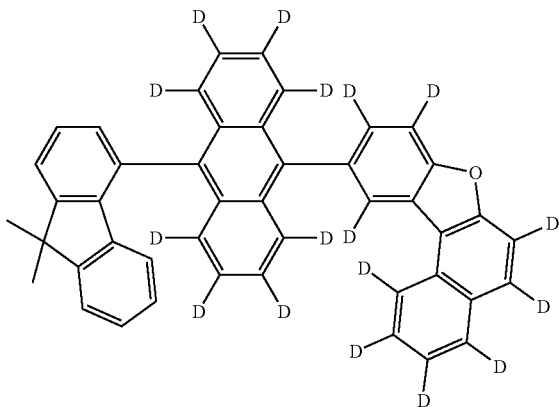
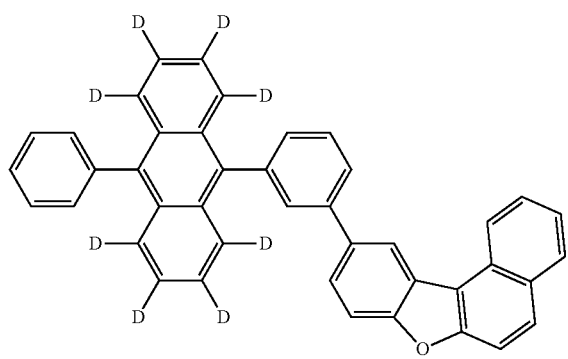
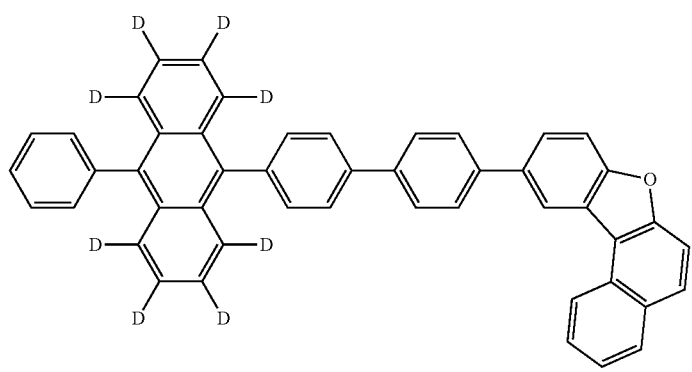
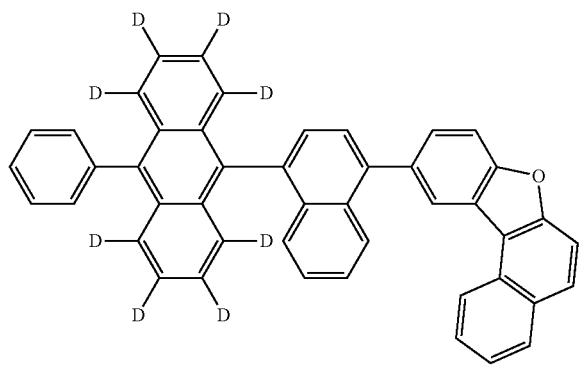

-continued
355
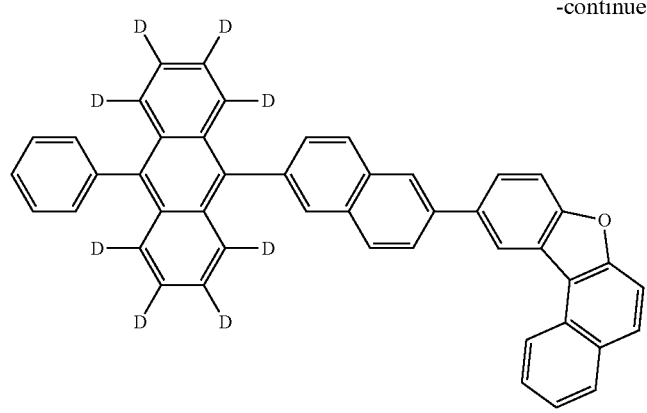
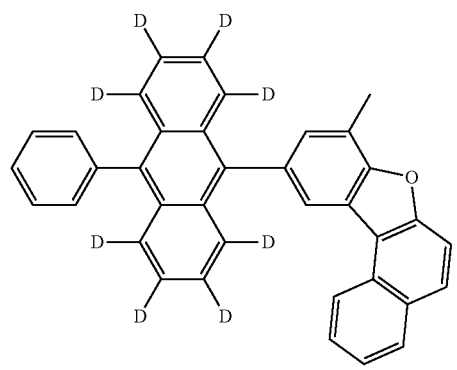
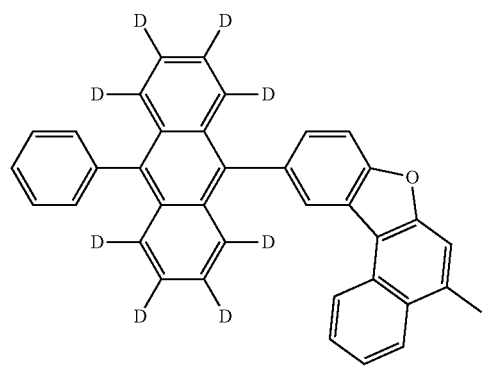
356
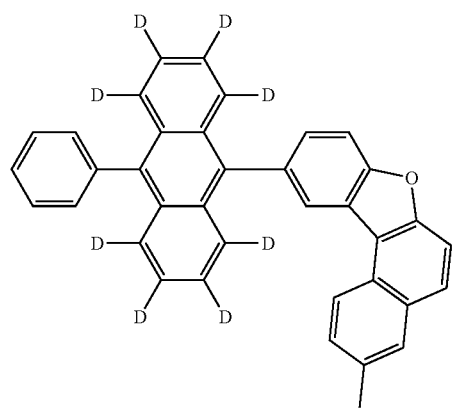
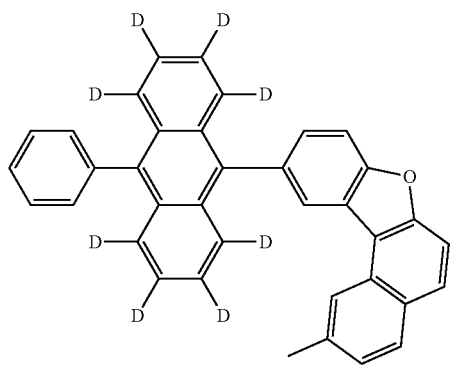
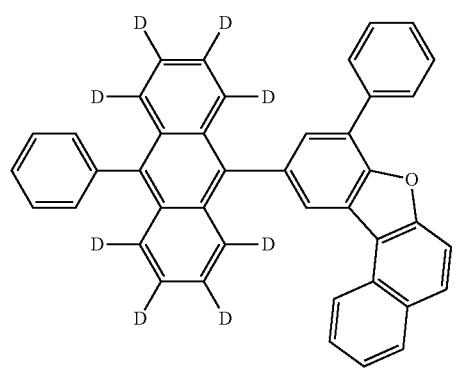
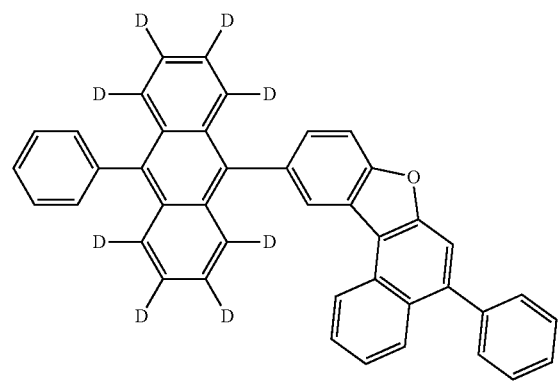

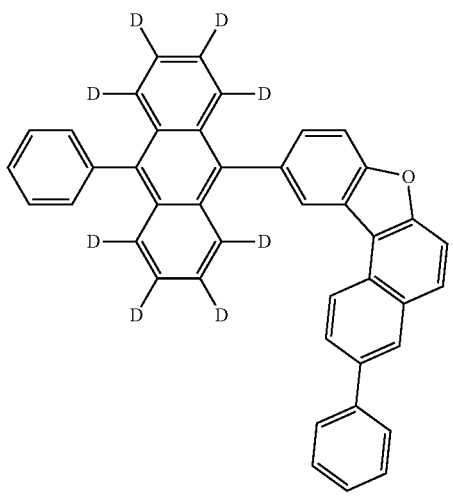

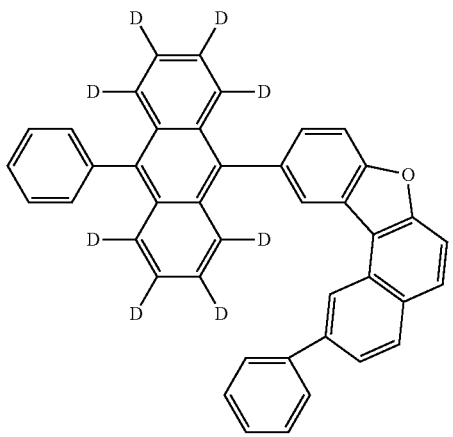

(Compound Represented by Formula (11))

The compound represented by the formula (11) is explained below,

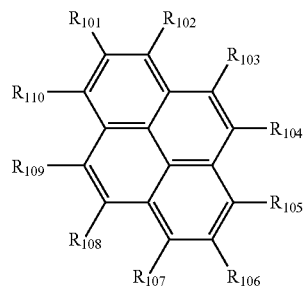

(11)

In the formula (11), one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;

at least one of $R_{101}$ to $R_{110}$ is a monovalent group represented by the formula (12);

$R_{90101}$ to $R_{110}$ that do not form the substituted or unsubstituted, saturated or unsaturated ring and that are not a monovalent group represented by the following formula (12) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

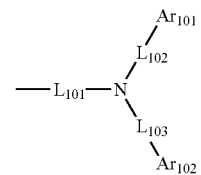

(12)

wherein, in the formula (12), $Ar_{101}$ and $Ar_{102}$ are independently a substituted or unsubstituted aryl group having 6 to 50 ring carbon atoms, or a substituted or unsubstituted monovalent heterocyclic group having 5 to 50 ring atoms;

$L_{101}$ to $L_{103}$ are independently a single bonded, a substituted or unsubstituted arylene group having 6 to 30 ring carbon atoms, or a substituted or unsubstituted divalent heterocyclic group having 5 to 30 ring atoms;

In the formula (11), it is preferable that two of $R_{101}$ to $R_{110}$ are the group represented by the formula (12).

In one embodiment, the compound represented by the formula (11) is represented by the following formula (13):

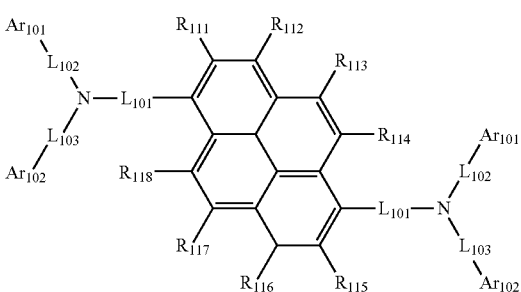

(13)

wherein in the formula (13), $R_{111}$ to $R_{118}$ are the same as $R_{101}$ to $R_{110}$ that is not a monovalent group represented by the formula (12) in the formula (11). $Ar_{101}$, $Ar_{102}$, $L_{101}$, $L_{102}$ and $L_{103}$ are as defined in the formula (12).

In the formula (11), $L_{101}$ is preferably a single bond and $L_{102}$ and $L_{103}$ are preferably a single bond.

In one embodiment, the compound represented by the formula (11) is represented by the formula (14) or (15).

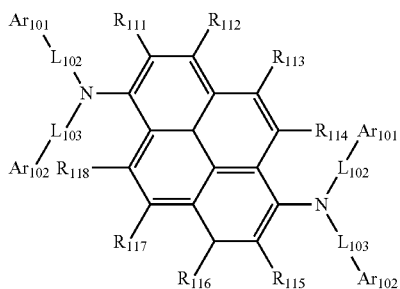
(14)

wherein in the formula (14), $R_{111}$ to $R_{118}$ are as defined in the formula (13). $Ar_{101}$, $Ar_{102}$, $L_{102}$ and $L_{103}$ are as defined in the formula (12).

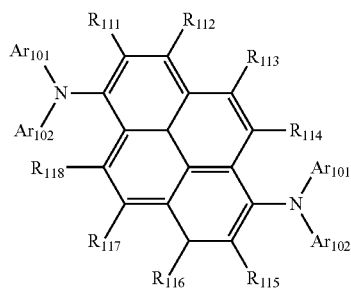
(15)

wherein in the formula (15), $R_{111}$ to $R_{118}$ are as defined in the formula (13). $A_{101}$ and $Ar_{102}$ are as defined in the formula (12)

In the formula (11) and formula (12), it is preferable that at least one $Ar_{101}$ and $Ar_{102}$ is the group represented by the following formula (16).

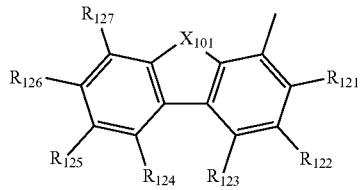
(16)

wherein in the formula (16).

$X_{101}$ is an oxygen atom or a sulfur atom;

One or more pairs of two or more adjacent groups of $R_{121}$ to $R_{127}$ are bonded with each other to form a substituted or unsubstituted, saturated or unsaturated ring, or do not form a substituted or unsubstituted, saturated or unsaturated ring;

$R_{121}$ to $R_{127}$ that do not form the substituted or unsubstituted, saturated or unsaturated ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

It is preferable that $X_{101}$ is an oxygen atom.

It is preferable that at least one of $R_{121}$ to $R_{127}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

It is preferable that in the formula (11) and formula (12), $Ar_{101}$ is a group represented by the formula (16) and $Ar_{102}$ is a substituted or unsubstituted aryl group having 6 to 50 ring carbon atoms.

In one embodiment, the compound represented by the formula (11) is represented by the following formula (17).

(17)

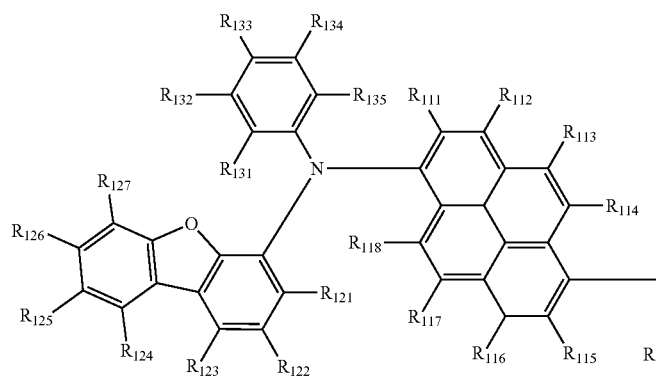

wherein in the formula (17), $R_{111}$ to $R_{118}$ are as defined in the formula (13), and $R_{121}$ to $R_{127}$ are as defined in the formula (16);

$R_{131}$ to $R_{135}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

As the compound represented by the formula (11), the following compounds can be given as specific examples, for example. In the following example compounds, Me represents a methyl group.

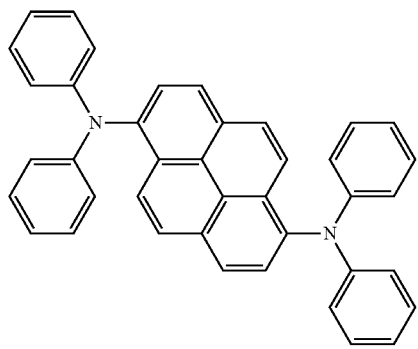

-continued

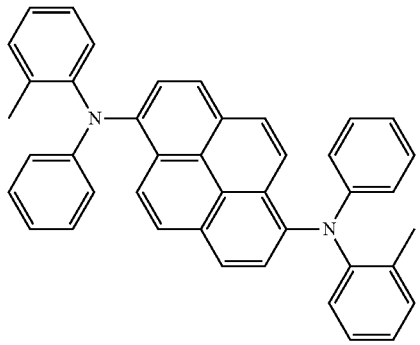

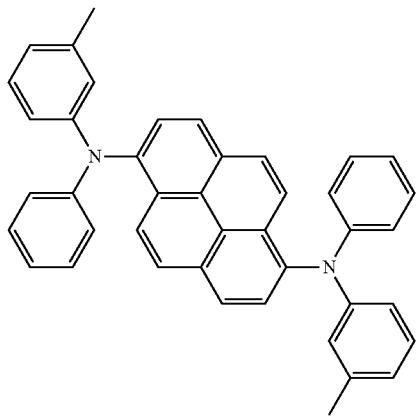

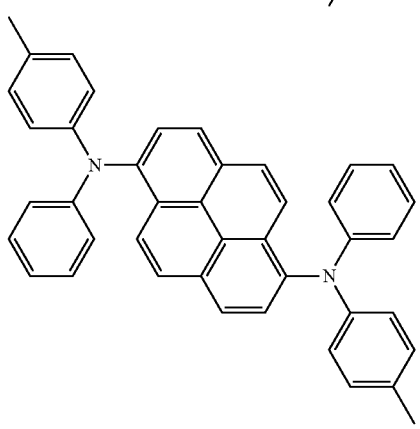

363
-continued
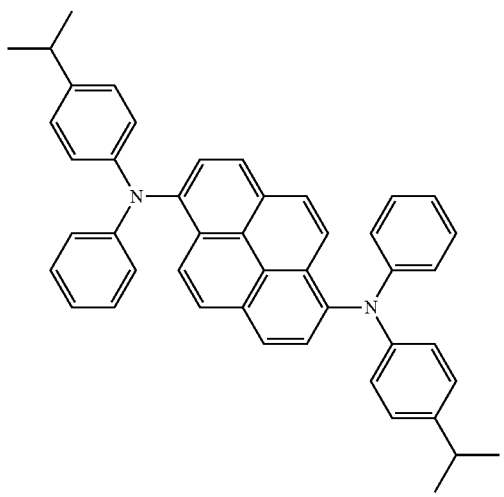
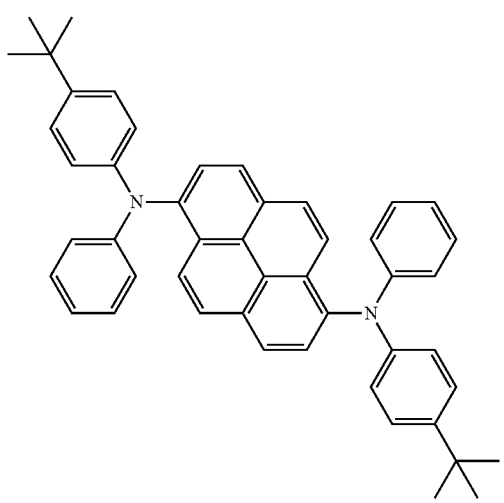
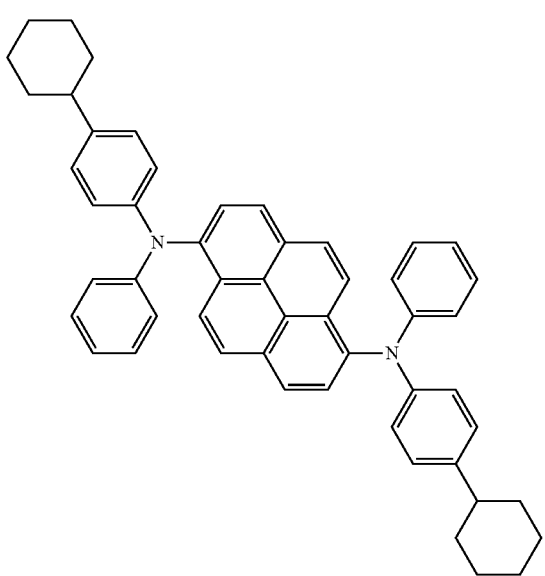
364
-continued
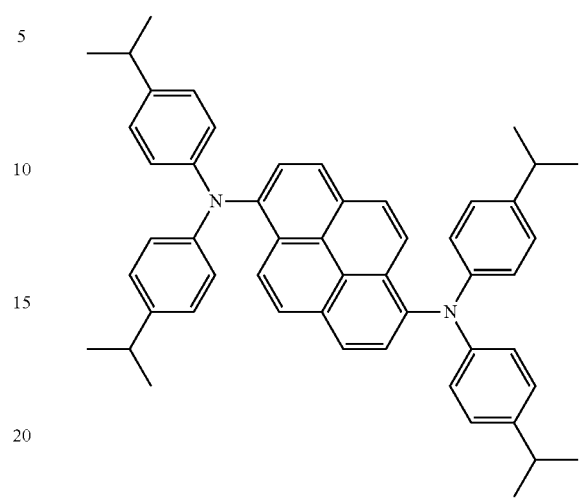
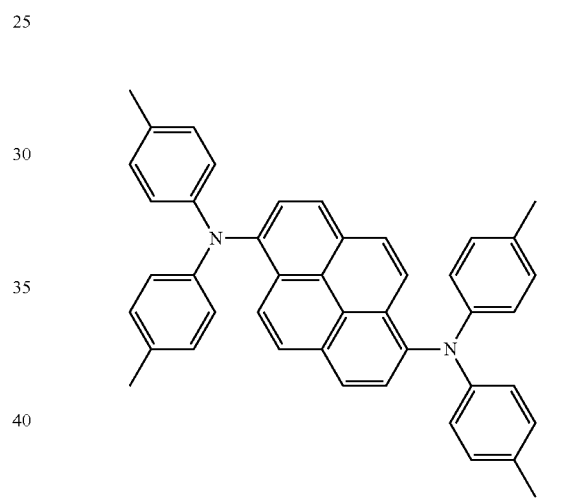
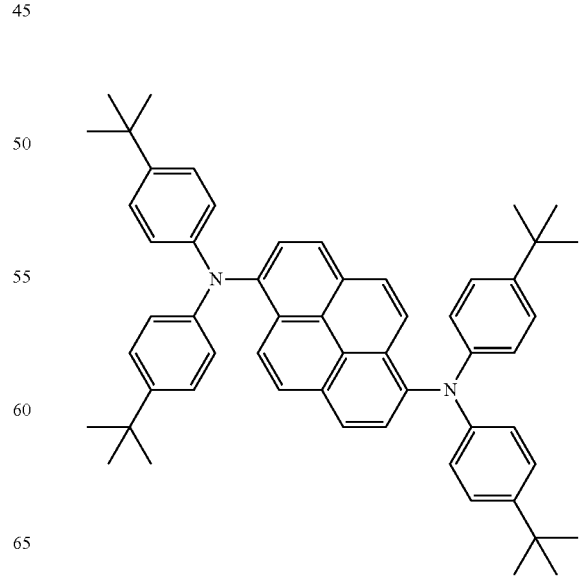

365
-continued
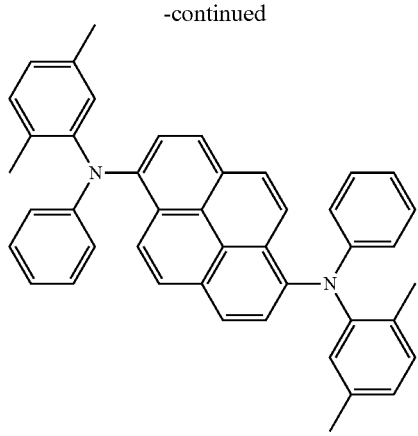
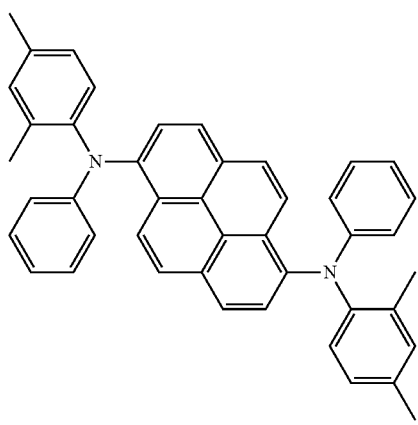
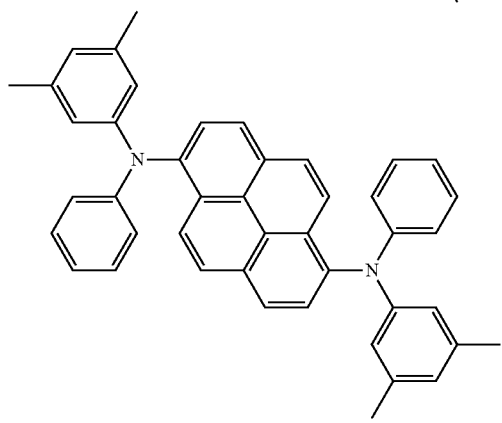
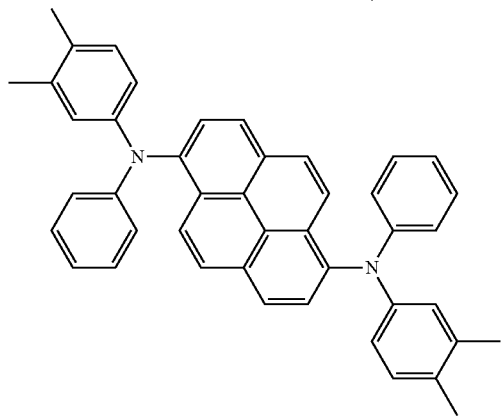
366
-continued
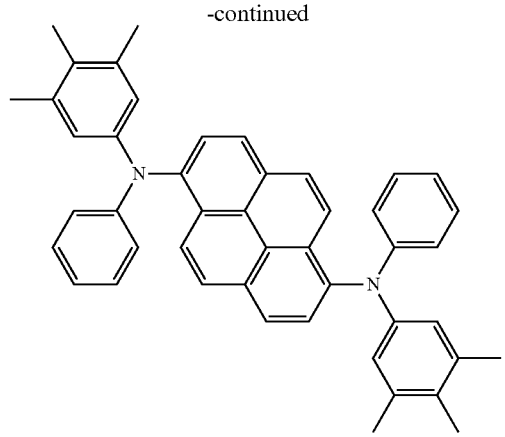
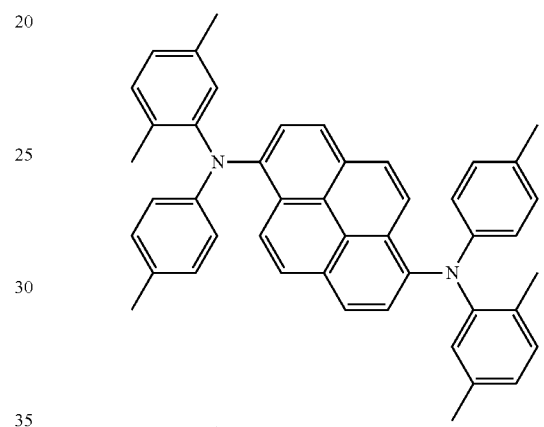
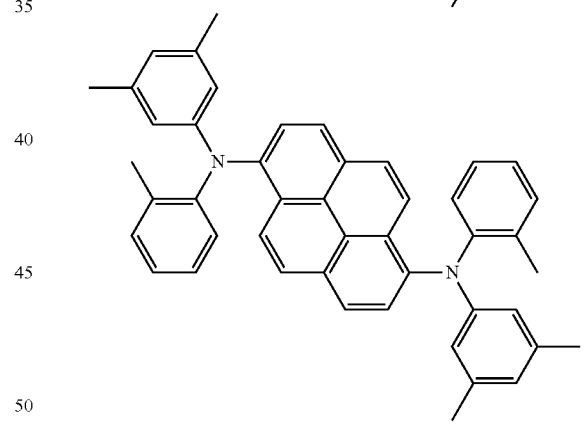
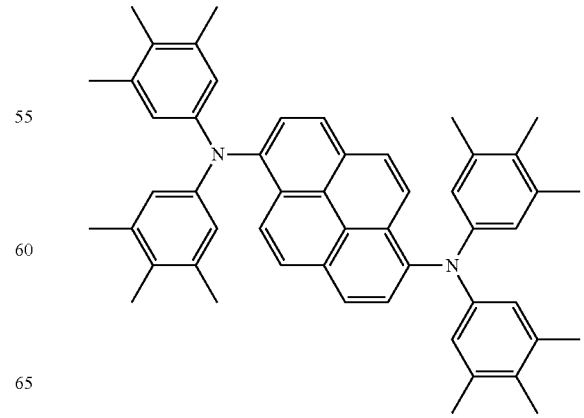

367
-continued
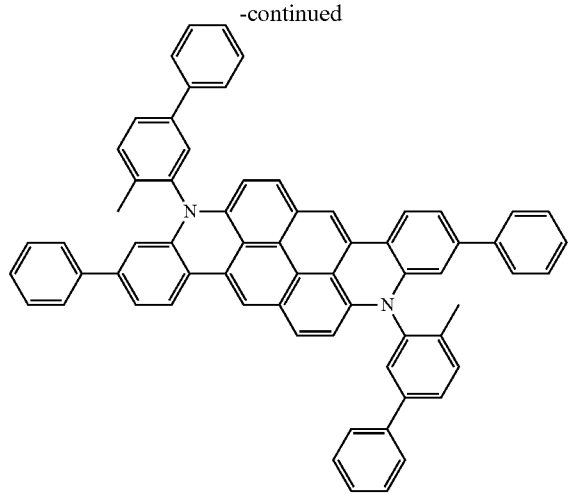
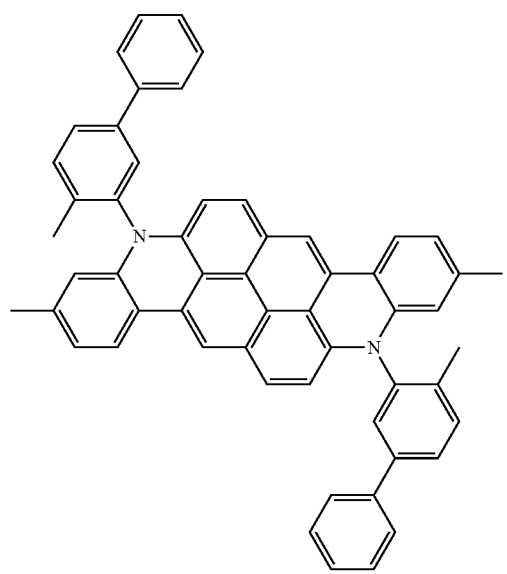
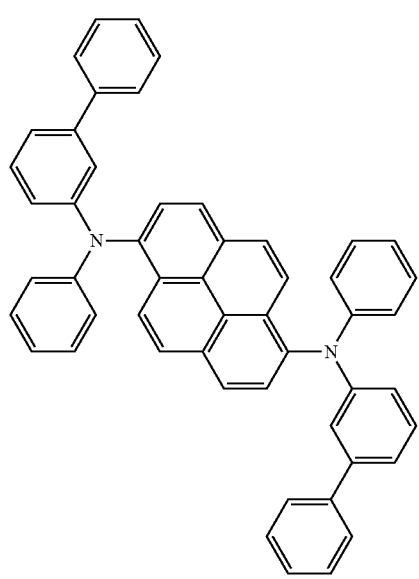
368
-continued
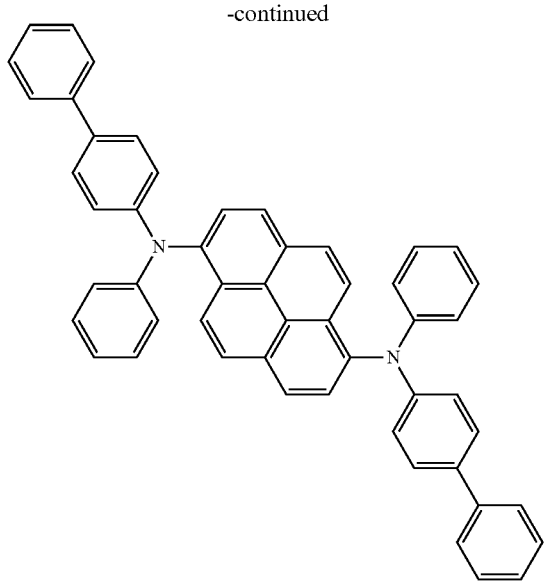
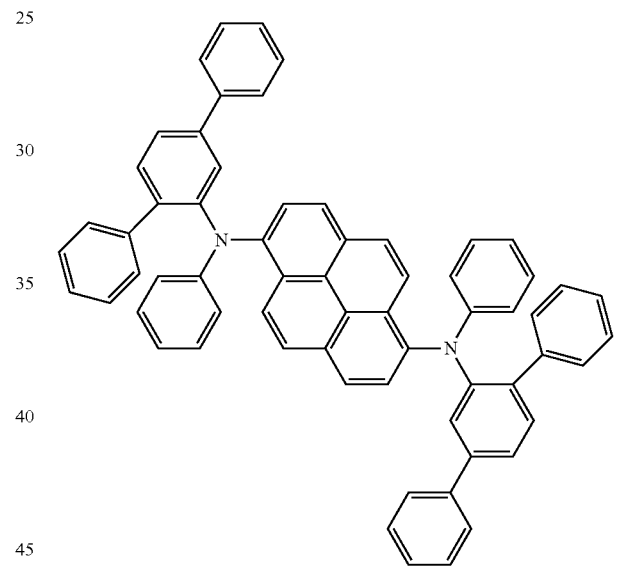

369
-continued
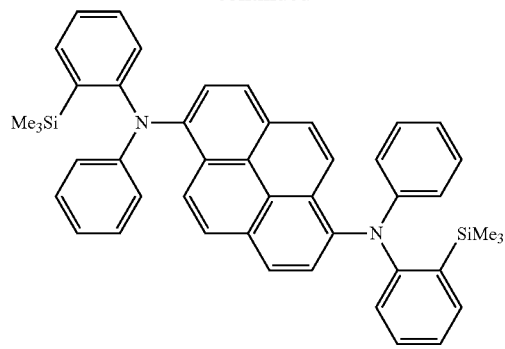
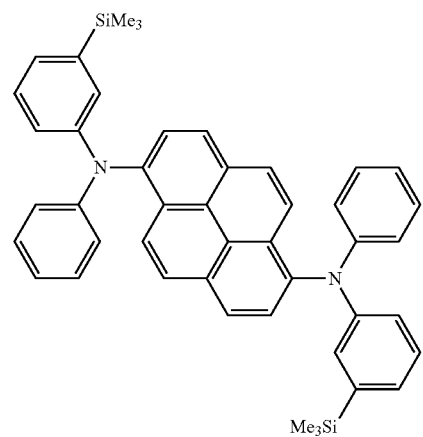
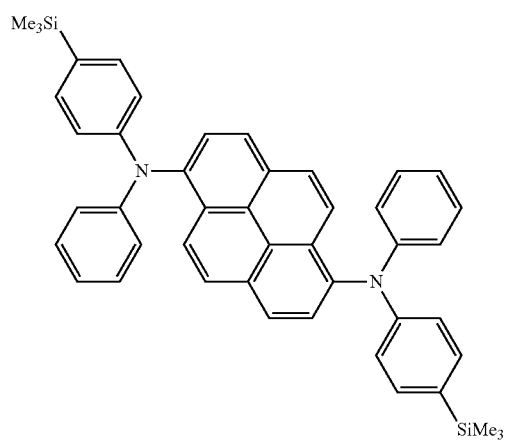
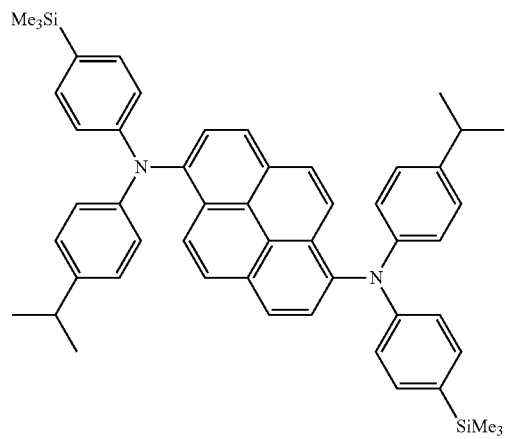
370
-continued
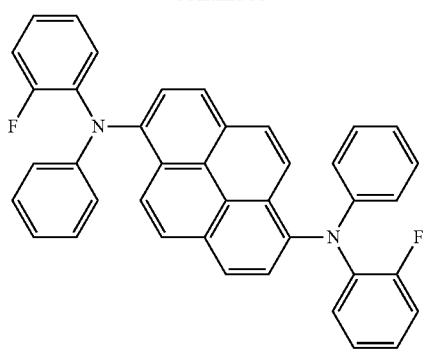
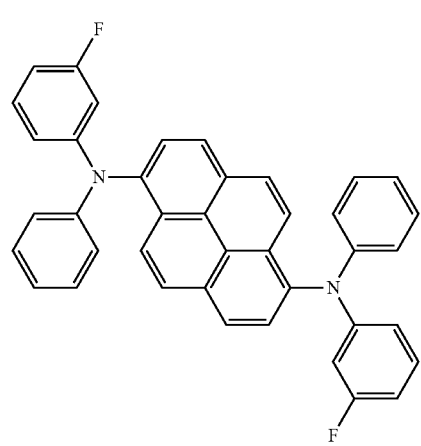
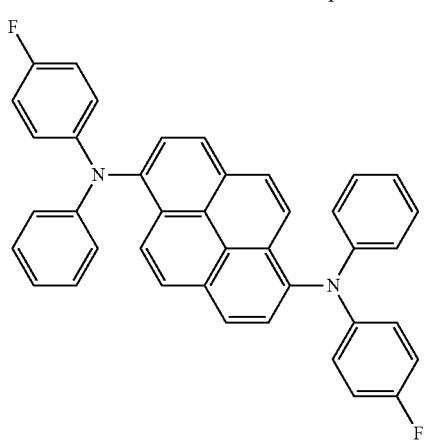
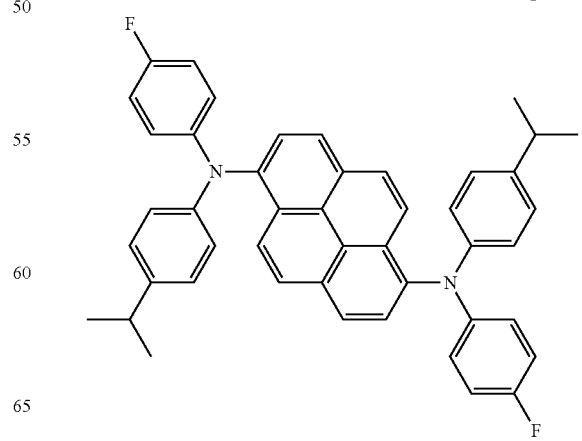

371
-continued
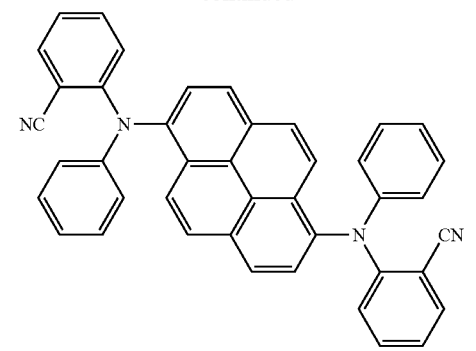
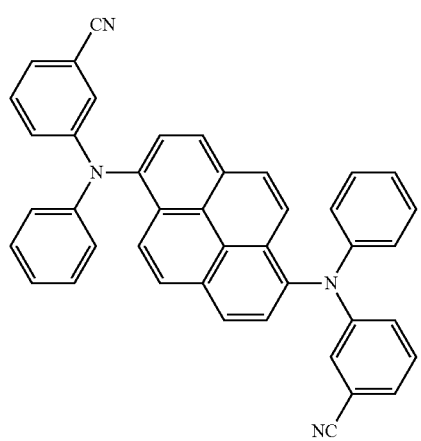
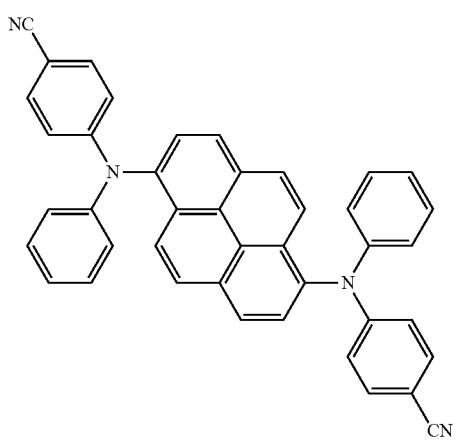
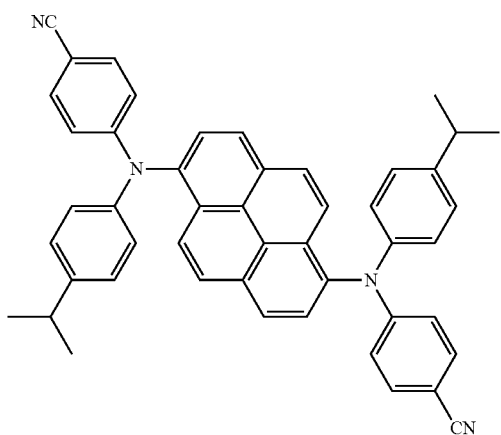
372
-continued
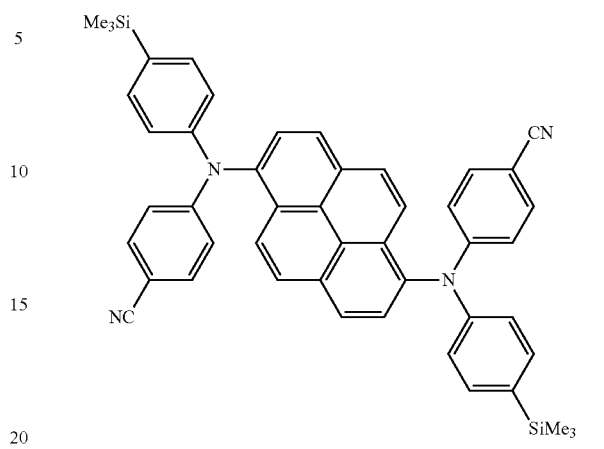
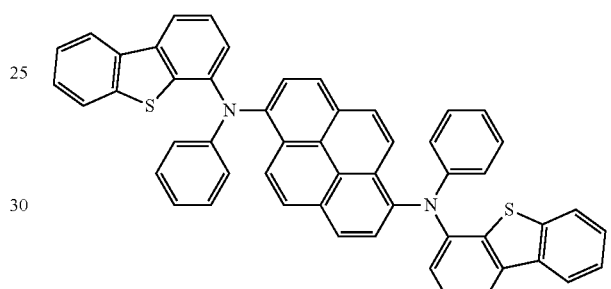
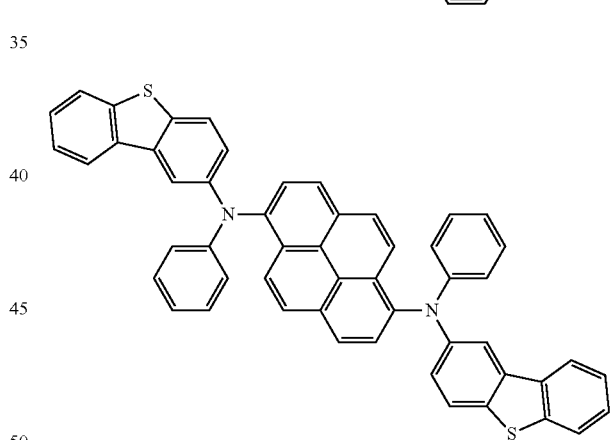
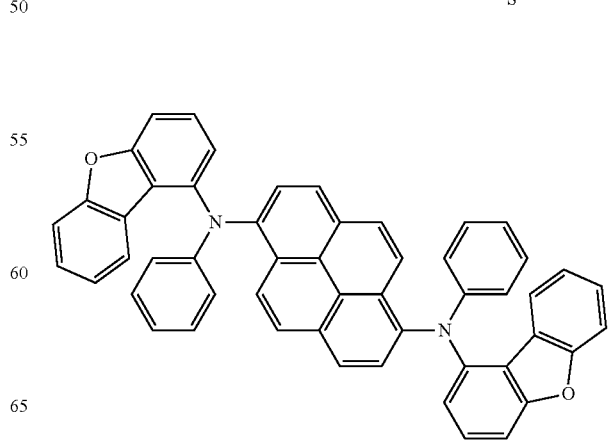

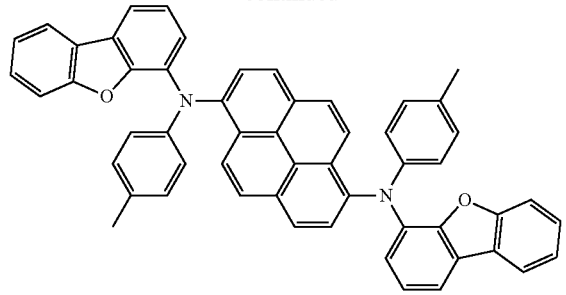
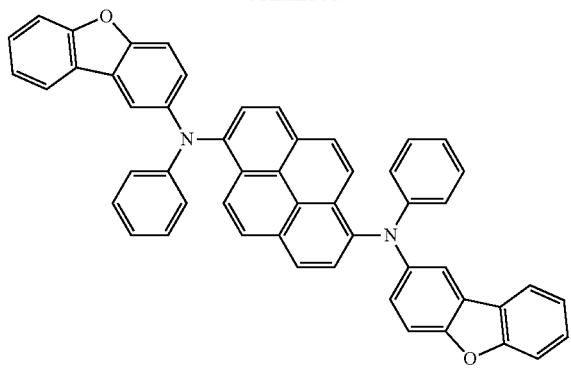
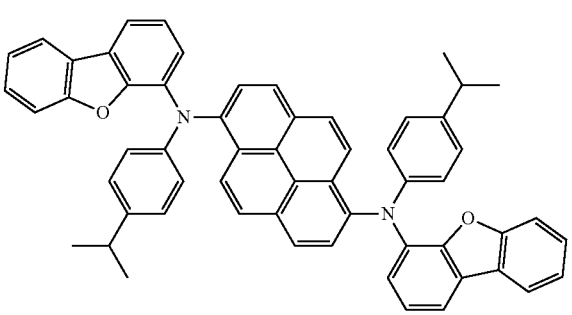
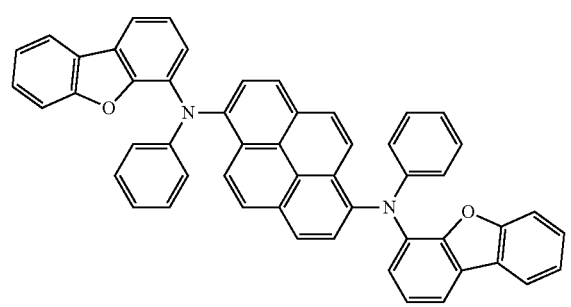
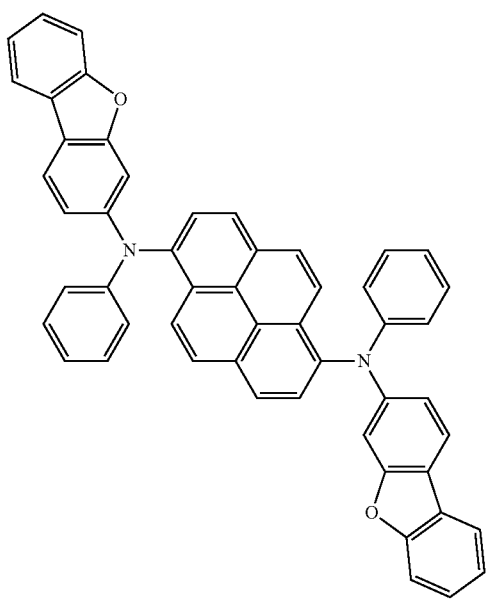
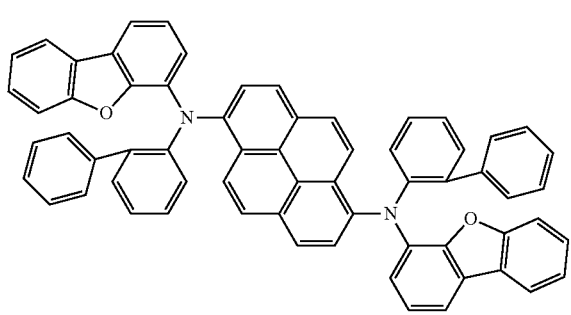
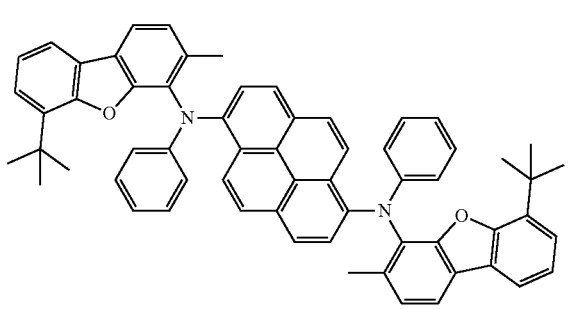

375
-continued
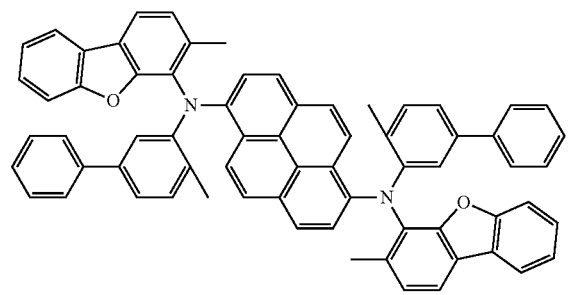
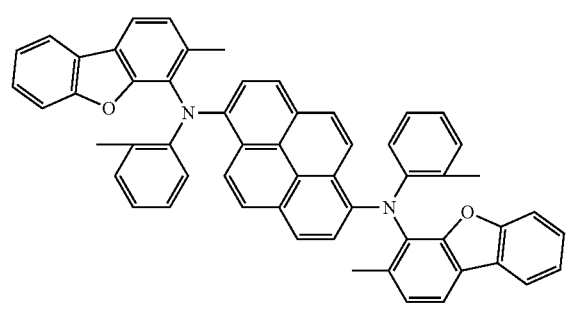
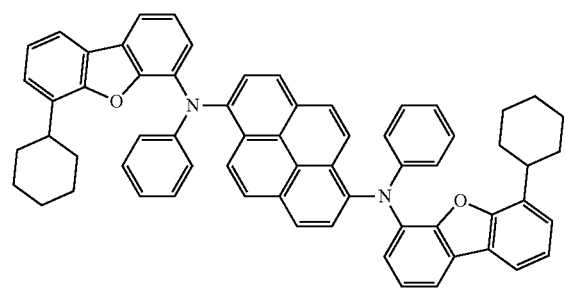
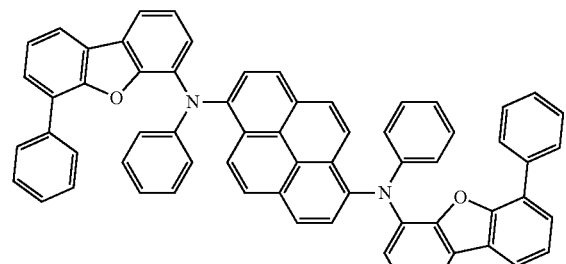
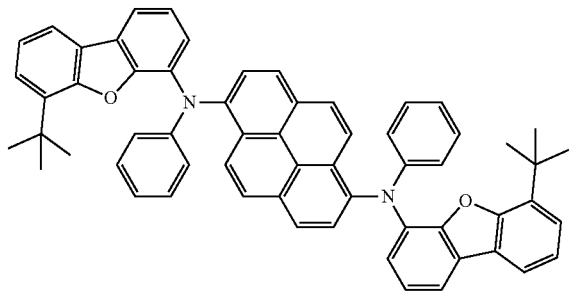
376
-continued
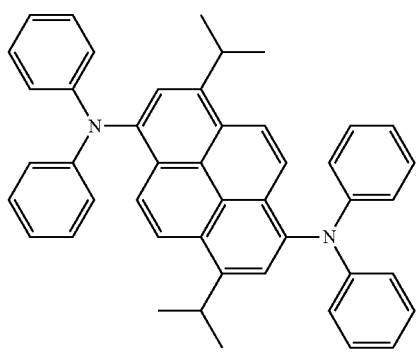
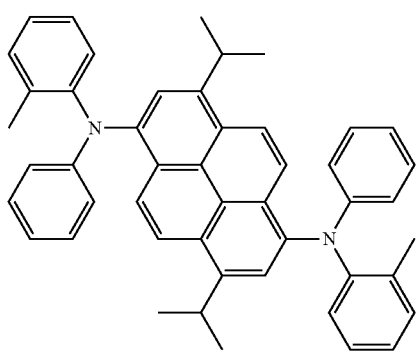
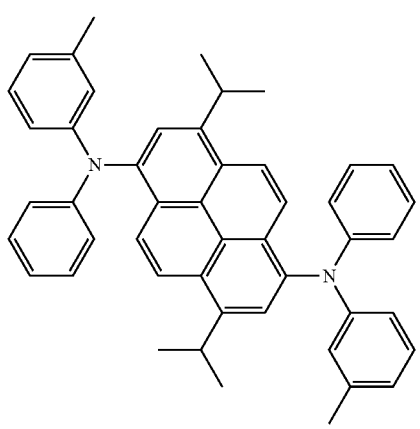
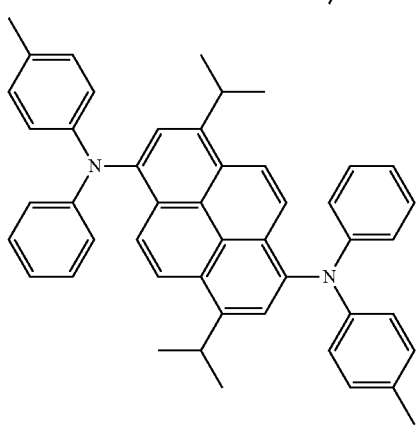

377
-continued
378
-continued
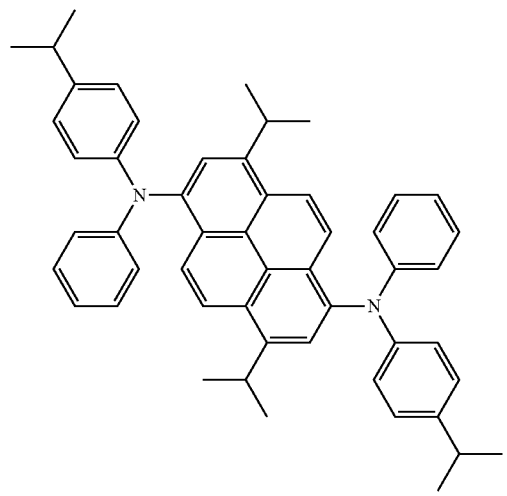
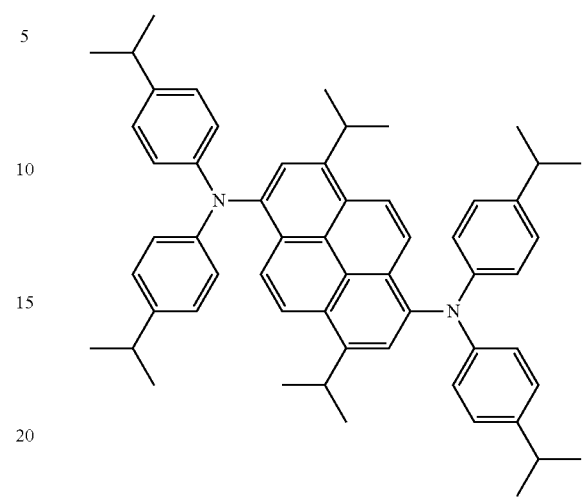
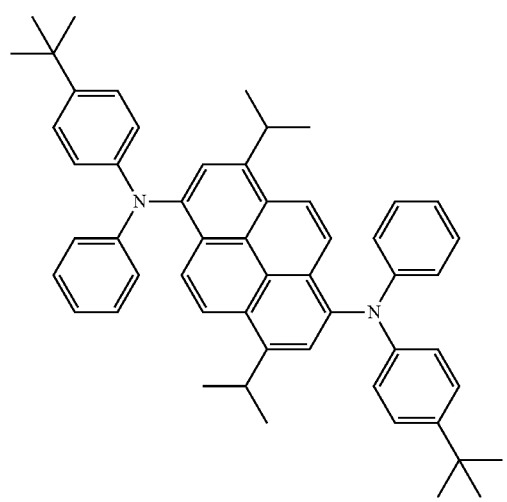
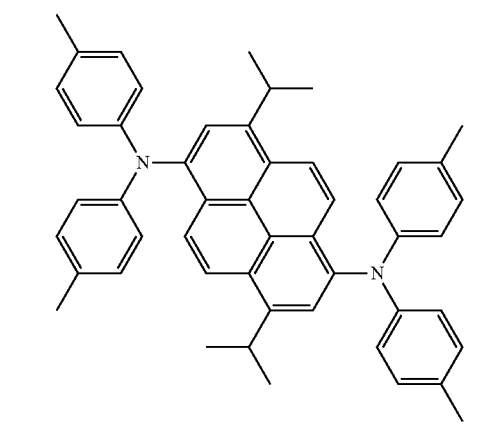
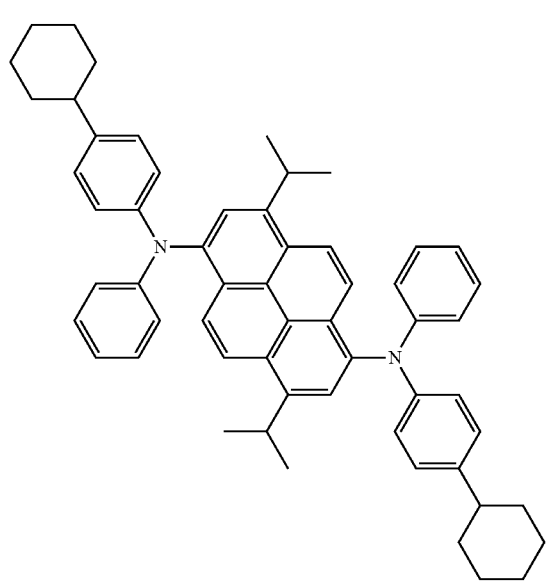
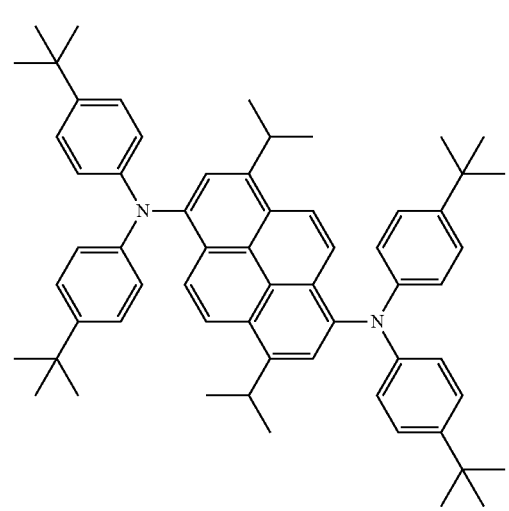

379
-continued
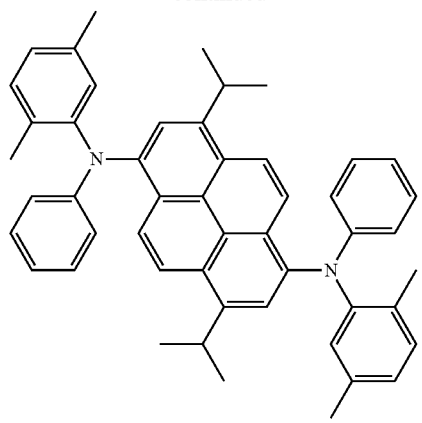
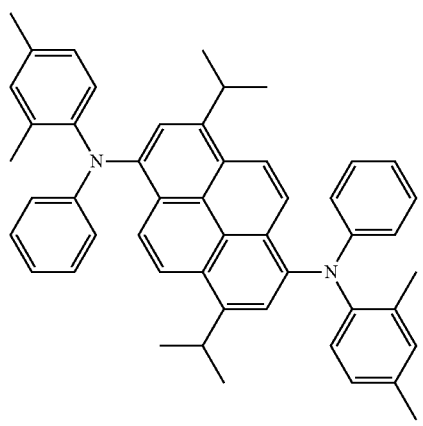
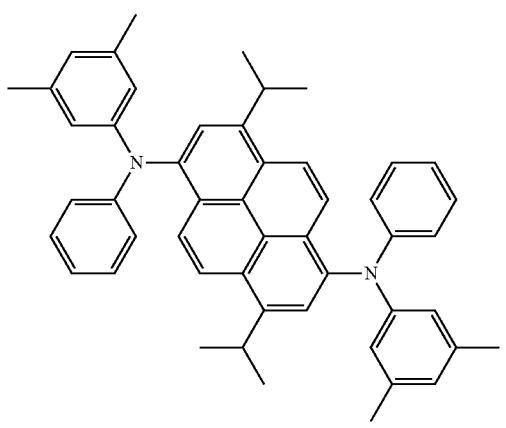
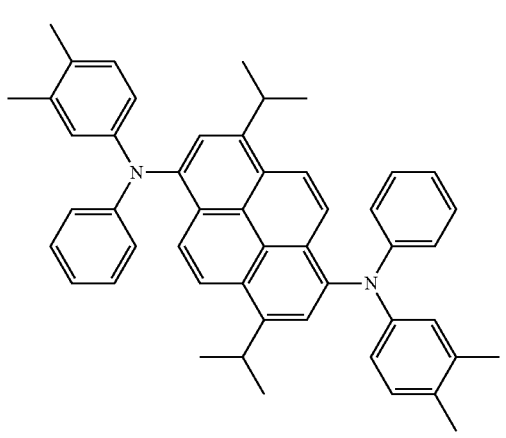
380
-continued

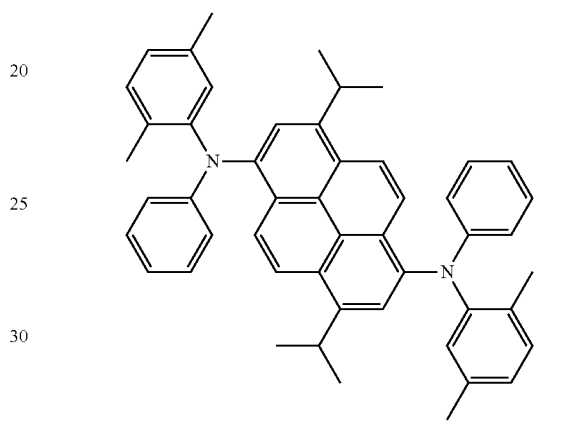
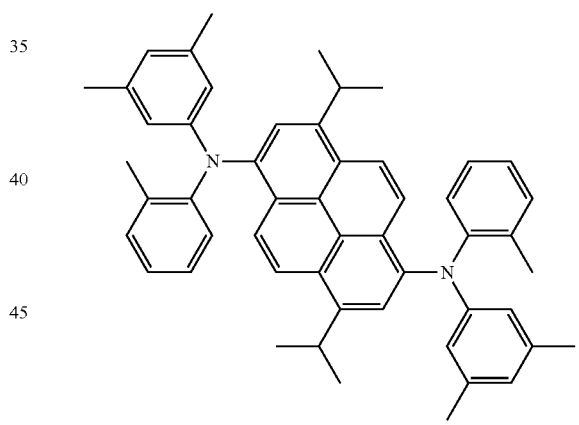
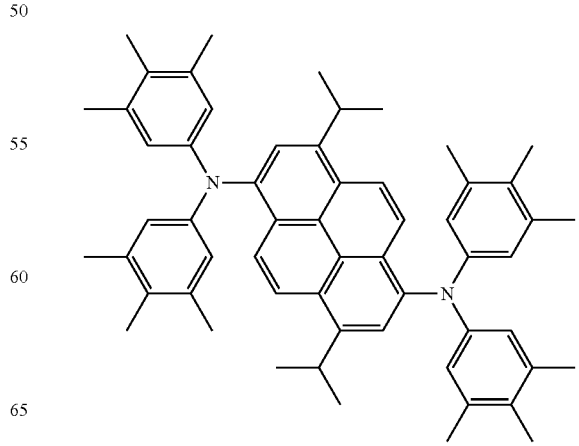

381
-continued
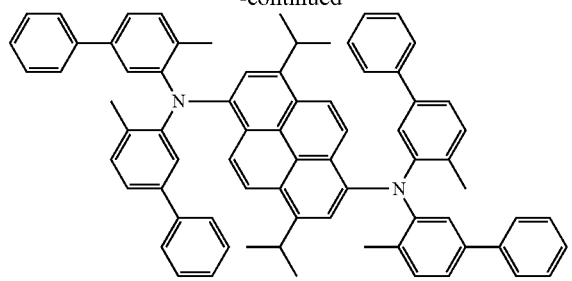
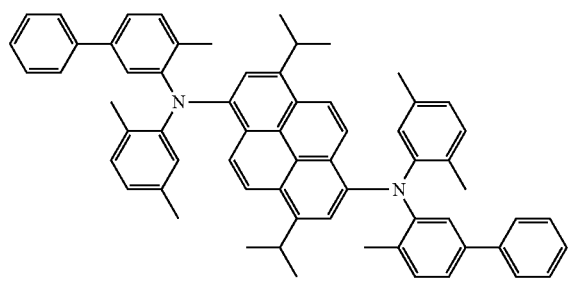
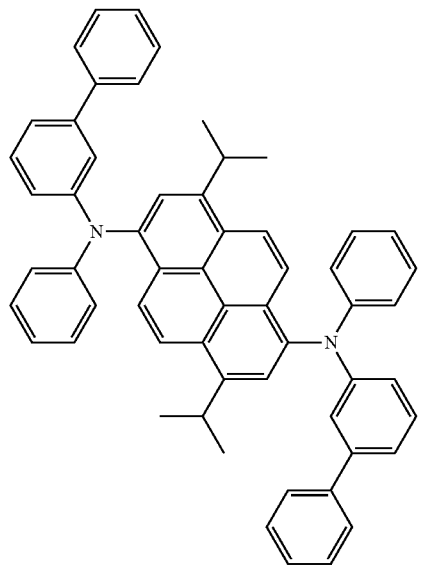
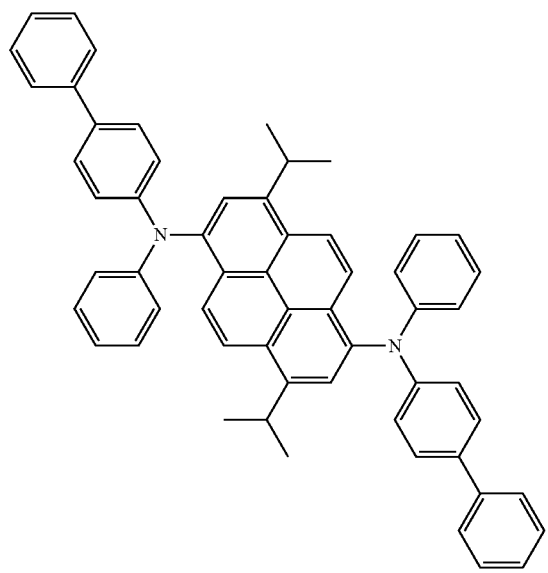
382
-continued
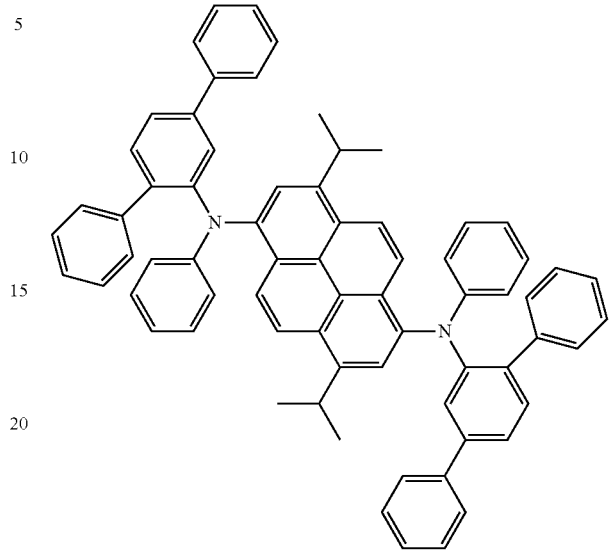
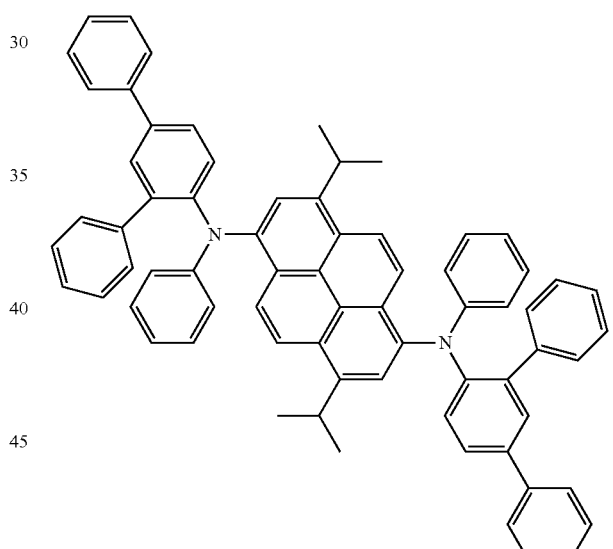
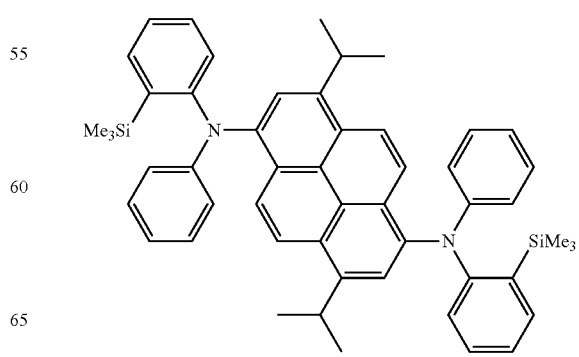

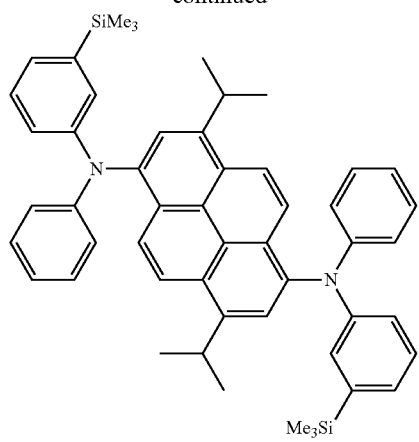
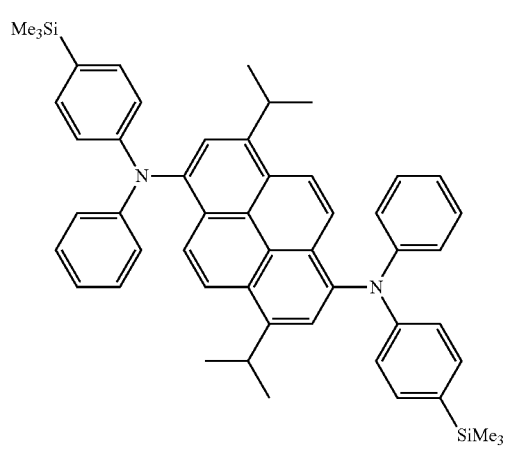
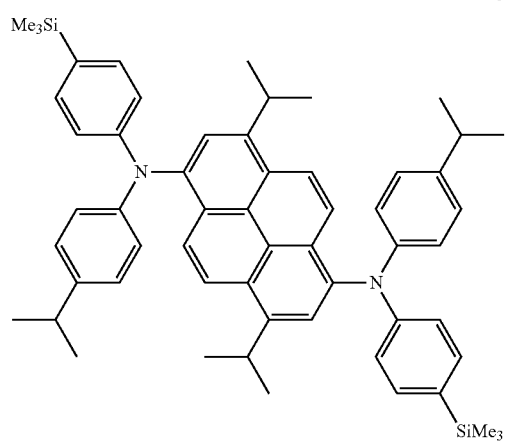
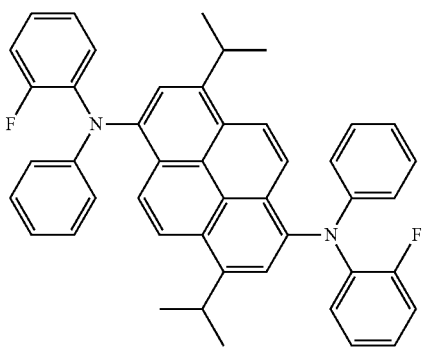
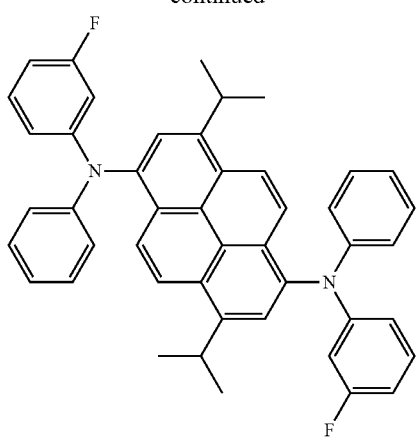
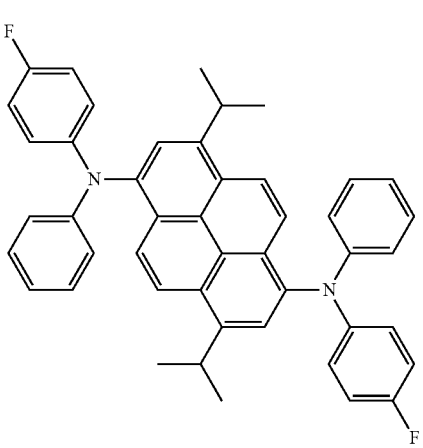
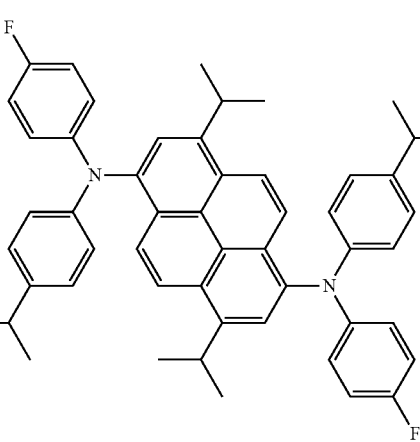
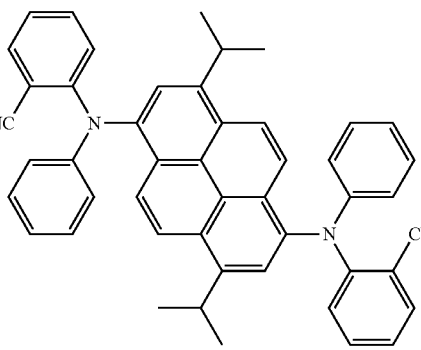

385
-continued
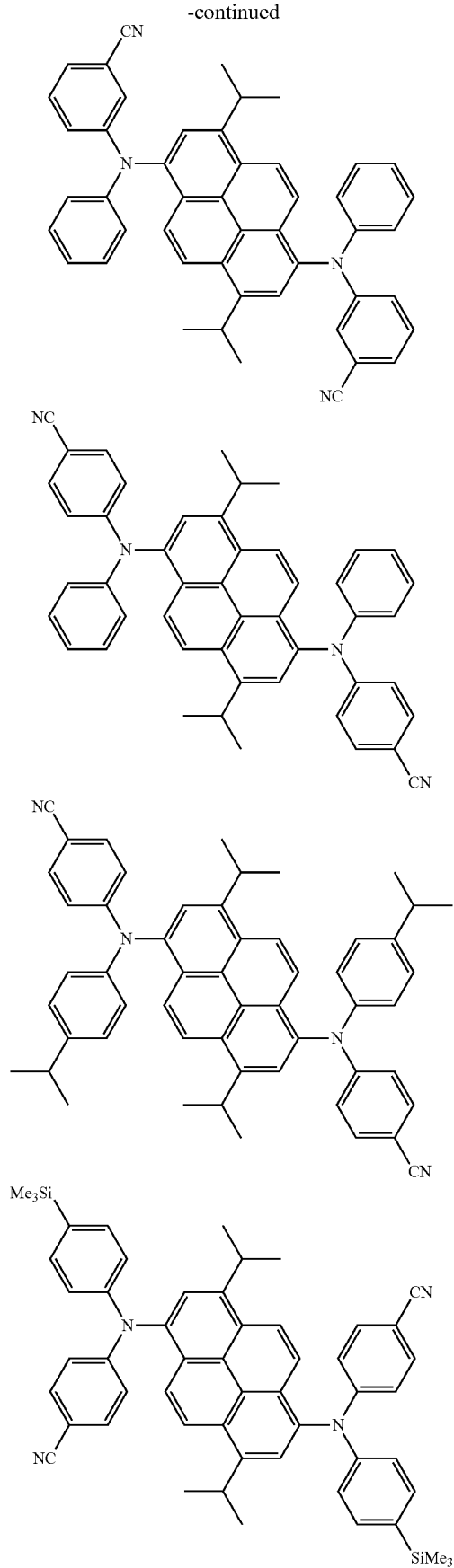
386
-continued
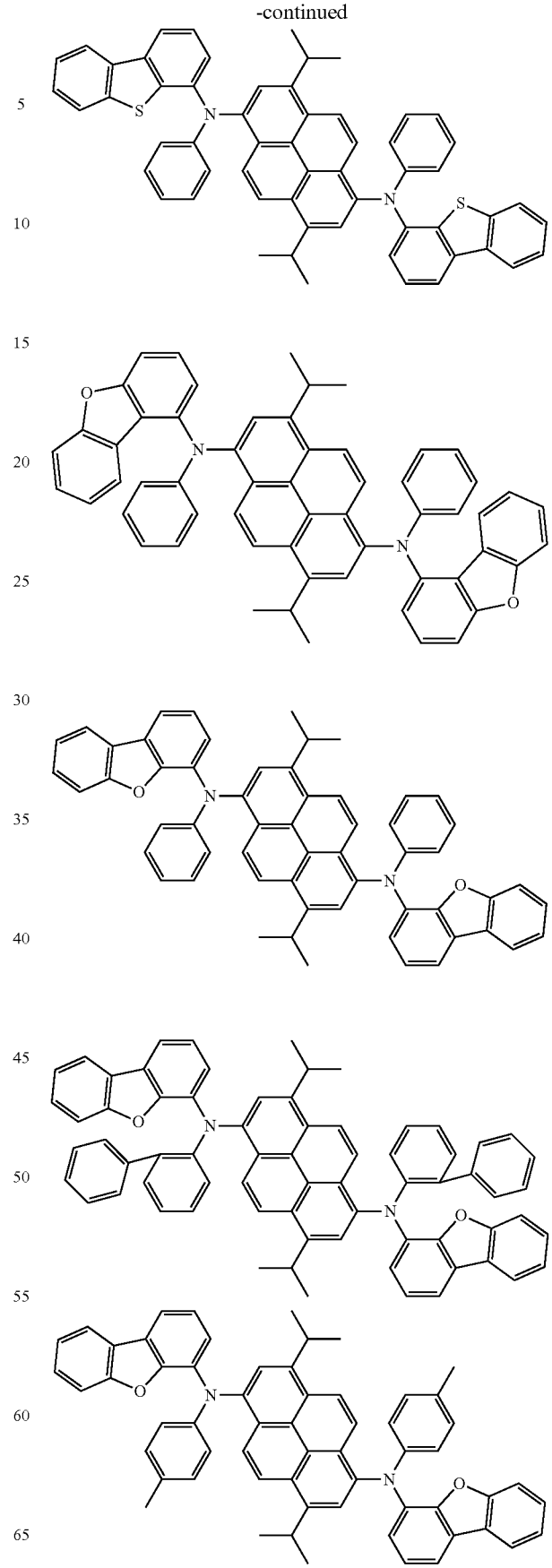

387
-continued
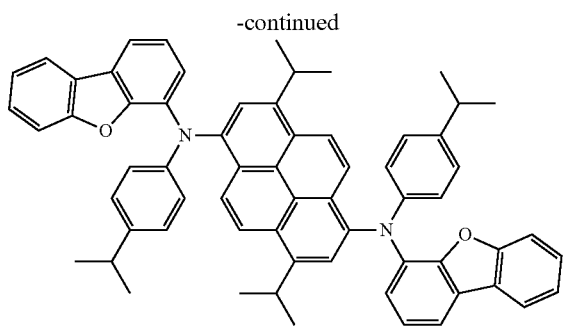
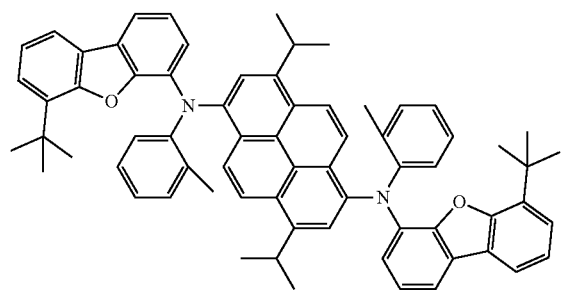
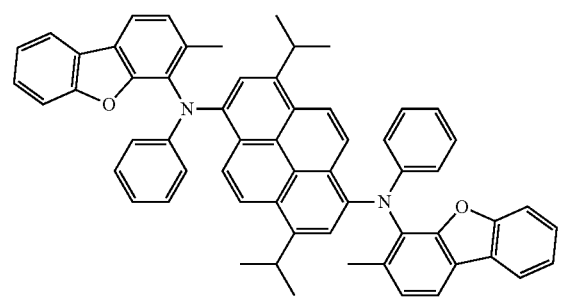
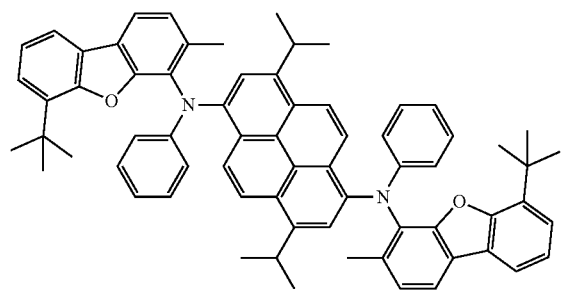
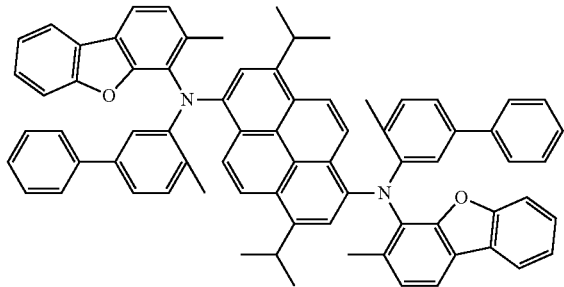
388
-continued
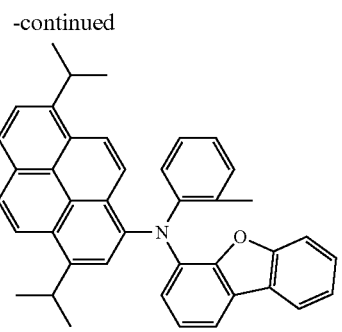
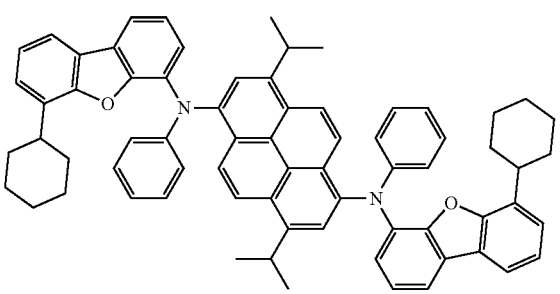
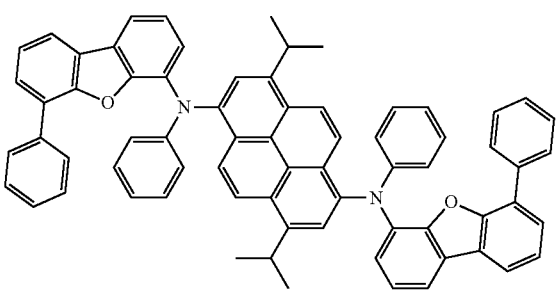
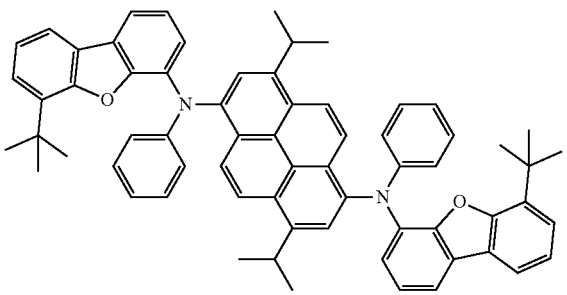
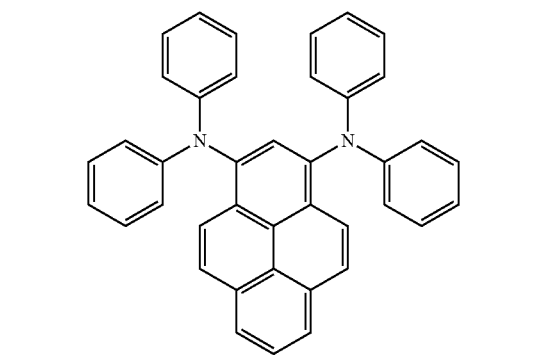

389
-continued
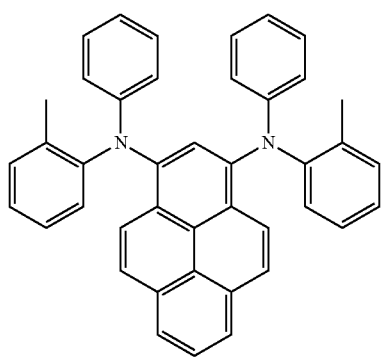
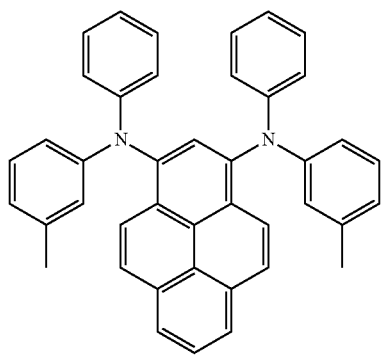
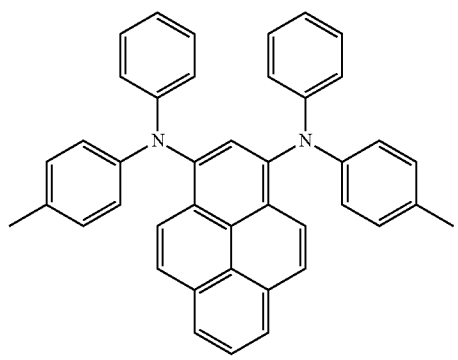
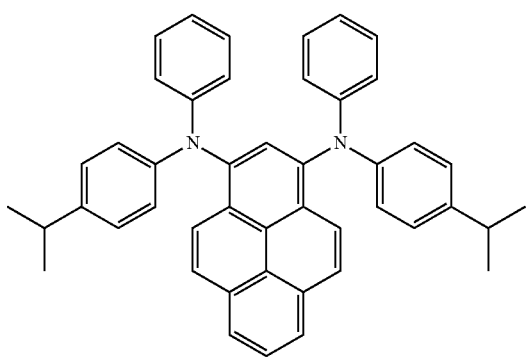
390
-continued
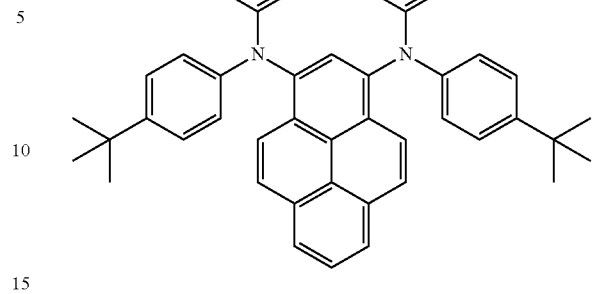
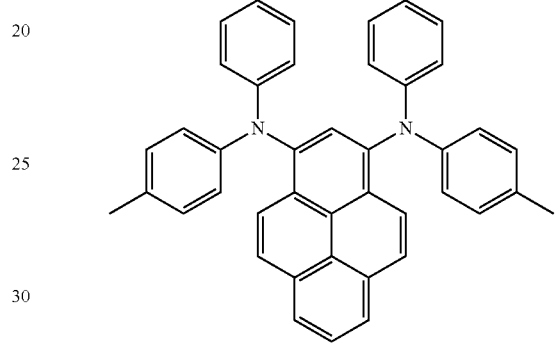
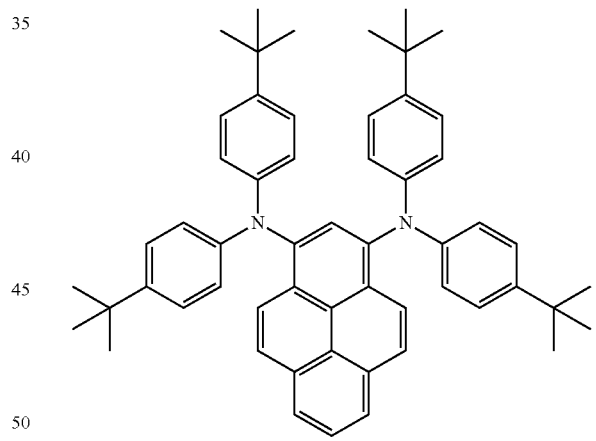
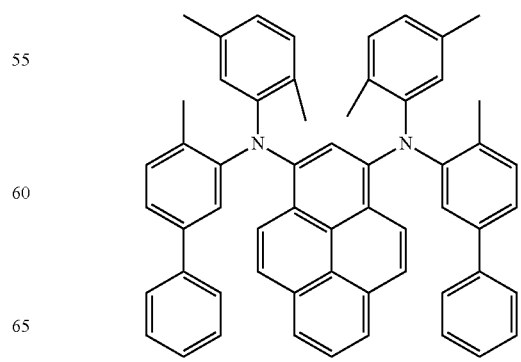

391
-continued
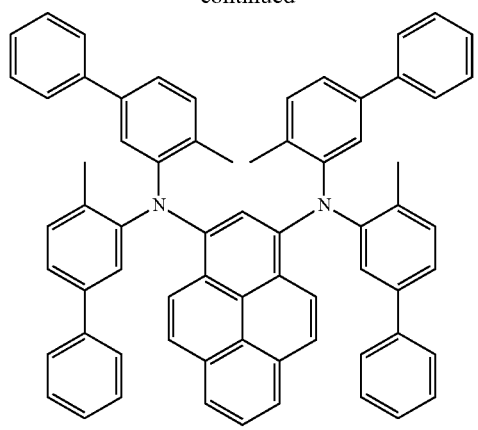
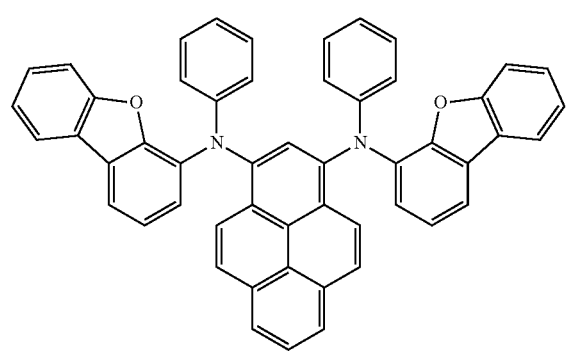
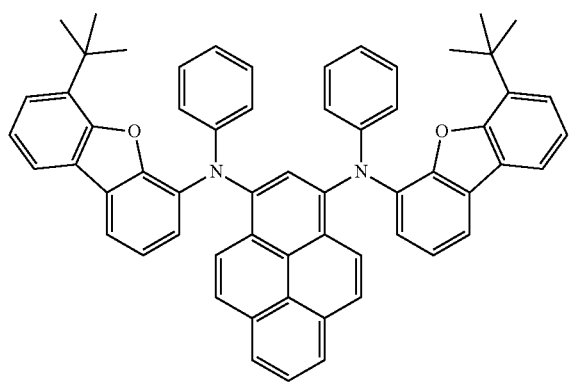
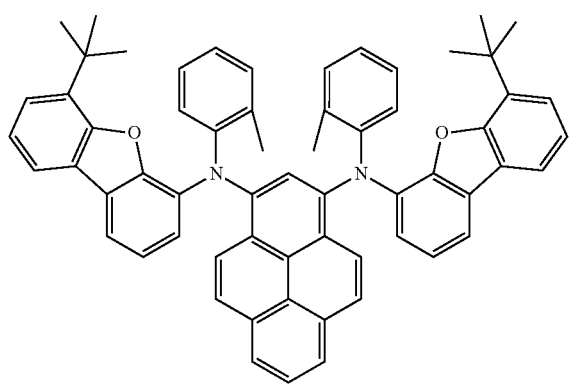
392
-continued
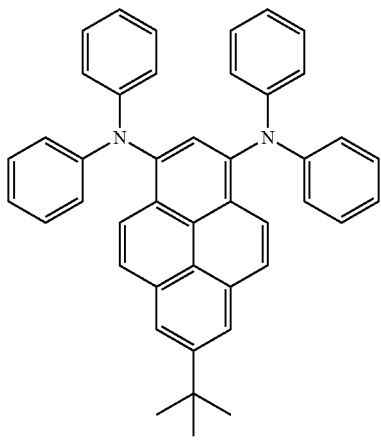
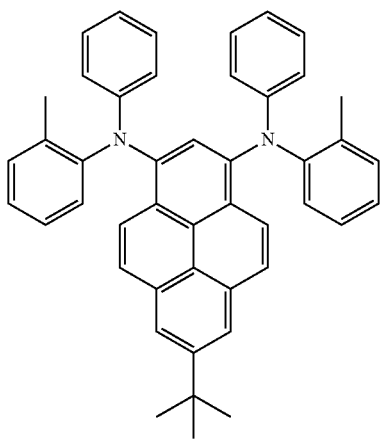
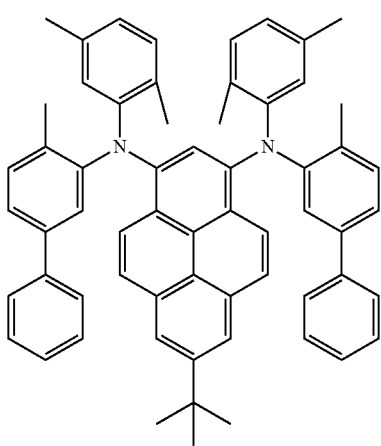

393
-continued
394
-continued
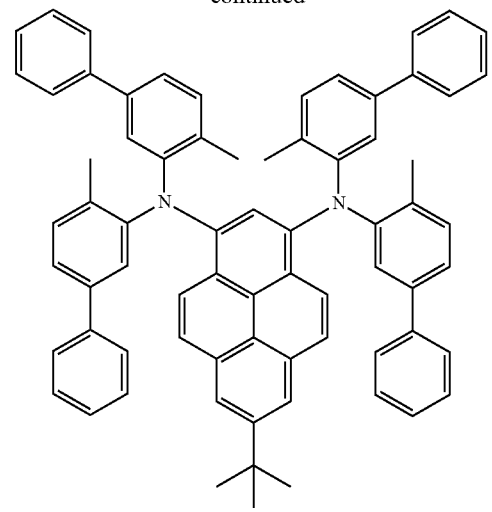
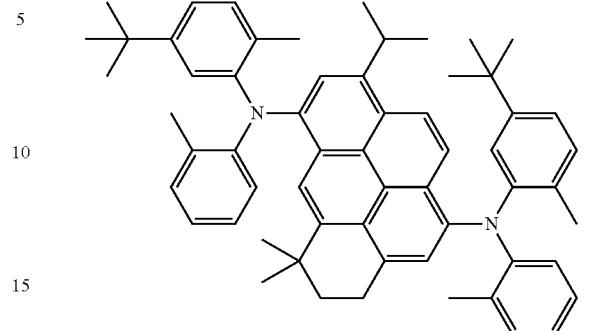
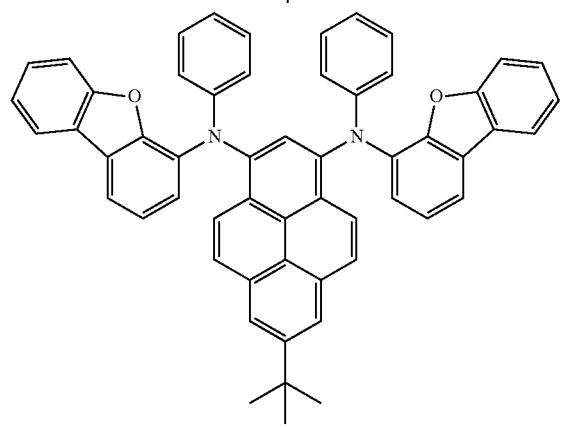
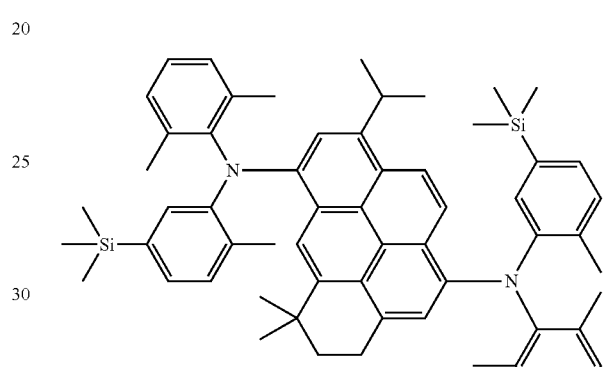
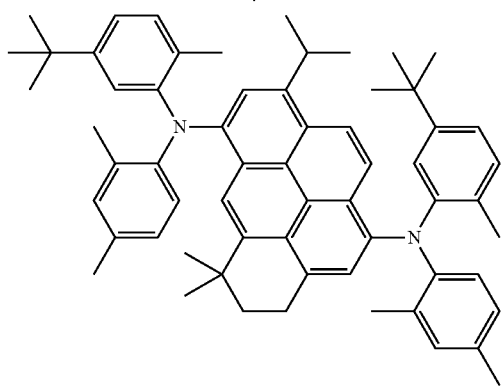
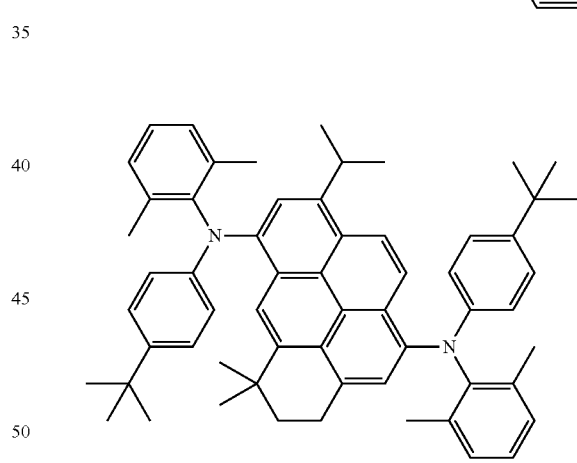
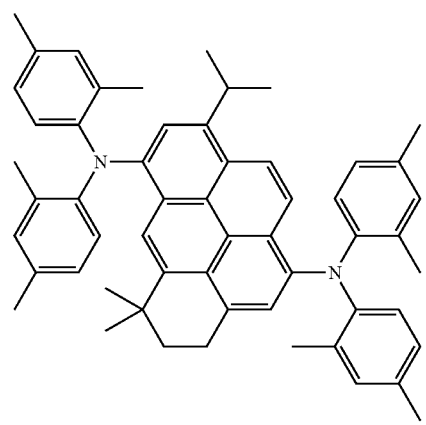
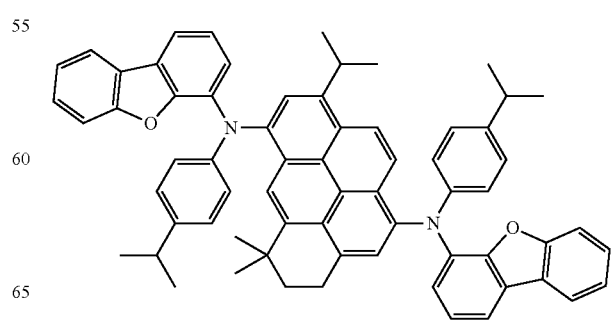

395
-continued
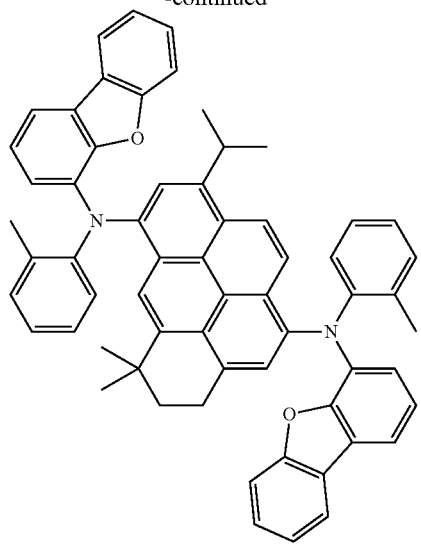
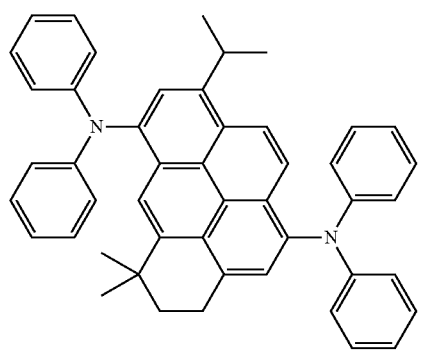
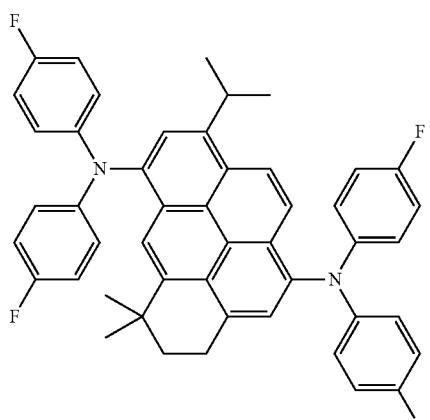
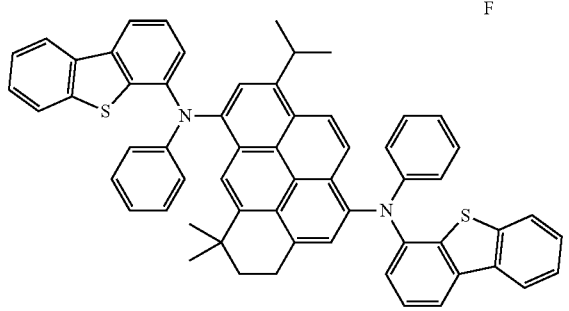
396
-continued
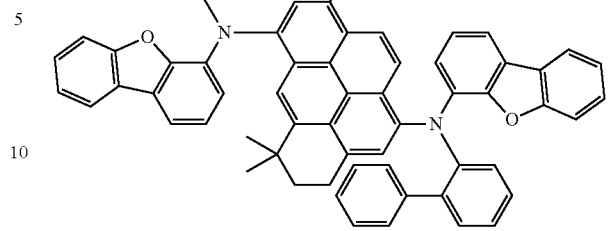
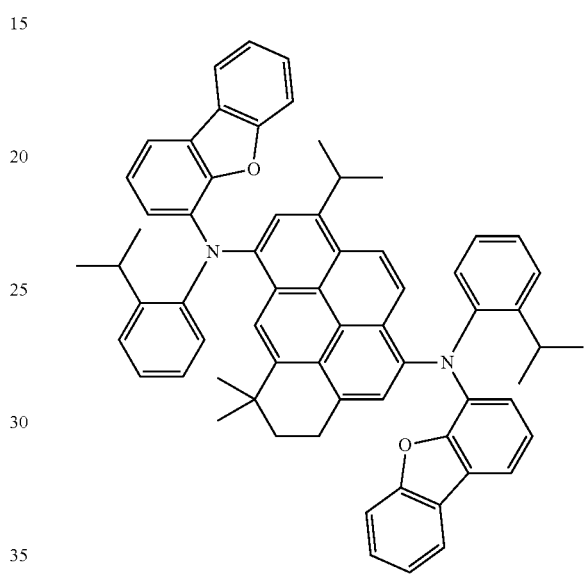
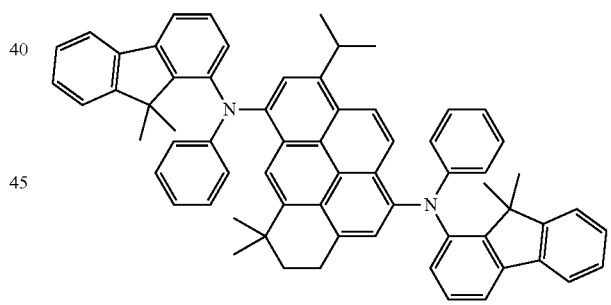
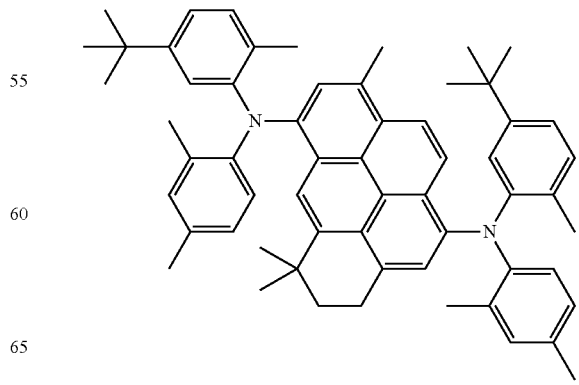

-continued

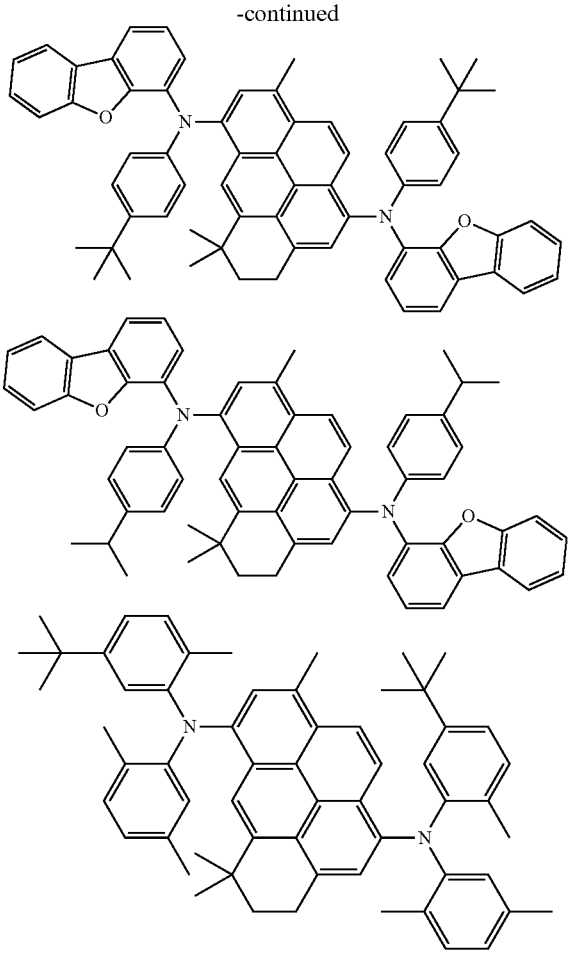

(Compound Represented by Formula (21))

The compound represented by formula (21) is explained below.

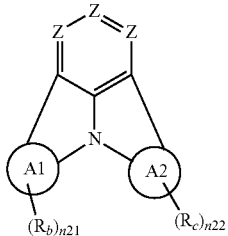

(21)

wherein, in the formula (21),

Zs are independently $CR_a$ or N;

A1 ring and A2 ring are independently a substituted or unsubstituted aromatic hydrocarbon ring having 6 to 50 ring carbon atoms, or a substituted or unsubstituted heterocyclic ring having 5 to 50 ring atoms;

when plural $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;

when plural $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;

when plural $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;

n21 and n22 are independently an integer of 0 to 4;

$R_a$ to $R_c$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

The "aromatic hydrocarbon ring" of A1 ring and A2 ring has the same structure as the compound obtained by introducing a hydrogen atom into the "aryl group" described above.

The "aromatic hydrocarbon ring" of the A1 ring and the A2 ring contains two carbon atoms in the fused bicyclic structure at the center of the formula (21) as ring atoms. Examples of "substituted or unsubstituted aromatic hydrocarbon ring having 6 to 50 ring carbon atoms" include compounds in which a hydrogen atom is introduced into the "aryl group" described in the example group G1.

The "heterocyclic ring" of A1 ring and A2 ring has the same structure as the compound obtained by introducing a hydrogen atom into the "heterocyclic group" described above. The "heterocyclic ring" of the A1 ring and the A2 ring contains two carbon atoms in the fused bicyclic structure at the center of the formula (21) as ring atoms. Examples of "substituted or unsubstituted heterocyclic ring having 5 to 50 ring atoms" include compounds in which a hydrogen atom is introduced into the "heterocyclic group" described in the example group G2.

$R_b$ is bonded to one of carbon atoms which form the aromatic hydrocarbon ring of A1 ring, or one of atoms which form the heterocycle of A1 ring.

$R_c$ is bonded to one of carbon atoms which form the aromatic hydrocarbon ring of A2 ring, or one of atoms which form the heterocycle of A2 ring.

It is preferable that at least one (preferably two) of $R_a$ to $R_C$ is a group represented by the following formula (21a).

-$L_{201}$-$Ar_{201}$ (21a)

wherein in the formula (21a), $L_{200}$ is a single bond, a substituted or unsubstituted arylene group having 6 to 30 ring carbon atoms, or a substituted or unsubstituted bivalent heterocyclic group having 5 to 30 ring atoms;

Ar$_{201}$ is
a substituted or unsubstituted arylene group having 6 to 50 ring carbon atoms,
a substituted or unsubstituted monovalent heterocyclic group having 5 to 50 ring atoms, or
a group represented by the following formula (21b):

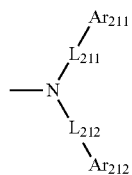

(21b)

wherein in the formula (21b),
L$_{211}$ and L$_{212}$ are independently
a single bond,
a substituted or unsubstituted arylene group having 6 to 30 ring carbon atoms, or
a substituted or unsubstituted divalent heterocyclic group having 5 to 30 ring atoms;
Ar$_{211}$ and Ar$_{212}$ are bonded with each other to form a substituted or unsubstituted, saturated or unsaturated ring, or do not form a substituted or unsubstituted, saturated or unsaturated ring; and
Ar$_{211}$ and Ar$_{212}$ that do not form a substituted or unsubstituted, saturated or unsaturated ring are independently
a substituted or unsubstituted aryl group having 6 to 50 ring carbon atoms or
a substituted or unsubstituted monovalent heterocyclic group having 5 to 50 ring atoms.

In one embodiment, the compound represented by the formula (21) is represented by the following formula (22).

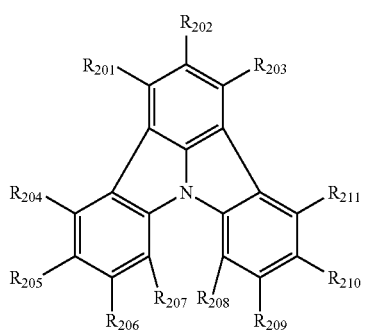

(22)

wherein in the formula (22),
one or more pairs of two or more adjacent groups of R$_{201}$ to R$_{211}$ are bonded with each other to form a substituted or unsubstituted, saturated or unsaturated ring, or do not form a substituted or unsubstituted saturated or unsaturated ring;
R$_{201}$ to R$_{211}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms, a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
R$_{901}$ to R$_{907}$ are as defined in the formula (1))

It is preferable that at least one (preferably two) of R$_{201}$ to R$_{211}$ is the group represented by the formula (21a). It is preferable that R$_{204}$ and R$_{211}$ are the group represented by the formula (21a).

In one embodiment, the compound represented by the formula (21) is a compound obtained by bonding the structure represented by the following formula (21-1) or (21-2) to A1 ring. In one embodiment, the compound represented by the formula (22) is a compound obtained by bonding the structure represented by the following formula (21-1) or (21-2) to the ring to which R$_{204}$ to R$_{207}$ bonds to.

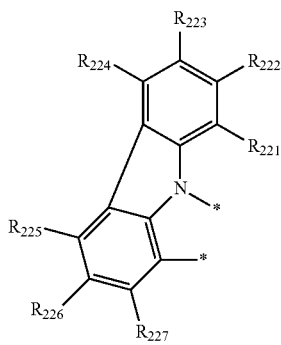

(21-1)

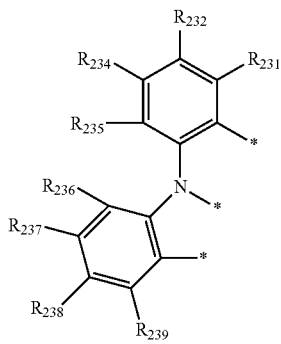

(21-2)

wherein in the formula (21-1), two bonds shown by * independently bond to a ring carbon atom in the aromatic hydrocarbon ring or a ring atom in the heterocyclic group in A1 ring in the formula (21), or bond to one of R$_{204}$ to R$_{207}$ in the formula (22);

wherein in the formula (21-2), three bonds shown by * independently bond to a ring carbon atom in the aromatic hydrocarbon ring or a ring atom in the heterocyclic group in A1 ring in the formula (21), or bond to one of R$_{204}$ to R$_{207}$ in the formula (22);

One or more pairs of two or more adjacent groups of $R_{221}$ to $R_{227}$ and $R_{221}$ to $R_{239}$ are bonded with each other to form a substituted or unsubstituted, saturated or unsaturated ring, or do not form a substituted or unsubstituted, saturated or unsaturated ring;

$R_{221}$ to $R_{227}$ and $R_{231}$ to $R_{239}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$).
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and $R_{901}$ to $R_{907}$ are as defined in the formula (1)

In one embodiment, the compound represented by the formula (21) is a compound represented by the following formula (21-3), (21-4), or (21-5).

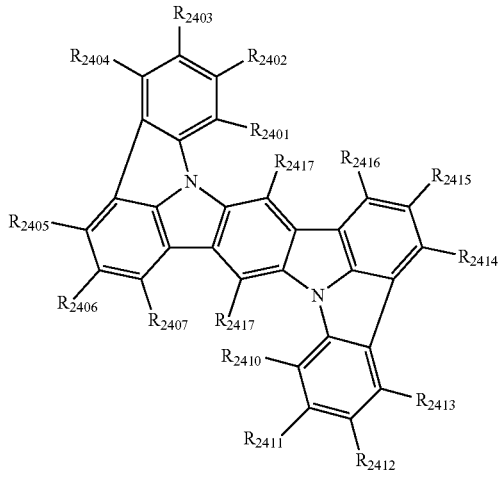

(21-3)

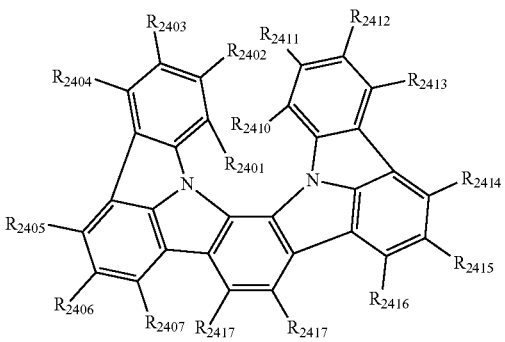

(21-4)

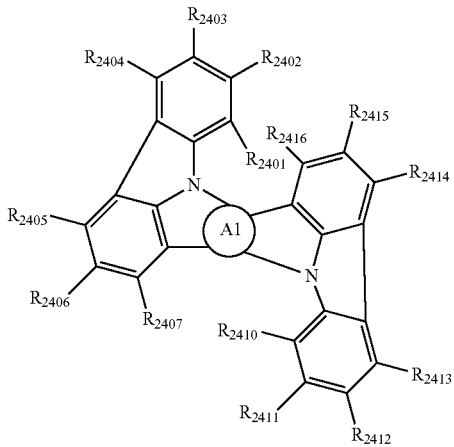

(21-5)

wherein in the formulas (21-3), (21-4) and (21-5),

A1 ring is as defined in the formula (21);

$R_{2401}$ to $R_{2407}$ are the same as $R_{221}$ to $R_{227}$ in the formulas (21-1) and (21-2);

$R_{2410}$ to $R_{2417}$ are the same as $R_{201}$ to $R_{211}$ in the formula (22); and the two $R_{2417}$s may be the same or different.

In one embodiment, the substituted or unsubstituted aromatic hydrocarbon ring having 6 to 50 ring carbon atoms of A1 ring in the formula (21-5) is a substituted or unsubstituted napthalene ring, or a substituted or unsubstituted fluorene ring.

In one embodiment, the substituted or unsubstituted heterocycle having 5 to 50 ring atoms of A1 ring in the formula (21-5) is a substituted or unsubstituted dibenzofuran ring, a substituted or unsubstituted carbazole ring, or a substituted or unsubstituted dibenzothiophene ring.

In one embodiment, the compound represented by the formula (21) or (22) is selected from the group consisting of the compounds represented by the following formulas (21-6-1) to (21-6-7).

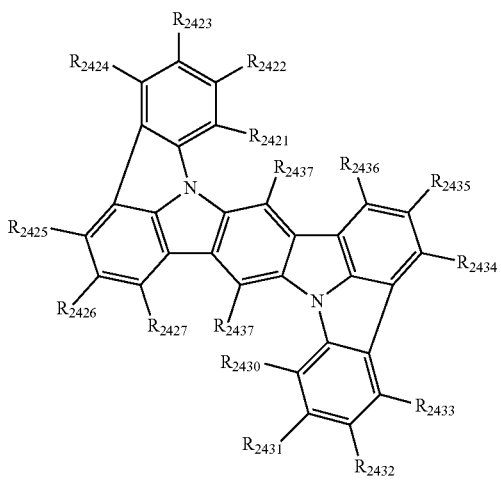

(21-6-1)

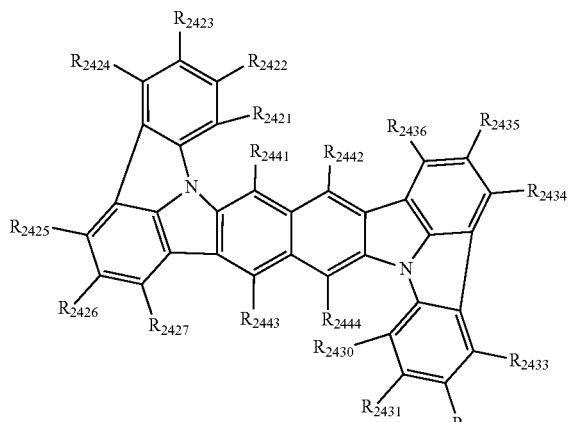

wherein in the formulas (21-6-1) to (21-6-7), $R_{2421}$ to $R_{2427}$ are the same as $R_{221}$ to $R_{227}$ in the formulas (21-1) and (21-2);

$R_{2430}$ to $R_{2437}$ and $R_{2441}$ to $R_{2444}$ are the same as $R_{201}$ to $R_{211}$ in the formula (22);

X is O, $NR_{901}$, or $C(R_{902})(R_{903})$; and $R_{901}$ to $R_{903}$ are as defined in the formula (1).

In one embodiment, in the compound represented by the formula (22), one or more pairs of two or more adjacent groups of $R_{201}$ to $R_{211}$ are bonded with each other to form a substituted or unsubstituted, saturated or unsaturated ring. This embodiment is described in the following formula (25).

(Compound Represented by Formula (25))

The compound represented by the formula (25) is explained below.

(25)

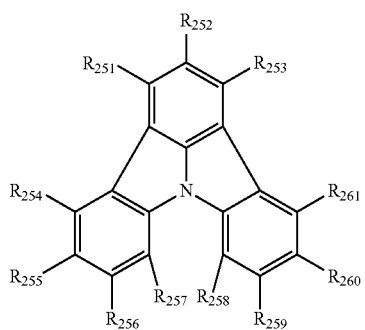

wherein in the formula (25), two or more pairs selected from a group consisting of $R_{251}$ and $R_{252}$, $R_{252}$ and $R_{253}$, $R_{254}$ and $R_{255}$, $R_{255}$ and $R_{256}$, $R_{256}$ and $R_{257}$, $R_{258}$ and $R_{259}$, $R_{259}$ and $R_{260}$, and $R_{260}$ and $R_{261}$ bond with each other to form a substituted or unsubstituted, saturated or unsaturated ring;

Provided that the pair of $R_{251}$ and $R_{252}$ and the pair of $R_{252}$ and $R_{253}$ do not form a ring simultaneously; the pair of $R_{254}$ and $R_{255}$ and the pair of $R_{255}$ and $R_{256}$ do not form a ring simultaneously; the pair of $R_{255}$ and $R_{256}$ and the pair of $R_{265}$ and $R_{257}$ do not form a ring simultaneously; the pair of $R_{25}$ and $R_{259}$ and the pair of $R_{259}$ and $R_{260}$ do not form a ring simultaneously; and the pair of $R_{259}$ and $R_{260}$ and the pair of $R_{260}$ and $R_{261}$ do not form a ring simultaneously;

When two or more rings are formed by $R_{251}$ to $R_{261}$, the rings may be the same or different;

$R_{251}$ to $R_{261}$ that do not form the substituted or unsubstituted, saturated or unsaturated ring are independently
a hydrogen atom,
a substituted or unsubstituted alkyl group having 1 to 50 carbon atoms,
a substituted or unsubstituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and $R_{901}$ to $R_{907}$ are as defined in the formula (1).

In the formula (25), $R_n$ and $R_{n+1}$ (n is an integer selected from 251, 252, 254 to 256 and 258 to 260) bond with each other to form a substituted or unsubstituted, saturated or unsaturated ring together with two ring carbon atoms to which $R_n$ and $R_{n+1}$ bond with. The ring is preferably configured with atoms selected from C atom, O atom, S atom and N atom, and the number of atoms is preferably 3 to 7, more preferably 5 or 6.

The number of the above-described ring structures in the compound represented by the formula (25) is, for example, 2, 3 or 4. Two or more ring structures may exist in the same benzene ring of the main skeleton in the formula (25), or may exist in different benzene rings. For example, the compound has three ring structures, one ring structure may exist in each of the three benzene rings in the formula (25).

As the above-mentioned ring structure in the compound represented by the formula (25), structures represented by the following formulas (251) to (260) can be given, for example.

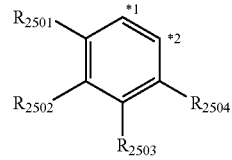
(251)

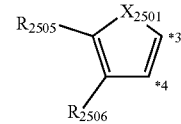
(252)

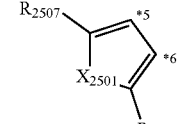
(253)

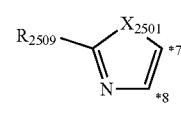
(254)

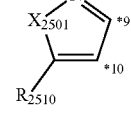
(255)

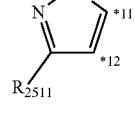
(256)

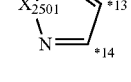
(257)

wherein in the formulas (251) to (257), each of *1 and *2, *3 and *4, *5 and *6, *7 and *8, *9 and *10, *11 and *12, and *13 and *14 represents two ring carbon atoms to which $R_n$ and $R_{n+1}$ bond, and $R_n$ may bond to either one of the two ring carbon atoms of *1 and *2, *3 and *4, *5 and *6, *7 and *8, *9 and *10, *11 and *12, and *13 and *14;

$X_{2501}$ is C($R_{2512}$)($R_{2513}$), $NR_{2514}$, O or S;

One or more pairs of two or more adjacent groups of $R_{2501}$ to $R_{2506}$ and $R_{2512}$ to $R_{2513}$ are bonded with each other to form a substituted or unsubstituted, saturated or unsaturated ring, or do not form a substituted or unsubstituted saturated or unsaturated ring; and $R_{2501}$ to $R_{2514}$ that do not form a substituted or unsubstituted saturated or unsaturated ring are the same as $R_{251}$ to $R_{21}$.

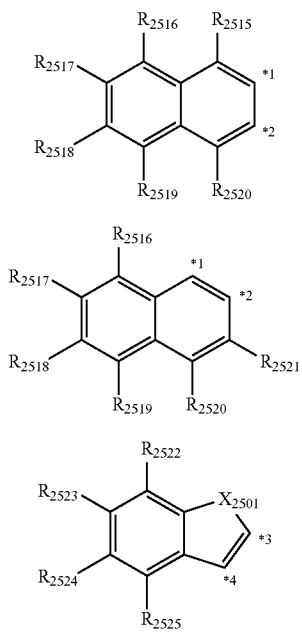

(258)

(259)

(260)

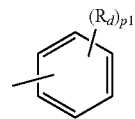

(261)

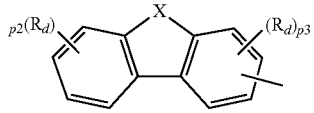

(262)

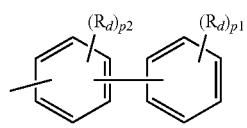

(263)

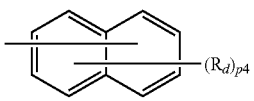

(264)

wherein in the formulas (258) to (260), each of *1 and *2, and *3 and *4 represents two ring carbon atoms to which $R_n$ and $R_{n+1}$ bond, and $R_n$ may bond to either one of the two ring carbon atoms of *1 and *2, or *3 and *4;

$X_{2501}$ is $C(R_{2512})(R_{2513})$, $NR_{2514}$, O or S;

One or more pairs of two or more adjacent groups of $R_{2515}$ to $R_{2525}$ bond to each other to form a substituted or unsubstituted, saturated or unsaturated ring, or do not form a substituted or unsubstituted saturated or unsaturated ring; and $R_{2515}$ to $R_{2521}$ and $R_{2522}$ to $R_{2525}$ that do not form a substituted or unsubstituted saturated or unsaturated ring are the same as $R_{251}$ to $R_{261}$.

In the formula (25), it is preferable that at least one of $R_{252}$, $R_{254}$, $R_{255}$, $R_{260}$ and $R_{261}$ (preferably at least one of $R_{252}$, $R_{255}$, and $R_{260}$, more preferably $R_{252}$) is a group which does not form a ring.

(i) Substituent in the case where the ring structure formed by $R_n$ and $R_{n+1}$ has a substituent in the formula (25), (ii) $R_{251}$ to $R_{261}$ that do not form a ring structure in the formula (25), and (iii) $R_{2501}$ to $R_{2514}$ and $R_{2515}$ to $R_{2525}$ in the formulas (251) to (260) are preferably independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$N(R_{906})(R_{907})$,
a substituted or unsubstituted aryl group having 6 to 50 ring carbon atoms,
a substituted or unsubstituted monovalent heterocyclic group having 5 to 50 ring atoms, or a group selected from the following groups.

wherein in the formulas (261) to (264), $R_d$s are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

X is $C(R_{901})(R_{902})$, $NR_{903}$, O, or S;

$R_{901}$ to $R_{907}$ are as defined in the formula (1); and p1 is independently an integer of 0 to 5, p2 is independently an integer of 0 to 4, p3 is an integer of 0 to 3, and p4 is an integer of 0 to 7.

In one embodiment, the compound represented by the formula (25) is represented by the following formulas (25-1) to (25-6).

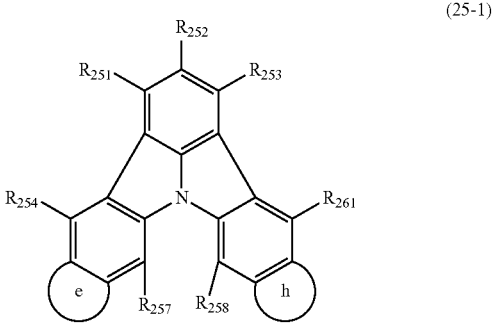

(25-1)

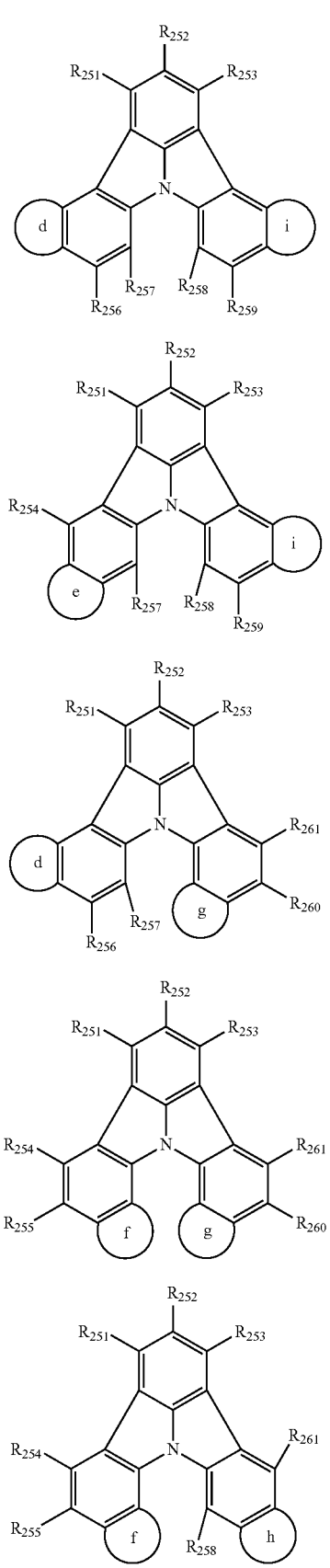
wherein in the formulas (25-1) to (25-6), ring d to ring i are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-7) to (25-12).
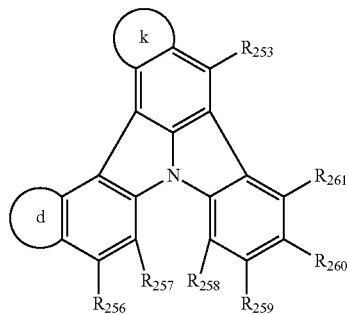
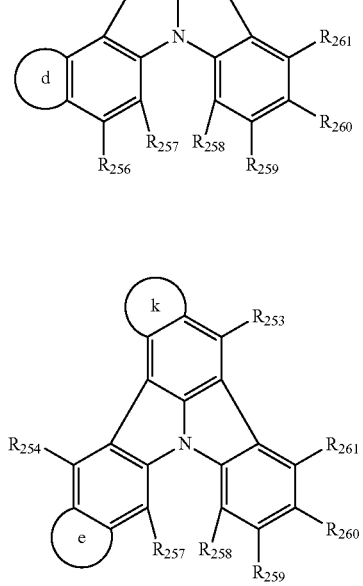
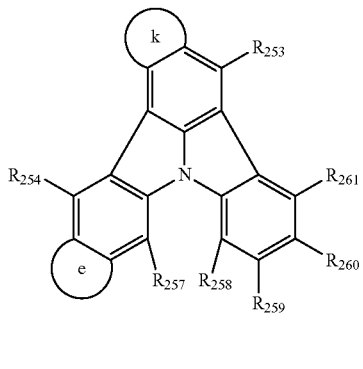
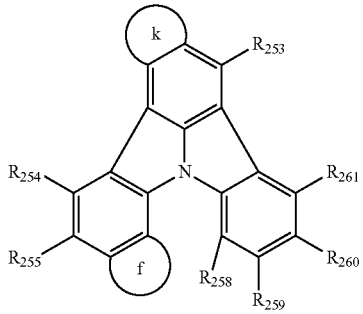

(25-11)
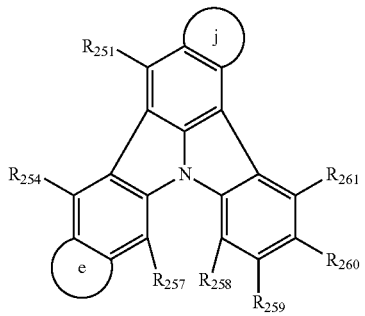
(25-12)
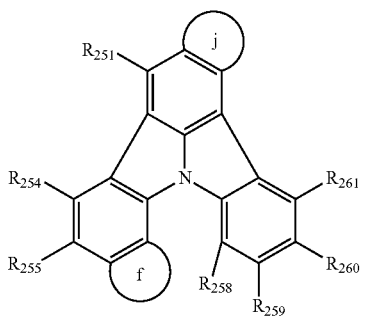
wherein in the formulas (25-7) to (25-12), ring d to ring f, ring k, and ring j are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-13) to (25-21).
(25-13)
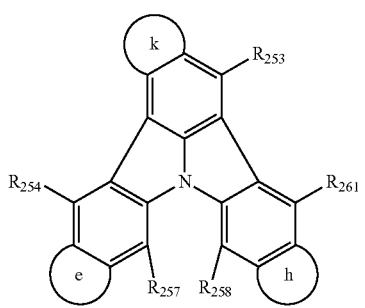
(25-14)
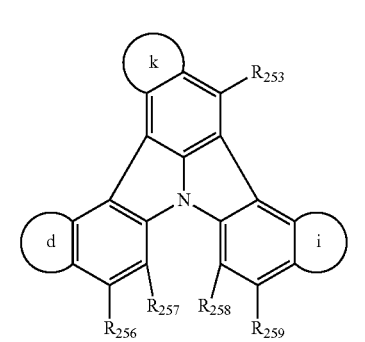
(25-15)
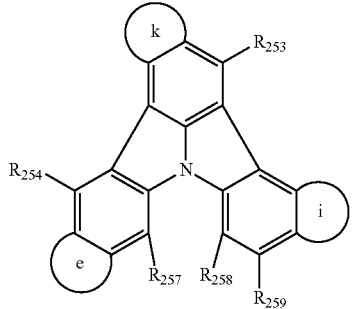
(25-16)
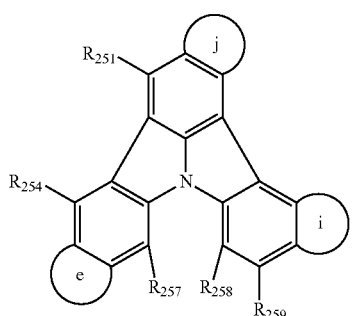
(25-17)
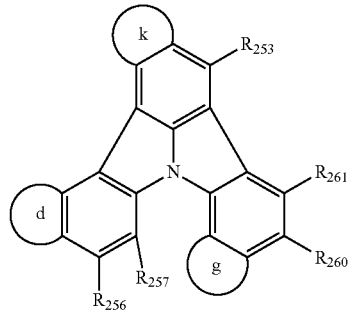
(25-18)
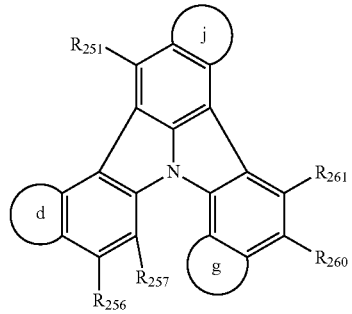
(25-19)
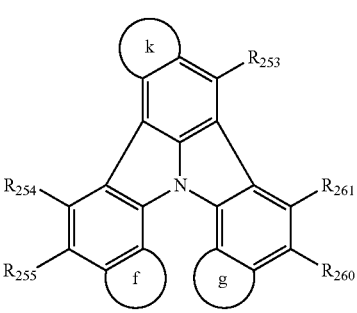

(25-20)

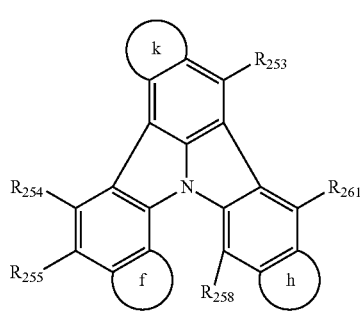

(25-21)

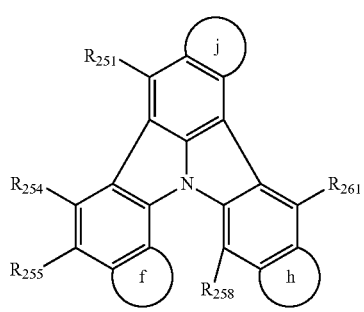

wherein in the formulas (25-13) to (25-21), ring d to ring k are independently a substituted or unsubstituted, saturated or unsaturated ring; and $R_{251}$ to $R_{261}$ are the same as defined in the formula (25).

As a substituent in the case where the ring g or ring h further has a substituent, a substituted or unsubstituted alkyl group having 1 to 50 carbon atoms, a substituted or unsubstituted aryl group having 6 to 50 ring carbon atoms, or a group represented by the formula (261), (263) or (264) can be given for example.

In one embodiment, the compound represented by the formula (25) is represented by one of the following formulas (25-22) to (25-25).

(25-22)

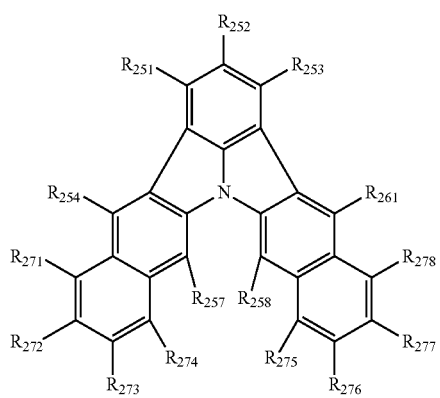

(25-23)

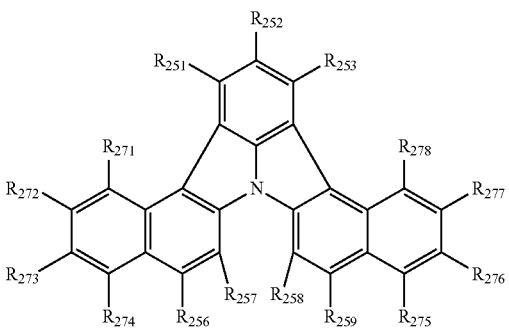

(25-24)

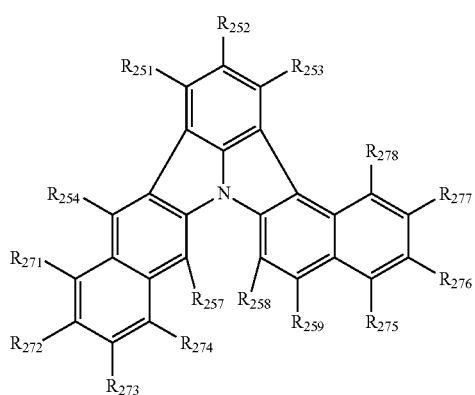

(25-25)

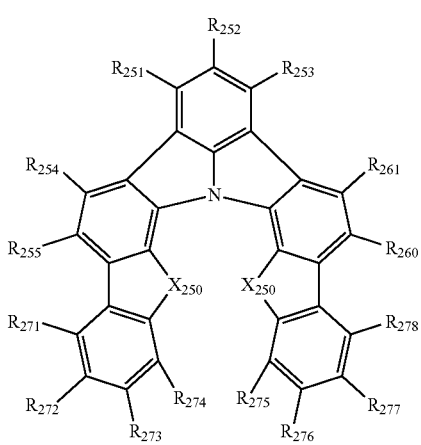

wherein in the formulas (25-22) to (25-25), $X_{250}$ is $C(R_{901})(R_{902})$, $NR_{903}$, O or S; $R_{251}$ to $R_{261}$, and $R_{271}$ to $R_{278}$ are the same as $R_{251}$ to $R_{261}$ in the formula (25); and $R_{901}$ to $R_{903}$ are as defined in the formula (1).

In one embodiment, the compound represented by the formula (25) is represented by the following formula (25-26).

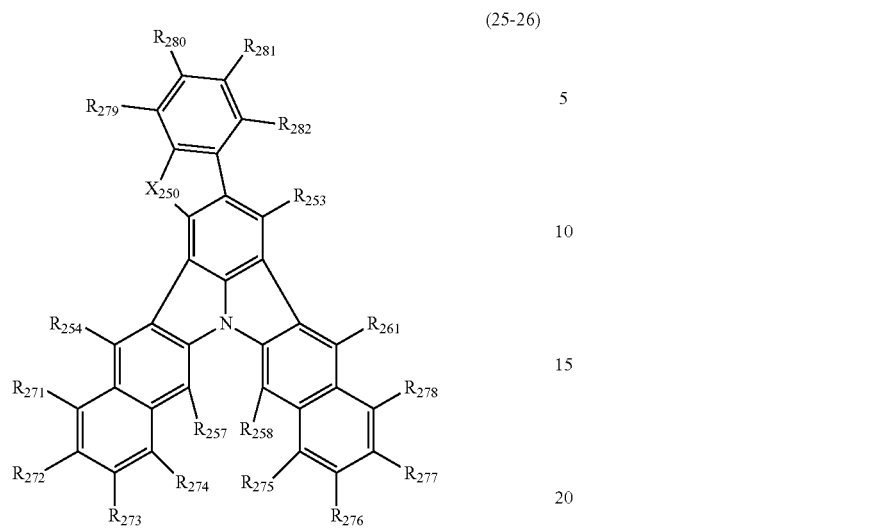
(25-26)
wherein in the formula (25-26), $X_{250}$ is $C(R_{901})(R_{902})$, $NR_{903}$, O or S; $R_{253}$, $R_{254}$, $R_{257}$, $R_{258}$, $R_{261}$, and $R_{271}$ to $R_{282}$ are the same as $R_{251}$ to $R_{261}$ in the formula (25); and $R_{901}$ to $R_{903}$ are as defined in the formula (1).
As the compound represented by the formula (21), the following compounds can be shown for example. In the following example compounds, Me represents methyl group.
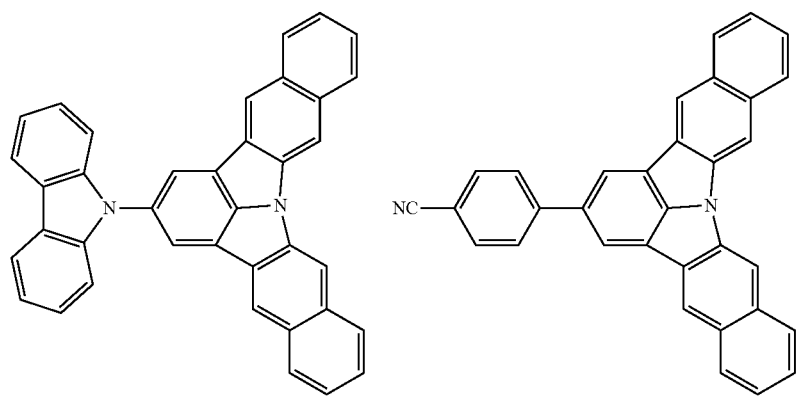
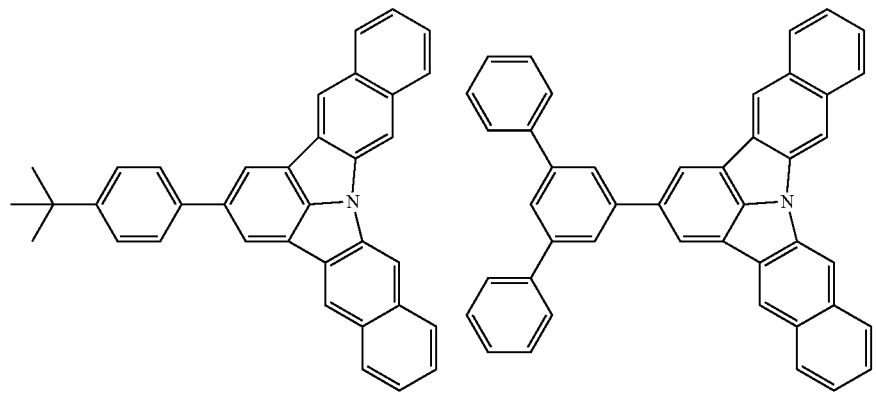

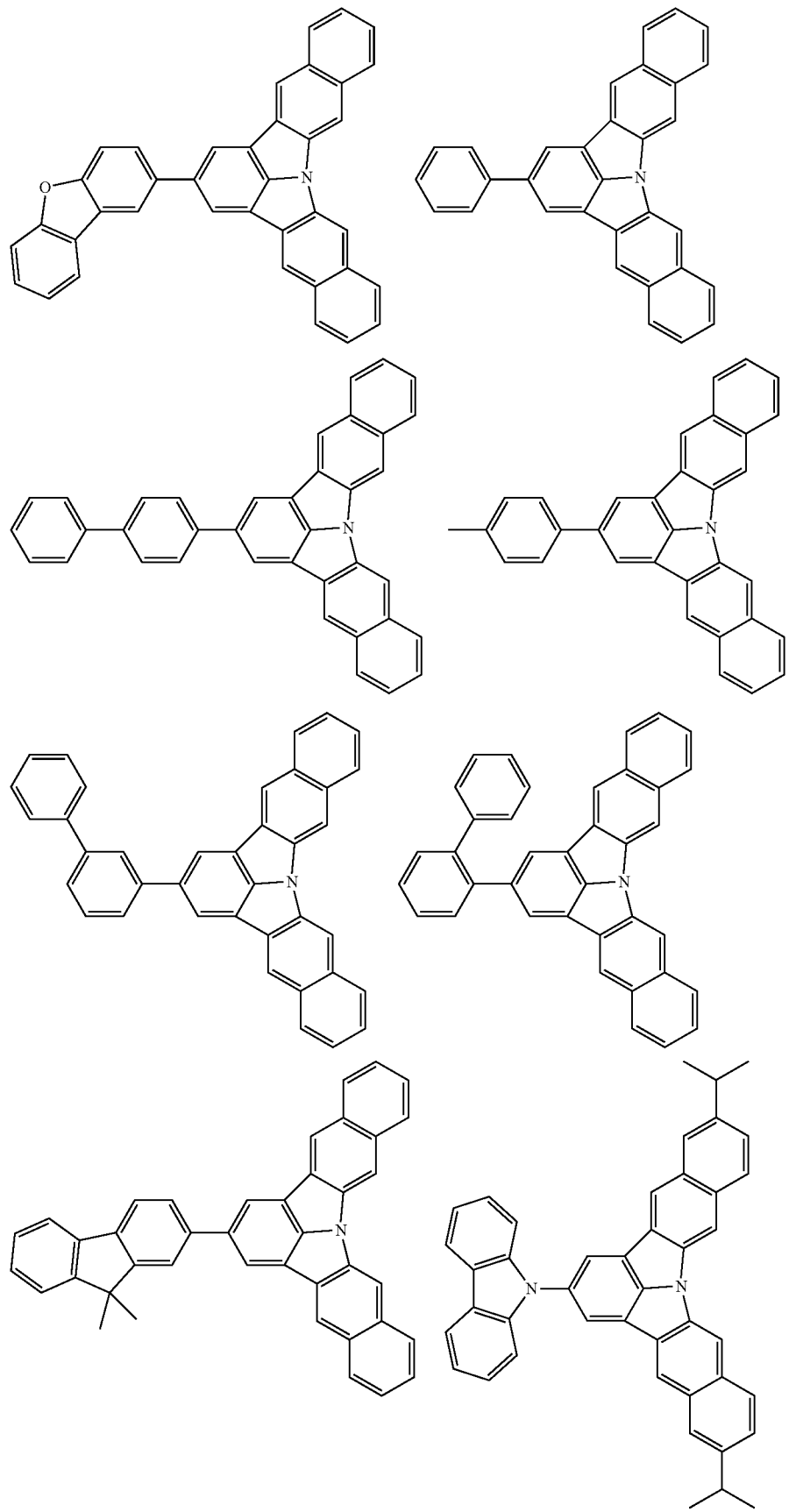

-continued
419
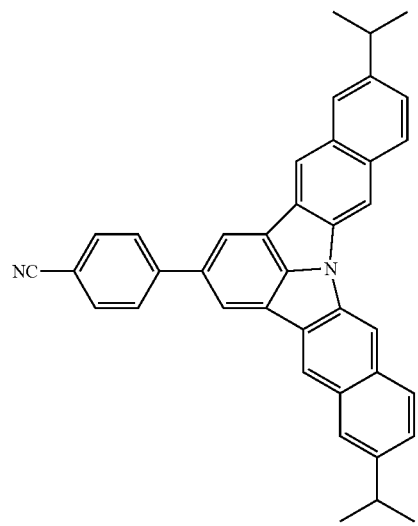
420
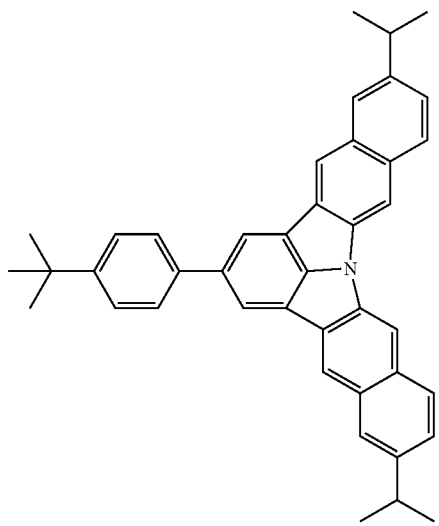
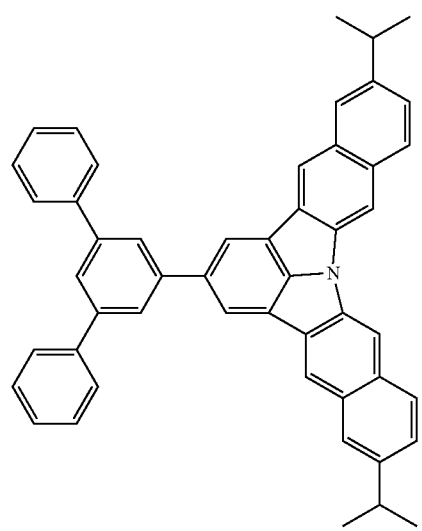
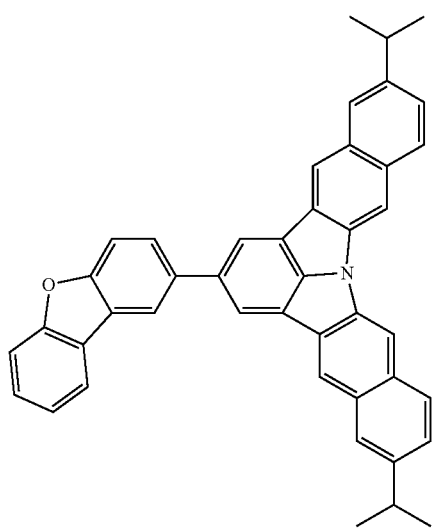
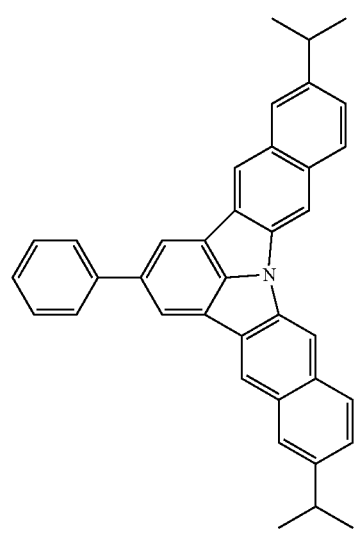
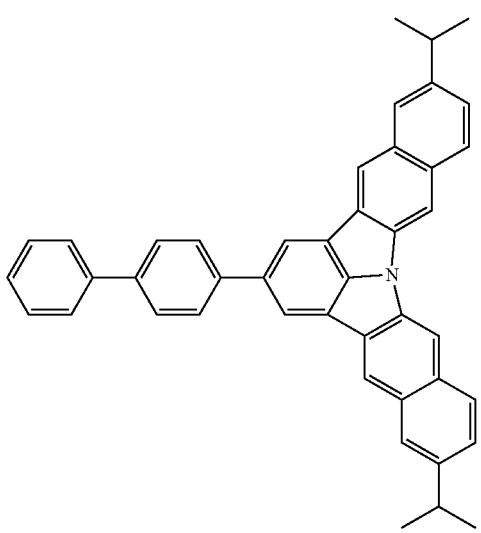

421
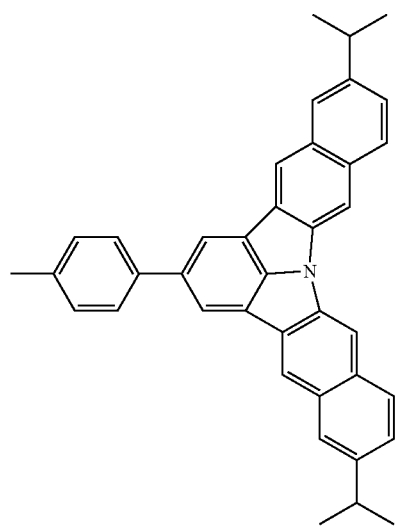
422
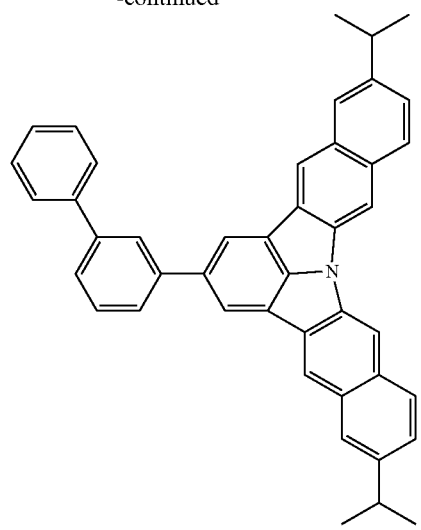
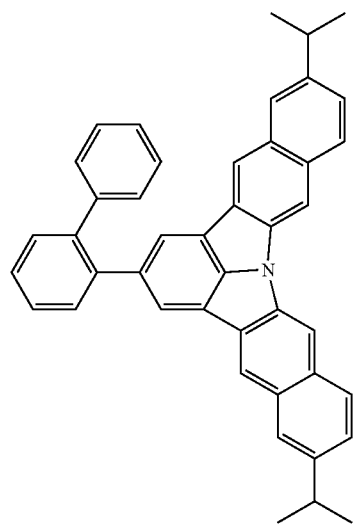
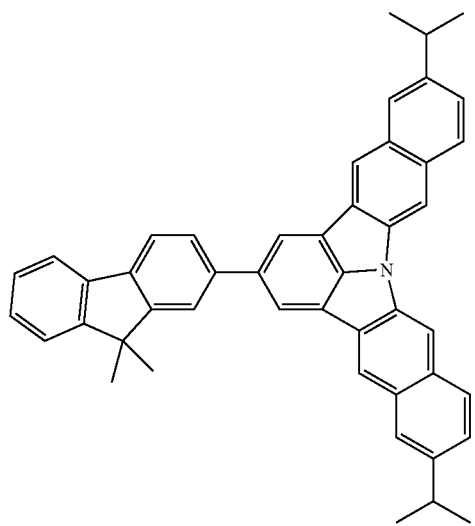
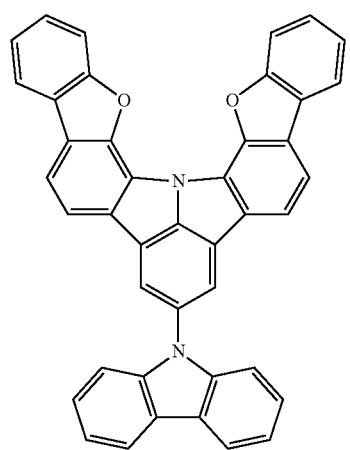
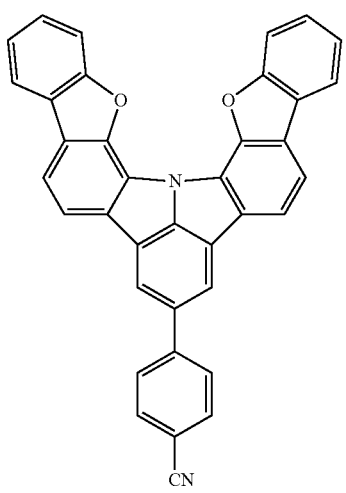
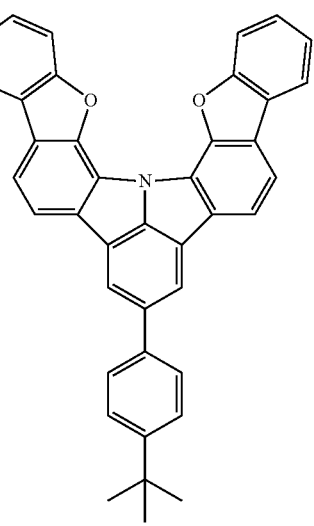

423
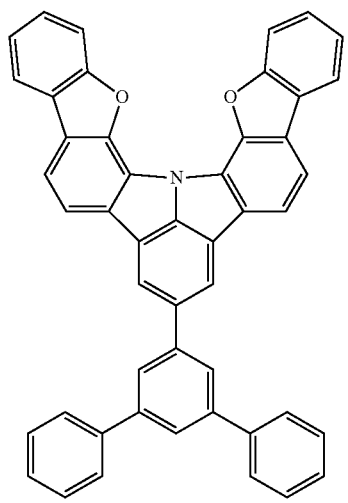
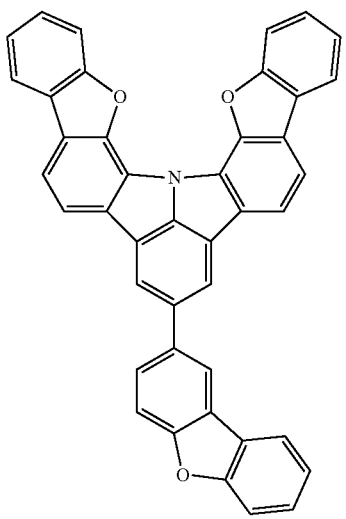
424
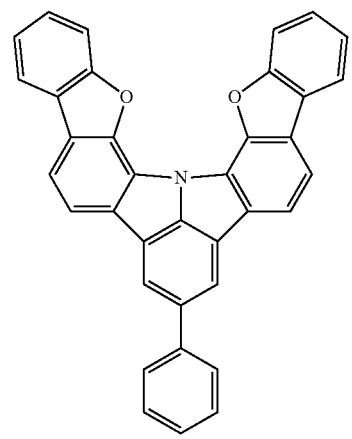
-continued
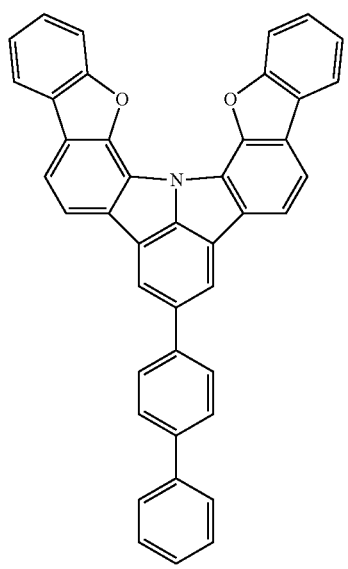
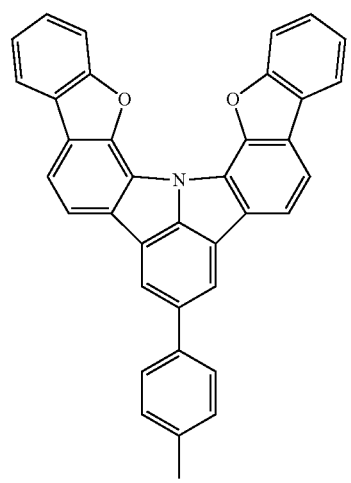
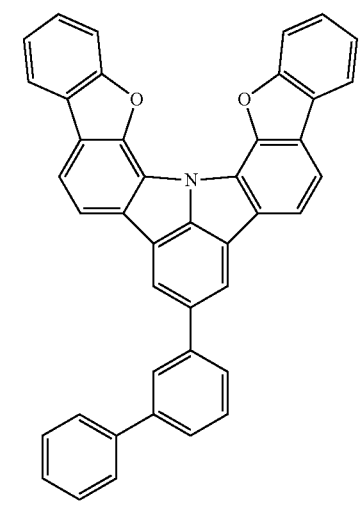
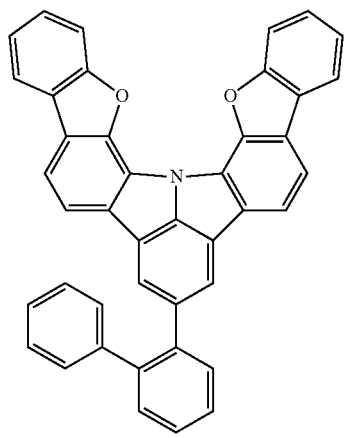
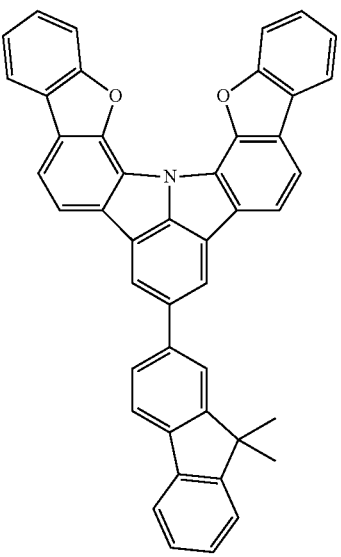

425 426
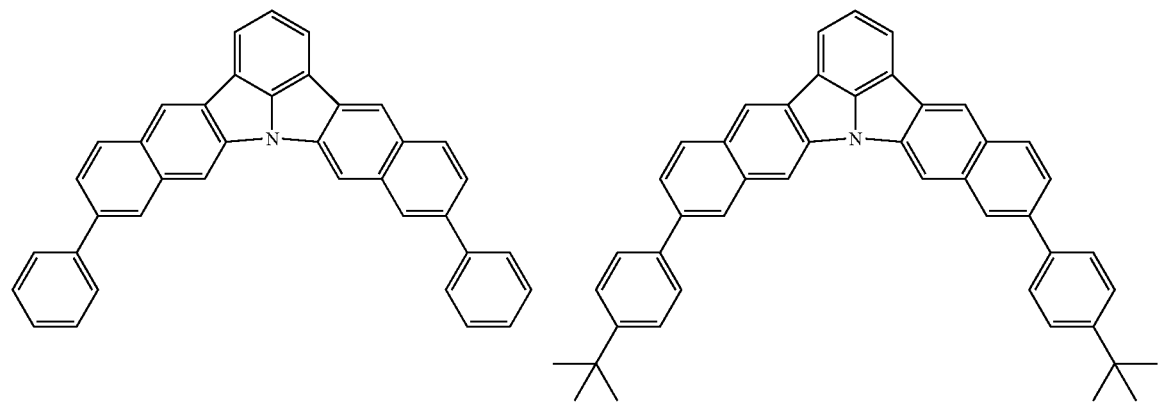
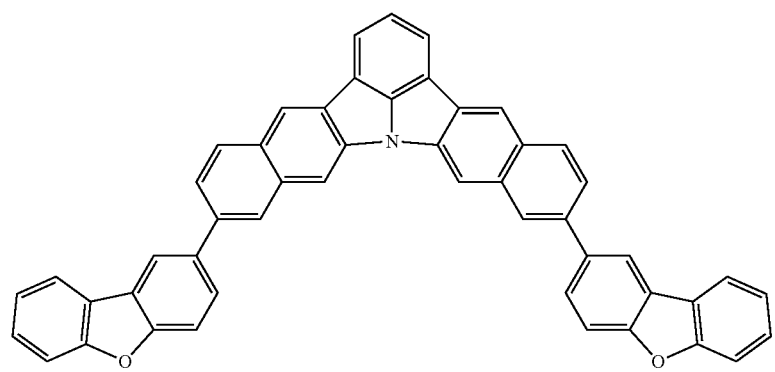
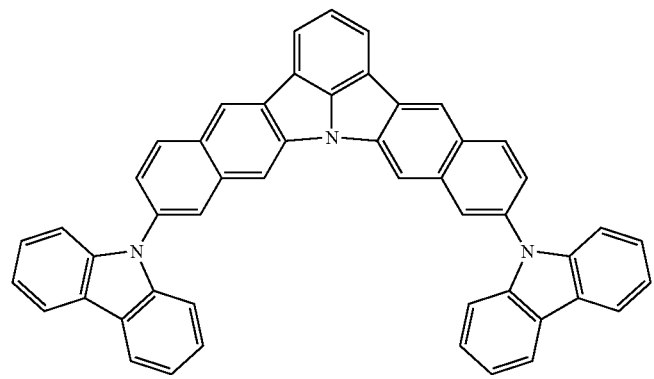
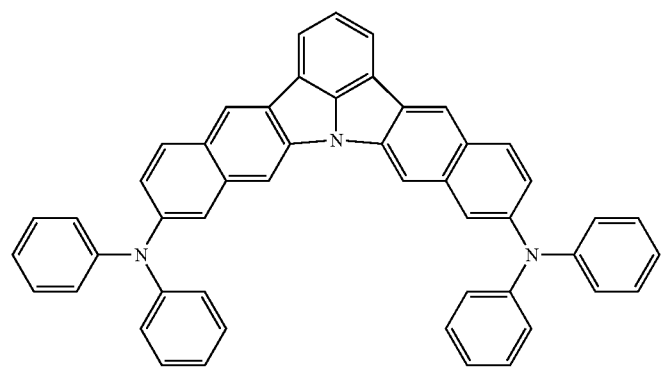

-continued
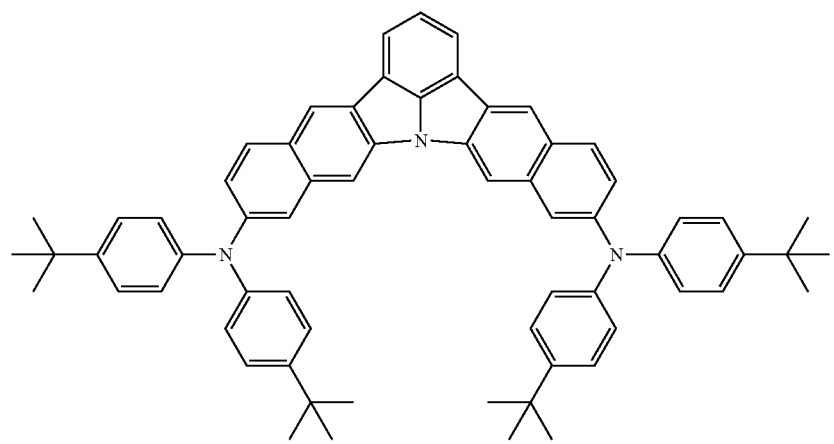
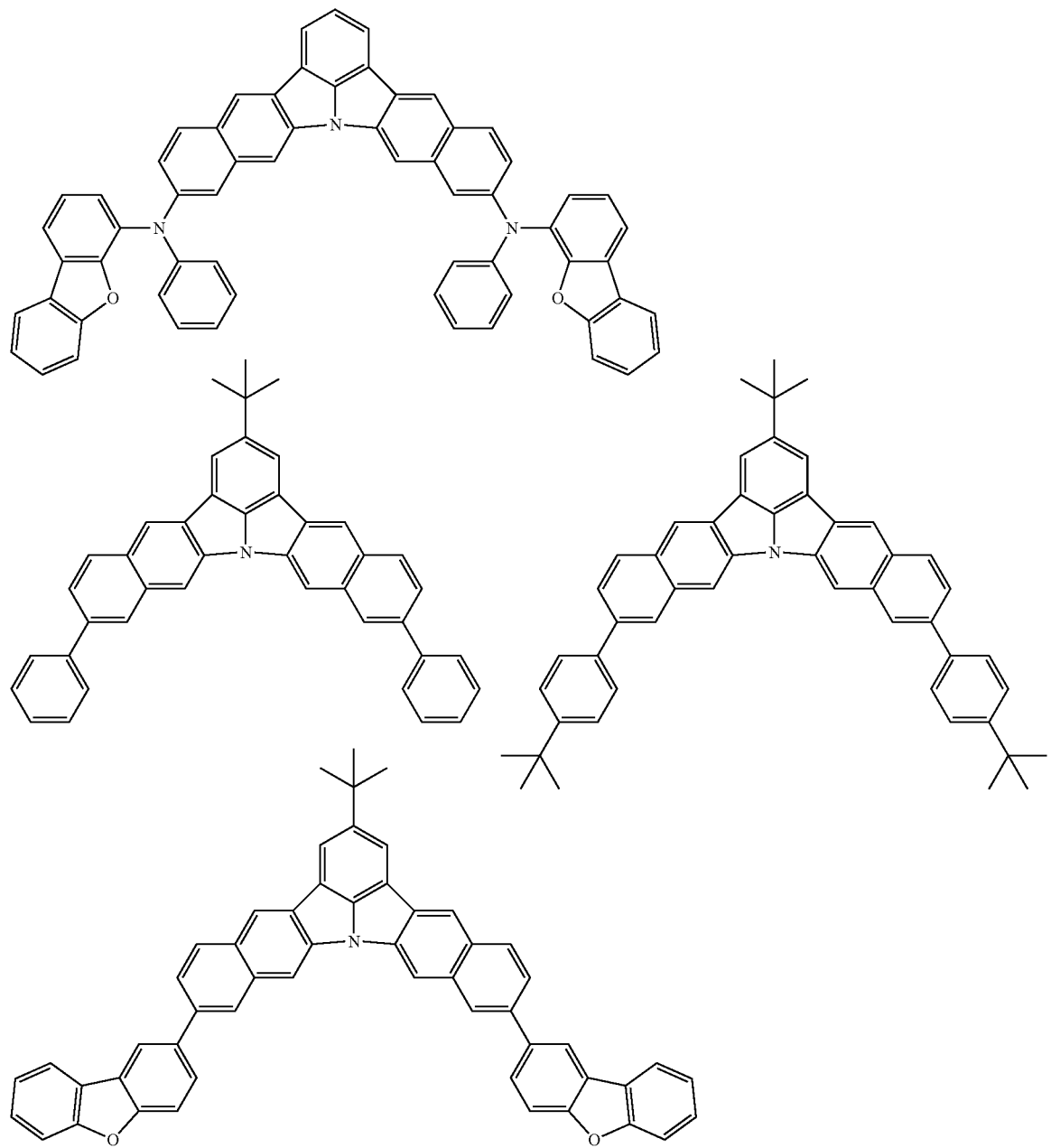

-continued
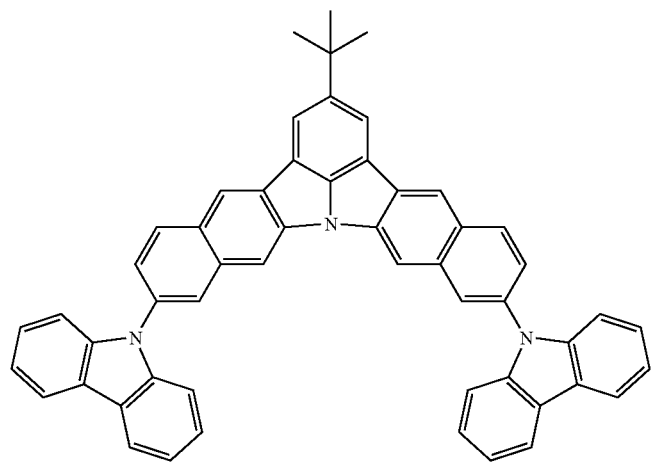
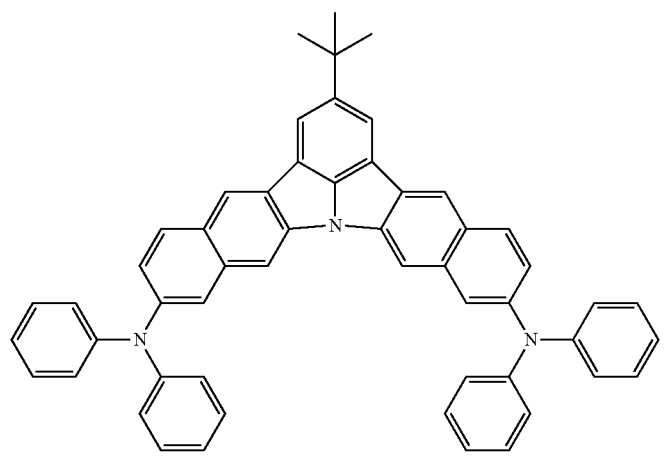
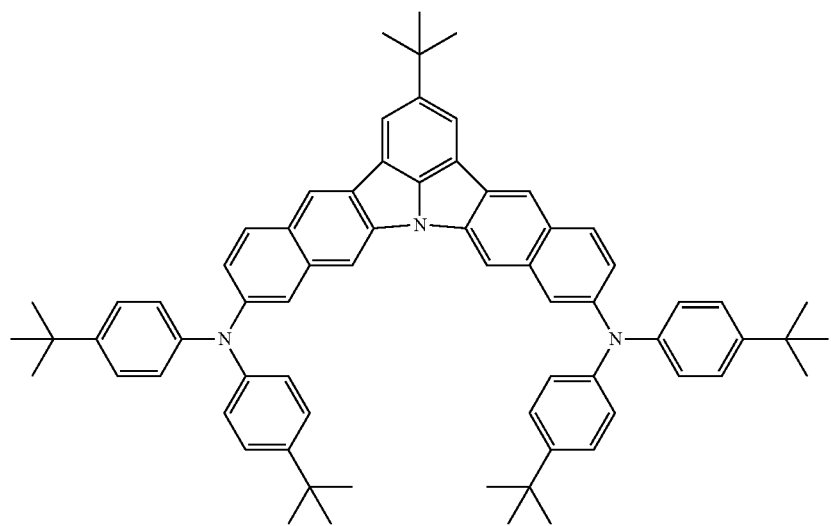

431
432
-continued
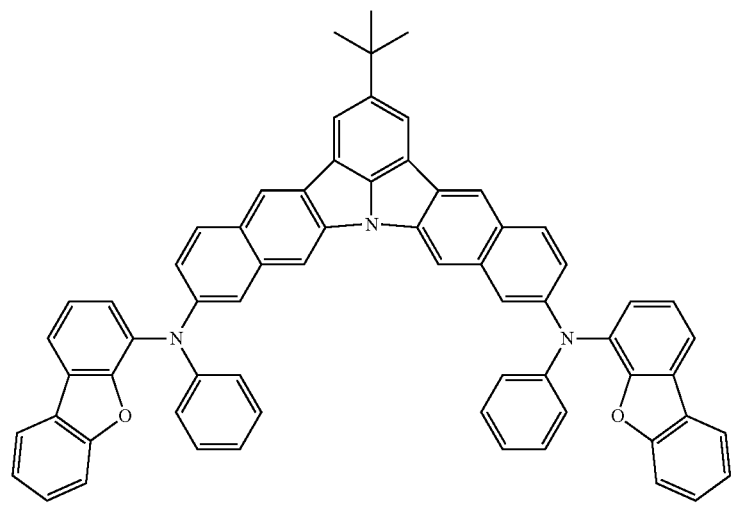
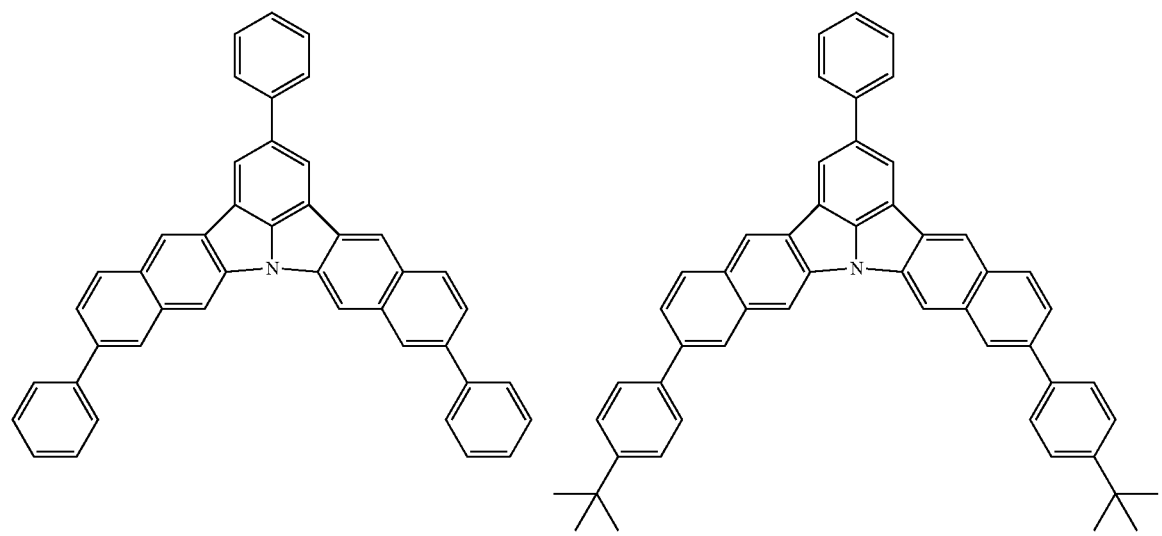
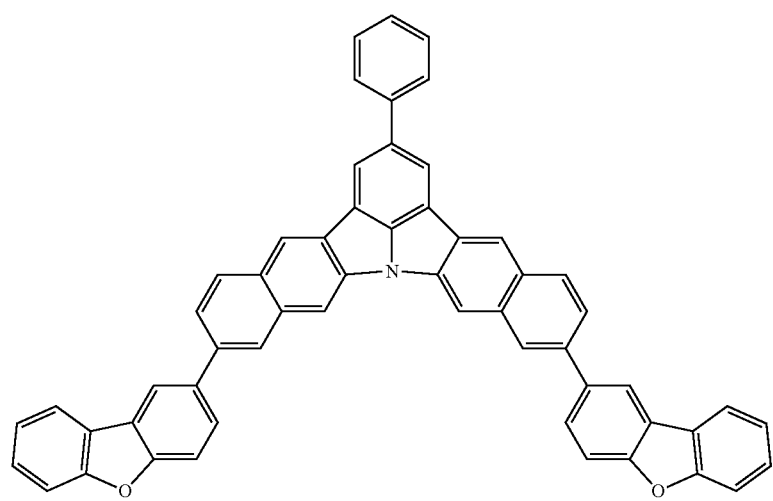 [SMILES: c1ccc(-c2cc3c4cc5ccc(-c6ccc7oc8ccccc8c7c6)cc5cc4n4c5cc6cc(-c7ccc8oc9ccccc9c8c7)ccc6cc5c(c2)c34)cc1]

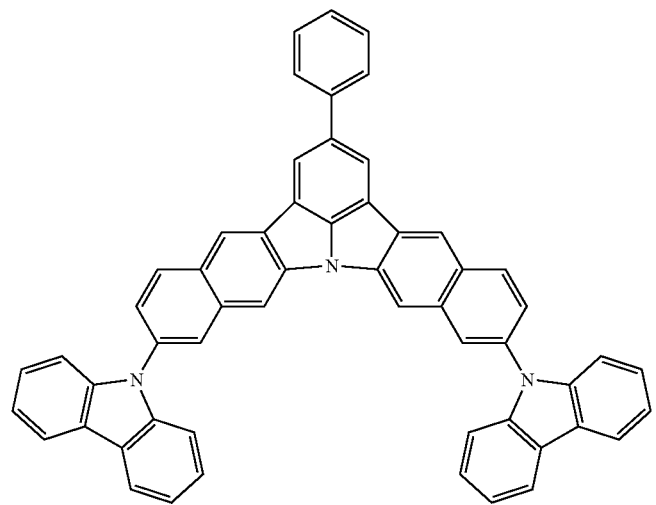
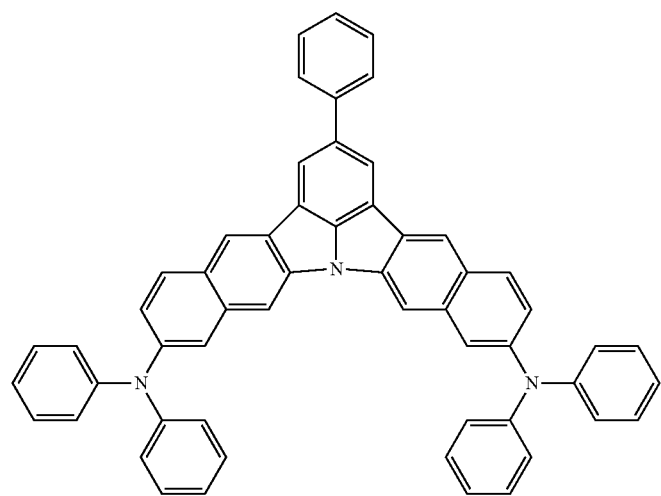
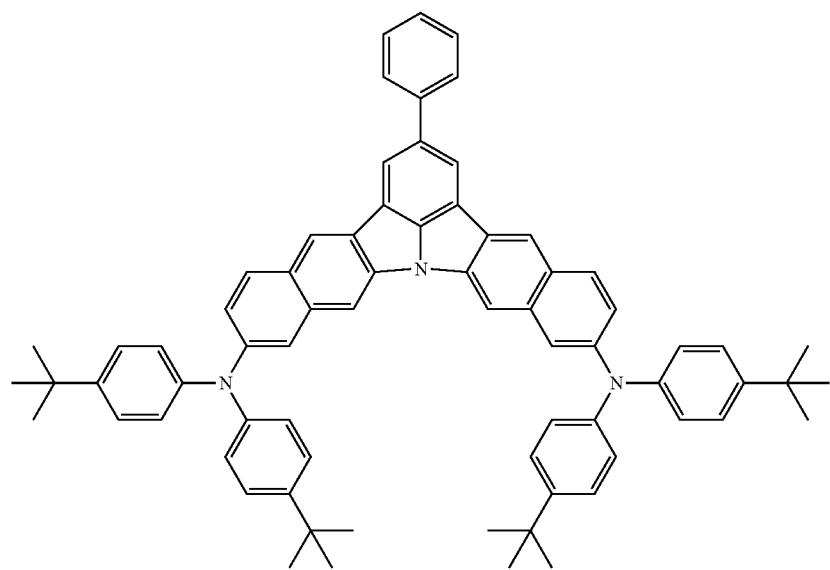

435 436
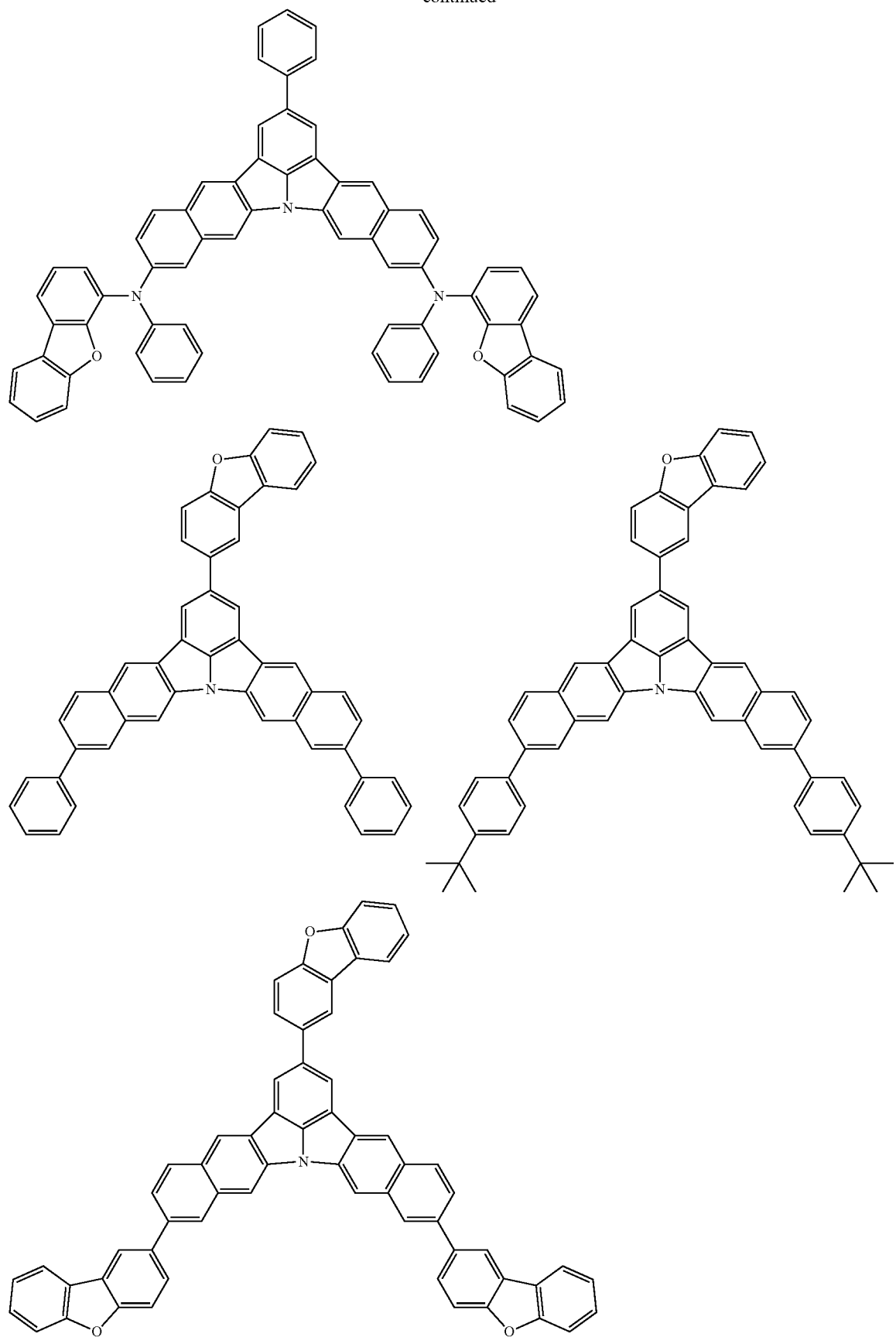
-continued

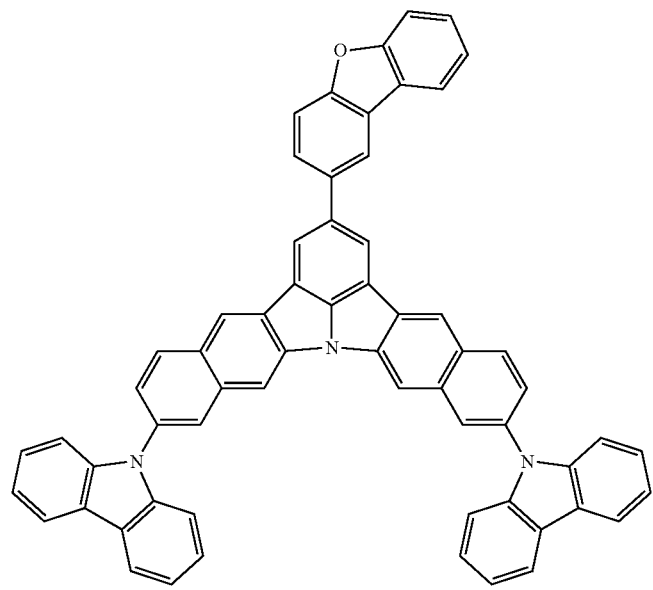
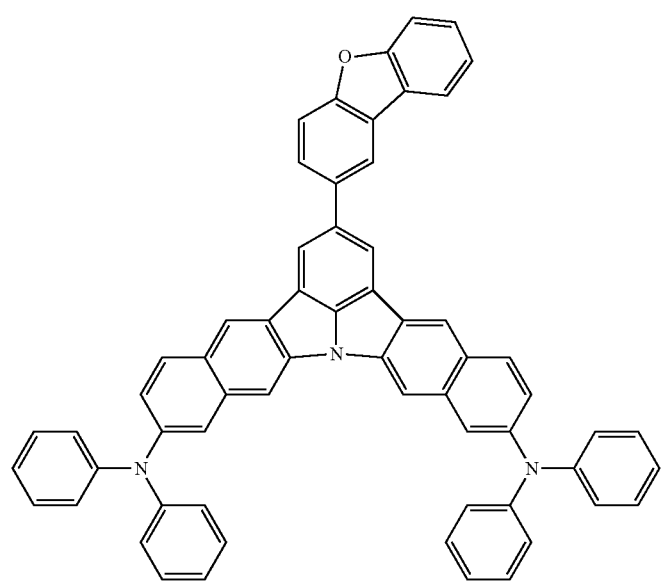

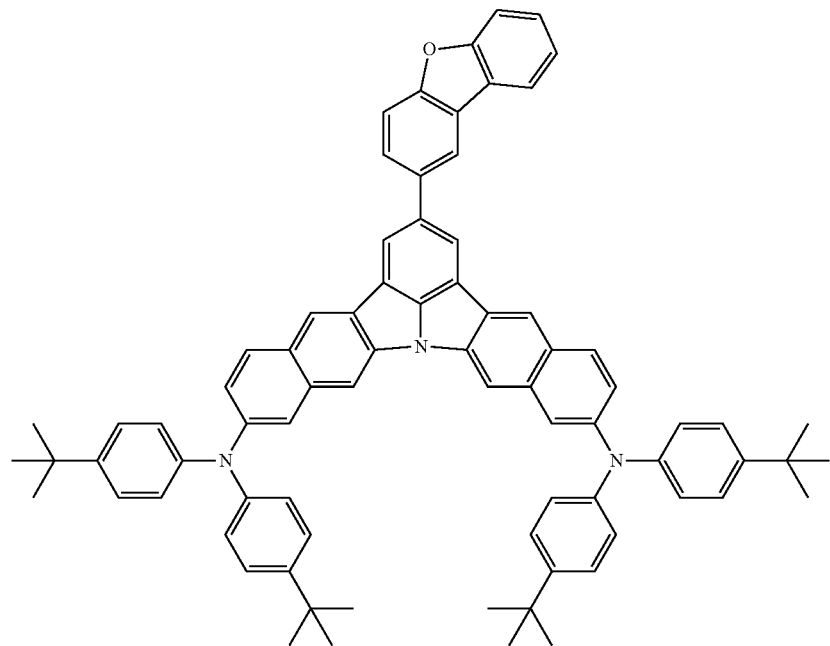
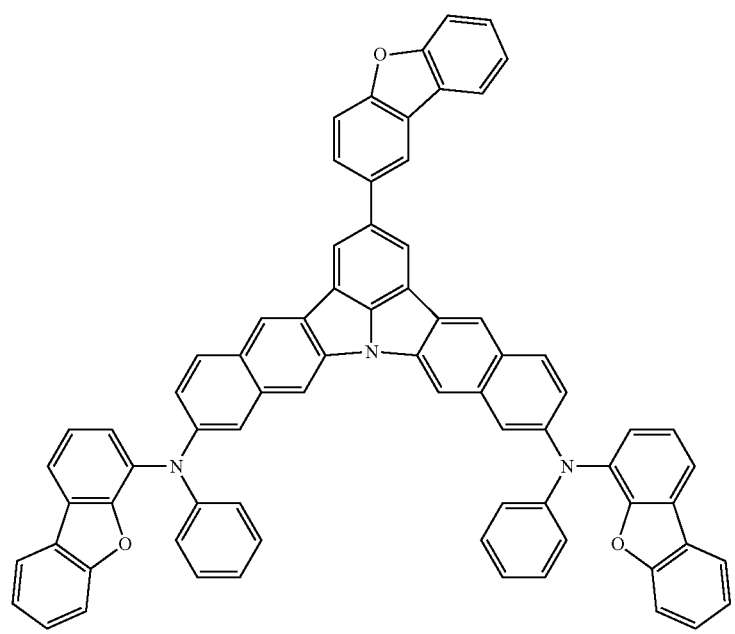

441 442
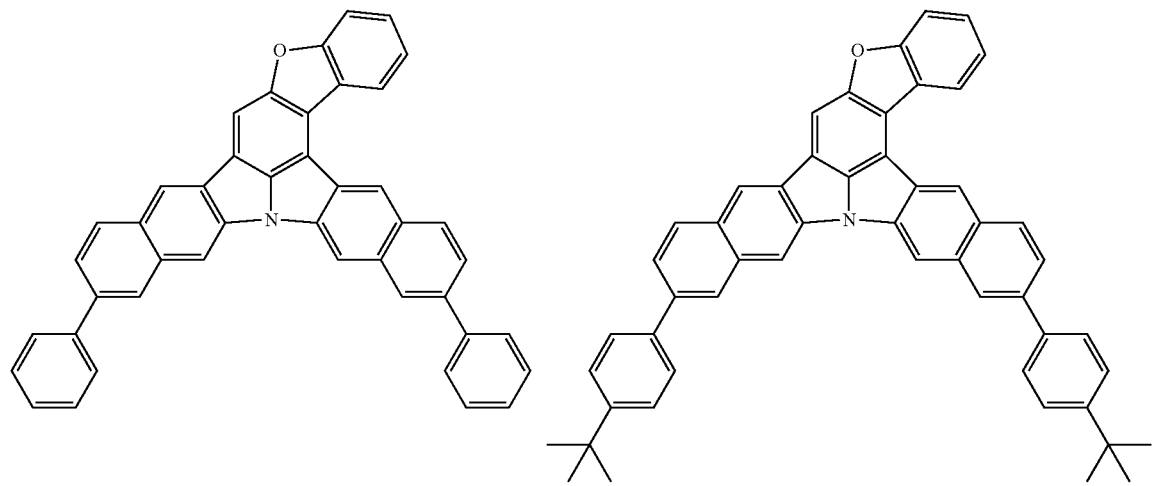
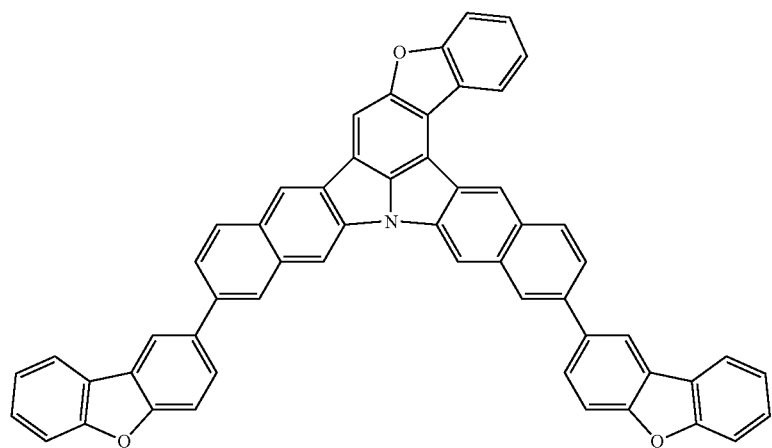 [SMILES: c1ccc2c(c1)oc1ccc(-c3ccc4cc5c6cc7oc8ccccc8c7c7c8cc9ccc(-c%10ccc%11oc%12ccccc%12c%11c%10)cc9cc8n(c5cc4c3)c67)cc12]
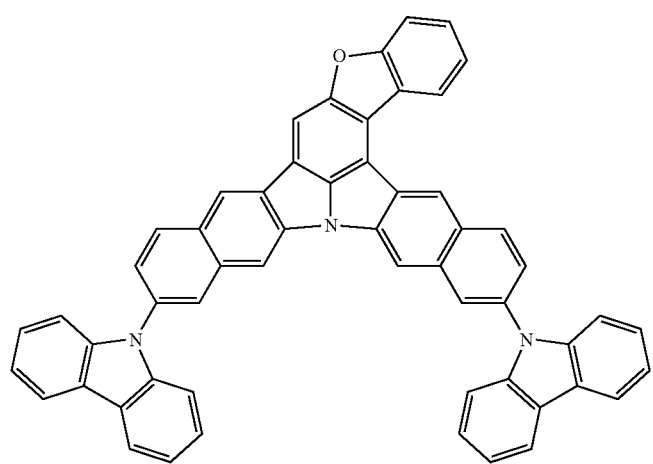

-continued
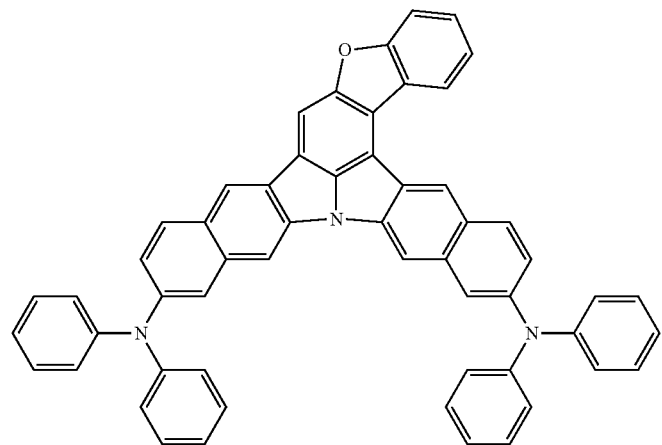
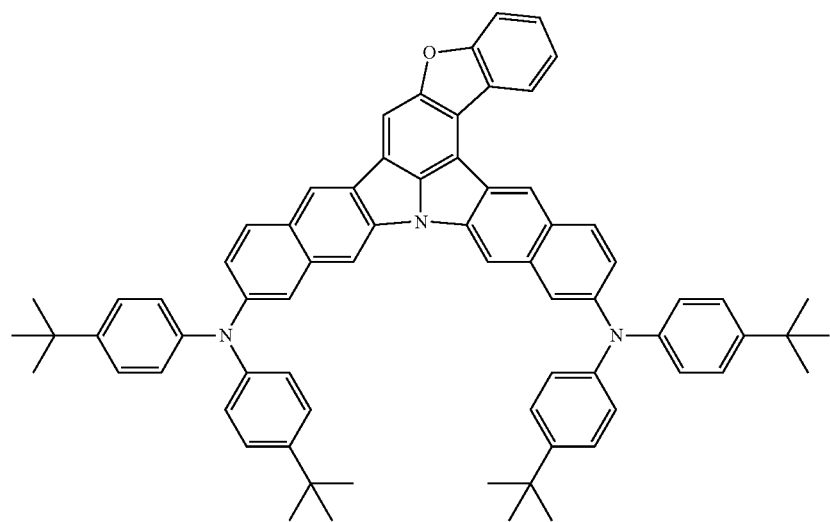
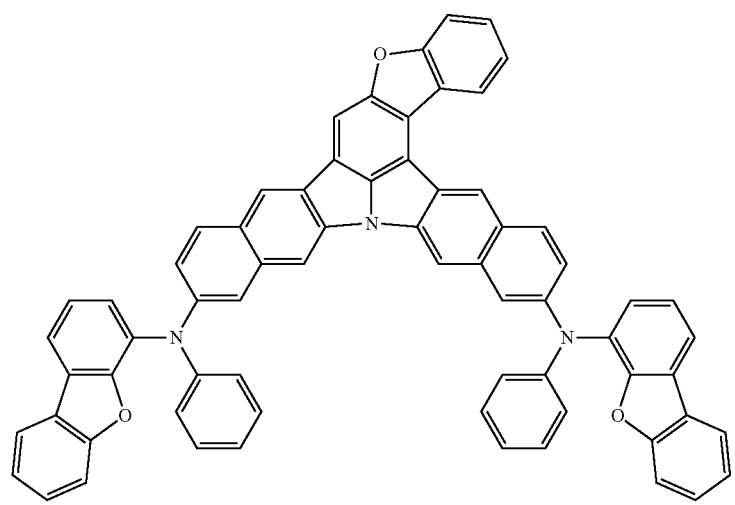

-continued
445 446
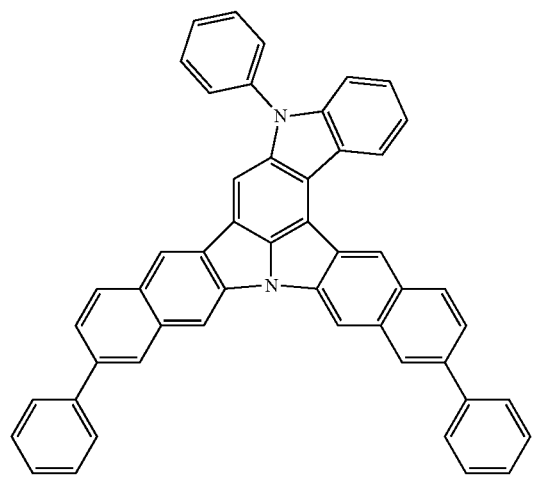 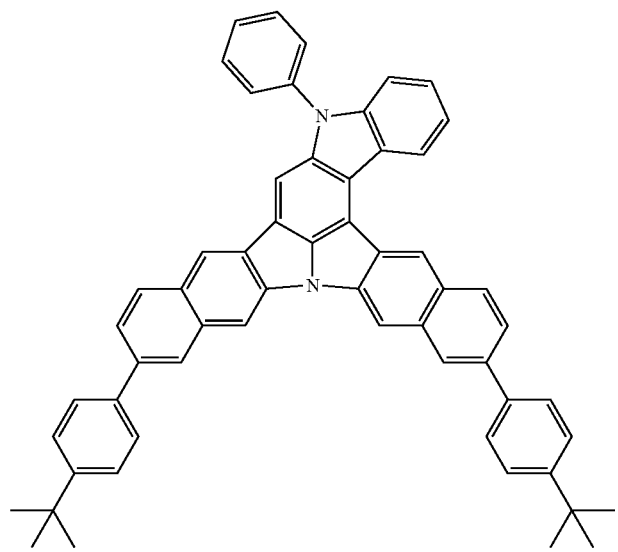
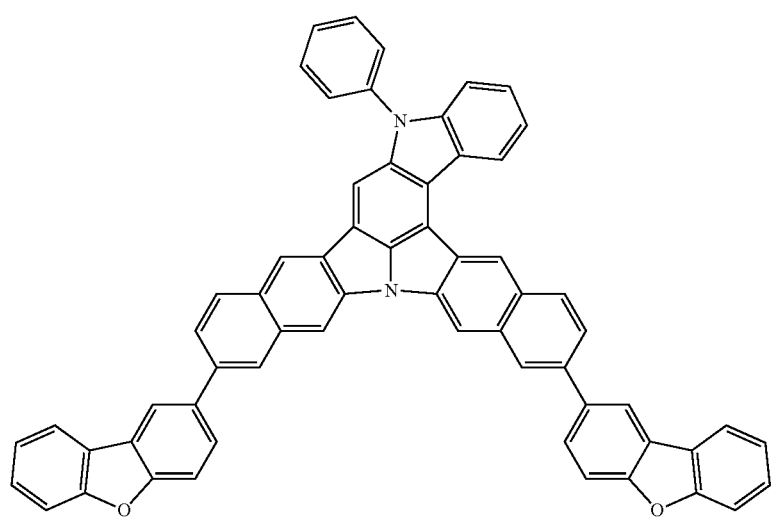 [SMILES: c1ccc(-n2c3ccccc3c3c4c5cc6ccc(-c7ccc8oc9ccccc9c8c7)cc6cc5n5c6cc7cc(-c8ccc9oc%10ccccc%10c9c8)ccc7cc6c(cc32)c45)cc1]
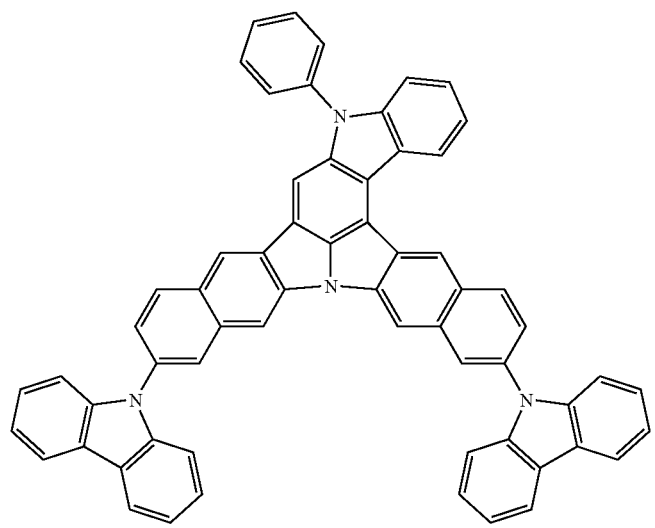

-continued
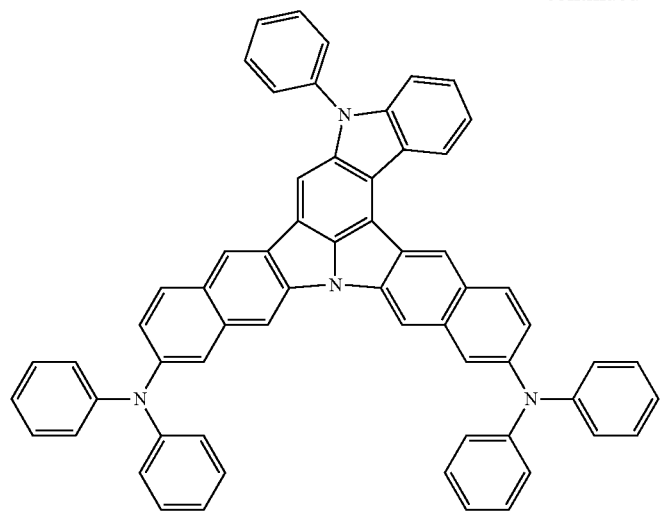
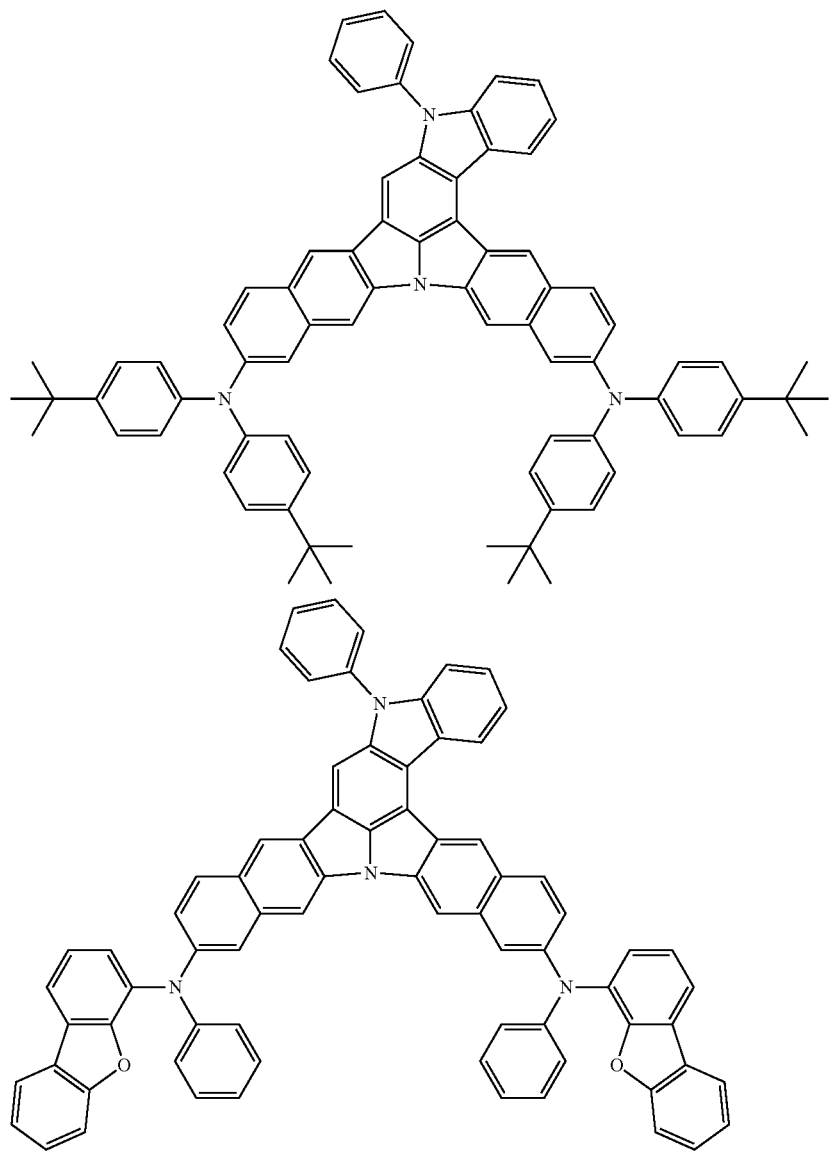

-continued
449 450
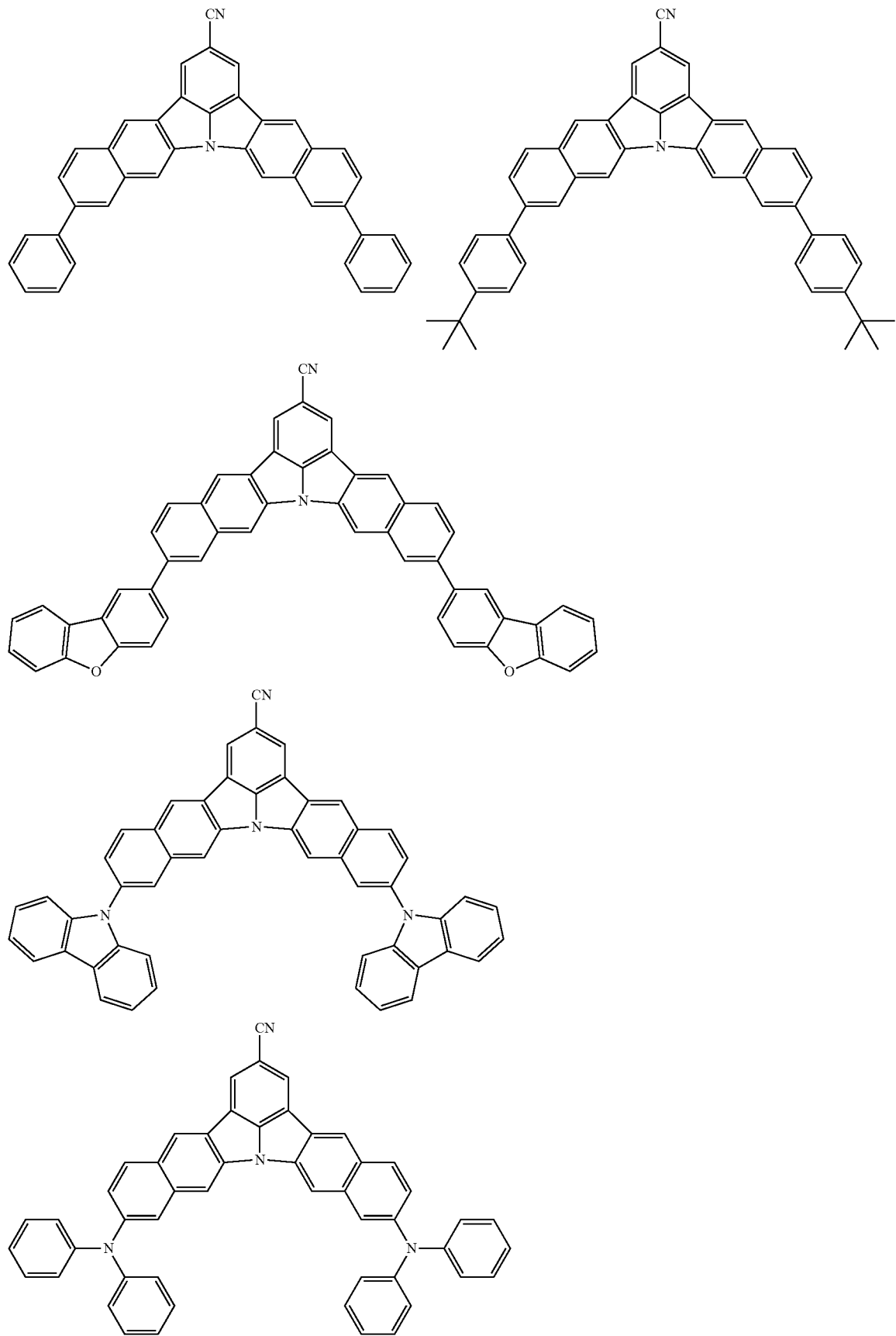

451
452
-continued
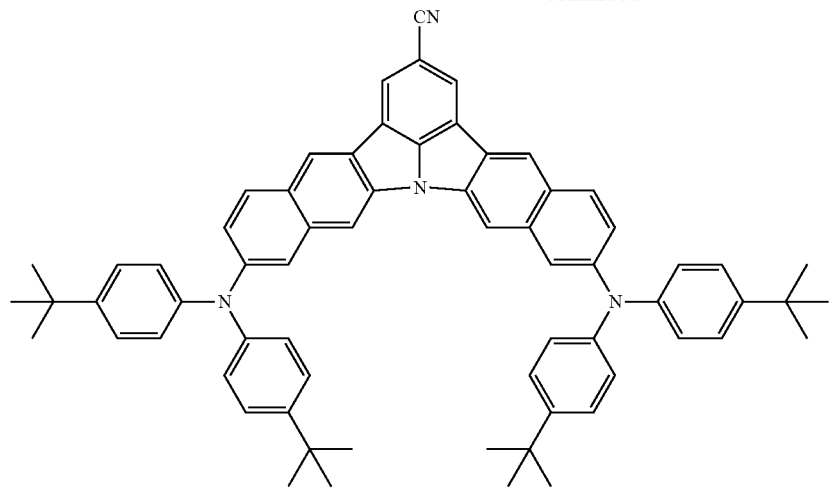
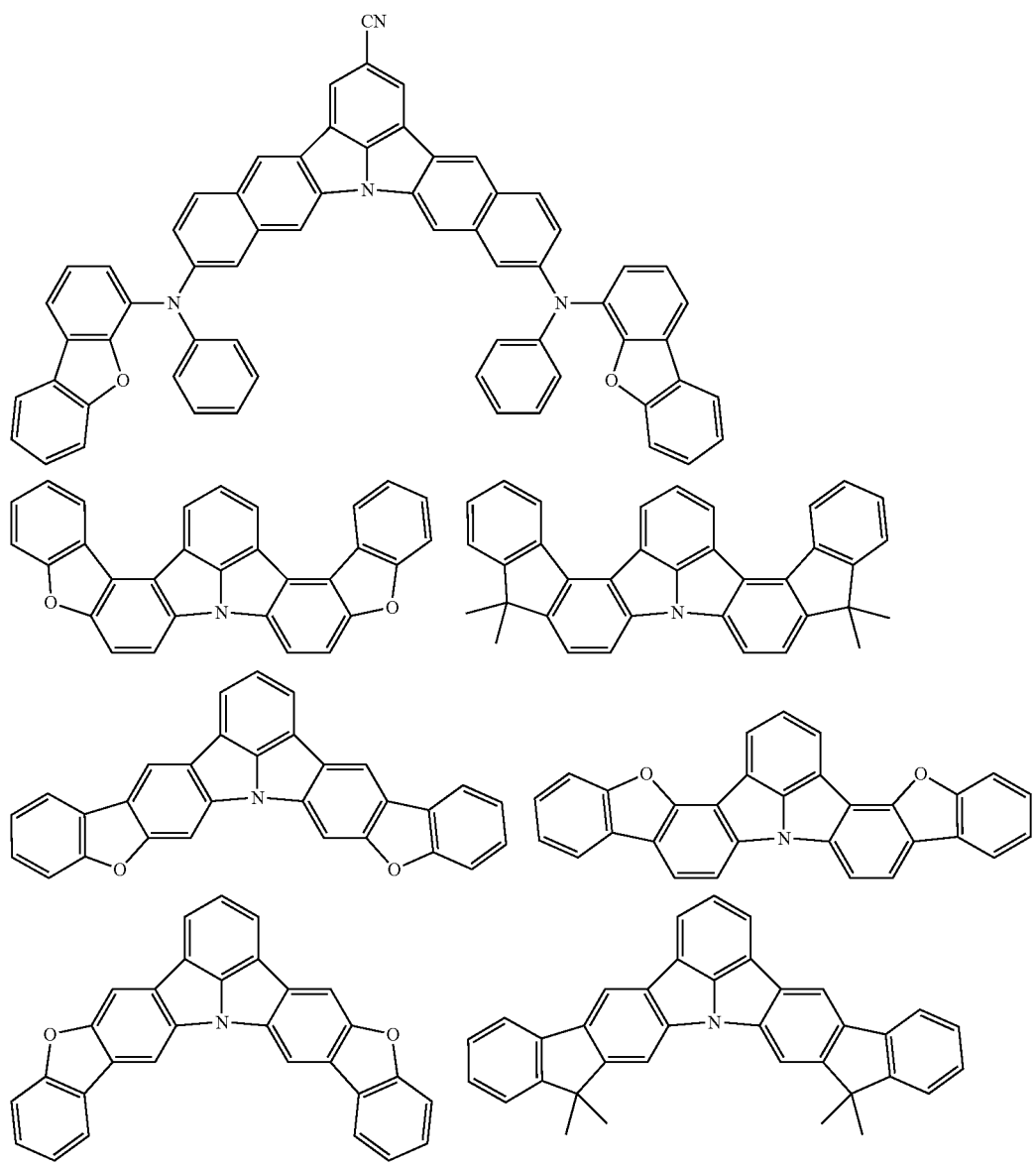

453
454
-continued
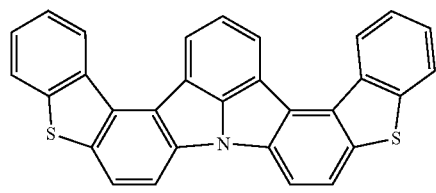
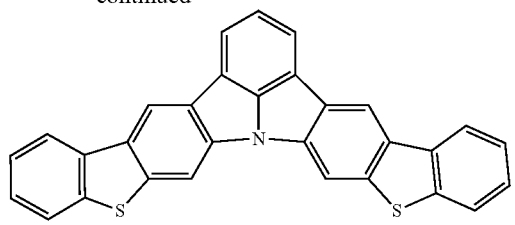
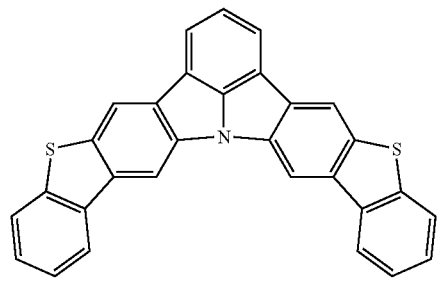
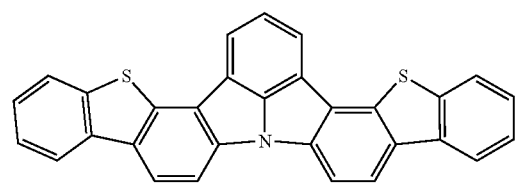
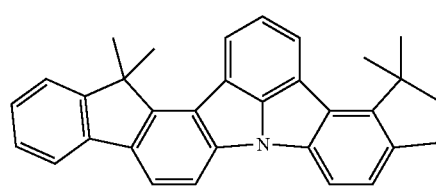
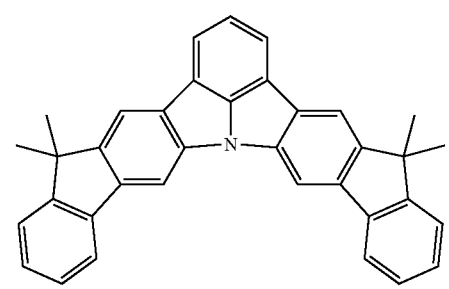
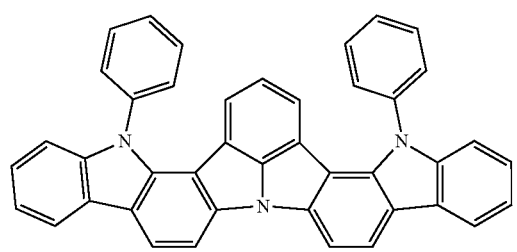
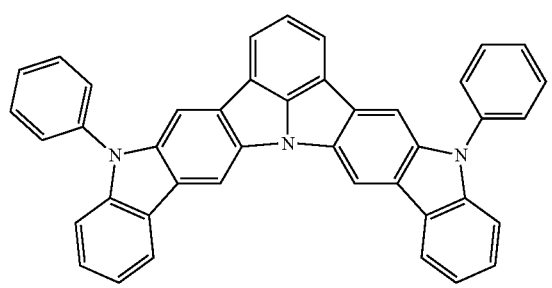
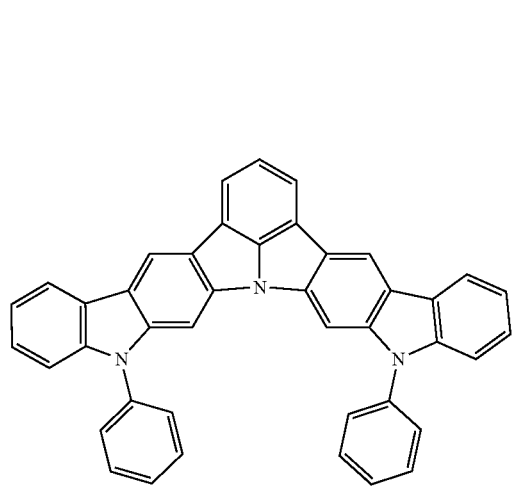
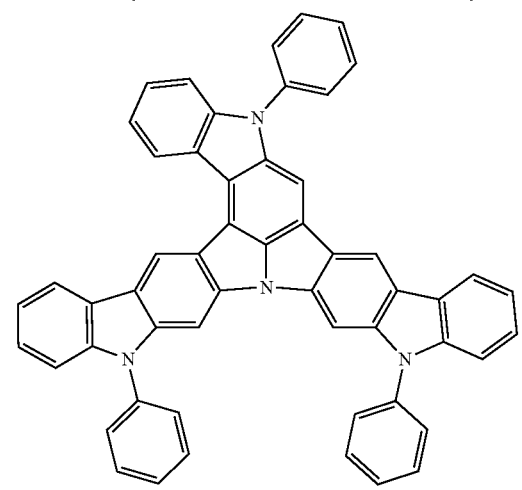

455
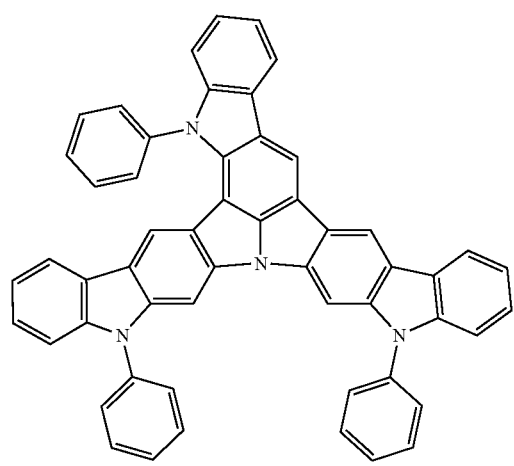
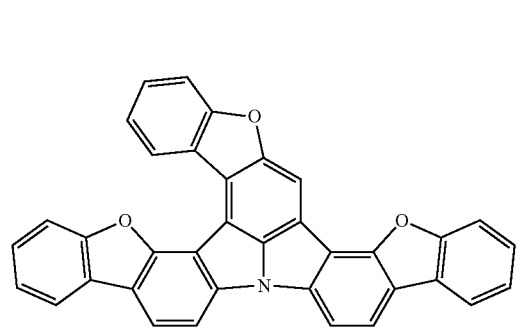
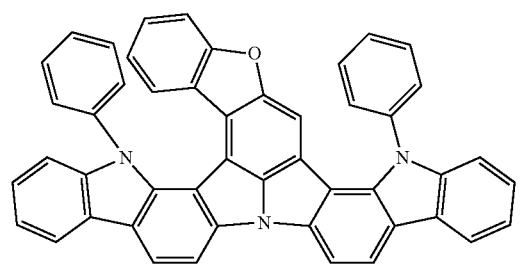
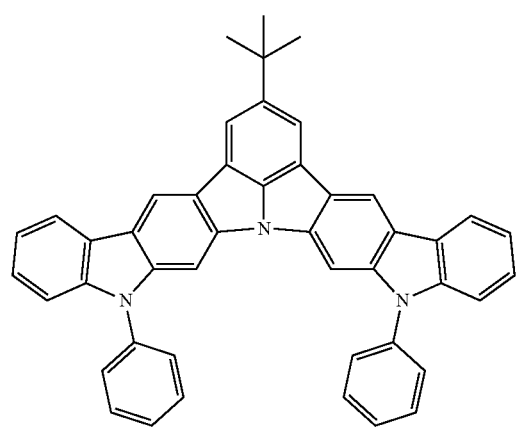
456
-continued
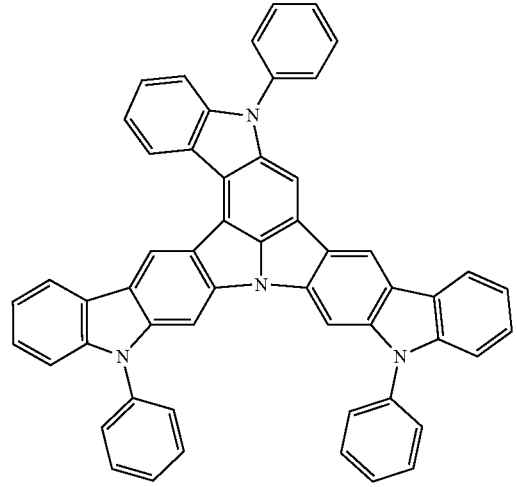
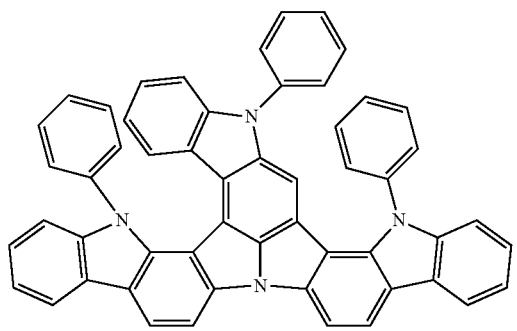
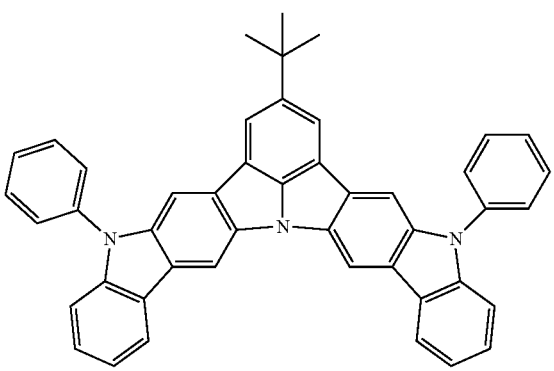
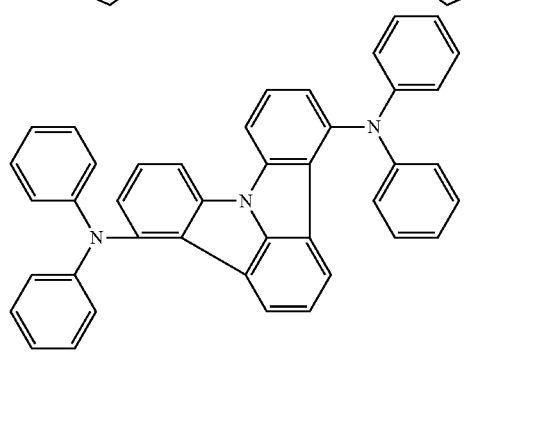

-continued
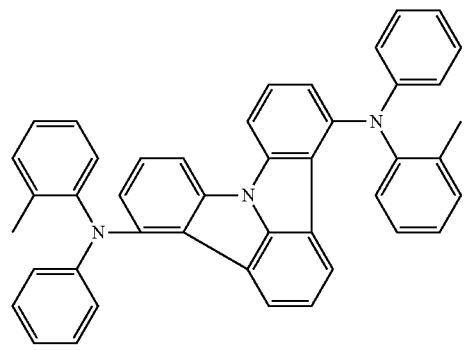
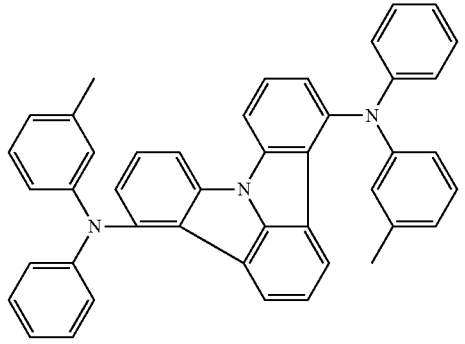
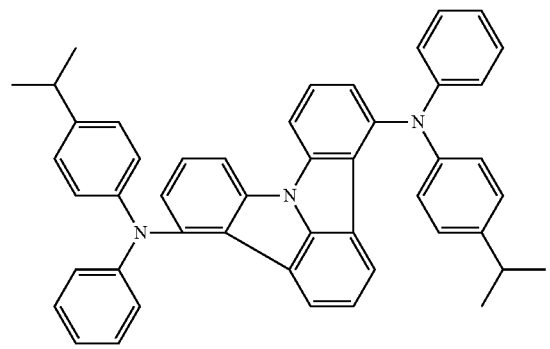
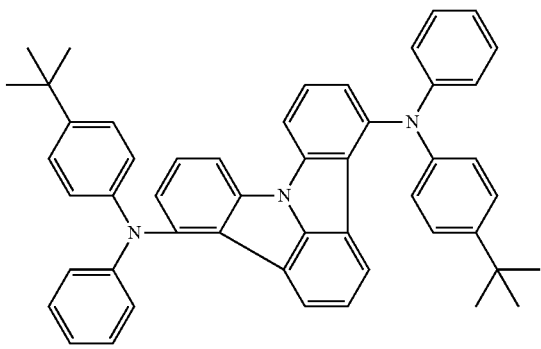
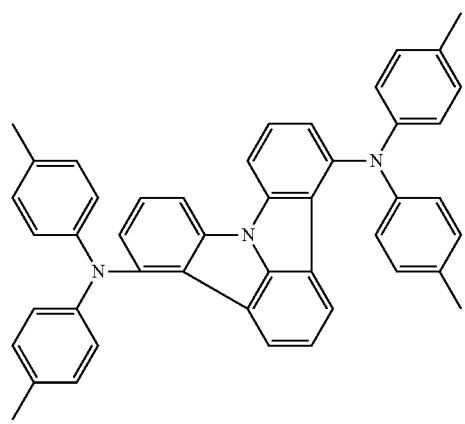
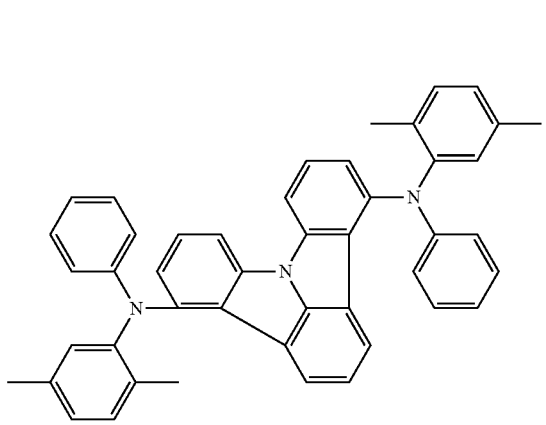
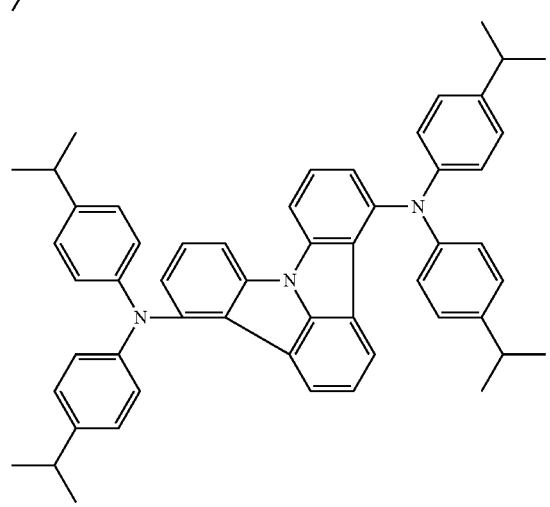
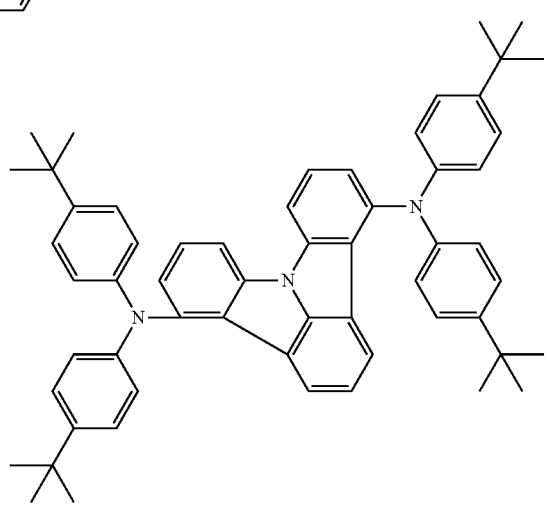

-continued
459 460
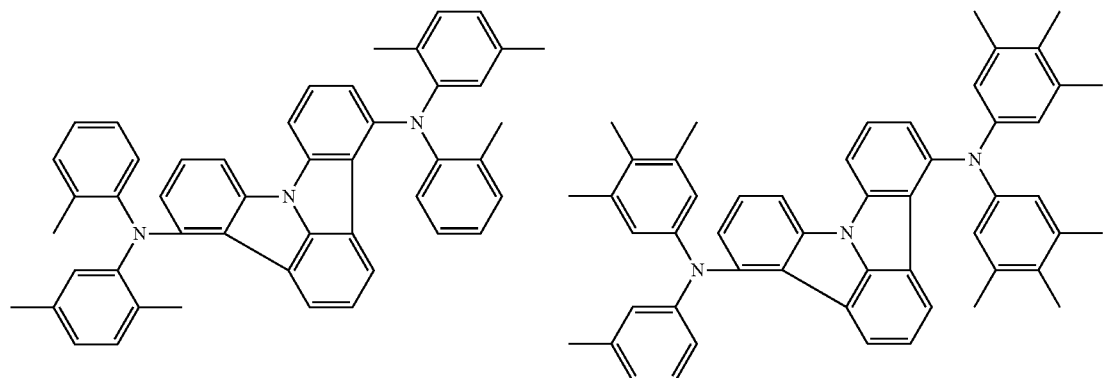
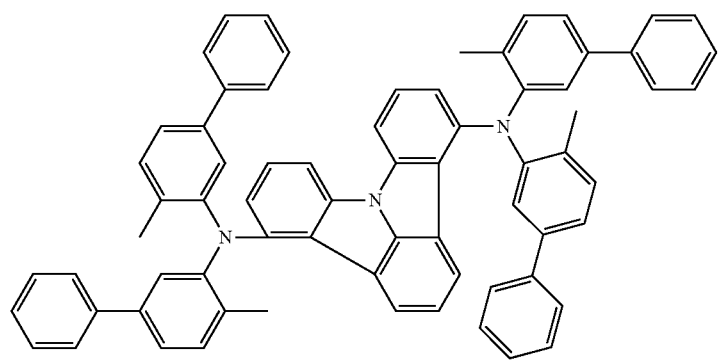
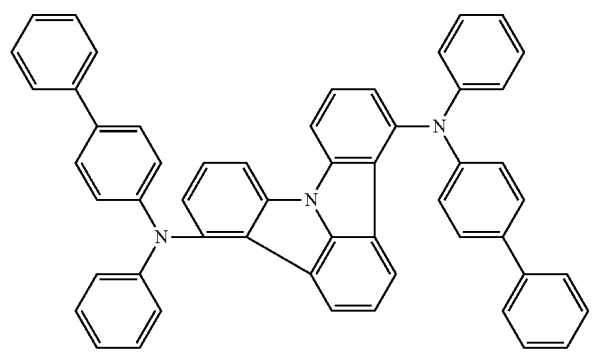
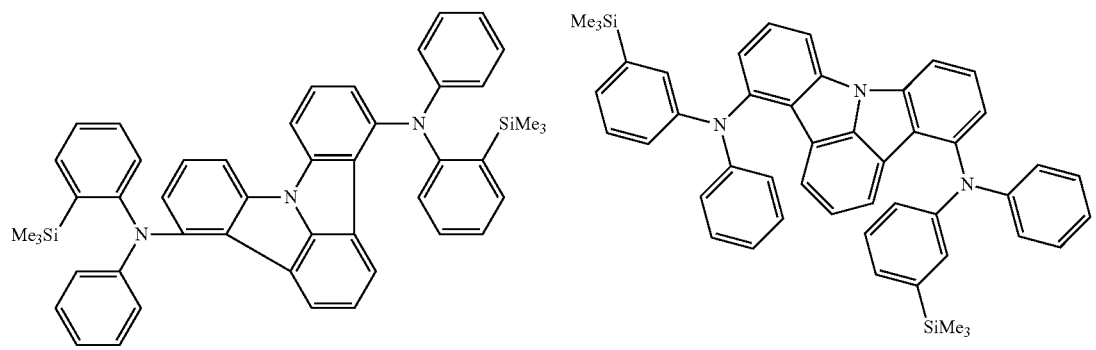

-continued
461
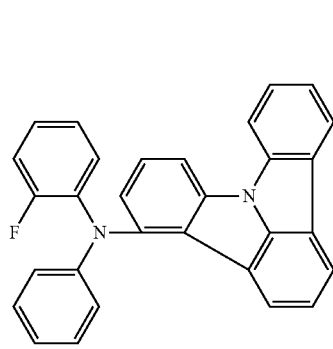
462
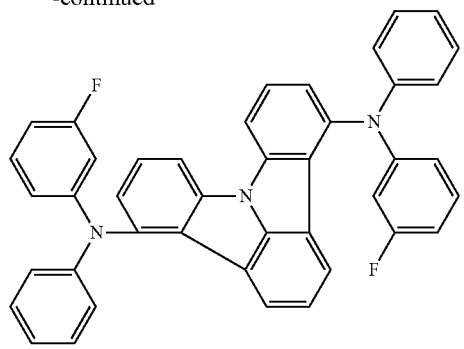
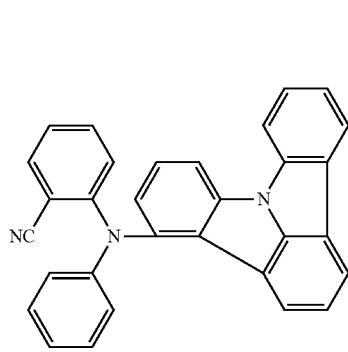
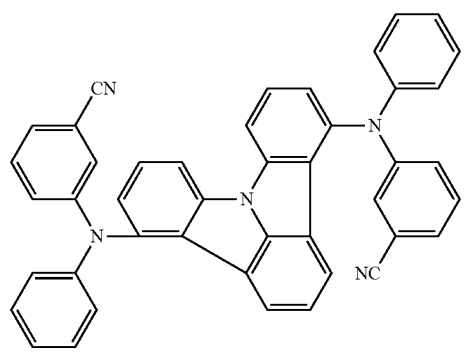
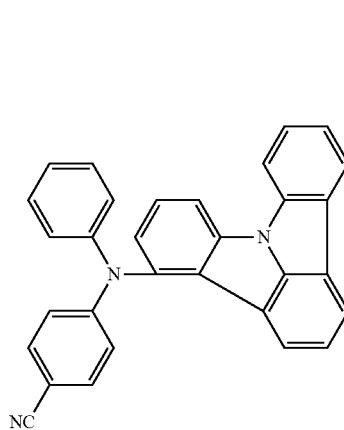
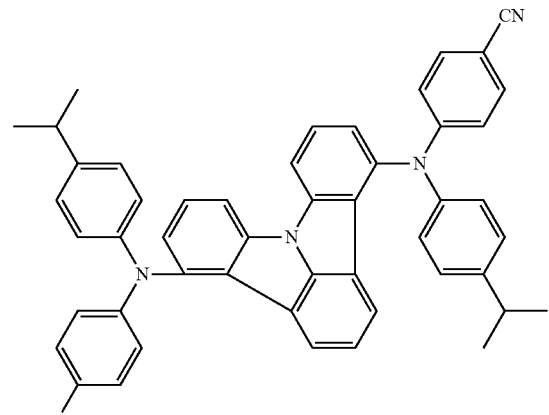
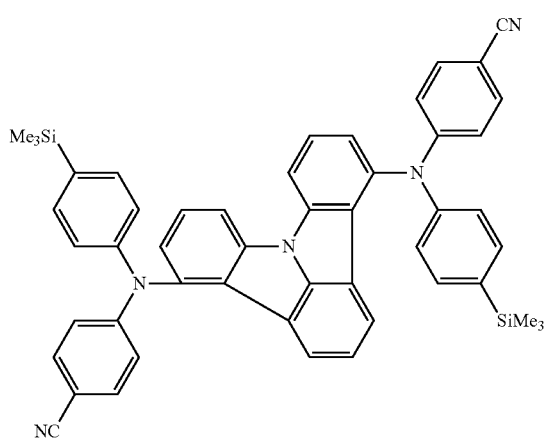

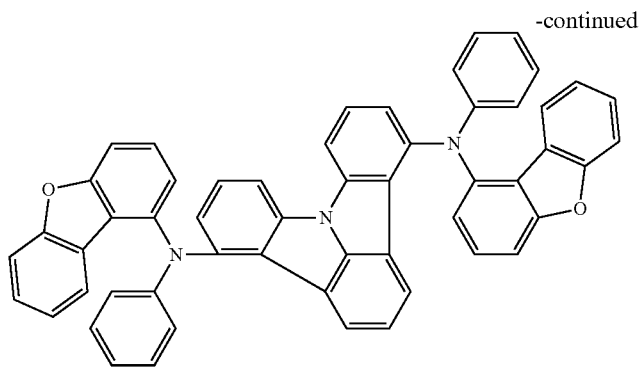
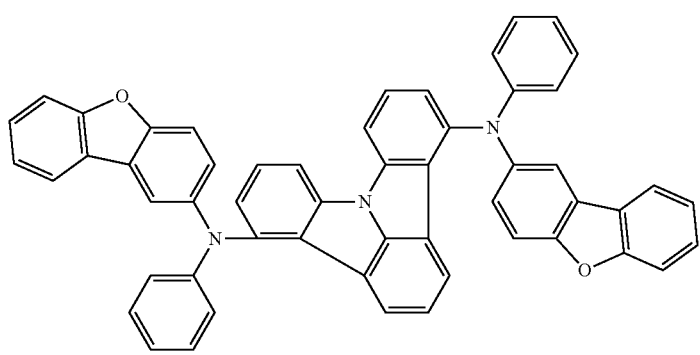
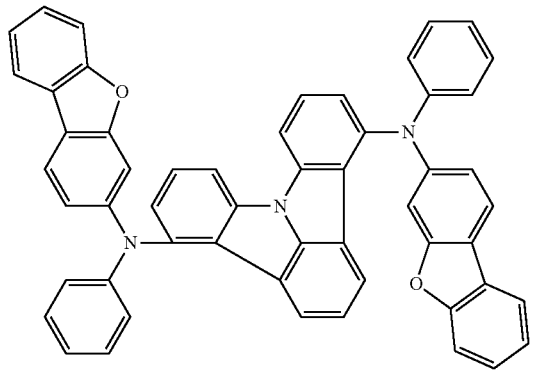
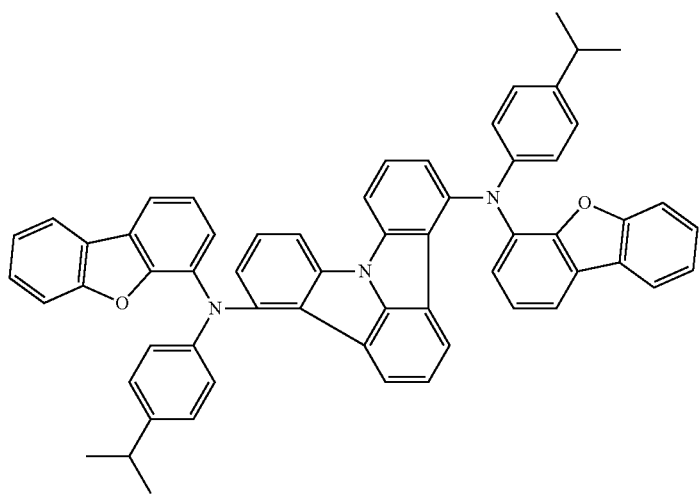

-continued
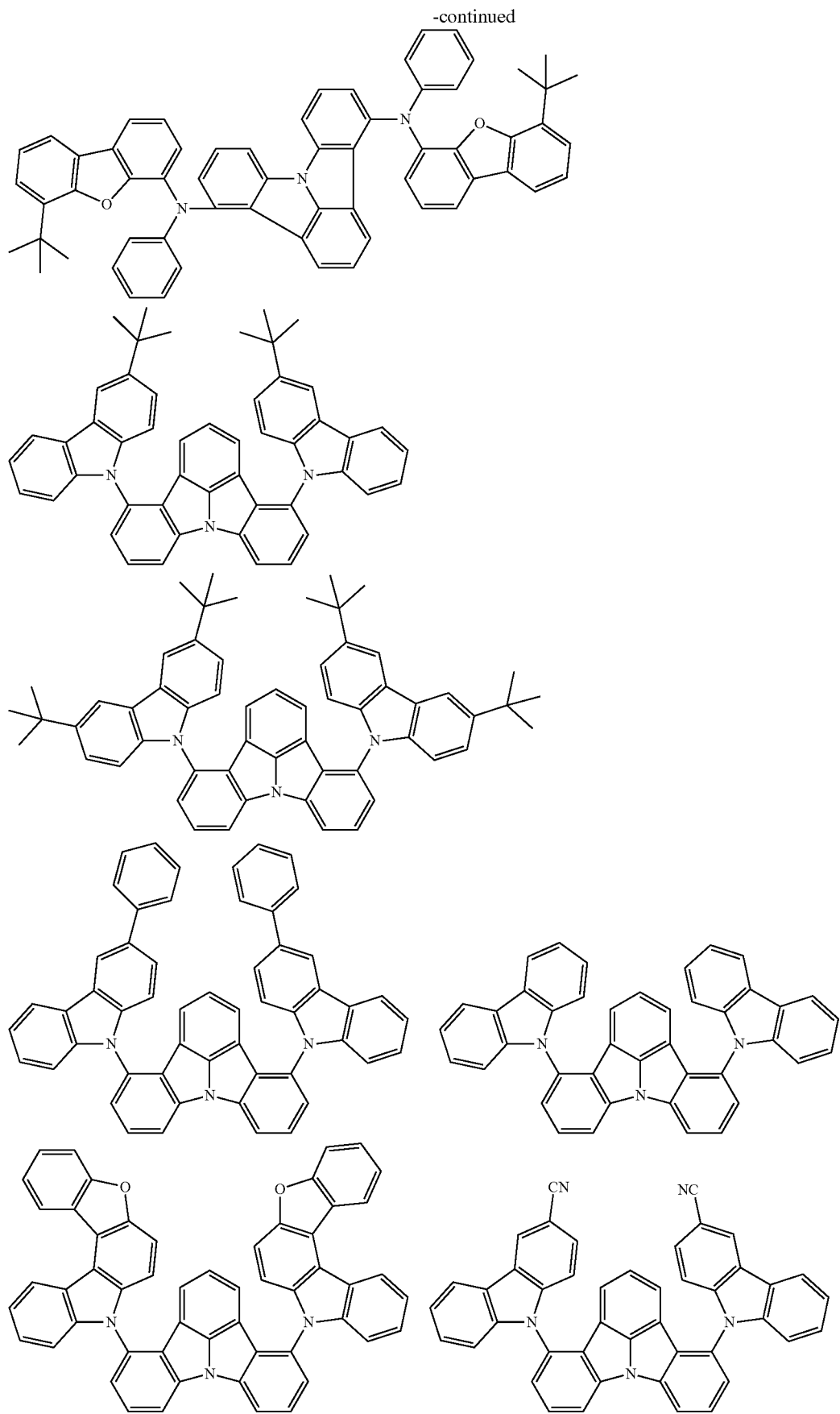

-continued
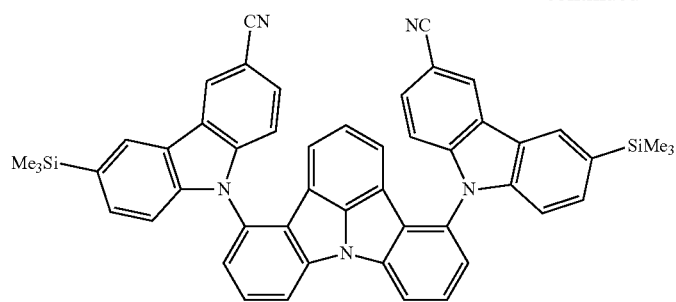
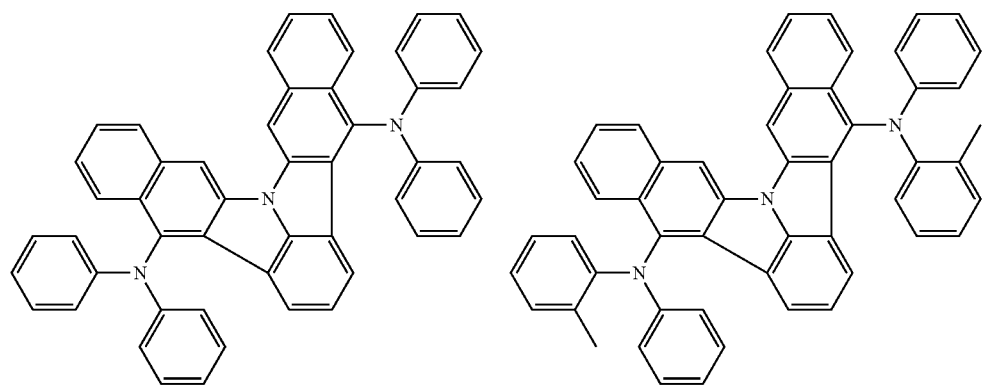
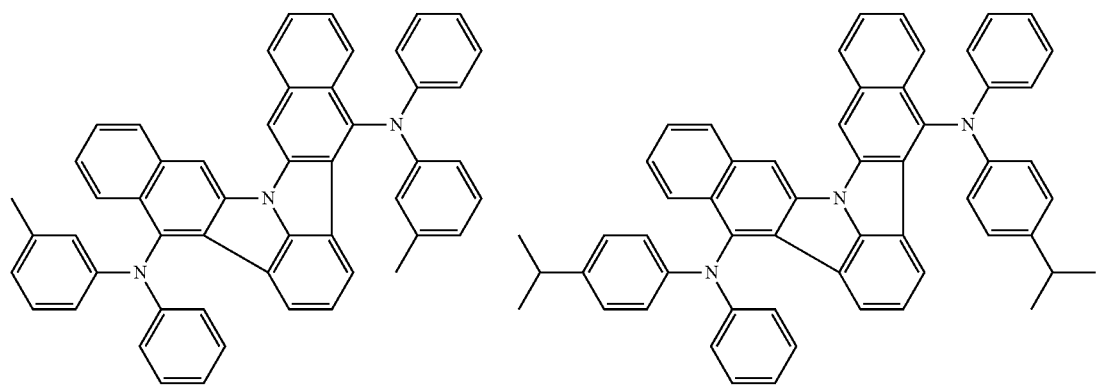
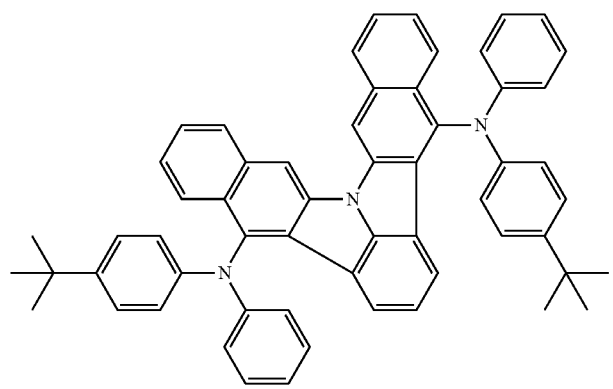

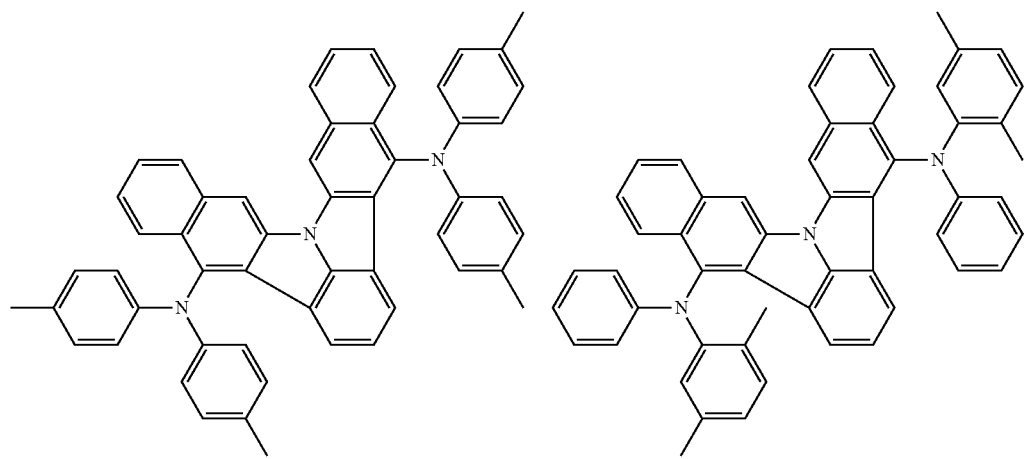
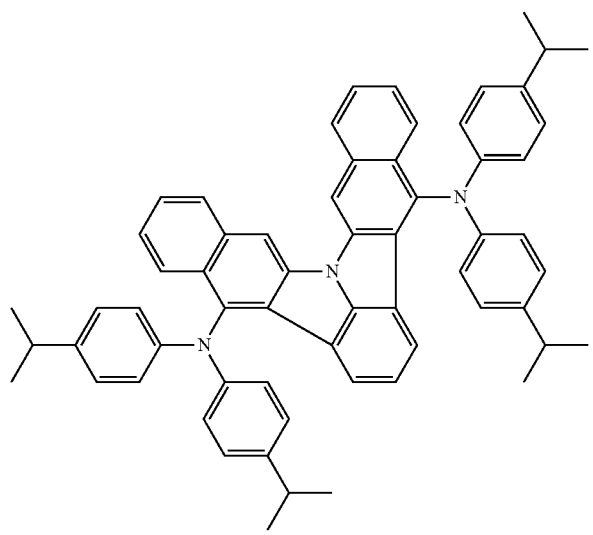
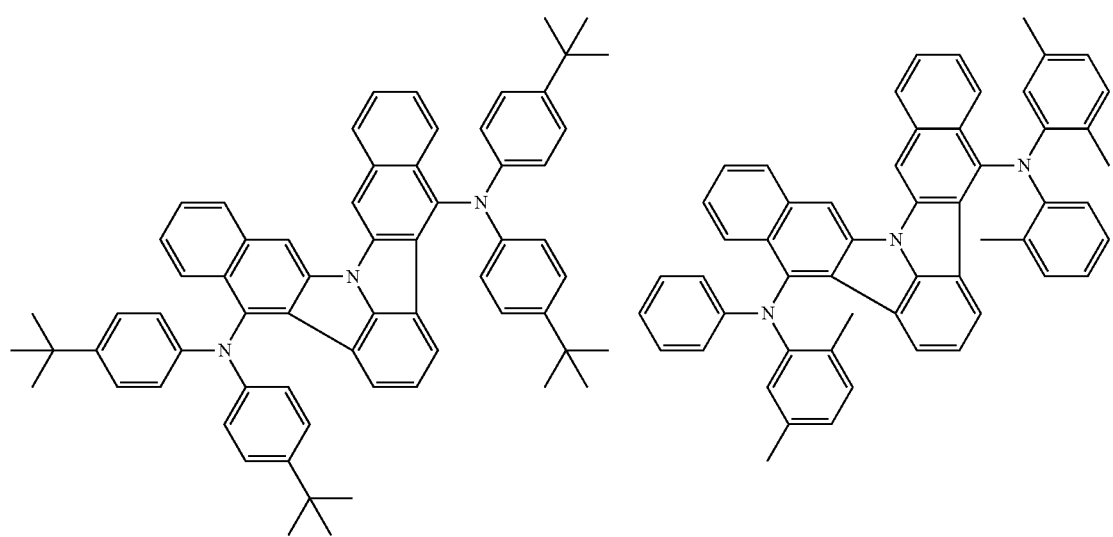

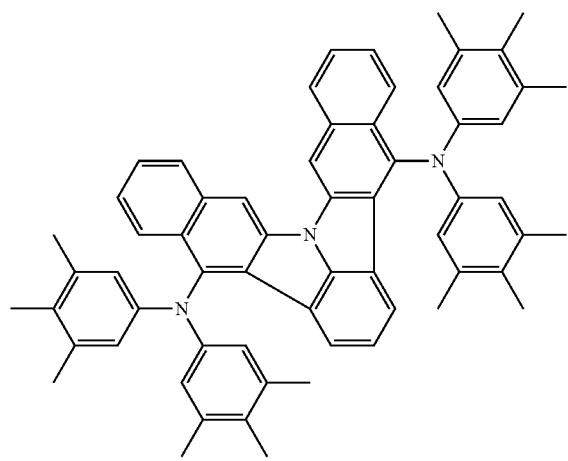
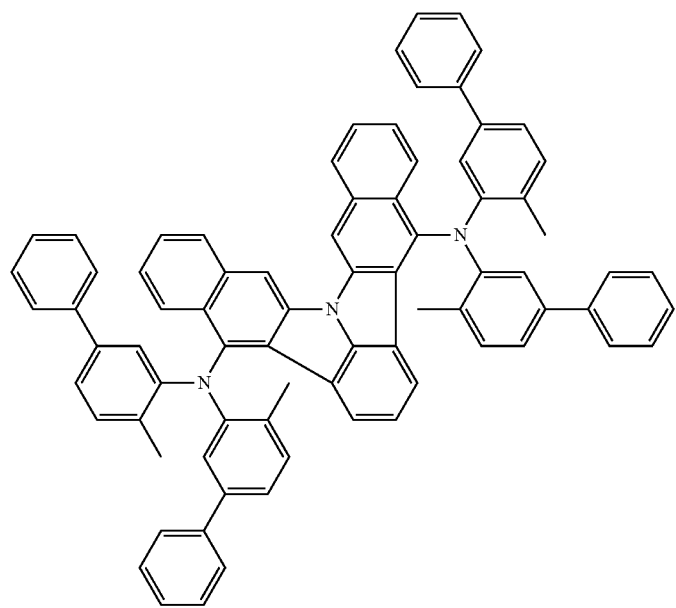
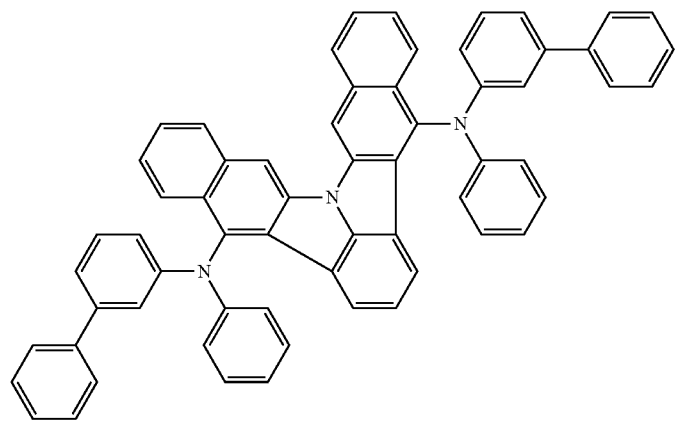

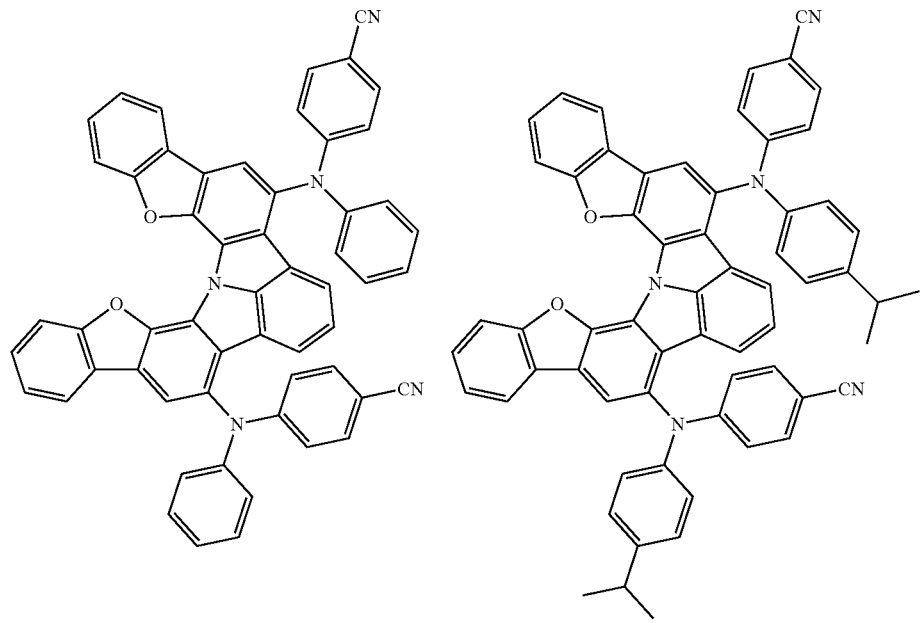
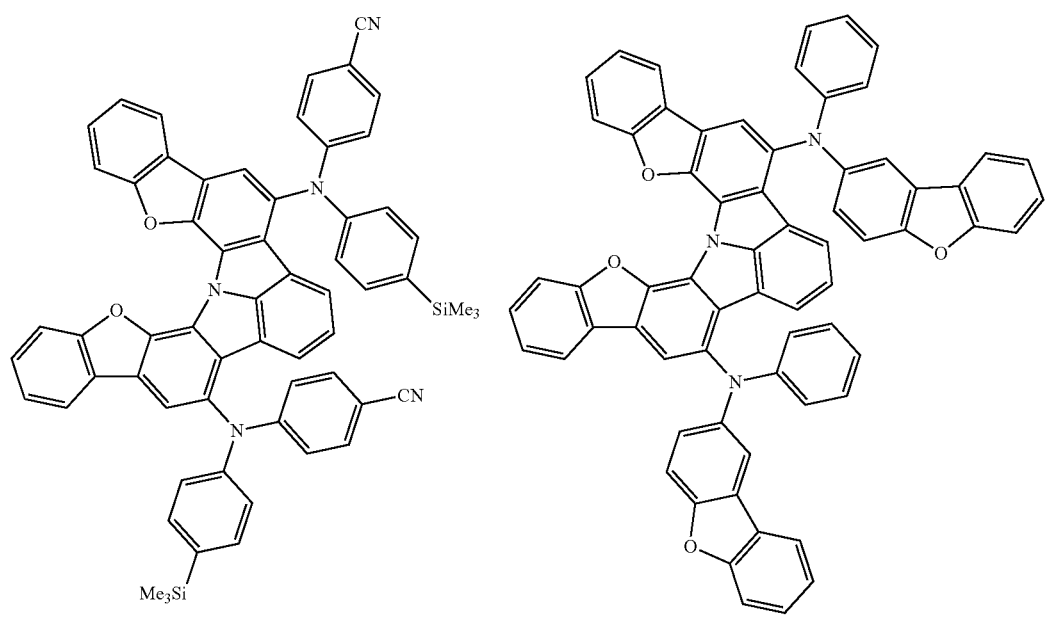

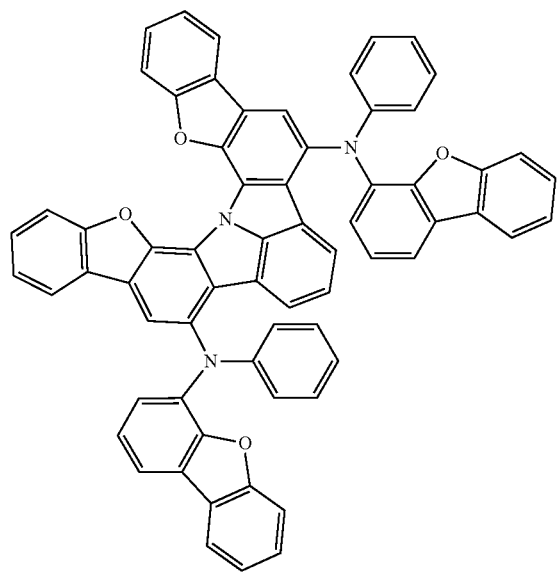
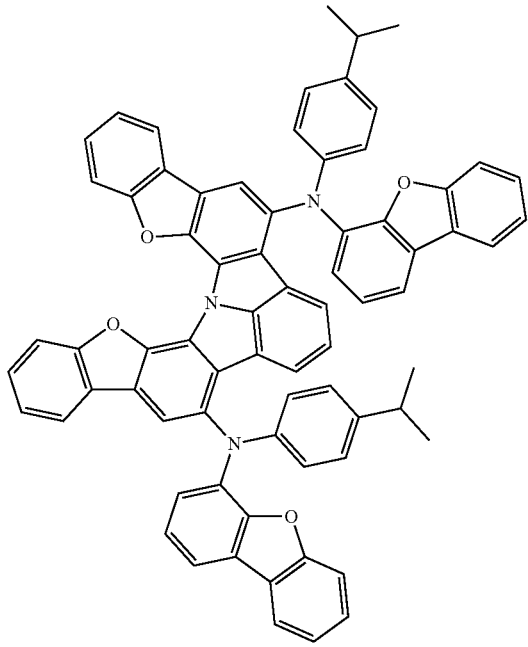
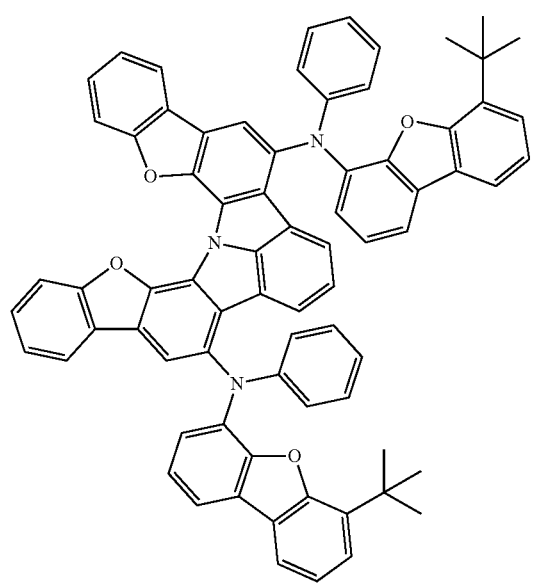
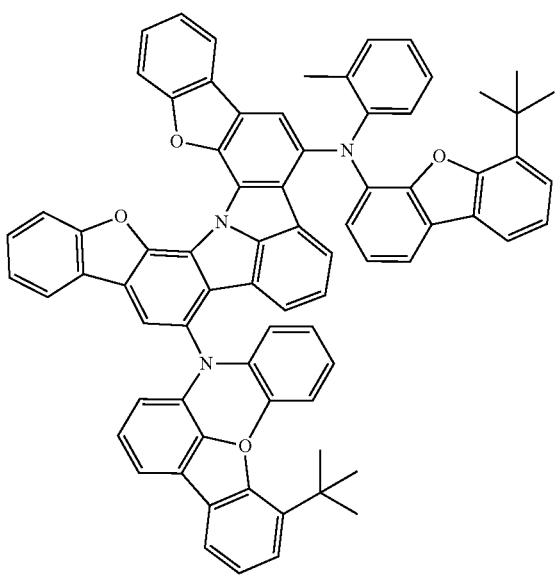

-continued
477
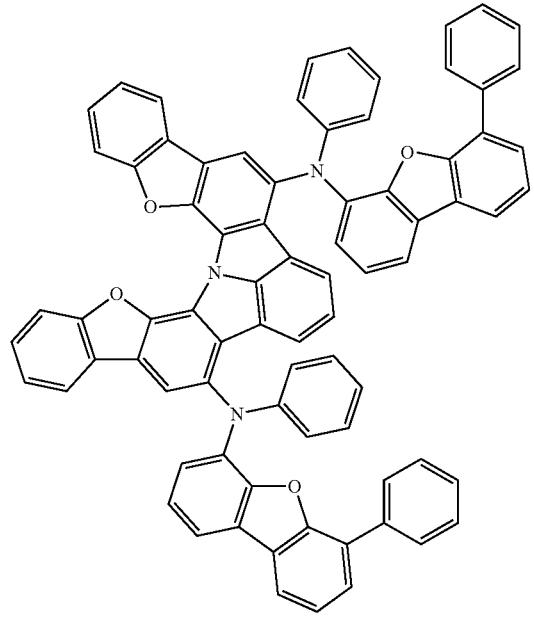
478
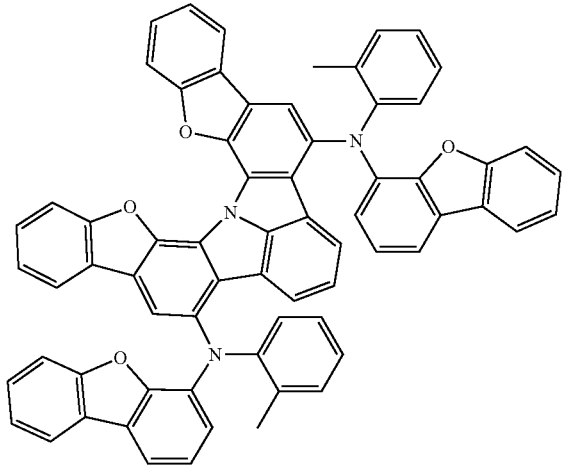
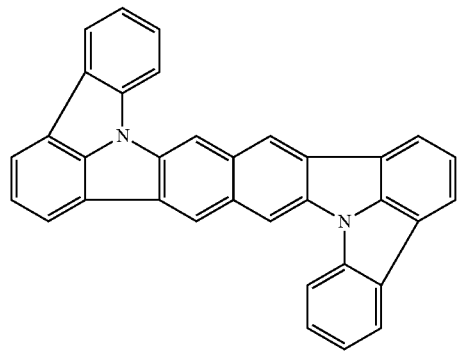
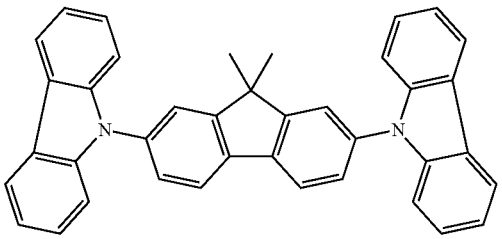
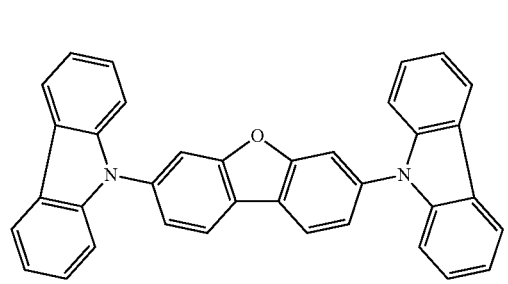
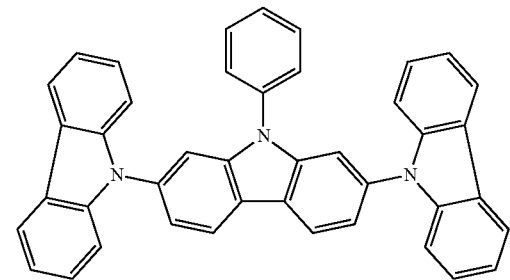
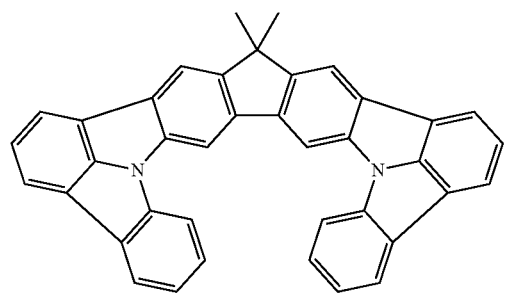
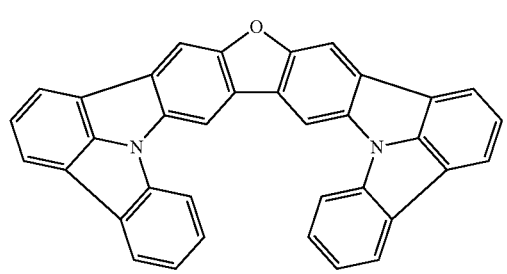

-continued

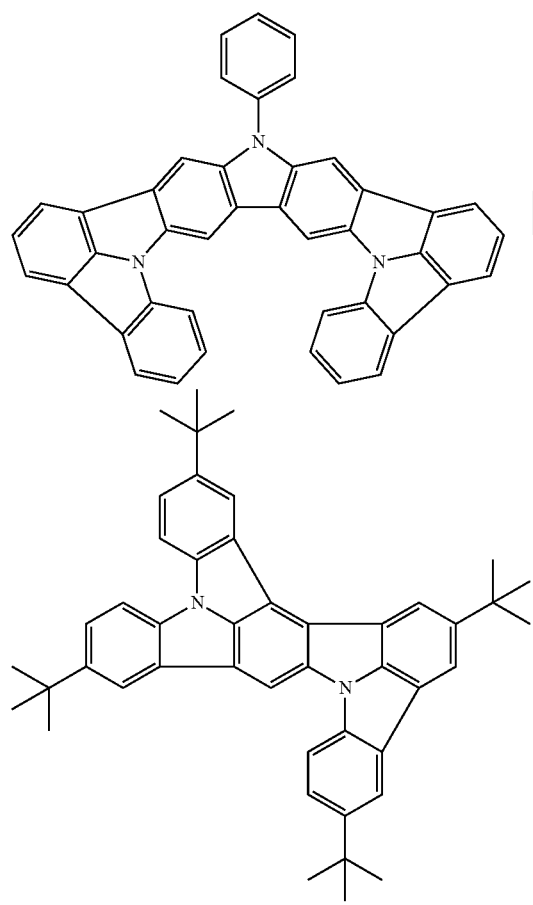
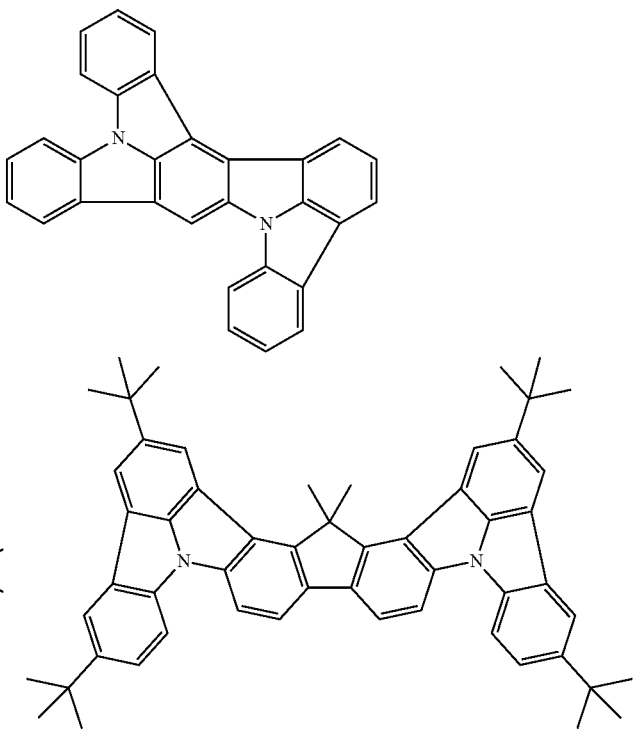

(Compound Represented by Formula (31))

The compound represented by the formula (31) is explained below.

The compound represented by formula (31) is a compound corresponding to the compound represented by the formula (21-3).

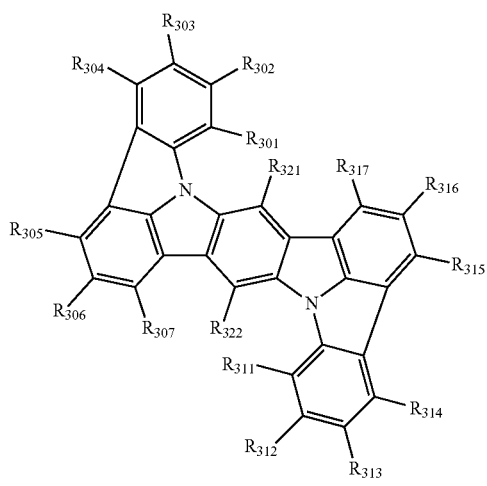

(31)

wherein in the formula (31), one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;

$R_{301}$ to $R_{307}$ and $R_{311}$ to $R_{317}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),
—O—($R_{904}$),
—S—($R_{905}$),
—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{321}$ and $R_{322}$ are independently a hydrogen atom, a substituted or unsubstituted alkyl group having 1 to 50 carbon atoms, a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{007}$ are as defined in the formula (1).

Example of "One pair of two or more adjacent groups of $R_{301}$ to $R_{307}$ and $R_{311}$ to $R_{317}$" is pairs of $R_{301}$ and $R_{302}$, $R_{302}$ and $R_{303}$, $R_{303}$ and $R_{304}$, $R_{305}$ and $R_{306}$, $R_{306}$ and $R_{307}$, and $R_{301}$, $R_{302}$ and $R_{303}$, and the like.

In one embodiment, at least one of $R_{301}$ to $R_{307}$ and $R_{311}$ to $R_{317}$, preferably two of $R_{301}$ to $R_{317}$ and $R_{311}$ to $R_{317}$ is a group represented by —N($R_{906}$)($R_{907}$).

In one embodiment, $R_{301}$ to $R_{307}$ and $R_{311}$ to $R_{317}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the following formula (32).

(32)

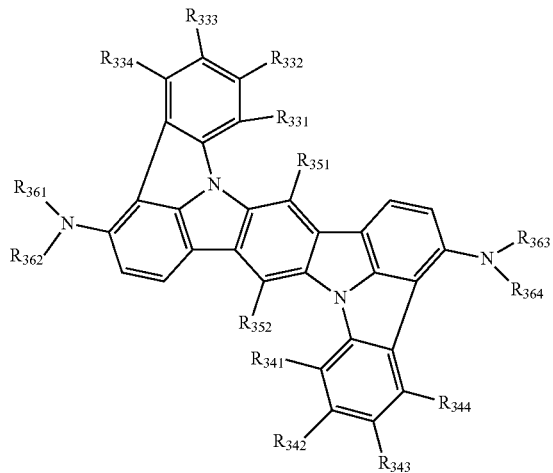

wherein in the formula (32),
one or more pairs of two or more adjacent groups of $R_{331}$ to $R_{334}$ and $R_{341}$ to $R_{344}$ form a substituted or unsubstituted, saturated or unsaturated ring, or do not form a substituted or unsubstituted saturated or unsaturated ring;
$R_{331}$ to $R_{334}$ and $R_{341}$ to $R_{344}$ that do not form the substituted or unsubstituted, saturated or unsaturated ring and $R_{351}$ and $R_{352}$ are independently a hydrogen atom,
a substituted or unsubstituted aryl group having 6 to 50 ring carbon atoms, or
a substituted or unsubstituted monovalent heterocyclic group having 5 to 50 ring atoms; and
$R_{361}$ to $R_{364}$ are independently
a substituted or unsubstituted aryl group having 6 to 50 ring carbon atoms, or
a substituted or unsubstituted monovalent heterocyclic group having 5 to 50 ring atoms.

In one embodiment, the compound represented by the formula (31) is a compound represented by the formula (33).

(33)

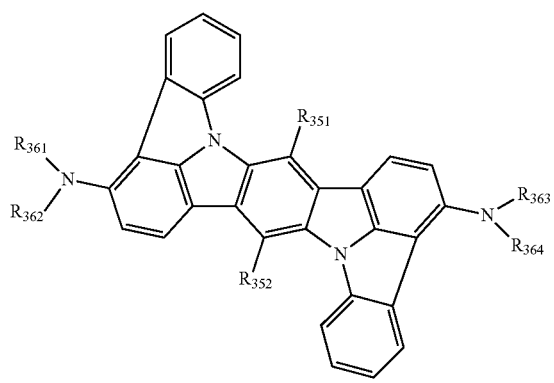

wherein in the formula (33), $R_{351}$, $R_{352}$, and $R_{361}$, to $R_{364}$ are as defined in the formula (32).

In one embodiment, the compound represented by the formula (31) is a compound represented by the formula (34) or (35).

(34)

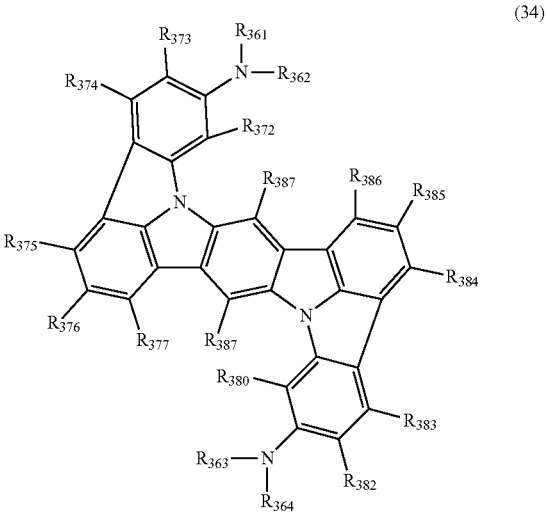

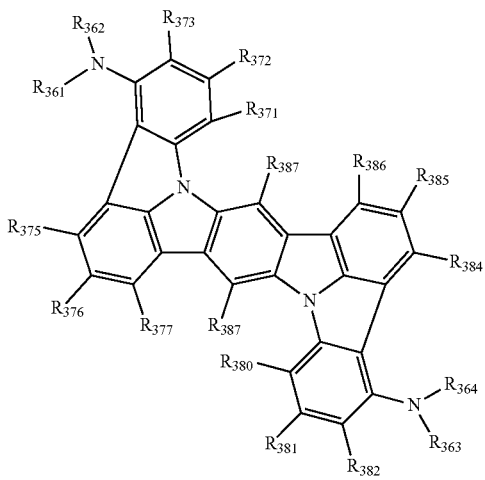

(35)

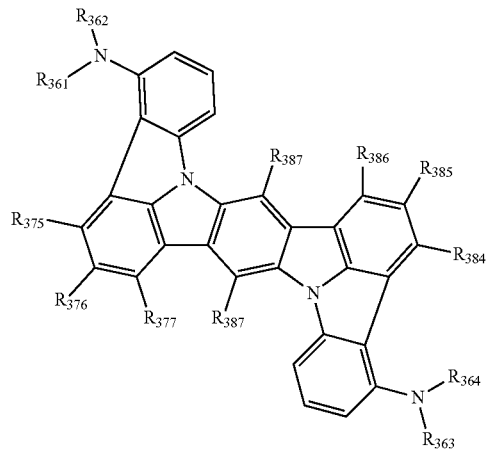

(35-2)

wherein in the formulas (34) and (35), $R_{361}$ to $R_{364}$ are as defined in the formula (32); one or more pairs of two or more adjacent groups of $R_{371}$ to $R_{377}$ and $R_{380}$ to $R_{386}$ form a substituted or unsubstituted, saturated or unsaturated ring, or do not form a substituted or unsubstituted saturated or unsaturated ring;

$R_{371}$ to $R_{377}$ and $R_{380}$ to $R_{386}$ that do not form the substituted or unsubstituted, saturated or unsaturated ring and $R_{387}$ are independently a hydrogen atom, a substituted or unsubstituted aryl group having 6 to 50 ring carbon atoms, or a substituted or unsubstituted monovalent heterocyclic group having 5 to 50 ring atoms; and two $R_{387}$s may be the same with or different from each other.

In one embodiment, the compound represented by the formula (31) is a compound represented by the formula (34-2) or (35-2).

wherein in the formulas (34-2) and (35-2), $R_{361}$ to $R_{364}$, $R_{375}$ to $R_{377}$ and $R_{384}$ to $R_{387}$ are as defined in the formulas (34) and (35).

In one embodiment, $R_{361}$ to $R_{364}$ in the formulas (32), (33), (34), (35), (34-2) and (35-2) are independently a substituted or unsubstituted aryl group having 6 to 50 ring carbon atoms (preferably a substituted or unsubstituted phenyl group).

In one embodiment, $R_{321}$ and $R_{322}$ in the formula (31) and $R_{351}$, $R_{352}$ and $R_{387}$ in the formulas (32), (33), (34), (35), (34-2) and (35-2) are independently a hydrogen atom or a substituted or unsubstituted aryl group having 6 to 50 ring carbon atoms (preferably a substituted or unsubstituted phenyl group).

In one embodiment, the compound represented by the formula (31) is one or more compounds selected from the group consisting of the following formulas (32-11), (34-11) and (35-11).

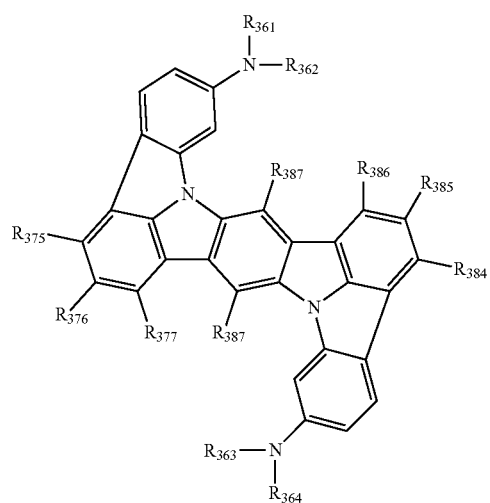

(34-2)

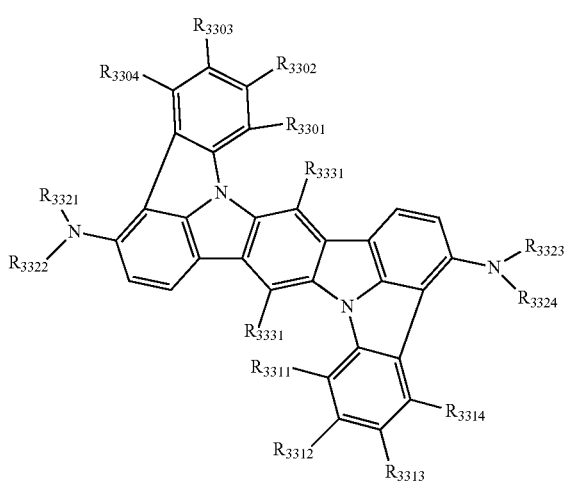

(32-11)

-continued (34-11)

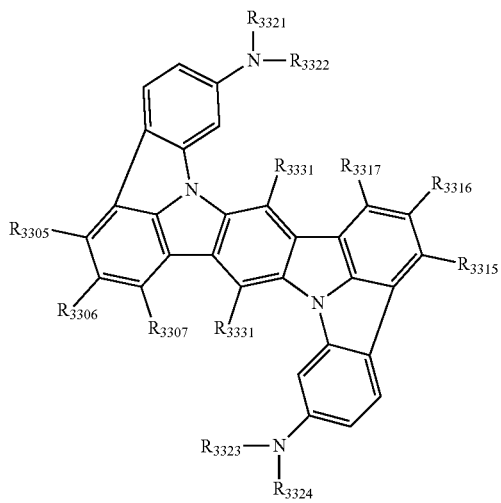

(35-11)

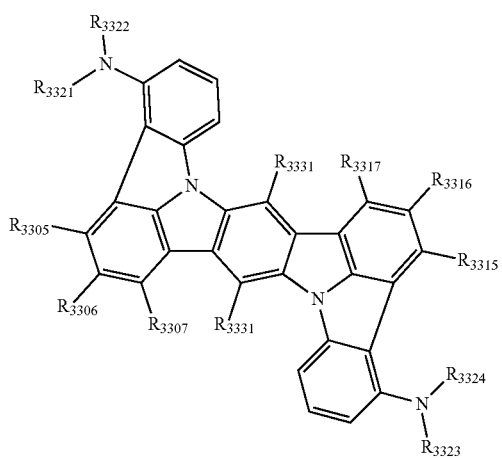

wherein in the formulas (32-11), (34-11) and (35-11), one or more pairs of two or more adjacent groups of $R_{3301}$ to $R_{3307}$ and $R_{3311}$ to $R_{3317}$ form a substituted or unsubstituted, saturated or unsaturated ring, or do not form a substituted or unsubstituted, saturated or unsaturated ring;

$R_{3301}$ to $R_{3307}$ and $R_{3311}$ to $R_{3317}$ that do not form the substituted or unsubstituted, saturated or unsaturated ring, and $R_{3331}$ are independently
a hydrogen atom,
a substituted or unsubstituted aryl group having 6 to 20 ring carbon atoms, or
a substituted or unsubstituted monovalent heterocyclic group having 5 to 20 ring atoms;

two $R_{3331}$s may be the same with or different from each other; and $R_{3321}$ to $R_{3324}$ are independently
a substituted or unsubstituted aryl group having 6 to 20 ring carbon atoms, or
a substituted or unsubstituted monovalent heterocyclic group having 5 to 20 ring atoms.

In one embodiment, the one or more compounds selected from the group consisting of the formulas (32-11), (34-11) and (35-11) is one or more compounds selected from a group consisting of the following formulas (32-12), (34-12) and (35-12).

(32-12)

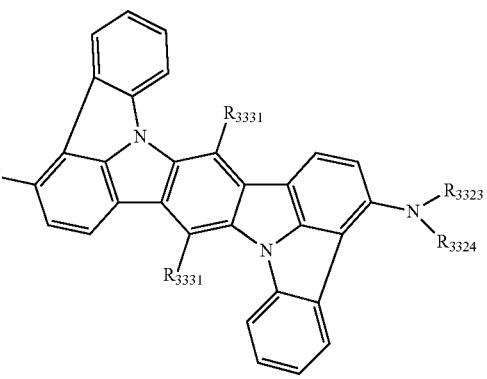

(34-12)

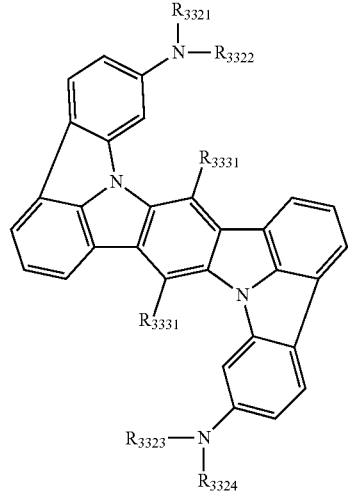

(35-12)

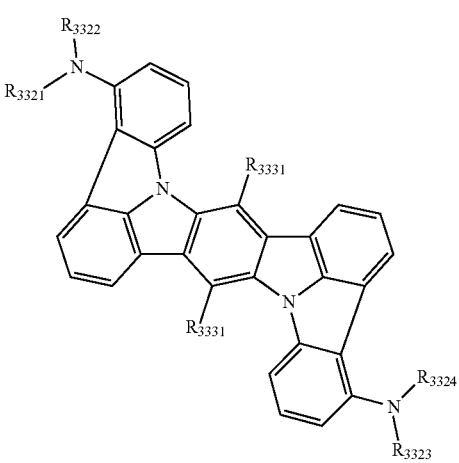

wherein in the formulas (32-12), (34-12) and (35-12), $R_{3321}$ to $R_{3324}$ and $R_{3331}$ are as defined in the formulas (32-11), (34-11) and (35-11).

In one embodiment, in the formulas (32-11), (3411), (35-11), (32-12), (34-12) and (35-12), $R_{3321}$ to $R_{3324}$ are independently a substituted or unsubstituted phenyl group.

In one embodiment, in the formulas (32-11), (34-11), (35-11), (32-12), (34-12) and (35-12), two $R_{3331}$s are independently a hydrogen atom.

In one embodiment, in the formulas (32-11), (34-11), (35-11), (32-12), (34-12) and (35-12), the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), the substituent in the case of "substituted or unsubstituted" is an alkyl group having 1 to 5 carbon atoms.

In one embodiment, in the formulas (32-11), (34-11), (35-11), (32-12), (34-12) and (35-12), $R_{3321}$ to $R_{3324}$ are independently a substituted or unsubstituted phenyl group, and two $R_{3331}$s are independently a hydrogen atom.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is an alkyl group having 1 to 5 carbon atoms.

In one embodiment, in the compound represented by the formula (31), one or more pairs of two or more adjacent groups of $R_{301}$ to $R_{307}$ and $R_{311}$ to $R_{317}$ form a substituted or unsubstituted, saturated or unsaturated ring.

In one embodiment, the compound represented by the formula (31) is one or more compounds selected from the group consisting of the following formulas (36-1) to (36-6).

(36-1)
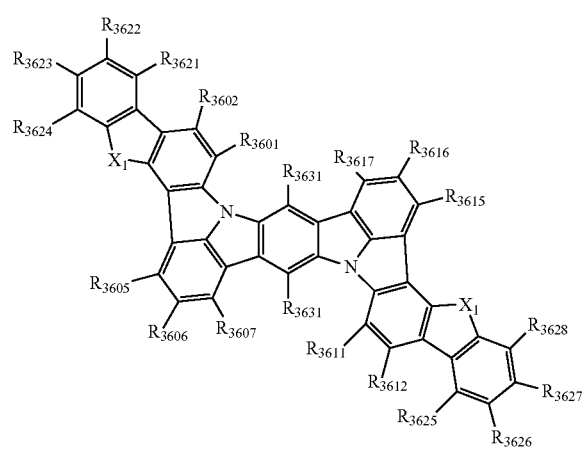

(36-2)
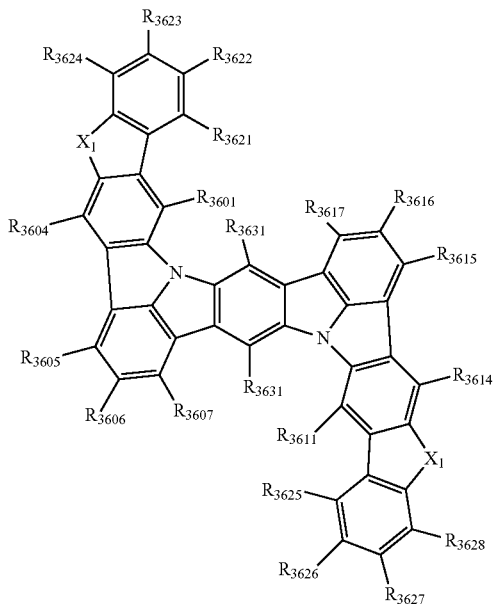

(36-3)
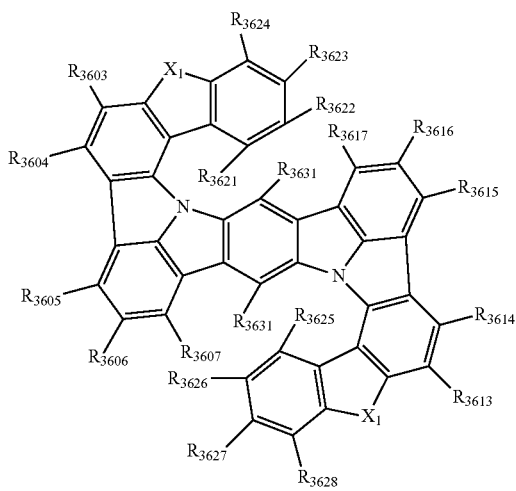

(36-4)
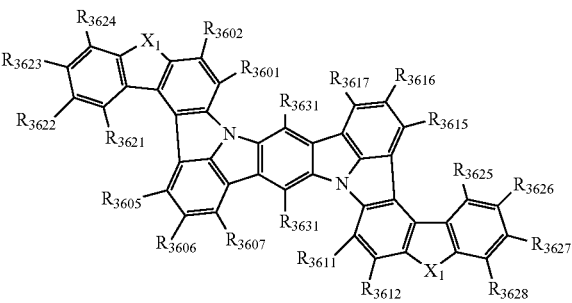

(36-5)

(36-6)

wherein in the formulas (36-1) to (36-6), one or more pairs of two or more adjacent groups of $R_{3605}$ to $R_{3607}$, $R_{3615}$ to $R_{3617}$ and $R_{3631}$ bond with each other to form a substituted or unsubstituted, saturated or unsaturated ring or do not form the ring;

one or more pairs of two or more adjacent groups of $R_{3601}$ to $R_{3604}$, $R_{3611}$ to $R_{3614}$ and $R_{3621}$ to $R_{3628}$ bond with each other to form a substituted or unsubstituted, saturated or unsaturated ring or do not form the ring;

$R_{3601}$ to $R_{3607}$, $R_{3611}$ to $R_{3617}$, $R_{3621}$ to $R_{3628}$ and $R_{3631}$ that do not form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to 50 ring atoms;

$R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

when two or more of $R_{901}$ to $R_{907}$ exist, two or more of $R_{901}$ to $R_{907}$ may be the same with or different from each other;

$X_1$ is selected from O, S and N($R_{3641}$), and two $X_1$s may be the same with or different from each other;

$R_{3641}$ and one or more groups selected from $R_{3601}$ to $R_{3640}$, $R_{3611}$ to $R_{3614}$, $R_{3624}$ and $R_{3628}$ bond with each other to form a substituted or unsubstituted, saturated or unsaturated ring or do not form the ring; and $R_{3641}$ that do not form the ring is a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the formula (36-1) or (36-2). In one embodiment, the compound represented by the formula (31) is a compound represented by the formula (36-1).

In one embodiment, in the compound represented by the formulas (36-1) to (36-6), two $R_{3631}$s are phenyl groups.

In one embodiment, in the compound represented by the formulas (36-1) to (36-6), $X_1$ is N($R_{3641}$).

In one embodiment, in the compound represented by the formulas (36-1) to (36-6), $R_{3641}$ is a substituted or unsubstituted aryl group having 6 to 50 ring carbon atoms.

In one embodiment, the compound represented by the formula (31) is a compound represented by the following formula (36-1-1).

(36-1-1)

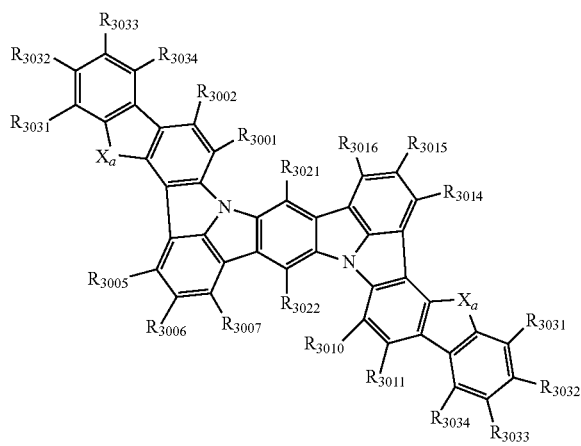

wherein in the formula (36-1-1), one or more pairs of two or more adjacent groups of $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3034}$ bond with each other to form a substituted or unsubstituted, saturated or unsaturated ring or do not form the ring;

$X_a$s are independently selected from O, S and N($R_{3035}$);

$R_{3035}$ and $R_{3031}$ bond with each other to form a substituted or unsubstituted, saturated or unsaturated ring or do not form the ring; and $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3035}$ that do not form the ring and $R_{3021}$ and $R_{3022}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, a substituent in the case of "substituted or unsubstituted" in the formulas (31) to (35), (34-2), (35-2), (32-11), (34-11), (35-11), (32-12), (34-12), (35-12), (36-1) to (36-6) and (36-1-1) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

As the compound represented by the formula (31), the following compounds can be given for example. In the following example compounds, Me represents methyl group.

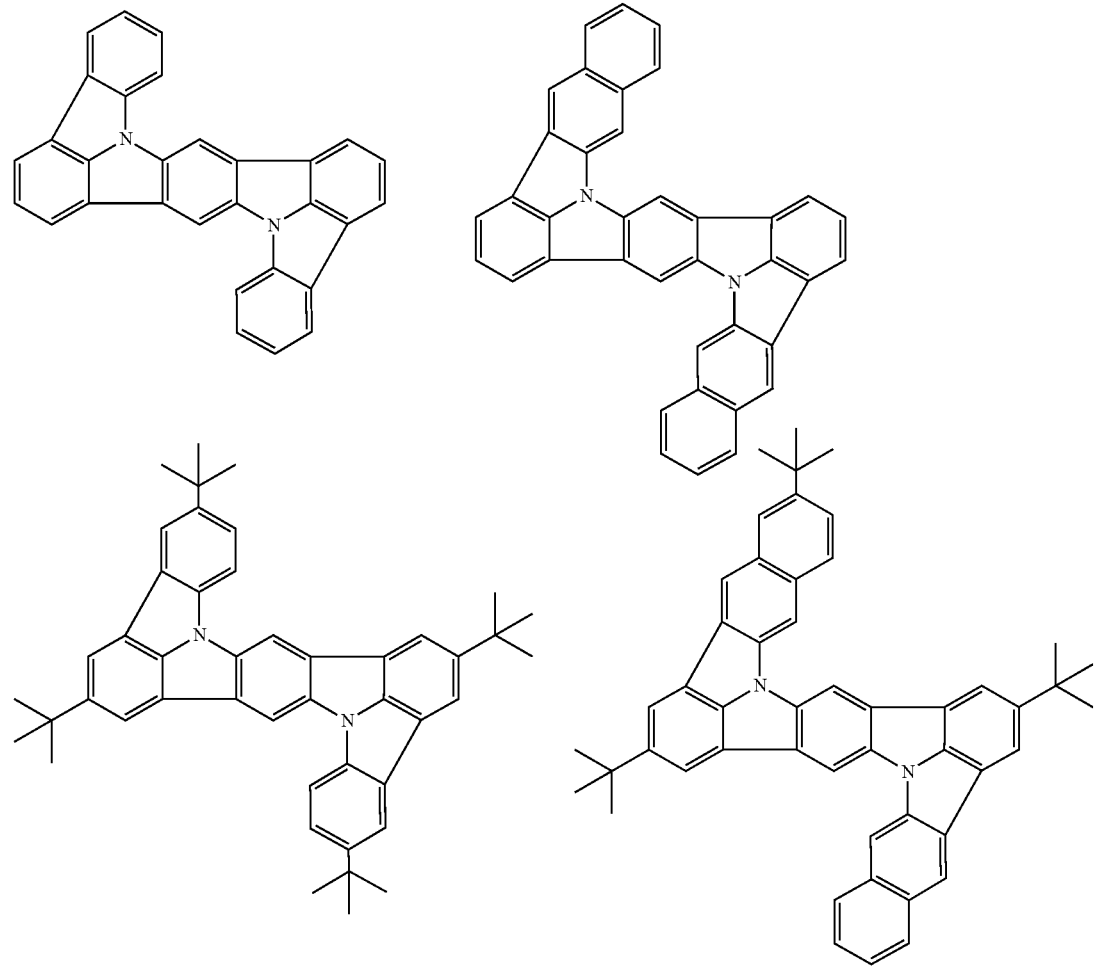

-continued
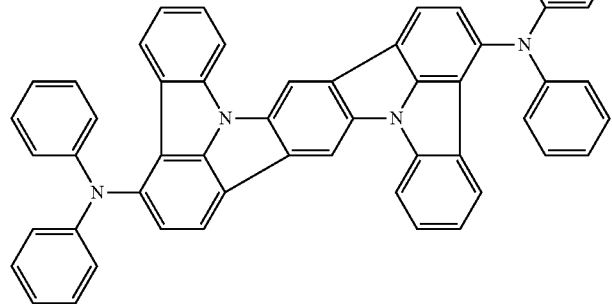
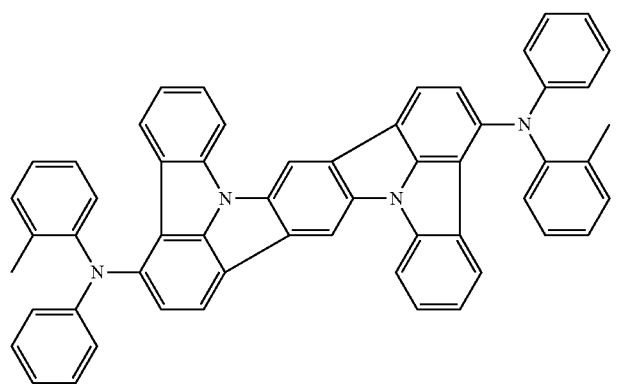
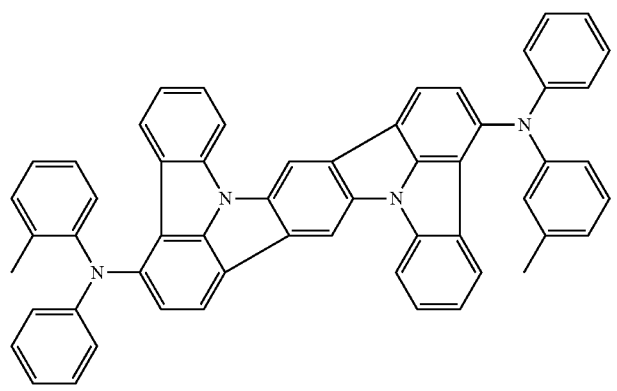
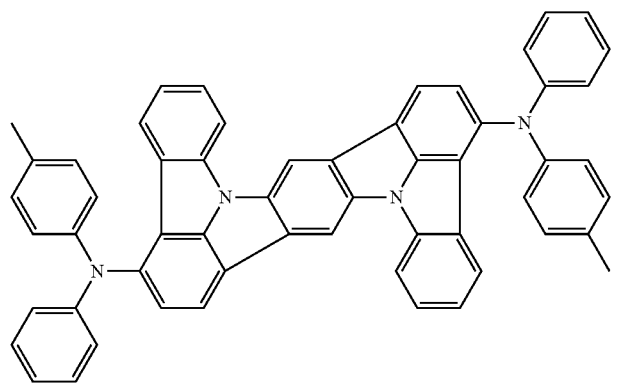

-continued
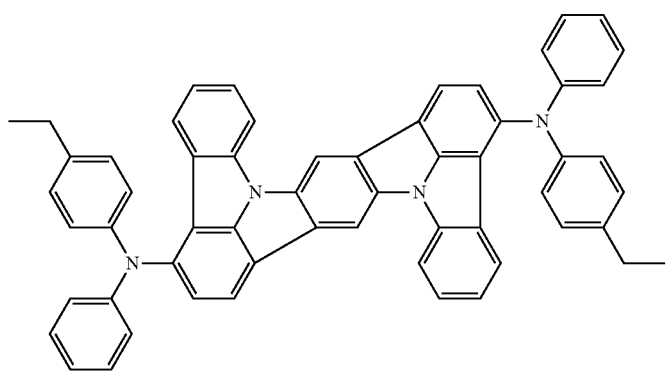
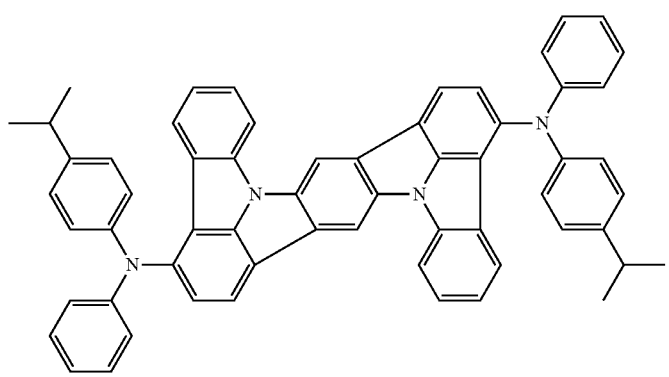
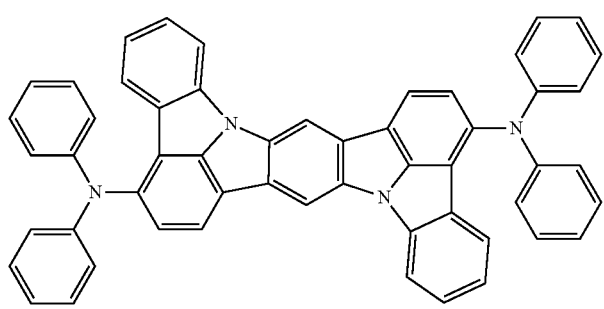
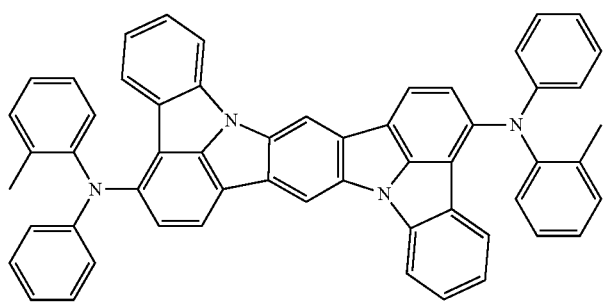
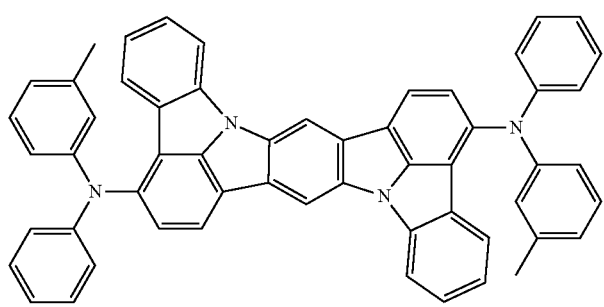

-continued
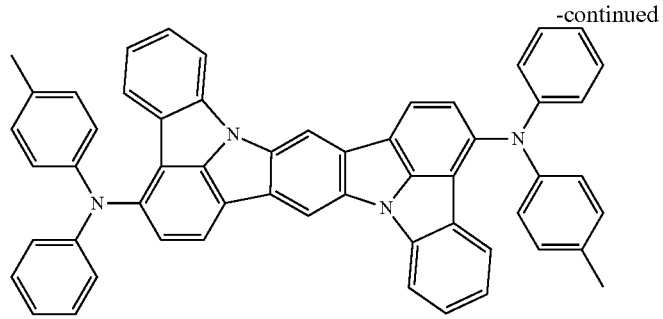
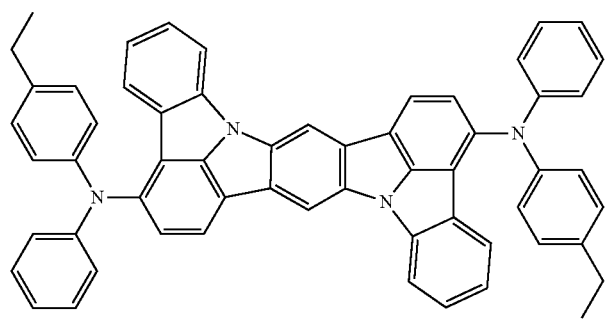
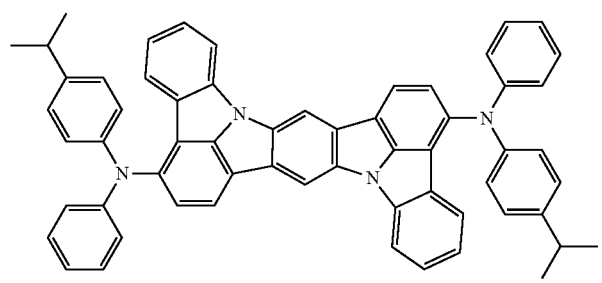
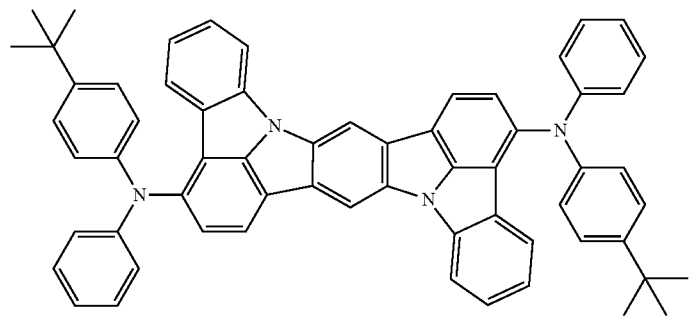
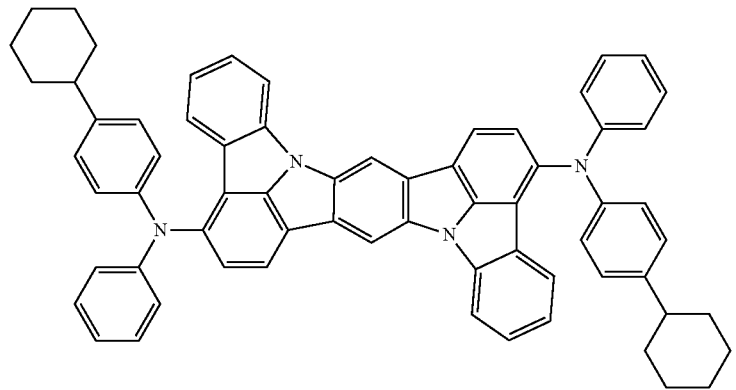

-continued
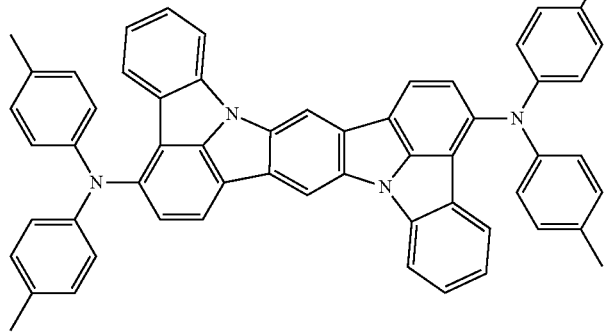
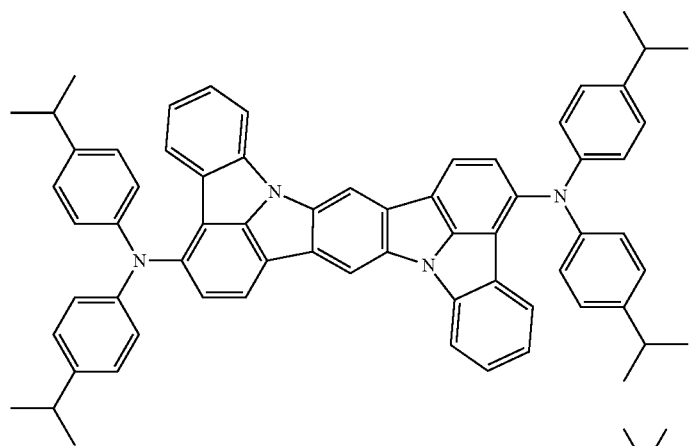
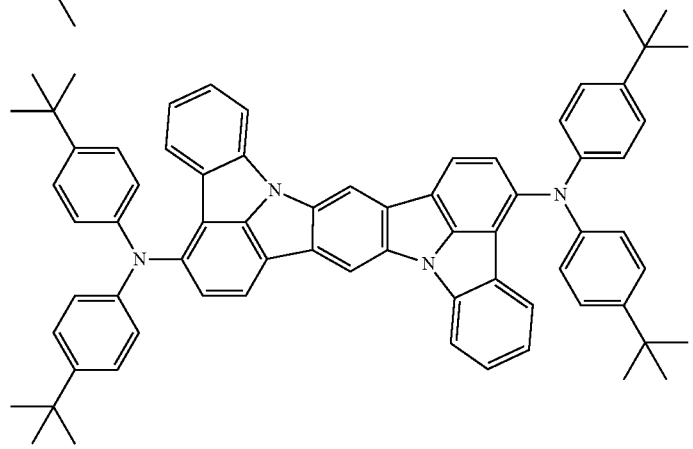
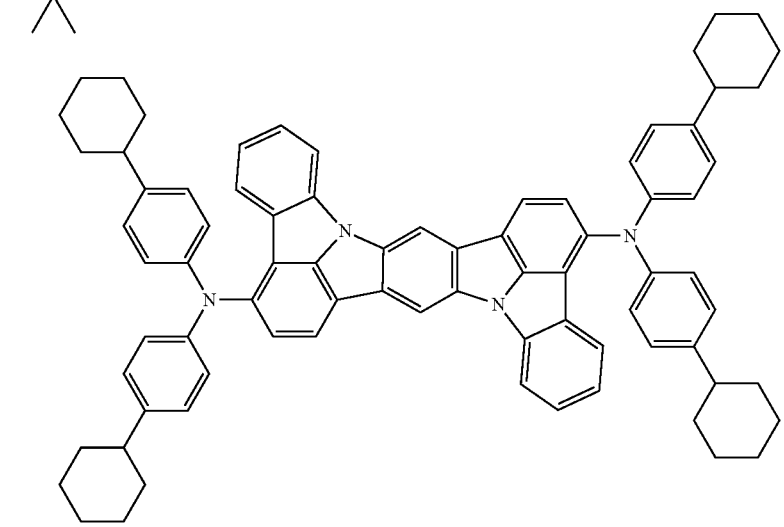

-continued
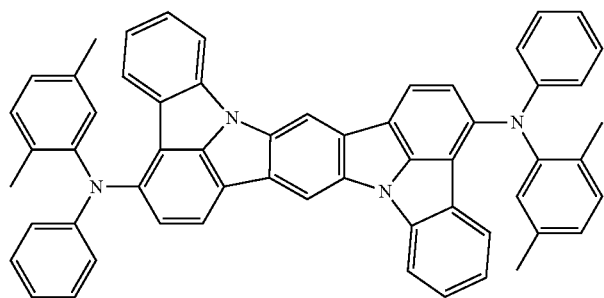
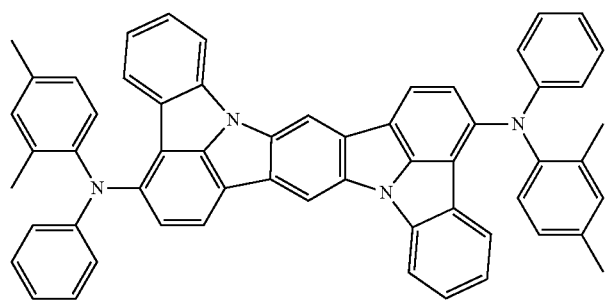
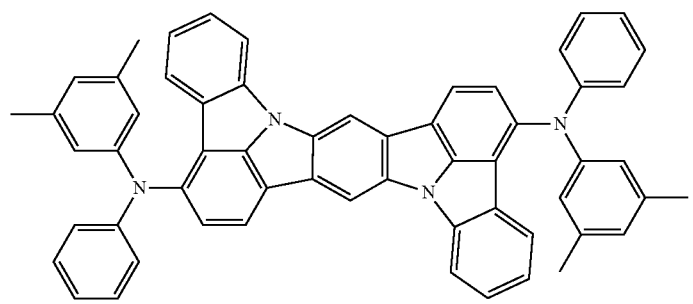
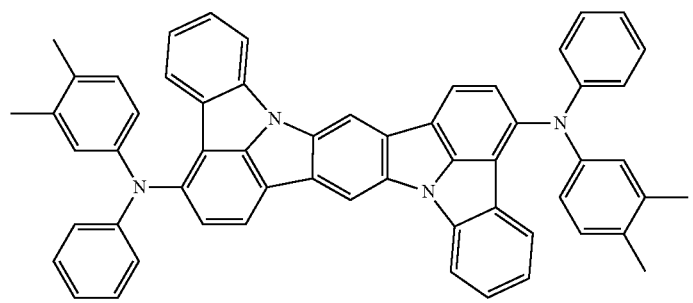
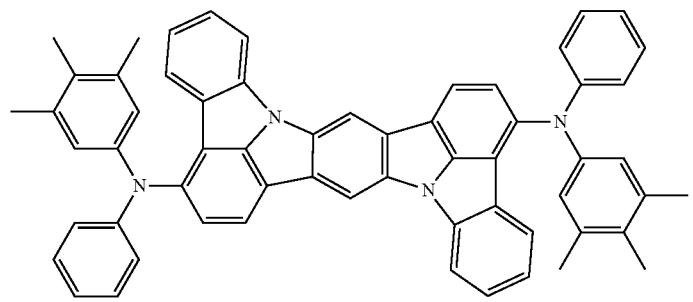

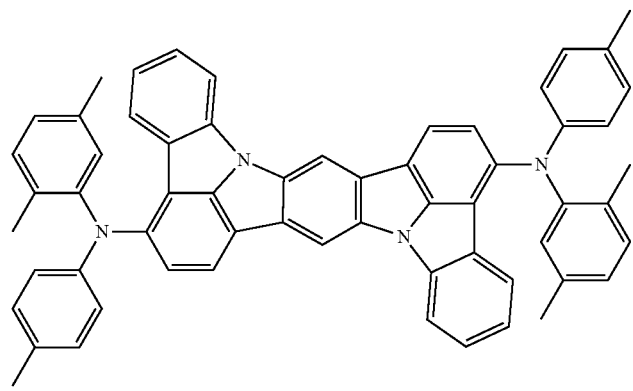
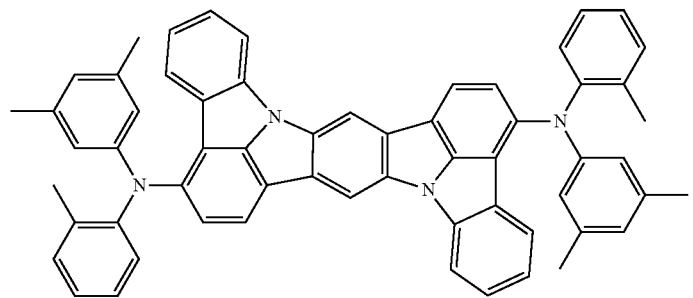
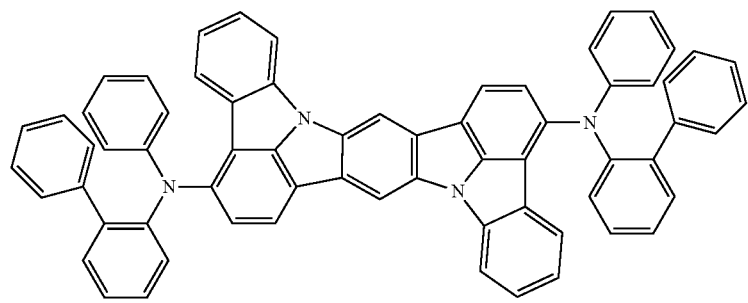
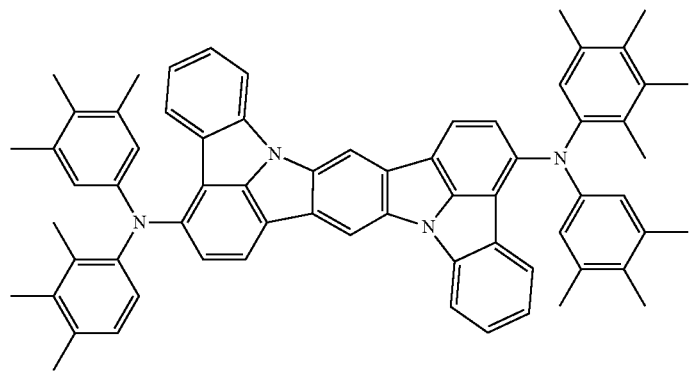

-continued
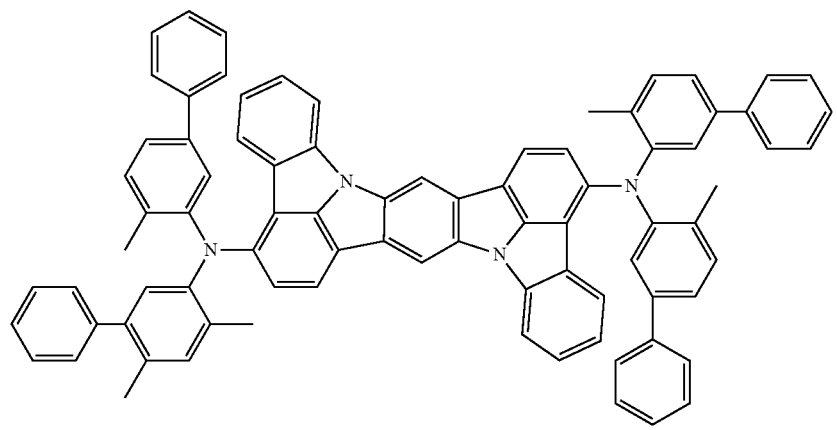
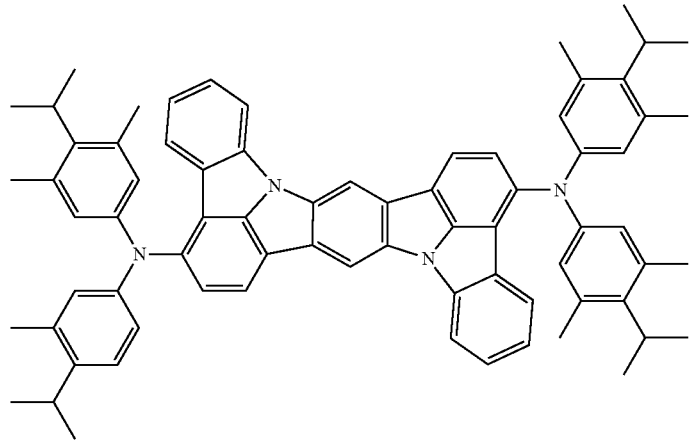
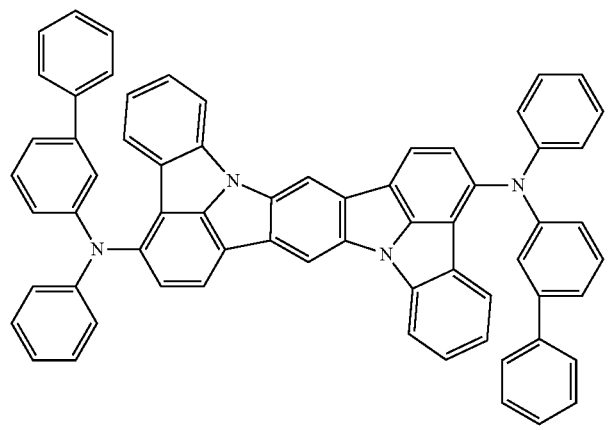
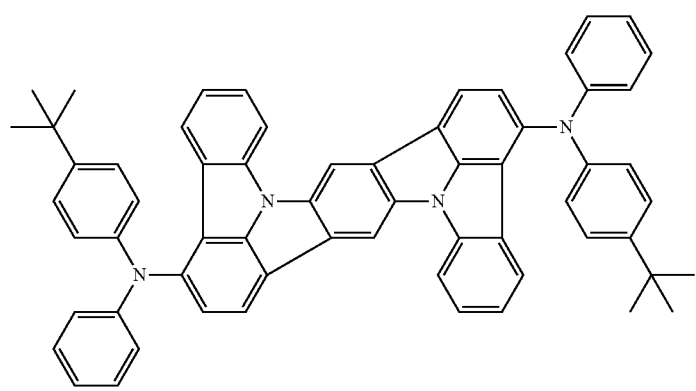

-continued
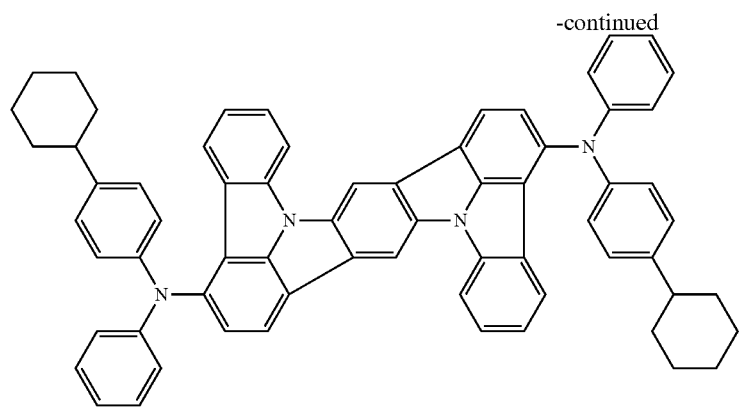
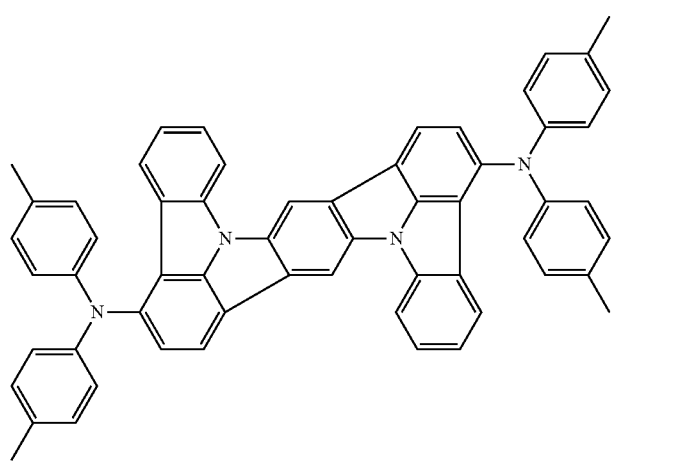
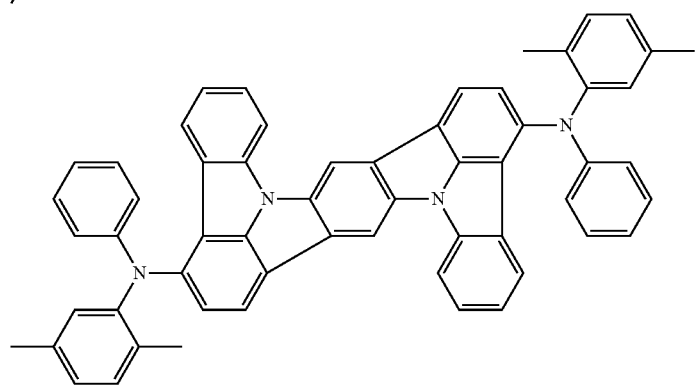
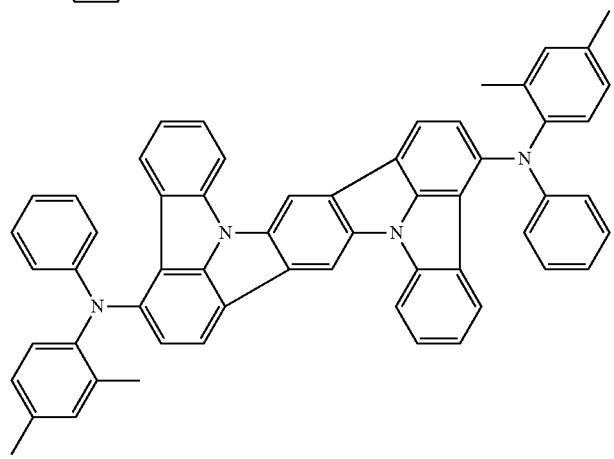

-continued
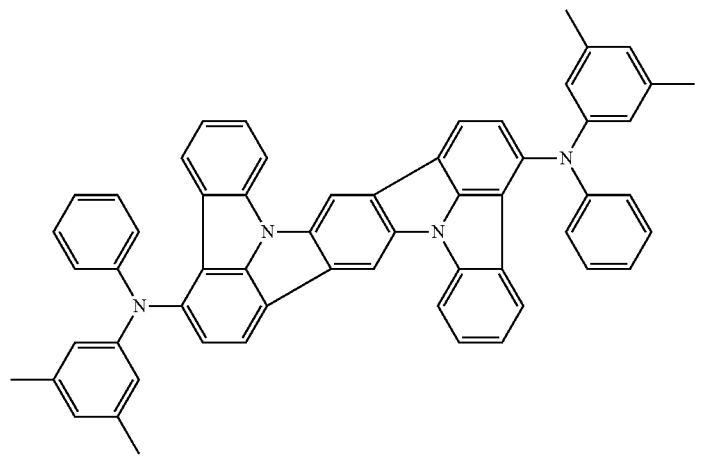
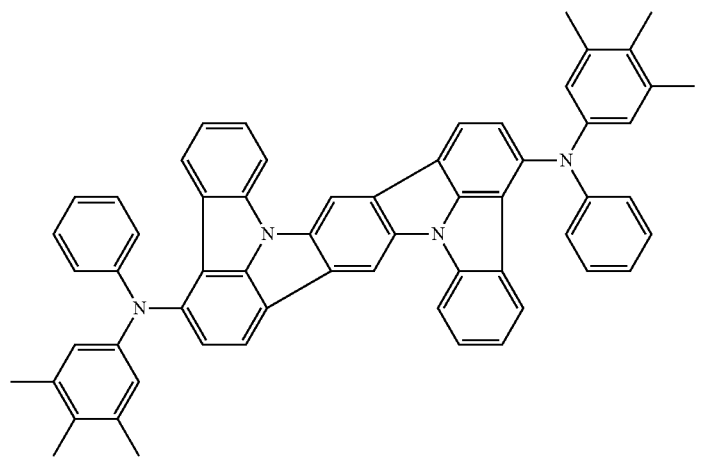
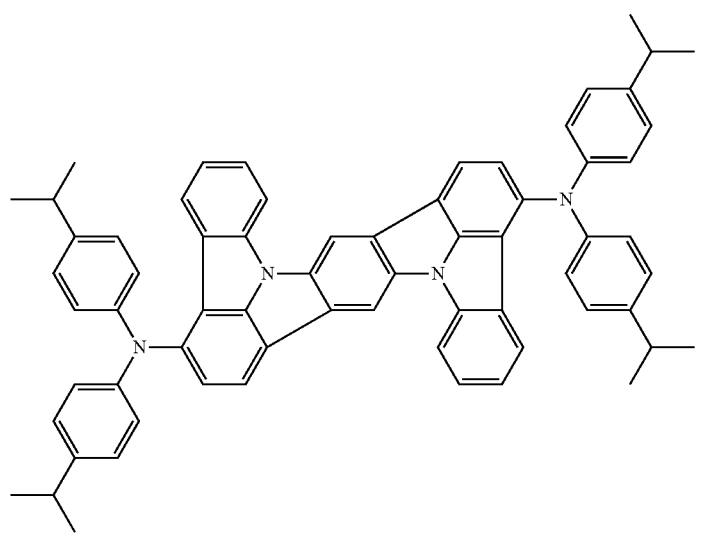

-continued
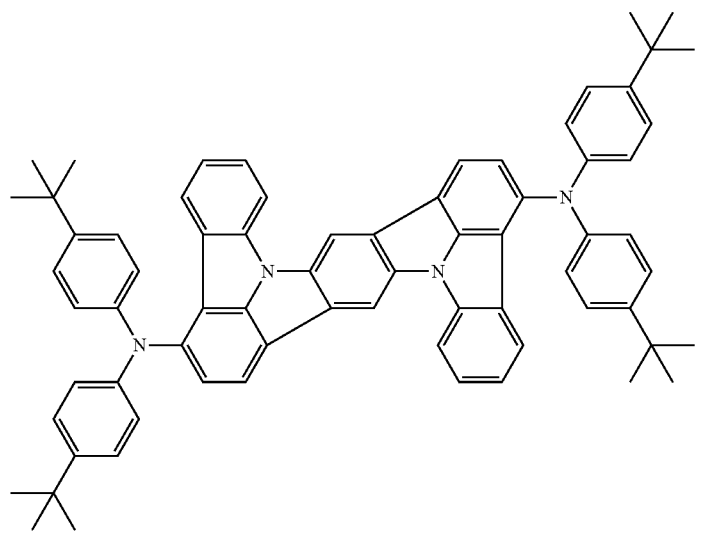
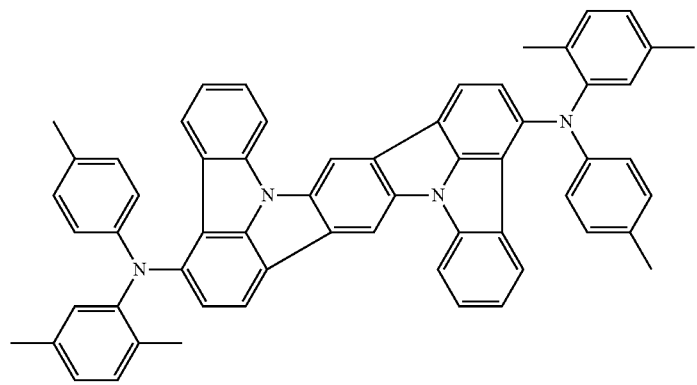
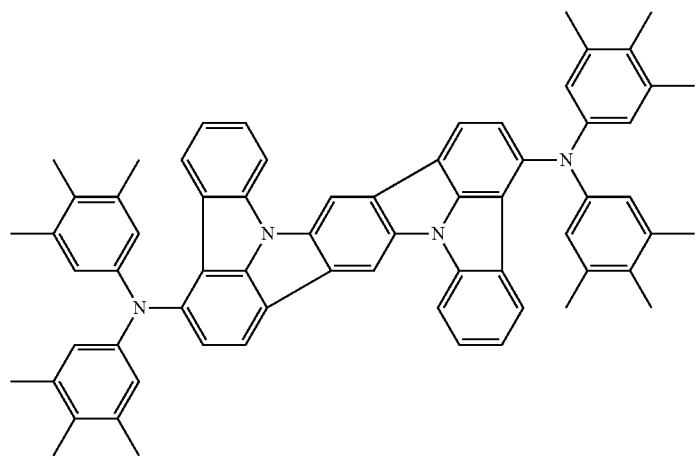
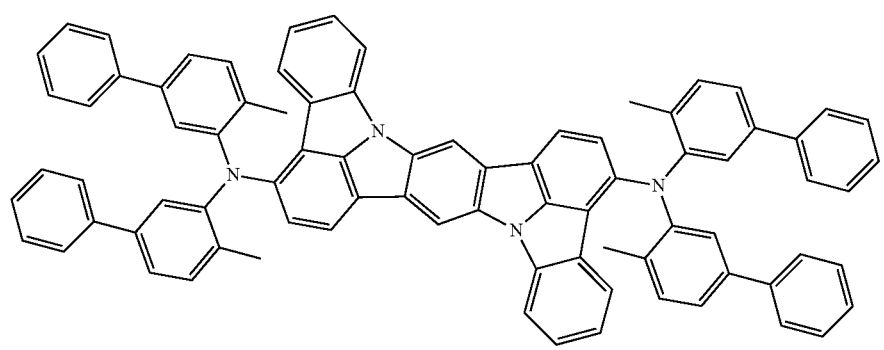

-continued
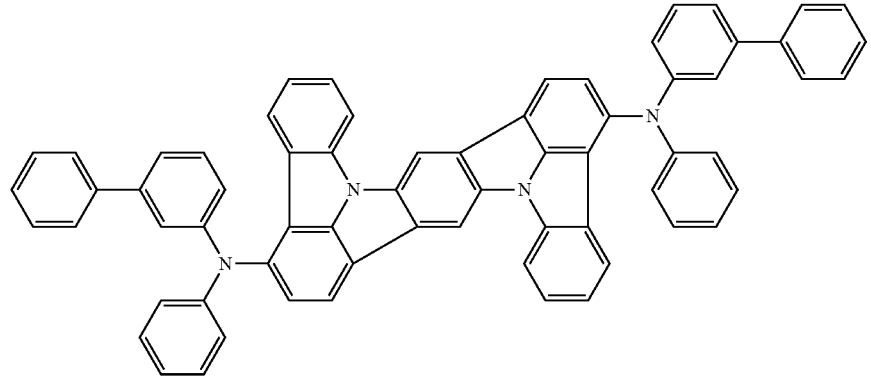
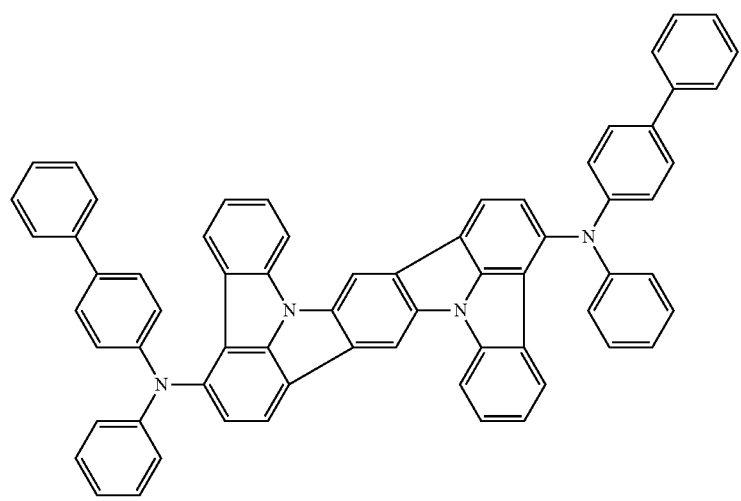
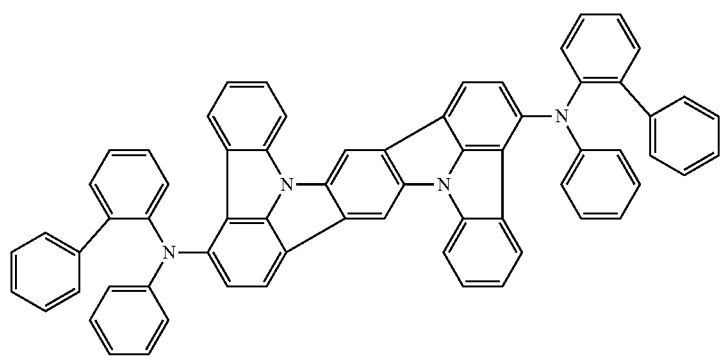
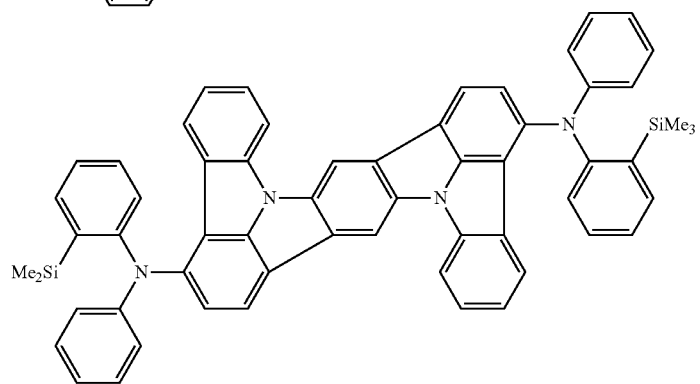

-continued
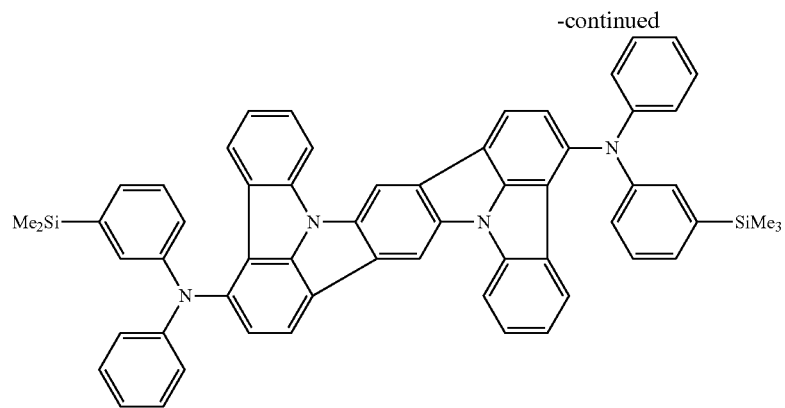
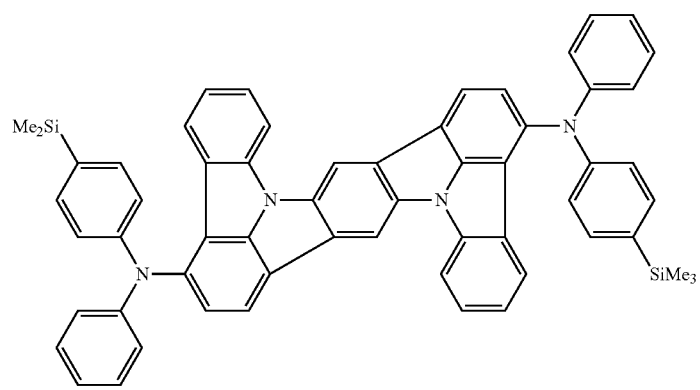
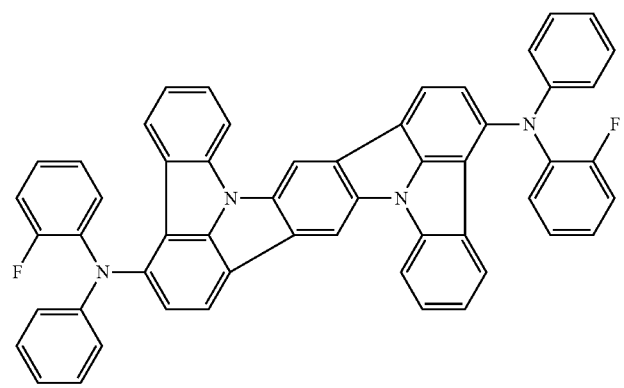
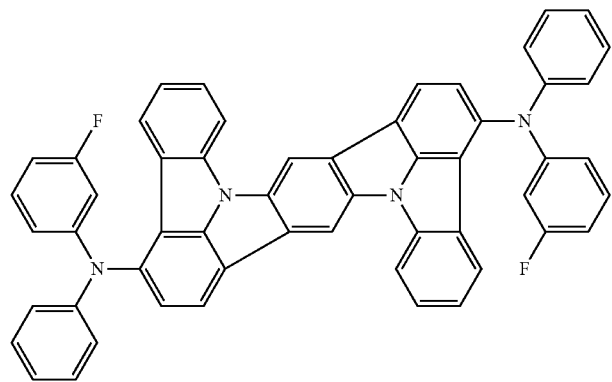

-continued
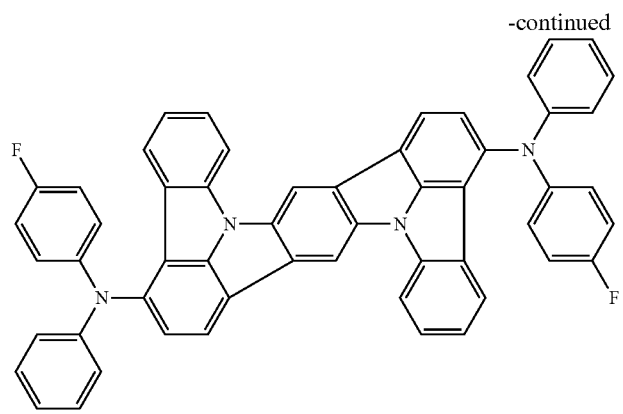
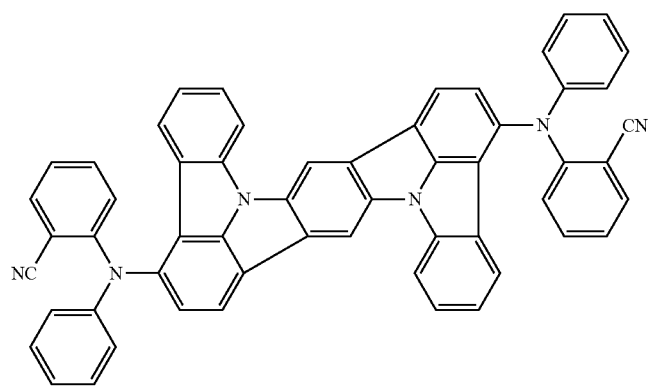
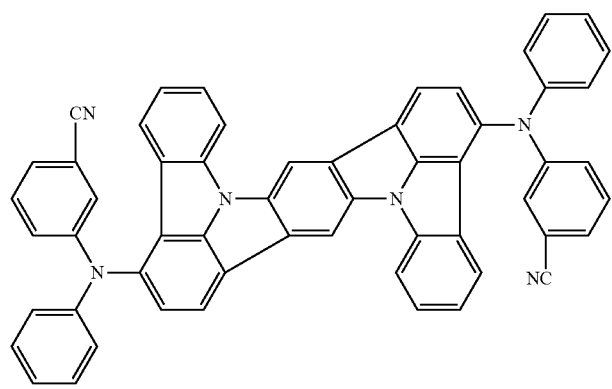
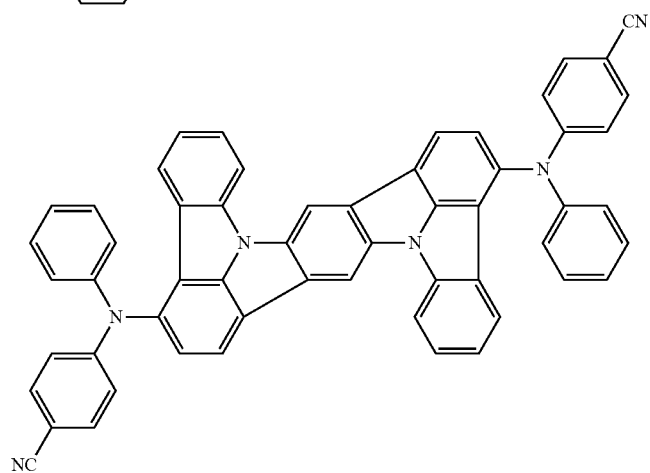

-continued
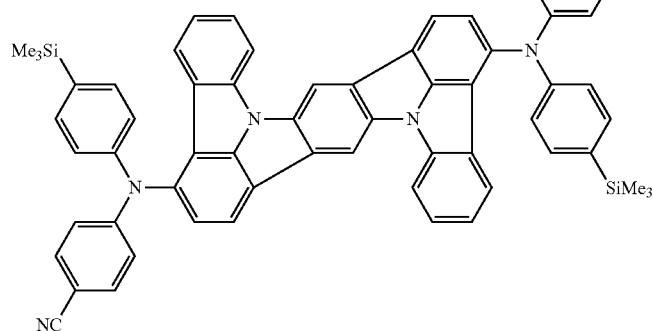
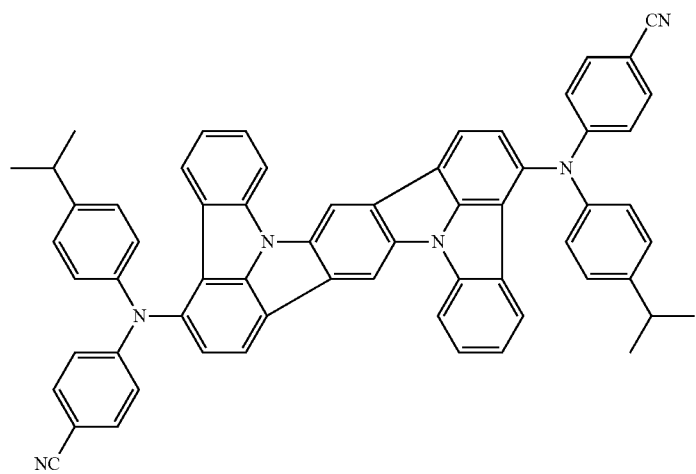
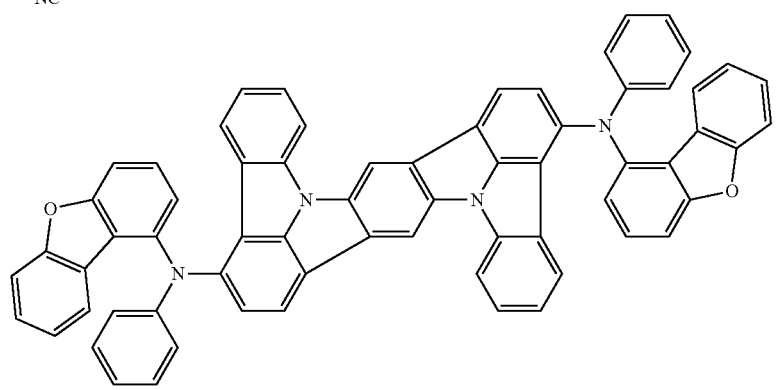
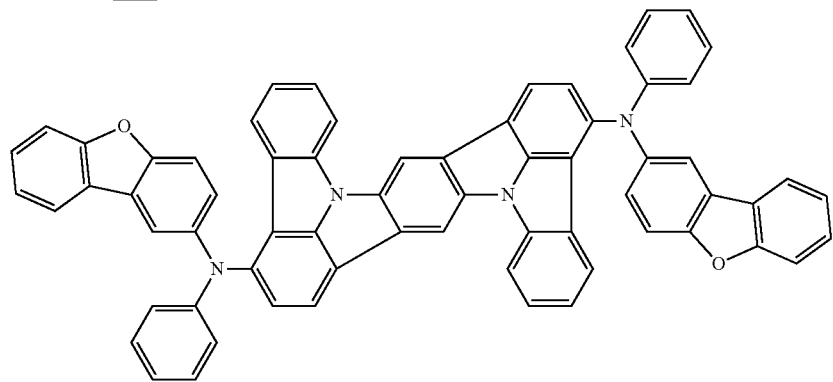

521
-continued
522
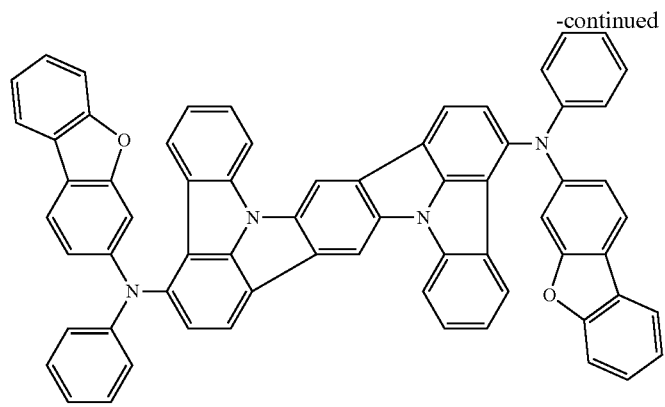
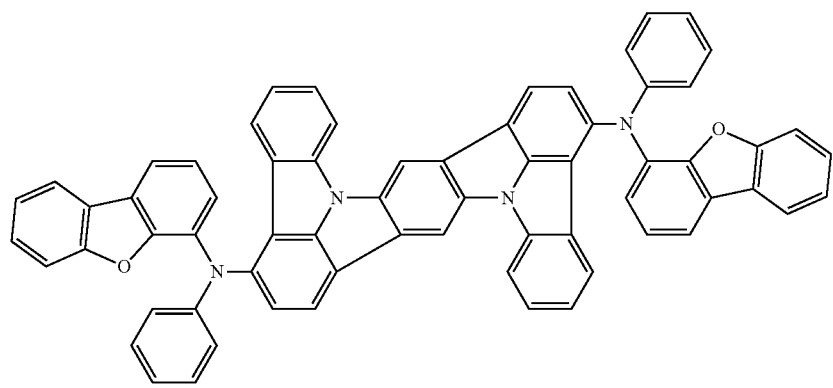
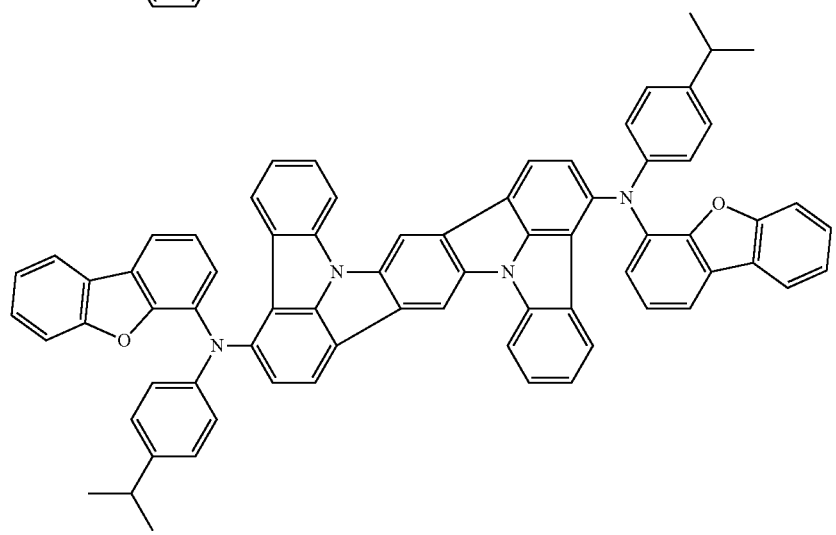
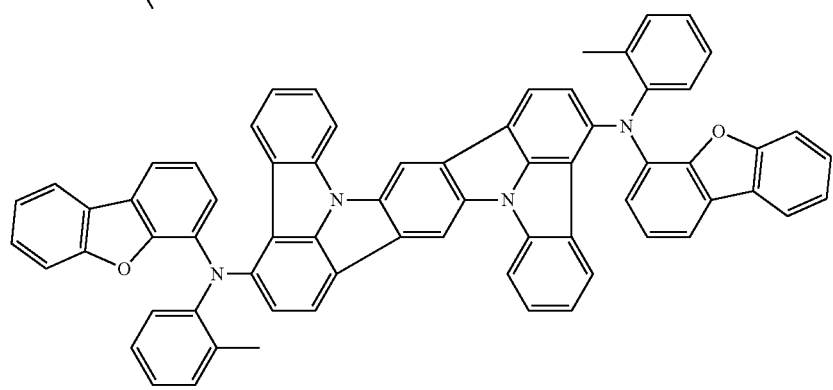

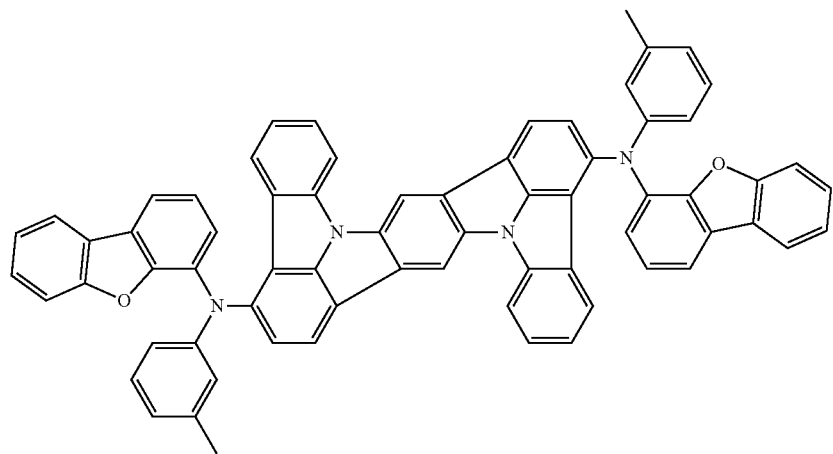
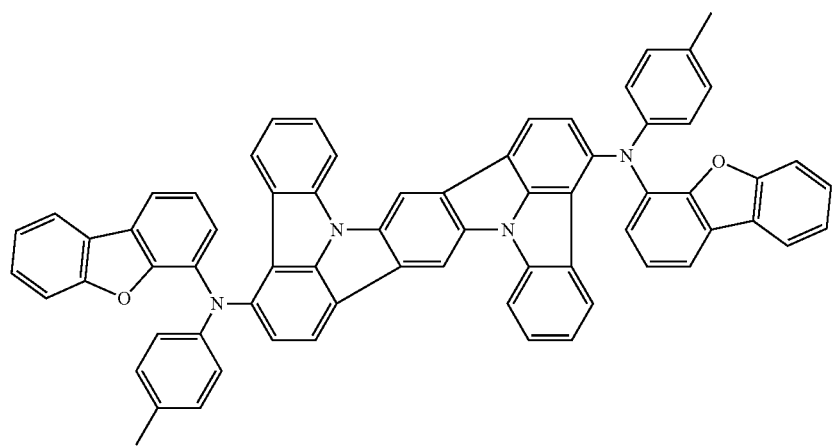
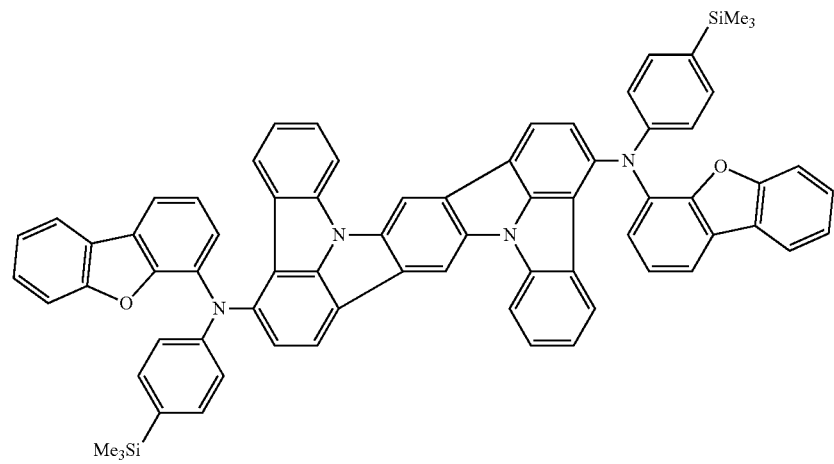

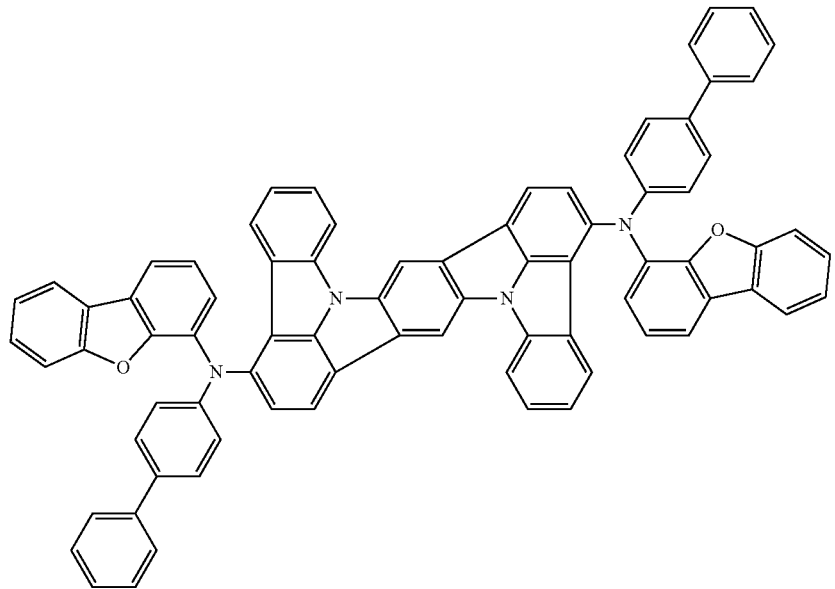
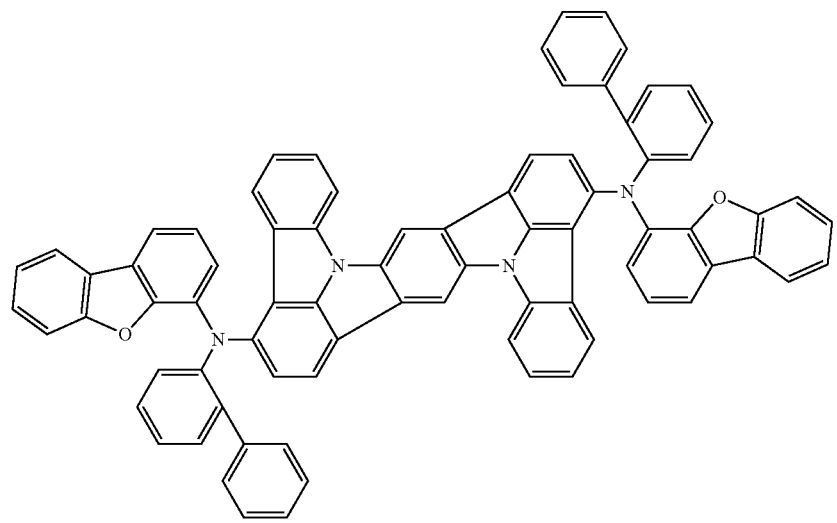
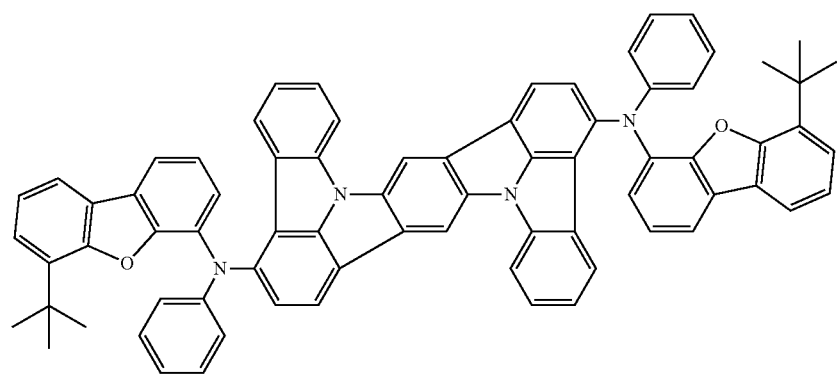

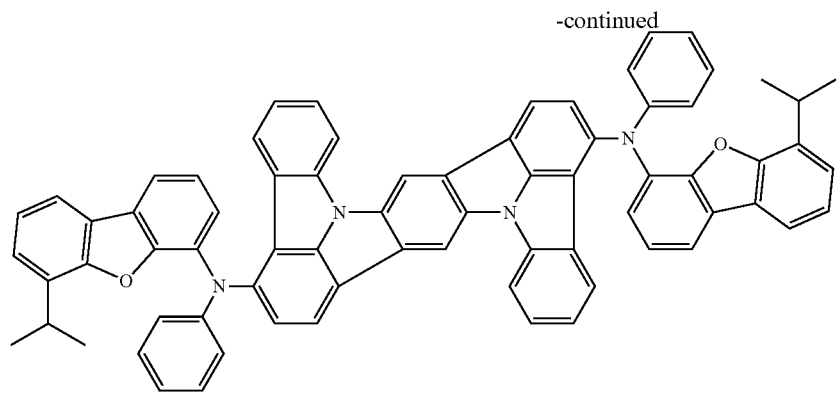
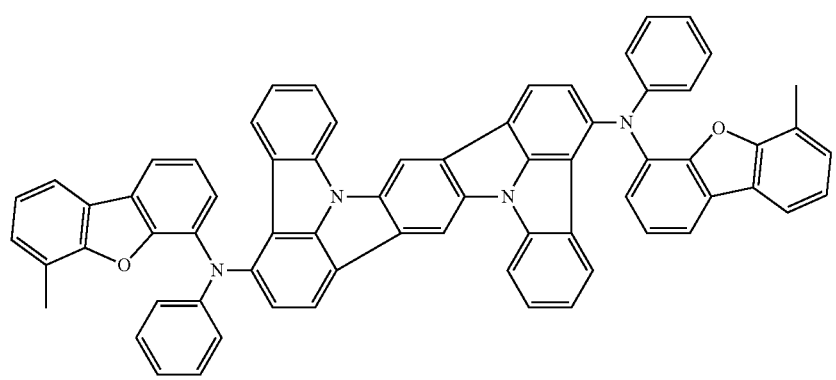
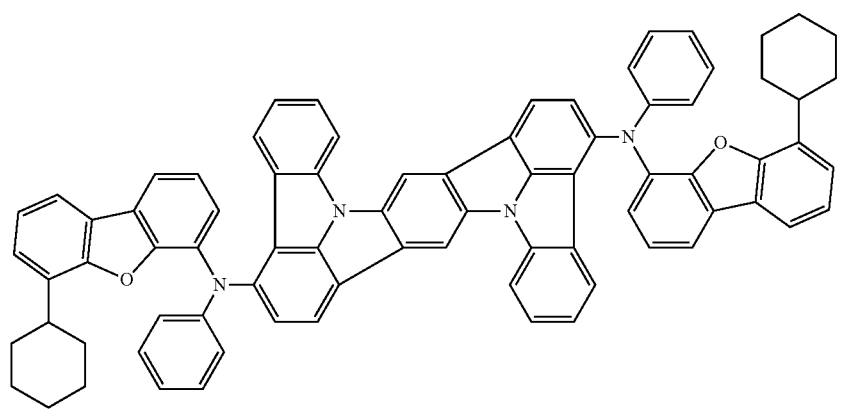
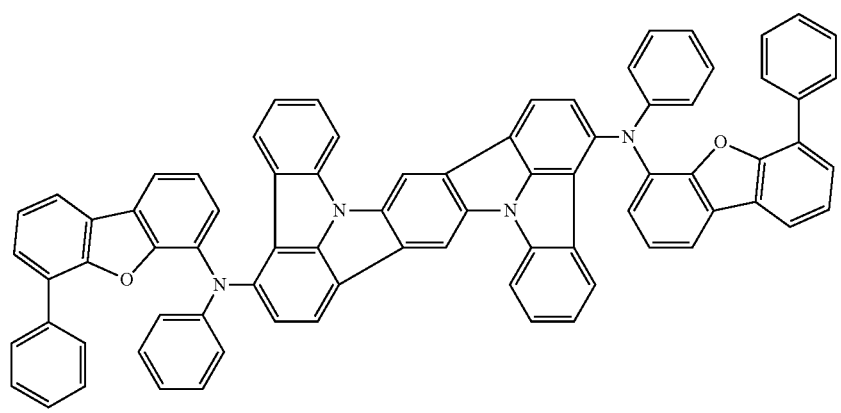

-continued
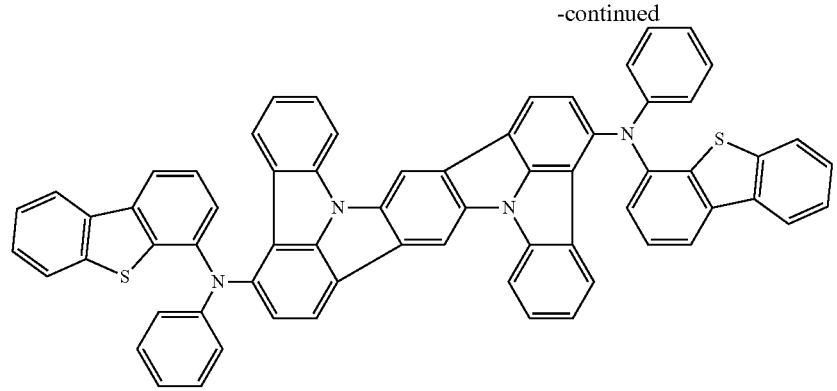
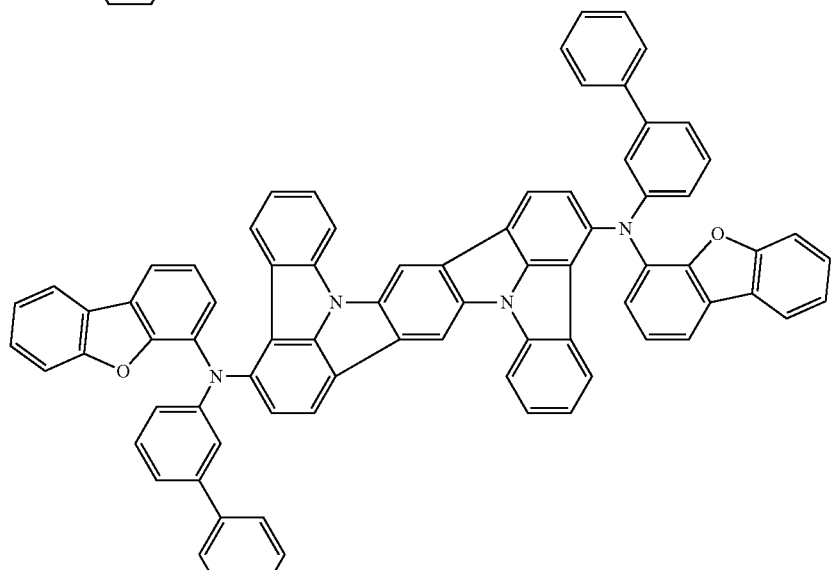
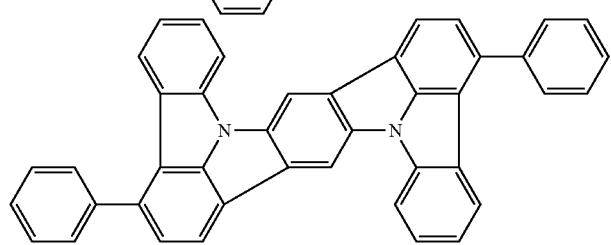
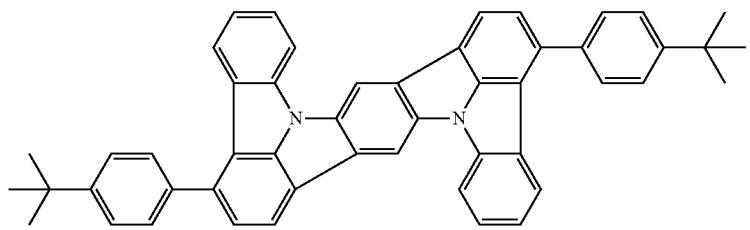
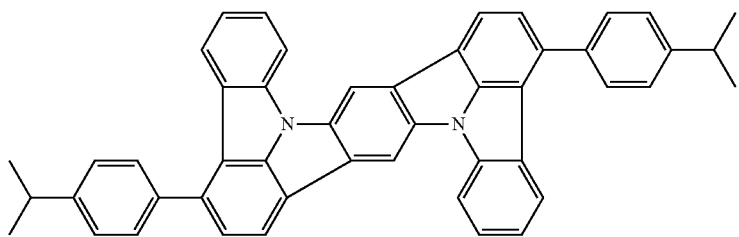

-continued
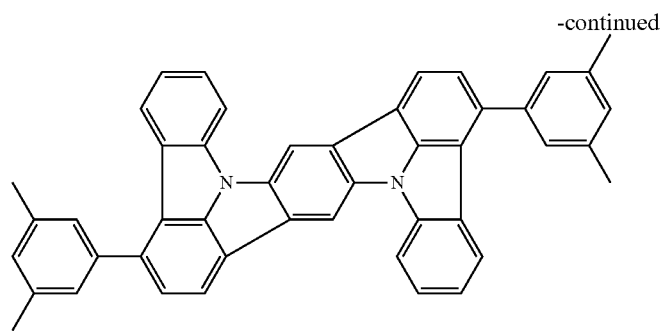
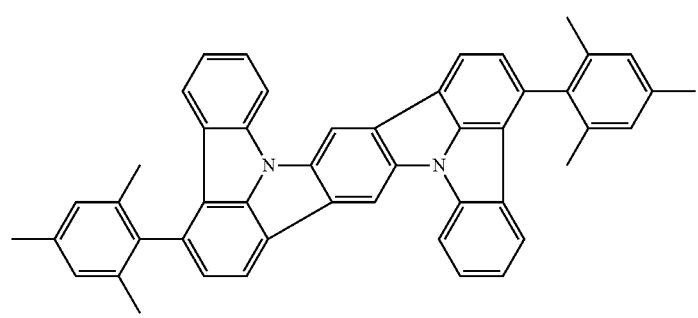
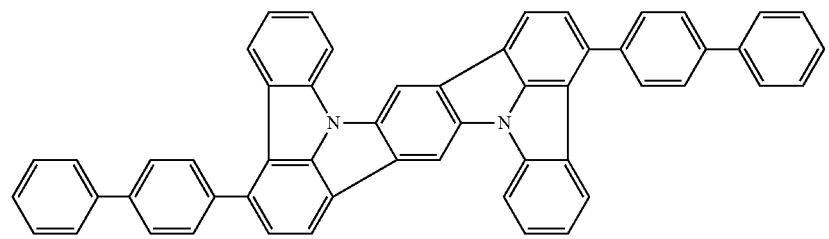
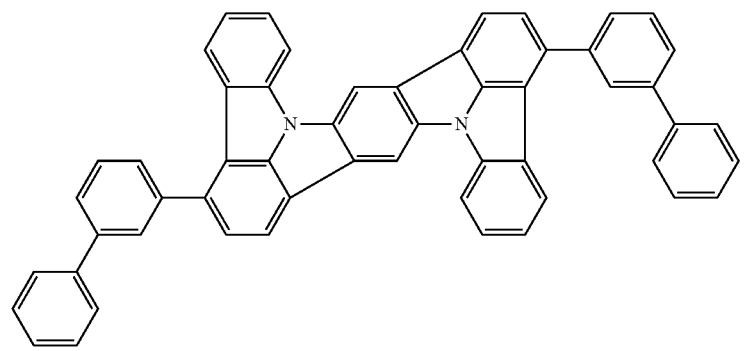
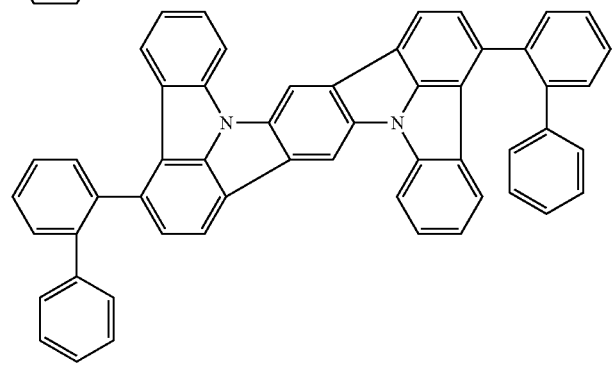

-continued
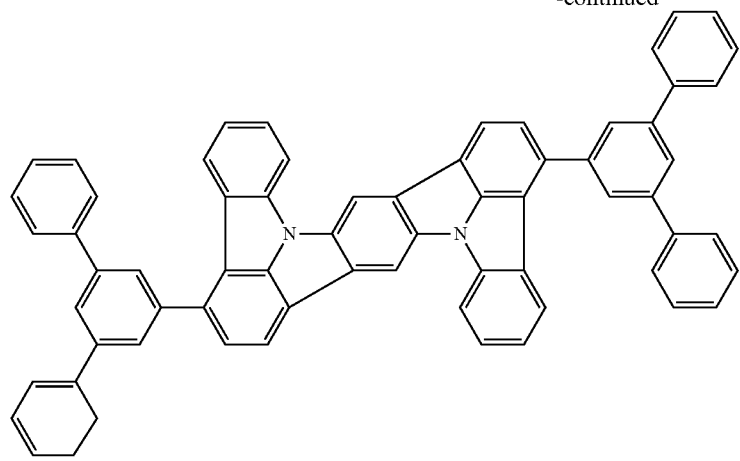
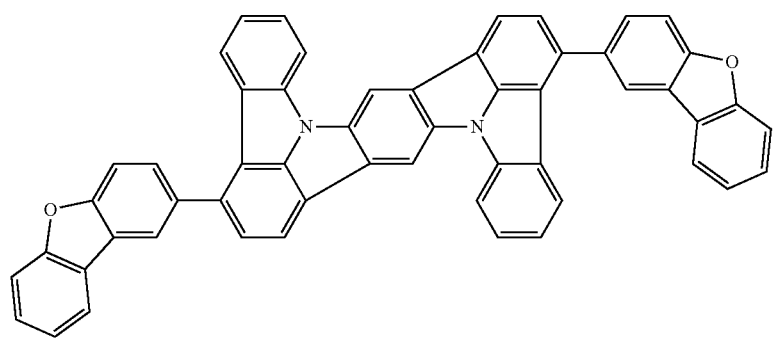
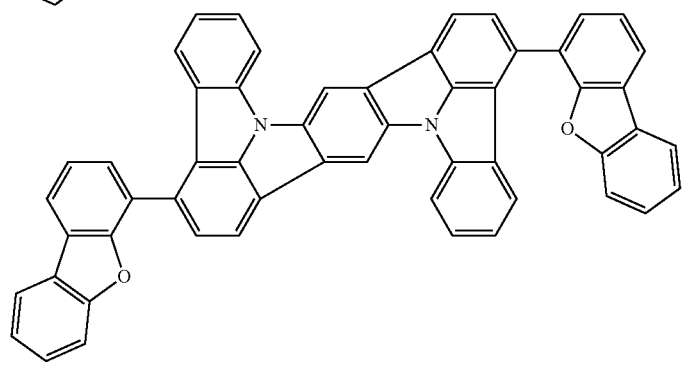
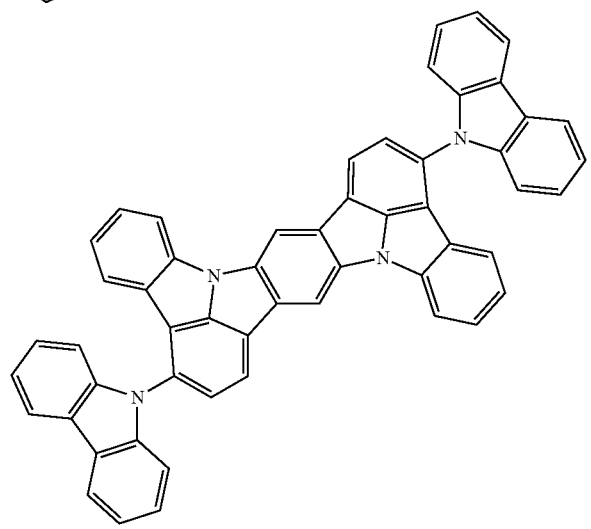

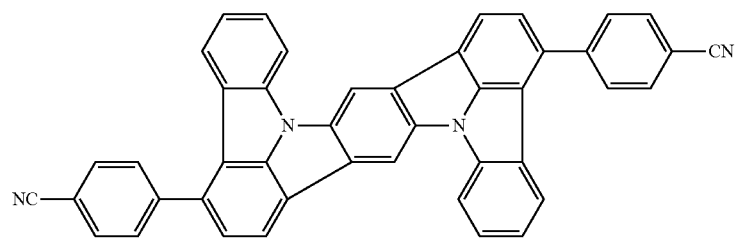
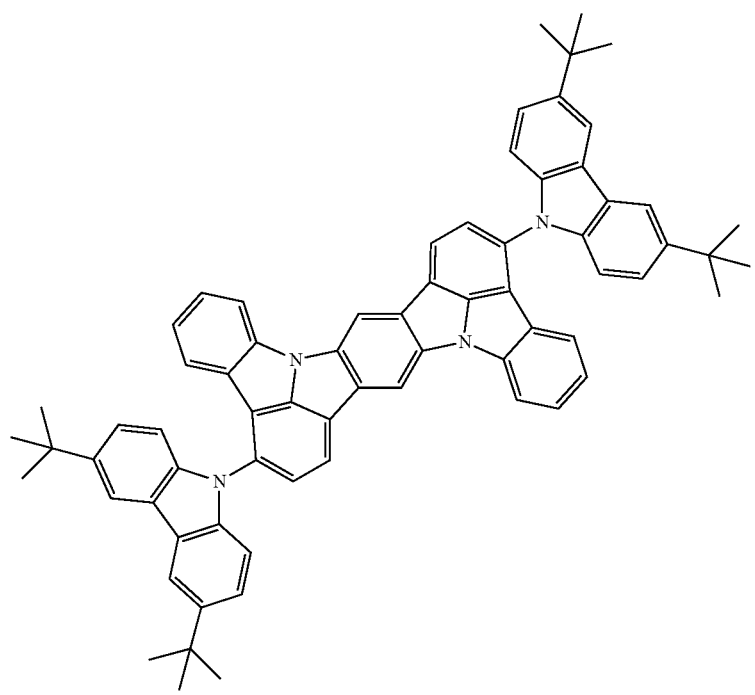
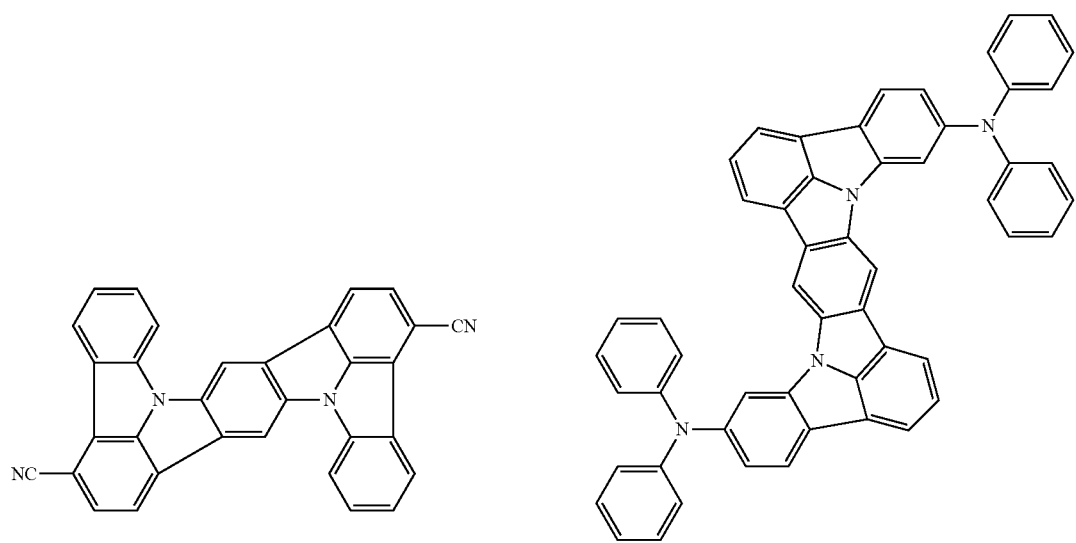

-continued
537
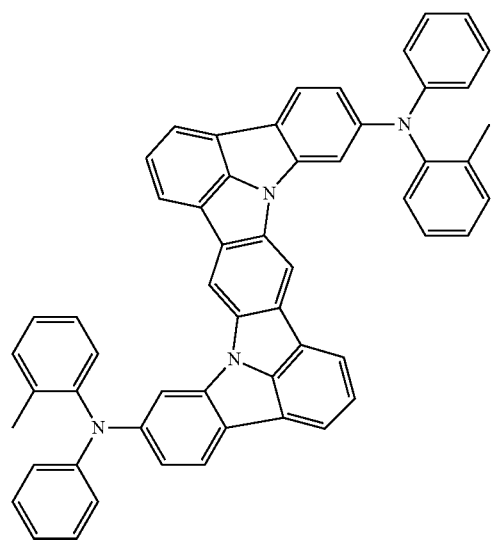
538
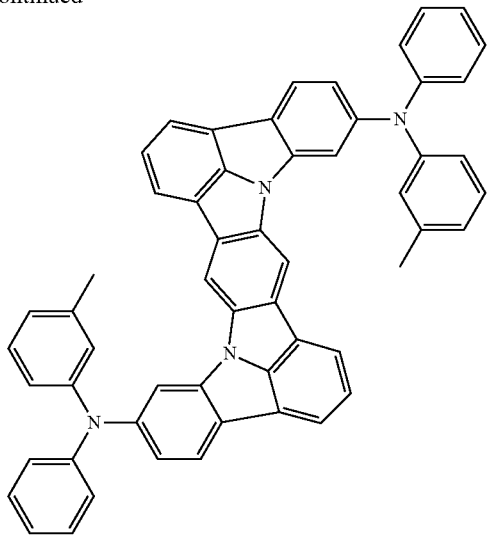
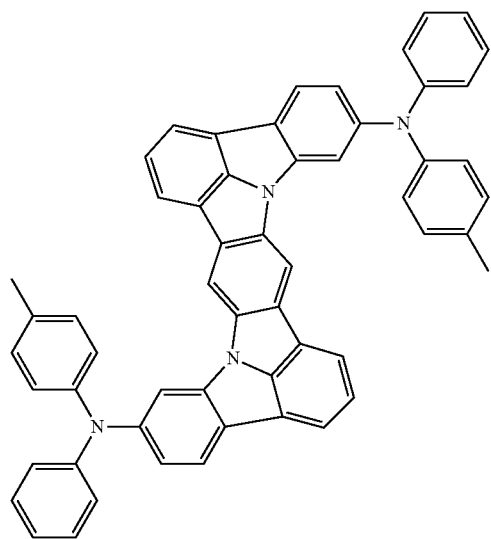
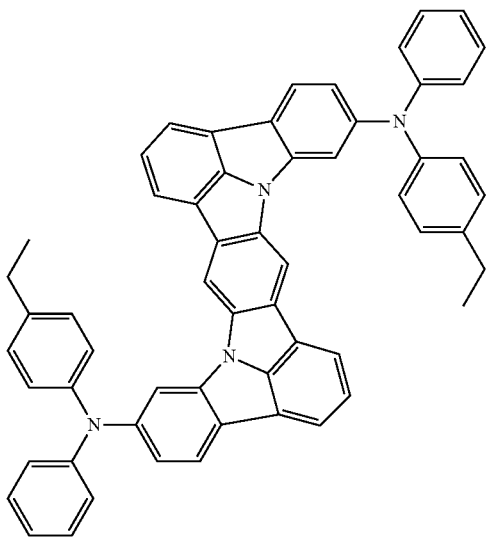
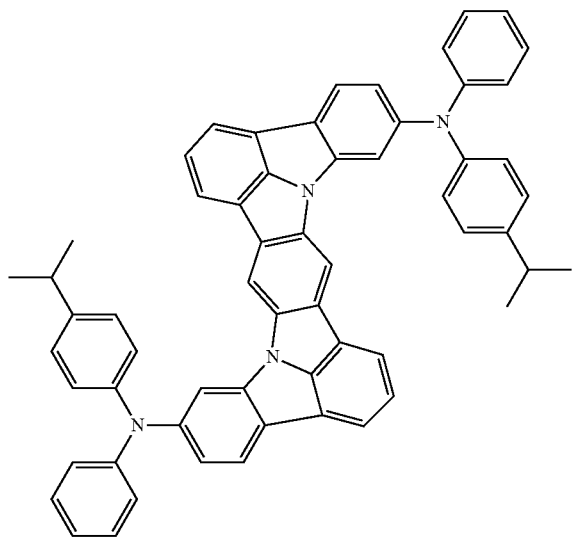
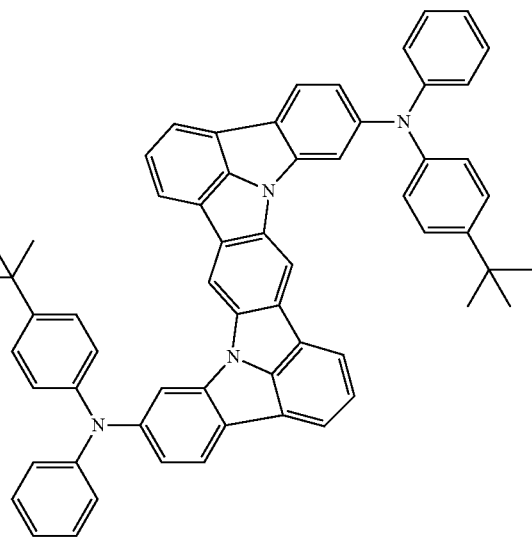

-continued
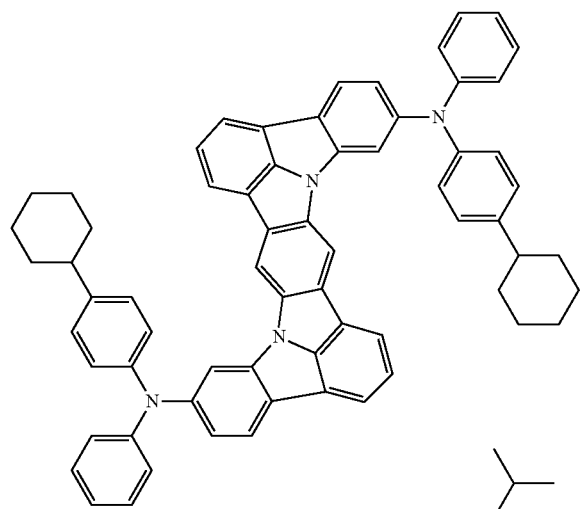
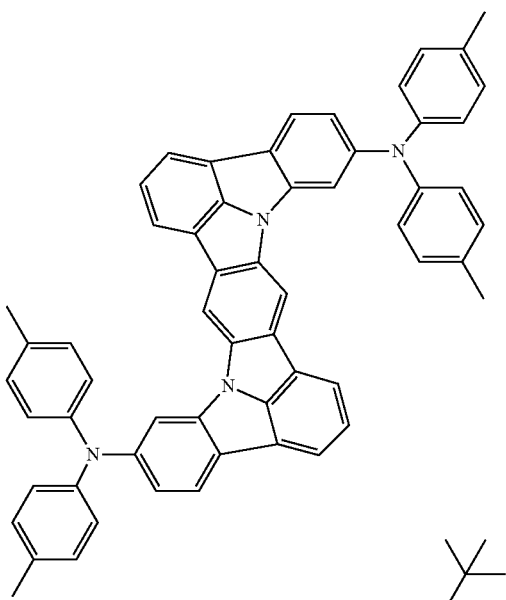
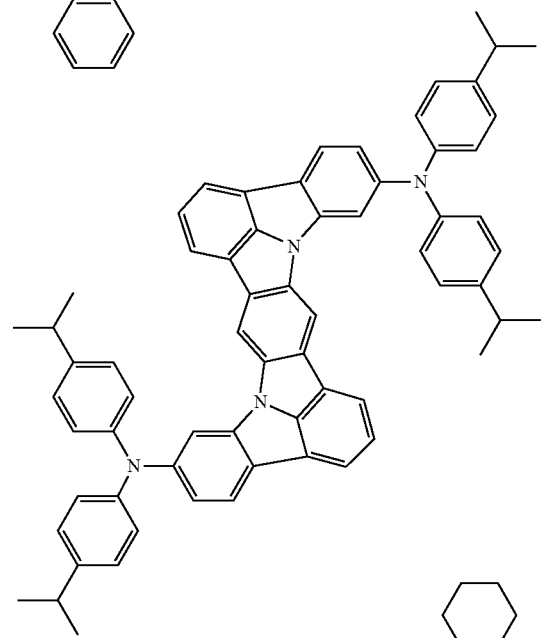
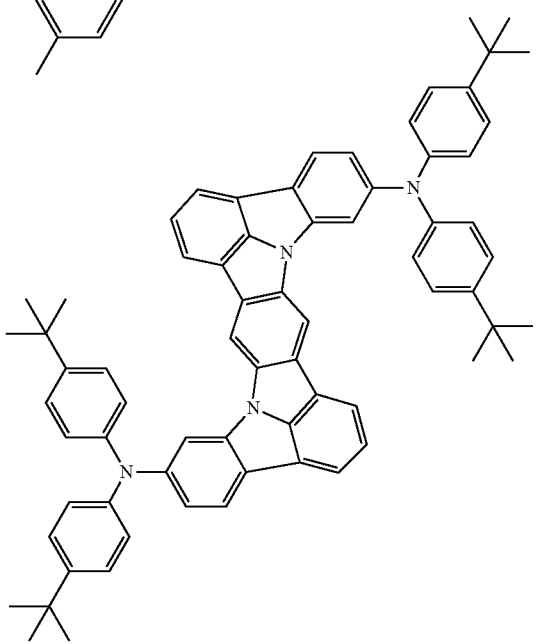
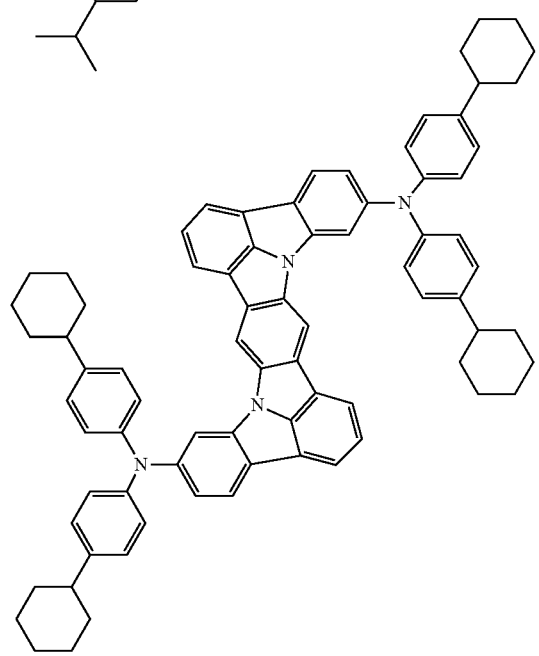
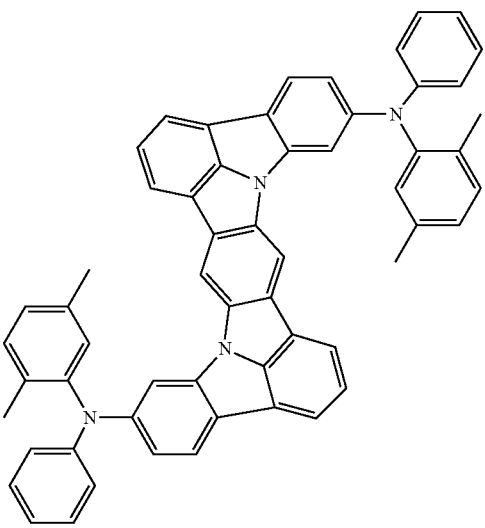

-continued
541 542
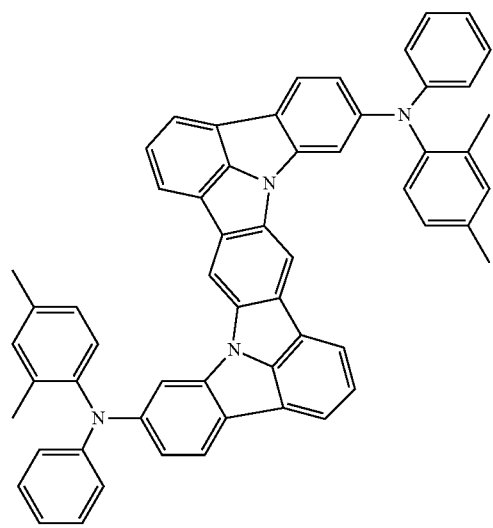
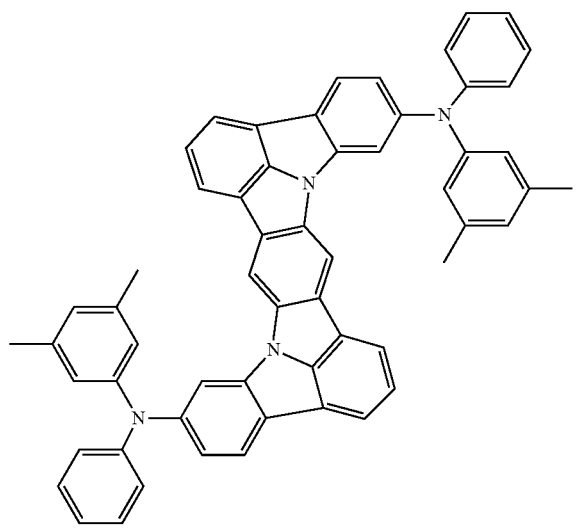
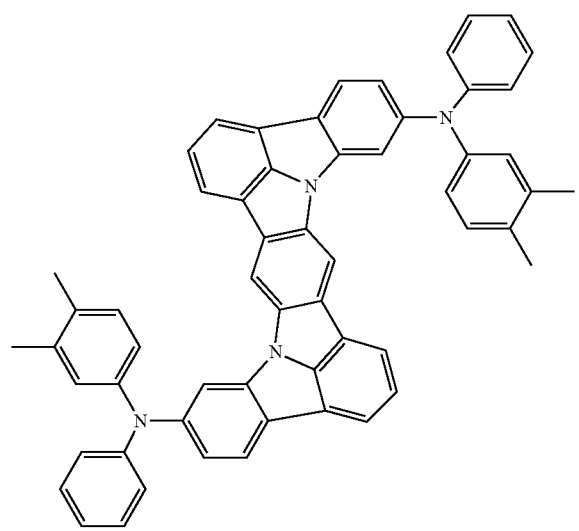
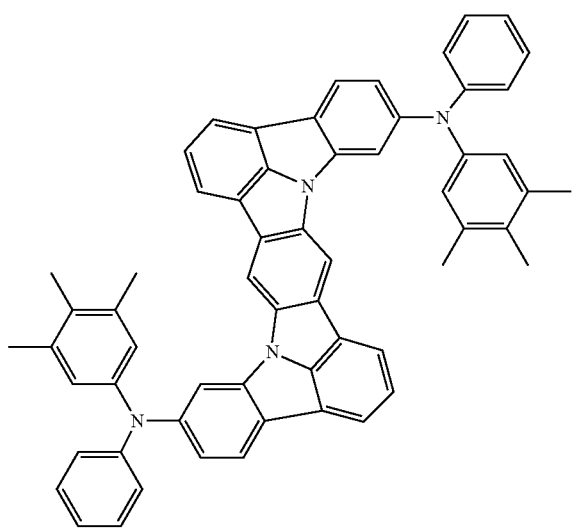
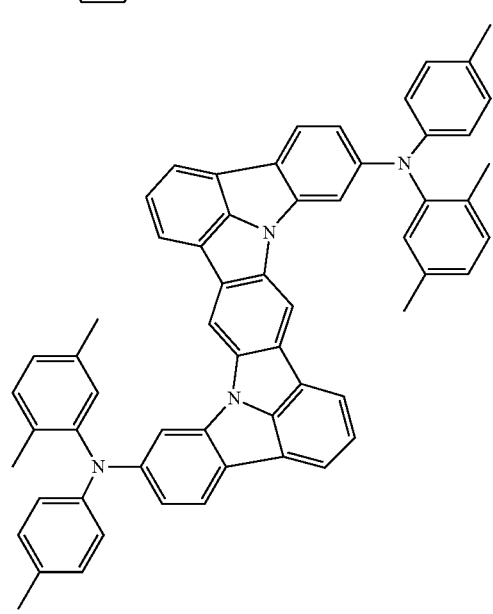
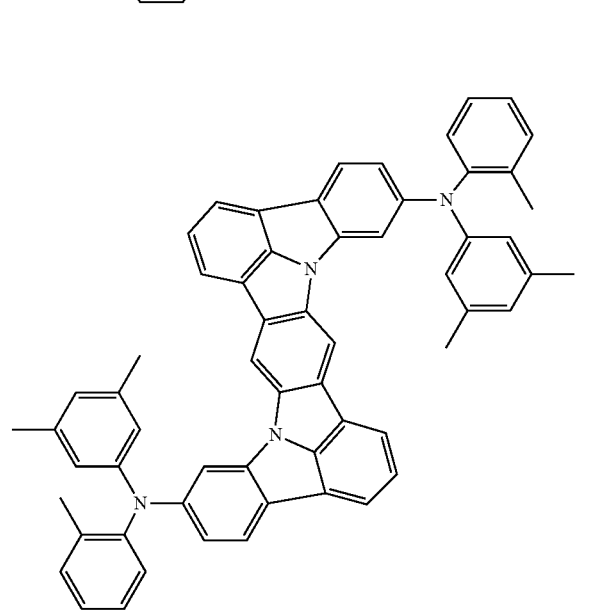

-continued
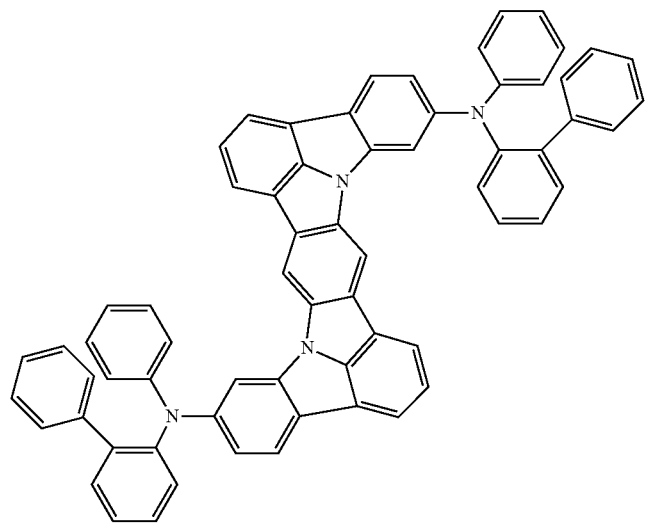
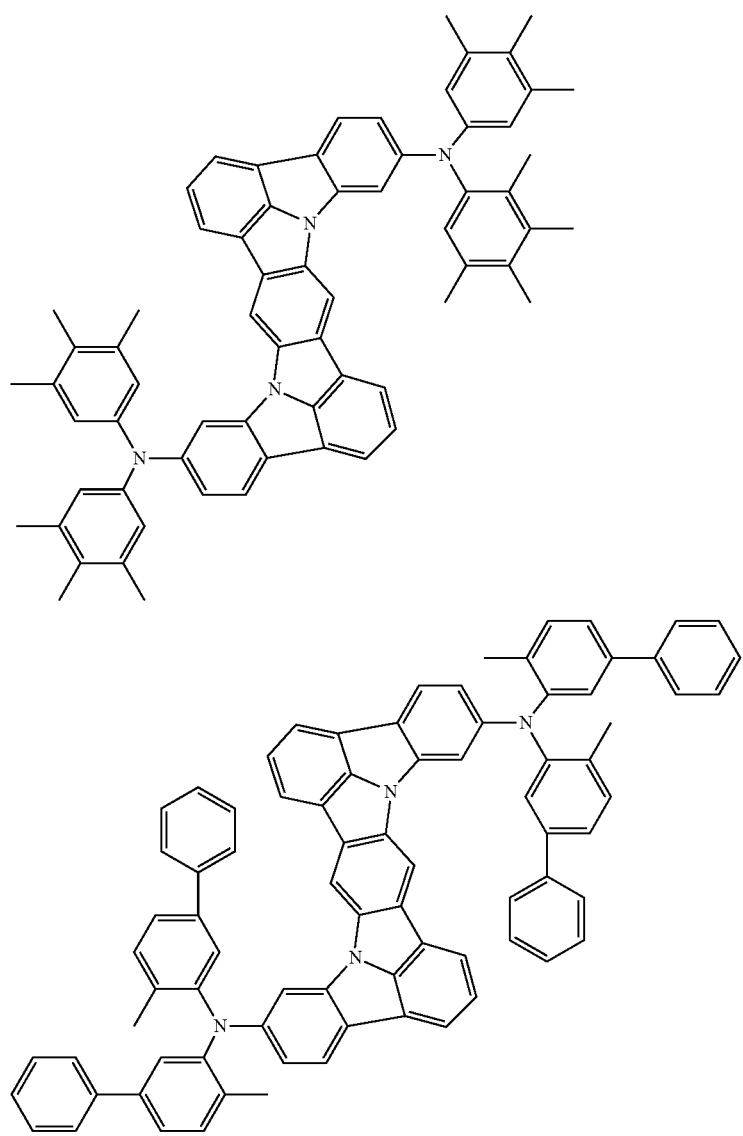

545
546
-continued
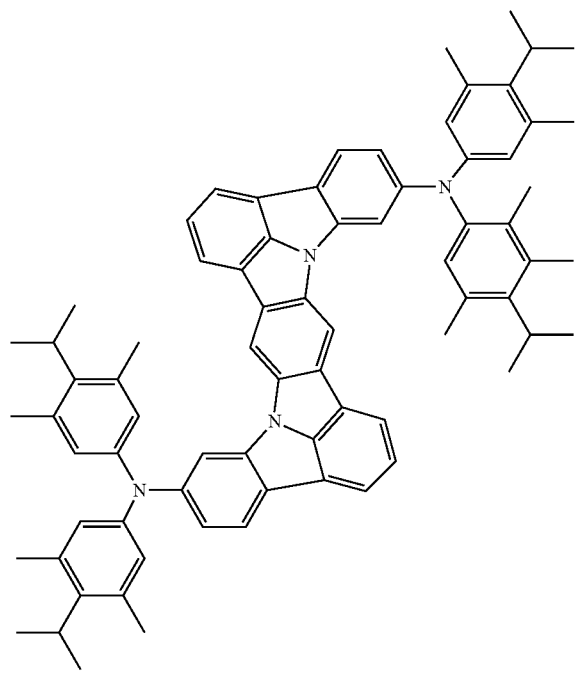
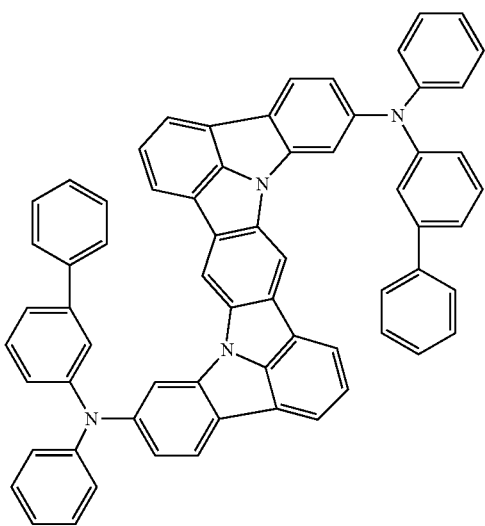
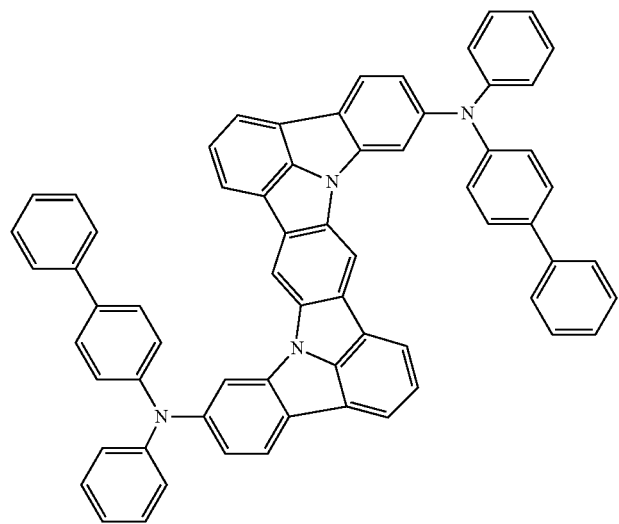
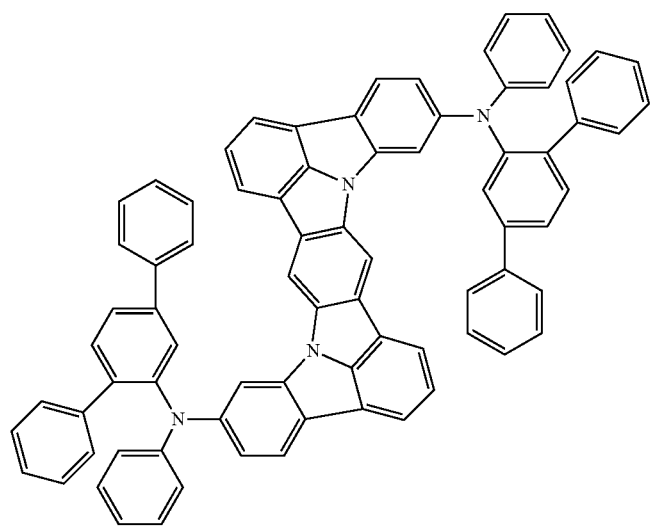

-continued
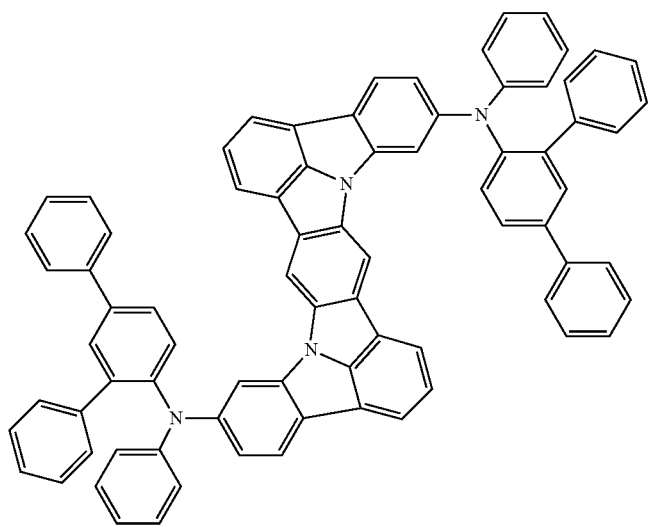
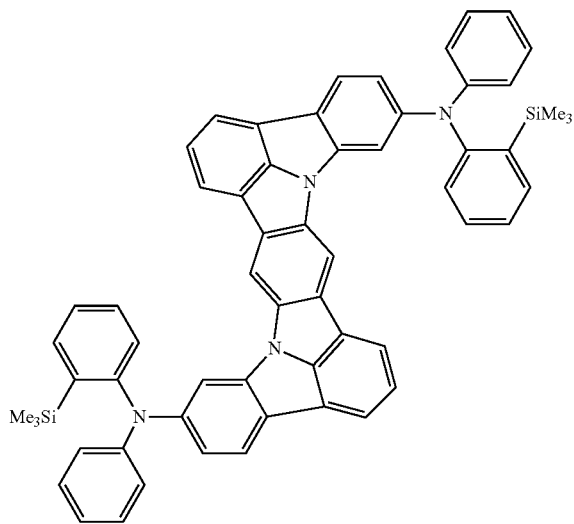
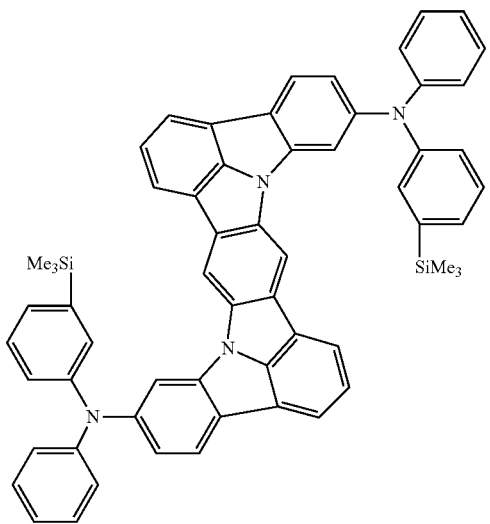
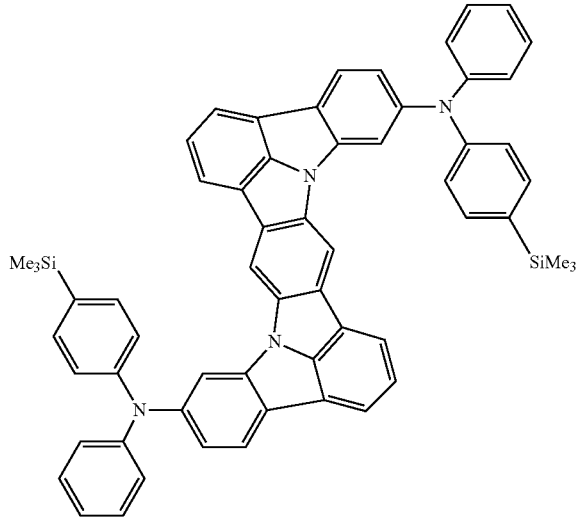
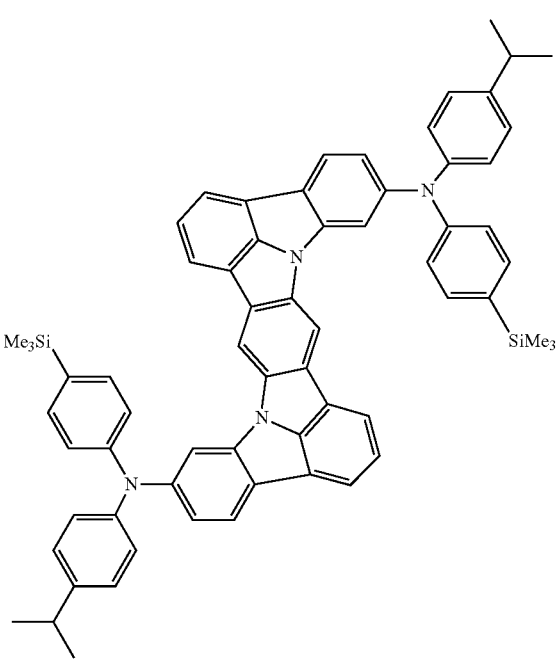

-continued
549
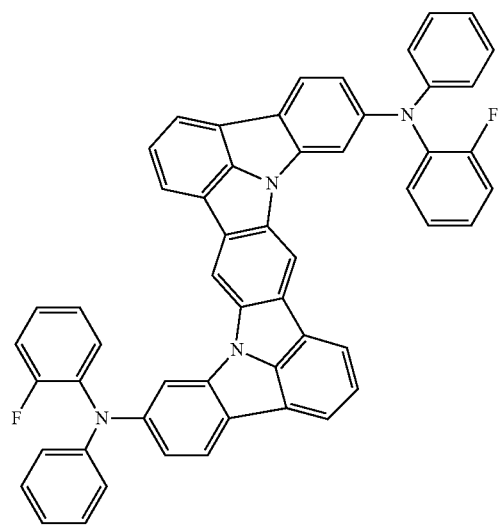
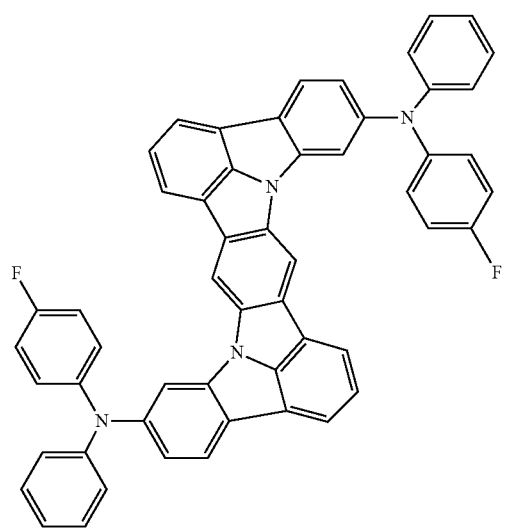
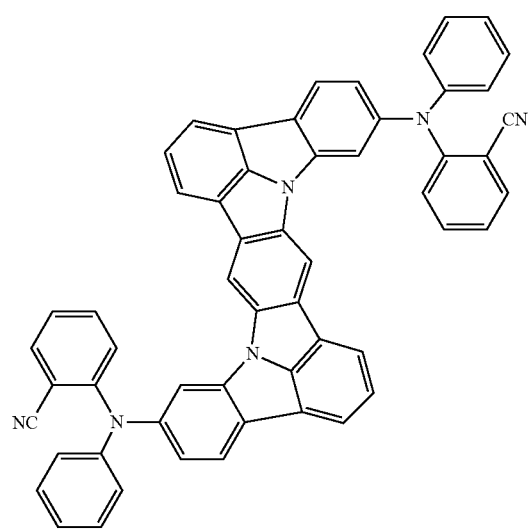
550
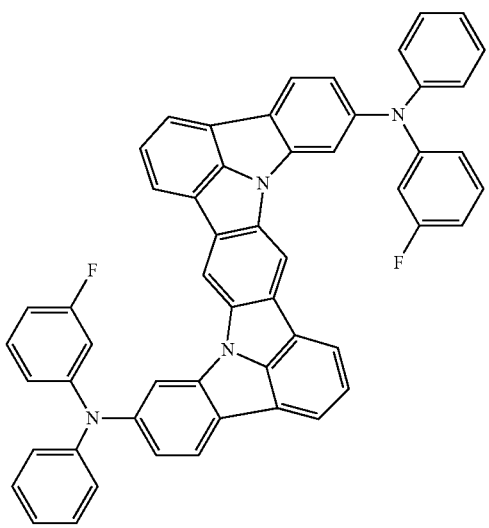
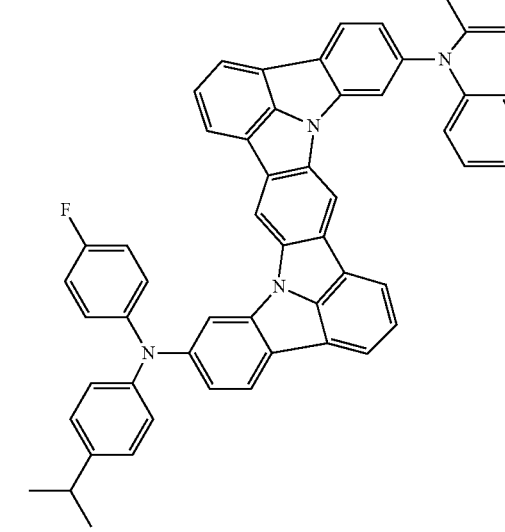
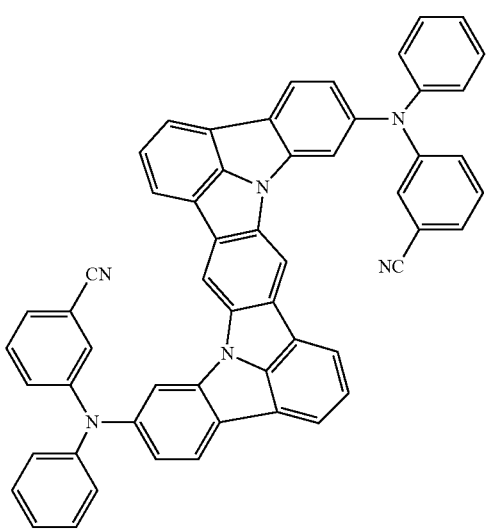

-continued
551
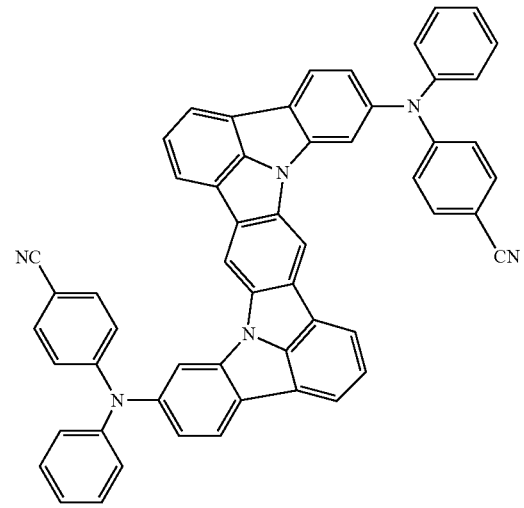
552
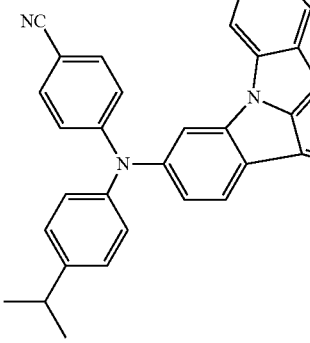
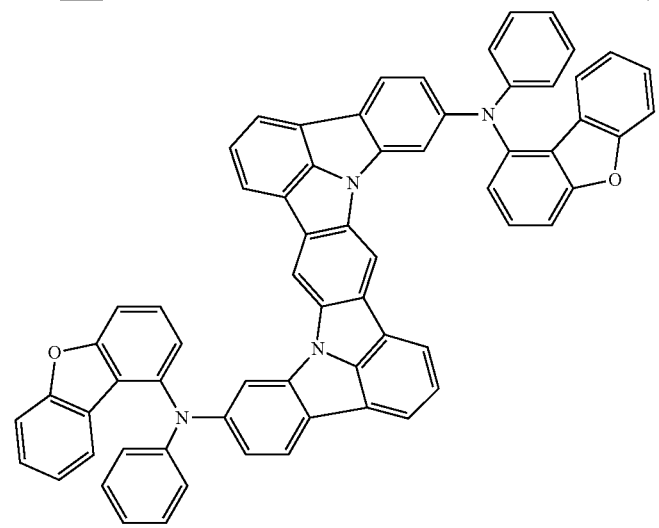
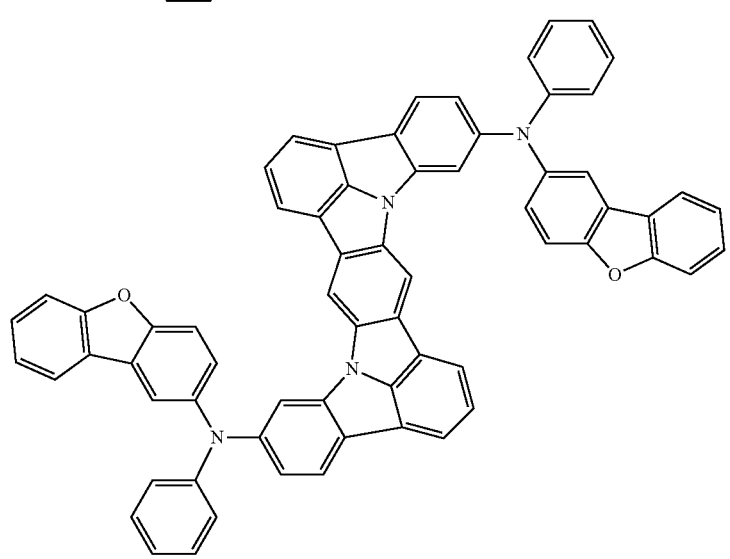

-continued
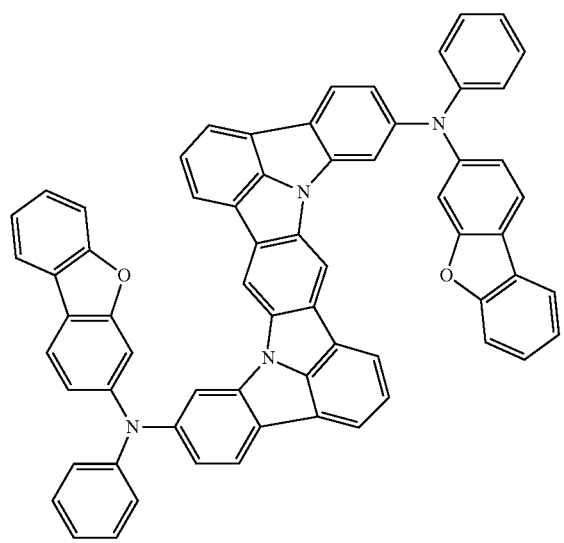
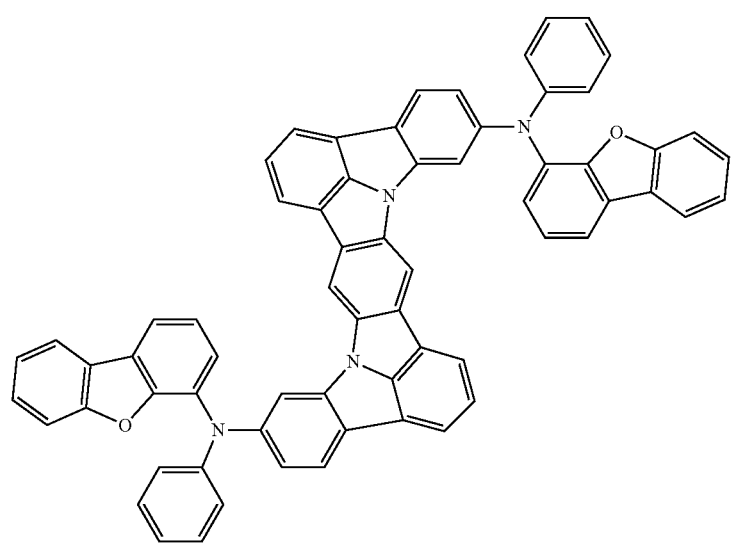
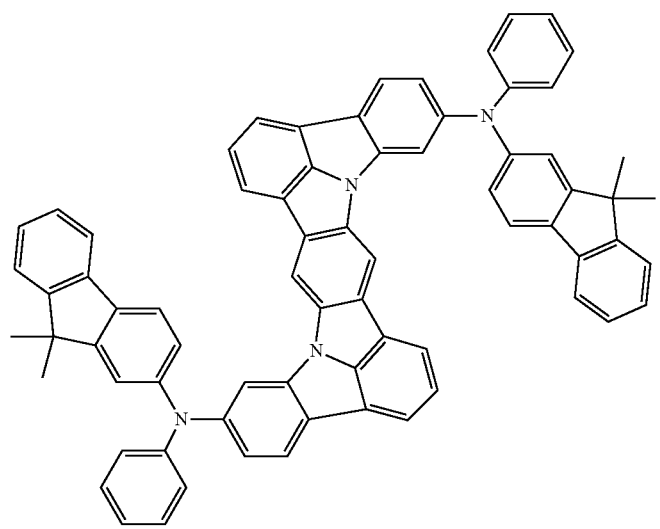

-continued
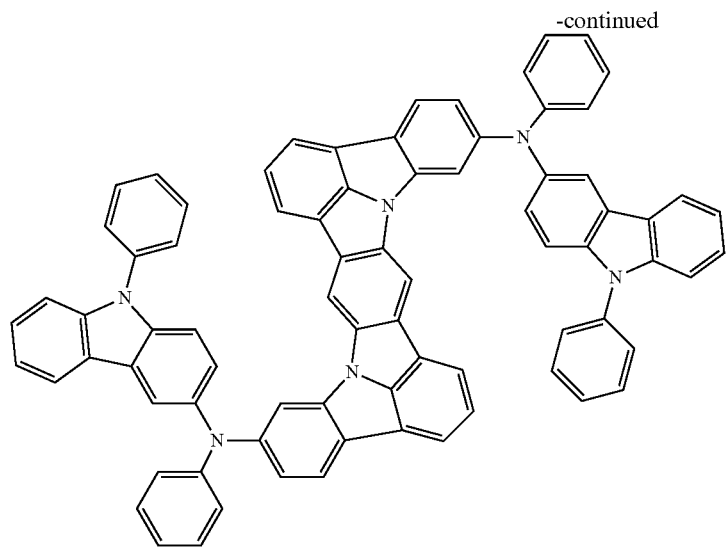
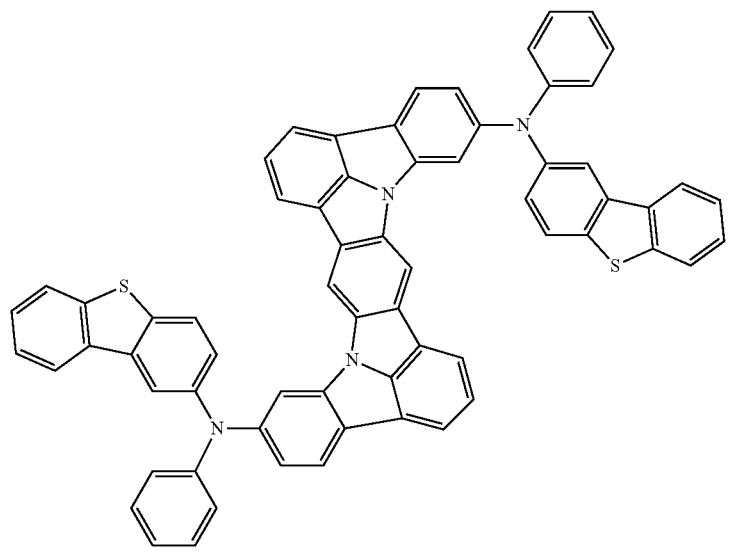
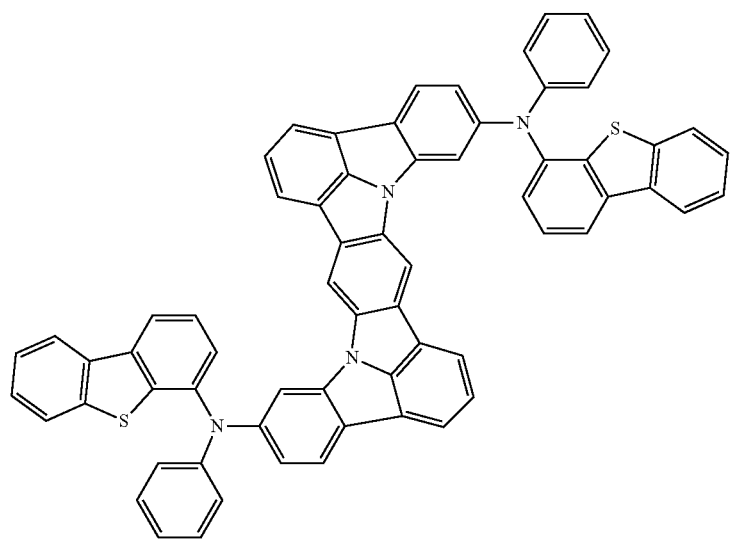

-continued
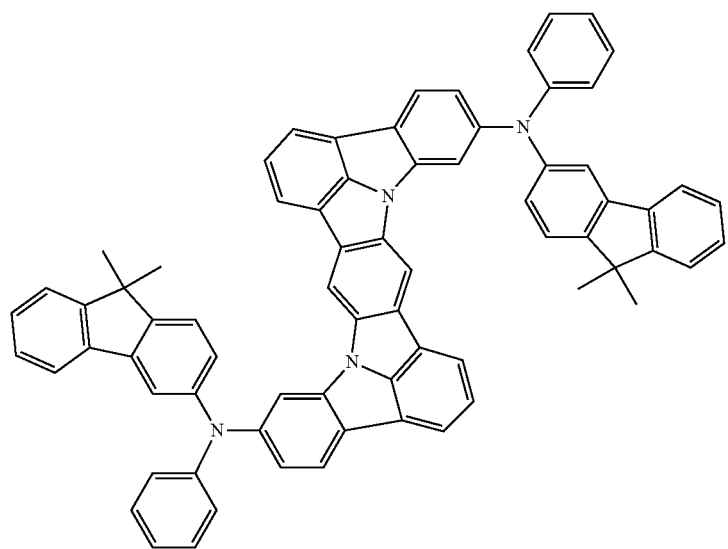
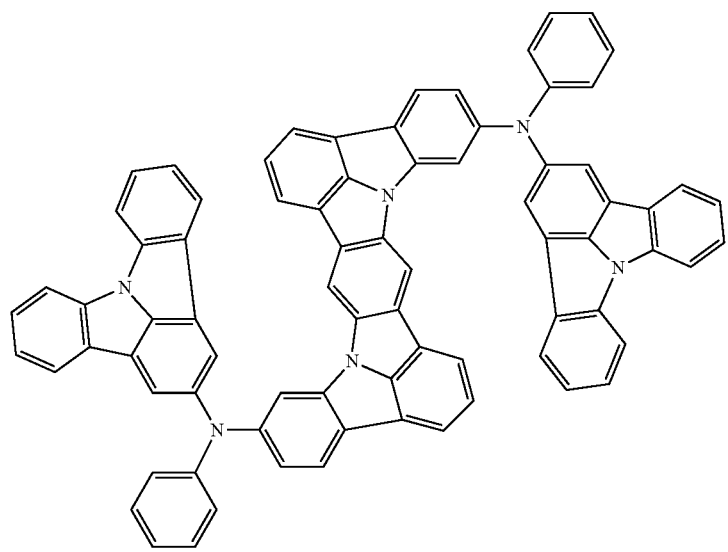
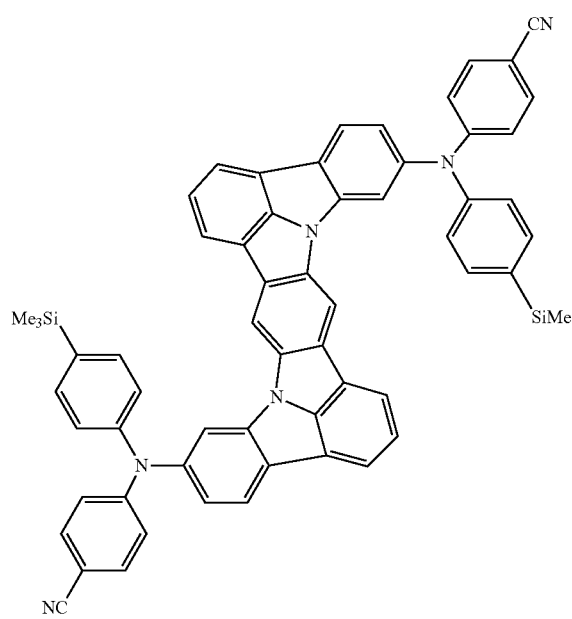

-continued
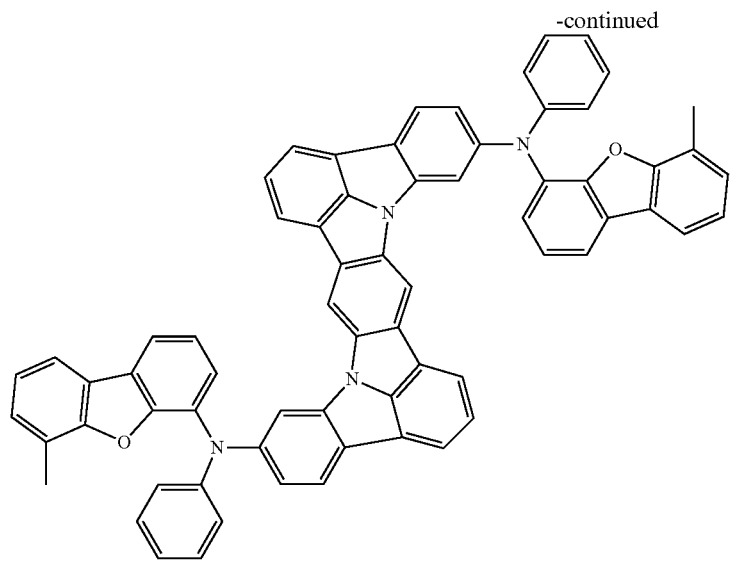
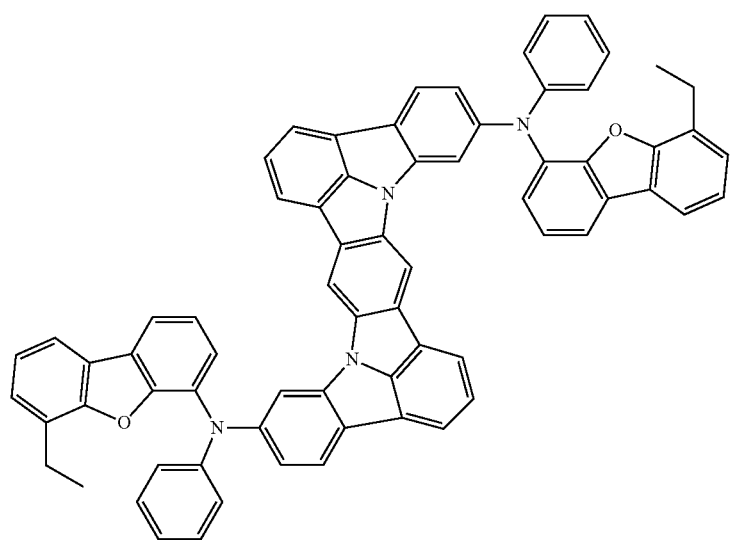
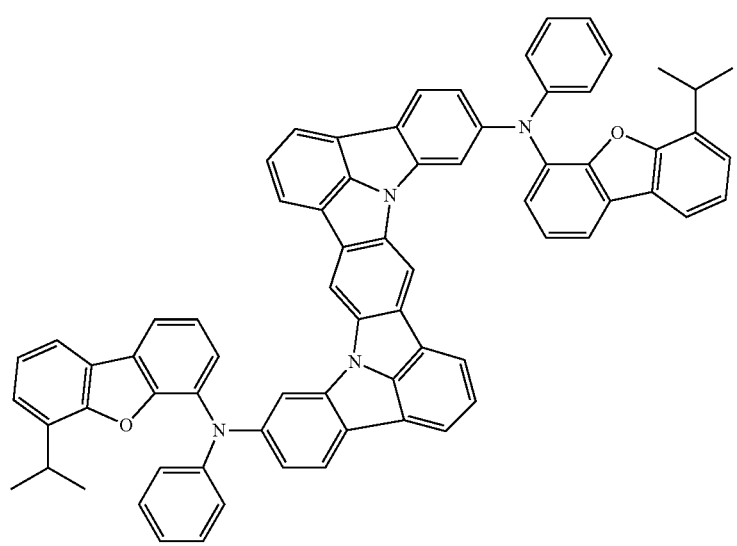

-continued
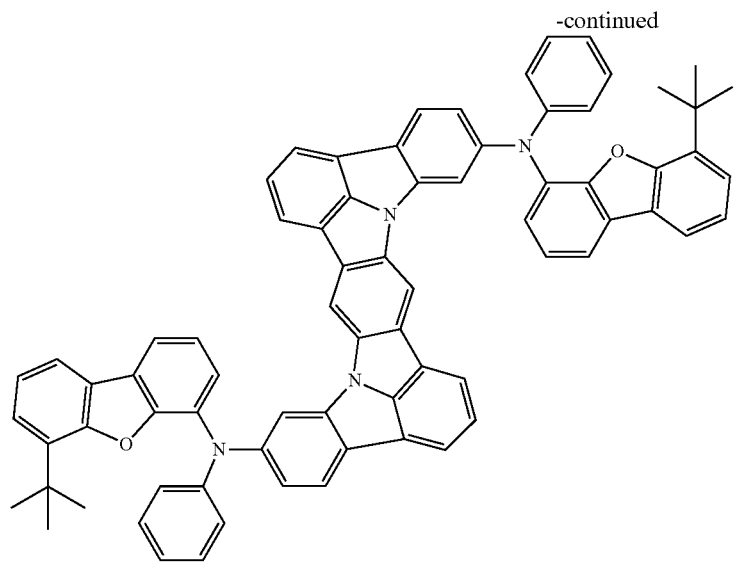
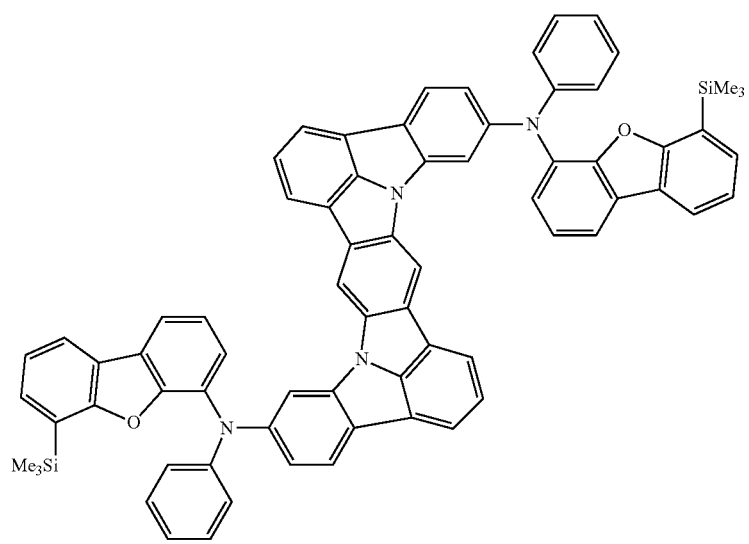
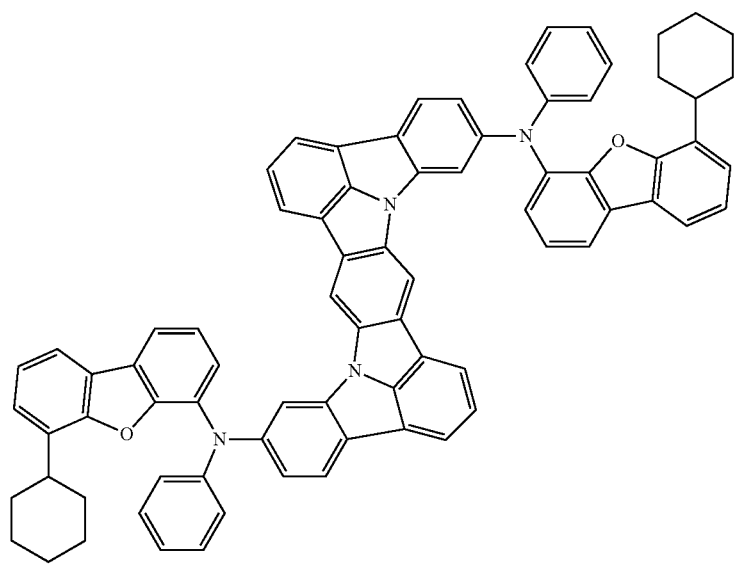

-continued
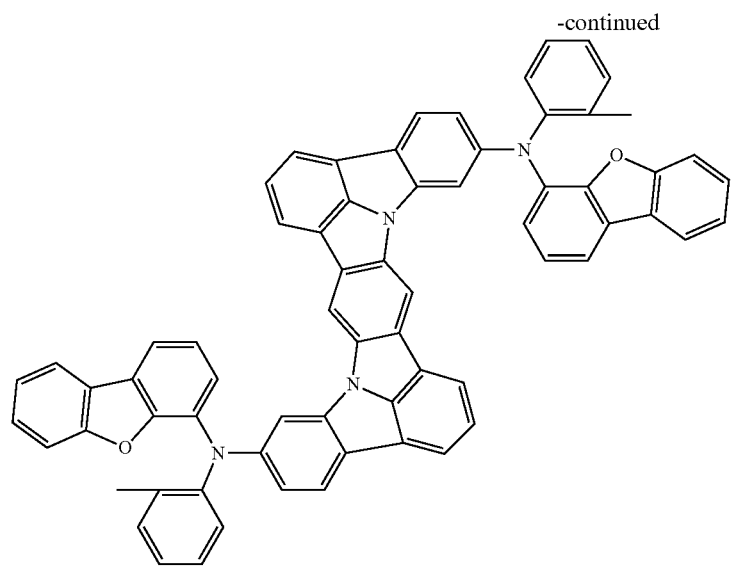
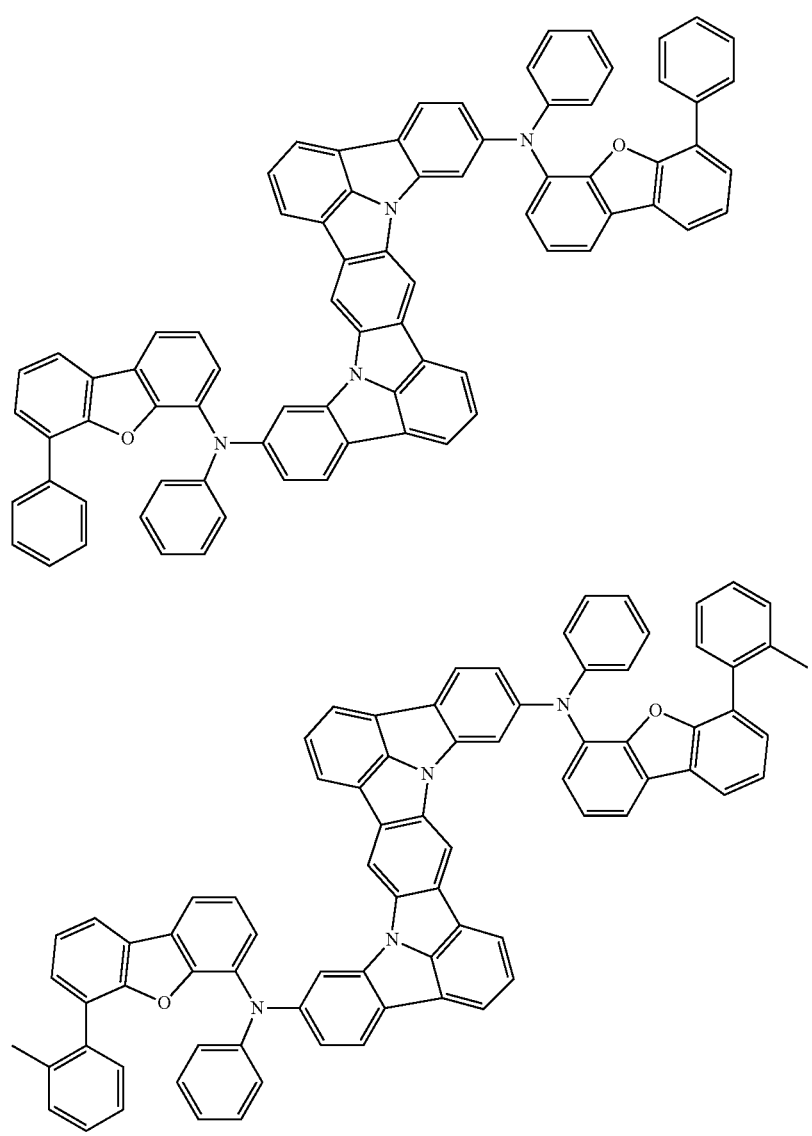

-continued
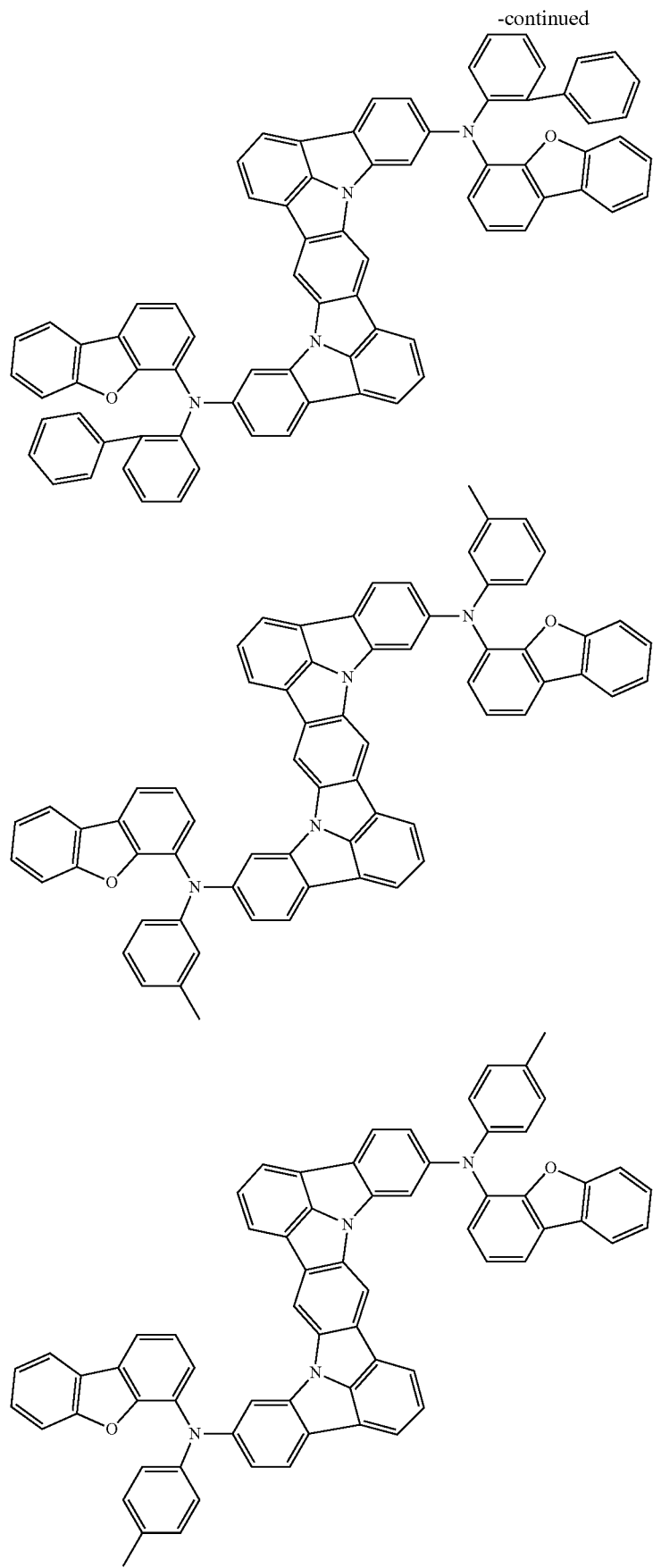

-continued
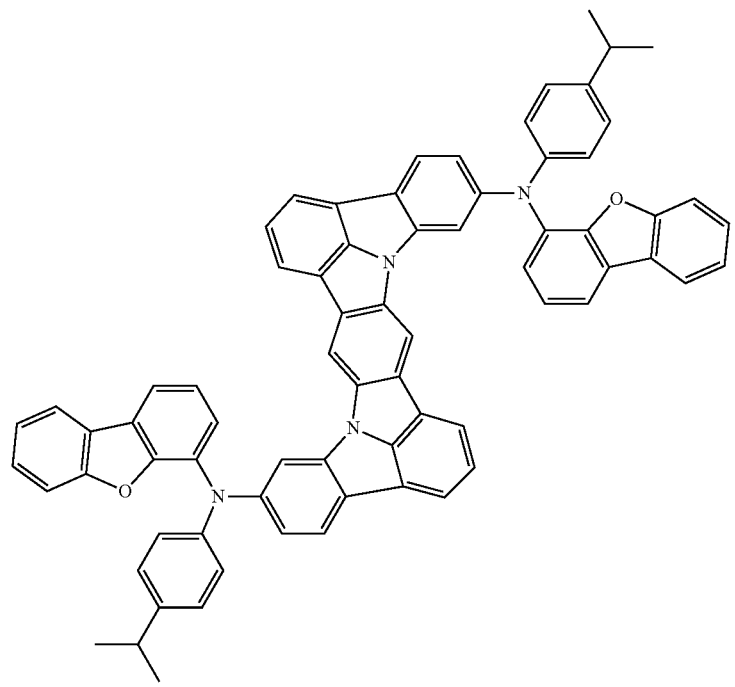
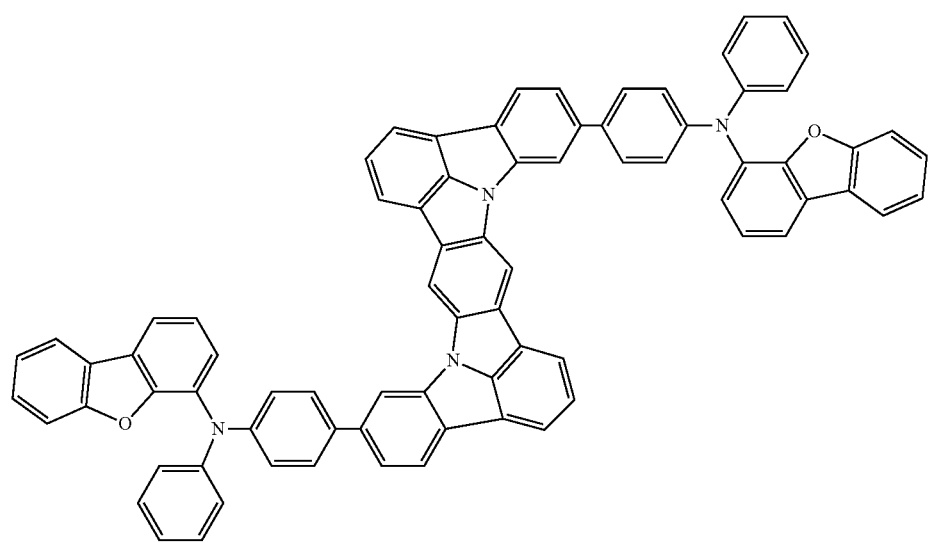

-continued
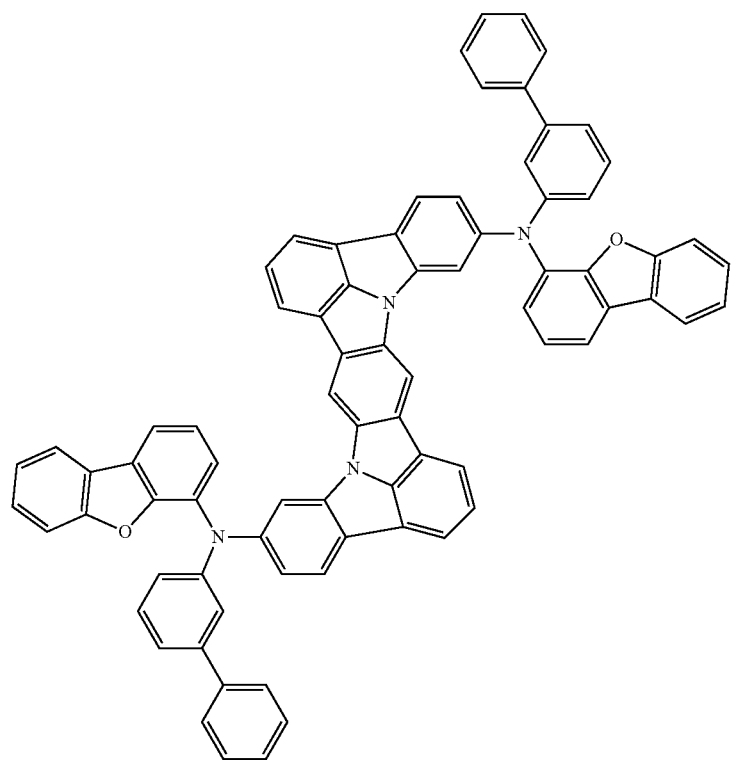
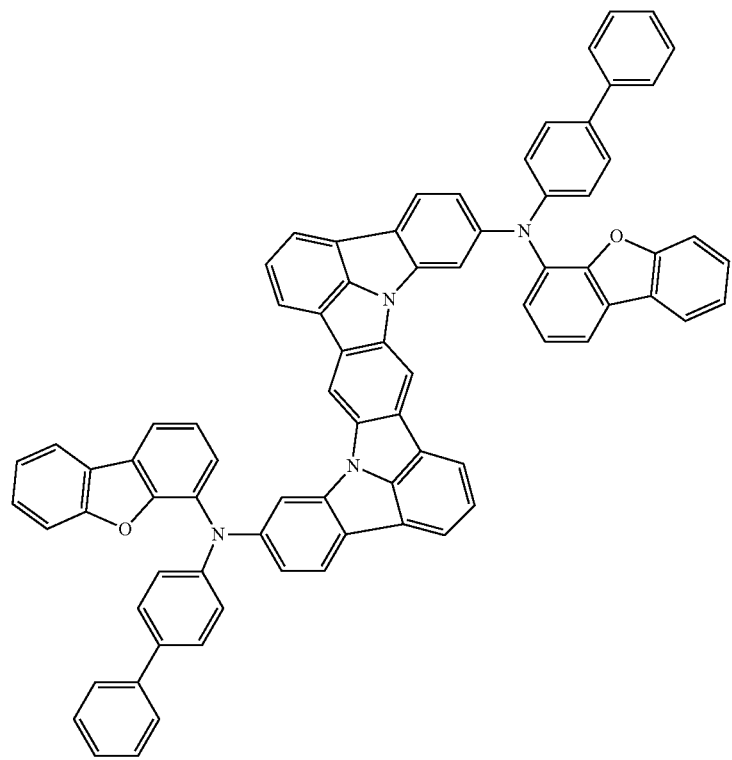

-continued
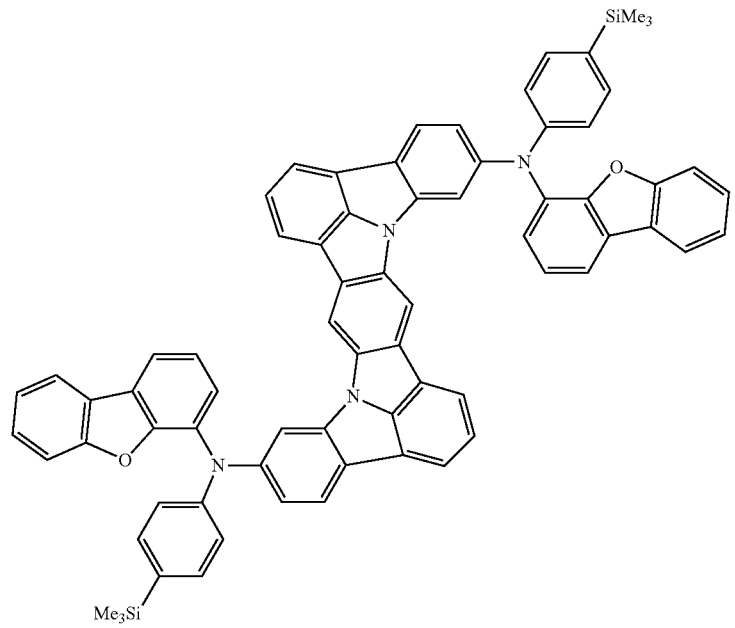
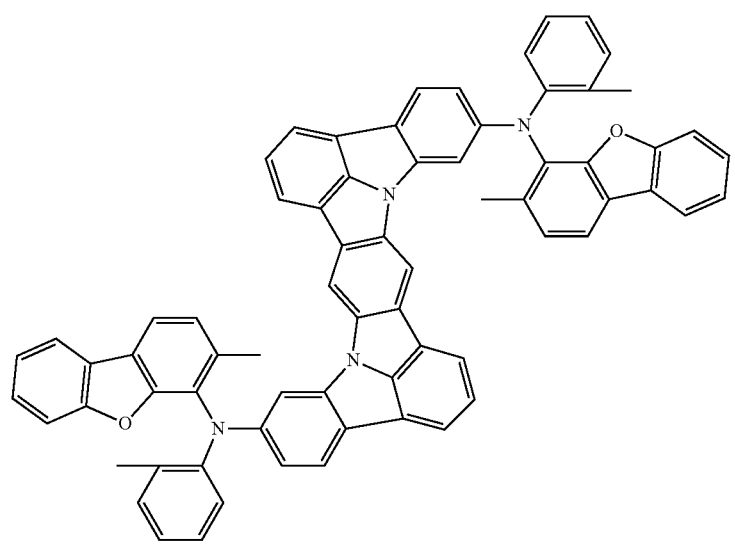
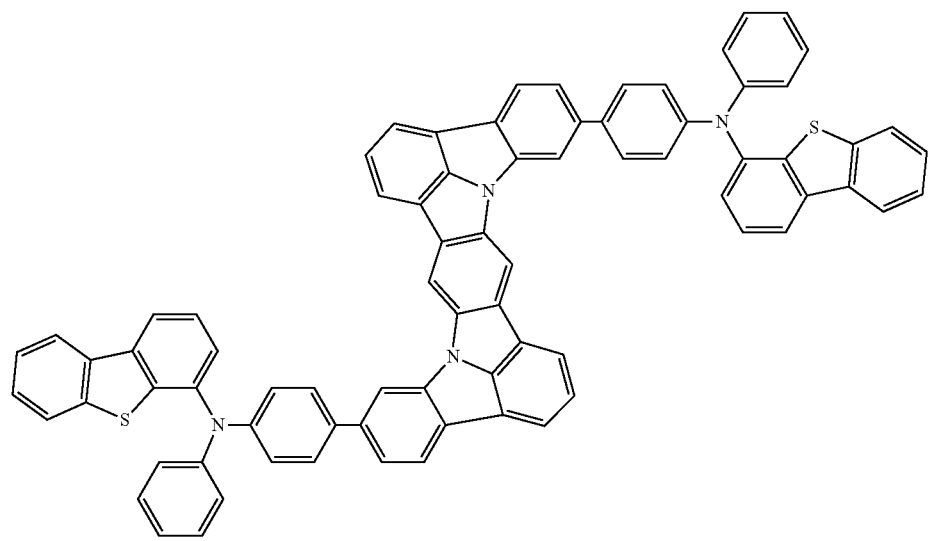

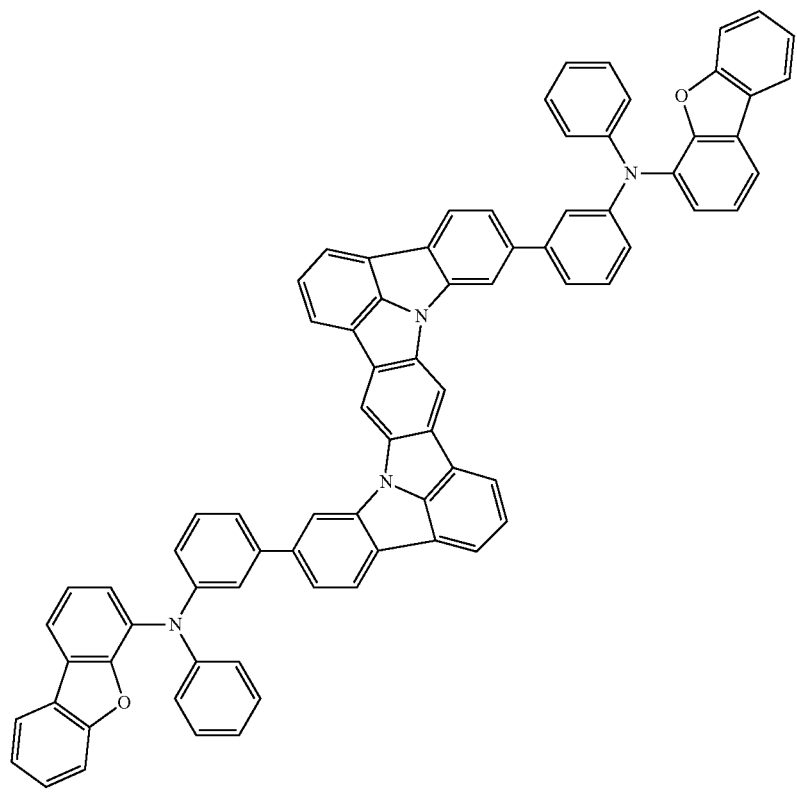
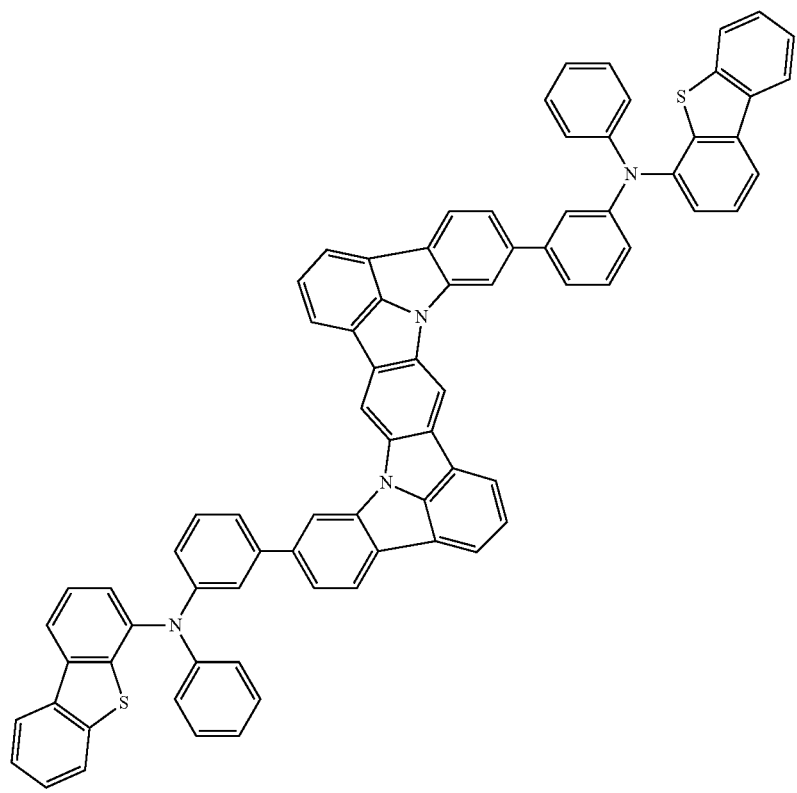

-continued
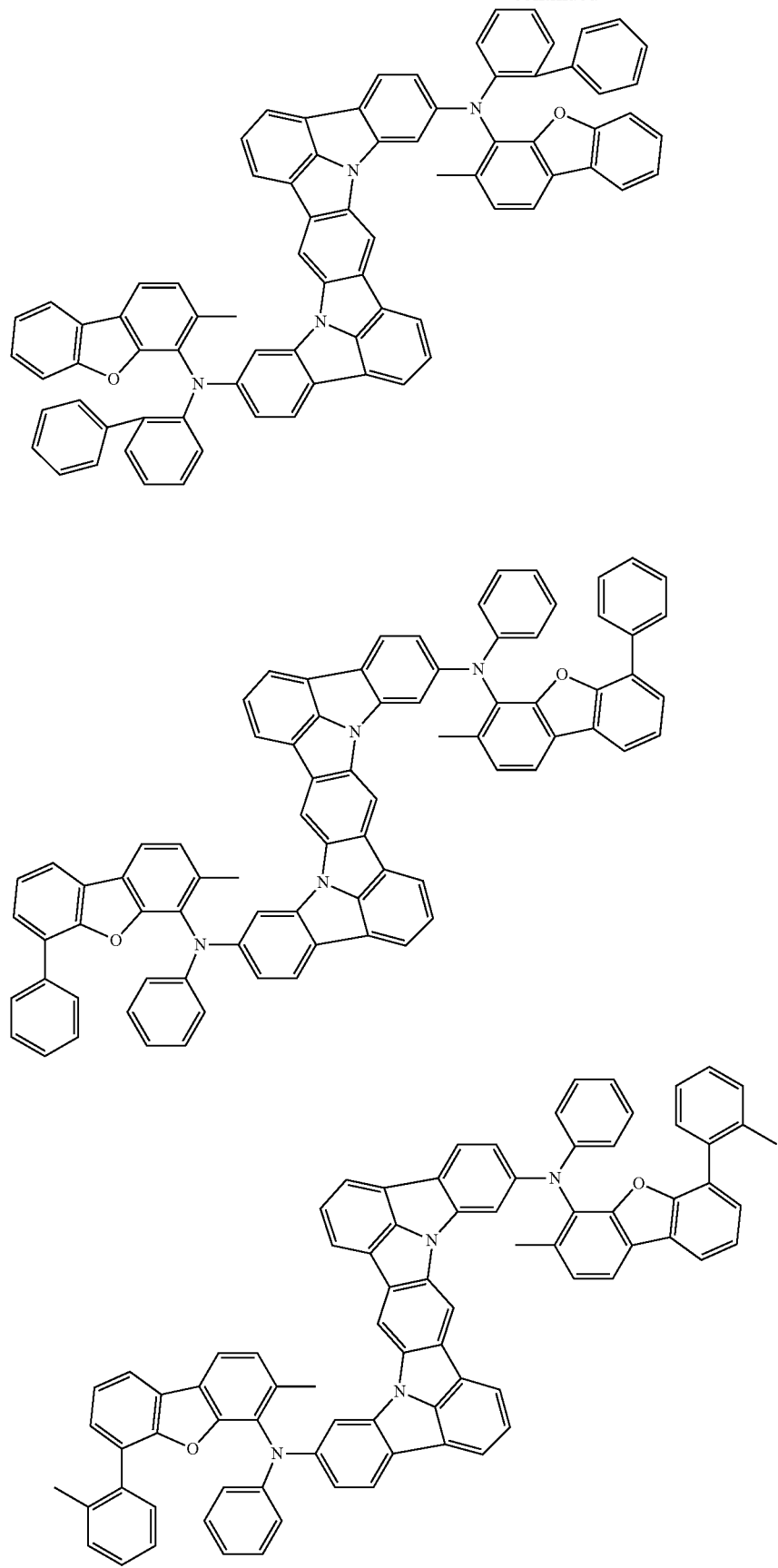

-continued
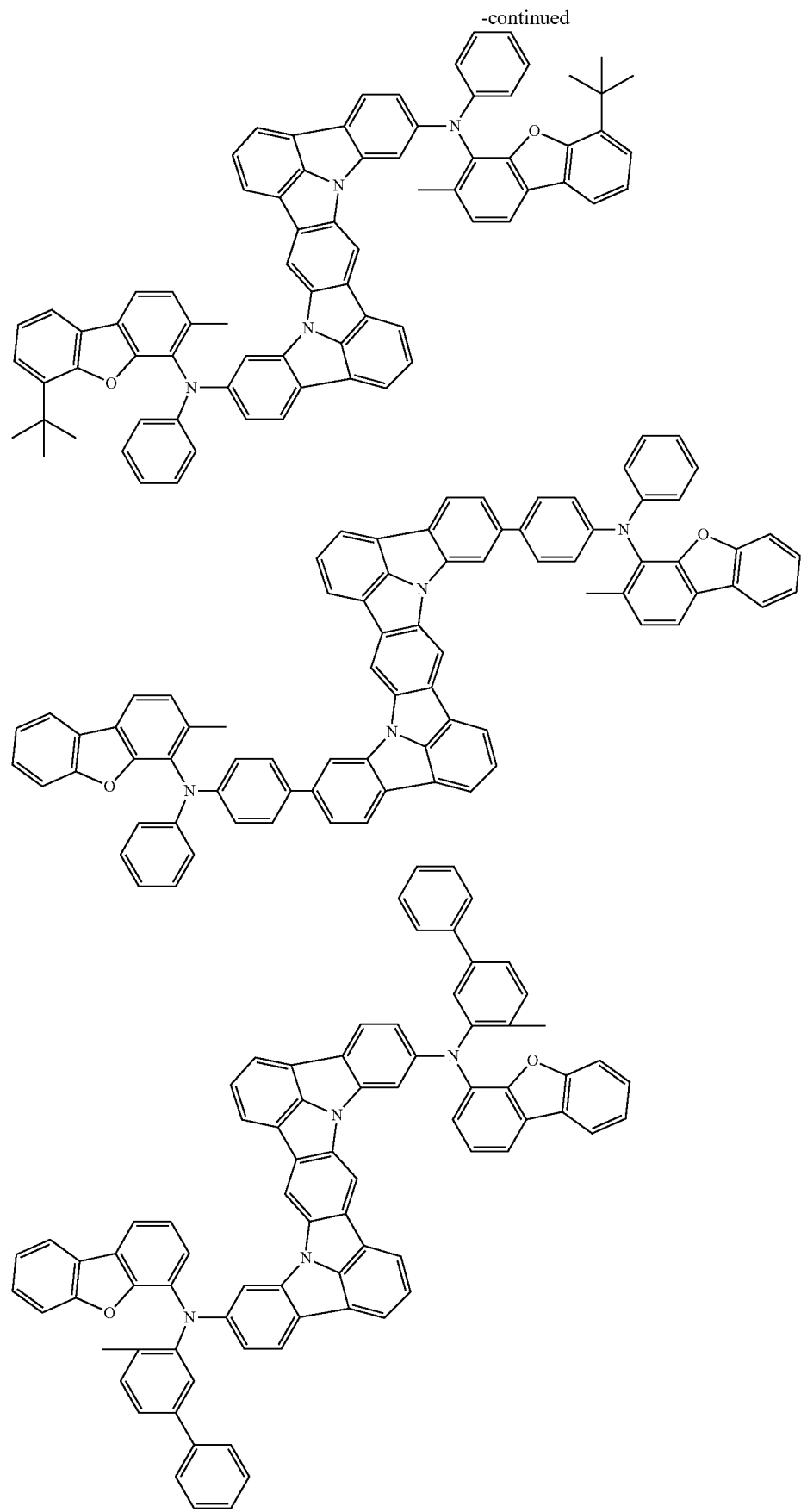

-continued
581
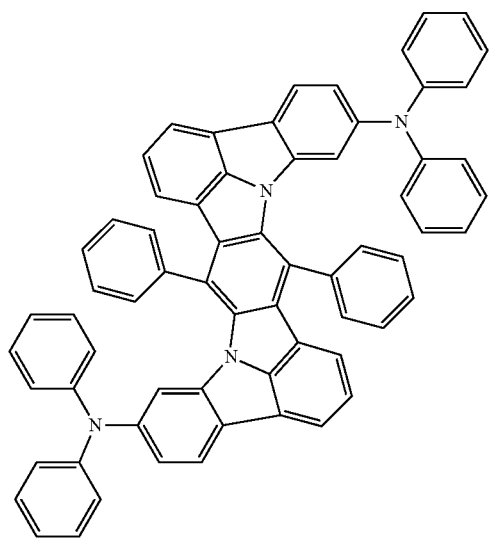
582
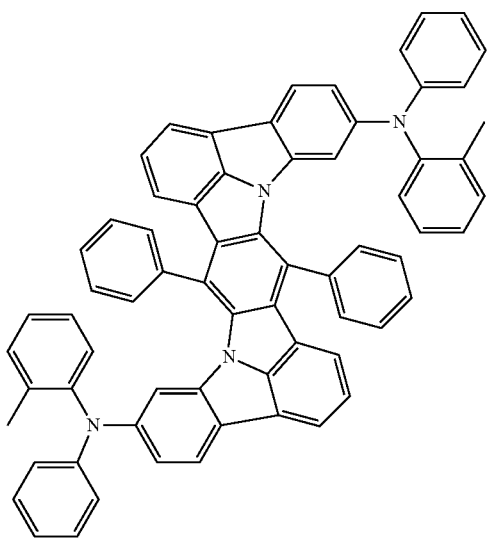
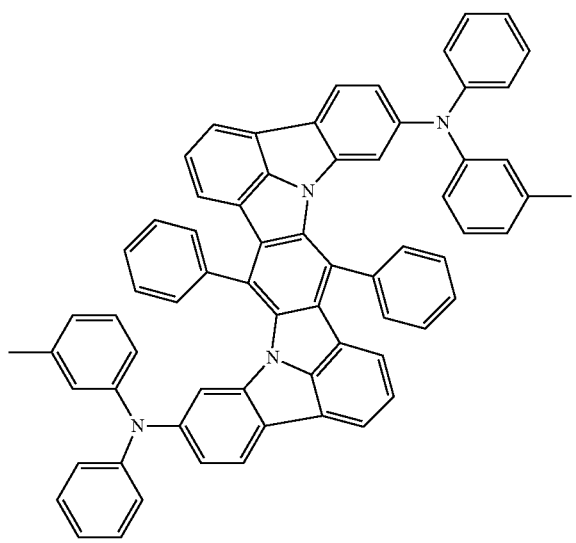
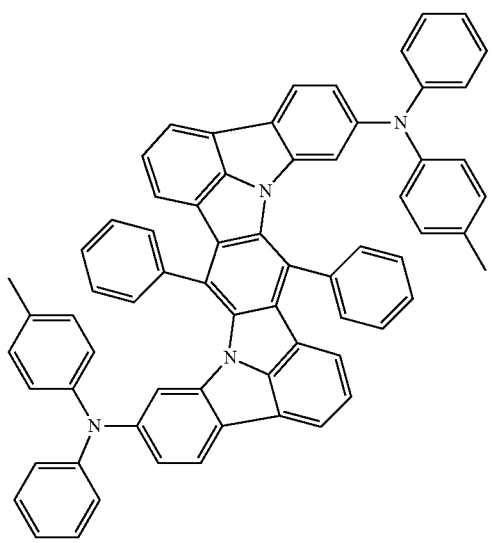
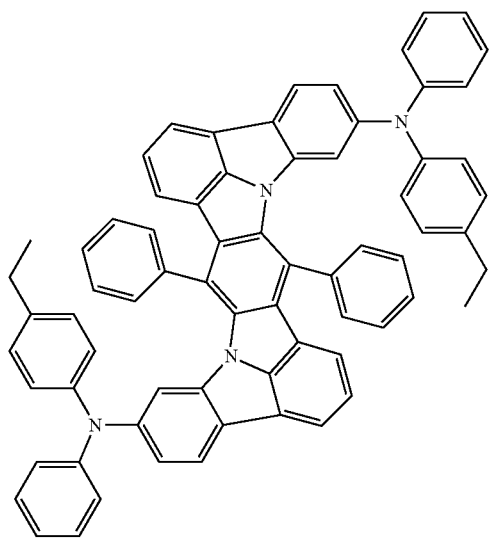
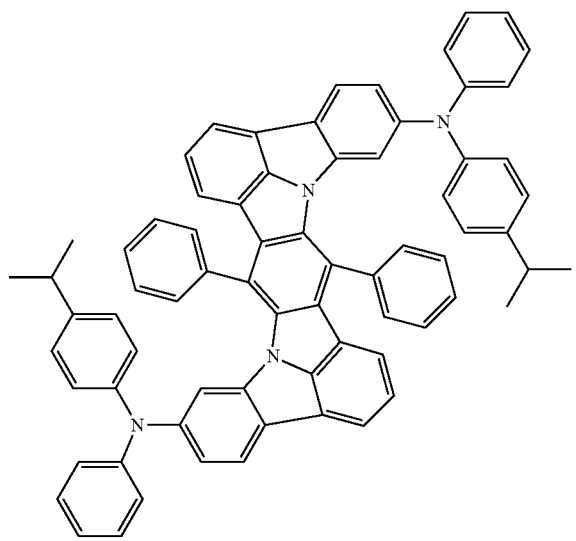

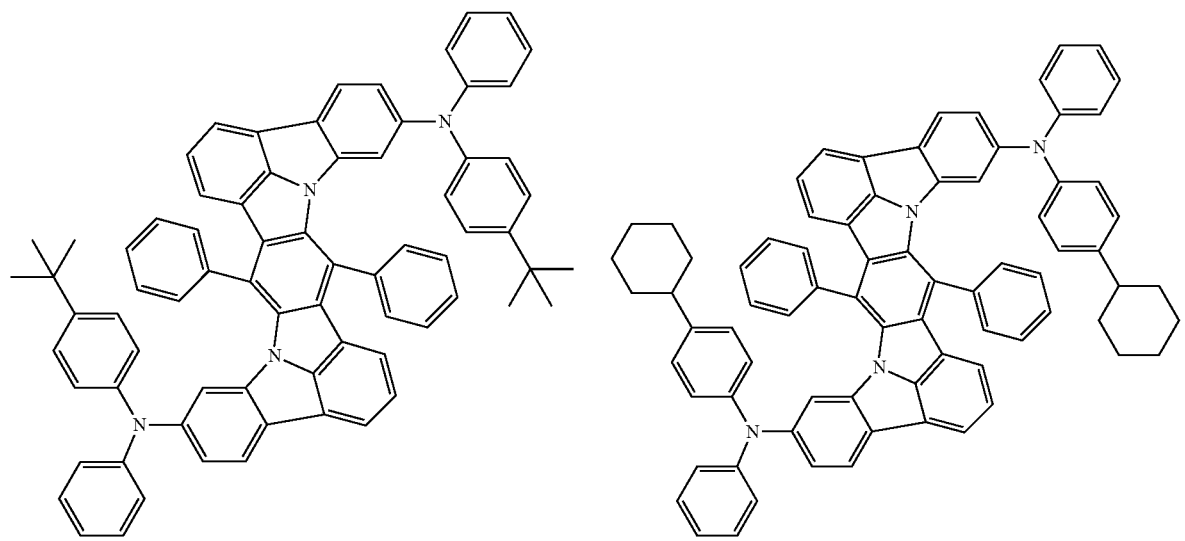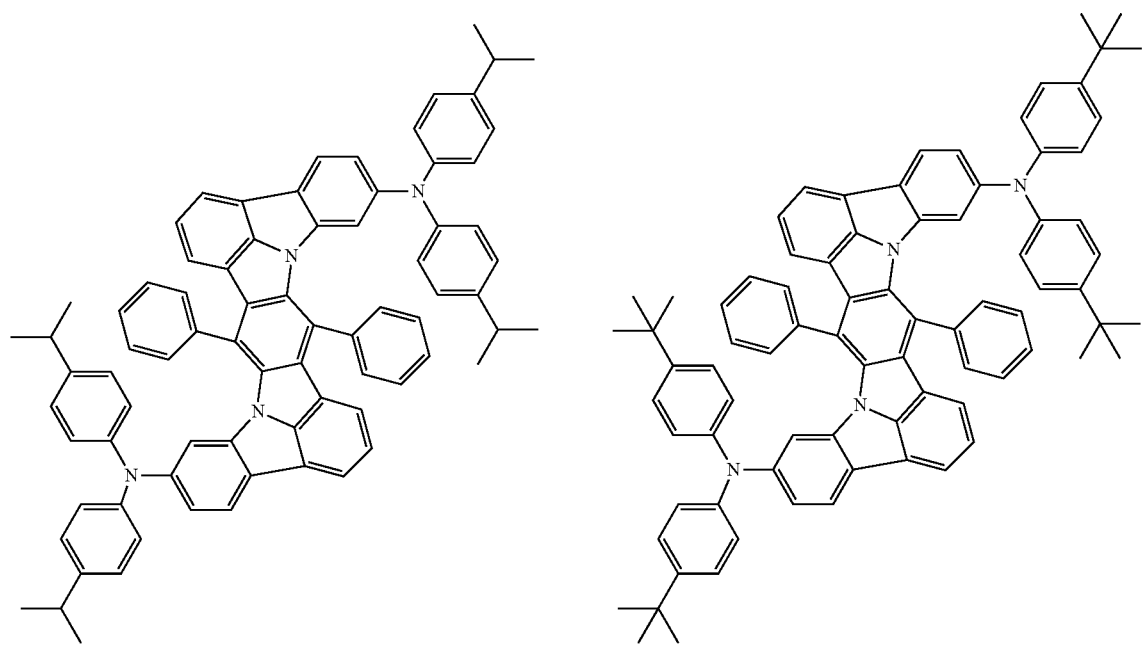

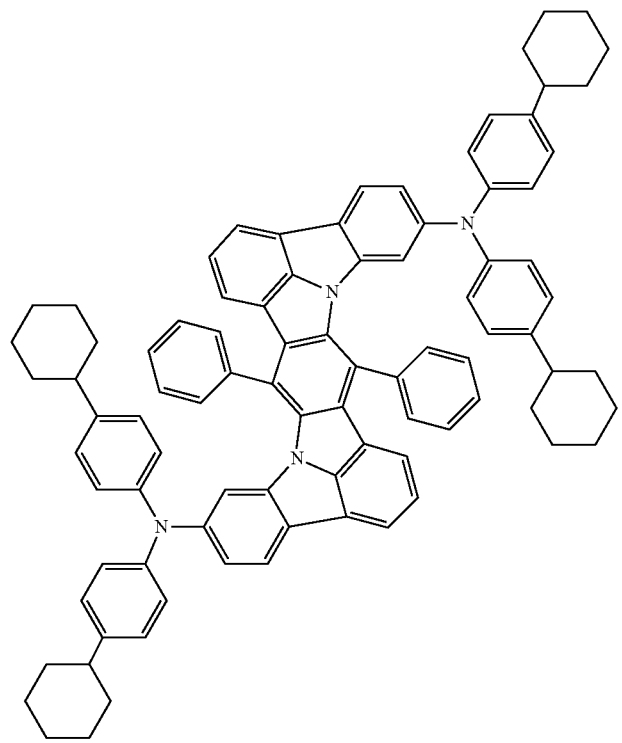
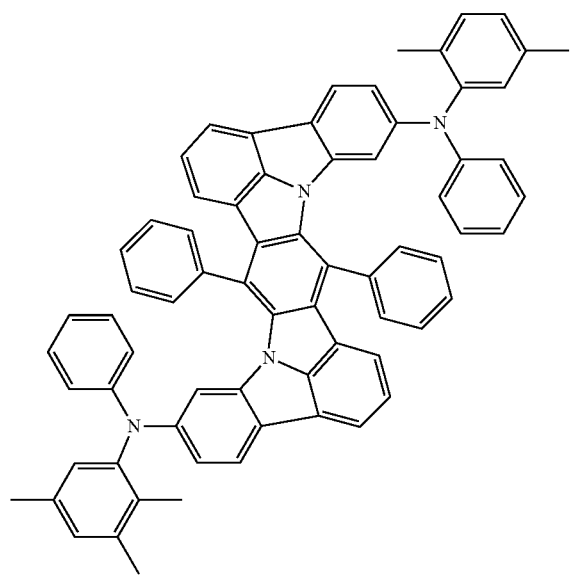
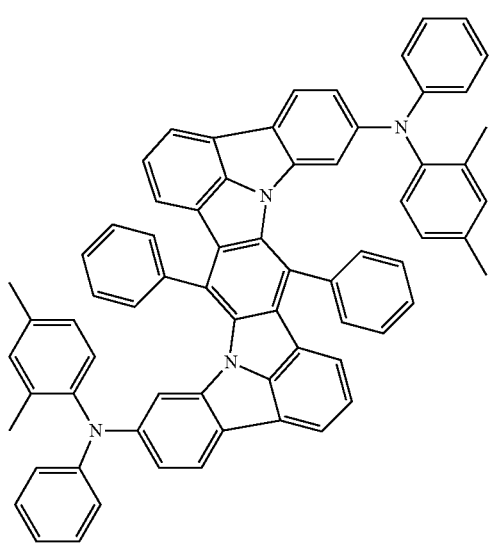

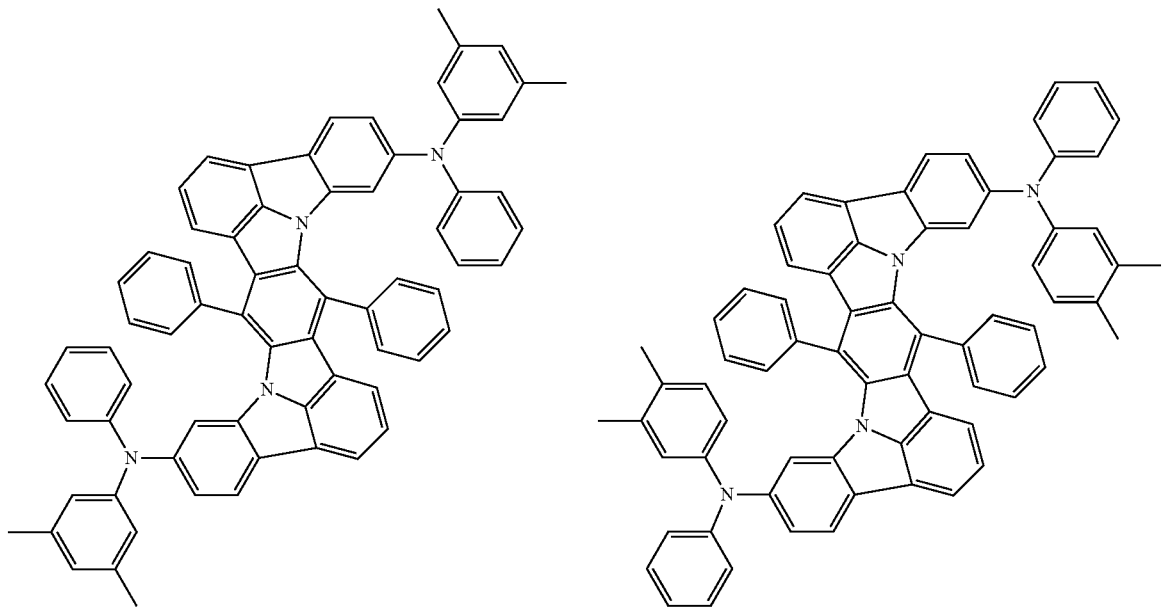
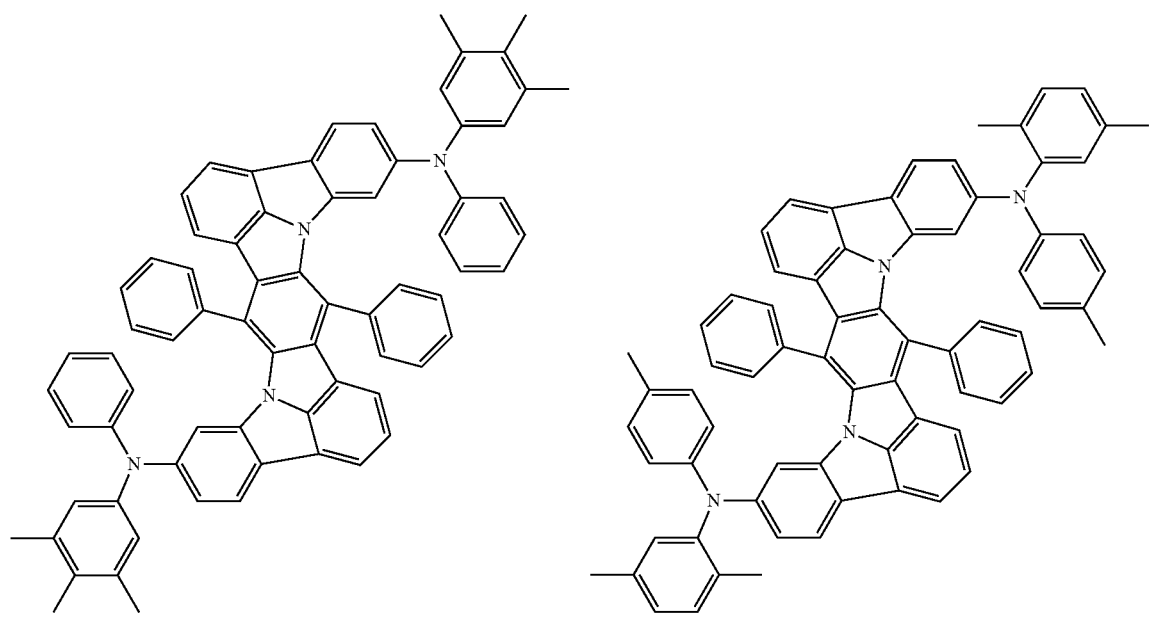

-continued
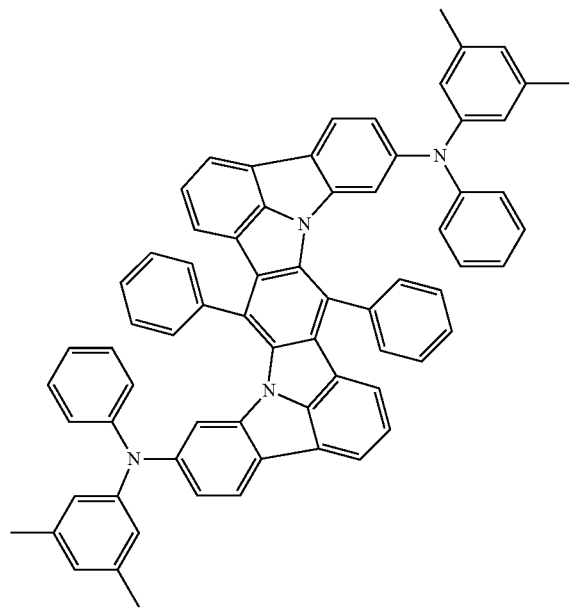
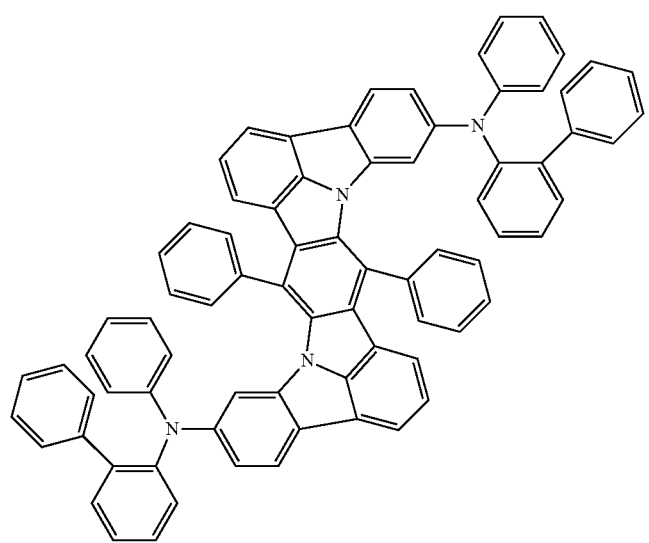
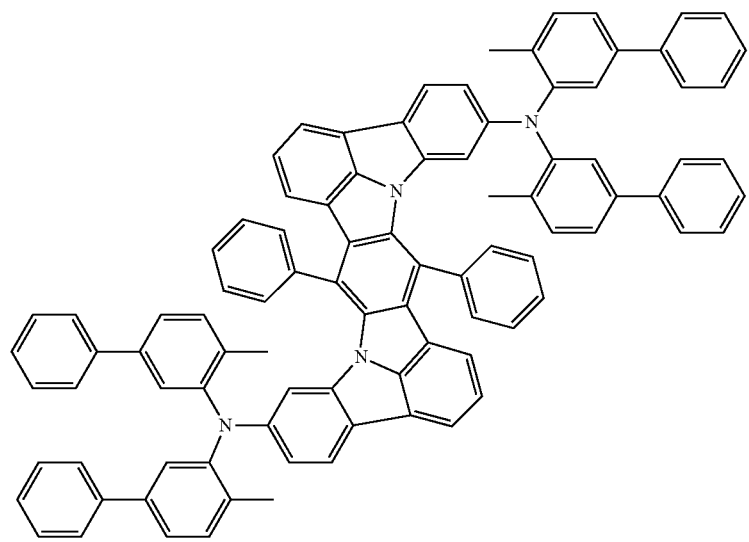

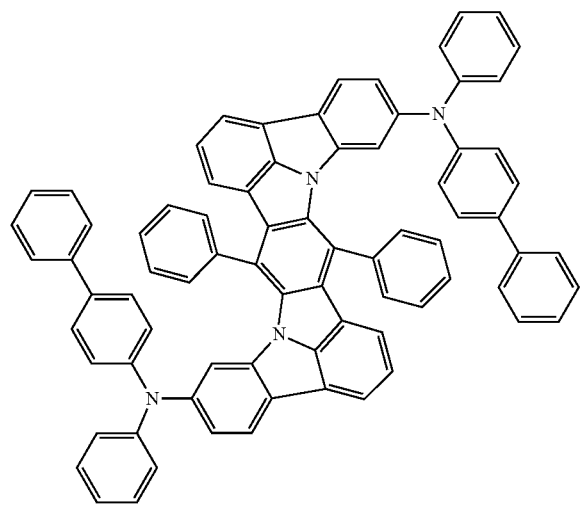
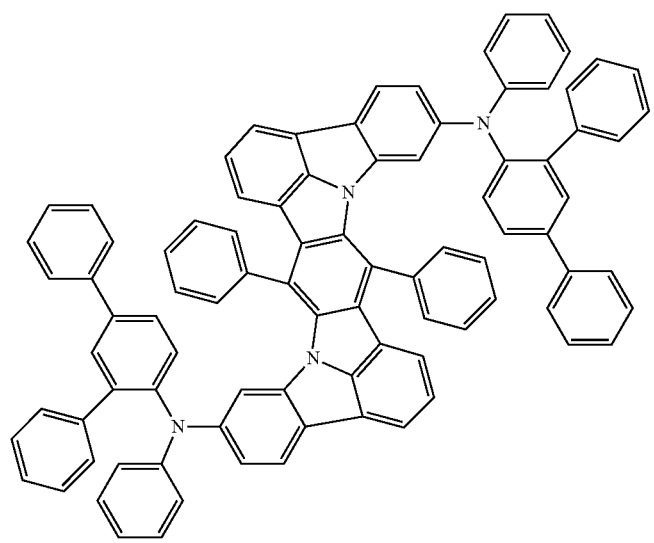
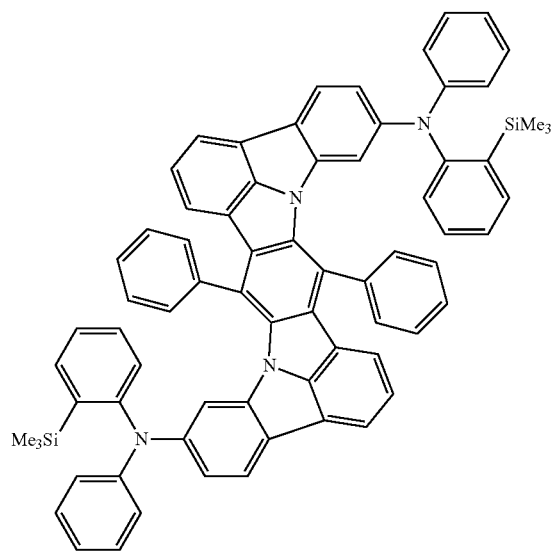

-continued
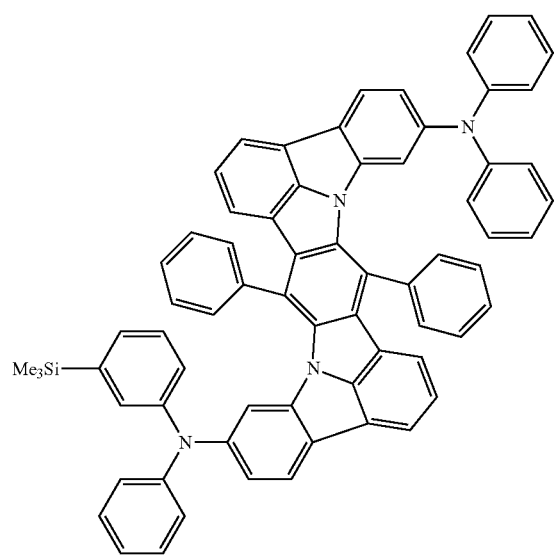

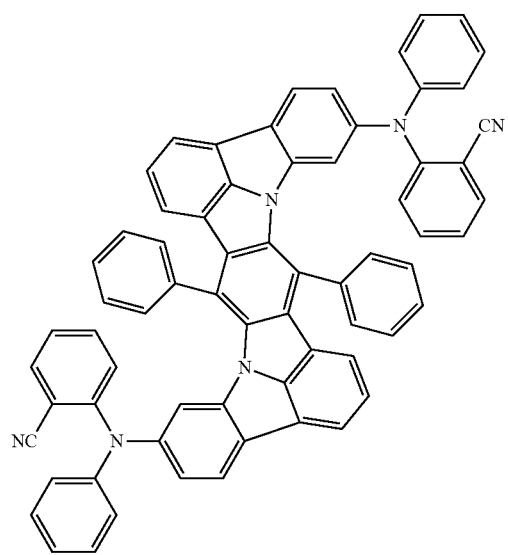

-continued
595 596
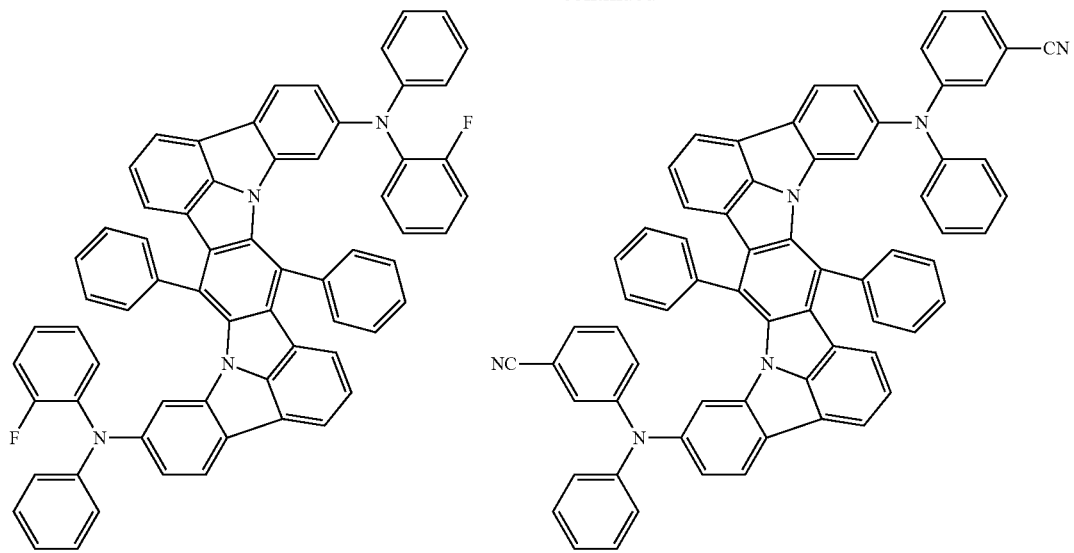
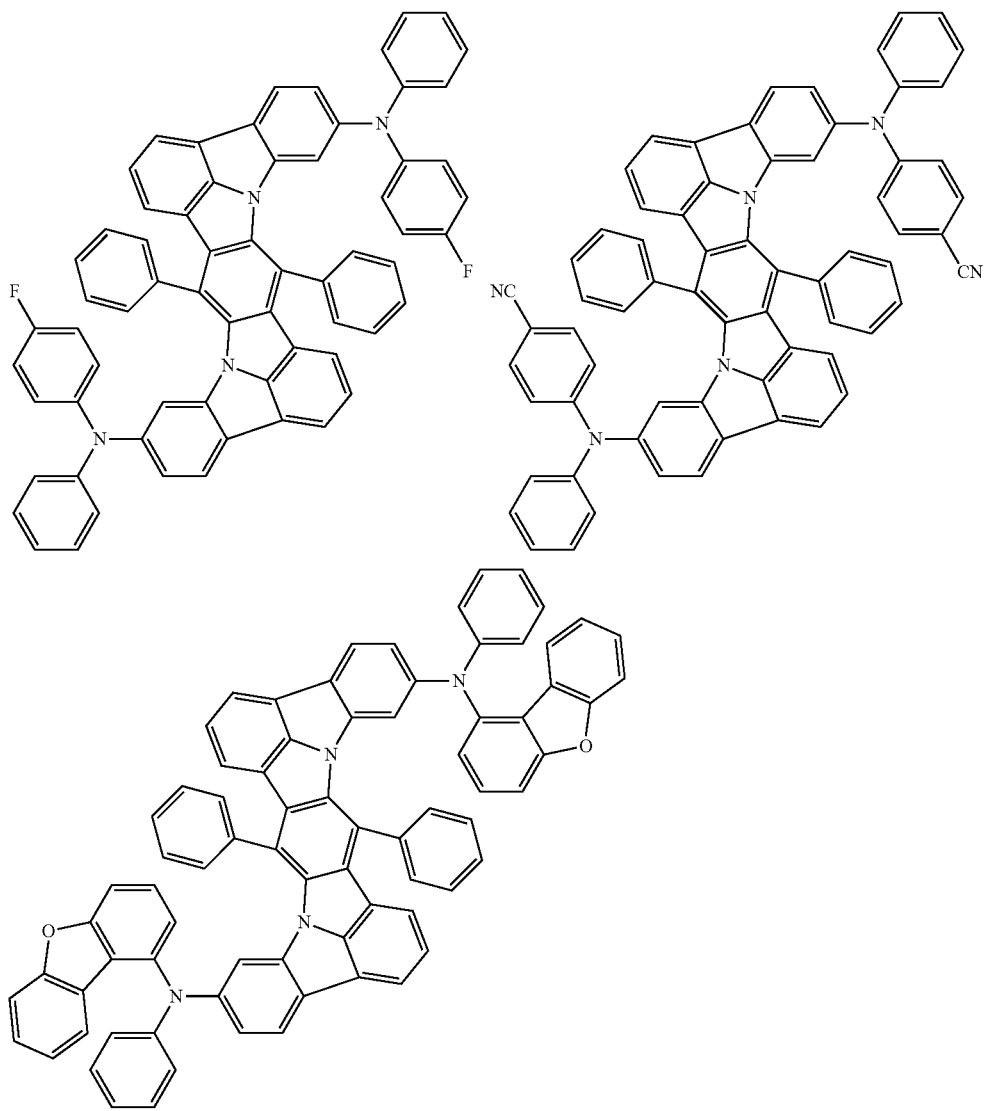

-continued
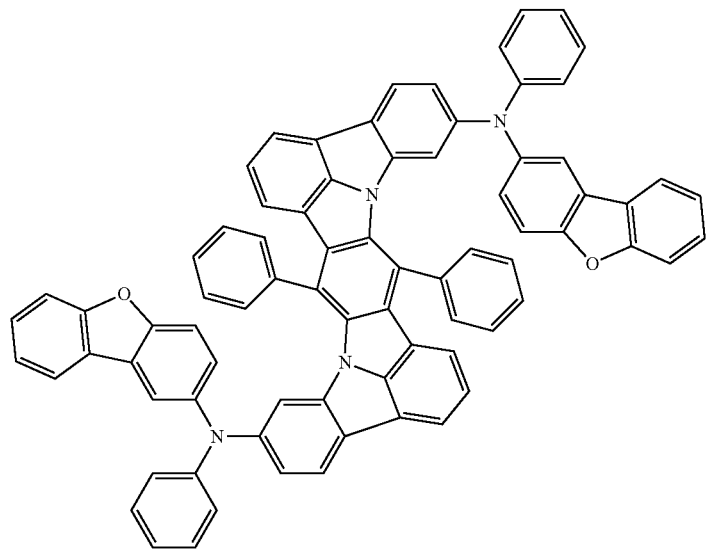
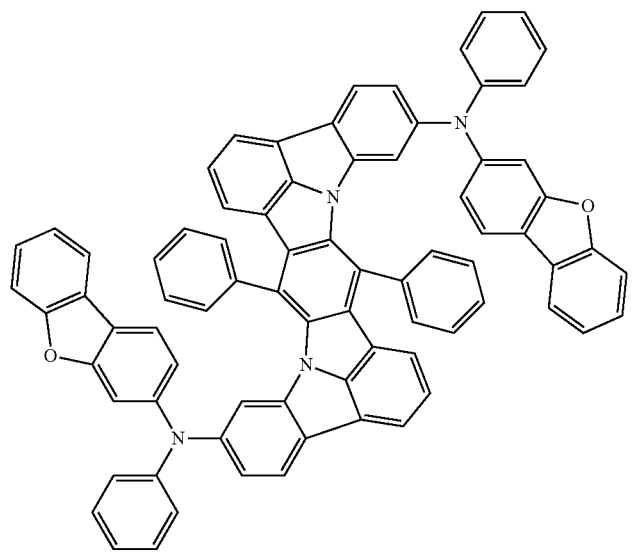
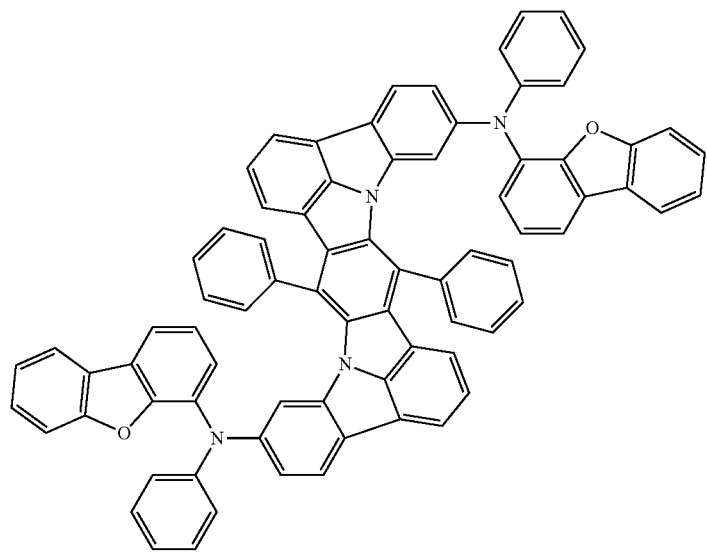

-continued
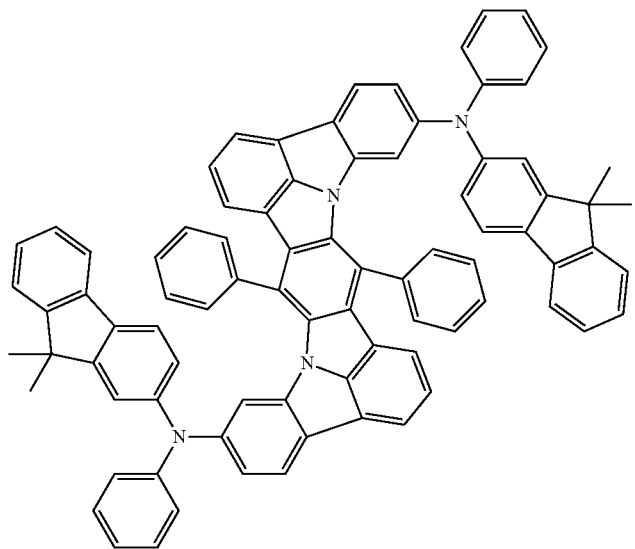
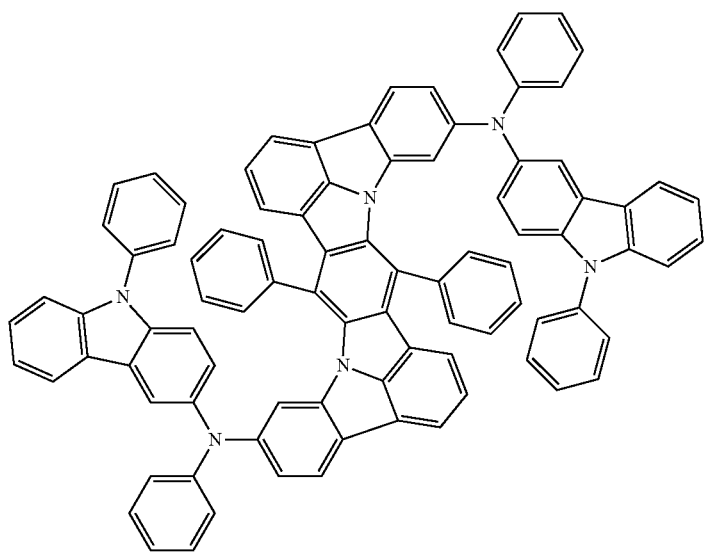
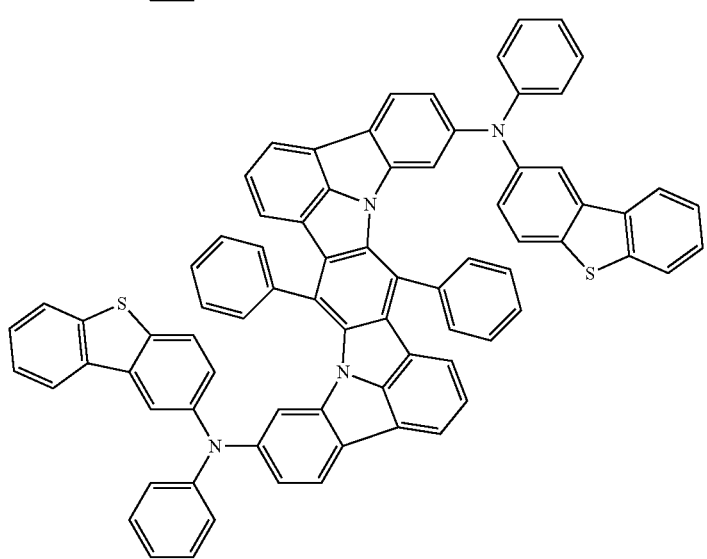

-continued
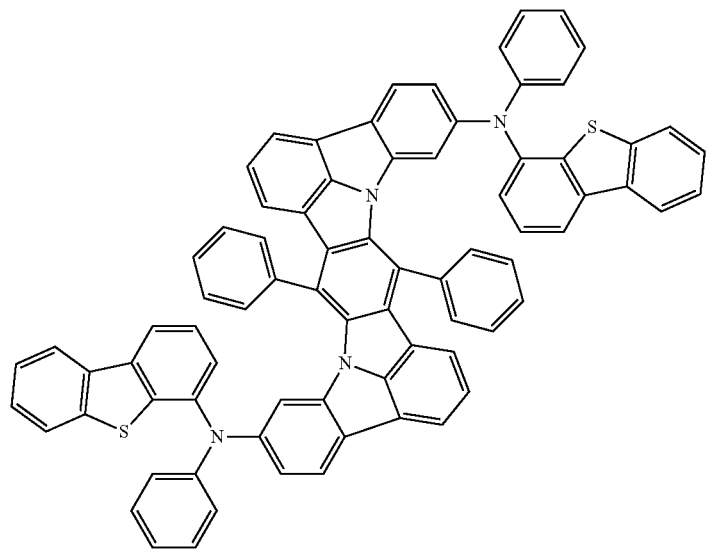
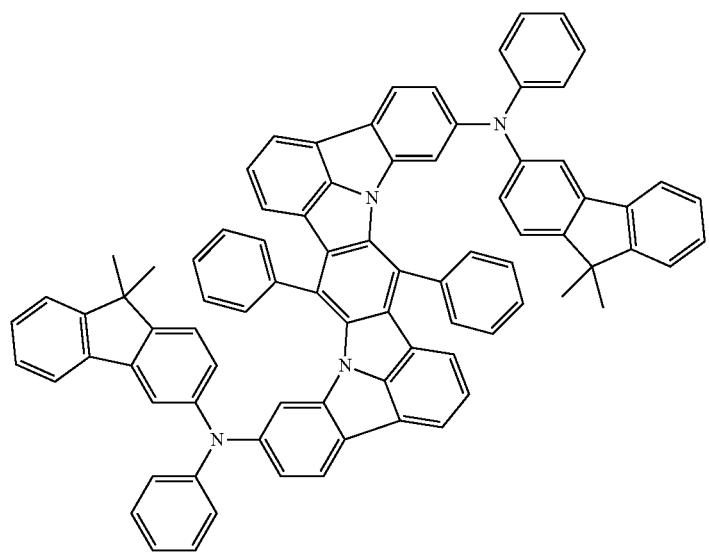
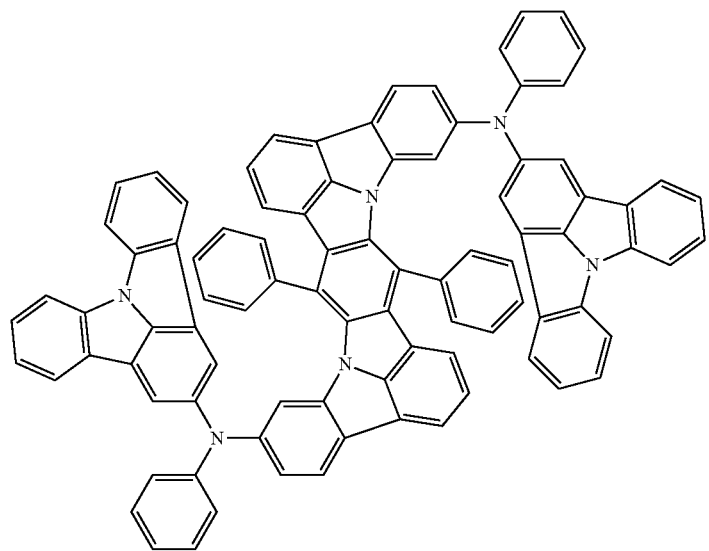

-continued
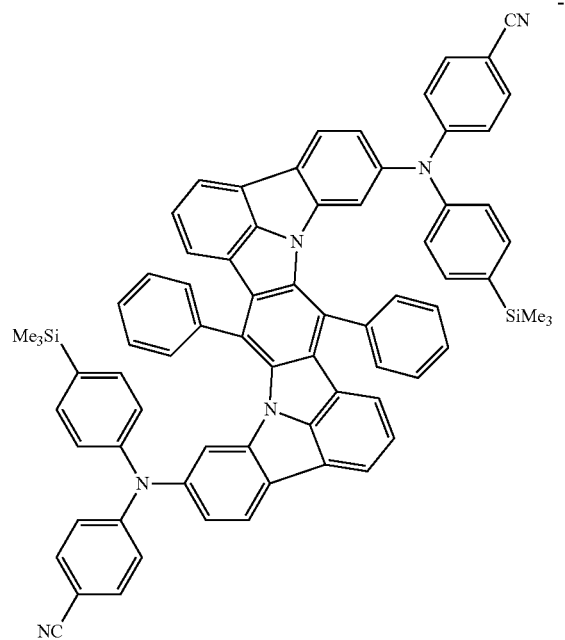
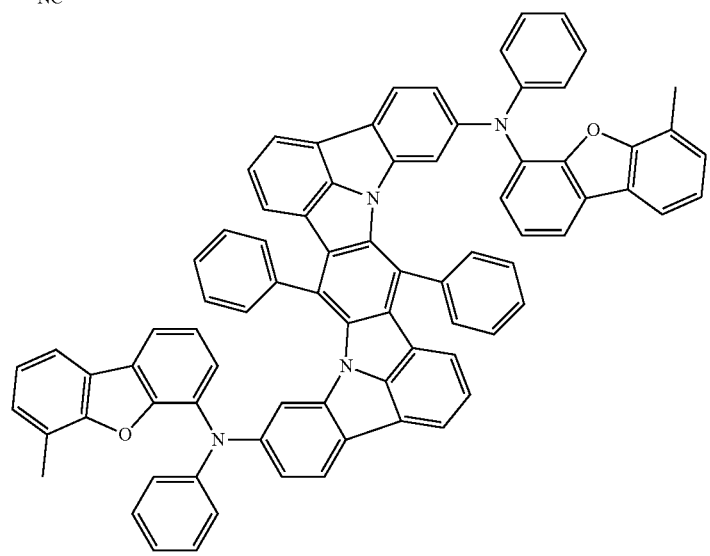
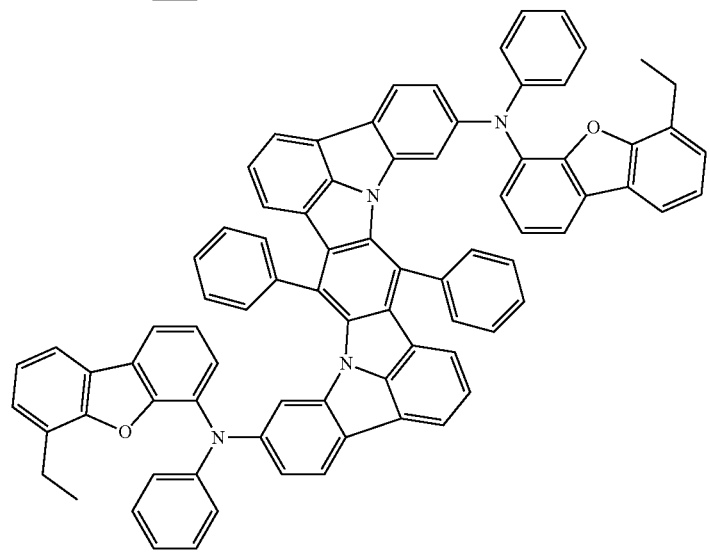

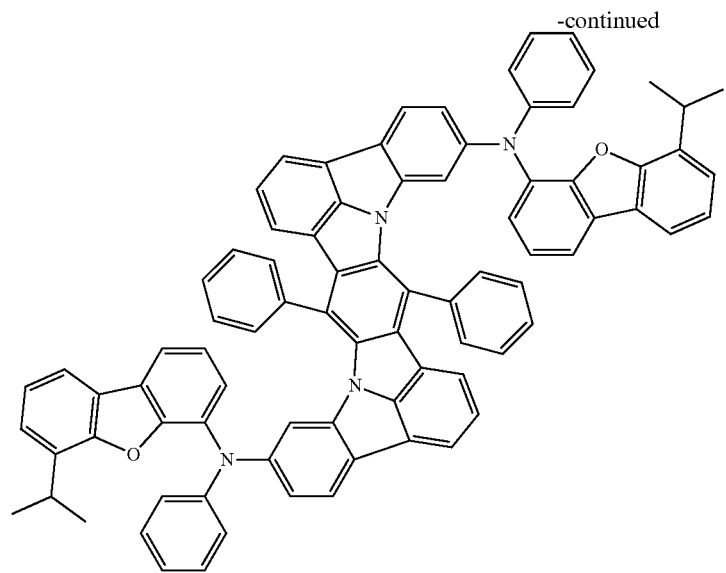
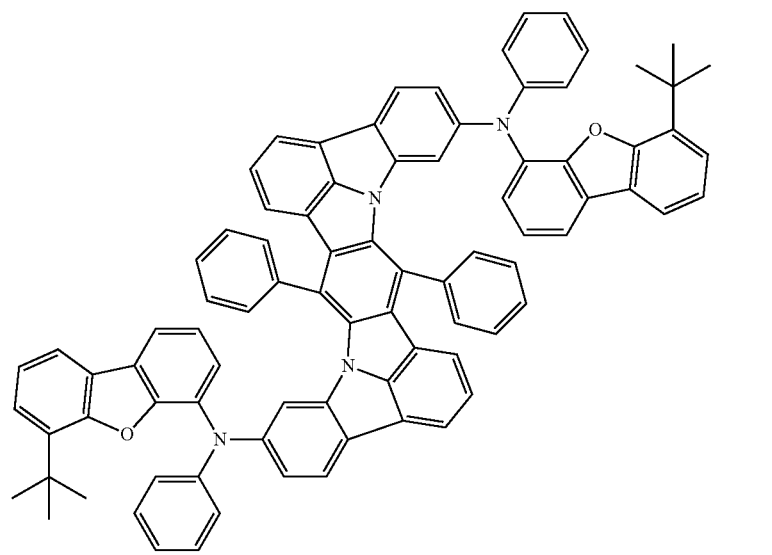
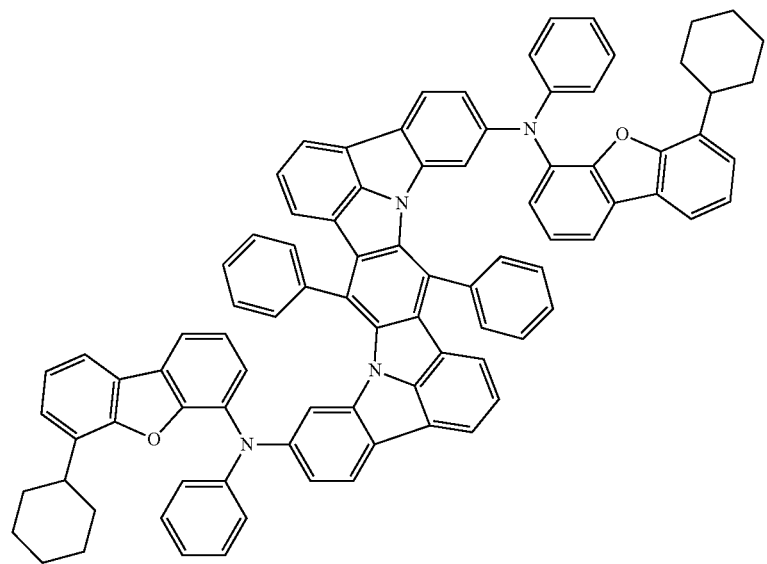

-continued
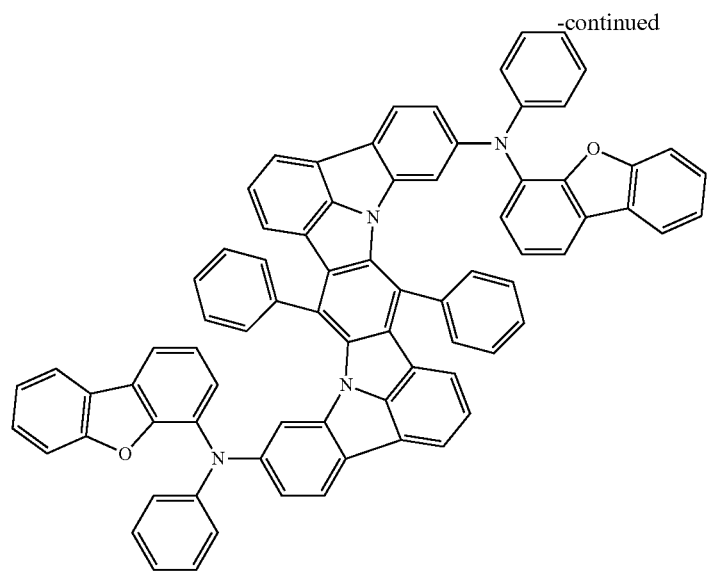
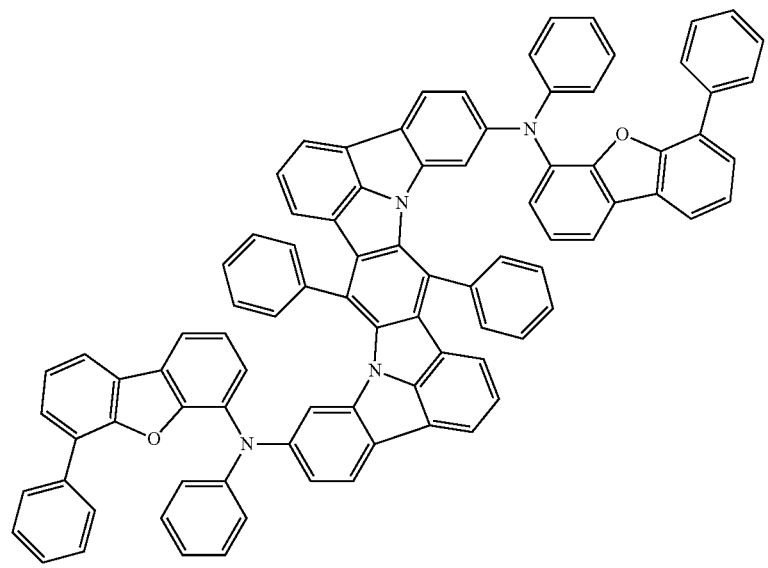
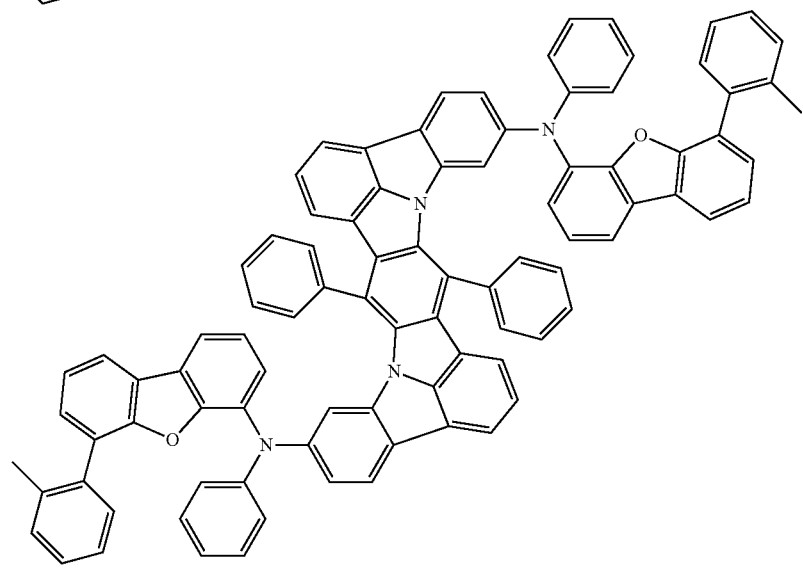

-continued
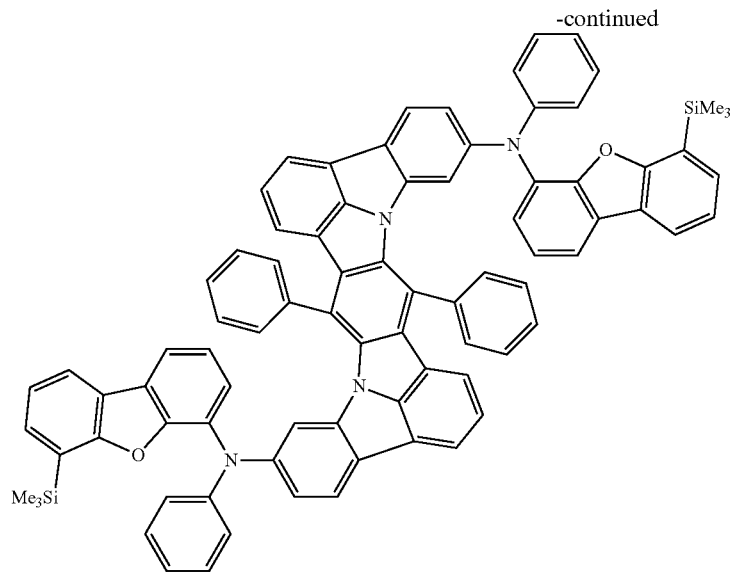
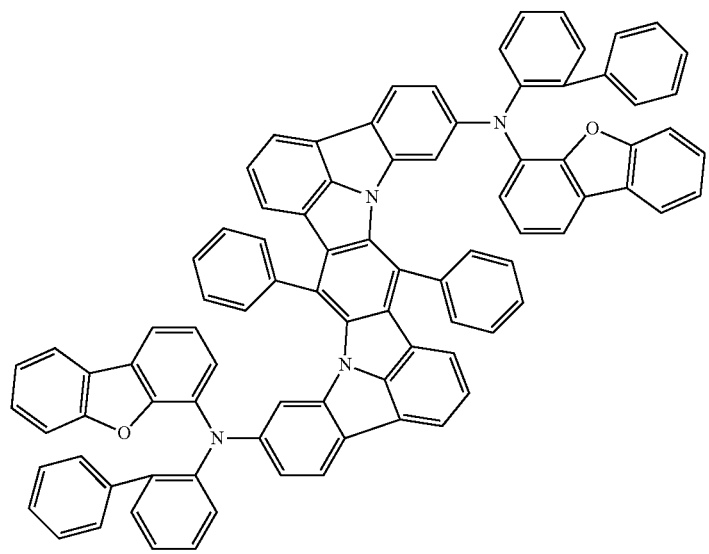
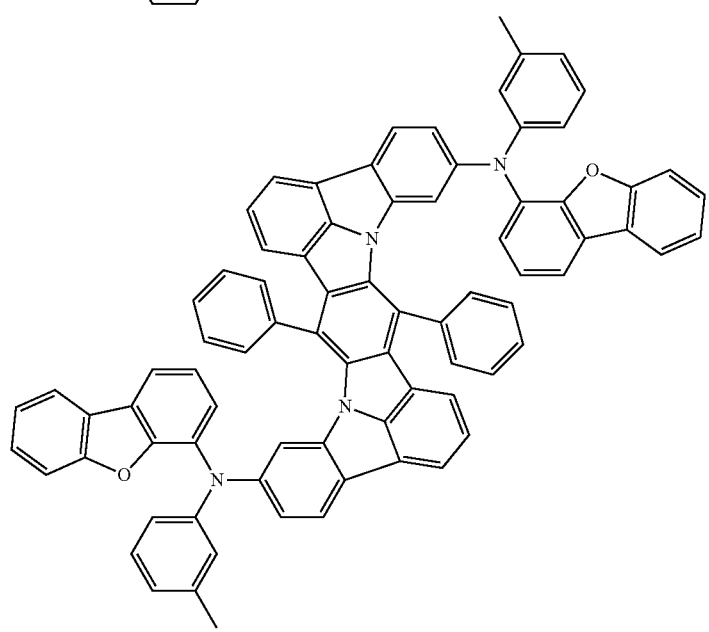

-continued
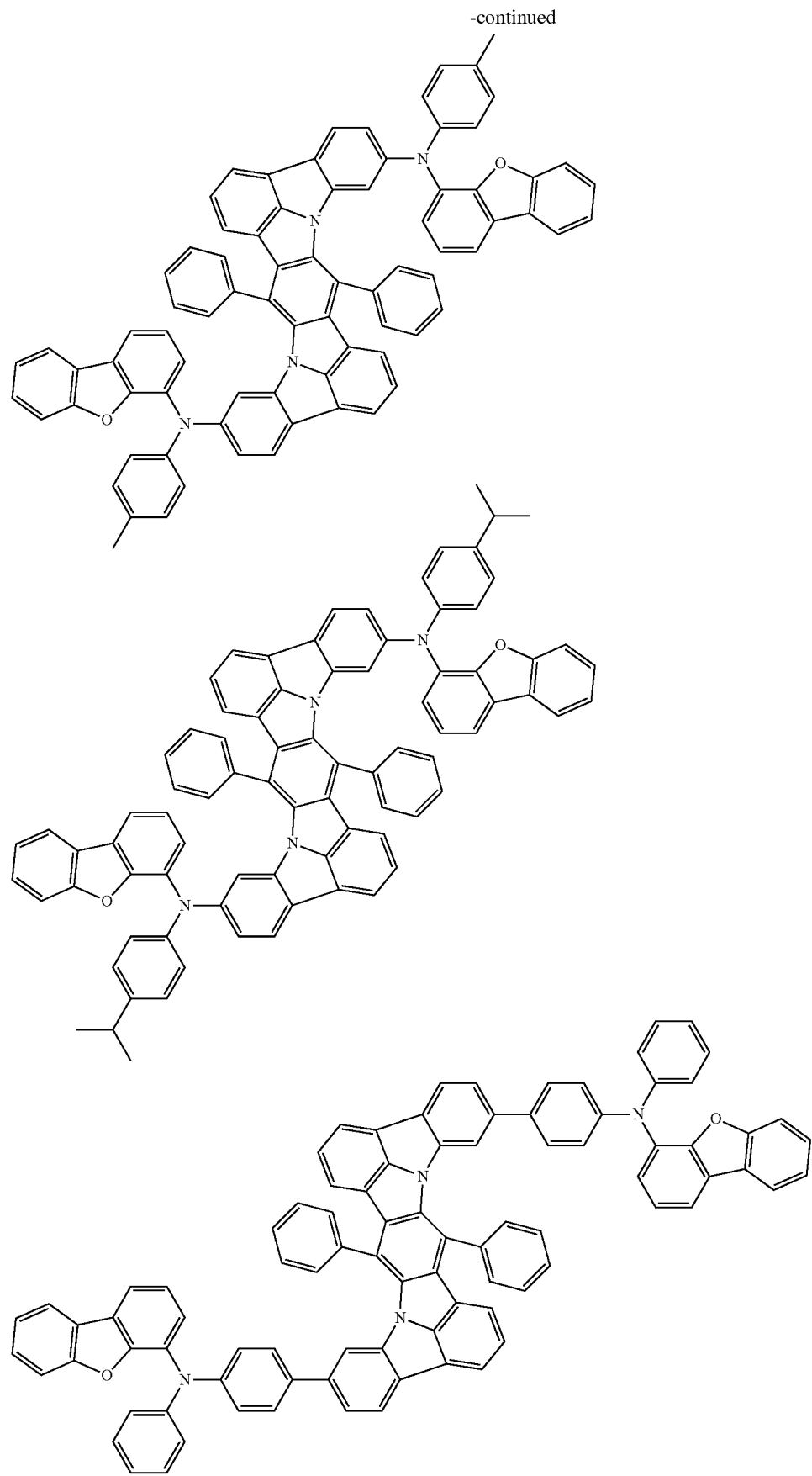

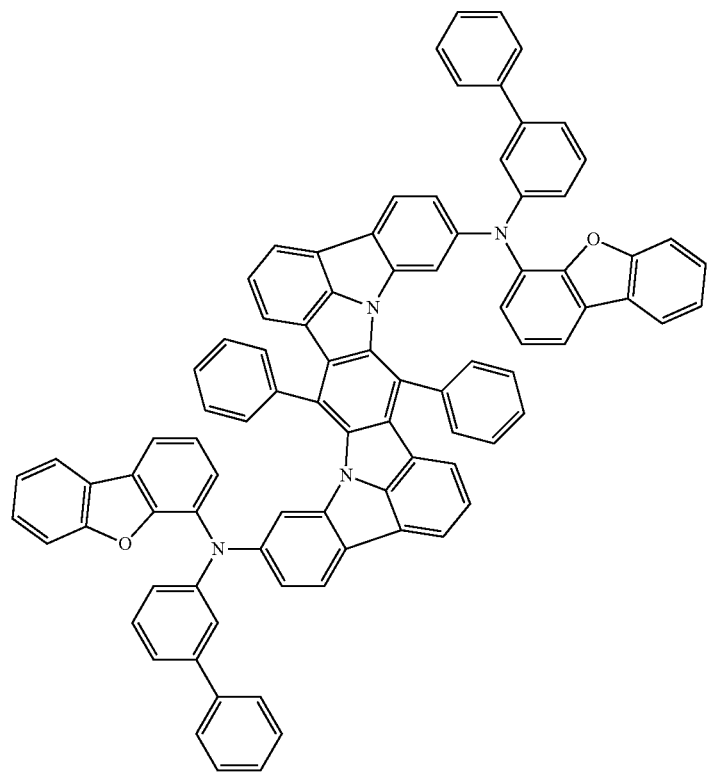
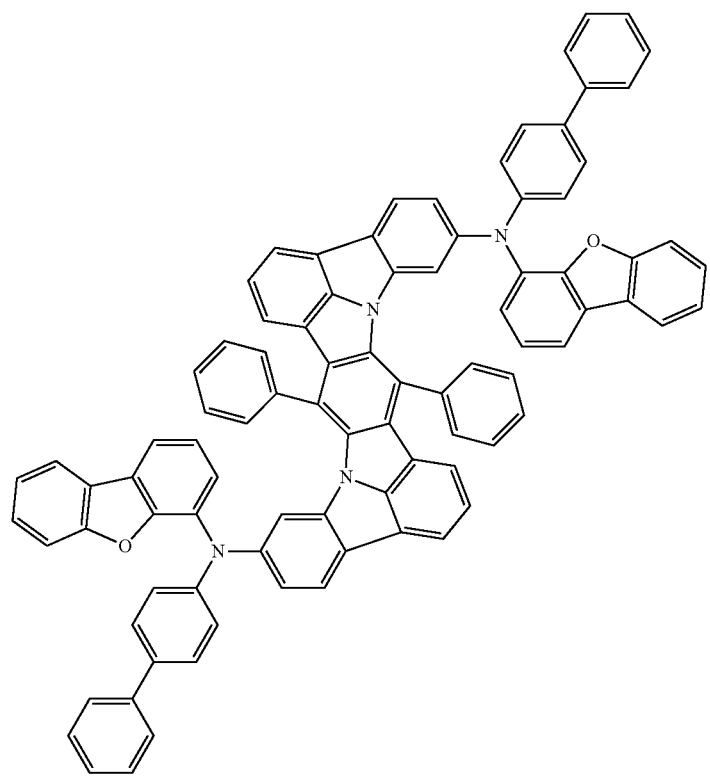

-continued
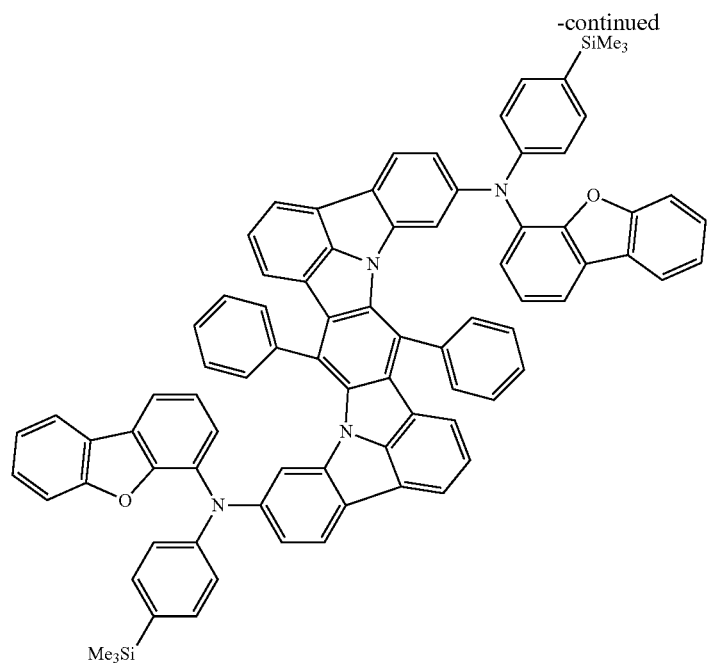
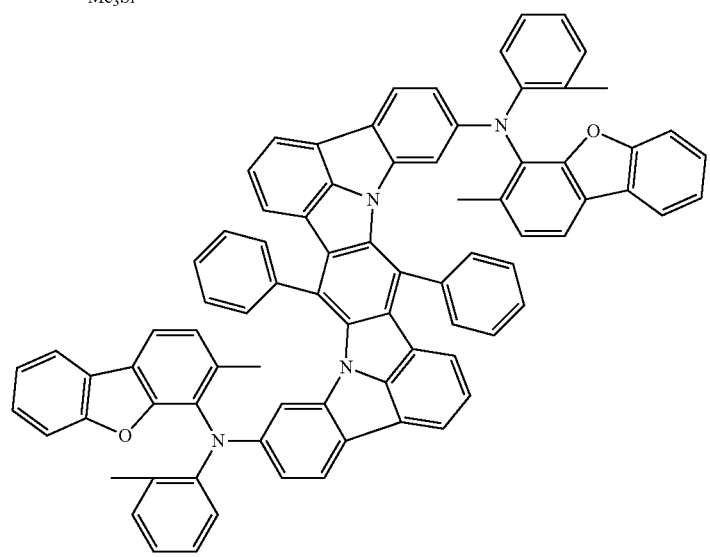
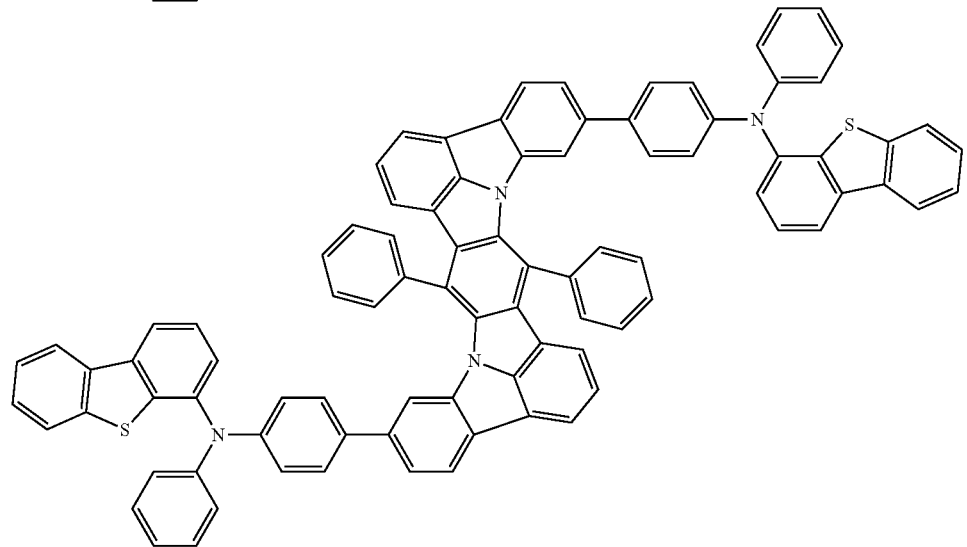

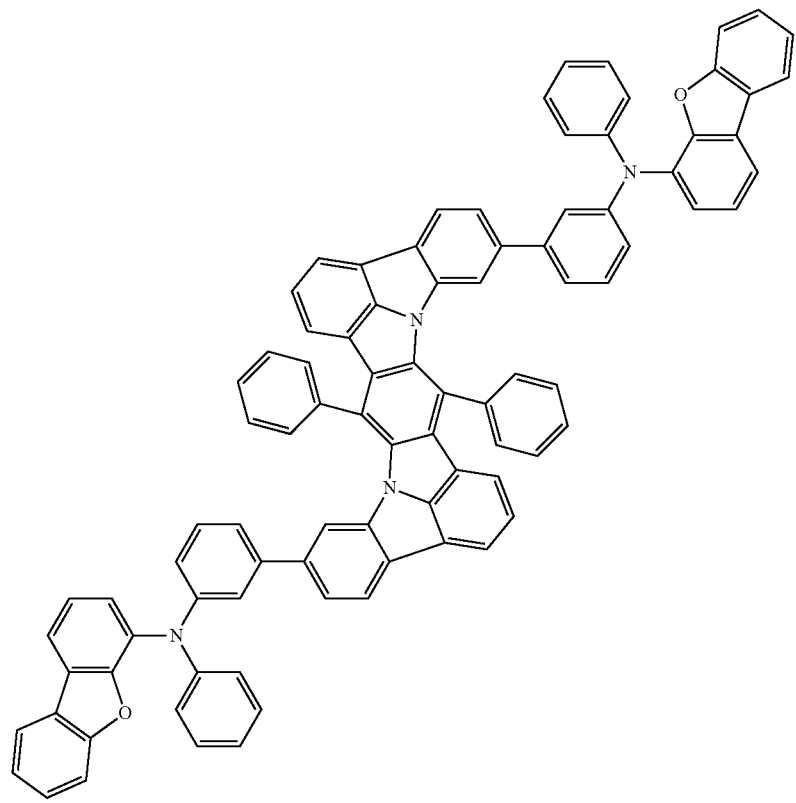
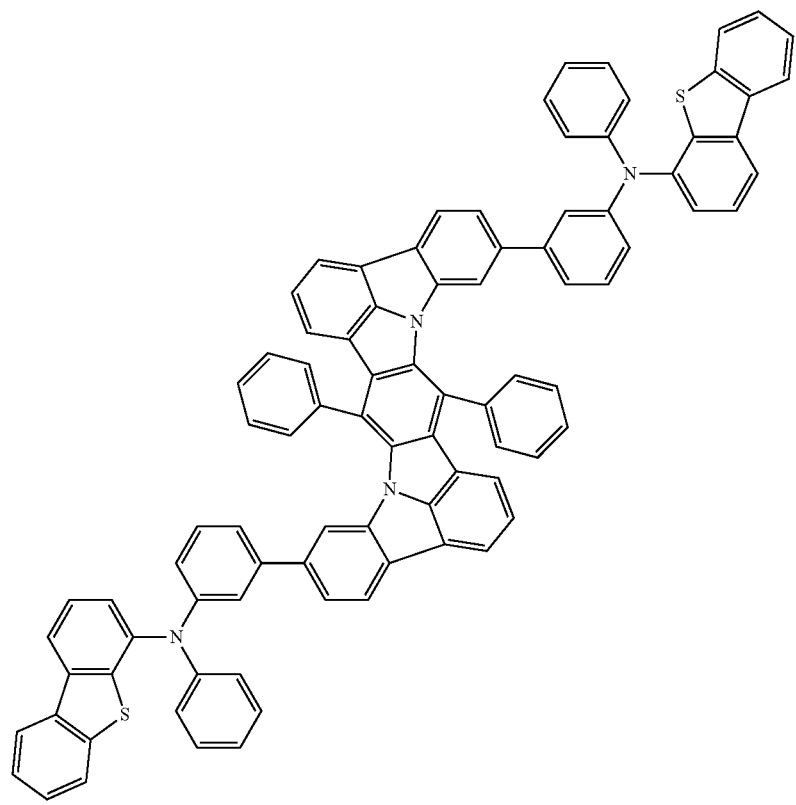

-continued
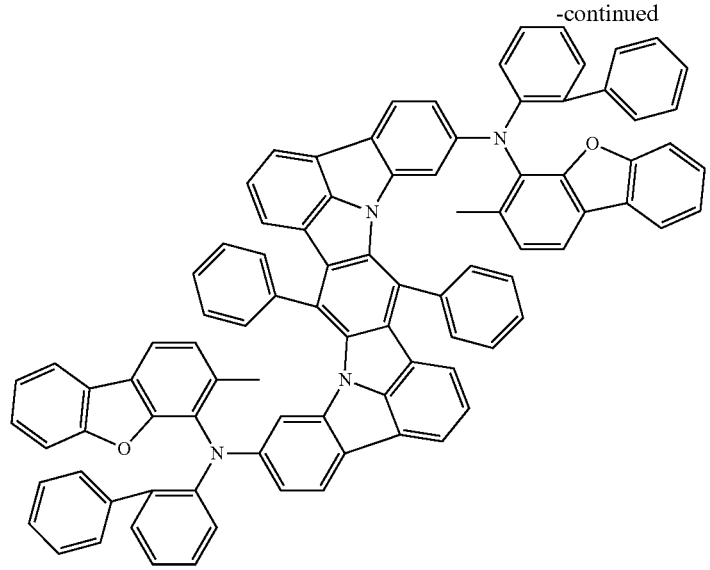
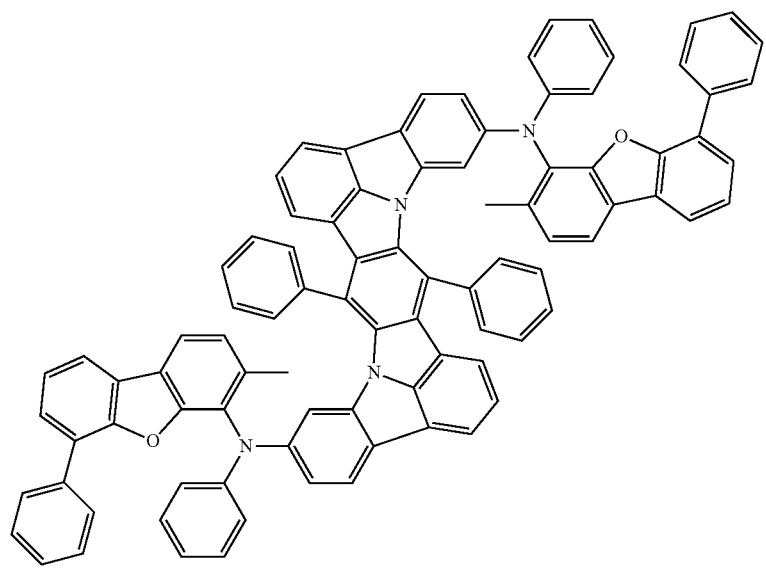
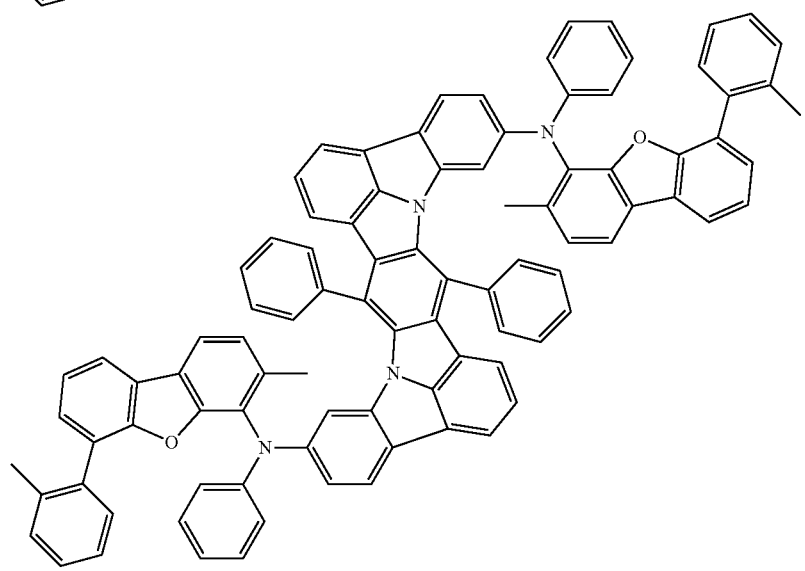

-continued
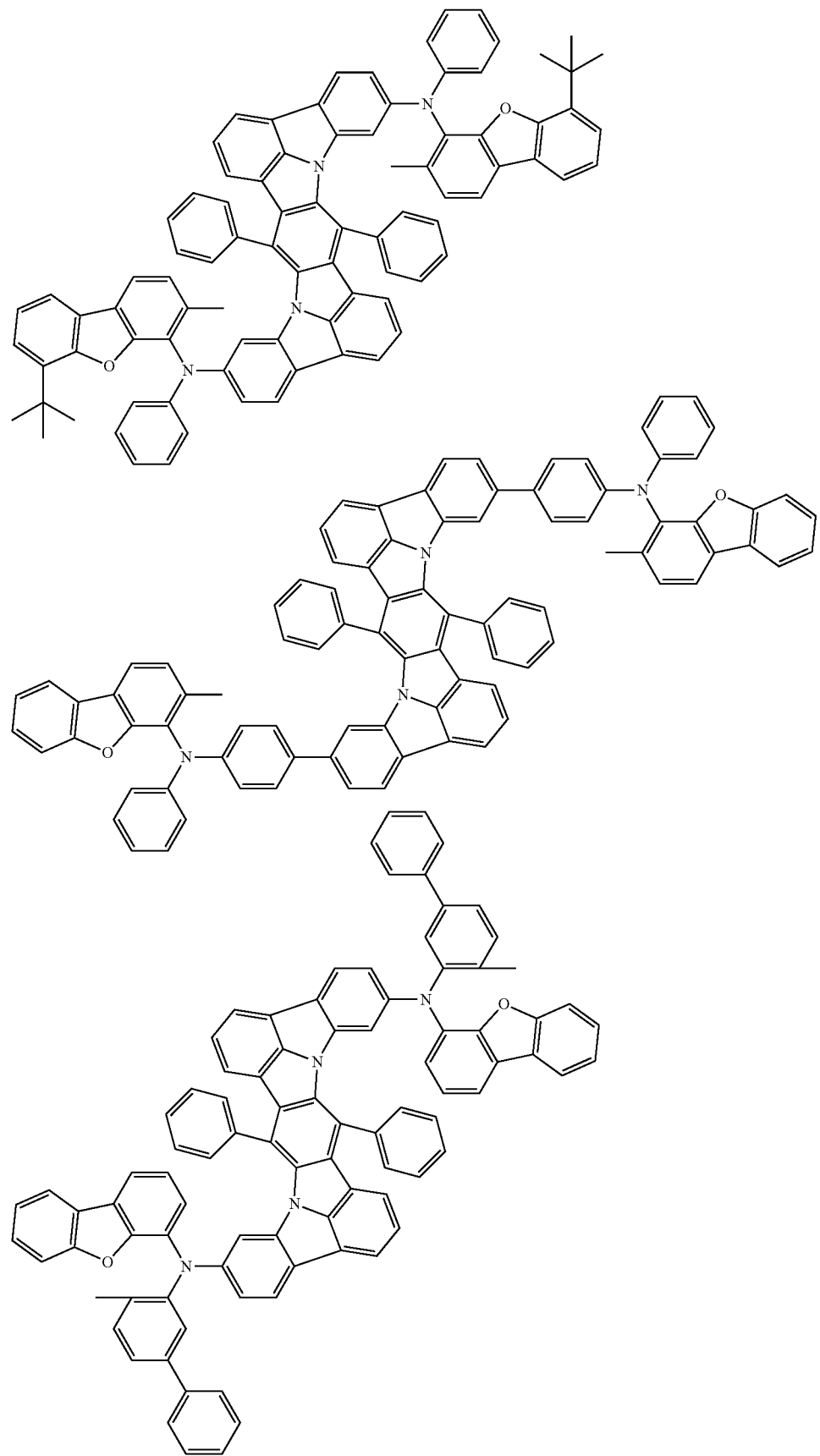

623 624
-continued
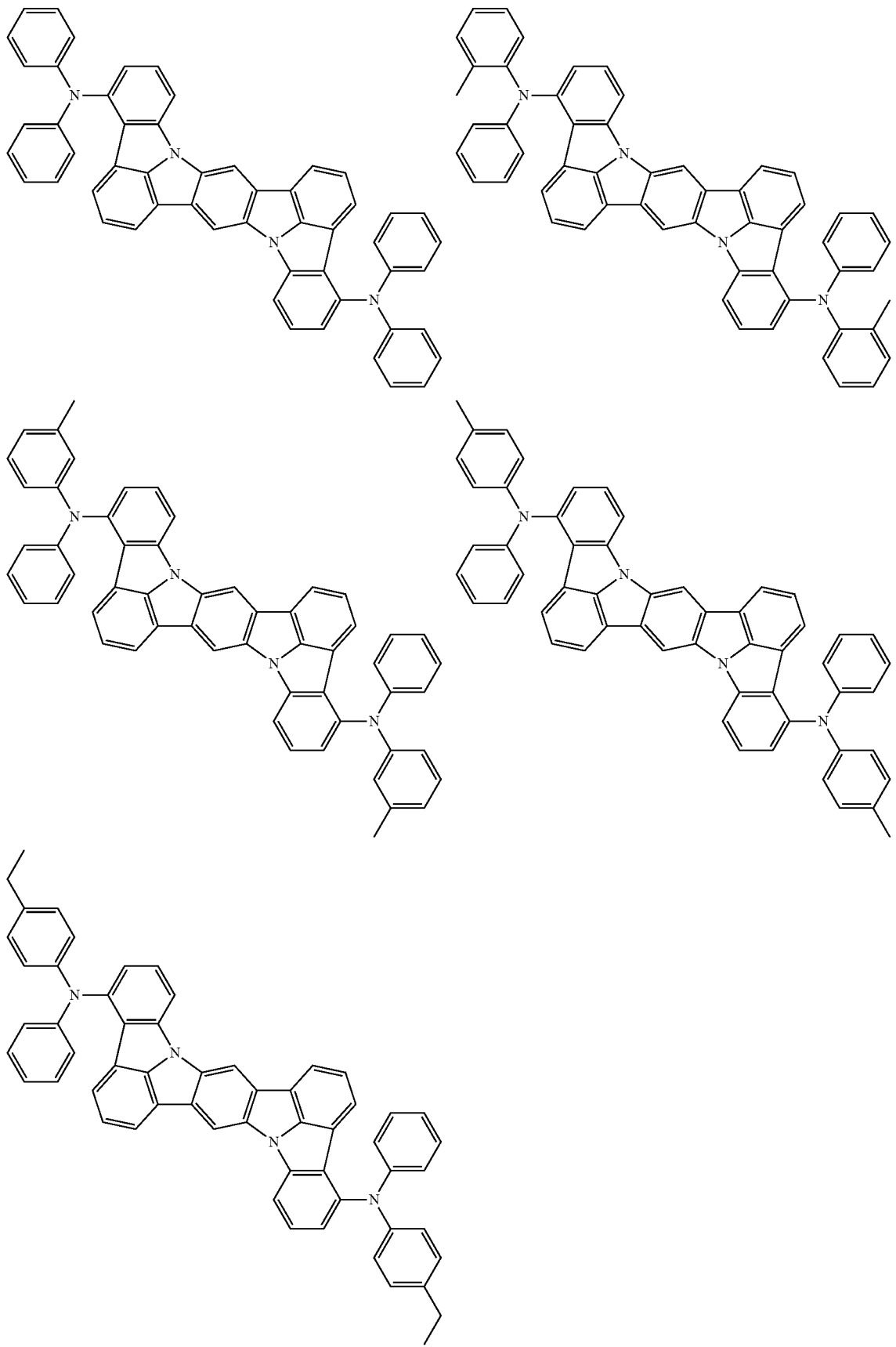 [SMILES: c1ccc(N(c2ccccc2)c2cccc3c2c2cccc4c5cc6c(cc5n3c42)c2cccc3c4c(N(c5ccccc5)c5ccccc5)cccc4n6c23)cc1 ; Cc1ccccc1N(c1ccccc1)c1cccc2c1c1cccc3c4cc5c(cc4n2c31)c1cccc2c3c(N(c4ccccc4)c4ccccc4C)cccc3n5c12 ; Cc1cccc(N(c2ccccc2)c2cccc3c2c2cccc4c5cc6c(cc5n3c42)c2cccc3c4c(N(c5ccccc5)c5cccc(C)c5)cccc4n6c23)c1 ; Cc1ccc(N(c2ccccc2)c2cccc3c2c2cccc4c5cc6c(cc5n3c42)c2cccc3c4c(N(c5ccccc5)c5ccc(C)cc5)cccc4n6c23)cc1 ; CCc1ccc(N(c2ccccc2)c2cccc3c2c2cccc4c5cc6c(cc5n3c42)c2cccc3c4c(N(c5ccccc5)c5ccc(CC)cc5)cccc4n6c23)cc1]

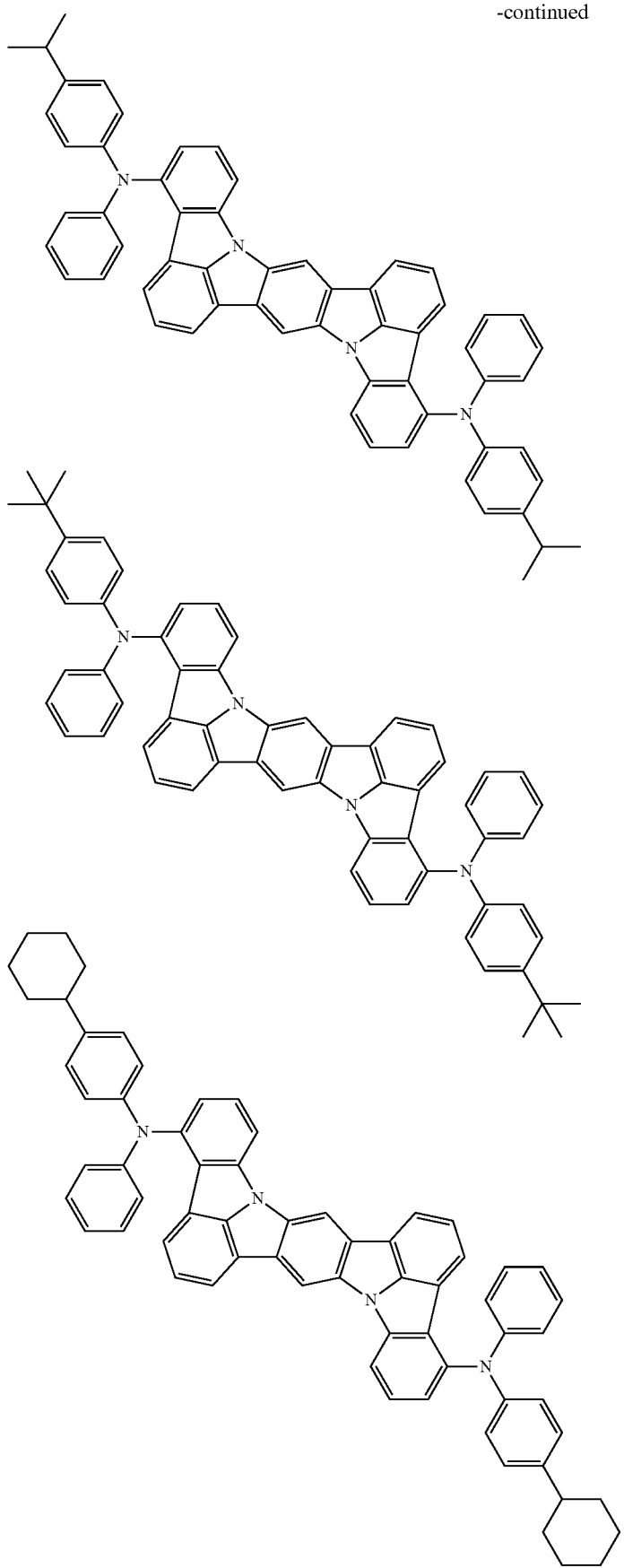

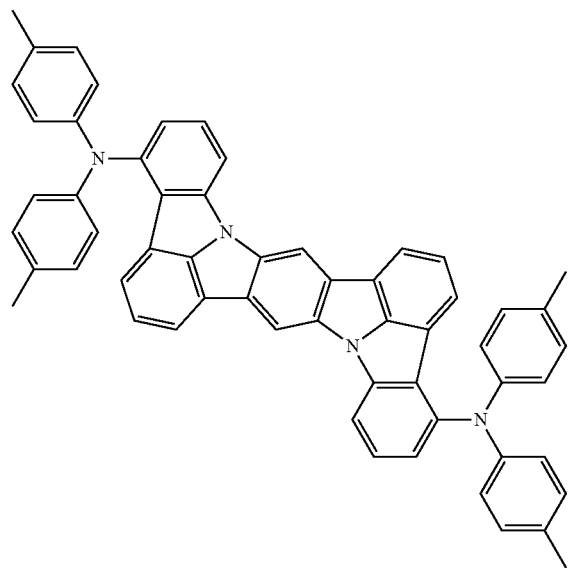
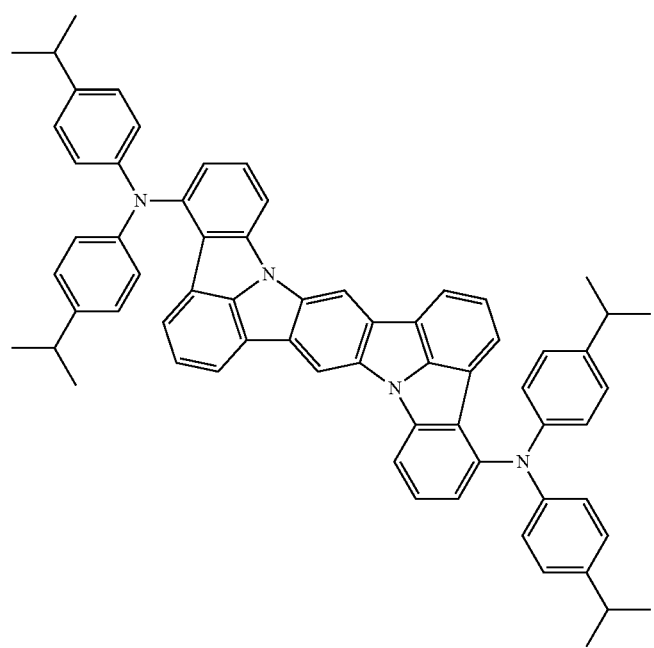

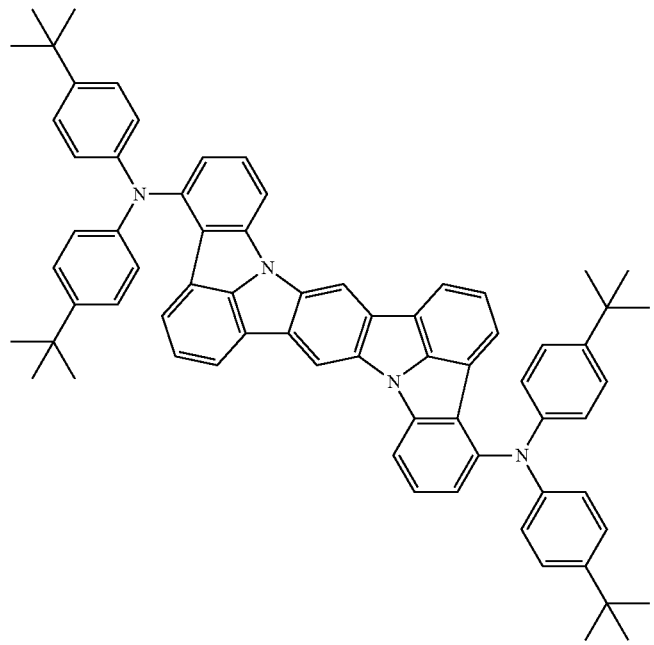
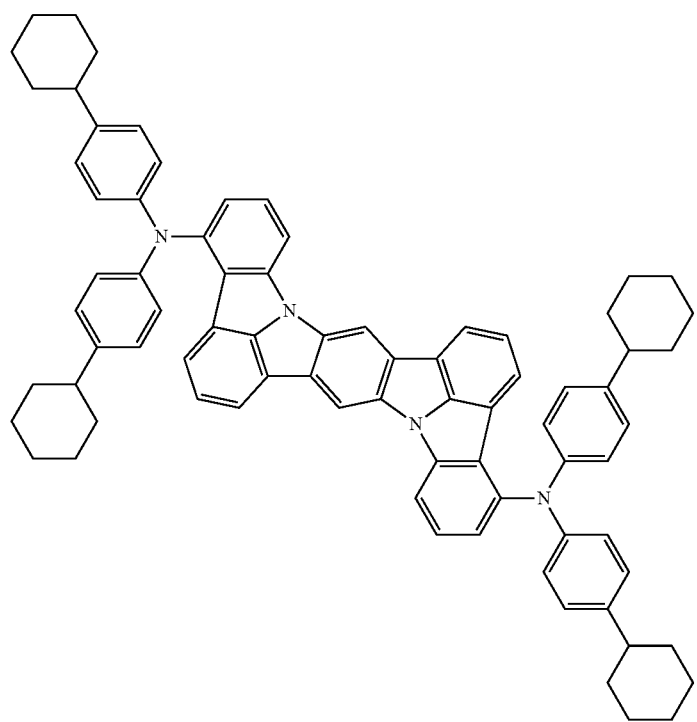

631
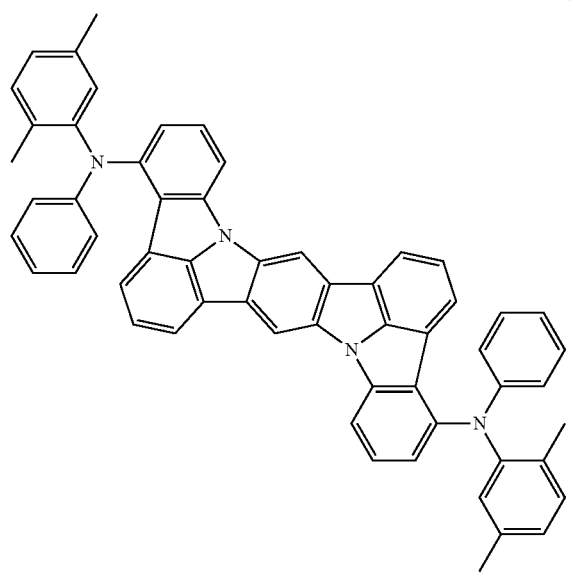
632
-continued
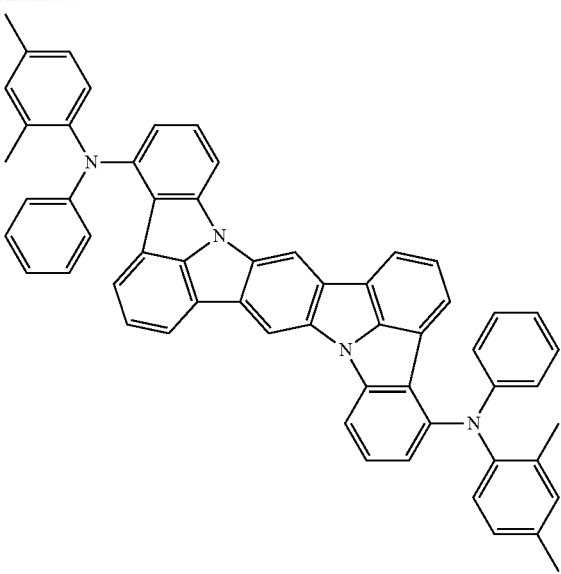
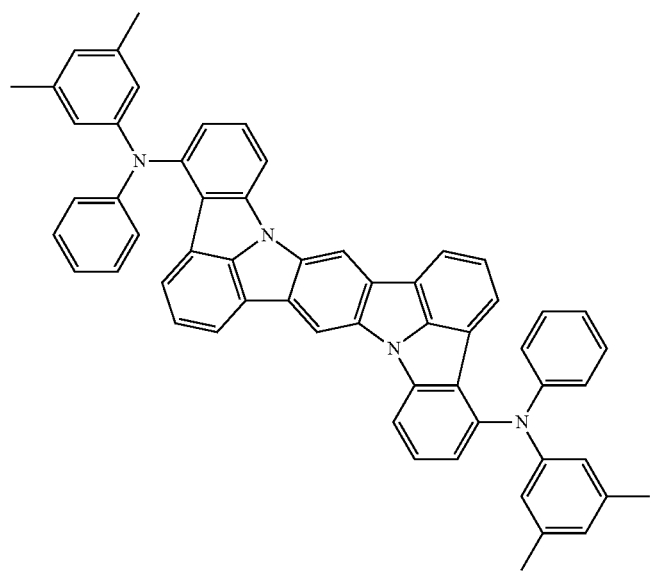
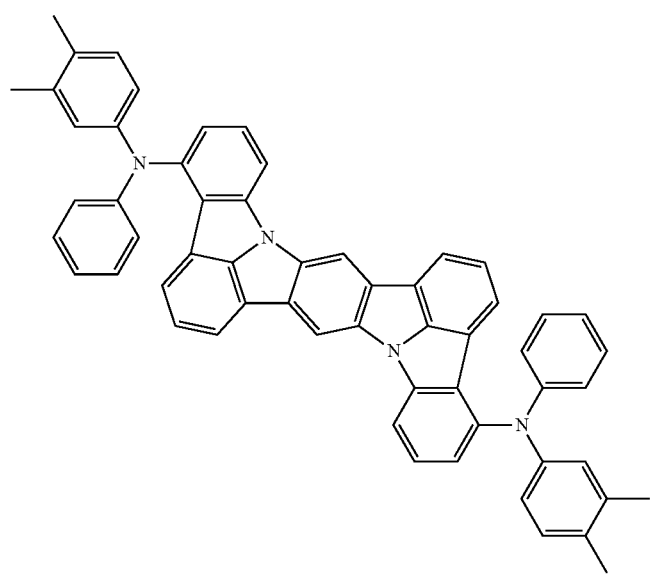

-continued
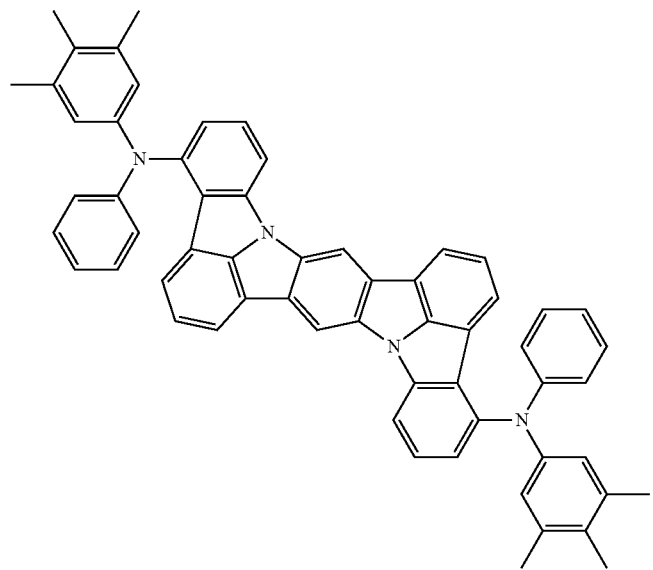
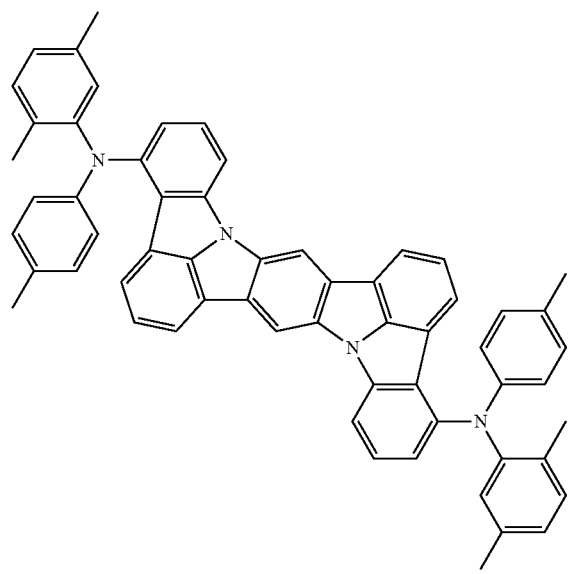
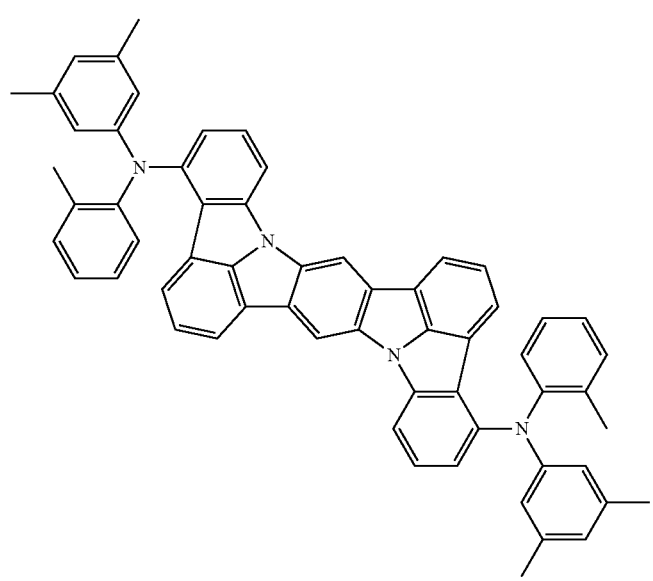

-continued
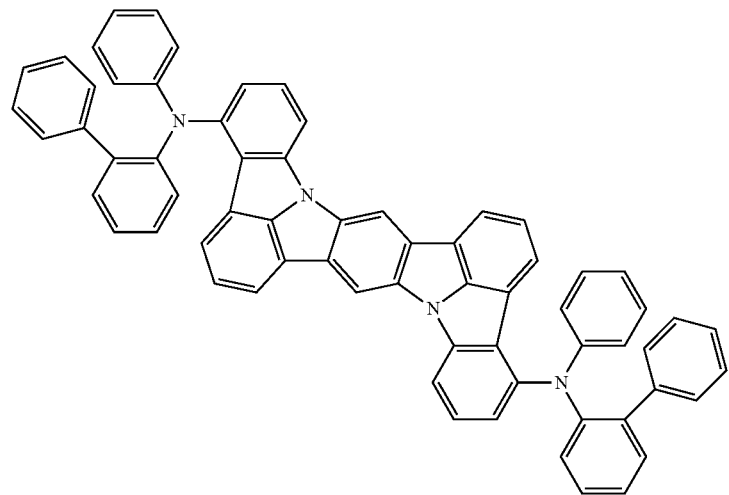
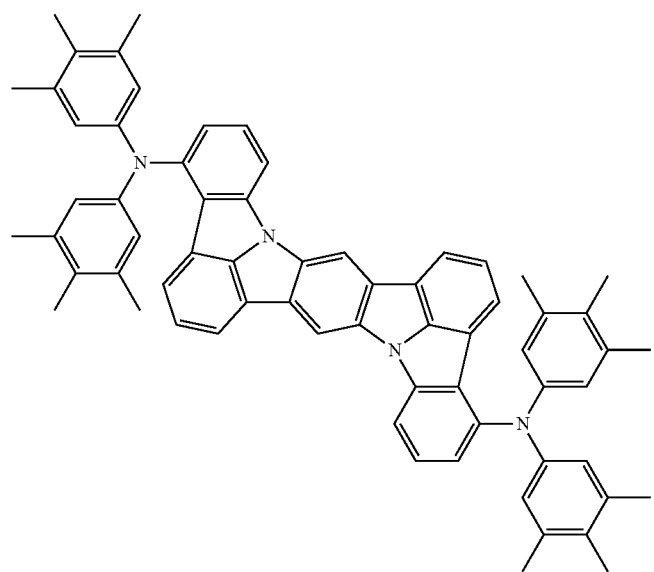

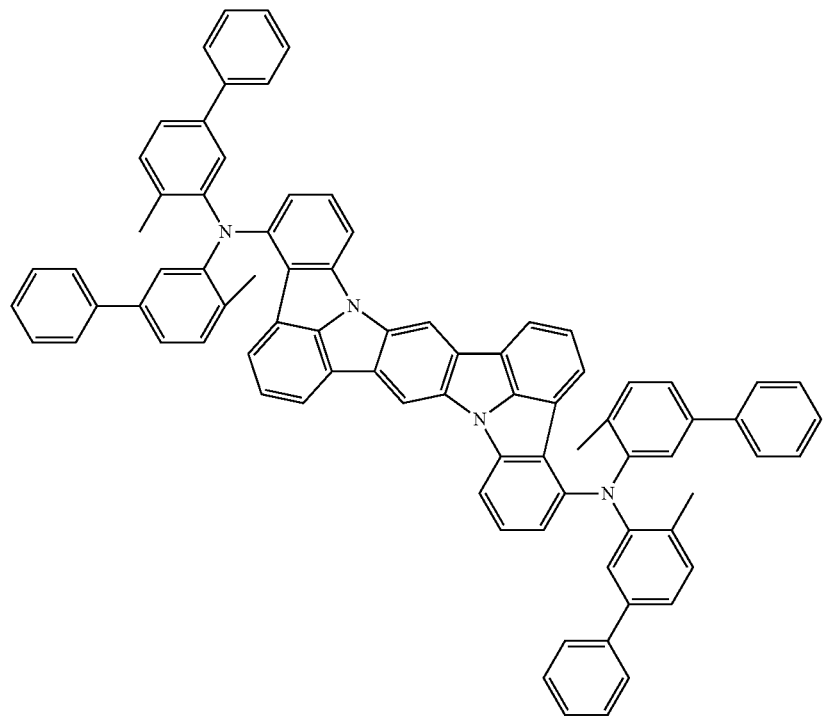
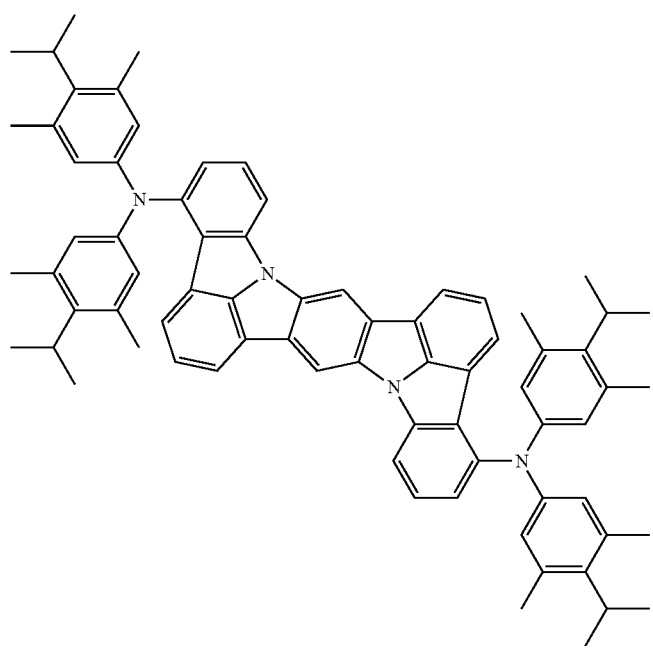

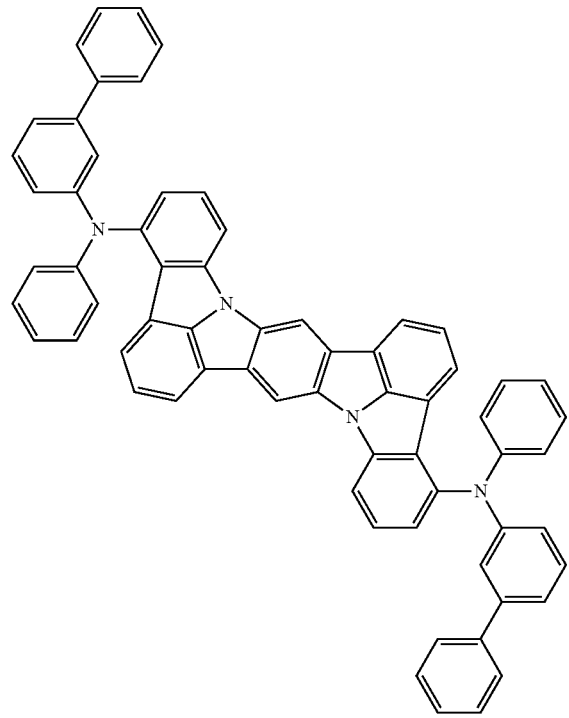
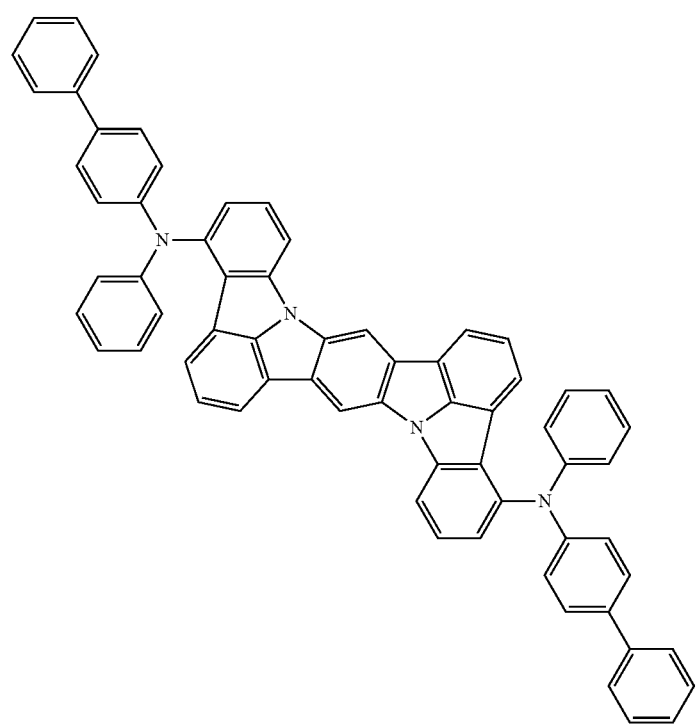

-continued
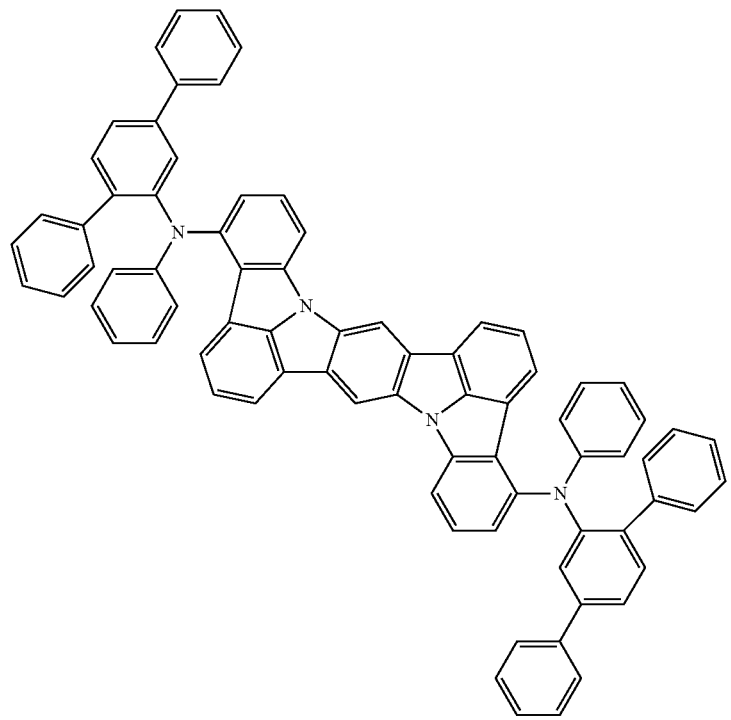
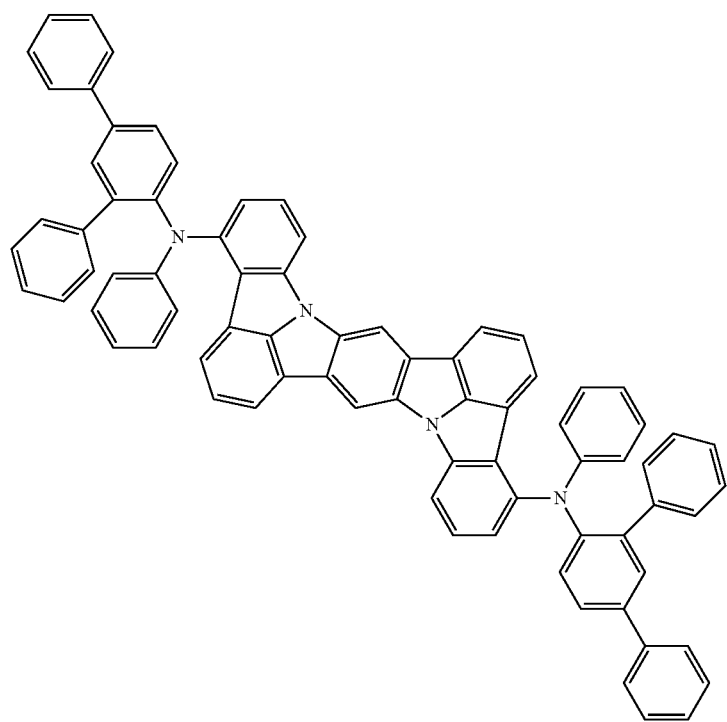

-continued
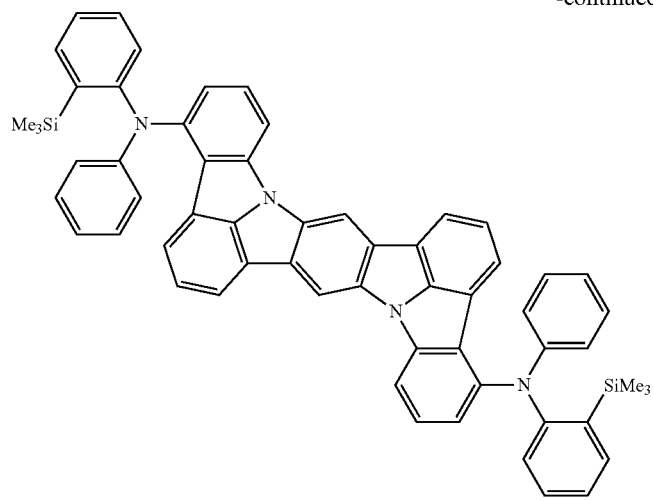
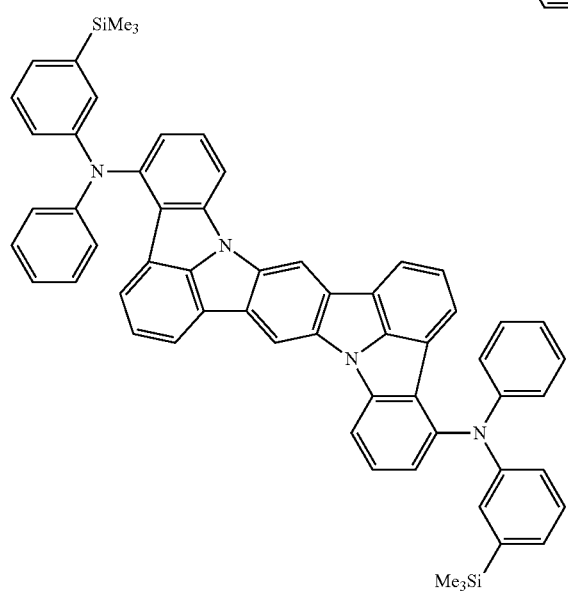
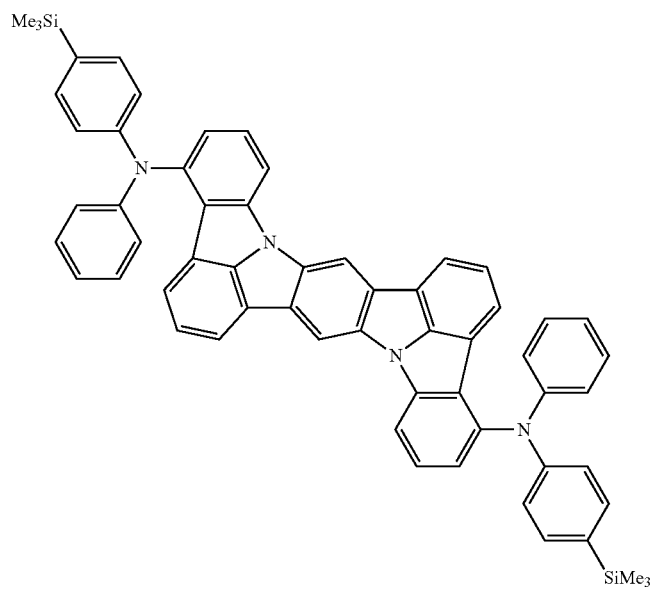

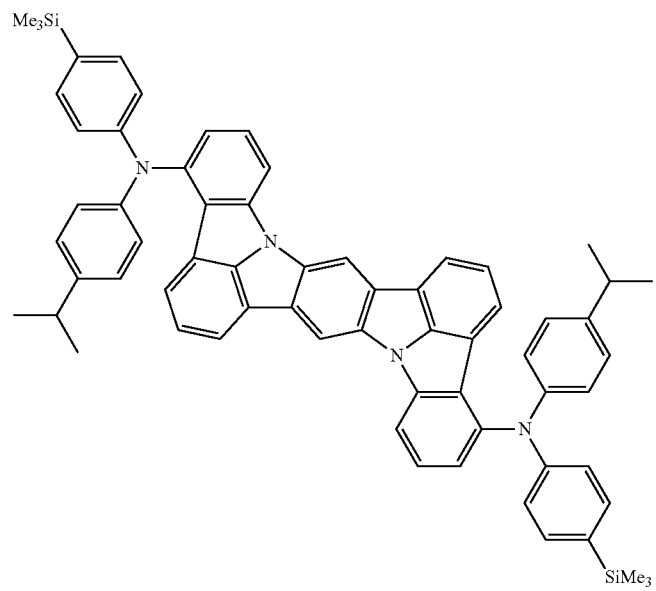
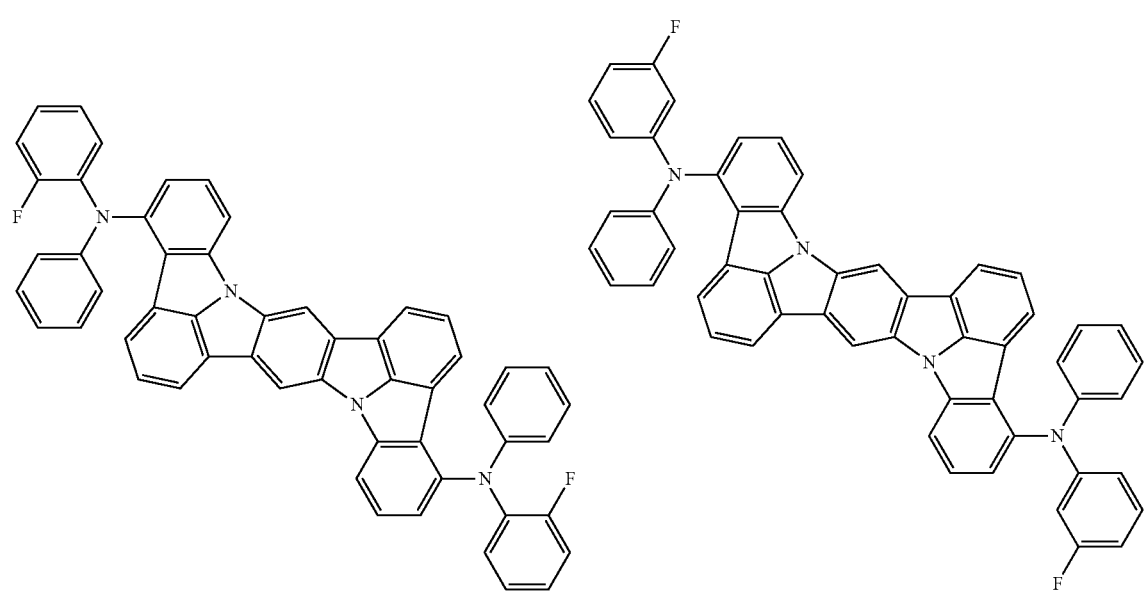

-continued
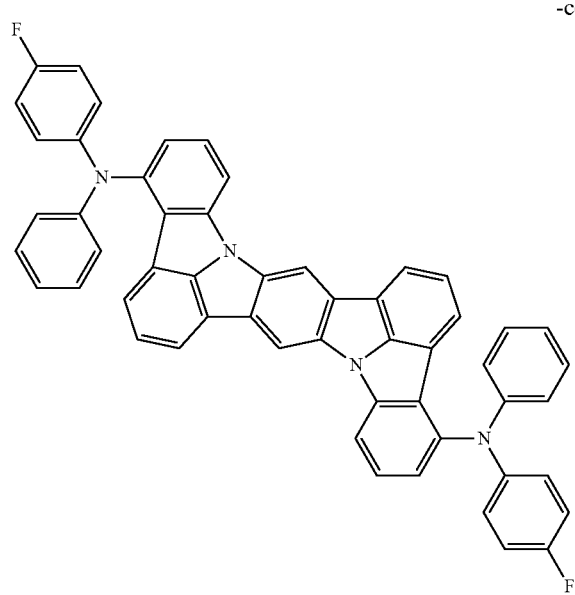
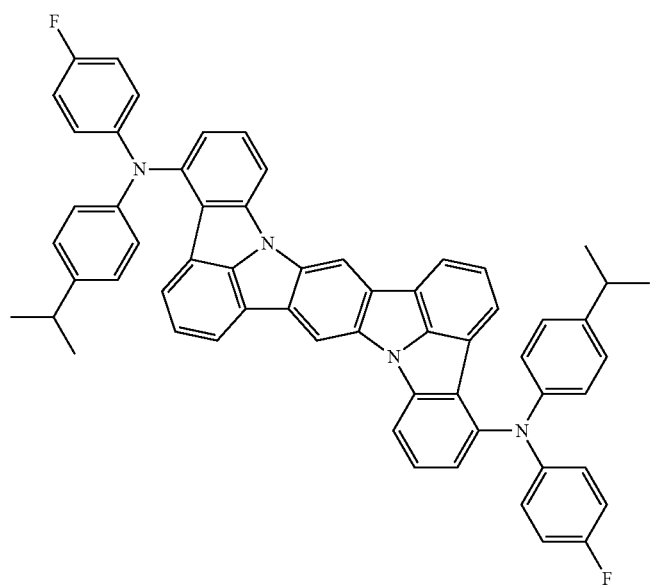
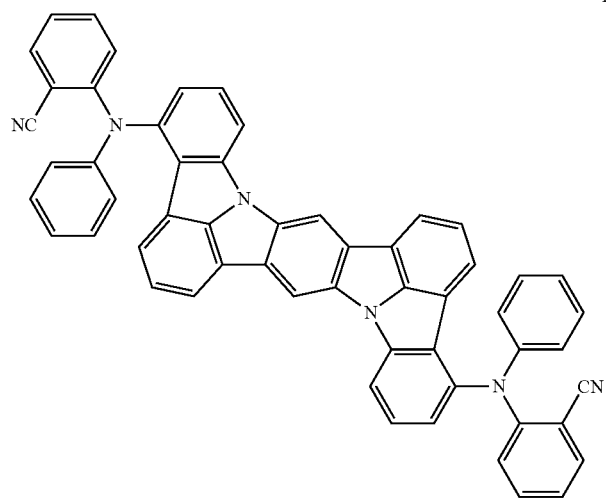

-continued
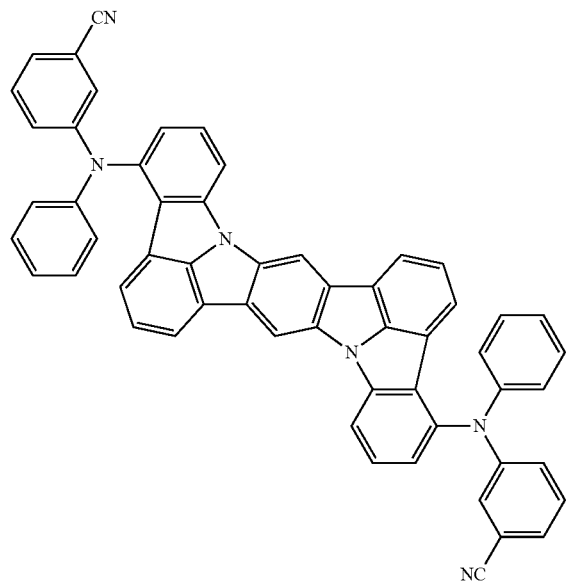
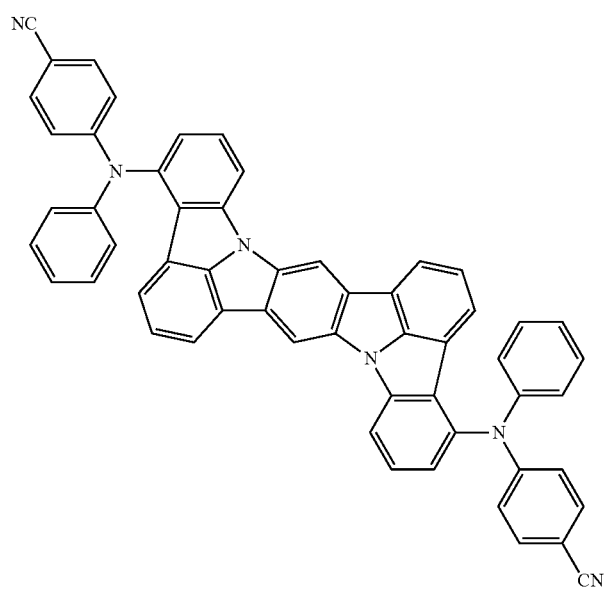

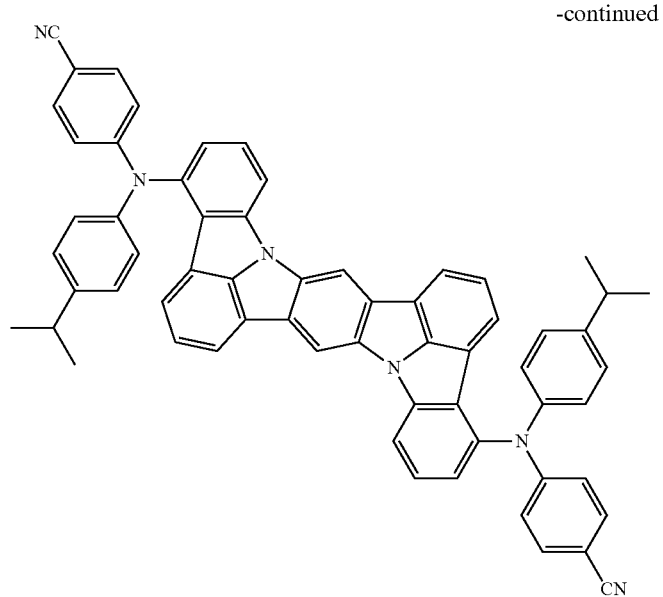
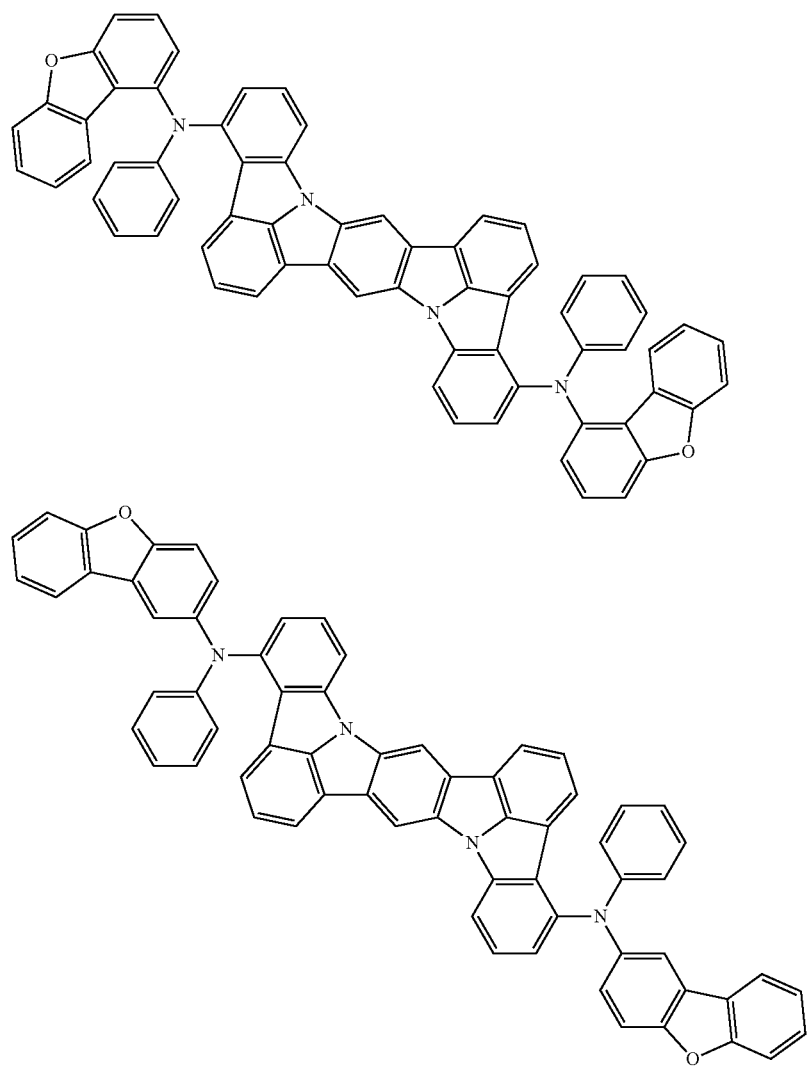

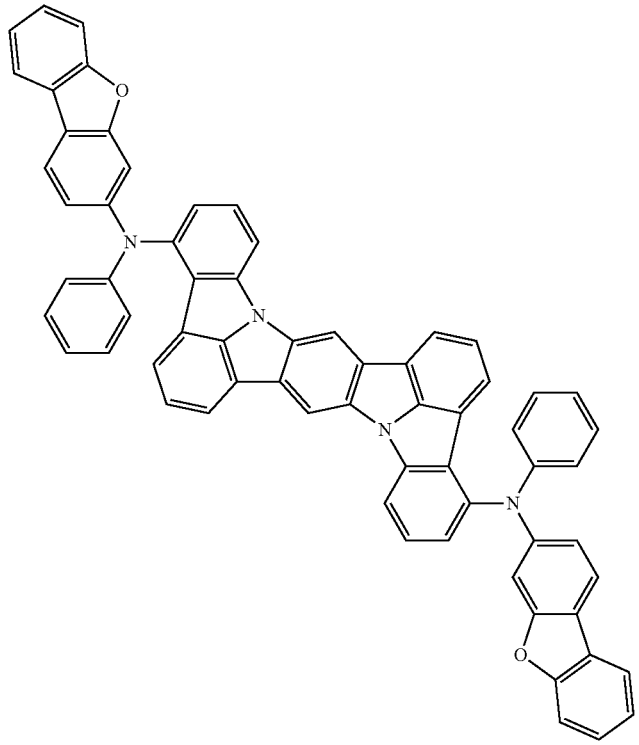
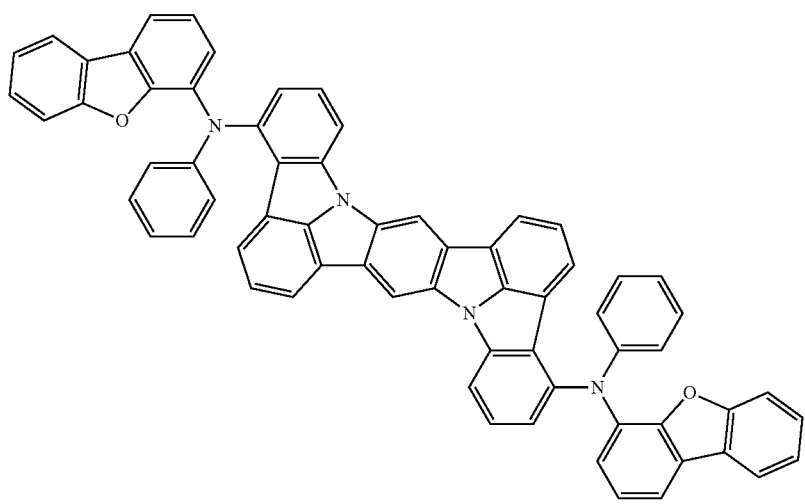

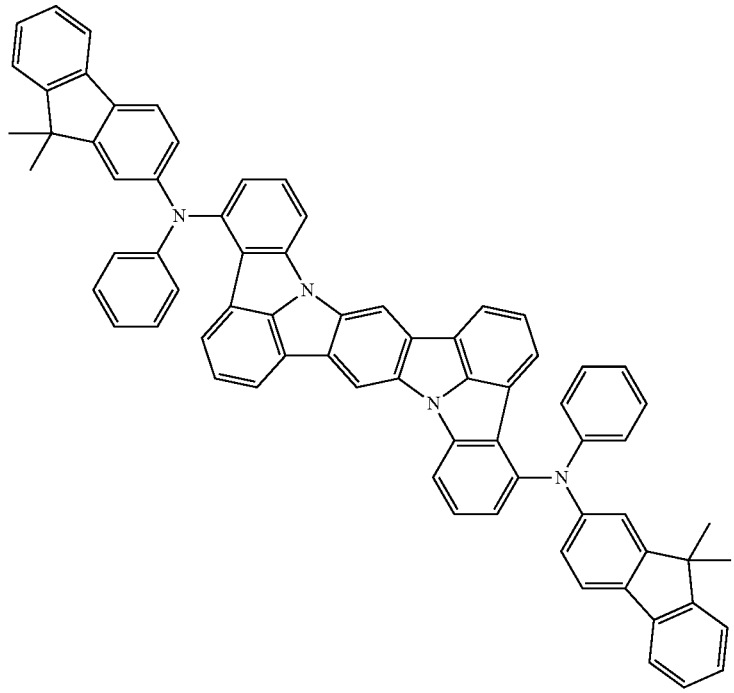
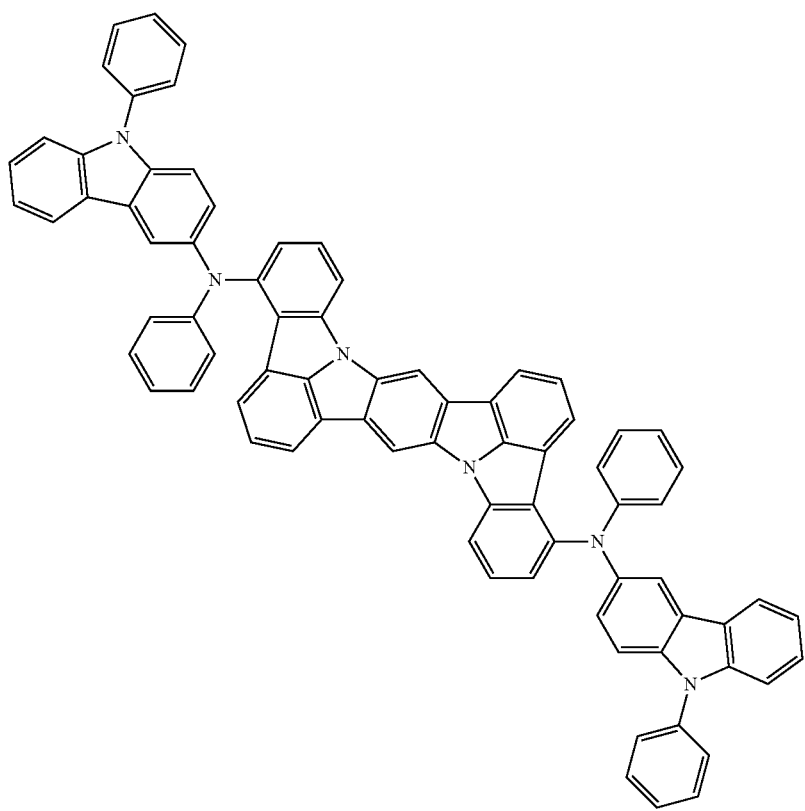

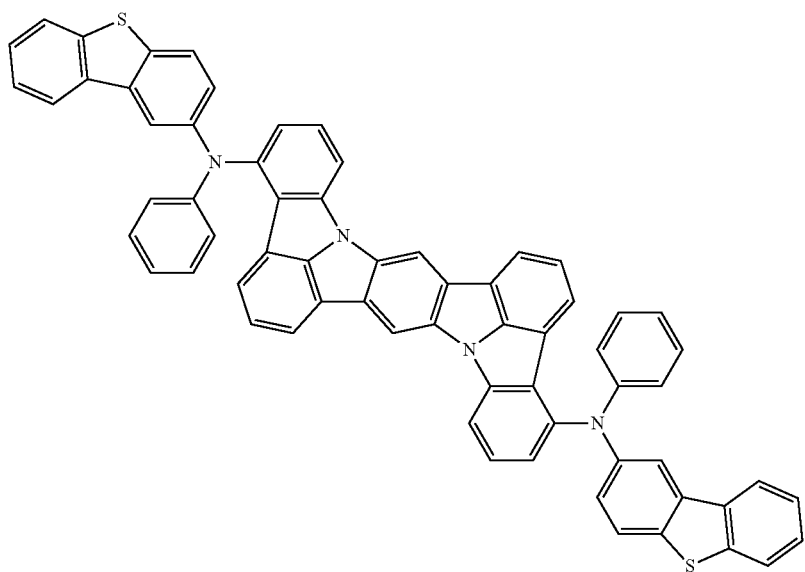
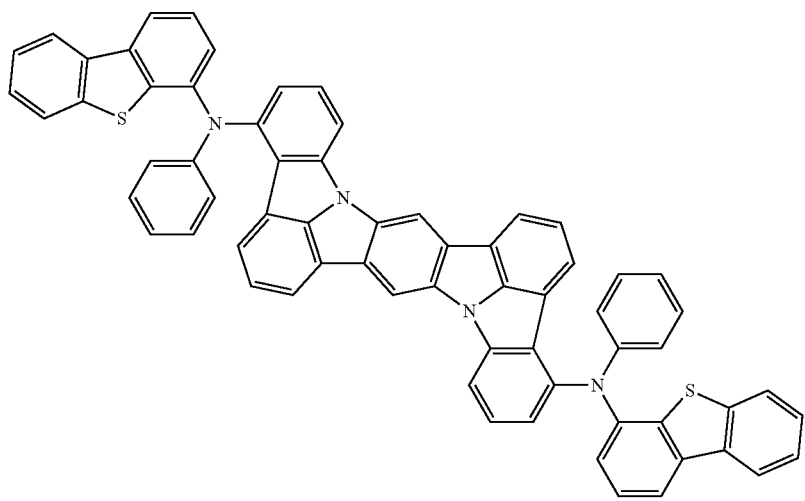
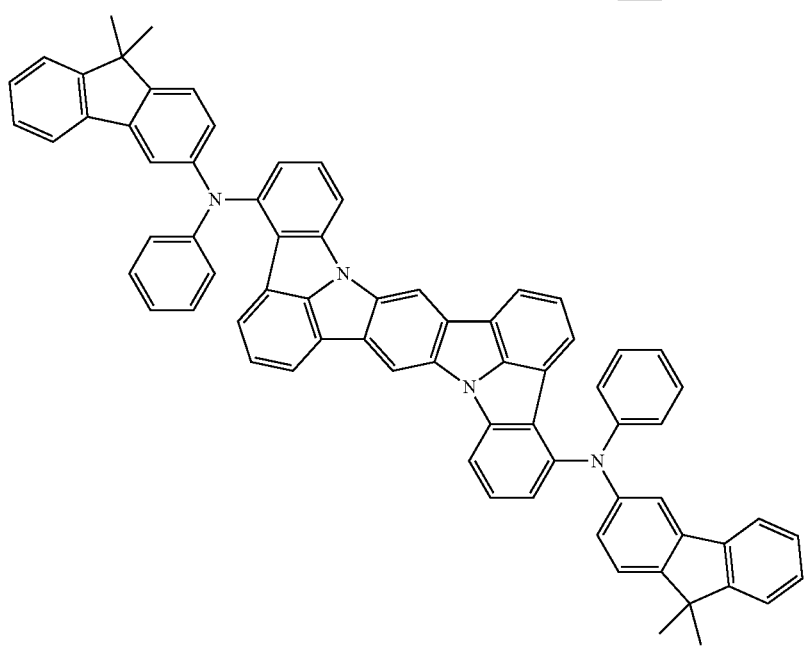

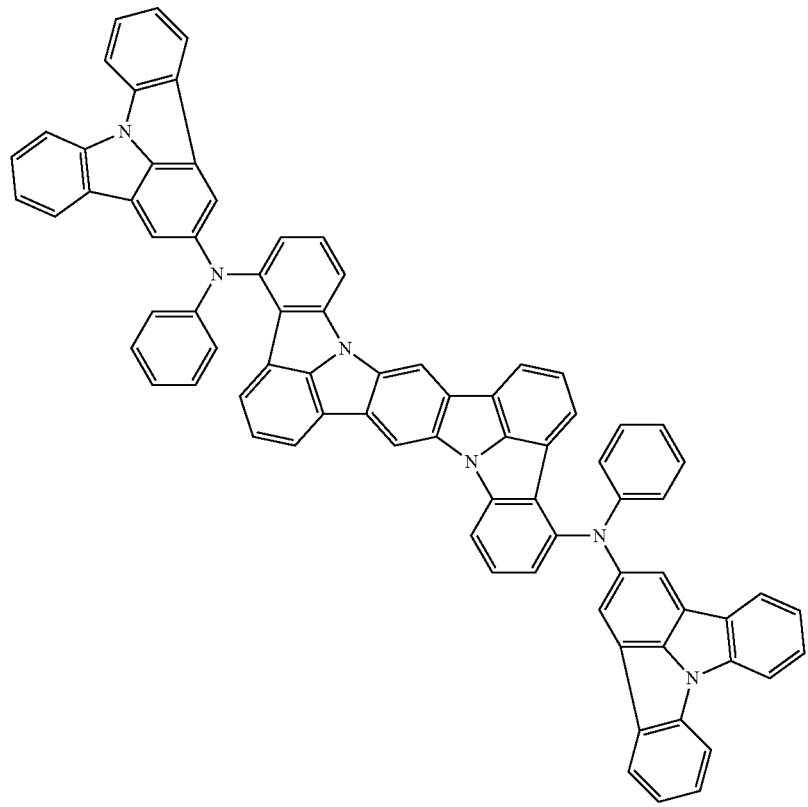
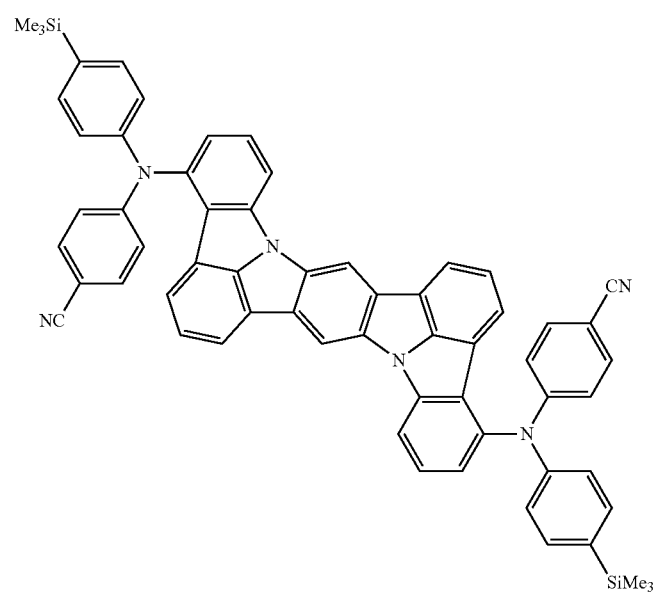

-continued
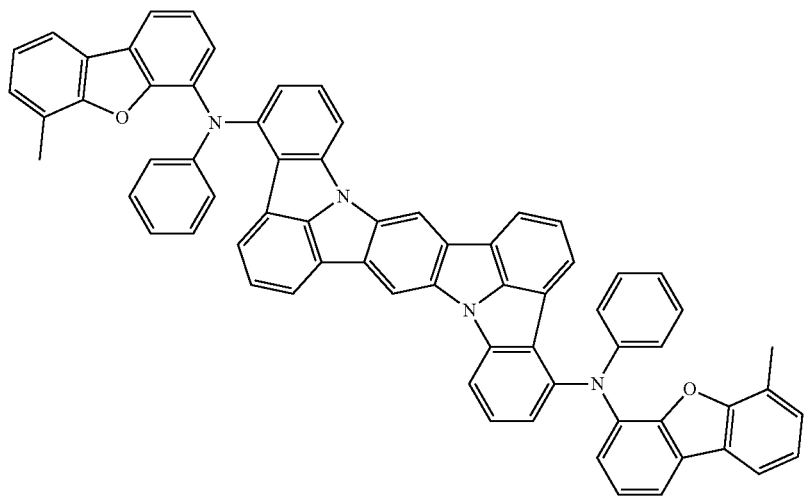
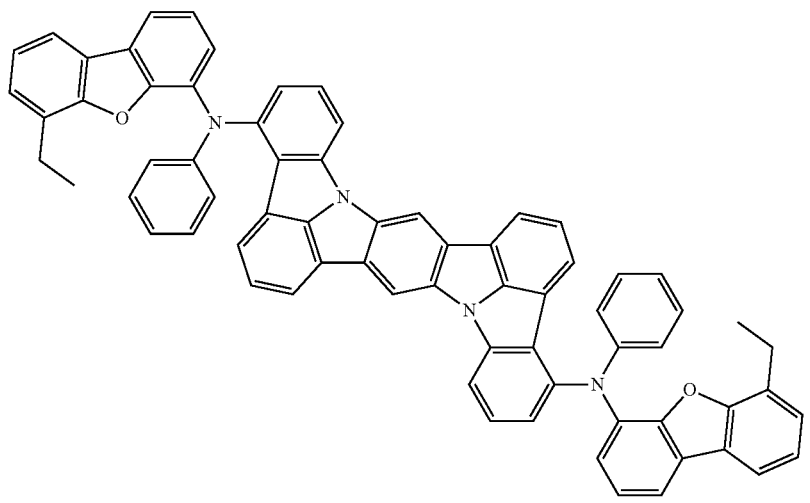
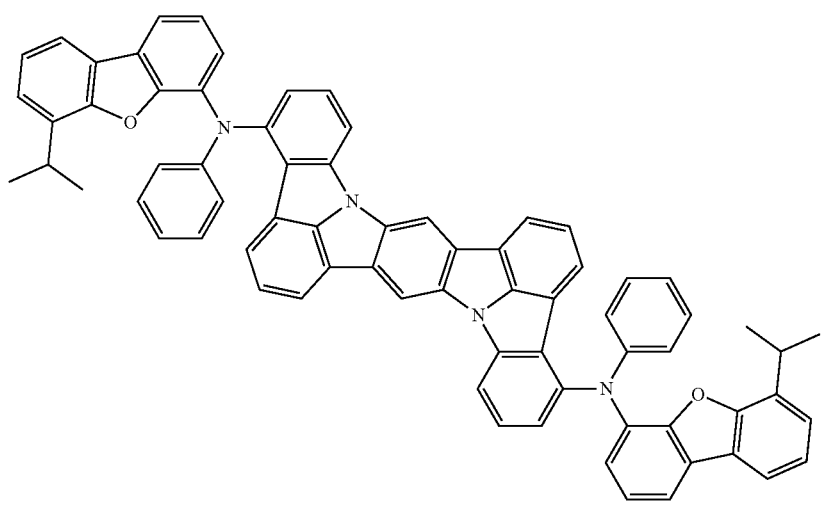

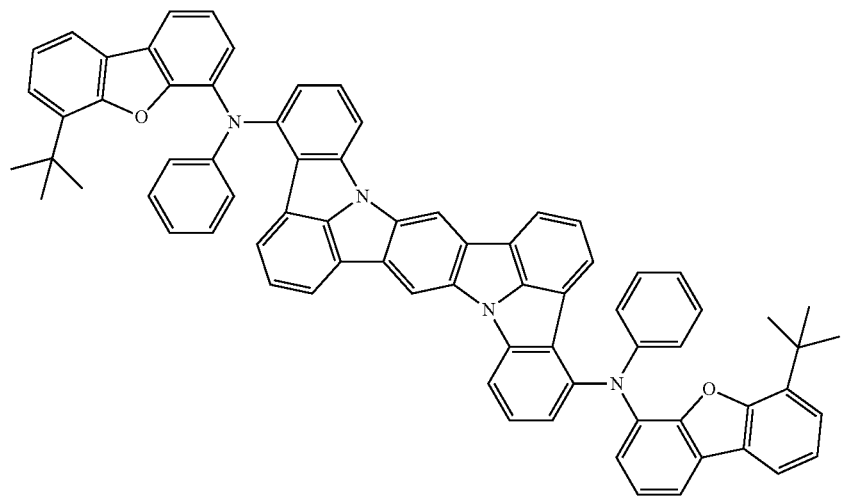 [SMILES: CC(C)(C)c1cccc2c1oc1c(N(c3ccccc3)c3cccc4c3c3cccc5c6cc7c(cc6n4c53)c3cccc4c5c(N(c6ccccc6)c6cccc8c6oc6c(C(C)(C)C)cccc68)cccc5n7c34)cccc12]
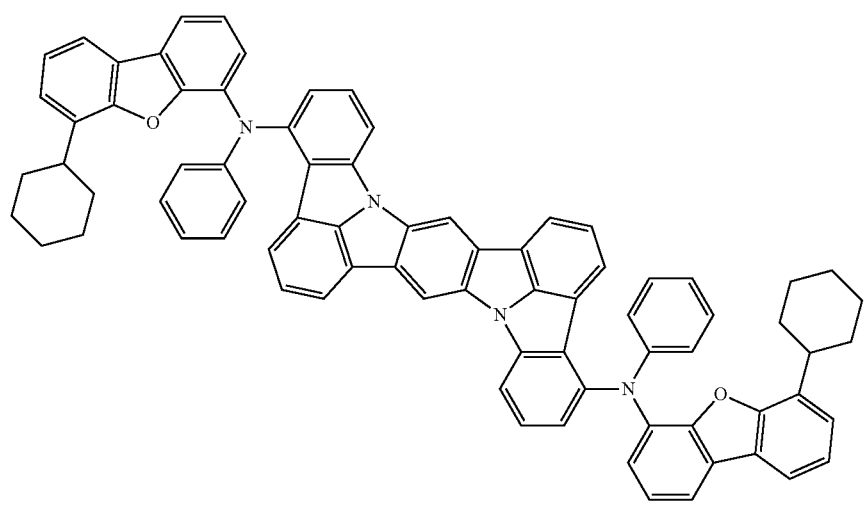
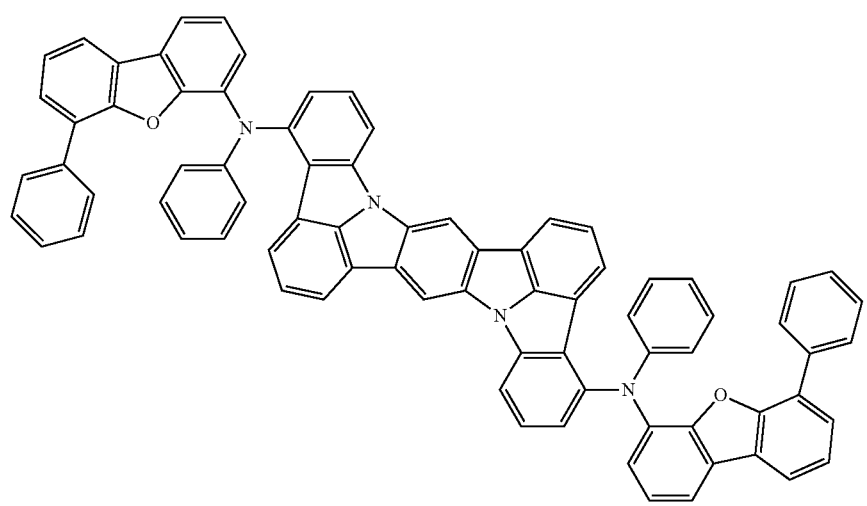

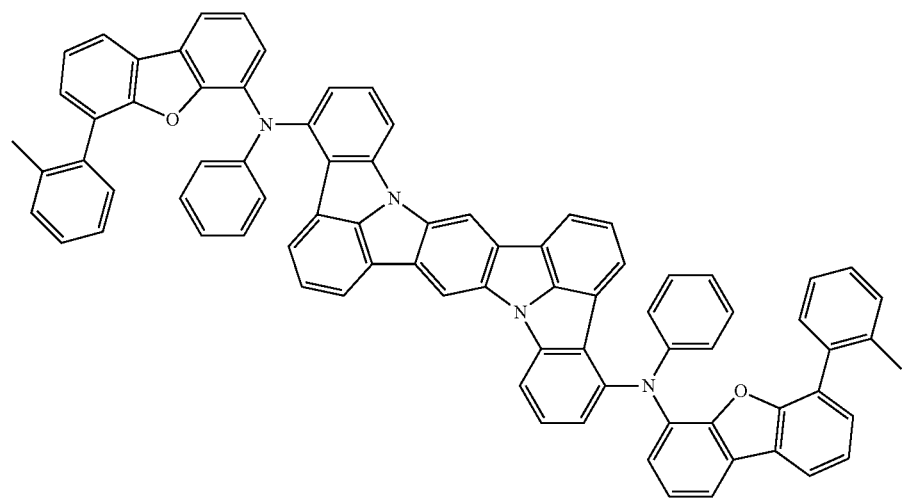
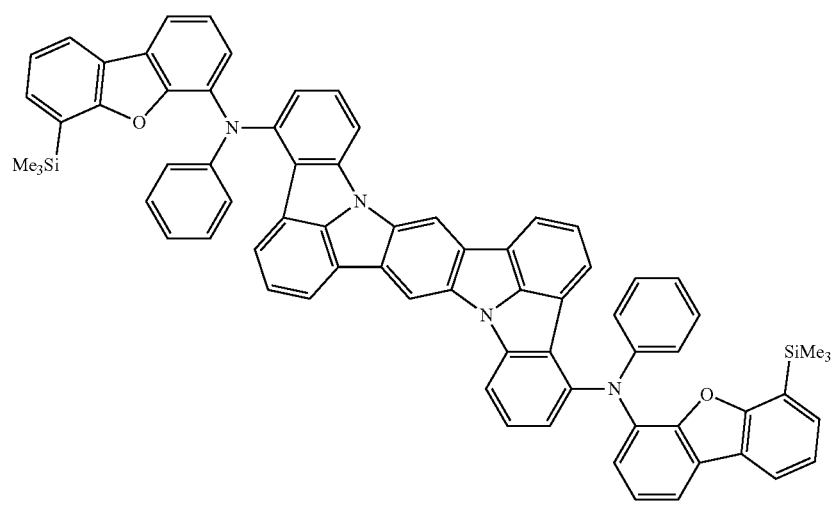
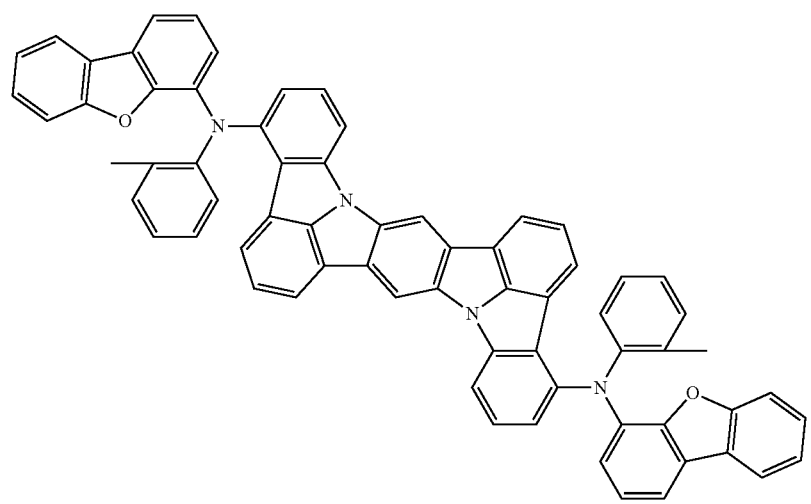

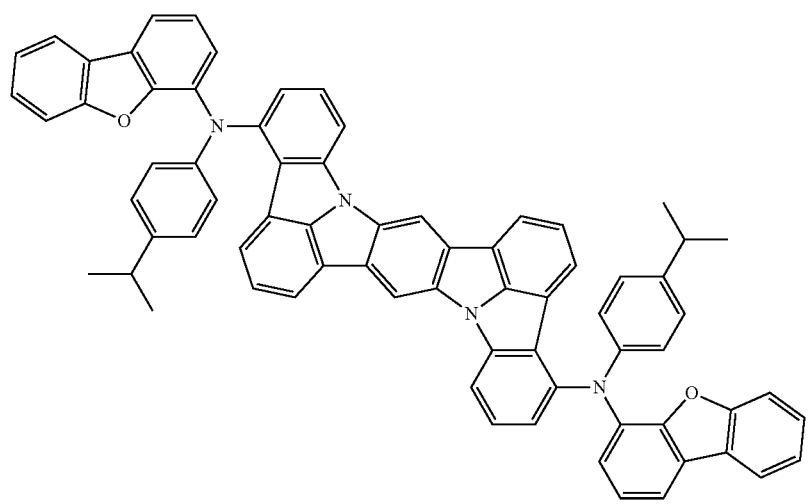

-continued
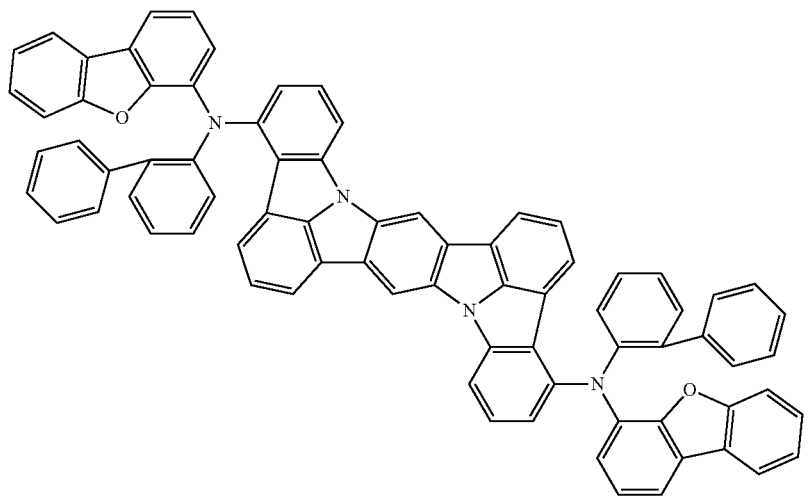
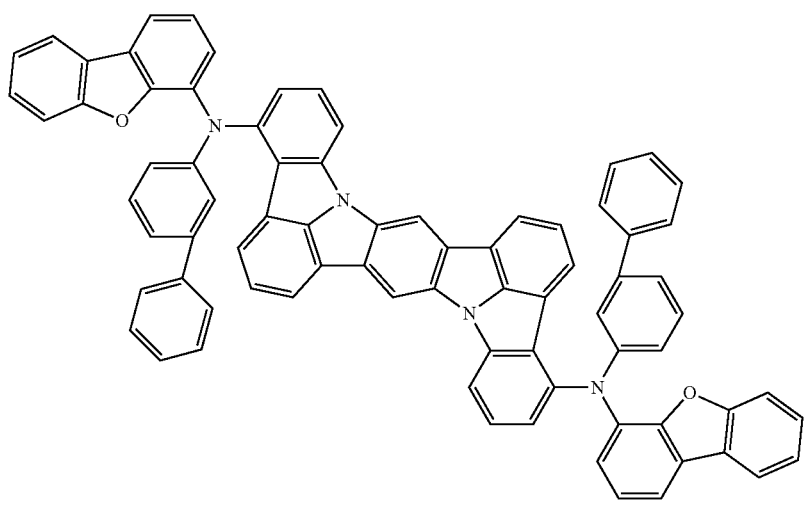
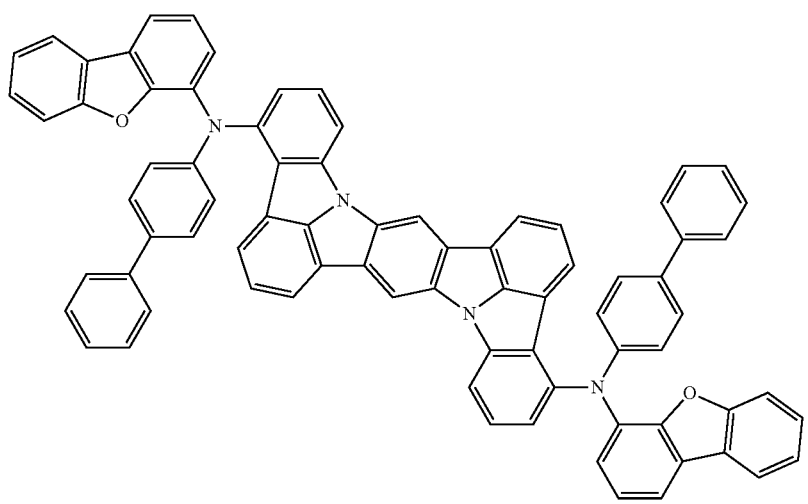

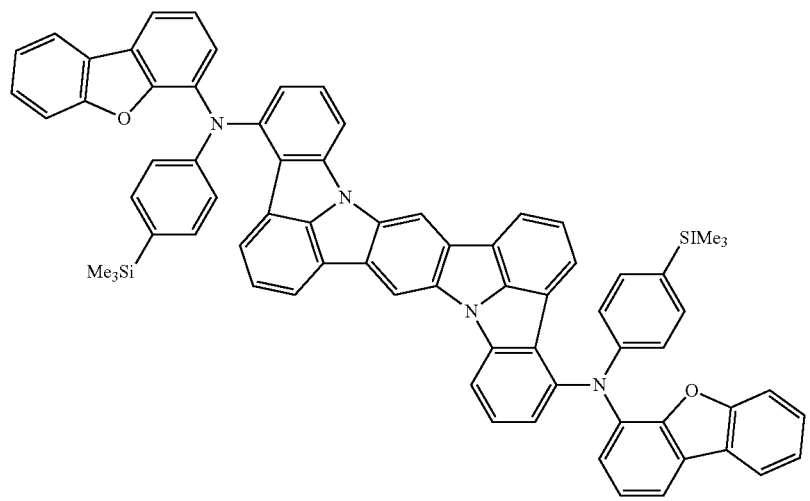
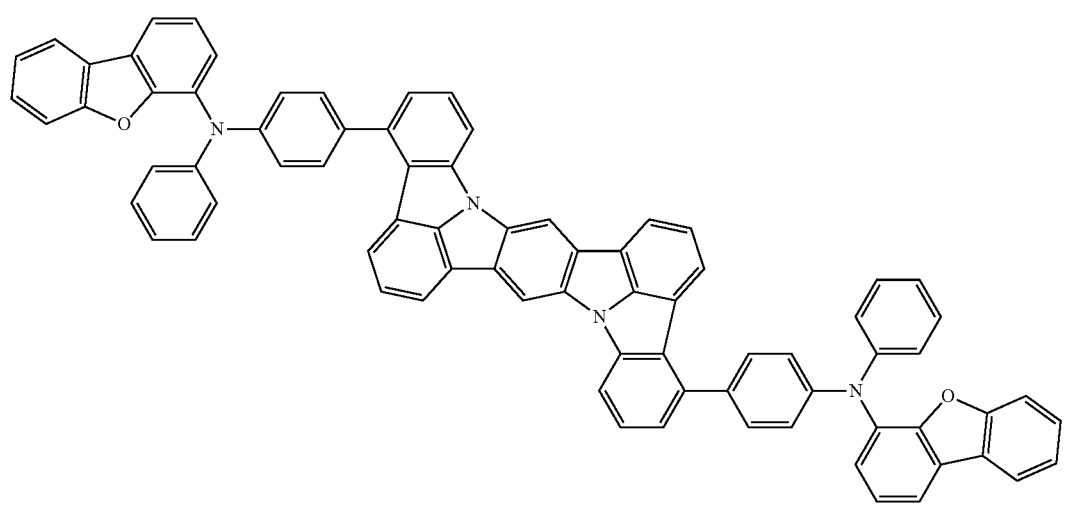
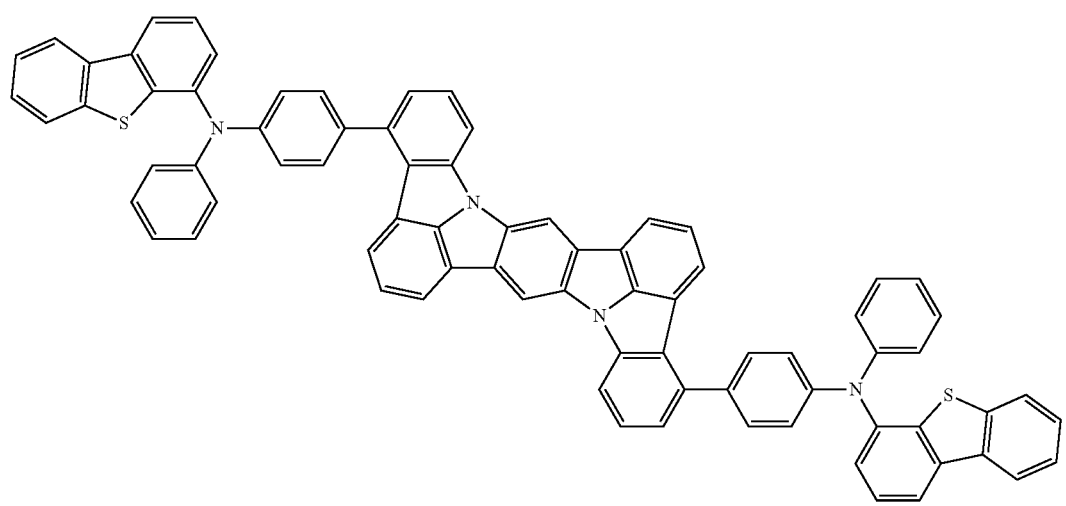

-continued
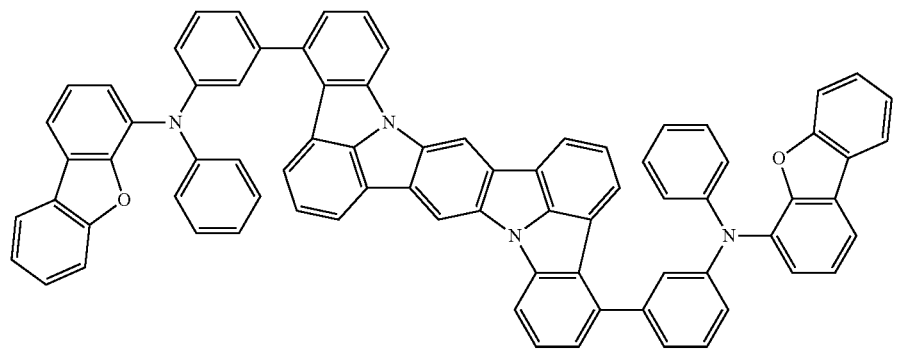
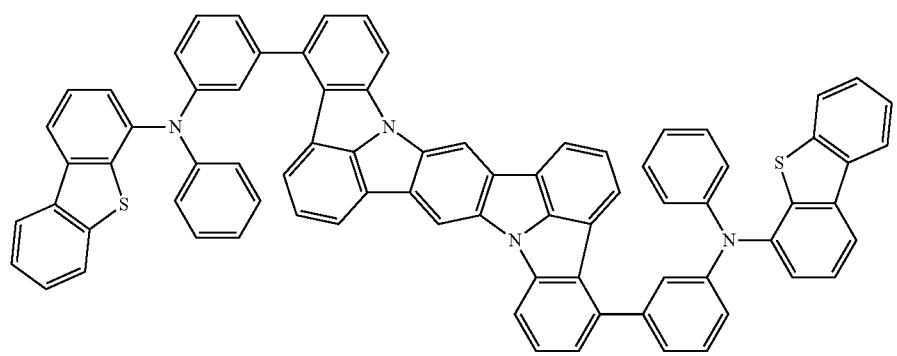
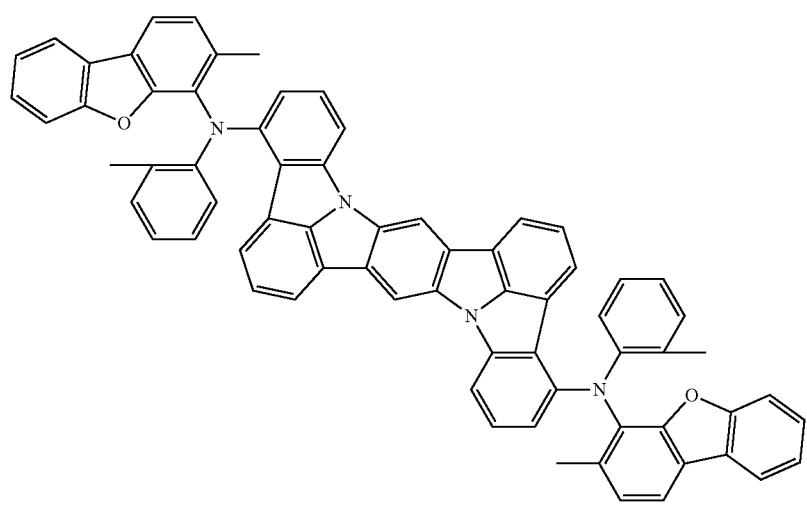
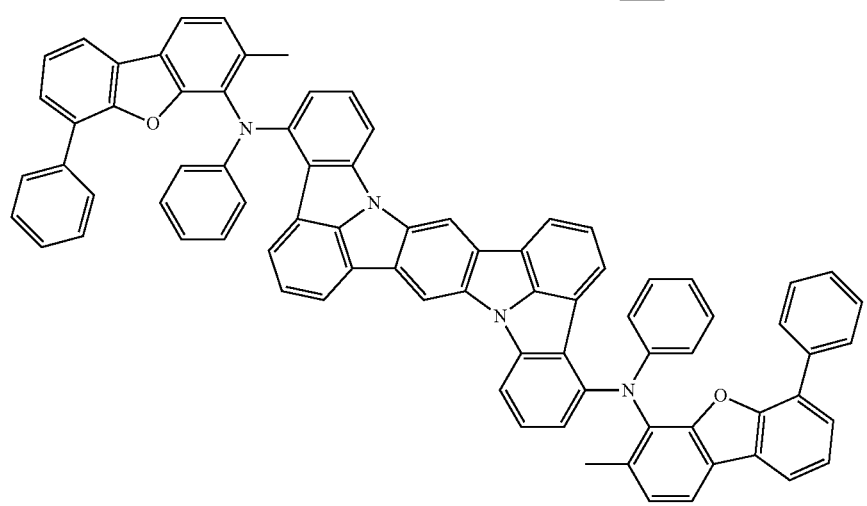

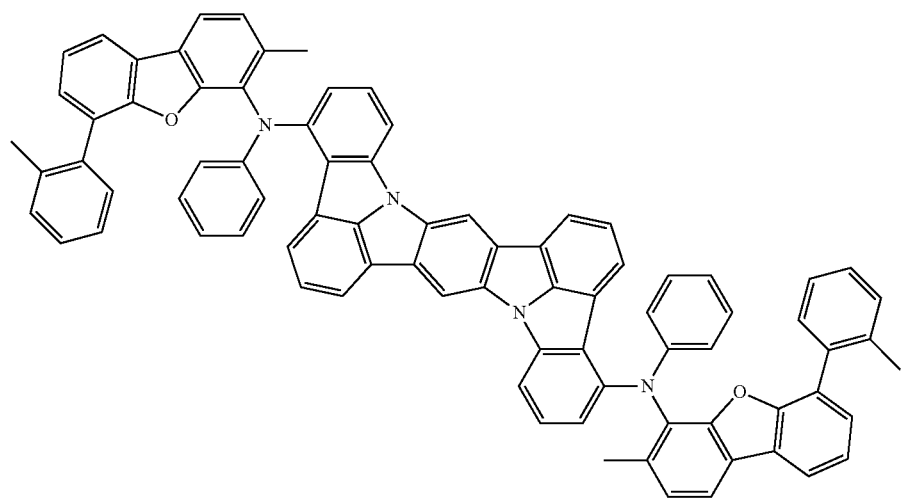
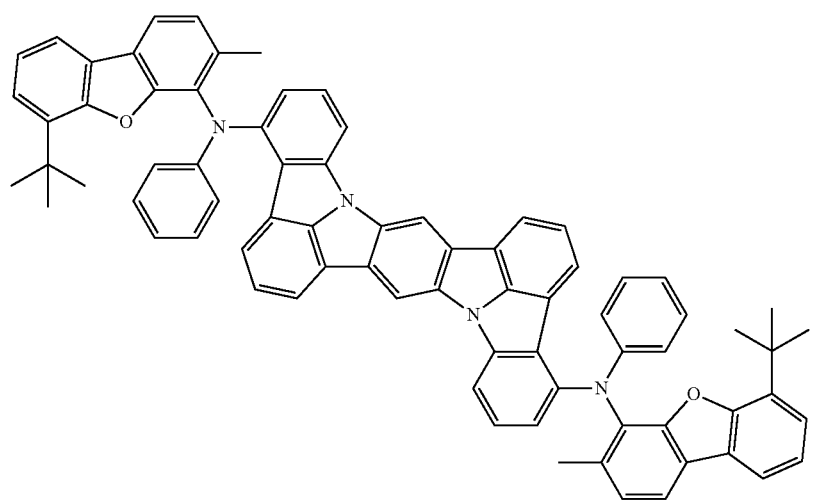
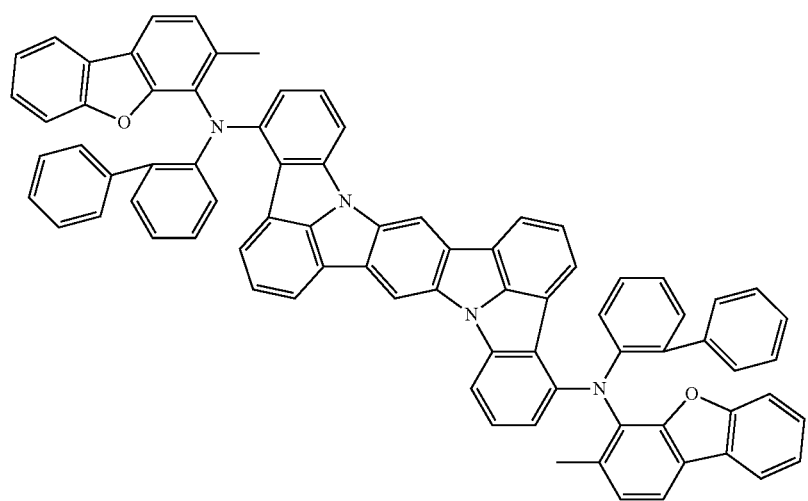

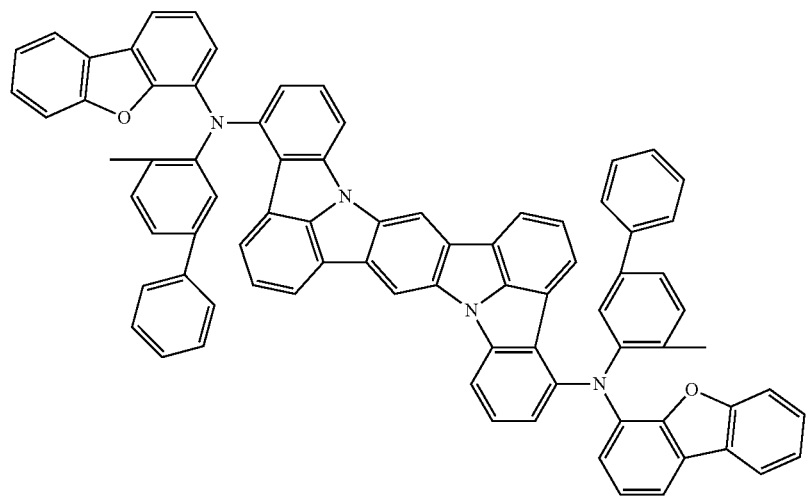
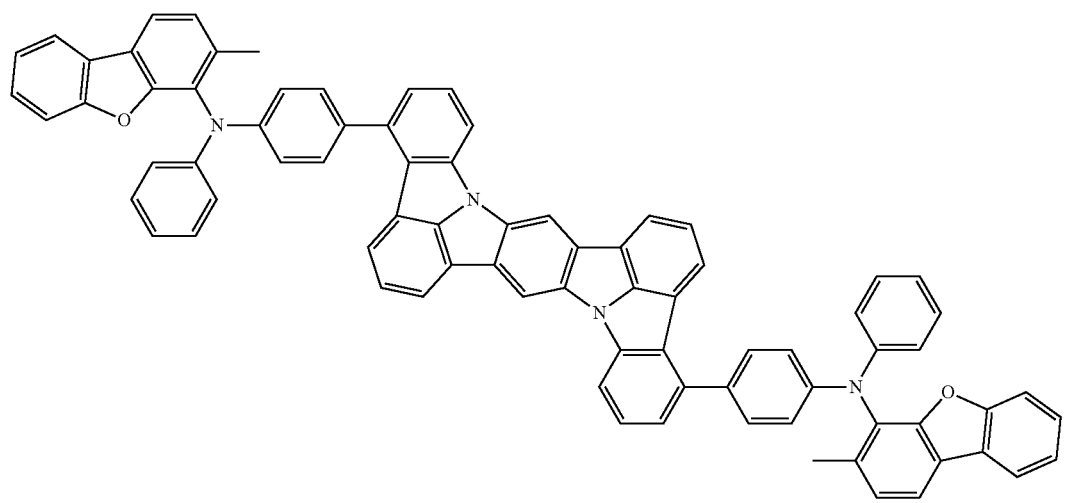
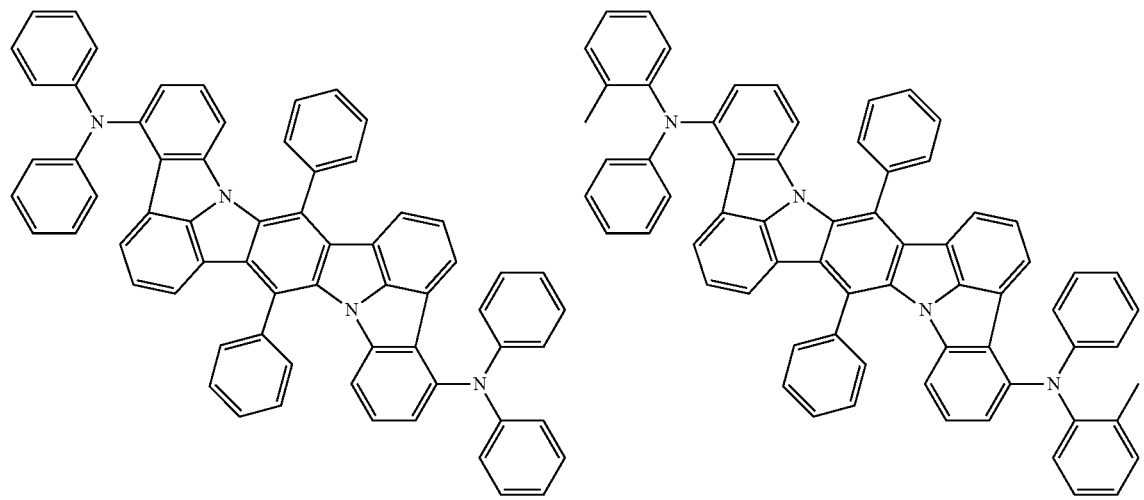

683
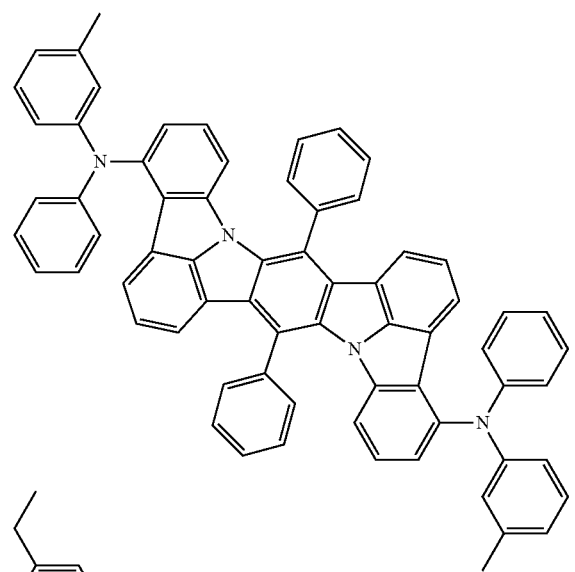
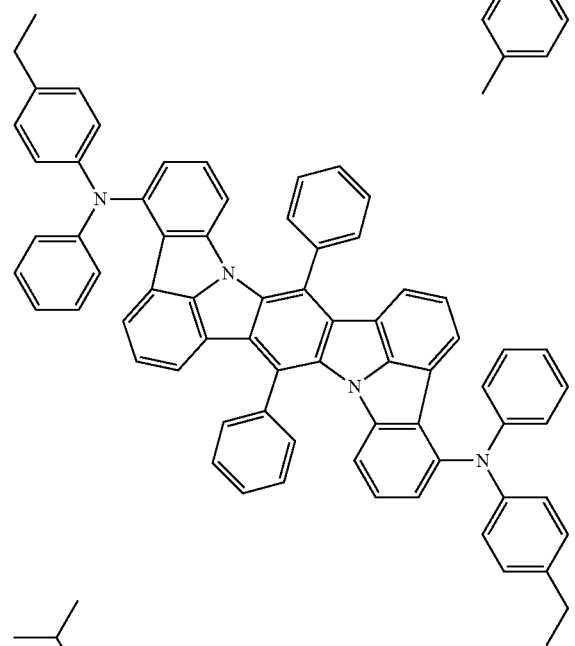
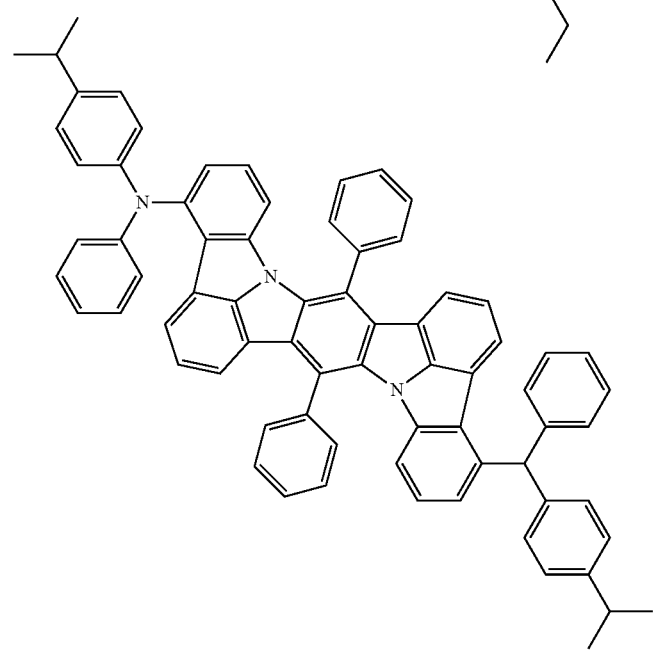
684
-continued
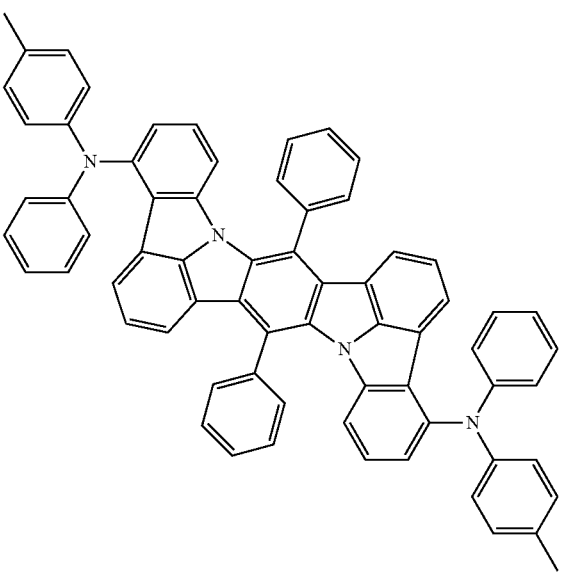

-continued
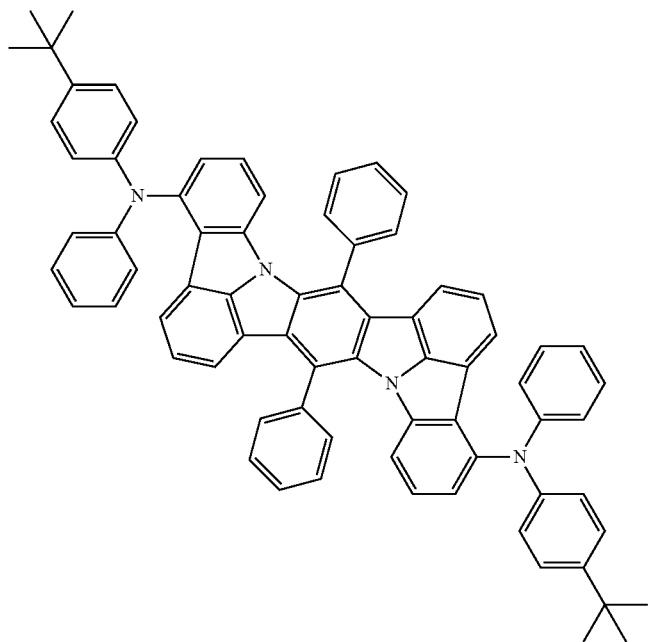
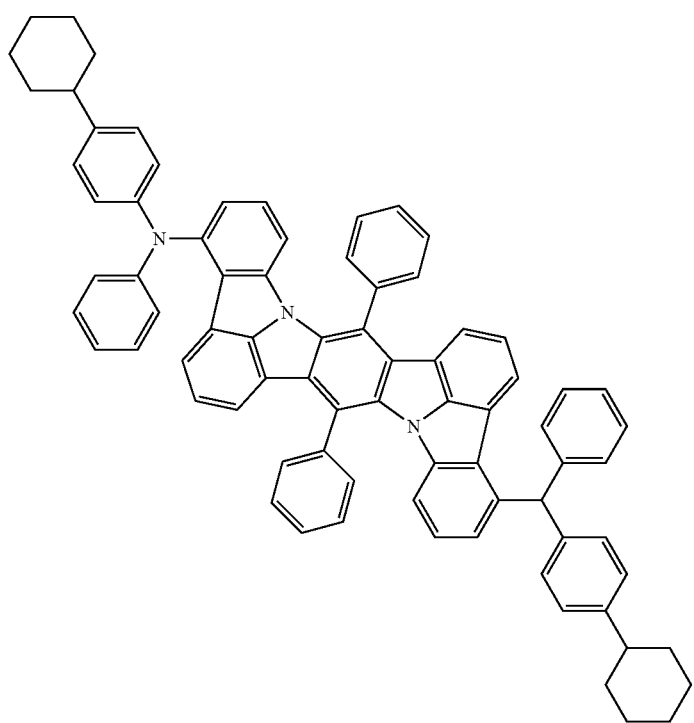

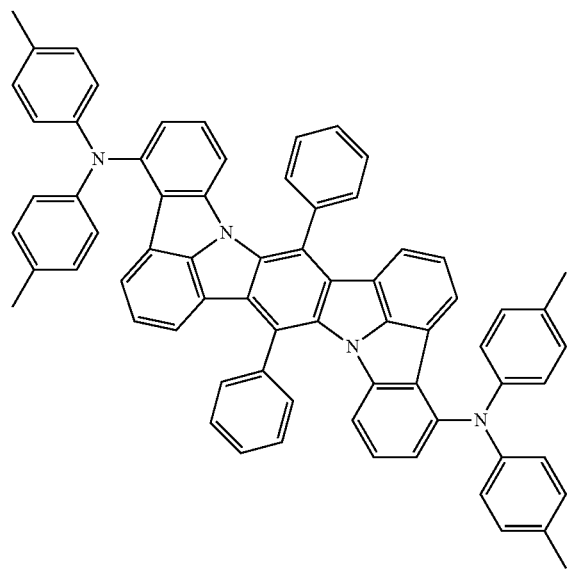
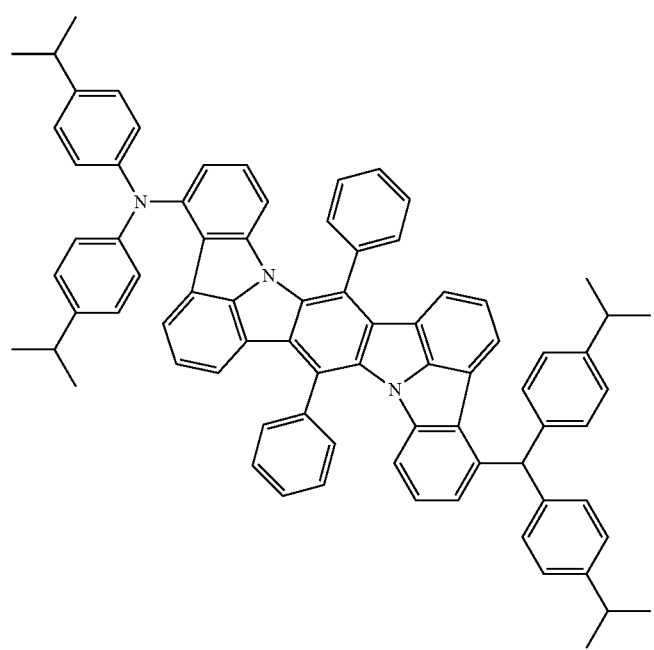

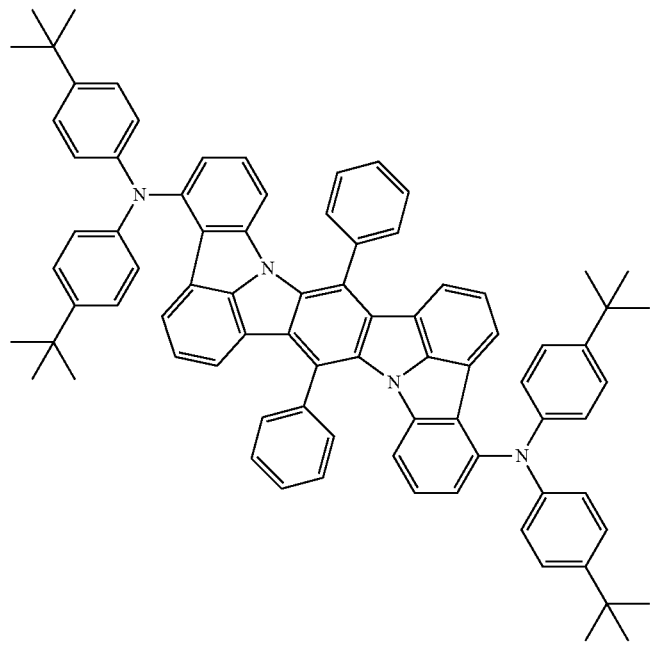
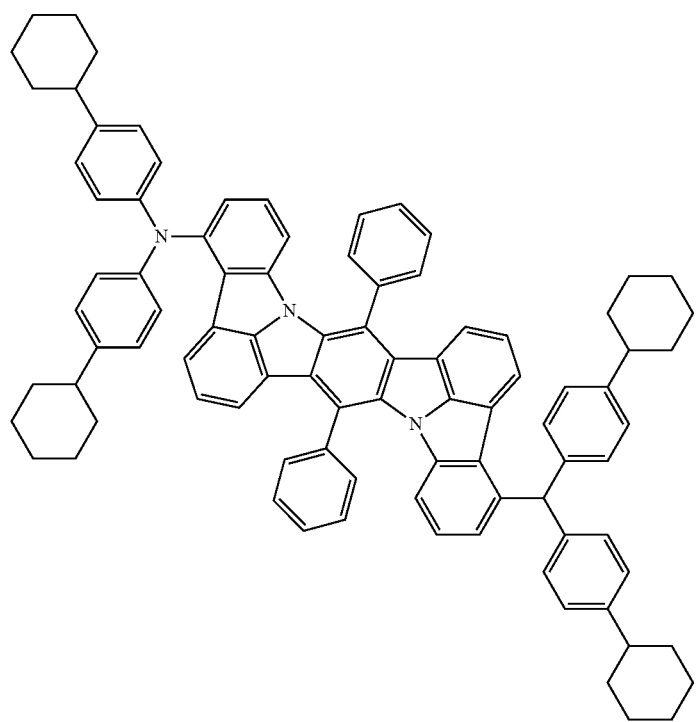

691
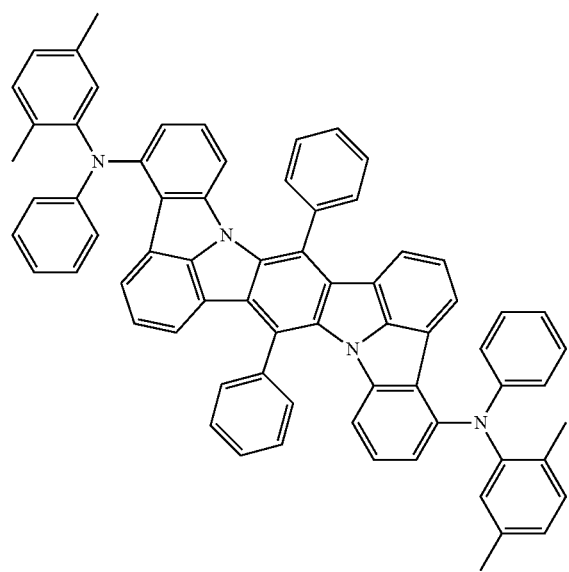
692
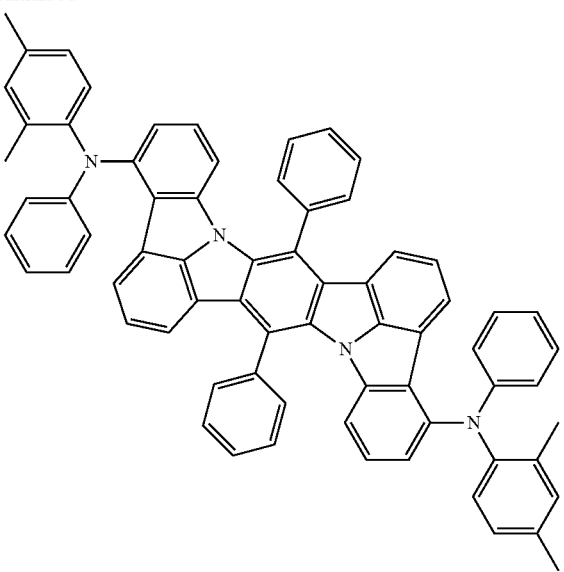
-continued
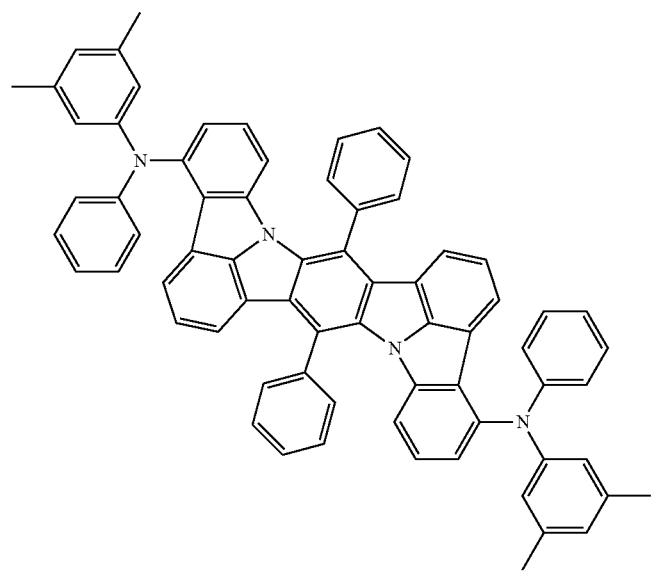
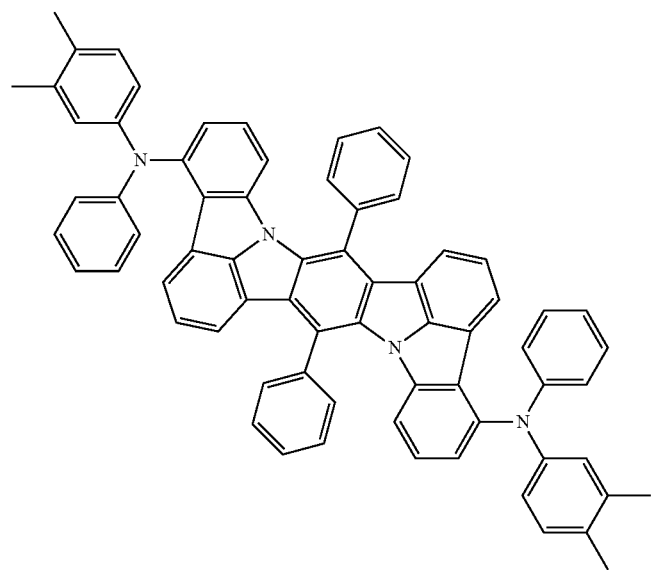

-continued
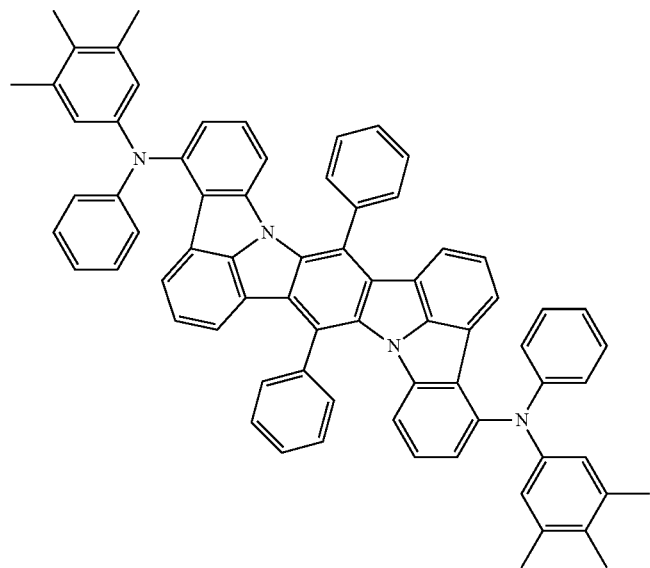
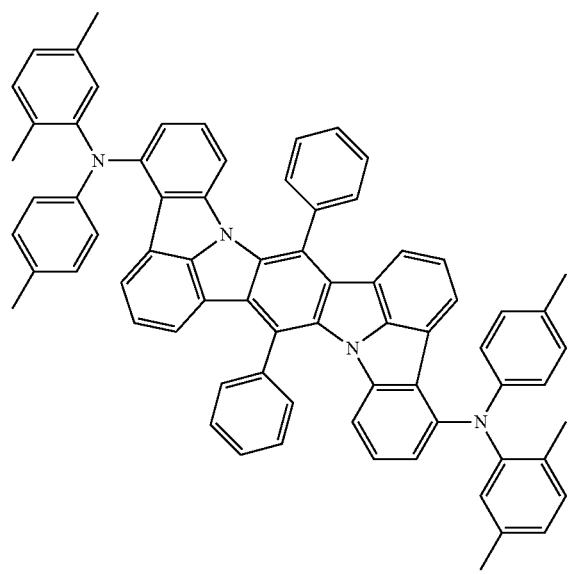
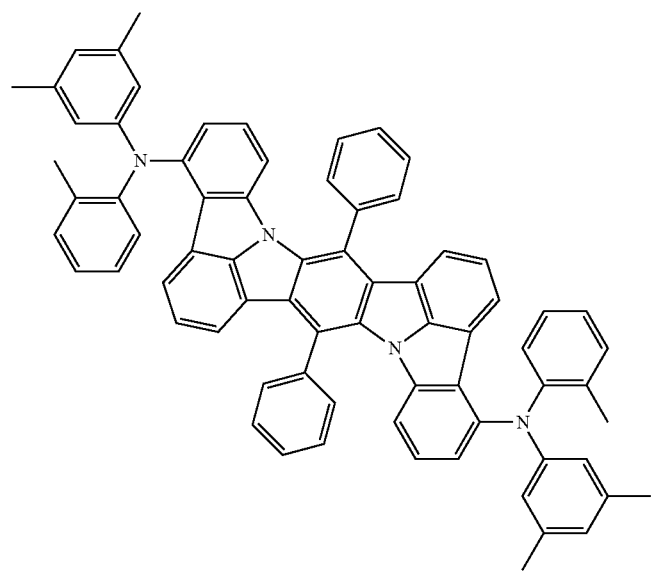

-continued
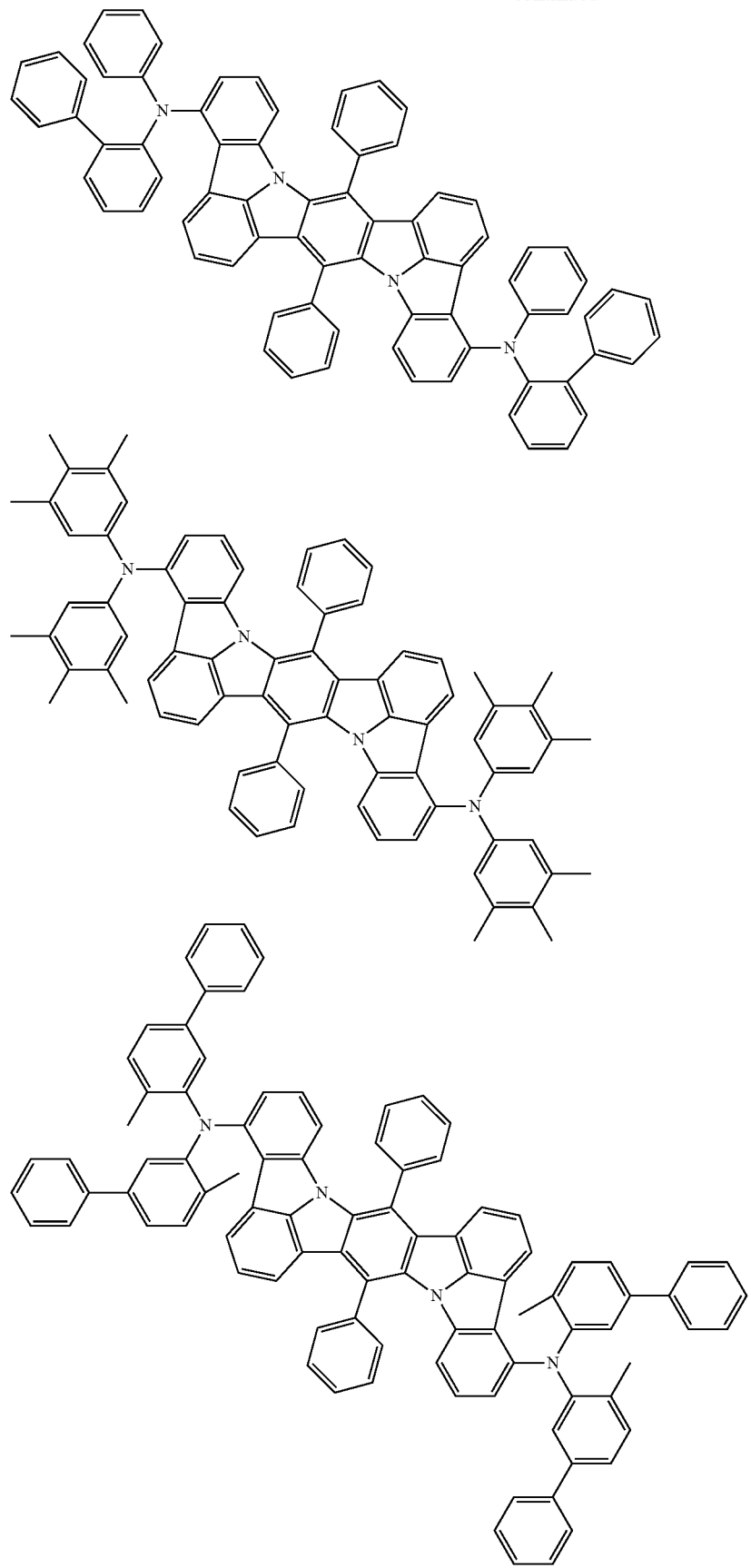

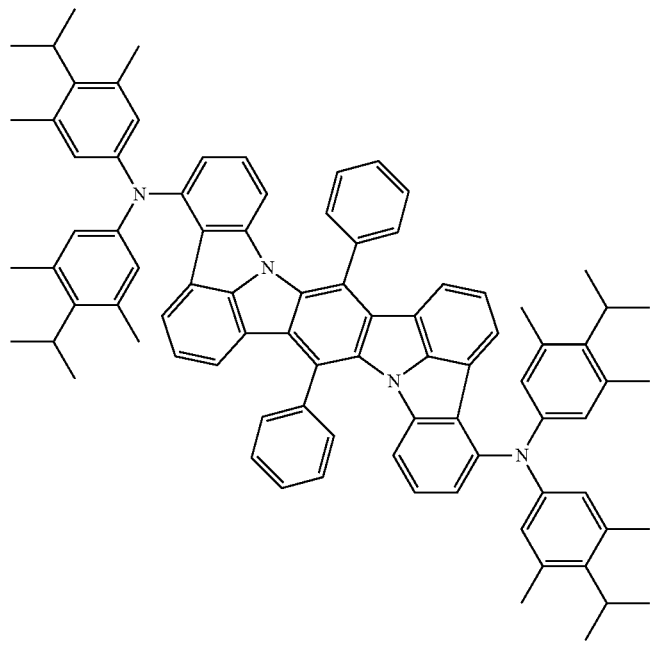
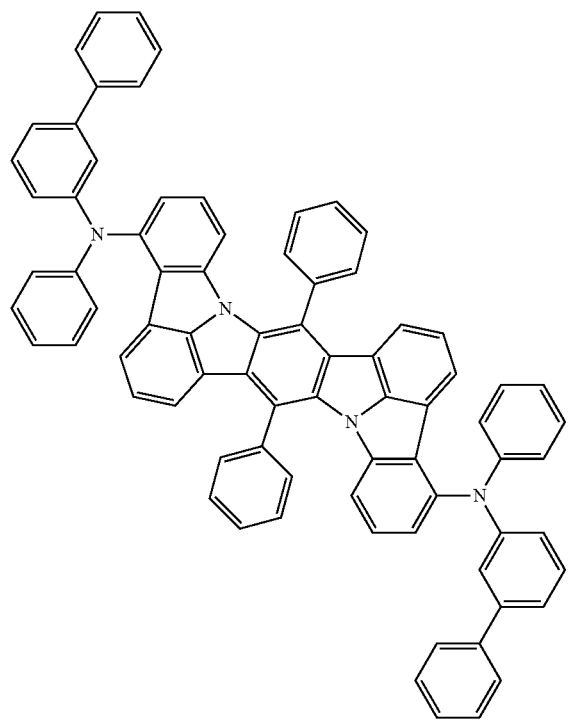

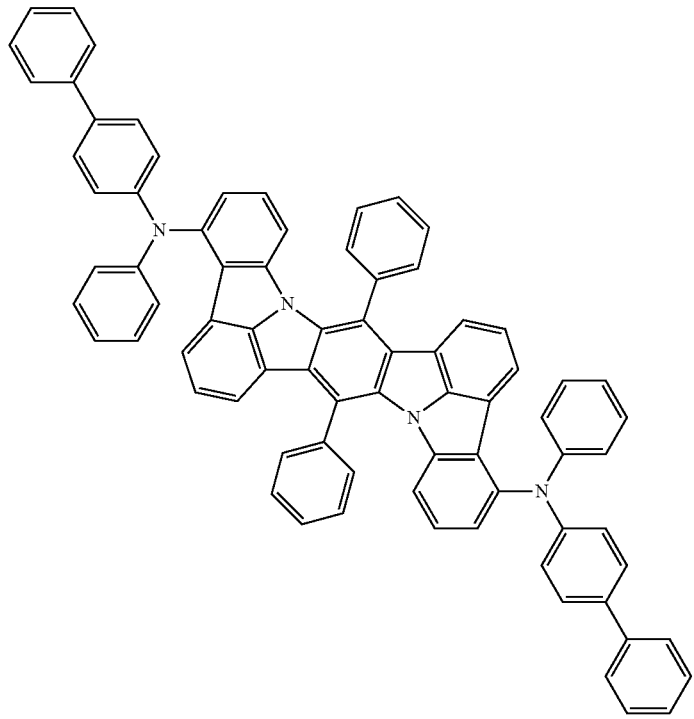
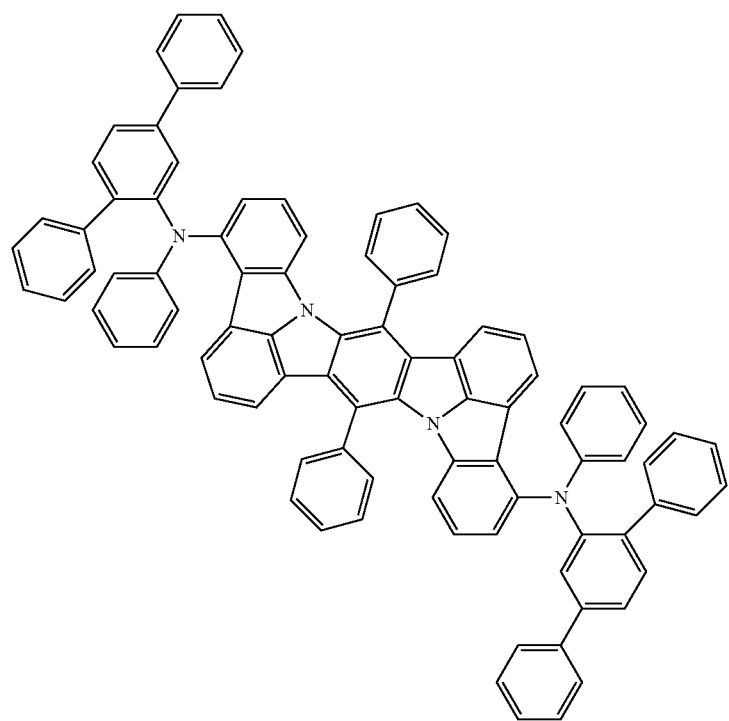

-continued
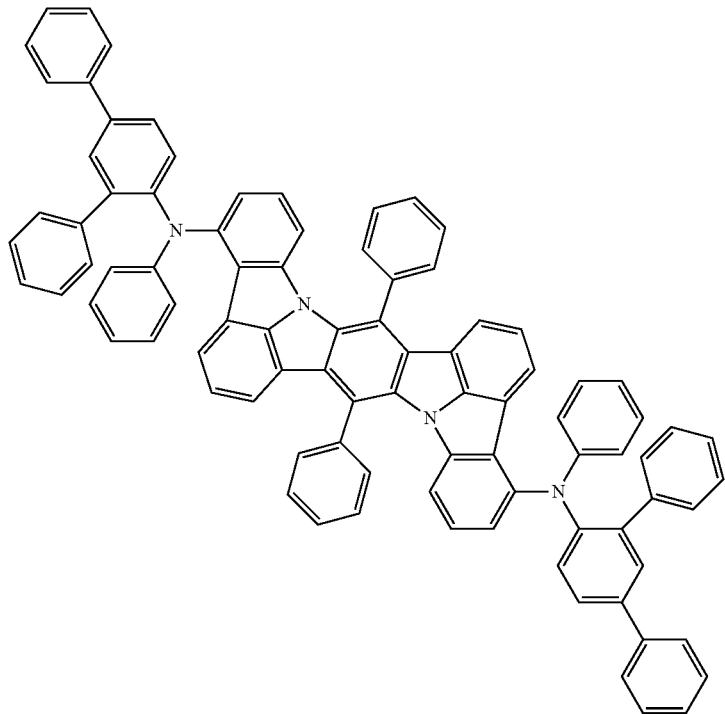 [SMILES: c1ccc(-c2ccc(N(c3ccccc3)c3cccc4c3c3cccc5c6c(-c7ccccc7)c7c(c(-c8ccccc8)c6n4c35)c3cccc4c5c(N(c6ccccc6)c6ccc(-c8ccccc8)cc6-c6ccccc6)cccc5n7c43)c(-c3ccccc3)c2)cc1]
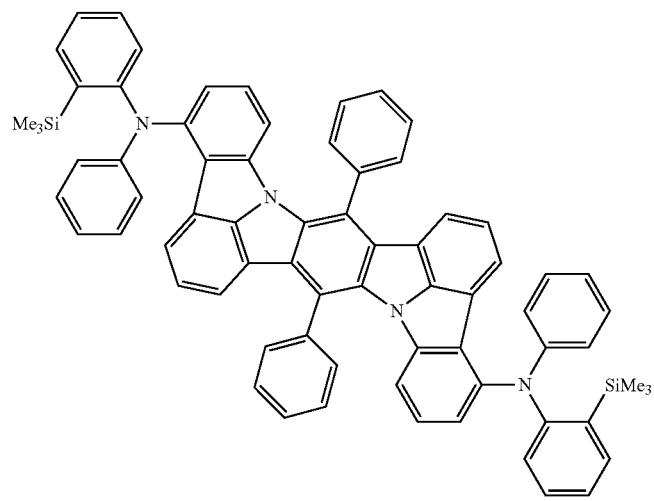

-continued
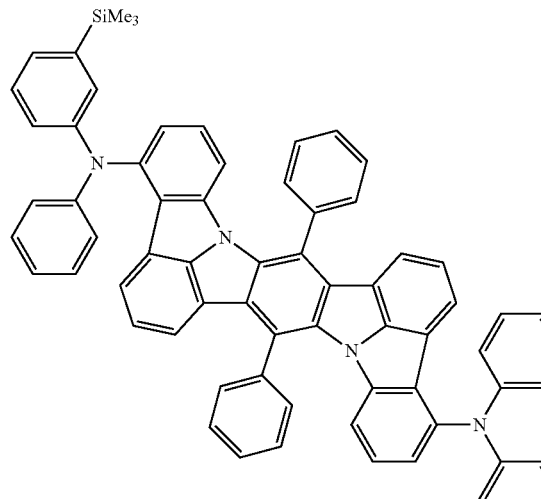
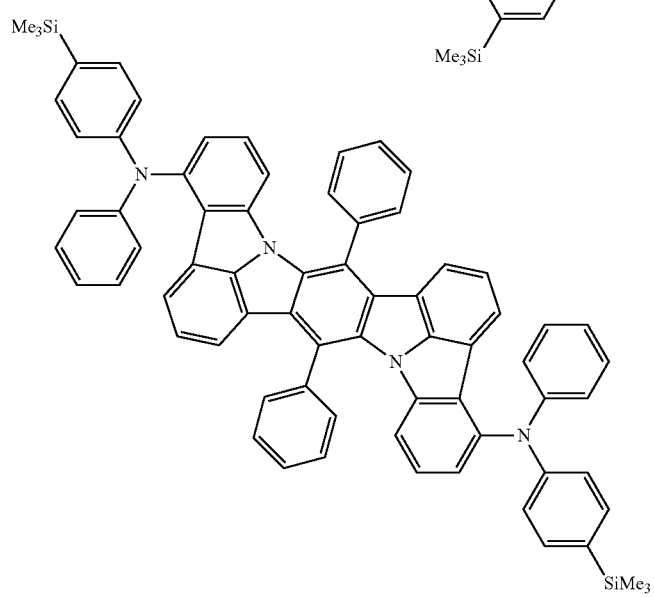
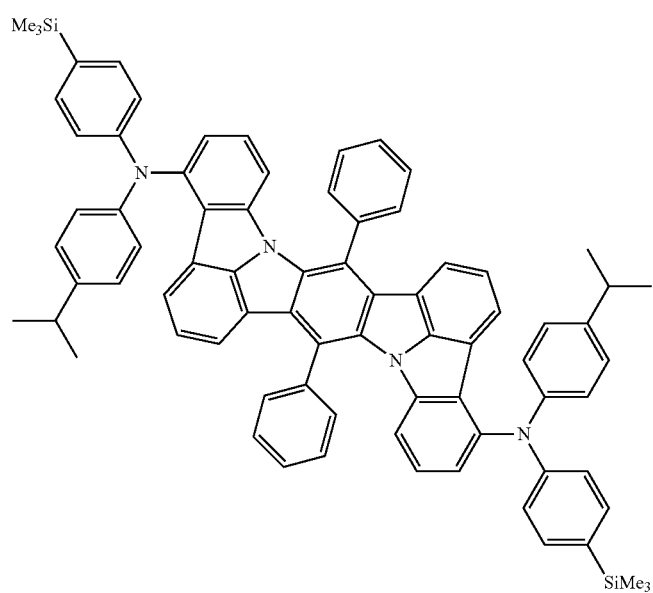

705
706
-continued
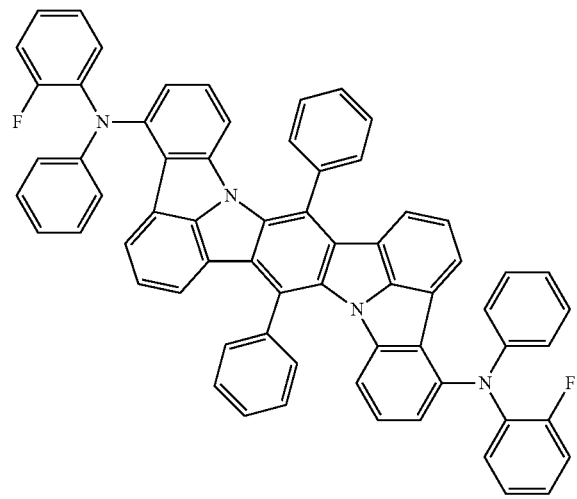
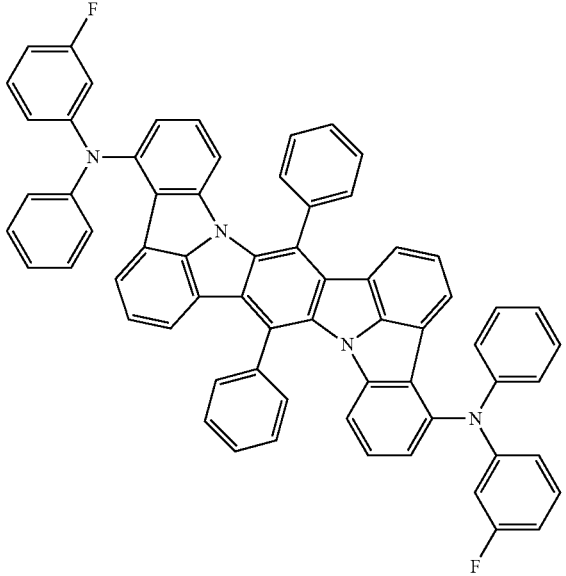
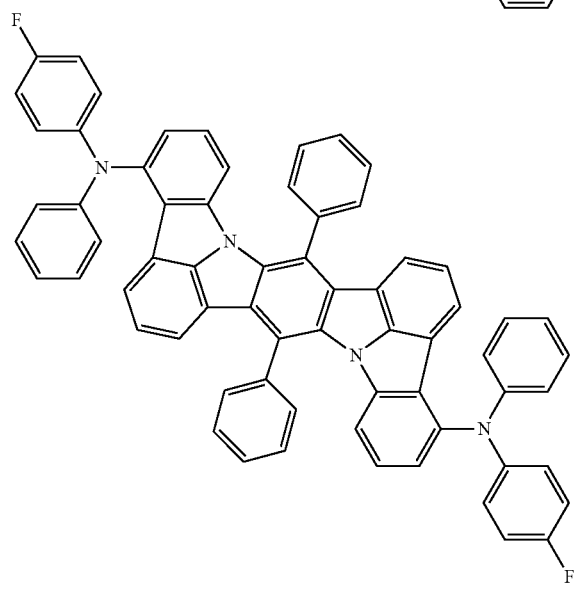
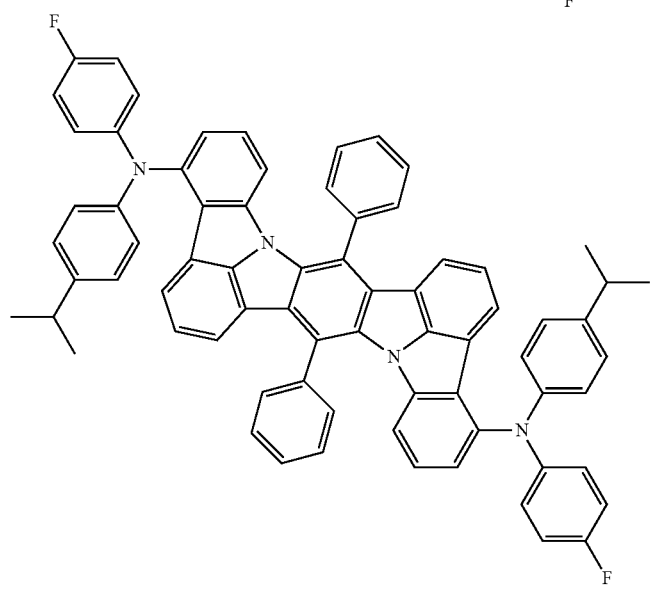

-continued
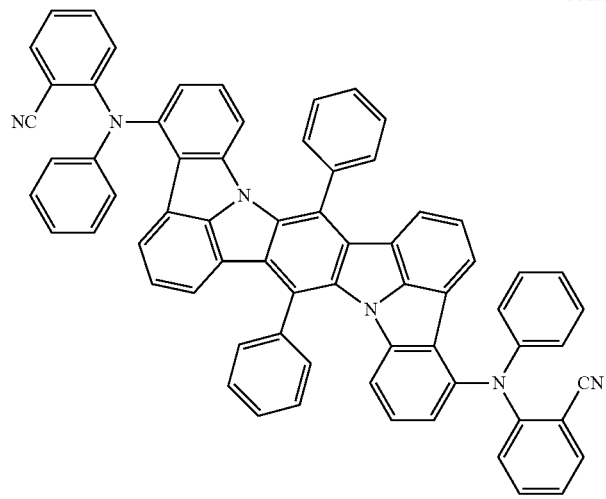
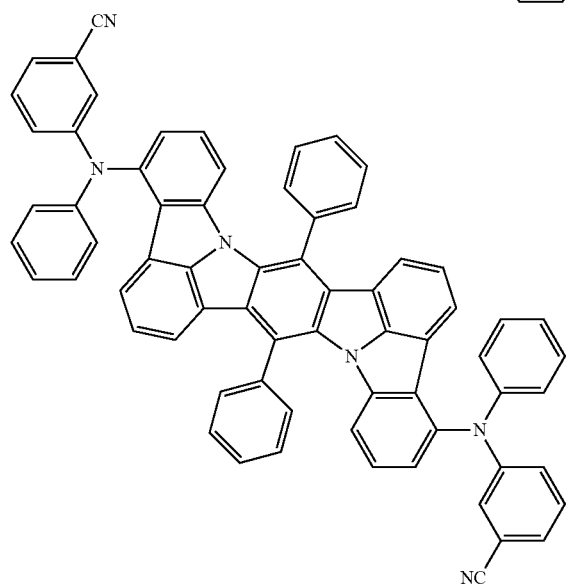
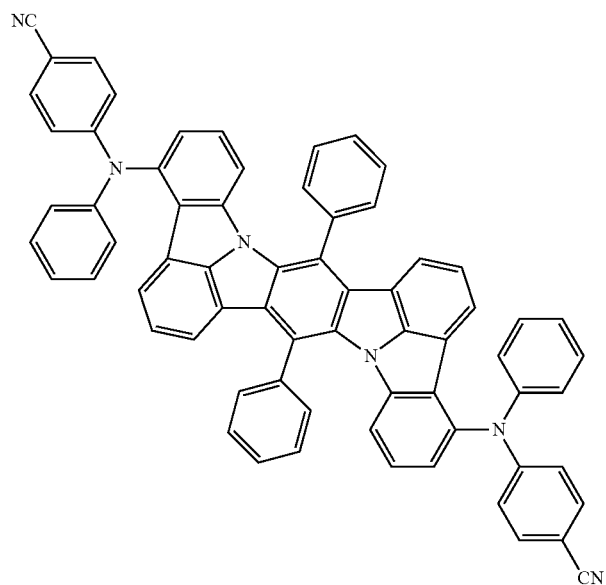

-continued
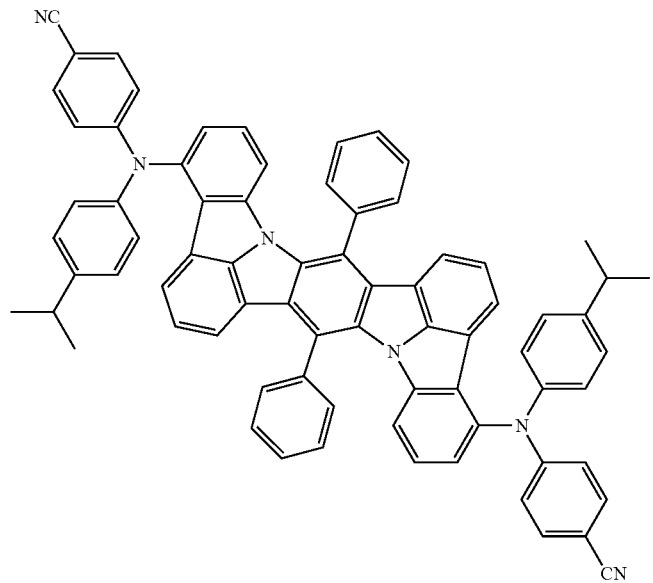
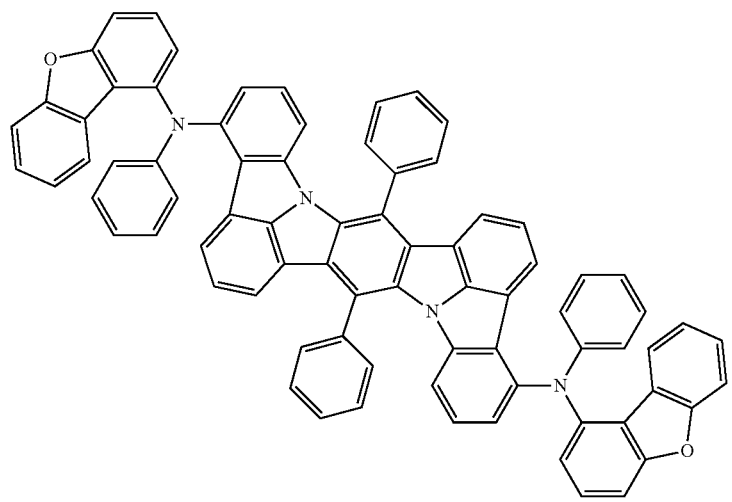
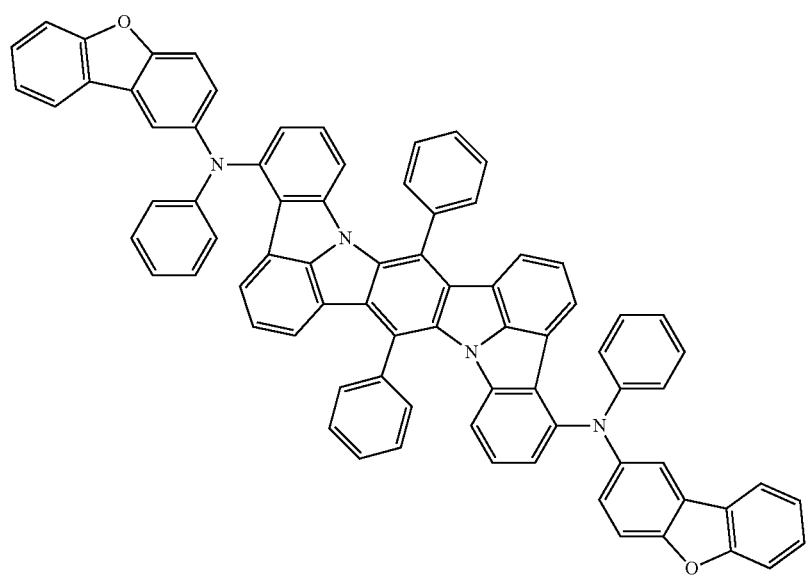

-continued
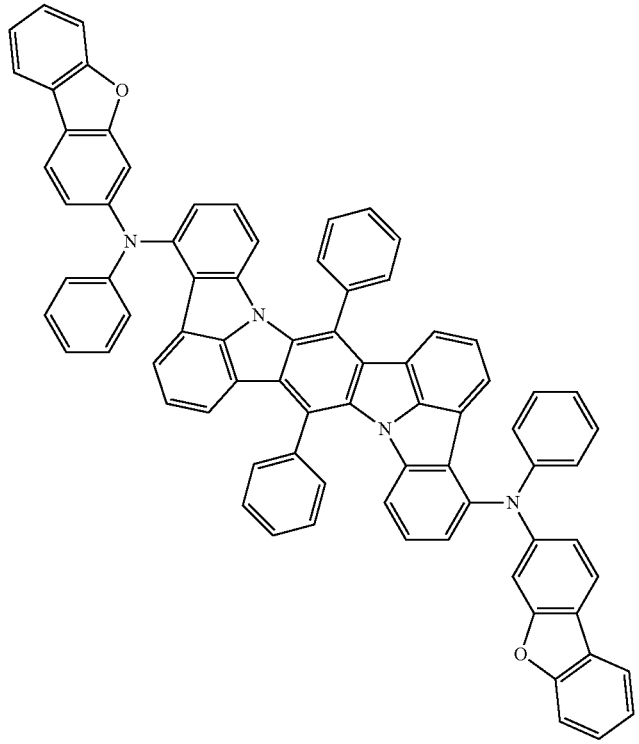
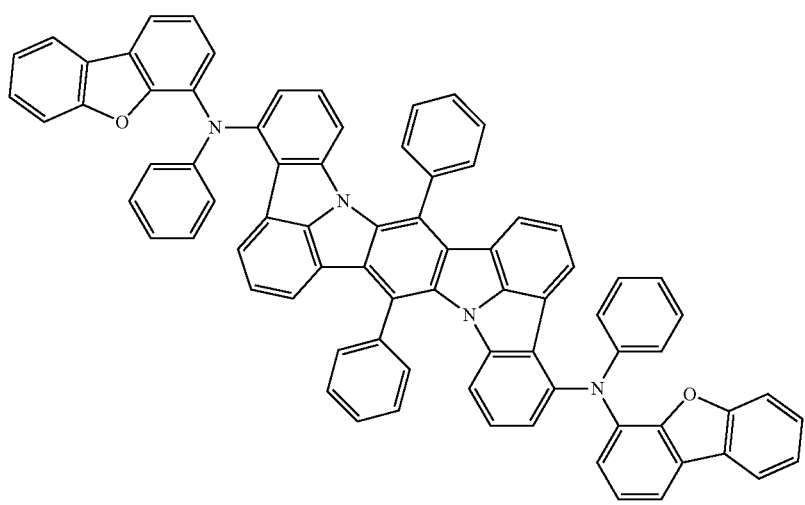

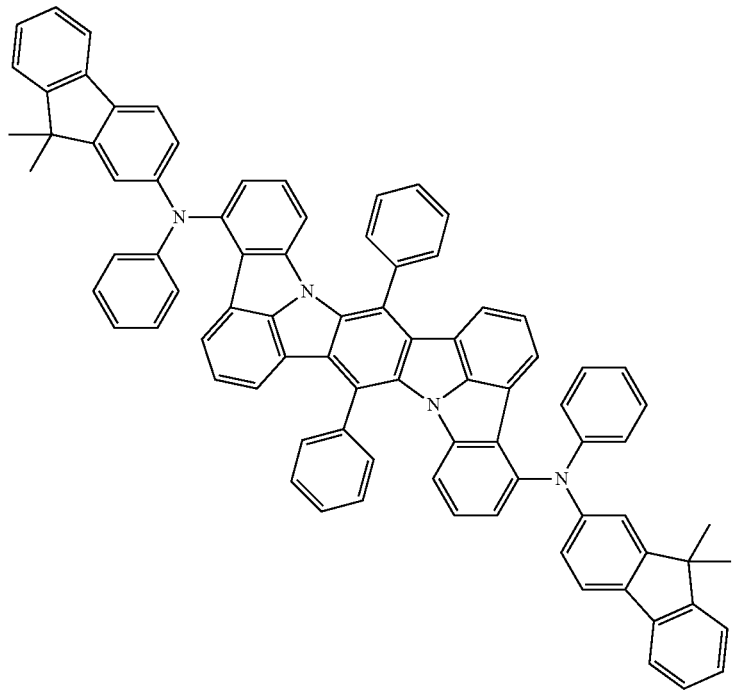
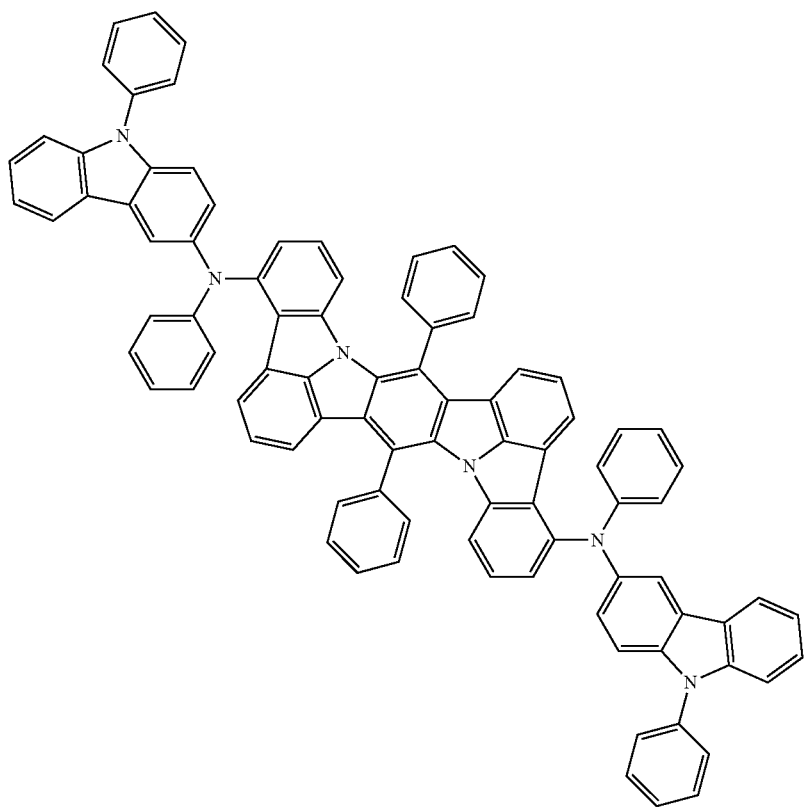

-continued
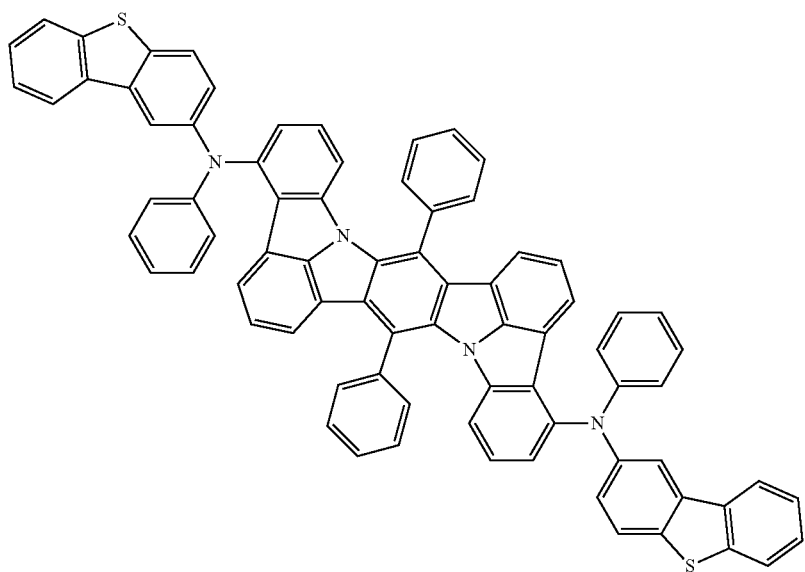
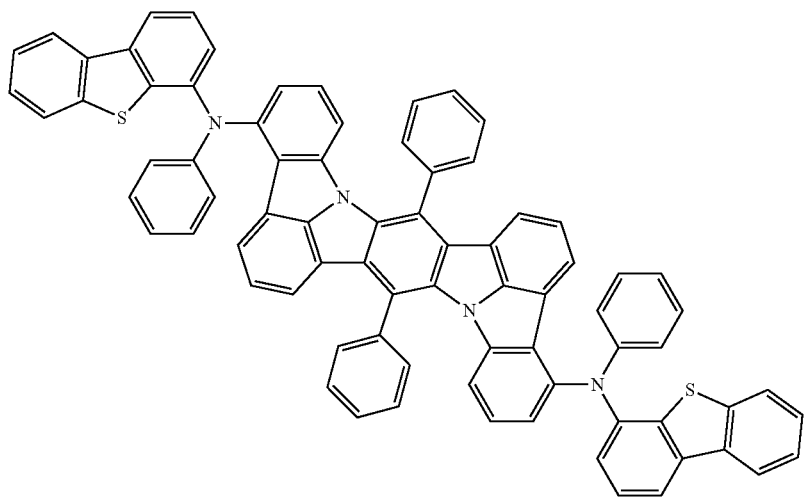
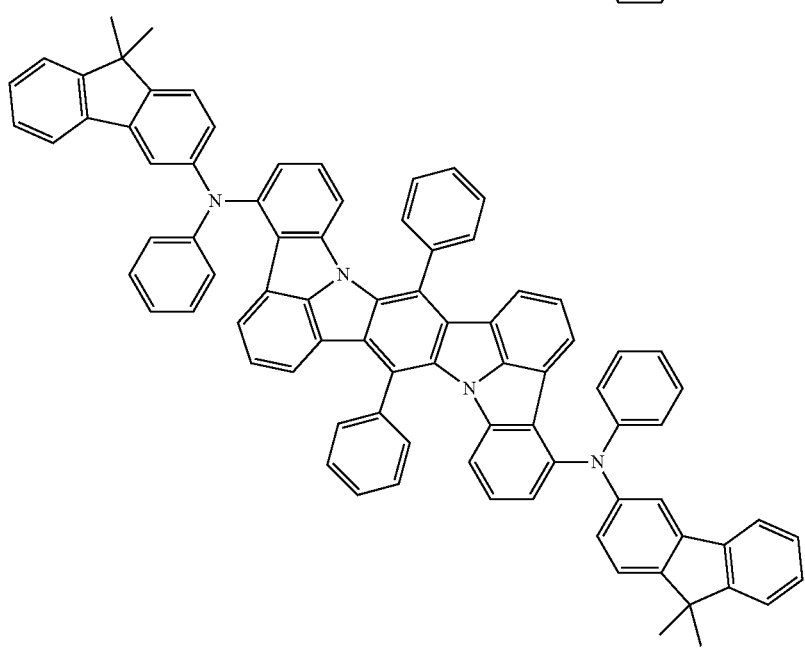

-continued
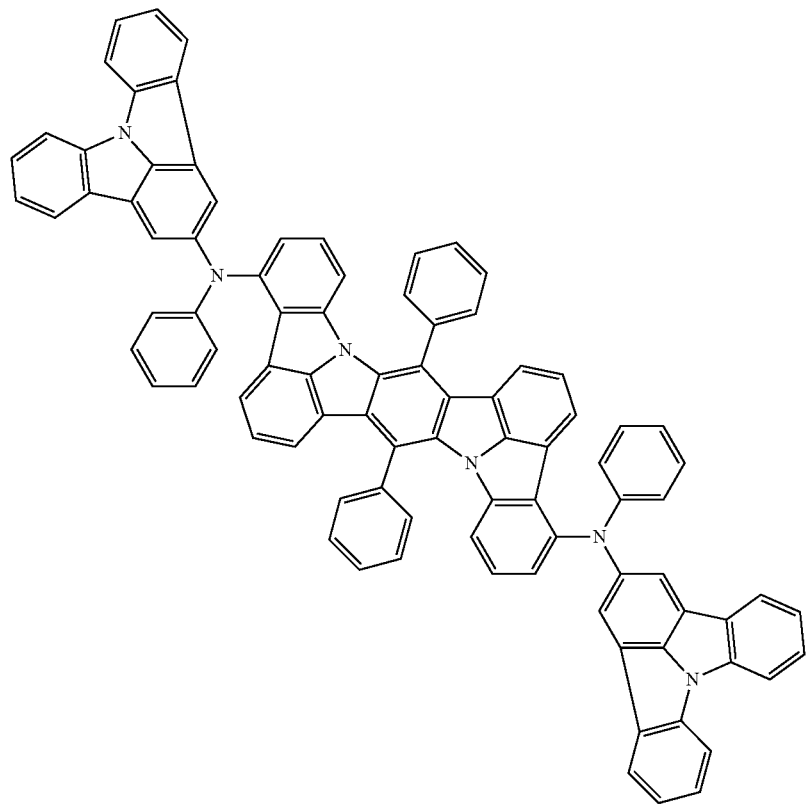
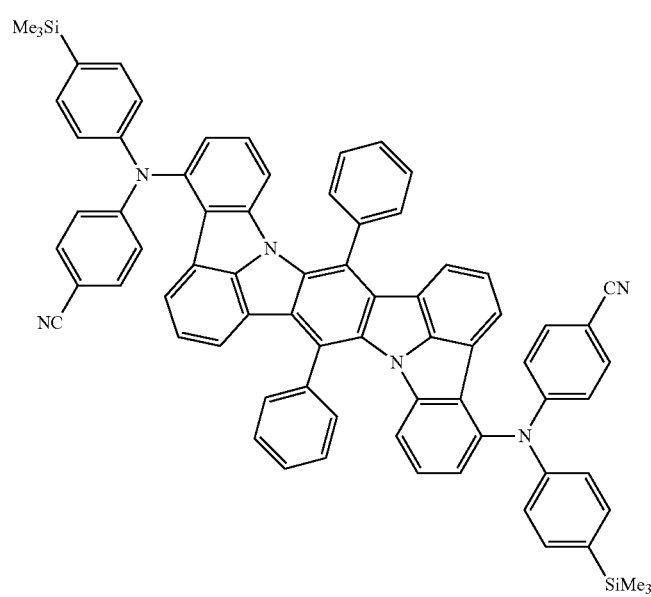

-continued
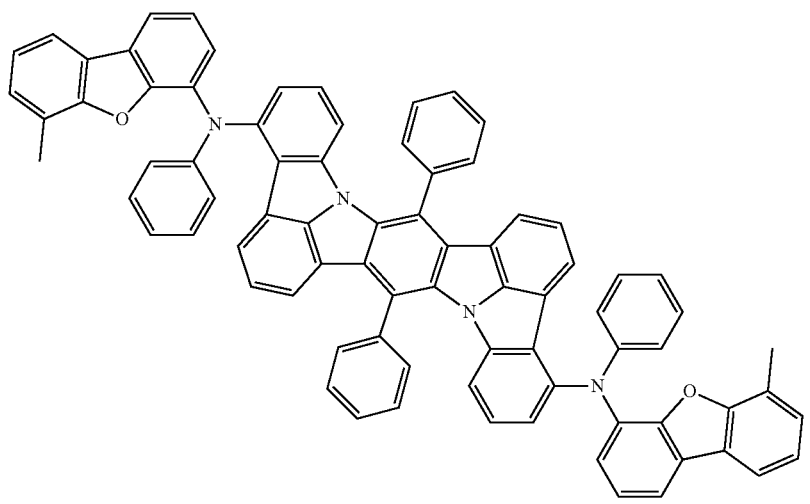
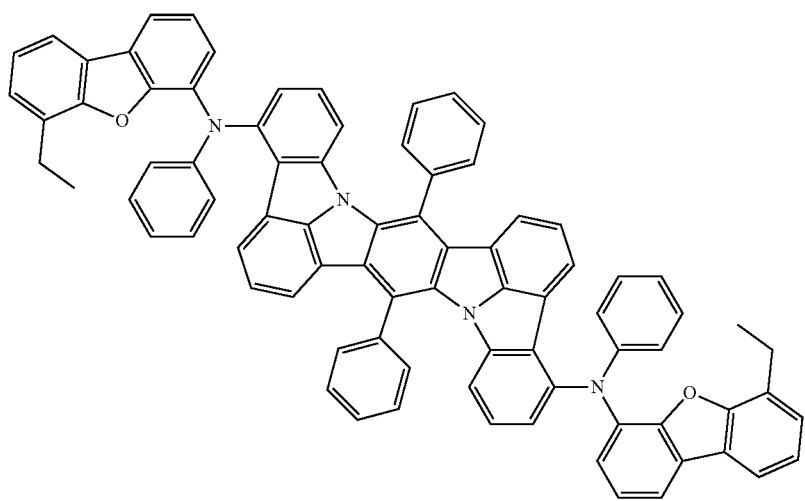
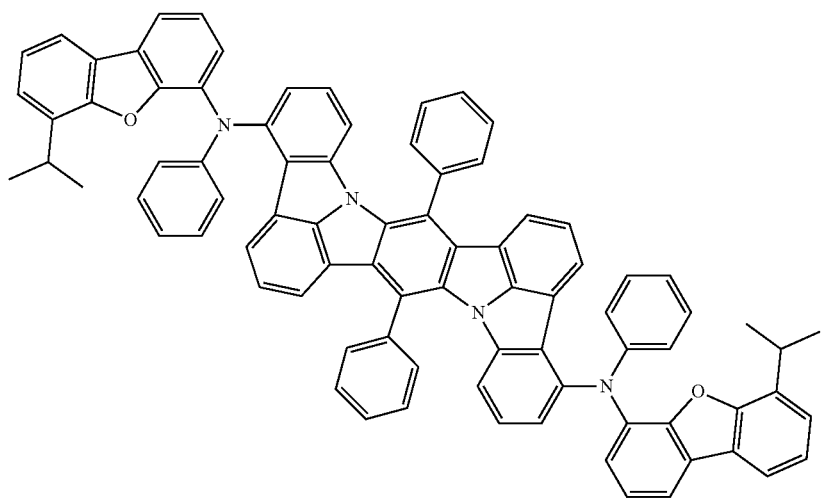

-continued
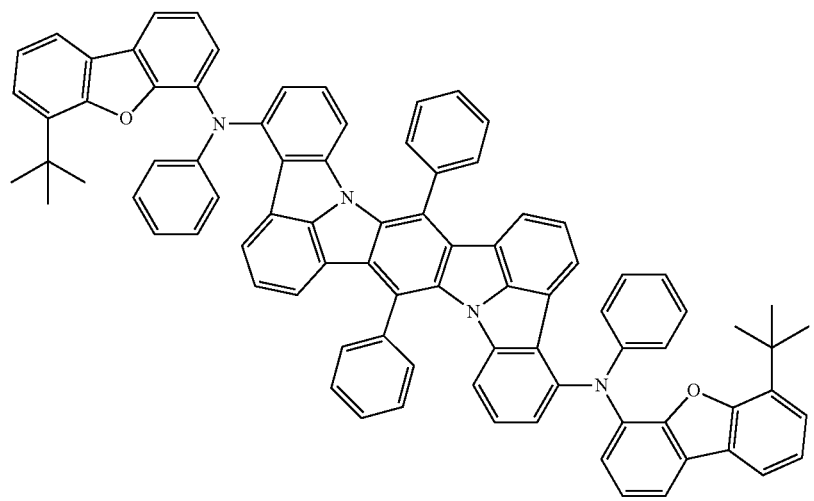
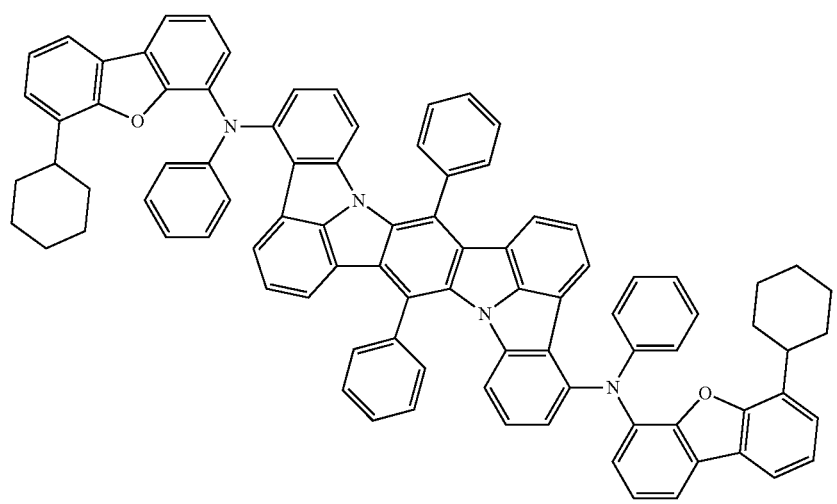
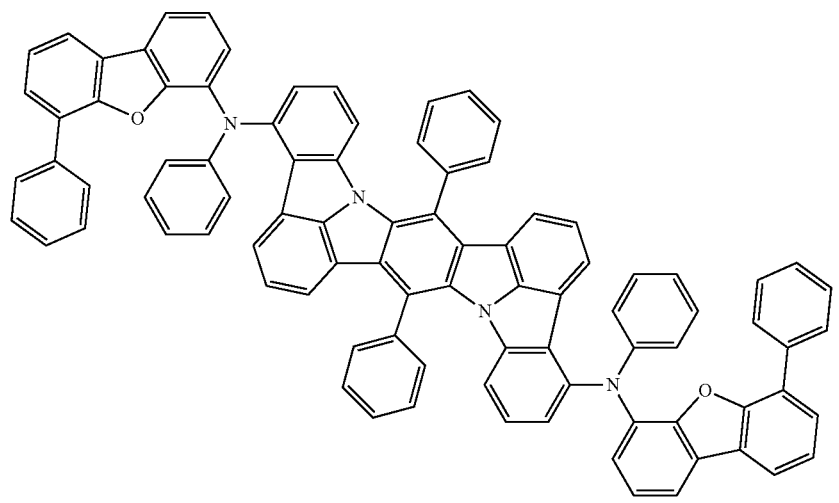

-continued
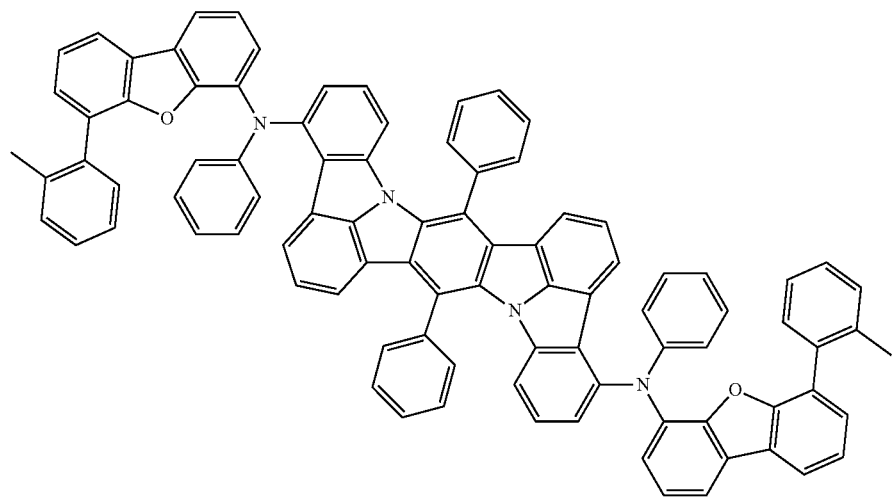
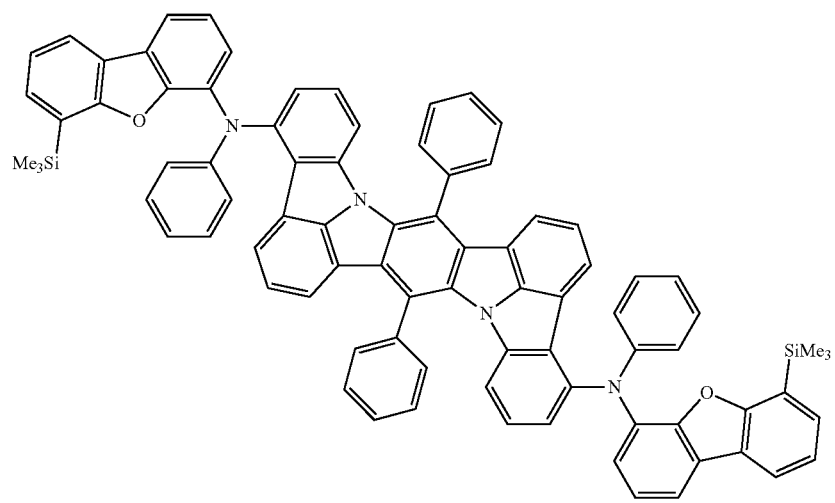
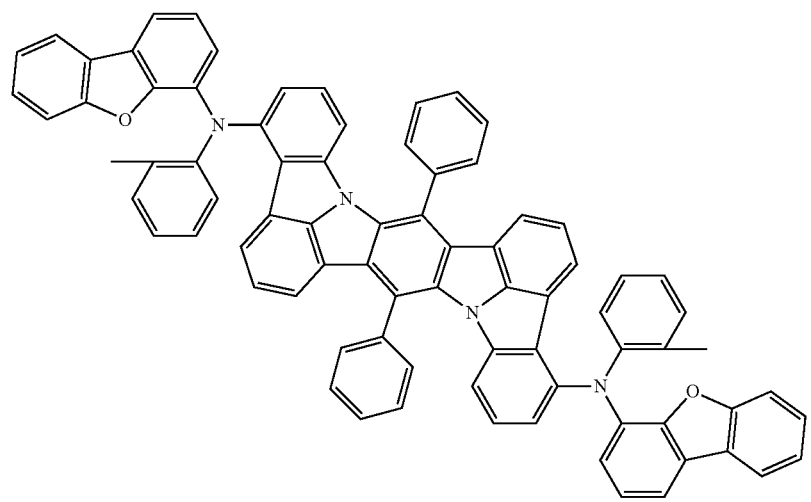

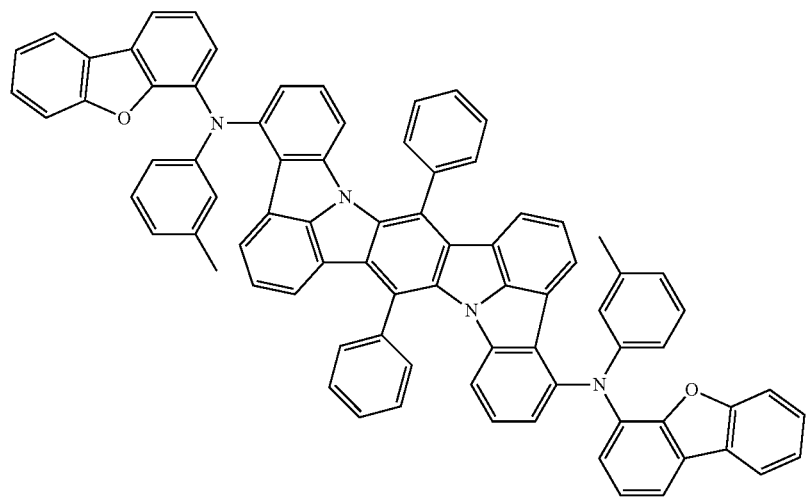
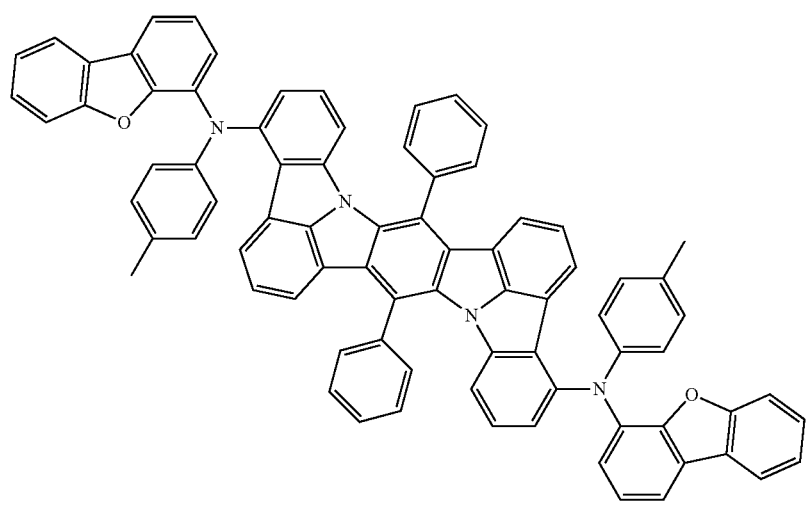
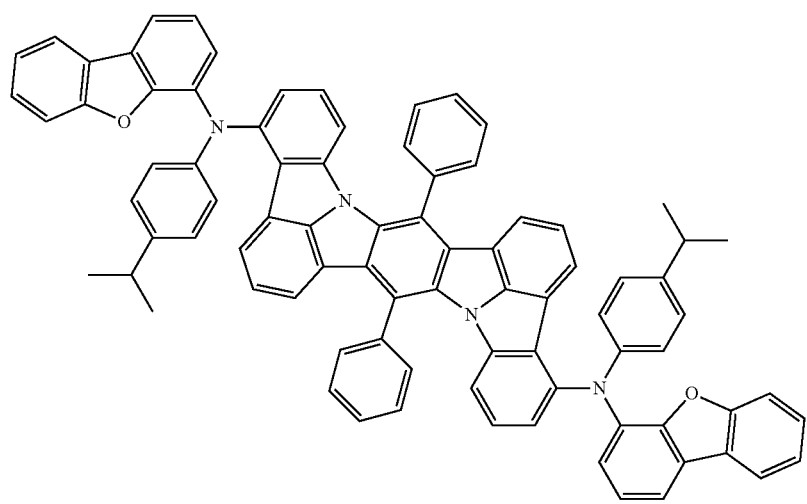

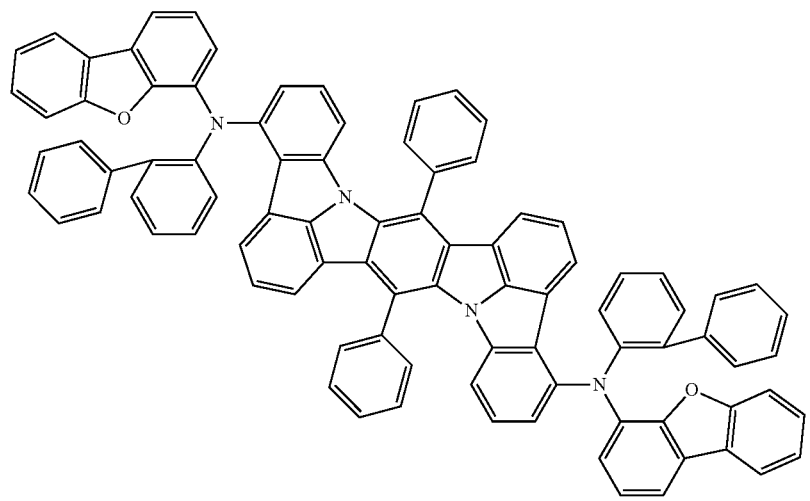
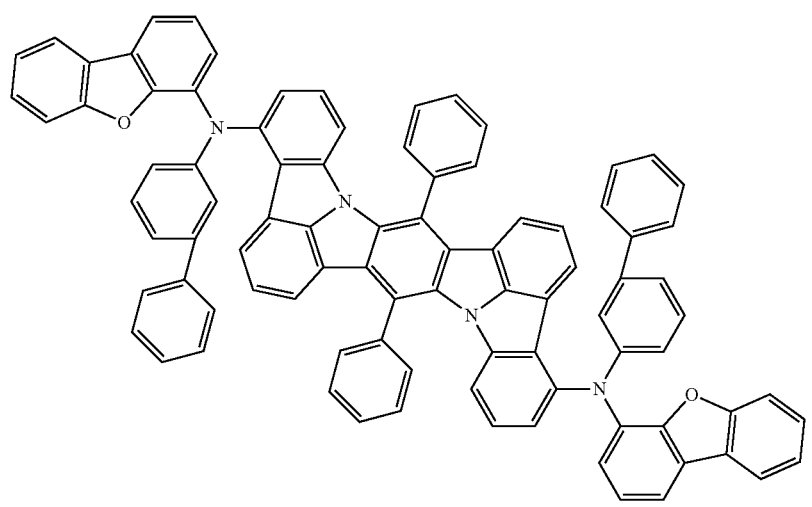
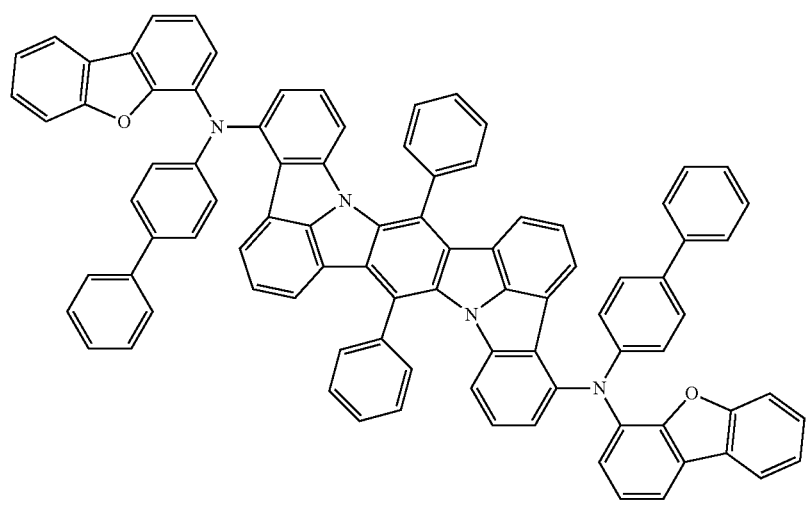

-continued
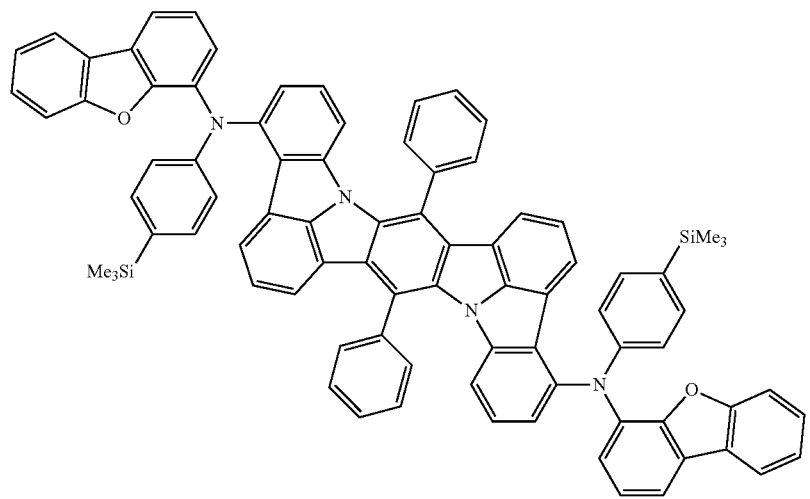
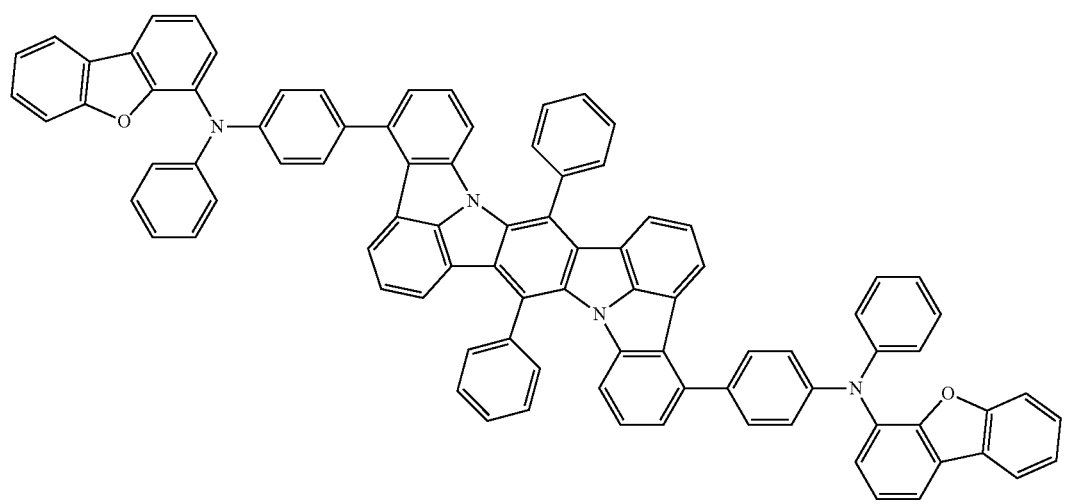
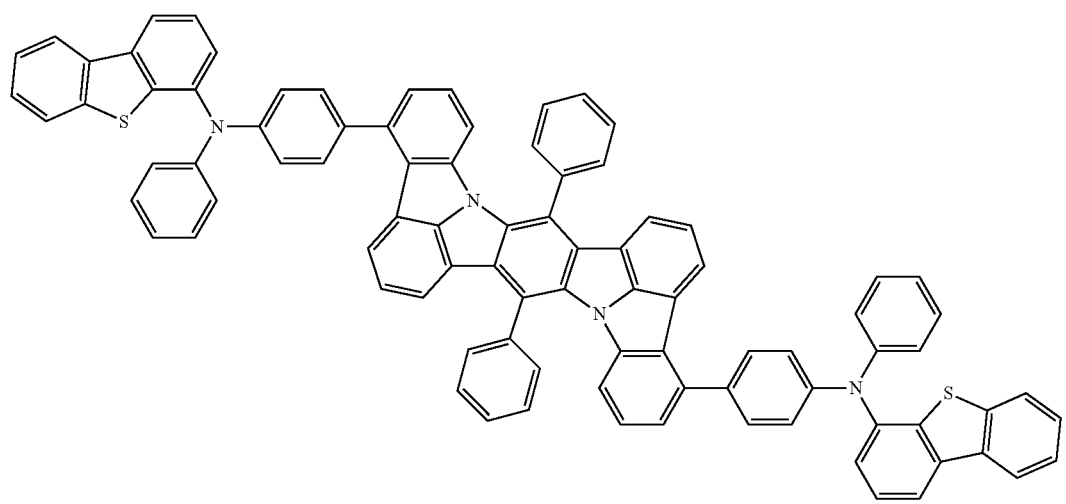

-continued
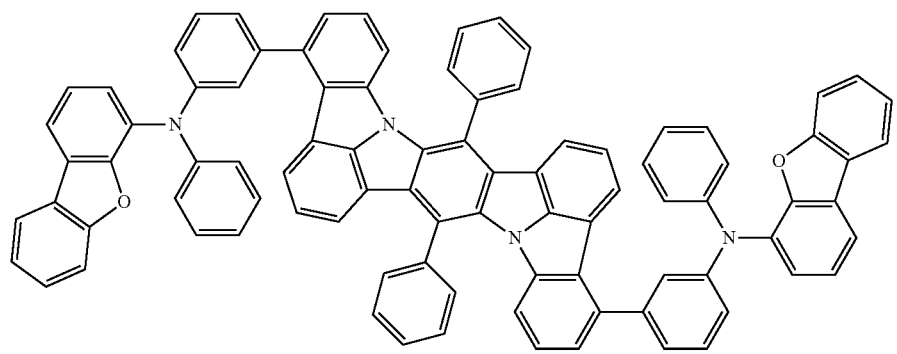
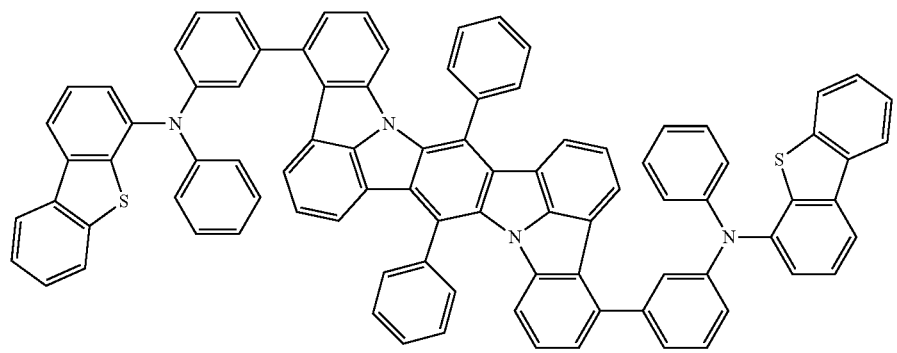
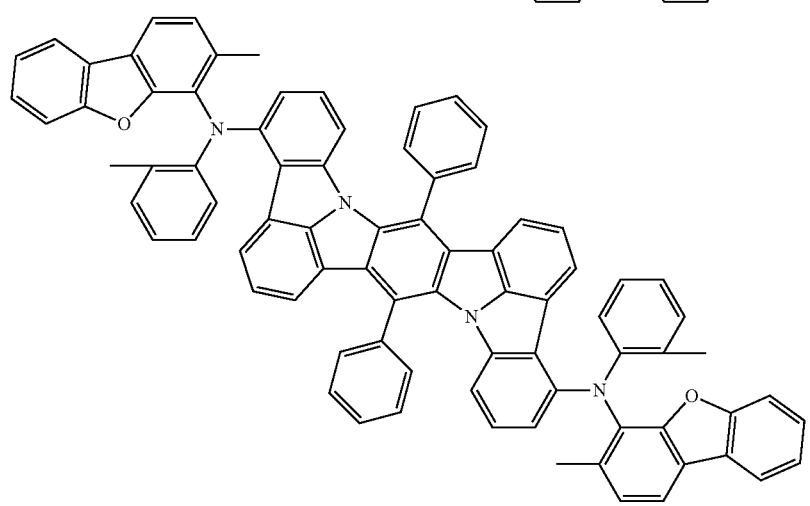
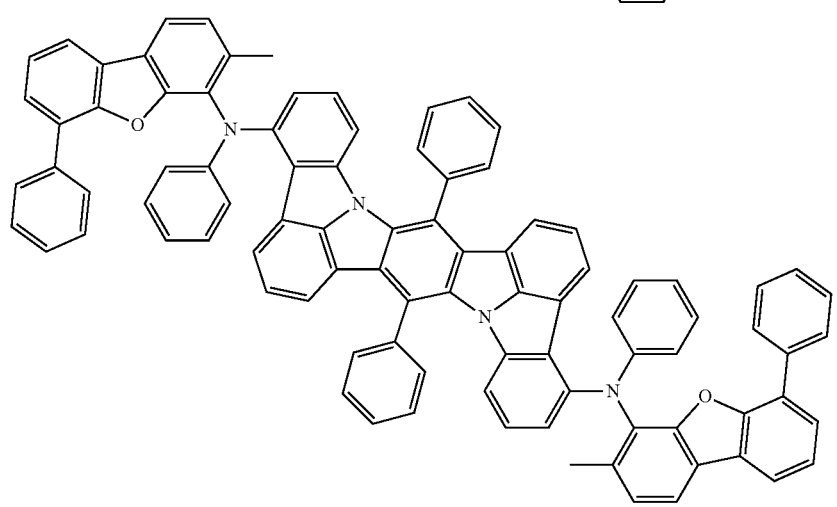

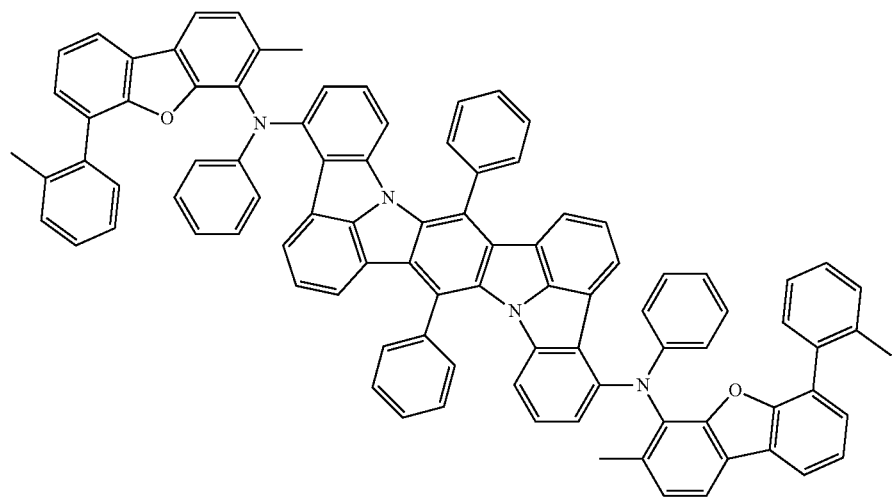
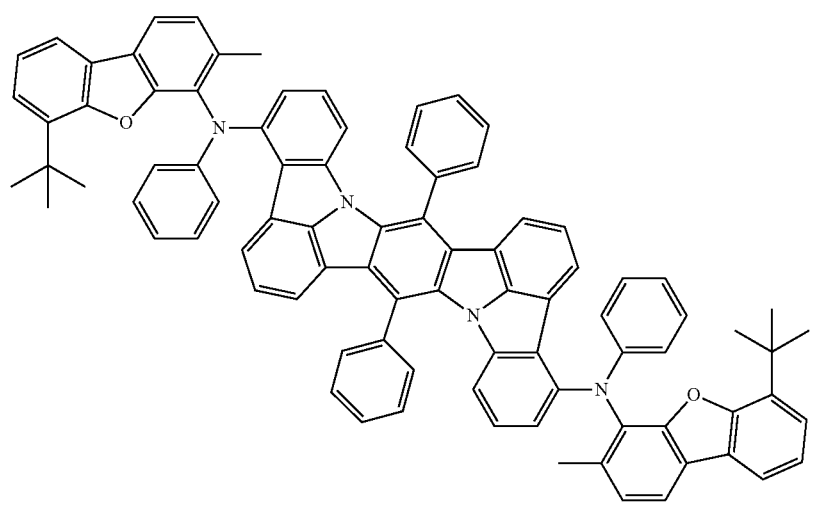
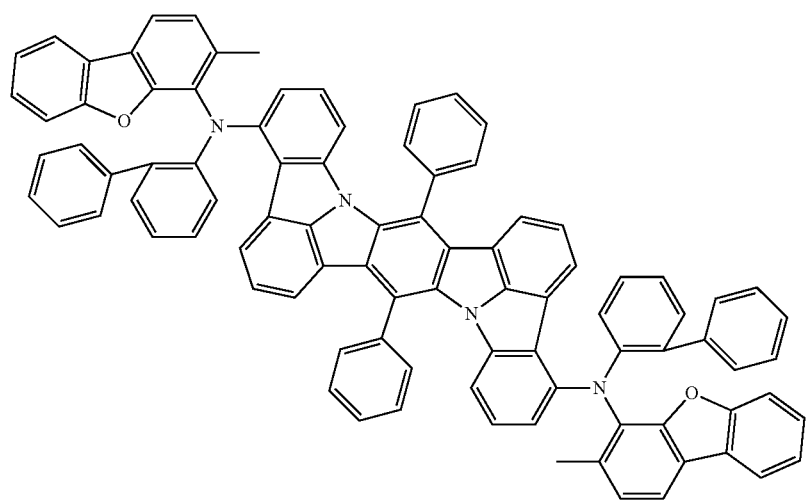

-continued
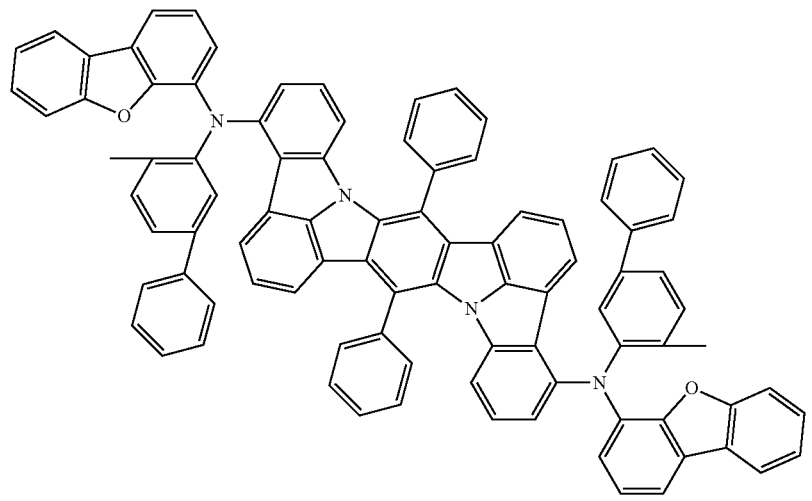
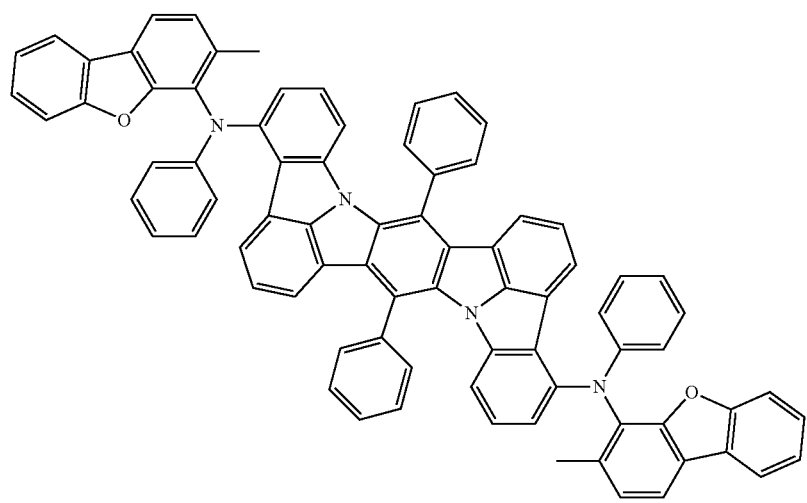
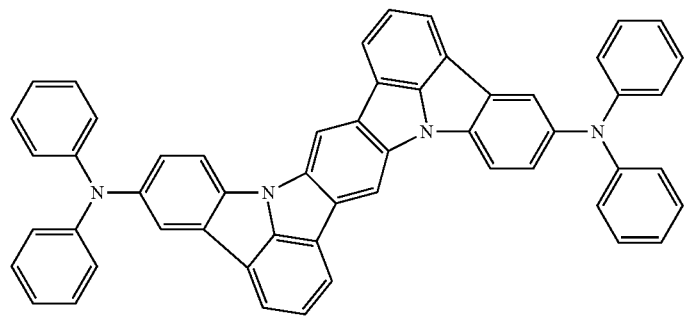
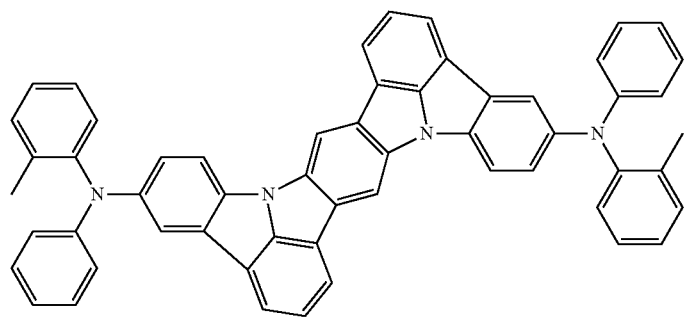

-continued
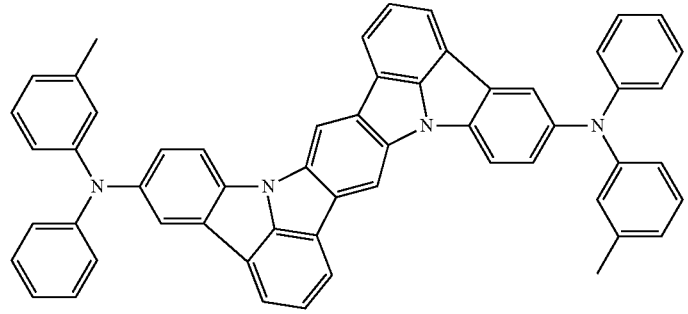
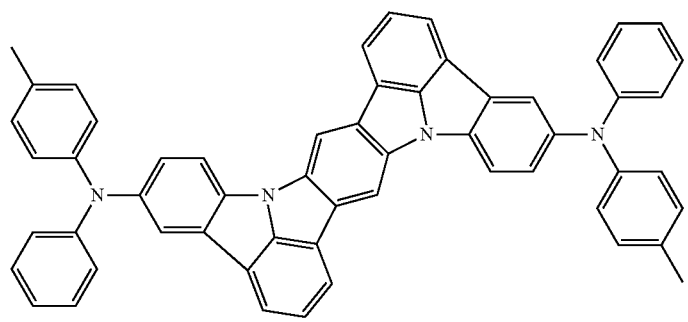
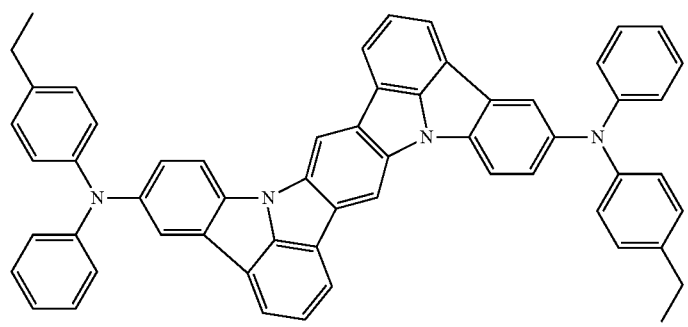
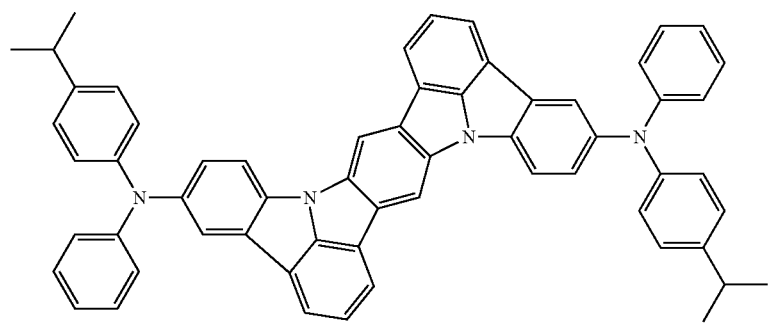
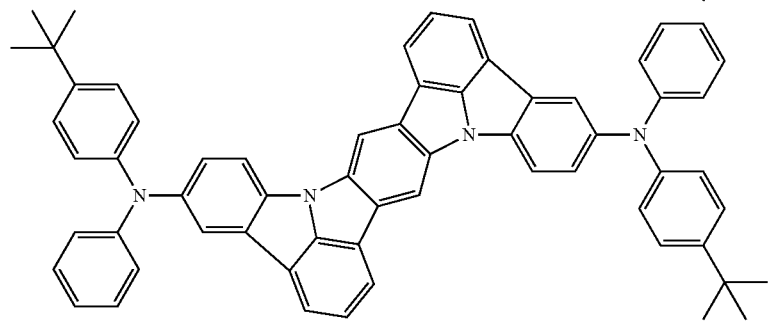

-continued
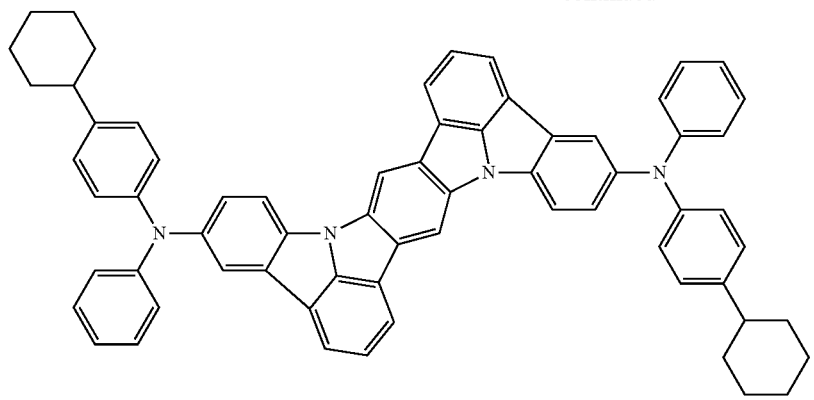
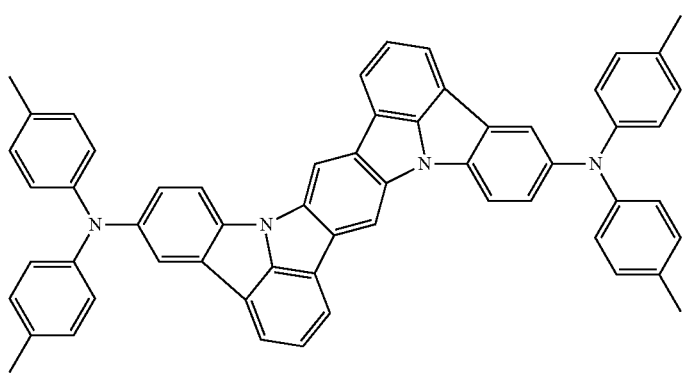
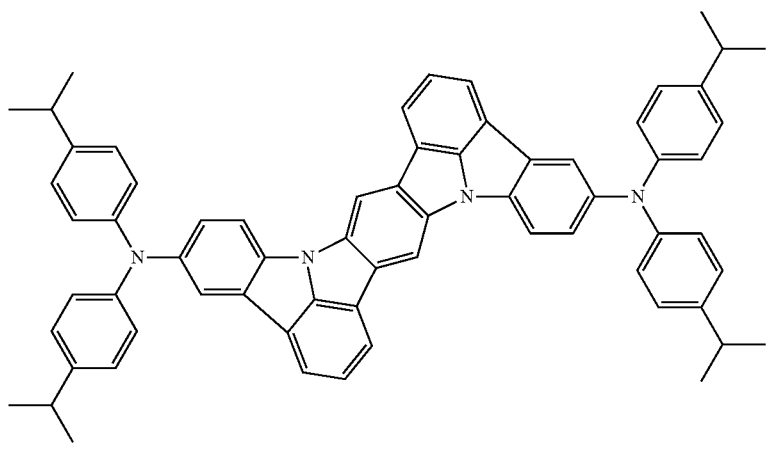

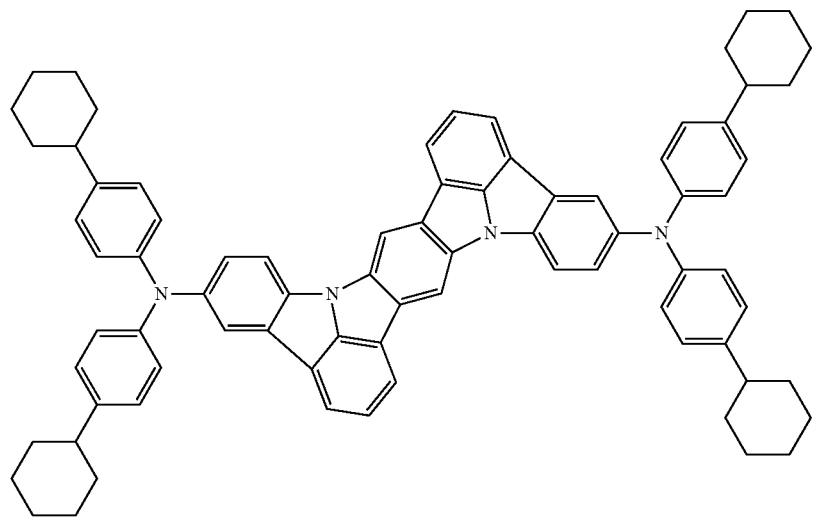
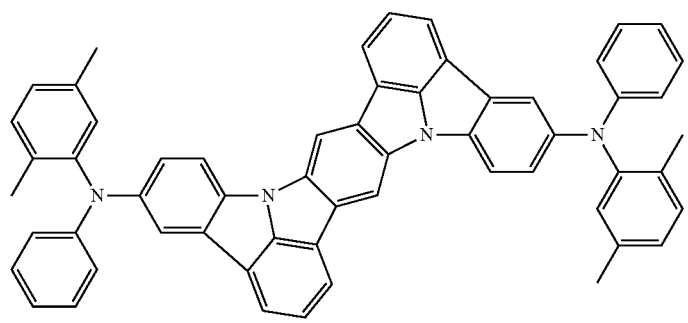
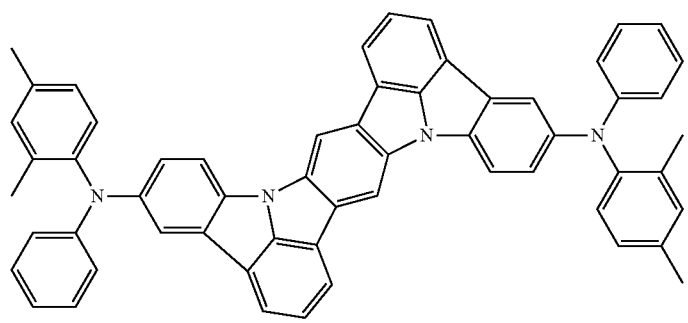
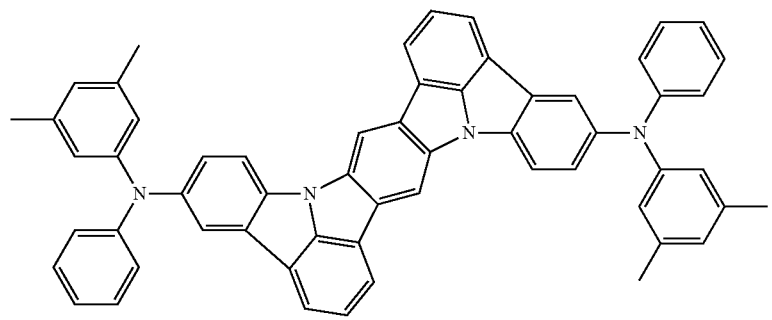

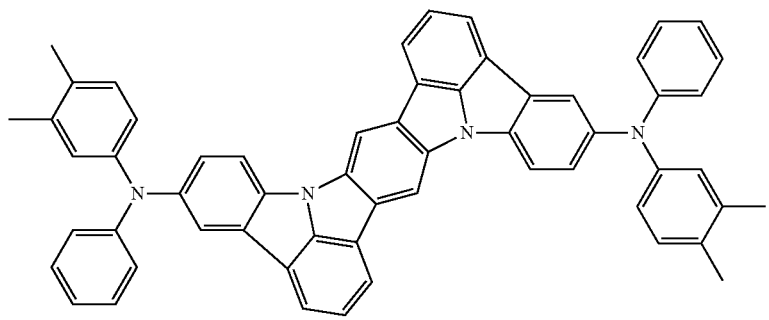
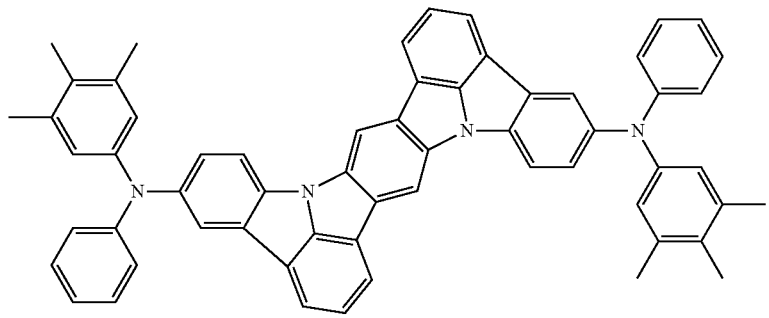
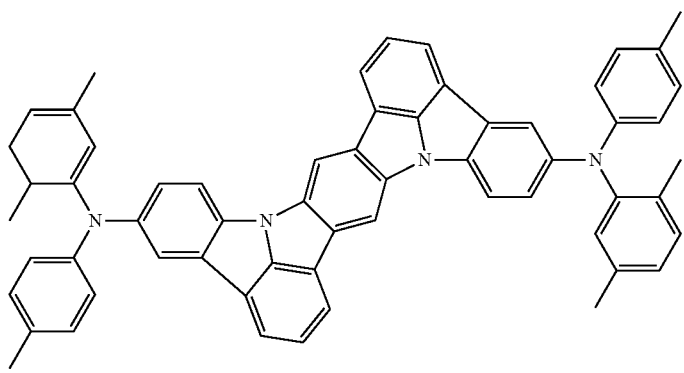
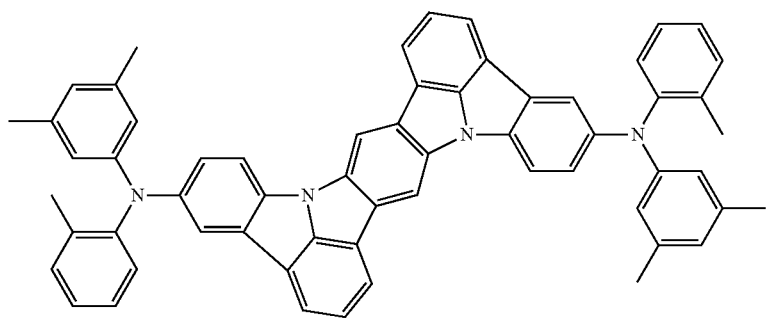
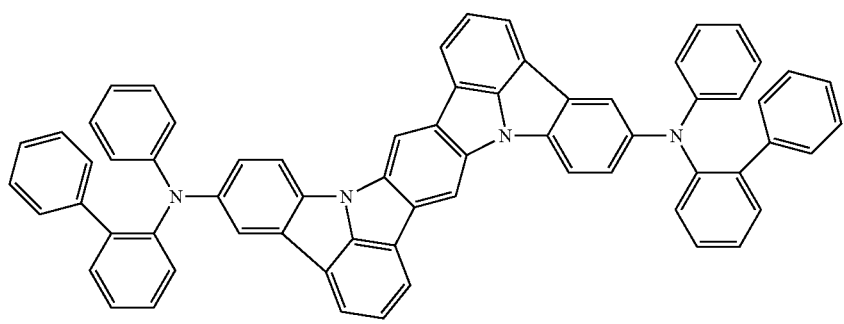

-continued
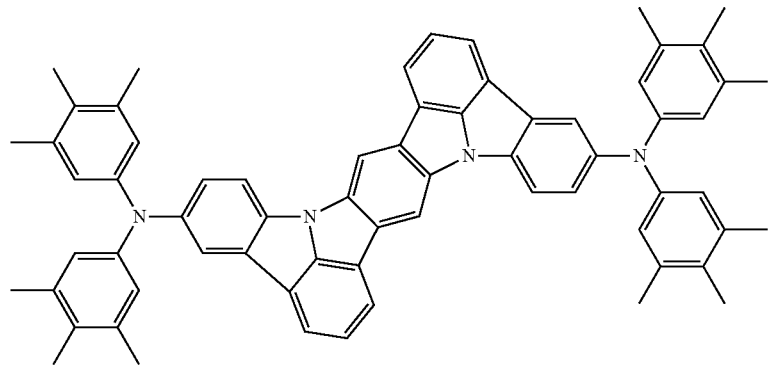
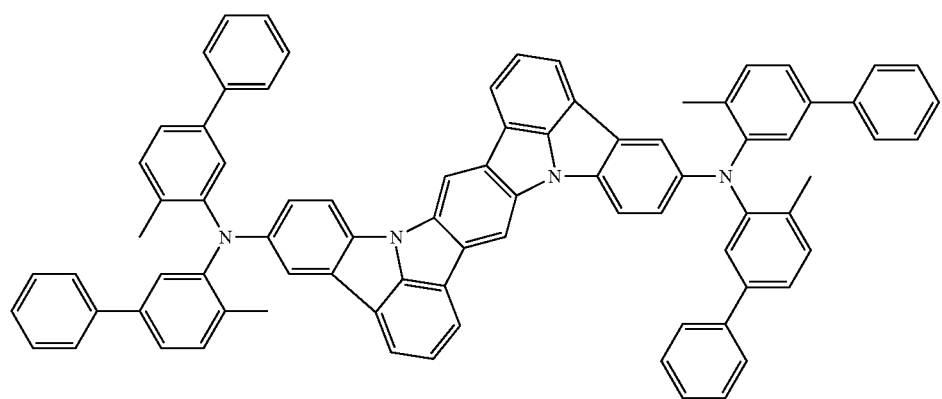
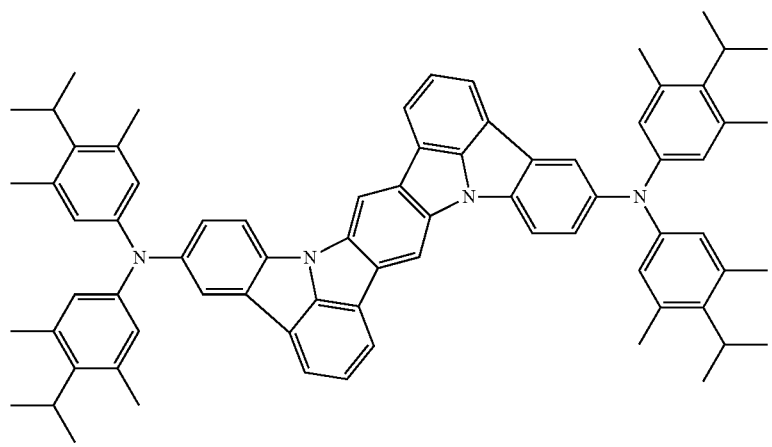
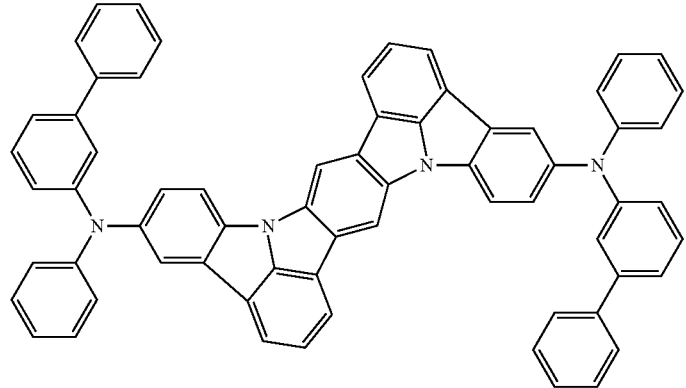

-continued
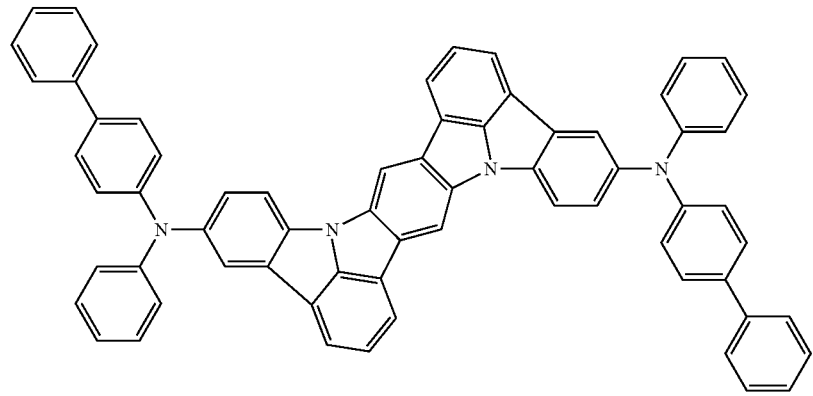
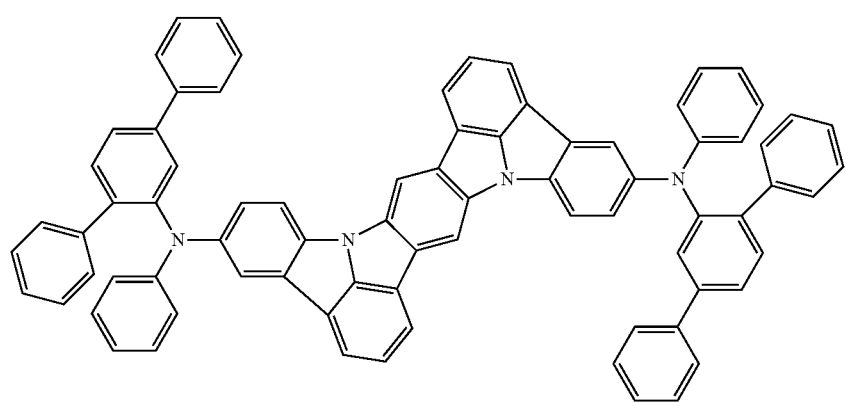
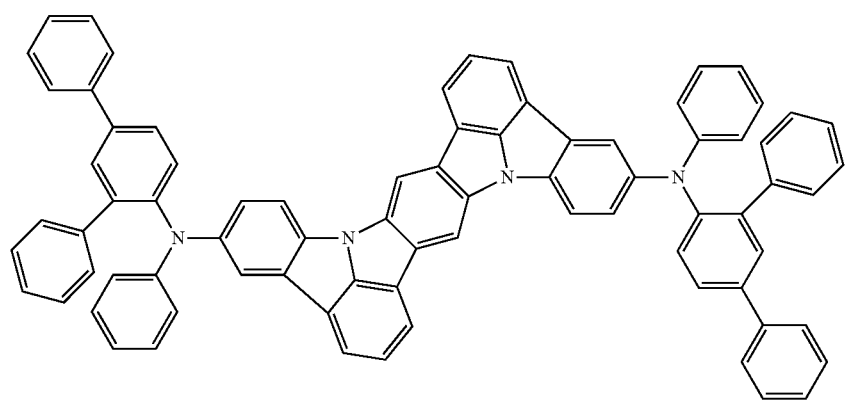
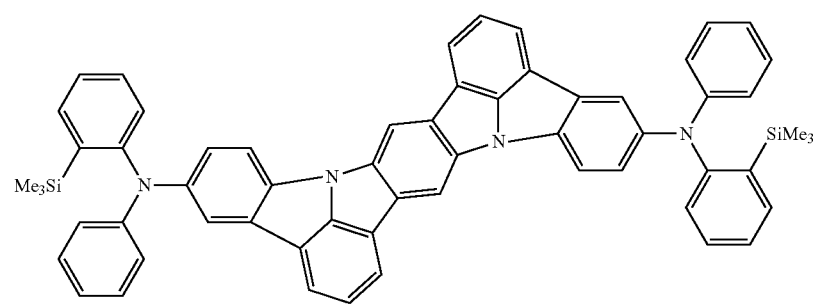

-continued
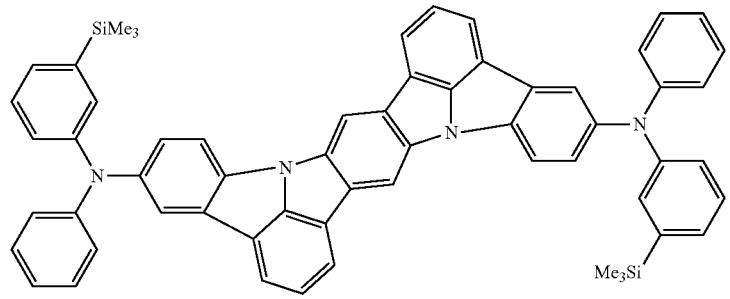
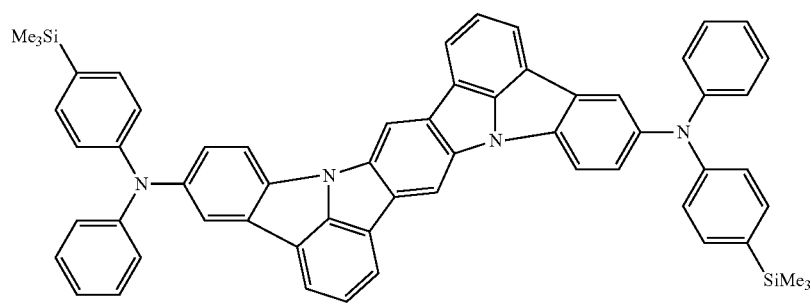
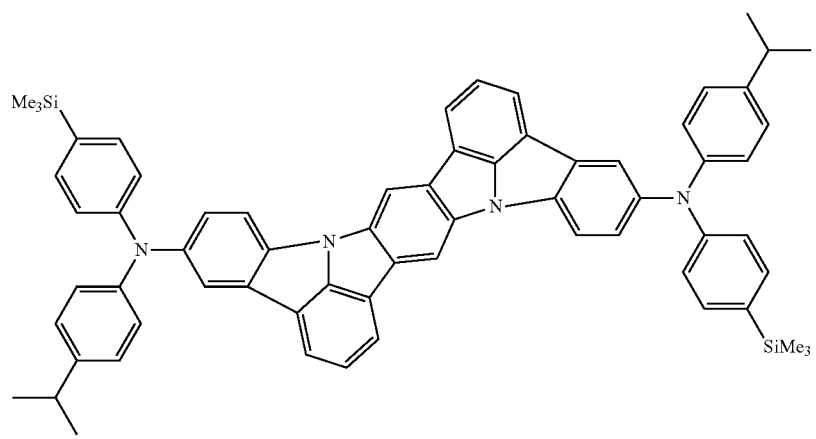
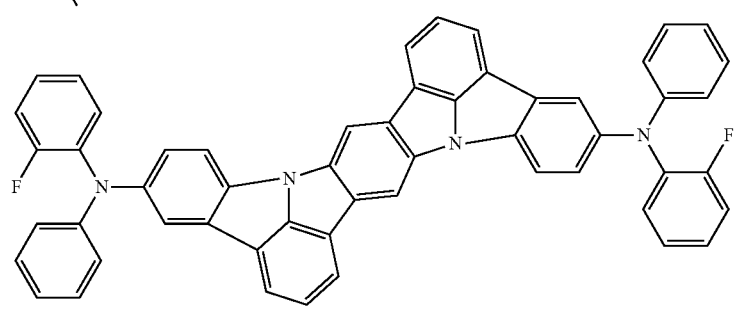
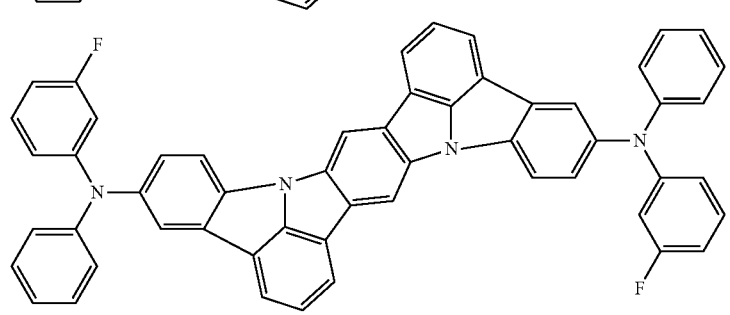

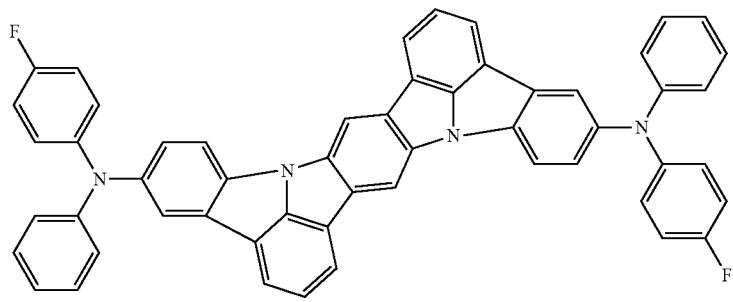
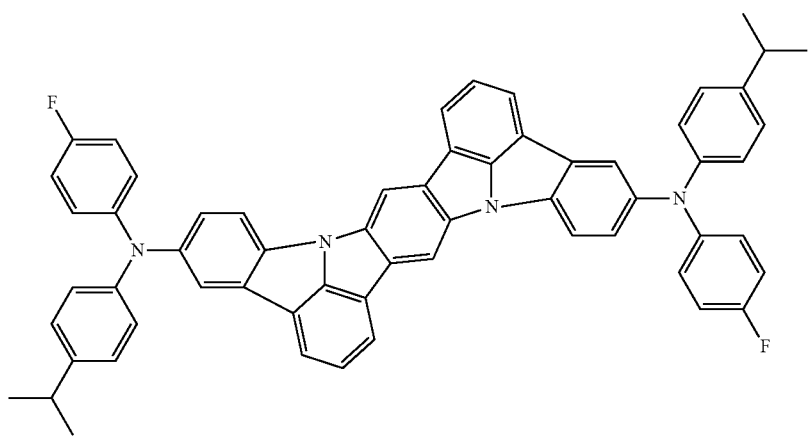
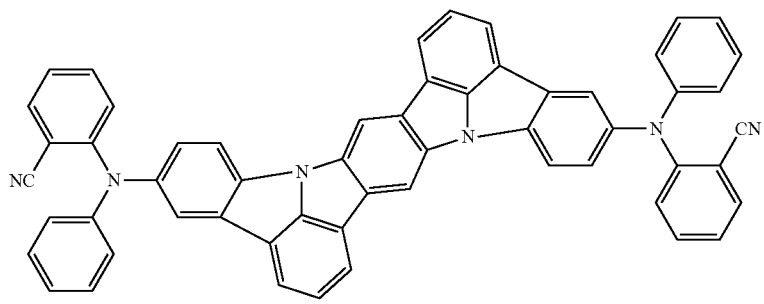
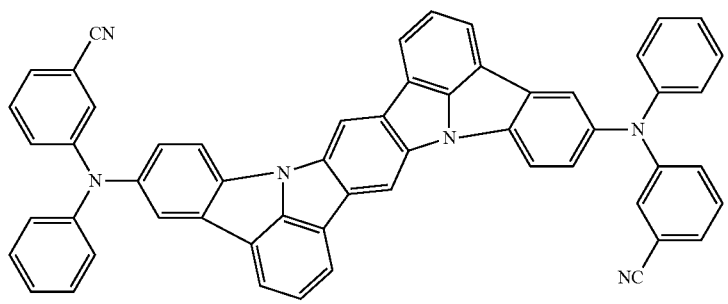
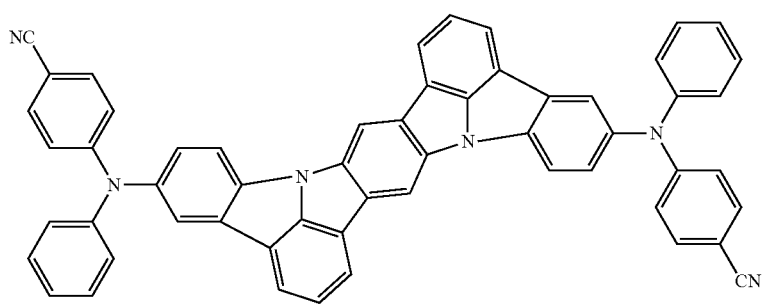

-continued
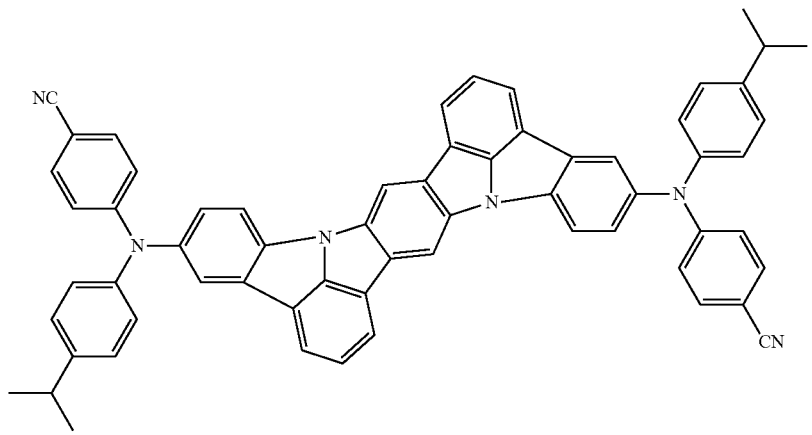
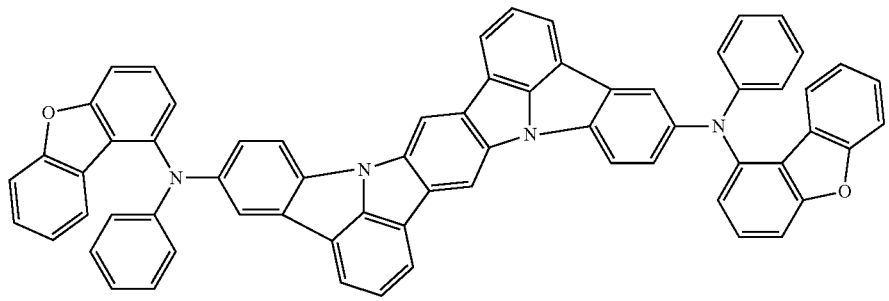
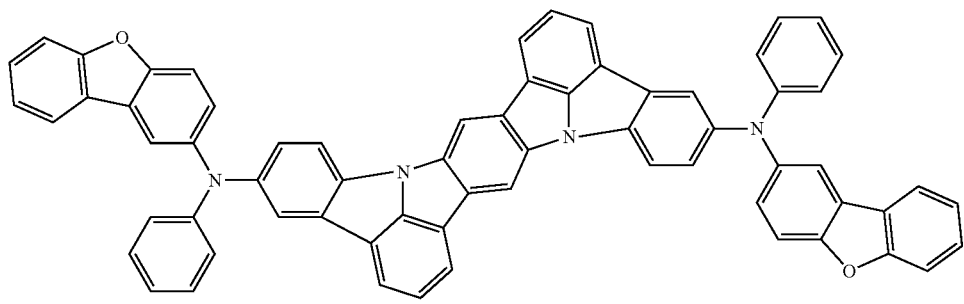
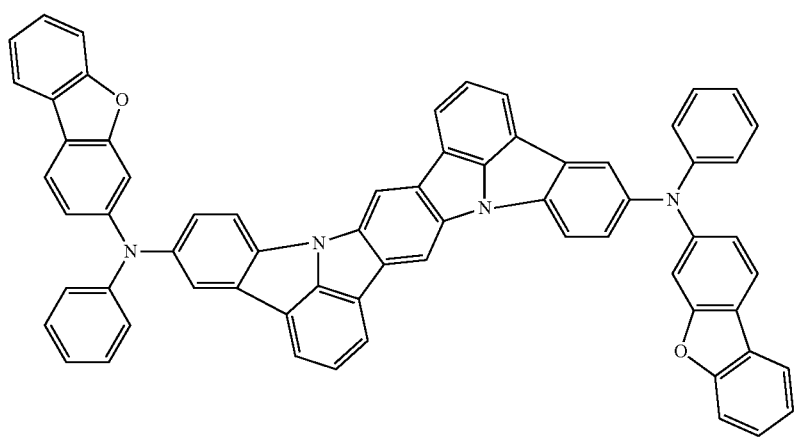

-continued
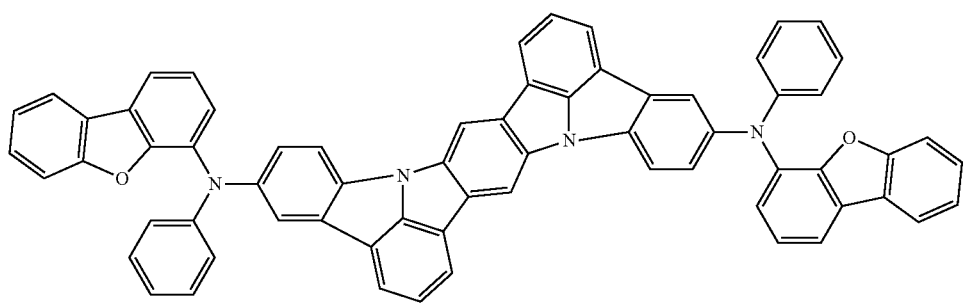
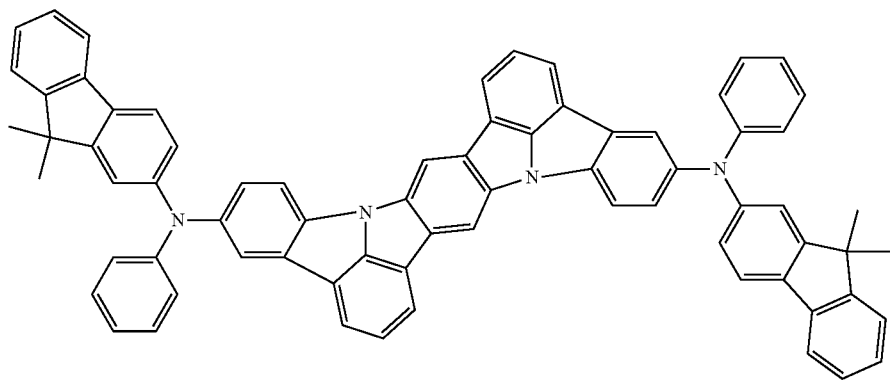
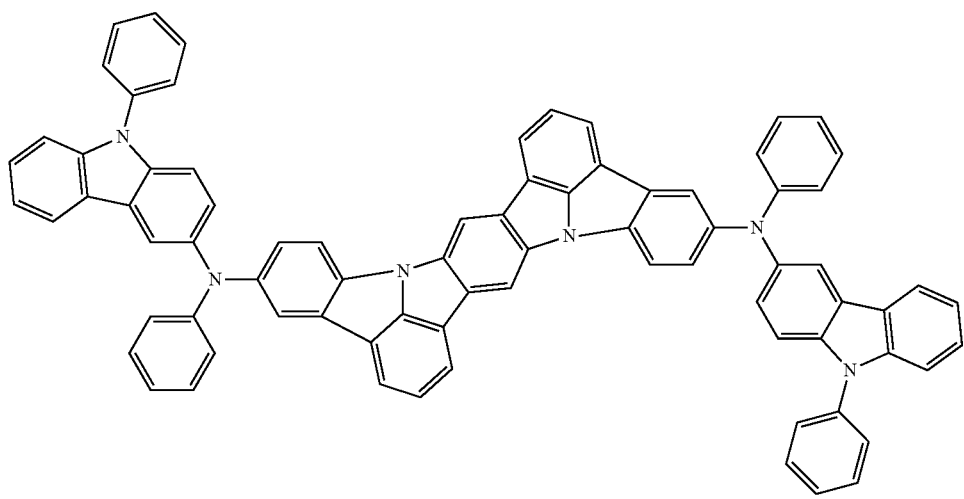
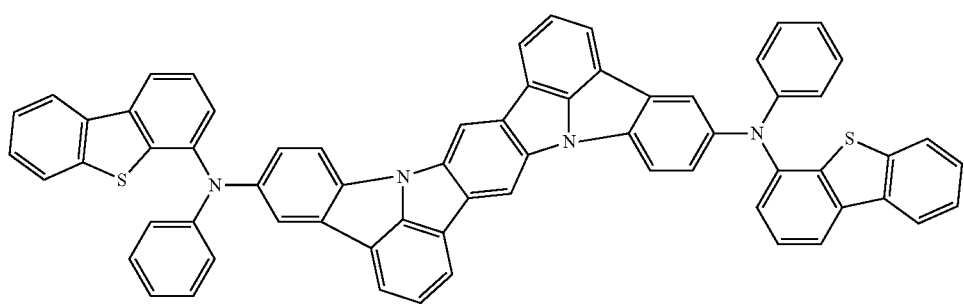

-continued
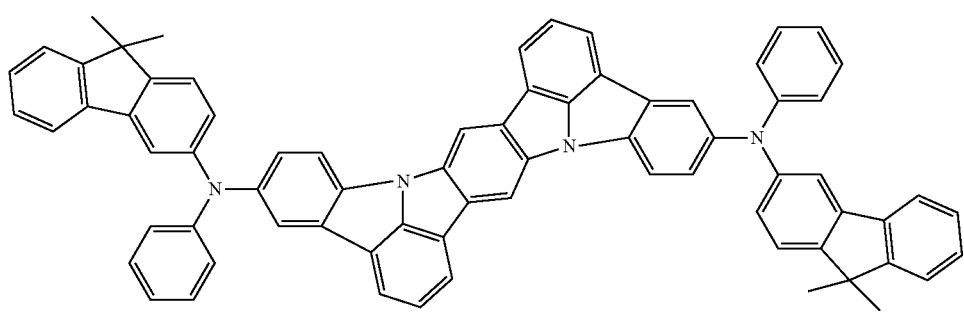
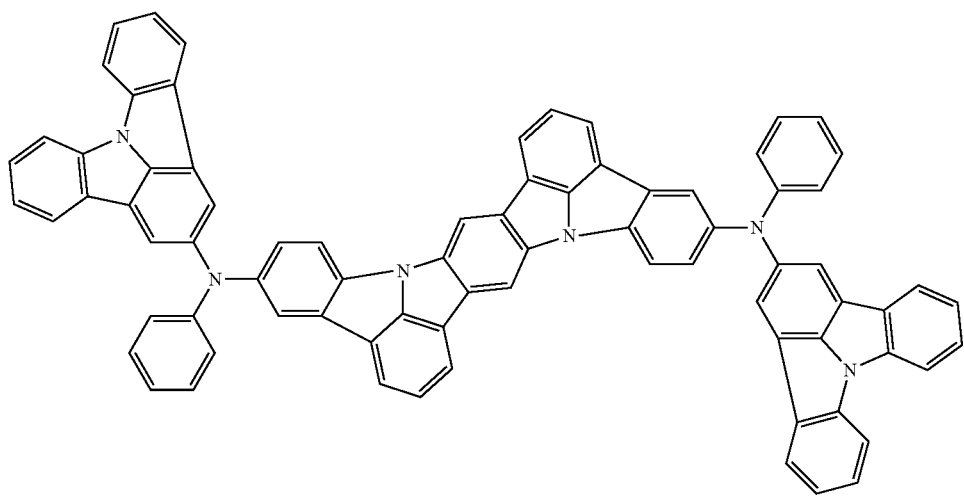
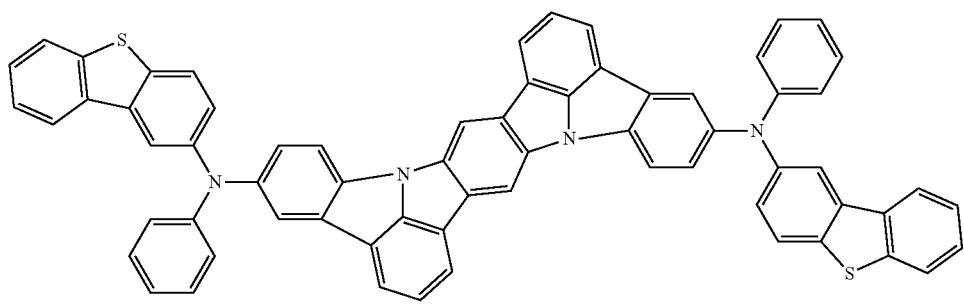
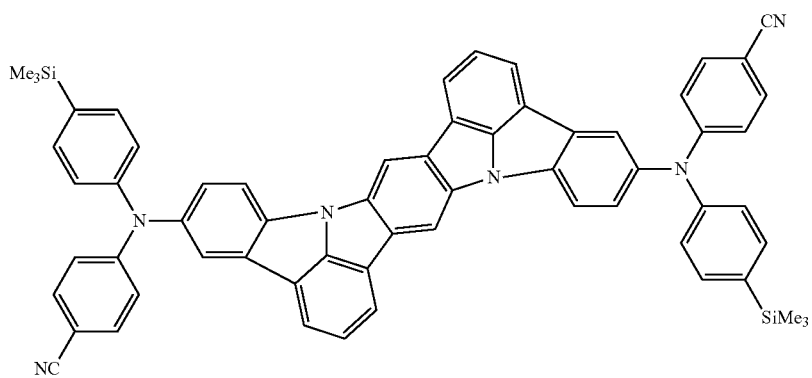

-continued
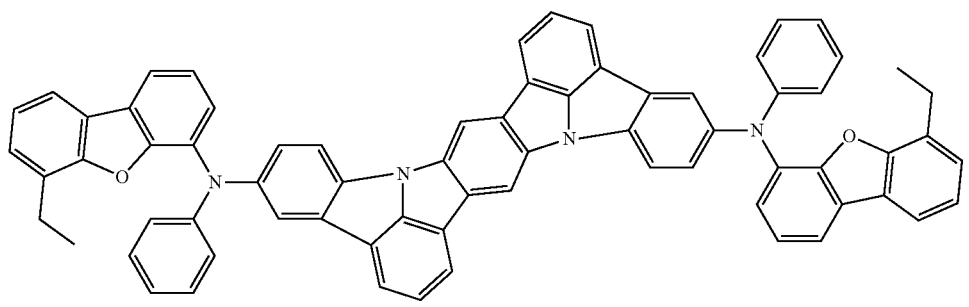
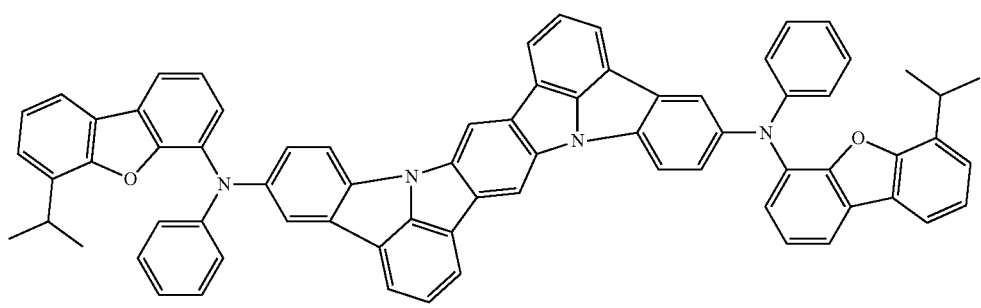
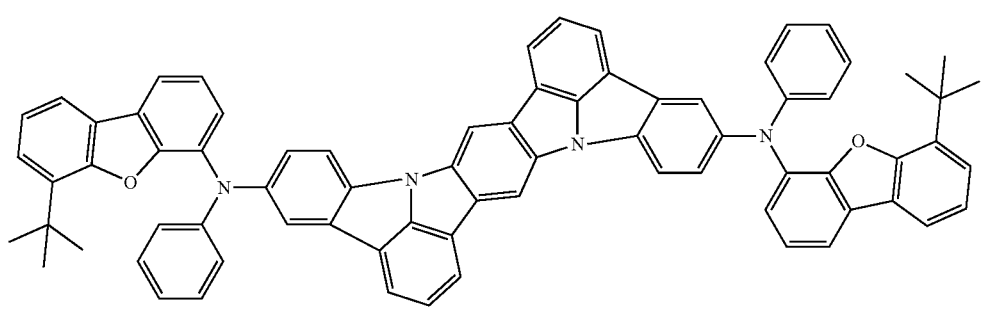
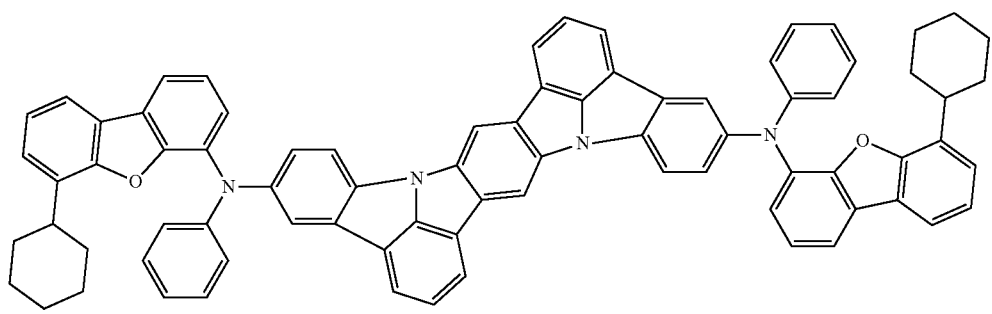

761
-continued
762
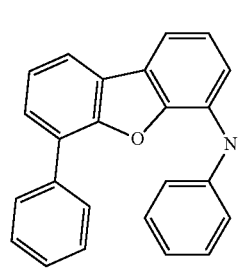 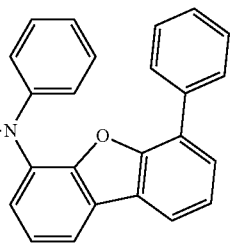
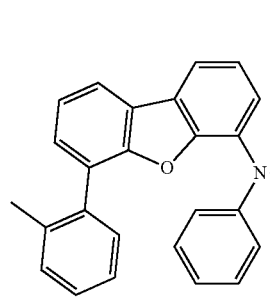 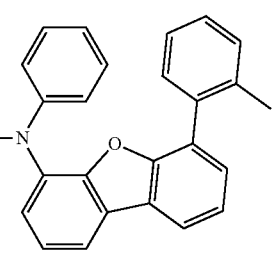
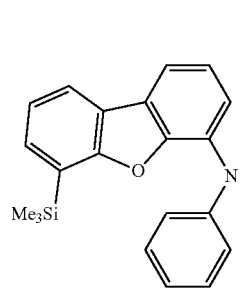 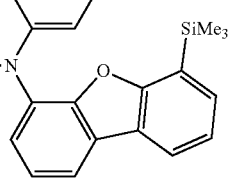
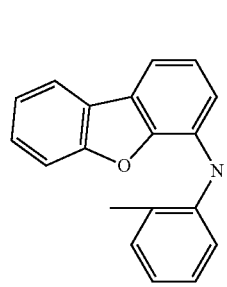 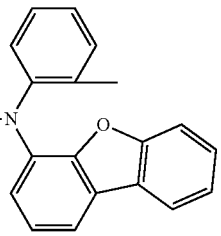
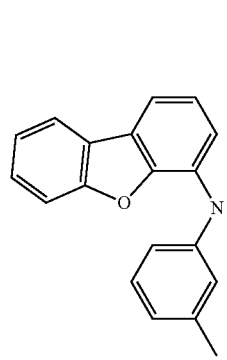 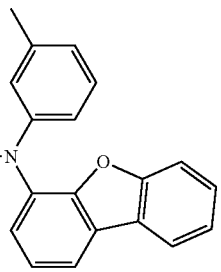

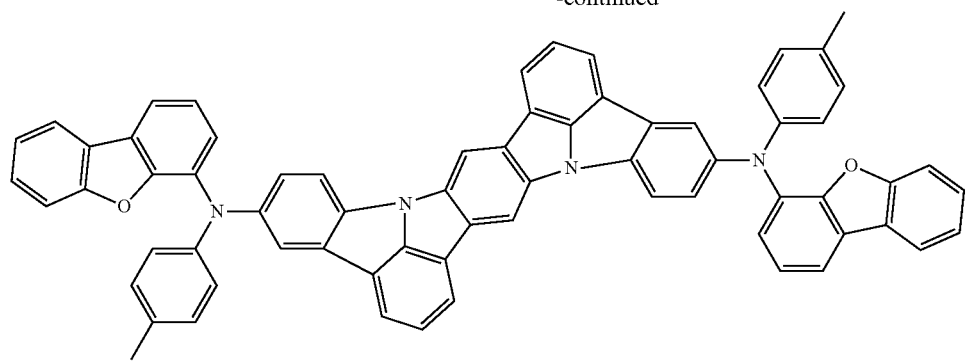
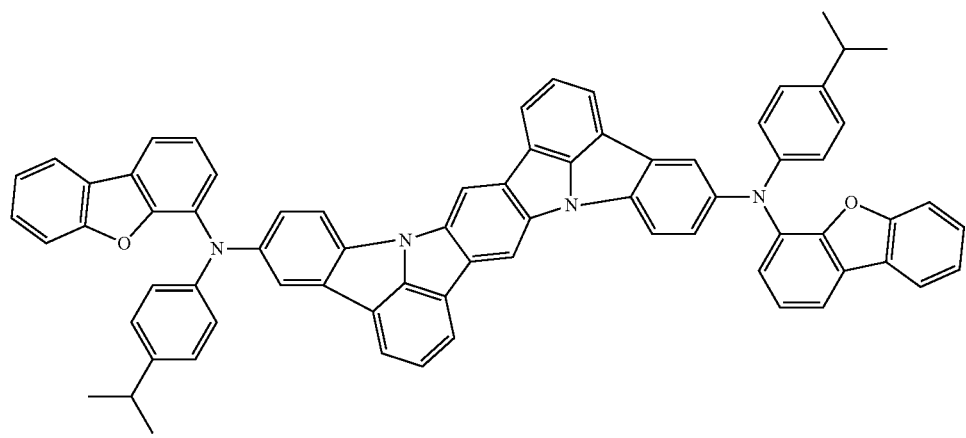
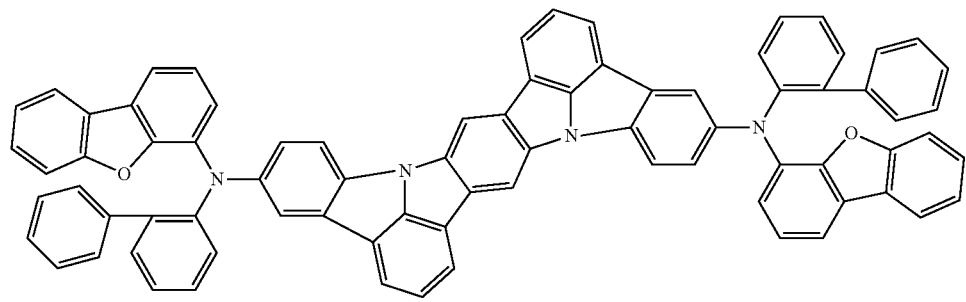
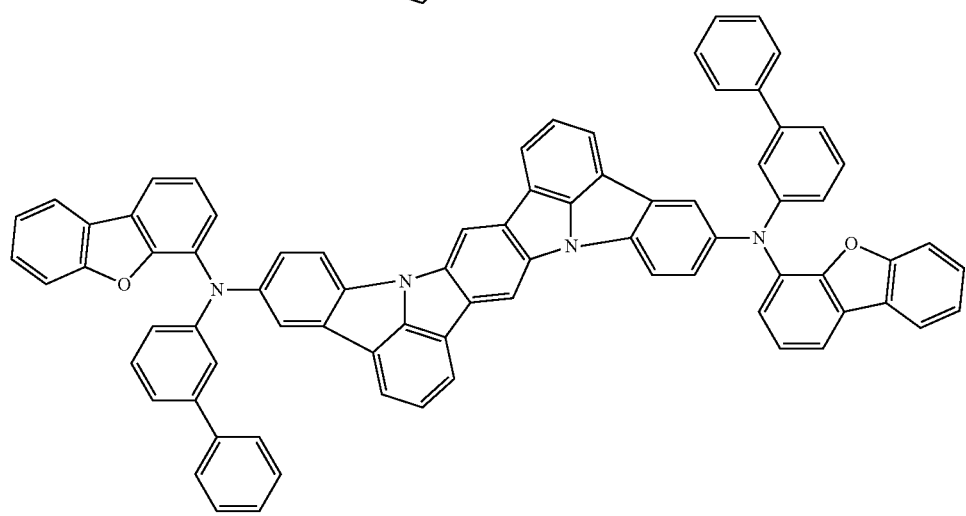

-continued
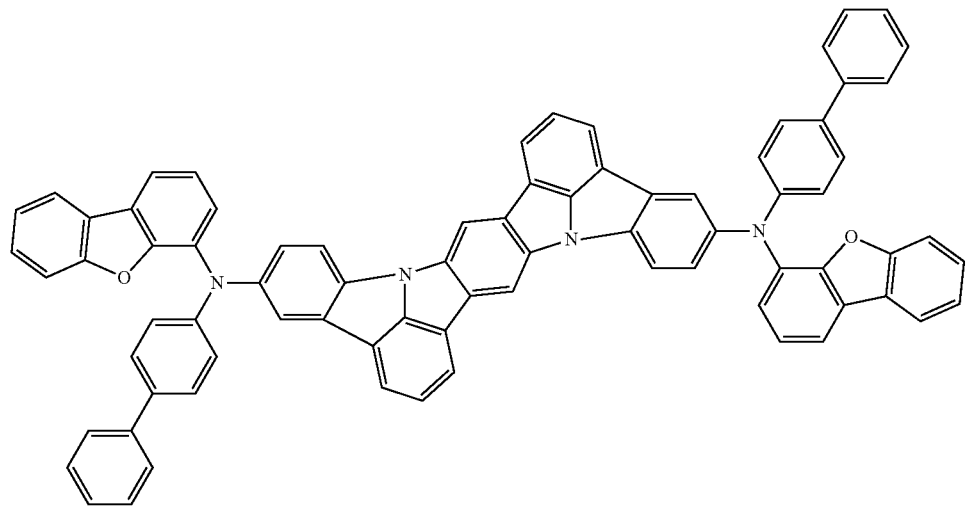
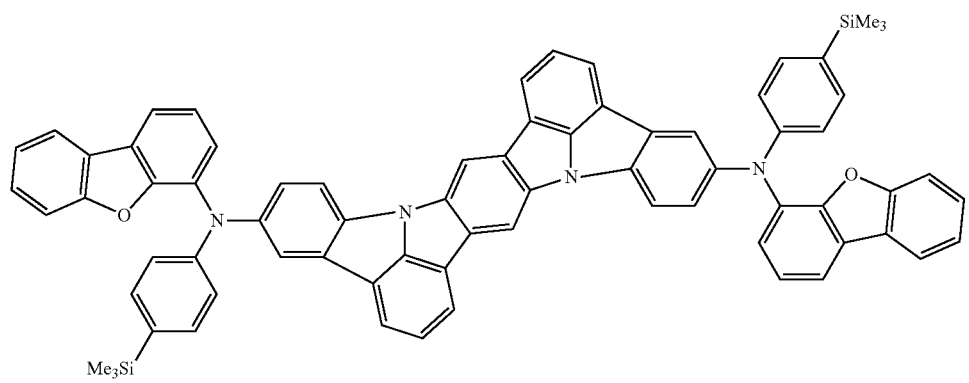
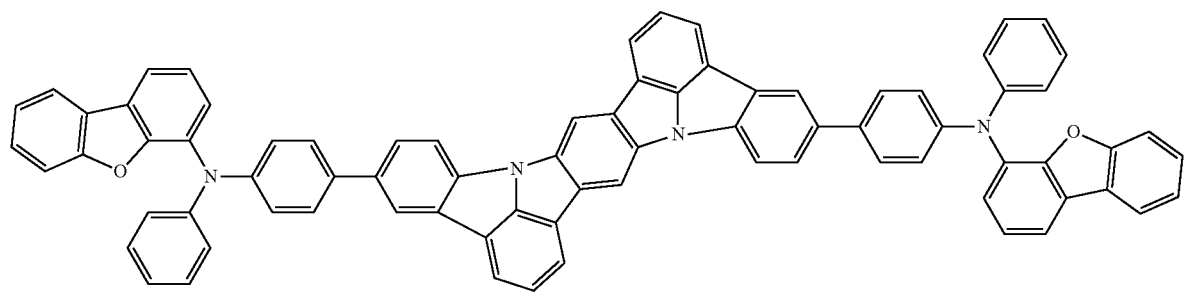
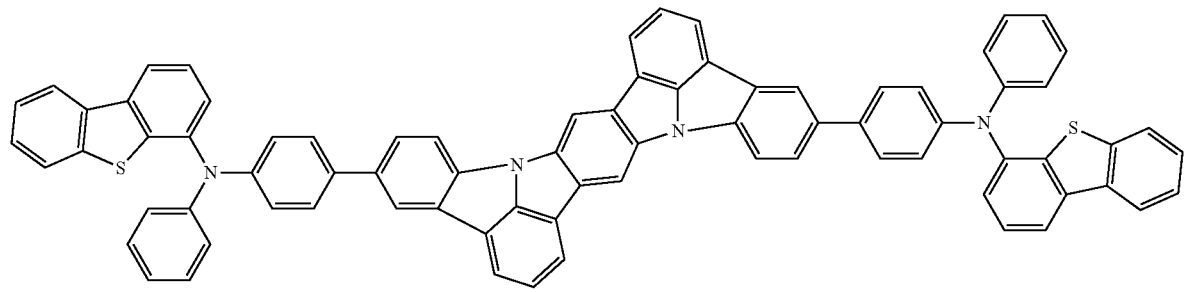

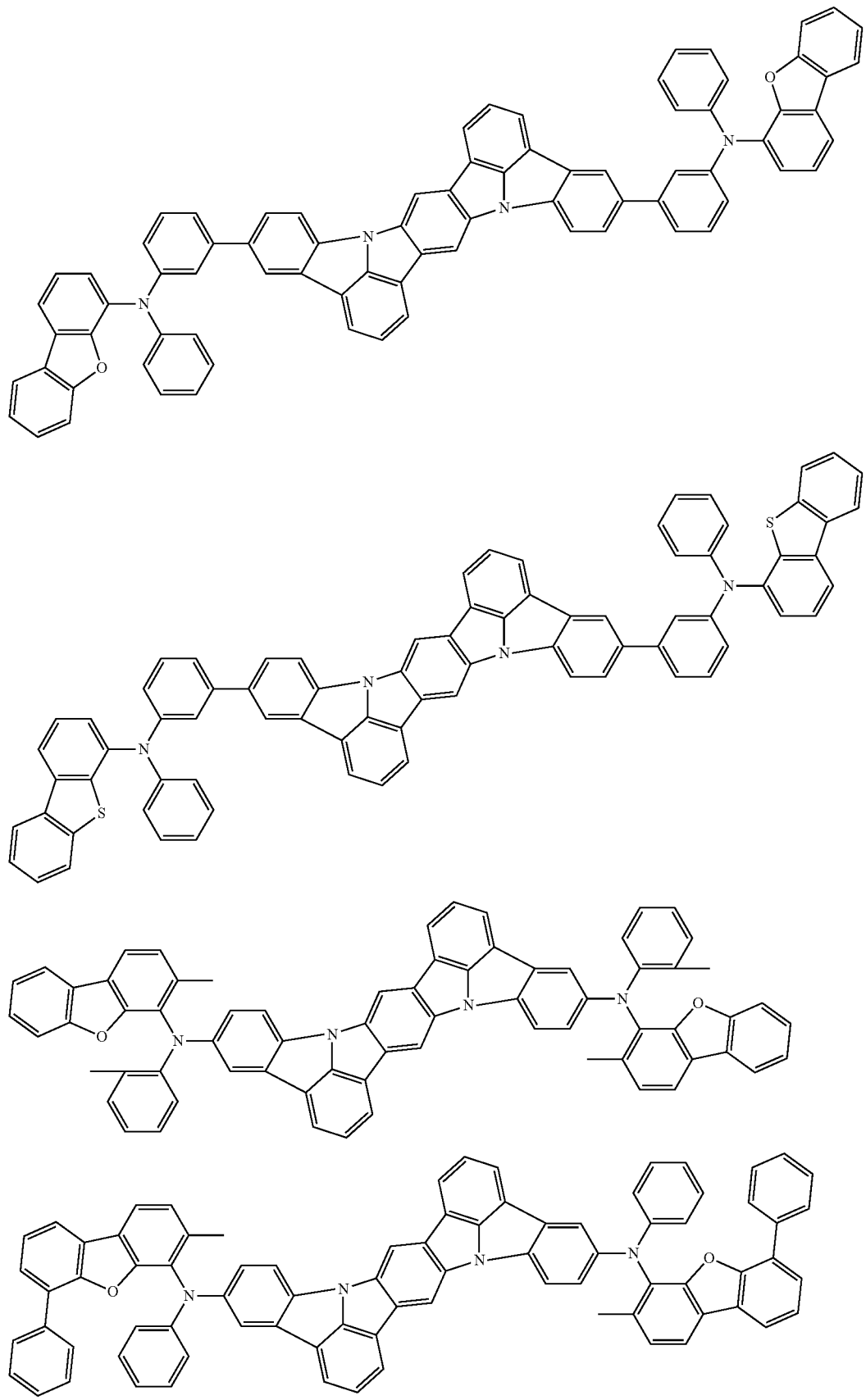

-continued
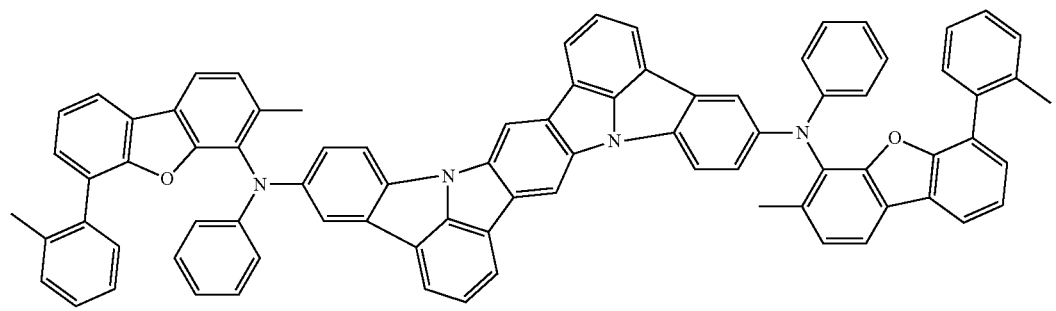
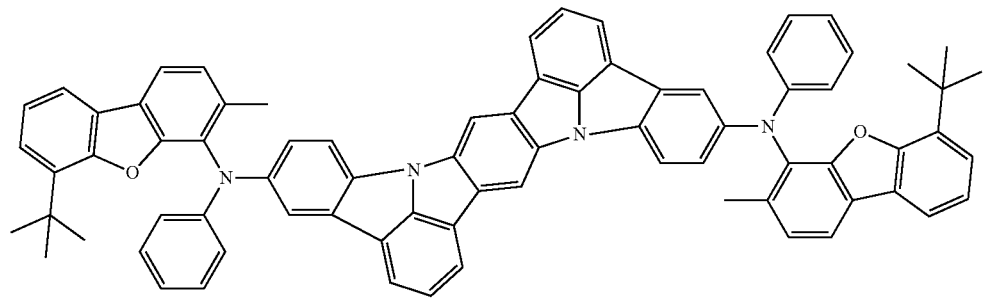
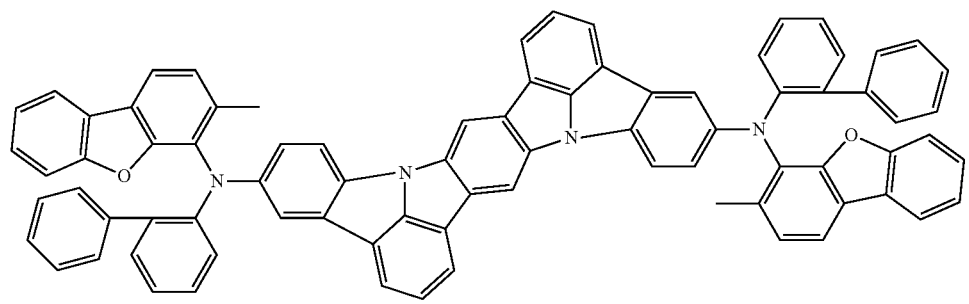
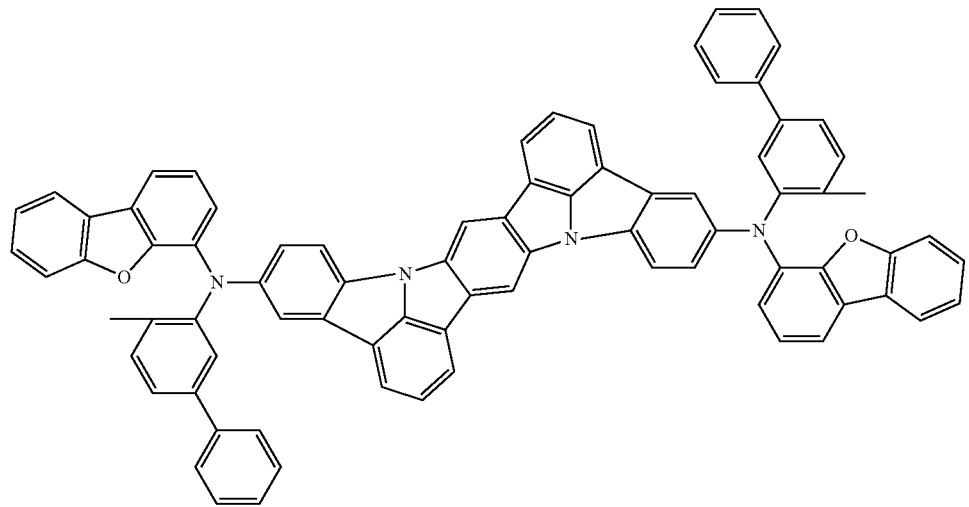
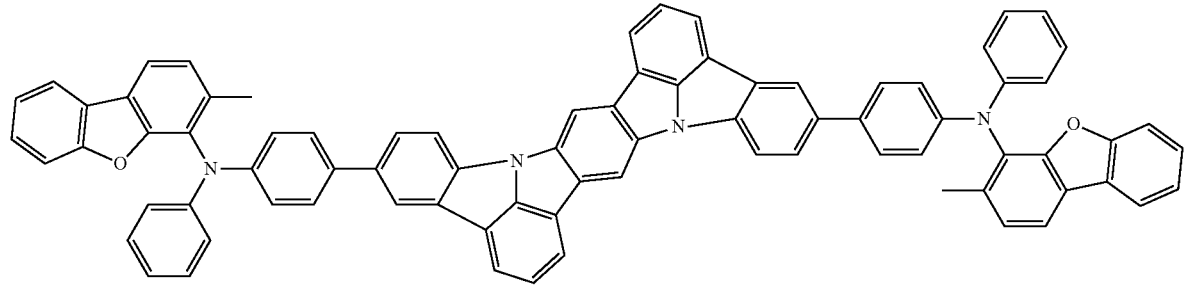

-continued
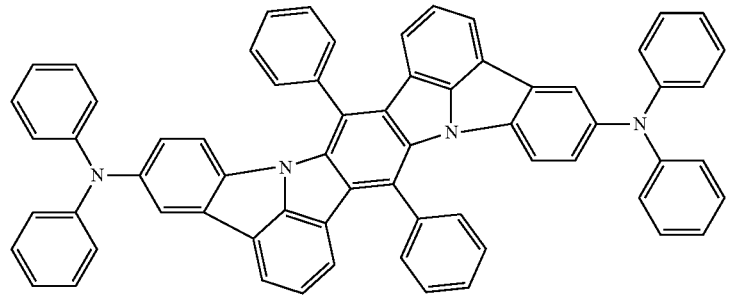
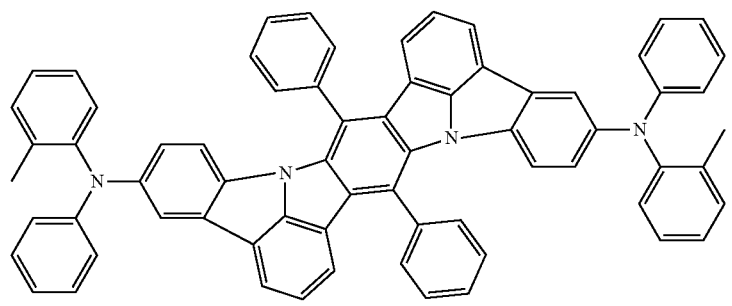
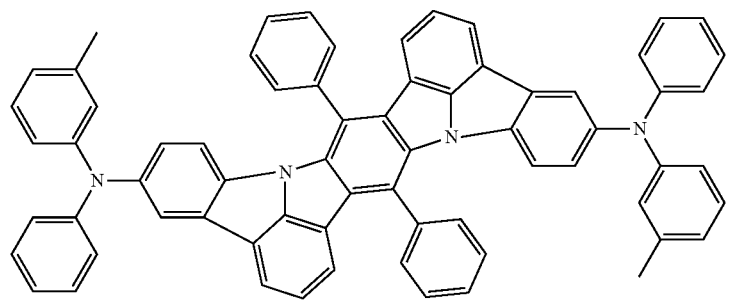
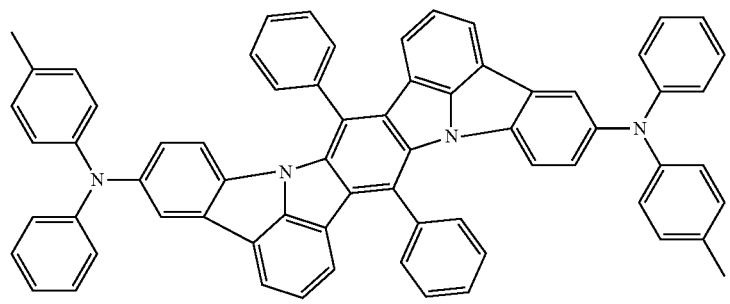
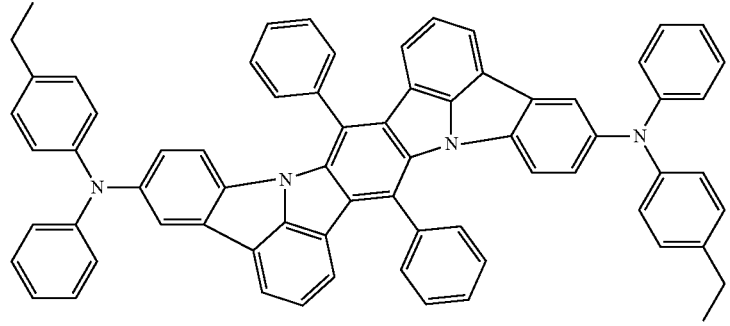

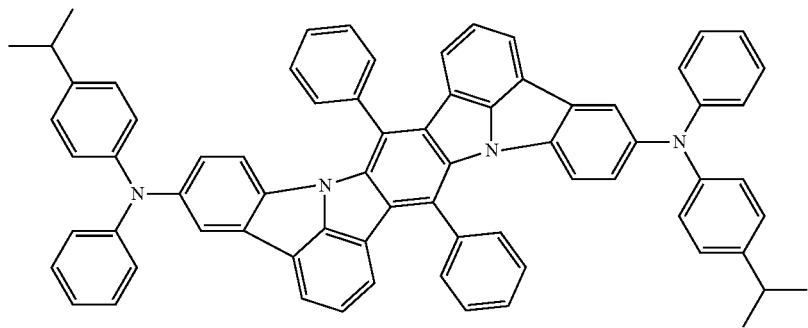
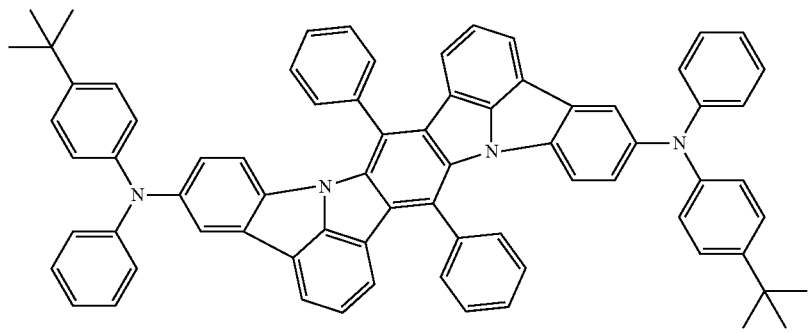
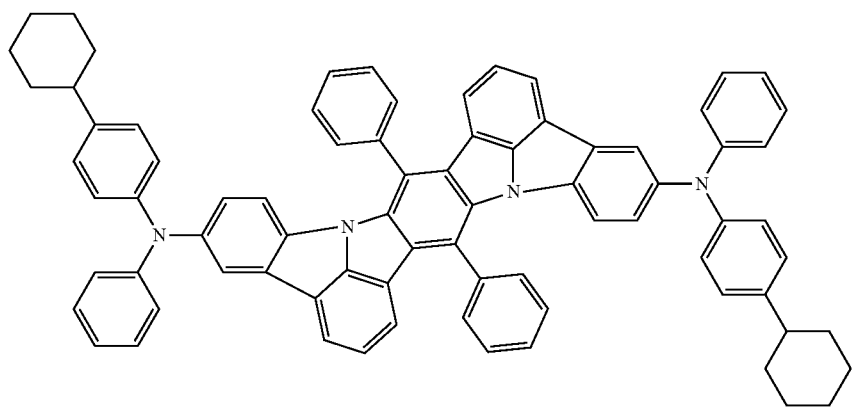
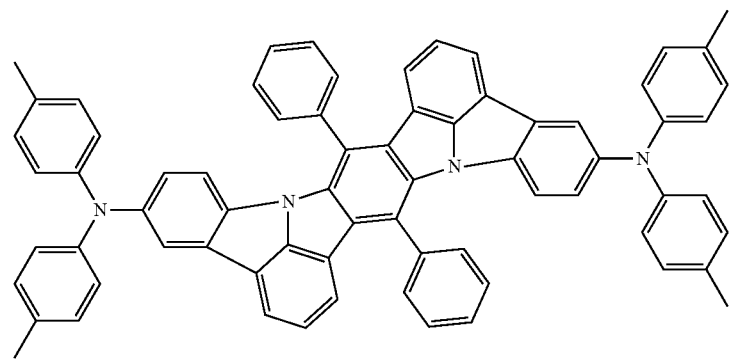

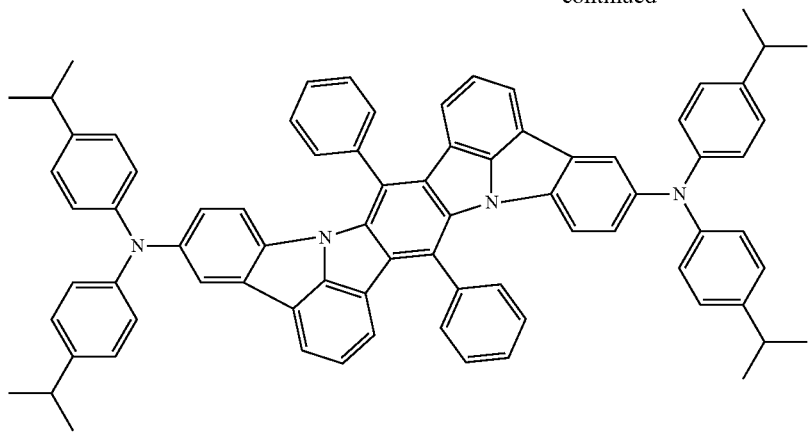
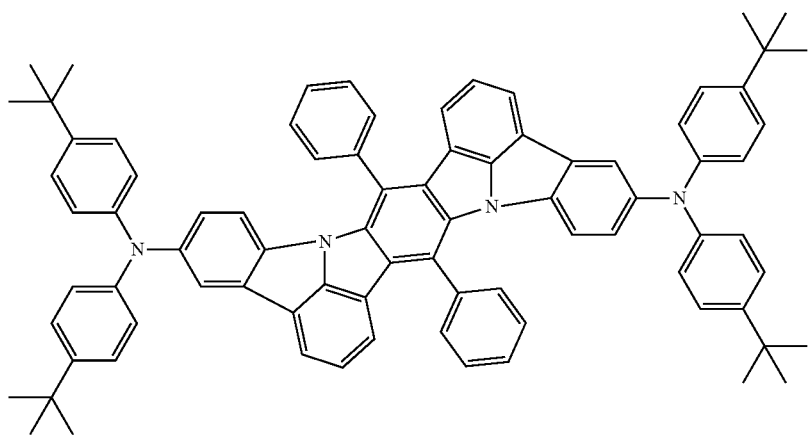
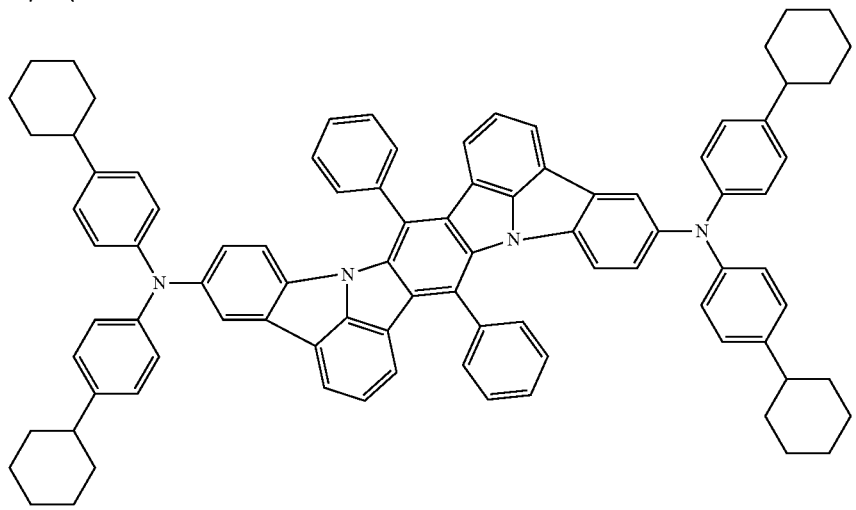
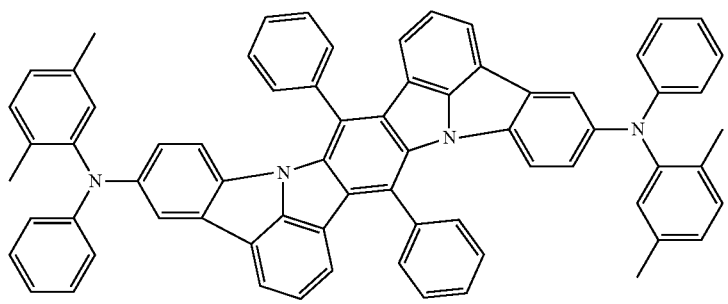

-continued
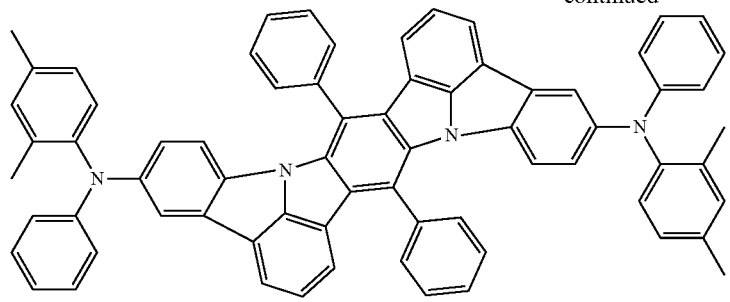
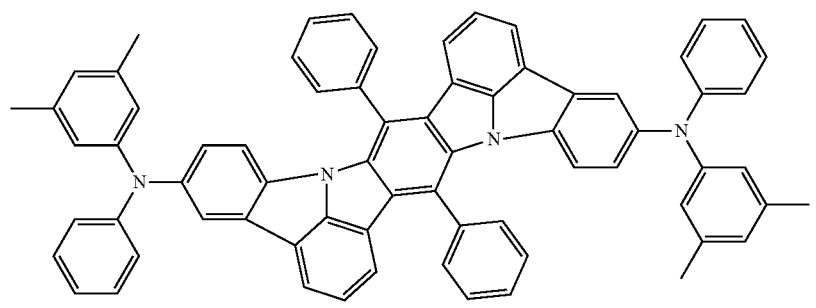
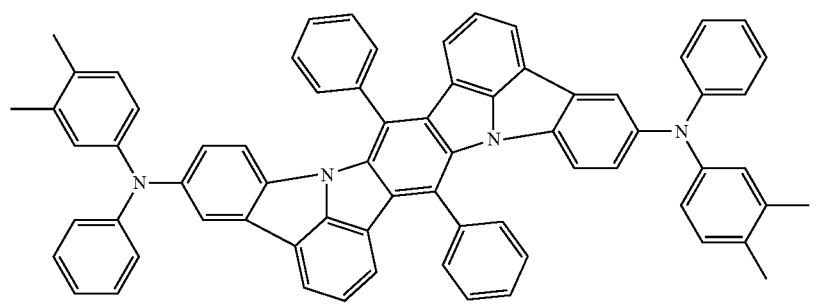
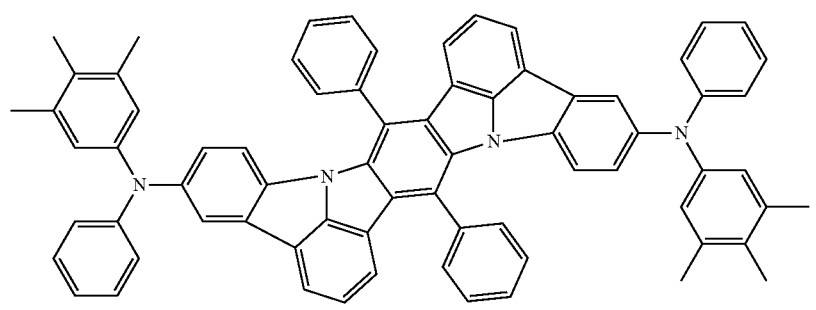
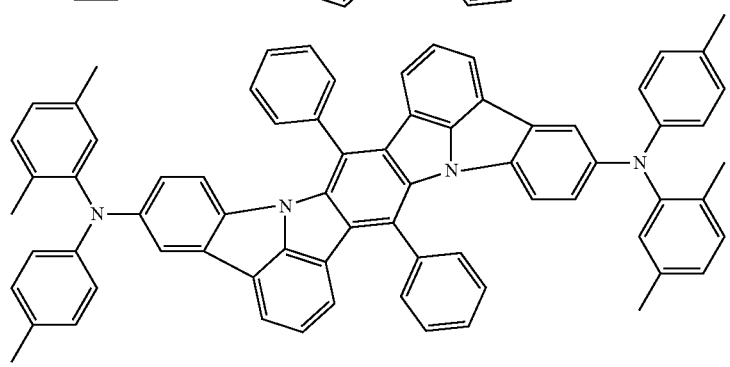

-continued
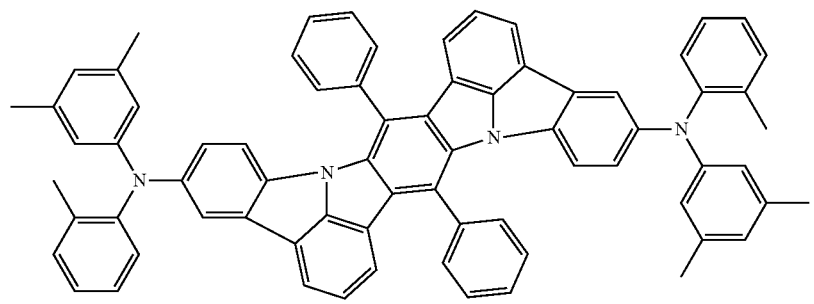
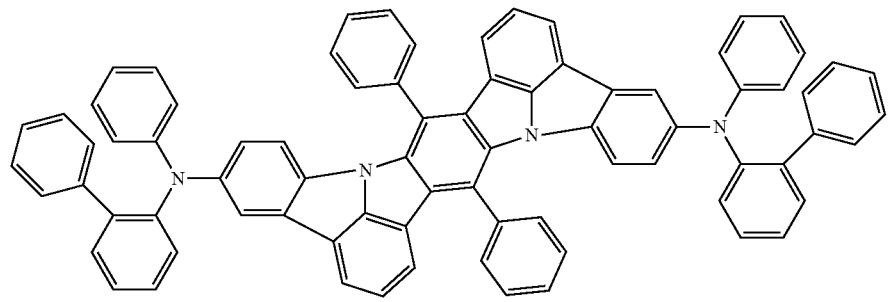
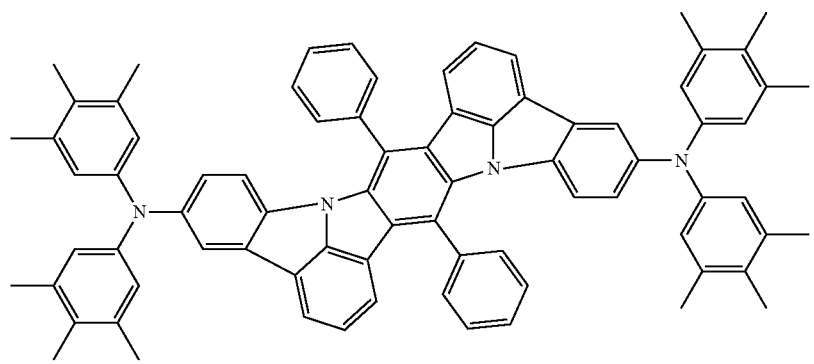
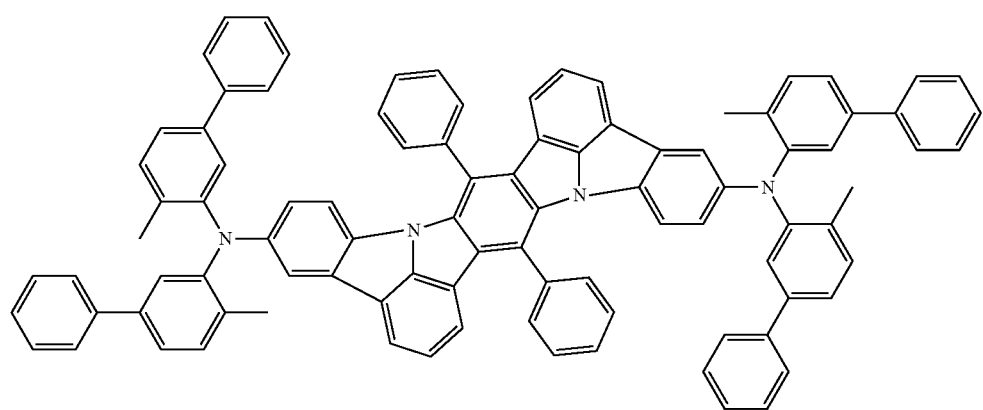

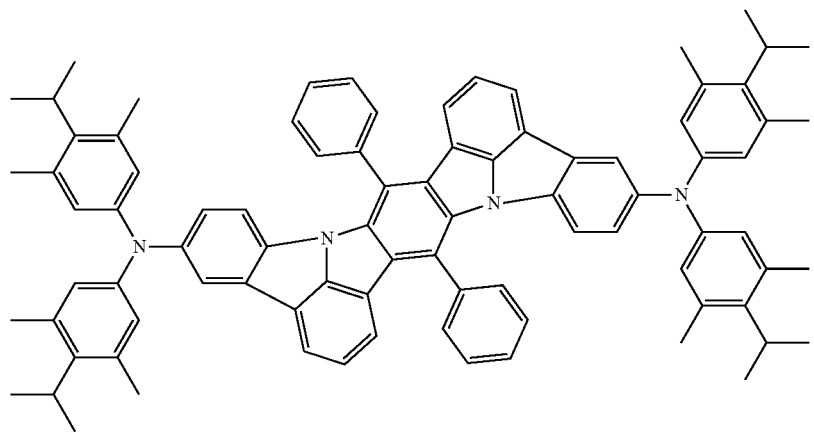
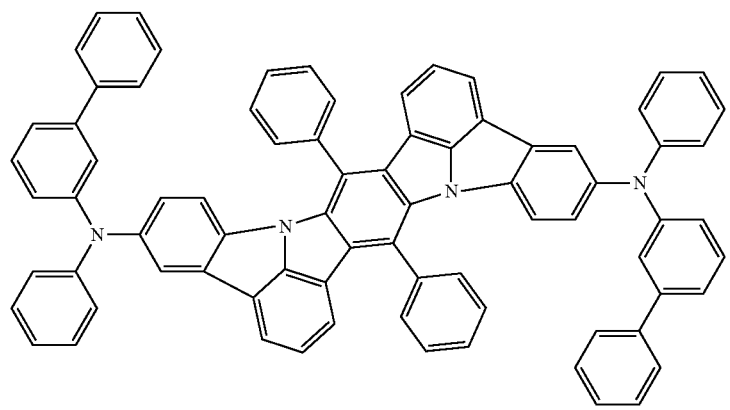
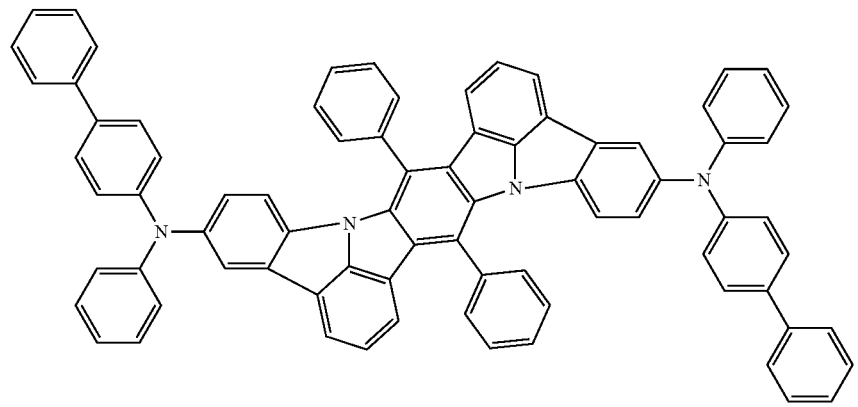
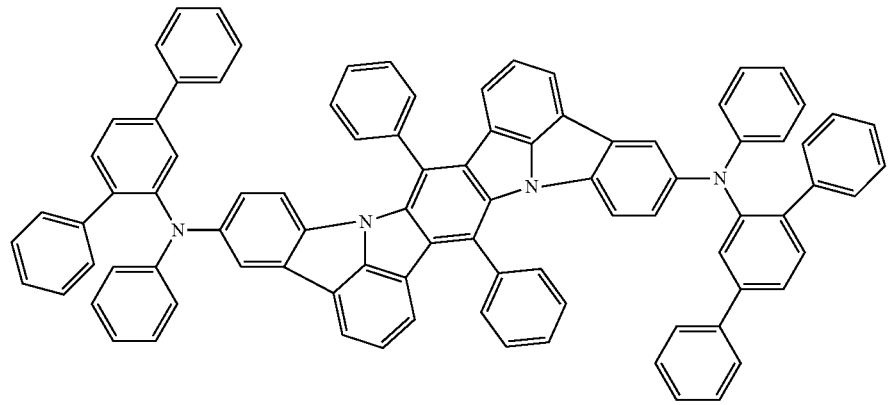

-continued
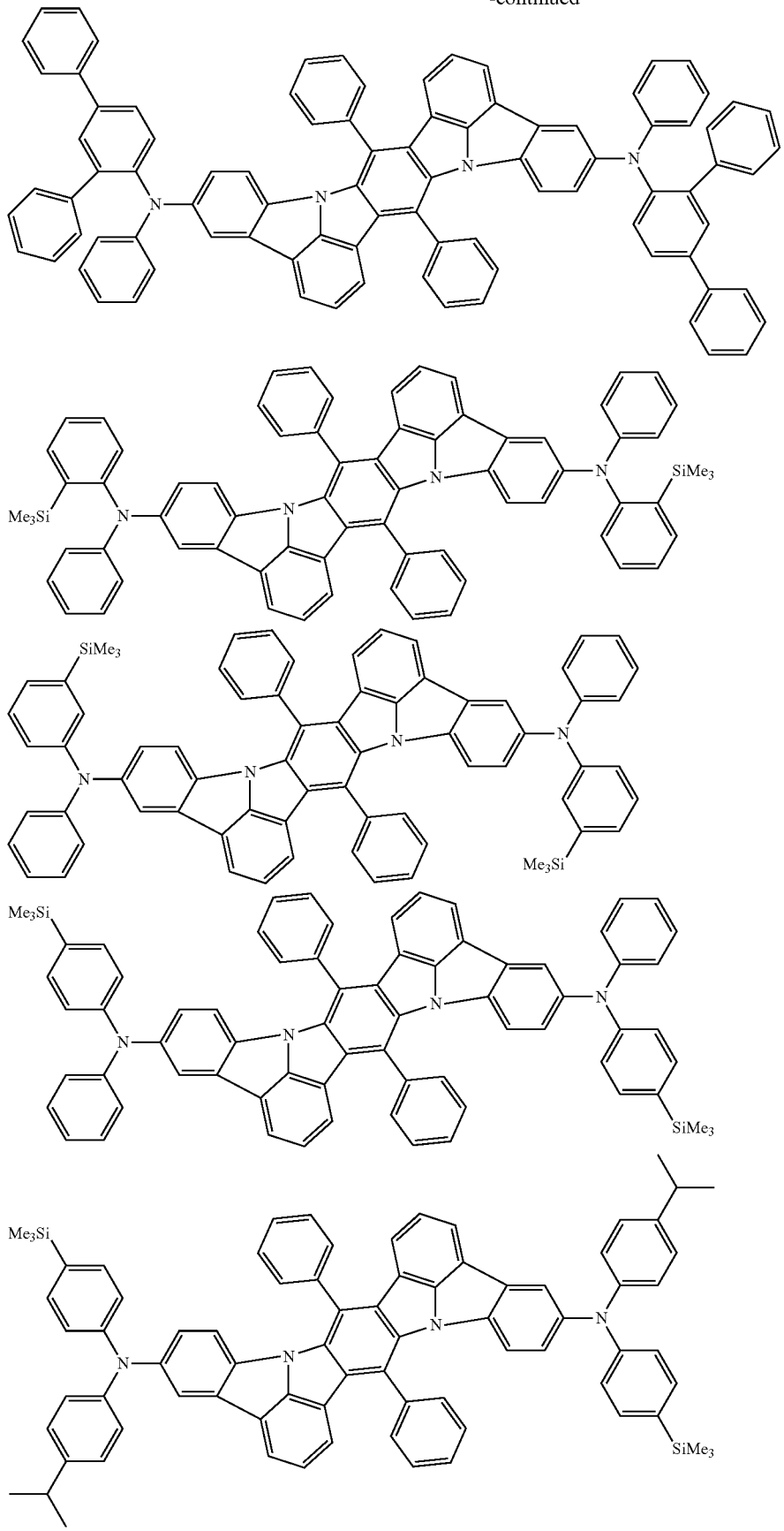

-continued
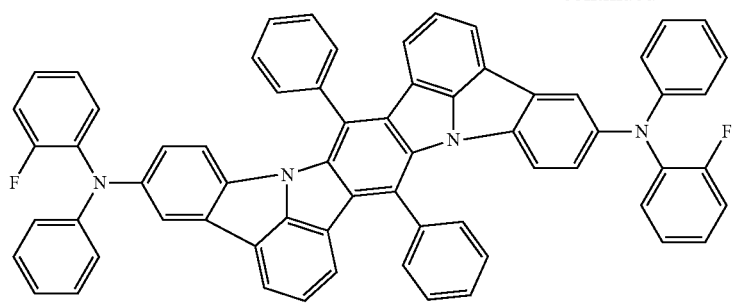
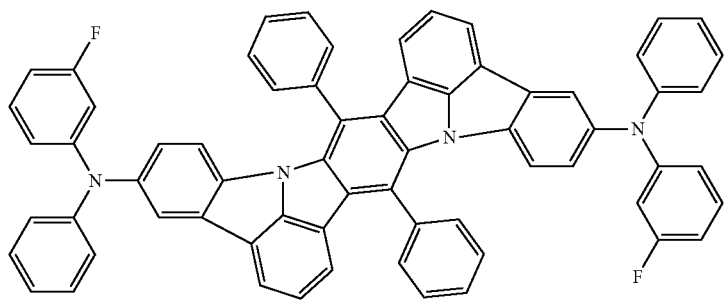
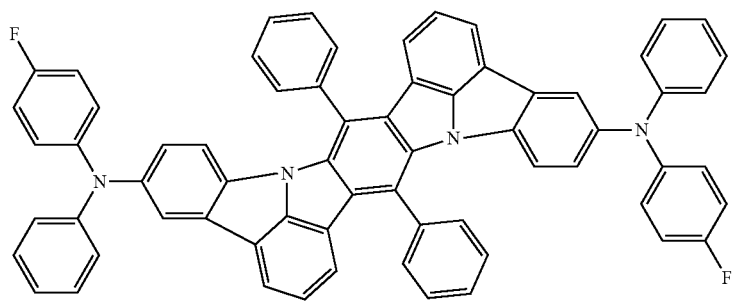
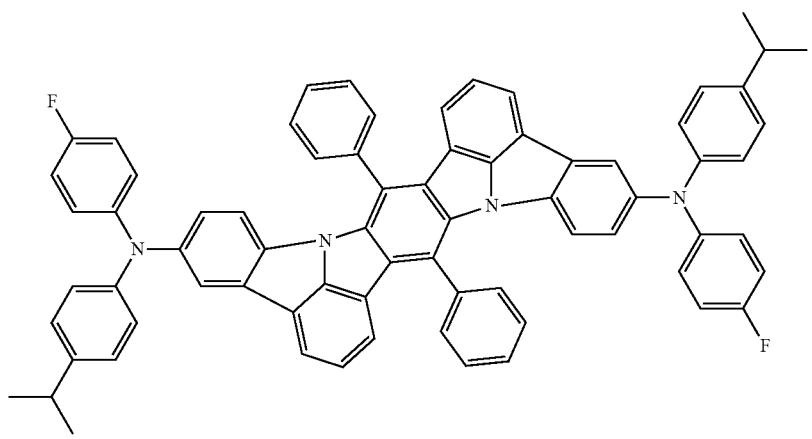
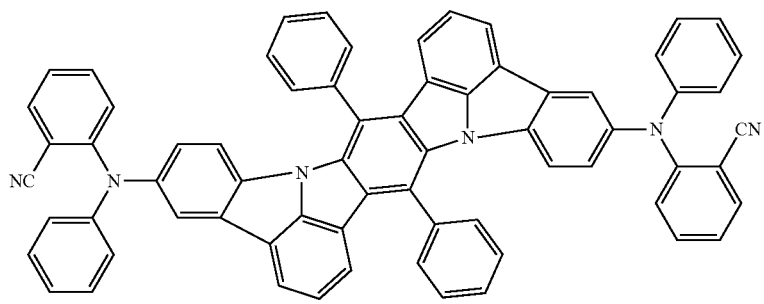

-continued
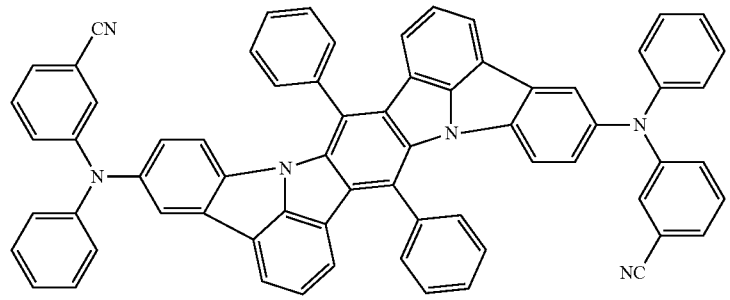
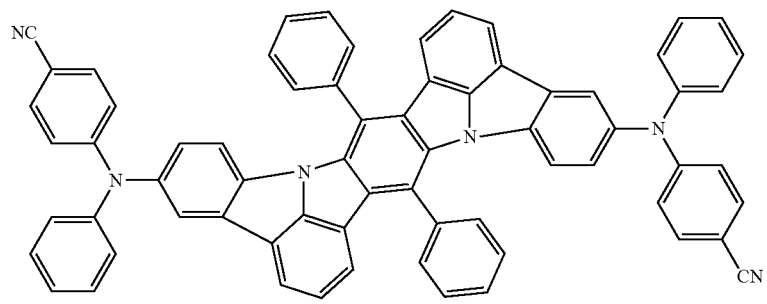
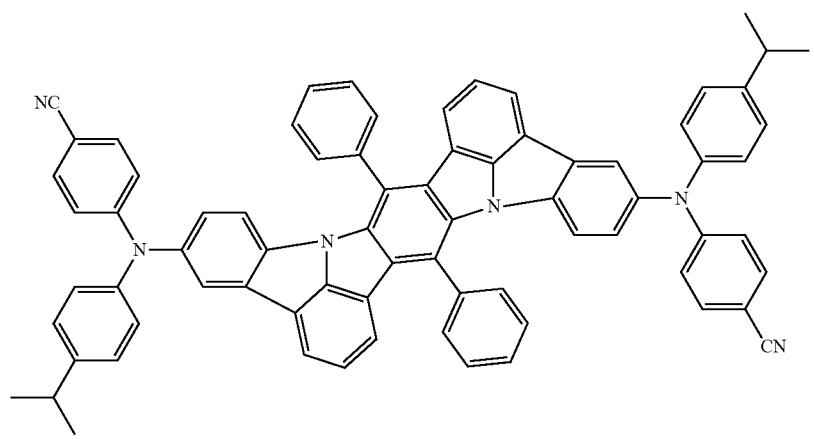
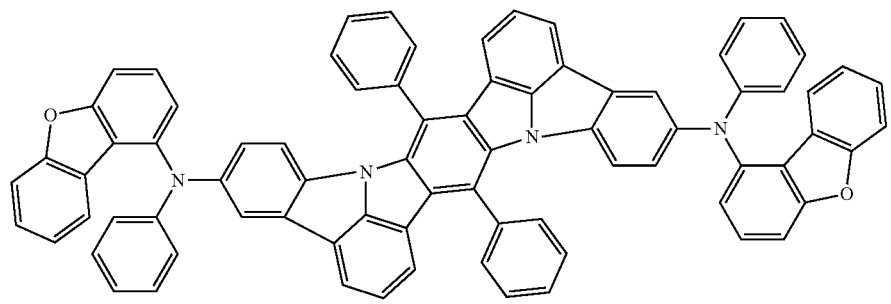
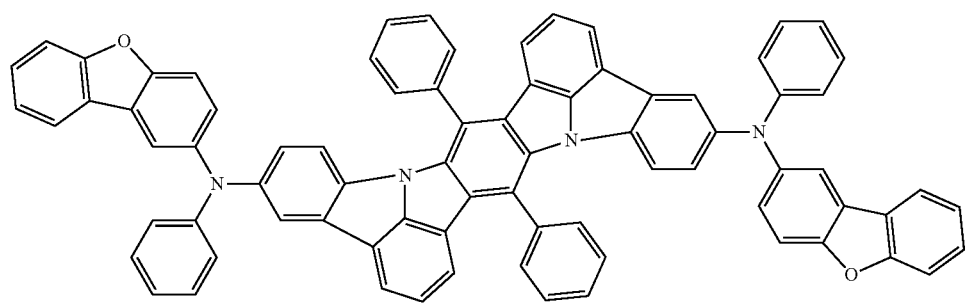

-continued
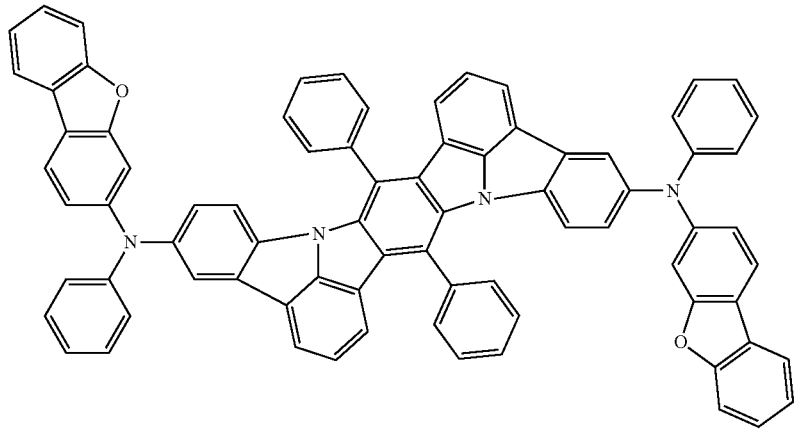
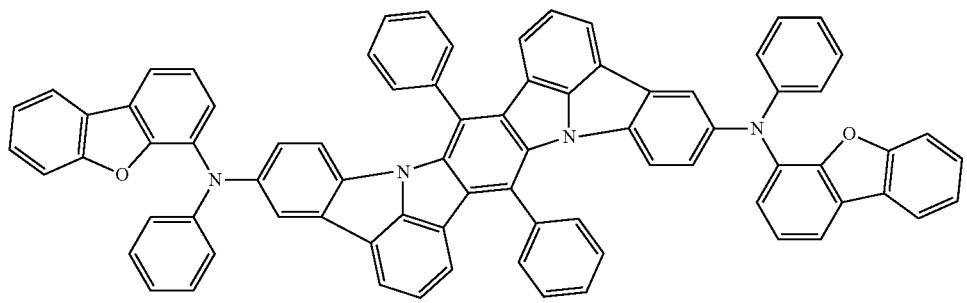
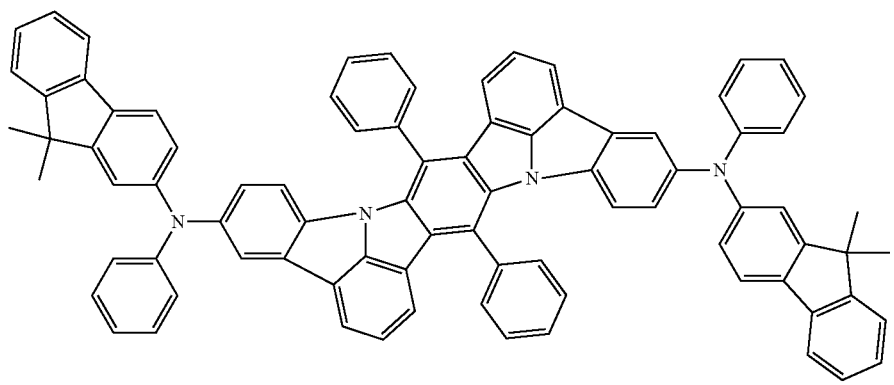
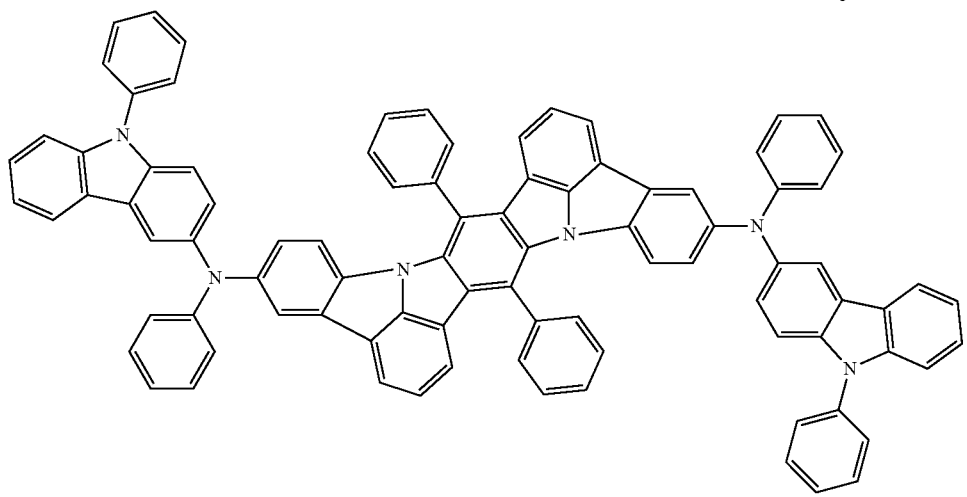

-continued
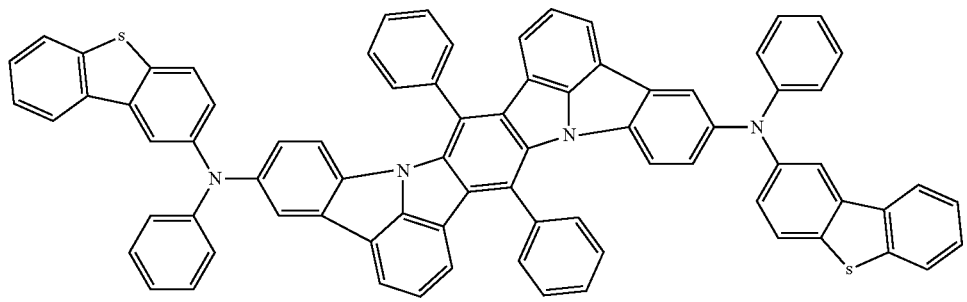
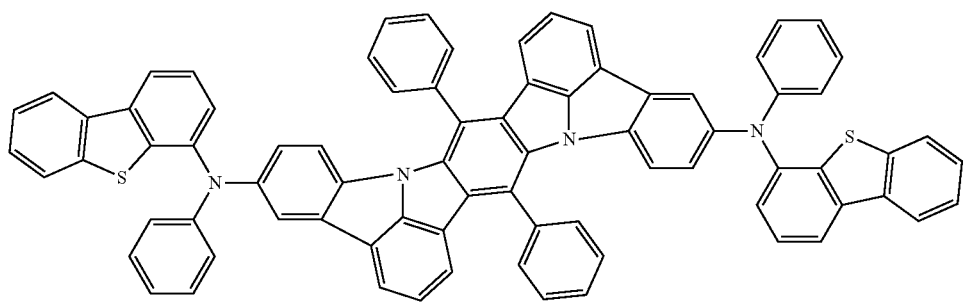
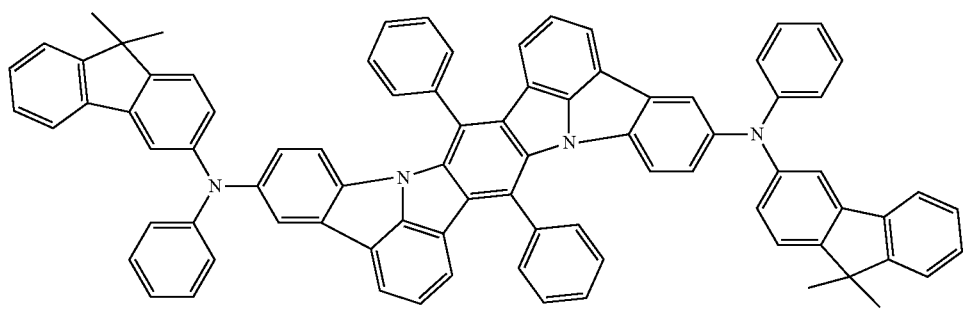
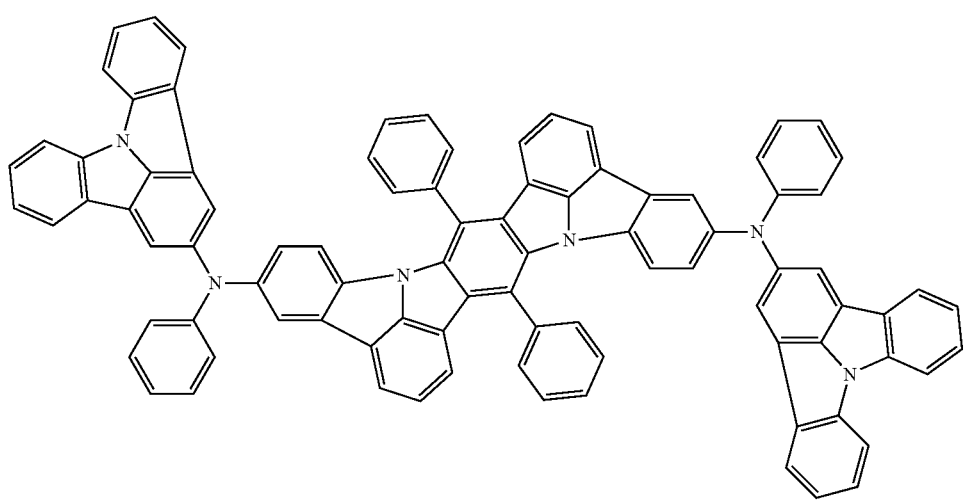

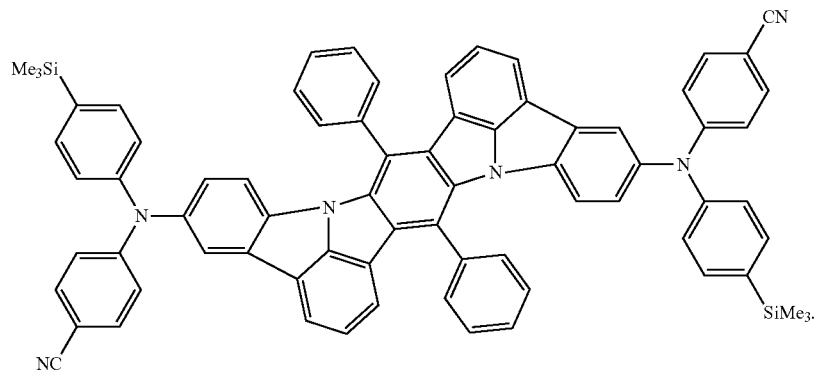
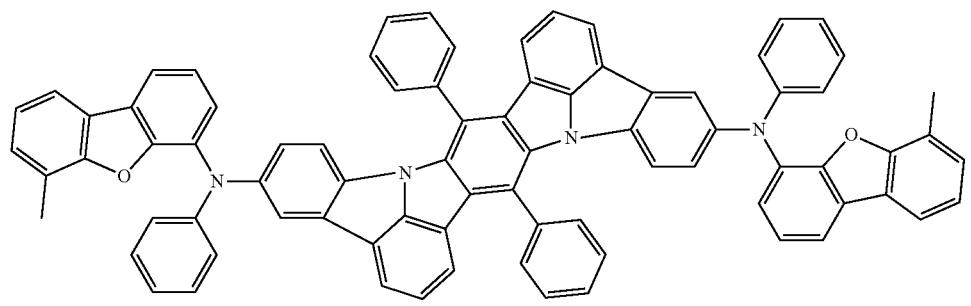
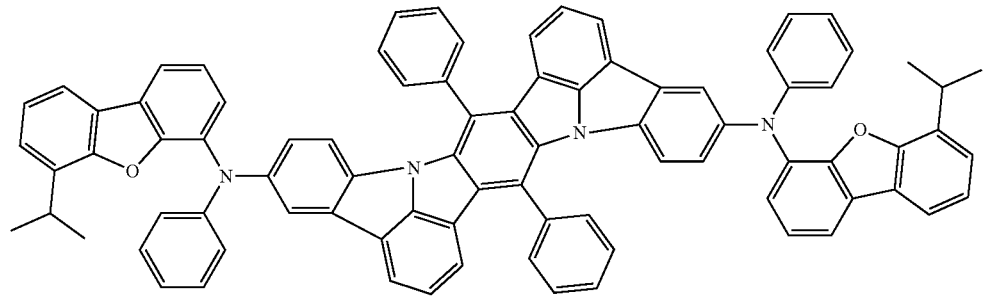
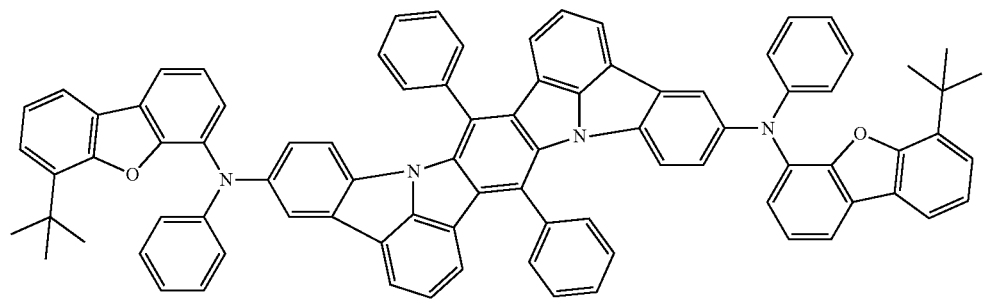

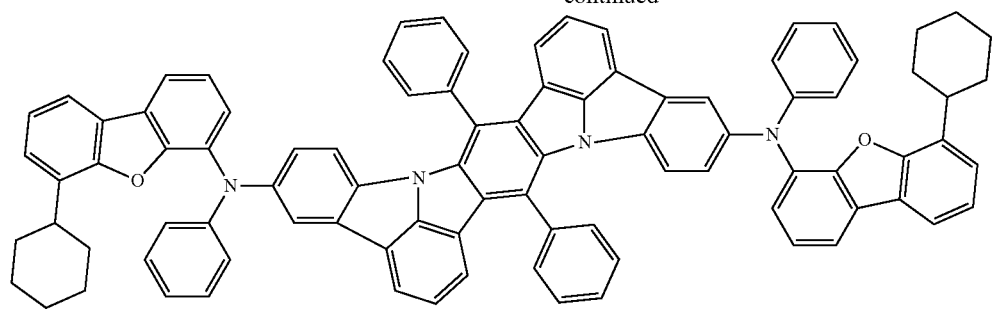
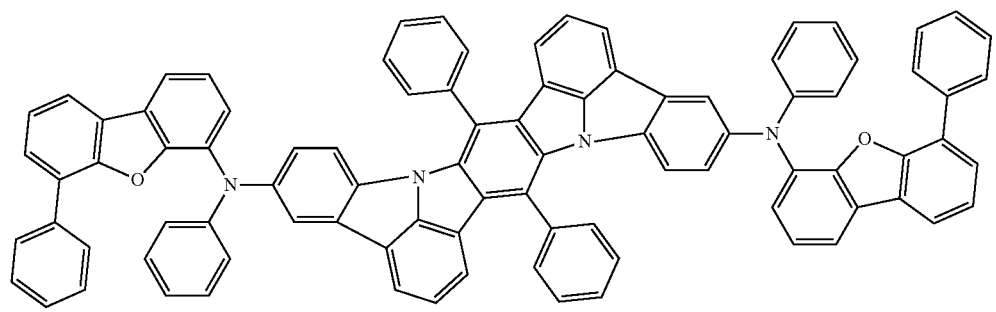
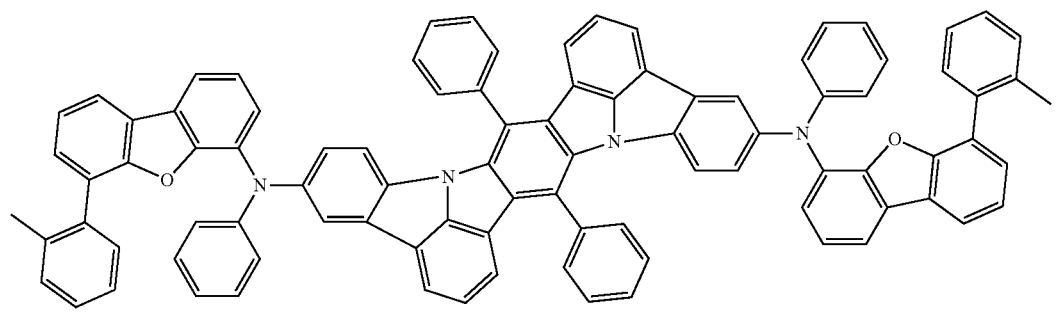
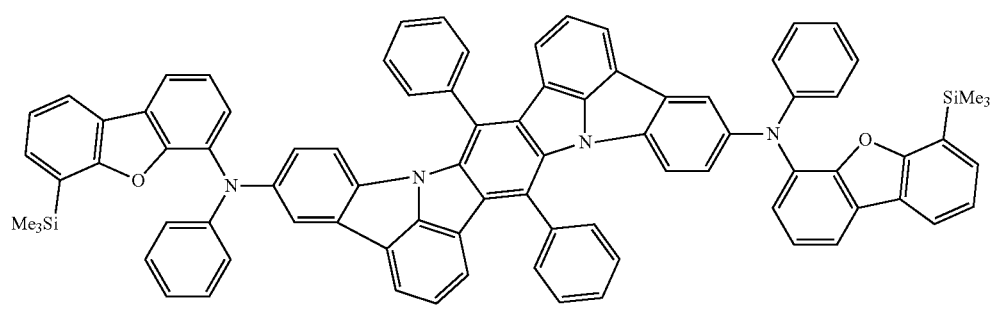
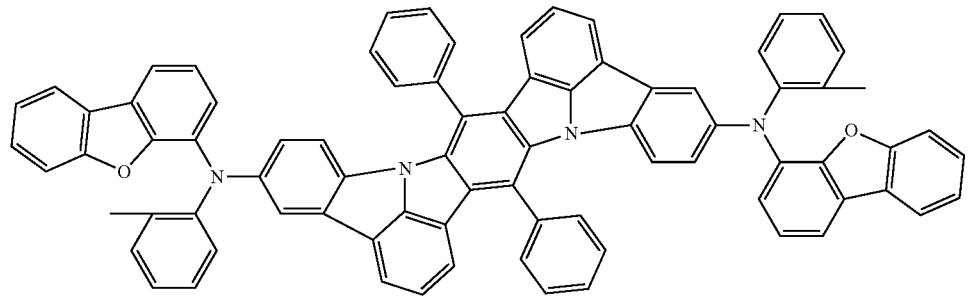

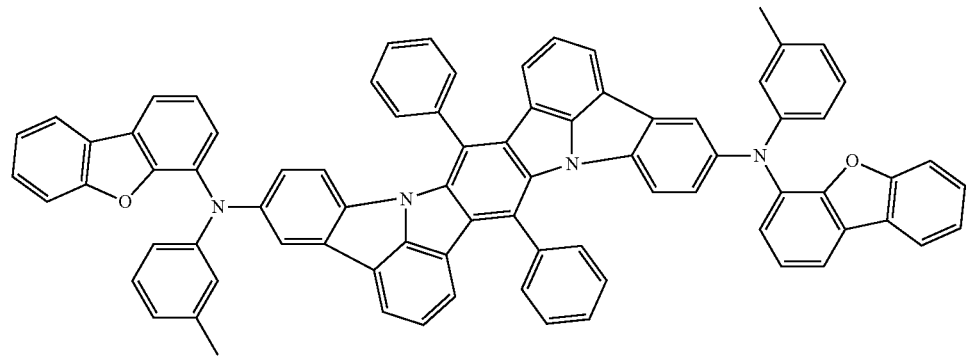
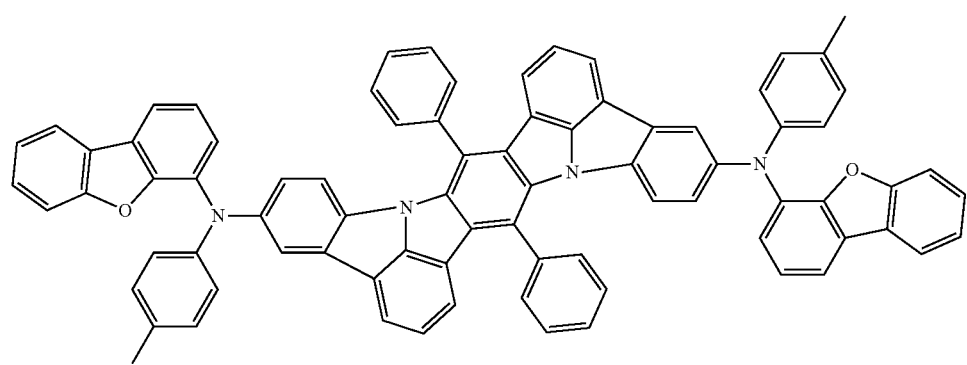
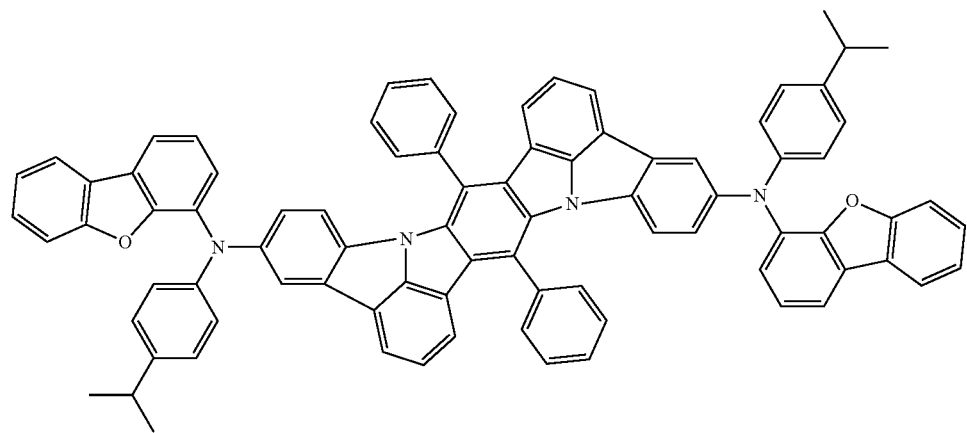
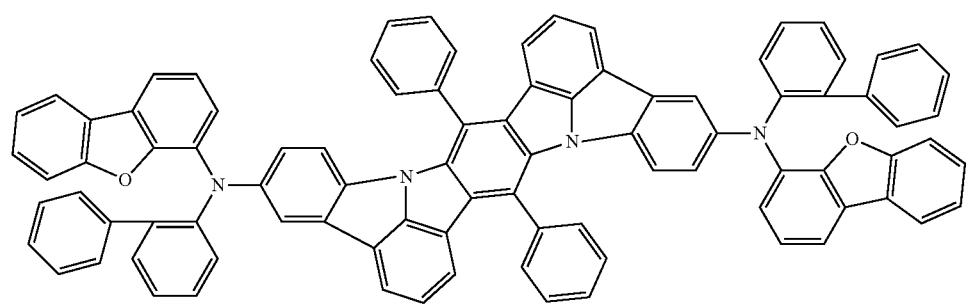

-continued
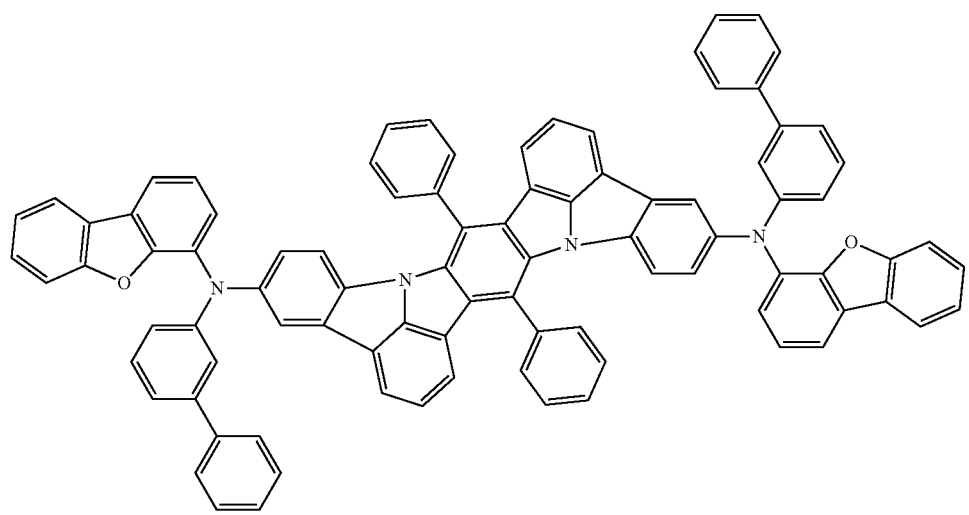
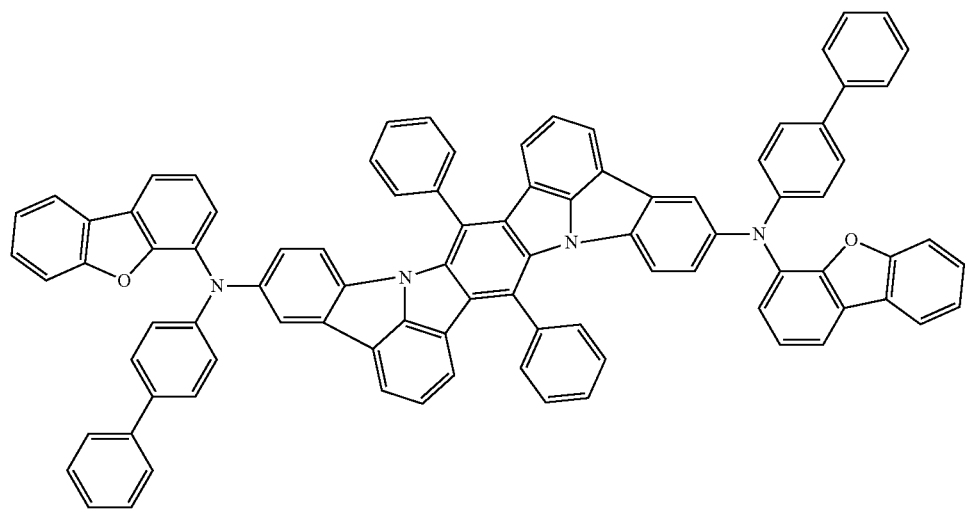
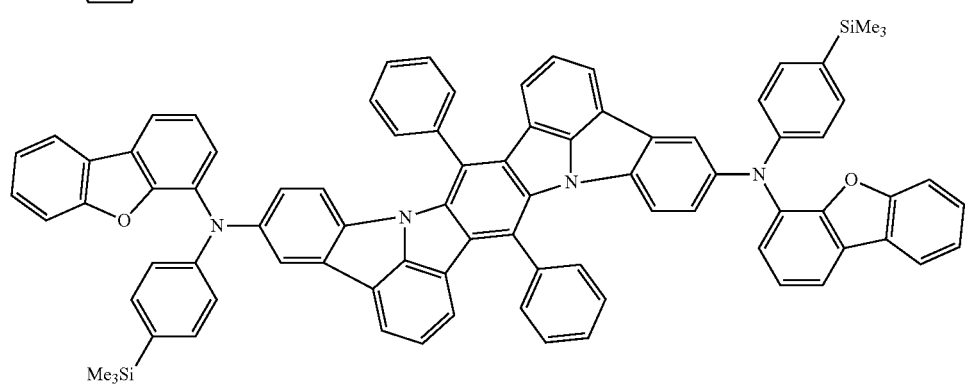
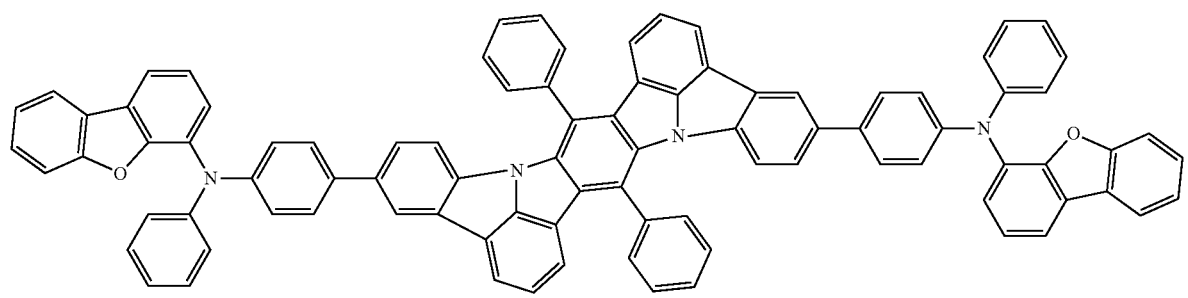

-continued
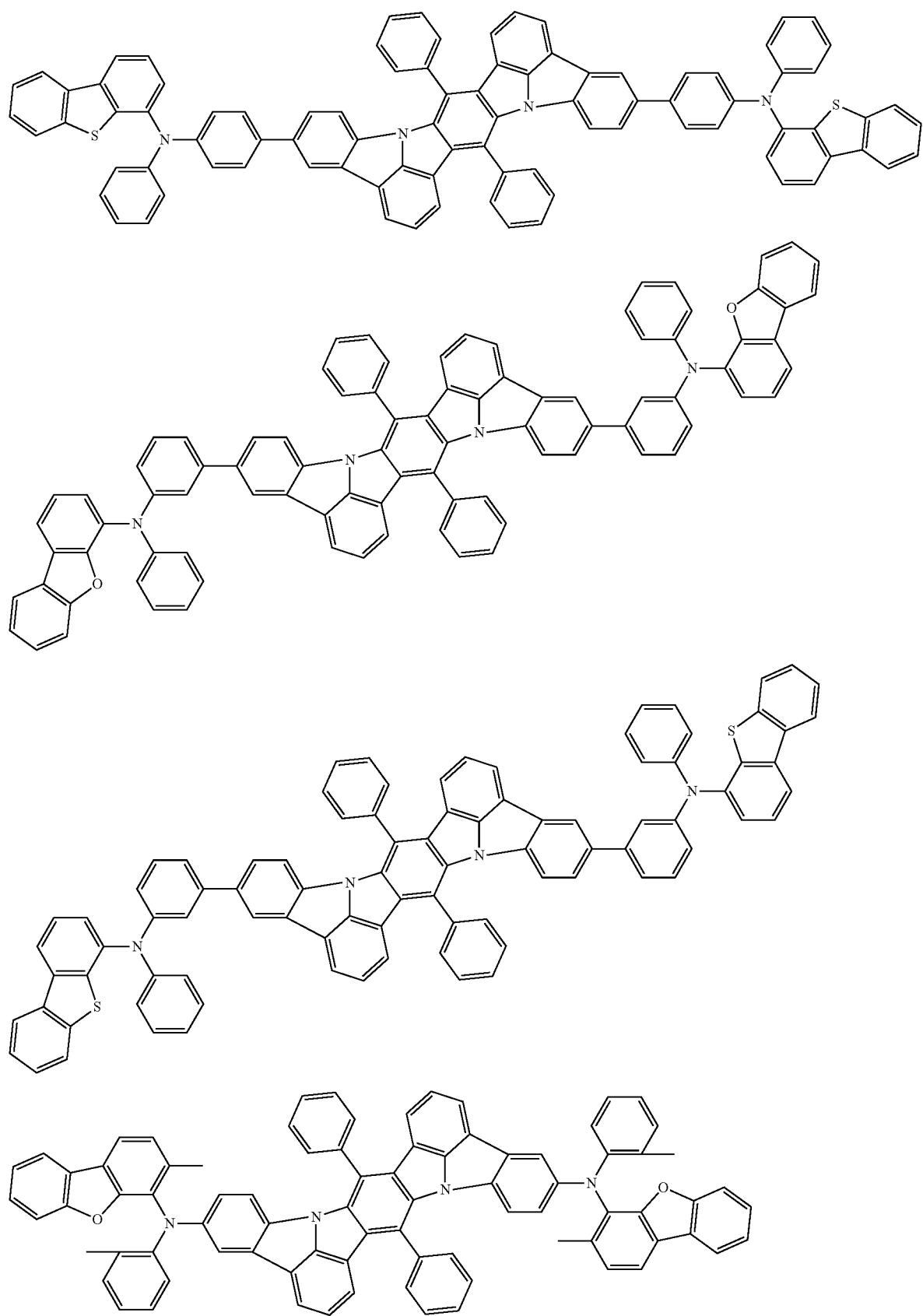

-continued
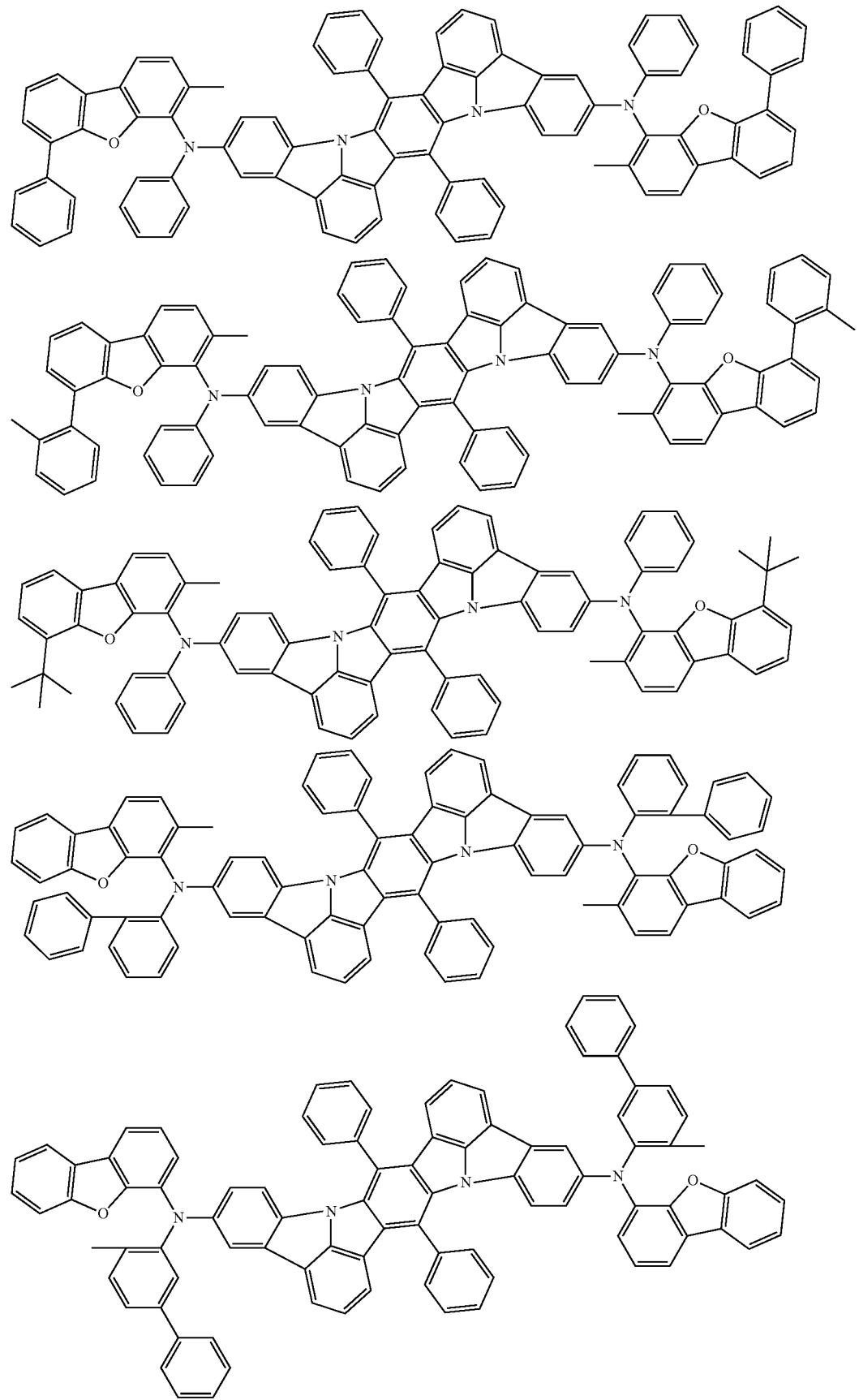

-continued
805 806
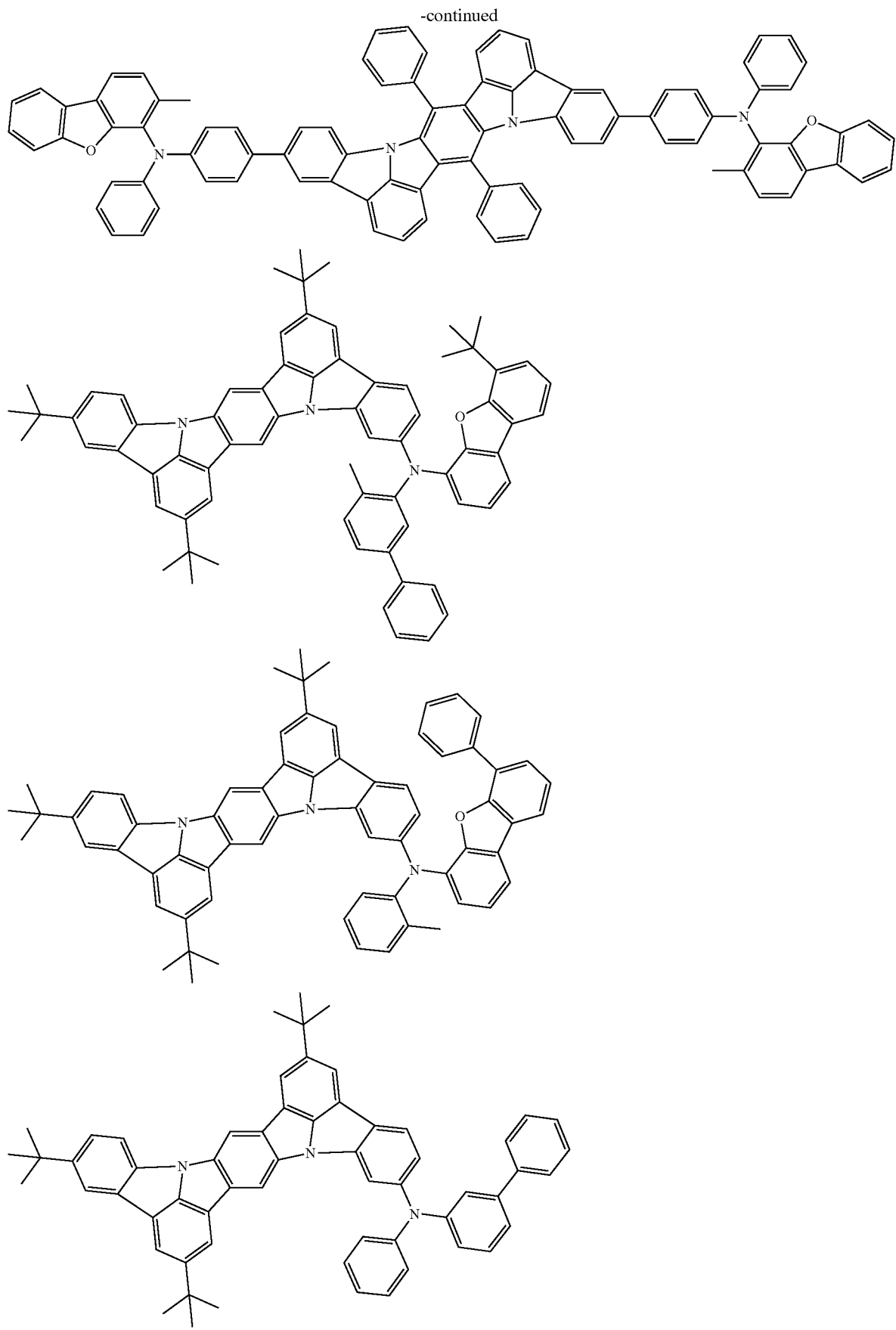

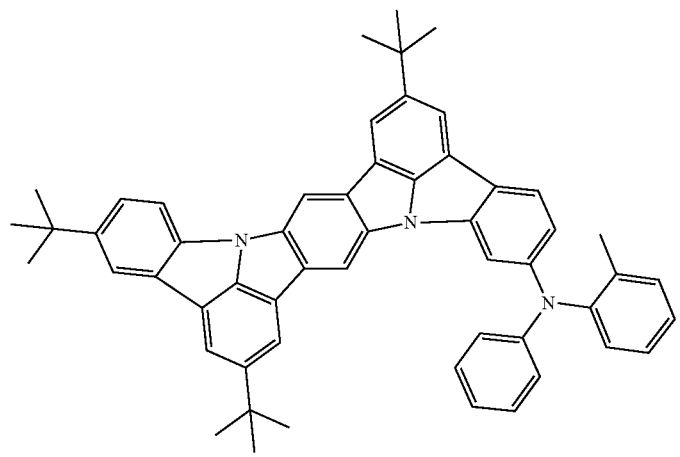
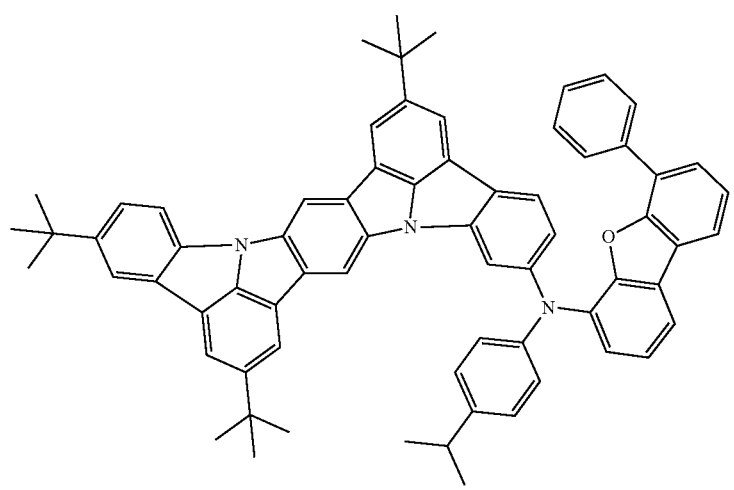
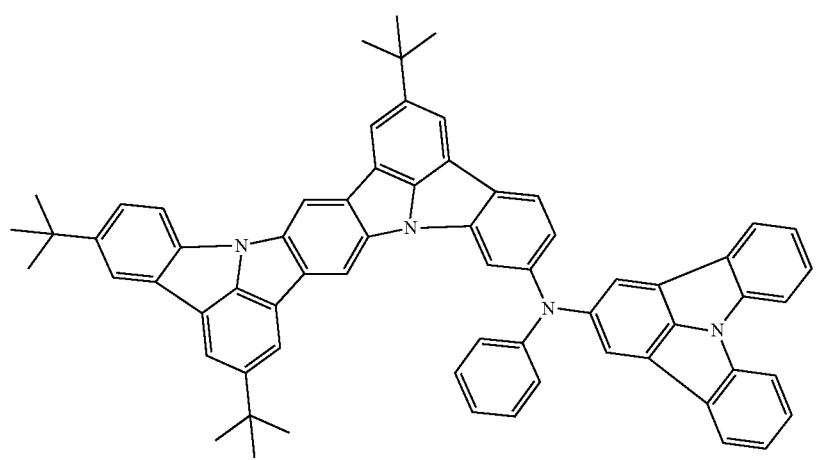

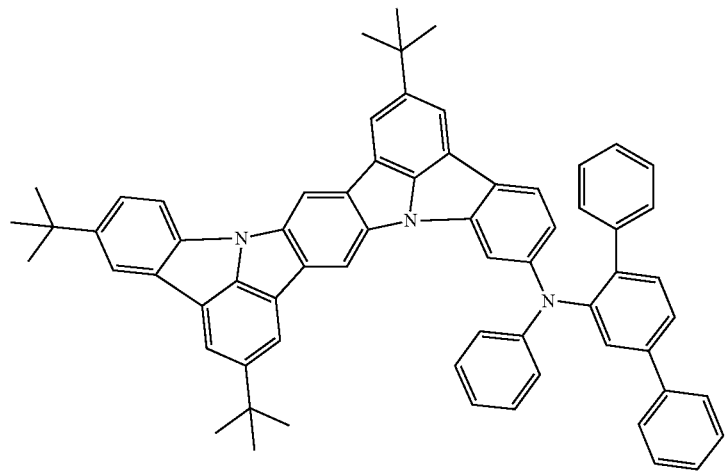
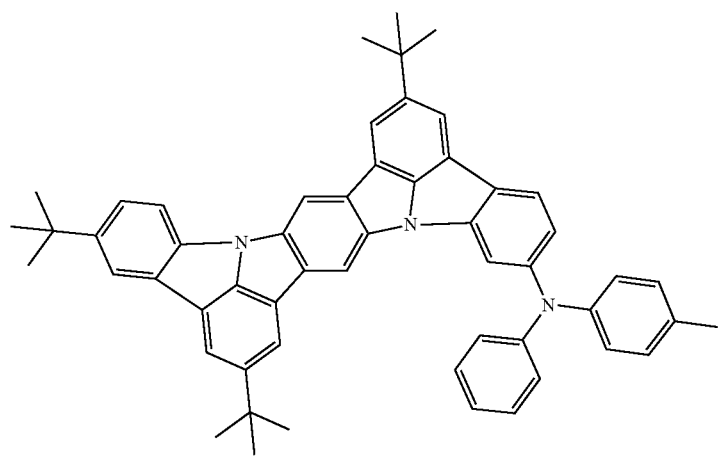
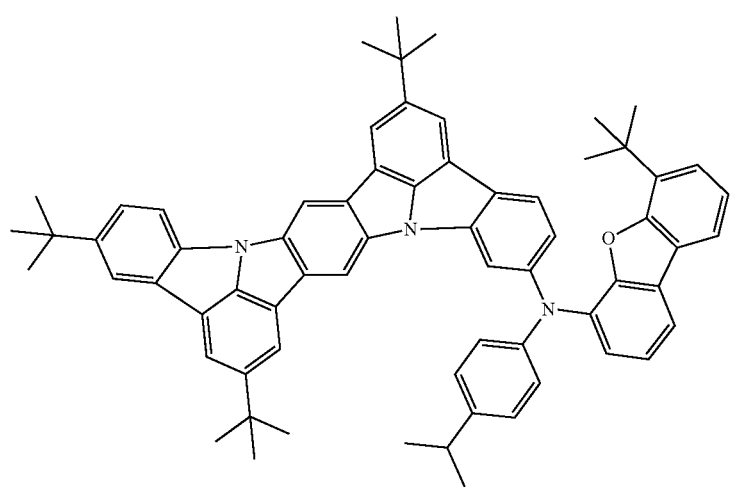

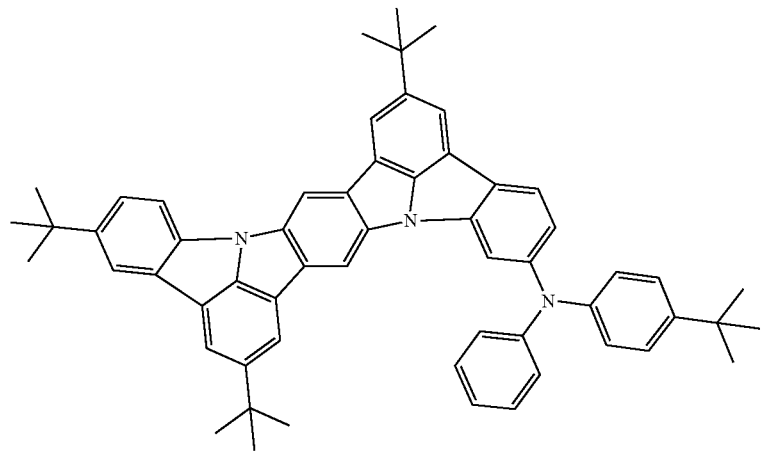
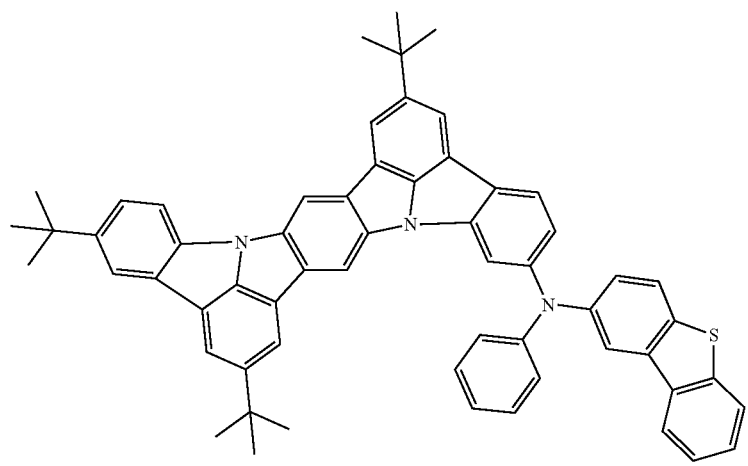
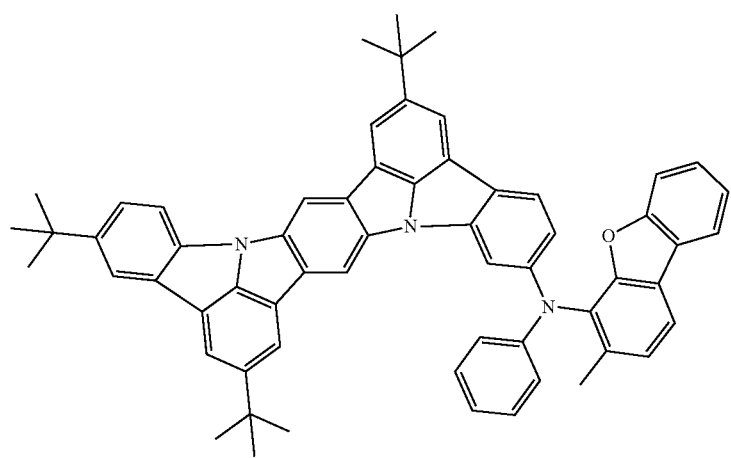

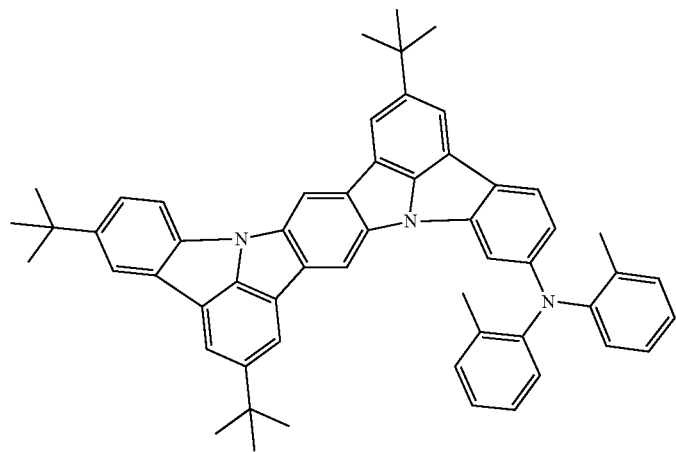
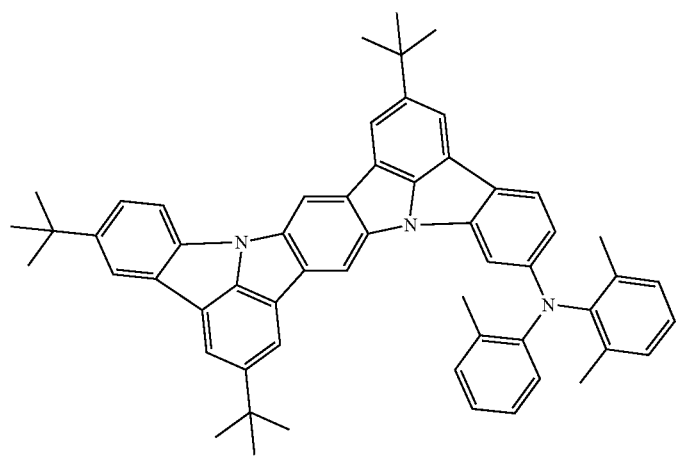
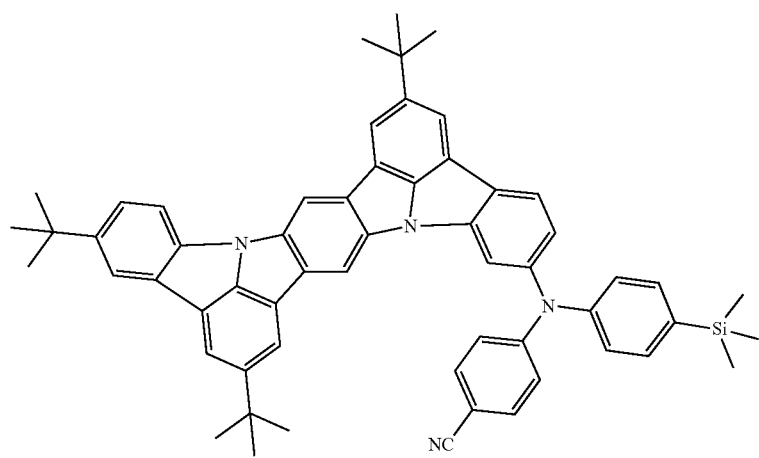

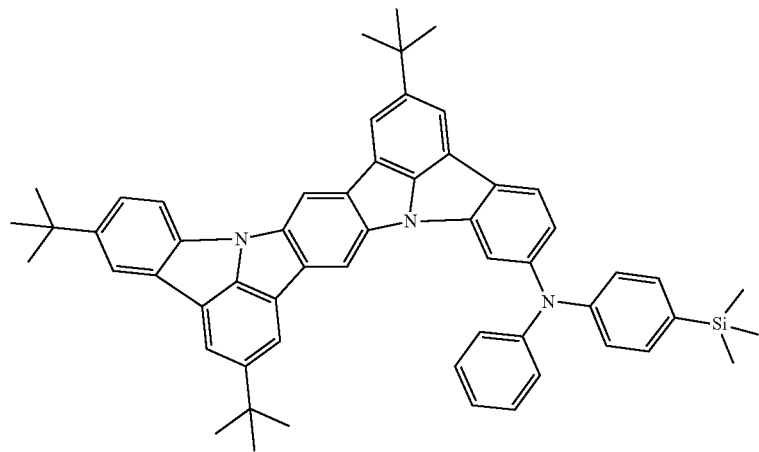
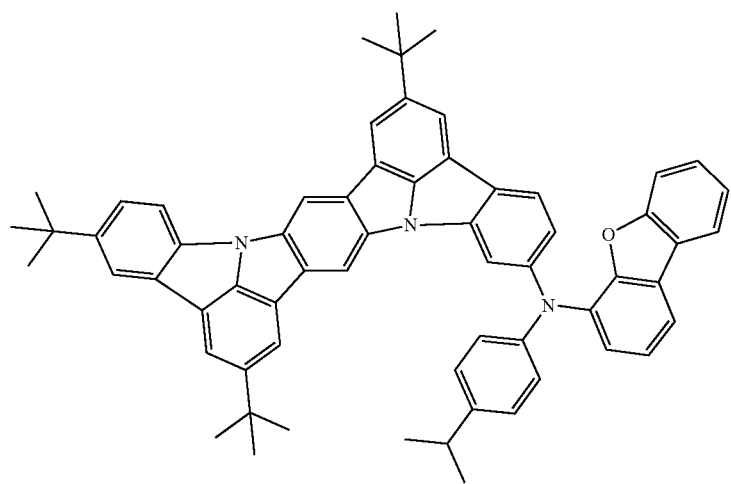
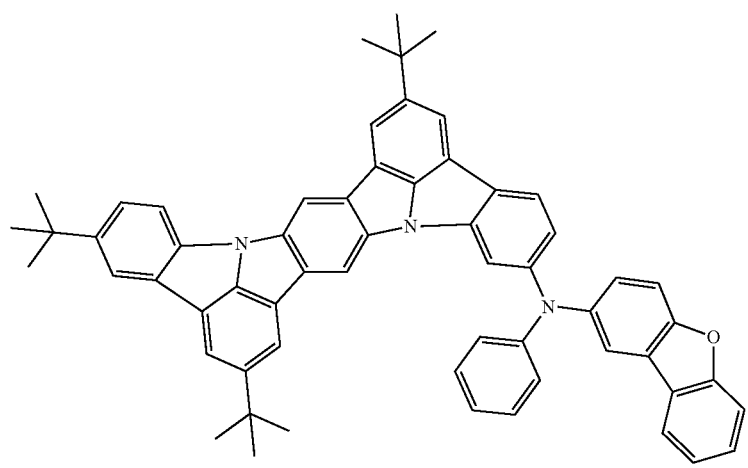

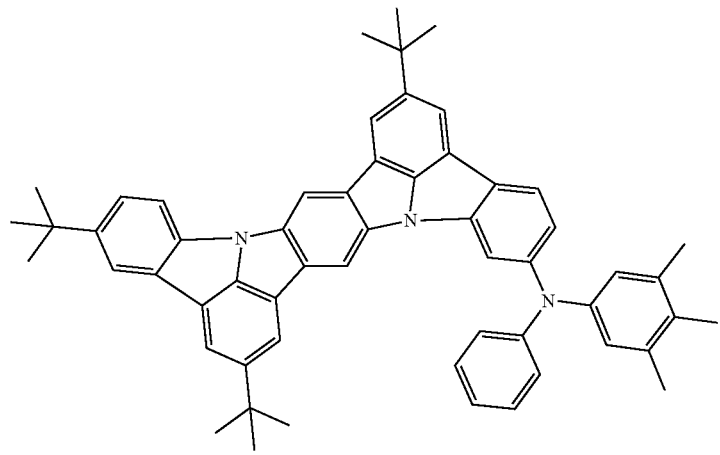
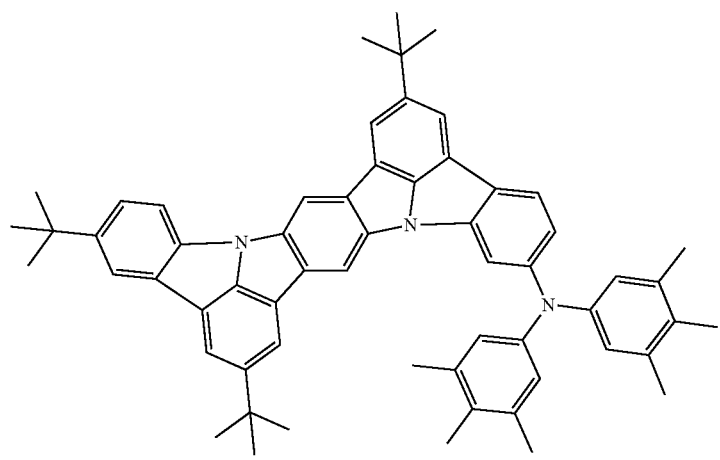
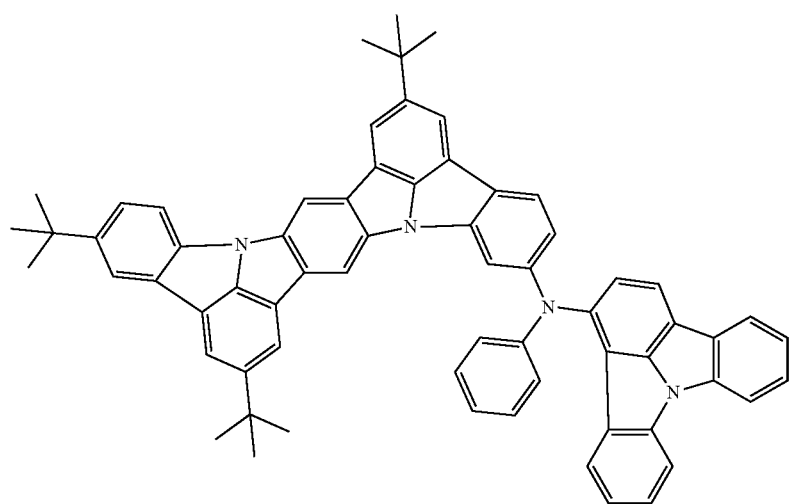

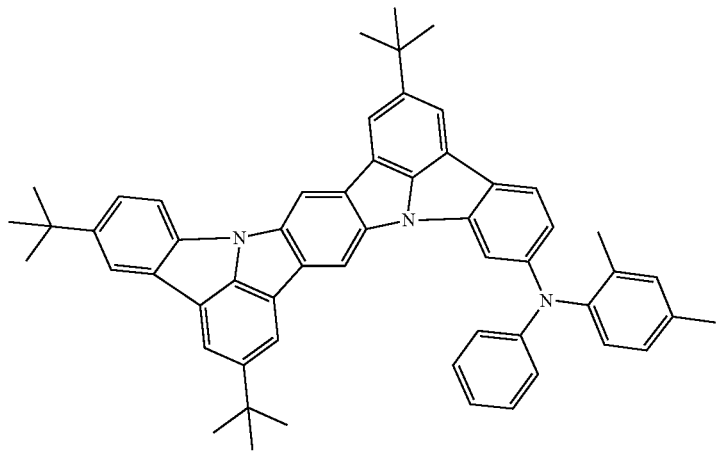
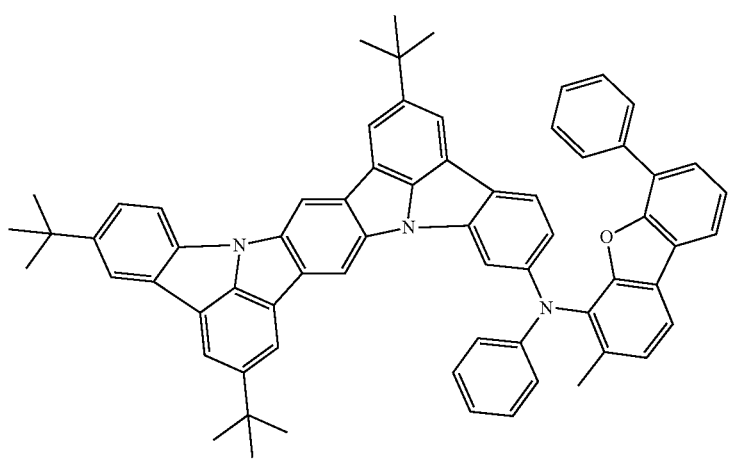
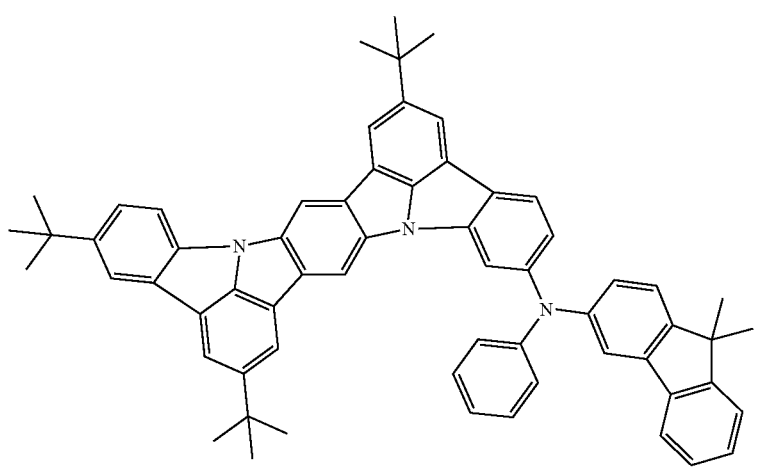

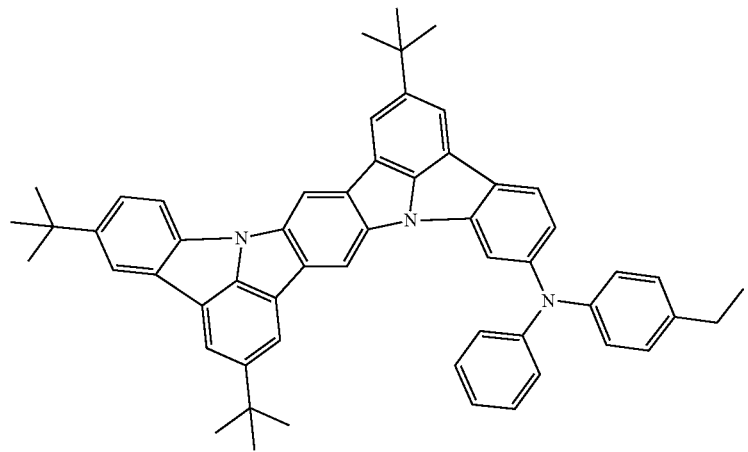
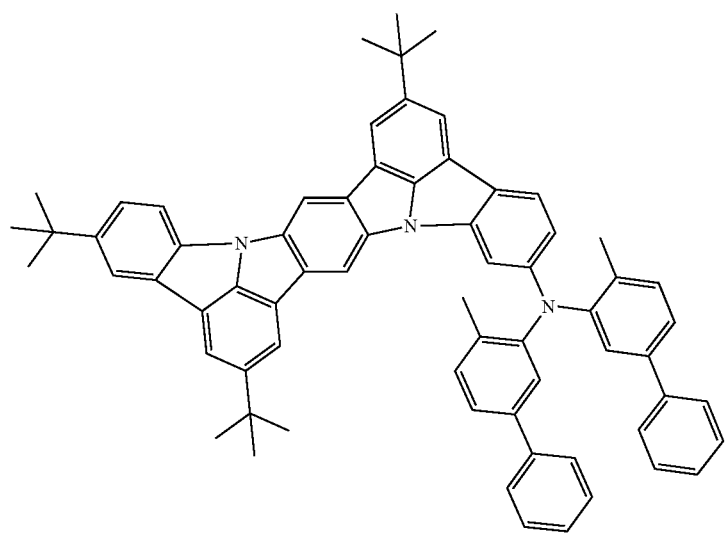
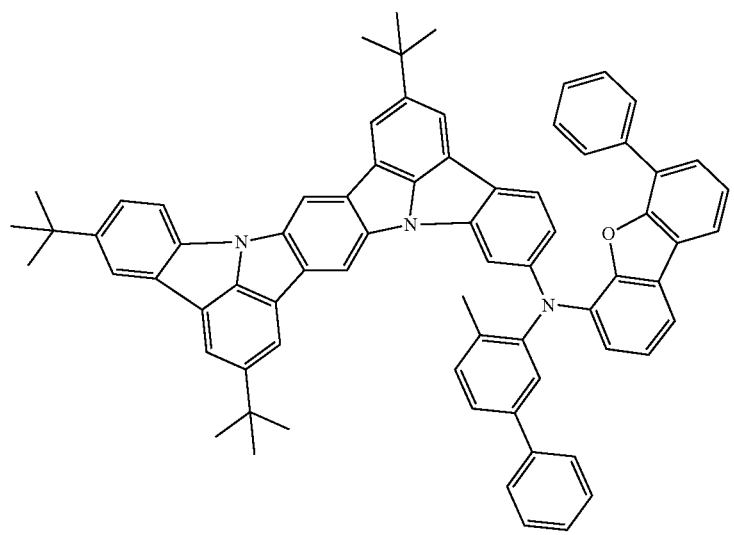

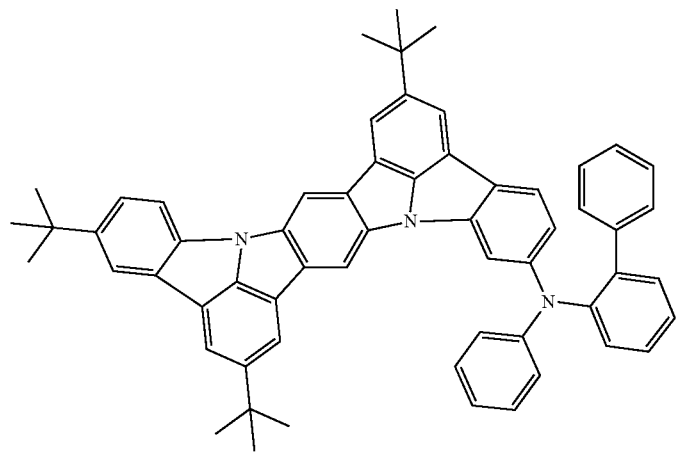
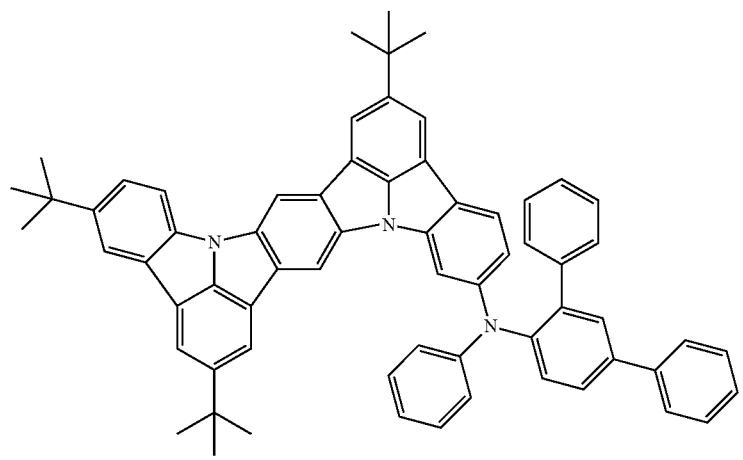
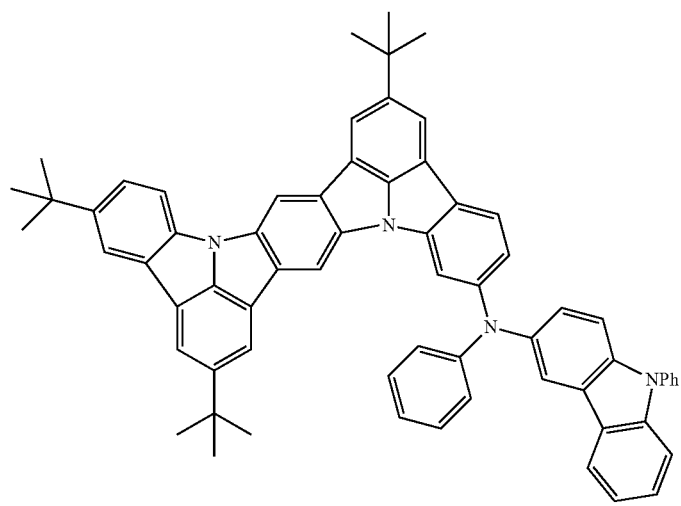

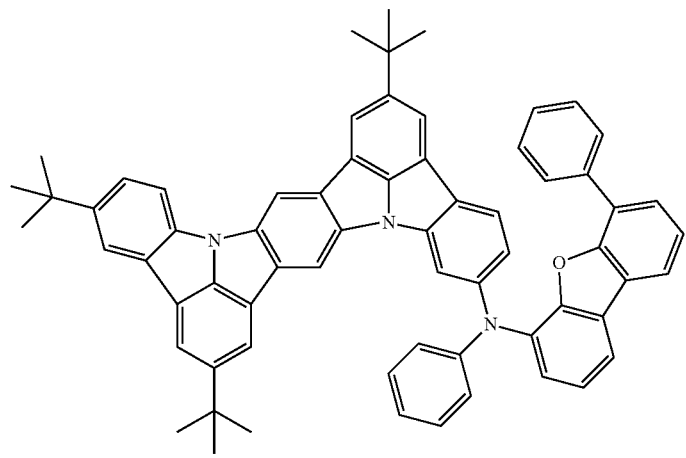
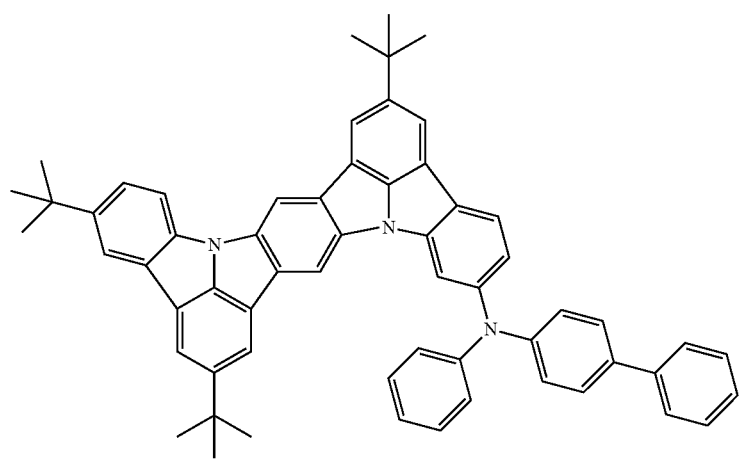
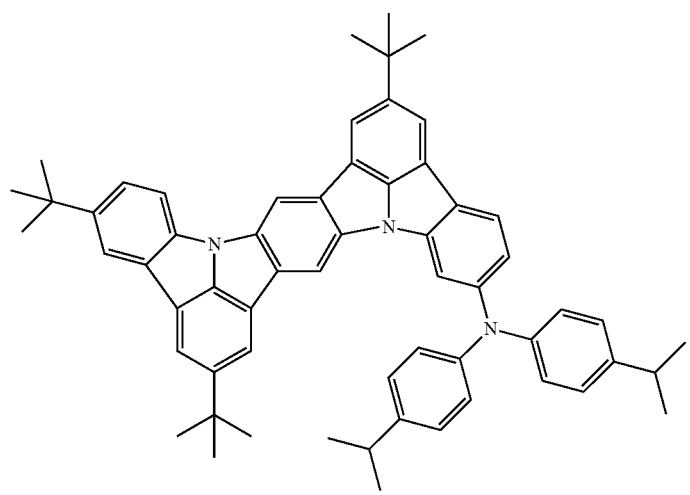

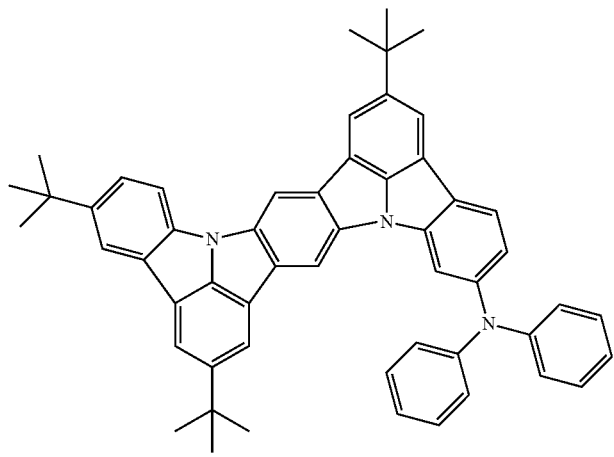
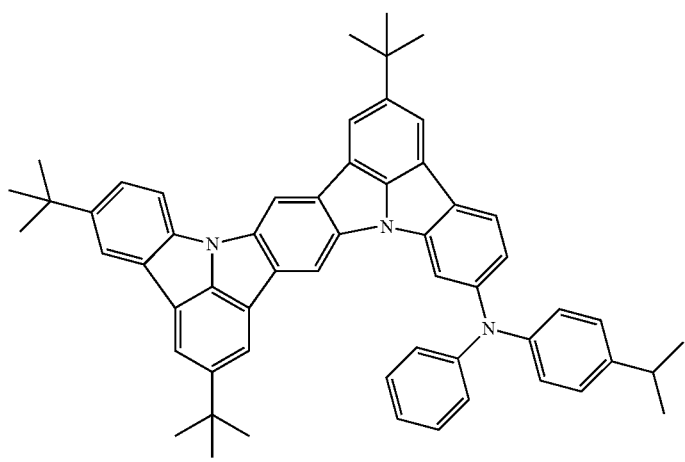
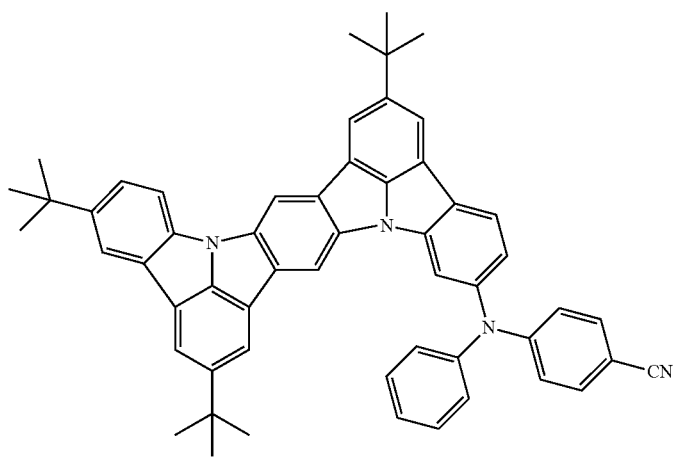

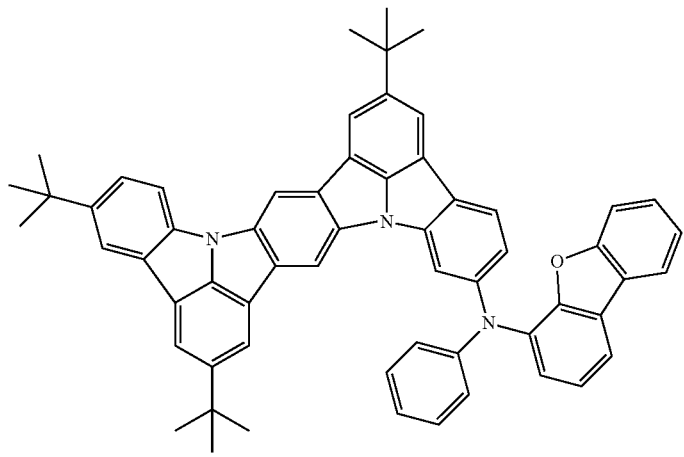
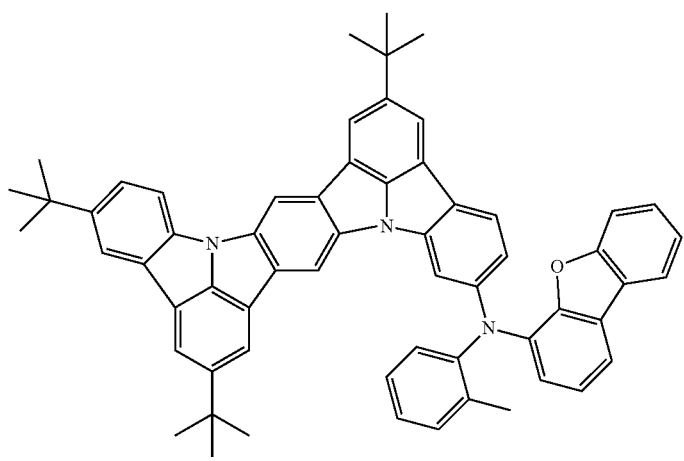
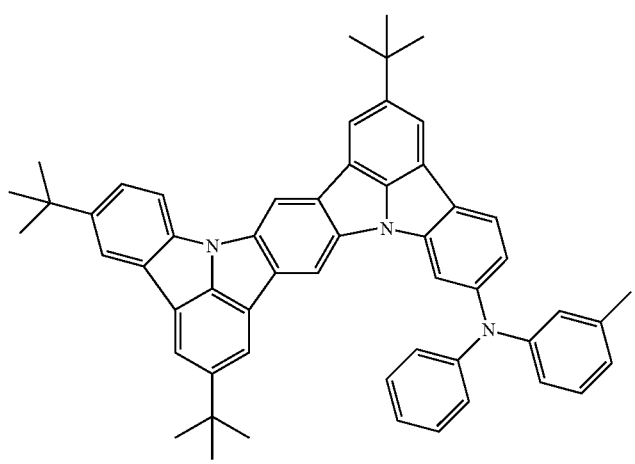

831
832
-continued
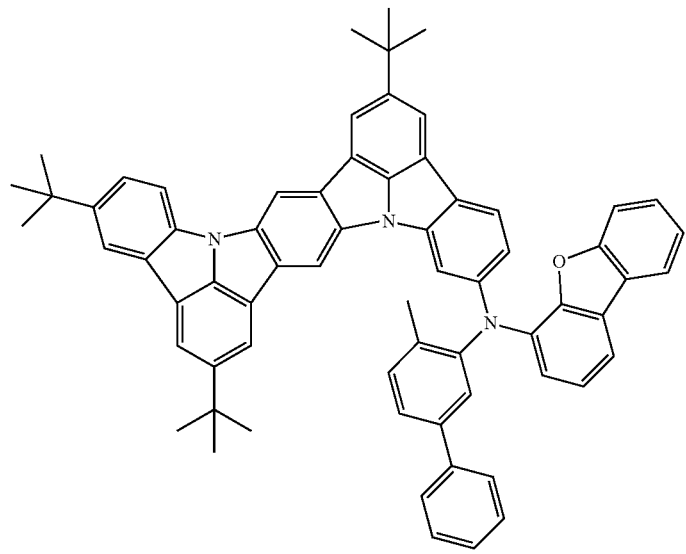
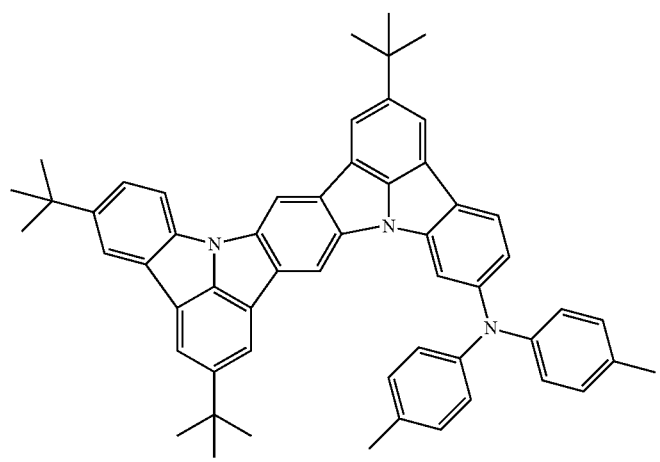
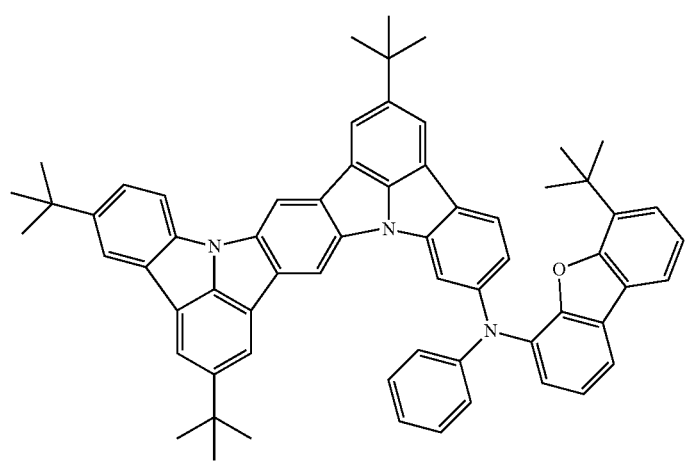

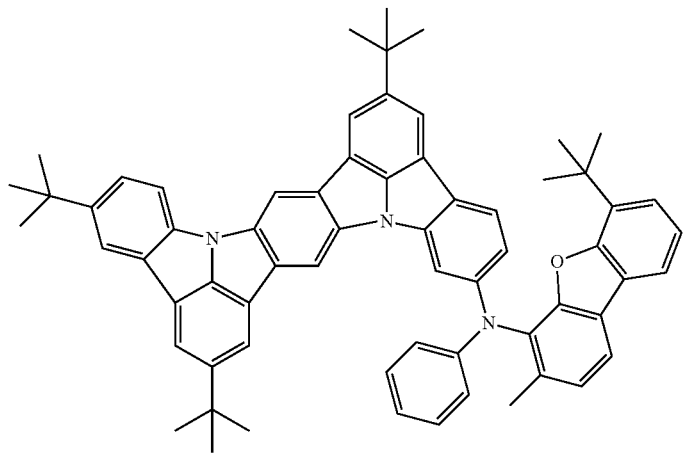
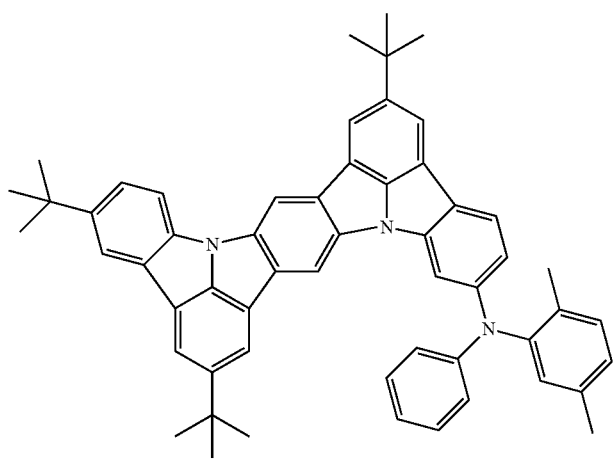
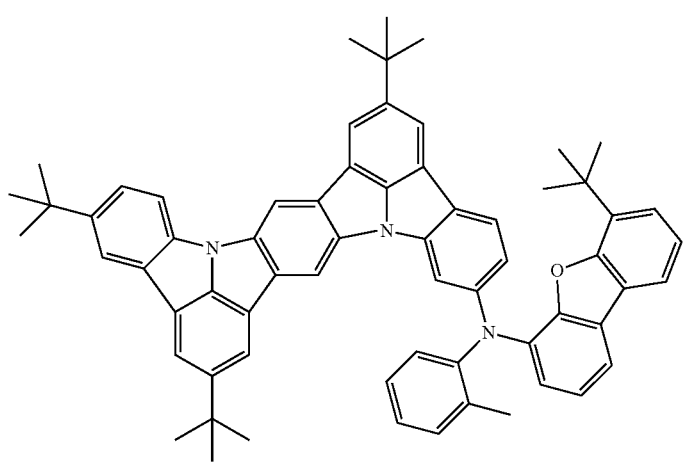

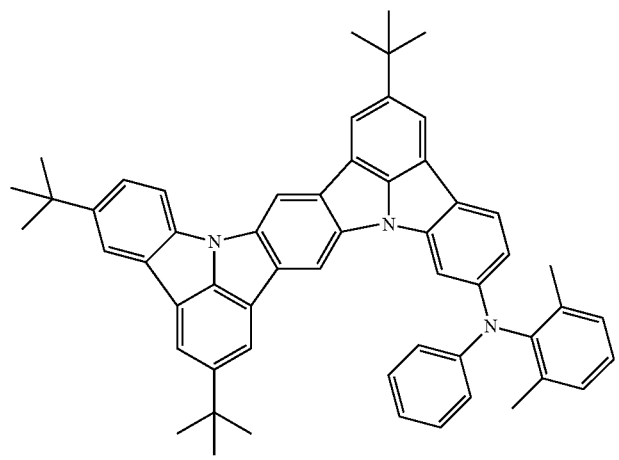
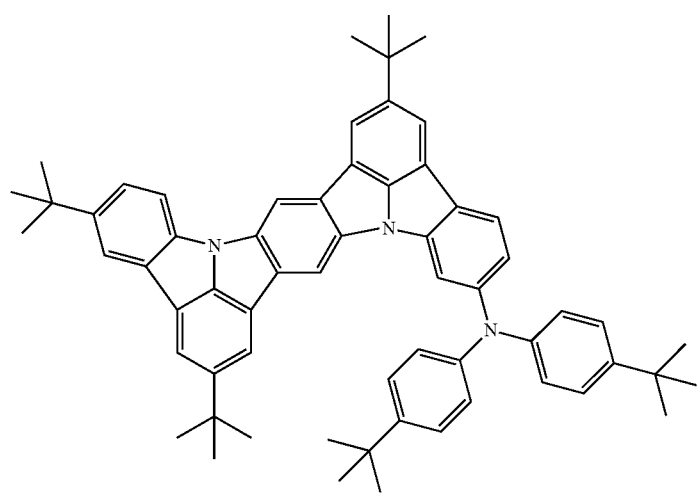
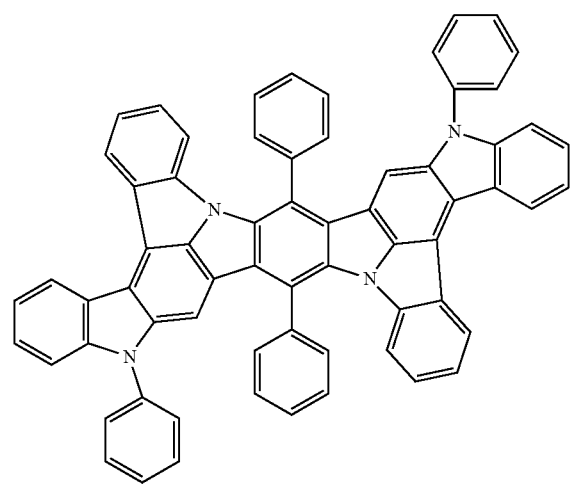

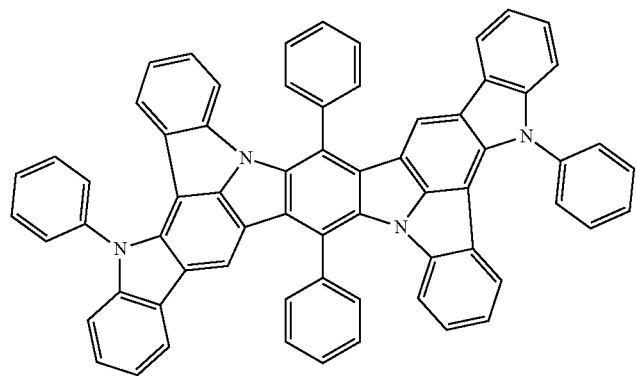
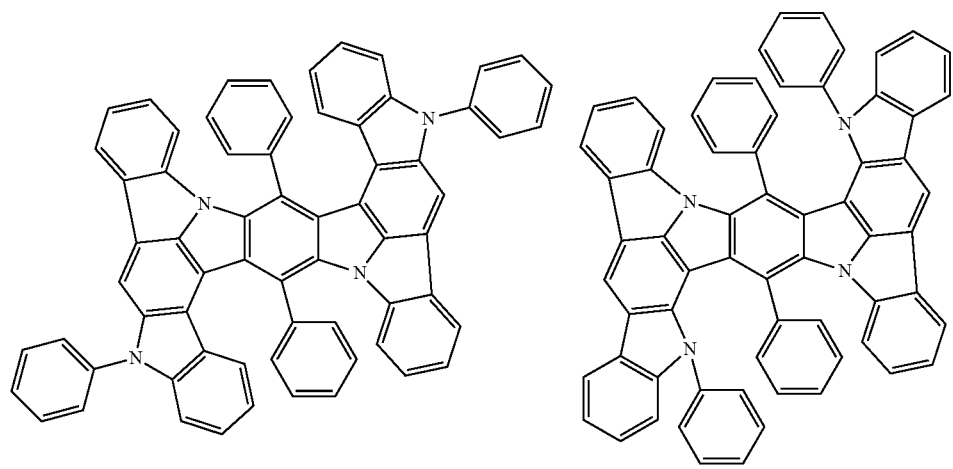
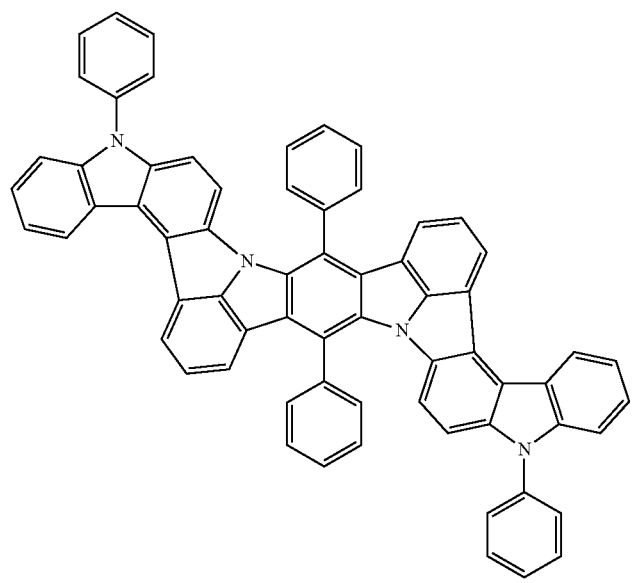

839
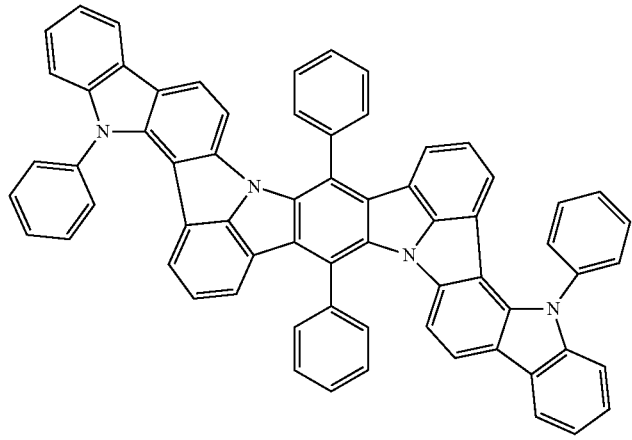
840
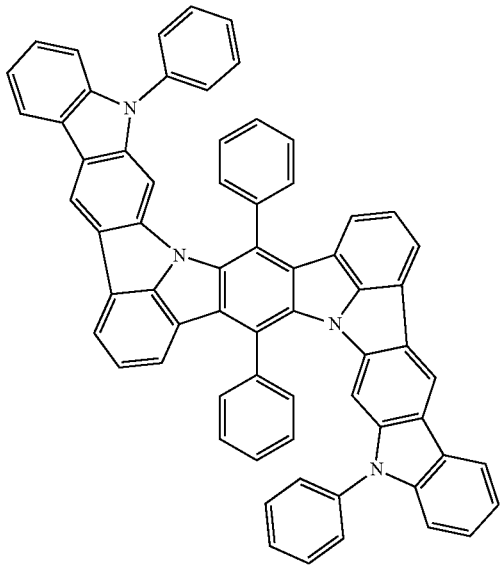
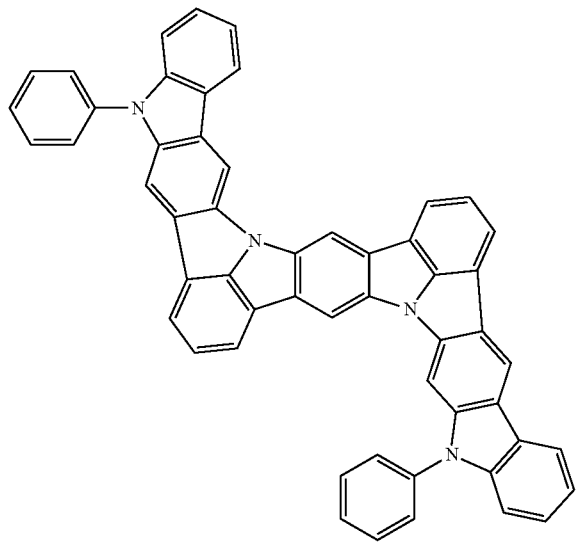
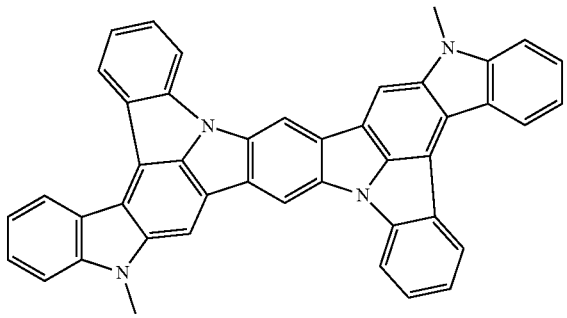
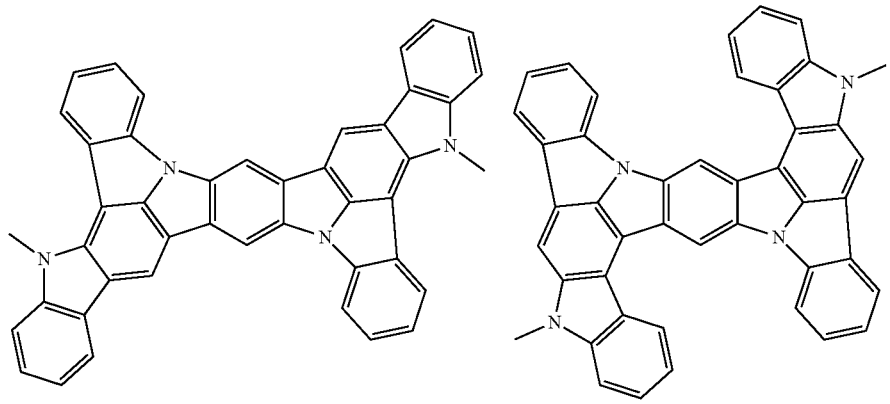

841
842
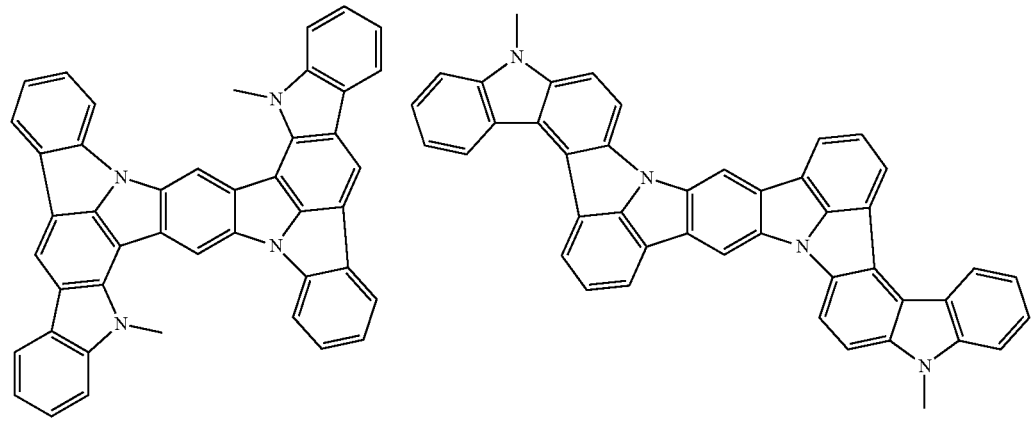
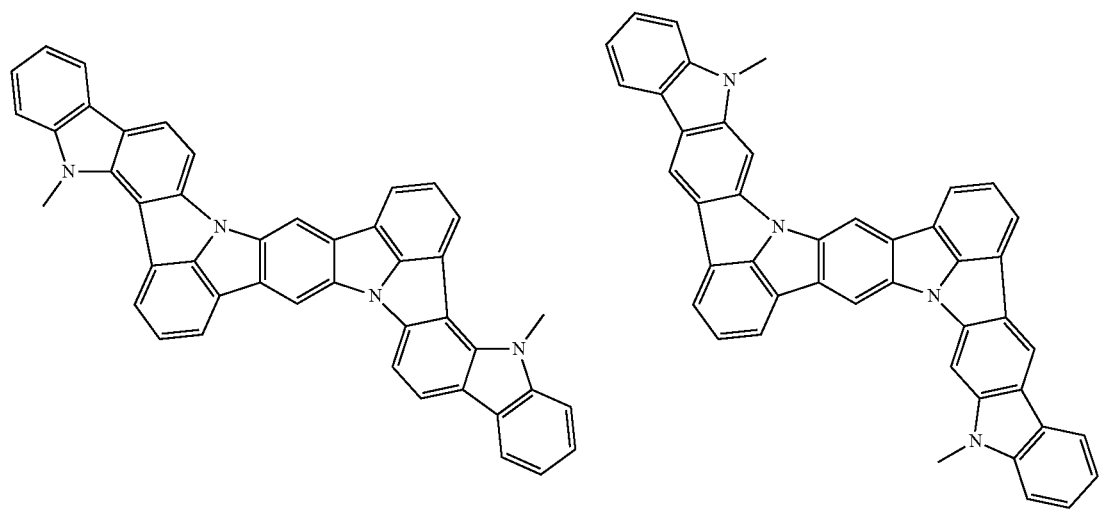 [SMILES: Cn1c2ccccc2c2ccc3c(c4cccc5c6cc7c(cc6n3c54)c3cccc4c5c6c(ccc5n7c34)c3ccccc3n6C)c21 ; Cn1c2ccccc2c2cc3c4cccc5c6cc7c(cc6n(c3cc21)c54)c1cccc2c3cc4c5ccccc5n(C)c4cc3n7c12]
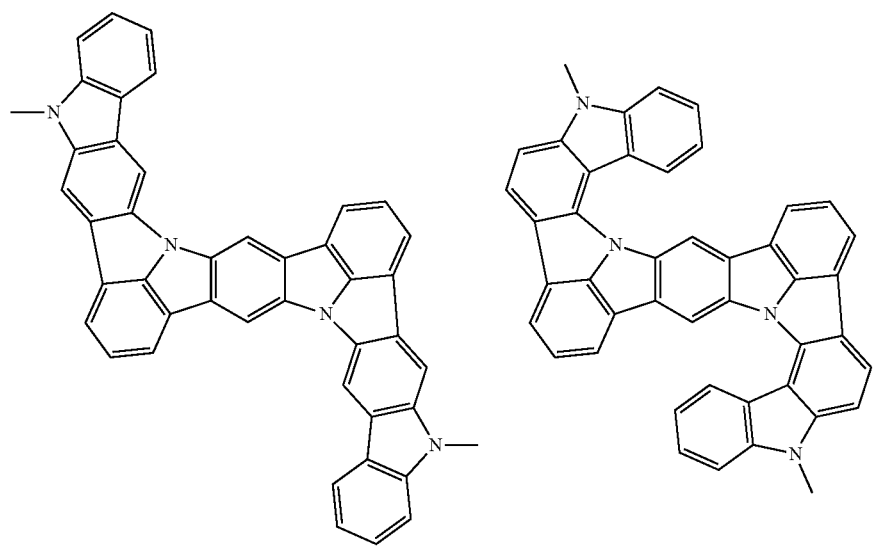

-continued
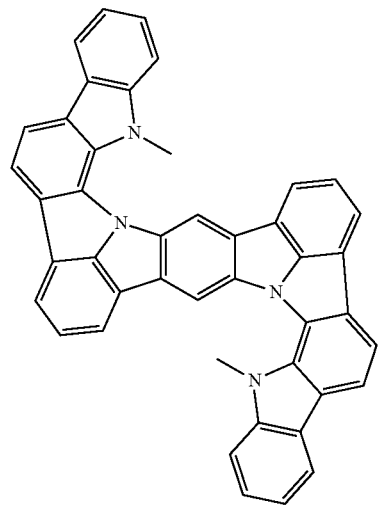
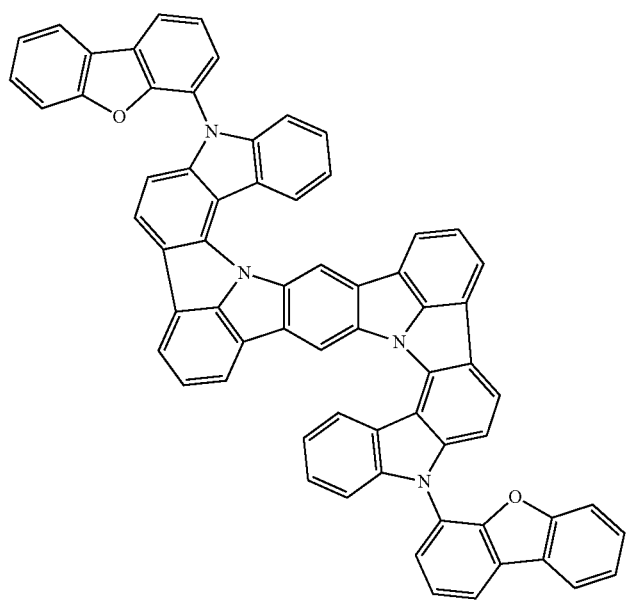
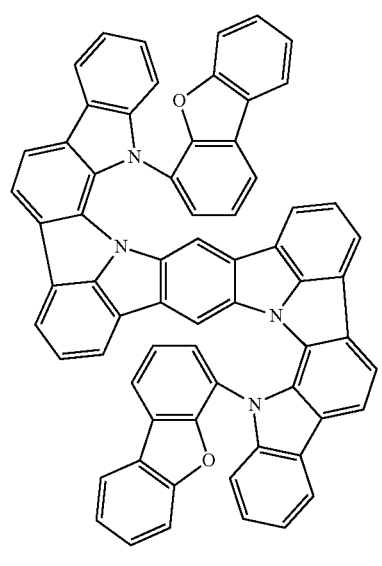
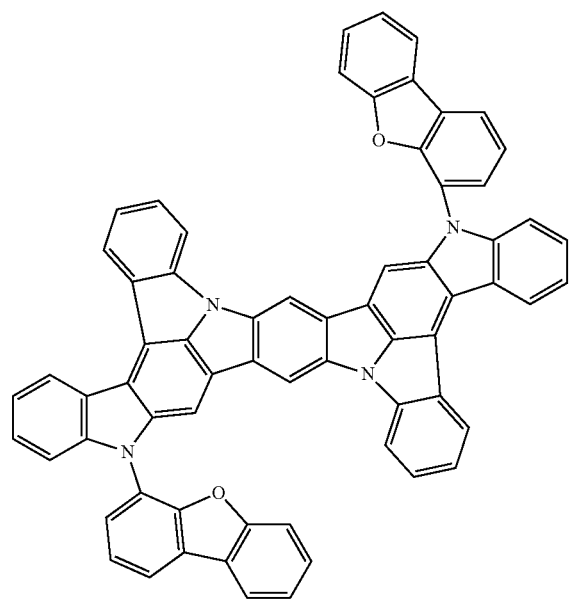
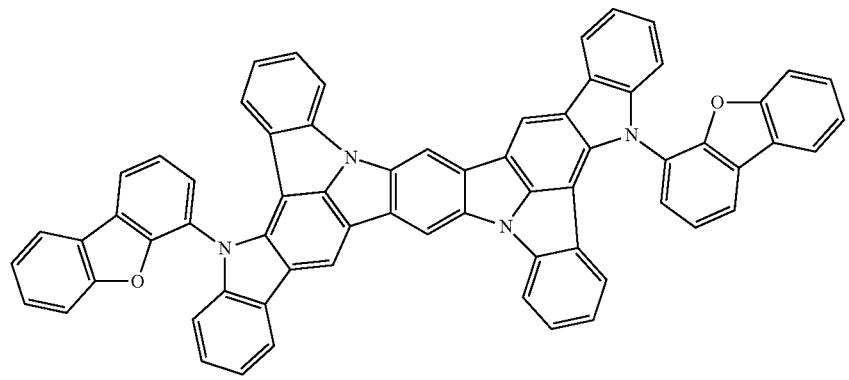

-continued
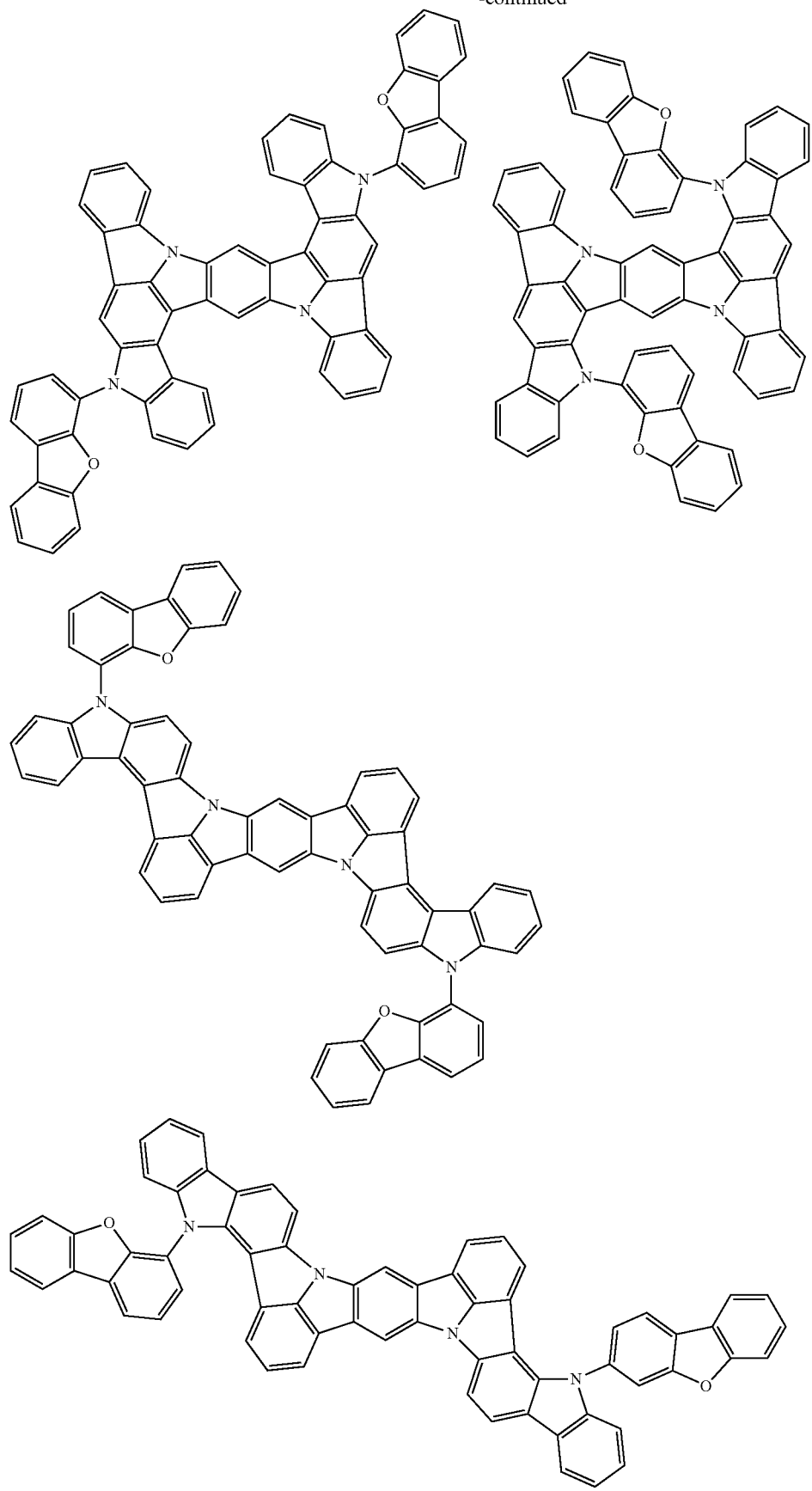

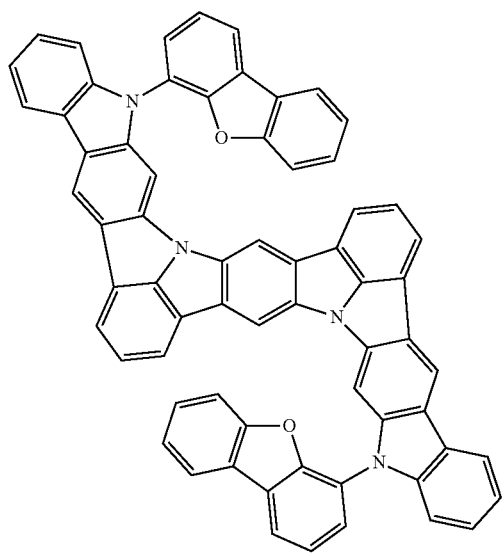
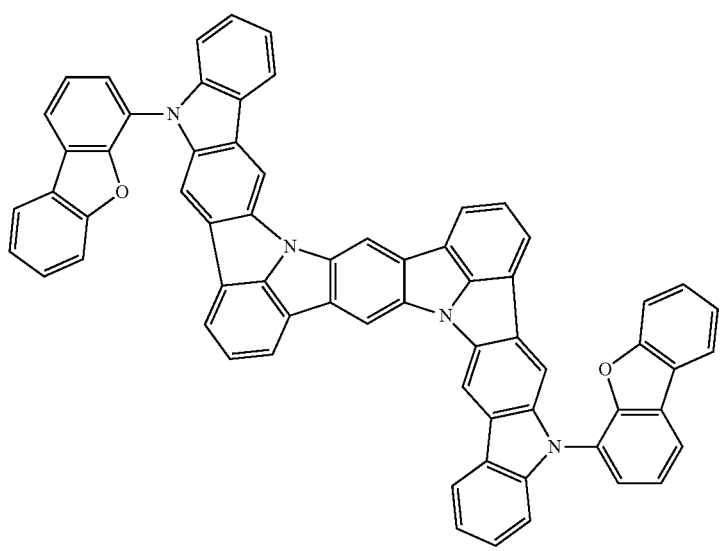
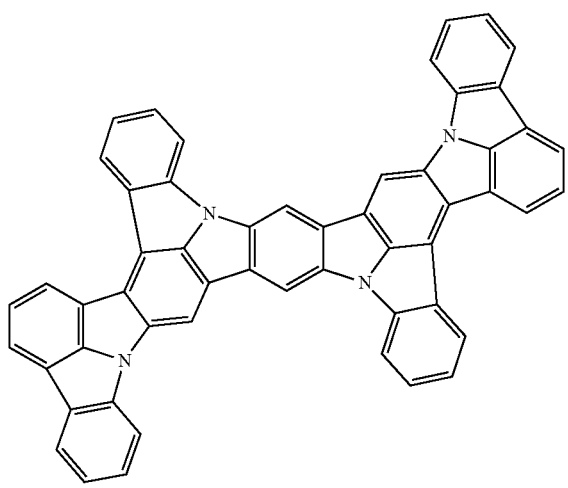

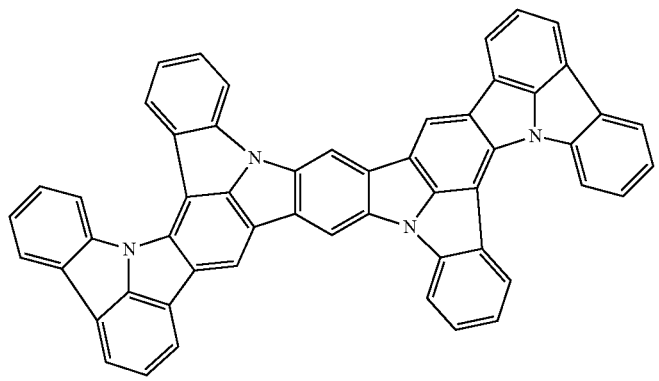
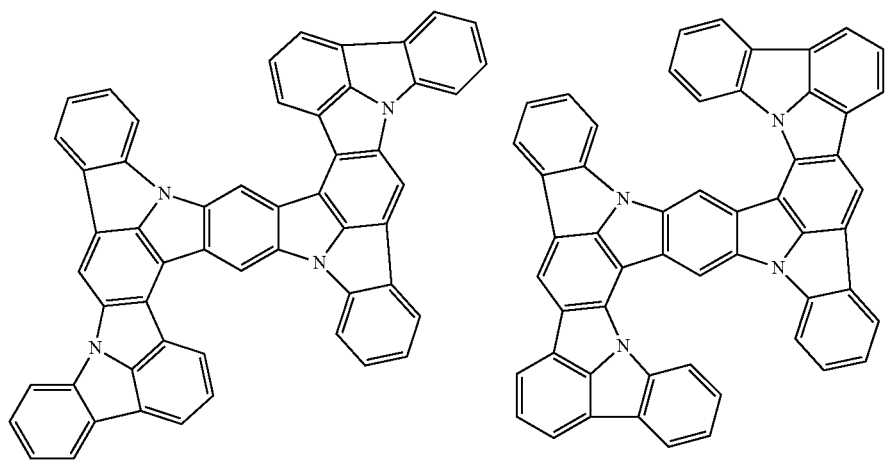
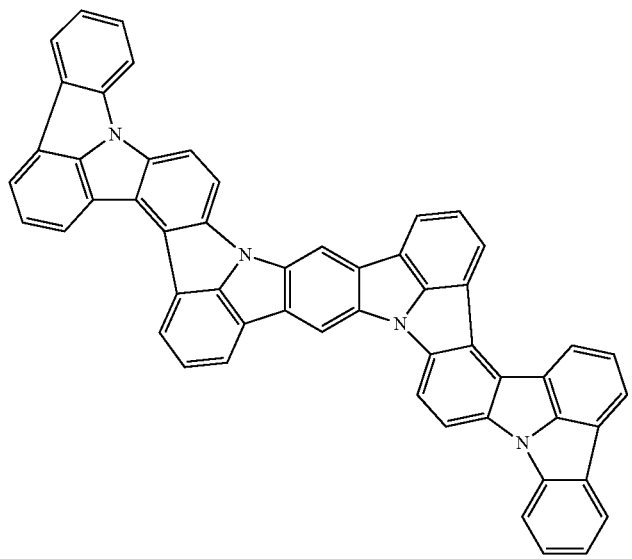

-continued
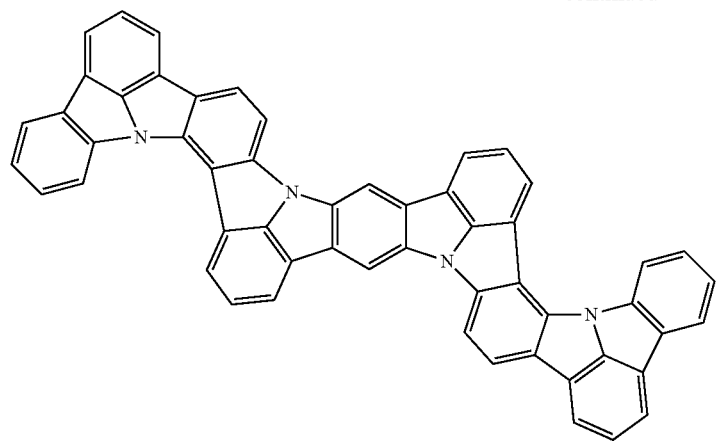
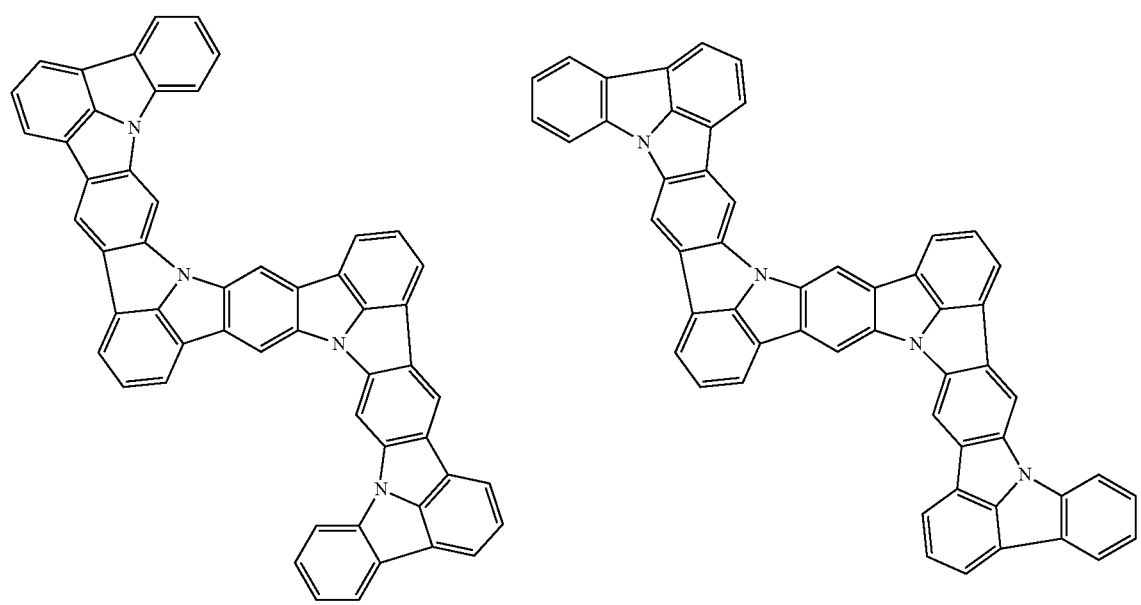
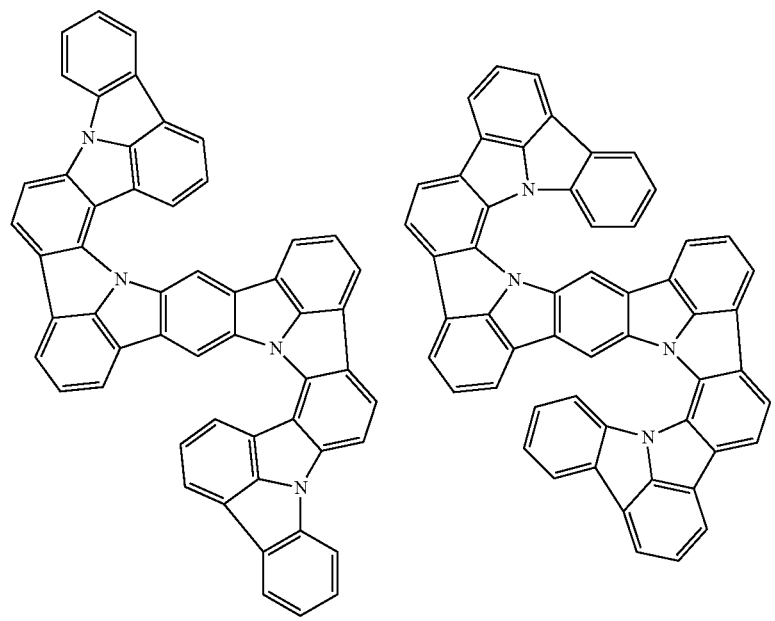

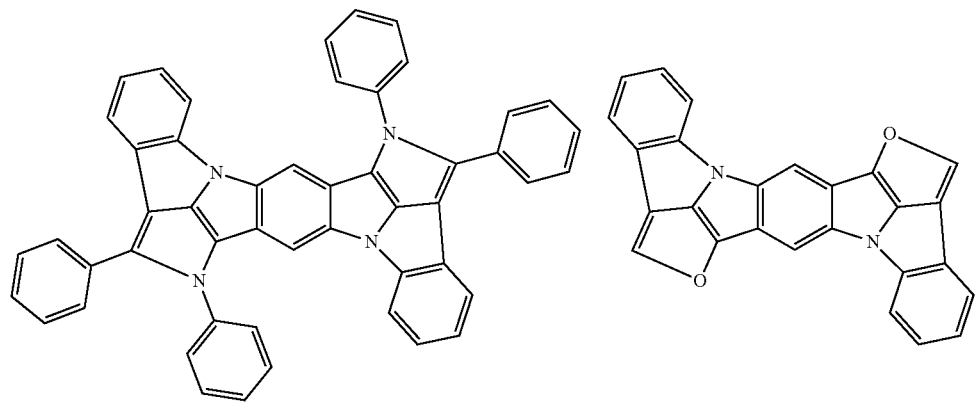
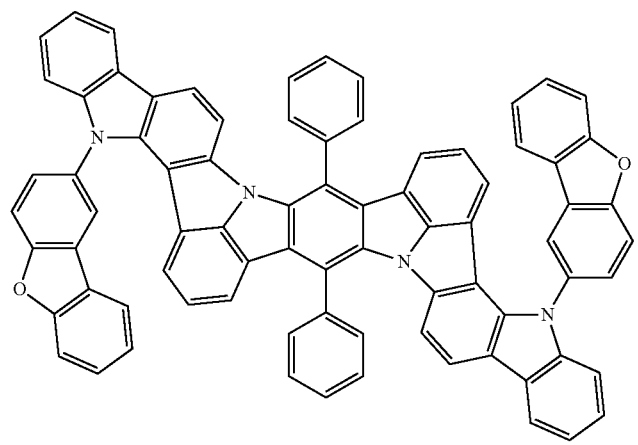
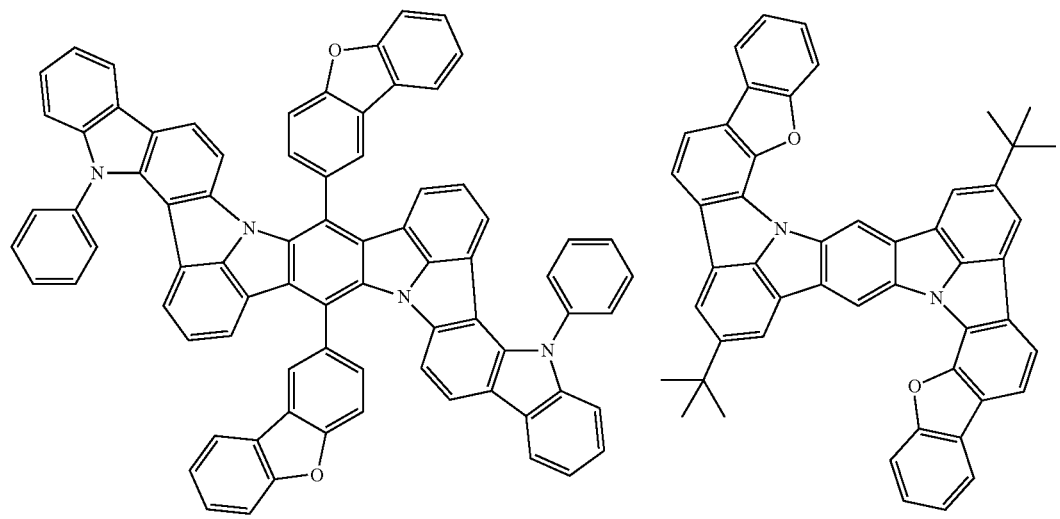

-continued
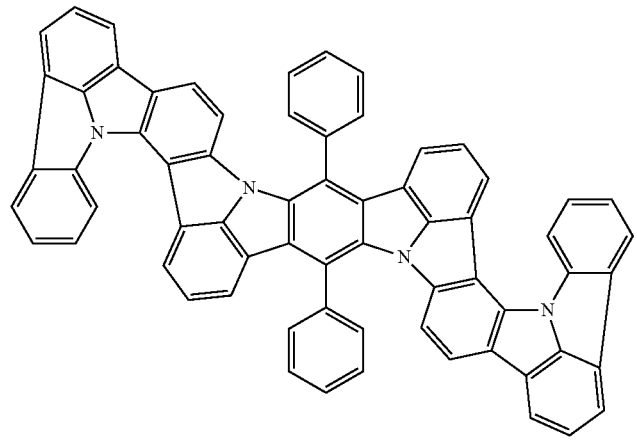
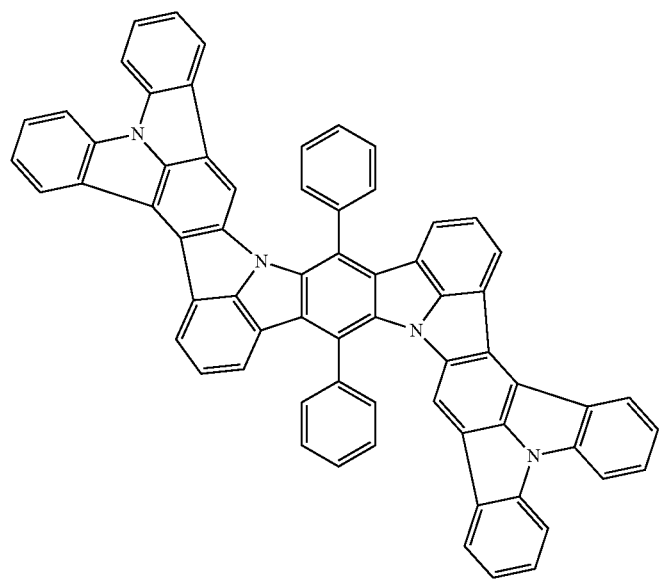
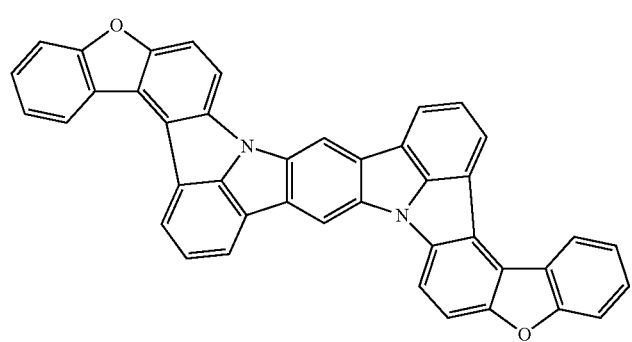

857 858
-continued
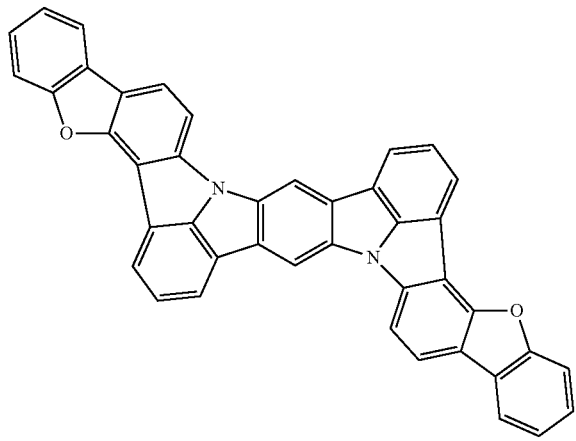
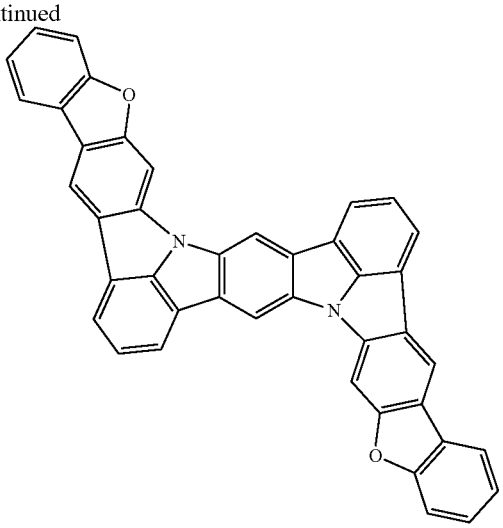
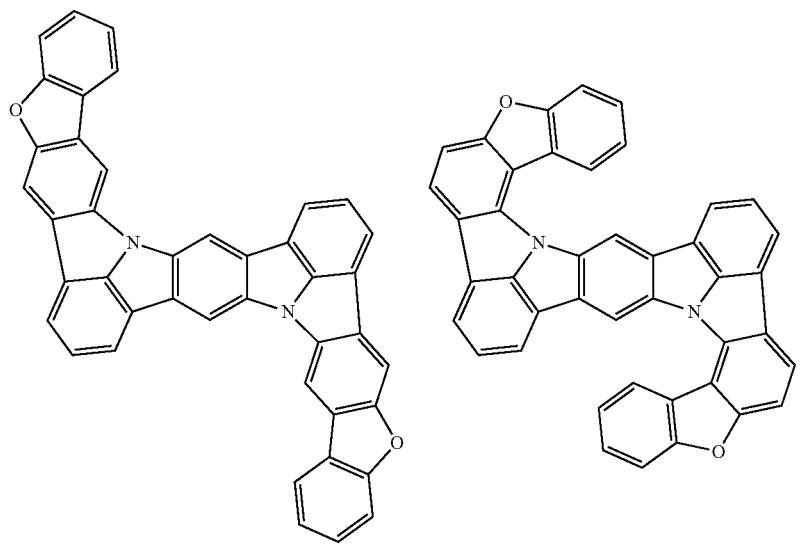
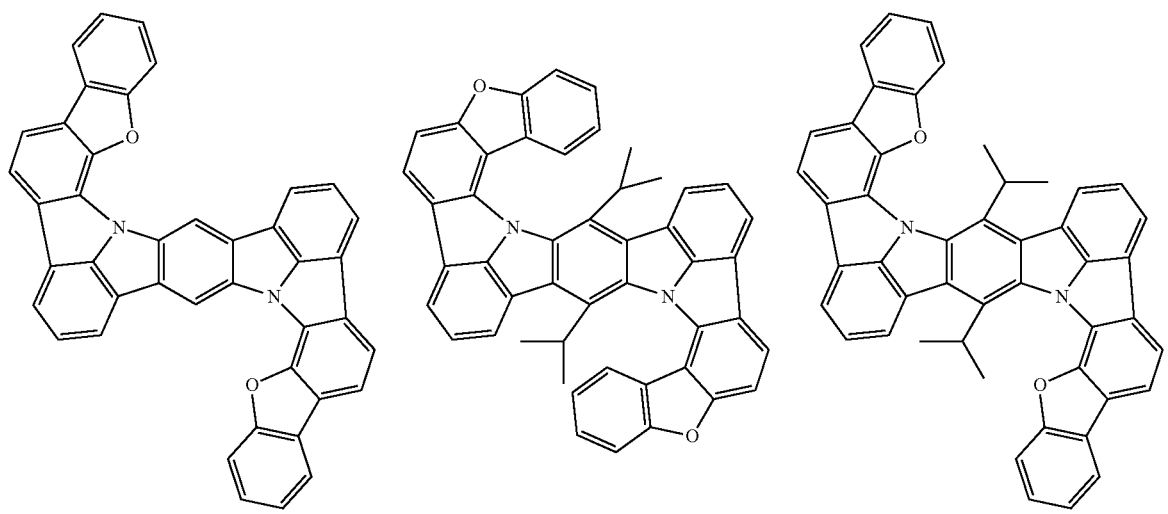

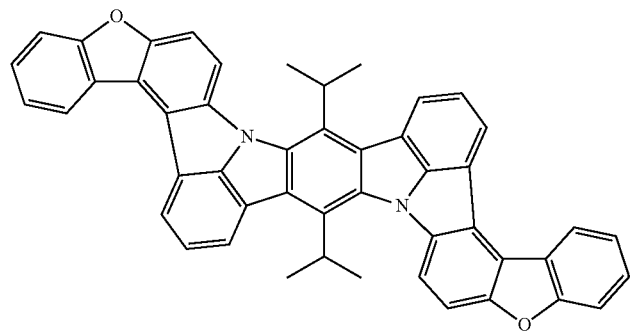
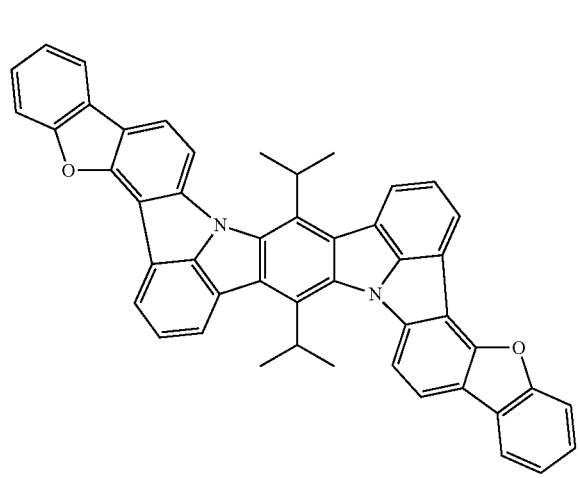
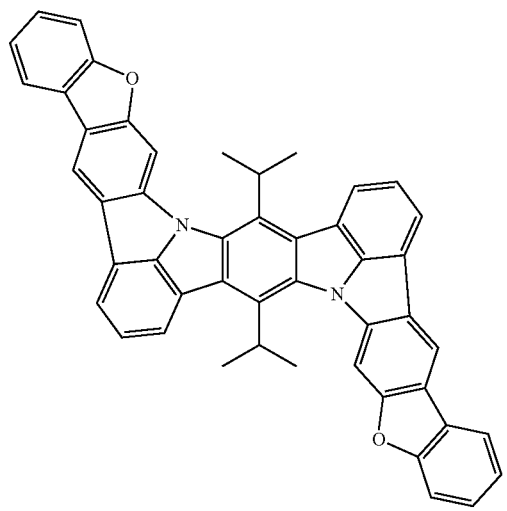
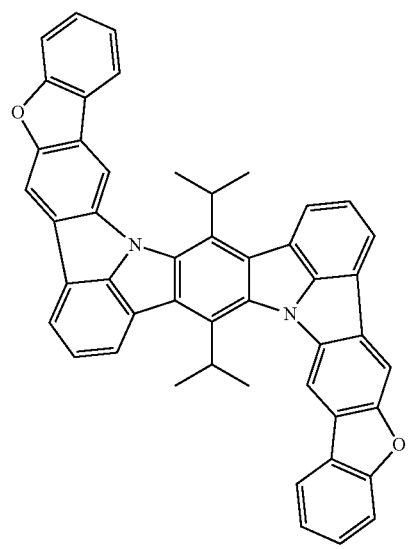

-continued
861
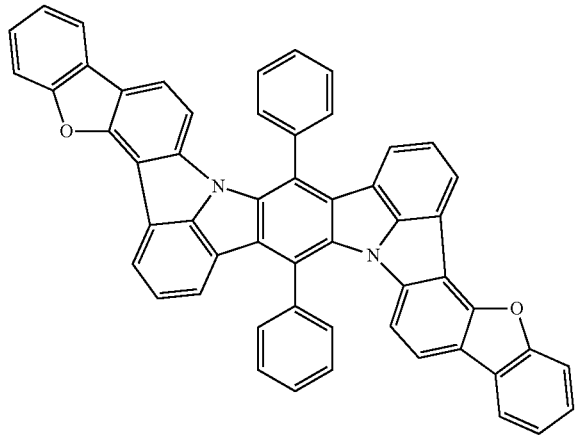
862
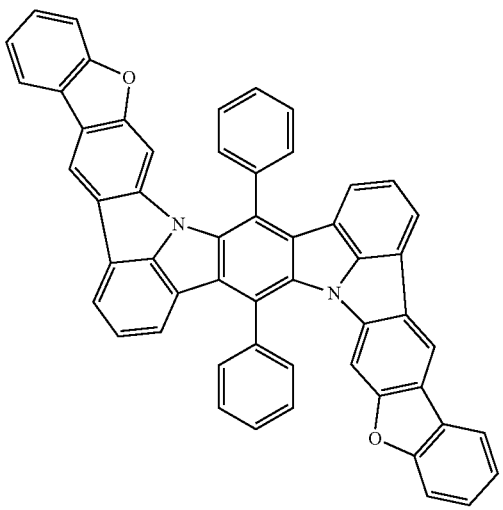
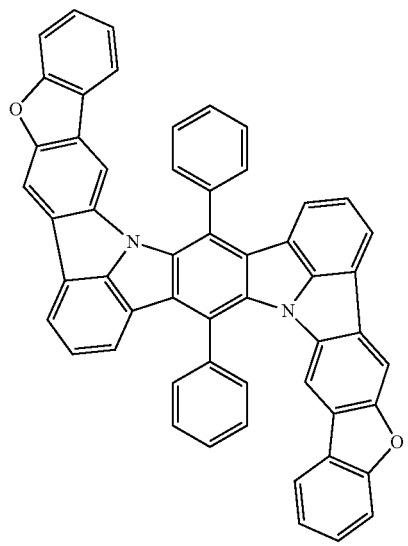
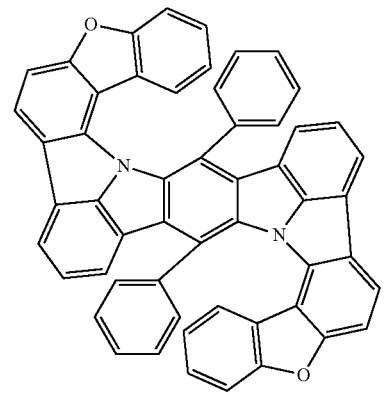
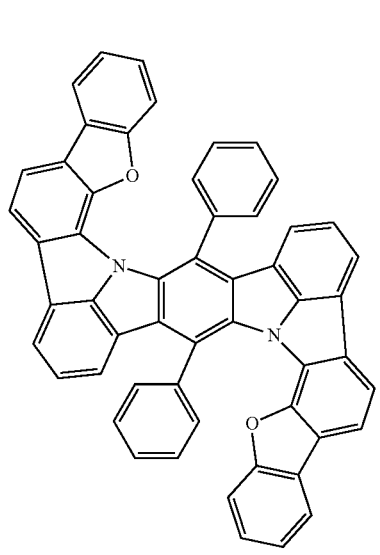
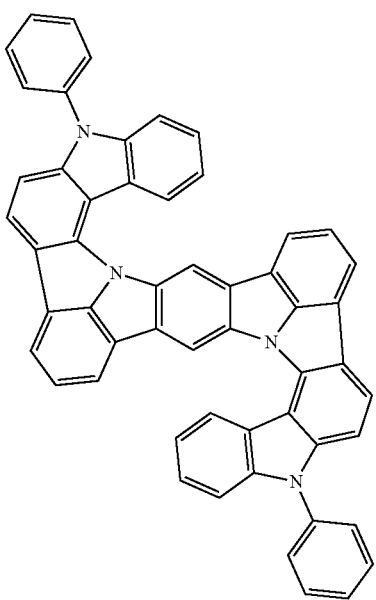

863
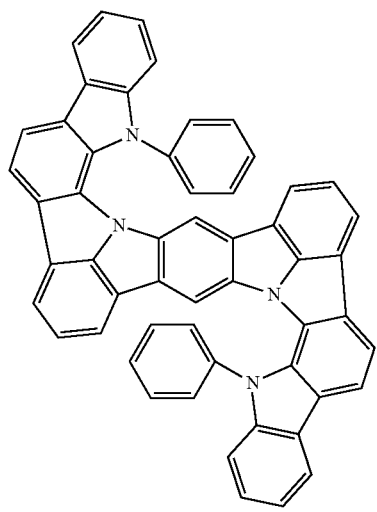
864
-continued
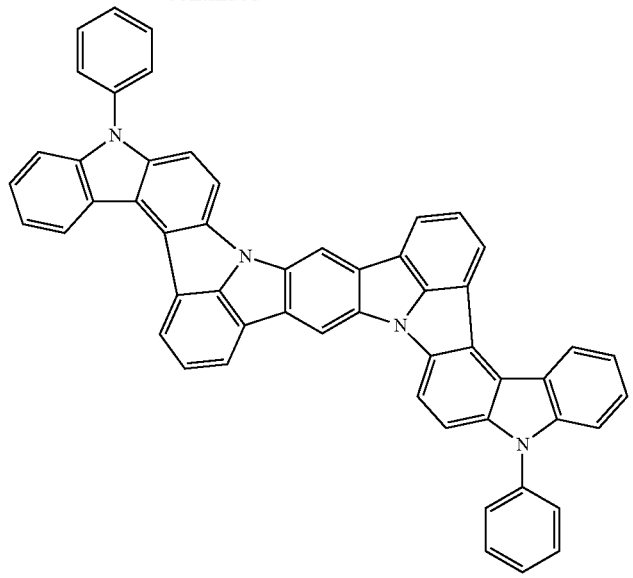
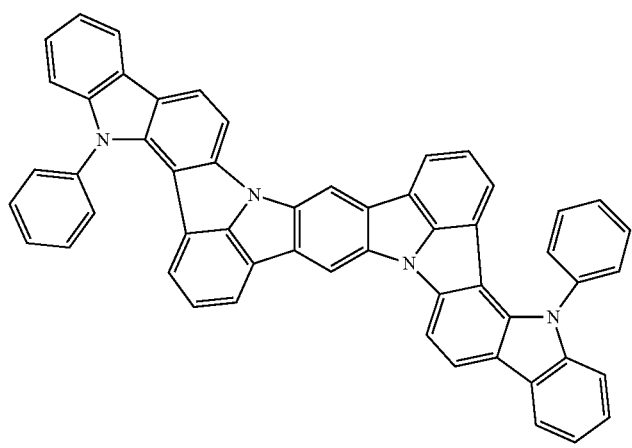
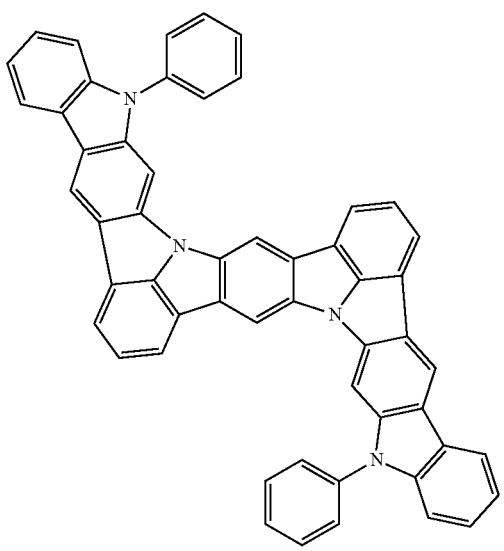
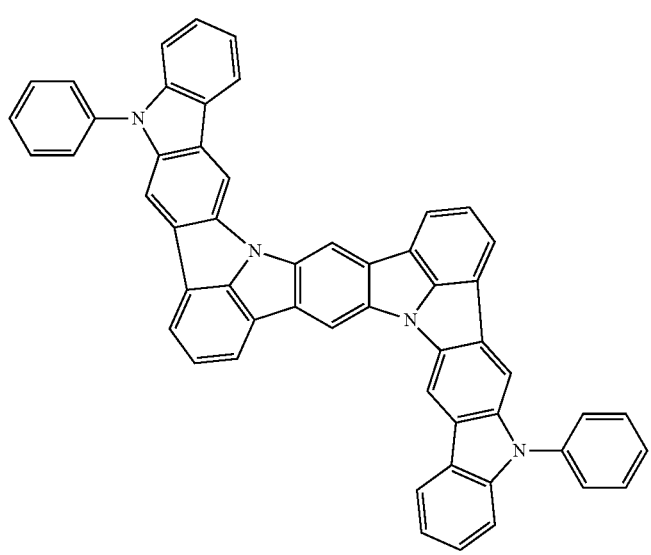

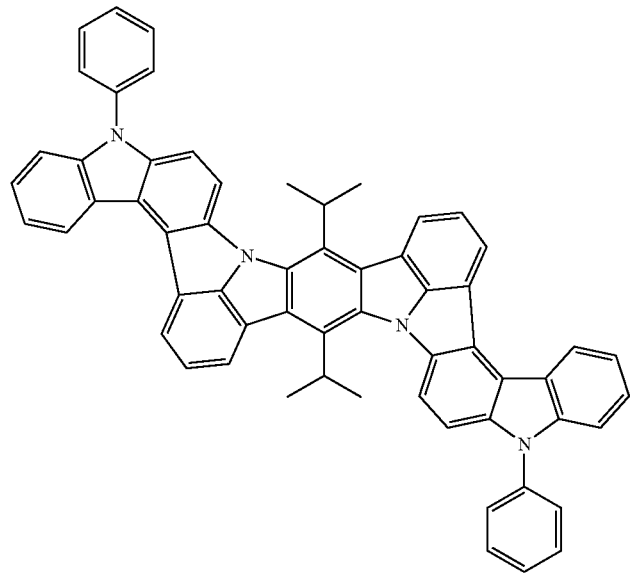
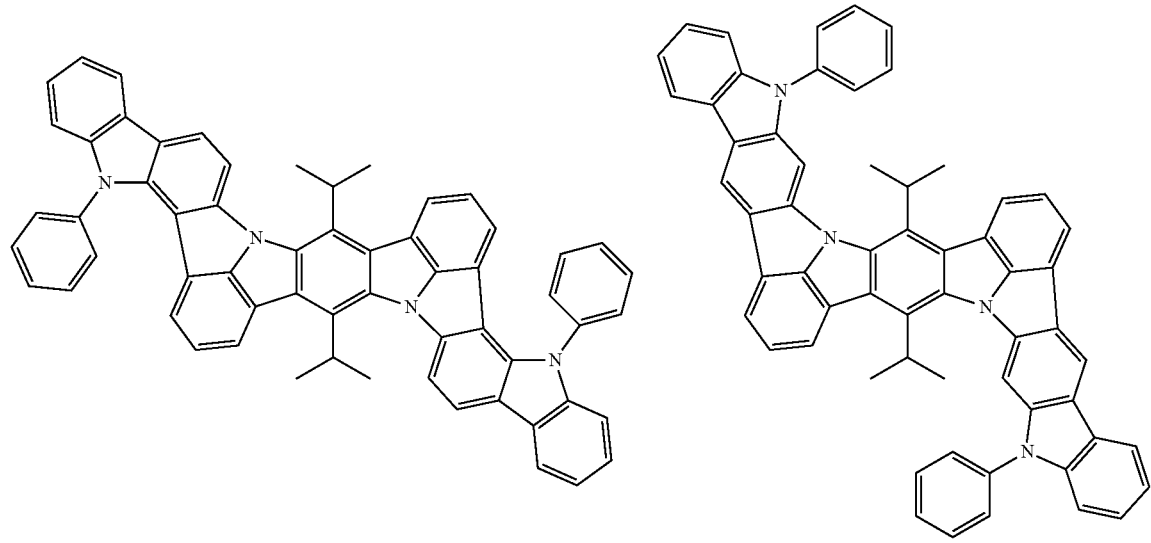
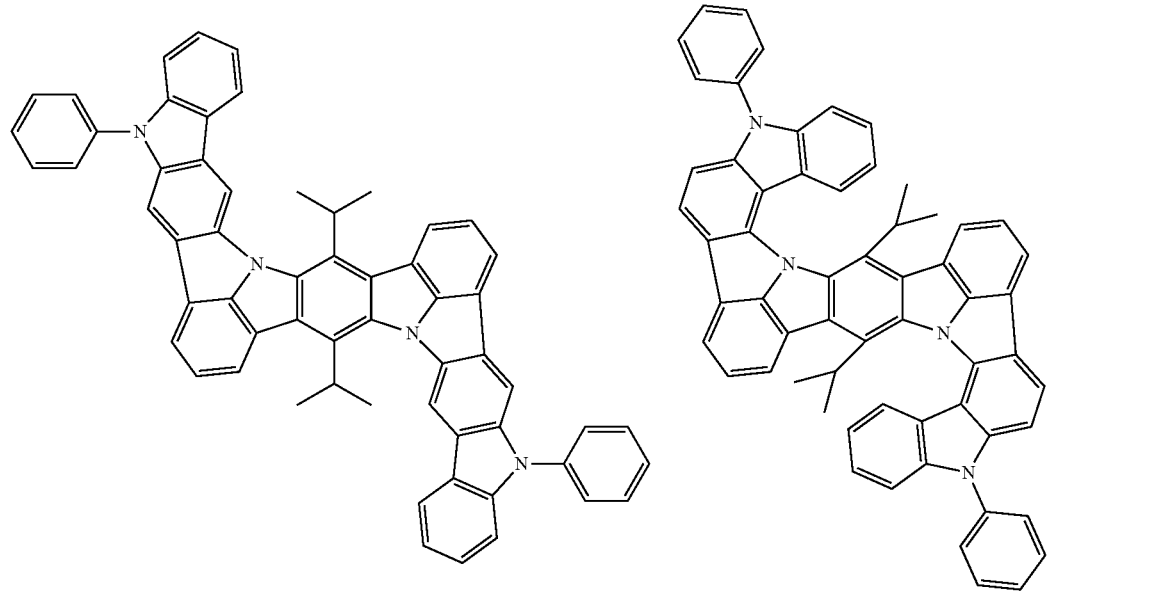

-continued
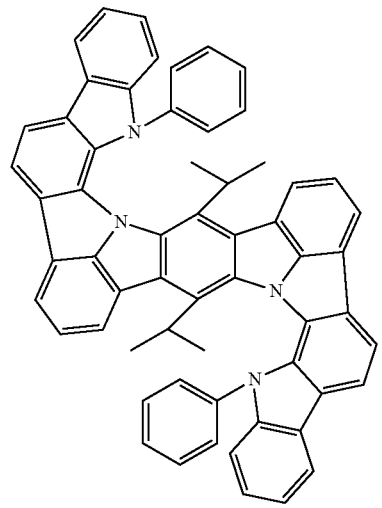
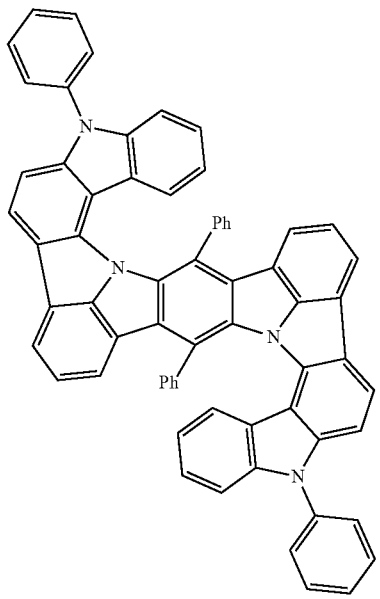
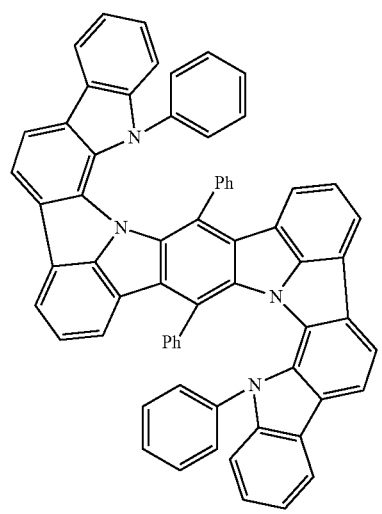
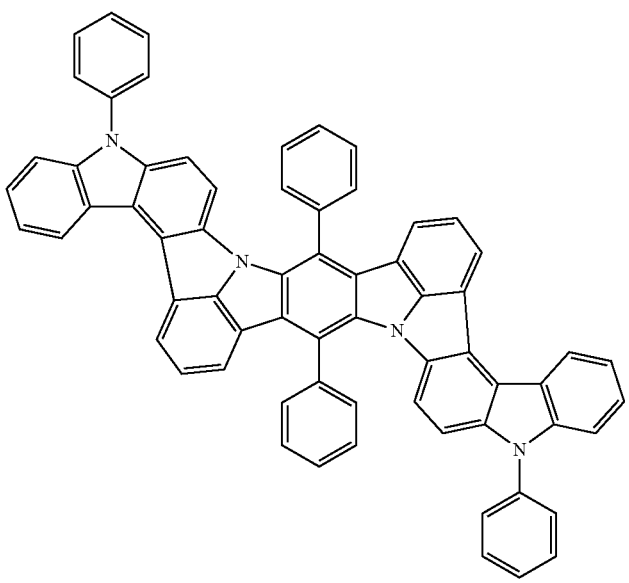
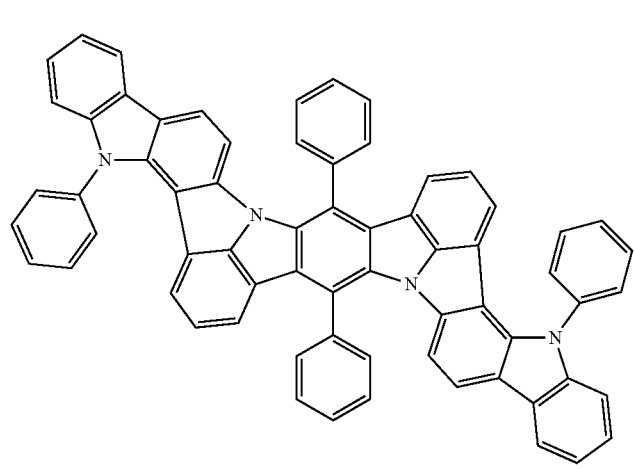
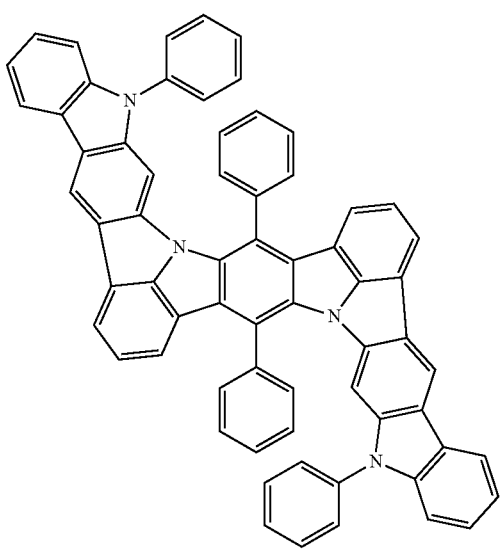

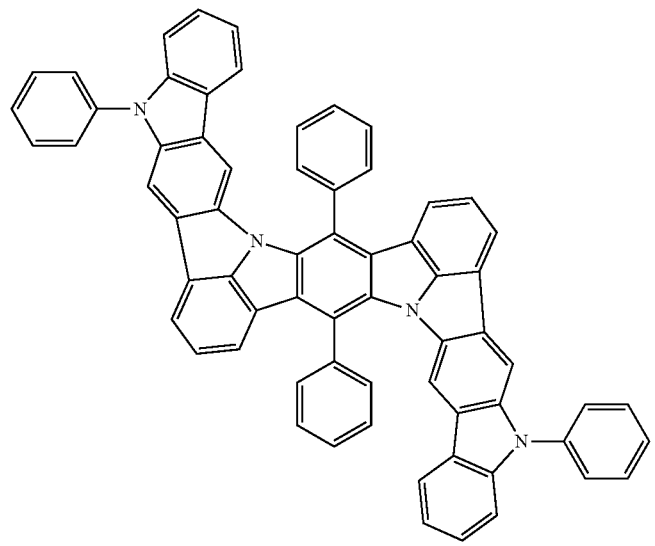
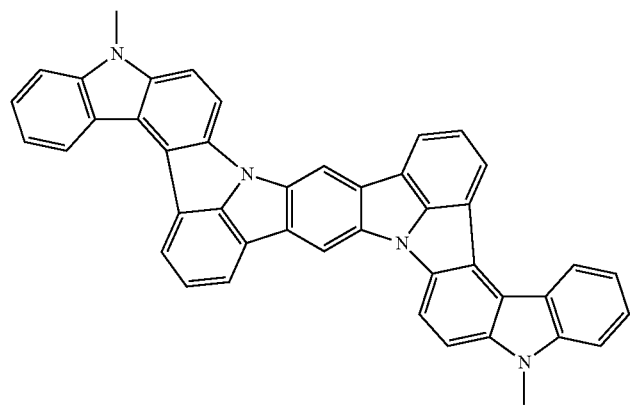
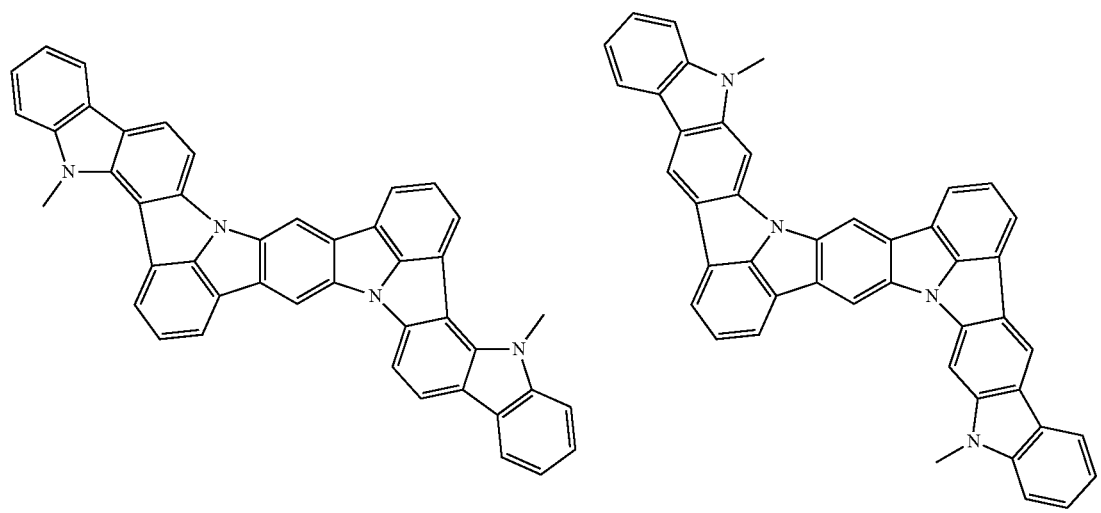

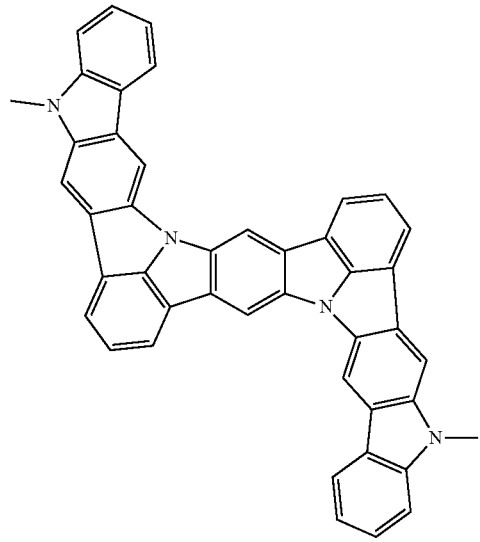
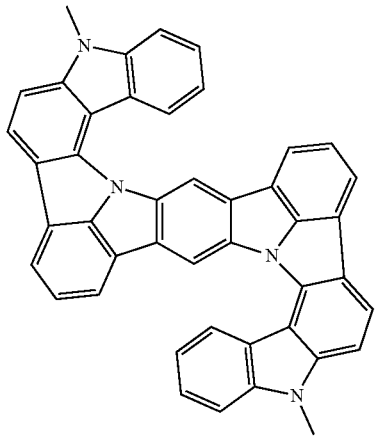
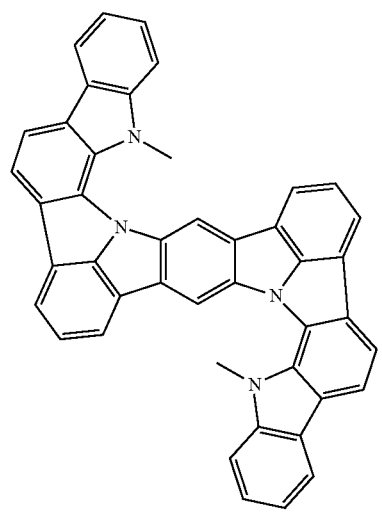
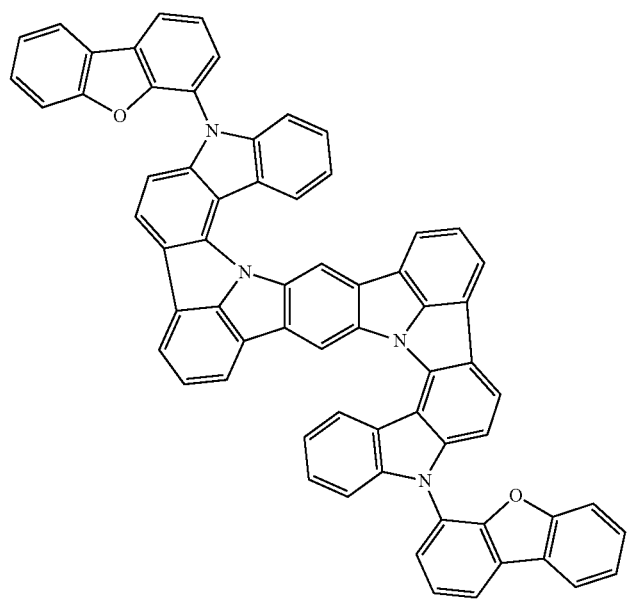

-continued
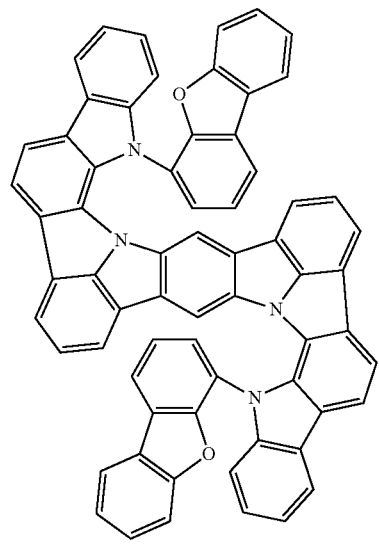
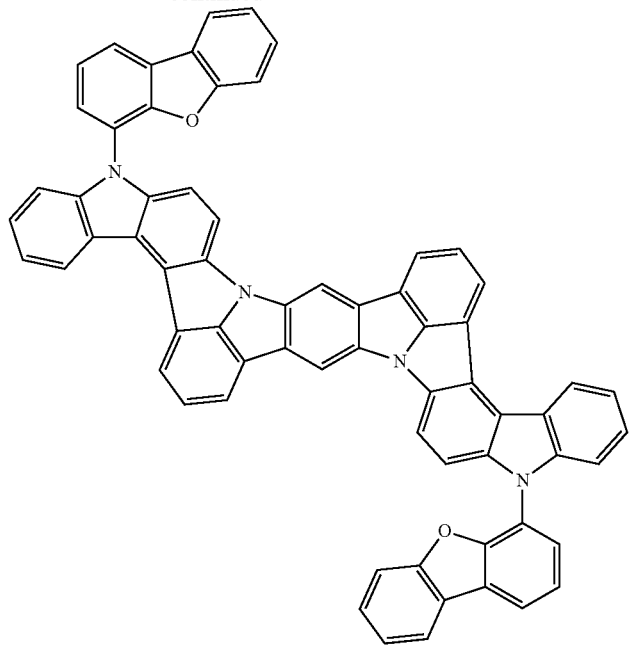
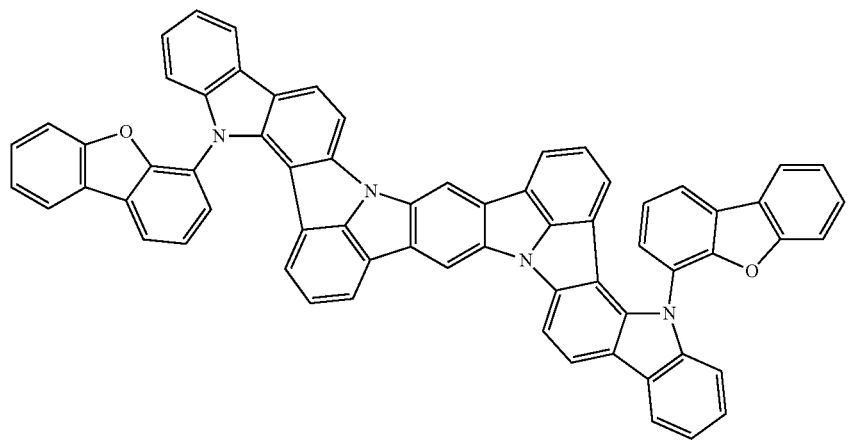
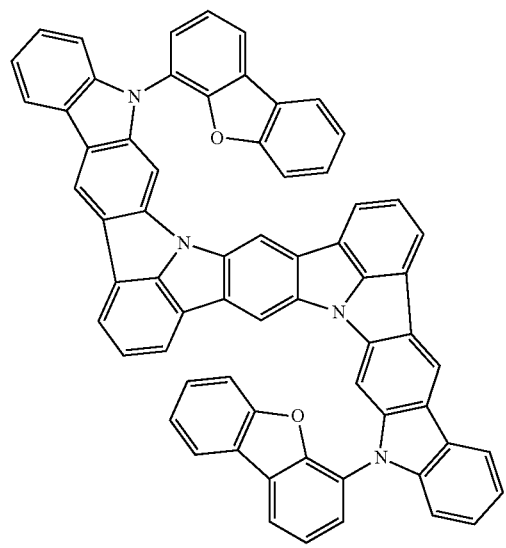

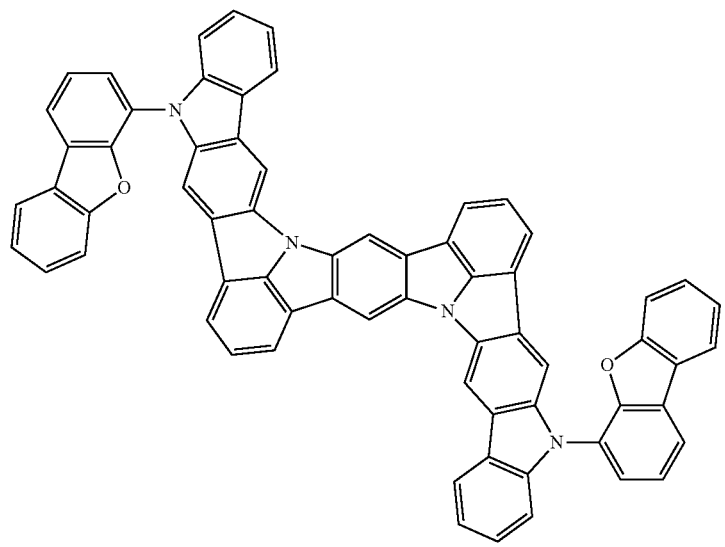
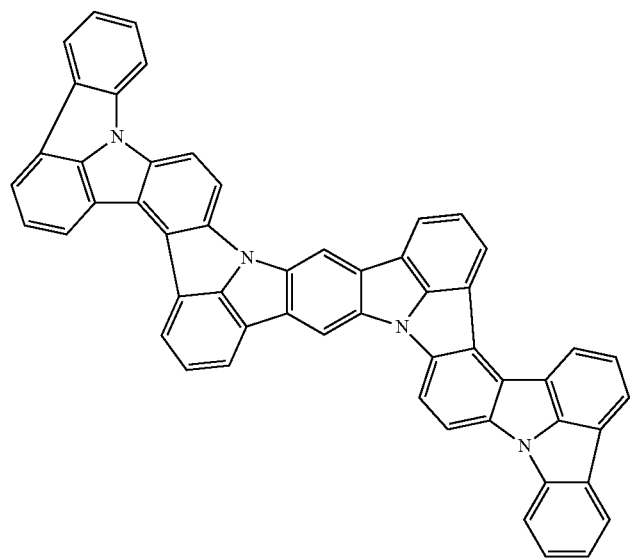
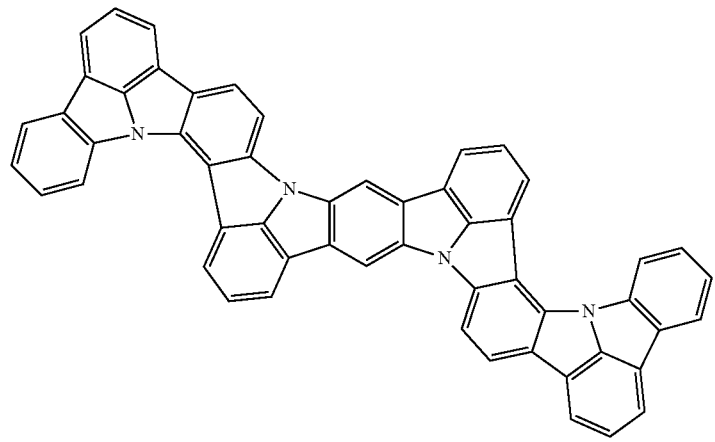

-continued
877          878
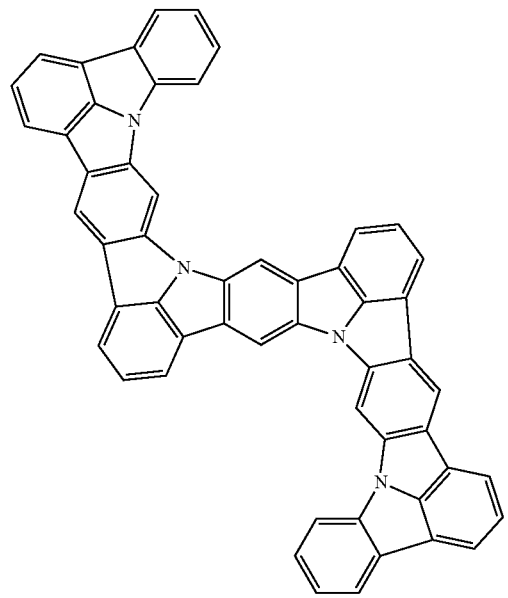
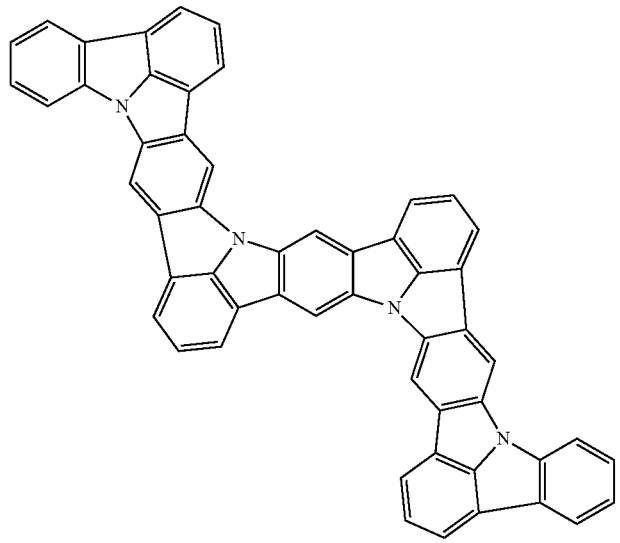
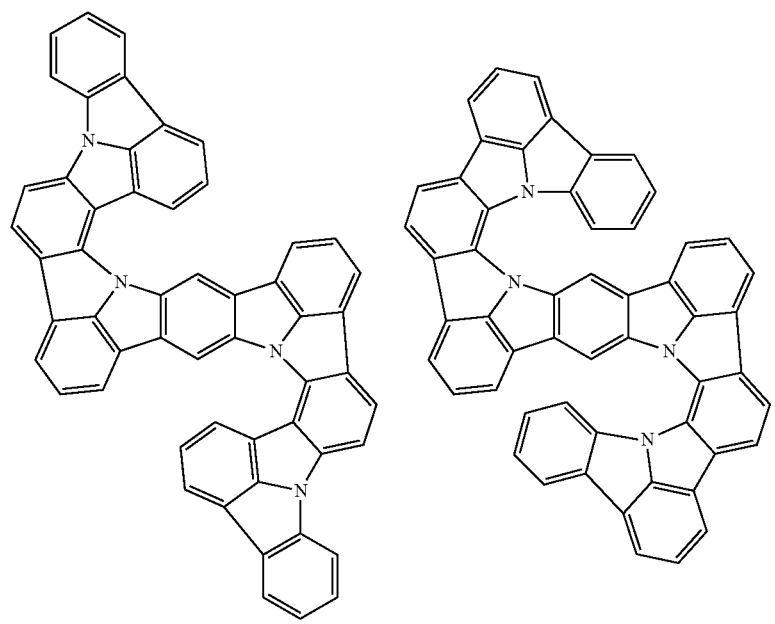
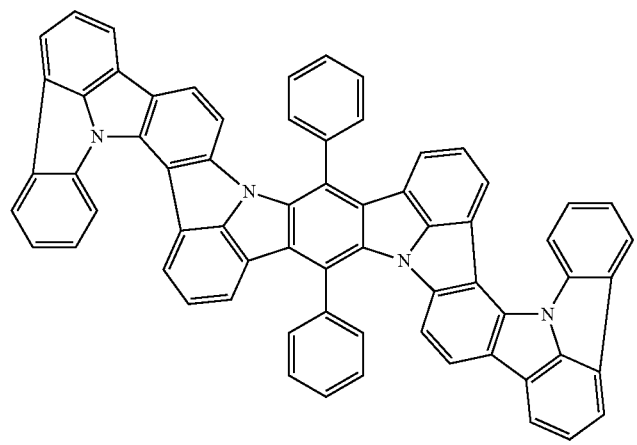

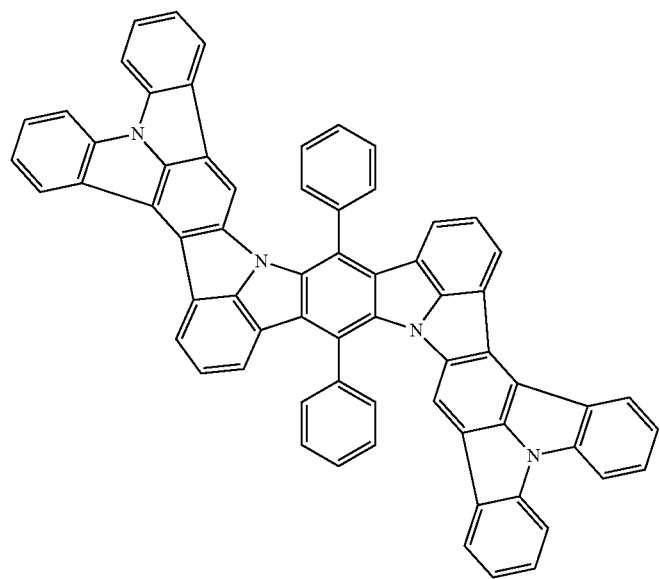
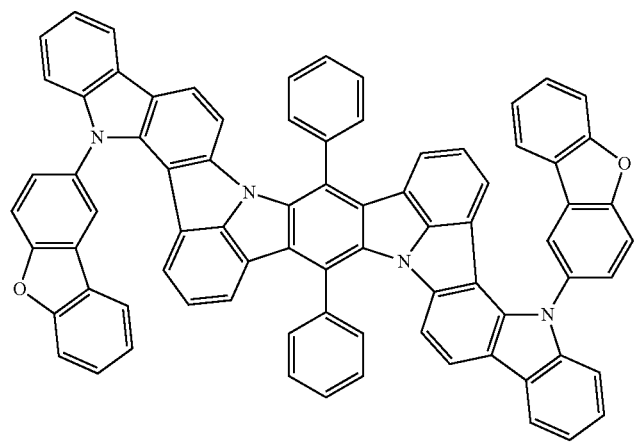
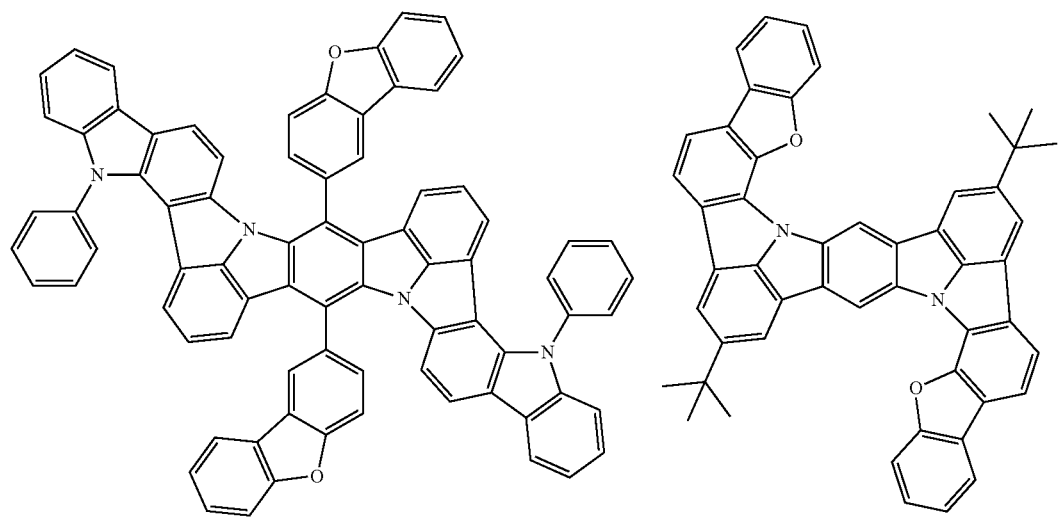

(Compound Represented by Formula (41))

The compound represented by the formula (41) is explained below.

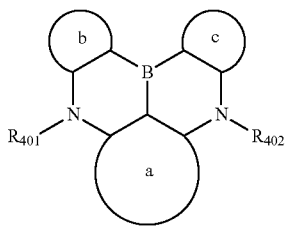

(41)

wherein, in the formula (41),
a ring, b ring and c ring are independently
a substituted or unsubstituted aromatic hydrocarbon ring having 6 to 50 ring carbon atoms, or
a substituted or unsubstituted heterocyclic ring having 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

The a ring, b ring and c ring are rings (a substituted or unsubstituted aromatic hydrocarbon ring having 6 to 50 ring carbon atoms or a substituted or unsubstituted heterocyclic ring having 5 to 50 ring atoms) fuse to the fused bicyclic structure composed of B atom and two N atoms in the center of the formula (41).

The "aromatic hydrocarbon ring" of the a ring, the b ring and the c ring has the same structure as the compound obtained by introducing a hydrogen atom into the "aryl group" described above. The "aromatic hydrocarbon ring" of the a ring contains three carbon atoms in the fused bicyclic structure in the center of the formula (41) as ring atoms. The "aromatic hydrocarbon ring" of the b ring and the c ring contain two carbon atoms in the fused bicyclic structure in the center of the formula (41) as ring atoms. As examples of "substituted or unsubstituted aromatic hydrocarbon ring having 6 to 50 ring carbon atoms", compounds in which a hydrogen atom is introduced into the "aryl group" described in the group G1 and the like can be given.

The "heterocyclic ring" of the a ring, the b ring and the c ring has the same structure as the compound obtained by introducing a hydrogen atom into the "heterocyclic group" described above. The "heterocyclic ring" of the a ring contains three carbon atoms in the fused bicyclic structure in the center of the formula (41) as ring atoms. The "heterocyclic ring" of the b ring and the c ring contain two carbon atoms in the fused bicyclic structure in the center of the formula (41) as ring atoms. As examples of "substituted or unsubstituted heterocyclic ring having 5 to 50 ring atoms", compounds in which a hydrogen atom is introduced into the "heterocyclic group" described in the group G2.

$R_{401}$ and $R_{402}$ may be independently bonded to the a ring, the b ring or the c ring to form a substituted or unsubstituted heterocyclic ring. This heterocyclic ring contains the nitrogen atom in the fused bicyclic structure in the center of the formula (41). This heterocyclic ring may contain a heteroatom other than the nitrogen atom. "$R_{401}$ and $R_{402}$ are bonded to the a ring, the b ring or the c ring" means, specifically, an atom forming the a ring, the b ring or the c ring is bonded to an atom forming $R_{401}$ and $R_{402}$. For example, it is possible that $R_{401}$ is bonded to the a ring to form a nitrogen-containing heterocyclic ring having a two-ring fused structure (or three or more rings fused structure) in which a ring containing $R_{401}$ and the a ring are fused.

The same applies to the case where $R_{401}$ is bonded to the b ring, $R_{402}$ is bonded to the a ring, and $R_{402}$ is bonded to the c ring.

In one embodiment, the a ring, the b ring and the c ring in the formula (41) are independently a substituted or unsubstituted aromatic hydrocarbon ring having 6 to 50 ring carbon atoms.

In one embodiment, the a ring, the b ring and the c ring in the formula (41) are independently a substituted or unsubstituted benzene ring or a substituted or unsubstituted naphthalene ring.

In one embodiment, $R_{401}$ and $R_{402}$ in the formula (41) are independently a substituted or unsubstituted aryl group having 6 to 50 ring carbon atoms, or a substituted or unsubstituted monovalent heterocyclic group having 5 to 50 ring atoms, and preferably a substituted or unsubstituted aryl group having 6 to 50 ring carbon atoms.

In one embodiment, the compound represented by the formula (41) is a compound represented by the following formula (42).

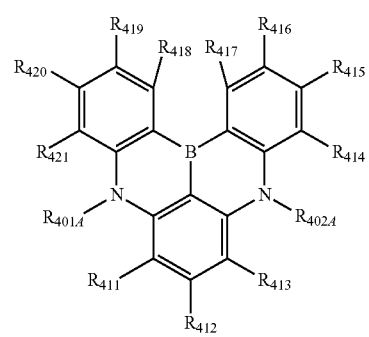

(42)

wherein in the formula (42),
$R_{401A}$ is bonded with one or more groups selected from $R_{411}$ or $R_{421}$ to form a substituted or unsubstituted heterocyclic ring, or does not form a substituted or unsubstituted heterocyclic ring; $R_{402A}$ is bonded with one or more group selected from $R_{413}$ or $R_{414}$ to form a substituted or unsubstituted heterocyclic ring, or does not form a substituted or unsubstituted heterocyclic ring;

$R_{401A}$ and $R_{402A}$ that do not form a substituted or unsubstituted heterocyclic ring are independently
a substituted or unsubstituted alkyl group having 1 to 50 carbon atoms, a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

One or more pairs of two or more adjacent groups of $R_{411}$ to $R_{421}$ are bonded with each other to form a substituted or unsubstituted, saturated or unsaturated ring, or do not form a substituted or unsubstituted, saturated or unsaturated ring;

$R_{411}$ to $R_{421}$ that do not form the substituted or unsubstituted heterocyclic ring or the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and $R_{901}$ to $R_{907}$ are as defined in the formula (1).

$R_{401A}$ and $R_{402A}$ in the formula (42) correspond to $R_{401}$ and $R_{402}$ in the formula (41).

$R_{401A}$ and $R_{411}$ may be bonded with each other to form a nitrogen-containing heterocyclic ring having two-ring fused structure (or three or more rings fused structure) which is a fused ring of a ring containing $R_{401A}$ and $R_{411}$ and the benzene ring of the a ring, for example. As examples of the nitrogen-containing heterocyclic ring, compounds correspond to nitrogen-containing heterocyclic group having two or more ring fused structure in the group G2 can be given. The same applies to the cases where $R_{401A}$ and $R_{412}$ are bonded, $R_{402A}$ and $R_{413}$ are bonded, and $R_{402A}$ and $R_{414}$ are bonded.

One or more pairs of two or more adjacent groups of $R_{411}$ to $R_{421}$ are bonded with each other to form a substituted or unsubstituted, saturated or unsaturated ring. For example, $R_{411}$ and $R_{412}$ are bonded to form a benzene ring, an indole ring, a pyrrole ring, a benzofuran ring, a benzothiophene ring or the like which fuses to the six-membered ring to which $R_{411}$ and $R_{412}$ bond, and the formed fused ring is a naphthalene ring, a carbazole ring, an indole ring, a dibenzofuran ring or a dibenzothiophene ring.

In one embodiment, $R_{411}$ to $R_{421}$ that do not contribute to form a ring are independently a hydrogen atom, a substituted or unsubstituted alkyl group having 1 to 50 carbon atoms, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom or a substituted or unsubstituted alkyl group having 1 to 50 carbon atoms.

In one embodiment, $R_{411}$ to $R_{421}$ that do not contribute to form a ring are independently a hydrogen atom, a substituted or unsubstituted alkyl group having 1 to 50 carbon atoms, and at least one of $R_{411}$ to $R_{421}$ is a substituted or unsubstituted alkyl group having 1 to 50 carbon atoms.

In one embodiment, the compound represented by the formula (42) is a compound represented by the following formula (43).

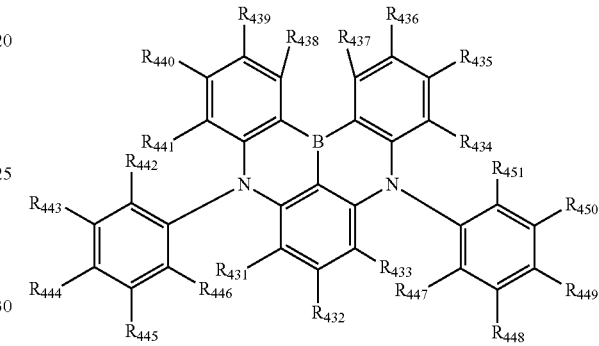

(43)

wherein in the formula (43), $R_{431}$ is bonded with $R_{446}$ to form a substituted or unsubstituted heterocyclic ring, or does not form a substituted or unsubstituted heterocyclic ring; $R_{433}$ is bonded with $R_{447}$ to form a substituted or unsubstituted heterocyclic ring, or does not form a substituted or unsubstituted heterocyclic ring; $R_{434}$ is bonded with $R_{451}$ to form a substituted or unsubstituted heterocyclic ring, or does not form a substituted or unsubstituted heterocyclic ring; $R_{441}$ is bonded with $R_{442}$ to form a substituted or unsubstituted heterocyclic ring, or does not form a substituted or unsubstituted heterocyclic ring;

One or more pairs of two or more adjacent groups of $R_{431}$ to $R_{451}$ are bonded with each other to form a substituted or unsubstituted, saturated or unsaturated ring, or do not form a substituted or unsubstituted, saturated or unsaturated ring;

$R_{431}$ to $R_{451}$ that do not form a substituted or unsubstituted heterocyclic ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

$R_{431}$ may bond to $R_{446}$ to form a substituted or unsubstituted heterocyclic ring. For example, $R_{431}$ may bonds with $R_{446}$ to form a nitrogen-containing heterocyclic ring with three or more fused rings of the benzene ring to which $R_{46}$ bond, a nitrogen-containing ring and the benzene ring of the a ring. As examples of the nitrogen-containing heterocyclic ring, compounds correspond to nitrogen-containing heterocyclic group having three or more ring fused structure in the group G2 can be given. The same applies to the cases where $R_{433}$ and $R_{447}$ are bonded, $R_{434}$ and $R_{451}$ are bonded, and $R_{441}$ and $R_{442}$ are bonded.

In one embodiment, $R_{431}$ to $R_{451}$ that do not contribute to form a ring are independently, a hydrogen atom, a substituted or unsubstituted alkyl group having 1 to 50 carbon atoms, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently, a hydrogen atom, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently a hydrogen atom or a substituted or unsubstituted alkyl group having 1 to 50 carbon atoms.

In one embodiment, $R_{431}$ to $R_{451}$ that do not contribute to form a ring are independently a hydrogen atom, a substituted or unsubstituted alkyl group having 1 to 50 carbon atoms, and at least one of $R_{431}$ to $R_{451}$ is a substituted or unsubstituted alkyl group having 1 to 50 carbon atoms.

In one embodiment, the compound represented by the formula (43) is a compound represented by the following formula (43A).

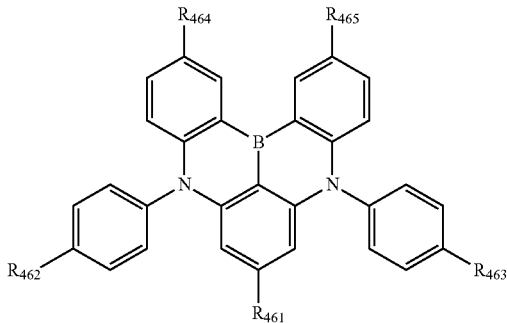

(43A)

wherein in the formula (43A), $R_{461}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{462}$ to $R_{465}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In one embodiment, $R_{461}$ to $R_{465}$ are independently a substituted or unsubstituted alkyl group having 1 to 50 carbon atoms or a substituted or unsubstituted aryl group having 6 to 50 ring carbon atoms.

In one embodiment, $R_{461}$ and $R_{465}$ are independently a substituted or unsubstituted alkyl group having 1 to 50 carbon atoms.

In one embodiment, the compound represented by the formula (43) is a compound represented by the following formula (43B).

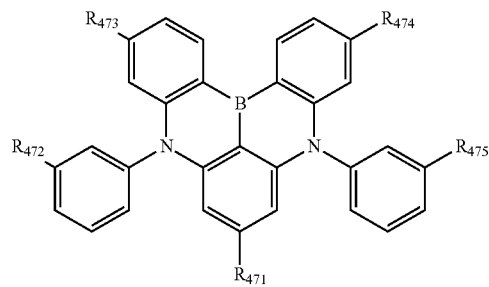

(43B)

wherein in the formula (43 B), $R_{471}$ and $R_{472}$ are independently, a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$)($R_{907}$), or a substituted or unsubstituted aryl group having 6 to 50 ring carbon atoms;

$R_{473}$ to $R_{475}$ are independently, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$)($R_{907}$), or a substituted or unsubstituted aryl group having 6 to 50 ring carbon atoms; and $R_{906}$ and $R_{907}$ are as defined in the formula (1).

In one embodiment, the compound represented by the formula (43) is the compound represented by the following formula (43B').

(43B′)

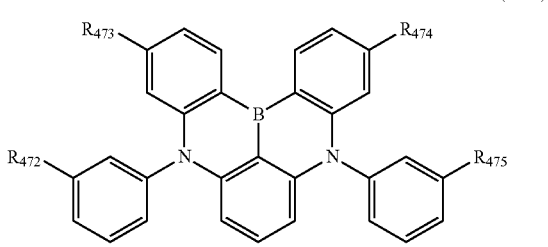

wherein in the formula (43B'), $R_{472}$ to $R_{475}$ are as defined in the formula (43 B).

In one embodiment, at least one of $R_{471}$ to $R_{475}$ is
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, —N($R_{906}$)($R_{907}$), or
a substituted or unsubstituted aryl group having 6 to 50 ring carbon atoms.

In one embodiment,
$R_{472}$ is
a hydrogen atom,
a substituted or unsubstituted alkyl group having 1 to 50 carbon atoms,
—N($R_{906}$)($R_{907}$), or
a substituted or unsubstituted aryl group having 6 to 50 ring carbon atoms; and
$R_{471}$ and $R_{473}$ to $R_{475}$ are independently
a substituted or unsubstituted alkyl group having 1 to 50 carbon atoms,
—N($R_{906}$)($R_{907}$), or
a substituted or unsubstituted aryl group having 6 to 50 ring carbon atoms.

In one embodiment, the compound represented by the formula (43) is a compound represented by the formula (43C).

(43C)

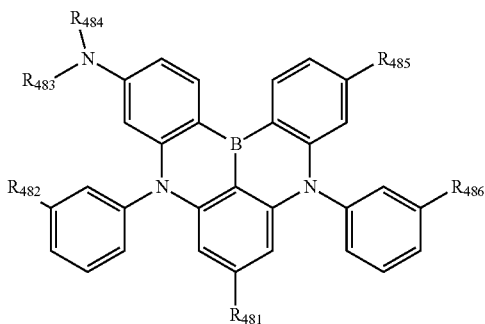

wherein in the formula (43C),
$R_{481}$ and $R_{482}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms; and
$R_{483}$ to $R_{486}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms.

In one embodiment, the compound represented by the formula (43) is the compound represented by the following formula (43C').

(43C′)

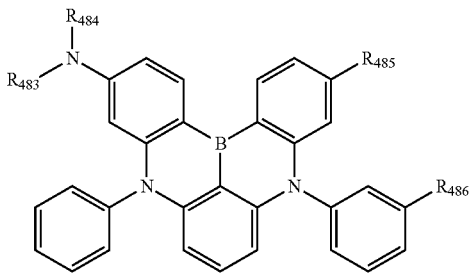

wherein in the formula (43C'), $R_{483}$ to $R_{484}$ are as defined in the formula (43C).

In one embodiment, $R_{481}$ to $R_{486}$ are independently a substituted or unsubstituted alkyl group having 1 to 50 carbon atoms or a substituted or unsubstituted aryl group having 6 to 50 ring carbon atoms.

In one embodiment, $R_{481}$ to $R_{486}$ are independently a substituted or unsubstituted aryl group having 6 to 50 ring carbon atoms.

In one embodiment, the compound represented by the formula (43) is a compound represented by the following formula (43D):

(43D)

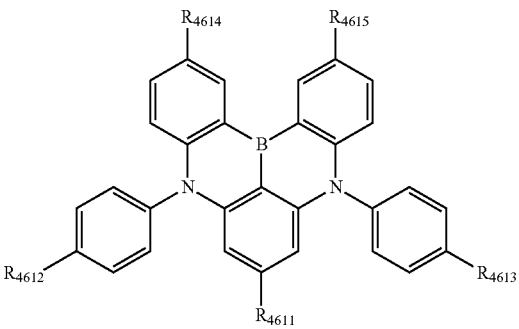

wherein in the formula (43D),
$R_{4611}$ is a hydrogen atom, an unsubstituted alkyl group including 1 to 6 carbon atoms, an unsubstituted cycloalkyl group including 3 to 10 ring carbon atoms, —Si(R$_{911}$)(R$_{912}$)(R$_{913}$), or —N(R$_{914}$)(R$_{915}$);

R$_{4612}$ to R$_{4615}$ are independently an unsubstituted alkyl group including 1 to 6 carbon atoms, an unsubstituted cycloalkyl group including 3 to 10 ring carbon atoms, or —Si(R$_{911}$)(R$_{912}$)(R$_{913}$);

R$_{911}$ to R$_{913}$ are independently an unsubstituted alkyl group including 1 to 6 carbon atoms or an unsubstituted aryl group including 6 to 18 ring carbon atoms;

R$_{914}$ to R$_{915}$ are independently an unsubstituted aryl group including 6 to 18 ring carbon atoms.

In one embodiment, in the formula (43D), R$_{4611}$ is a hydrogen atom, an unsubstituted alkyl group including 1 to 6 carbon atoms, or —N(R$_{914}$)(R$_{915}$).

In one embodiment, in the formula (43D), R$_{4612}$ to R$_{4615}$ are independently an unsubstituted alkyl group including 1 to 6 carbon atoms, or an unsubstituted cycloalkyl group including 3 to 10 ring carbon atoms.

In one embodiment, in the formula (43D), R$_{4611}$ is —N(R$_{914}$)(R$_{915}$), and R$_{4612}$ to R$_{4615}$ are independently an unsubstituted alkyl group including 1 to 6 carbon atoms.

In one embodiment, in the formula (43D), R$_{4611}$ is an unsubstituted alkyl group including 1 to 6 carbon atoms, and R$_{4612}$ to R$_{4615}$ are independently an unsubstituted alkyl group including 1 to 6 carbon atoms.

In one embodiment, in the formula (43D), R$_{4611}$ is a hydrogen atom, and R$_{4612}$ to R$_{4615}$ are independently an unsubstituted alkyl group including 1 to 6 carbon atoms, or an unsubstituted cycloalkyl group including 3 to 10 ring carbon atoms.

In one embodiment, in the formula (43D), at least one of the hydrogen atoms included in one or more selected from the group consisting of R$_{914}$ and R$_{915}$ is a deuterium atom.

The compound represented by the formula (41) can be synthesized by the following method: An intermediate is obtained by bonding the a ring, the b ring and the c ring with linking groups (a group containing N—R$_1$ and a group containing N—R$_2$) (first reaction), and a final compound is obtained by bonding the a ring, the b ring and the c ring with a linking group (a group containing B) (second reaction). In the first reaction, an amination reaction such as Buchwald-Hartwig reaction can be applied. In the second reaction, tandem hetero-Friedel-Crafts reaction or the like can be applied.

Examples of the compound represented by the formula (41) are described below. They are just exemplified compounds and the compound represented by the formula (41) is not limited to the following examples. In the following example compounds, Me represents methyl group, and tBu represents tert-butyl group.

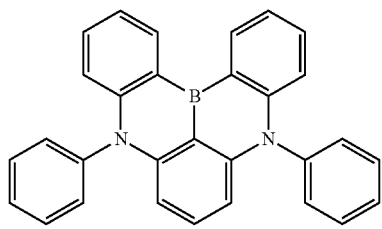

-continued

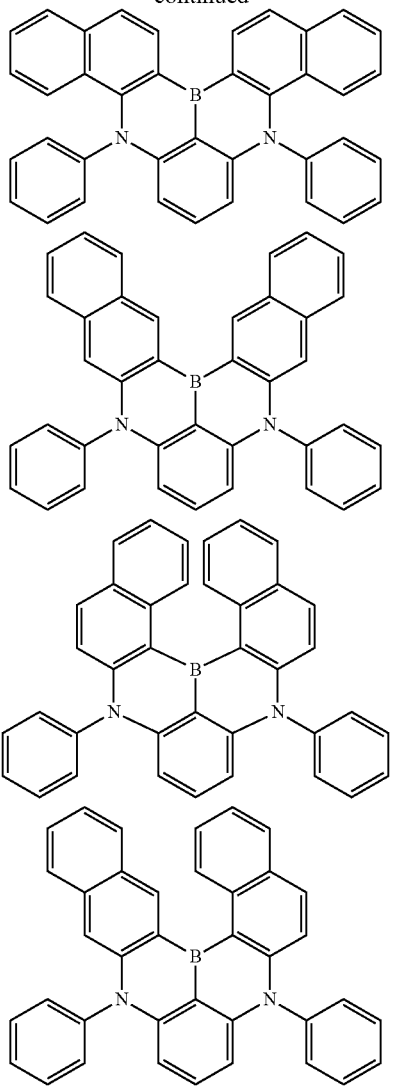

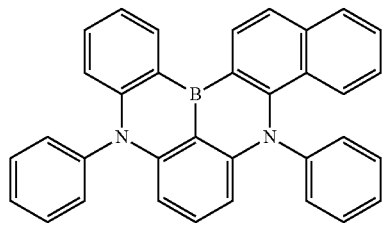

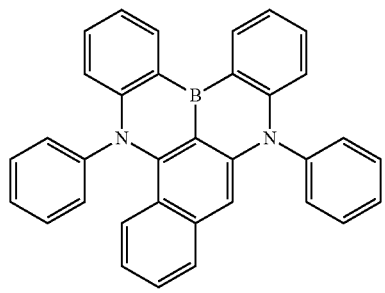

891
-continued
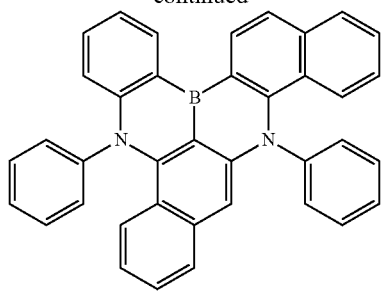
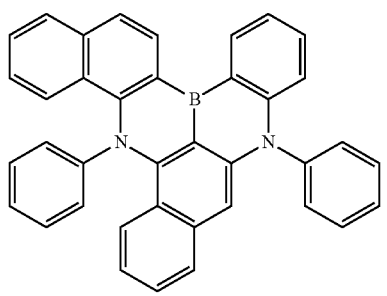
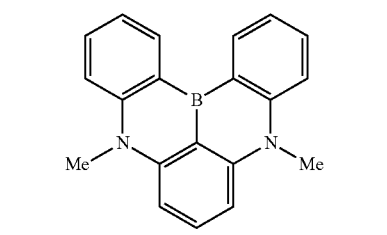
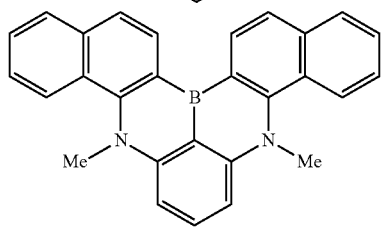
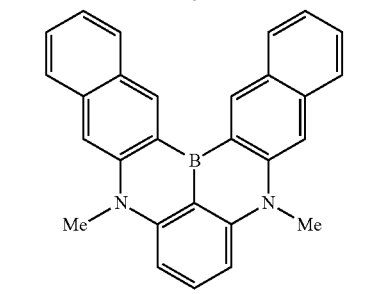
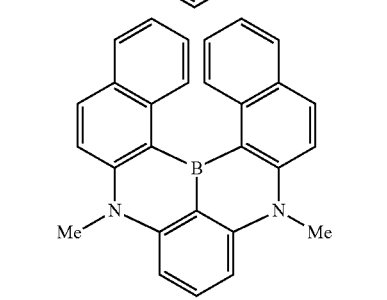
892
-continued
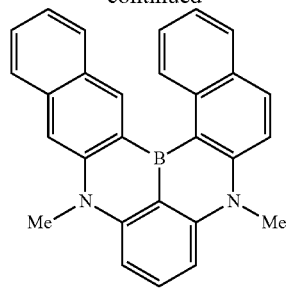
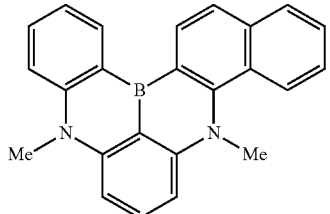
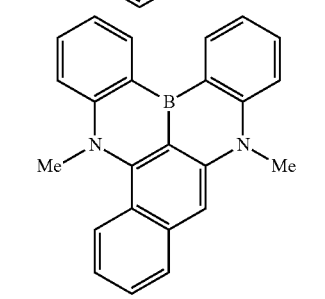
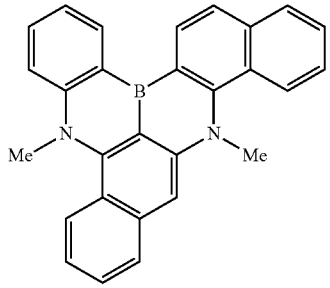
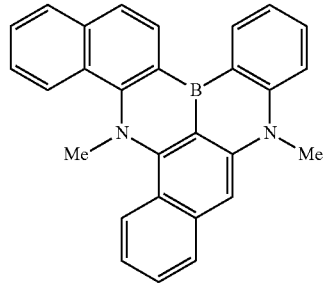
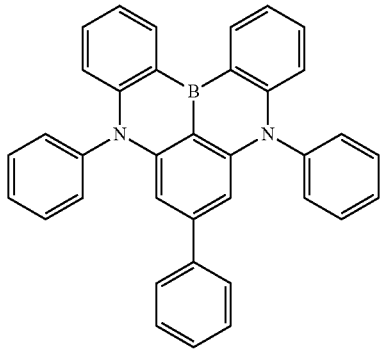

893
-continued
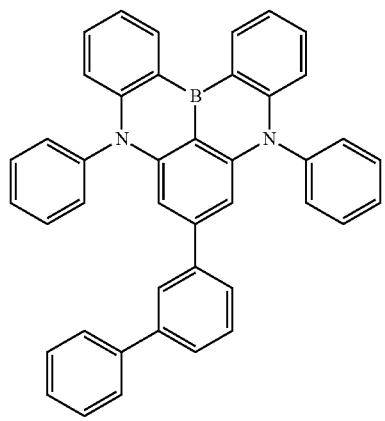
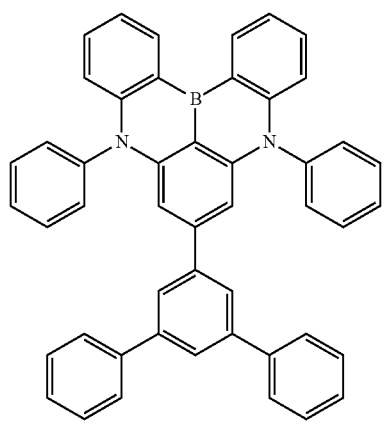
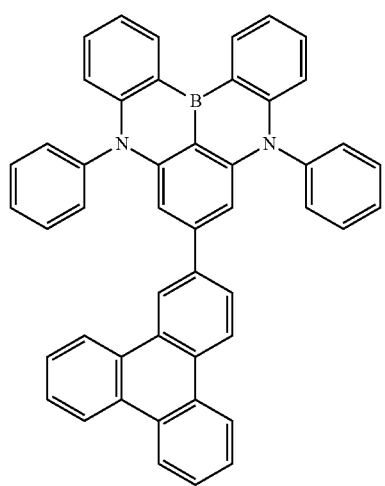
894
-continued
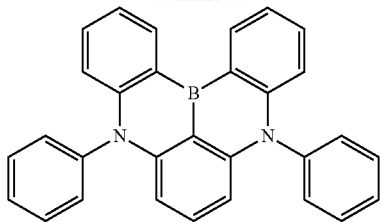
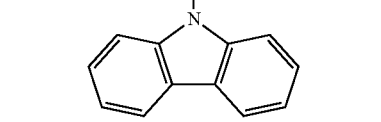
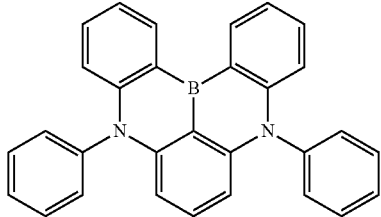
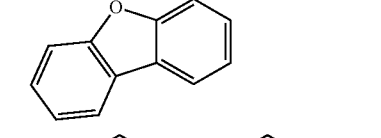
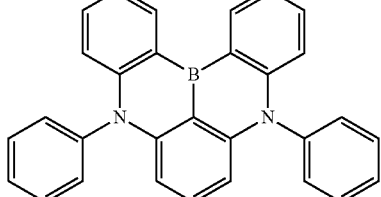
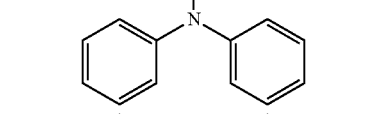
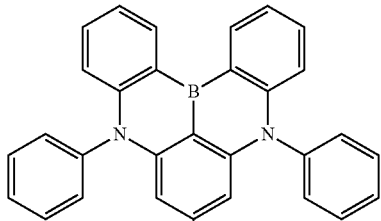
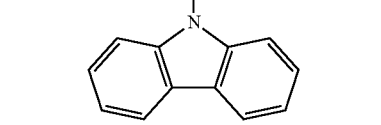

895
-continued
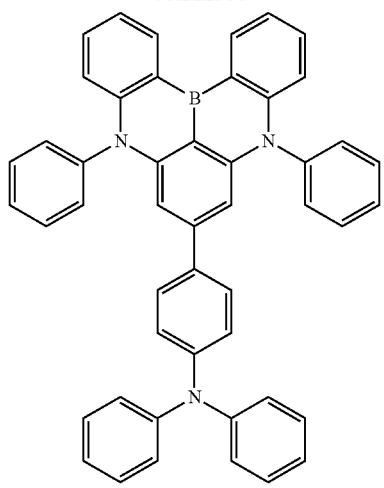
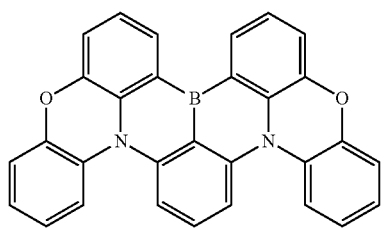
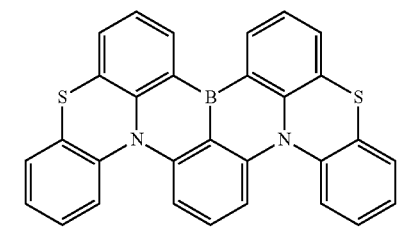
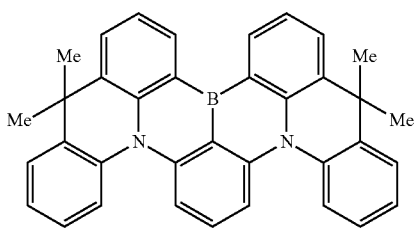
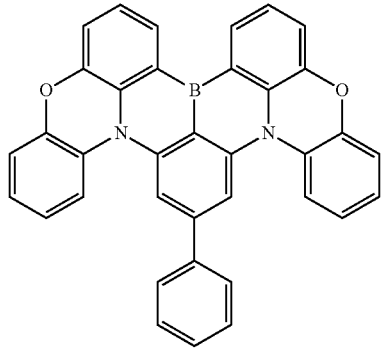
896
-continued
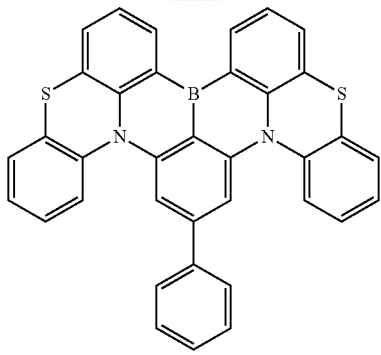
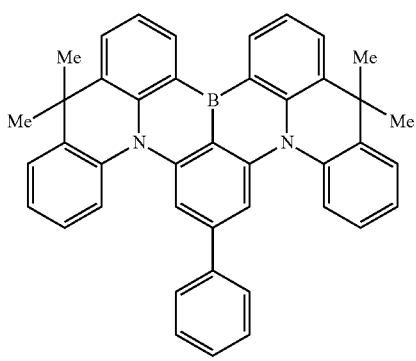
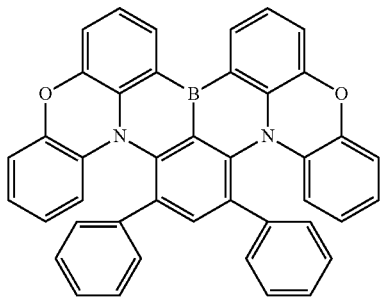
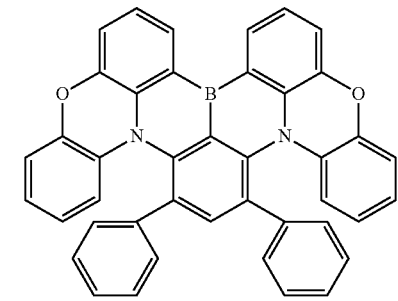
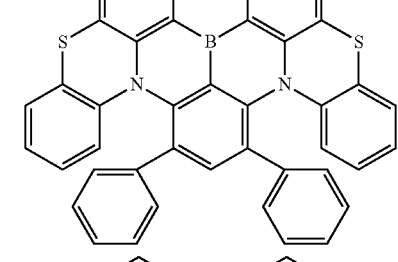
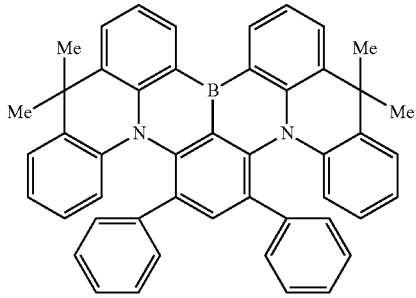

897
-continued
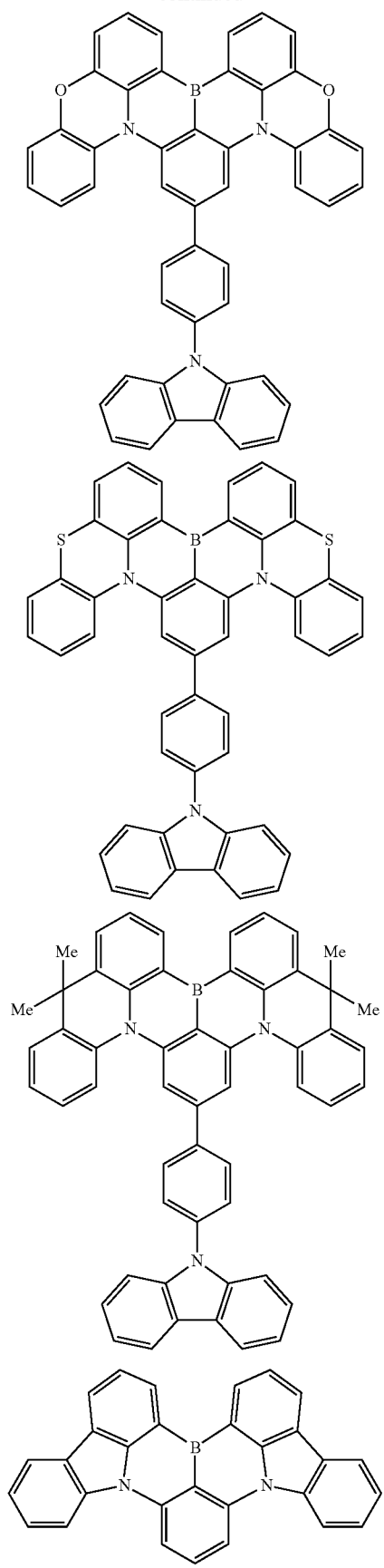
898
-continued
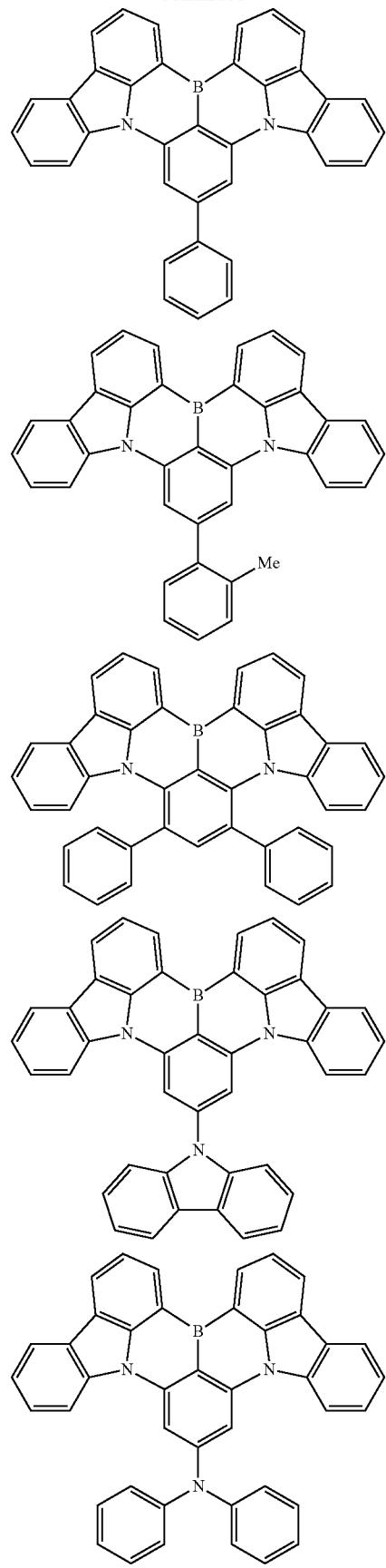

899
-continued
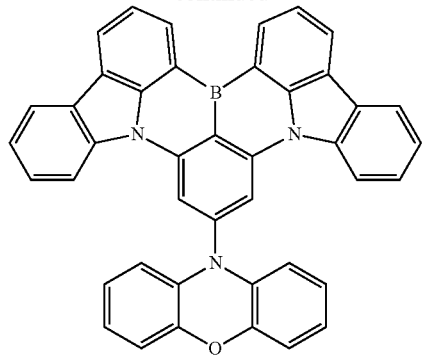
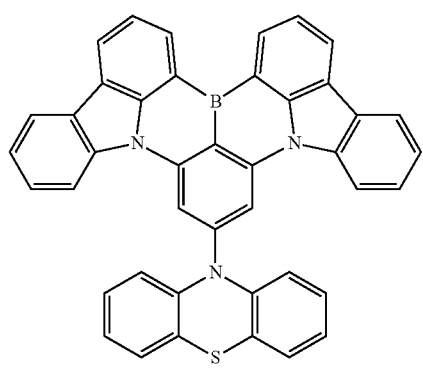
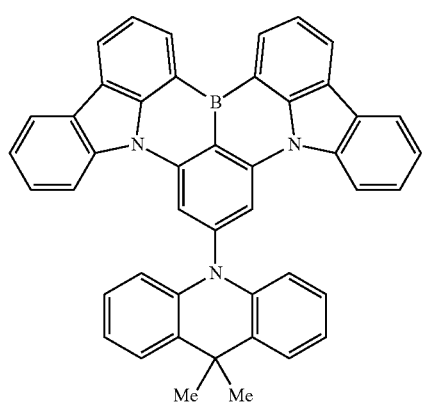
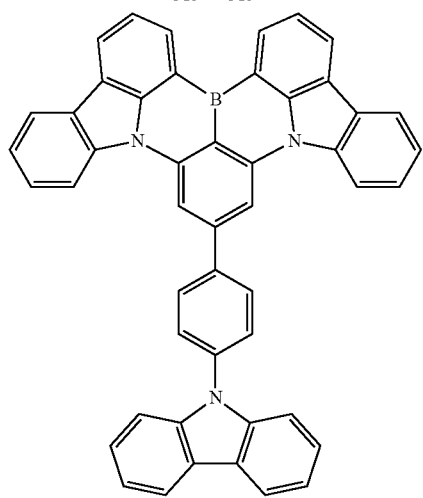
900
-continued
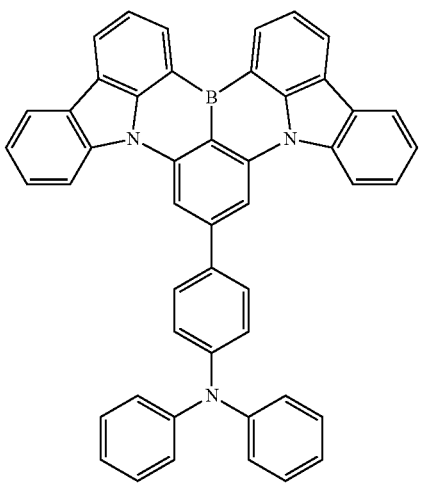
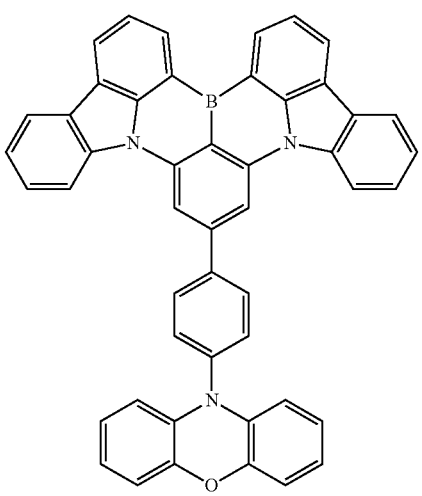
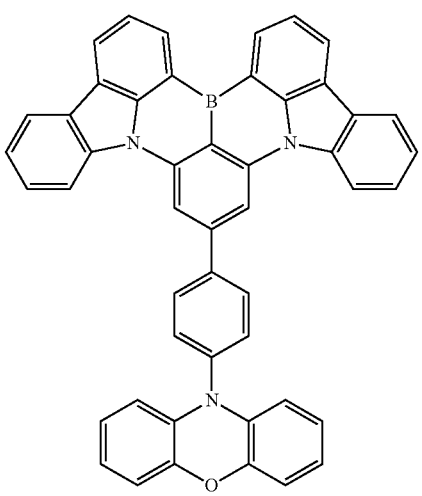
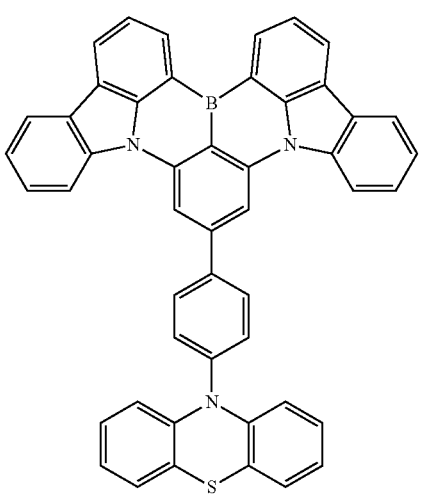

901
-continued
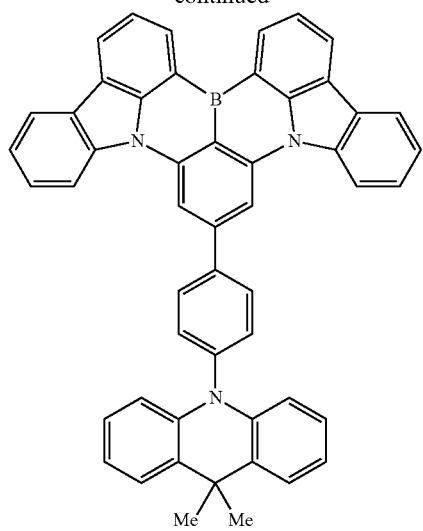
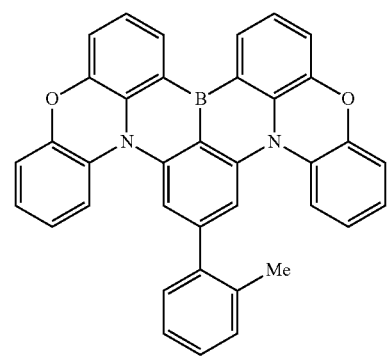
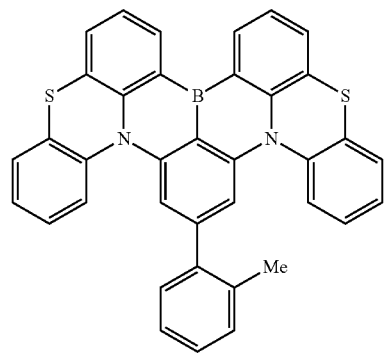
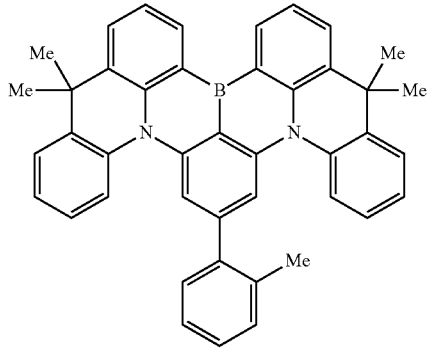
902
-continued
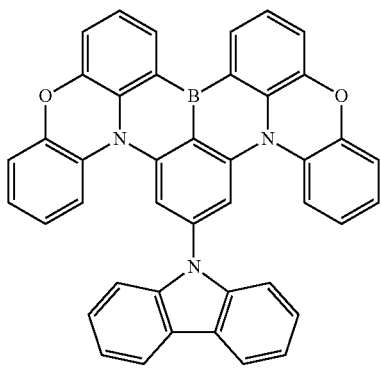
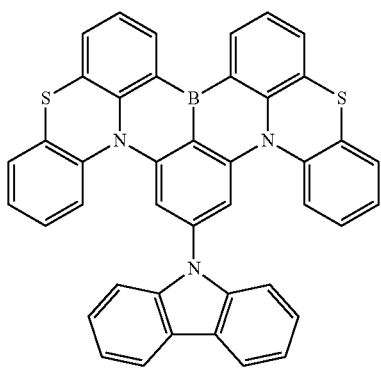
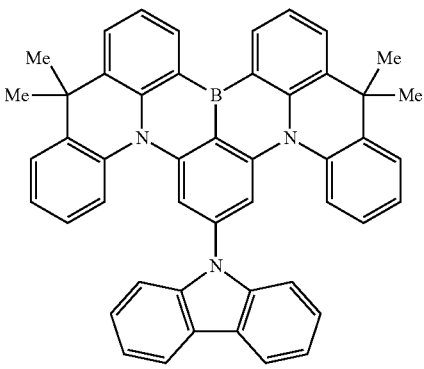
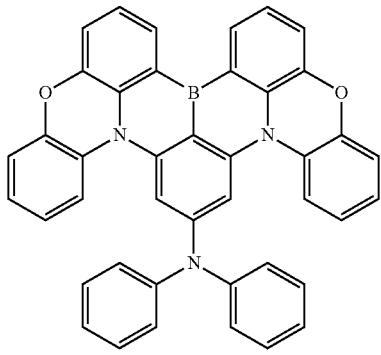

903
-continued
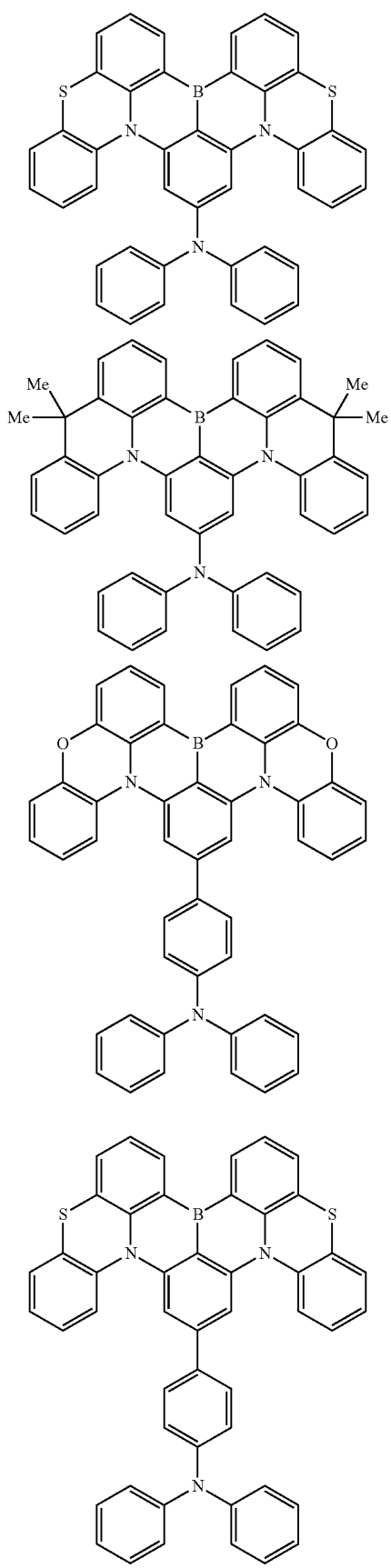
904
-continued
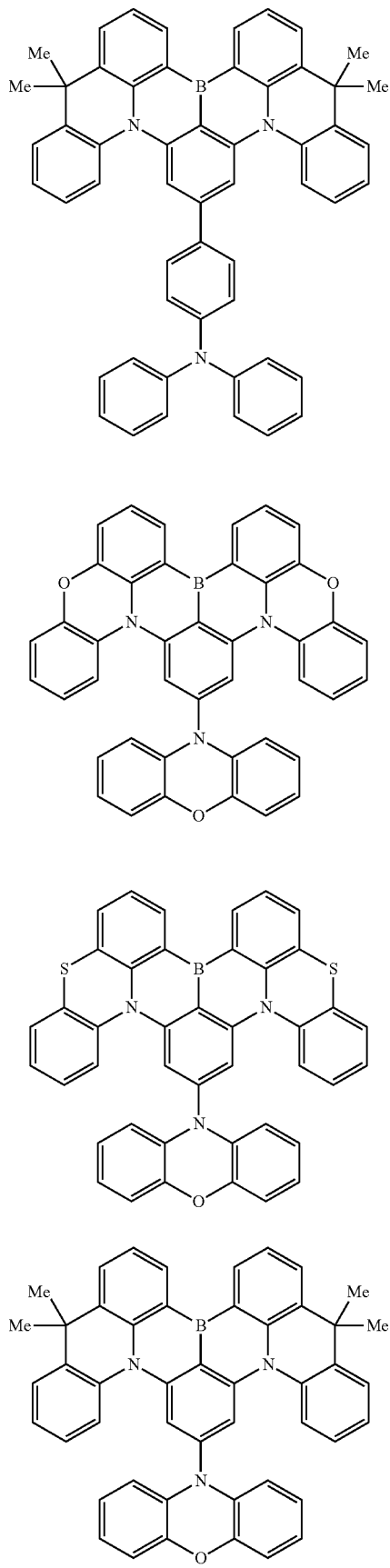

905
-continued
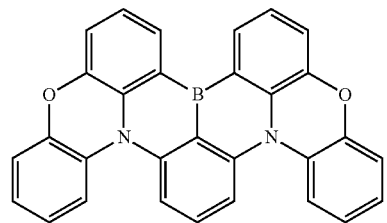
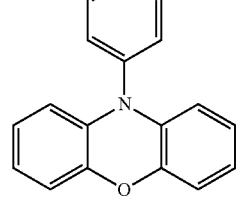
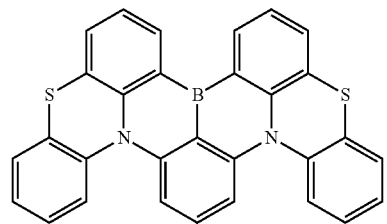
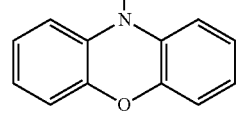
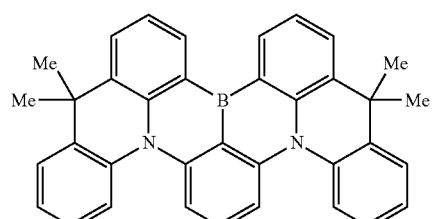
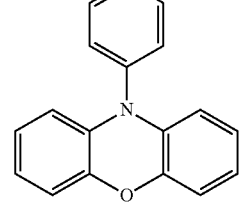
906
-continued
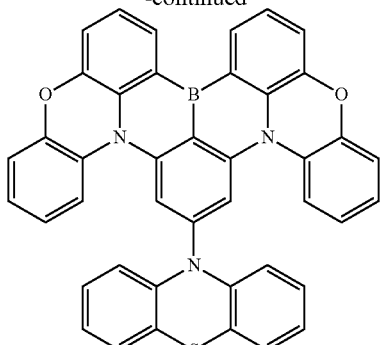
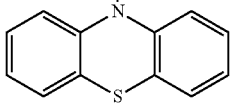
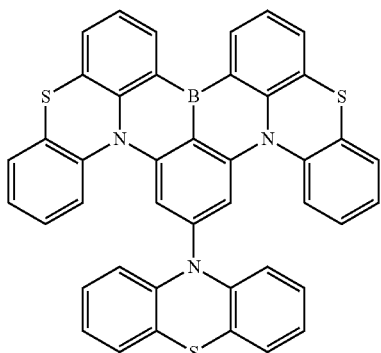
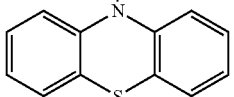
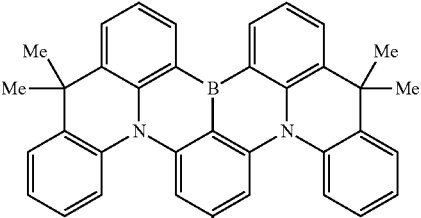
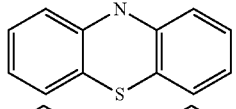
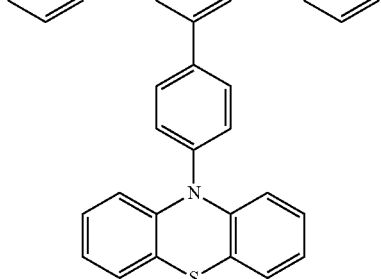
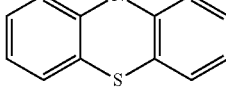

907
-continued
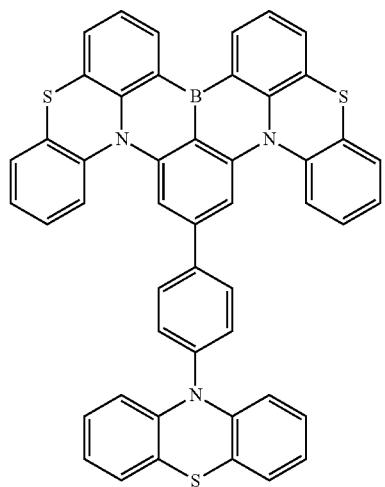
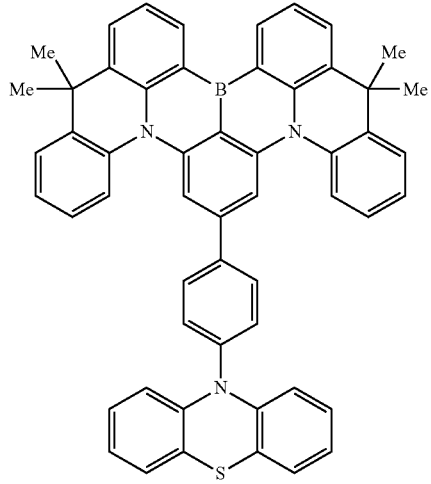
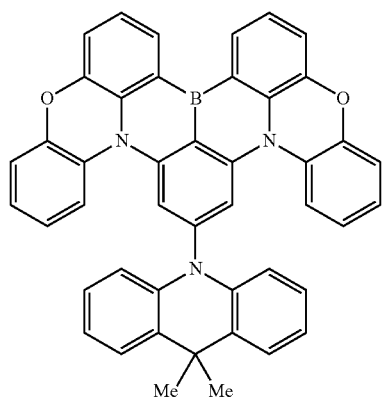
908
-continued
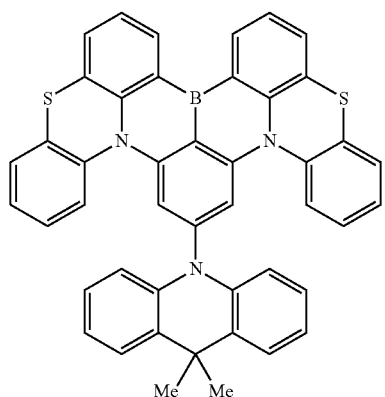
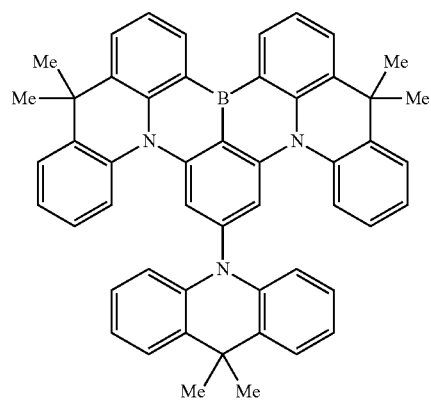
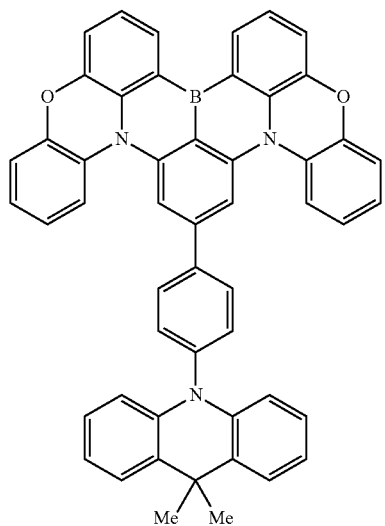

909
-continued
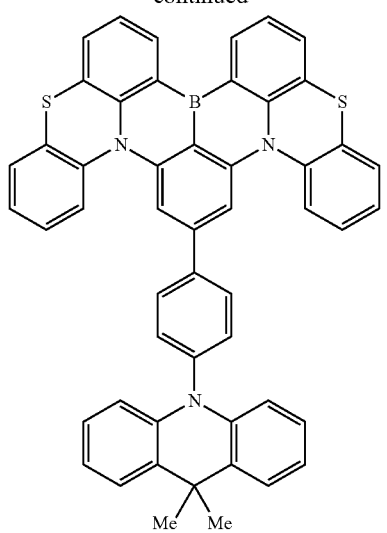
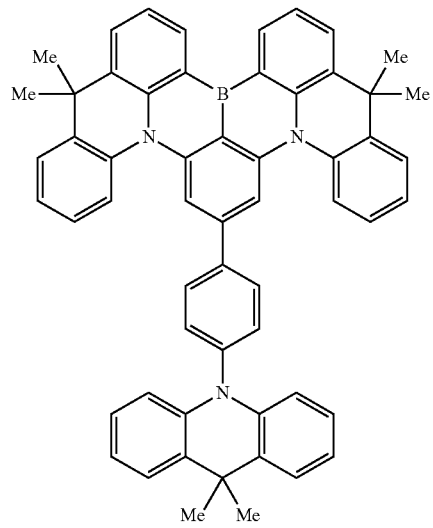
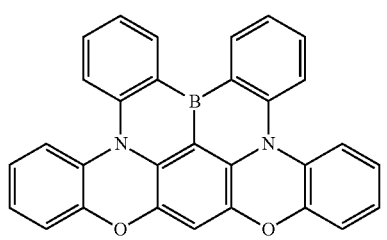
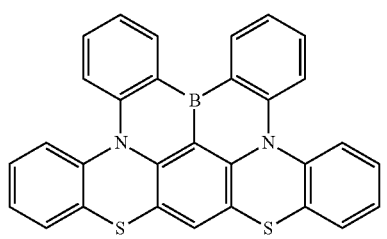
910
-continued
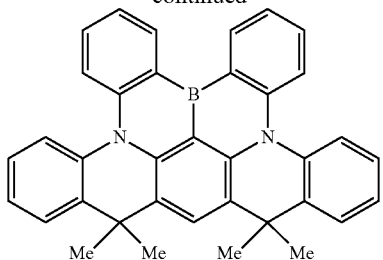
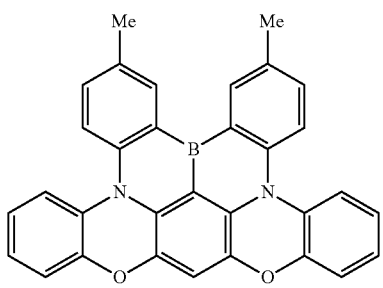
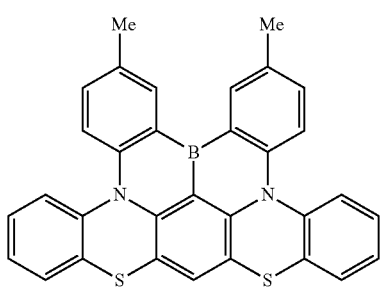
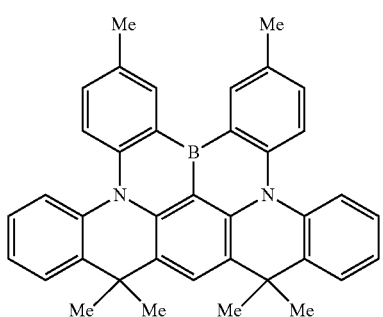
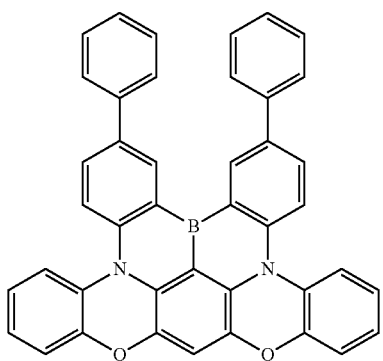

911
-continued
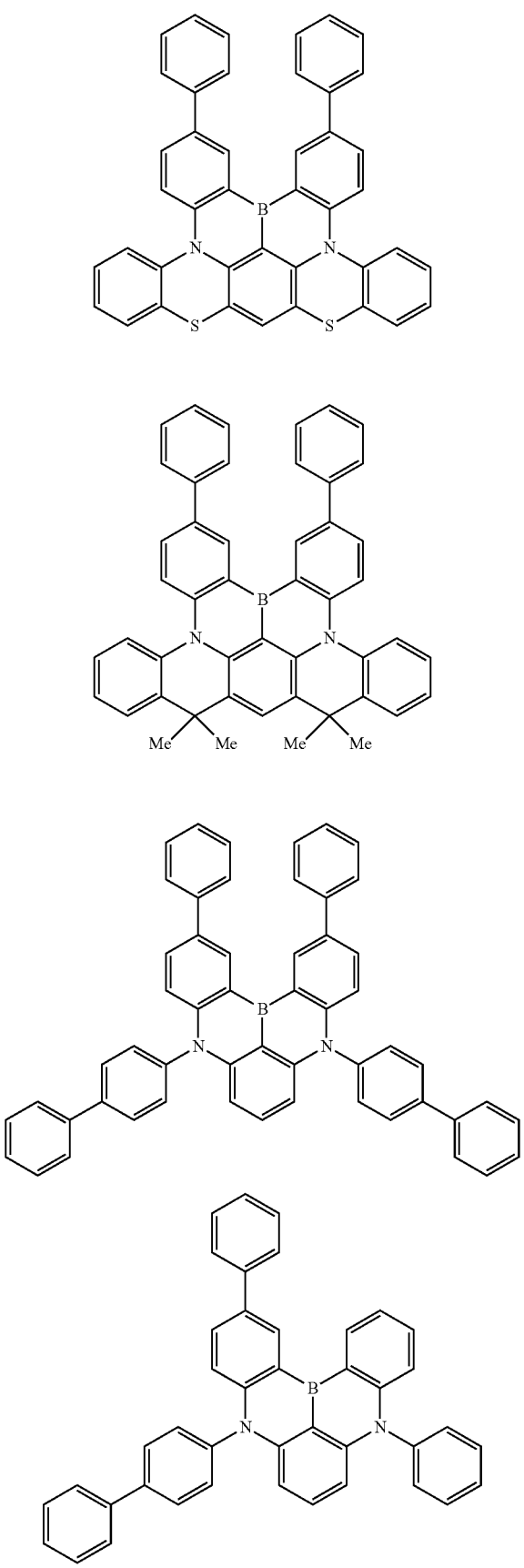
912
-continued
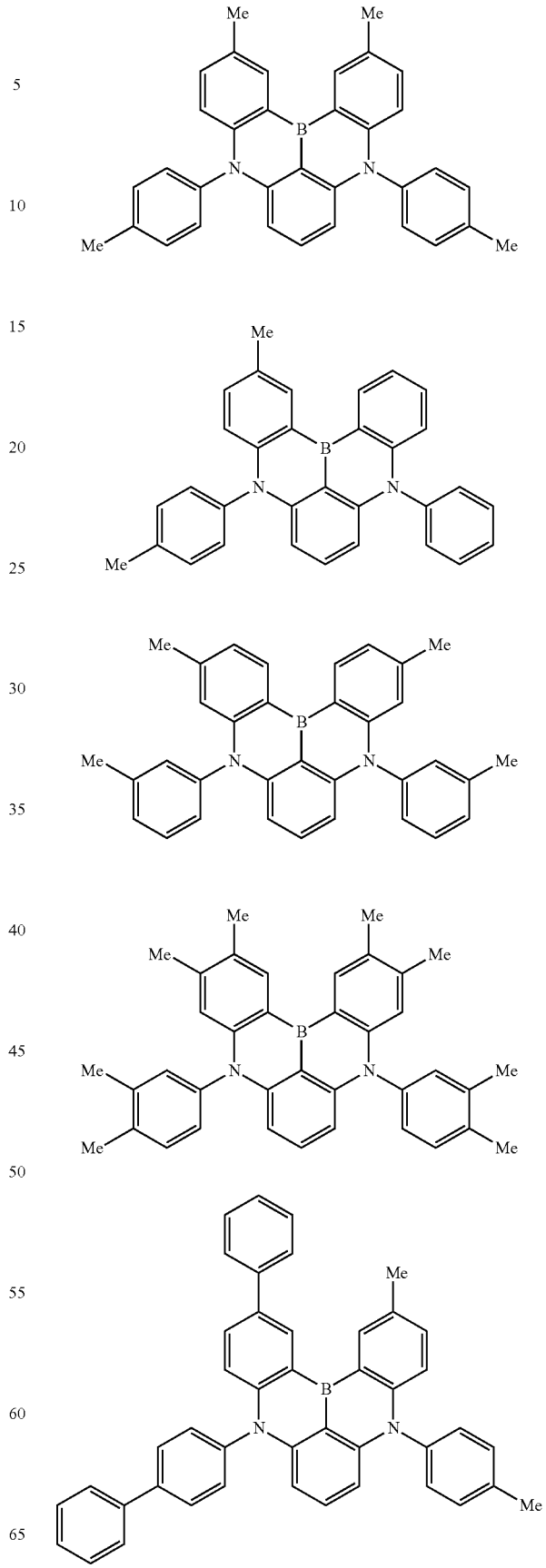

913
-continued
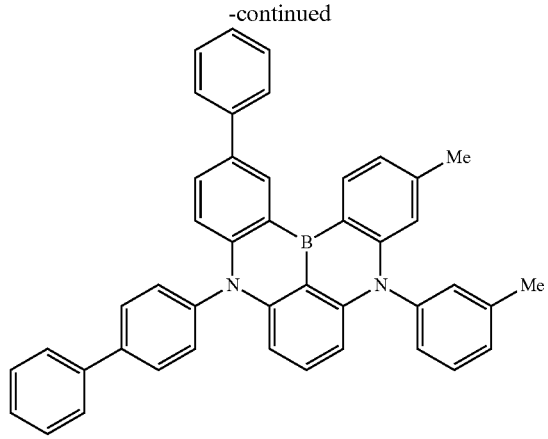
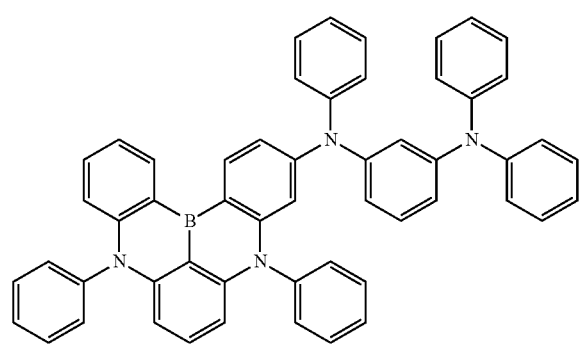
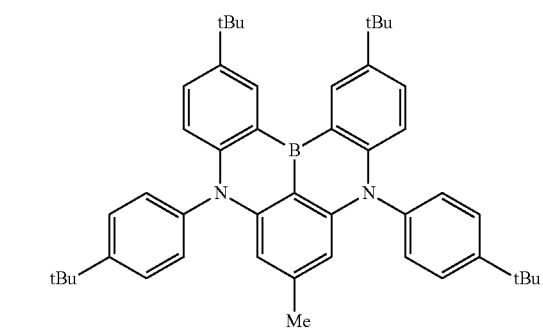
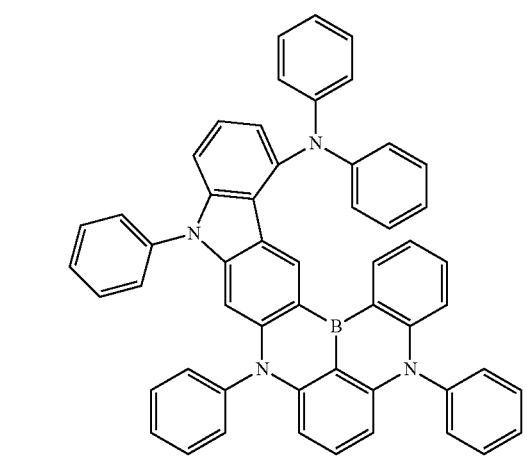
914
-continued
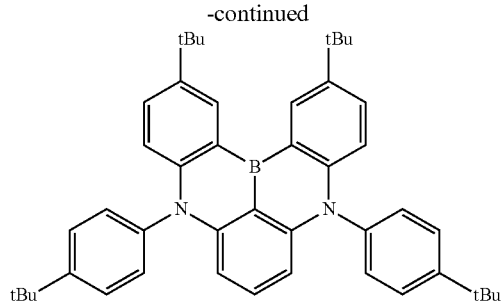
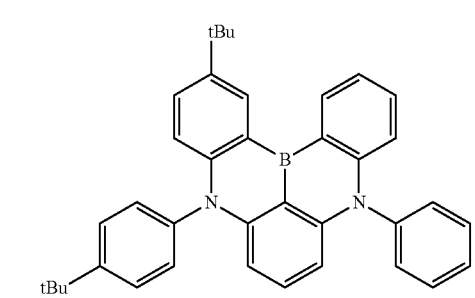
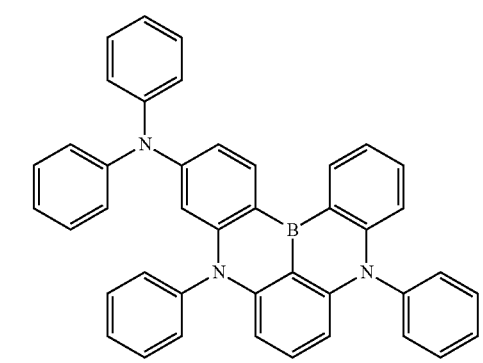
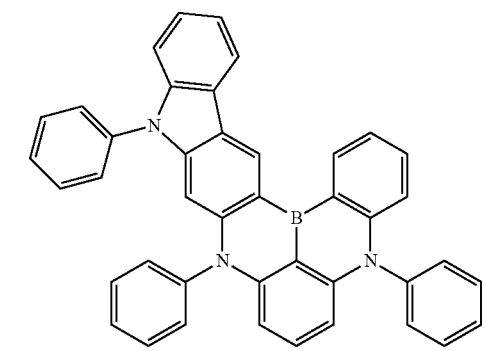

| 915 -continued | 916 -continued |
|---|---|
| 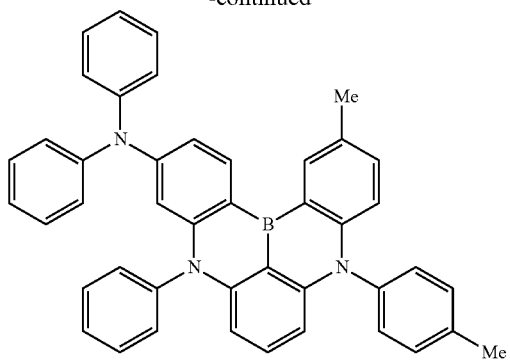 | 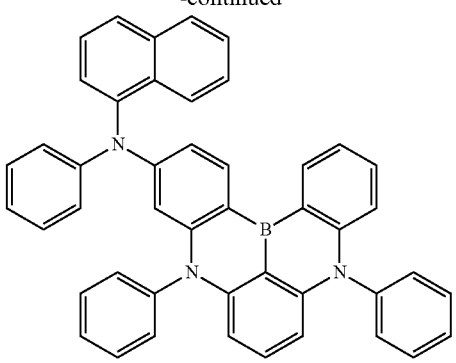 |
| 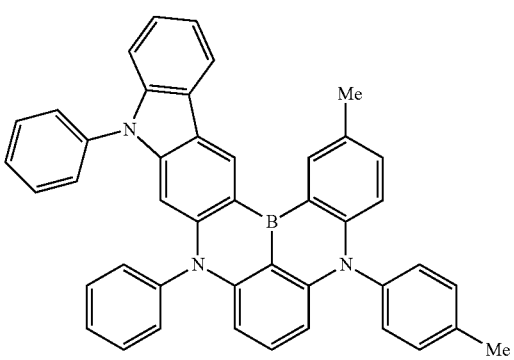 | 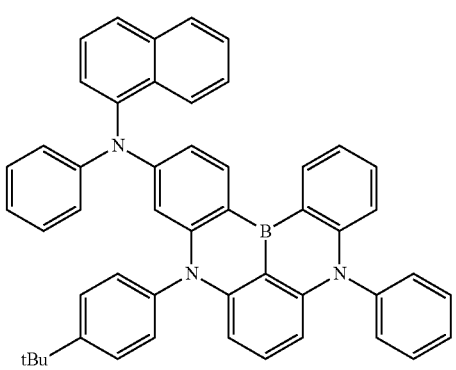 |
| 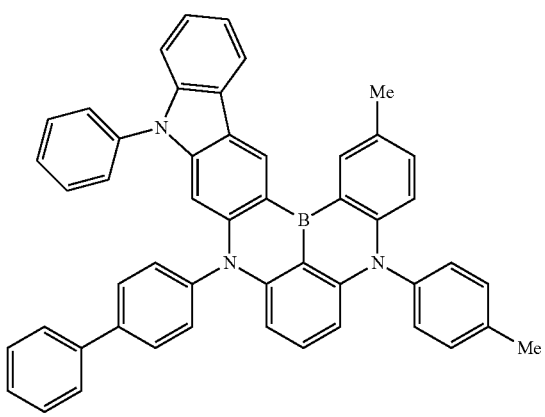 | 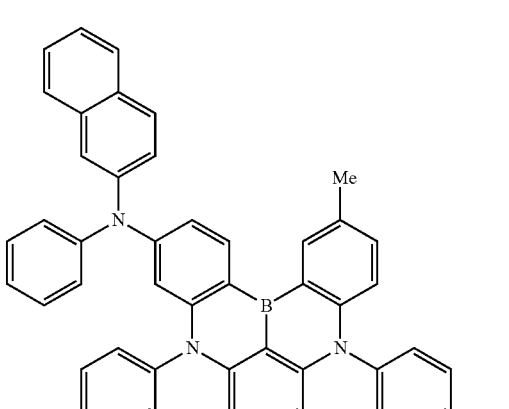 |
| 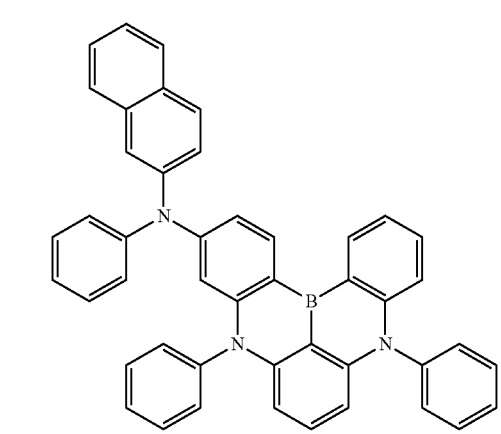 | 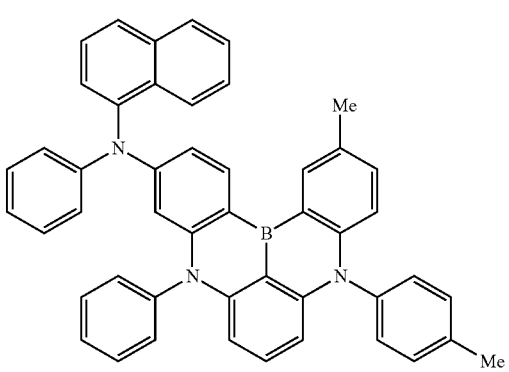 |

917
-continued
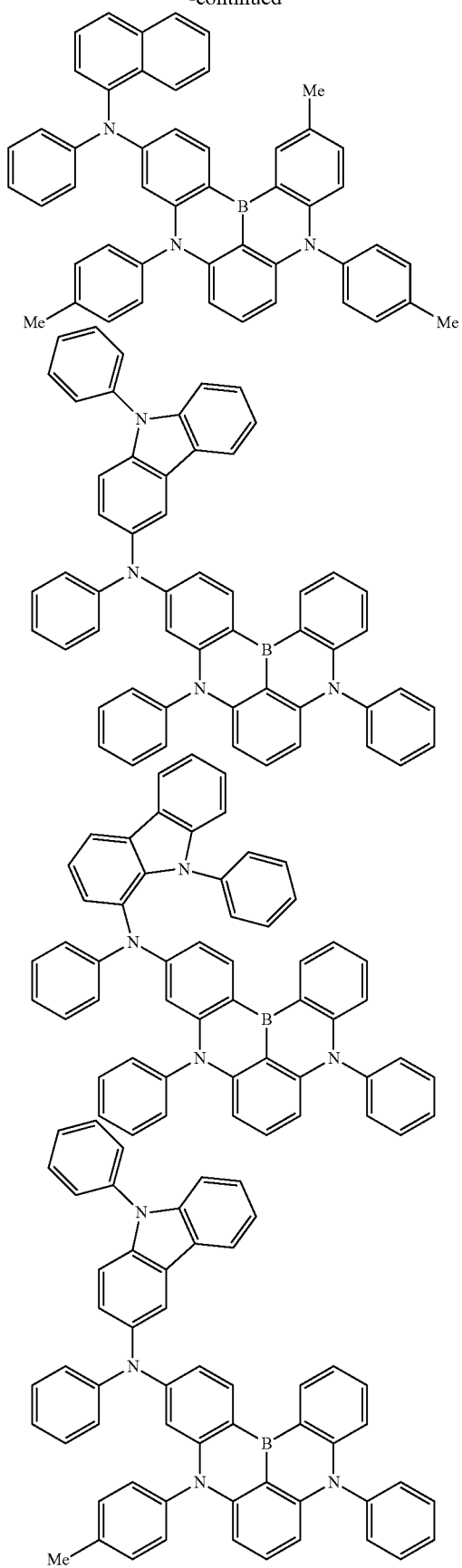
918
-continued
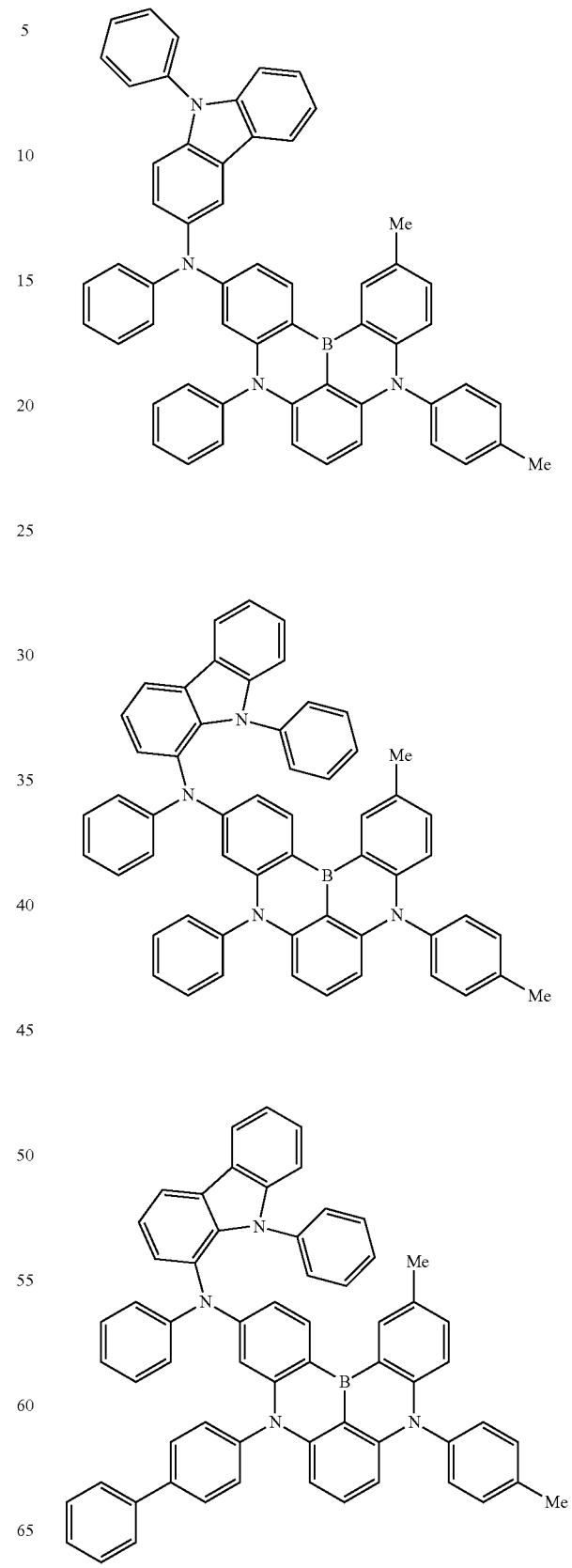

919
-continued
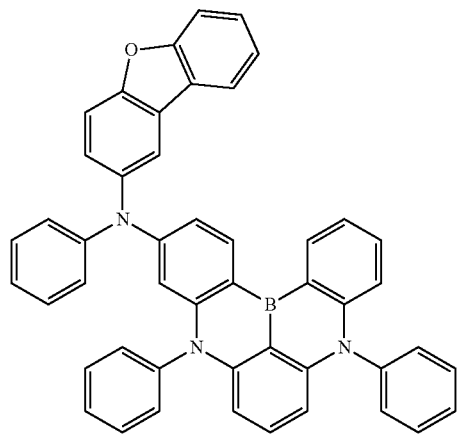
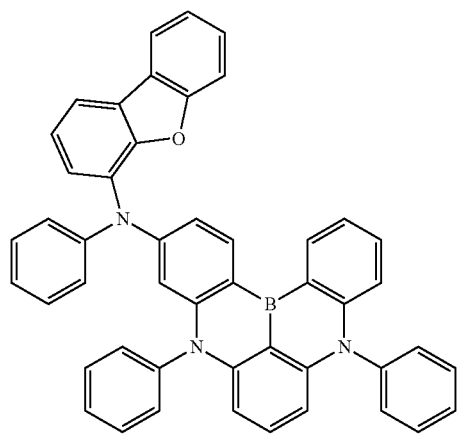
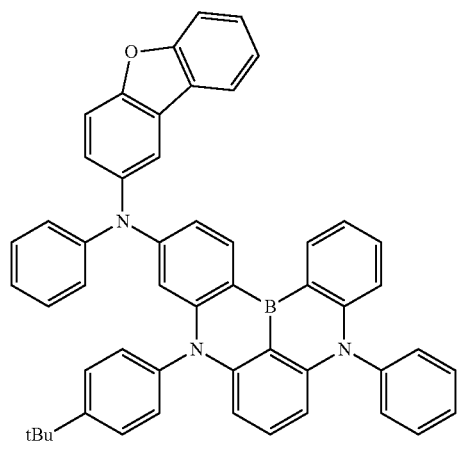
920
-continued
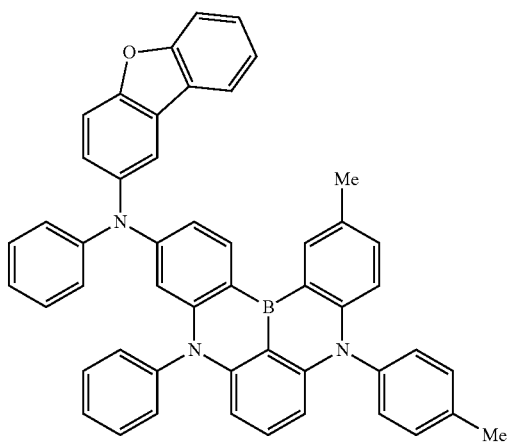
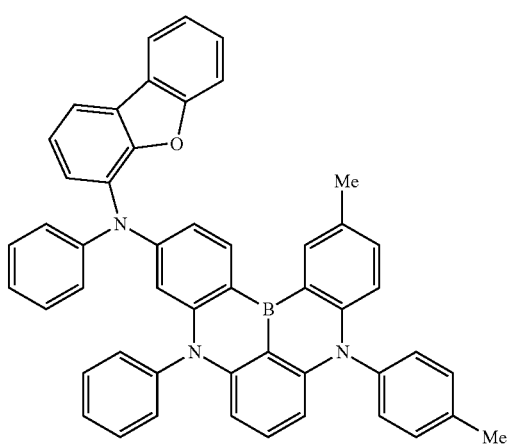
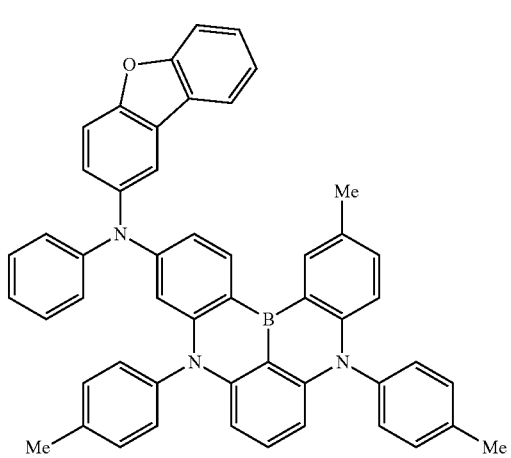

921
-continued
922
-continued
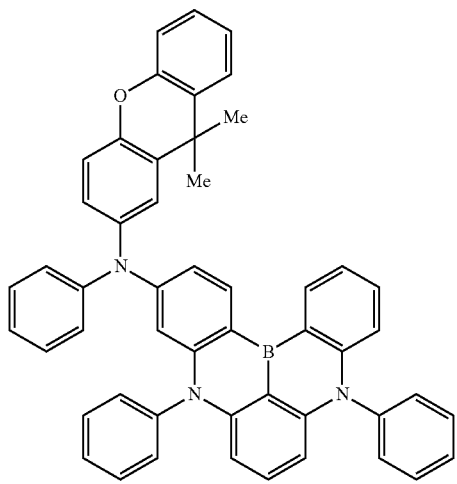
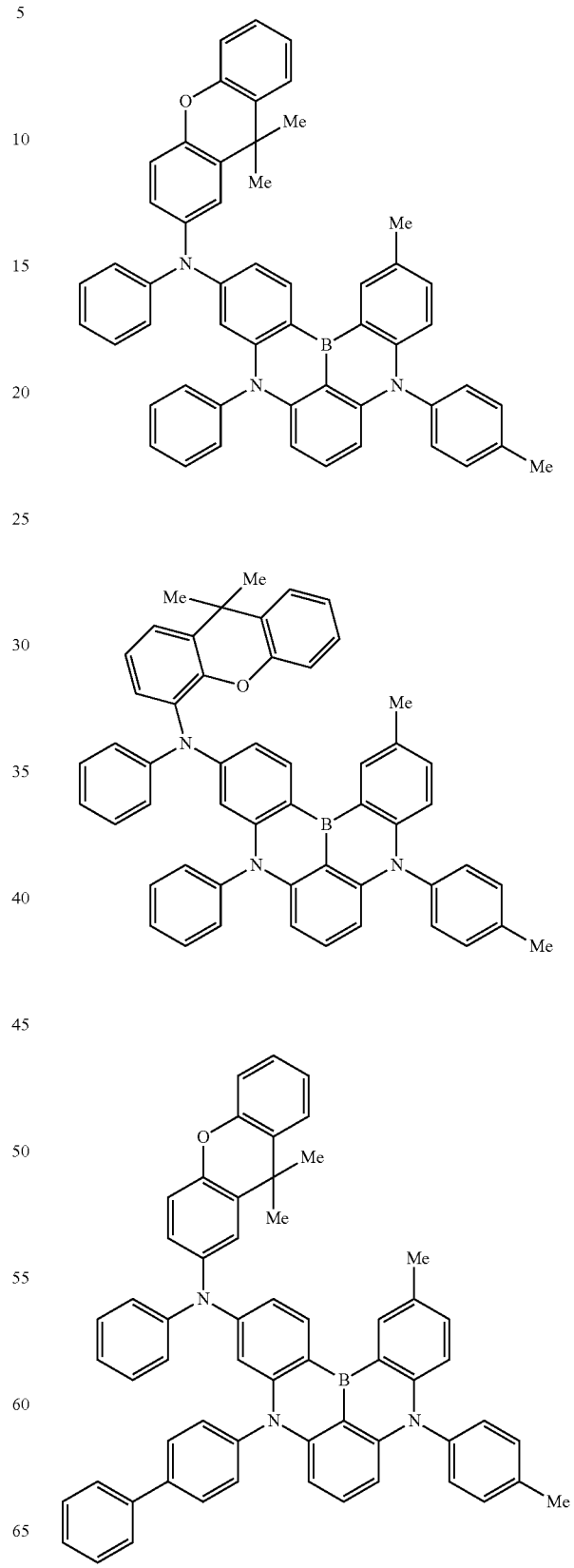

923
-continued
924
-continued
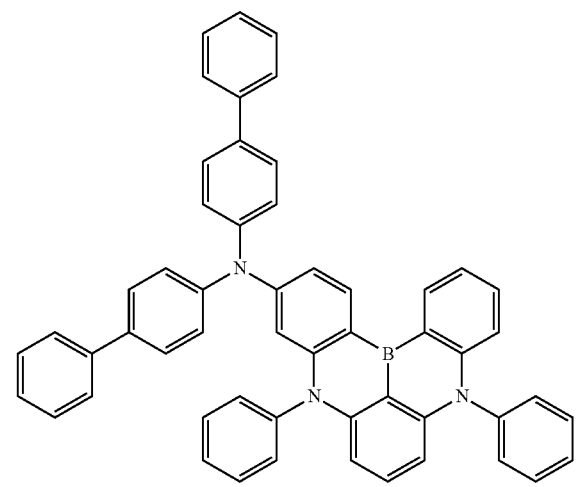
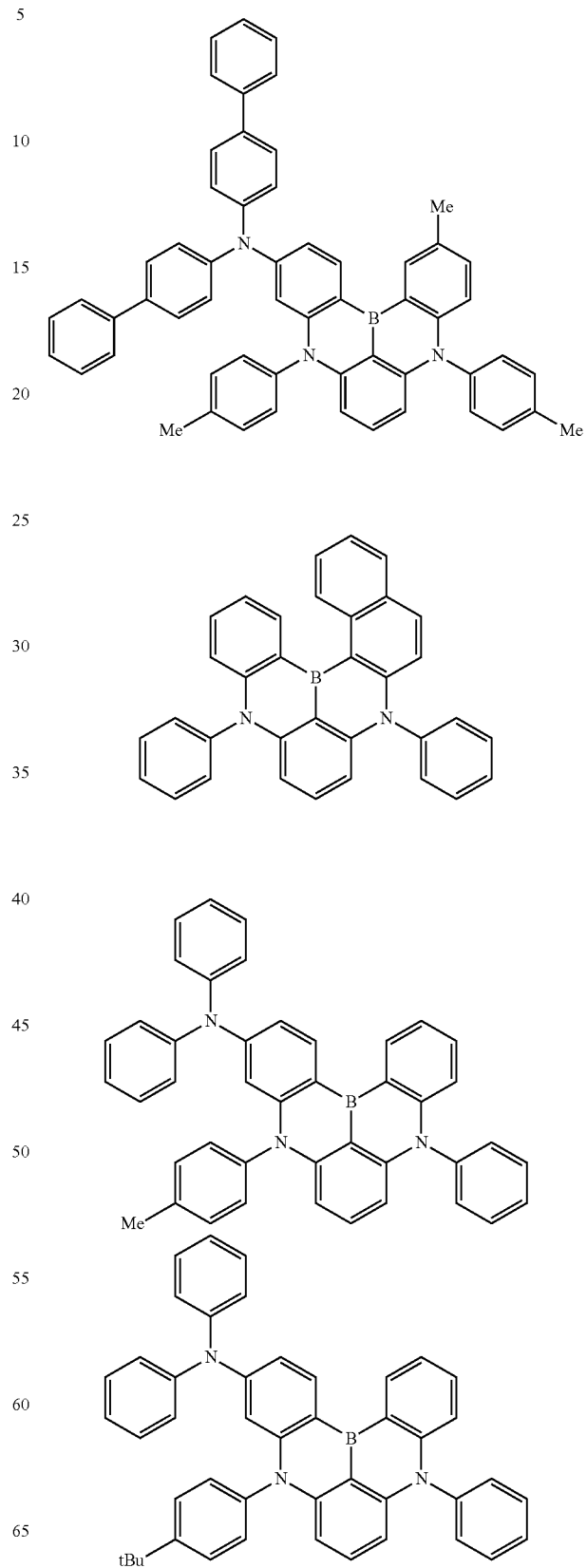

925
-continued
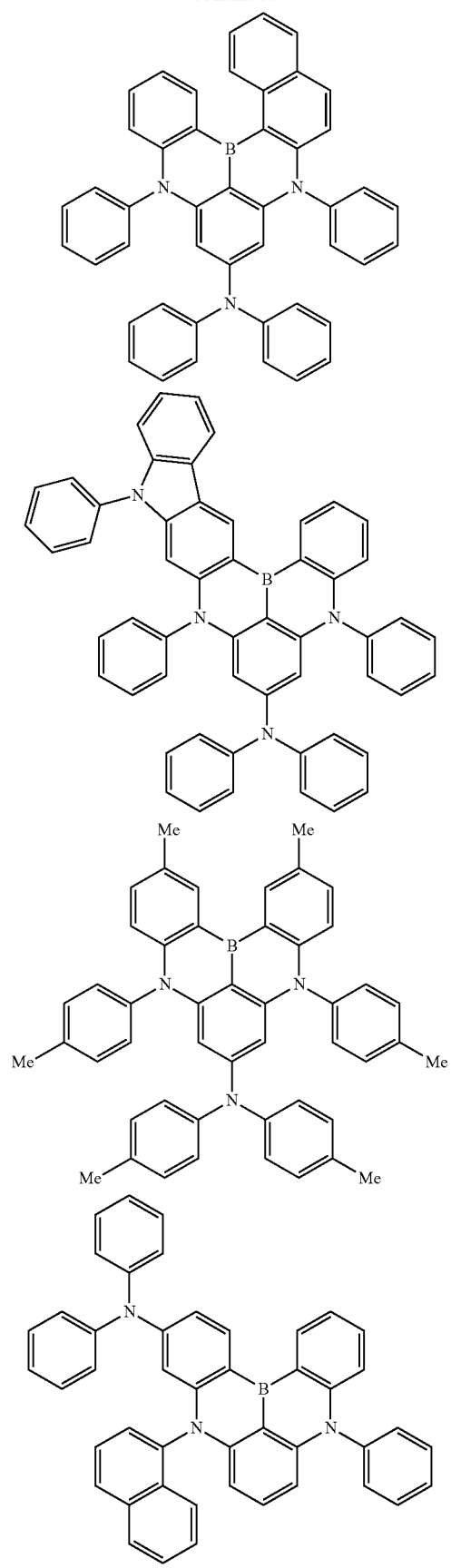
926
-continued
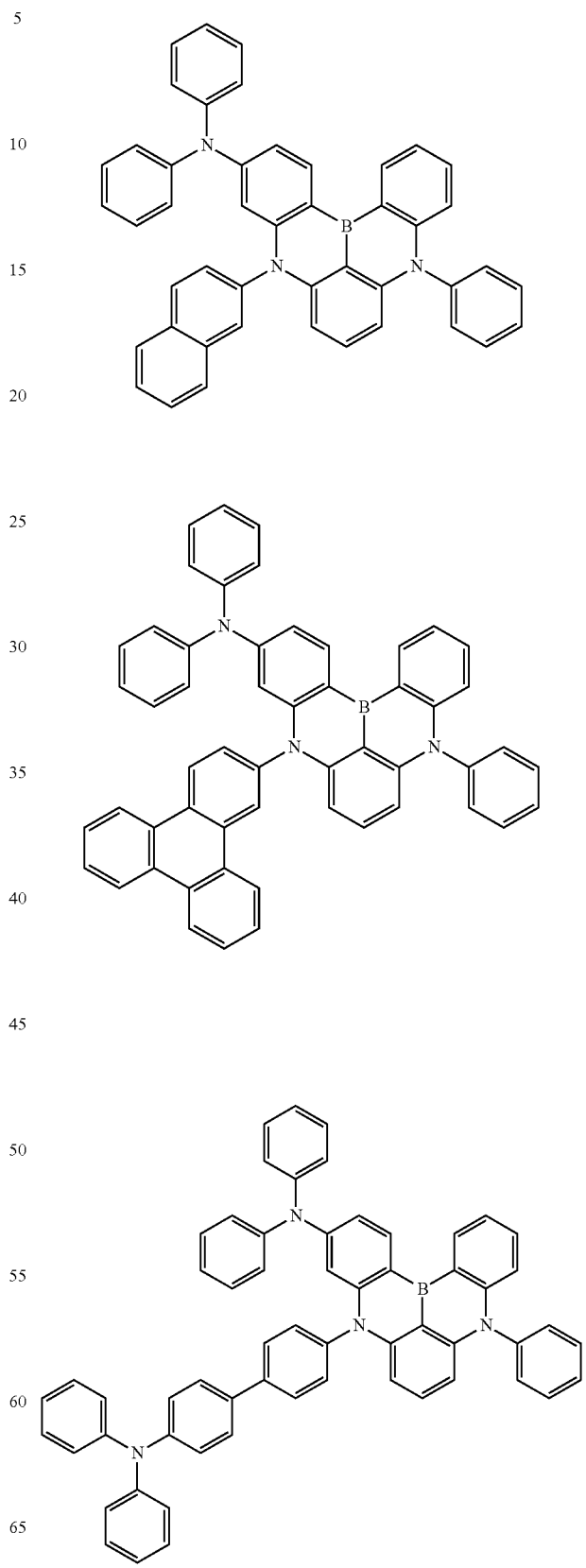

927
-continued
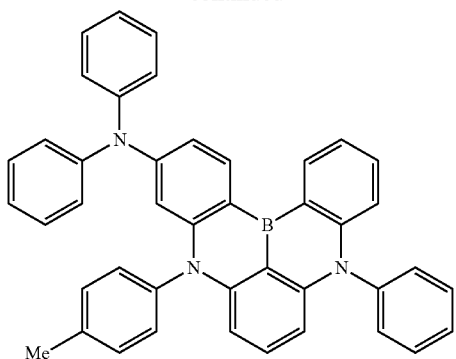
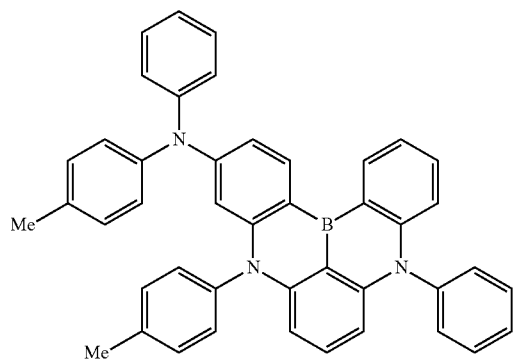
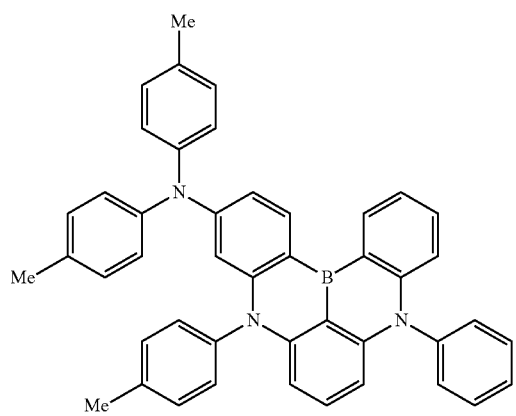
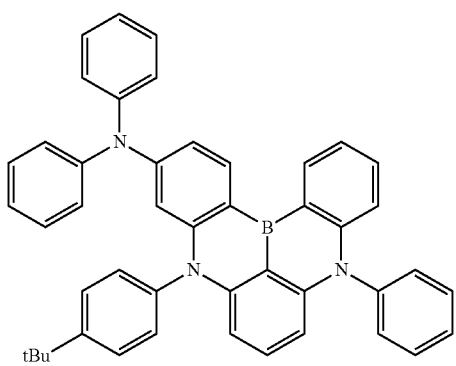
928
-continued
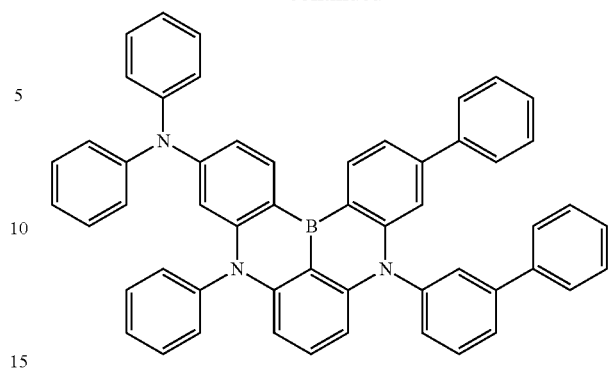
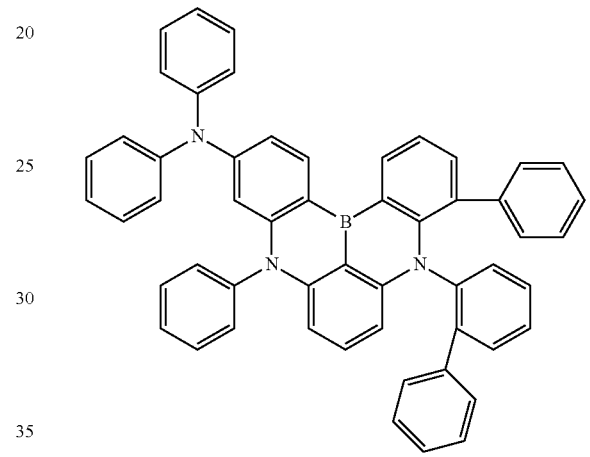
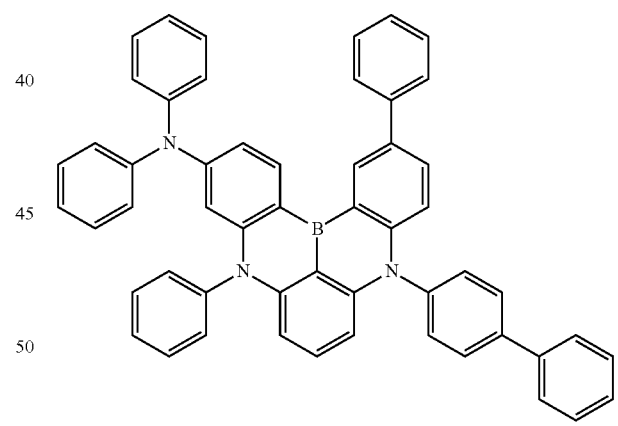

929
-continued
930
-continued
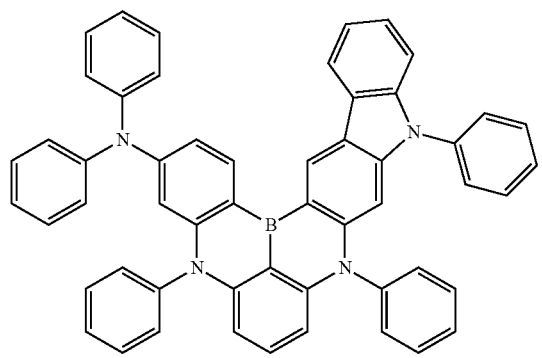
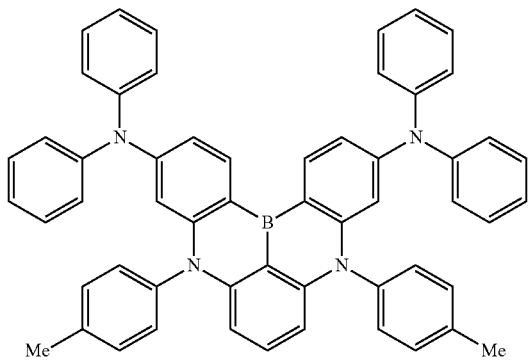
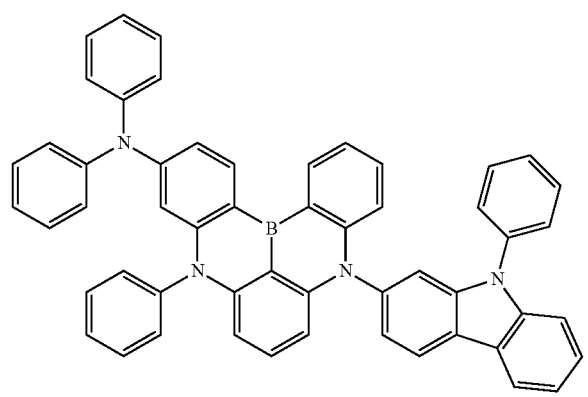
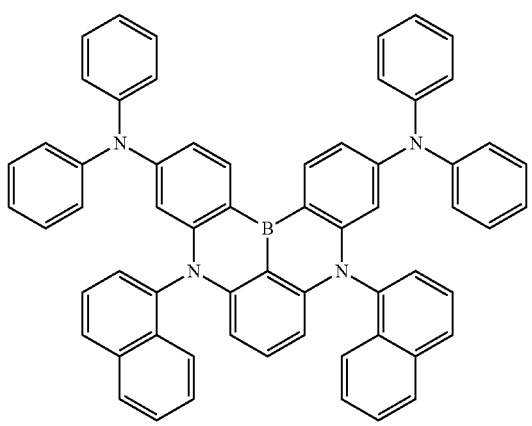
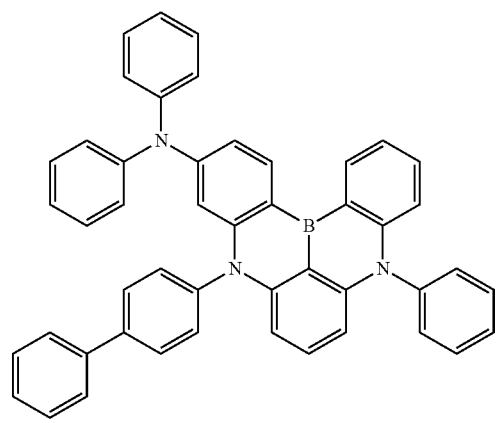
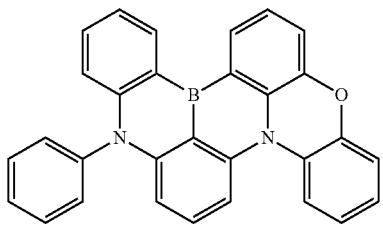
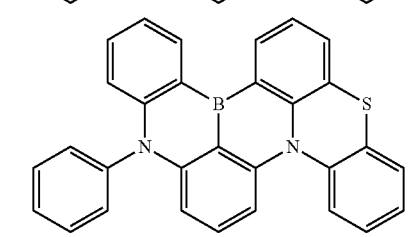
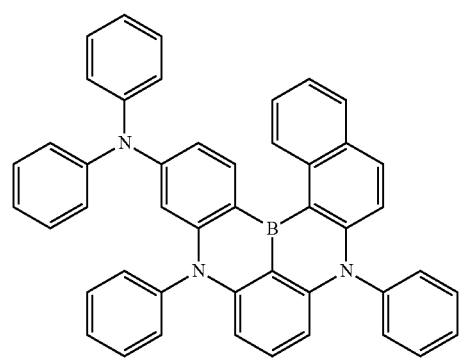
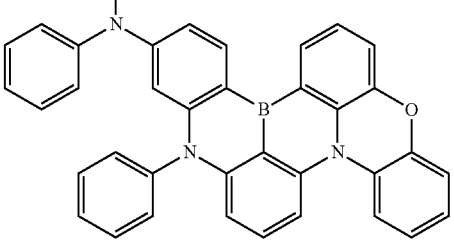

931
-continued
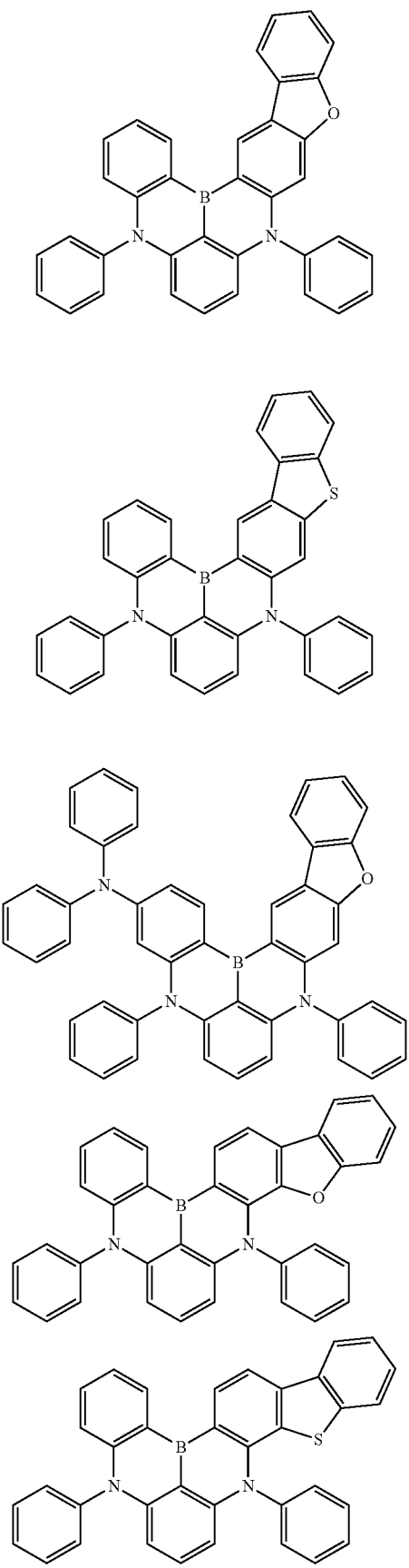
932
-continued
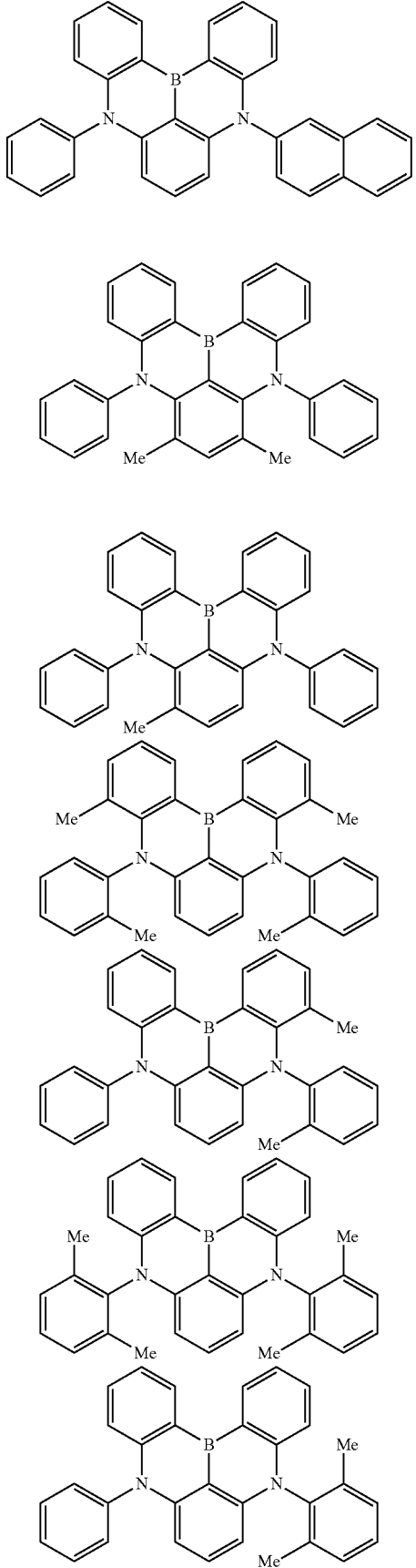

933
-continued
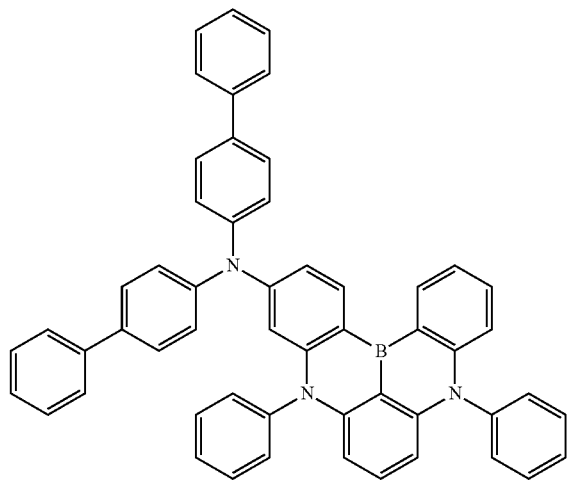
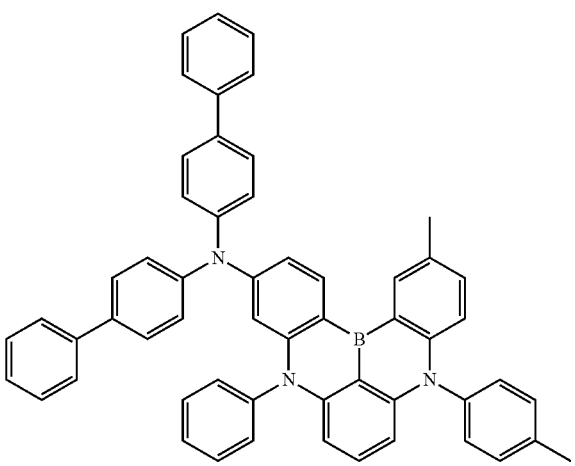
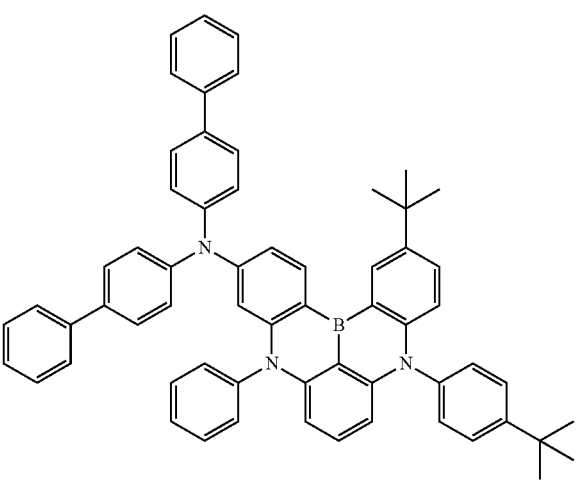
934
-continued
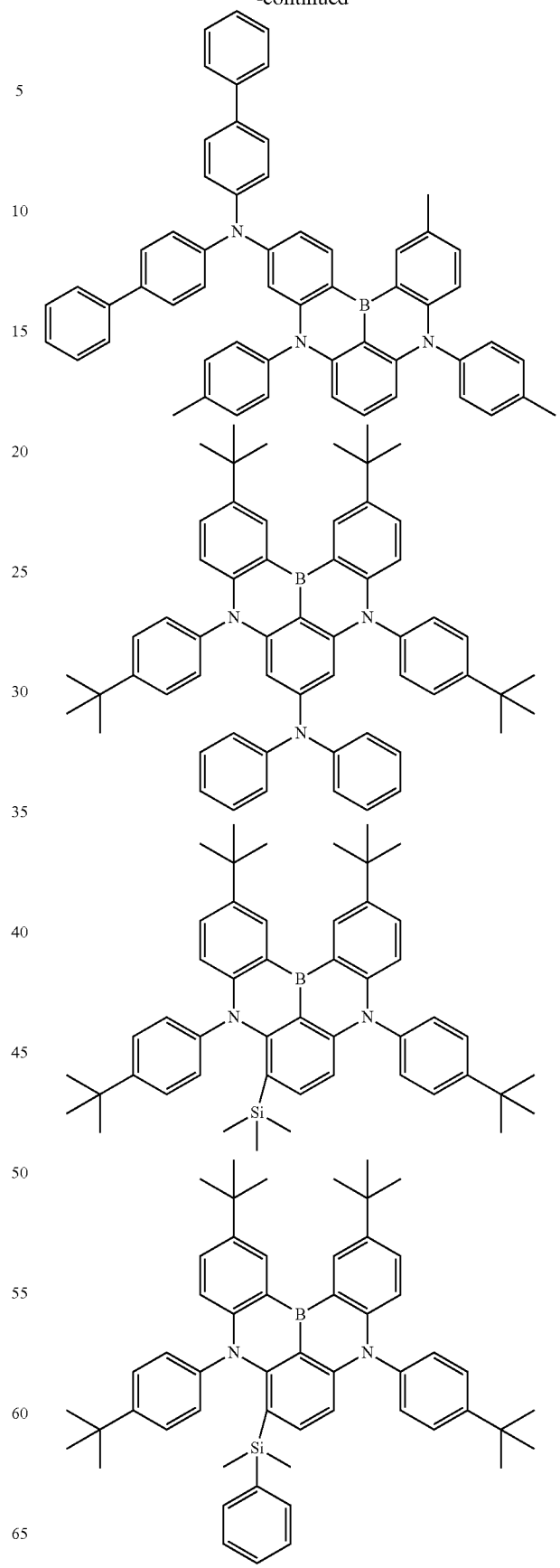

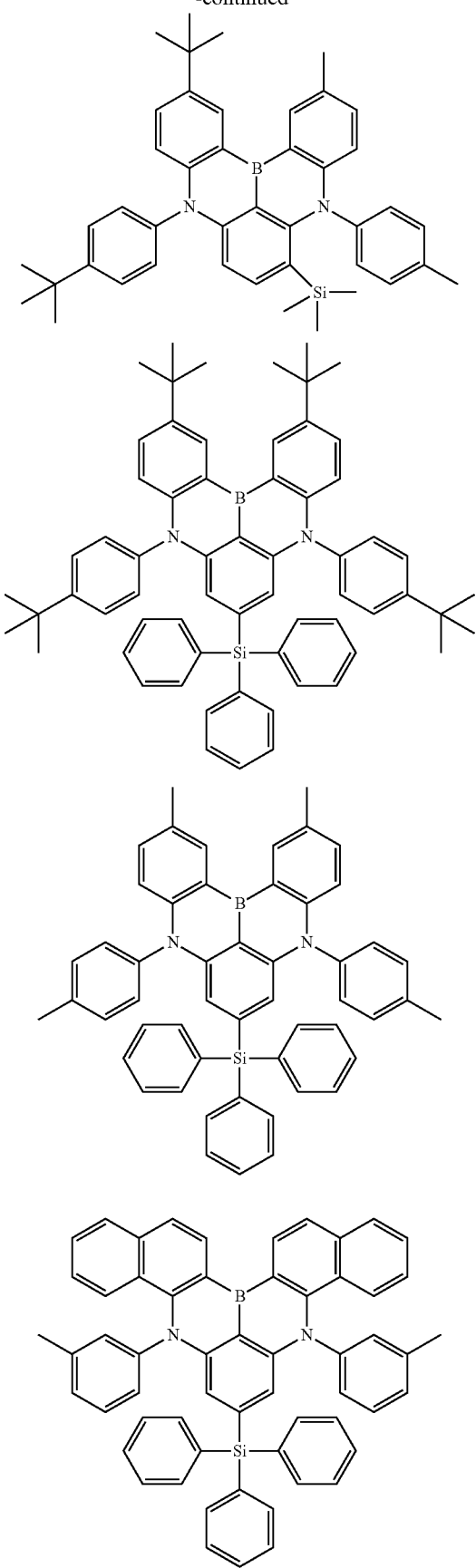

937
-continued
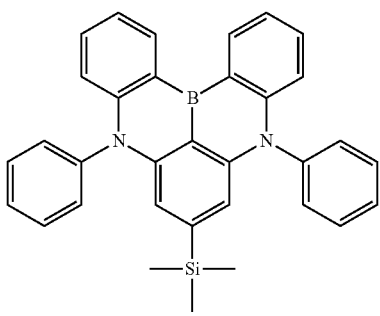
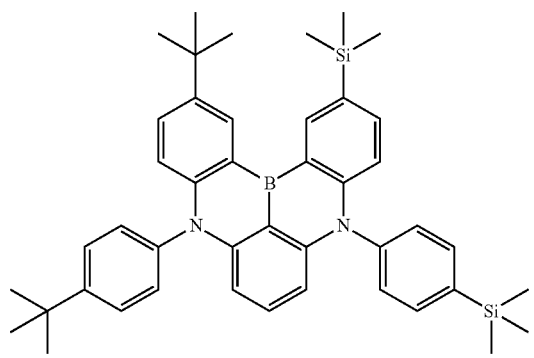
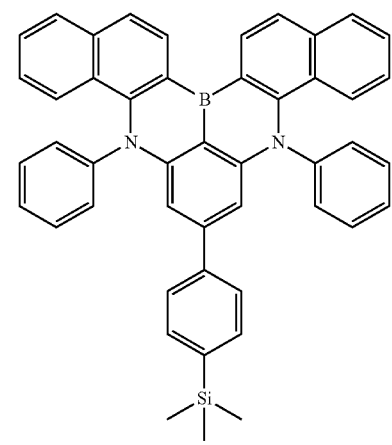
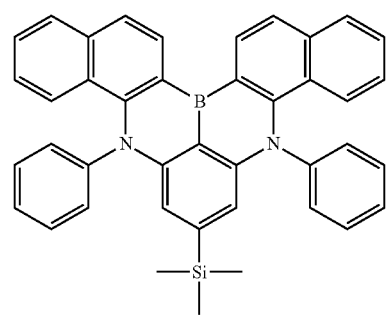
938
-continued
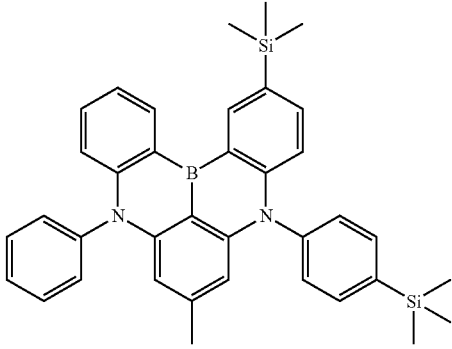
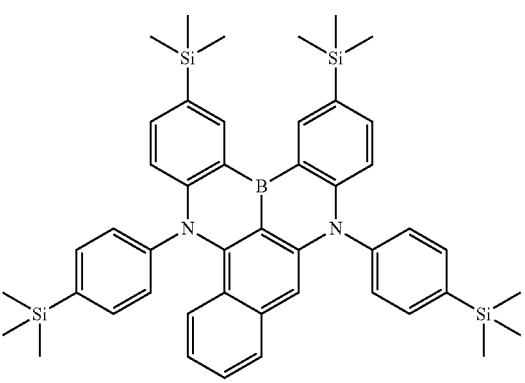
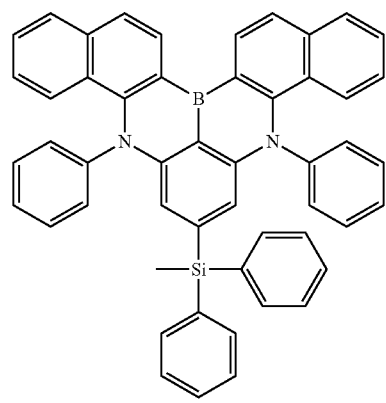
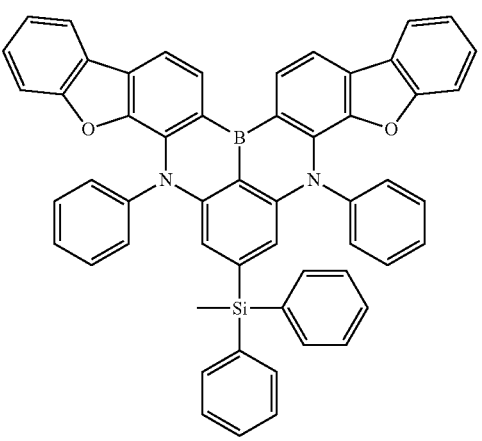

939
-continued
940
-continued
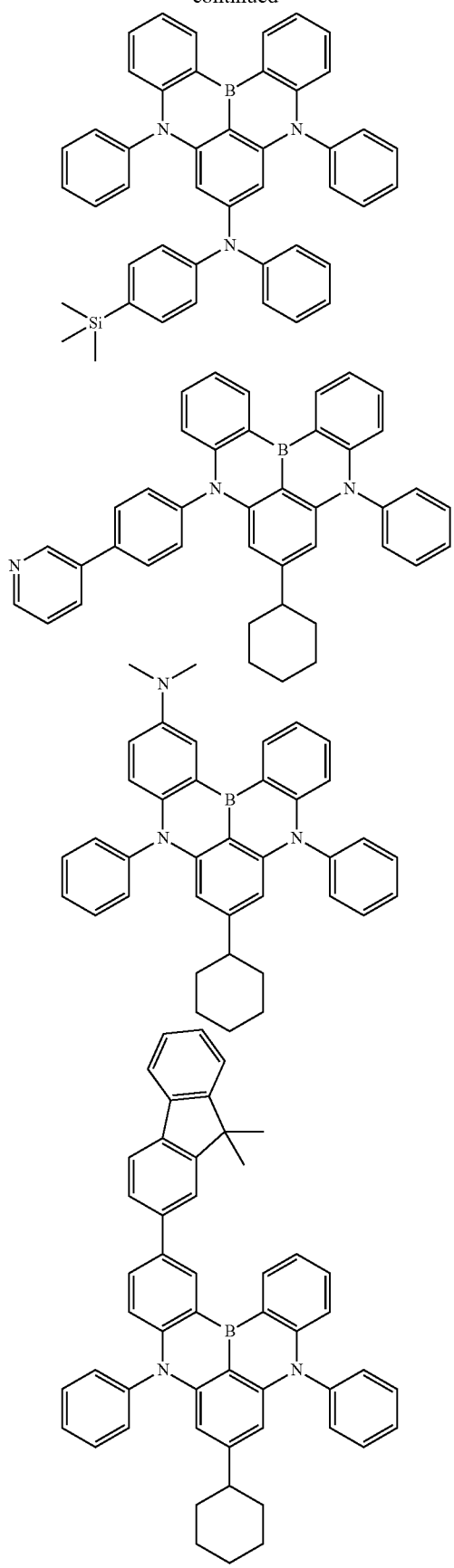
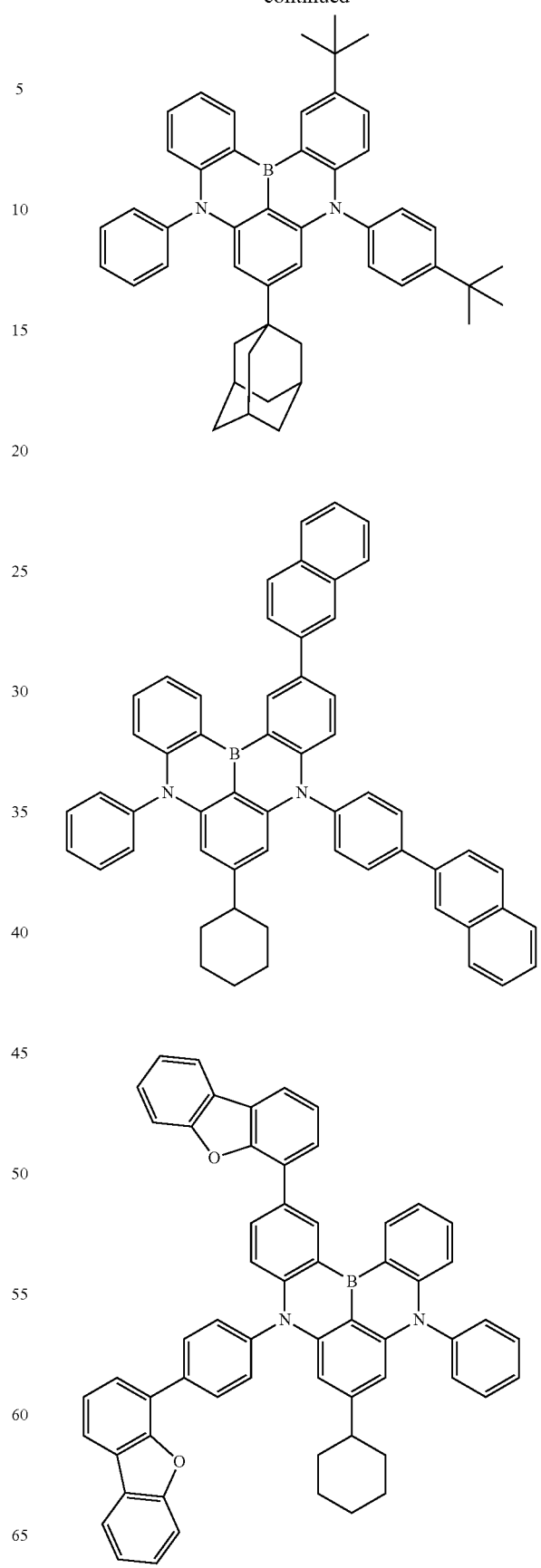

| 941 -continued | 942 -continued |
|---|---|
| 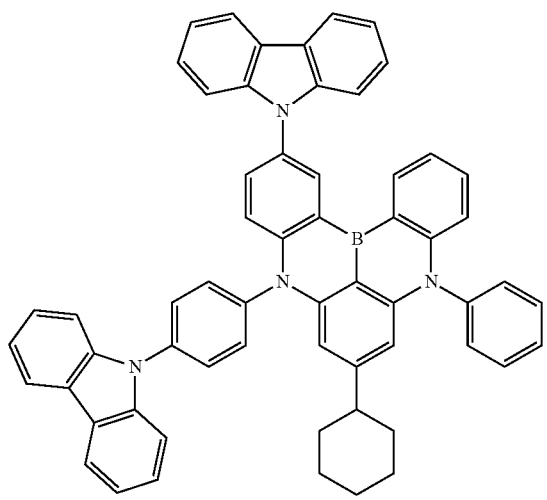 | 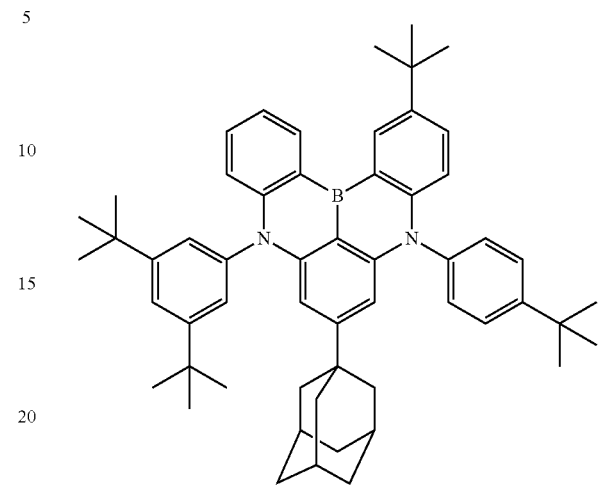 |
| 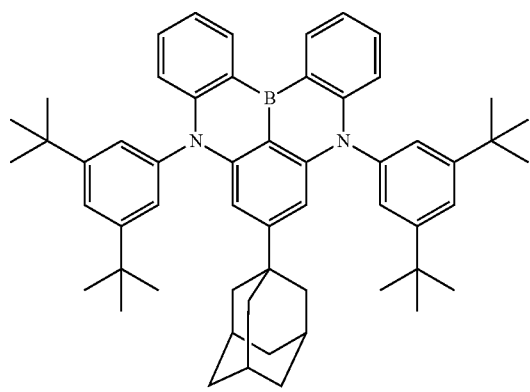 | 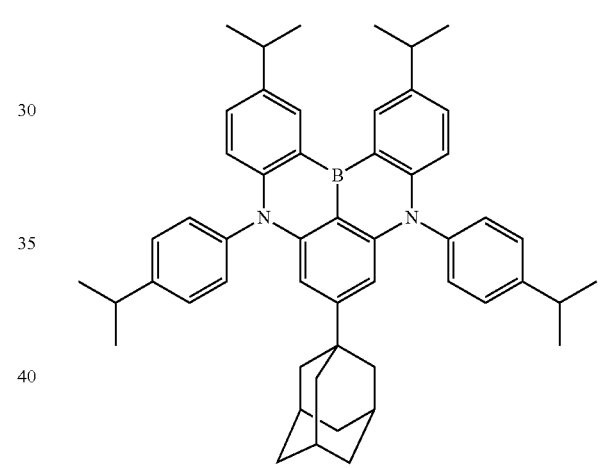 |
| 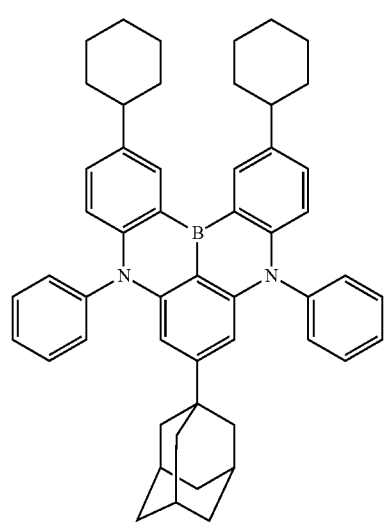 | 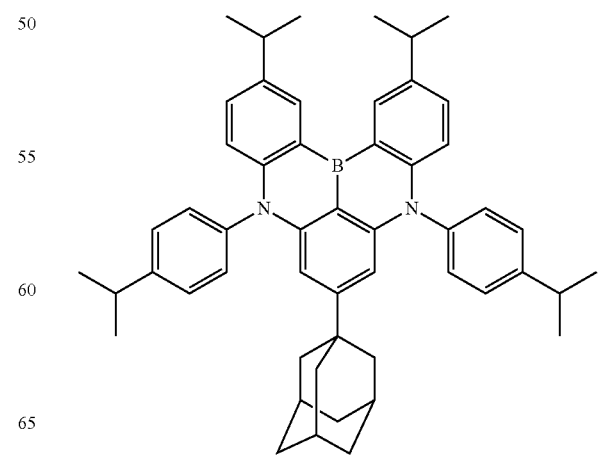 |

943
-continued
944
-continued
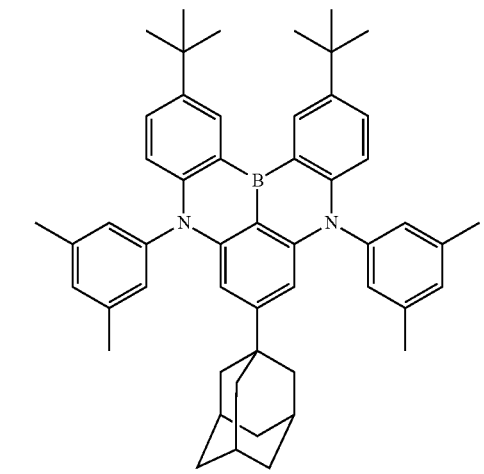
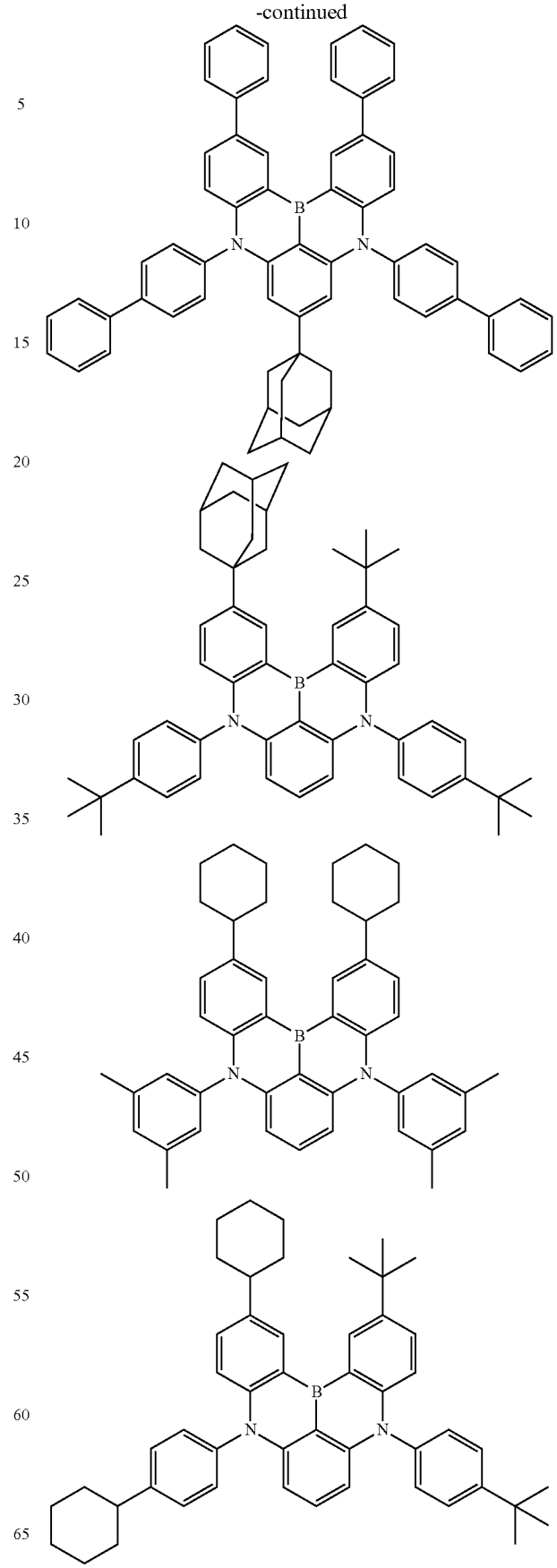

| 945 -continued | 946 -continued |
|---|---|
| 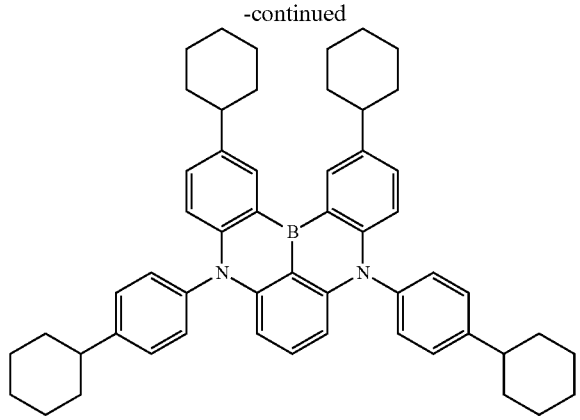 | 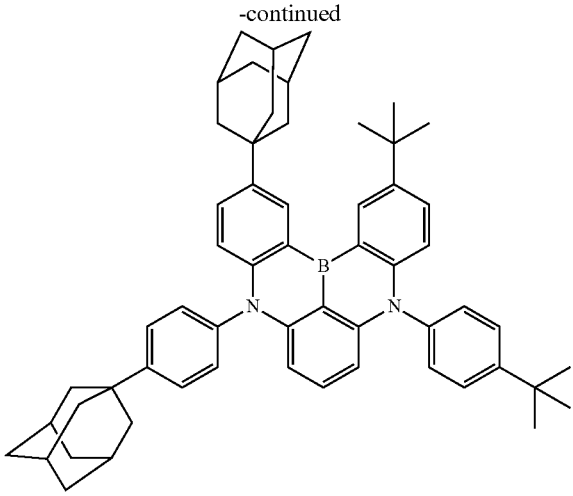 |
| 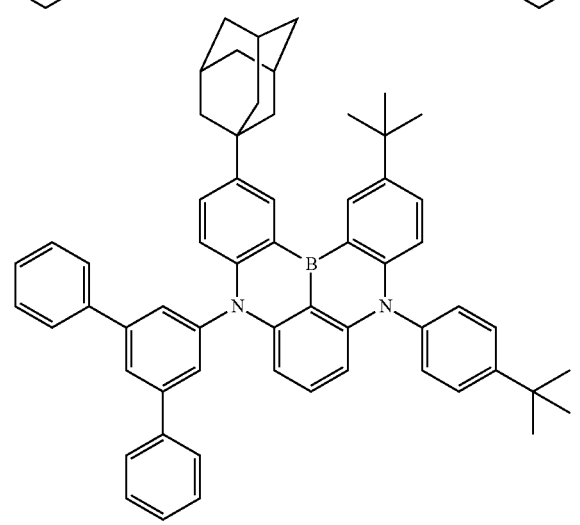 | 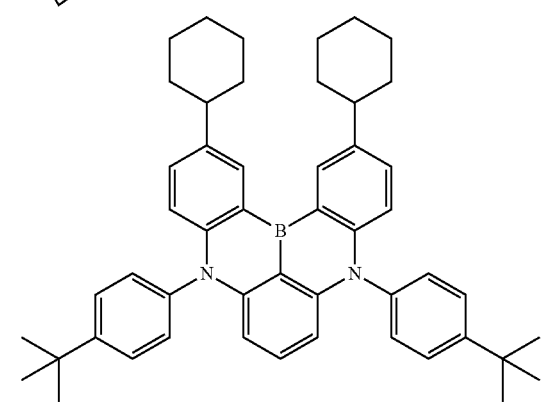 |
| 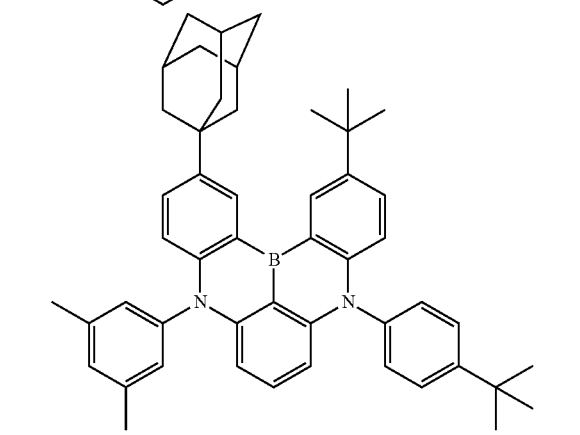 | 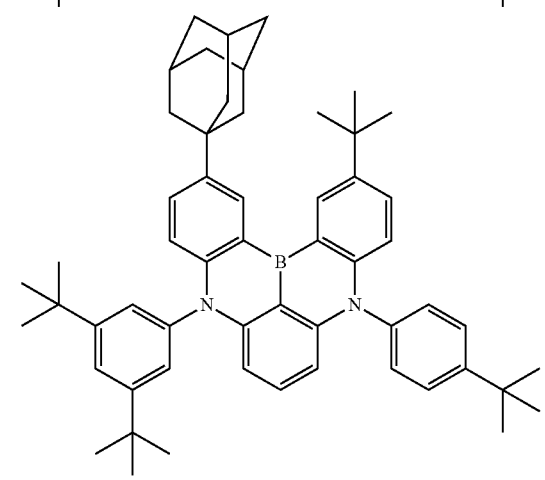 |
| 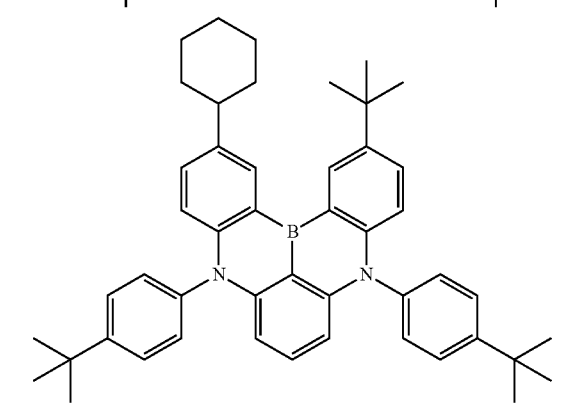 | 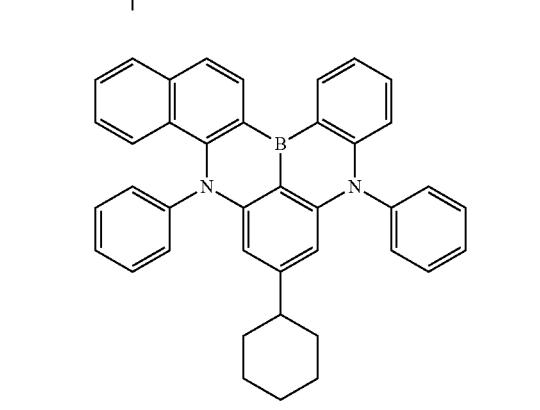 |

947
-continued
948
-continued
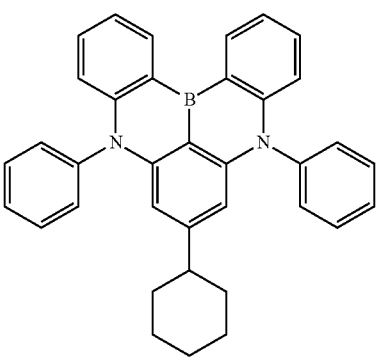
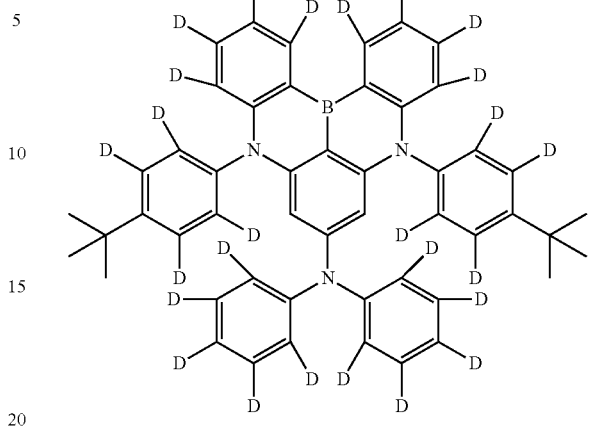
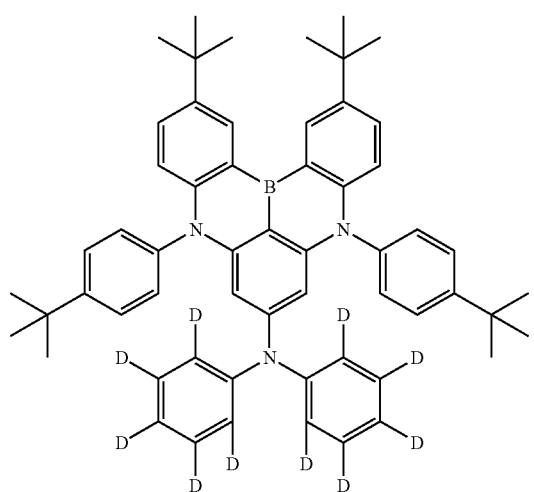
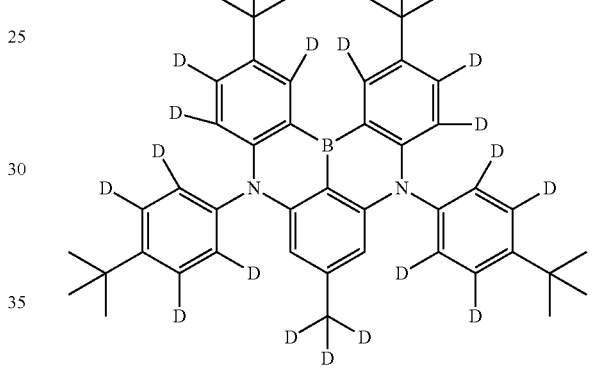
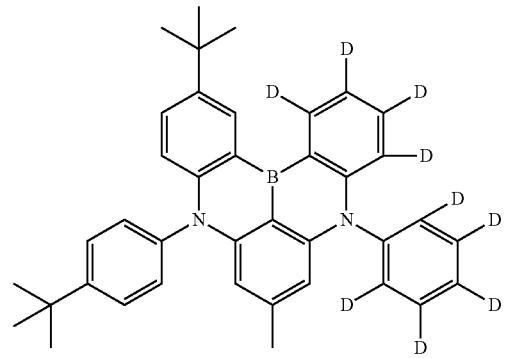
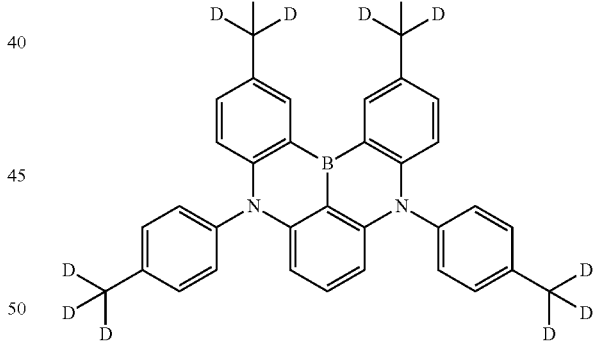
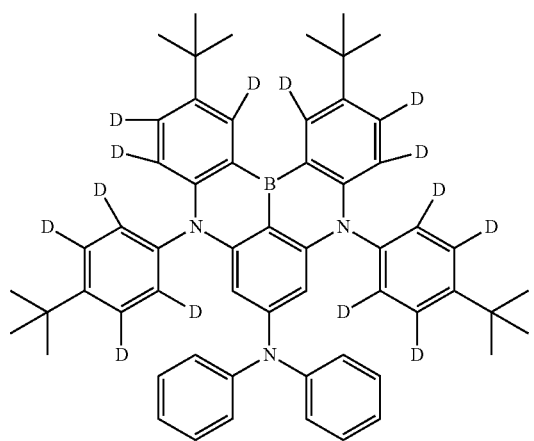

-continued

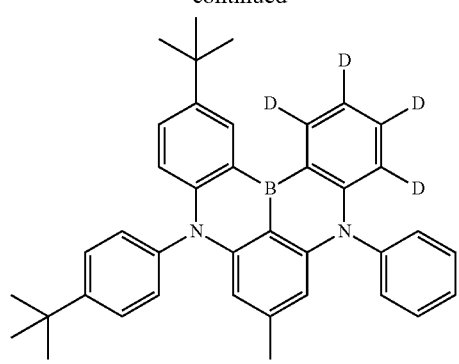

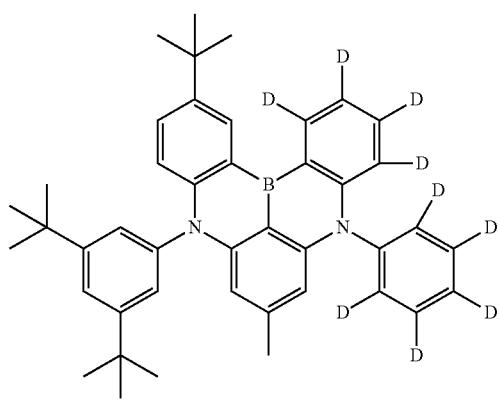

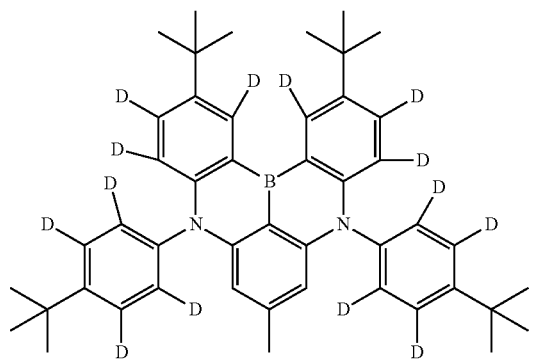 [SMILES: [2H]c1c([2H])c(C(C)(C)C)c([2H])c([2H])c1N1c2cc(C)cc3c2B(c2c([2H])c(C(C)(C)C)c([2H])c([2H])c21)c1c([2H])c(C(C)(C)C)c([2H])c([2H])c1N3c1c([2H])c([2H])c(C(C)(C)C)c([2H])c1[2H]]

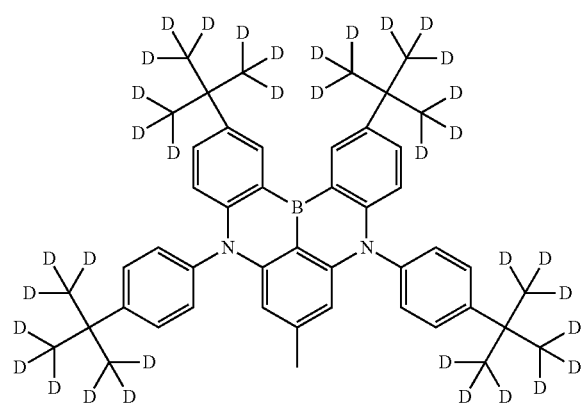

-continued

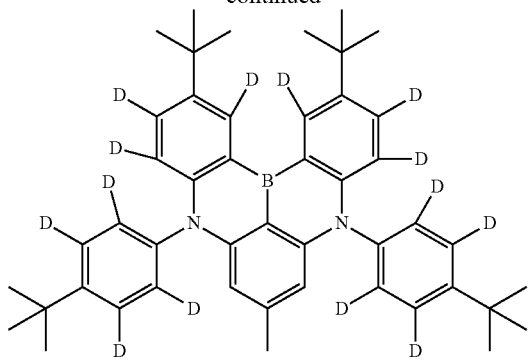

(Compound represented by formula (51))

The compound represented by the formula (51) is explained below.

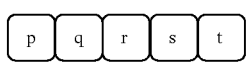

(51)

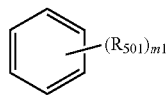

(52)

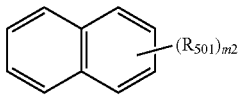

(53)

(54)

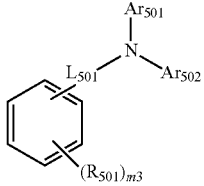

(55)

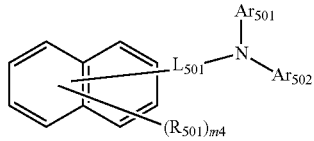

(56)

wherein, in the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when plural $R_{501}$s exist, adjacent plural $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
$Ar_{501}$ and $Ar_{502}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
$L_{501}$ is
a substituted or unsubstituted alkylene group having 1 to 50 carbon atoms,
a substituted or unsubstituted alkenylene group having 2 to 50 carbon atoms,
a substituted or unsubstituted alkynylene group having 2 to 50 carbon atoms,
a substituted or unsubstituted cycloalkylene group having 3 to 50 ring carbon atoms,
a substituted or unsubstituted arylene group having 6 to 50 ring carbon atoms, or
a substituted or unsubstituted divalent heterocyclic group having 5 to 50 ring atoms;
m1 is independently an integer of 0 to 2, m2 is independently an integer of 0 to 4, m3s are independently an integer of 0 to 3, and m4s are independently an integer of 0 to 5; when plural $R_{501}$s exist, the plural $R_{501}$s may be the same or different;

In the formula (51), each of the p ring to the t ring is fused to an adjacent ring by sharing two carbon atoms. The position and direction of fusing are not limited, and condensation is possible at any position and direction.

In one embodiment, in the formula (52) or (53) of the r ring, $R_{501}$ is a hydrogen atom.

In one embodiment, the compound represented by the formula (51) is represented by any one of the following formulas (51-1) to (51-6).

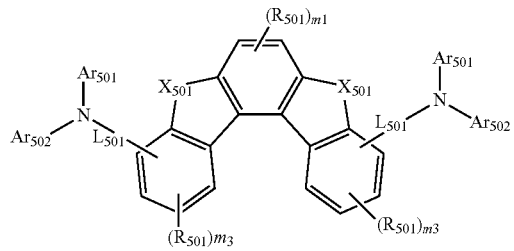
(51-1)

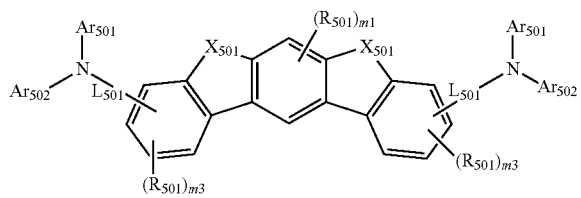
(51-2)

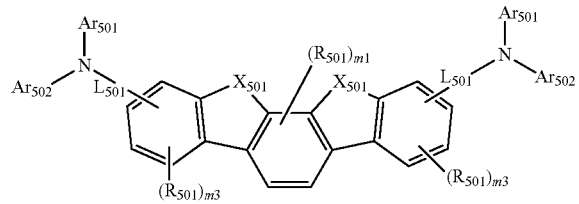
(51-3)

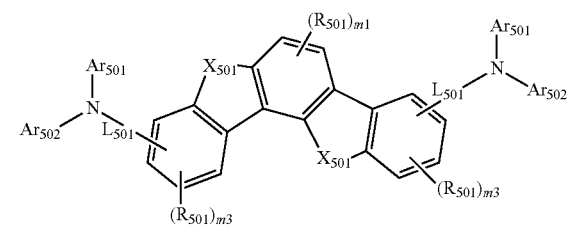
(51-4)

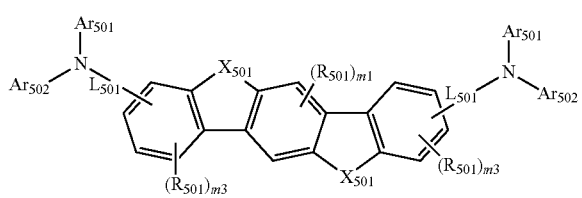
(51-5)

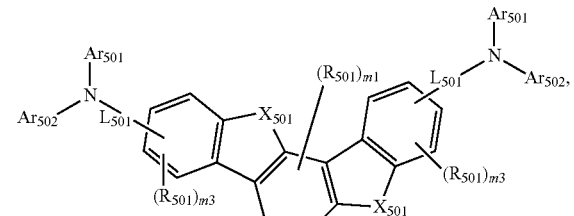
(51-6)

wherein in the formulas (51-1) to (51-6), $R_{501}$, $X_{501}$, $Ar_{501}$, $Ar_{502}$, $L_{501}$, m1 and m3 are as defined in the formula (51).

In one embodiment, the compound represented by the formula (51) is represented by any one of the following formulas (51-11) to (51-13).

(51-11)
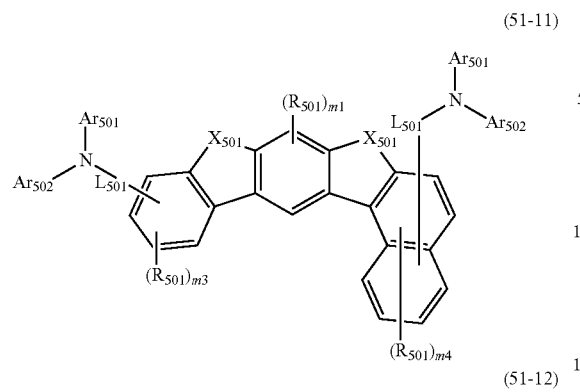
(51-13)
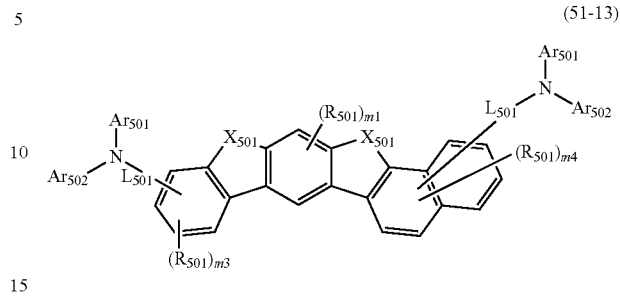
(51-12)
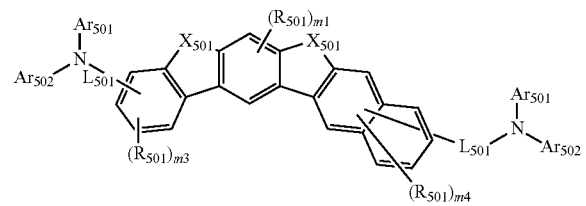
wherein in the formulas (51-11) to (51-13), $R_{501}$, $X_{501}$, $Ar_{501}$, $Ar_{502}$, $L_{501}$, m1, m3 and m4 are as defined in the formula (51).
In one embodiment, the compound represented by the formula (51) is represented by any one of the following formulas (51-21) to (51-25).
(51-21)
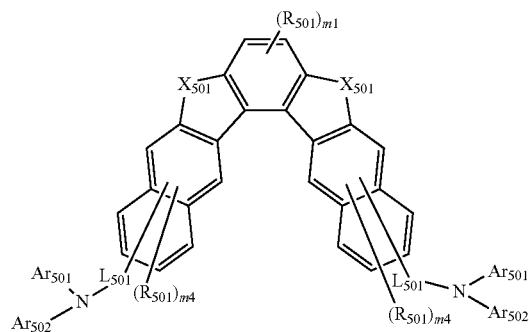
(51-22)
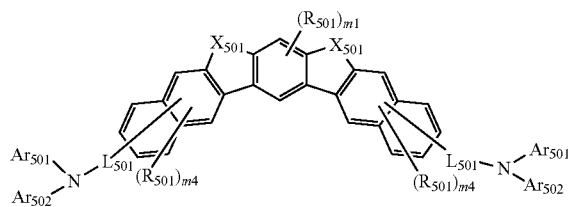
(51-23)
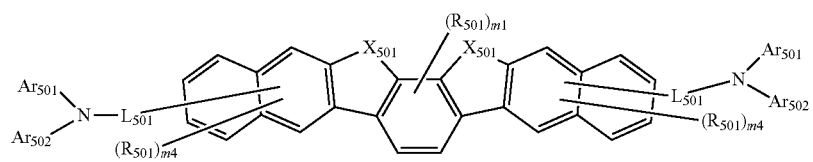
(51-24)
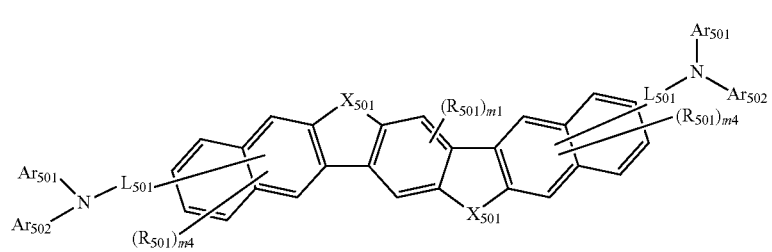

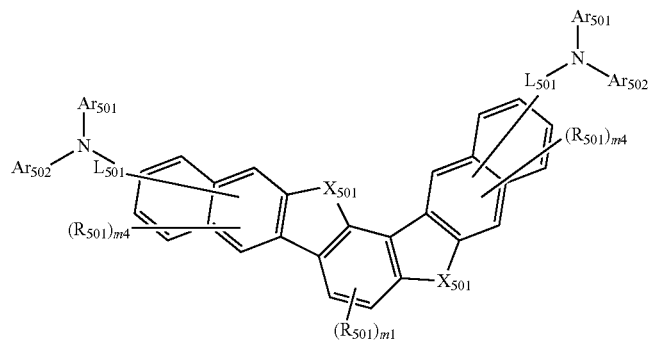
(51-25)
wherein in the formulas (51-21) to (51-25), $R_{501}$, $X_{501}$, $Ar_{501}$, $Ar_{502}$, $L_{501}$, m1 and m4 are as defined in the formula (51).
In one embodiment, the compound represented by the formula (51) is represented by any one of the following formulas (51-31) to (51-33).
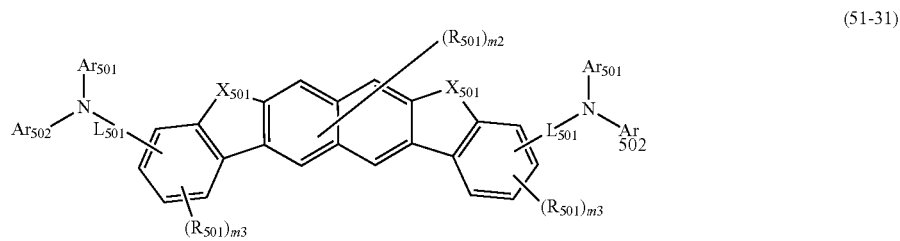
(51-31)
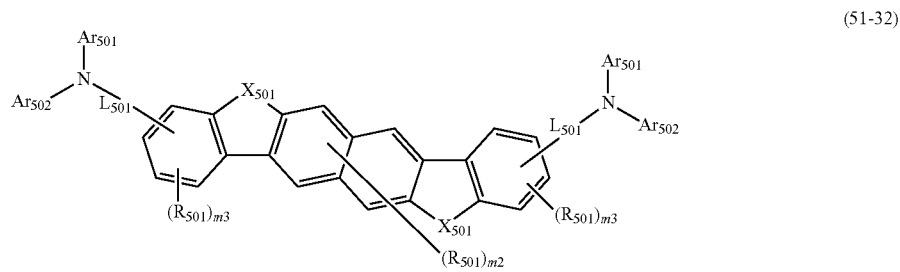
(51-32)
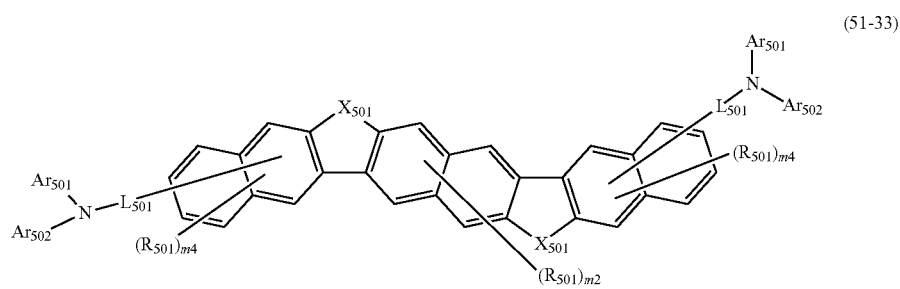
(51-33)
wherein in the formulas (51-31) to (51-33), $R_{501}$, $X_{501}$, $Ar_{501}$, $Ar_{502}$, $L_{501}$, m2 to m4 are as defined in the formula (51).

In one embodiment, $Ar_{501}$ and $Ar_{502}$ are independently a substituted or unsubstituted aryl group having 6 to 50 ring carbon atoms.

In one embodiment, one of $Ar_{501}$ and $Ar_{502}$ is a substituted or unsubstituted aryl group having 6 to 50 ring carbon atoms and the other is a substituted or unsubstituted monovalent heterocyclic ring having 5 to 50 ring atoms.

As examples of the compound represented by the formula (51), the following compounds can be given, for example. In the following example compounds, Me represents methyl group.

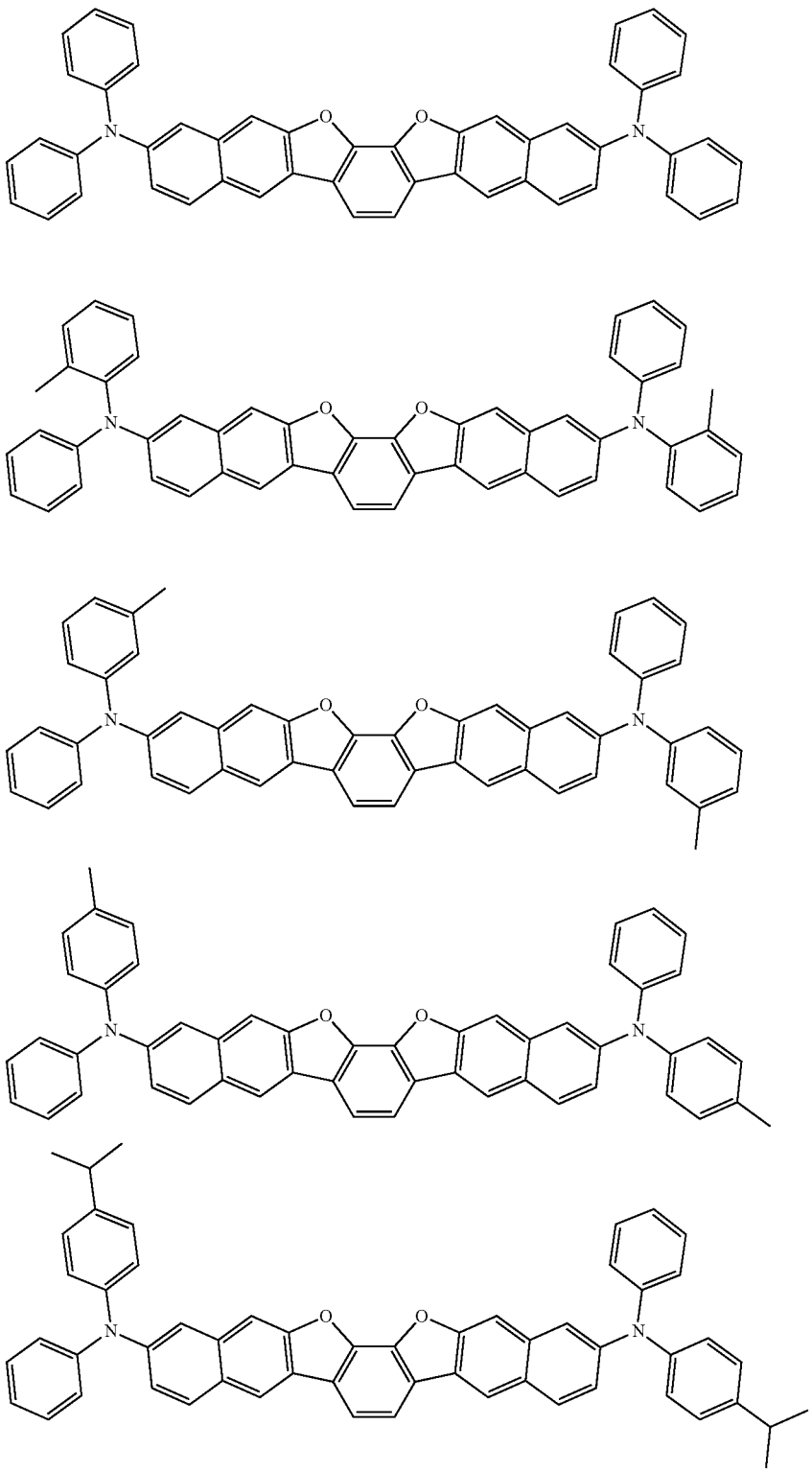

-continued
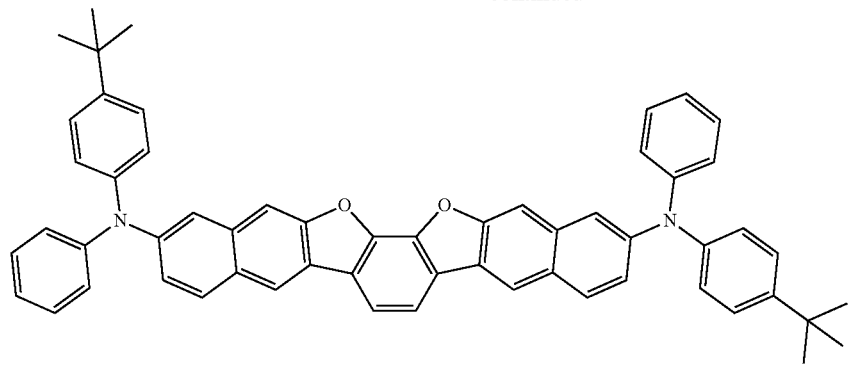
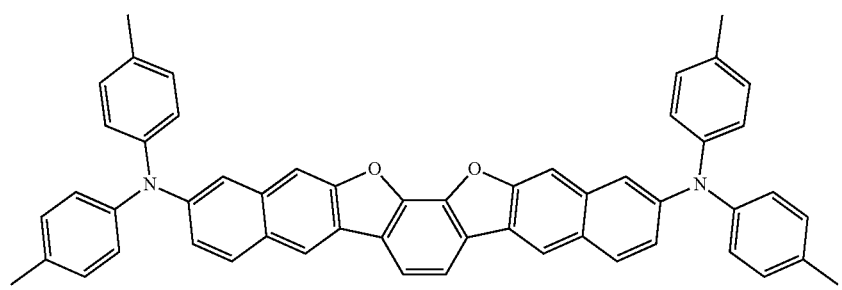
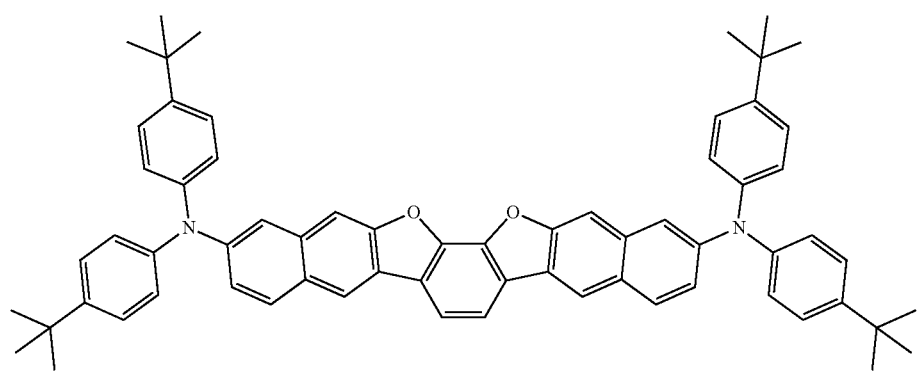
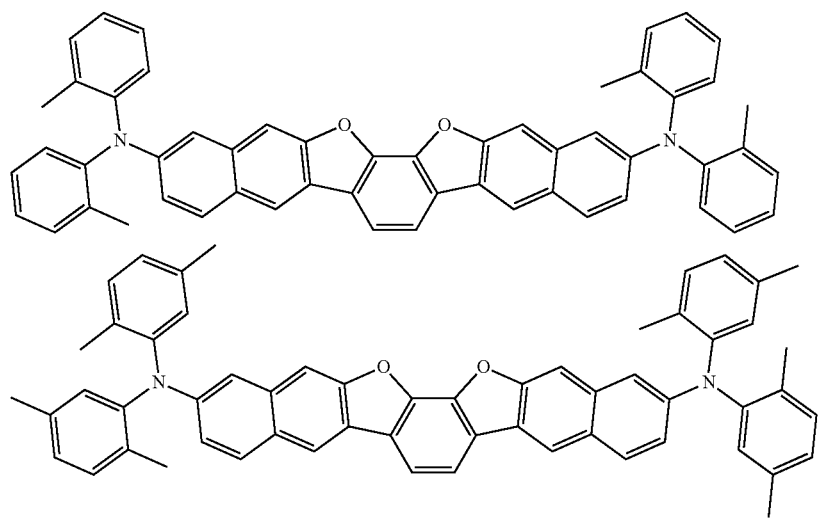

-continued
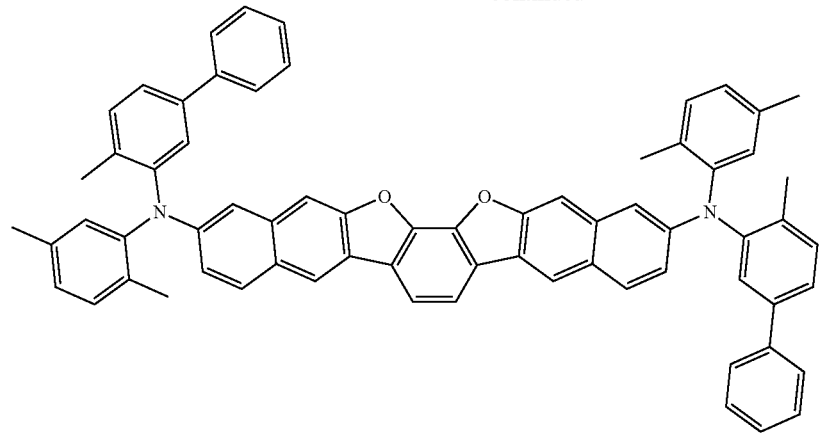
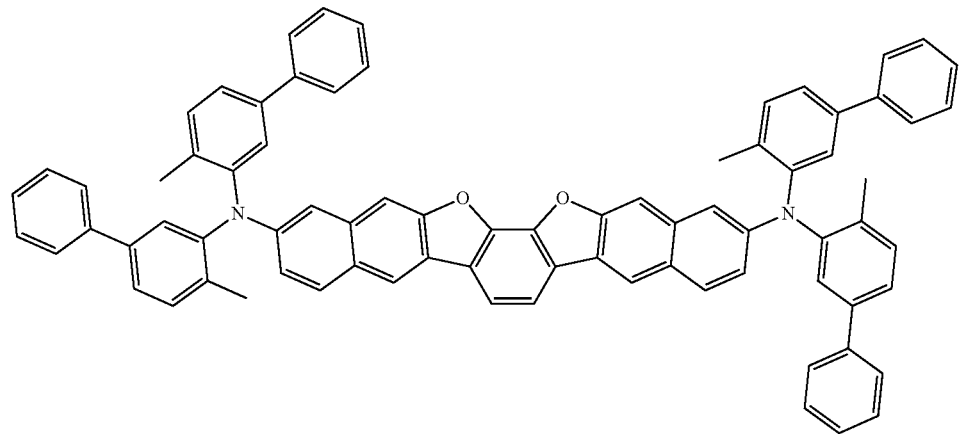
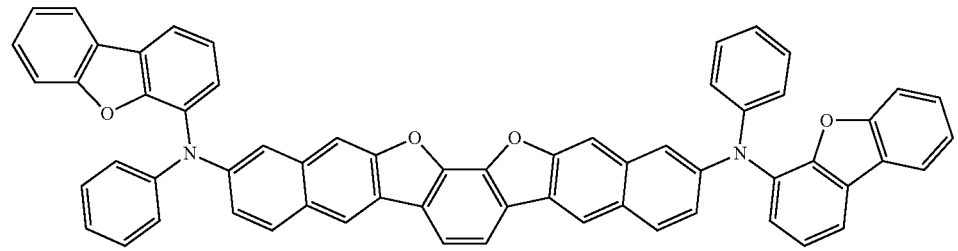
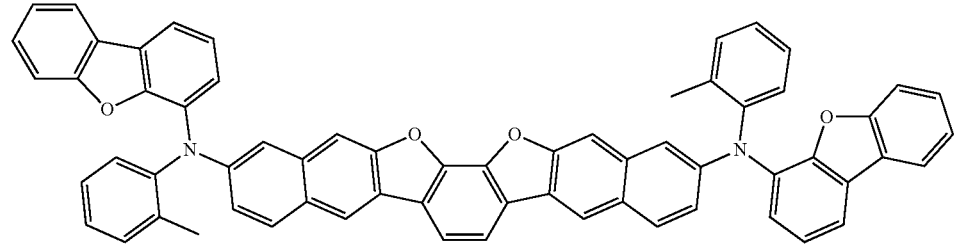
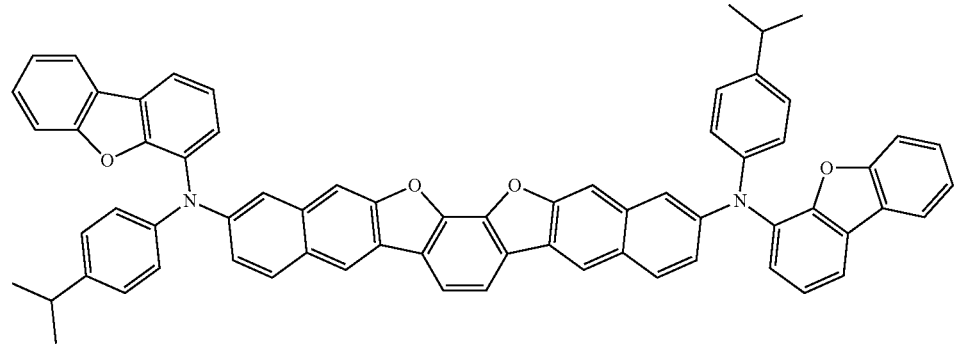

963 964
-continued
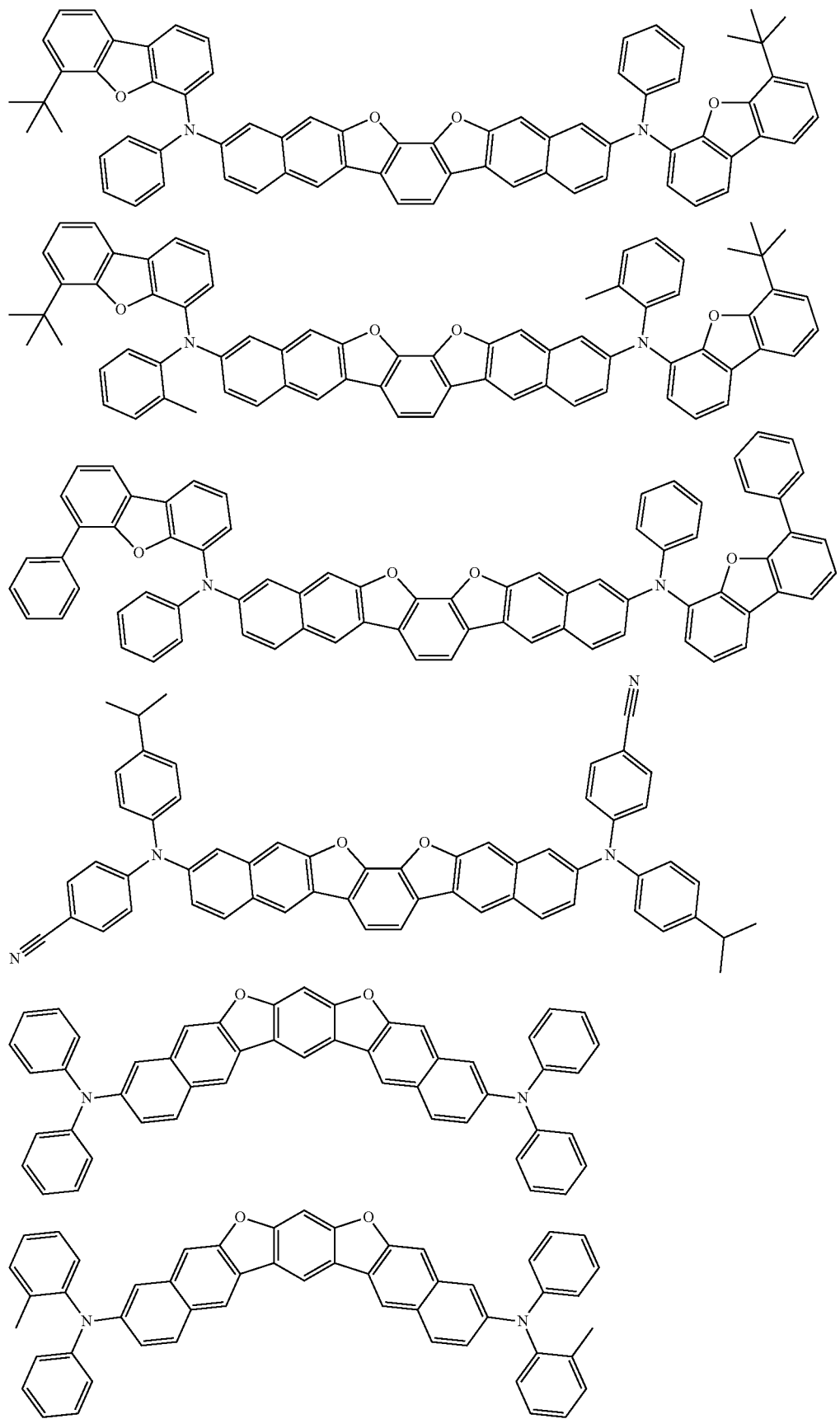

-continued
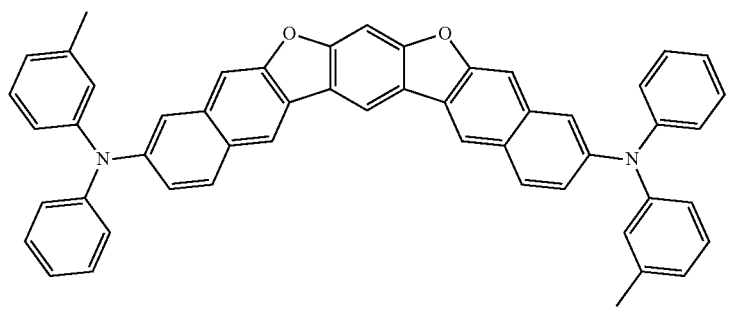
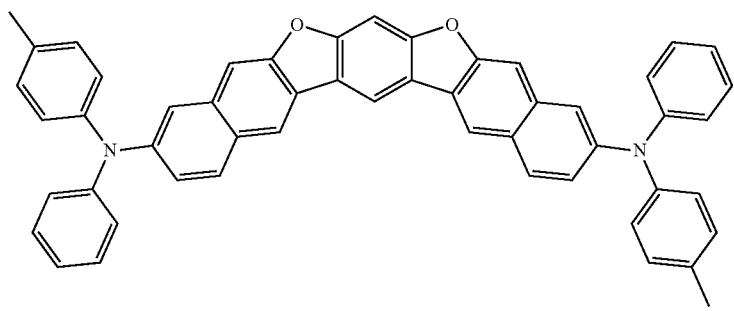
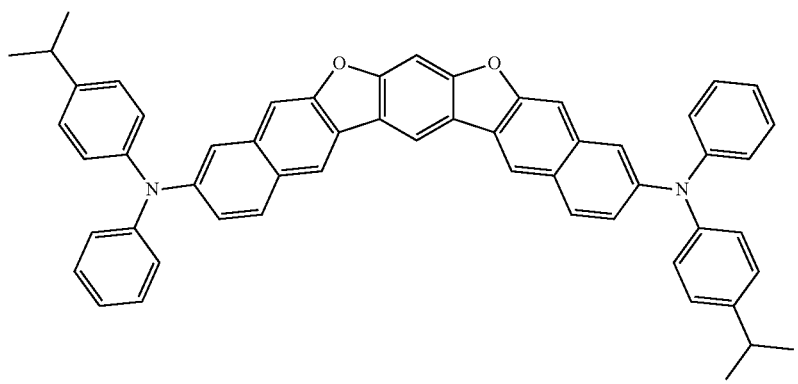
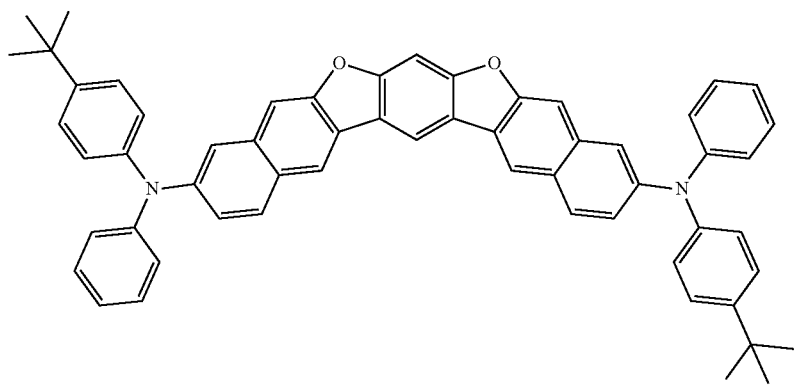
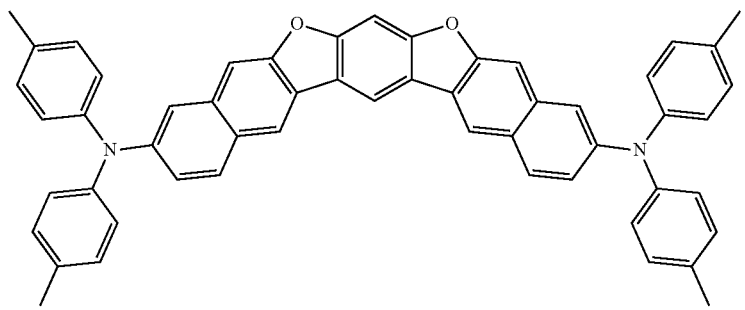

-continued
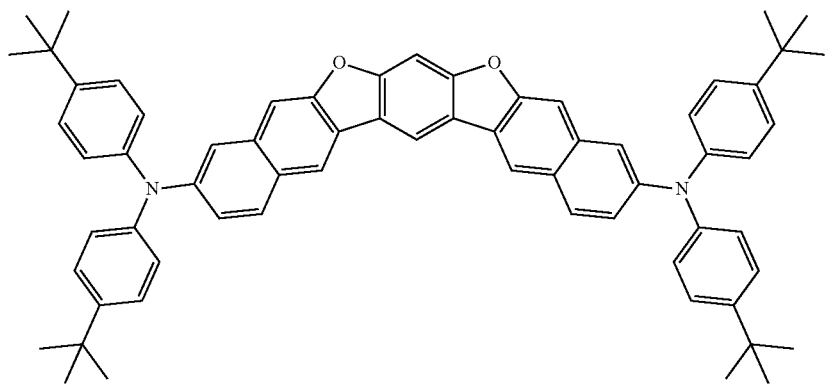
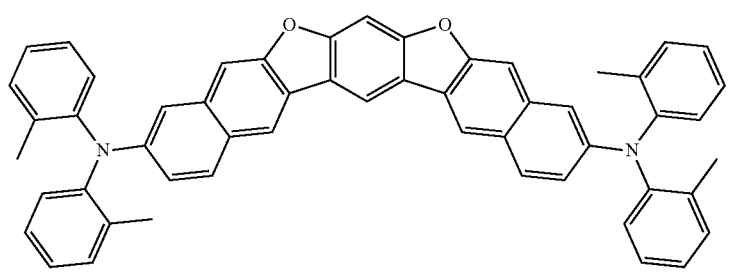
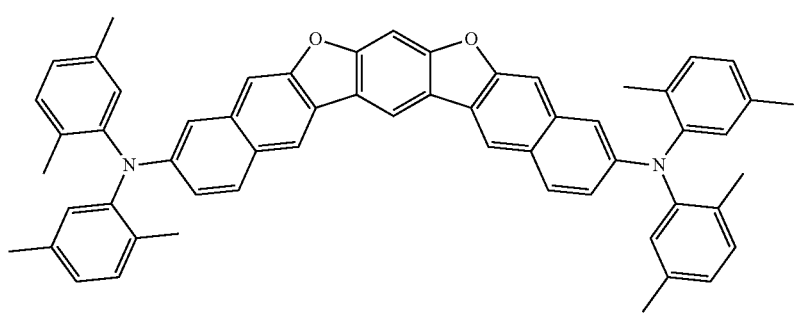
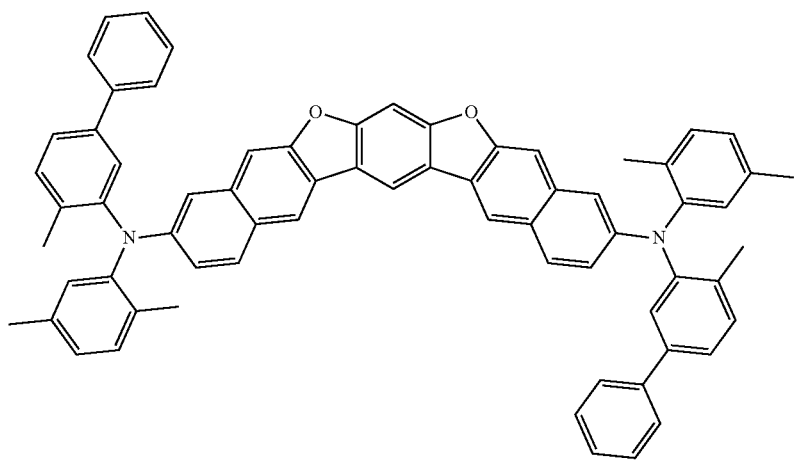

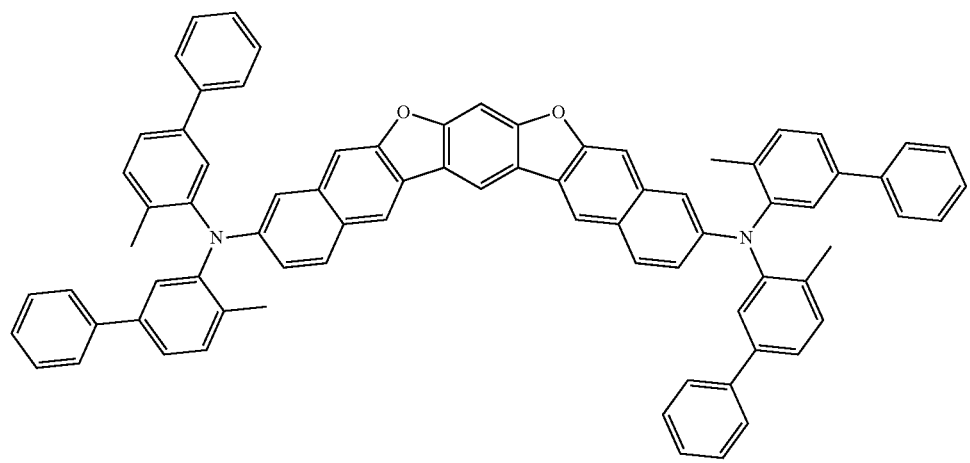
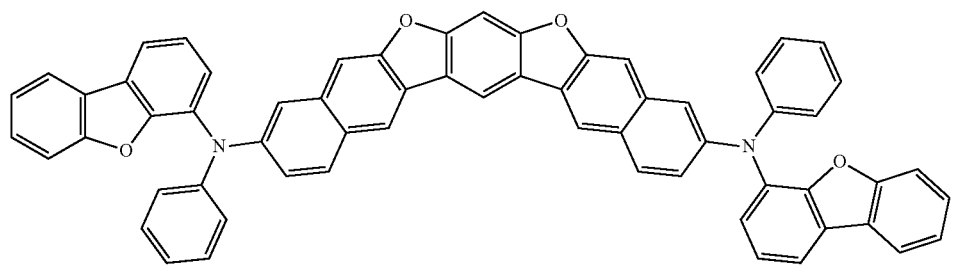
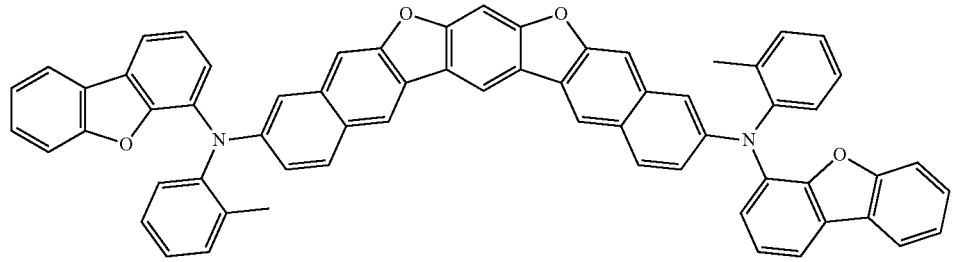
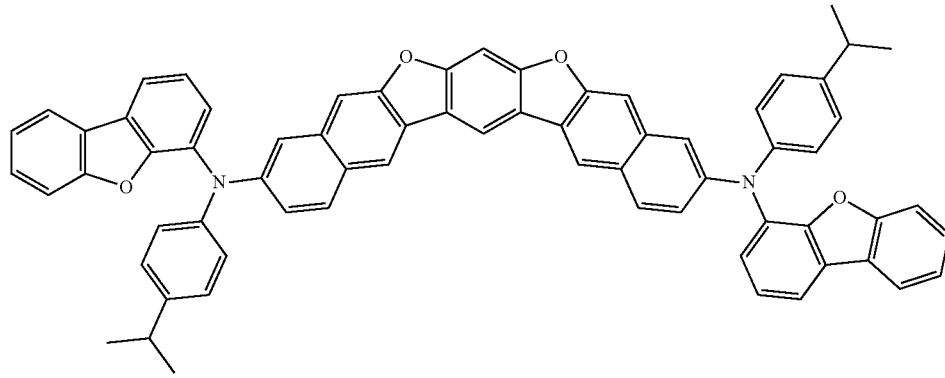
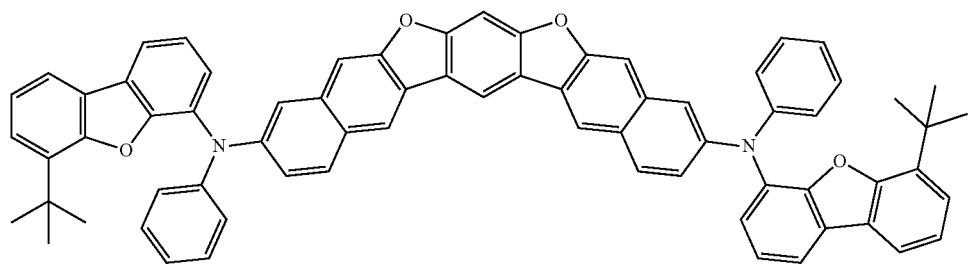

971
-continued
972
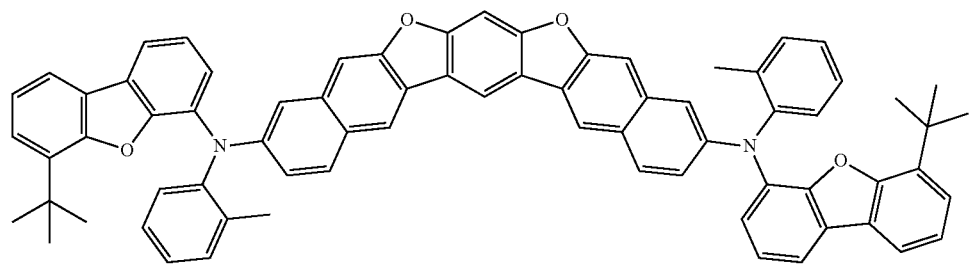
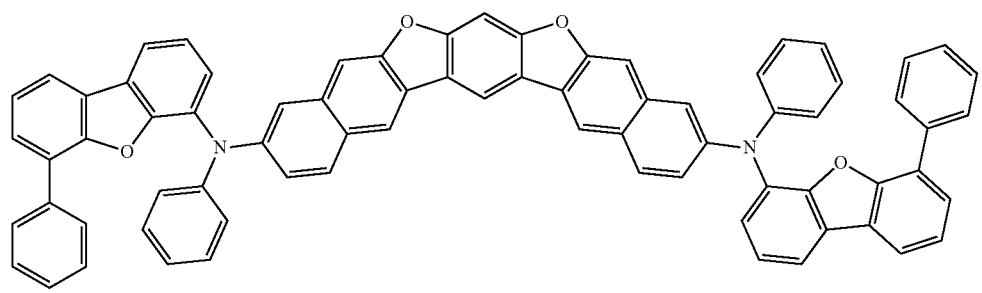
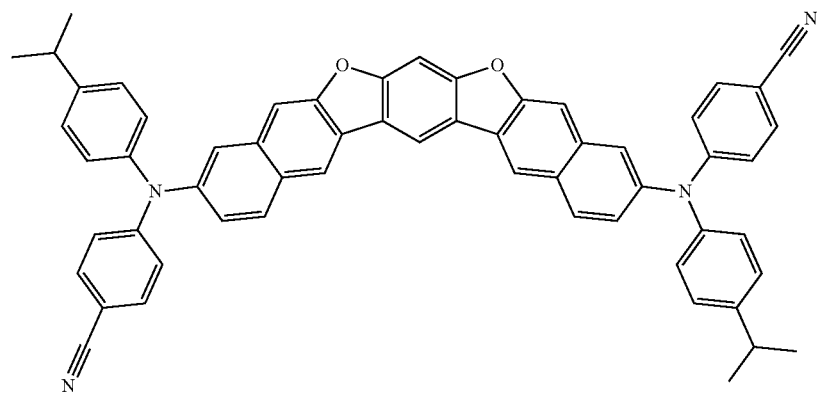
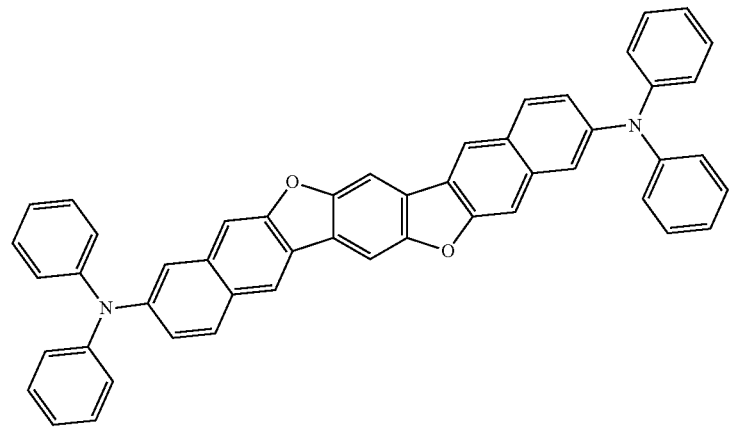

-continued
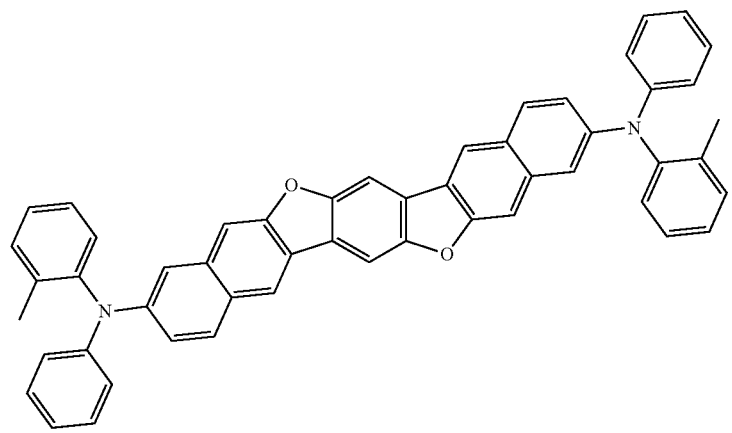
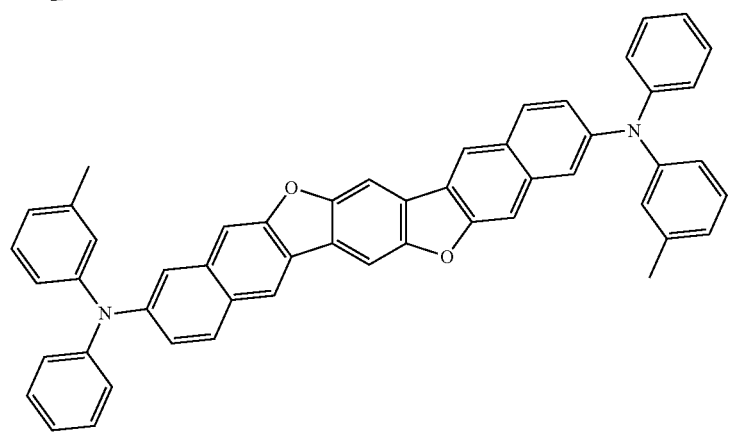
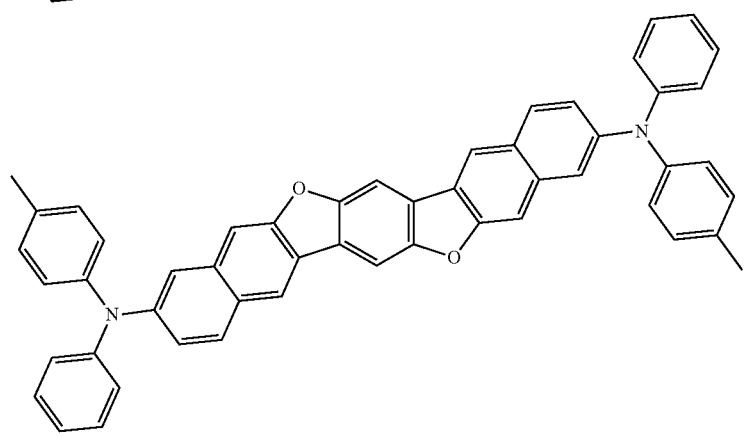
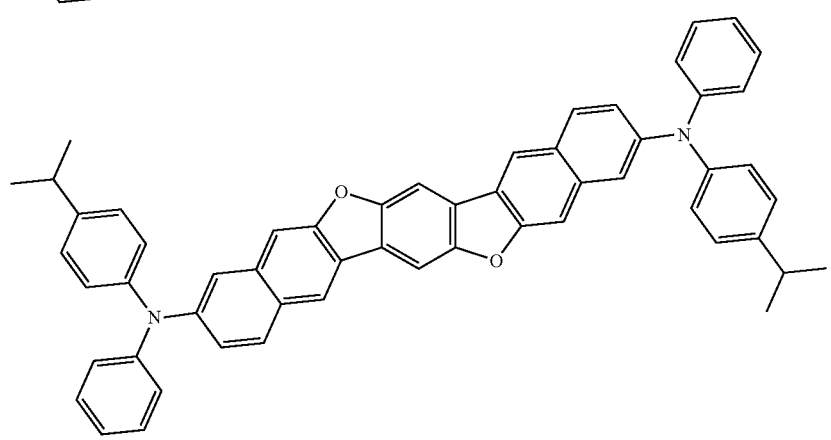

-continued
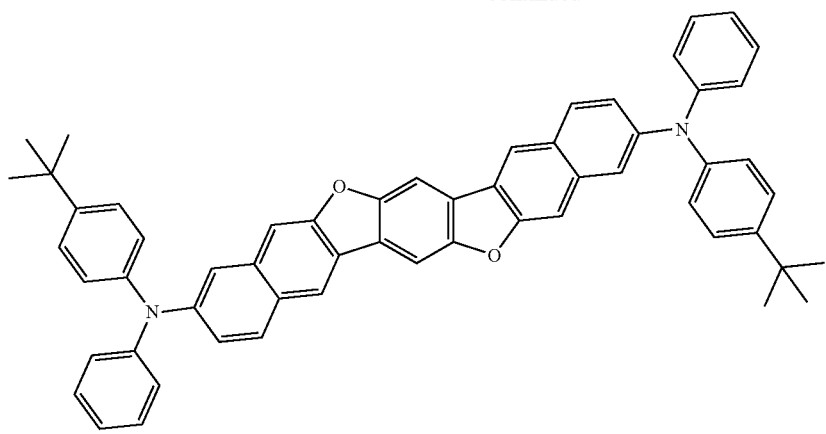
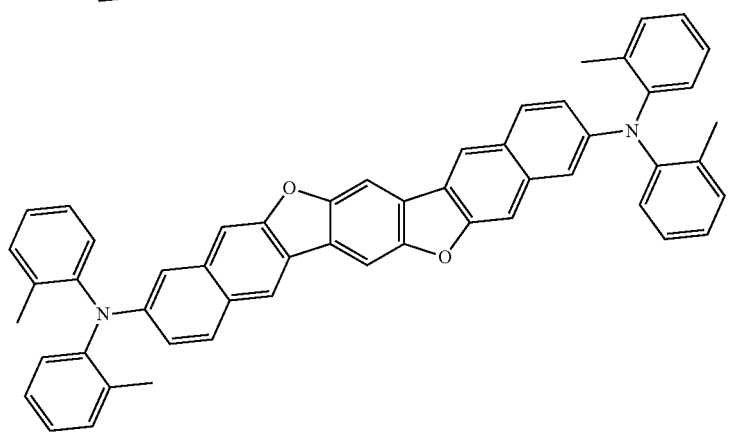
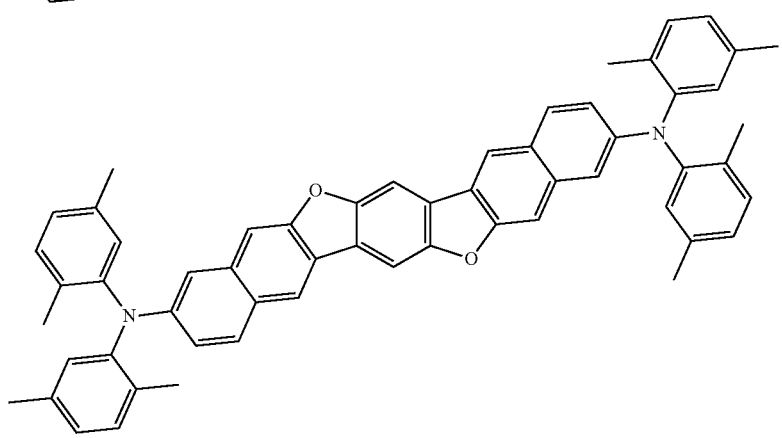
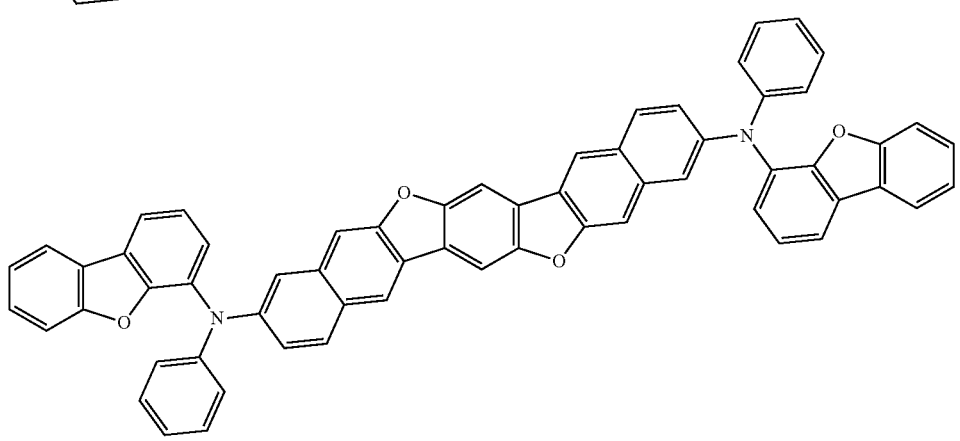

-continued
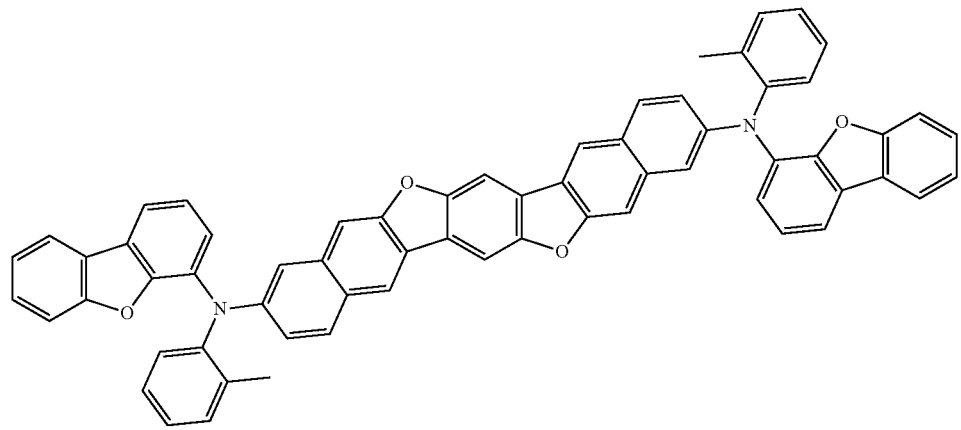
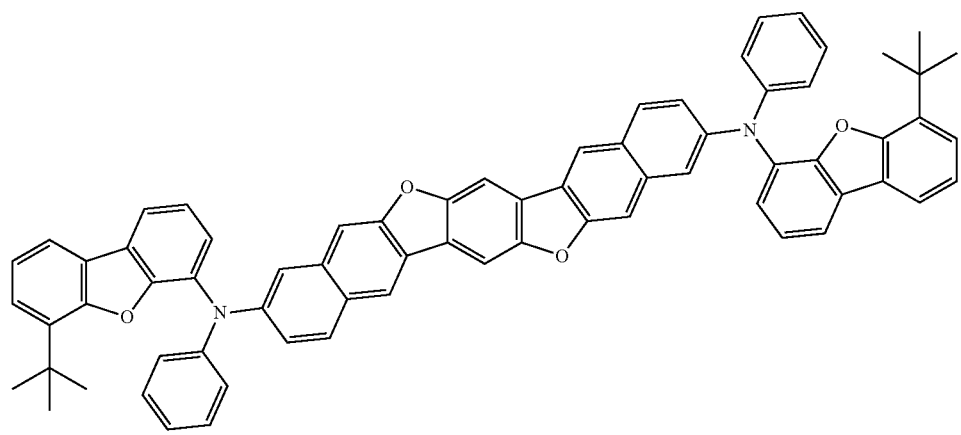
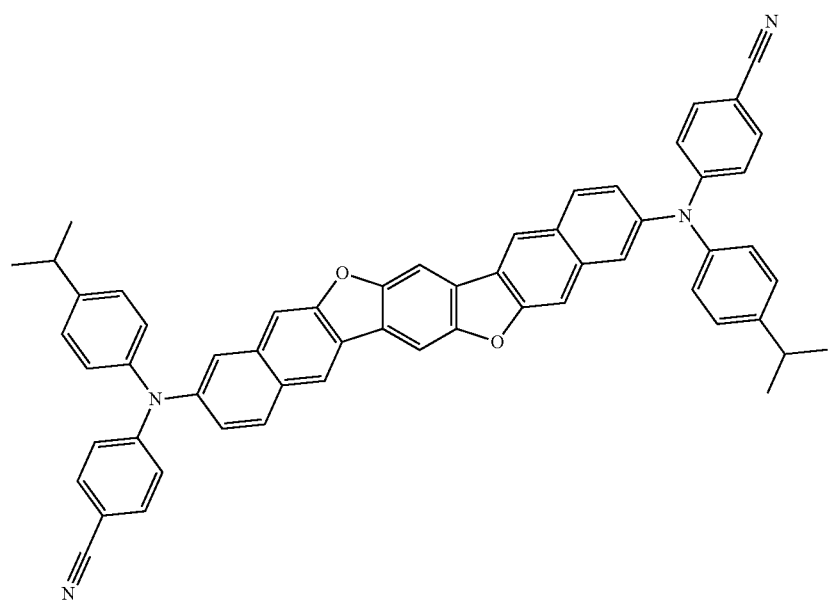

-continued
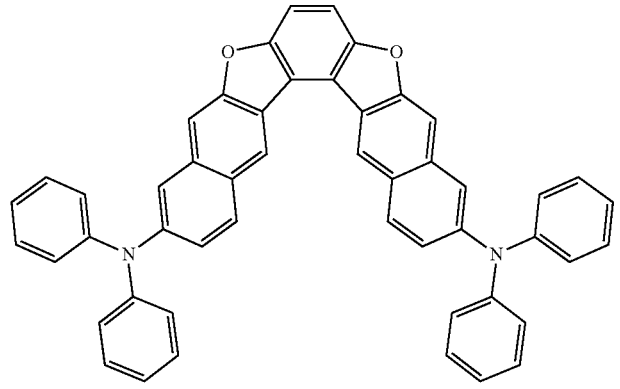
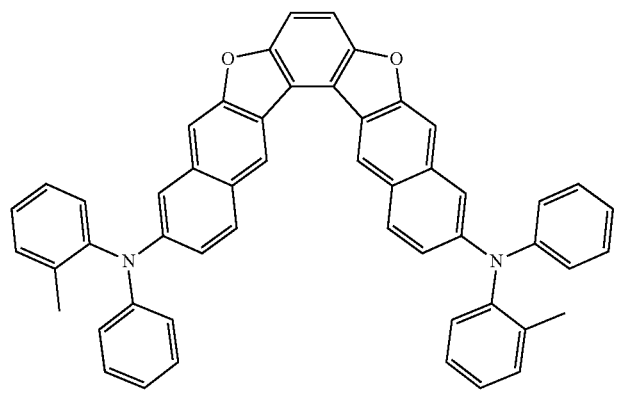
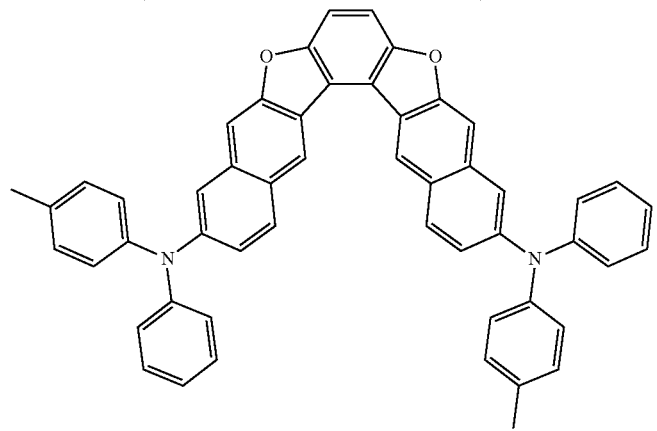
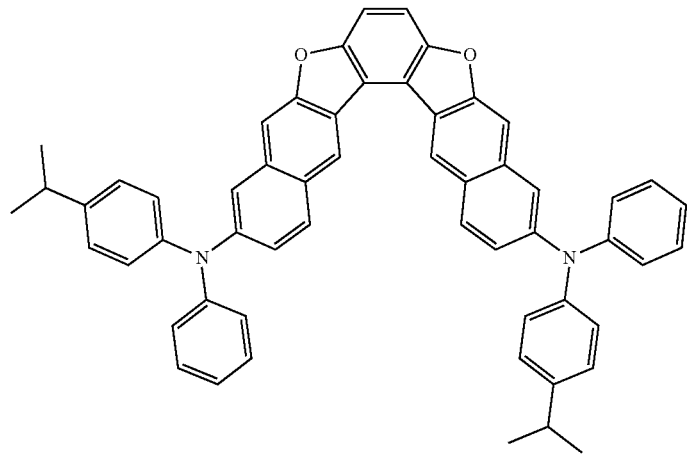

-continued
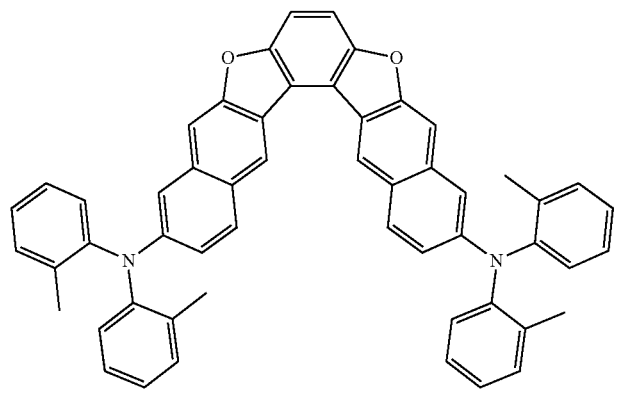
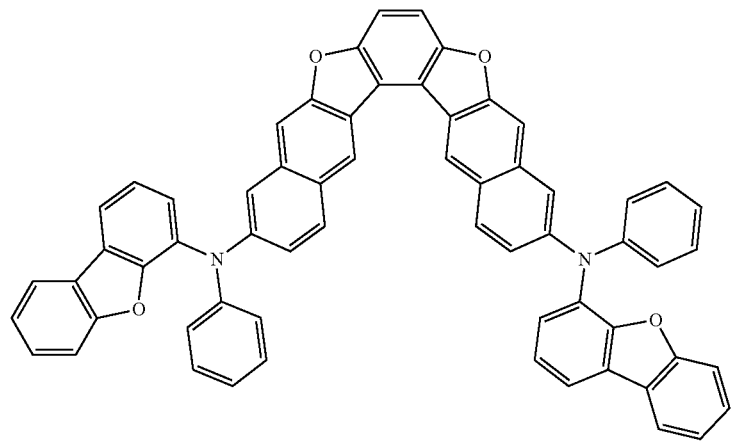
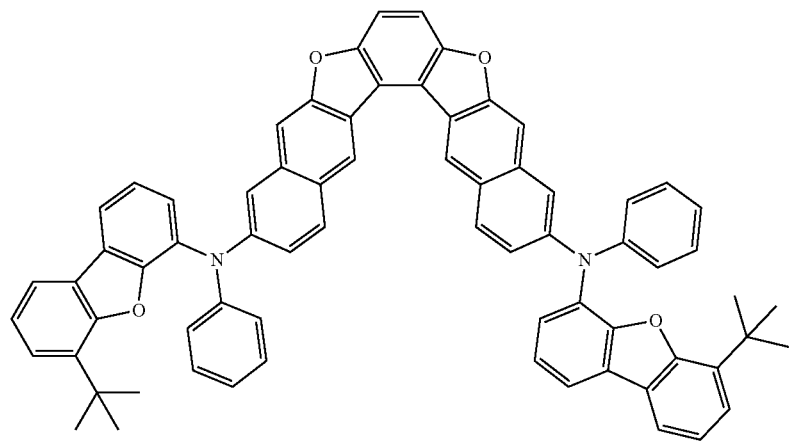
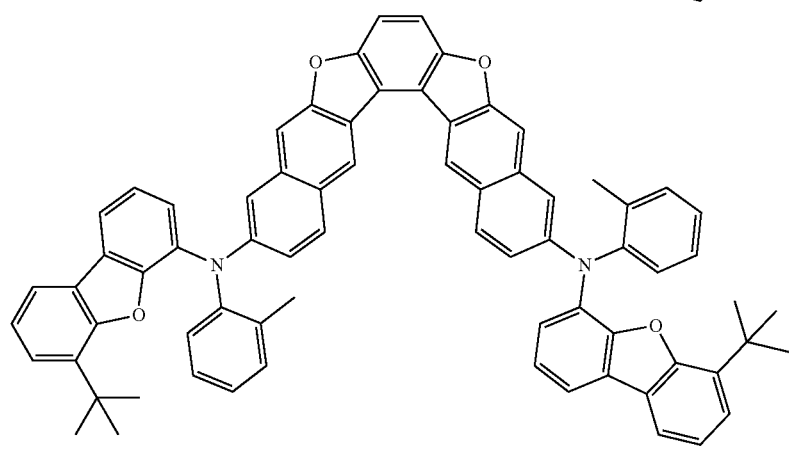

983 984
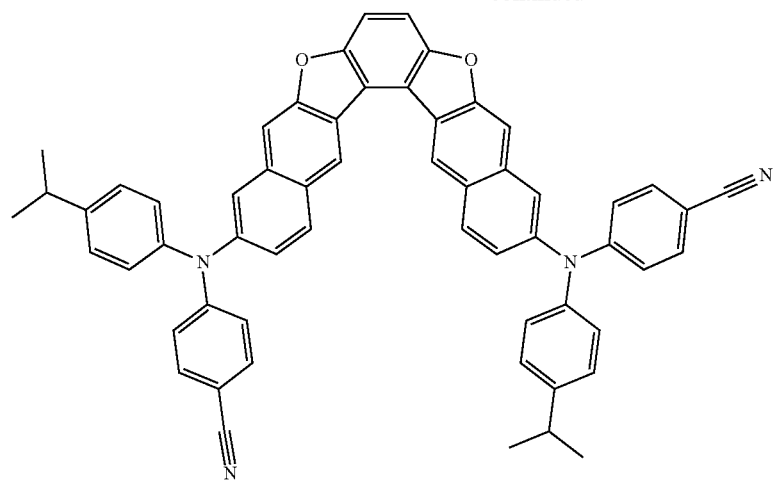
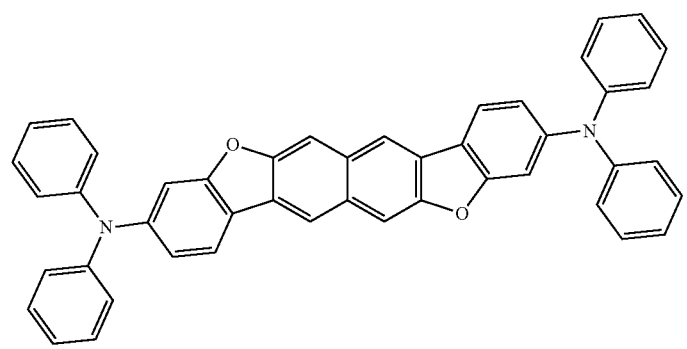
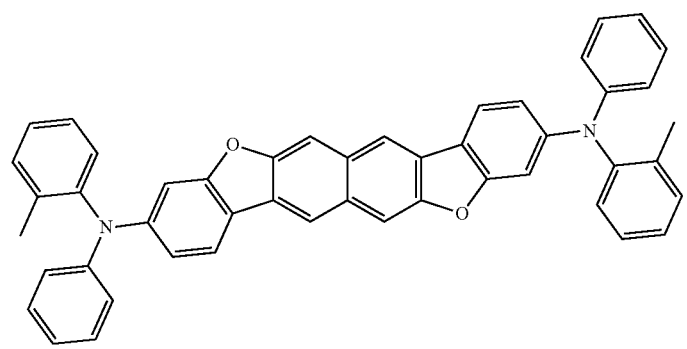
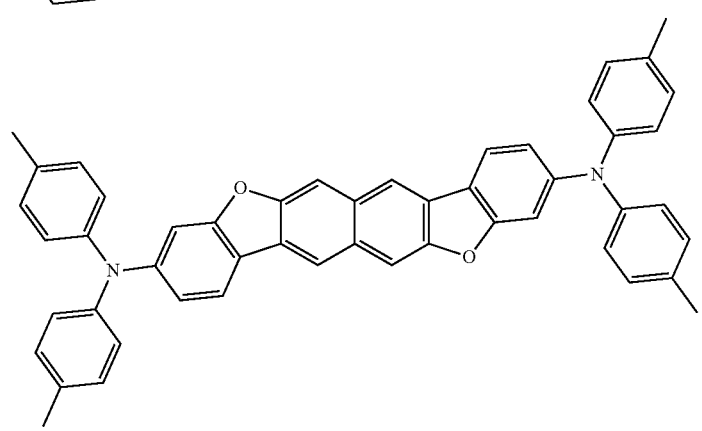

-continued
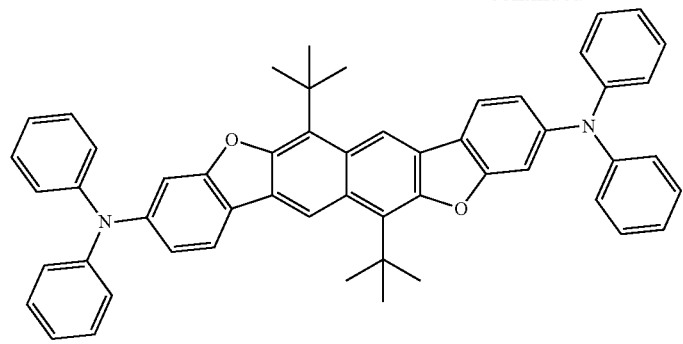
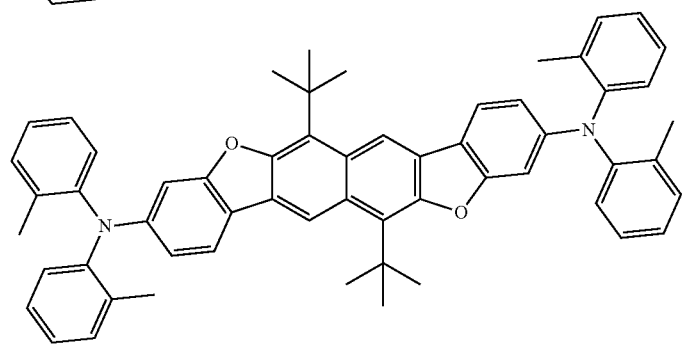
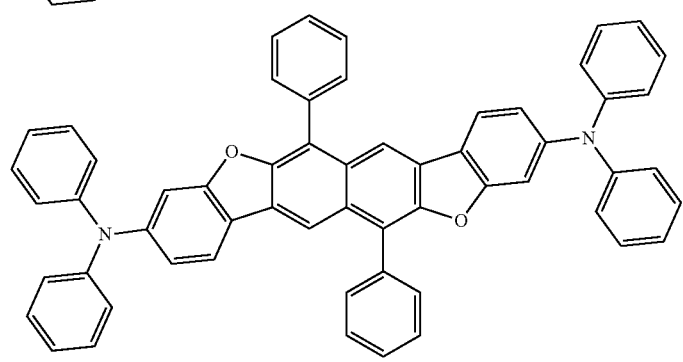
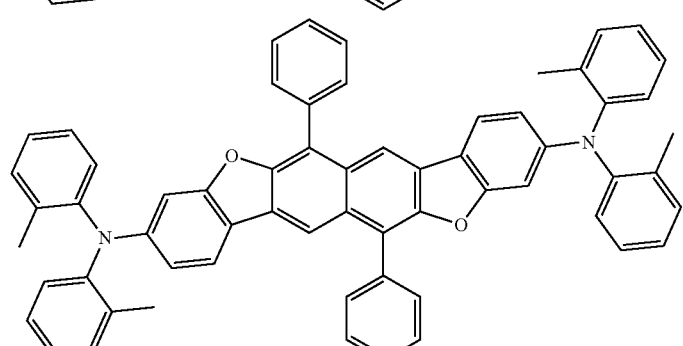
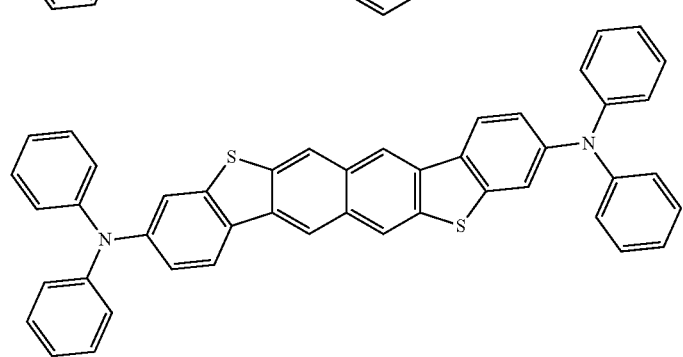

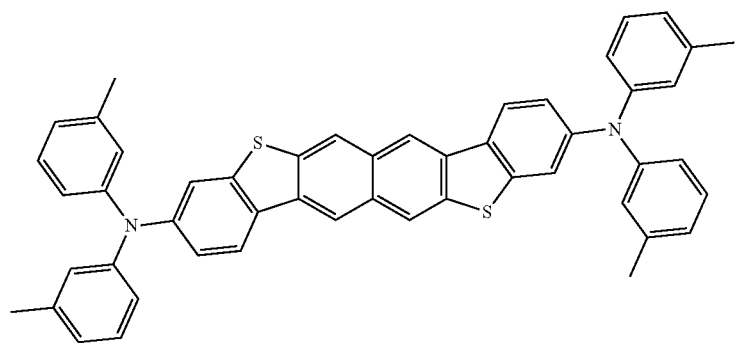
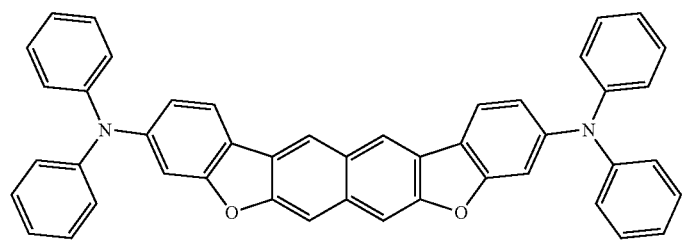
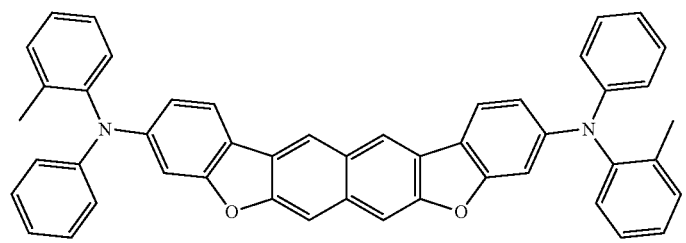
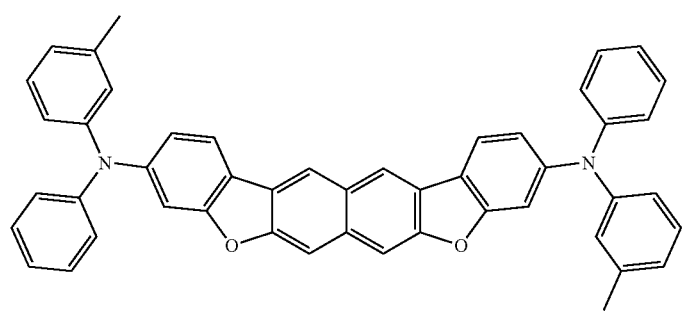
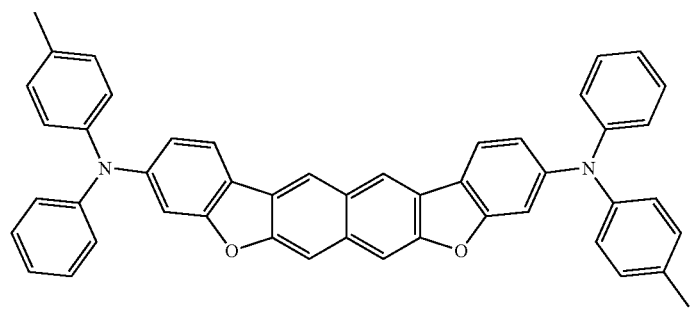

-continued
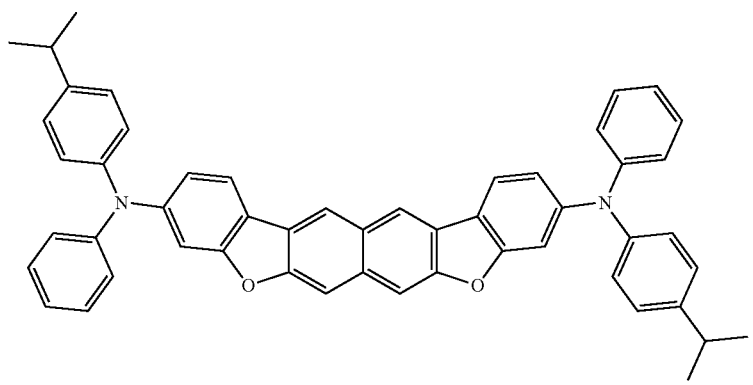
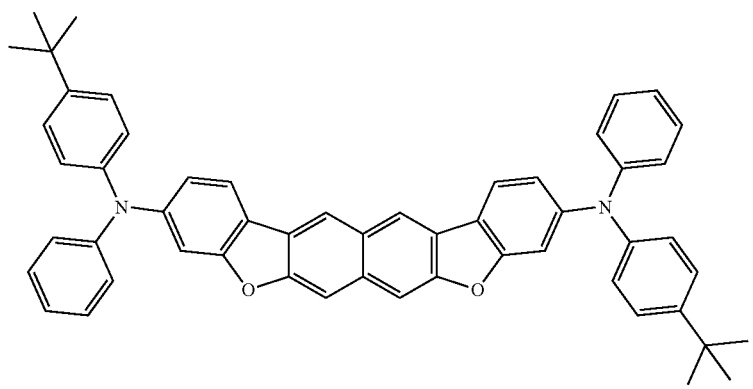
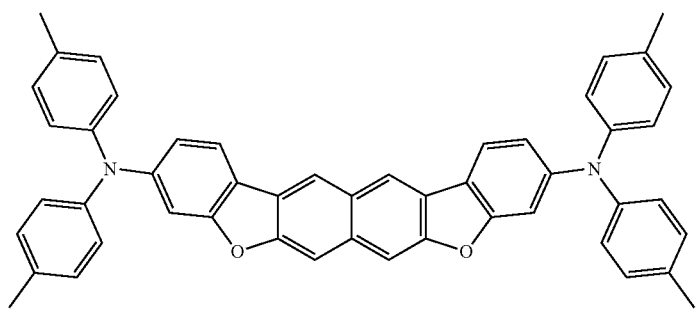
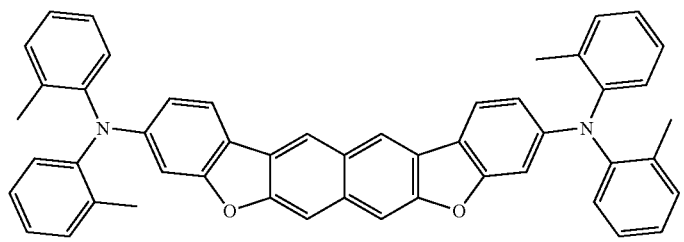
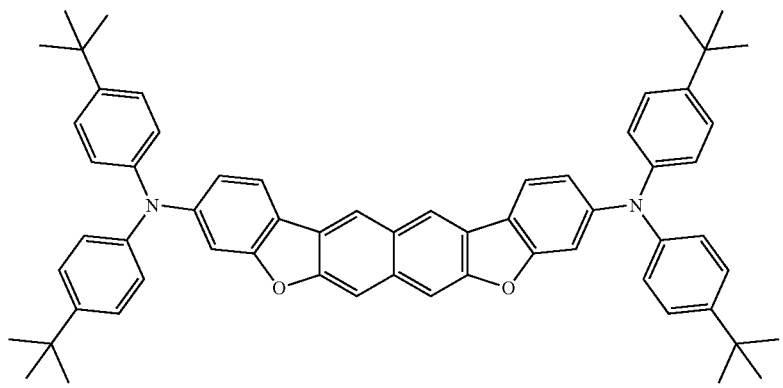

-continued
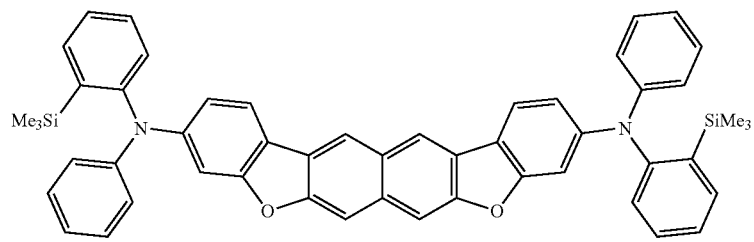
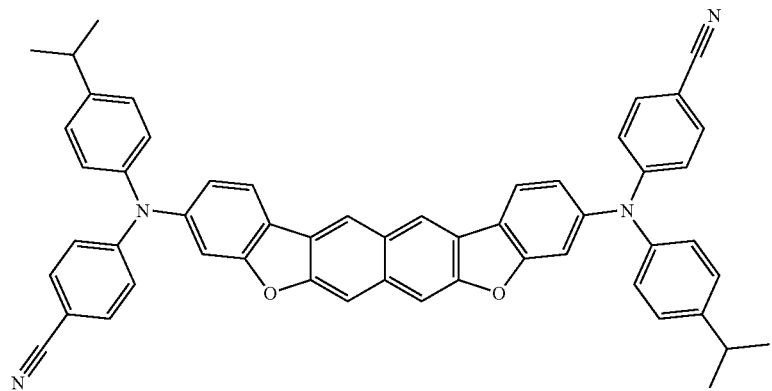
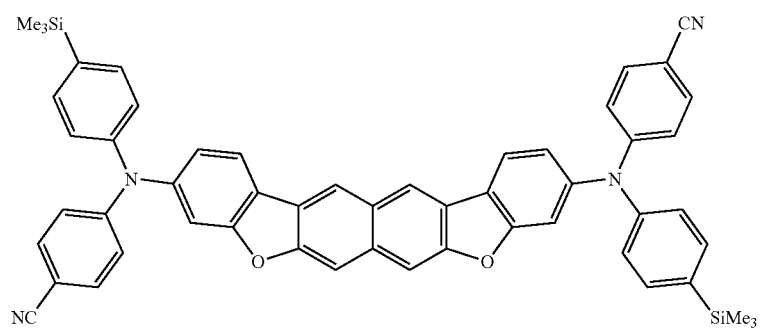
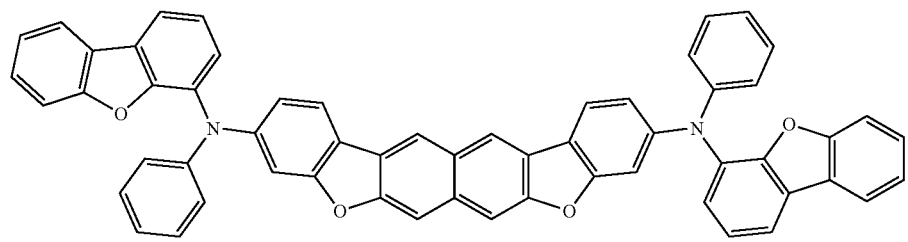
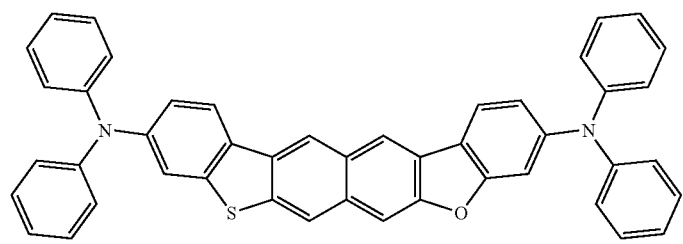

-continued
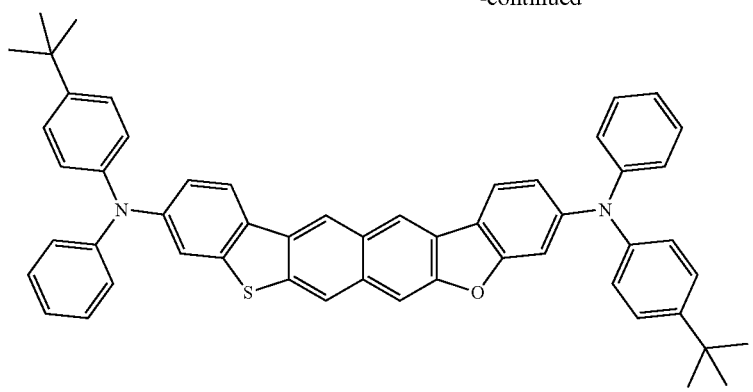
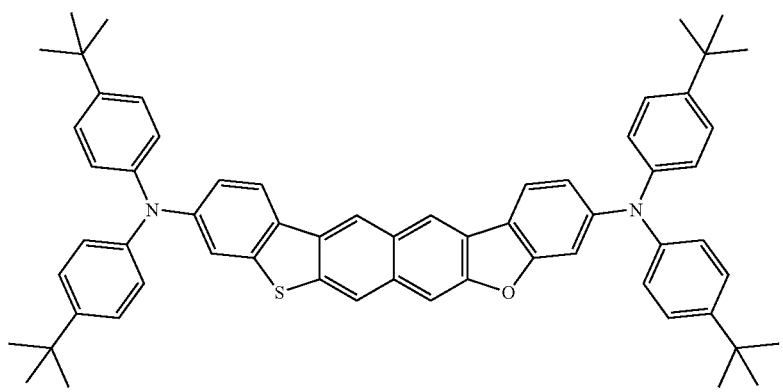
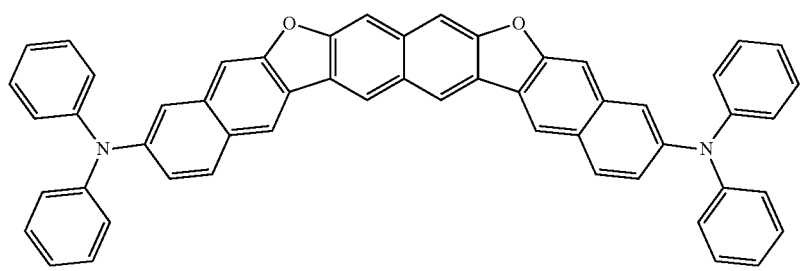
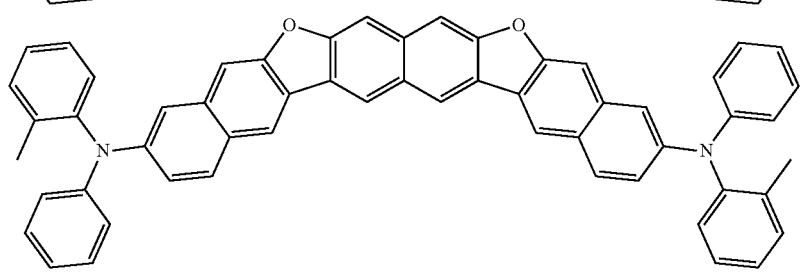
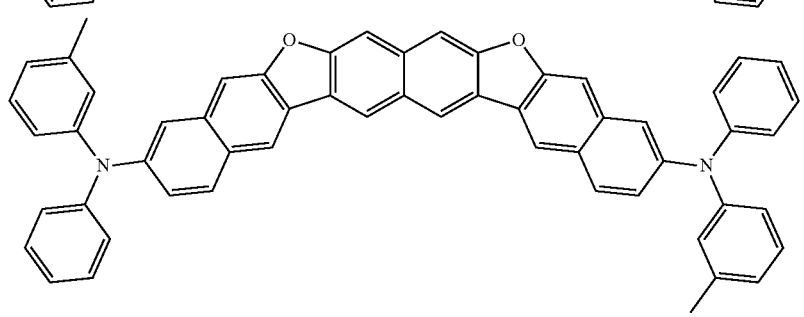

-continued
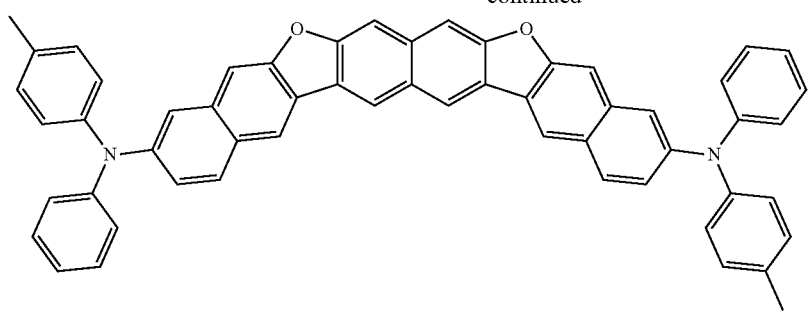
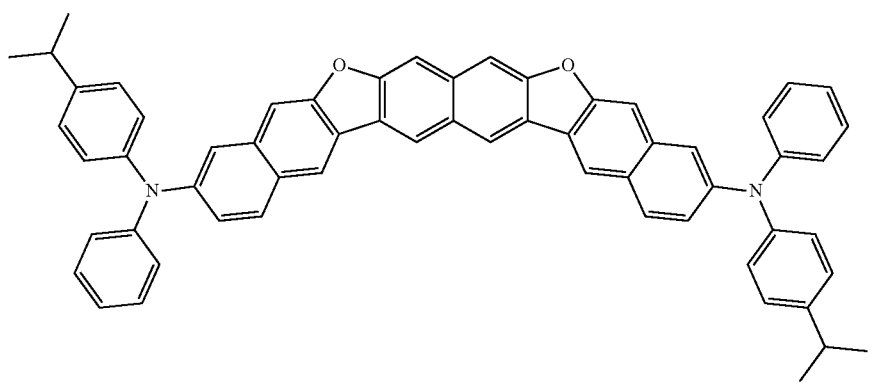
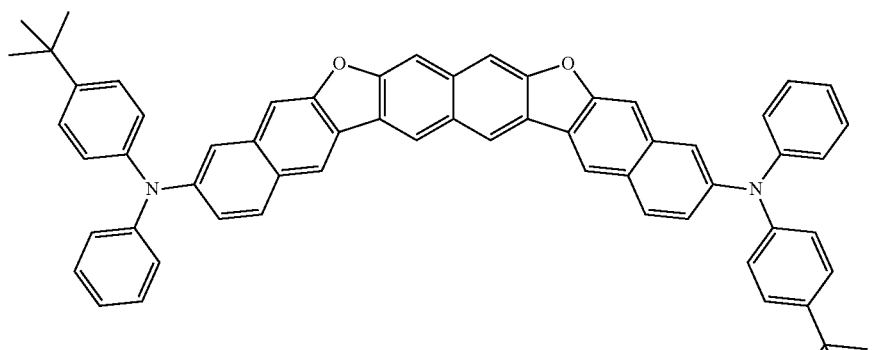
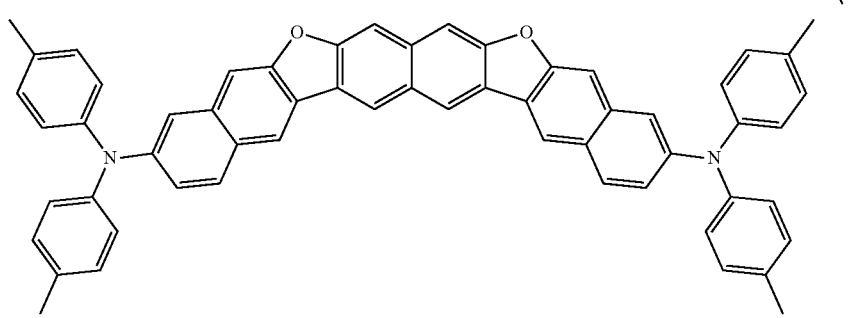
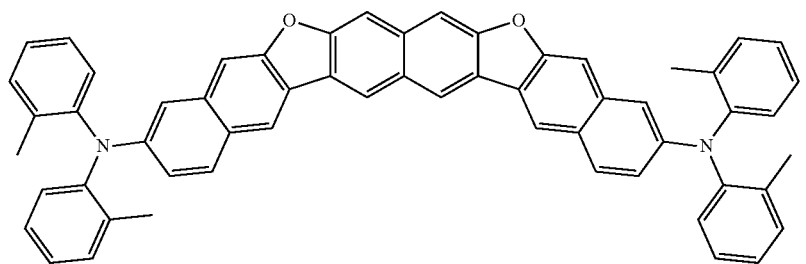

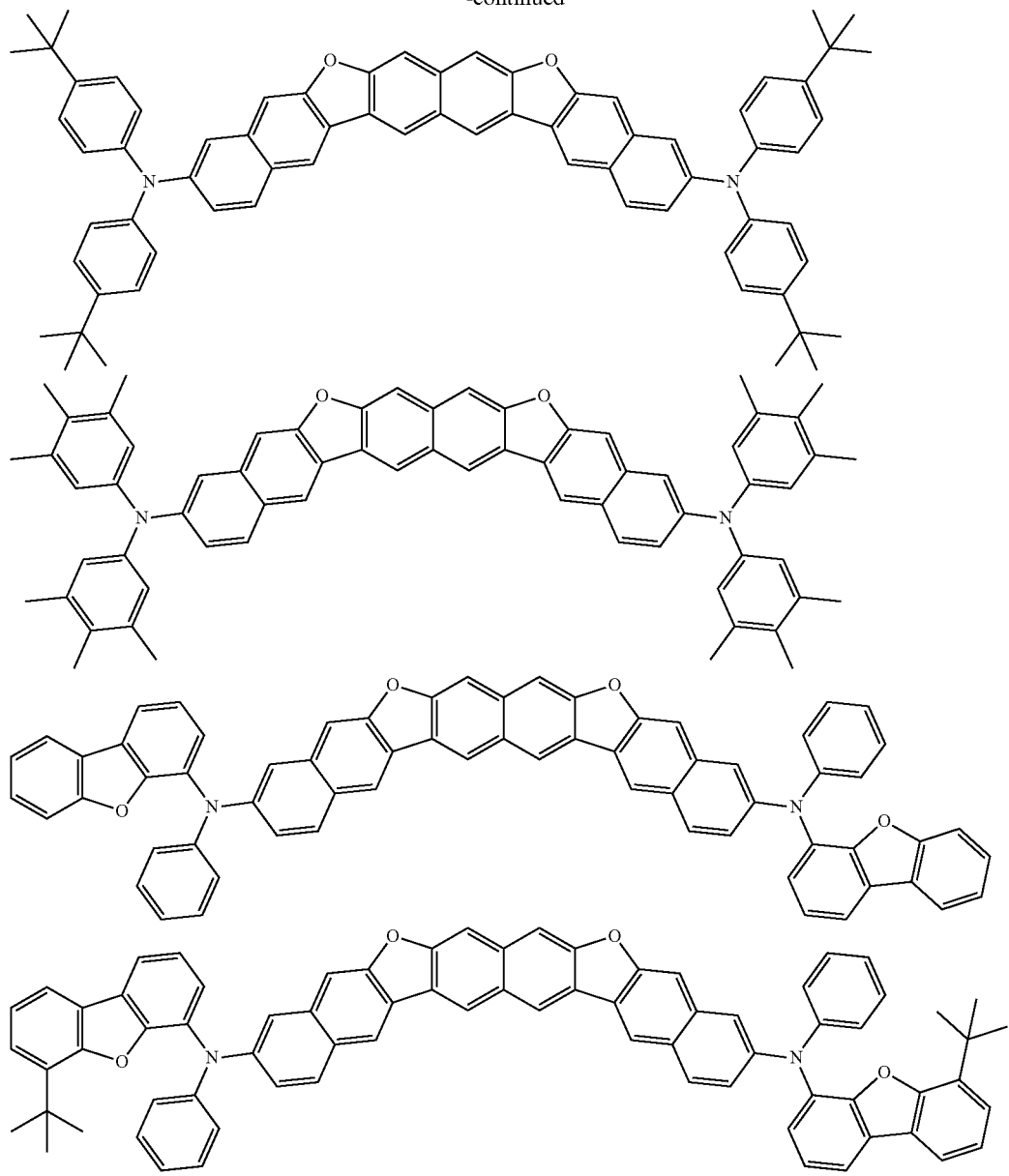

(Compound represented by formula (61))

The compound represented by the formula (61) is explained below.

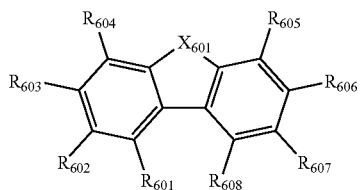

wherein, in the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63);

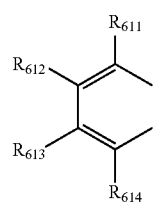

(63)

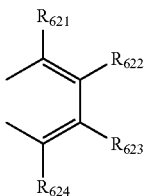

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{606}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

(64)

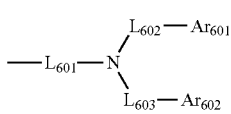

wherein, in the formula (64), $Ar_{601}$ and $Ar_{602}$ are independently
a substituted or unsubstituted aryl group having 6 to 50 ring carbon atoms, or
a substituted or unsubstituted monovalent heterocyclic group having 5 to 50 ring atoms;

$L_{601}$ to $L_{603}$ are independently
a single bonded,
a substituted or unsubstituted arylene group having 6 to 30 ring carbon atoms,
a substituted or unsubstituted divalent heterocyclic group having 5 to 30 ring atoms, or a divalent linking group formed by bonding 2 to 4 above mentioned groups;

In the formula (61), positions at which the divalent group represented by the formula (62) and the divalent group represented by the formula (63) are formed are not limited, and said groups can be formed at possible positions in $R_{601}$ to $R_{608}$.

In one embodiment, the compound represented by the formula (61) is represented by any one of the following formulas (61-1) to (61-6).

(61-1)

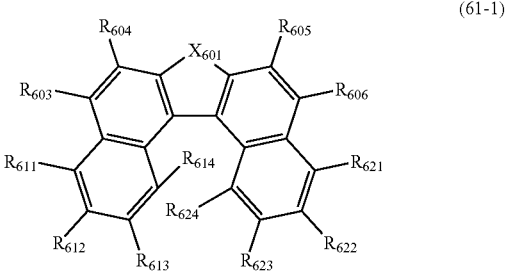

(61-2)

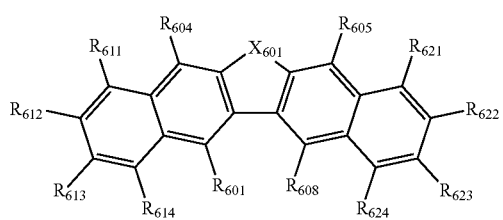

(61-3)

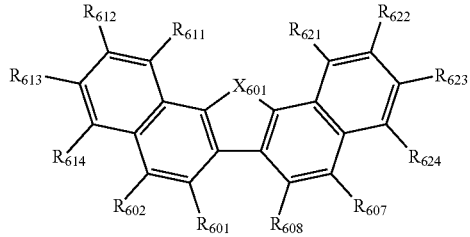

(61-4)

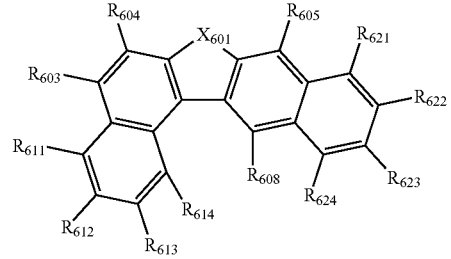

(61-5)

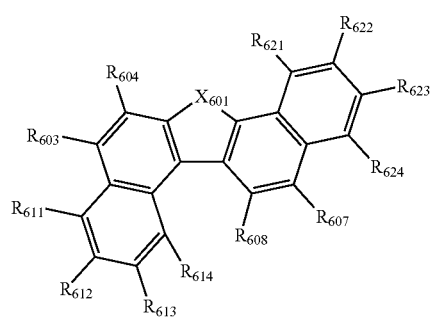

(61-6)

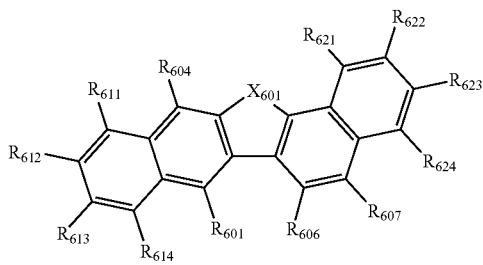

wherein in the formulas (61-1) to (61-6), $X_{601}$ is as defined in the formula (61);

at least two of $R_{601}$ to $R_{624}$ are monovalent groups represented by the formula (64);

$R_{601}$ to $R_{624}$ that are not monovalent groups represented by the formula (64) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si$(R_{901})(R_{902})(R_{903})$,

—O—$(R_{904})$,

—S—$(R_{905})$,

—N$(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In one embodiment, the compound represented by the formula (61) is represented by any one of the following formulas (61-7) to (61-18).

(61-7)

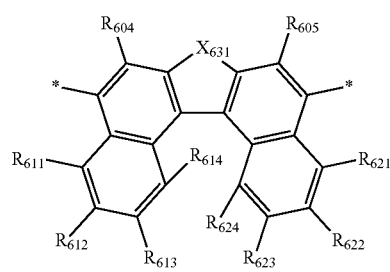

(61-8)

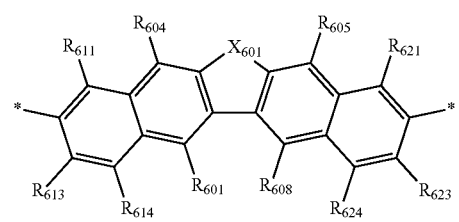

(61-9)

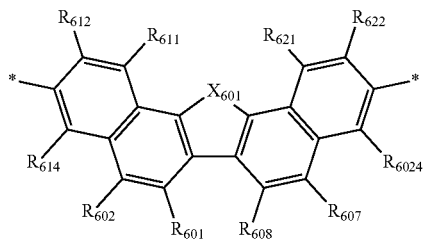

(61-10)

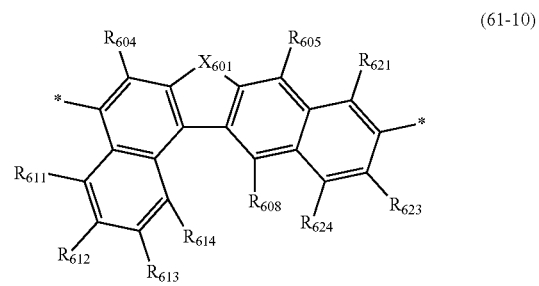

(61-11)

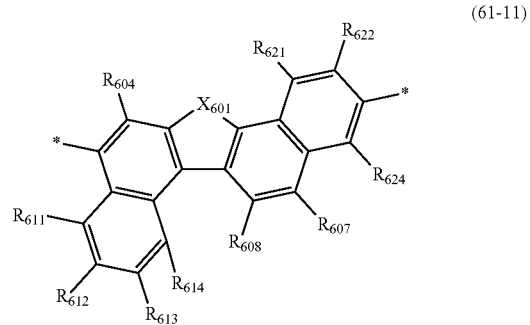

(61-12)

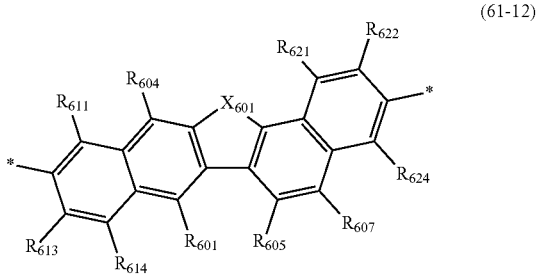

(61-13)

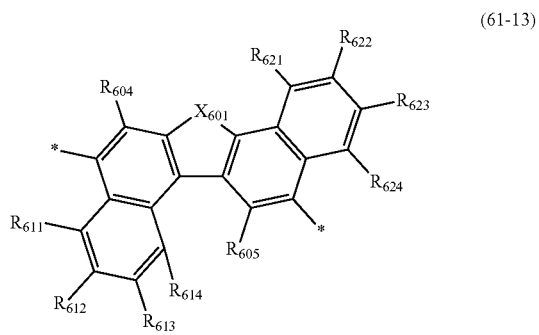

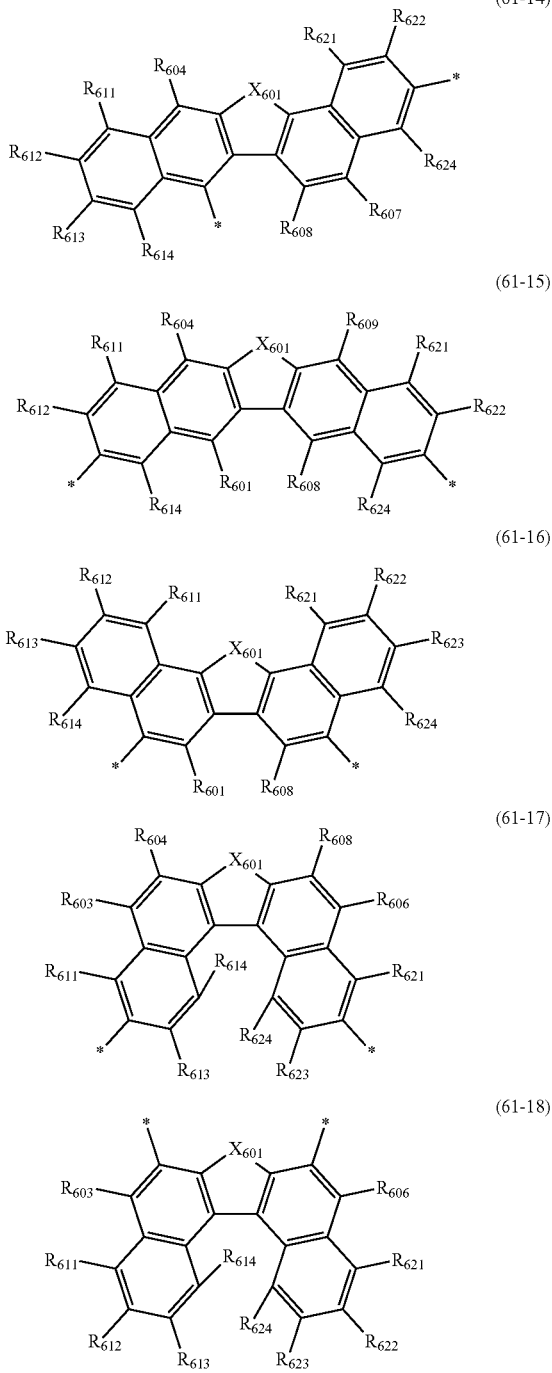

(61-14)
(61-15)
(61-16)
(61-17)
(61-18)

wherein in the formulas (61-7) to (61-18), $X_{601}$ is as defined in the formula (61); * is a single bond bonding to the monovalent group represented by the formula (64; and $R_{601}$ to $R_{624}$ are the same as $R_{601}$ to $R_{624}$ that are monovalent groups represented by the formula (64).

$R_{601}$ to $R_{624}$ which do not form the divalent group represented by the formula (62) and (63) and are not monovalent groups represented by the formula (64), and $R_{611}$ to $R_{614}$ and $R_{621}$ to $R_{624}$ which are not monovalent groups represented by the formula (64) are preferably independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

The monovalent group represented by the formula (64) is preferably represented by the following formulas (65) or (66).

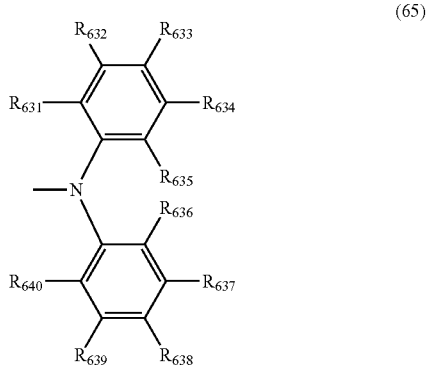

(65)

wherein in the formula (65), $R_{631}$ to $R_{640}$ are independently
a hydrogen atom,
a substituted or unsubstituted alkyl group having 1 to 50 ring carbon atoms, or
a substituted or unsubstituted alkenyl group having 2 to 50 carbon atoms;
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

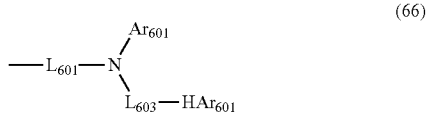

(66)

wherein in the formula (66), $Ar_{601}$, $L_{601}$ and $L_{603}$ are as defined in the formula (64); and $HAr_{601}$ is a structure represented by the following formula (67);

(67)

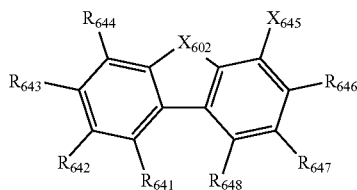

wherein in the formula (67) $X_{602}$ is an oxygen atom or a sulfur atom;

any one of $R_{641}$ to $R_{648}$ is a single bond bonding to $L_{603}$;

$R_{641}$ to $R_{648}$ which are not single bonds are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).)

As specific example of the compound represented by the formula (61), in addition to the compounds described in WO2014/104144, the following compounds can be given, for example. In the following example compounds, Me represents methyl group.

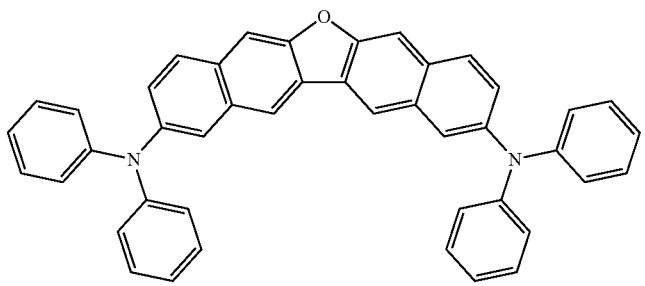

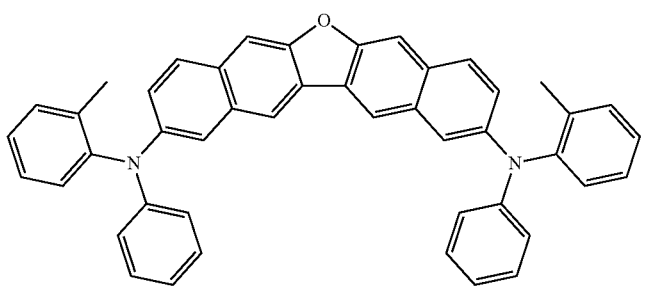

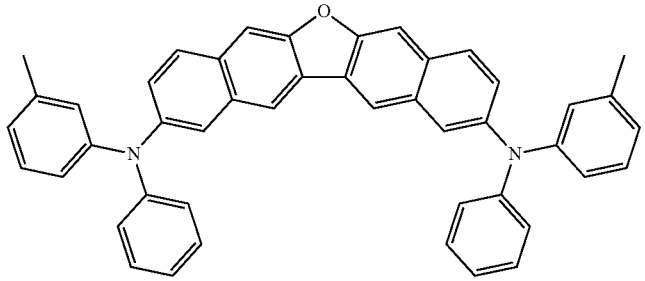

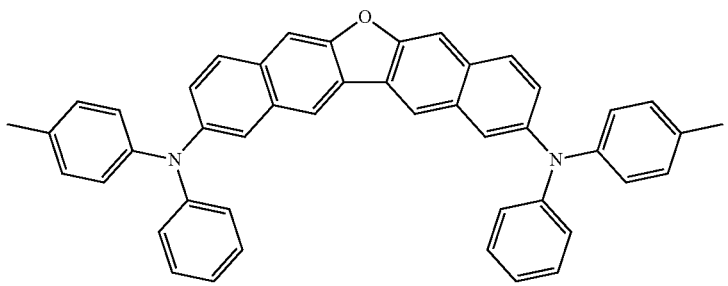

1007 1008
-continued
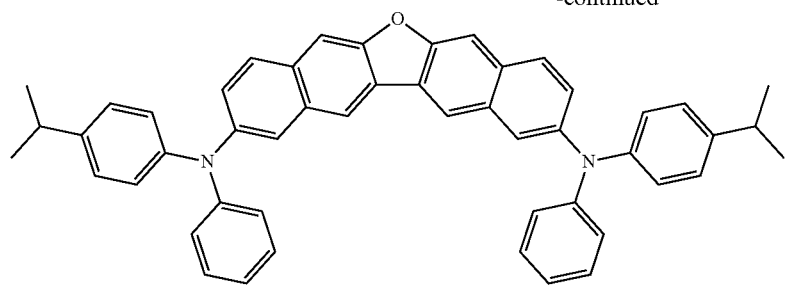
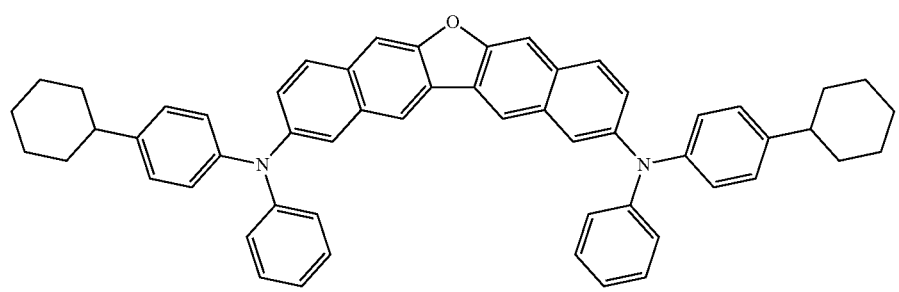
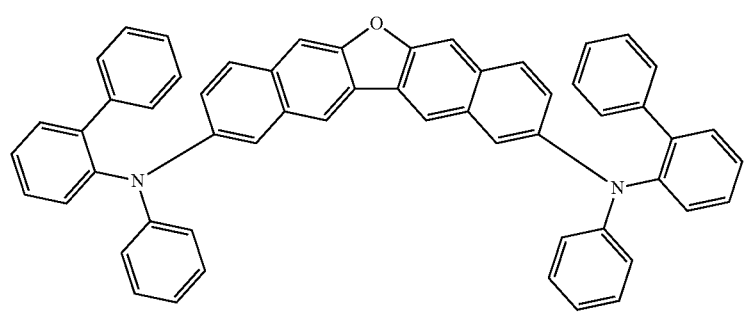
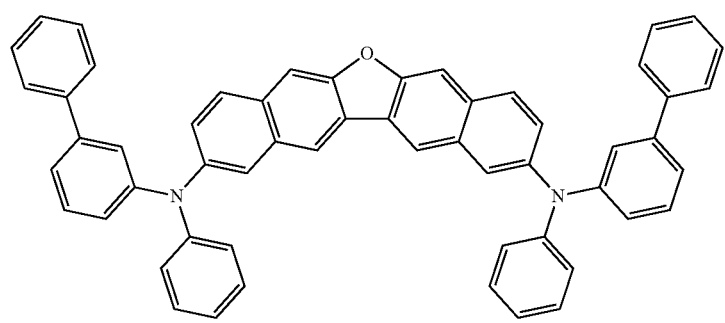
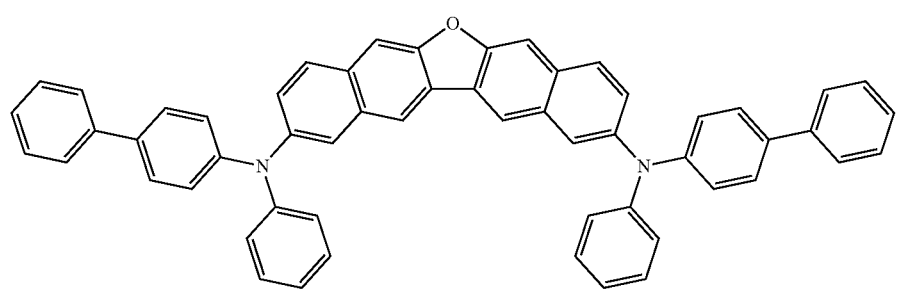

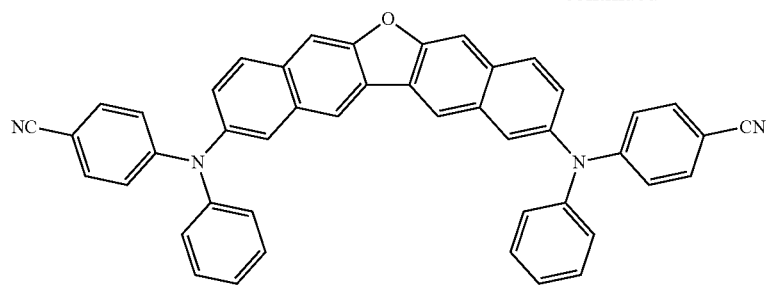
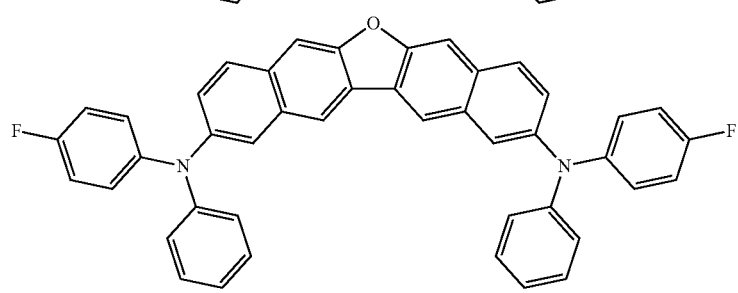
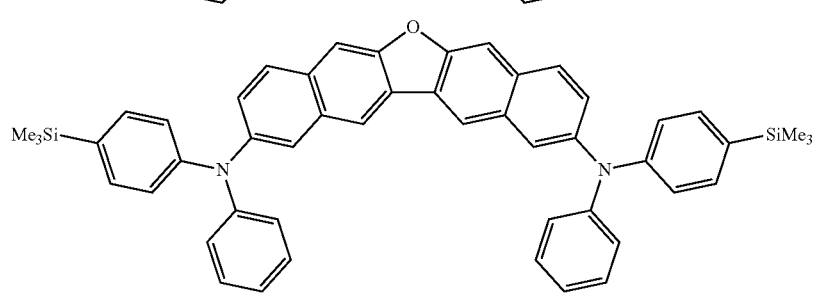
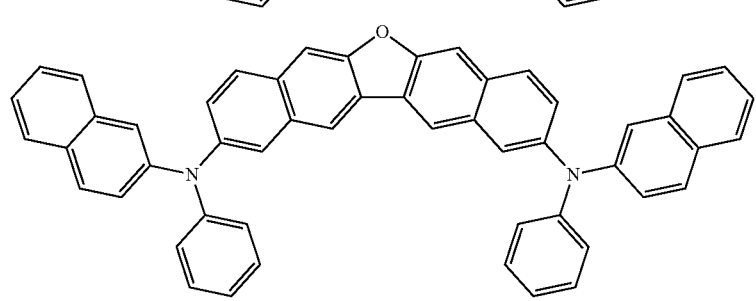
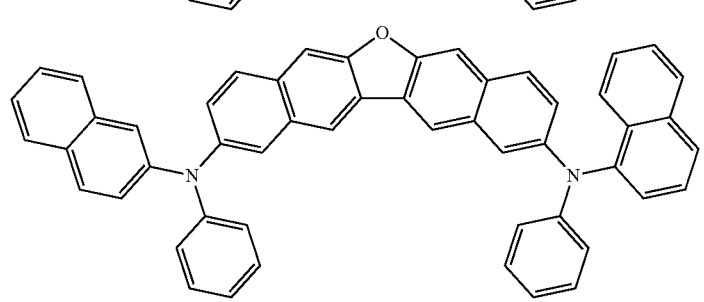
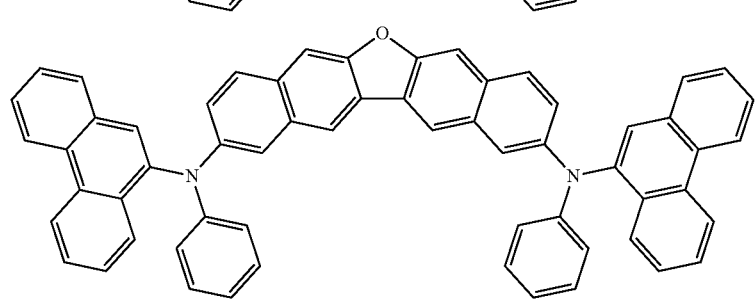

-continued
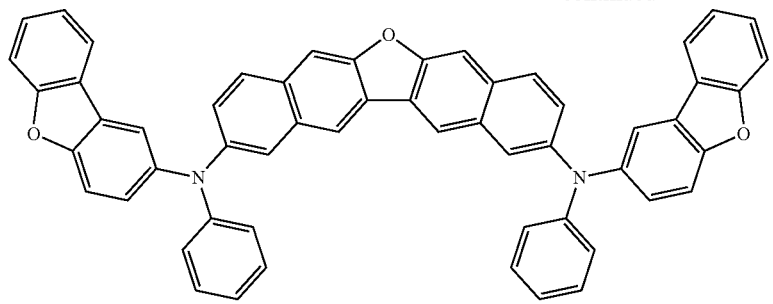
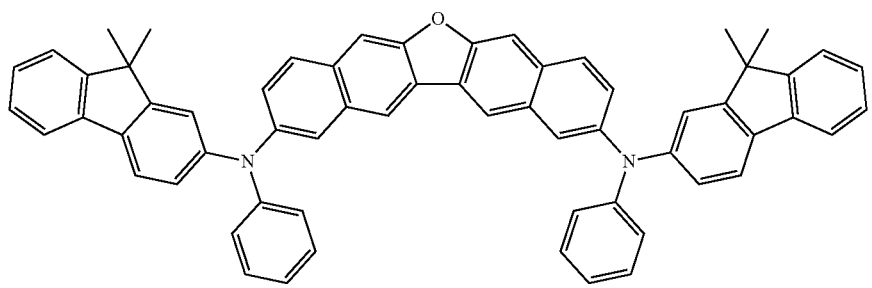
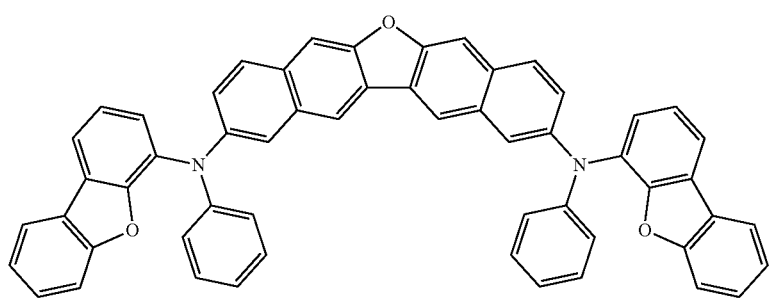
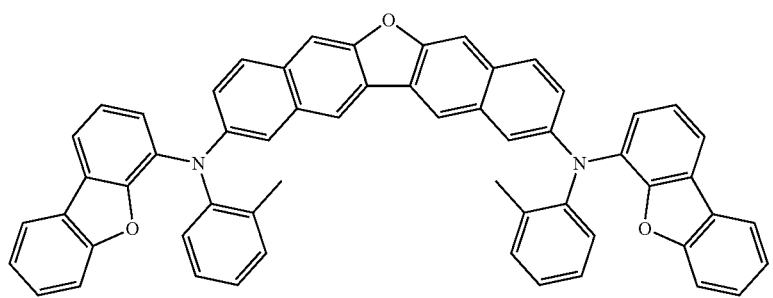
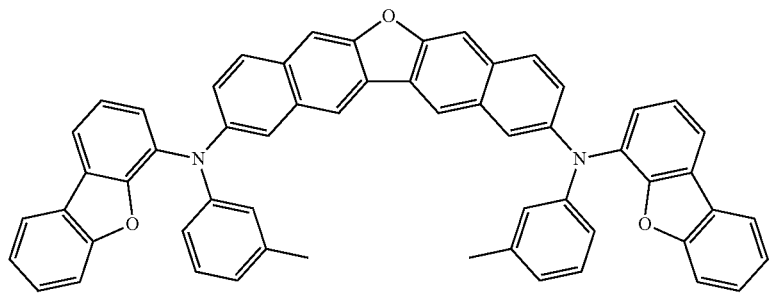

-continued
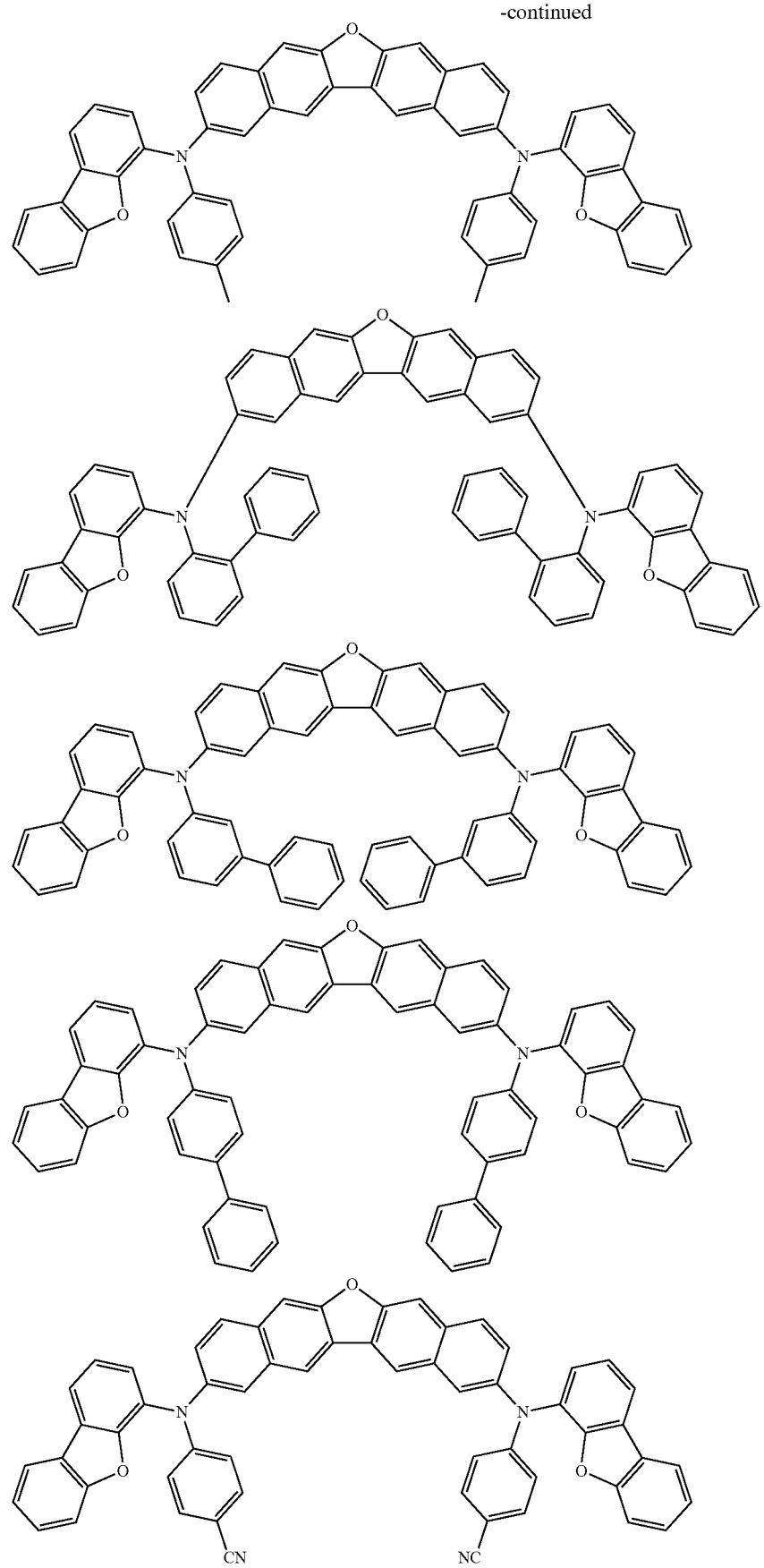

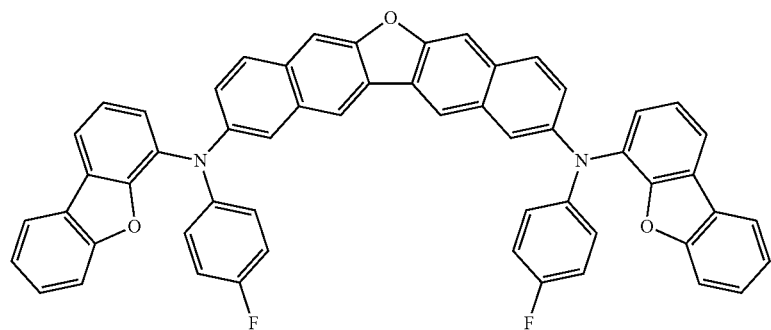
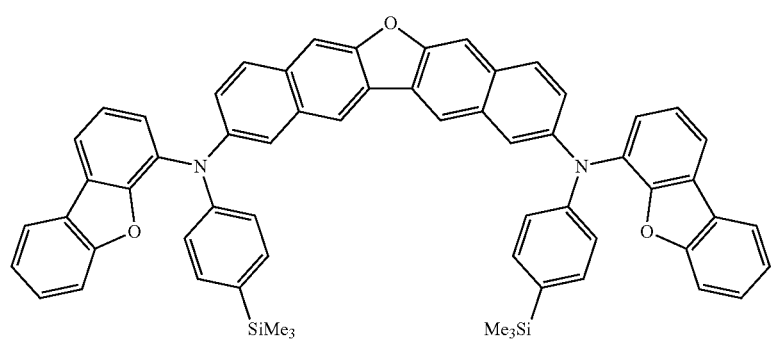
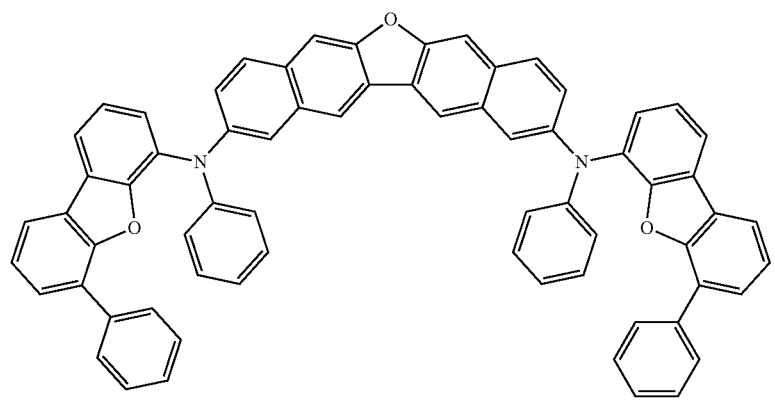
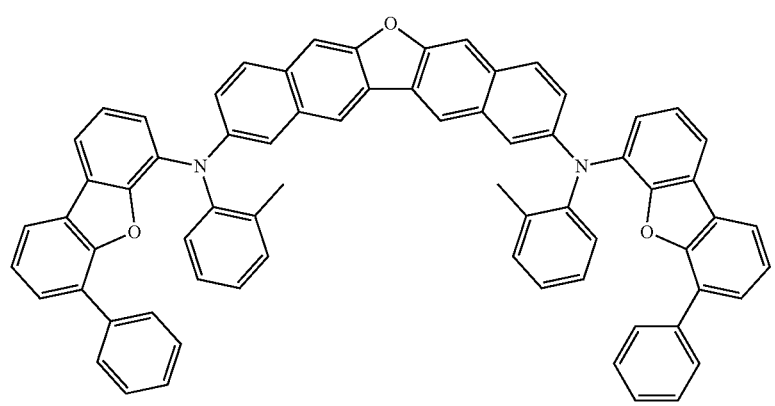

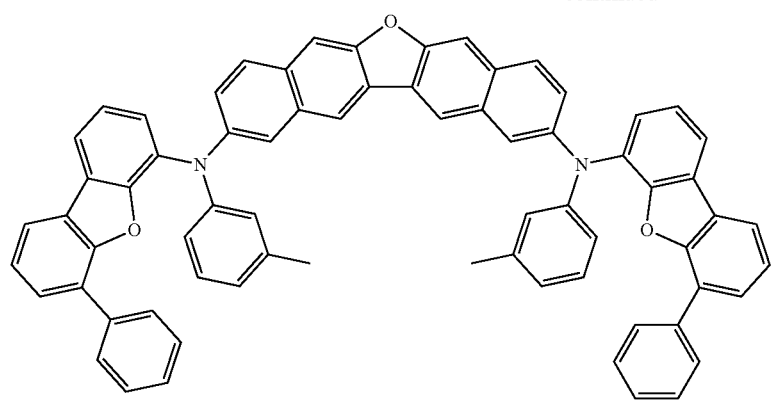
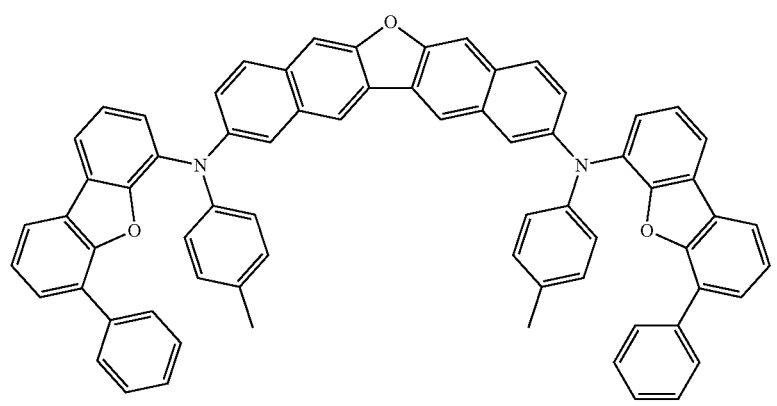
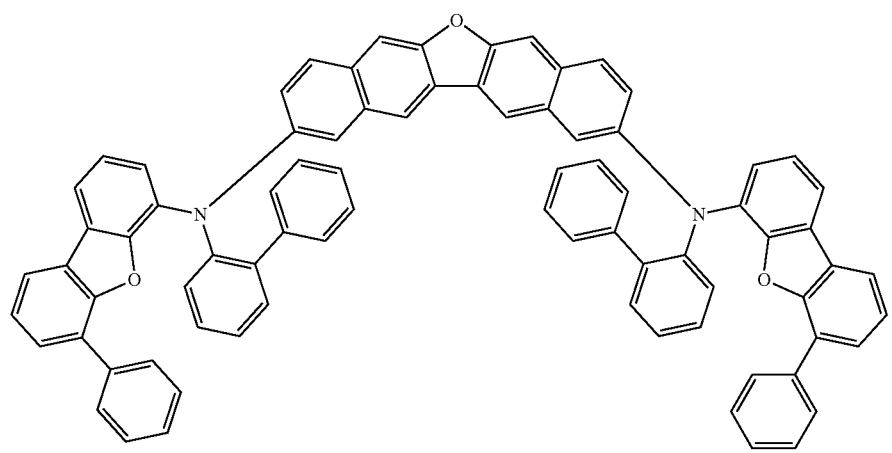
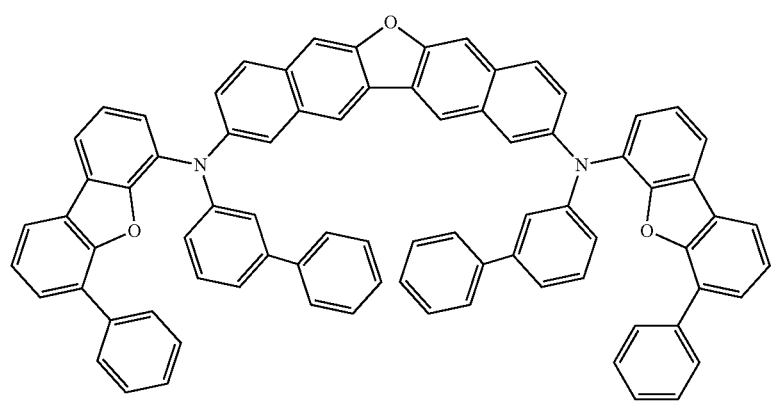

1019
-continued
1020
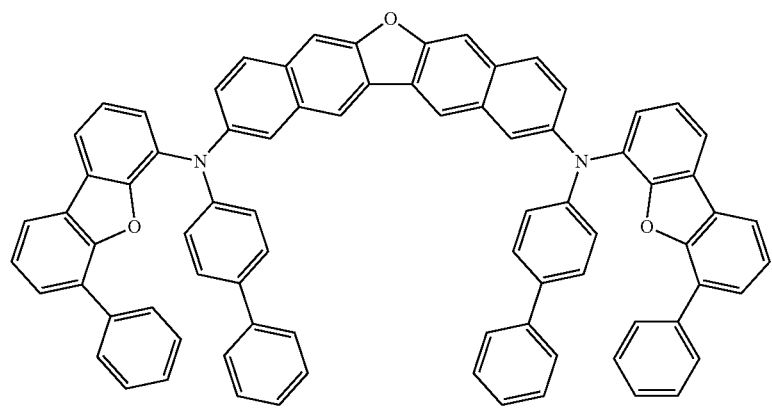
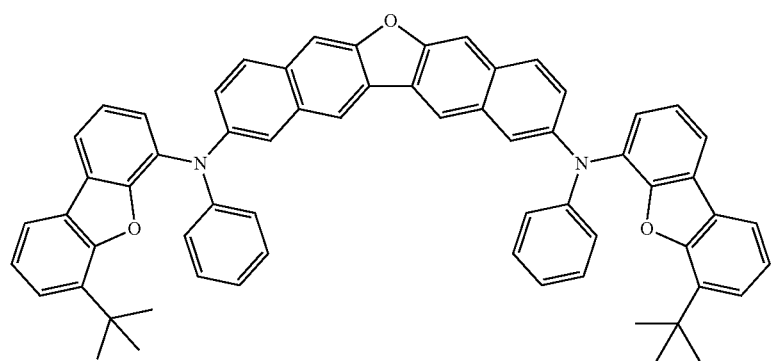
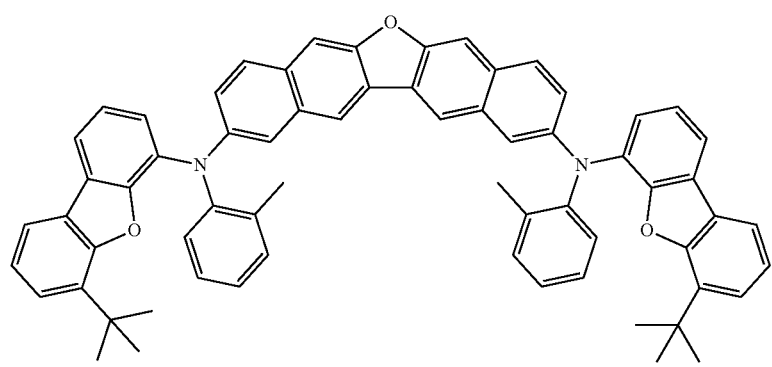
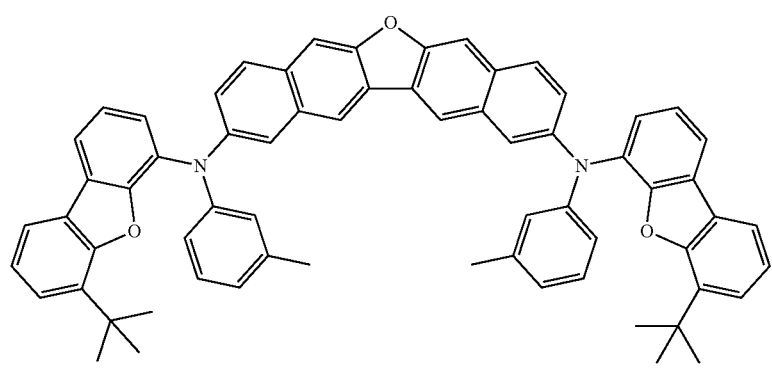

1021
1022
-continued
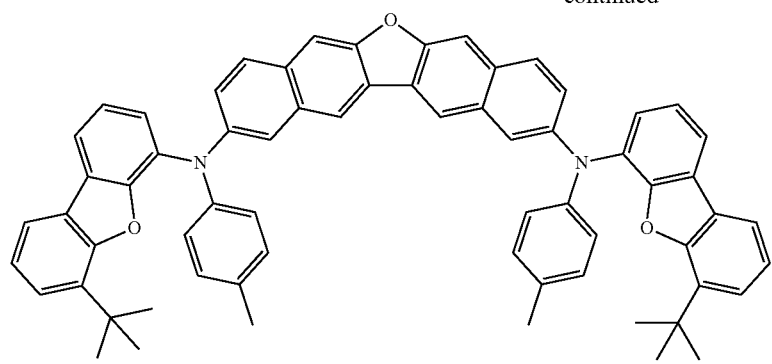
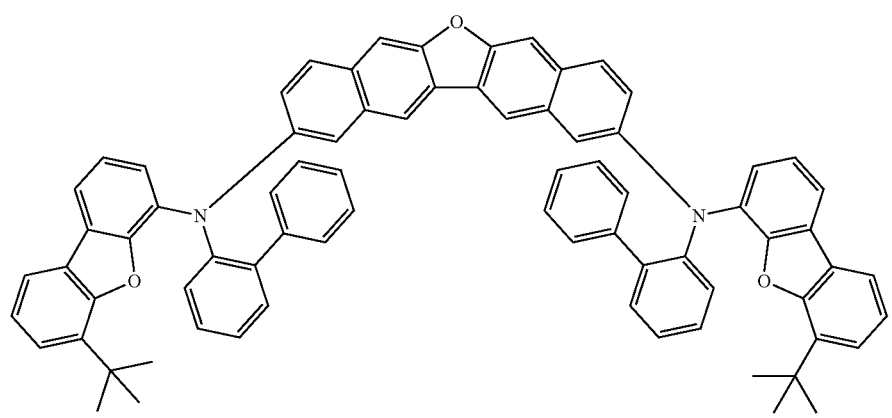
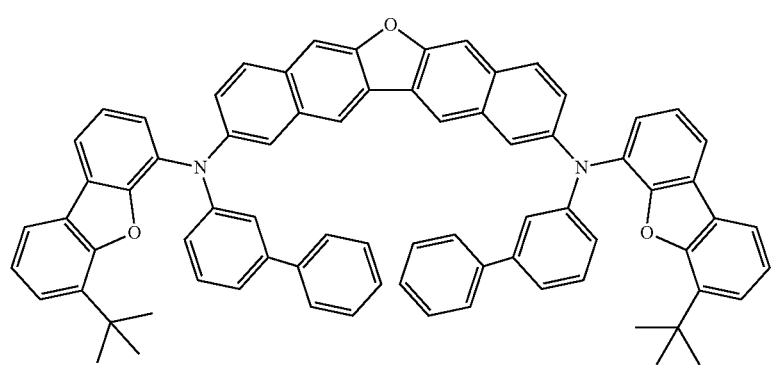
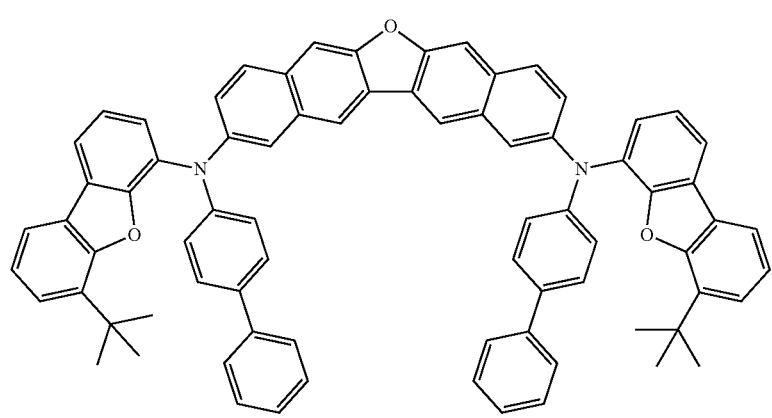

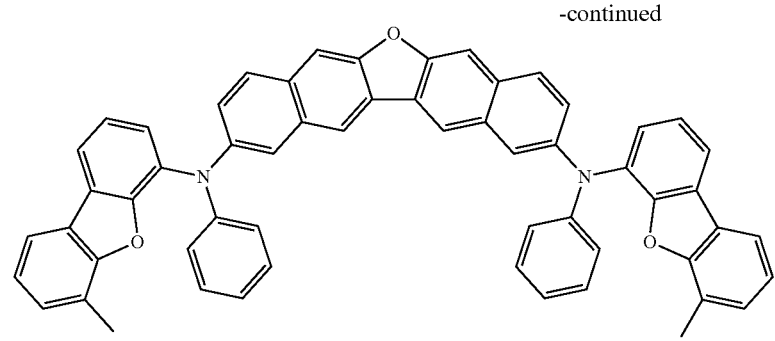
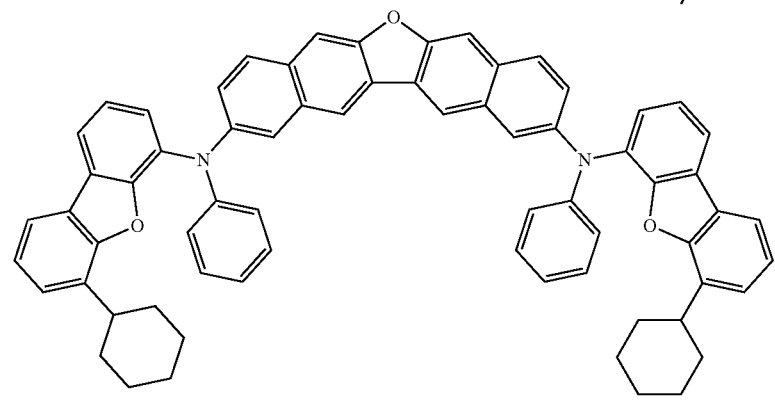
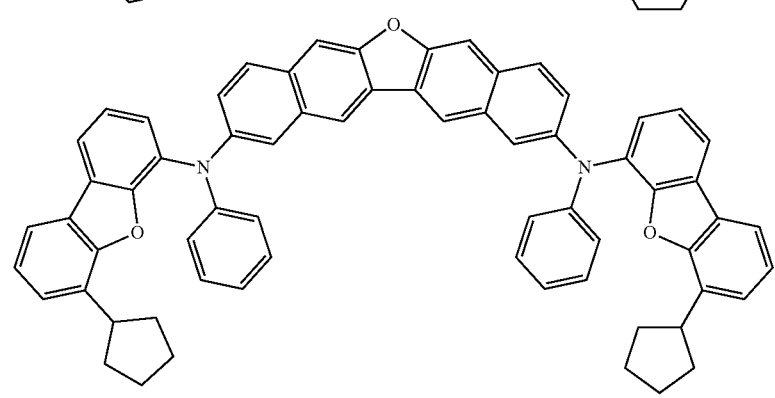
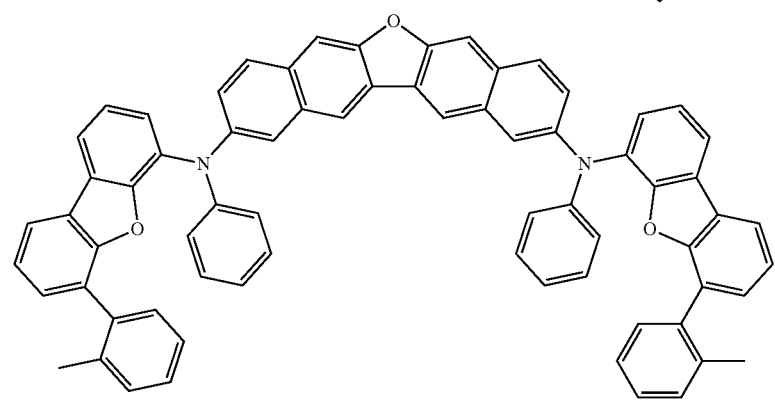
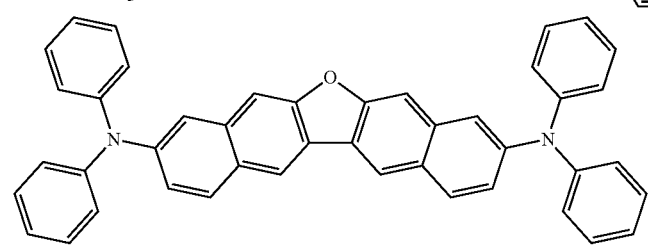

1025
-continued
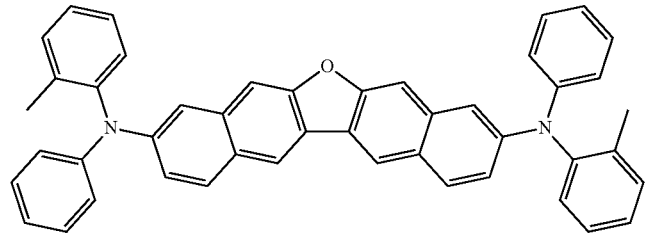
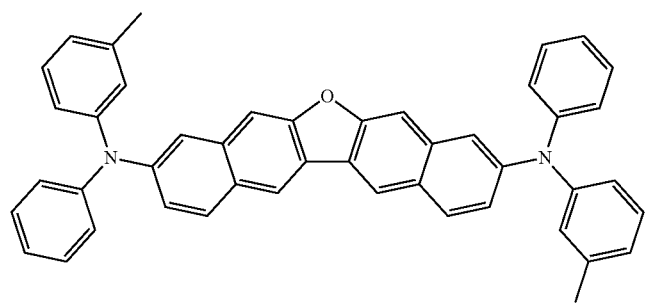
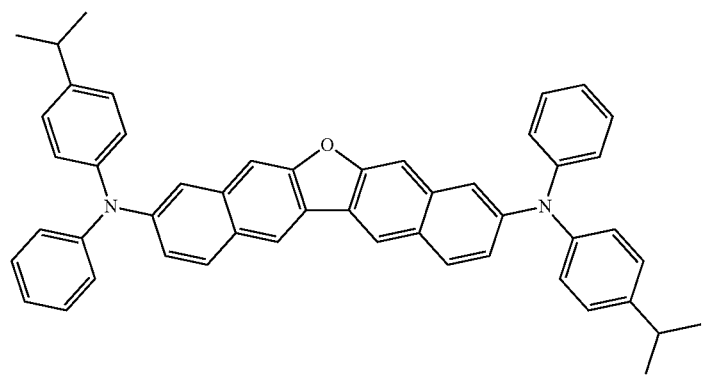
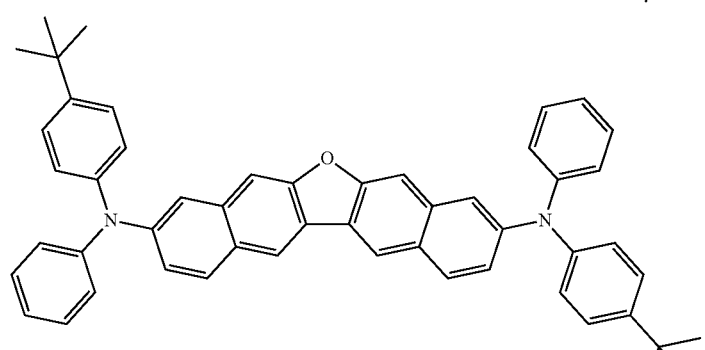
1026
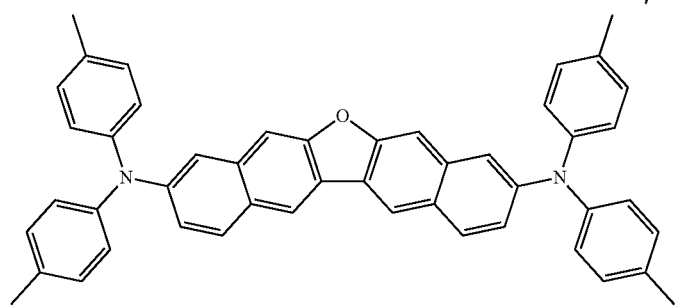

1027
-continued
1028
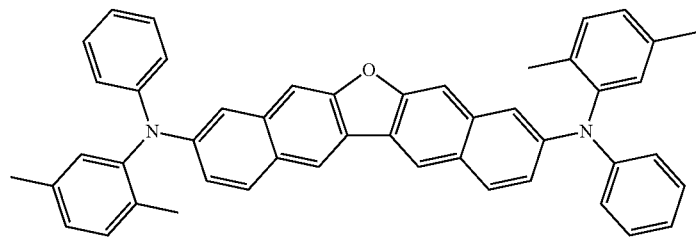
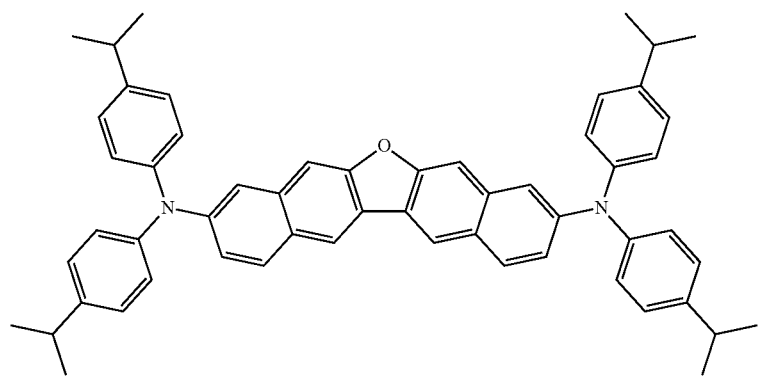
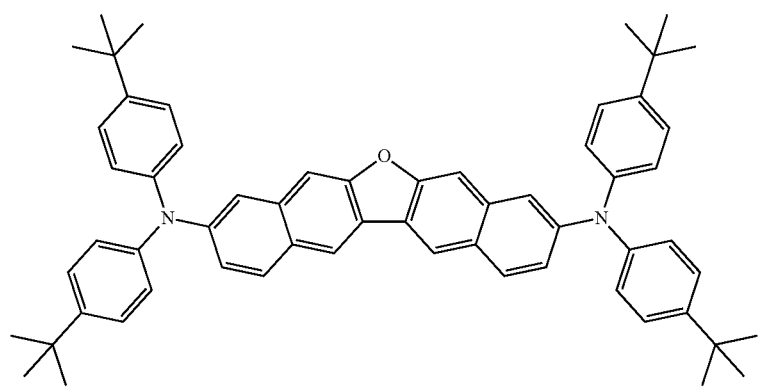
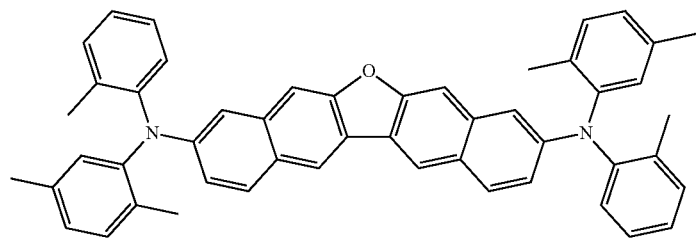
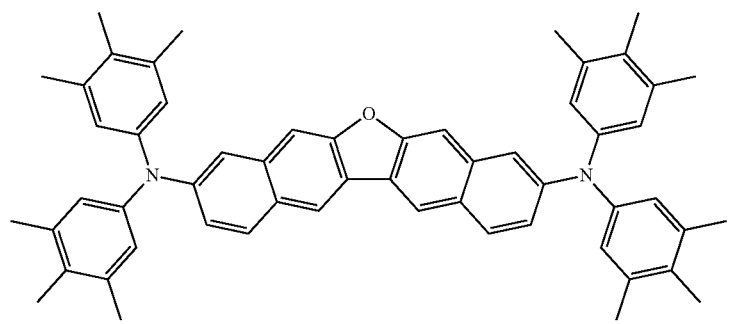

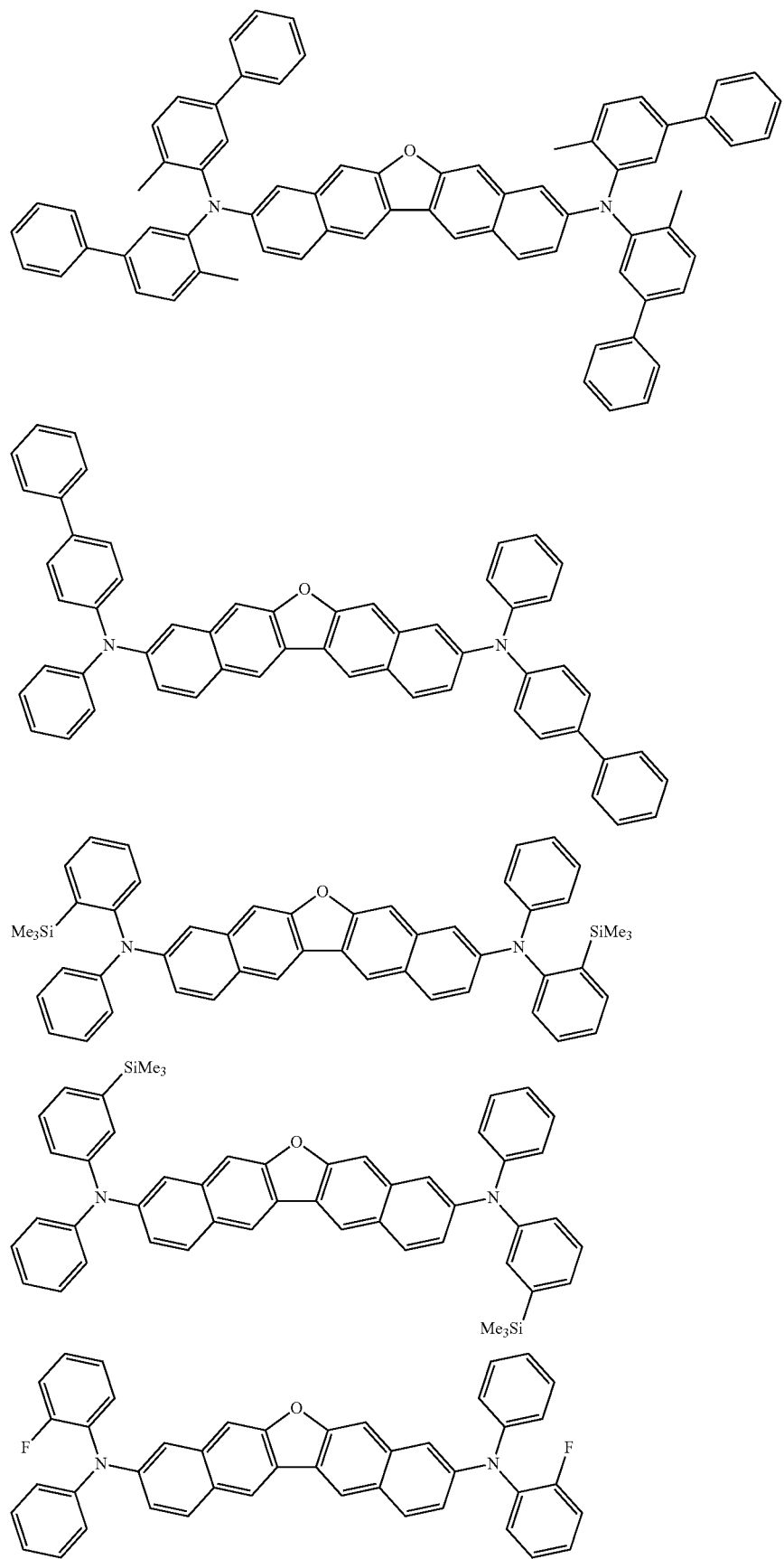

1031
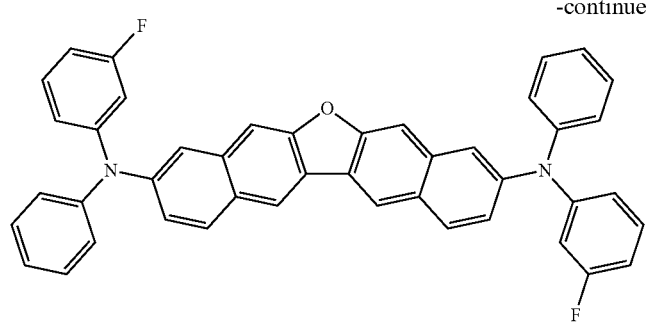
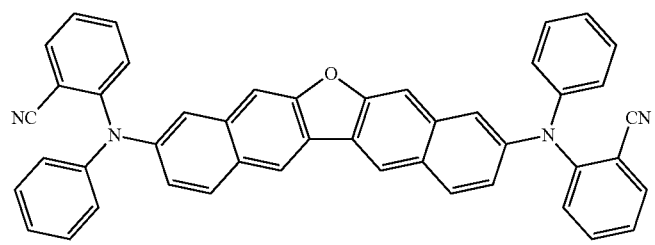
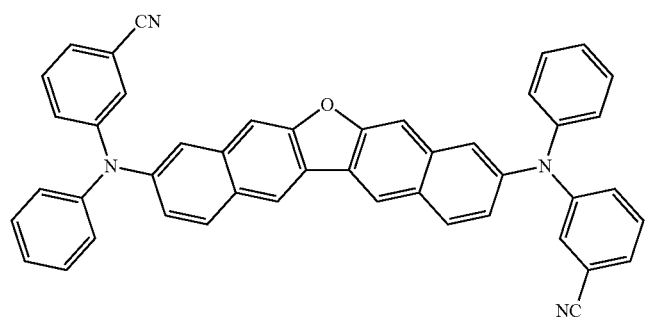
1032
-continued
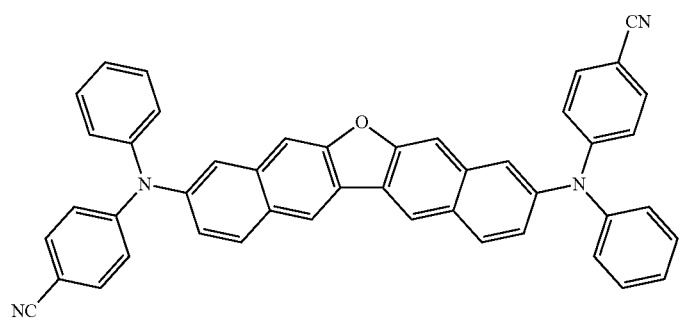
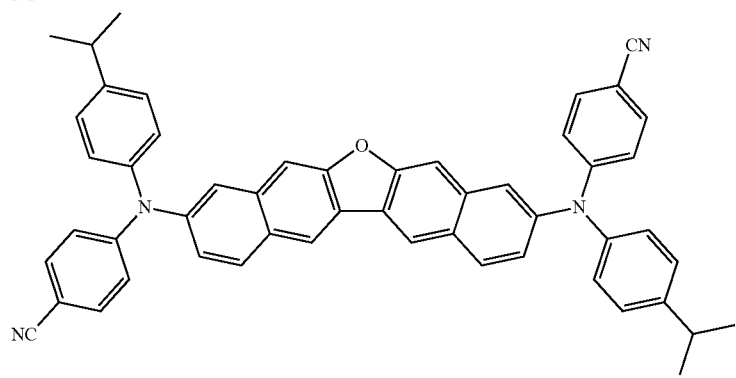

-continued
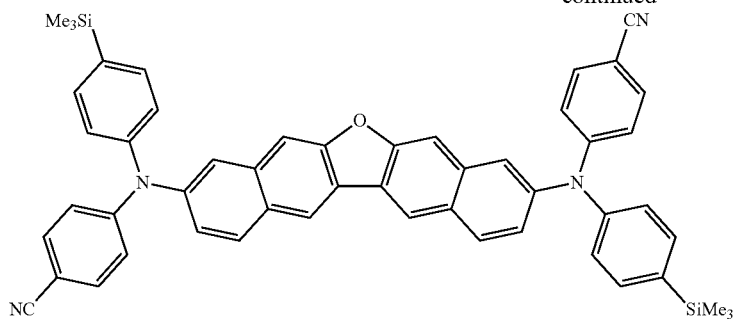
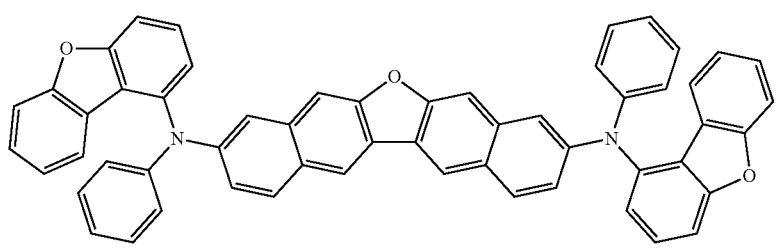
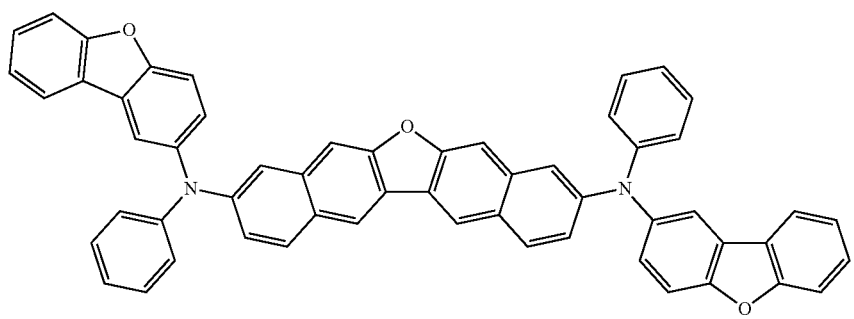
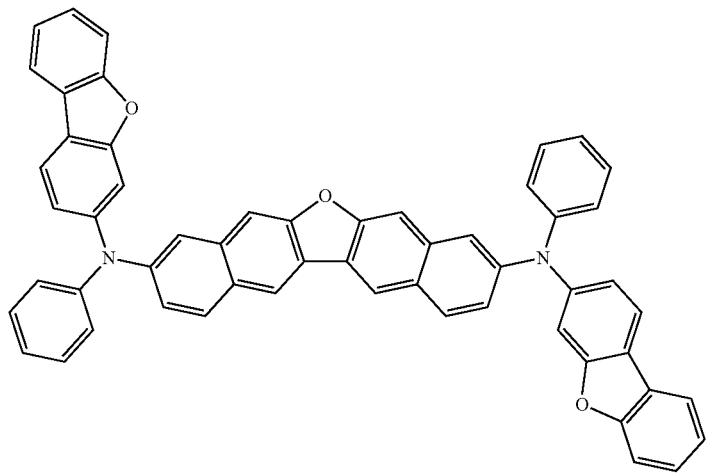
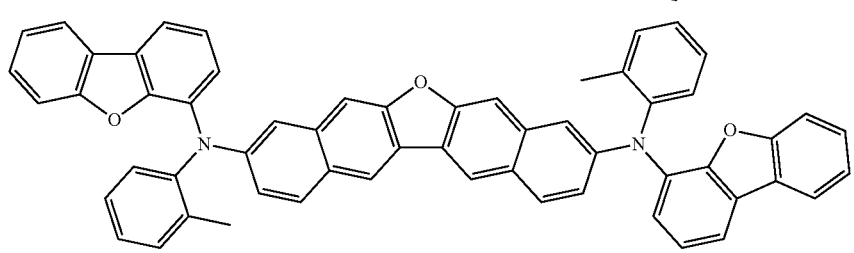

1035    -continued    1036
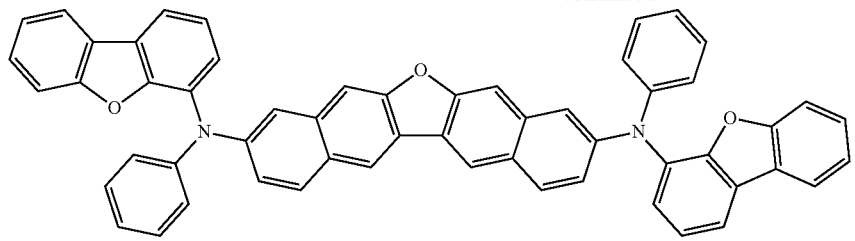
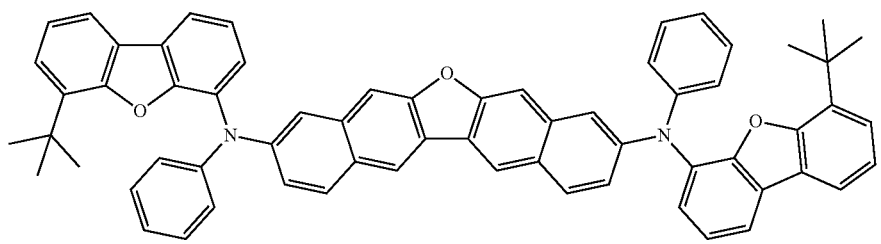
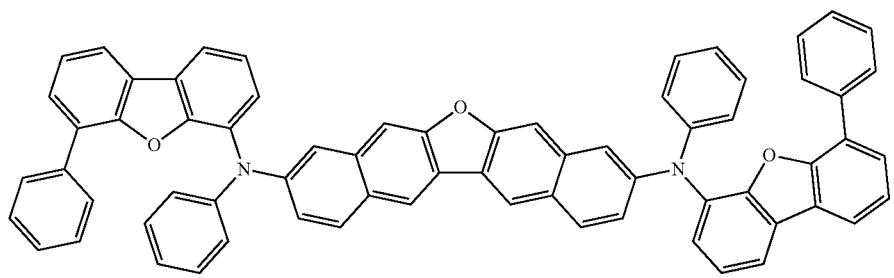
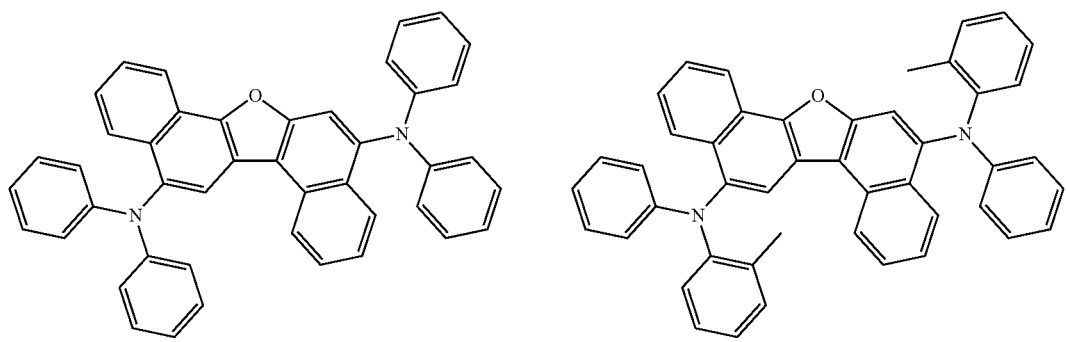
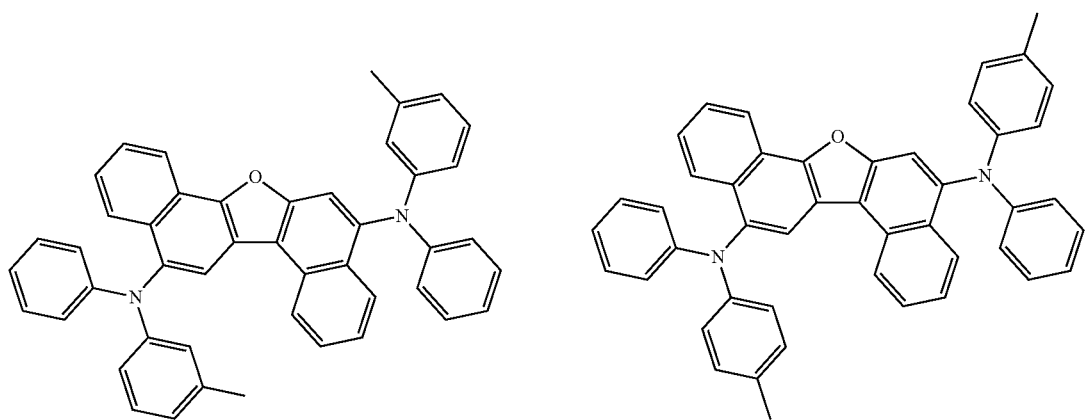

-continued
1037
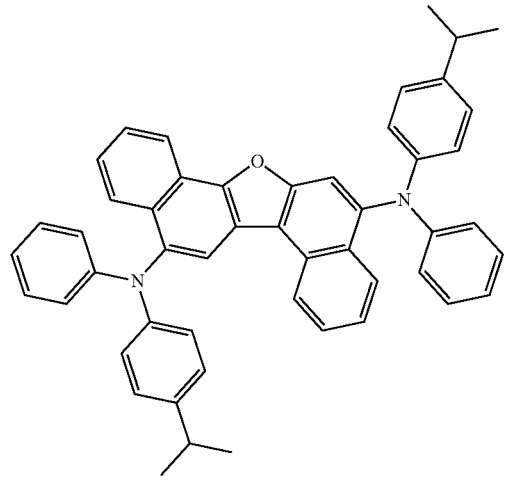
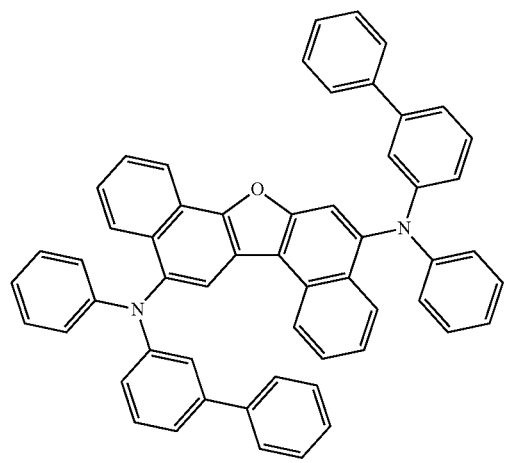
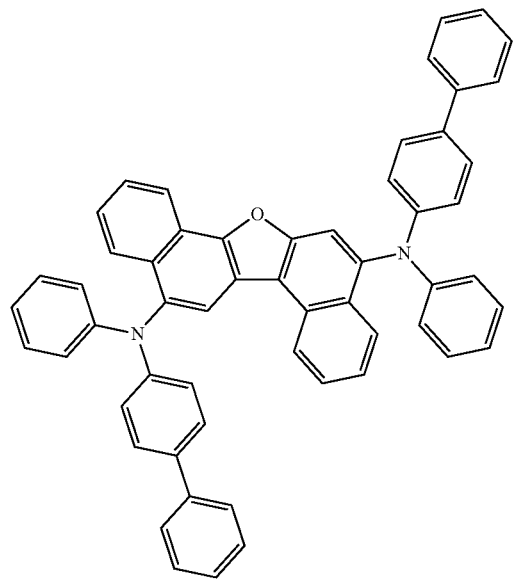
1038
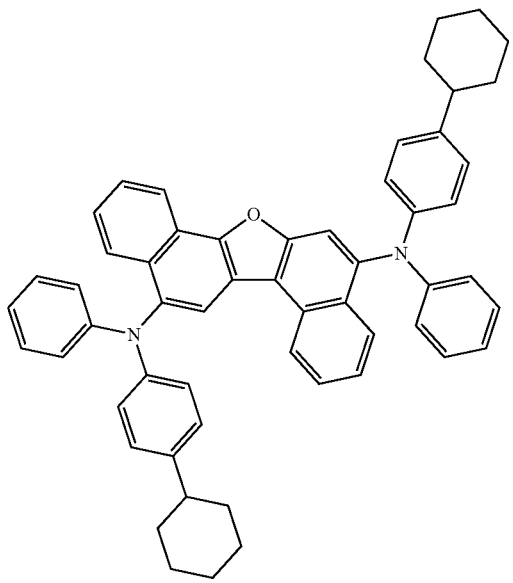
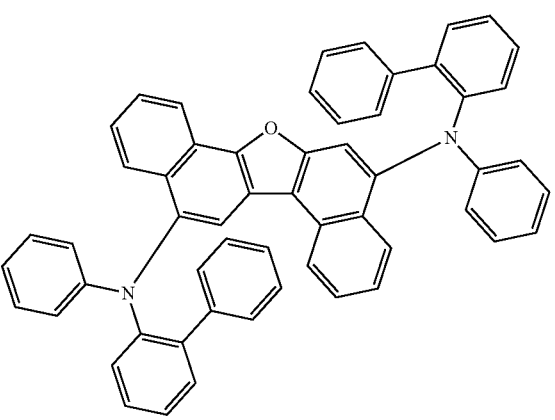
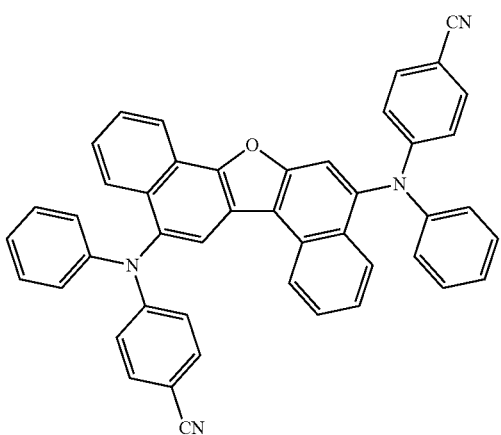

-continued
1039
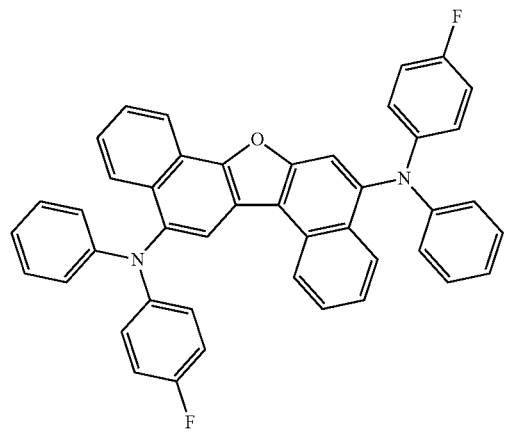
1040
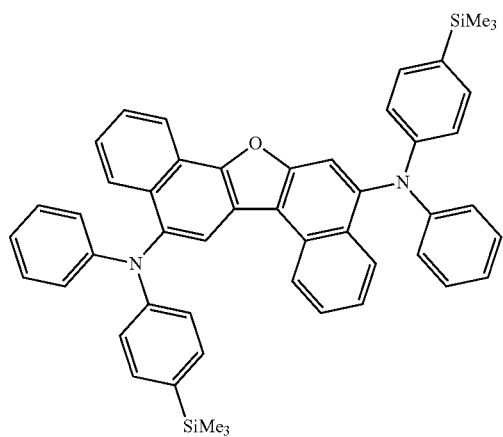
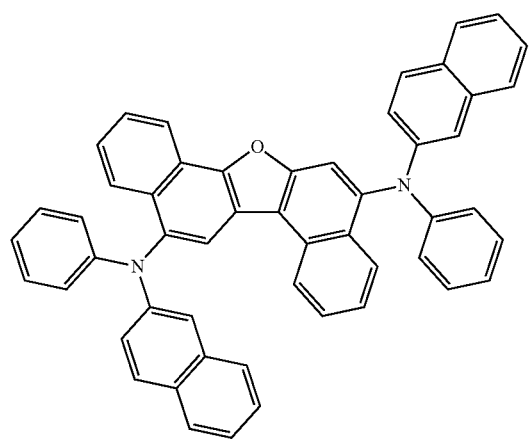
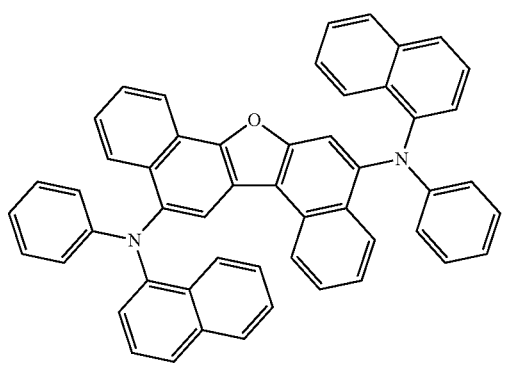
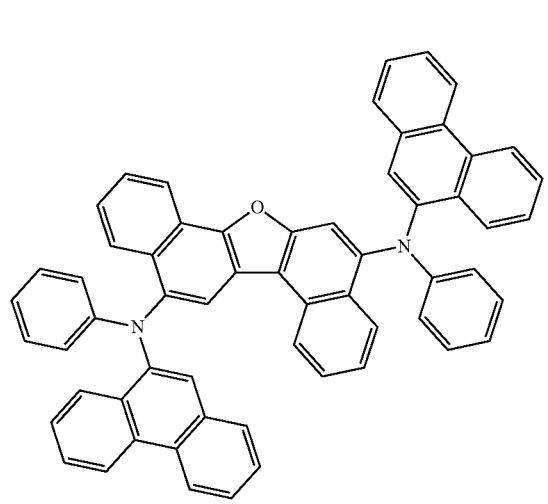
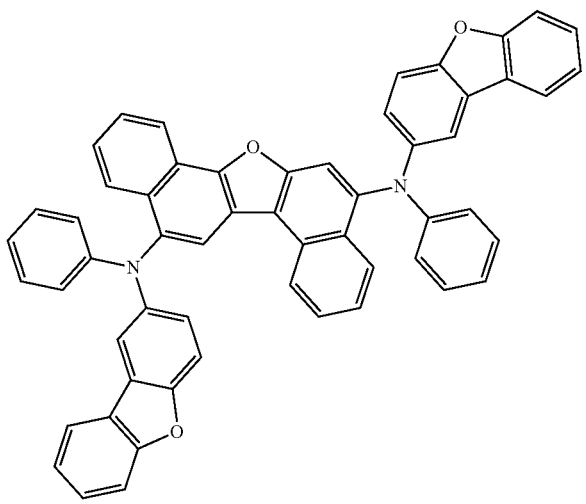

1041 1042
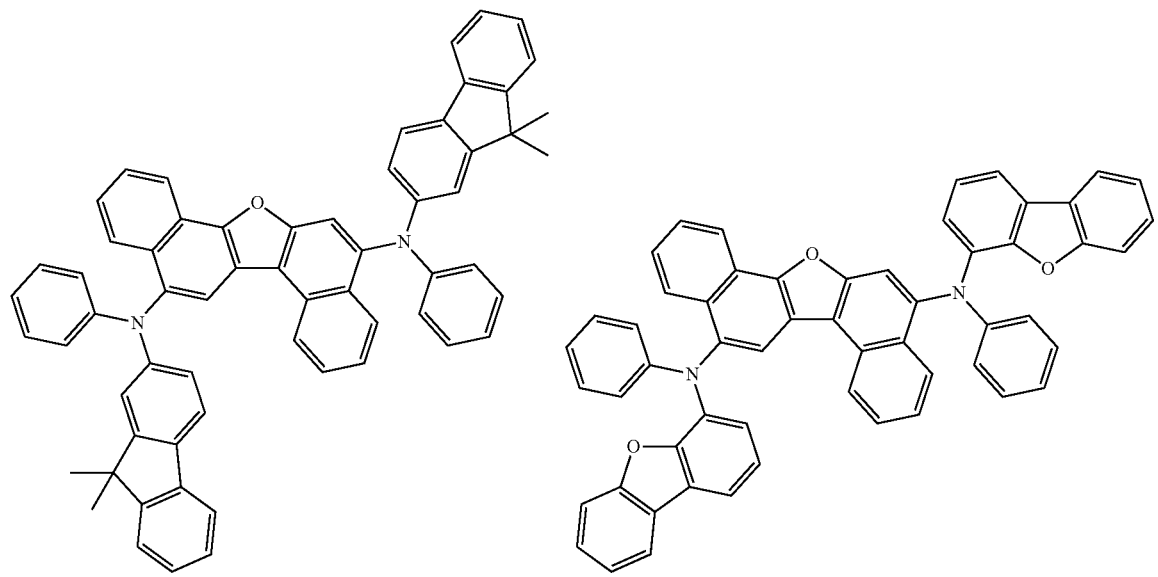
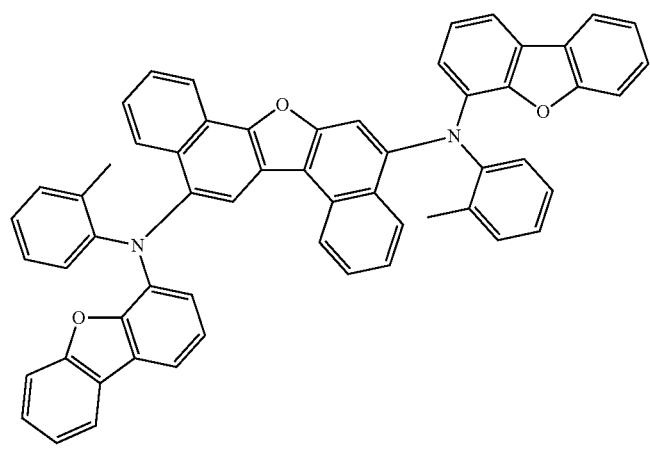
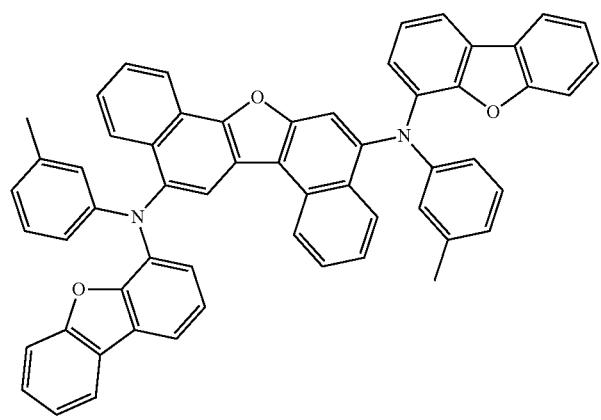

-continued
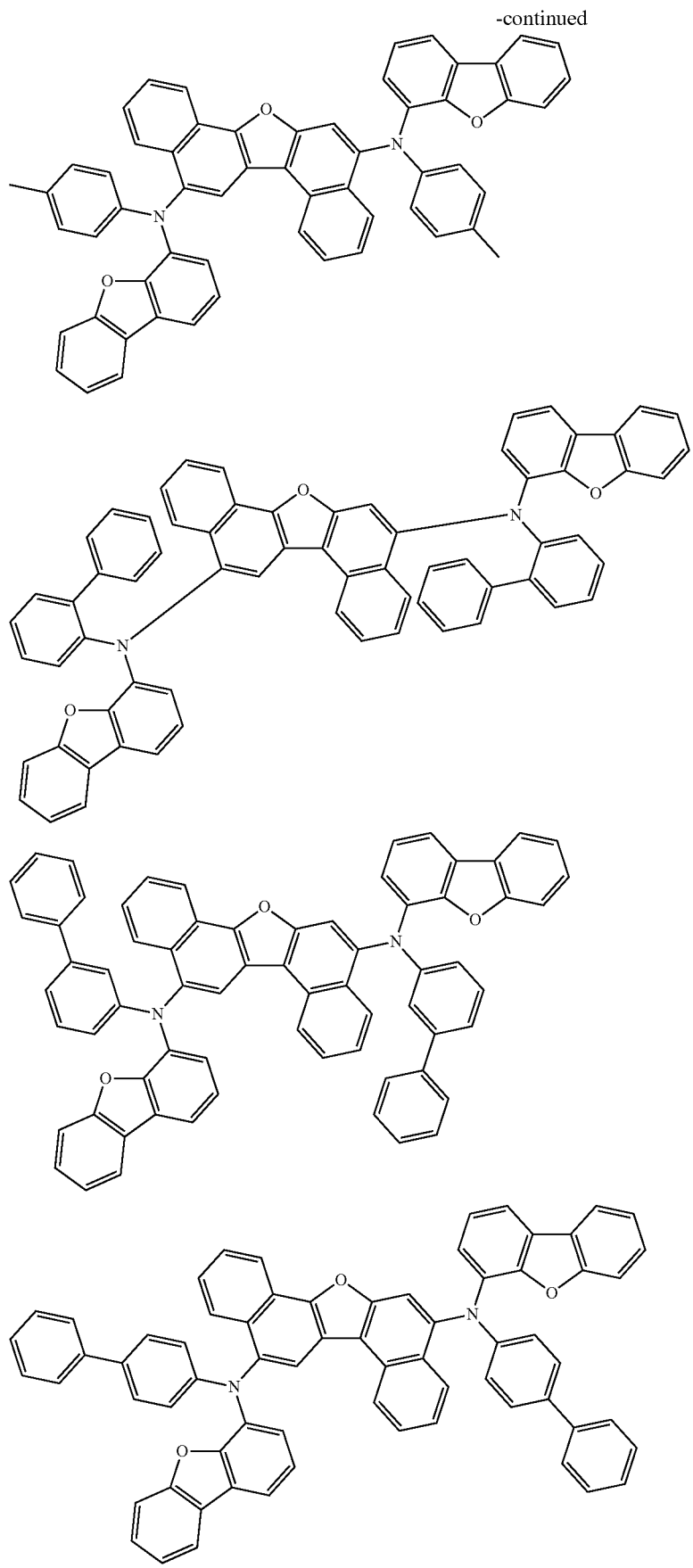

-continued
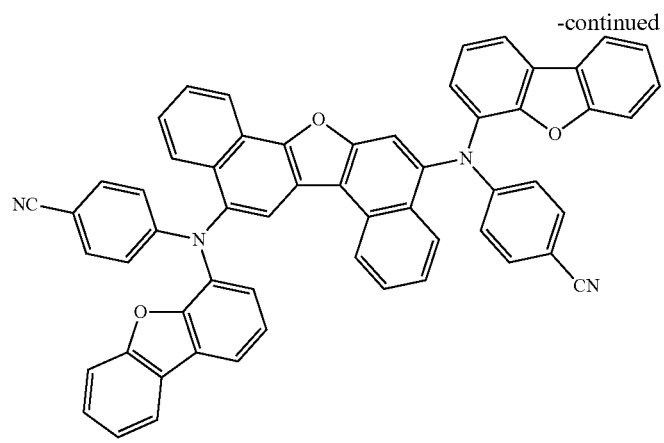
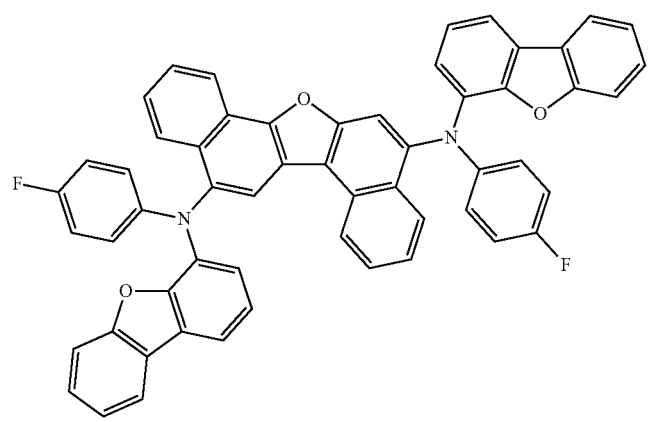
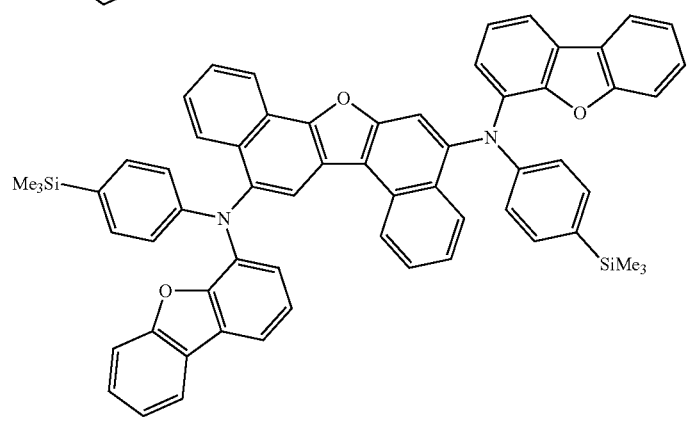
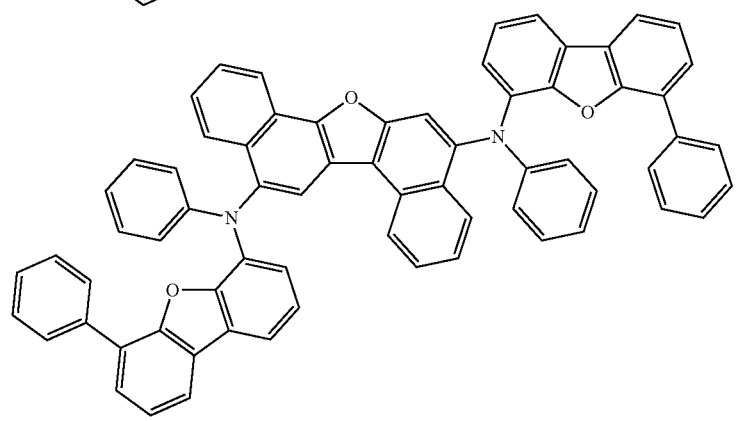

-continued
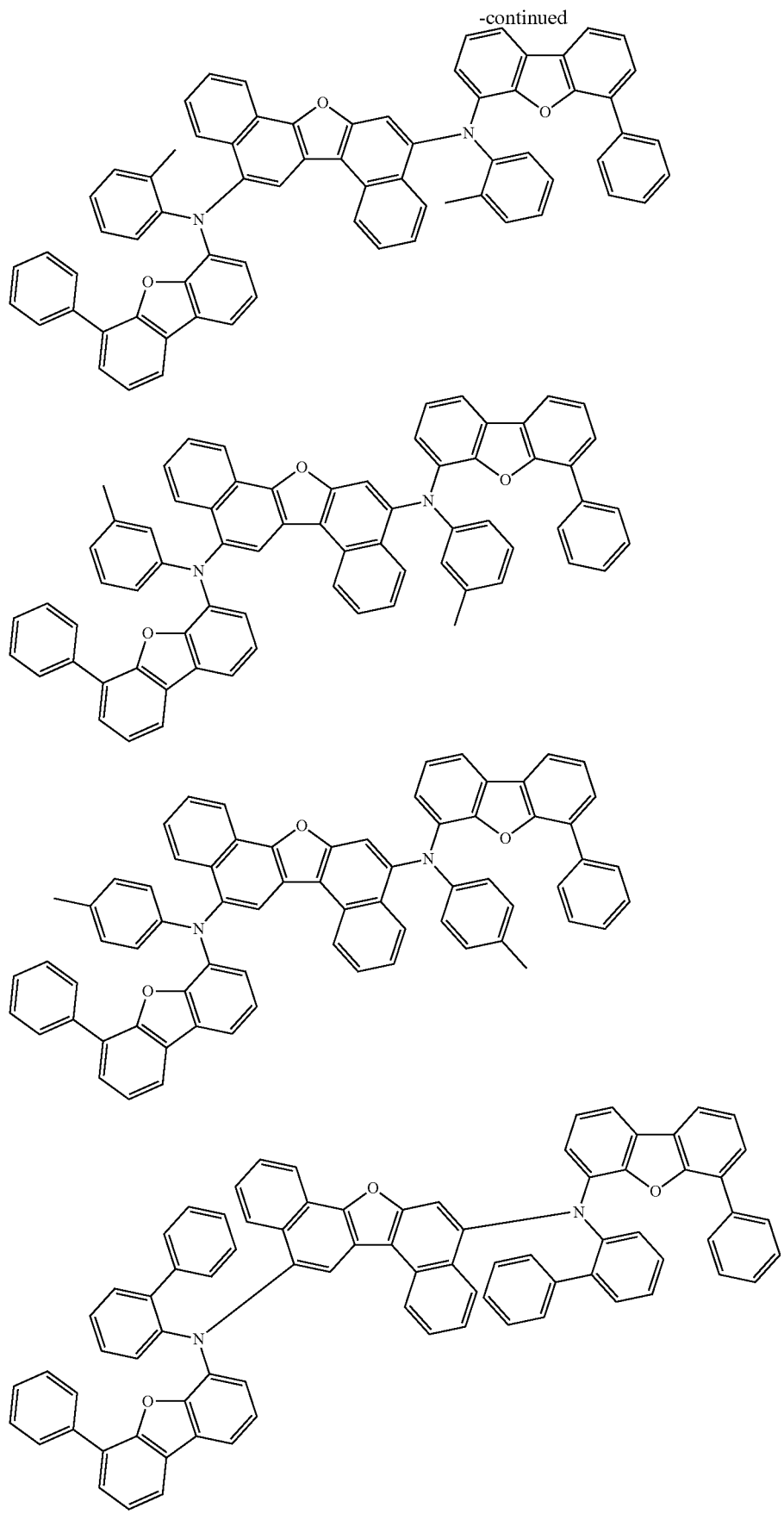

1049
-continued
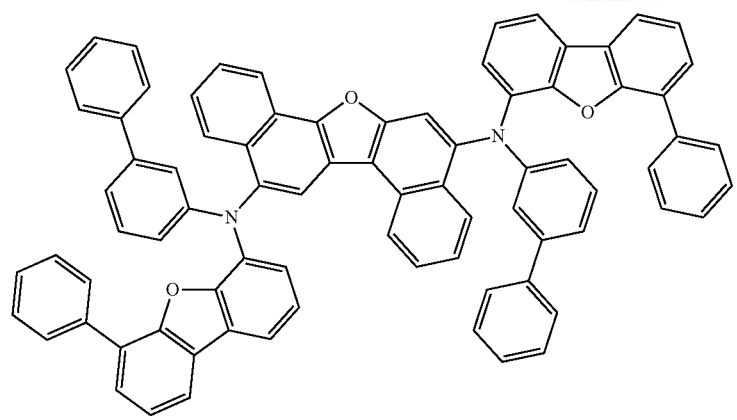
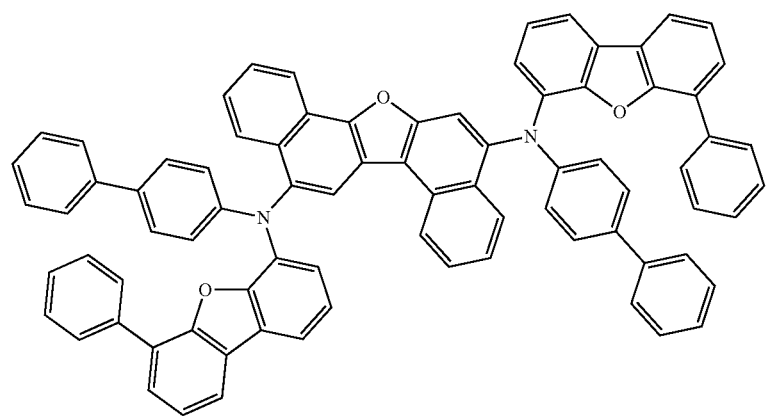
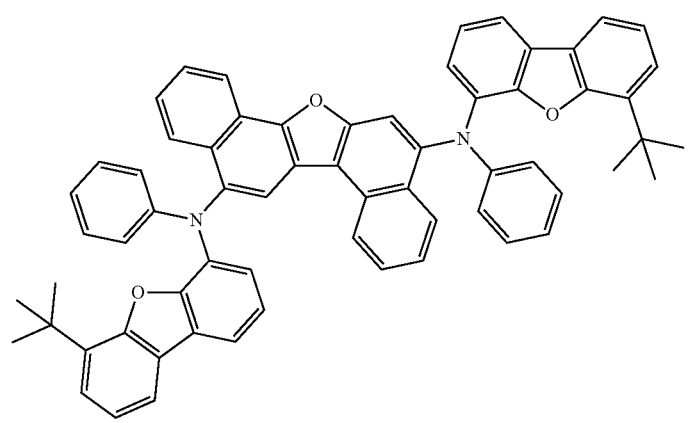
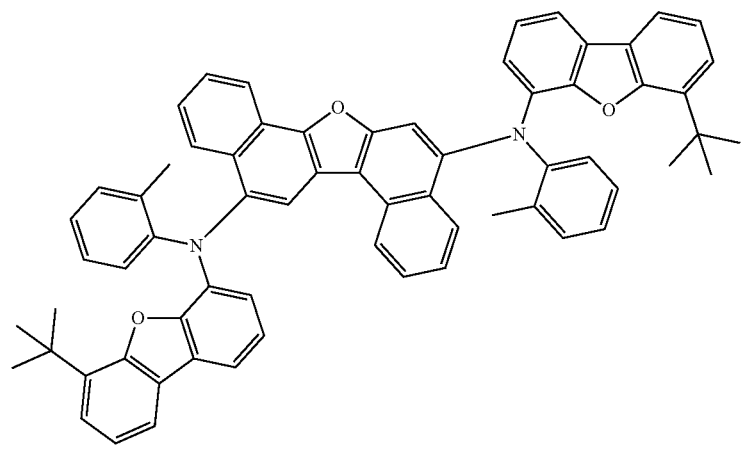
1050

1051  1052
-continued
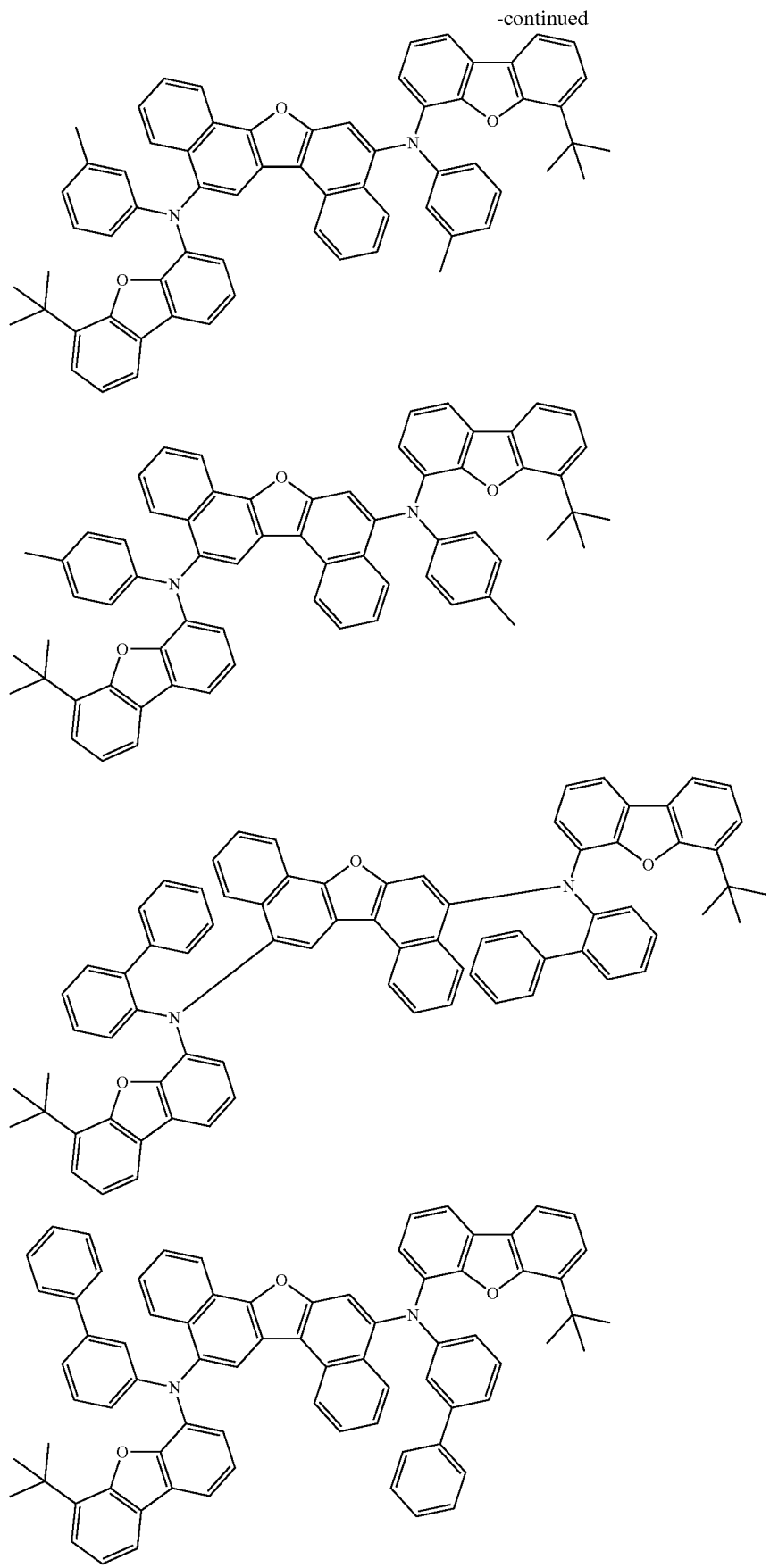

1053
-continued
1054
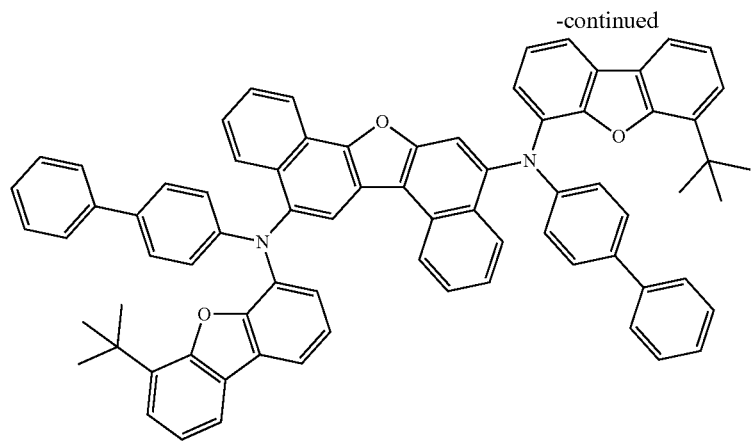
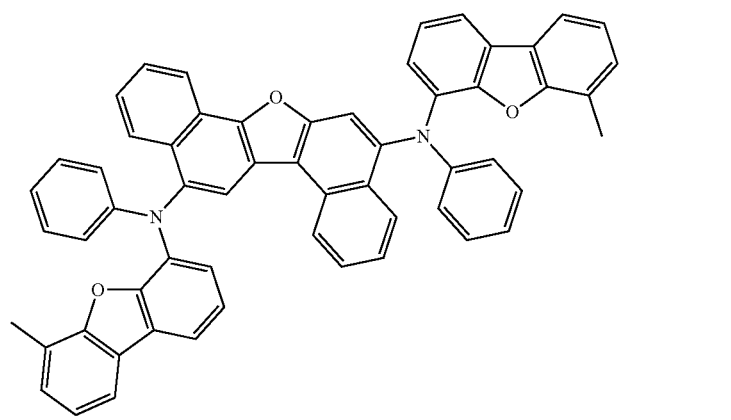
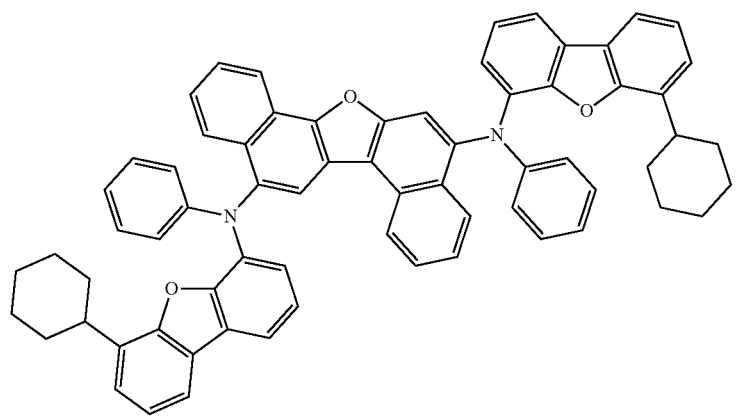
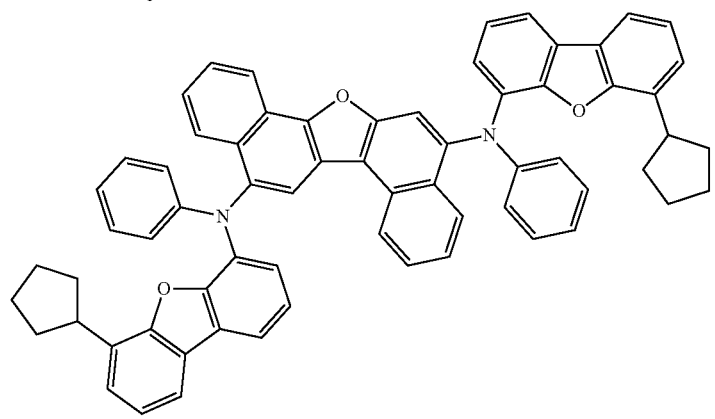

1055   1056
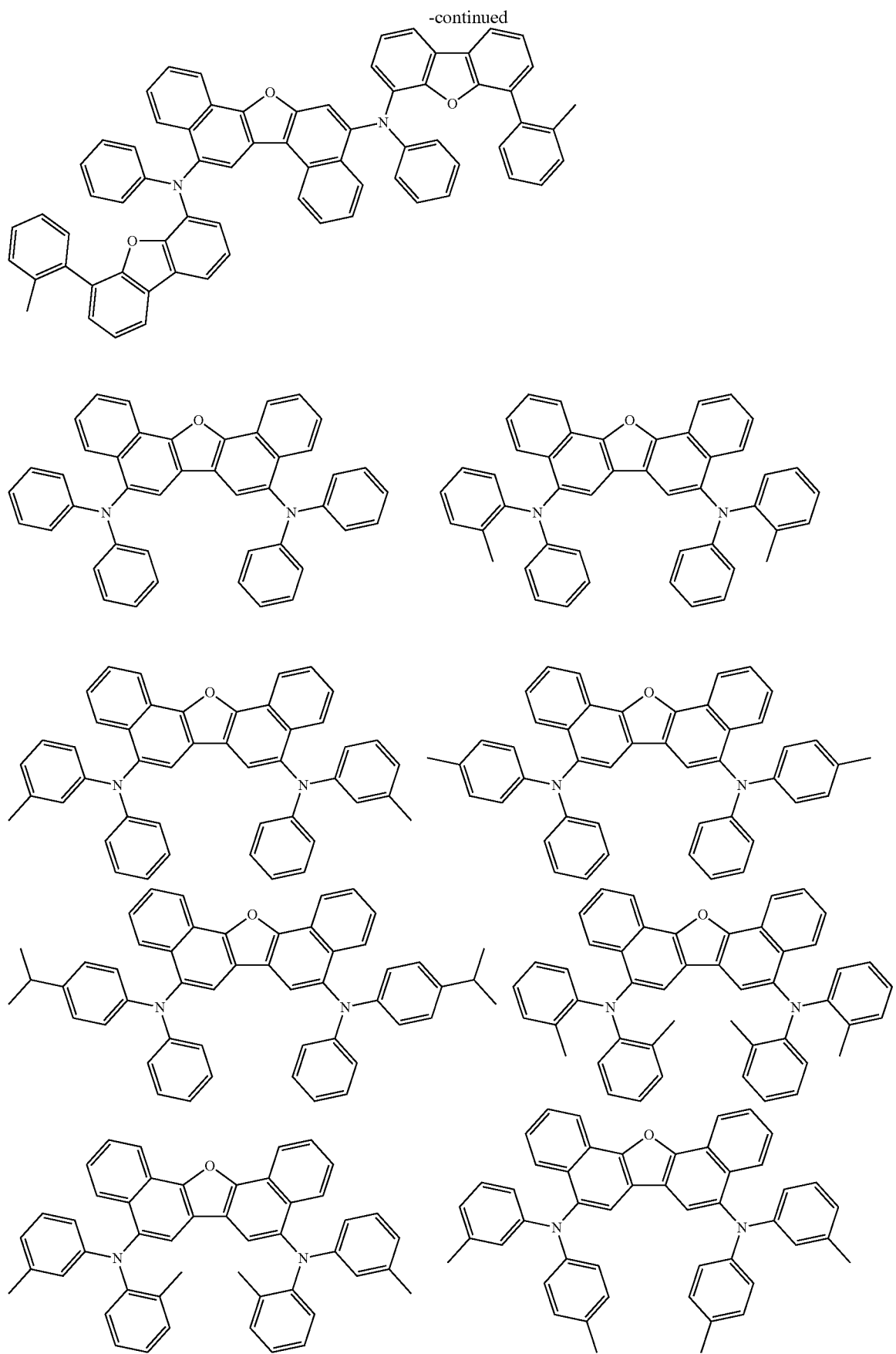
-continued 1057 1058
-continued
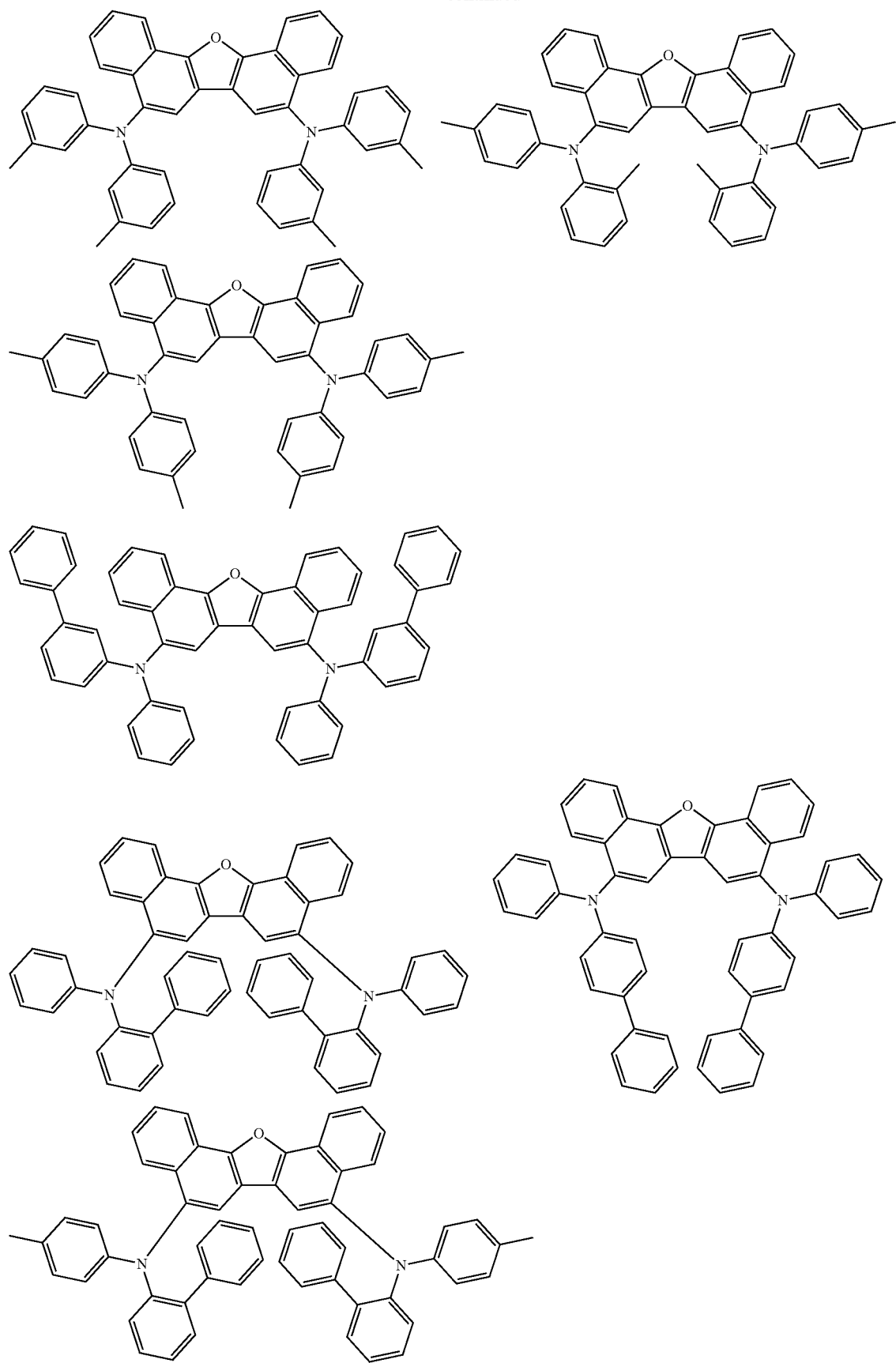

-continued
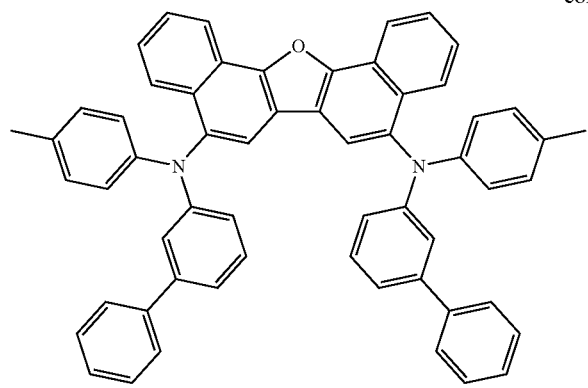
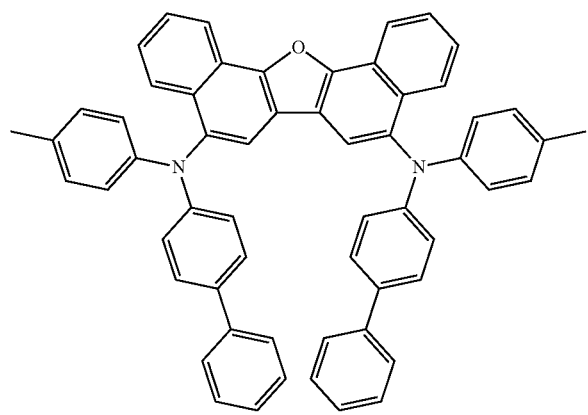
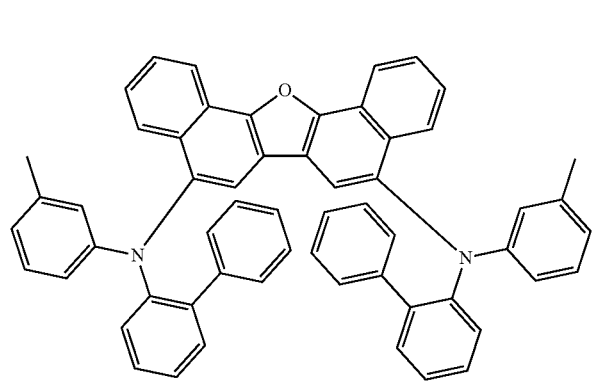
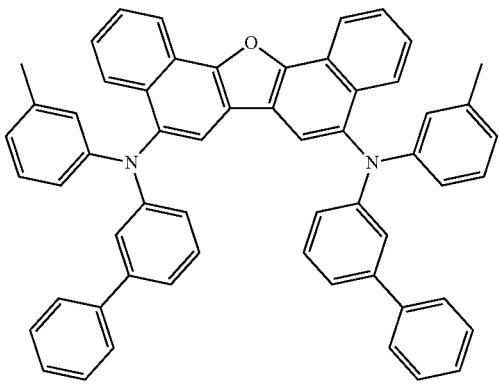
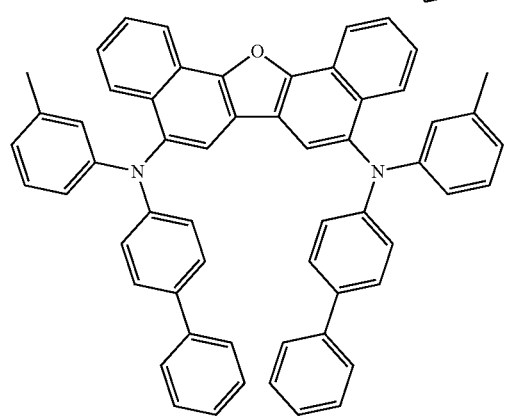
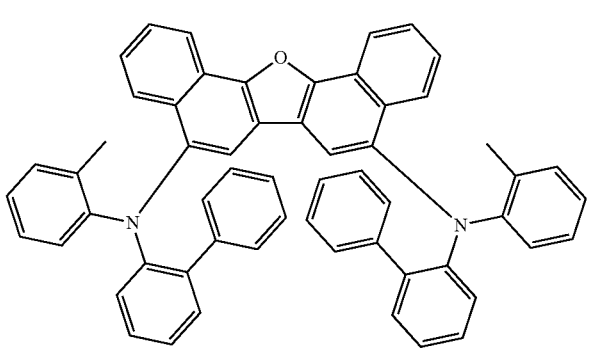

1061
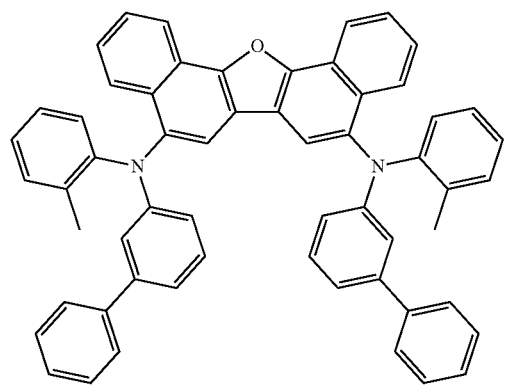
1062
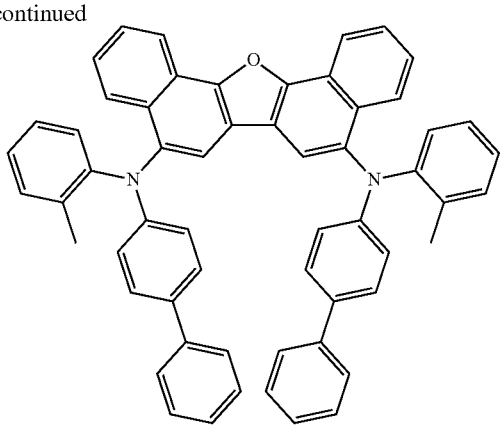
-continued
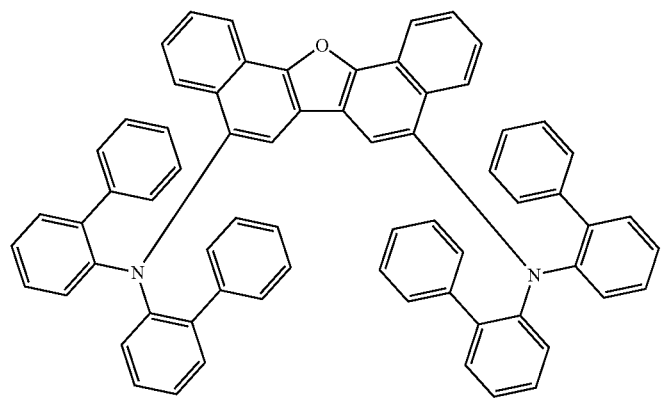
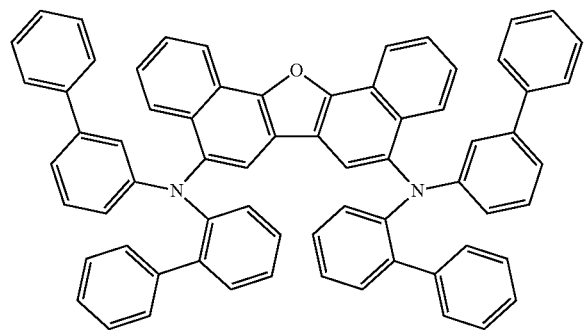
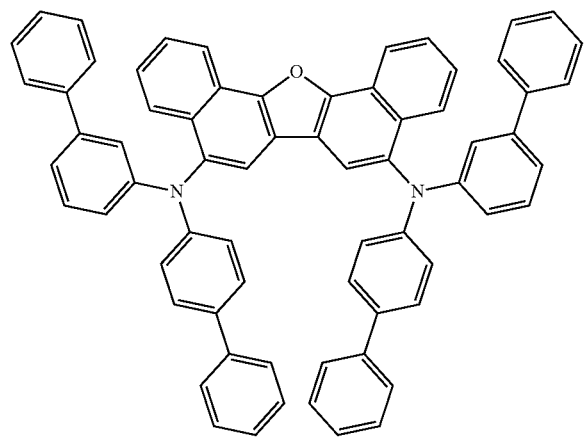

-continued
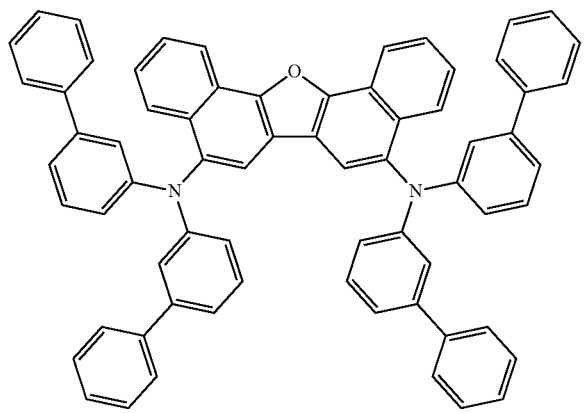
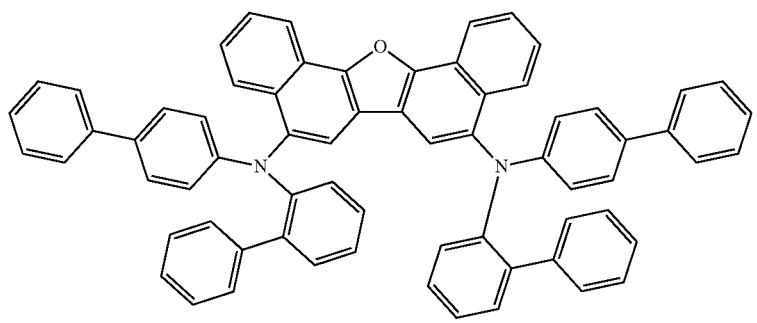
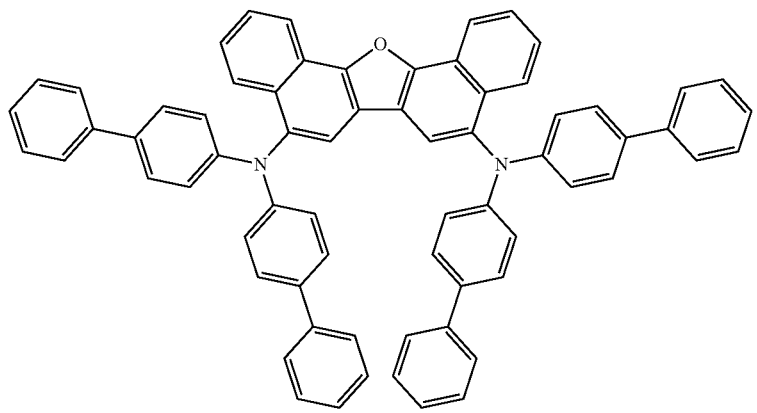
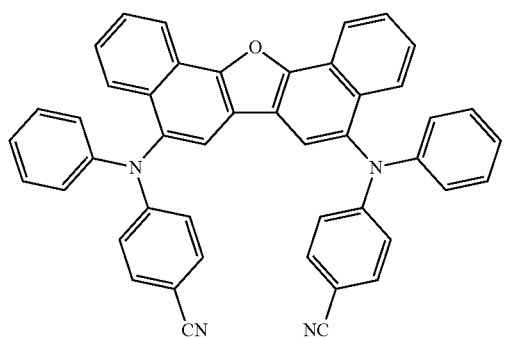
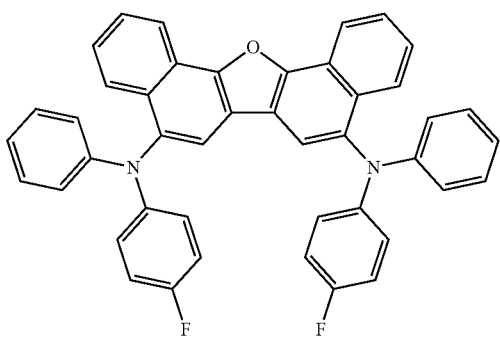

1065 1066
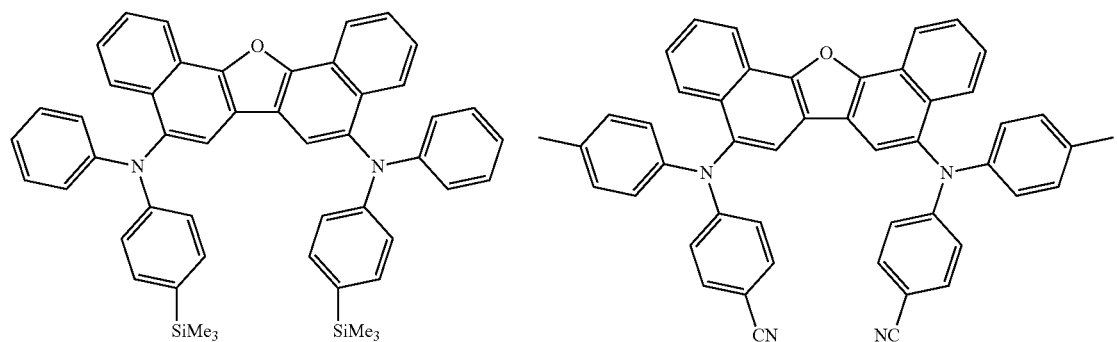
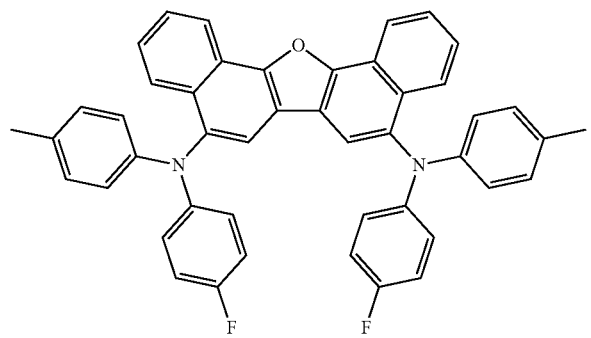
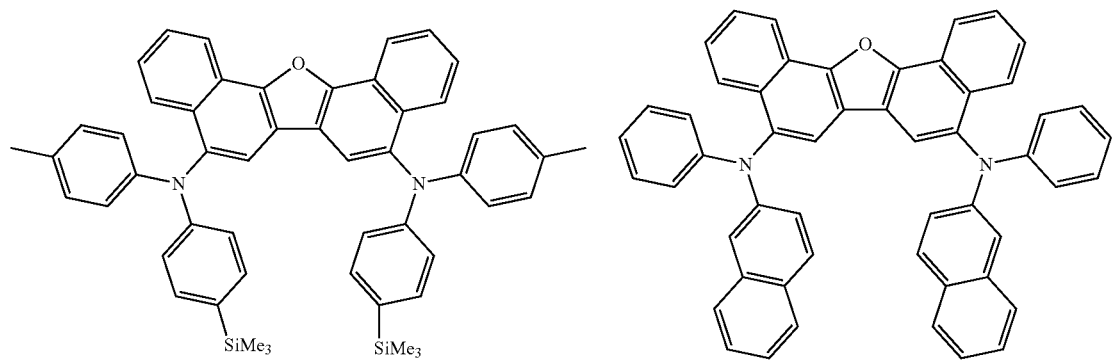
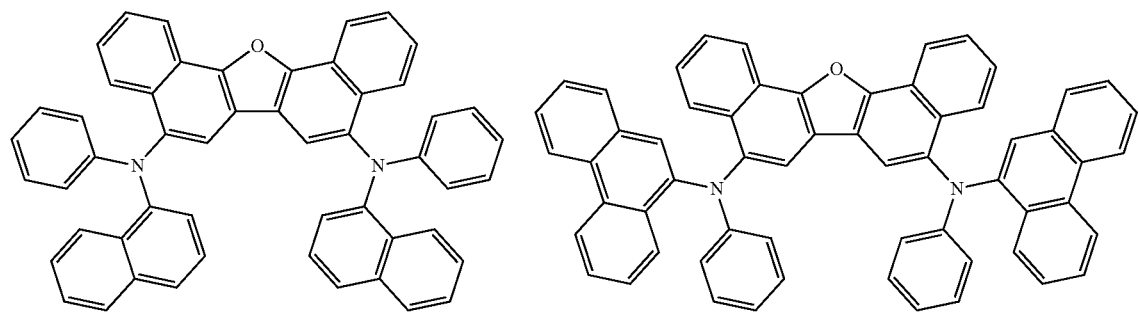

-continued
1067 1068
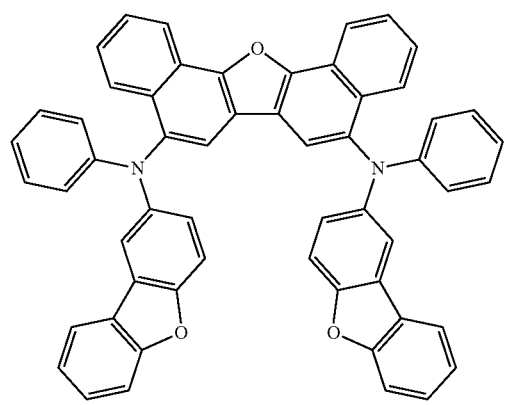
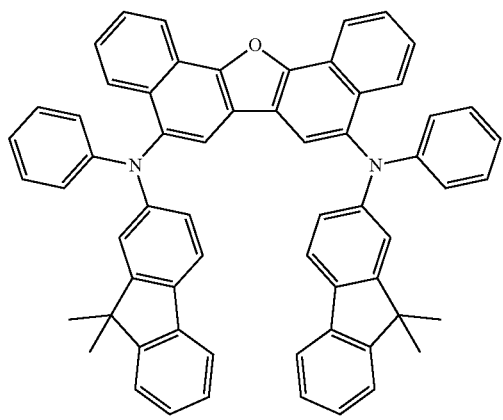
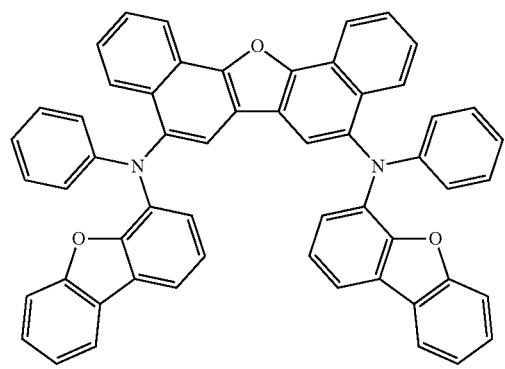
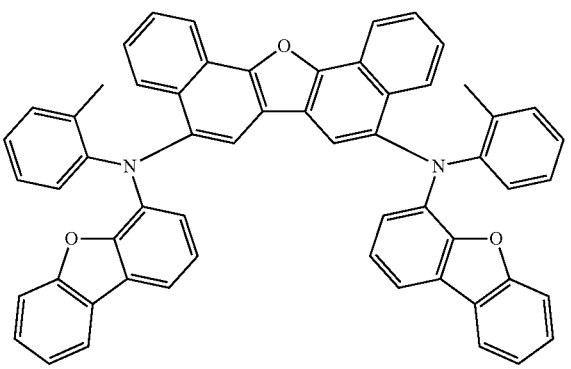
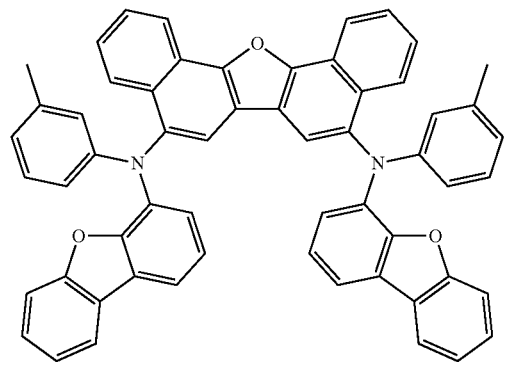
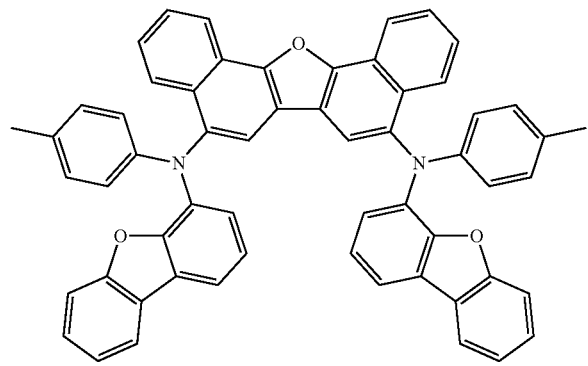
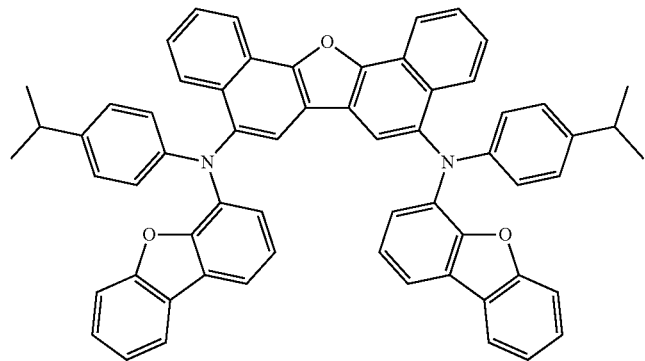

1069 1070
-continued
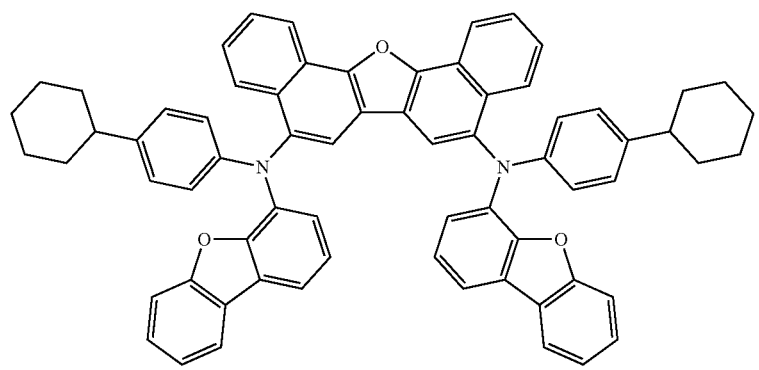
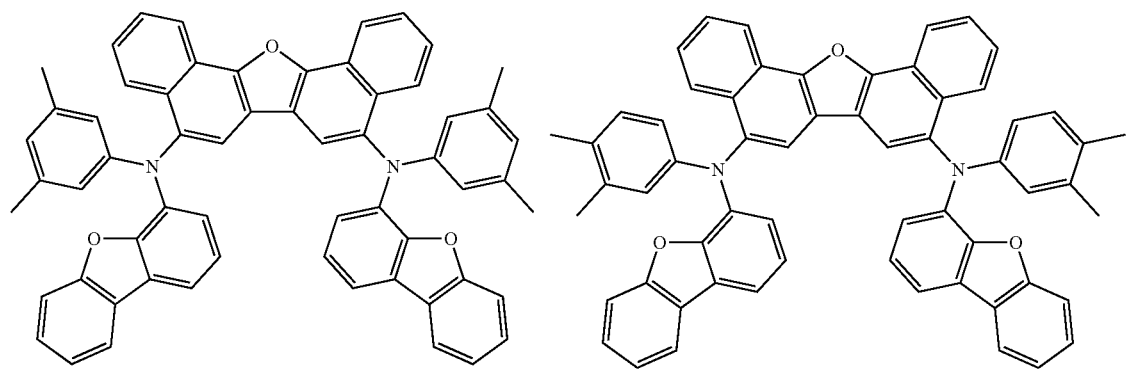
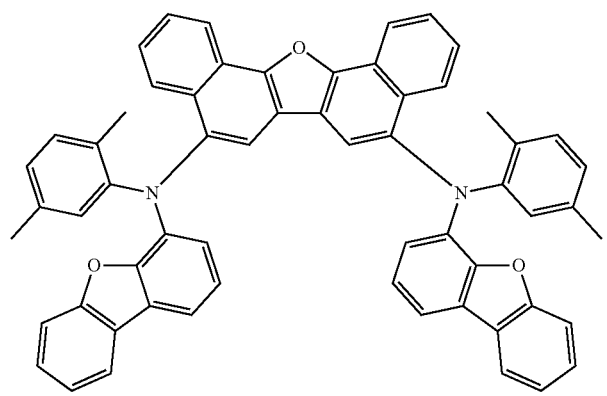
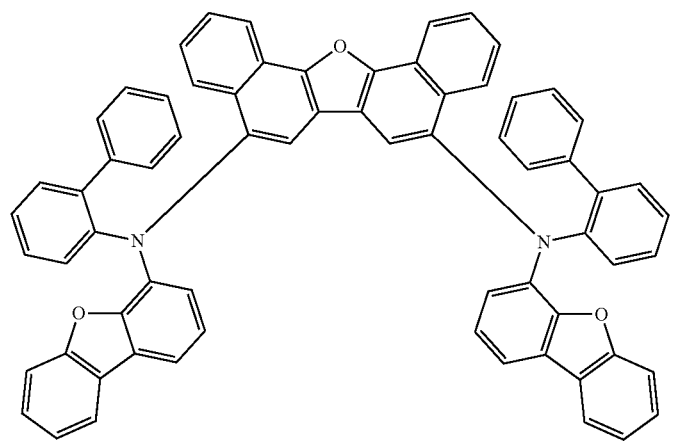

1071 1072
-continued
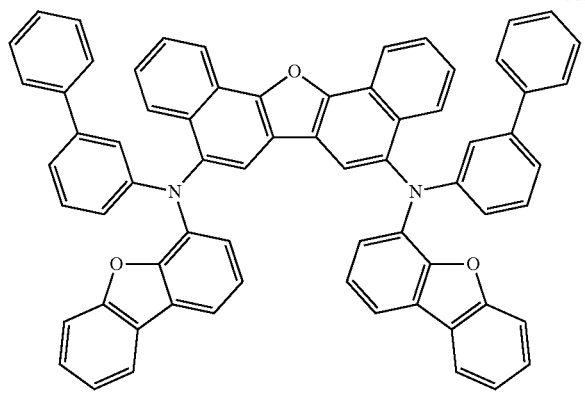

-continued
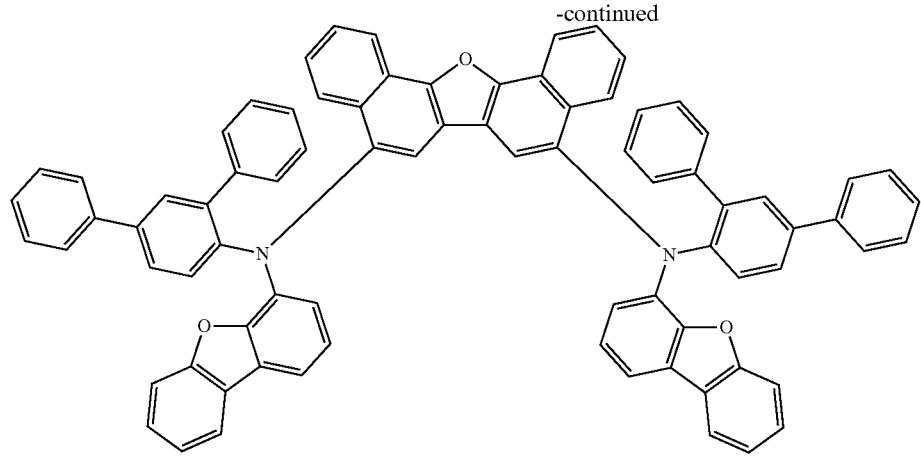
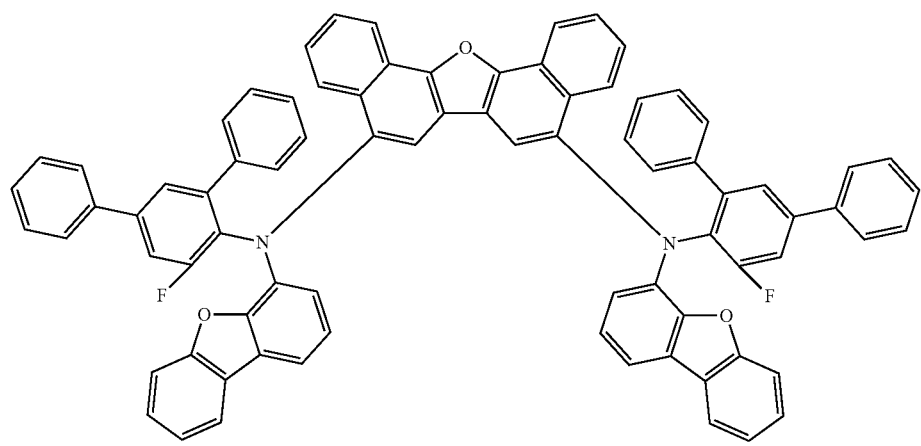
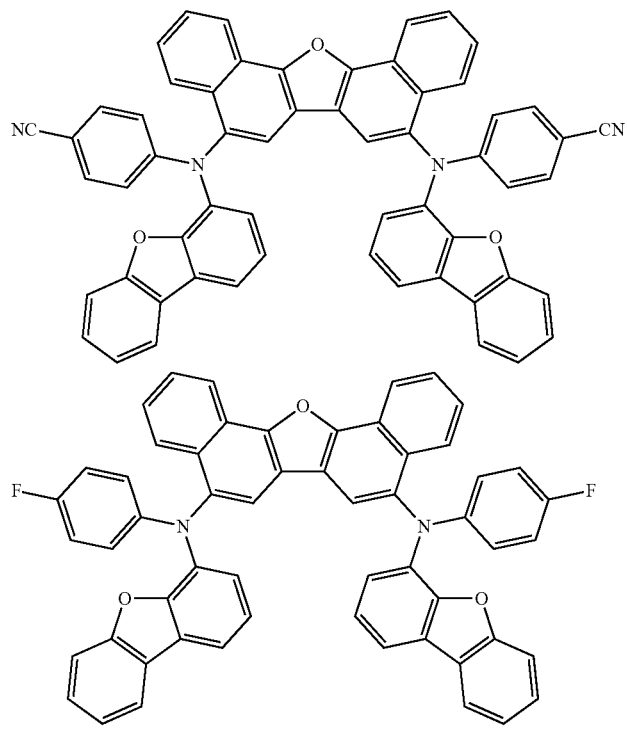

1075
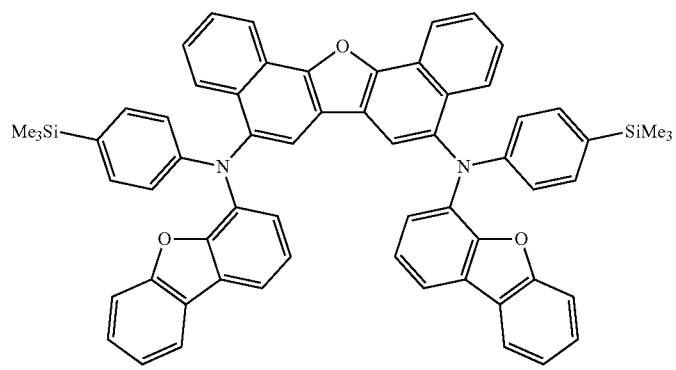
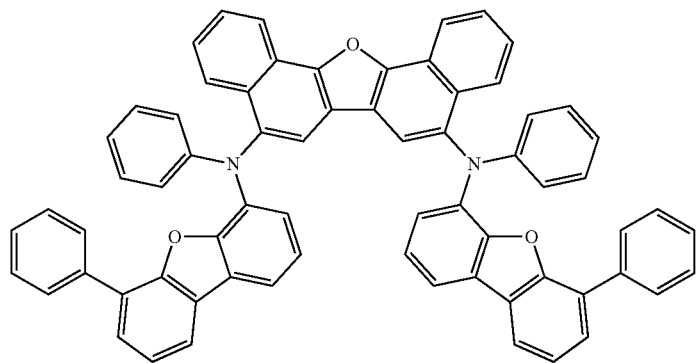
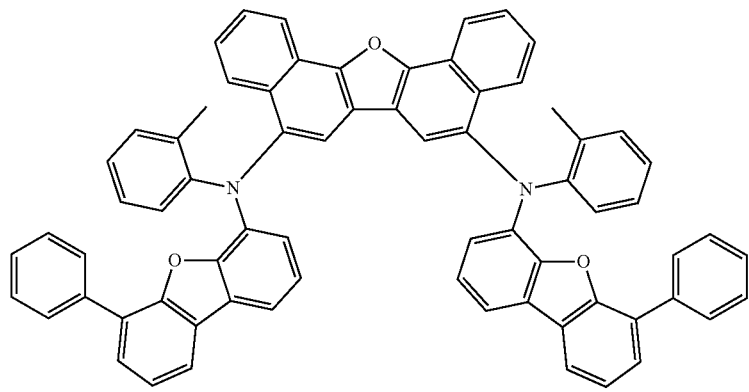
1076
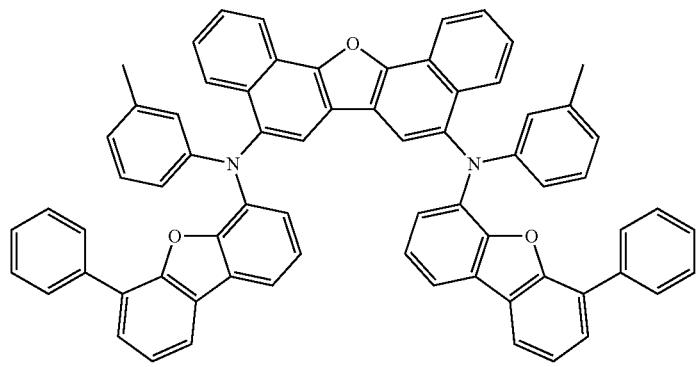

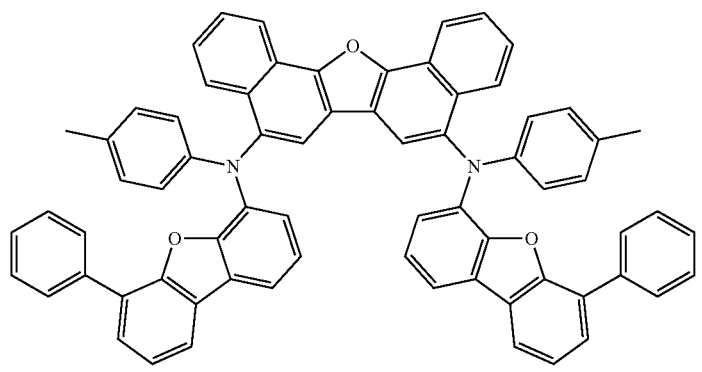
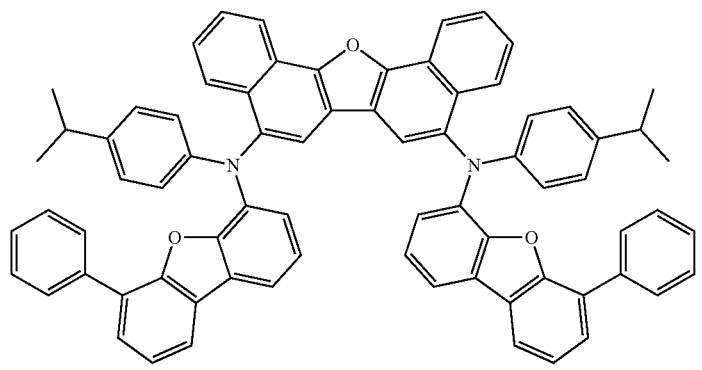
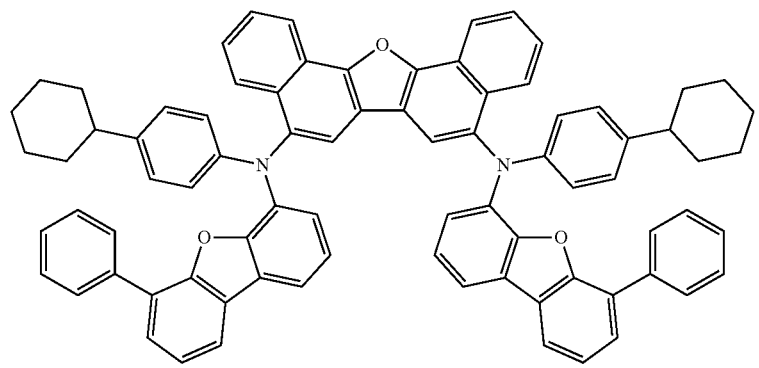
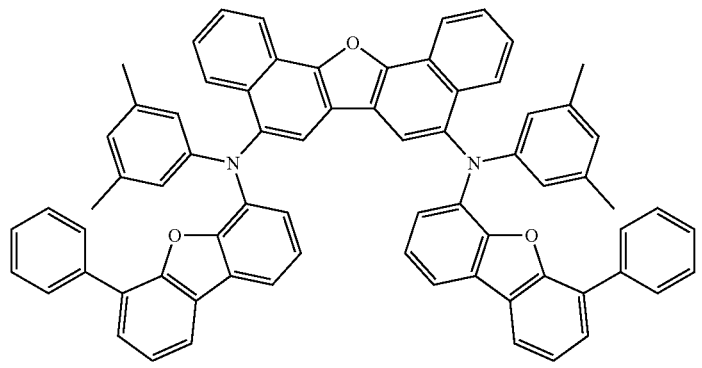

-continued
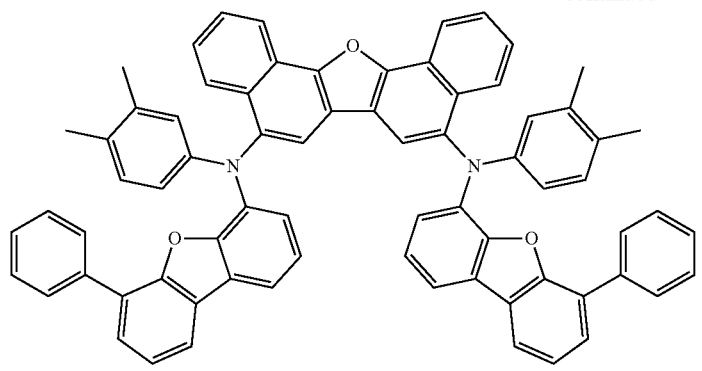
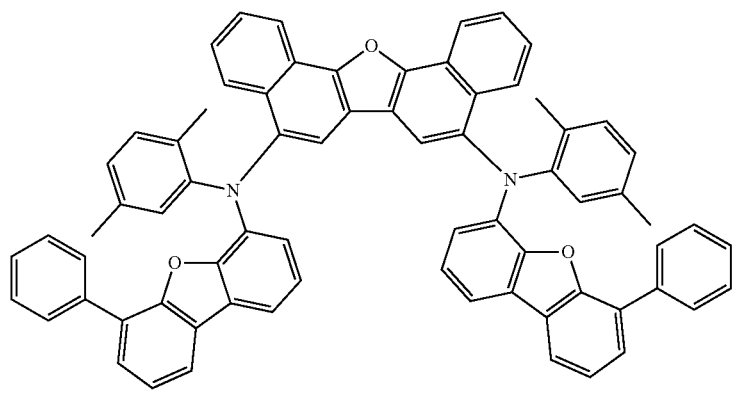
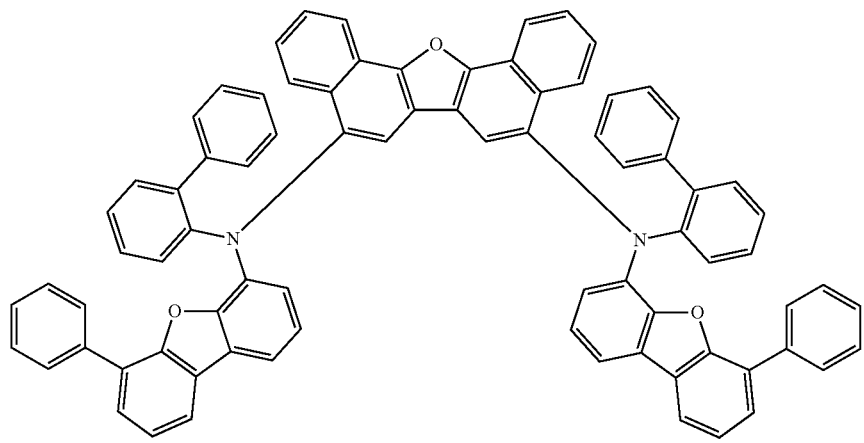
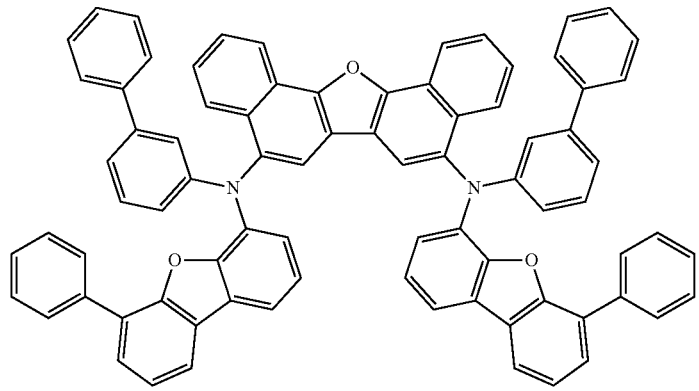

1081
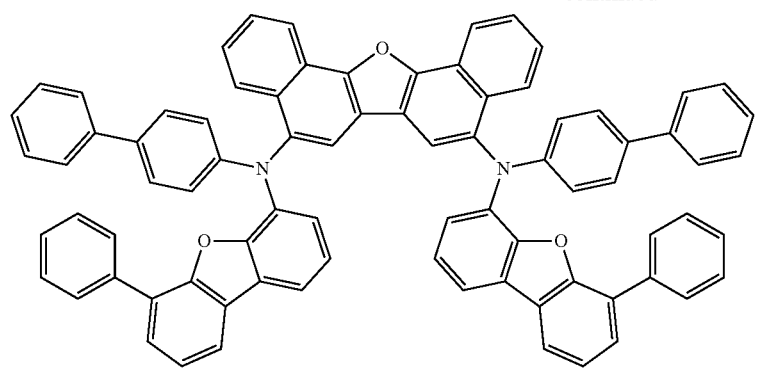
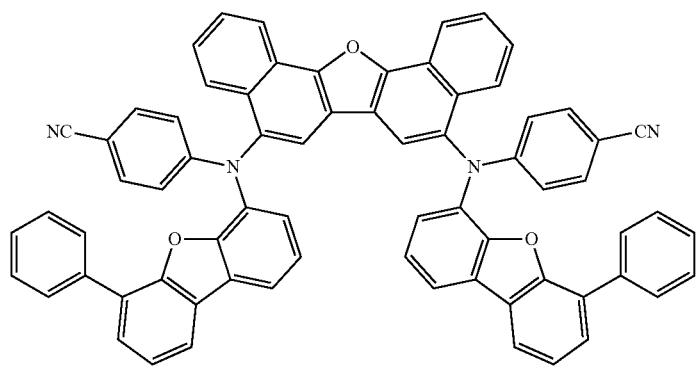
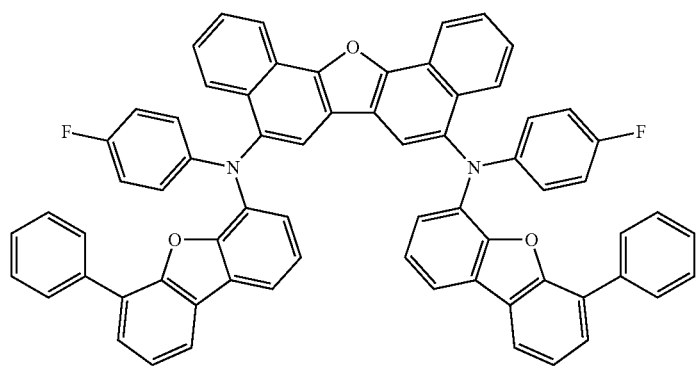
1082
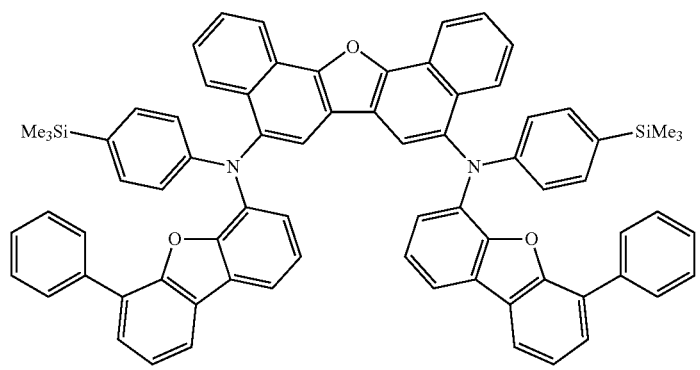

1083
-continued
1084
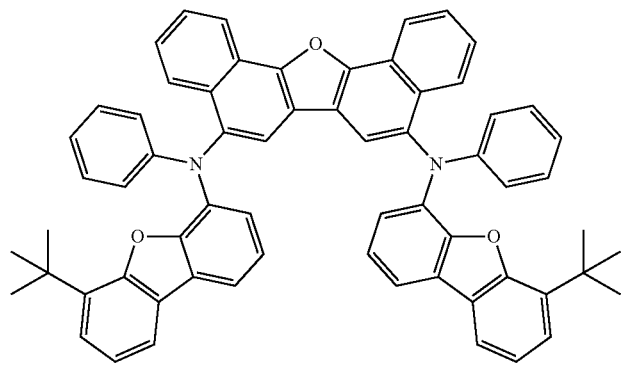
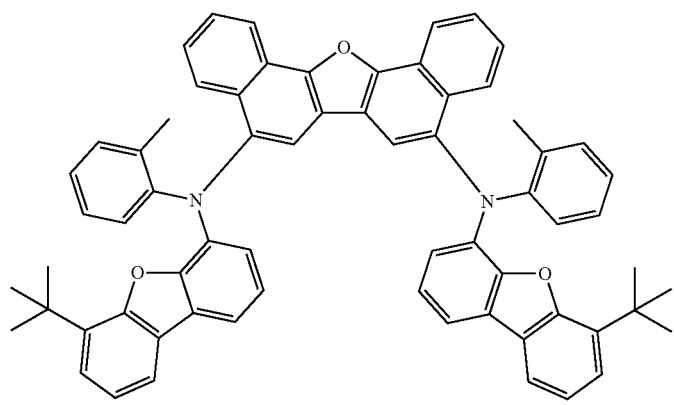
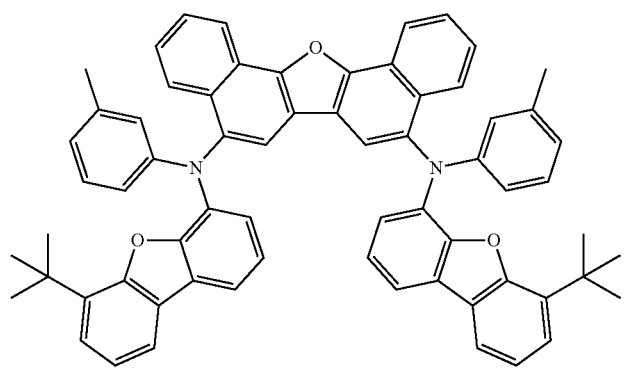
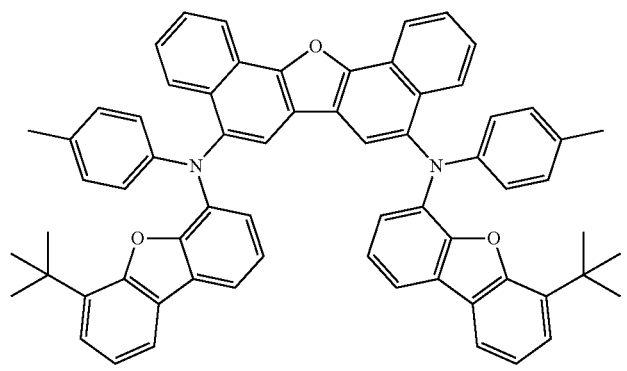

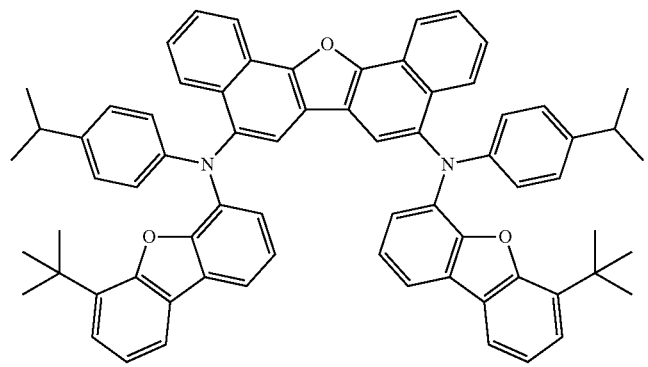
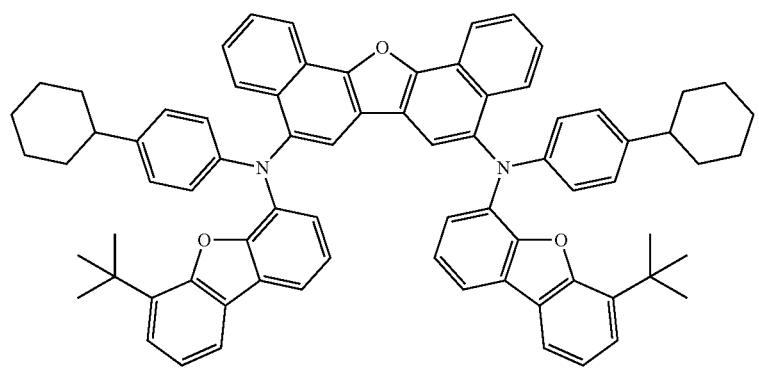
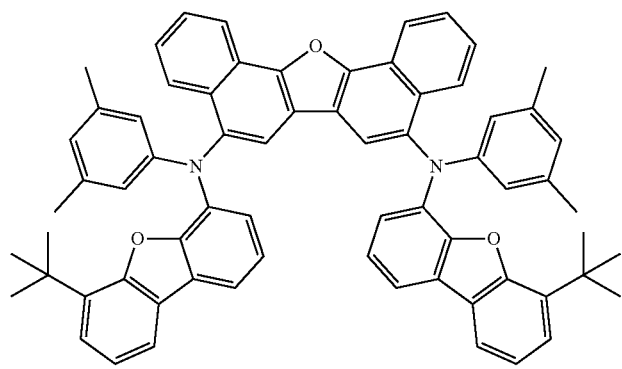
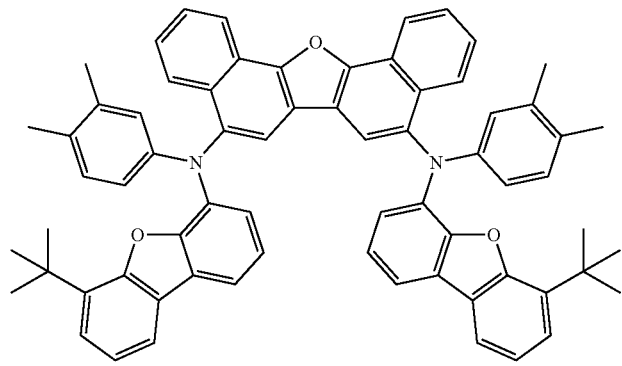

1087 1088
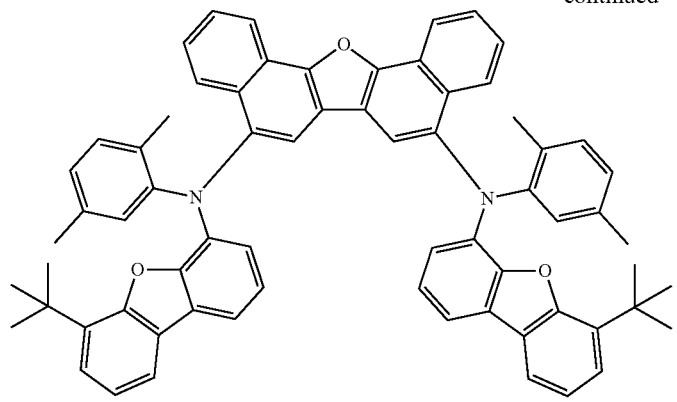
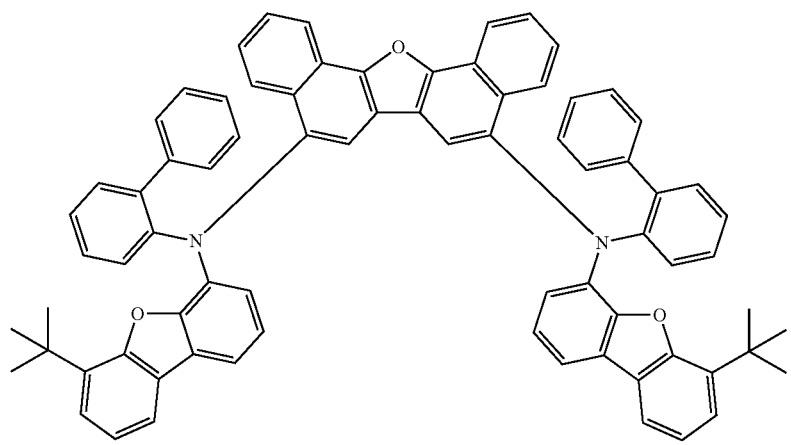
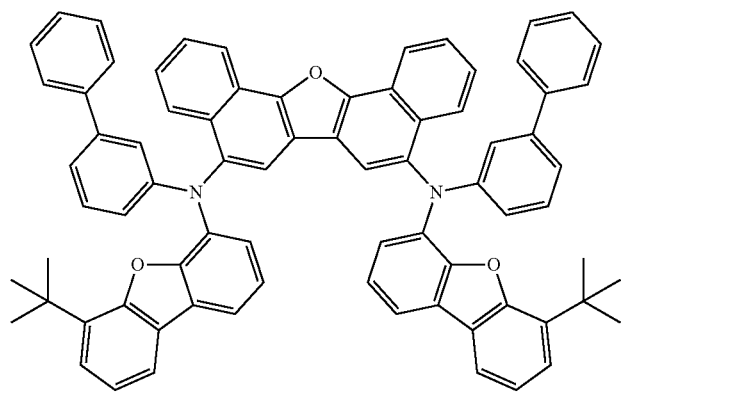
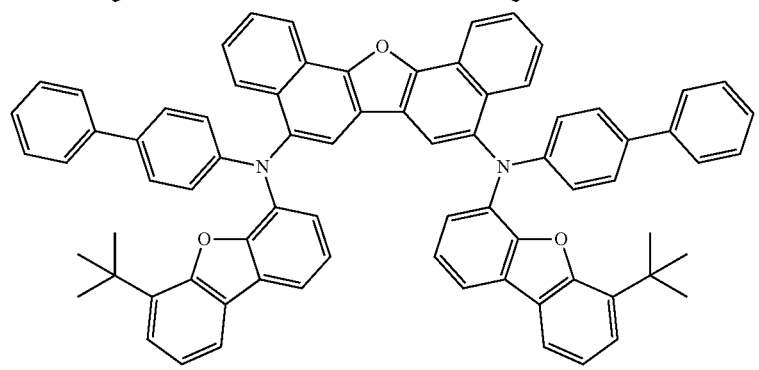

1089 1090
-continued
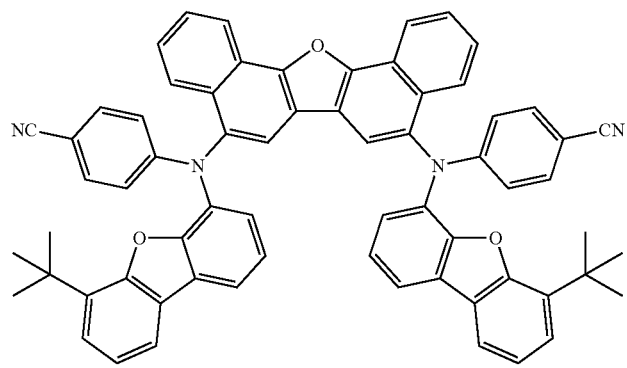
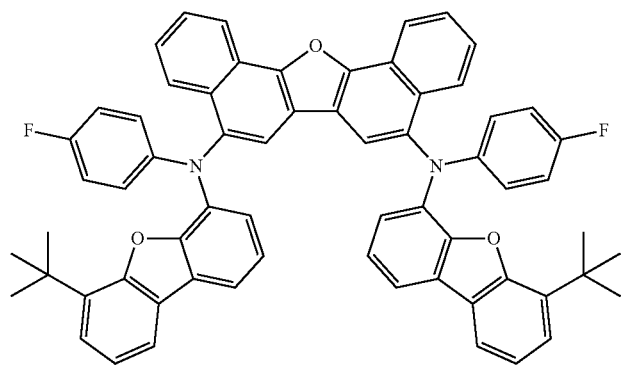
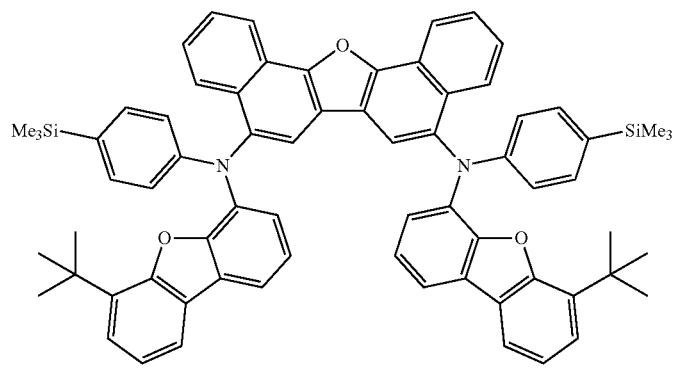
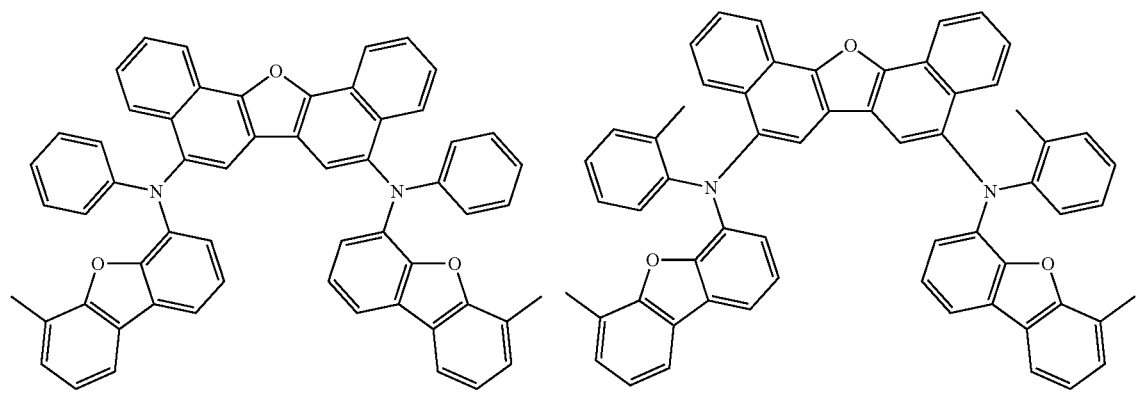

-continued
1091 1092
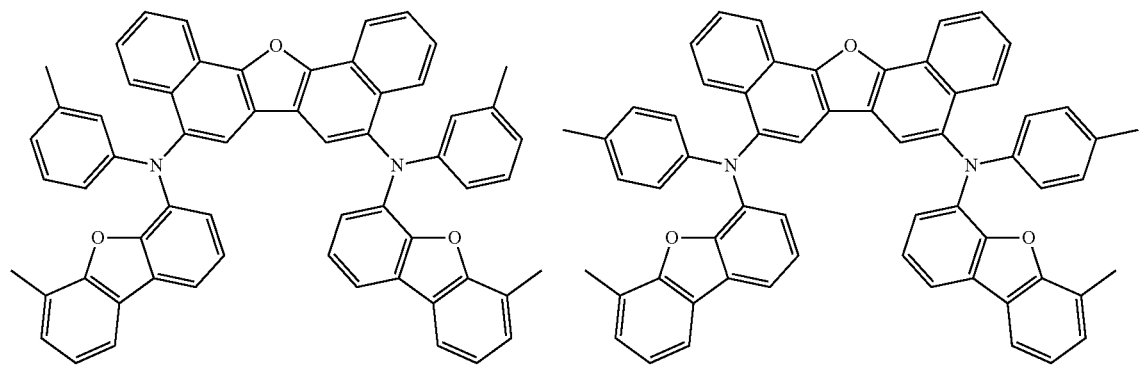
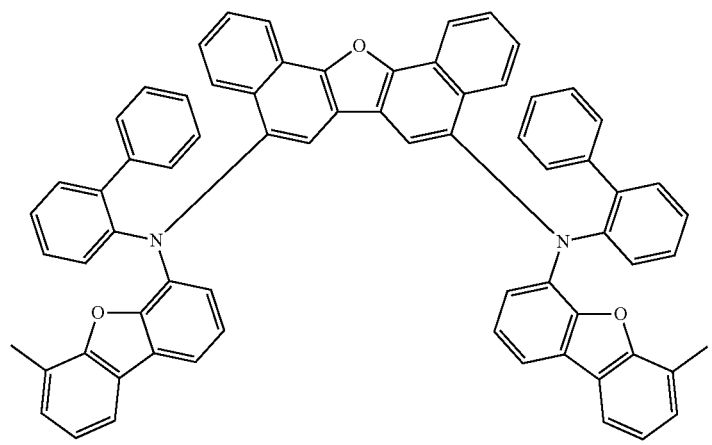
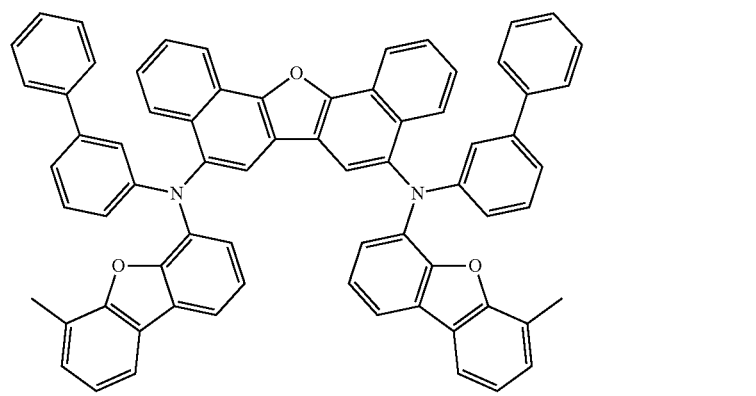
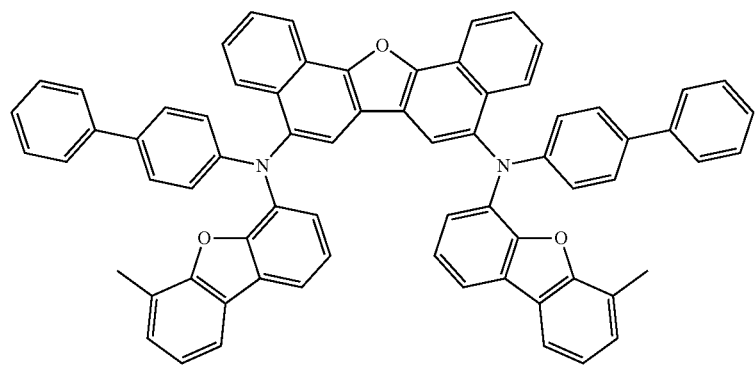

1093 1094
-continued
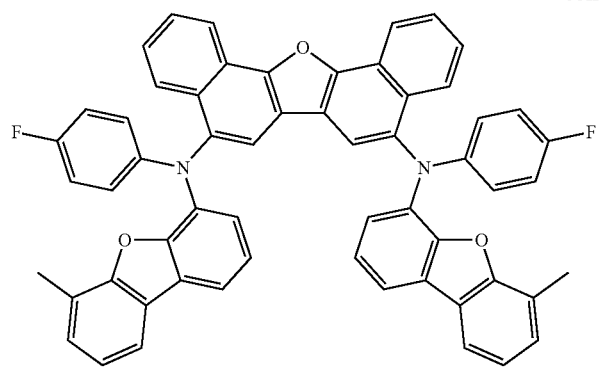
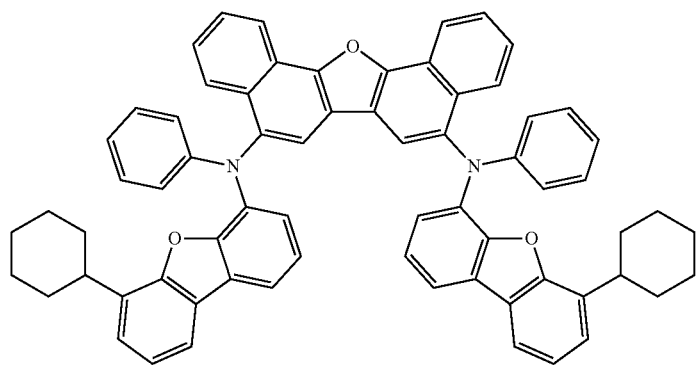
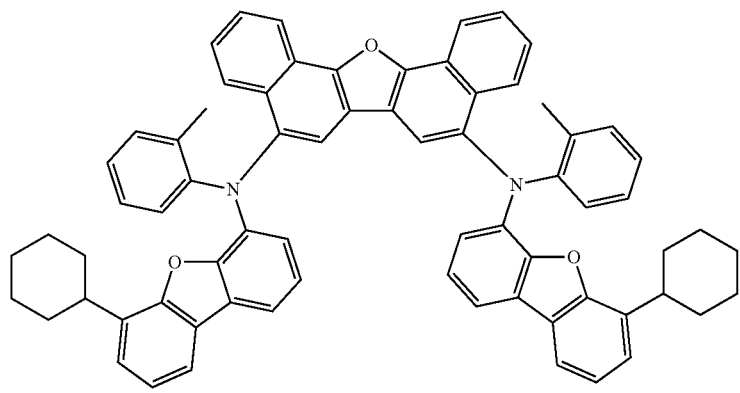
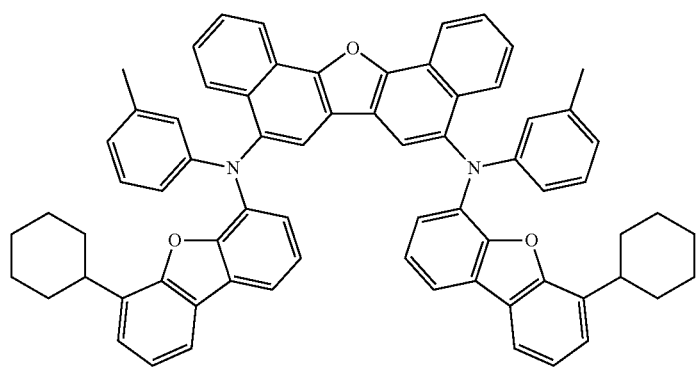

1095
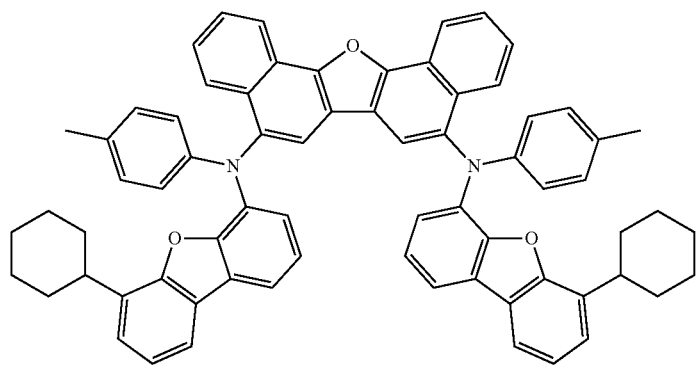
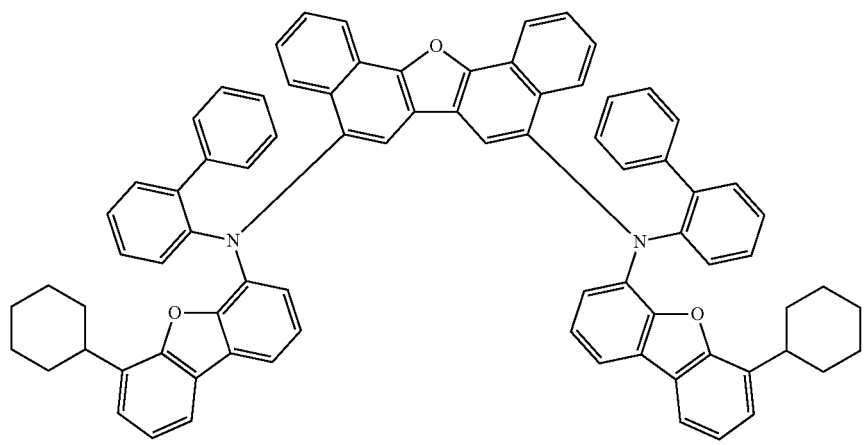
1096
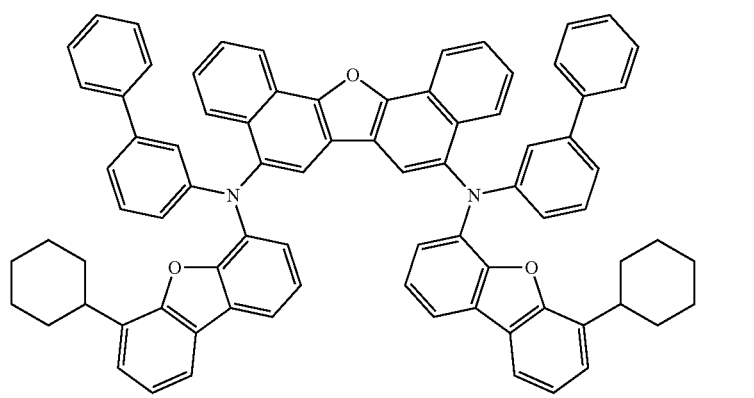
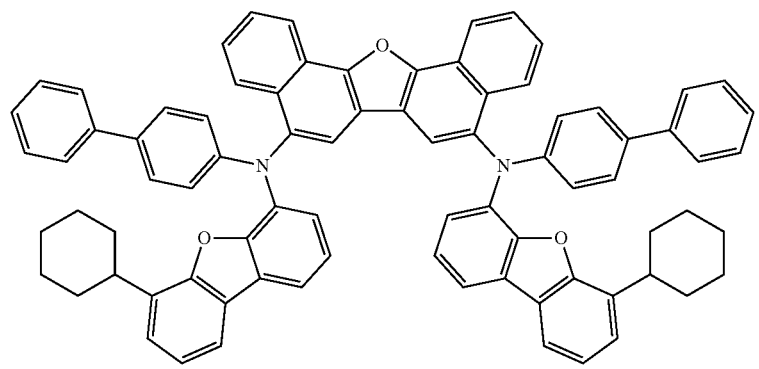

1097 1098
-continued
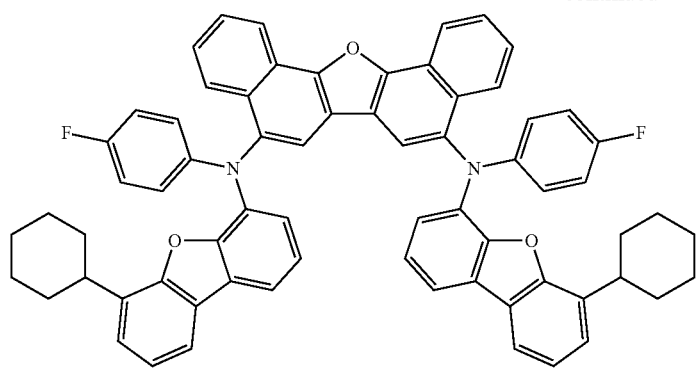
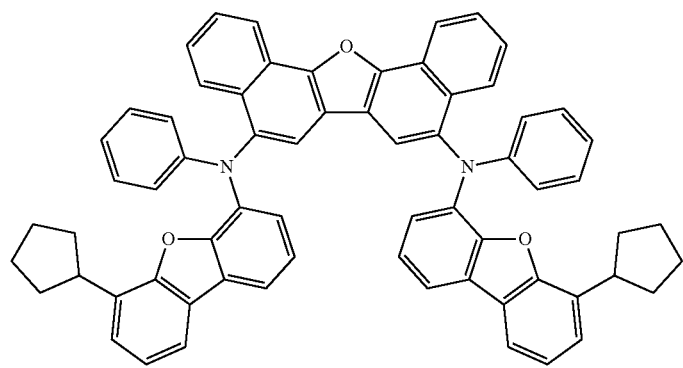
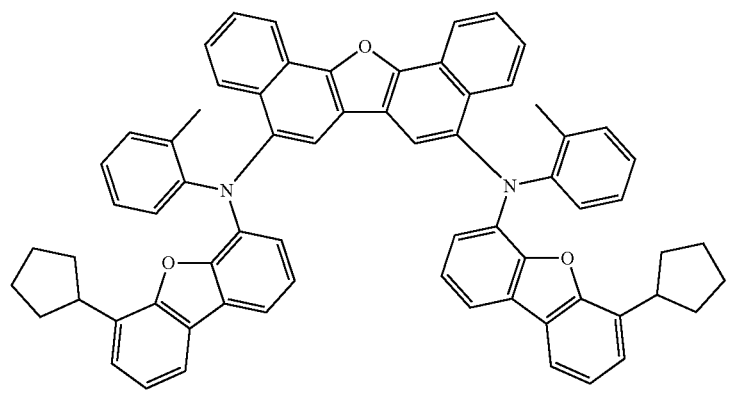
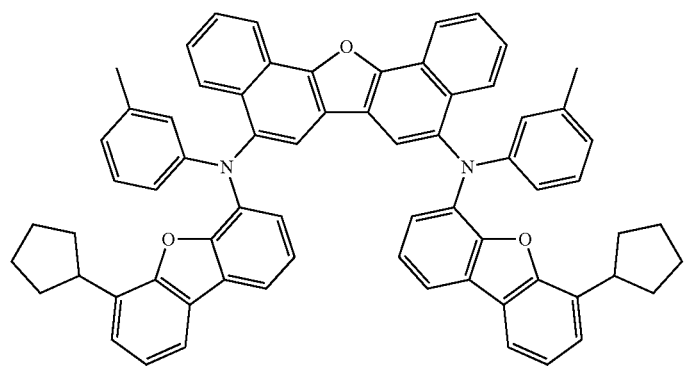

1099
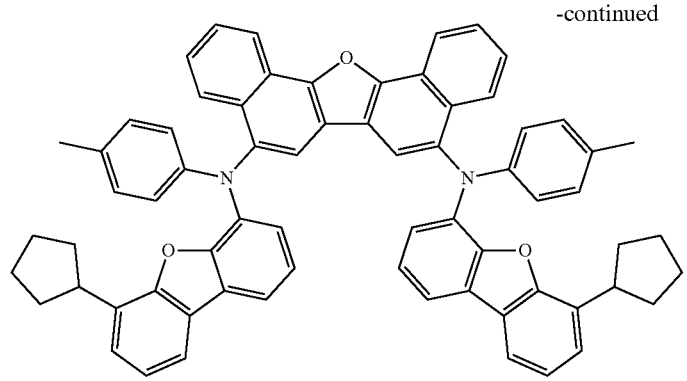
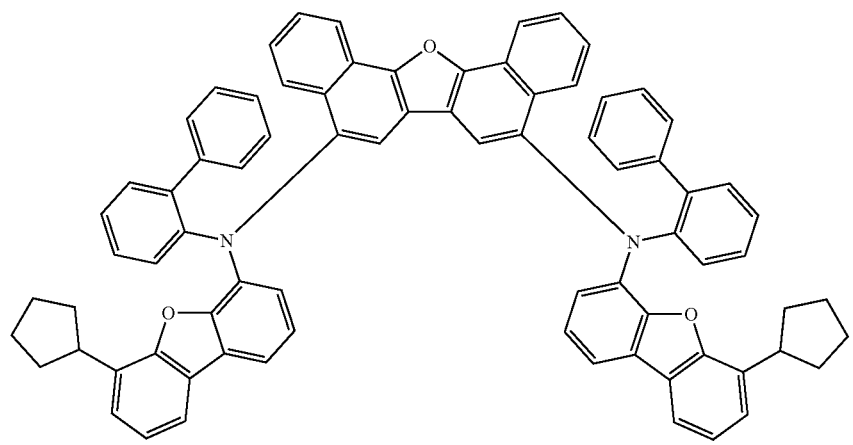
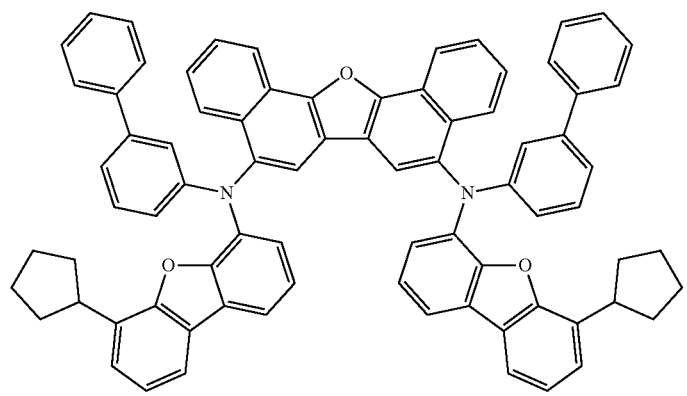
1100
-continued
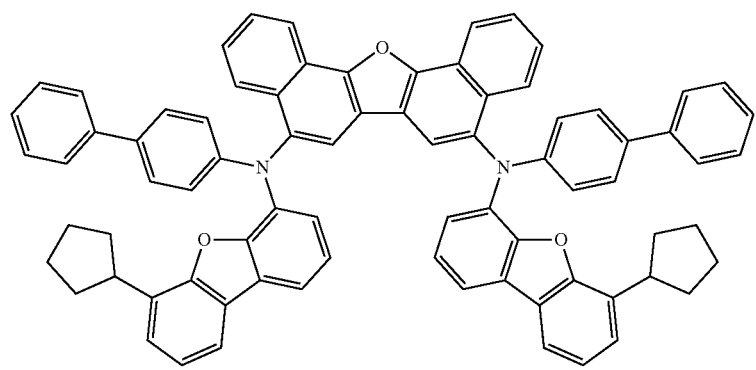

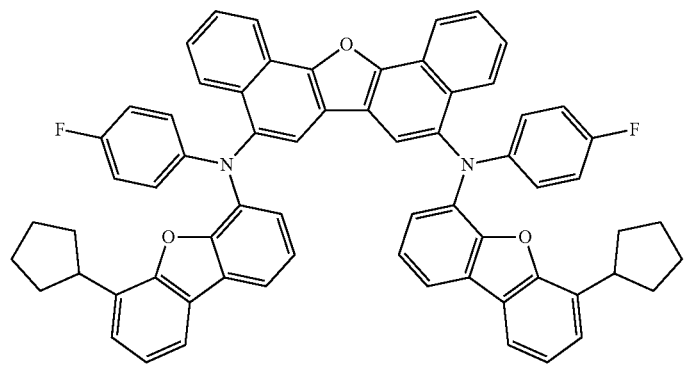
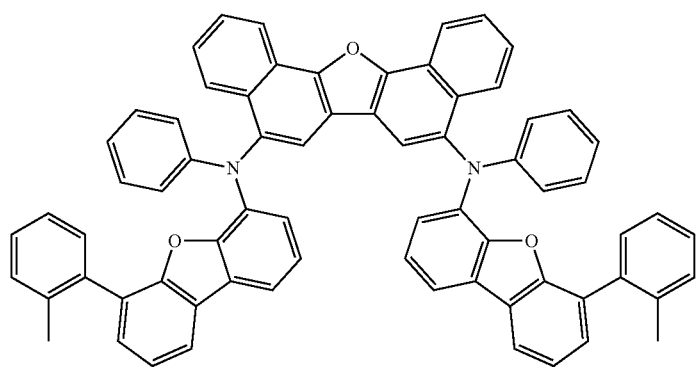
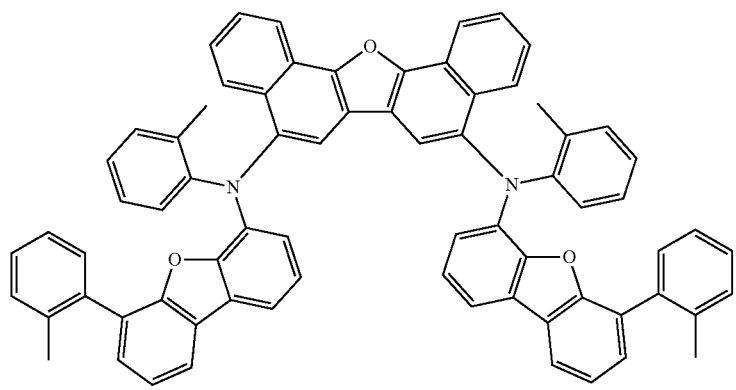
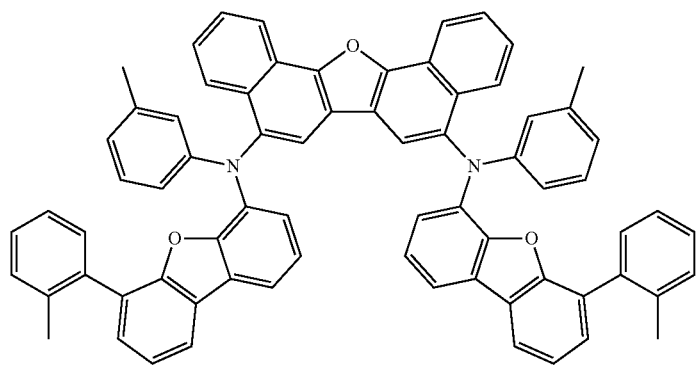

1103 1104
-continued
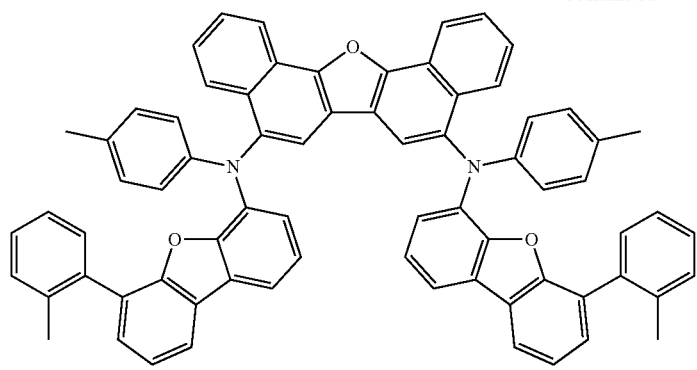
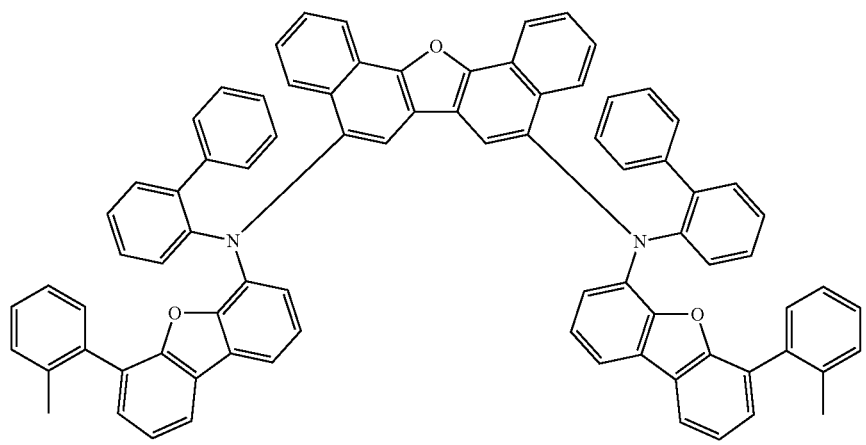
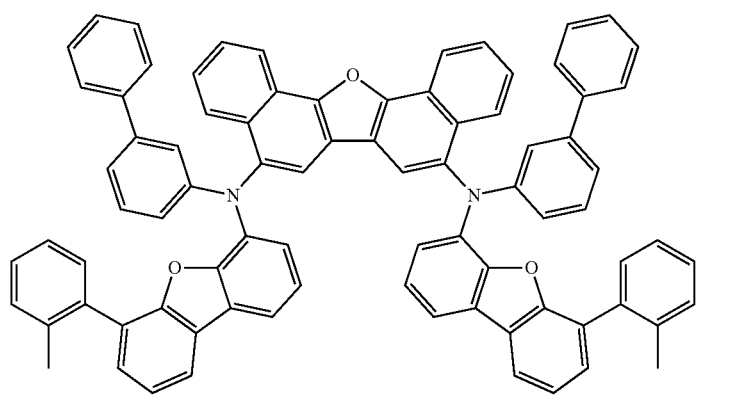
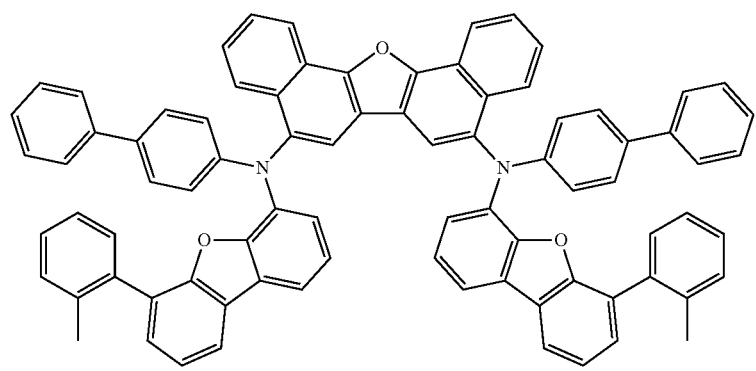

-continued
1105 1106
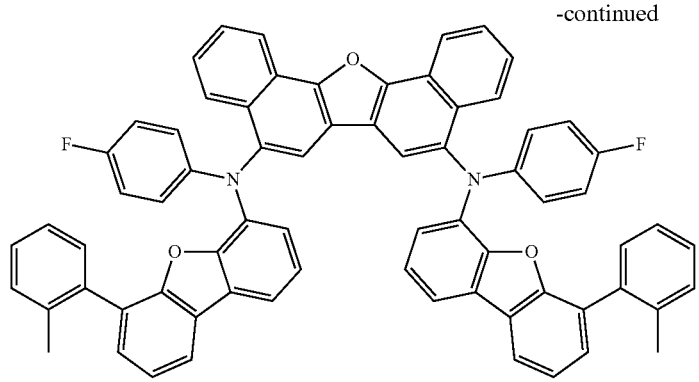
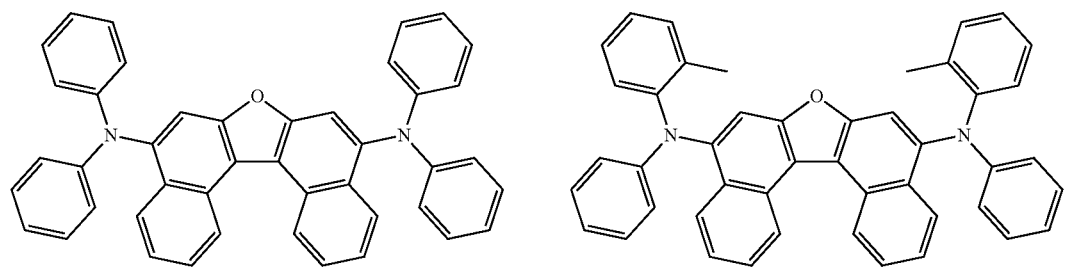
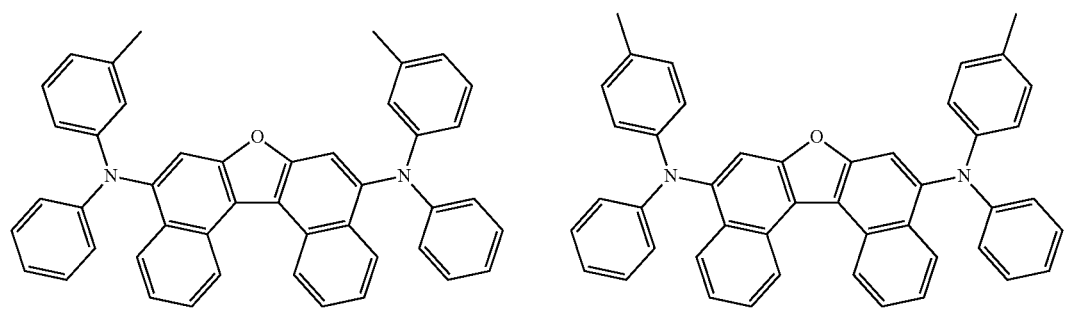
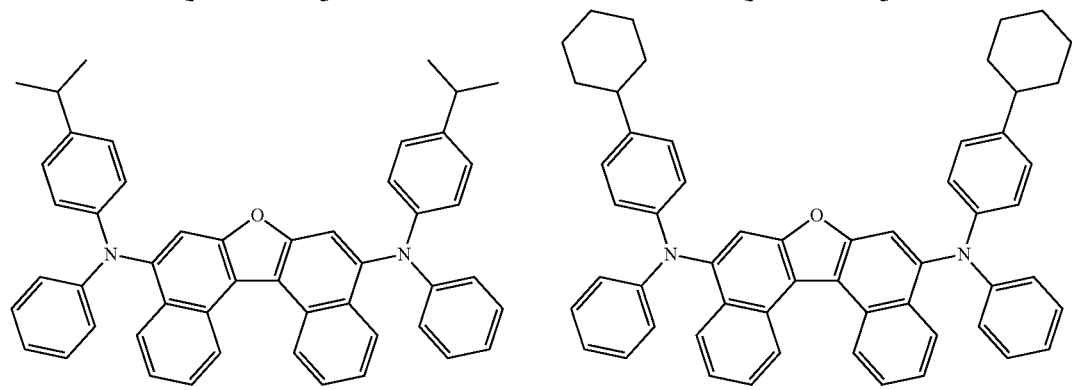
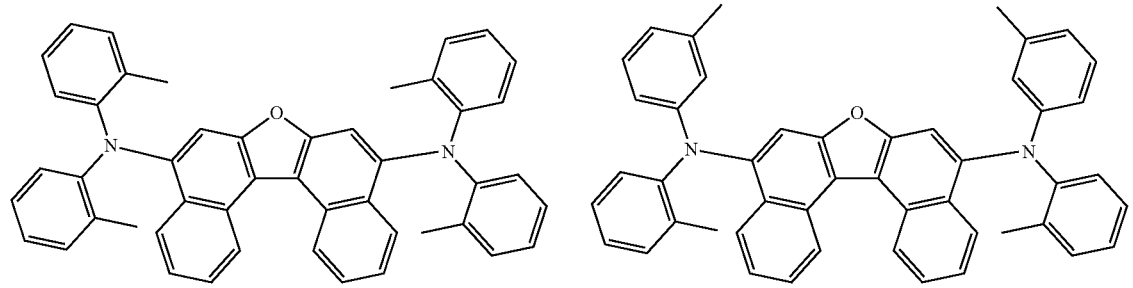

1107
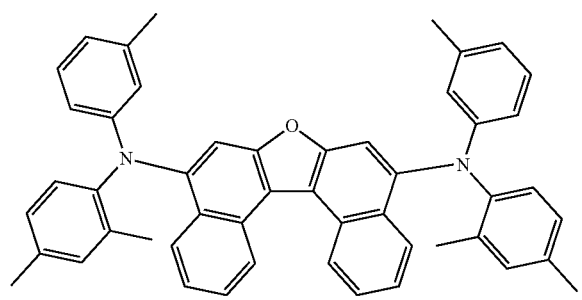
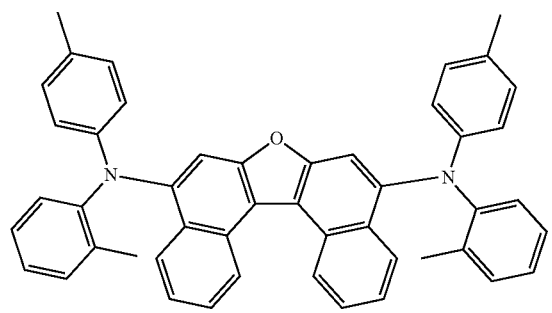
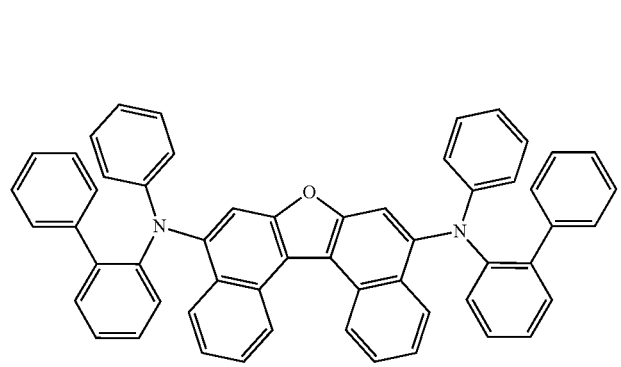
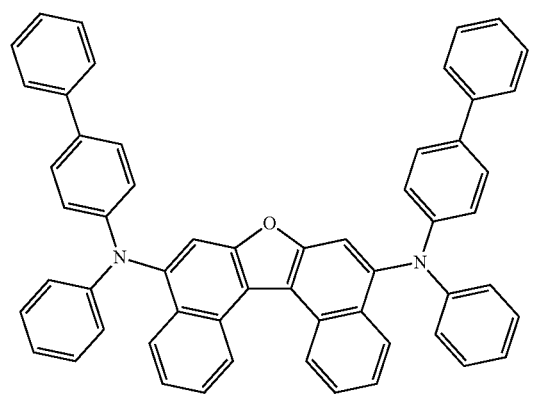
1108
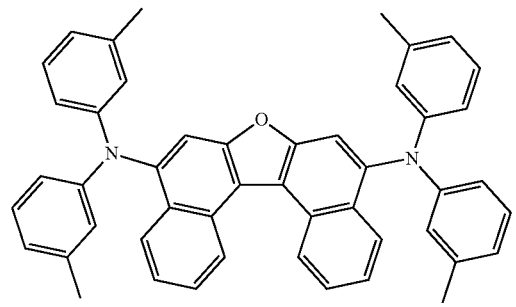
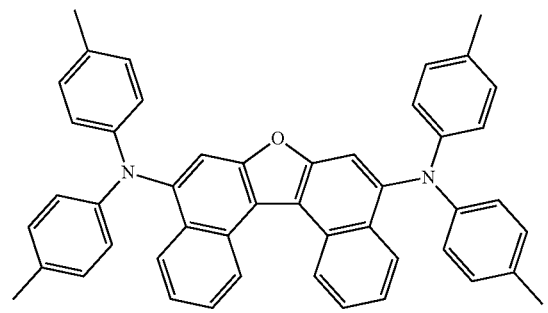
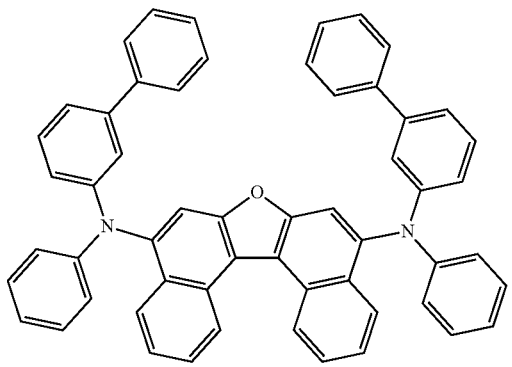
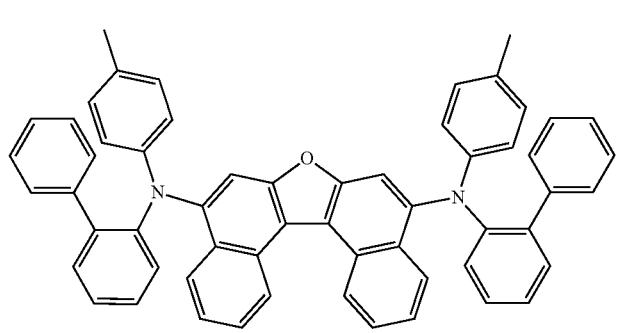
-continued -continued
| 1109 | 1110 |
|---|---|
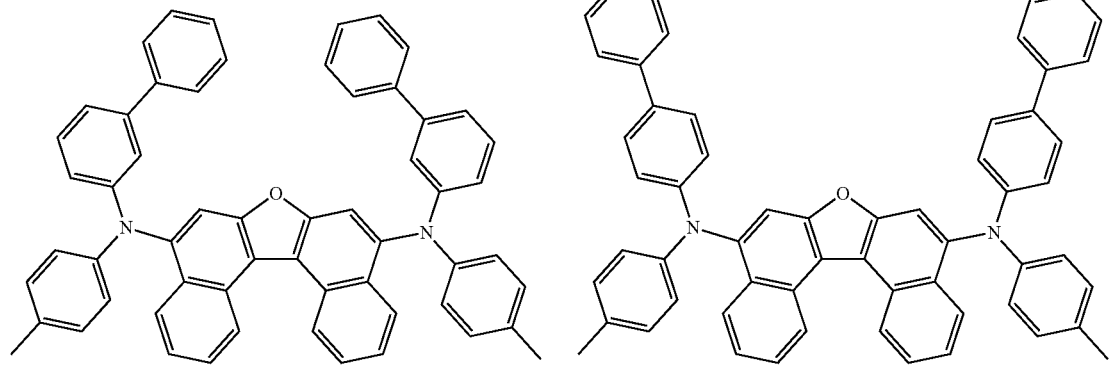
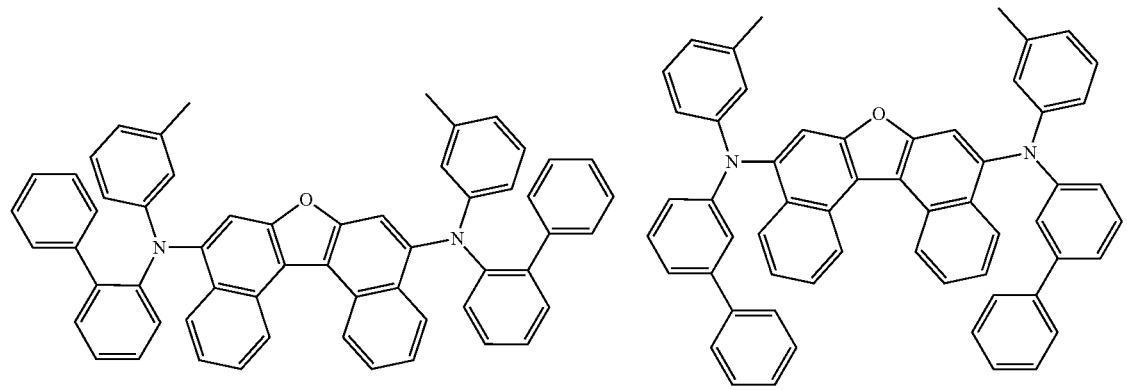
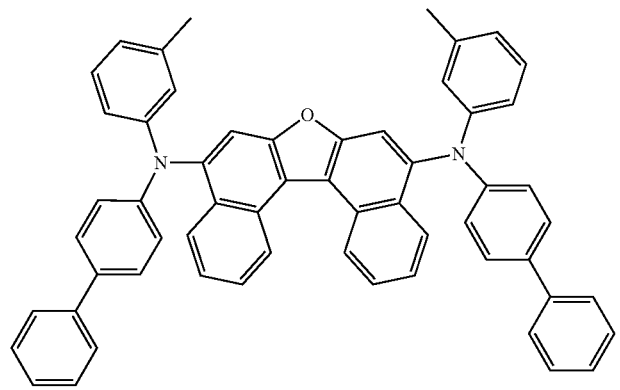
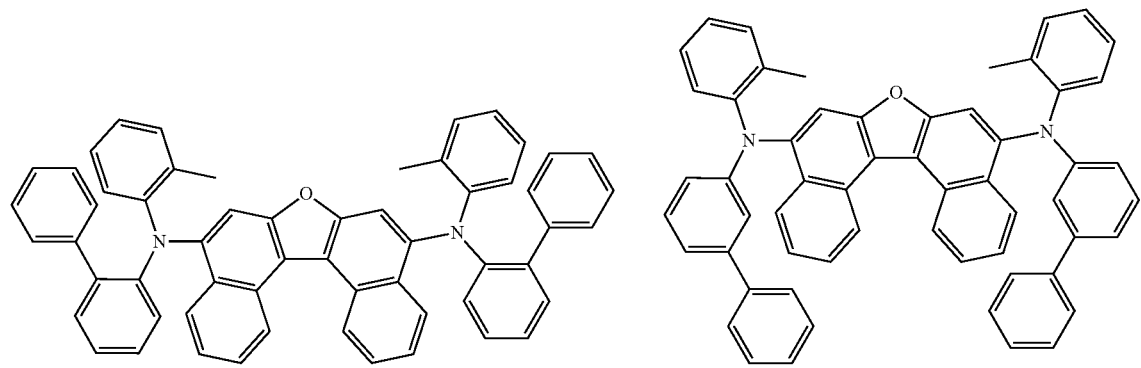

-continued
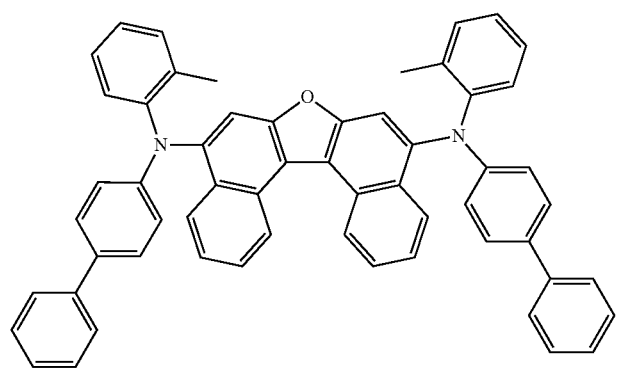
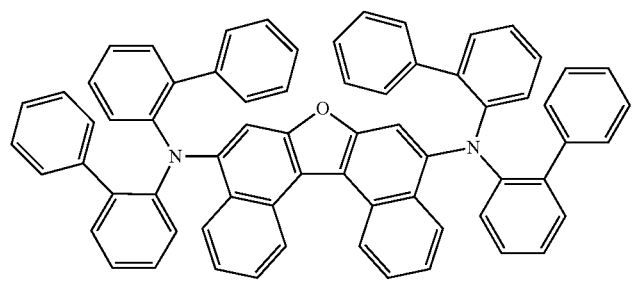
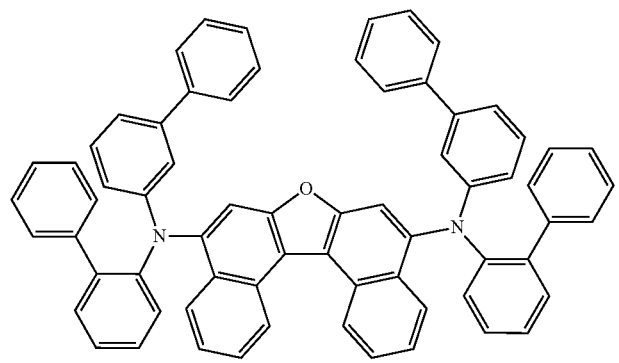
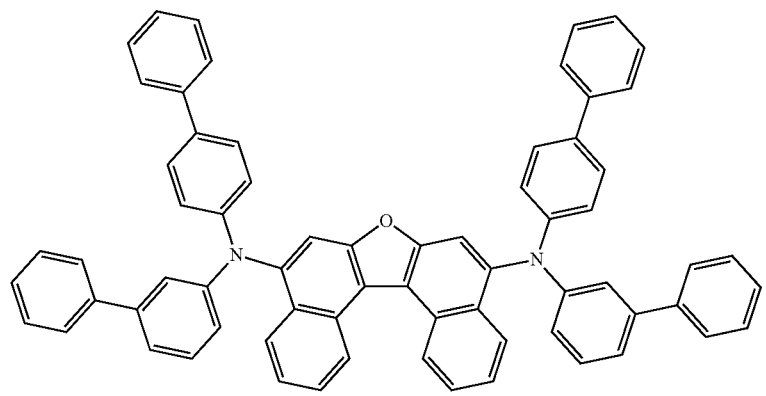

|1113|1114|
|---|---|
-continued
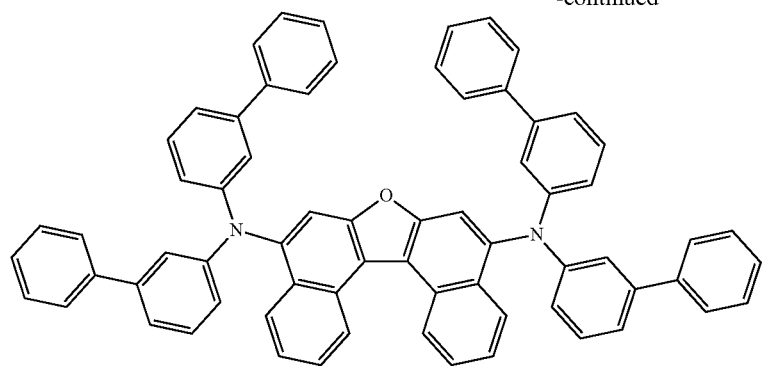
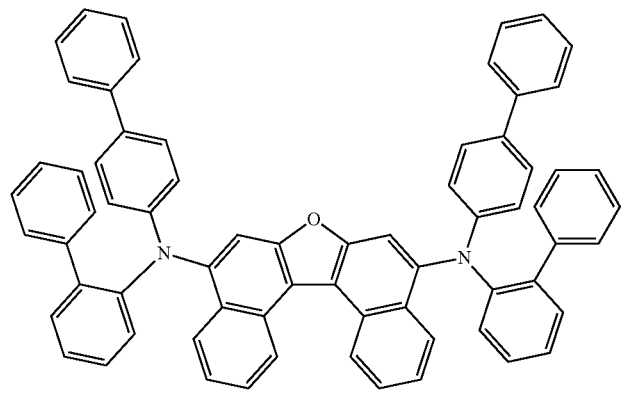
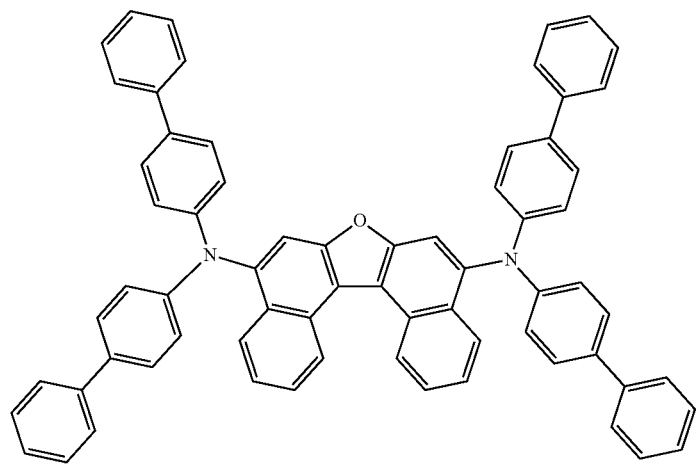
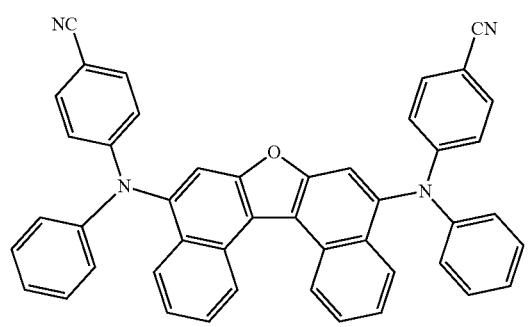 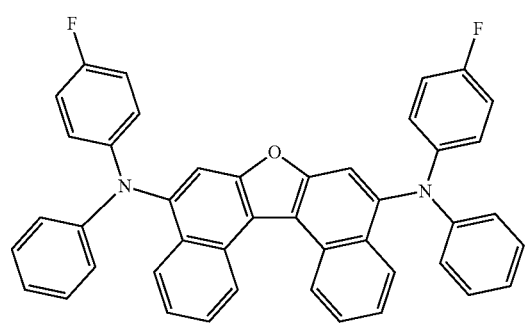

-continued
| 1115 | 1116 |
|---|---|
| 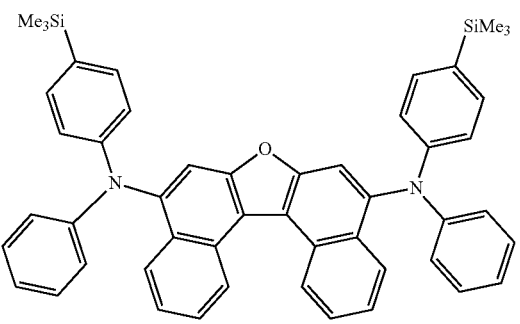 | 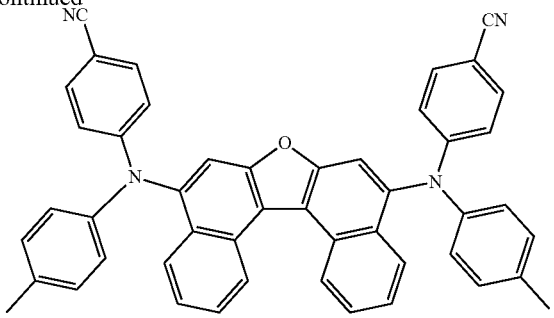 |
| 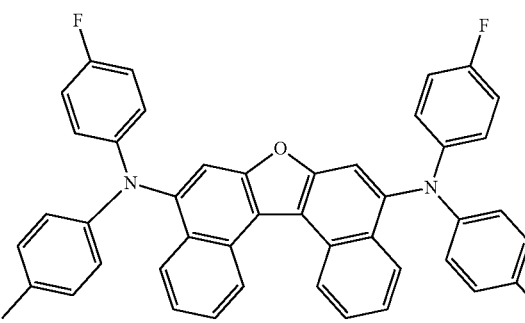 | 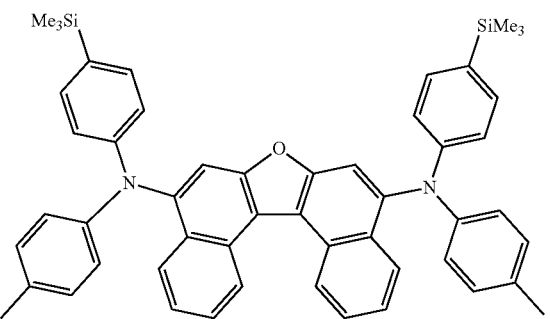 |
| 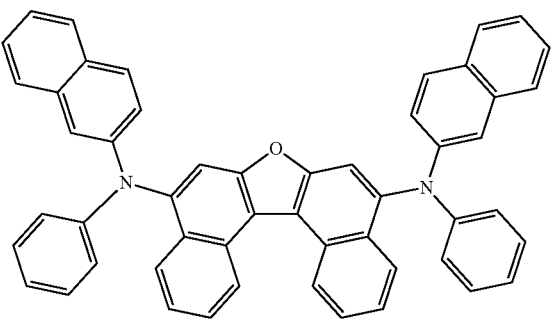 | 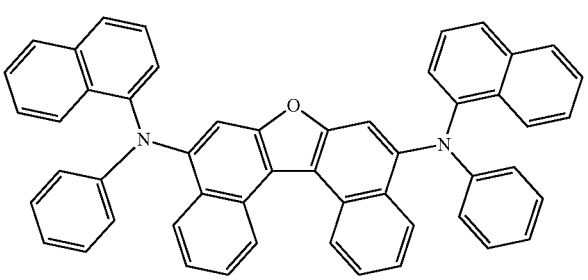 |
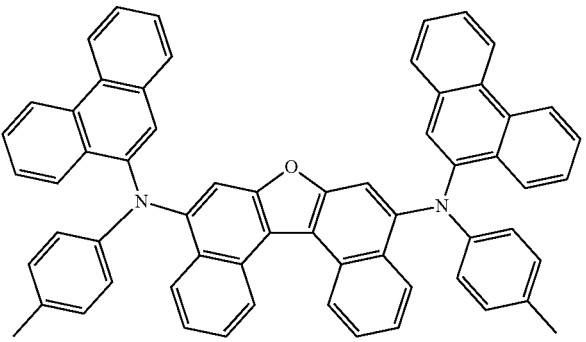
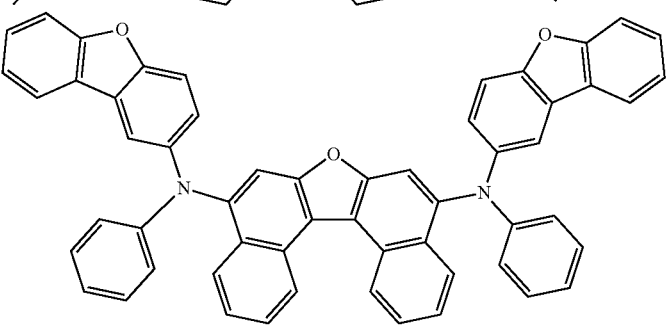

1117                                                      1118
-continued
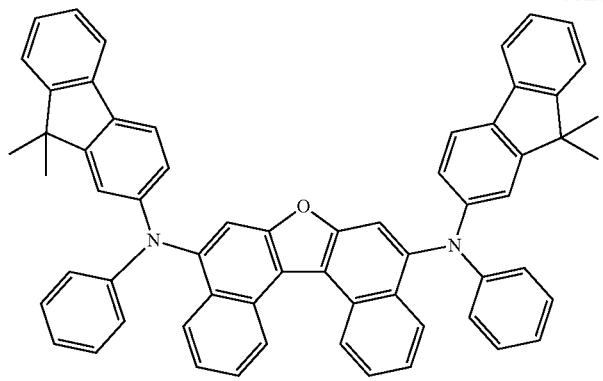
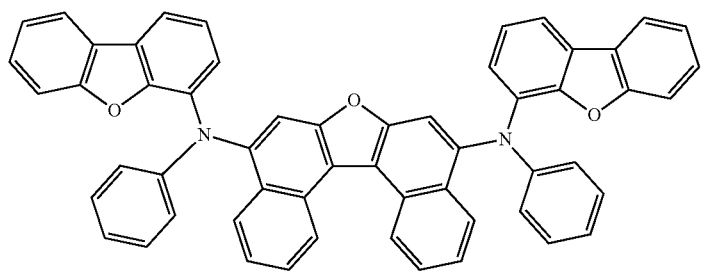
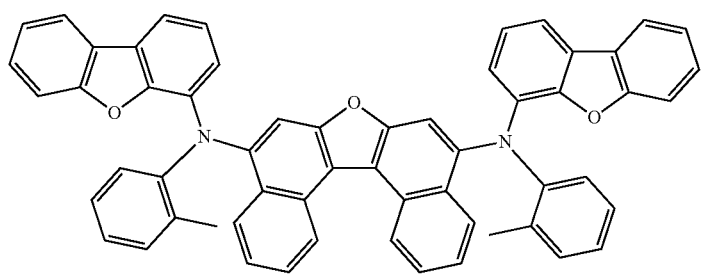
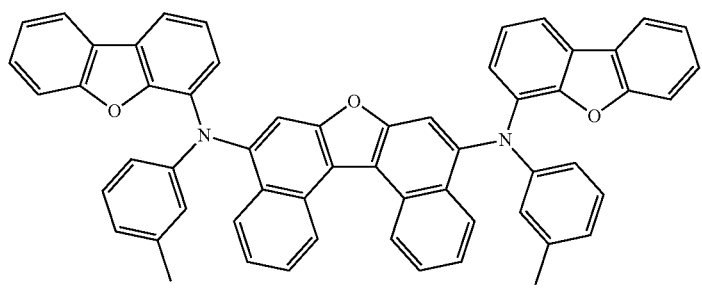
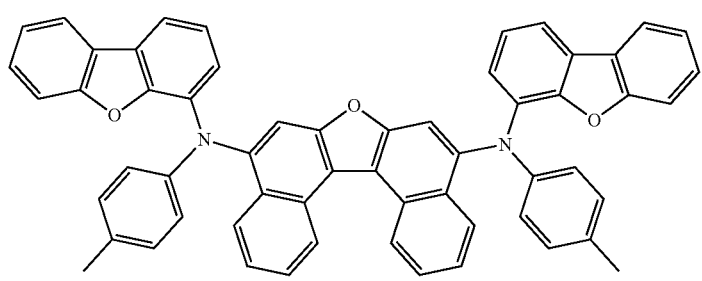

1119
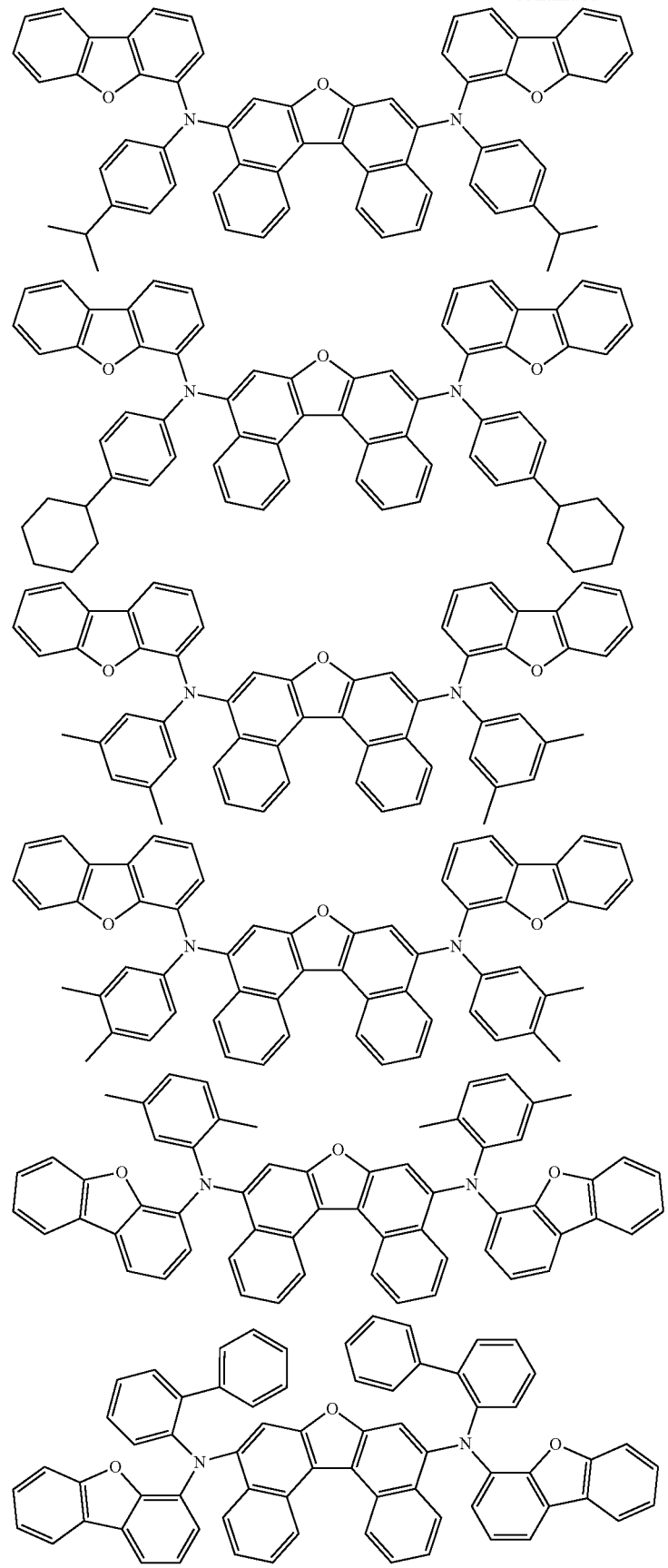
1120
-continued 1121 1122
-continued
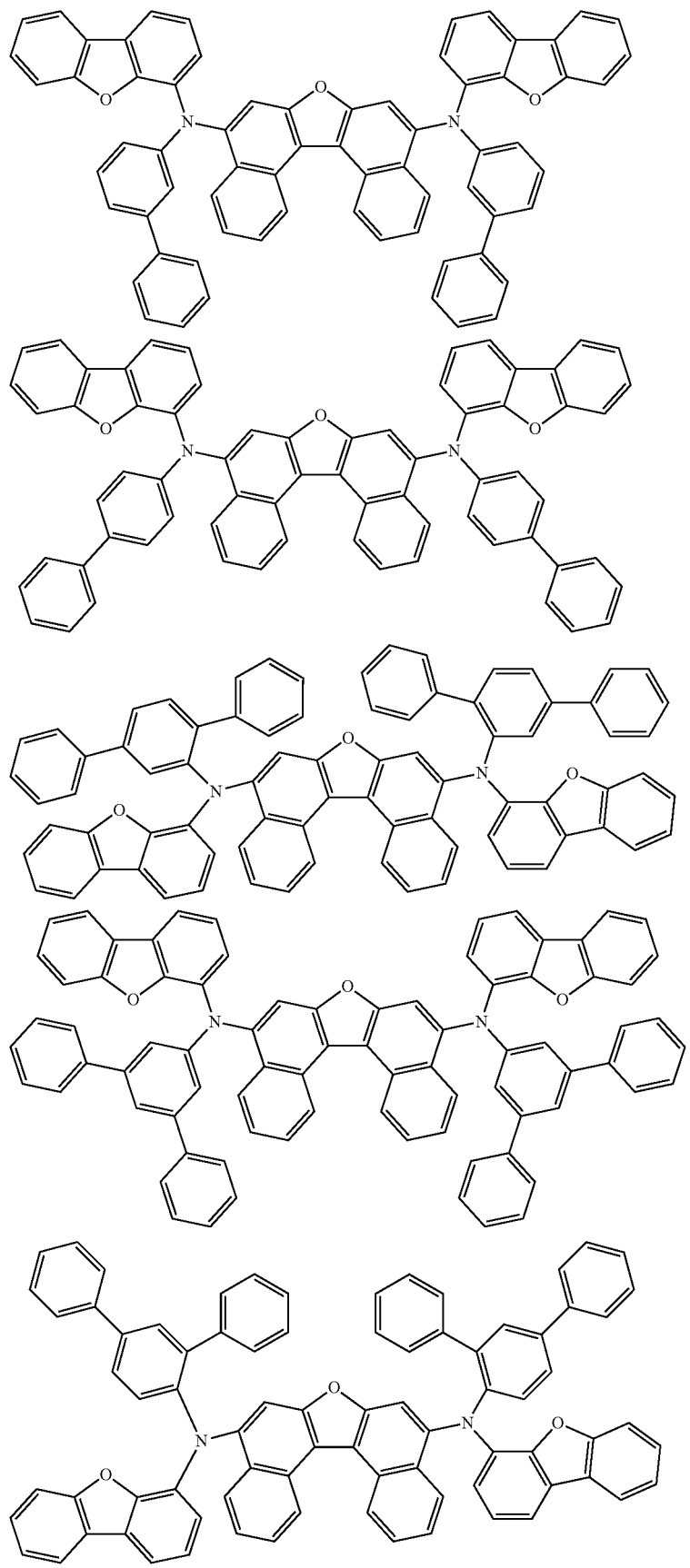

1123 1124
-continued
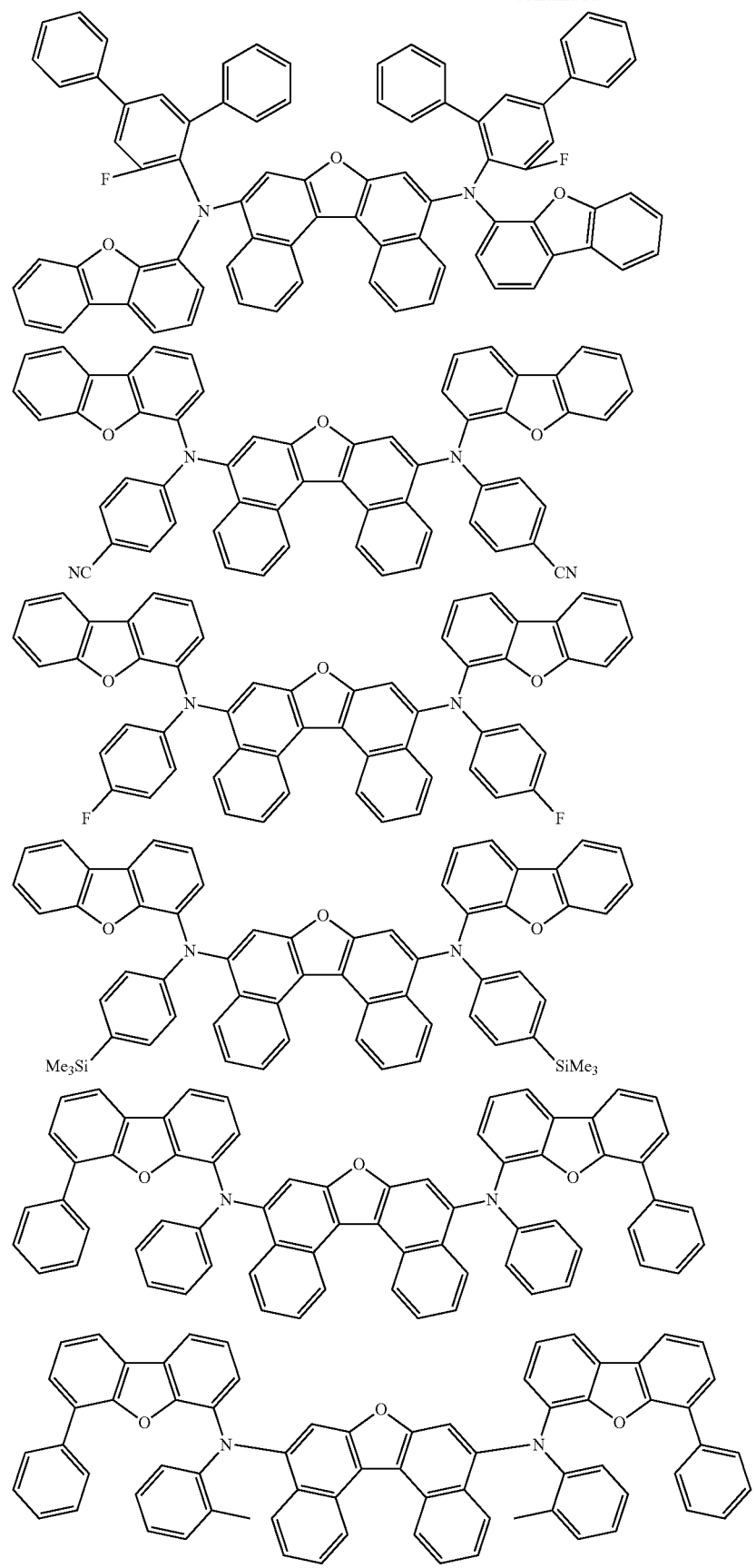

1125
1126
-continued
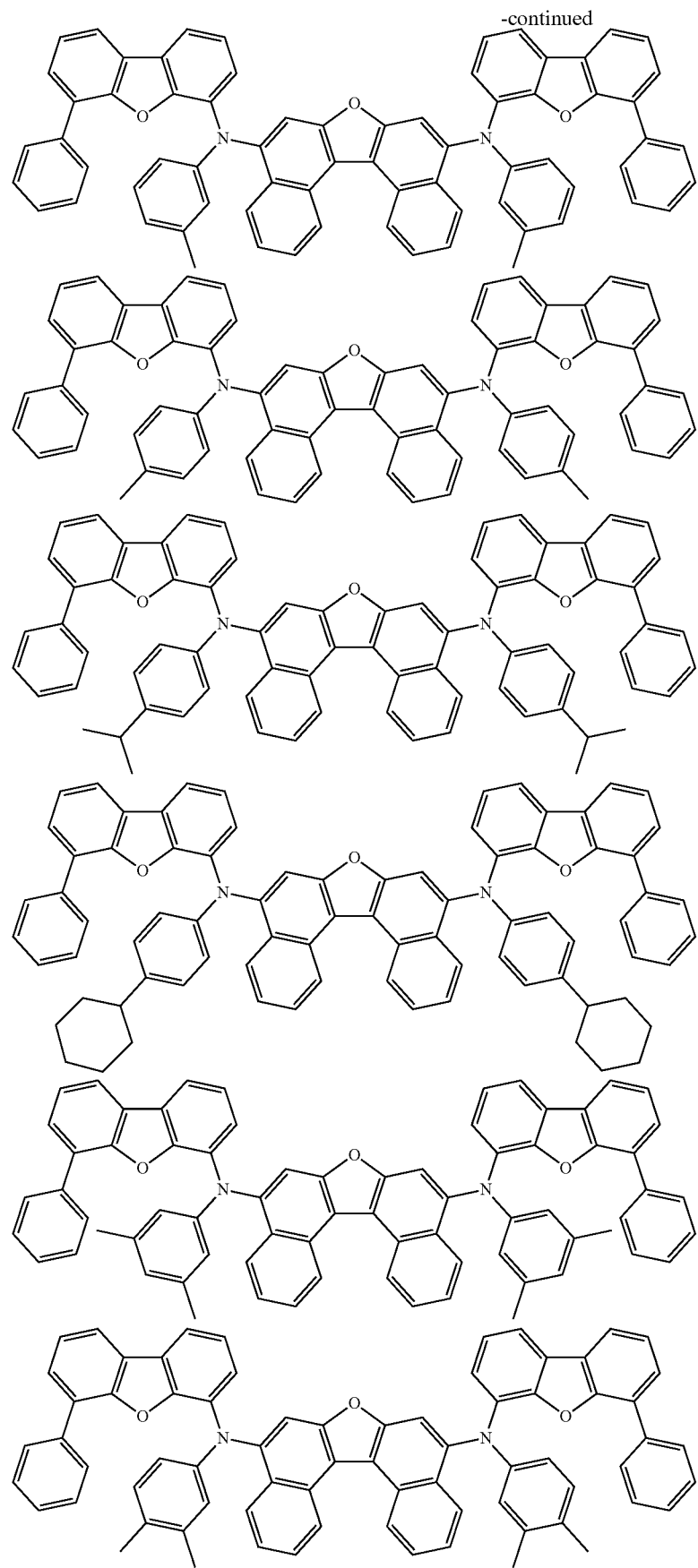

-continued
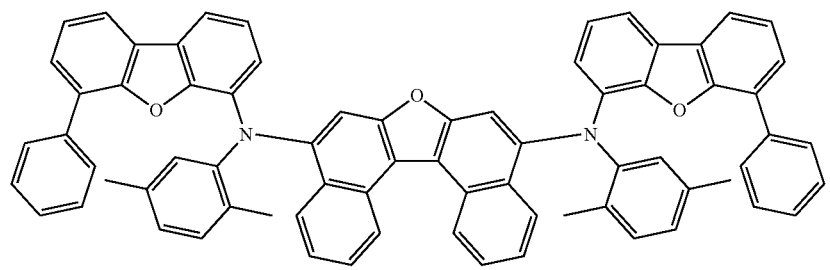
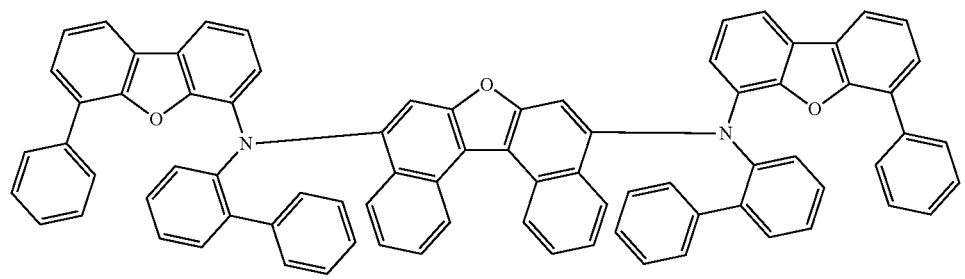
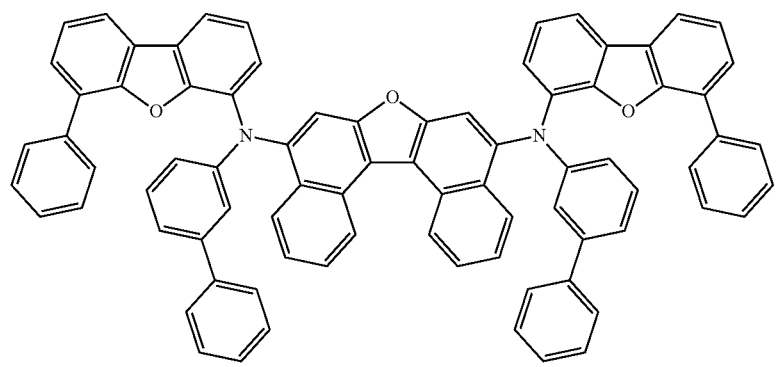
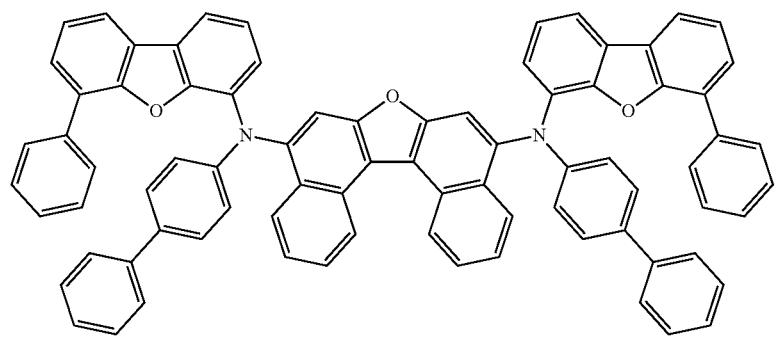
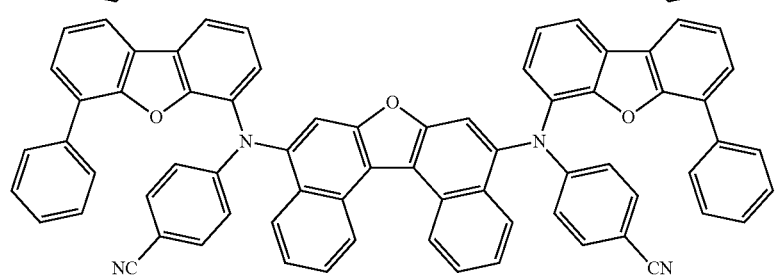

-continued
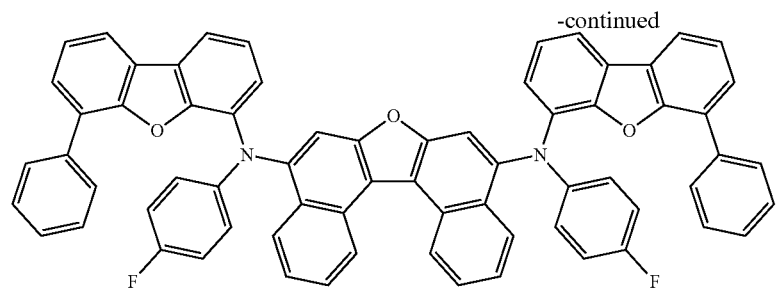
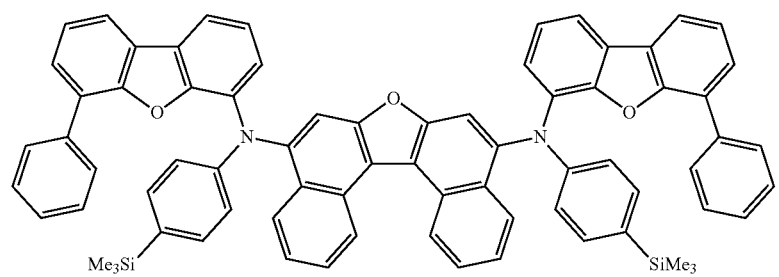
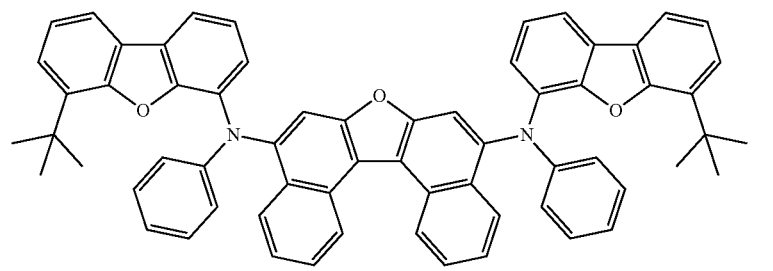
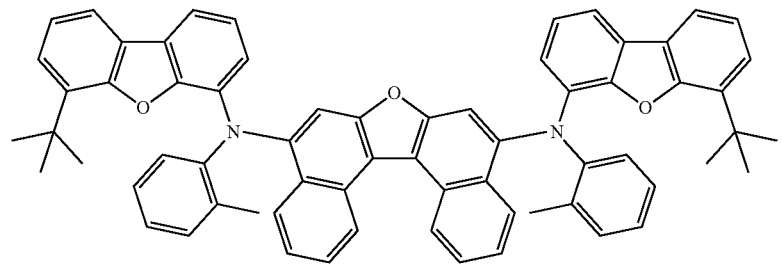
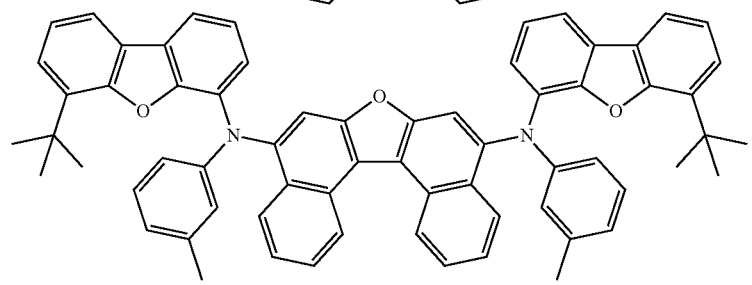
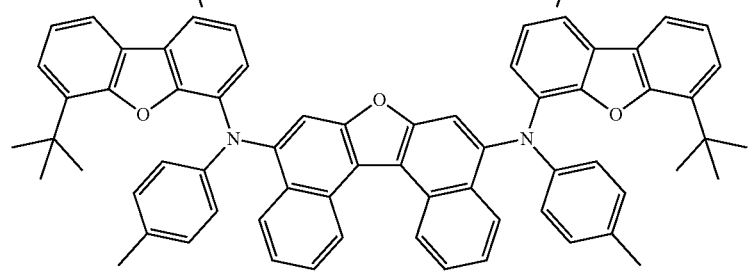

1131
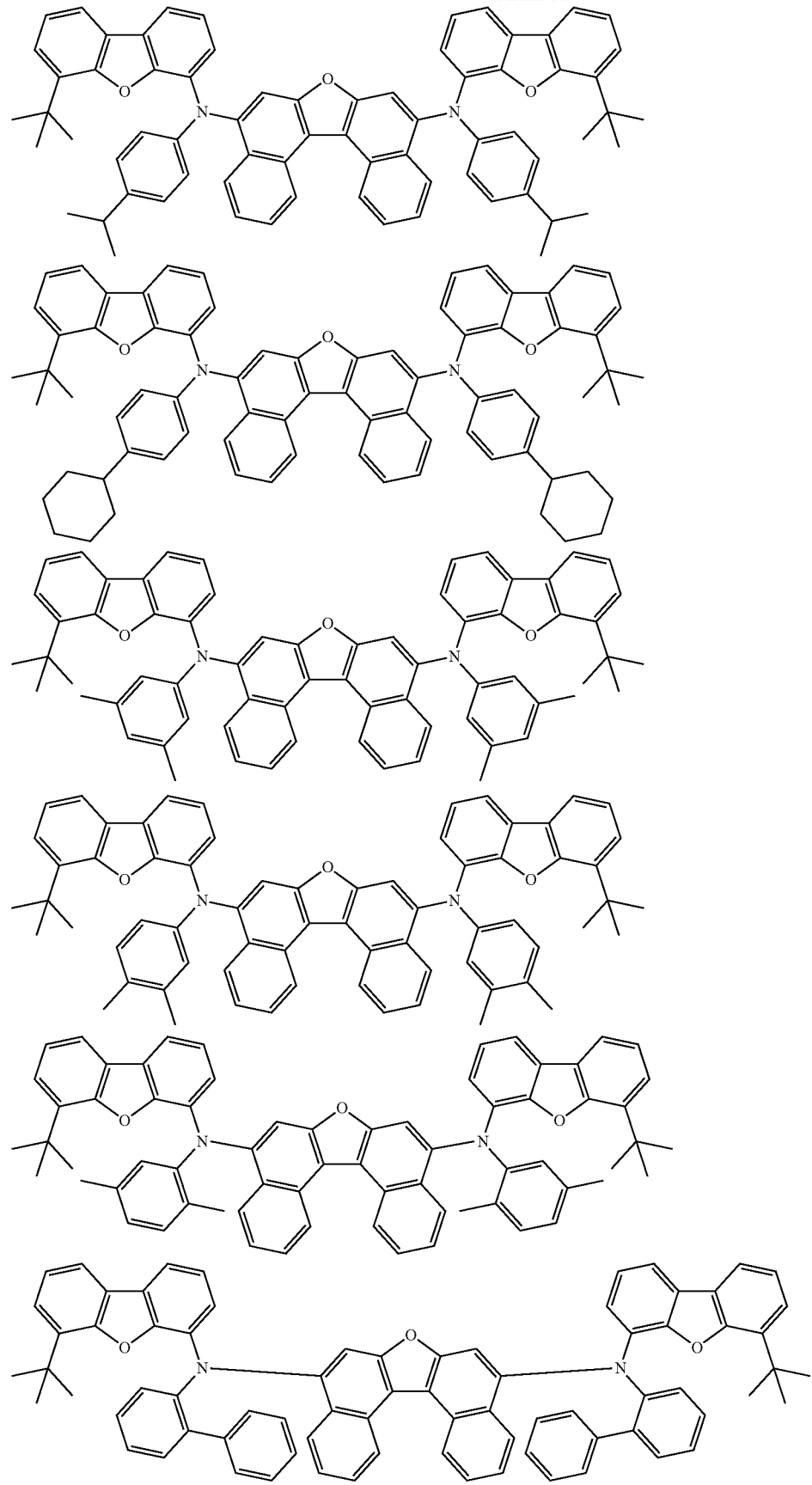
1132

1133
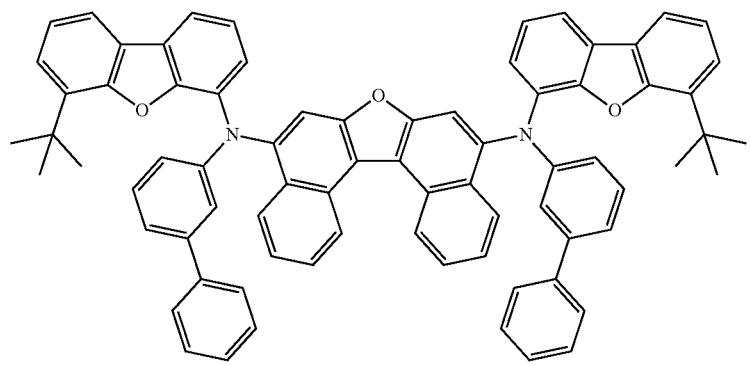
-continued
1134
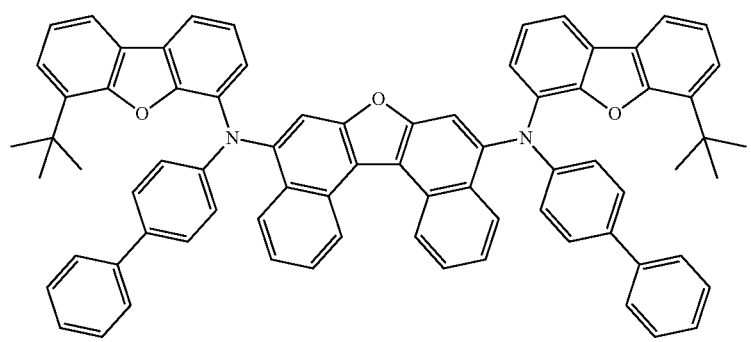
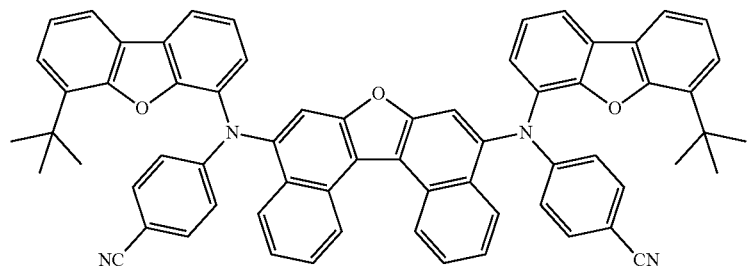
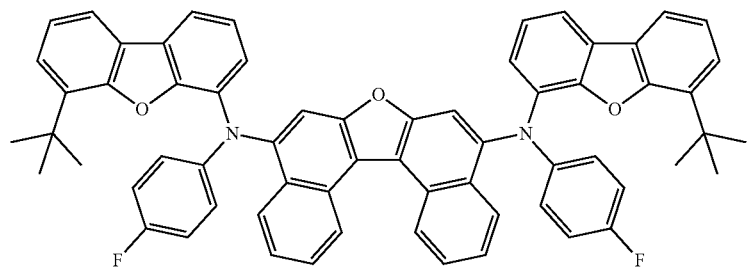
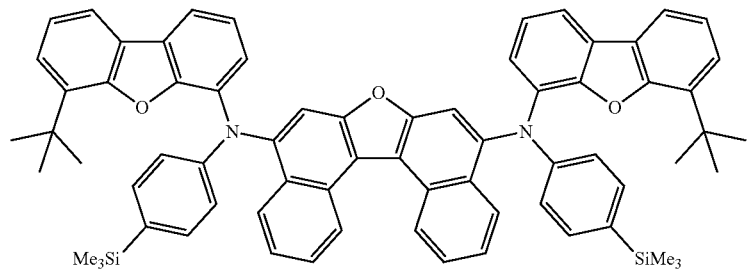

1135 1136
-continued
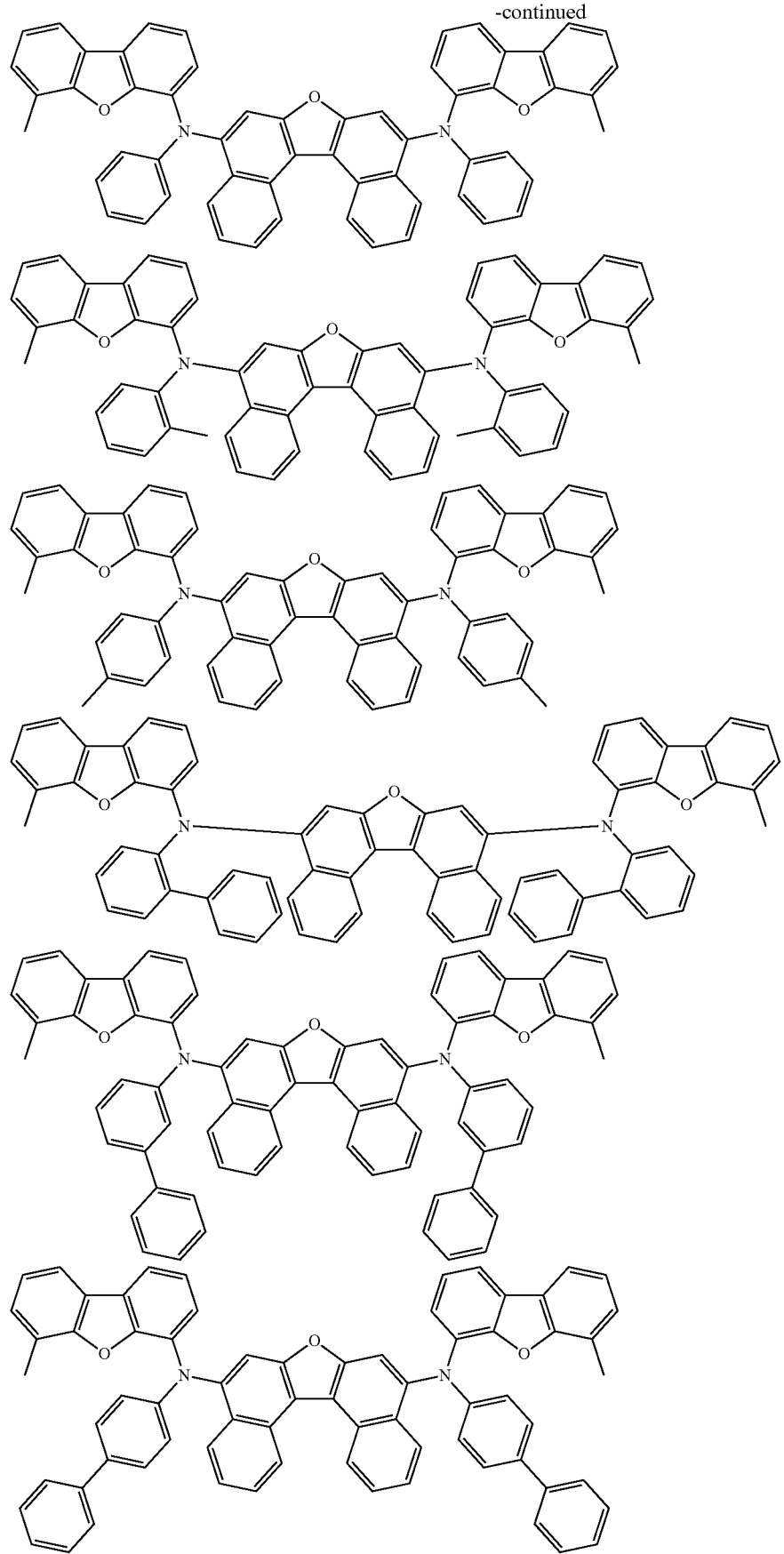

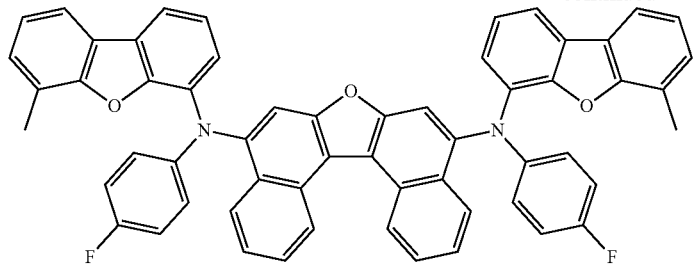
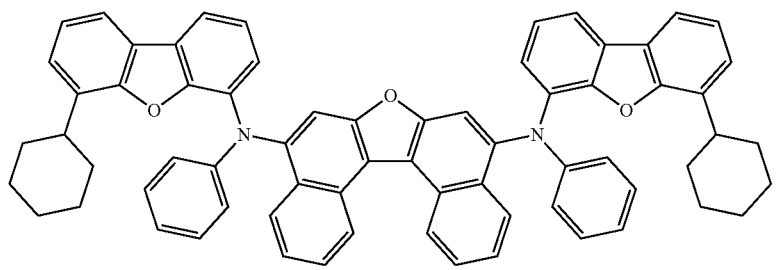
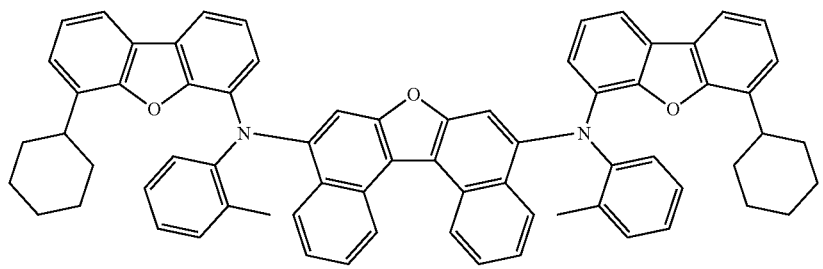
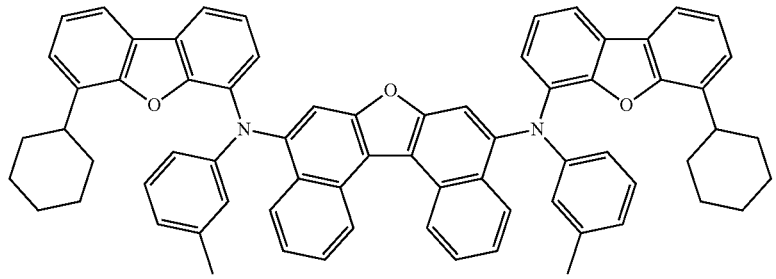
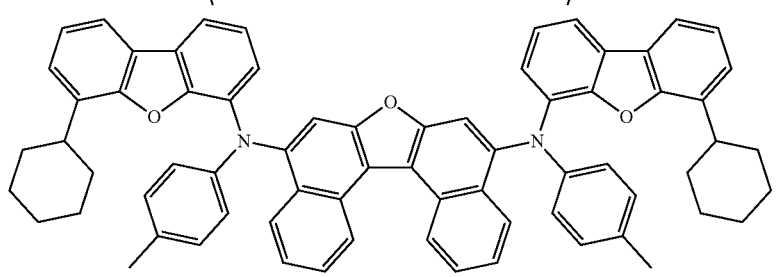
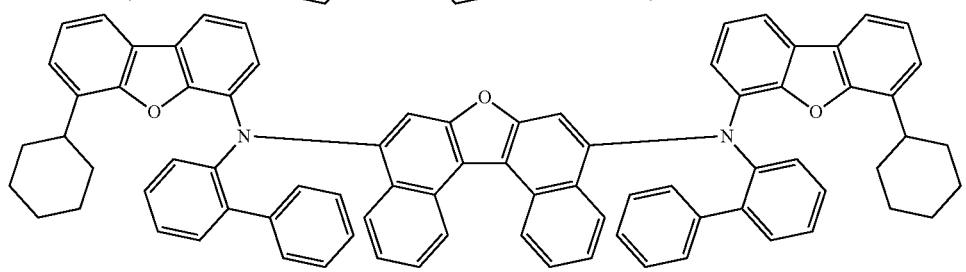

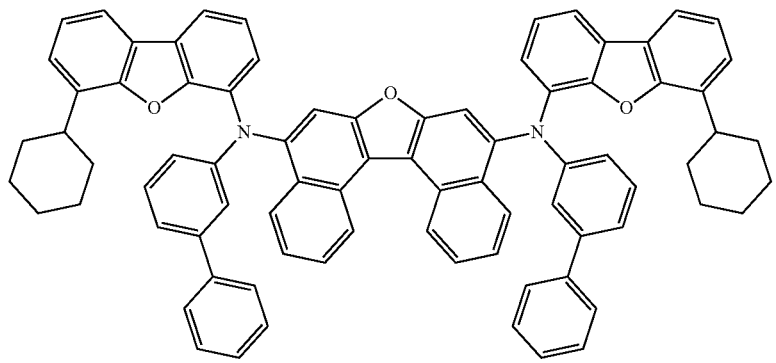
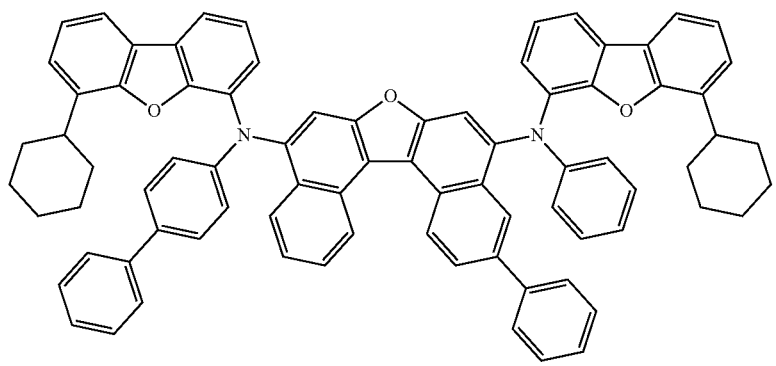
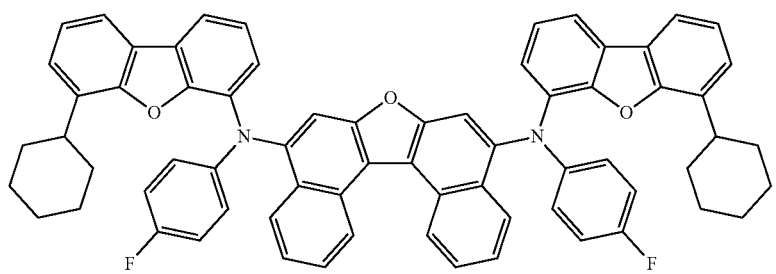
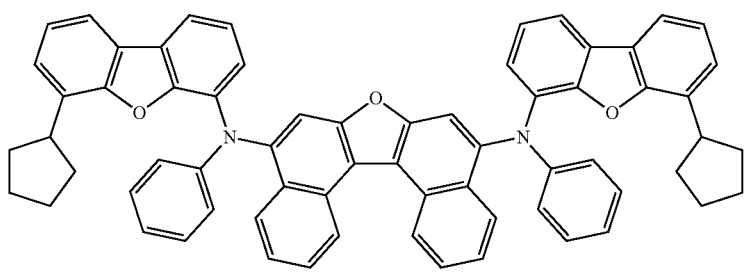
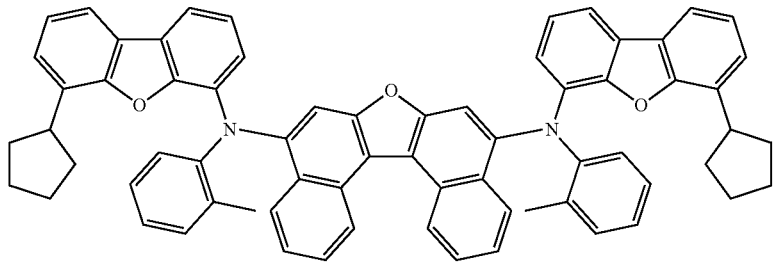

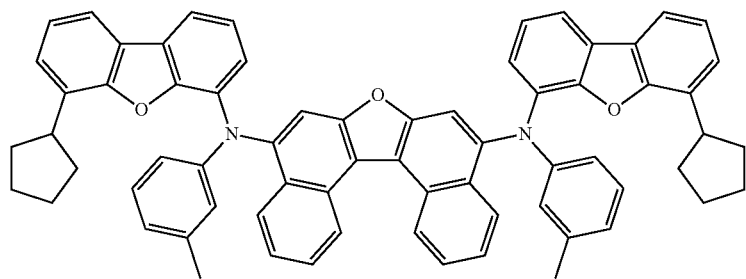
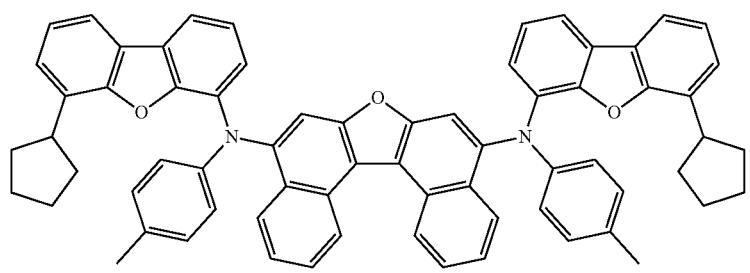
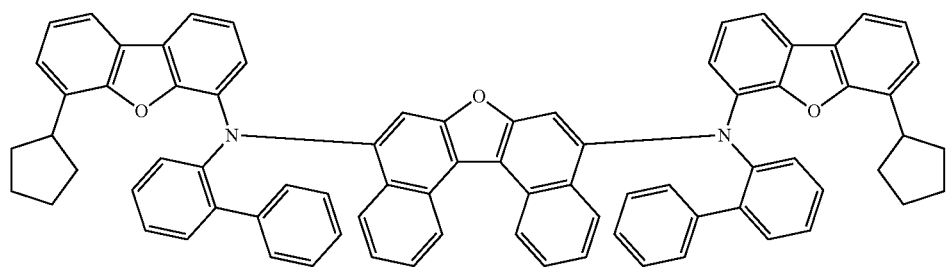
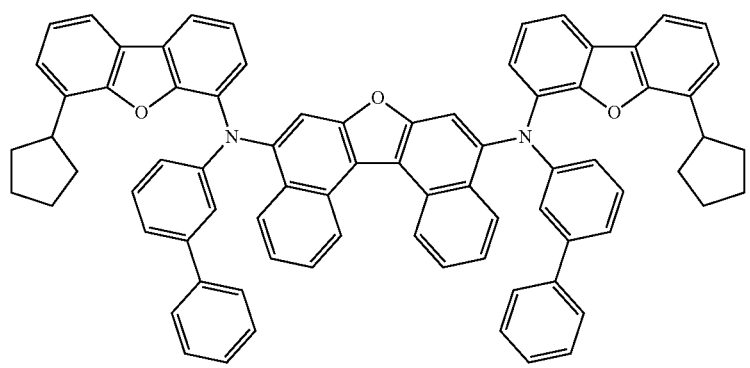
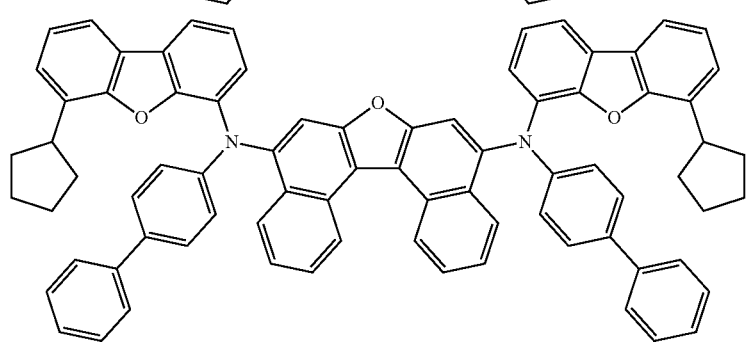

1143
-continued
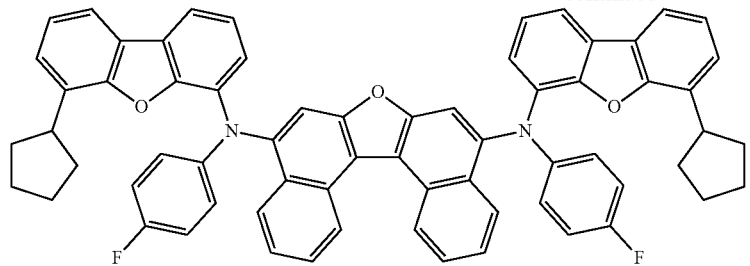
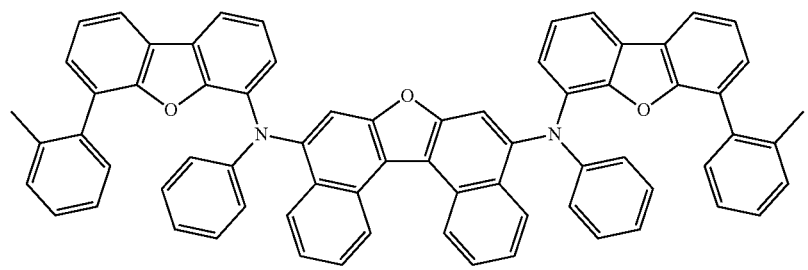
1144
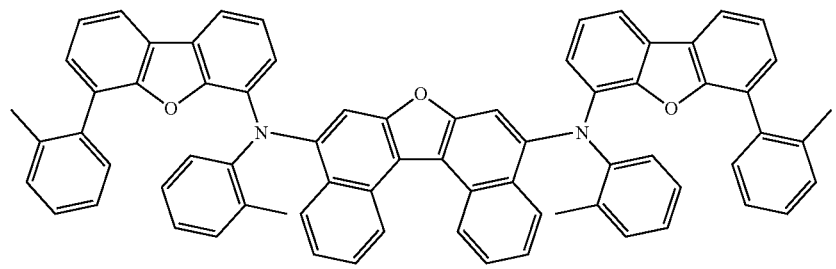
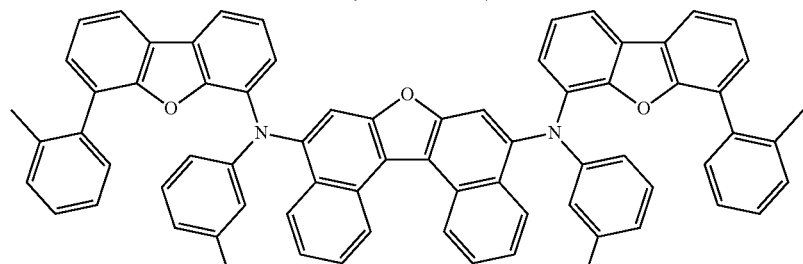
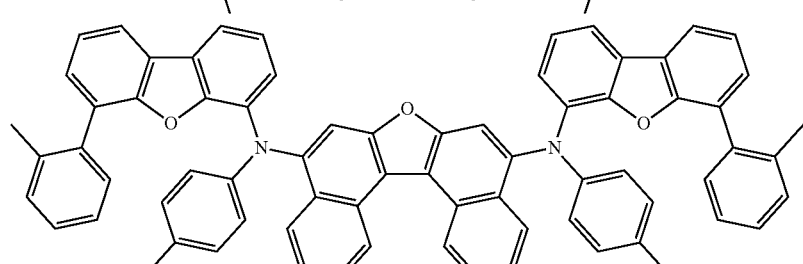
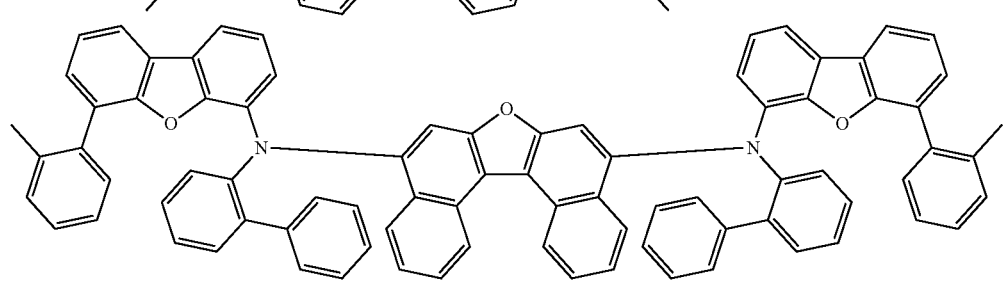

1145
-continued
1146
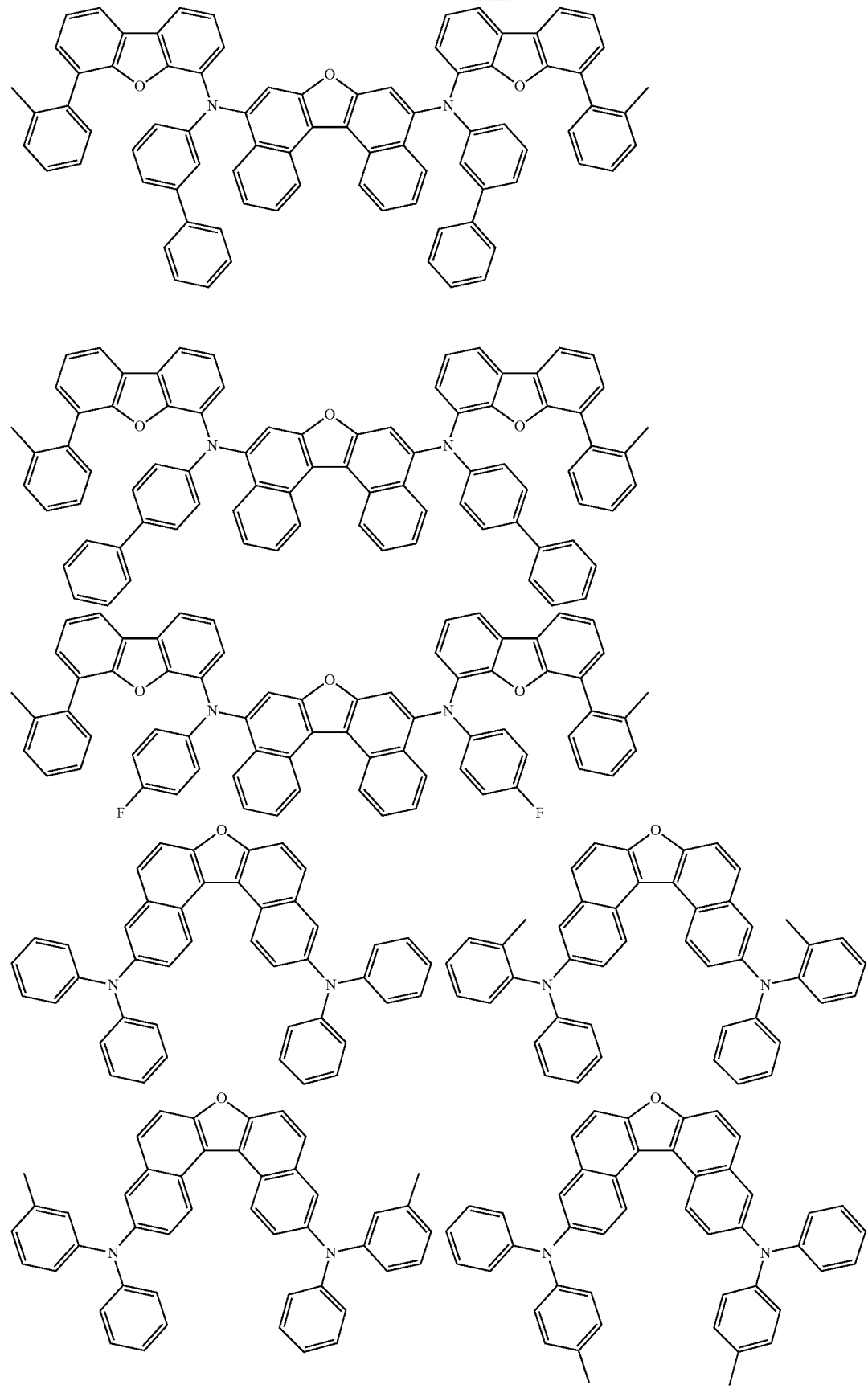

1147 1148
-continued
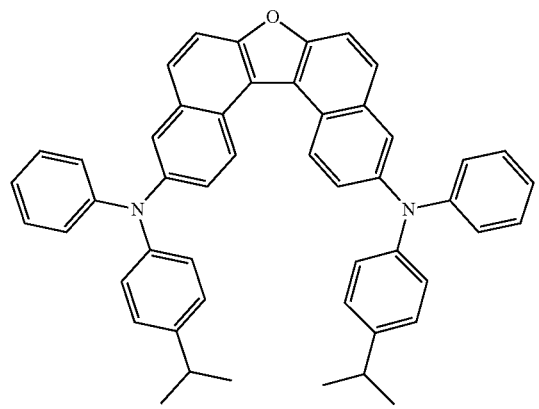 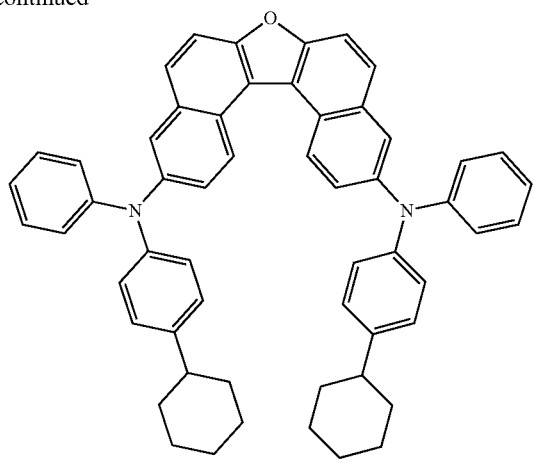
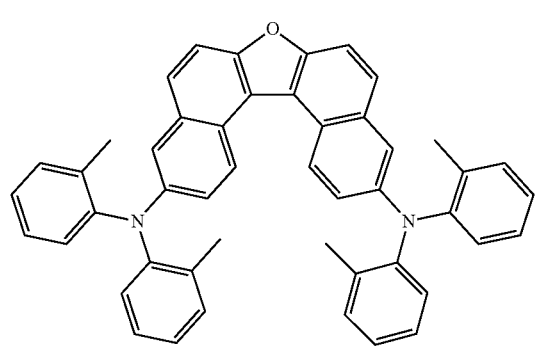 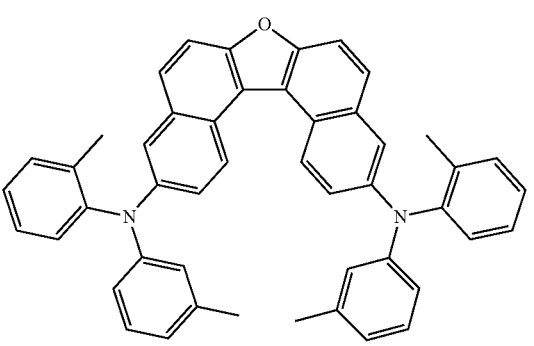
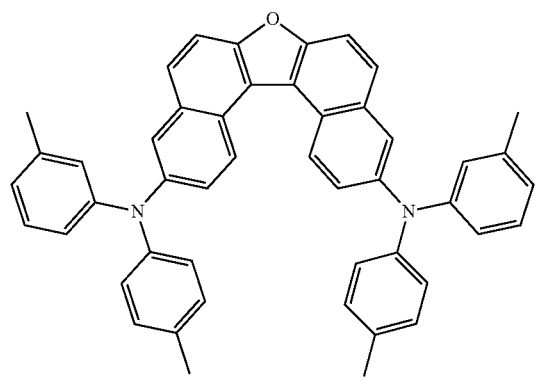 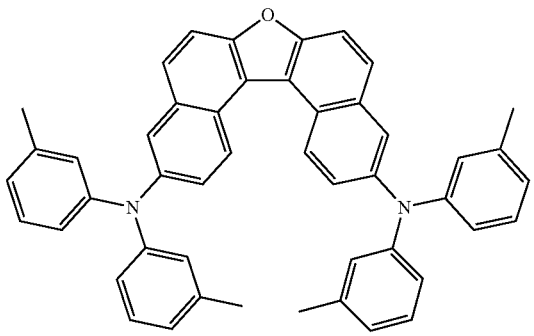
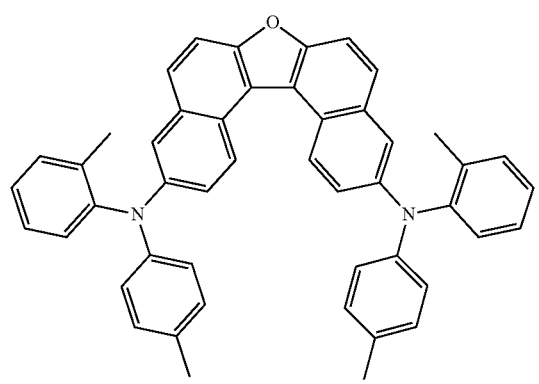 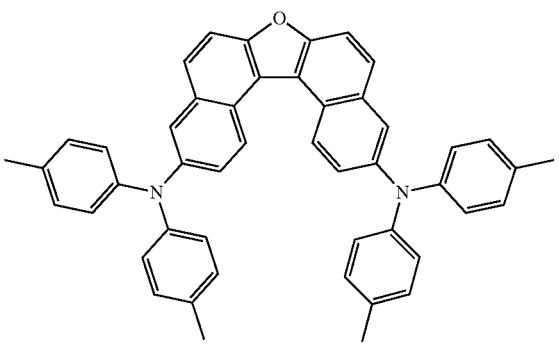

1149 1150
-continued
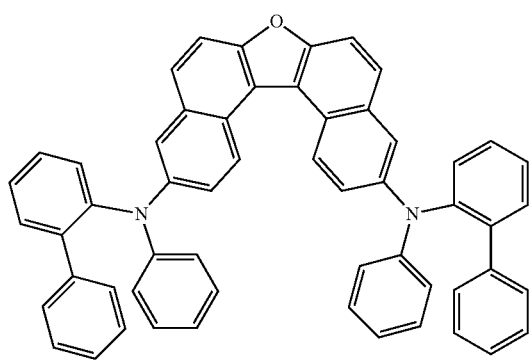 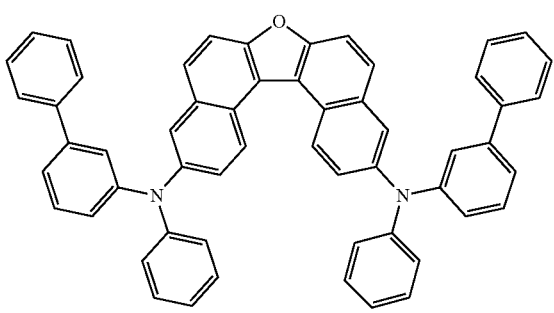
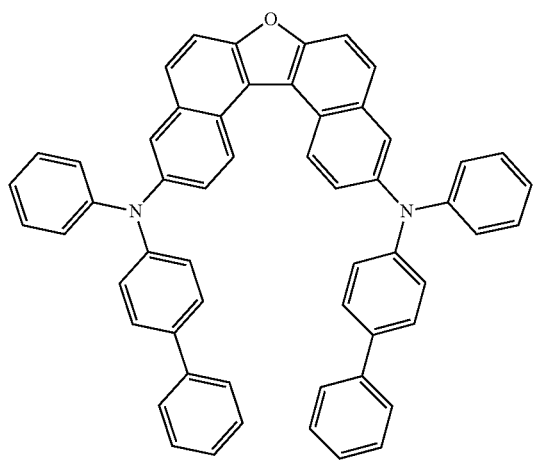 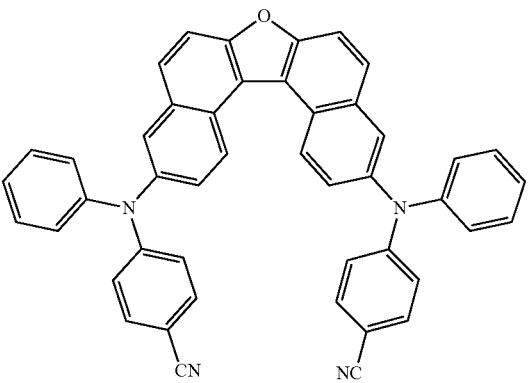
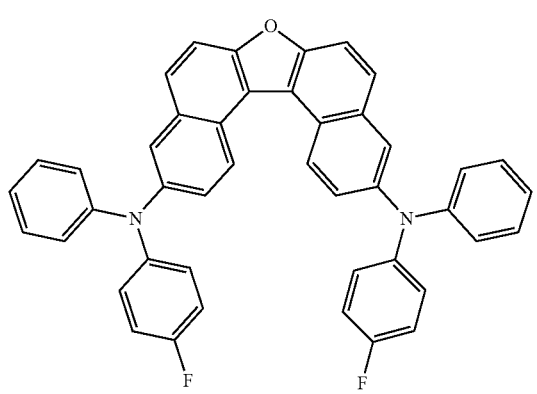 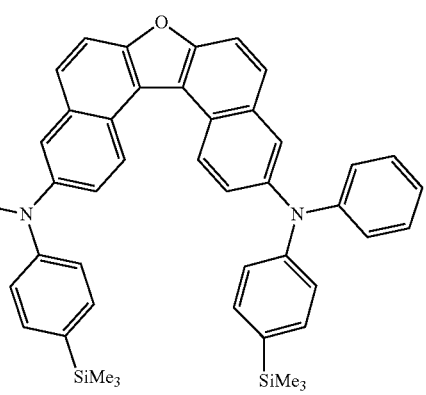
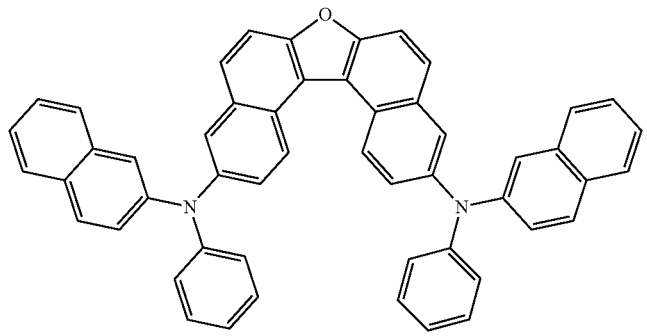 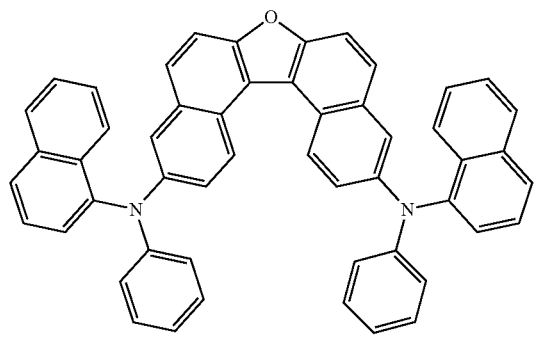

1151 1152
-continued
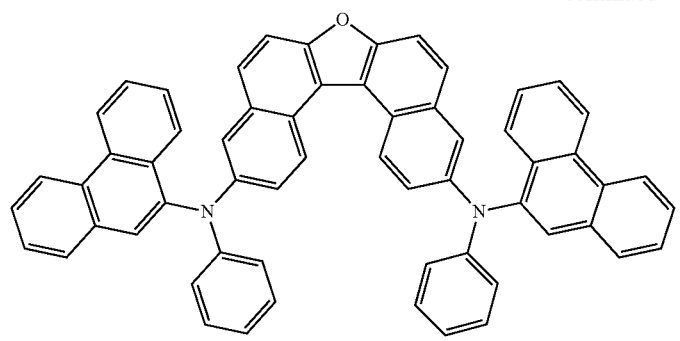
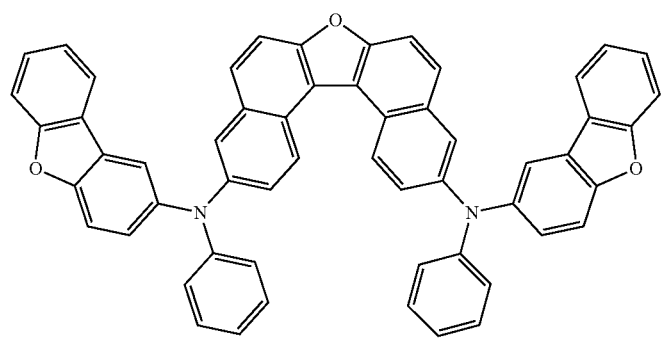
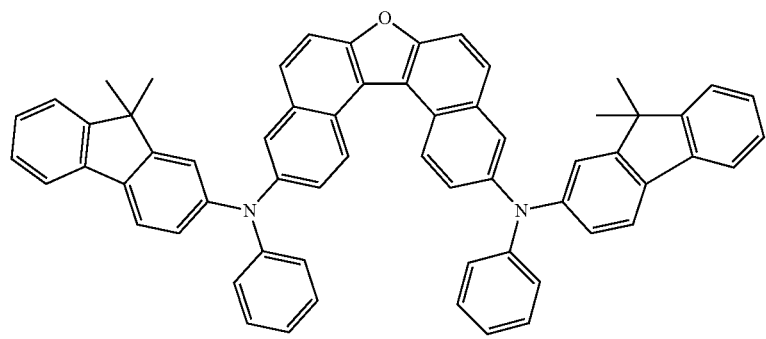
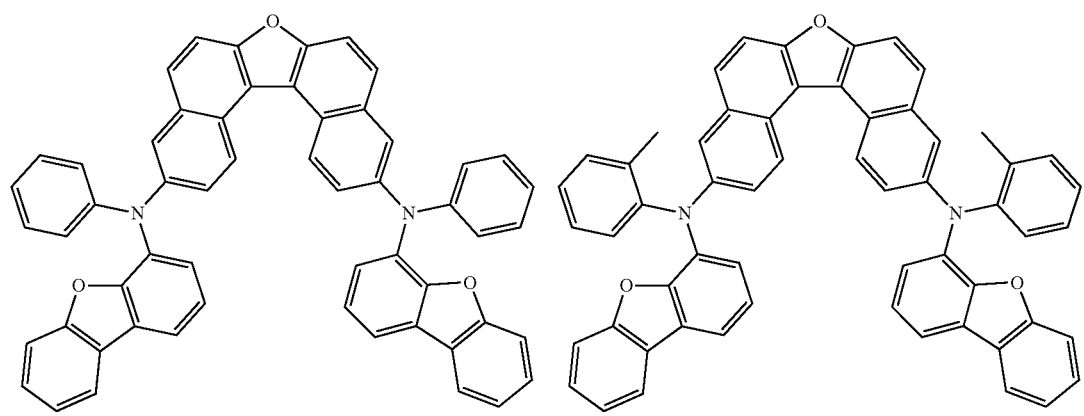

-continued
1153 1154
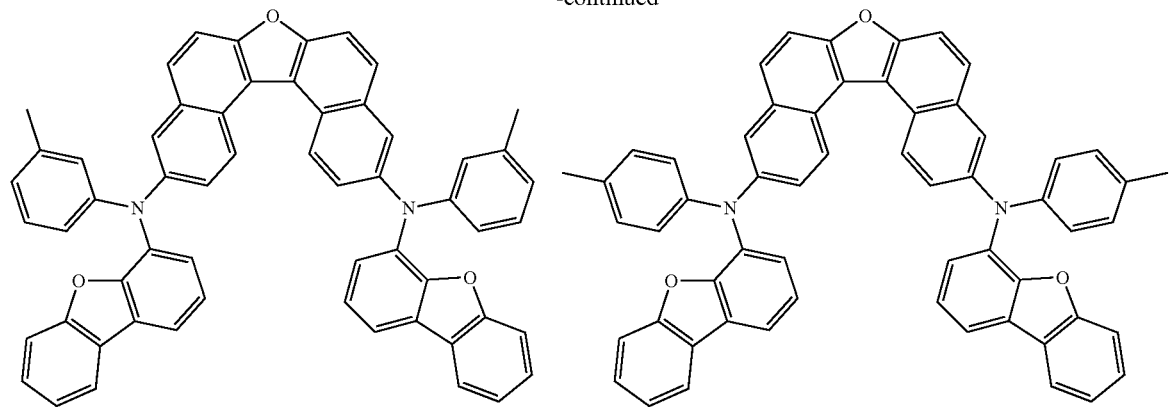
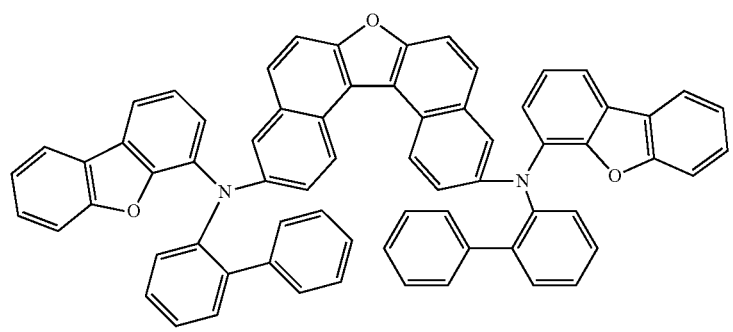
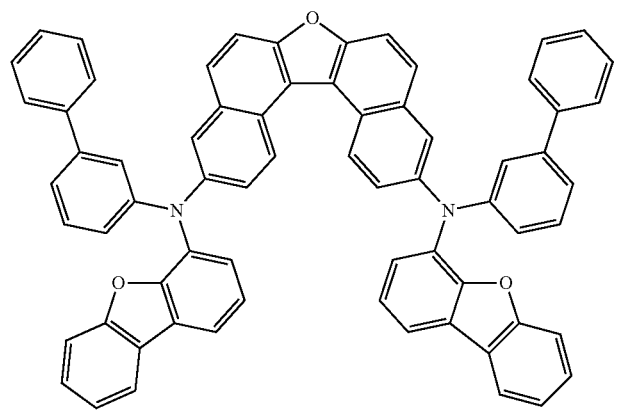
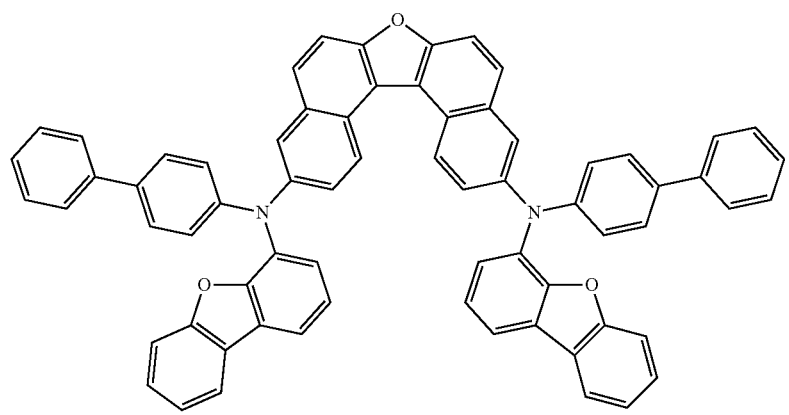

1155
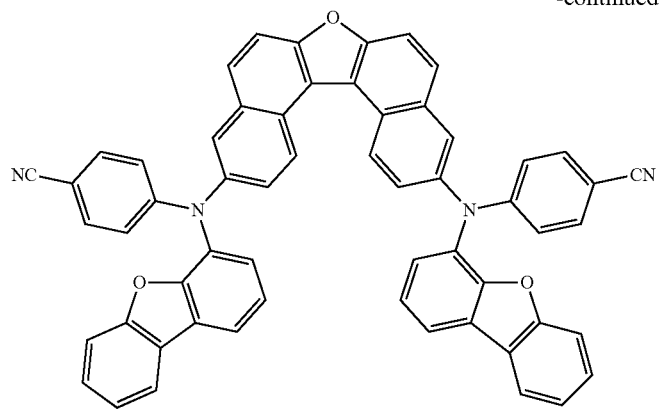
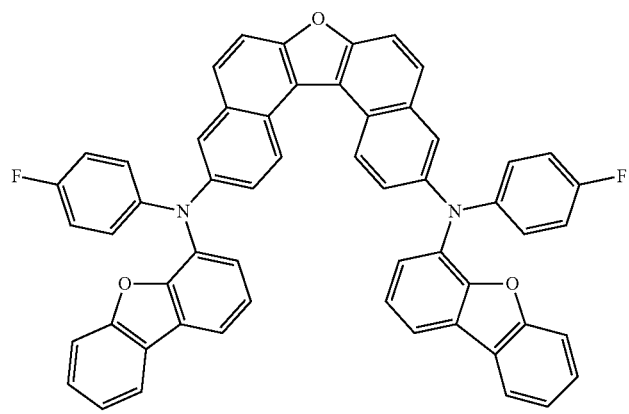
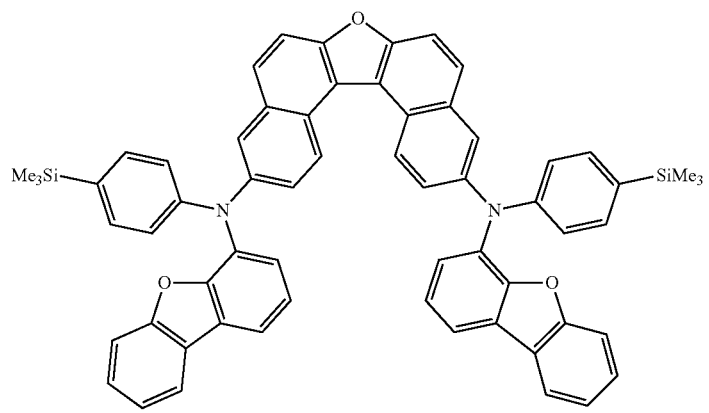
1156
-continued
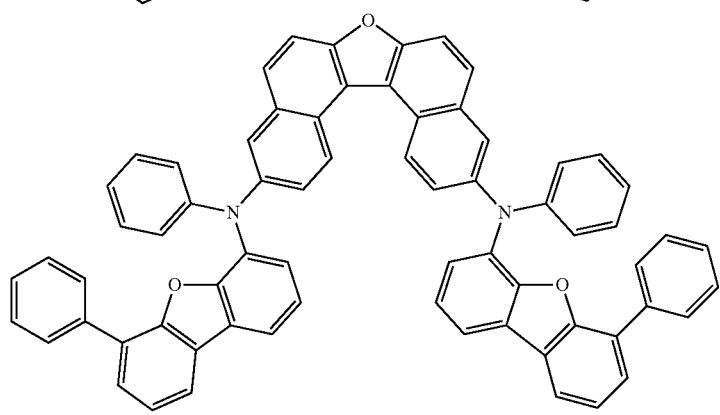

1157 1158
-continued
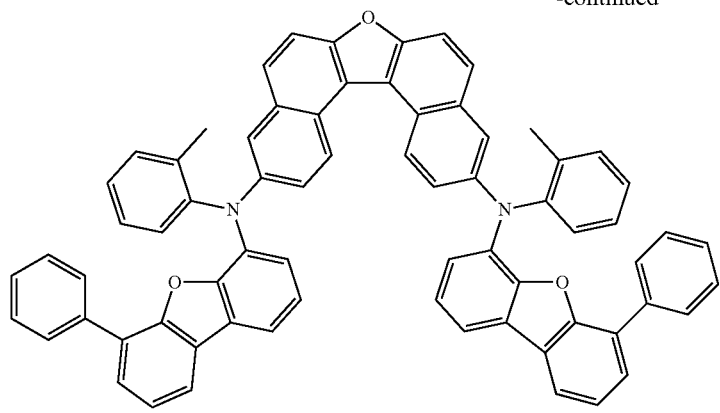
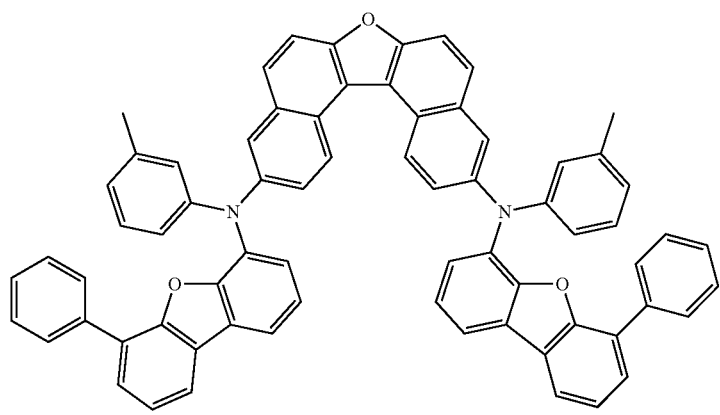
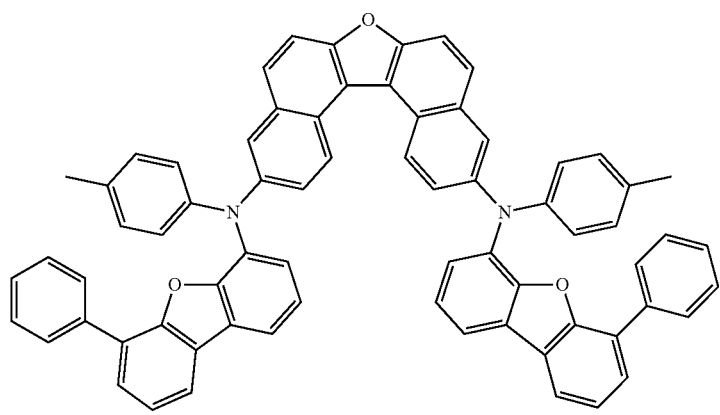
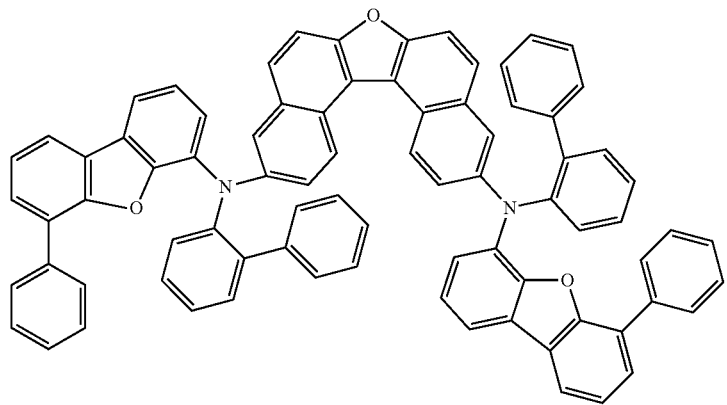

-continued
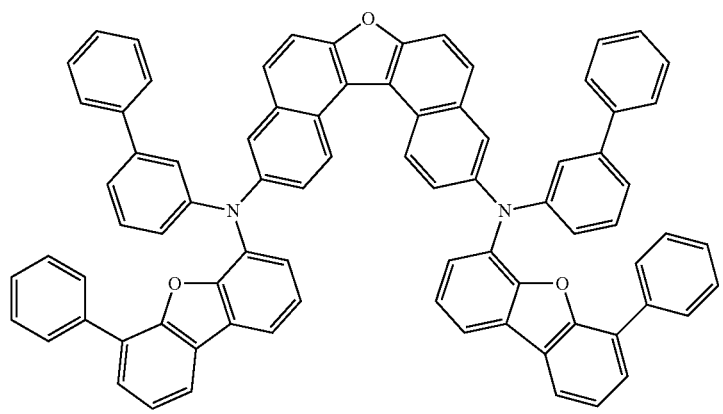
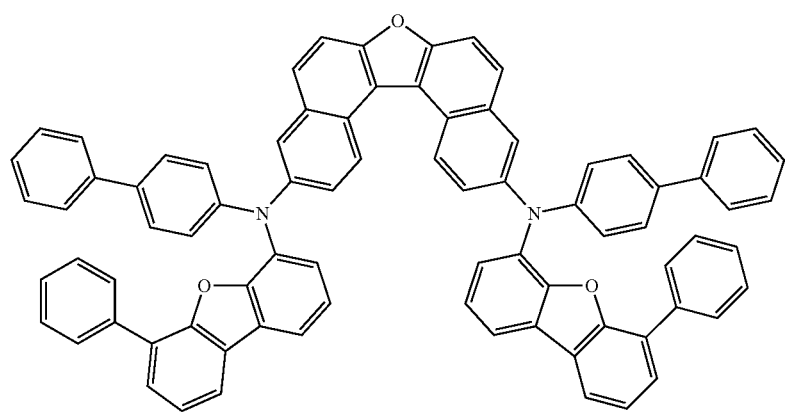
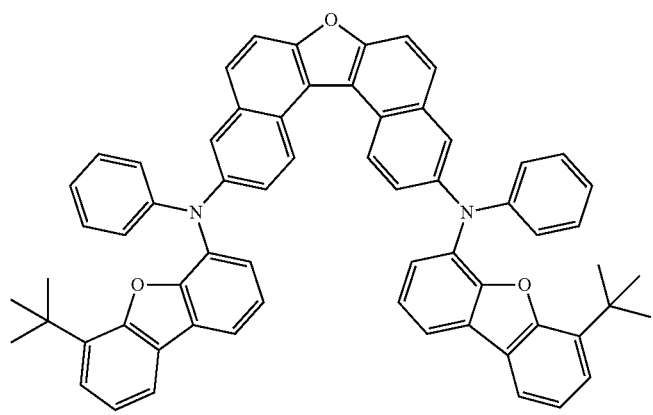
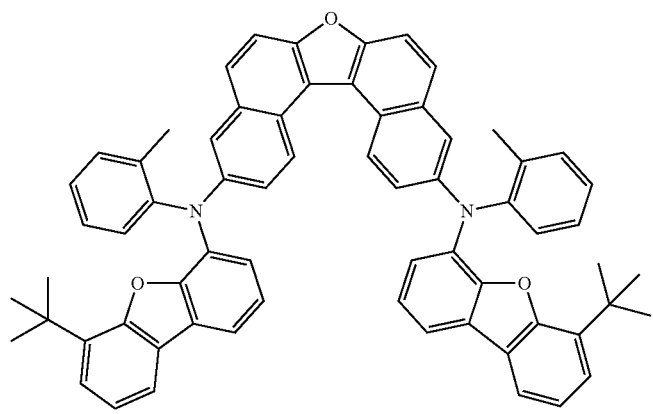

1161
1162
-continued
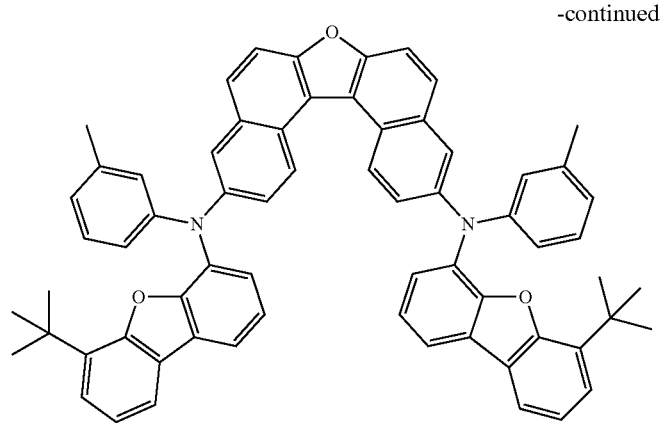
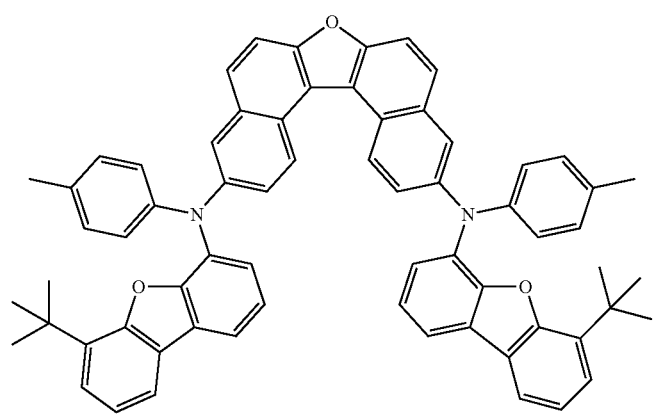
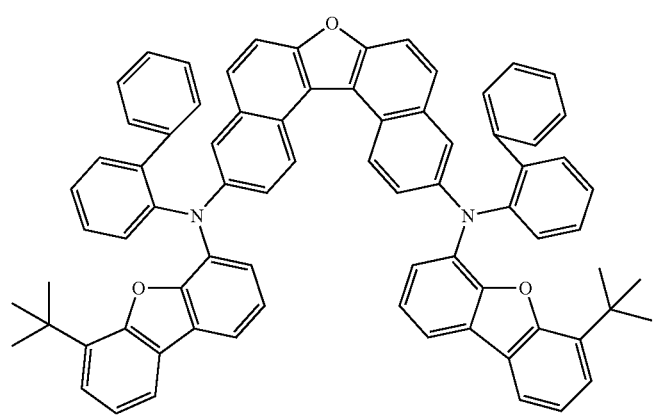
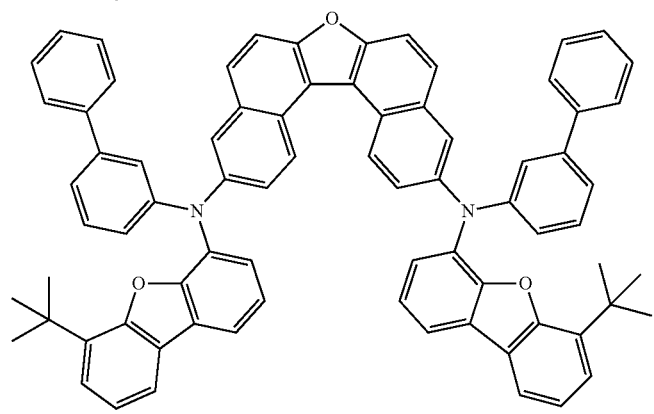

-continued
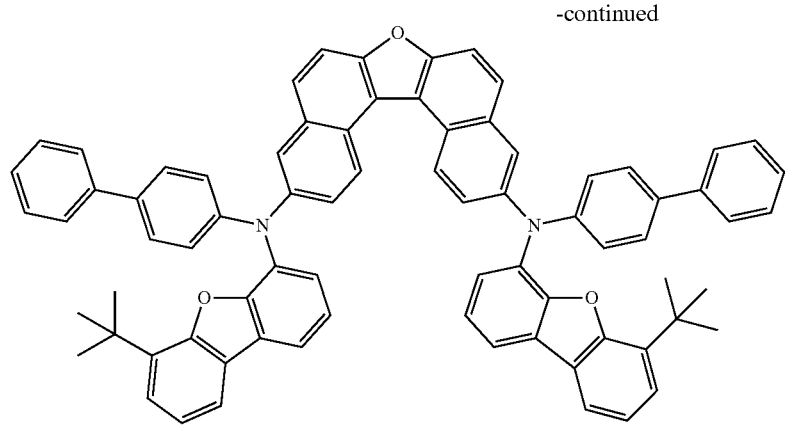
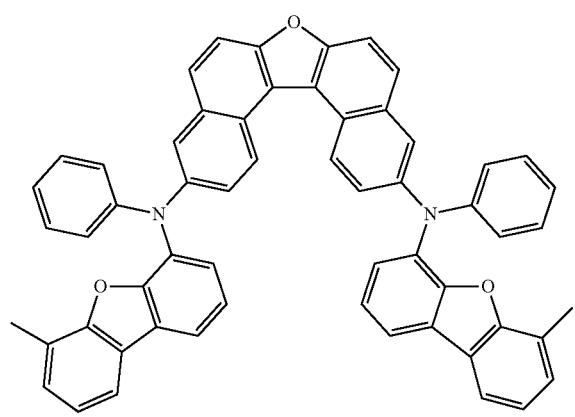
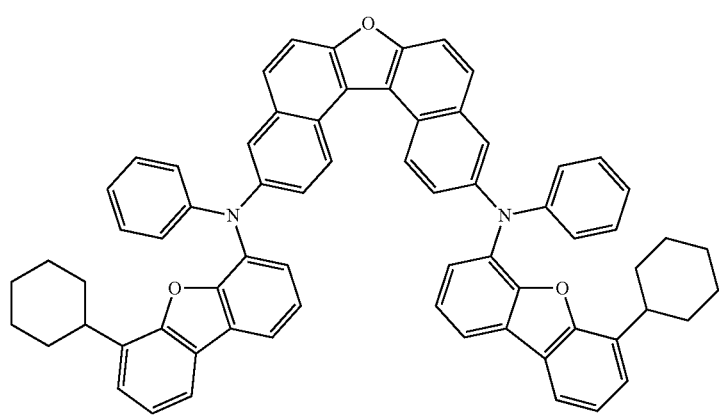
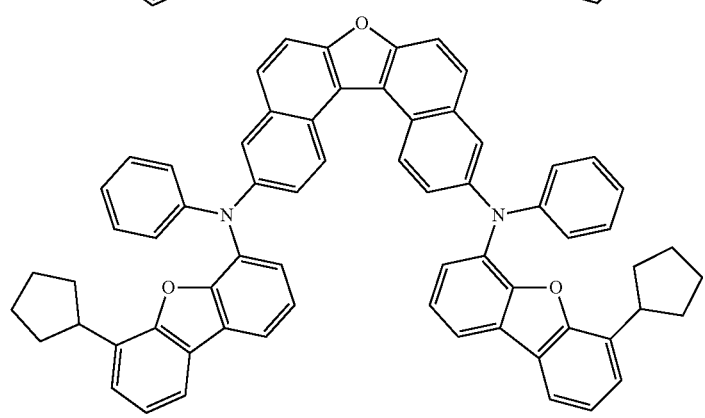

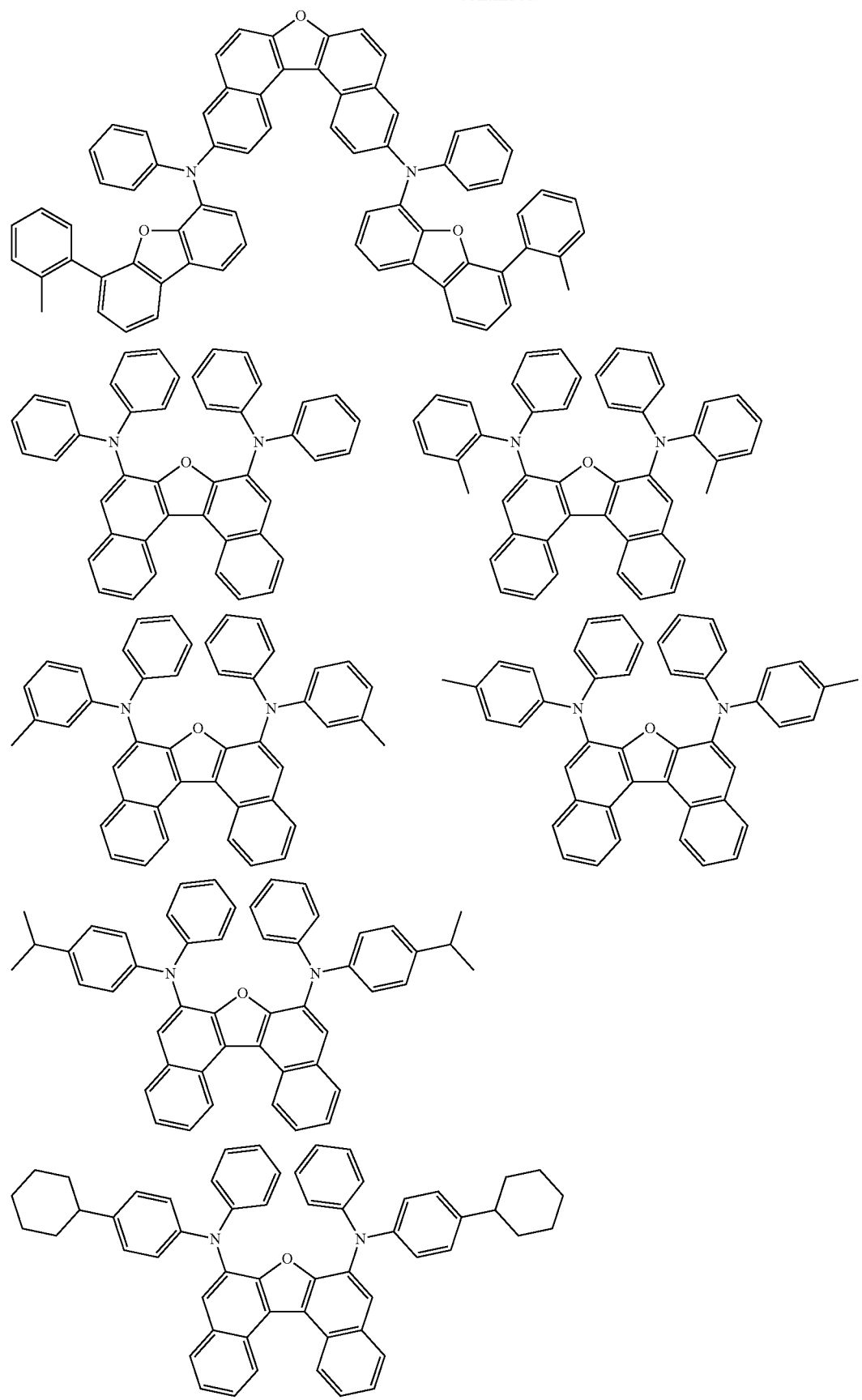

1167 -continued 1168
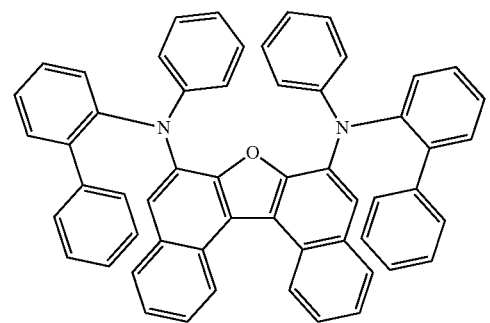
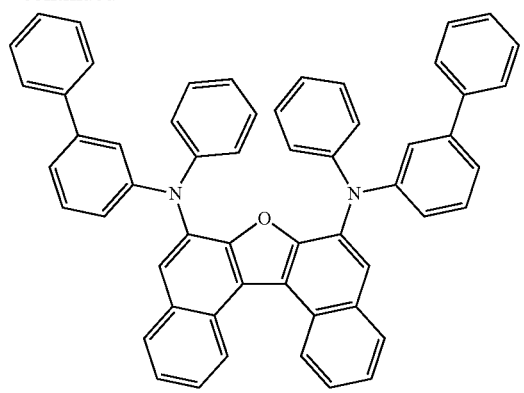
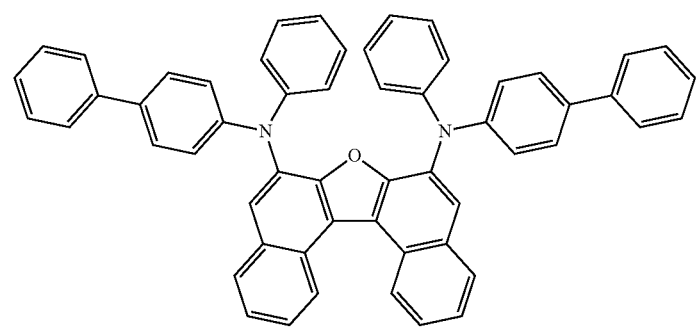
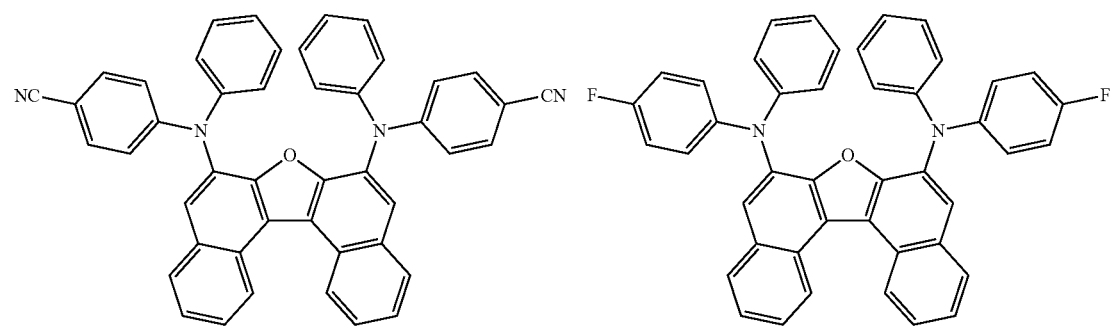
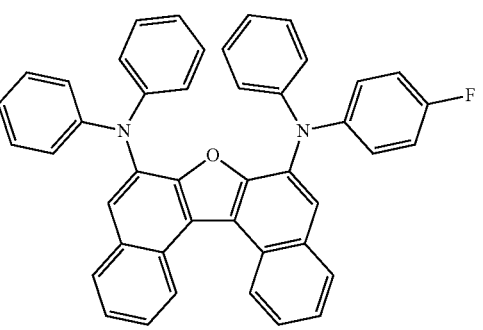
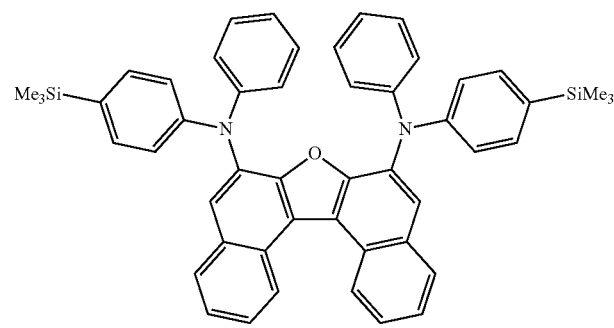
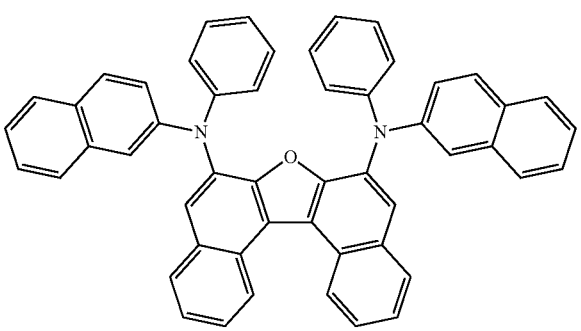
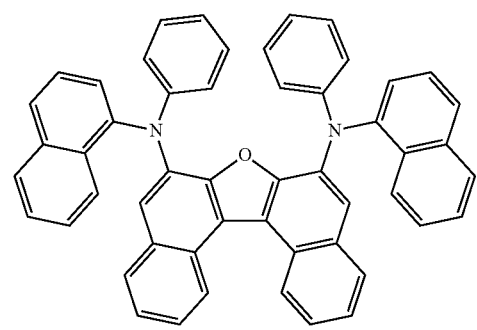
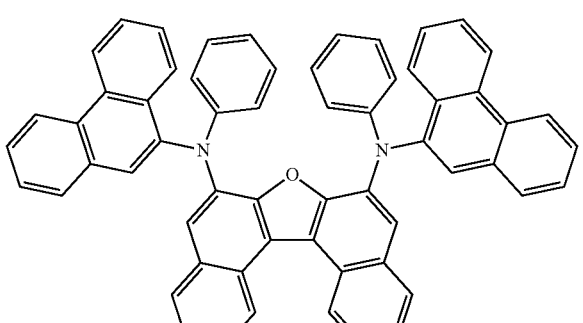

1169 1170
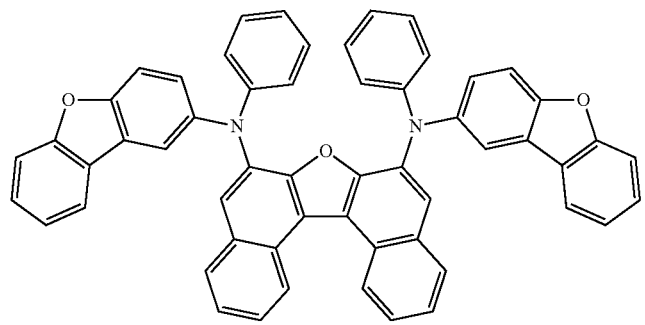
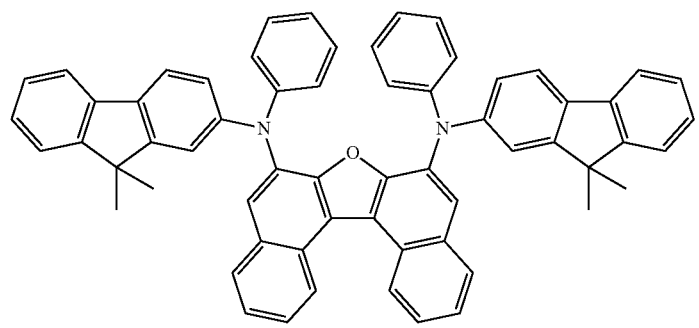
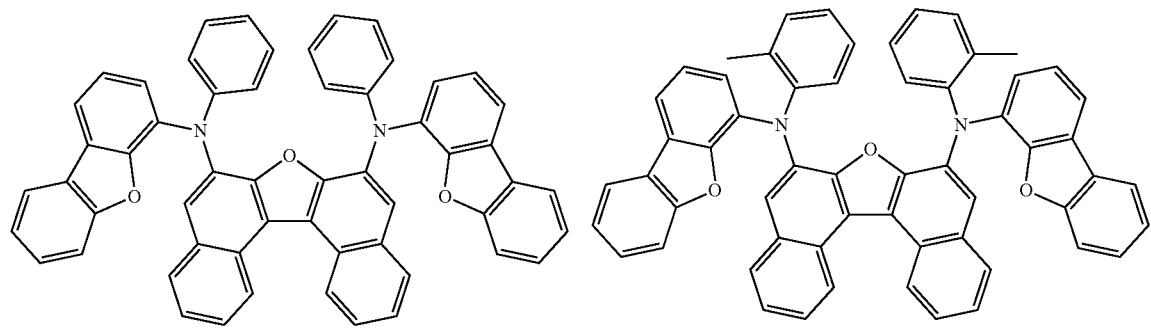
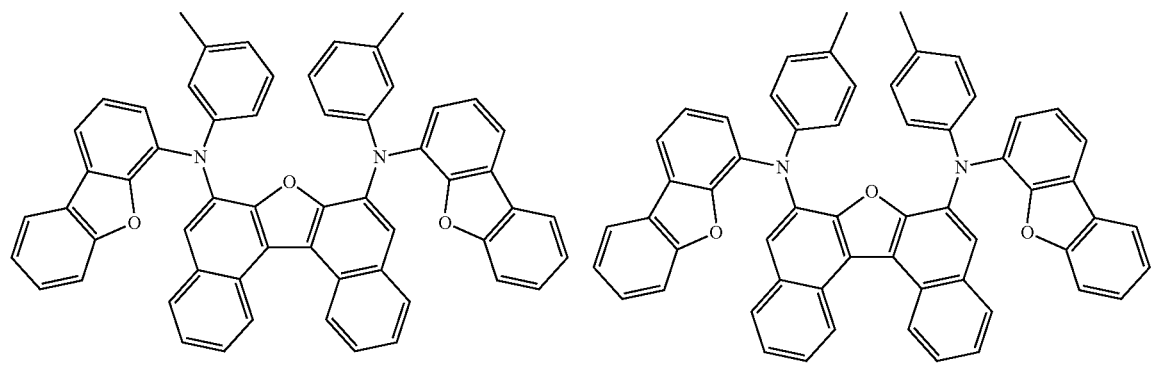

-continued
1171 1172
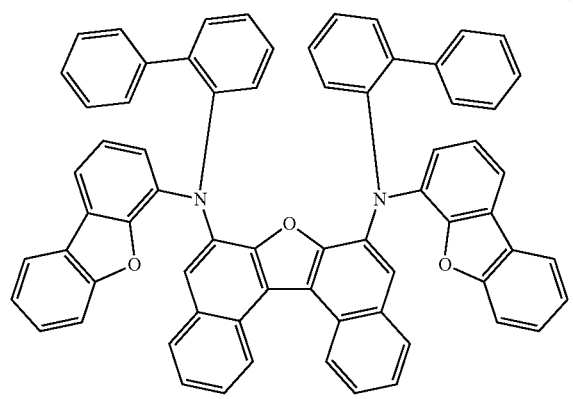 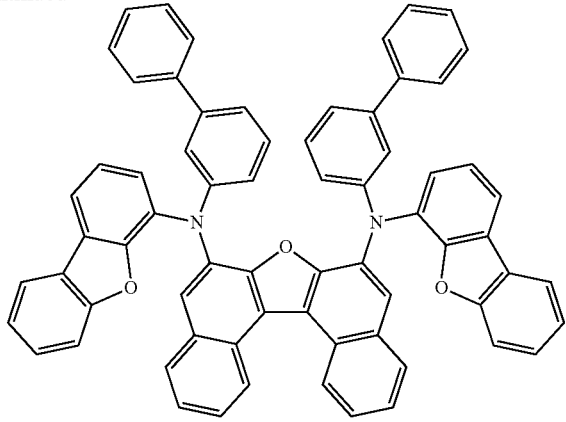
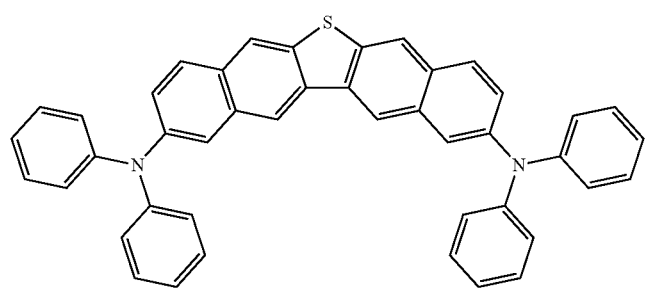
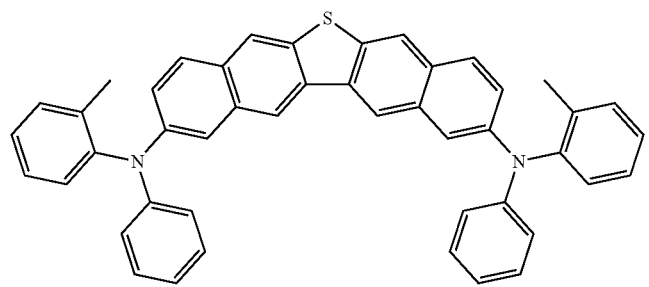
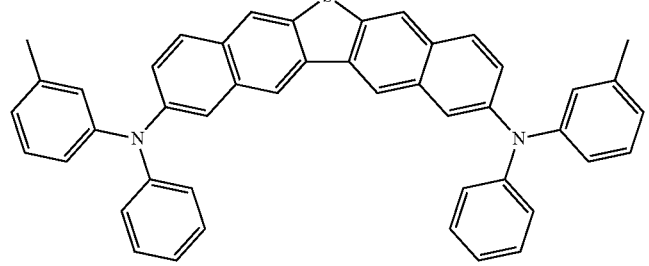
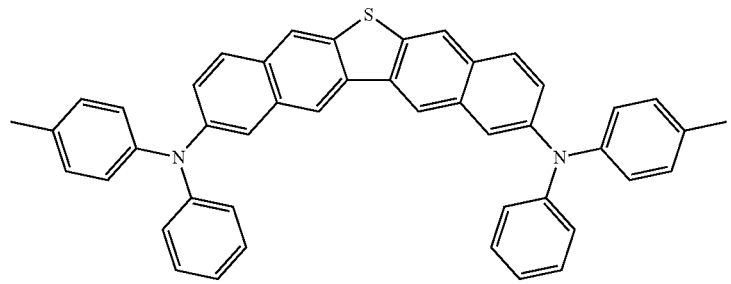

-continued
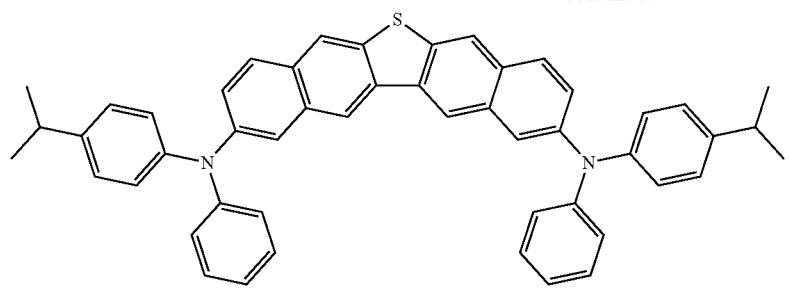
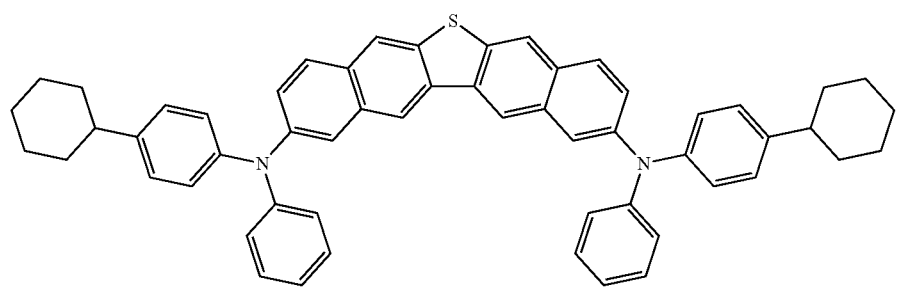
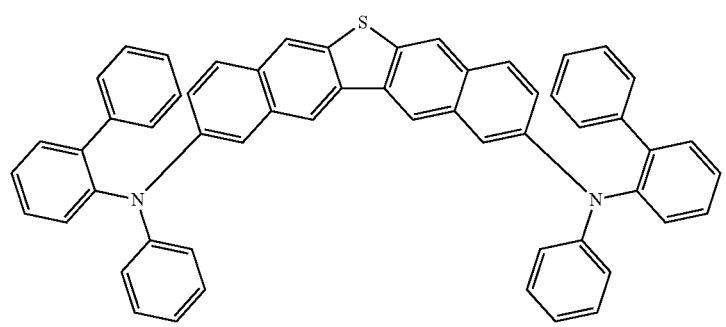
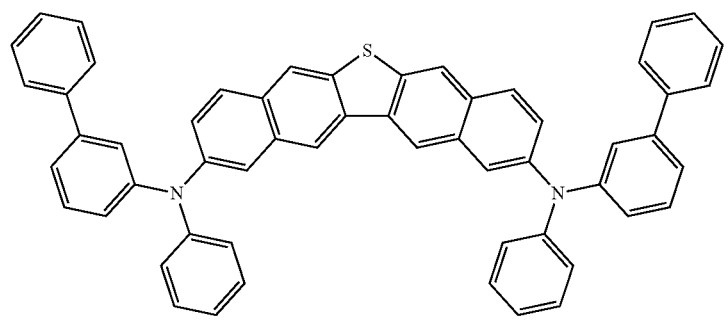
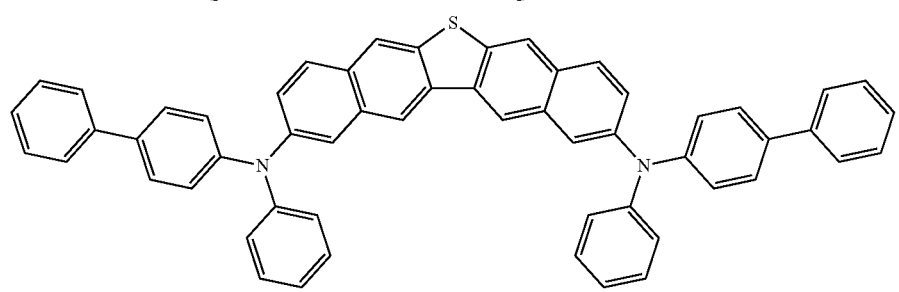

-continued
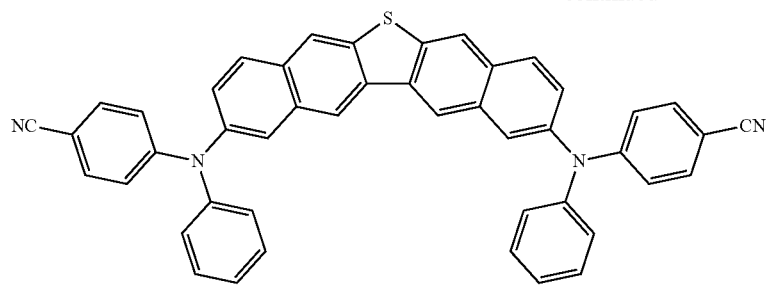
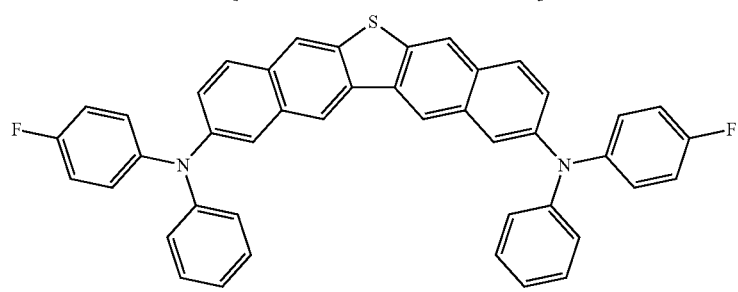
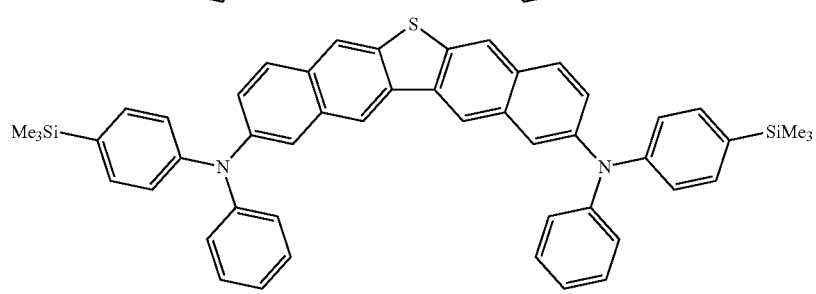
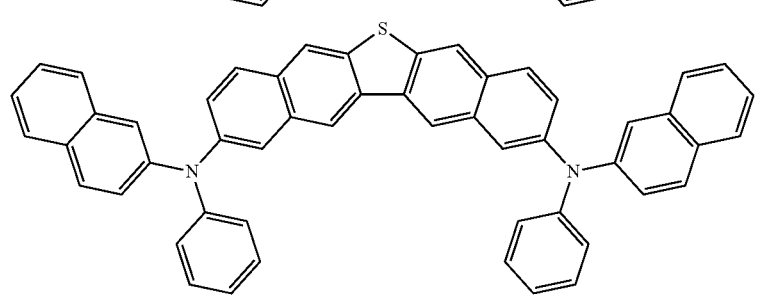
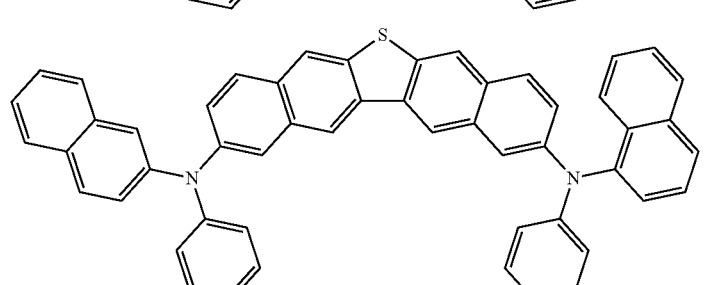
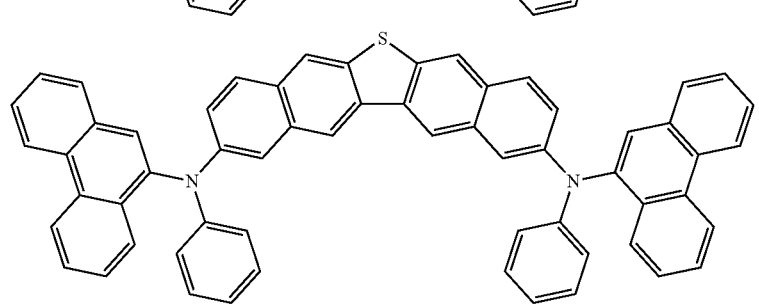

-continued
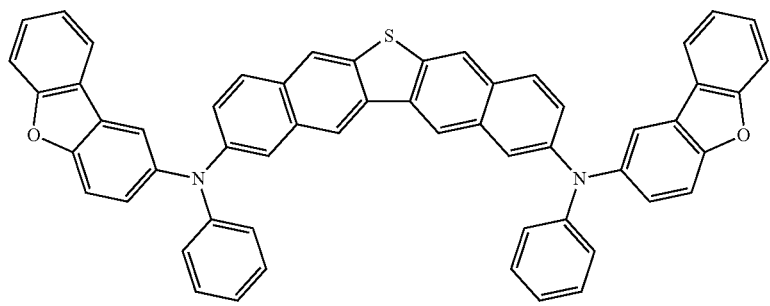
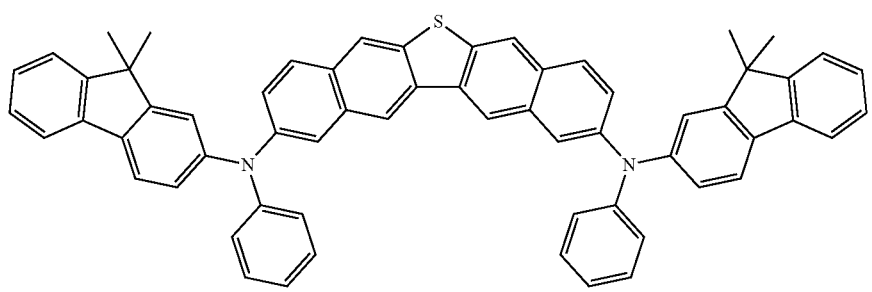
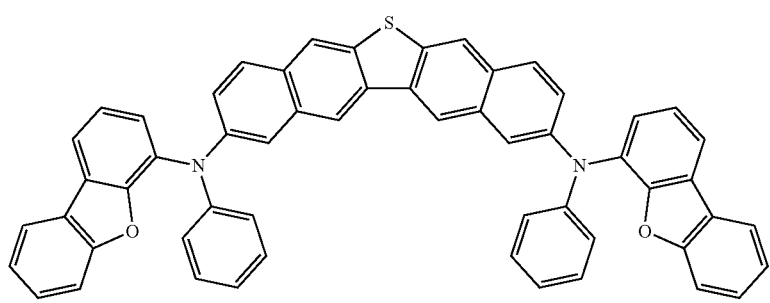
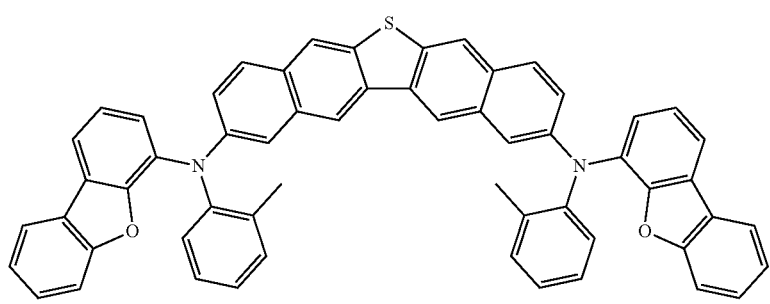
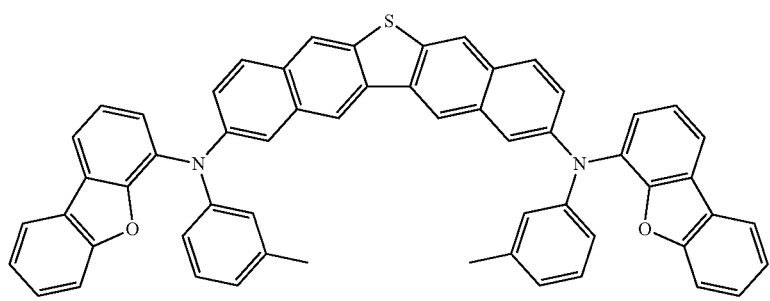

1179 1180
-continued
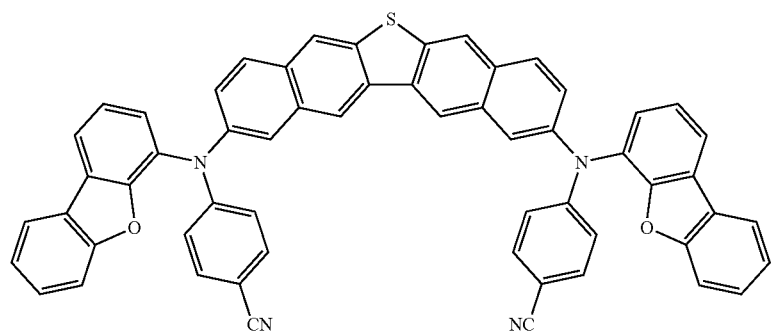
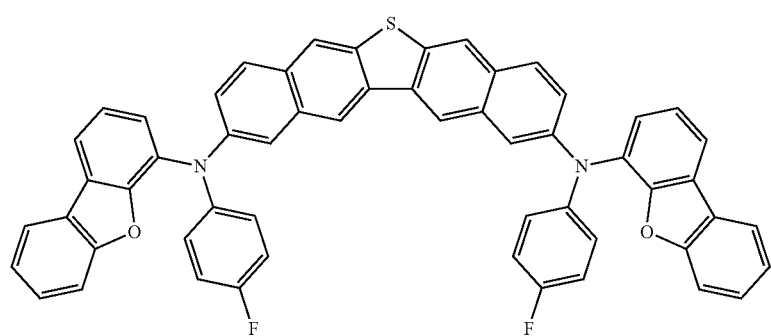
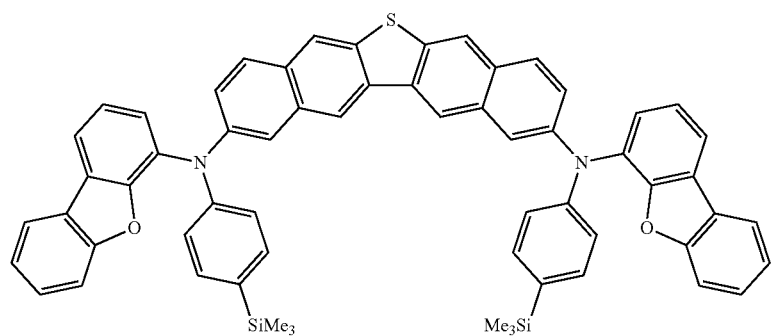
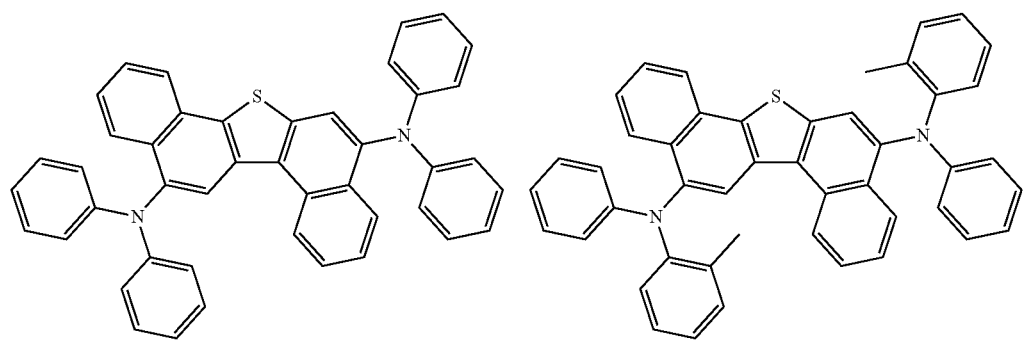

1181 1182
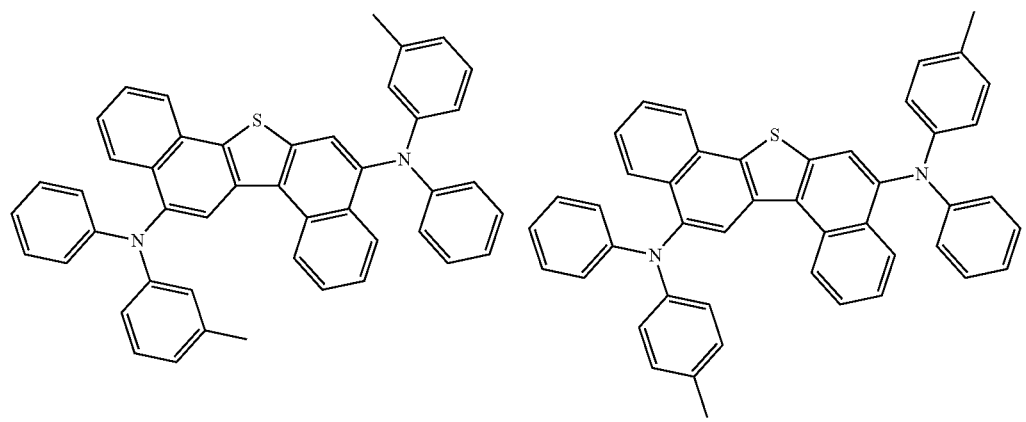
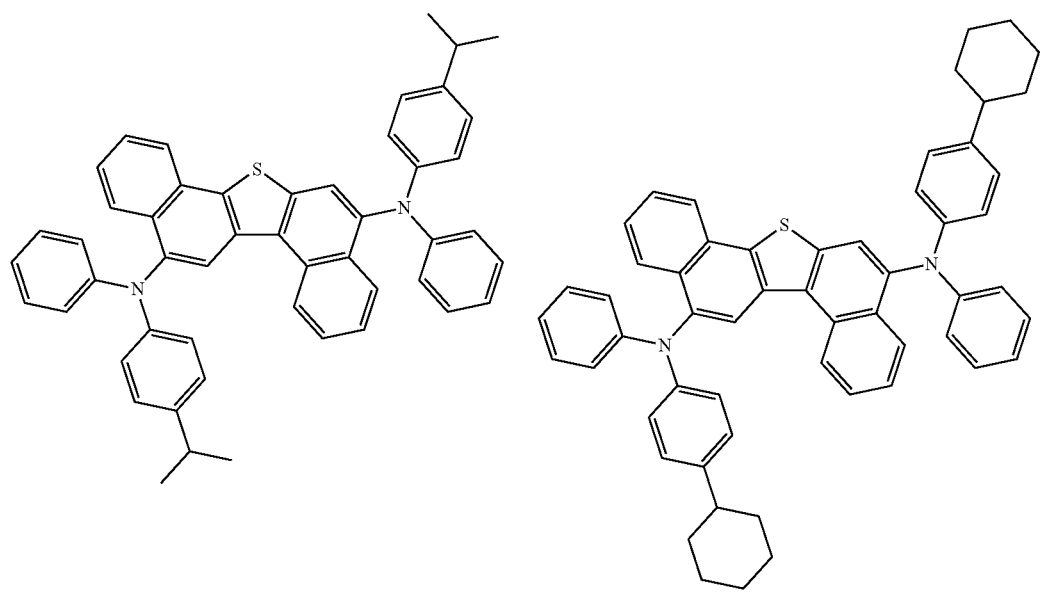
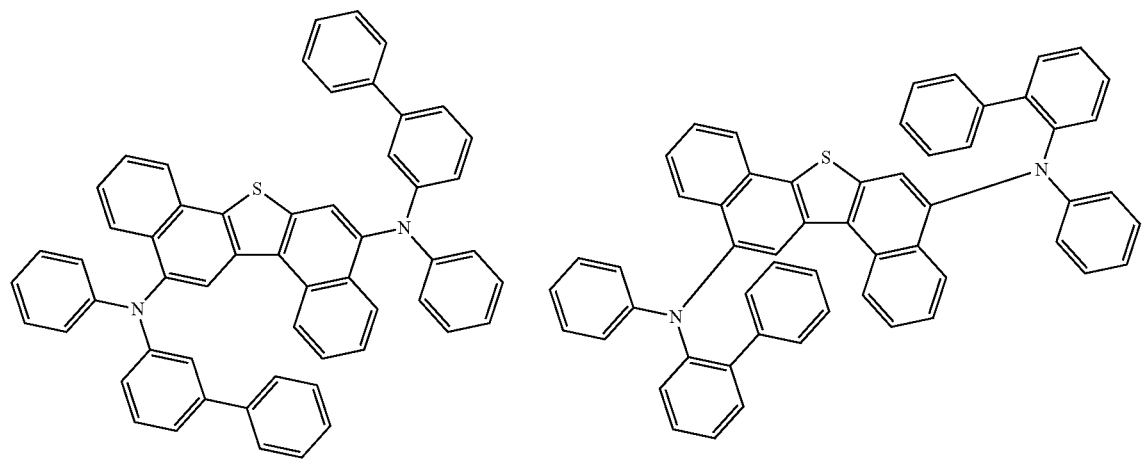

-continued
1183
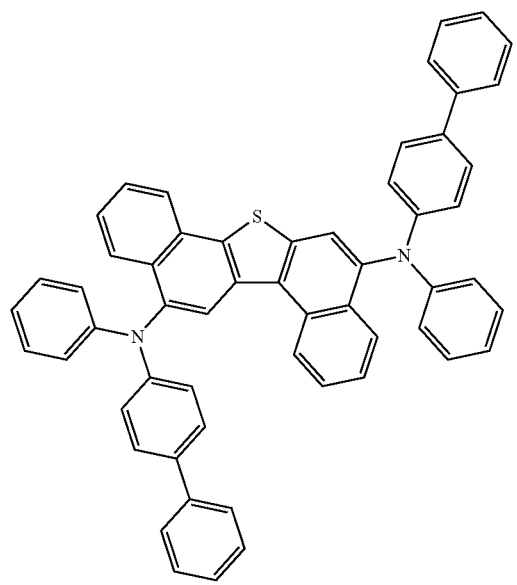
1184
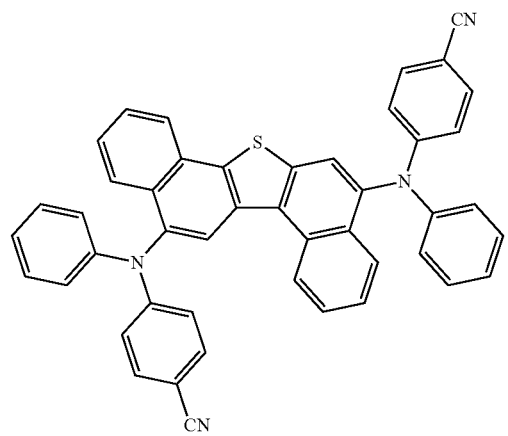
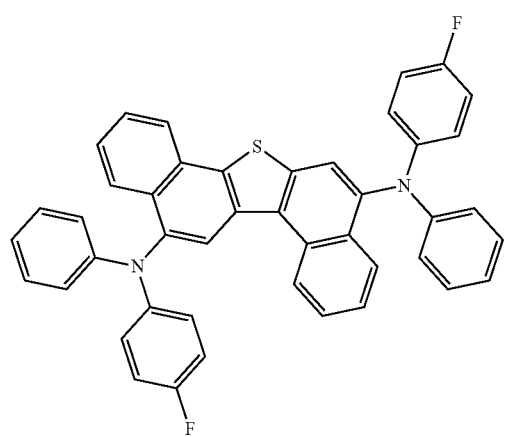
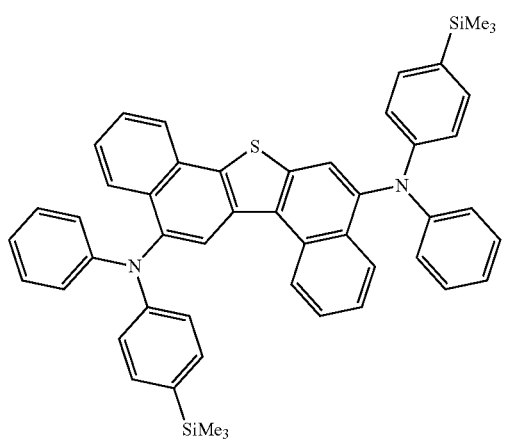
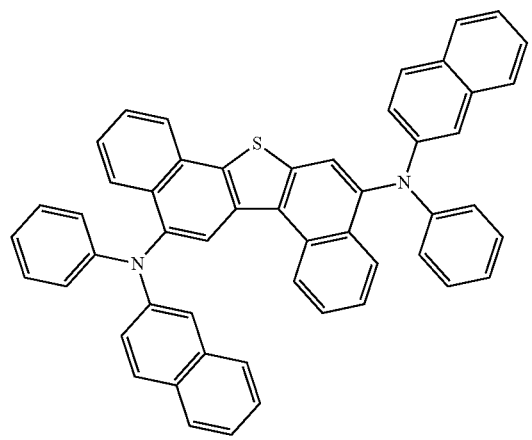
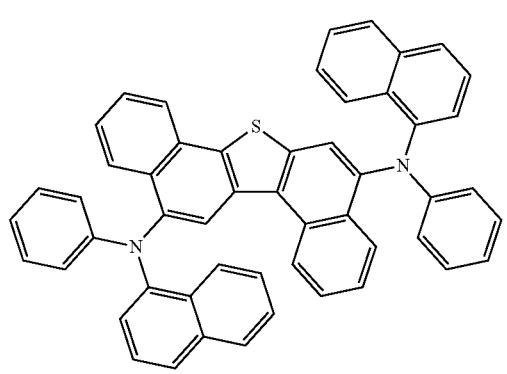

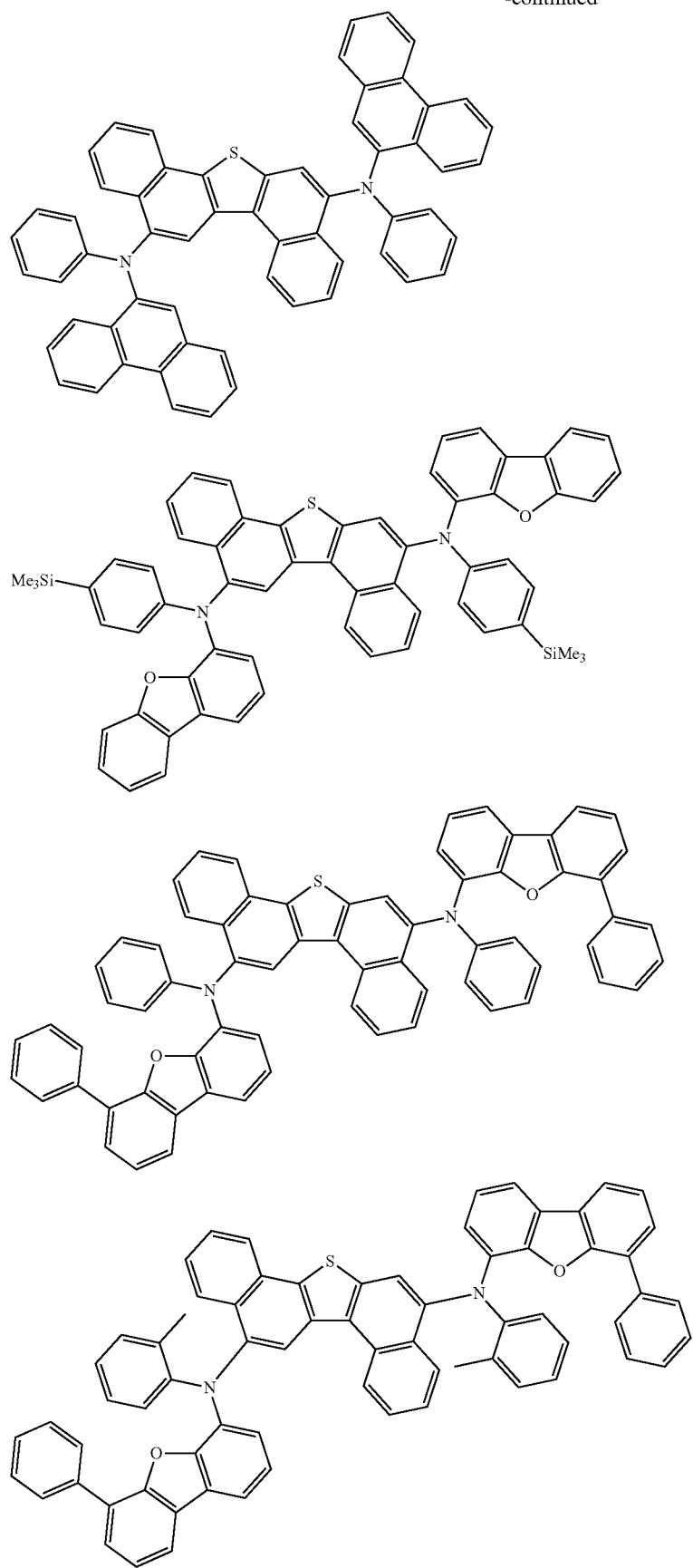

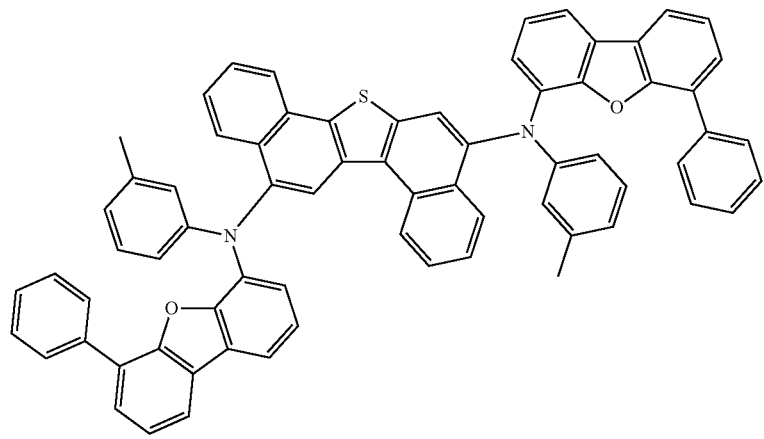
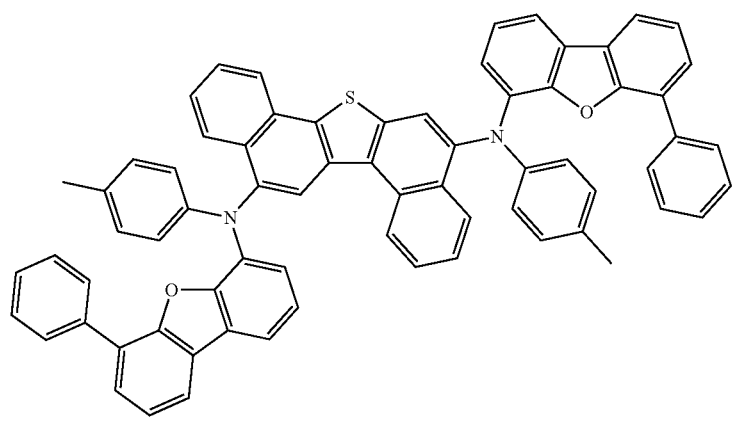
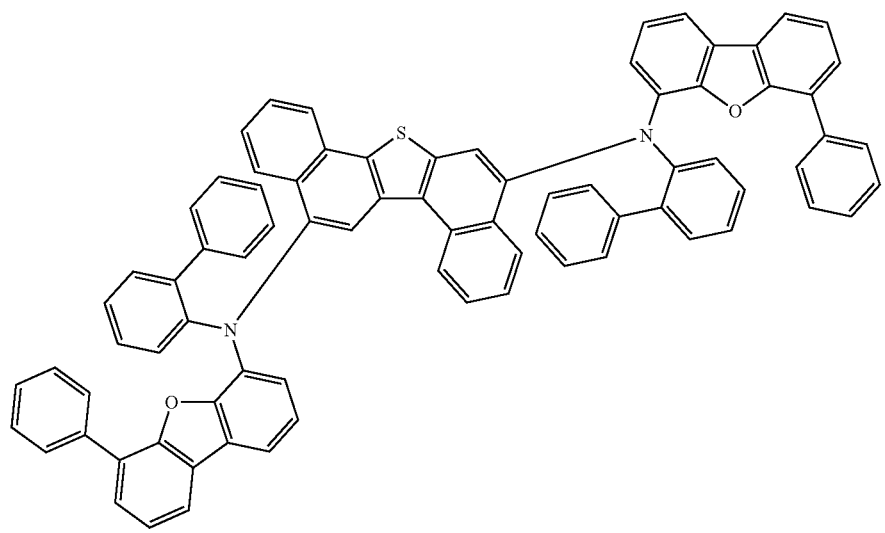

-continued
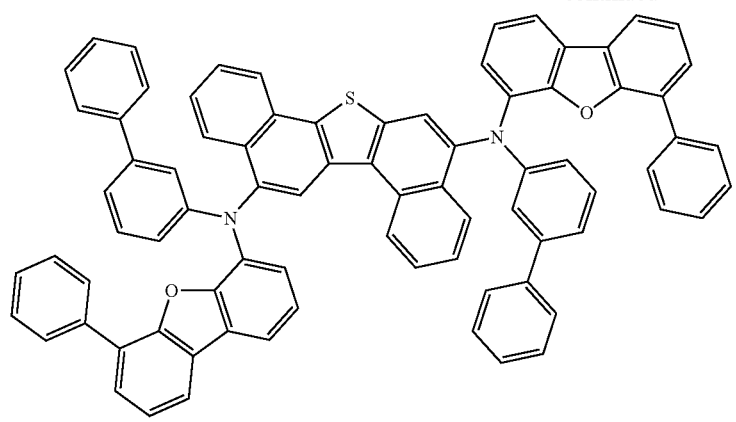
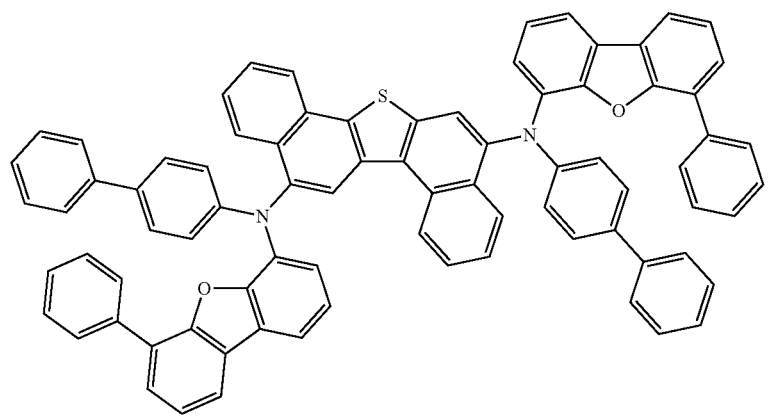
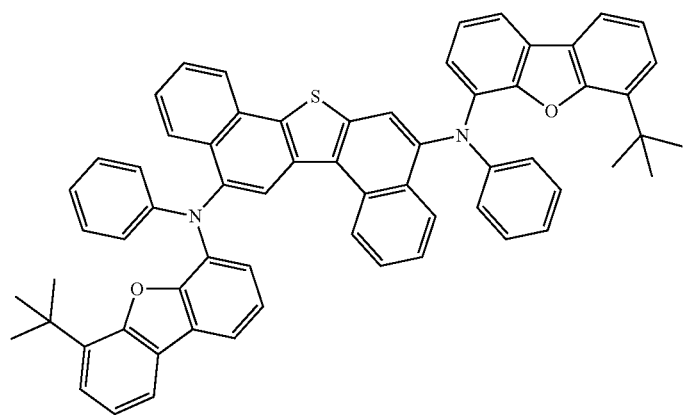
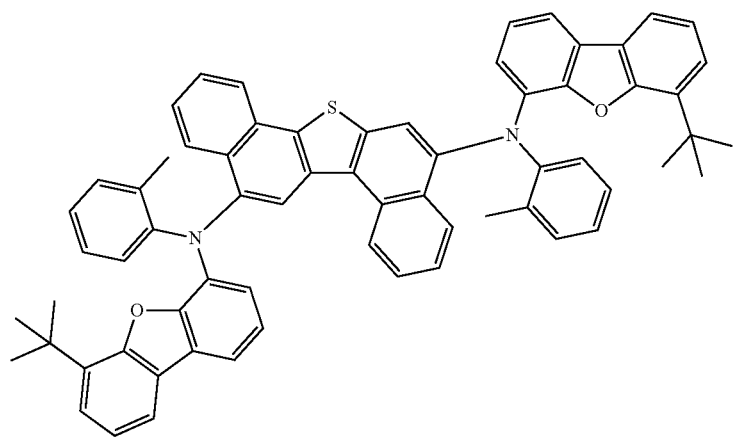

1191
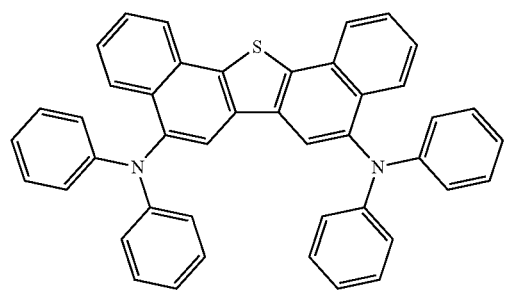
1192
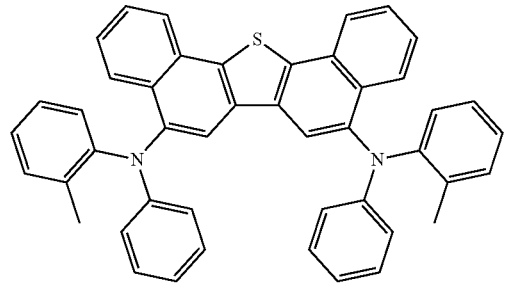
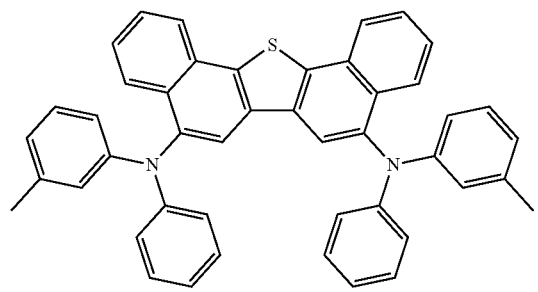
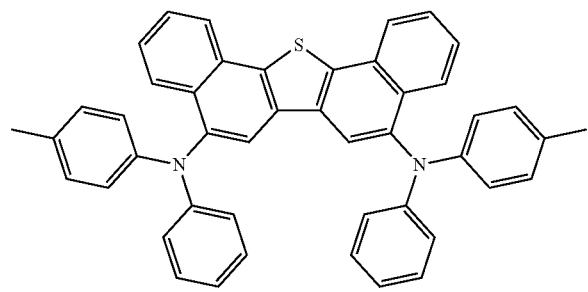
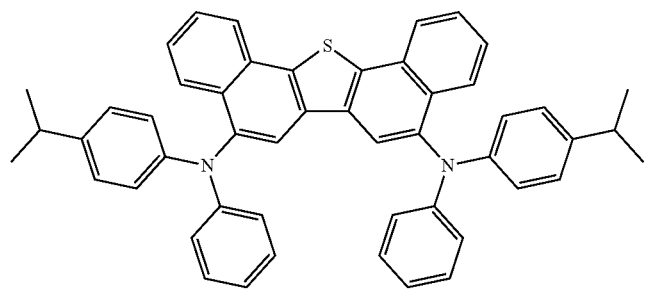
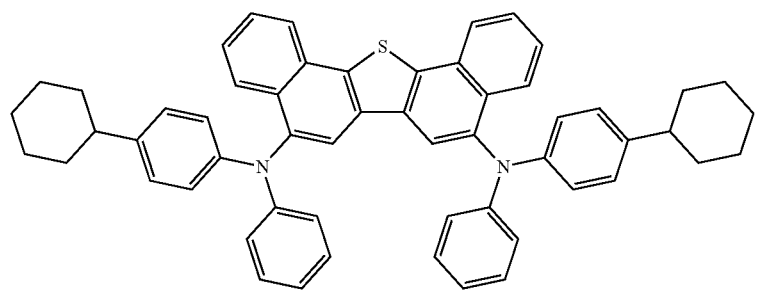
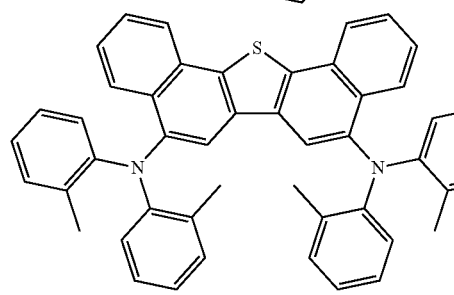
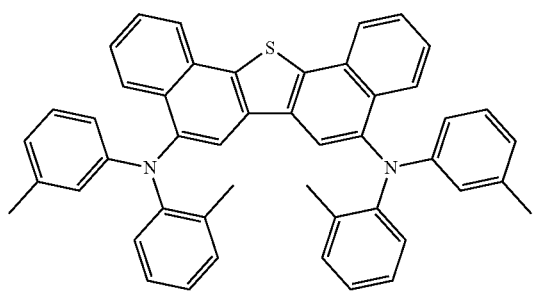

-continued
1193 1194
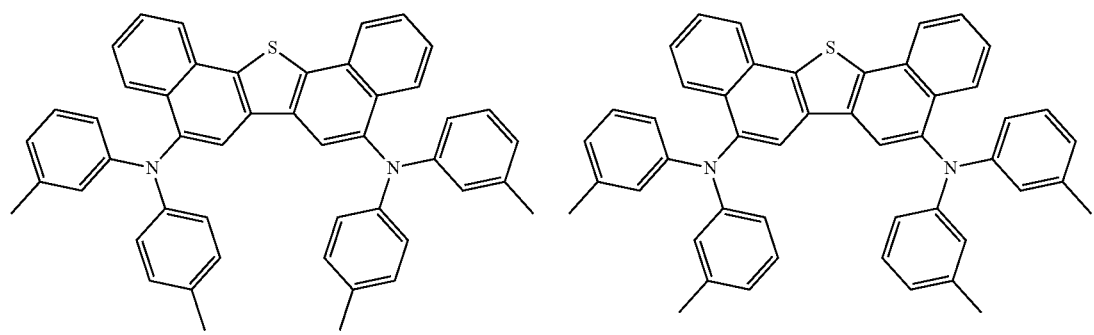
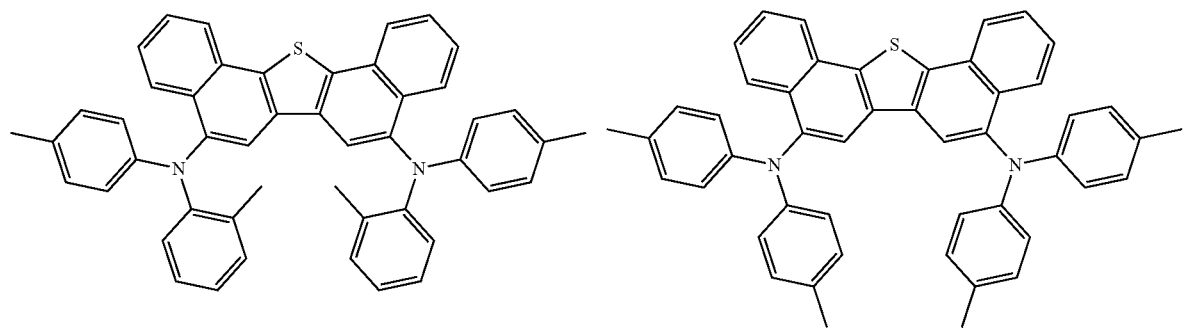
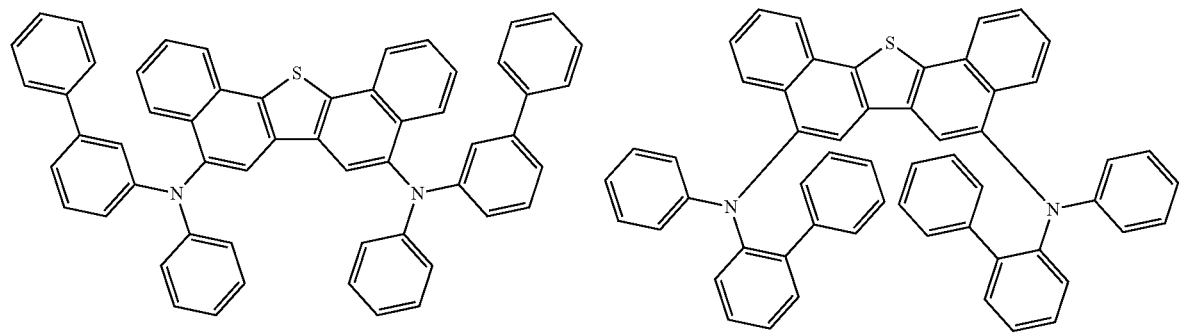
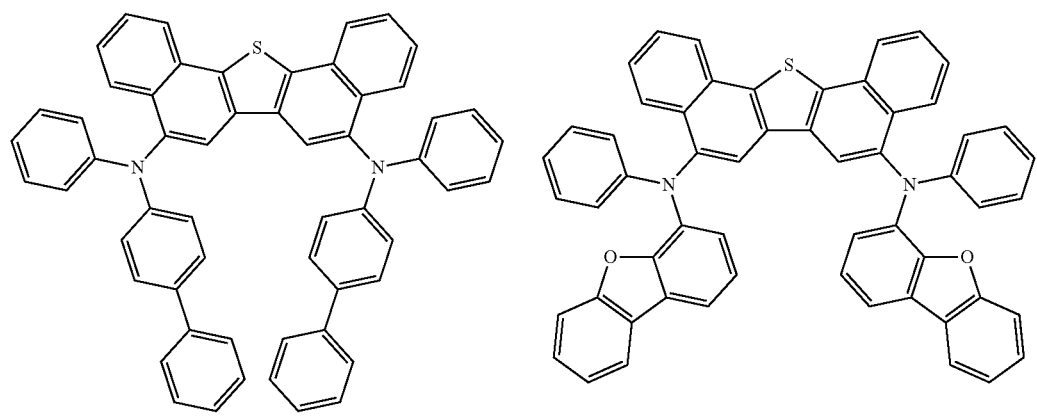

-continued
| 1195 | 1196 |
|---|---|
| 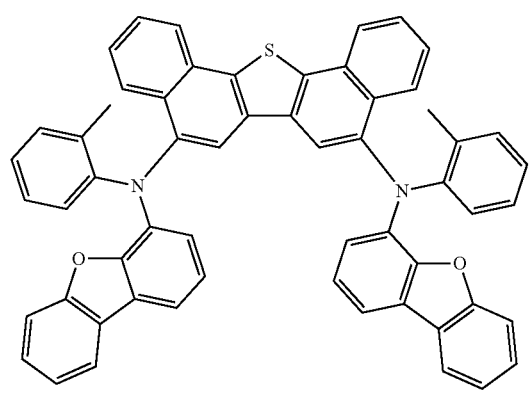 | 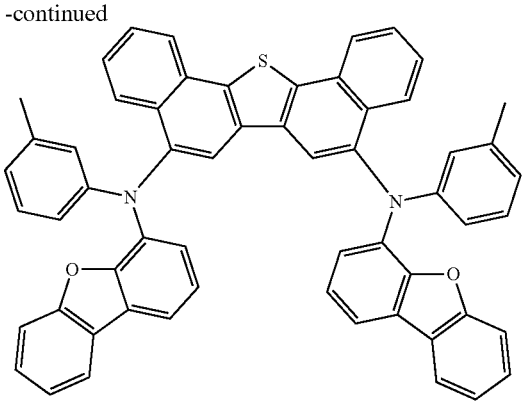 |
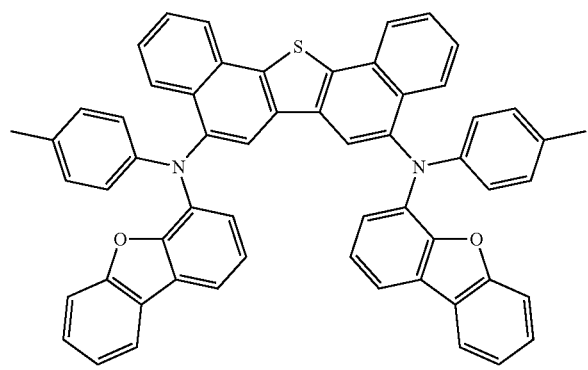
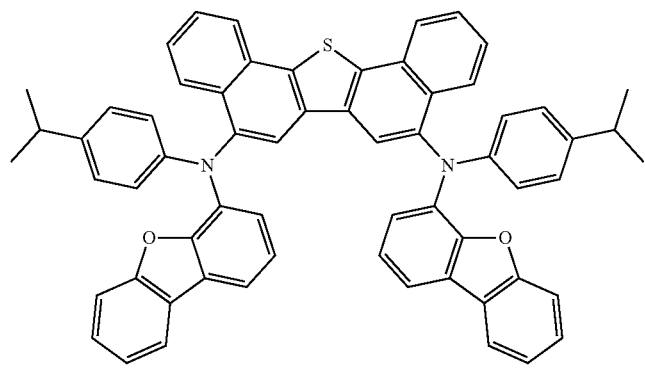
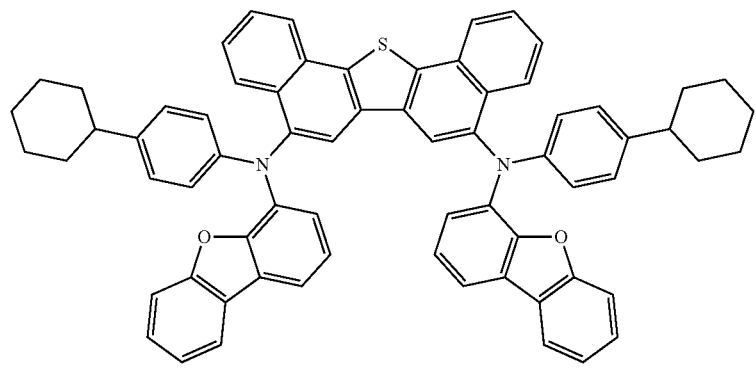

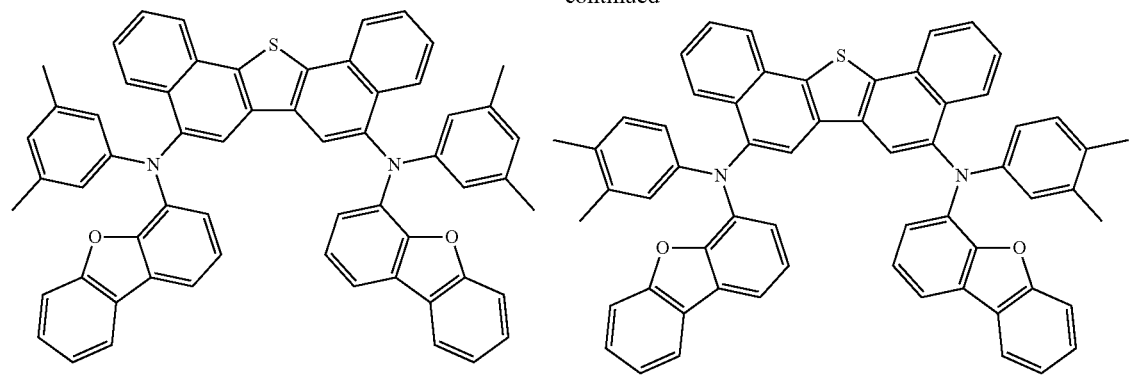

-continued
| 1199 | 1200 |
|---|---|
| 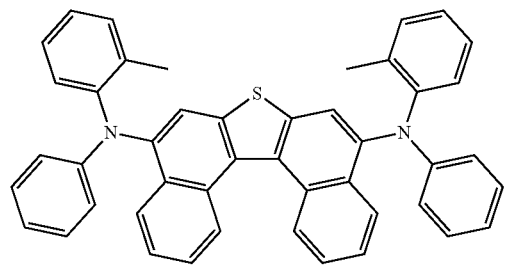 | 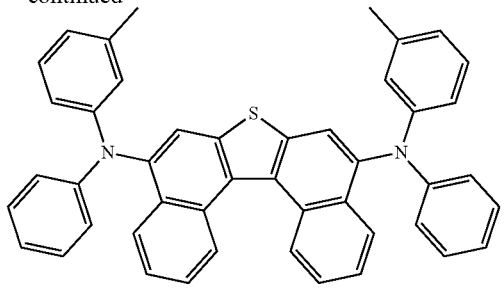 |
| 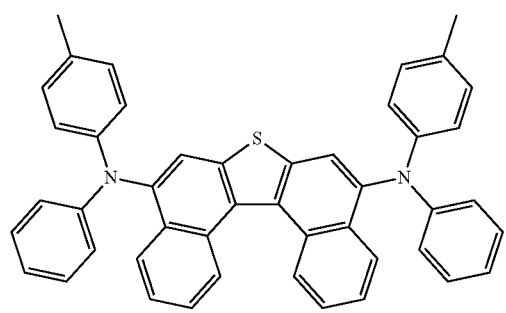 | 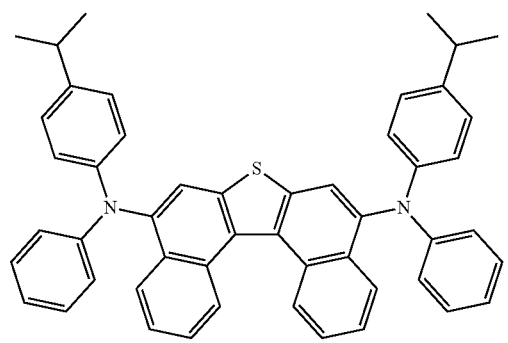 |
| 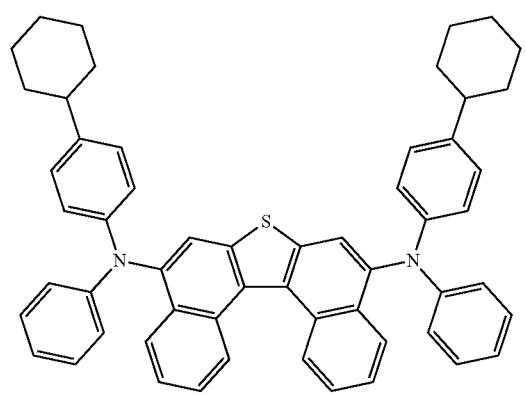 | 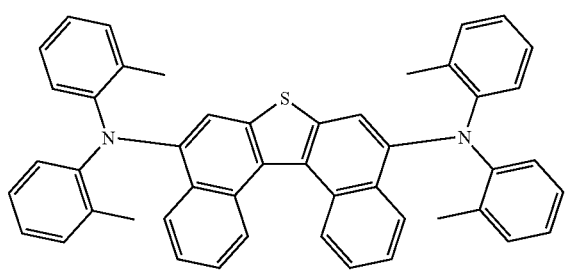 |
| 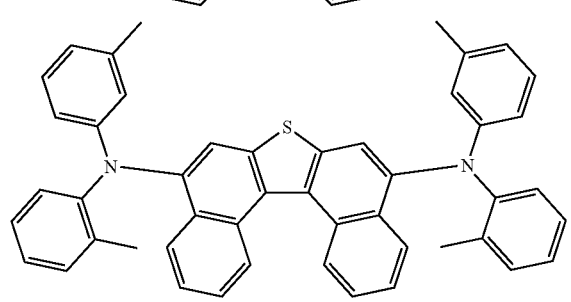 | 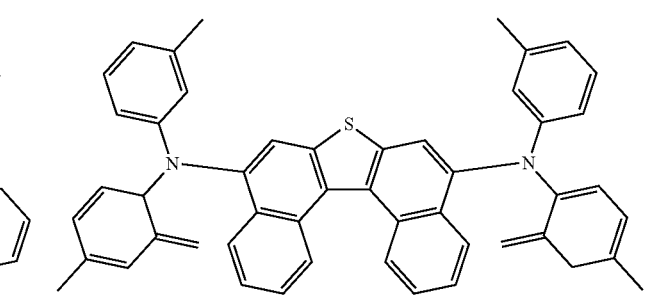 |
| 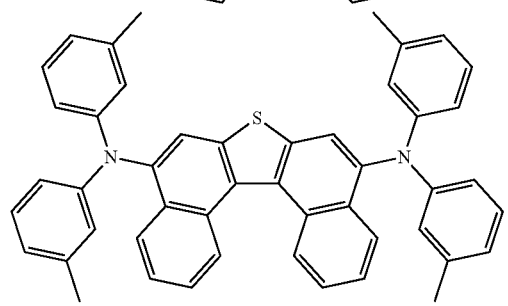 | 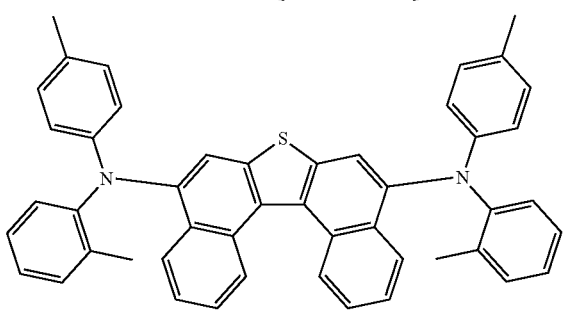 |

-continued
| 1201 | 1202 |
|---|---|
| 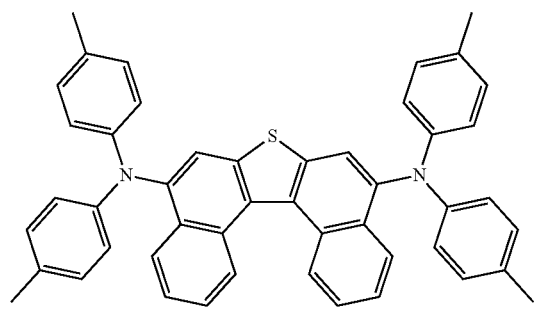 | 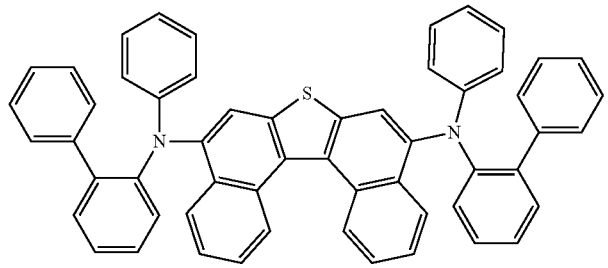 |
| 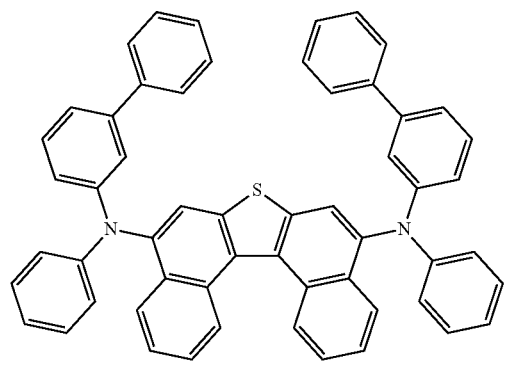 | 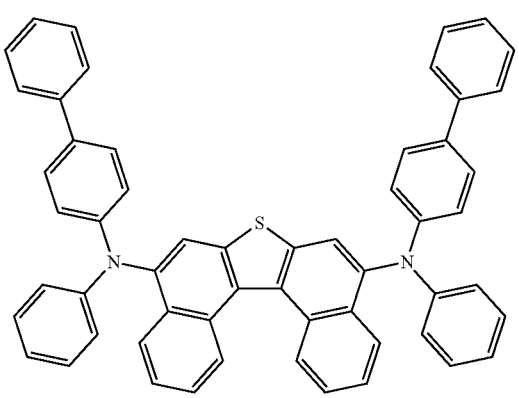 |
| 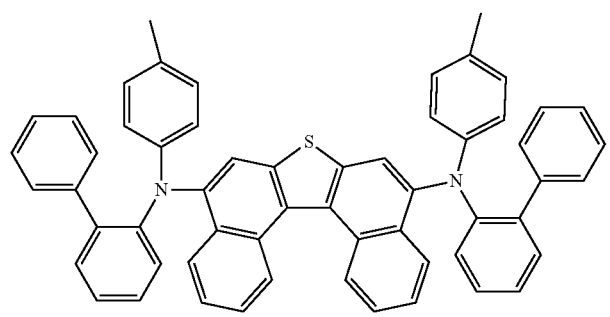 | 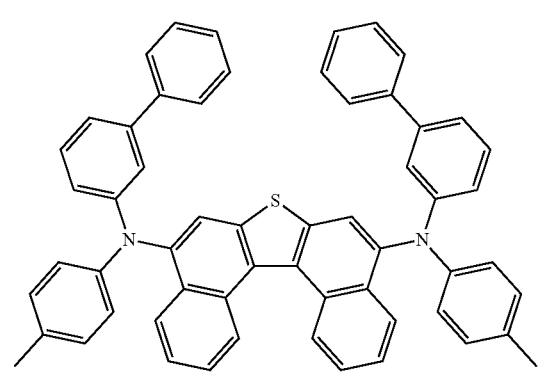 |
| 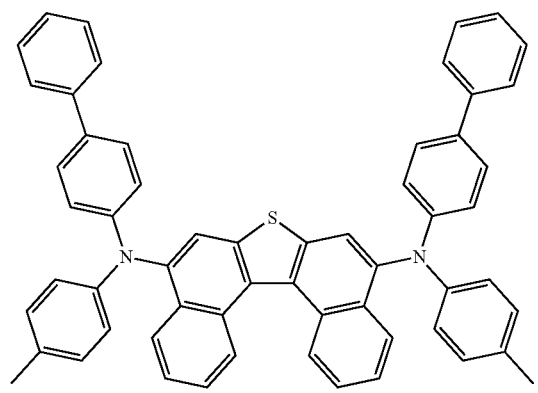 | |

1203 1204
-continued
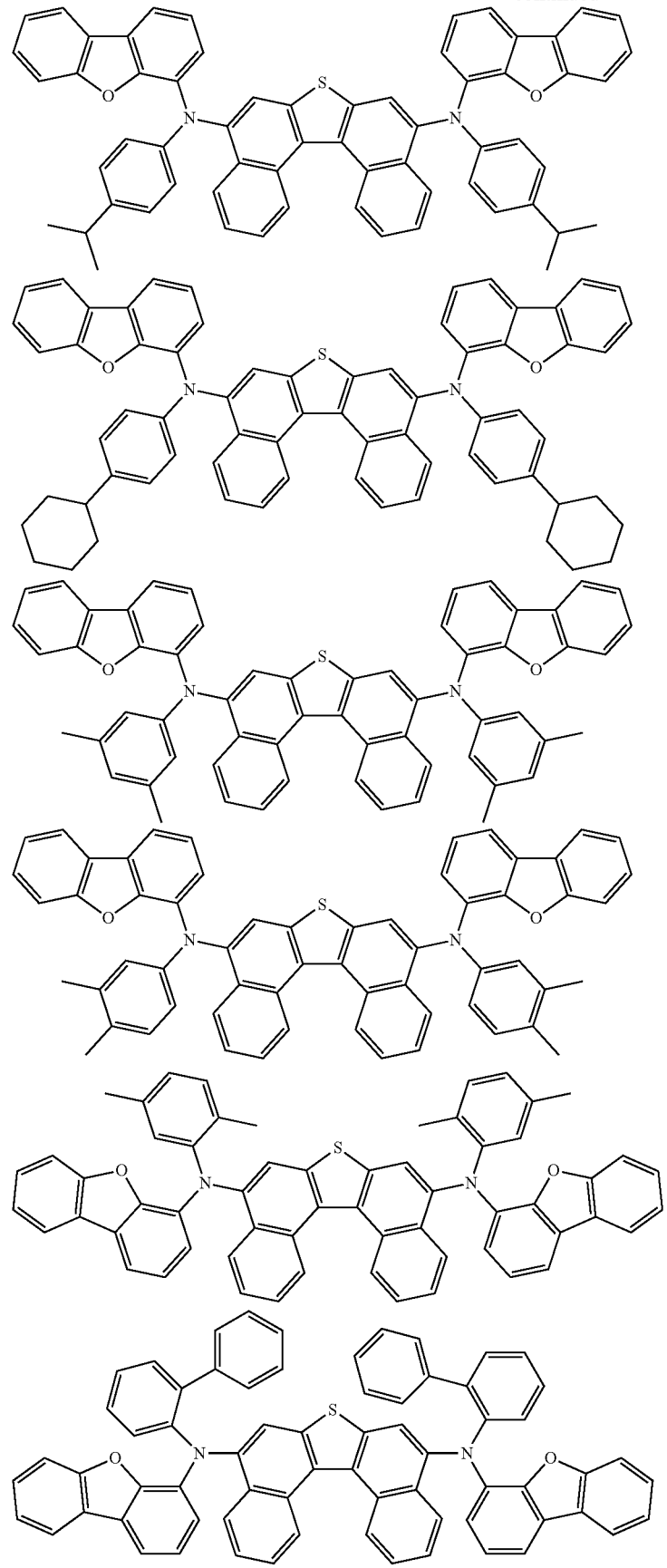

-continued
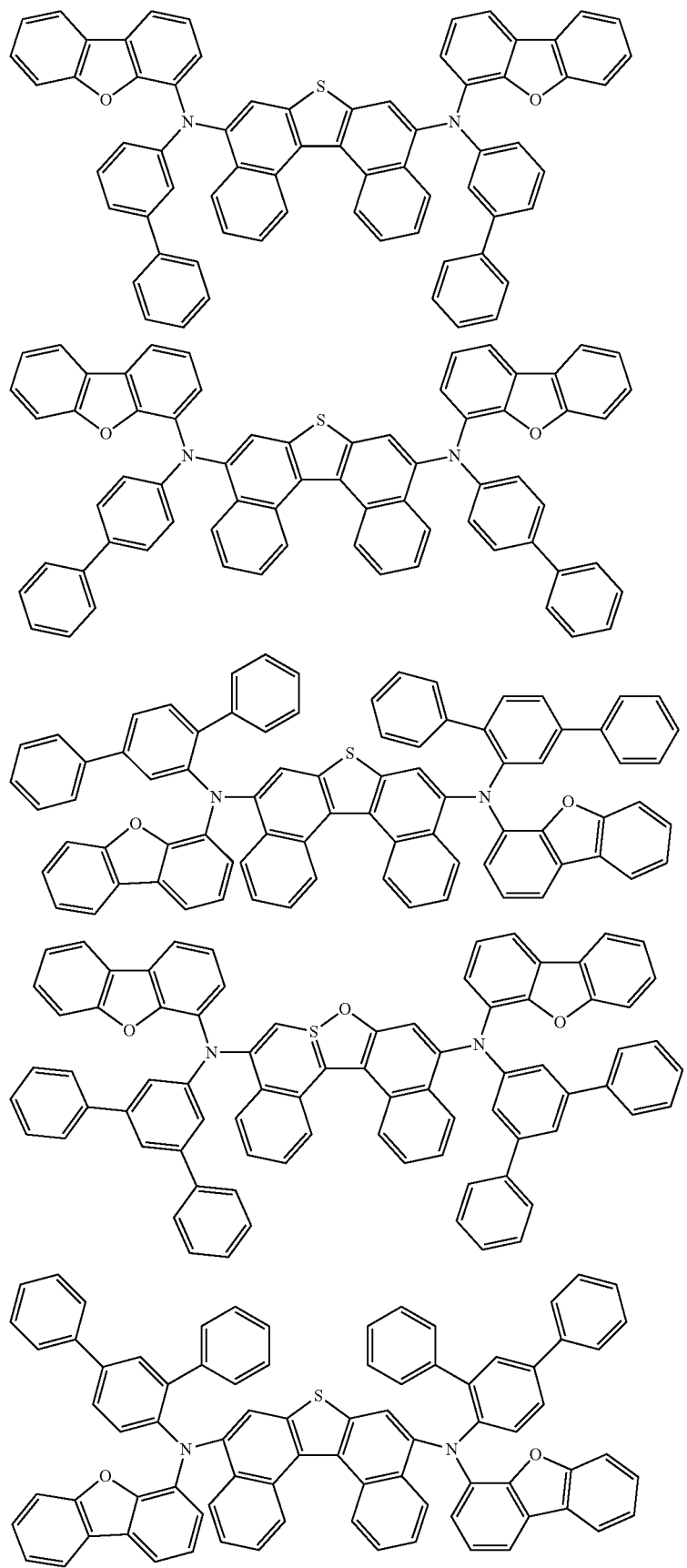

-continued
1207 1208
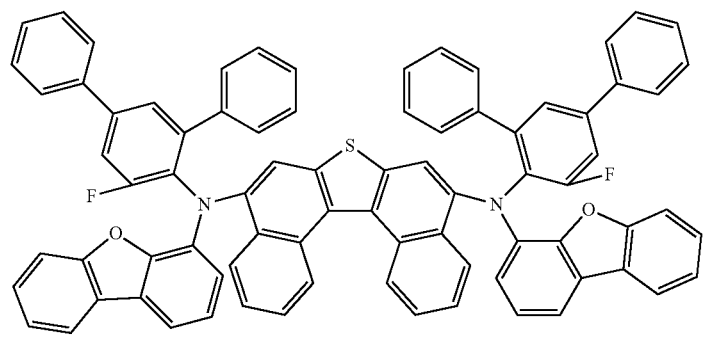
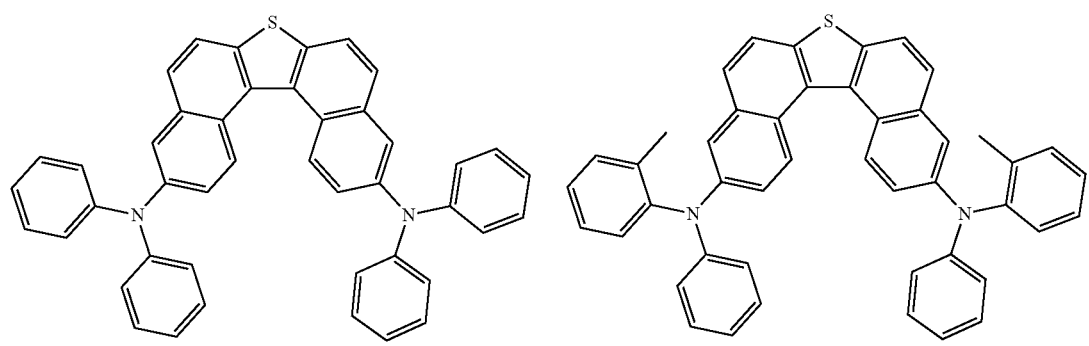
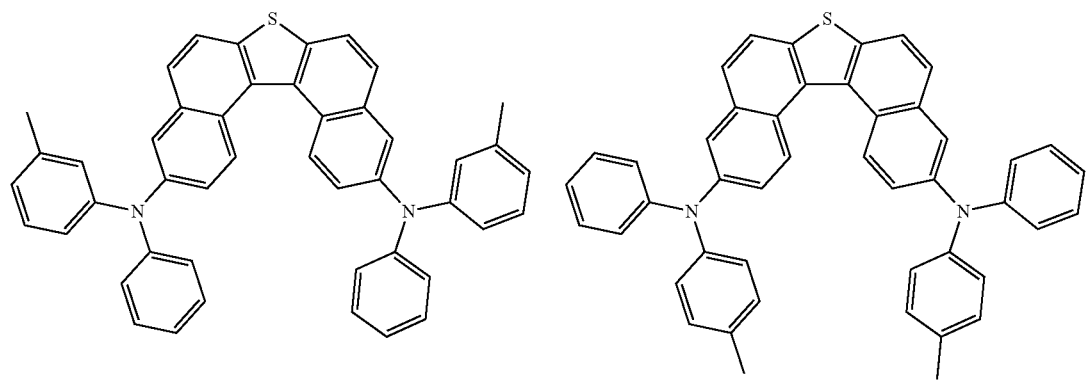
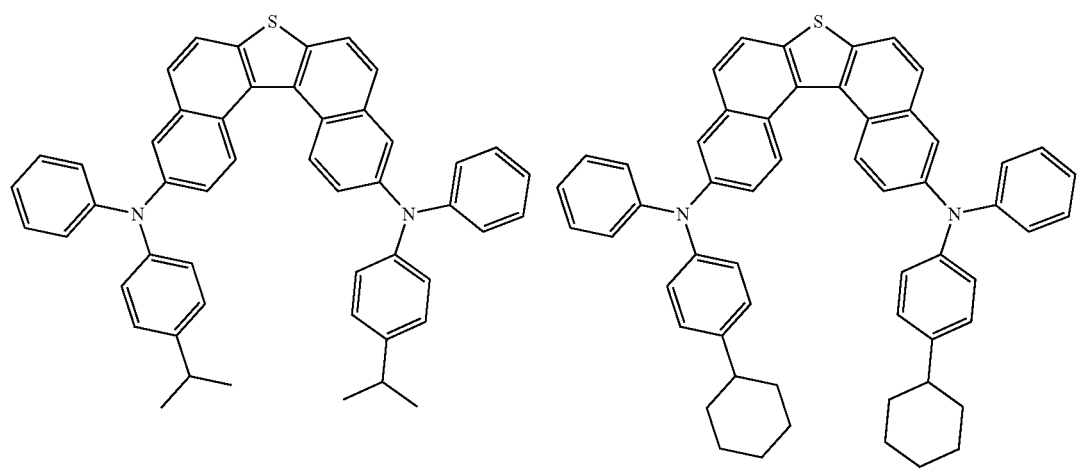

1209 1210
-continued
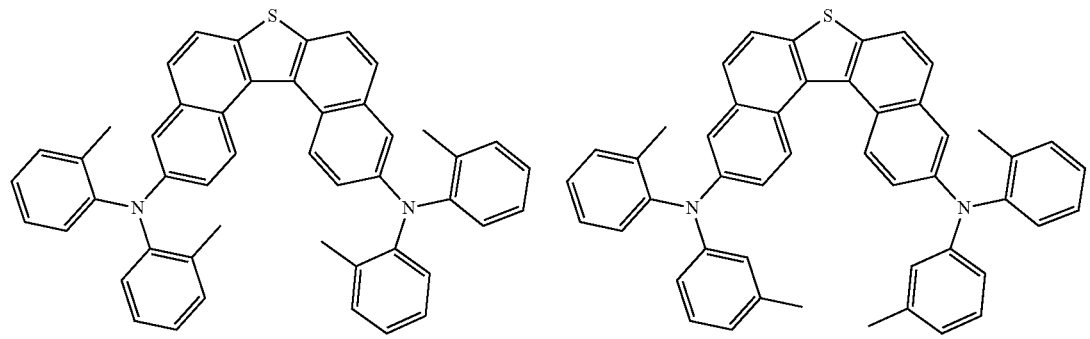
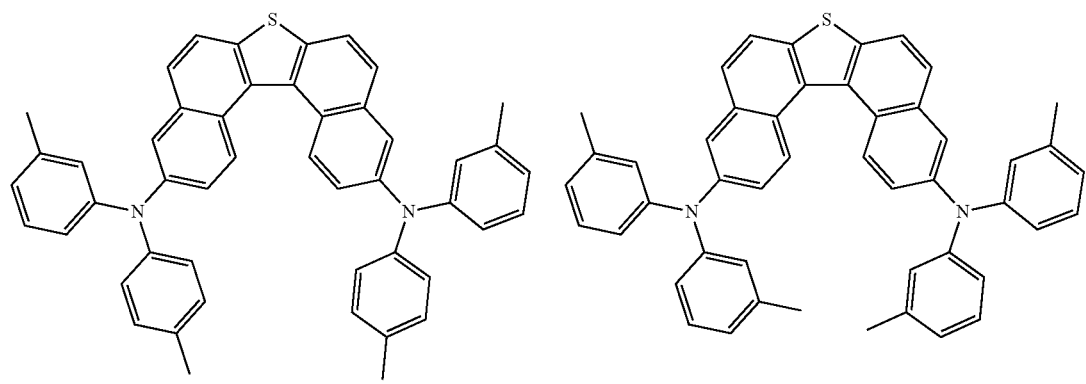
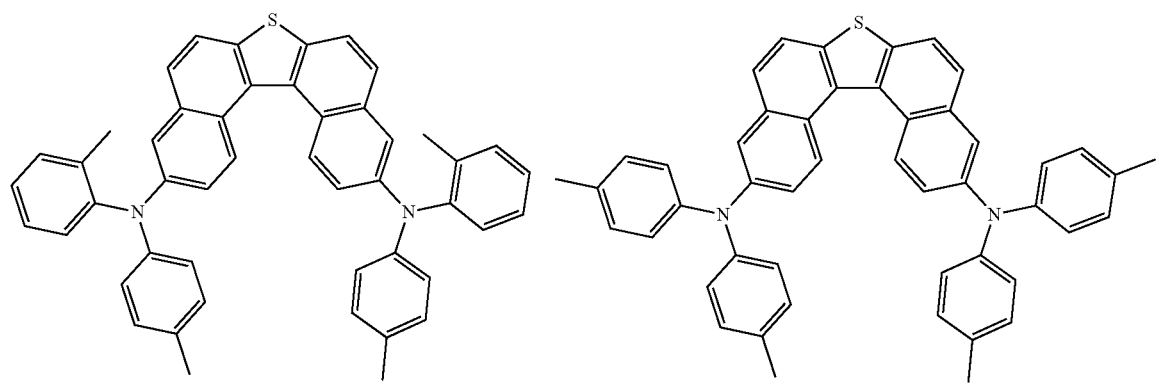
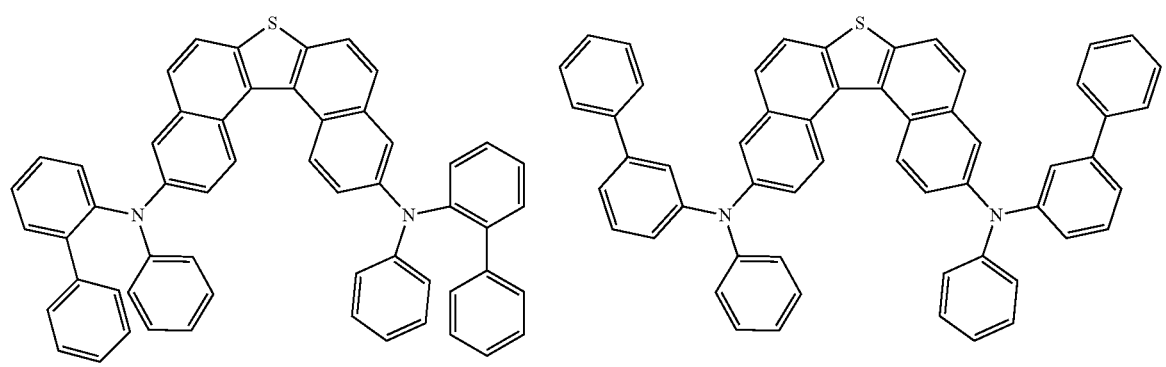

1211 1212
-continued
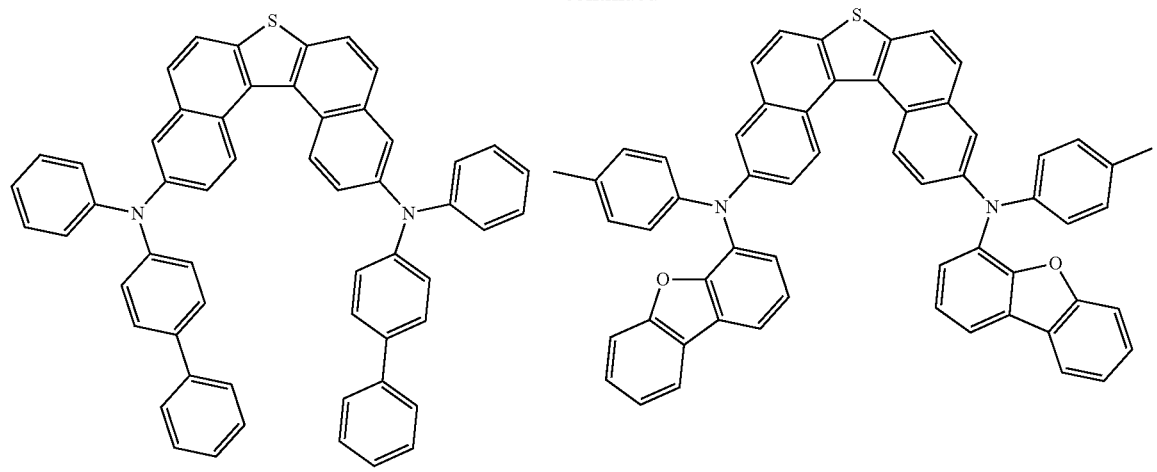
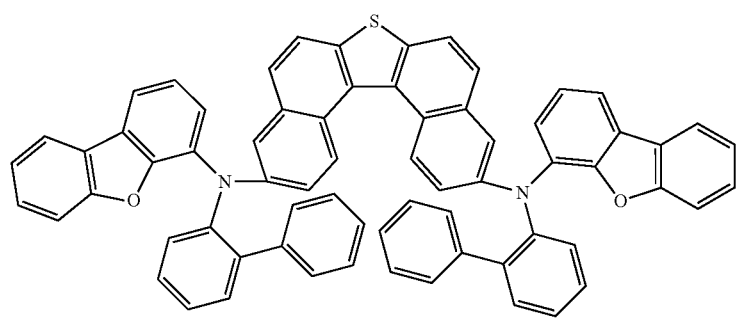
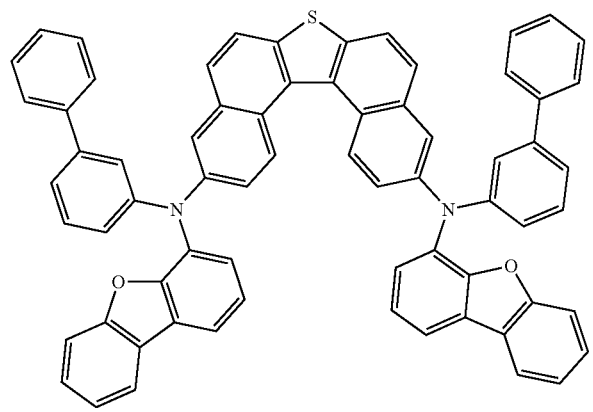
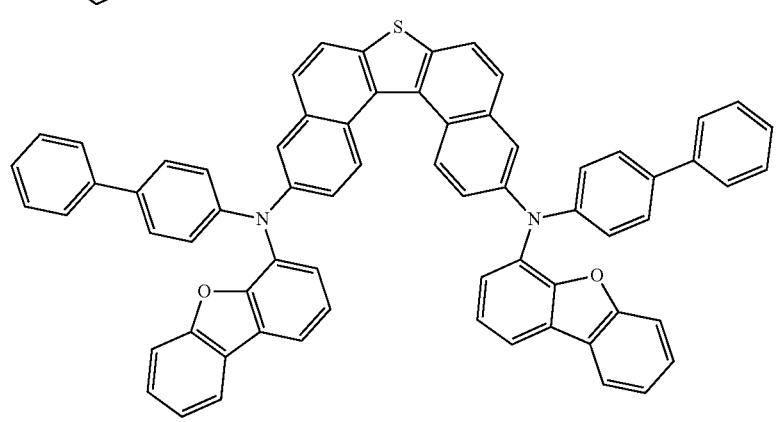

1213
-continued
1214
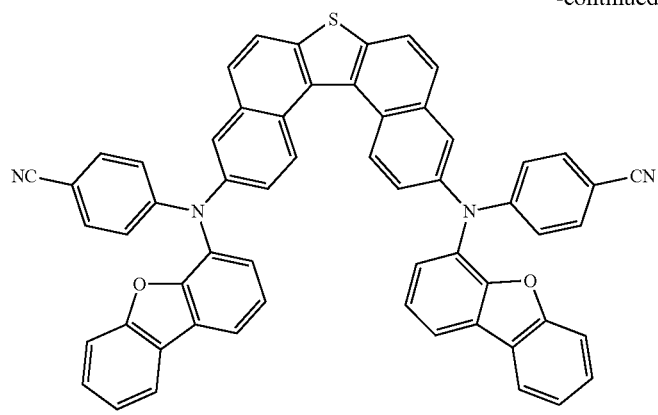
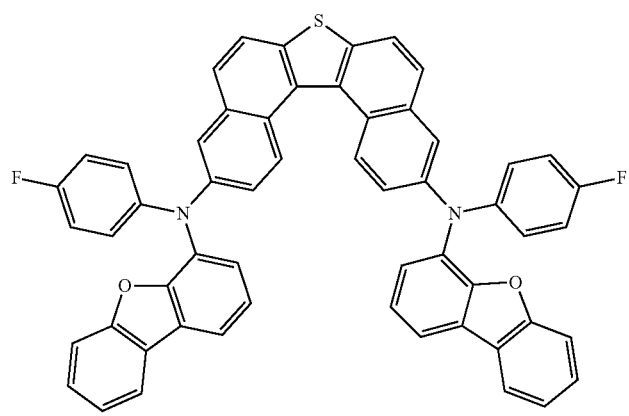
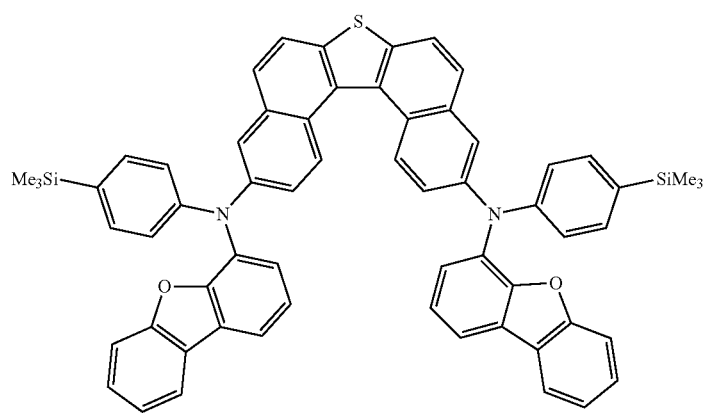
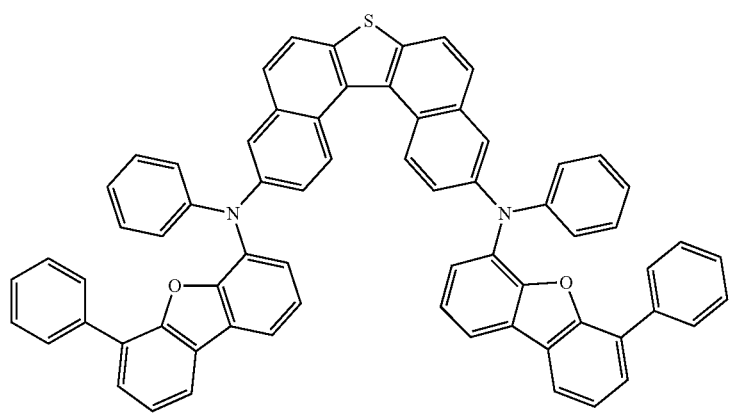

-continued
1215　　　1216
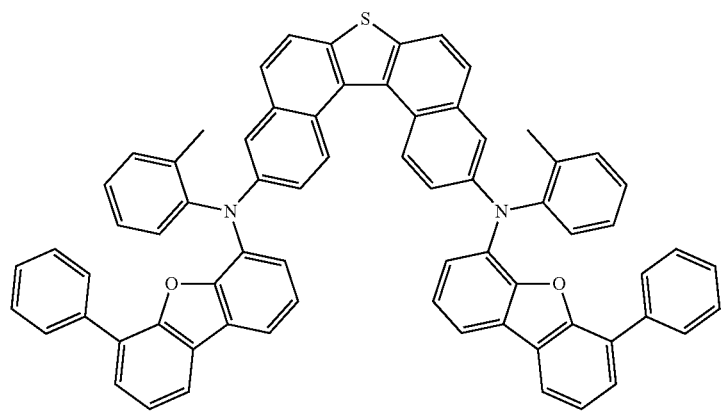
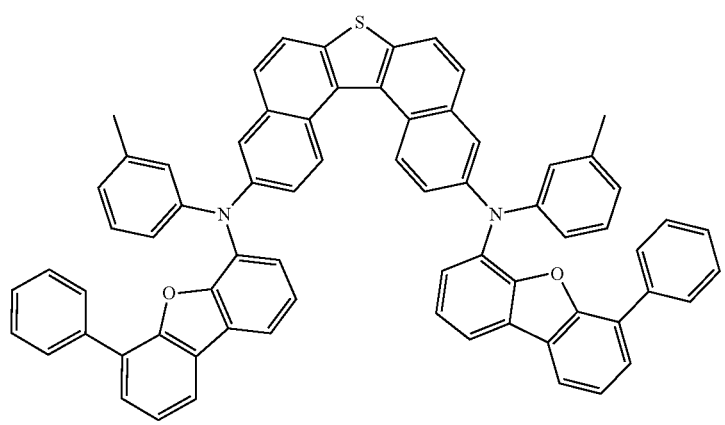
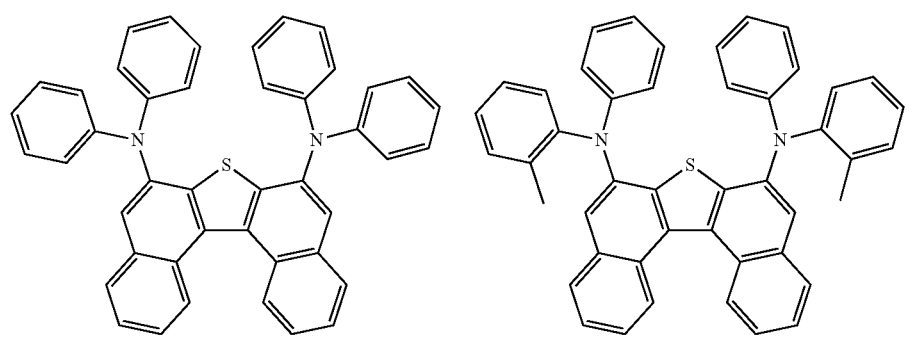
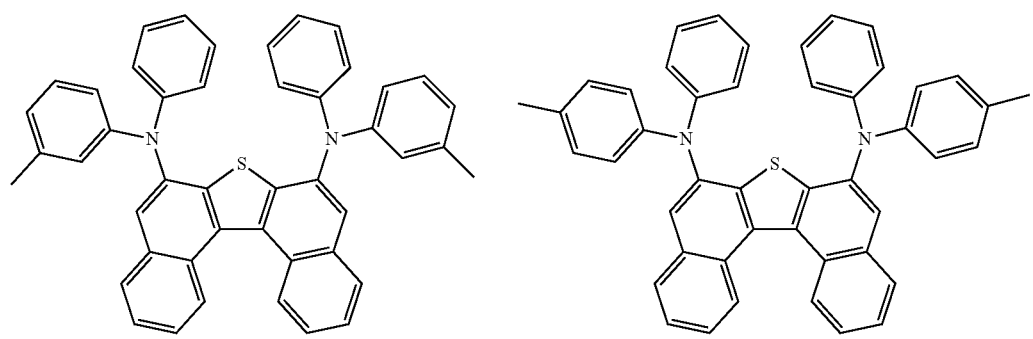

1217 1218
-continued
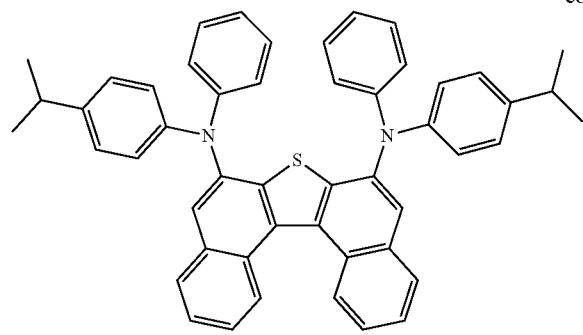
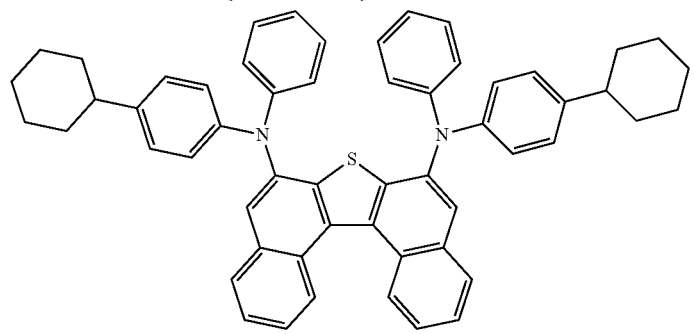
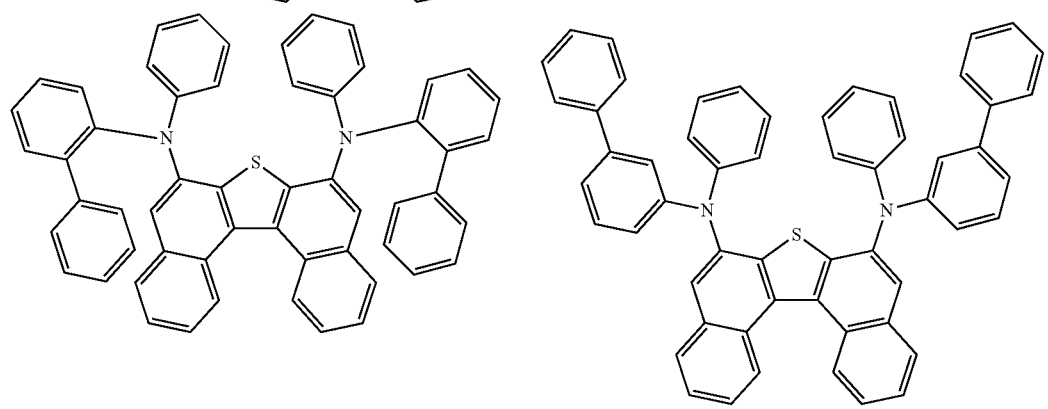
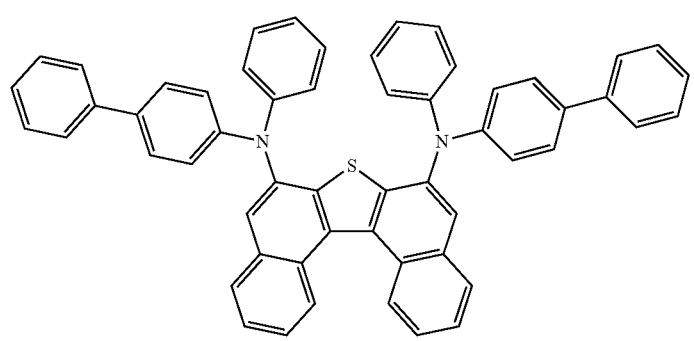
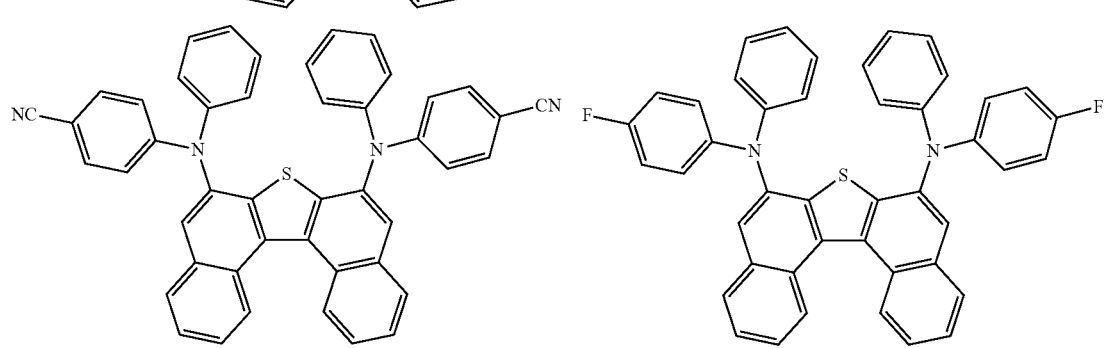

1219
1220
-continued
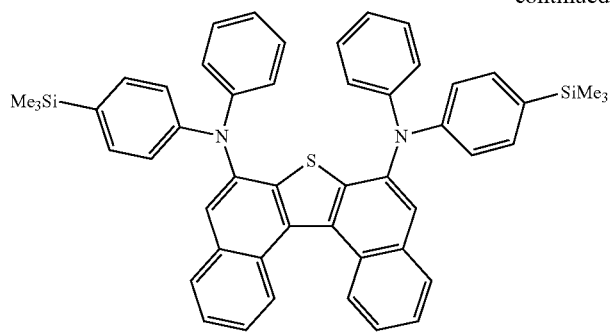
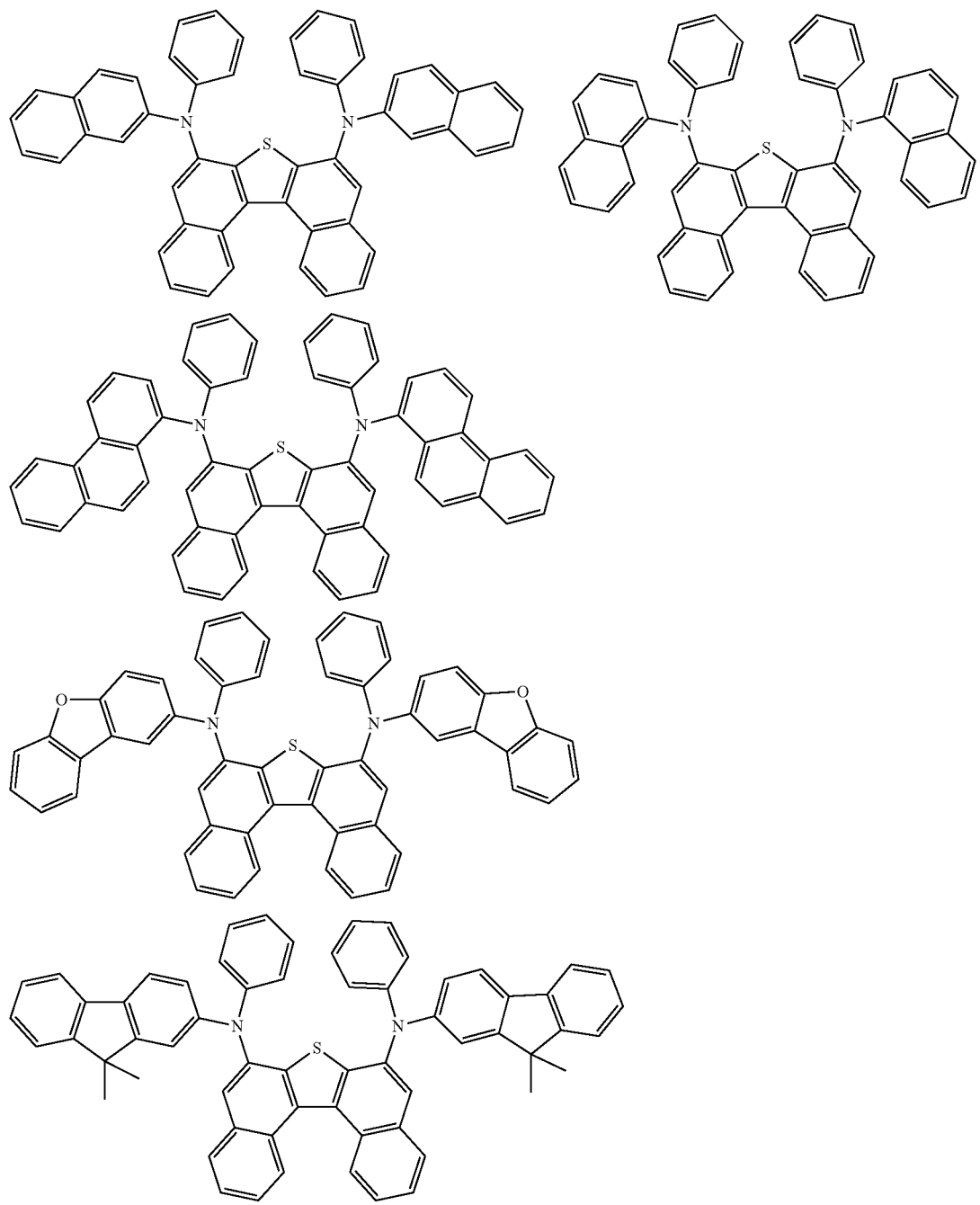

1221      1222

-continued

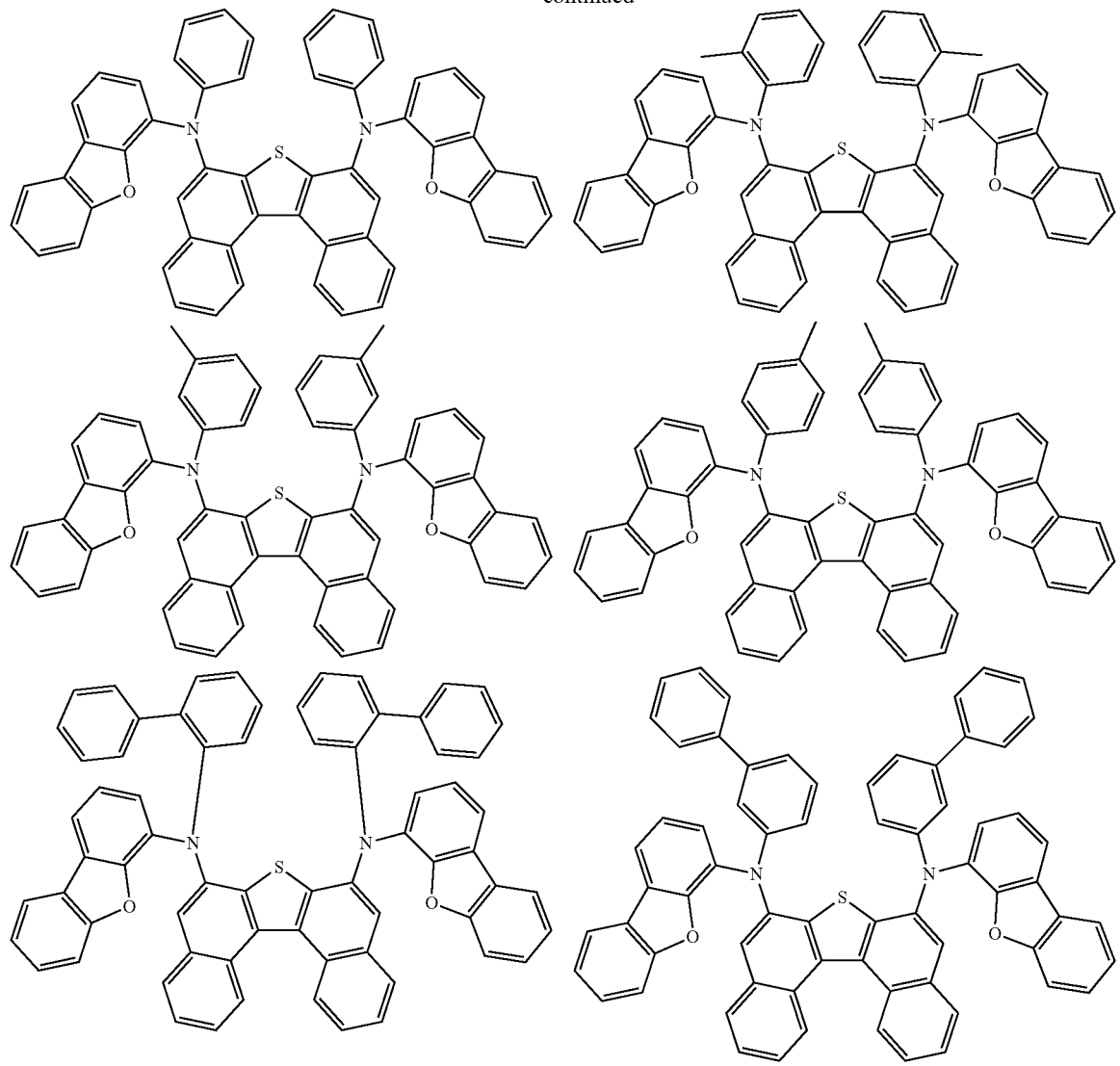

(Compound represented by formula (71))

The compound represented by the formula (71) is explained below.

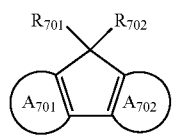
(71)

wherein, in the formula (71), $A_{701}$ ring and $A_{702}$ ring are independently a substituted or unsubstituted aromatic hydrocarbon ring having 6 to 50 ring carbon atoms, or a substituted or unsubstituted heterocyclic ring having 5 to 50 ring atoms;

One or more tings selected from the group consisting of $A_{701}$ ring and $A_{702}$ ring are bonded to the bond * of the structure represented by the following formula (72);

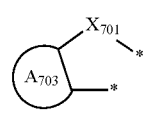
(72)

wherein, in the formula (72), $A_{703}$ rings are independently
a substituted or unsubstituted aromatic hydrocarbon ring having 6 to 50 ring carbon atoms, or
a substituted or unsubstituted heterocyclic ring having 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

One or more selected from the group consisting of $A_{7001}$ ring and $A_{7002}$ ring is bonded to * in the structure represented by the formula (72). That is, in one embodiment, the ring carbon atom of the aromatic hydrocarbon ring or the ring atom of the heterocyclic ring of $A_{701}$ ring is bonded to * in the structure represented by the formula (72). In one embodiment, the ring carbon atom of the aromatic hydrocarbon ring or the ring atom of the heterocyclic ring of $A_{702}$ ring is bonded to * in the structure represented by the formula (72).

In one embodiment, the group represented by the formula (73) is bonded to one or both of $A_{701}$ ring and $A_{702}$ ring.

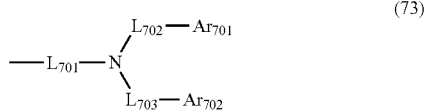

(73)

wherein in the formula (73), $Ar_{701}$ and $Ar_{702}$ are independently
a substituted or unsubstituted aryl group having 6 to 50 ring carbon atoms, or
a substituted or unsubstituted monovalent heterocyclic group having 5 to 50 ring atoms; and $L_{701}$ to $L_{703}$ are independently
a single bonded,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups.

In one embodiment, in addition to $A_{701}$ ring, the ring carbon atom of the aromatic hydrocarbon ring or the ring atom of the heterocyclic ring of $A_{702}$ ring is bonded to * in the structure represented by the formula (72). In this case, the structures represented by formula (72) may be the same or different.

In one embodiment, $R_{701}$ and $R_{702}$ are independently a substituted or unsubstituted aryl group having 6 to 50 ring carbon atoms.

In one embodiment, $R_{701}$ and $R_{702}$ are bonded with each other to form a fluorene structure.

In one embodiment, $Ar_{701}$ ring and $Ar_{702}$ ring are substituted or unsubstituted aromatic hydrocarbon rings having 6 to 50 ring carbon atoms, and they are substituted or unsubstituted benzene rings, for example.

In one embodiment, $Ar_{703}$ ring is a substituted or unsubstituted aromatic hydrocarbon ring having 6 to 50 ring carbon atoms, and it is a substituted or unsubstituted benzene ring, for example.

In one embodiment, $X_{701}$ is O or S.

As specific example of the compound represented by the formula (71), the following compounds can be given, for example. In the following example compounds, Me represents methyl group.

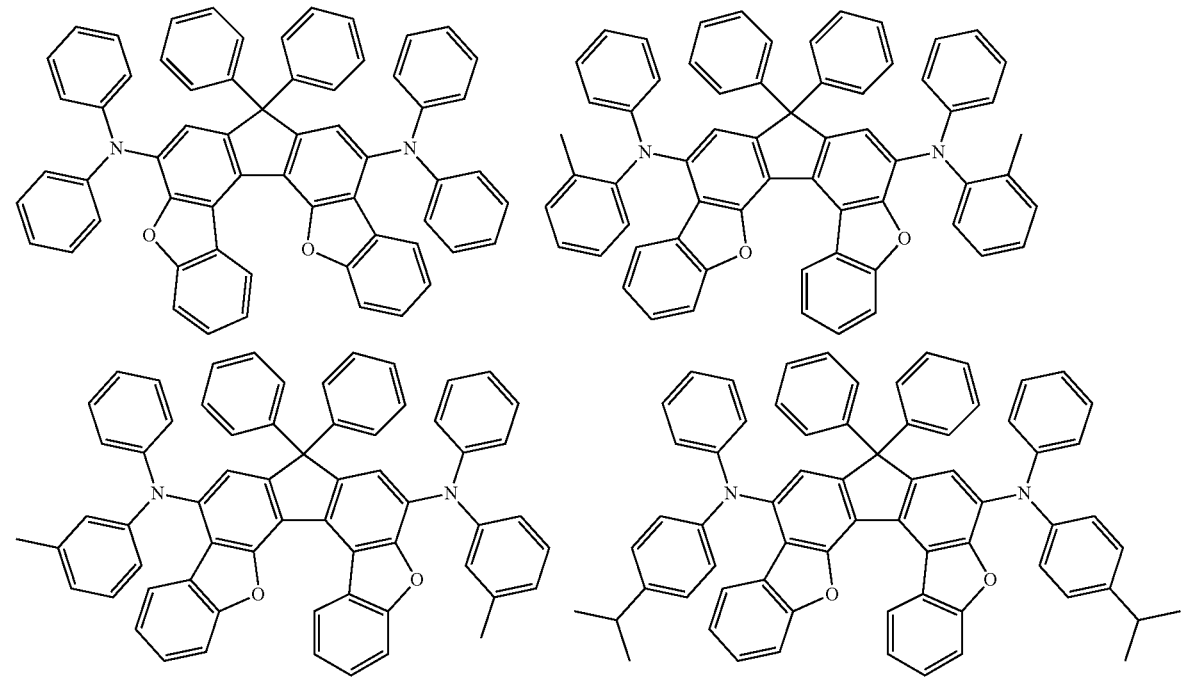

1225                    1226
-continued
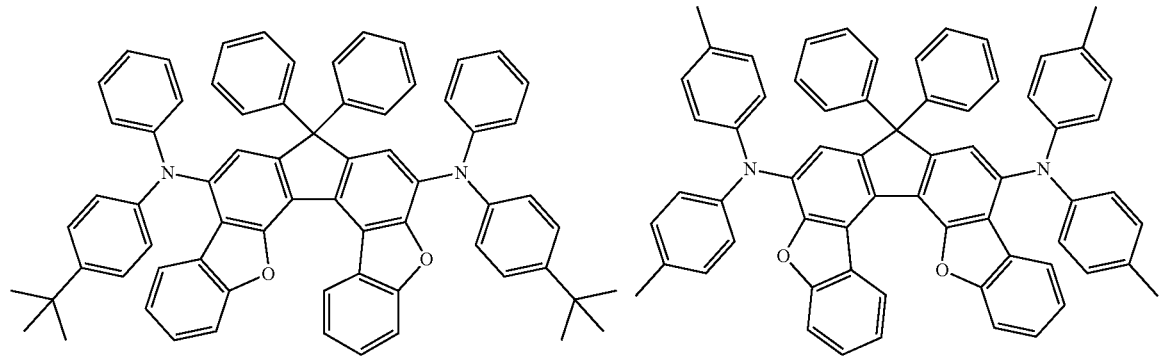
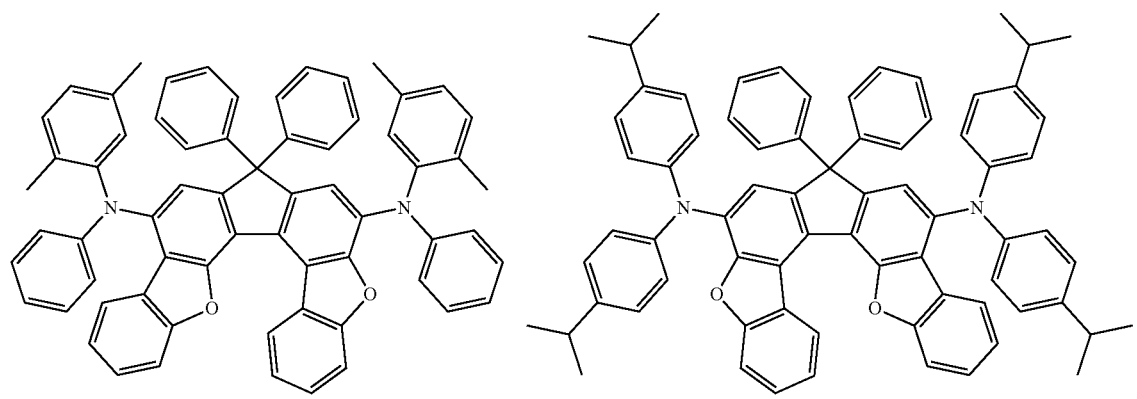
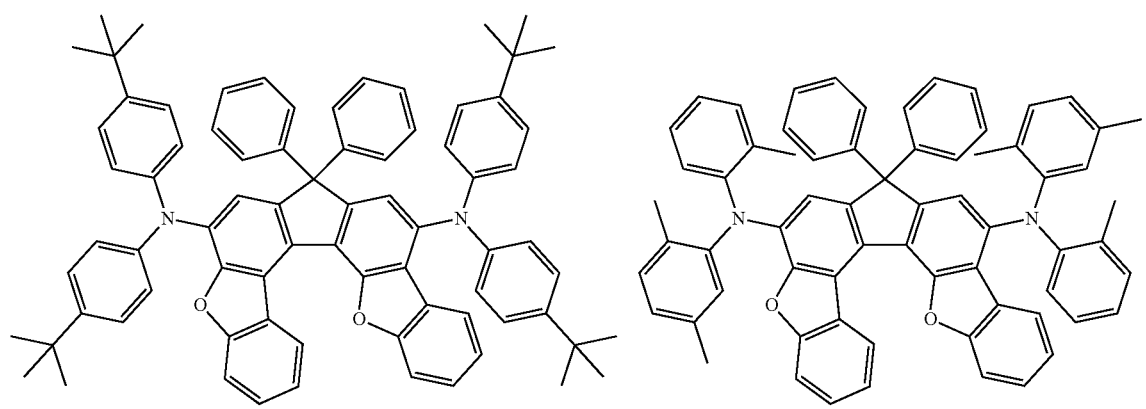
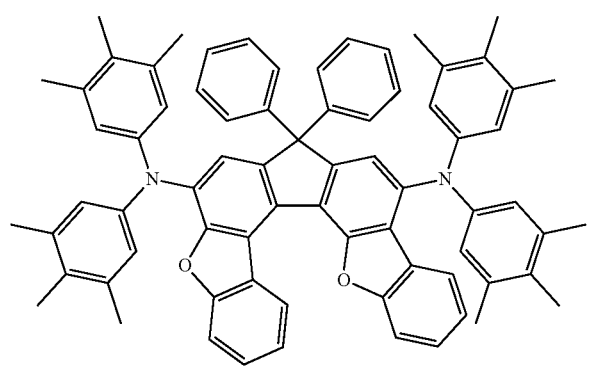

1227 1228
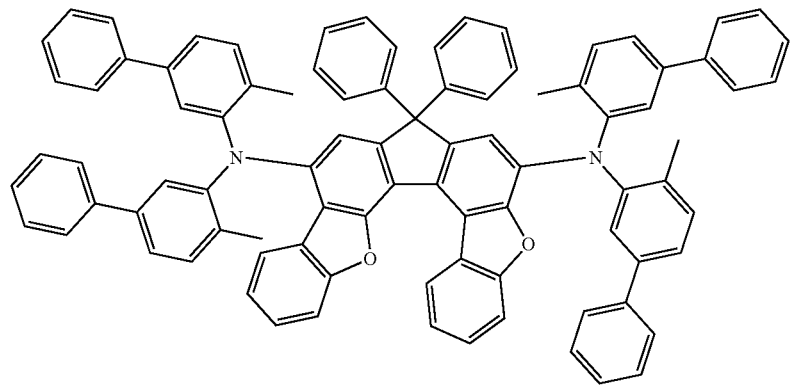
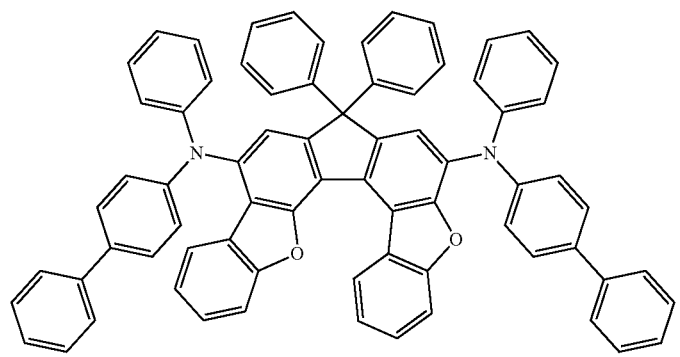
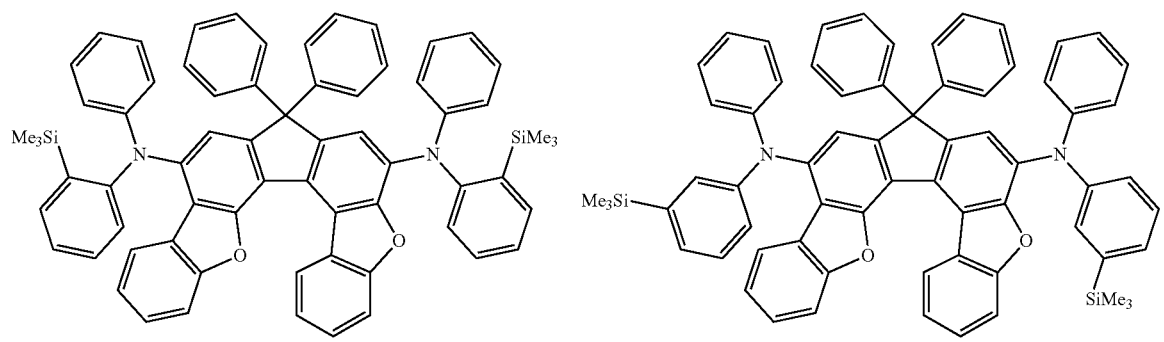
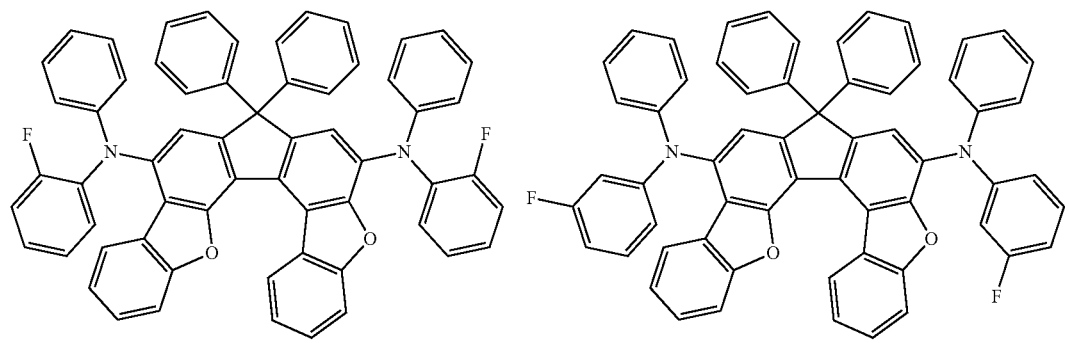

1229 1230
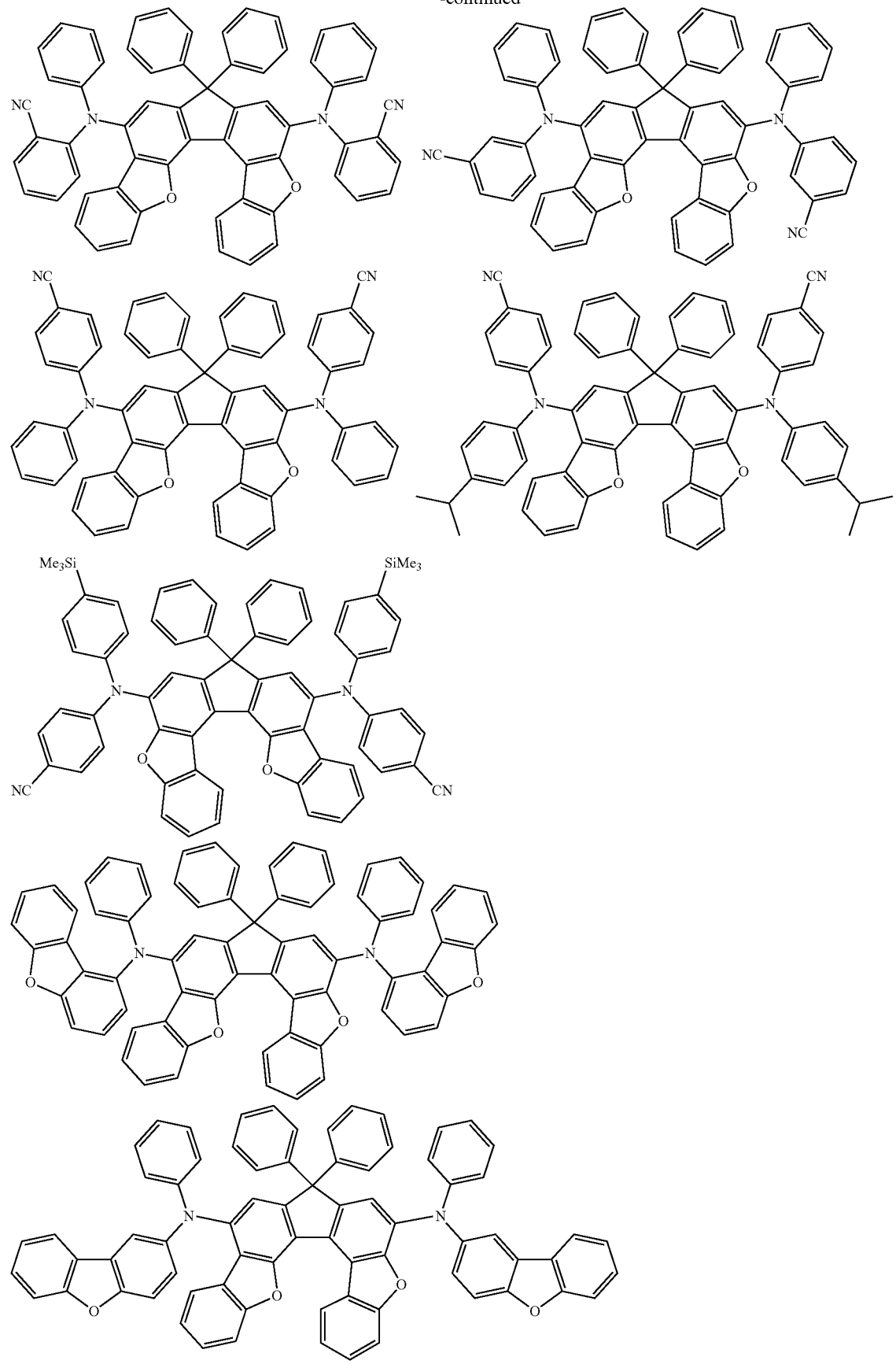

1231 1232
-continued
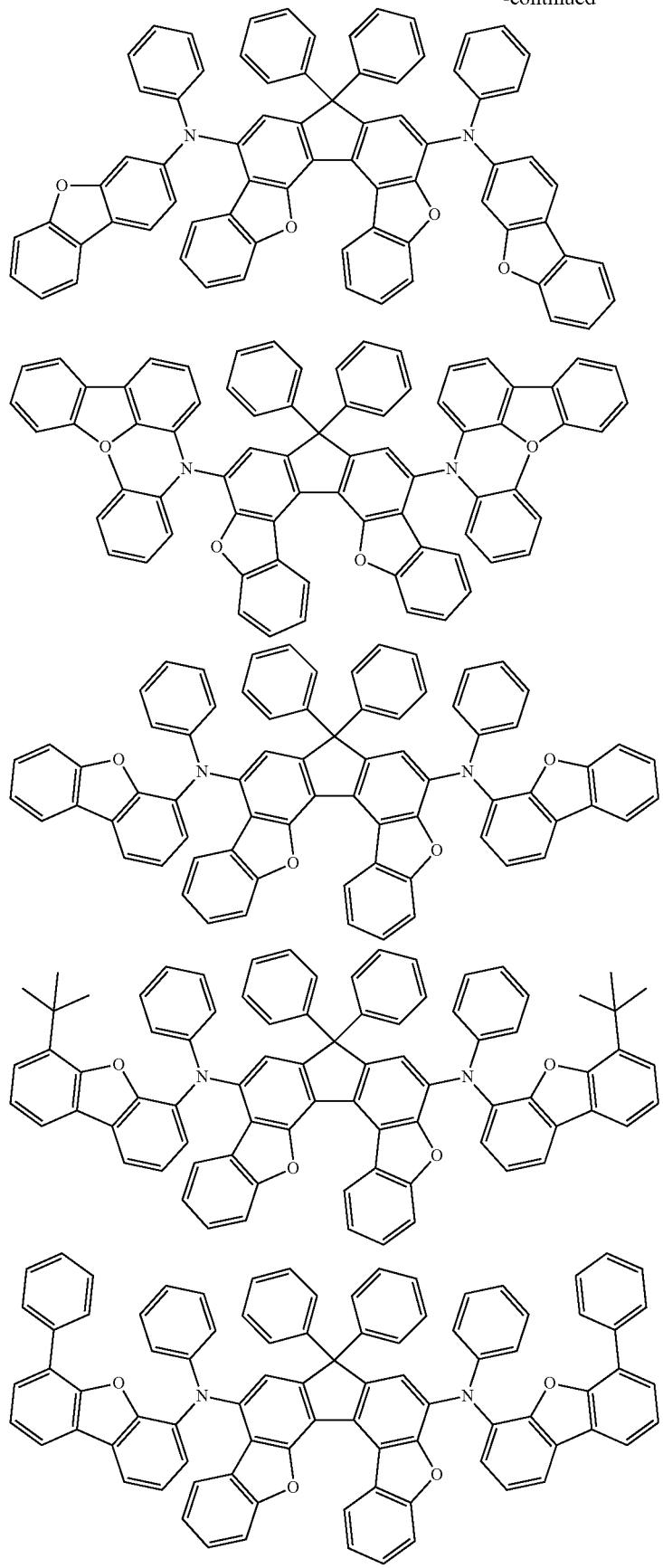

1233
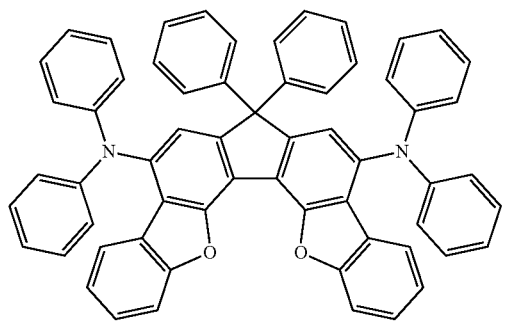
1234
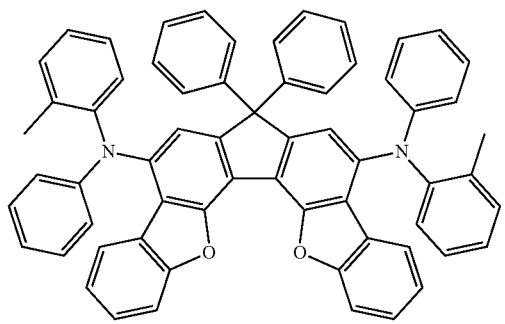
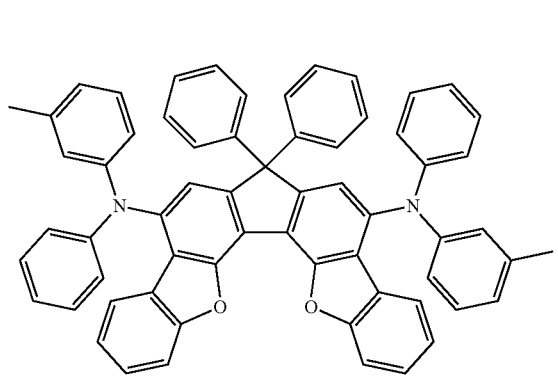
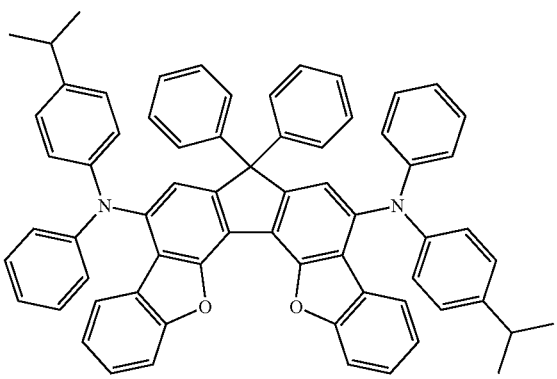
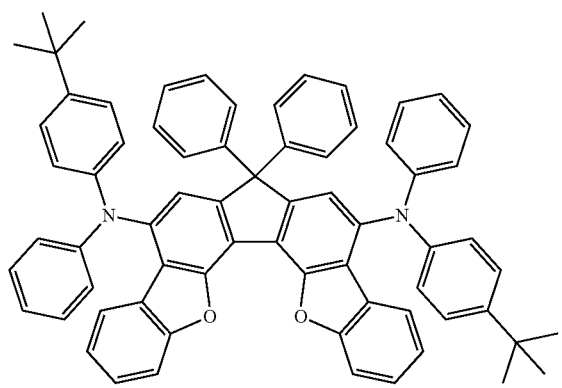
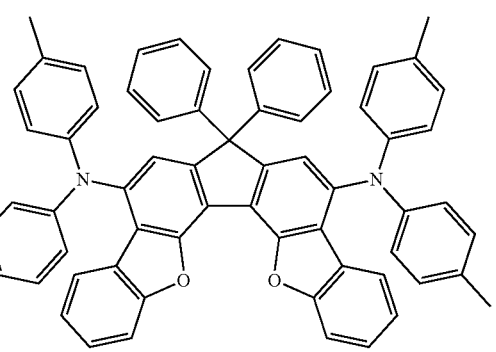
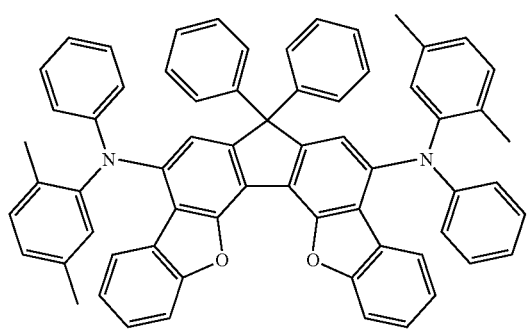

1235 1236
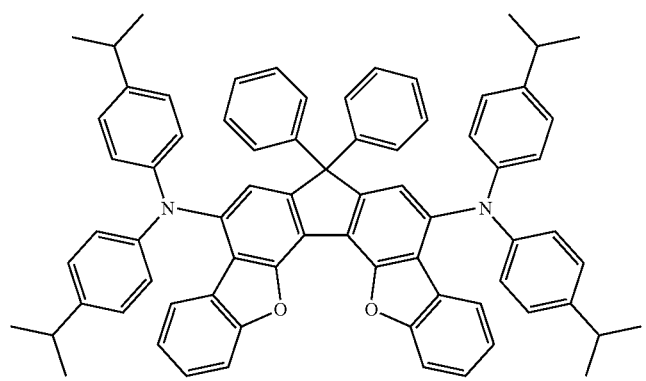
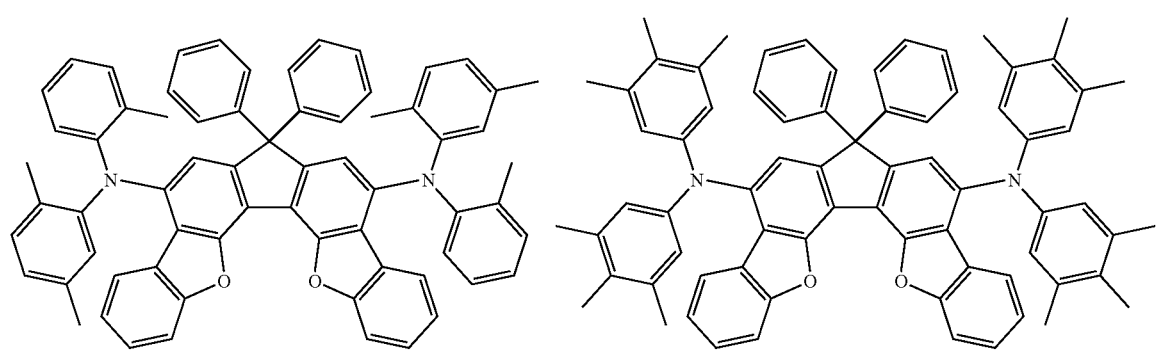
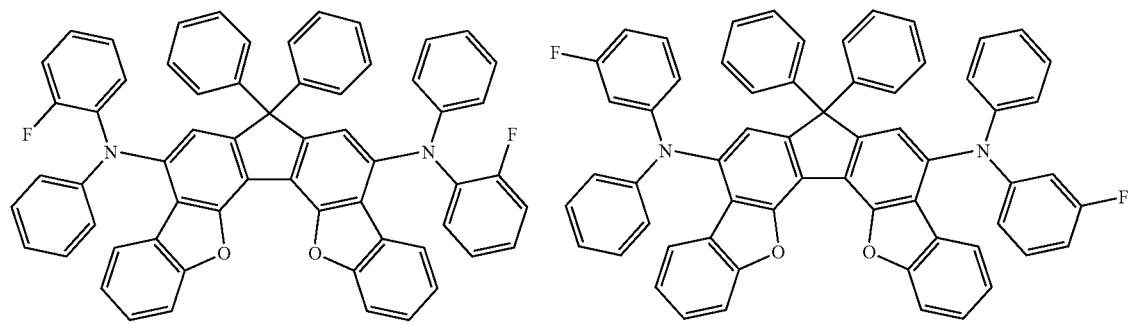
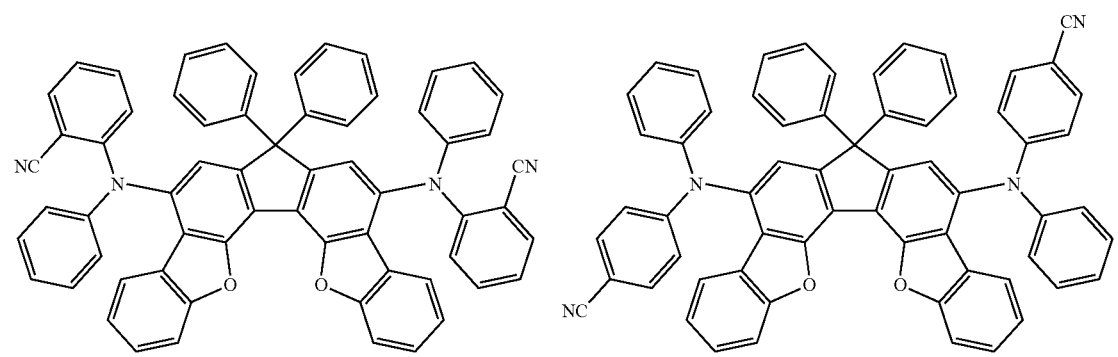

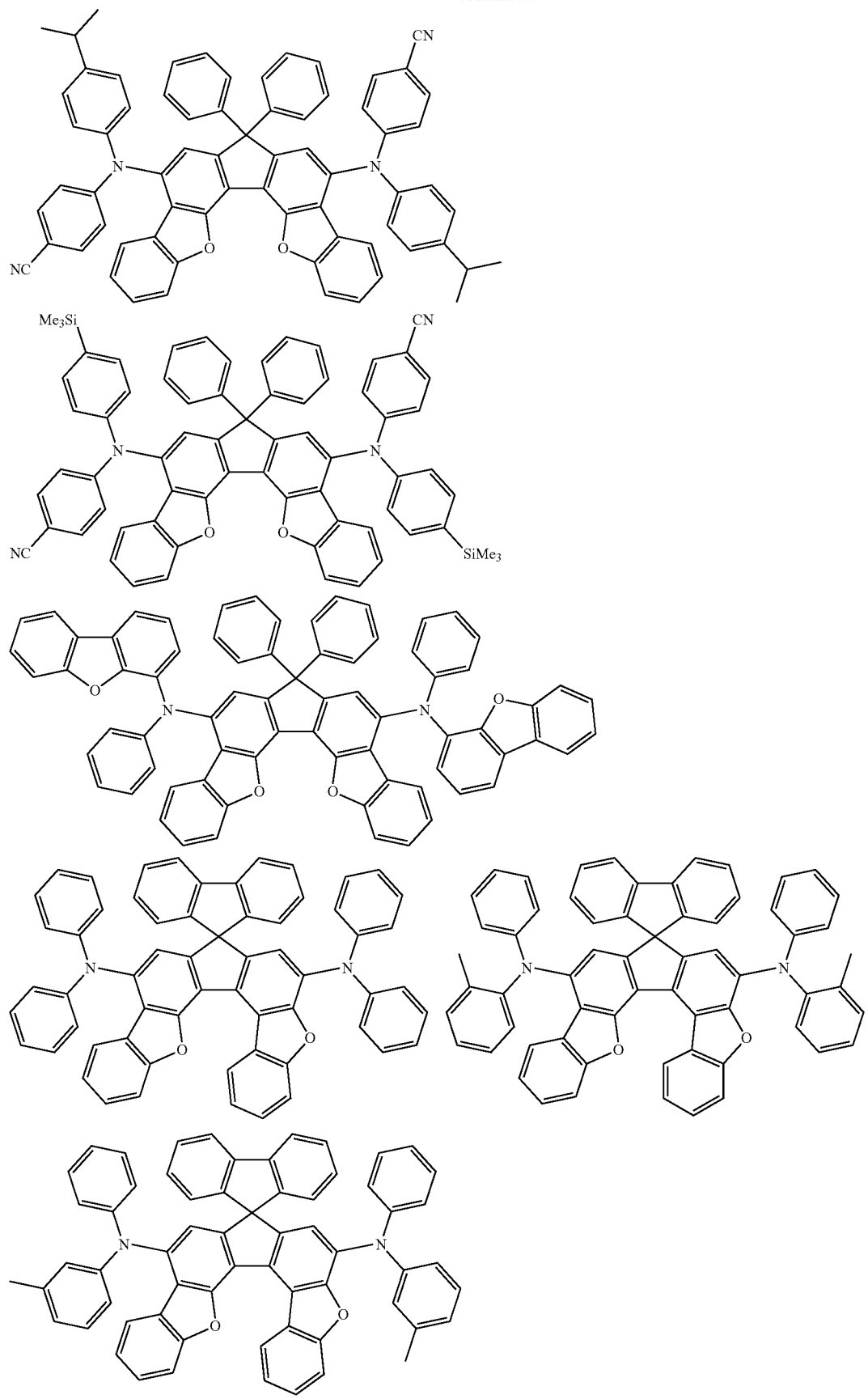

1239 1240
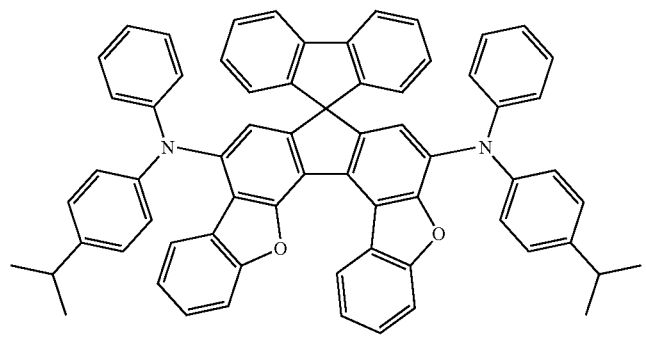
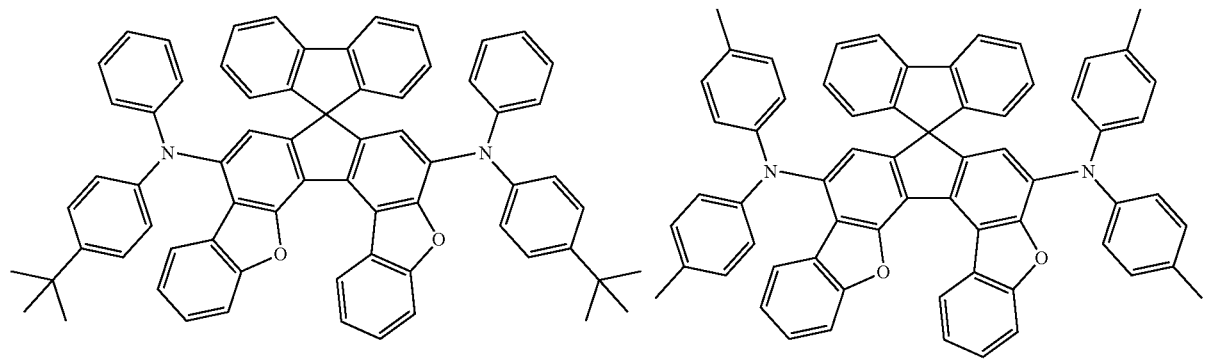
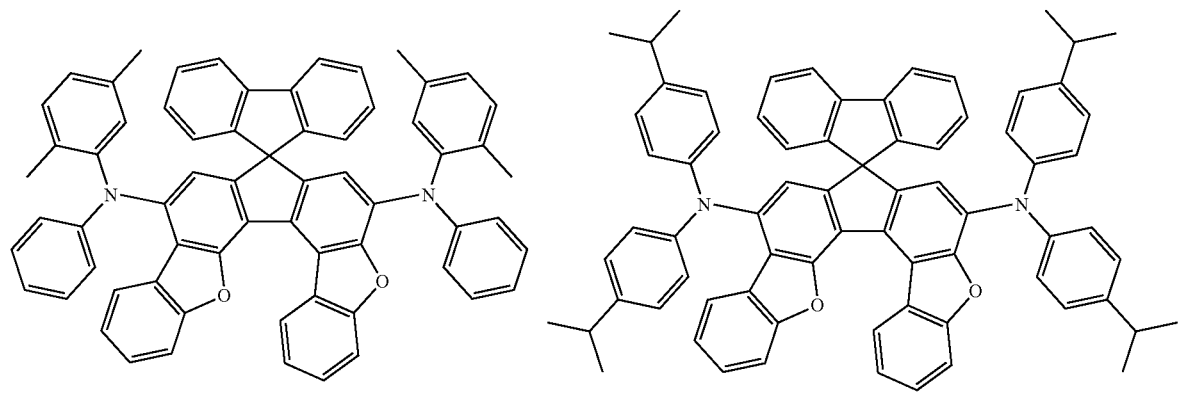
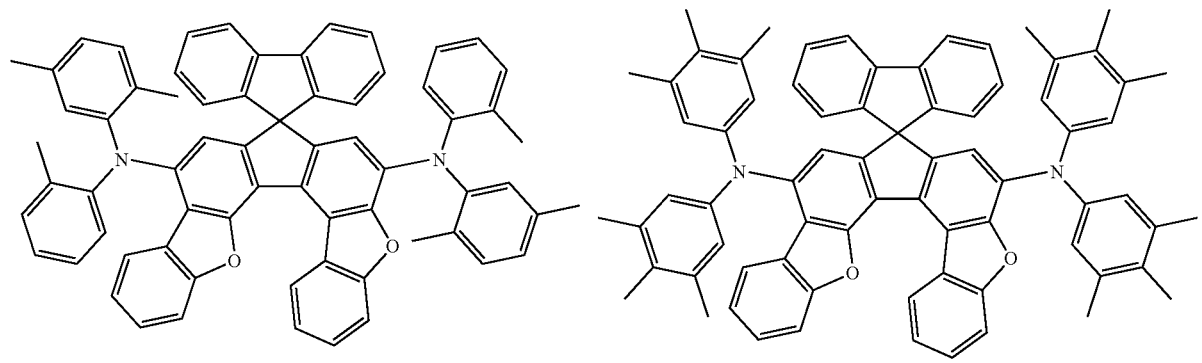

-continued
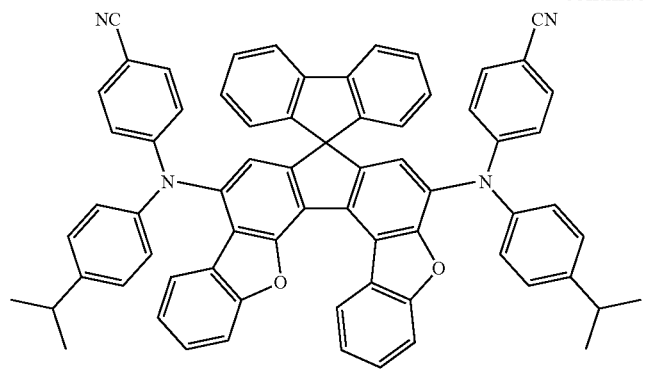
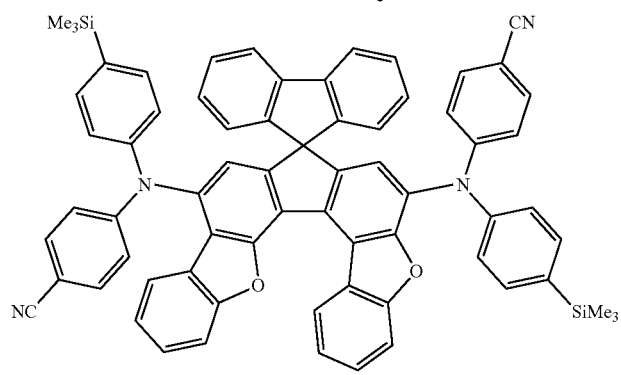
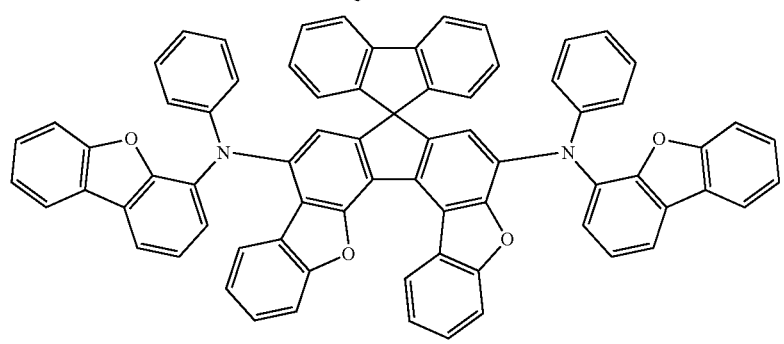
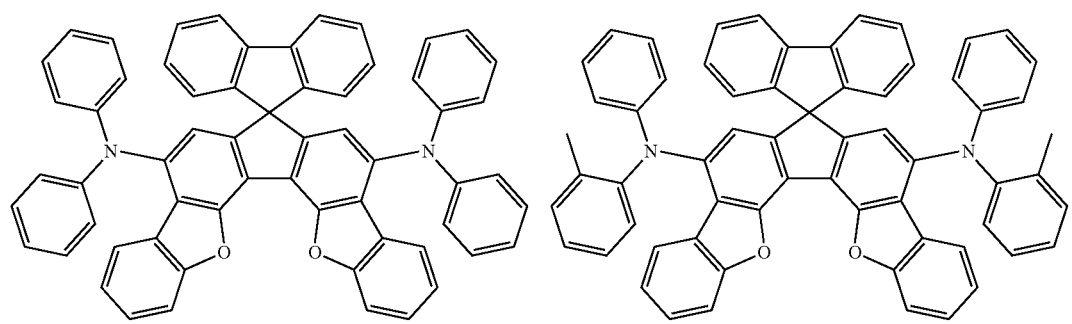
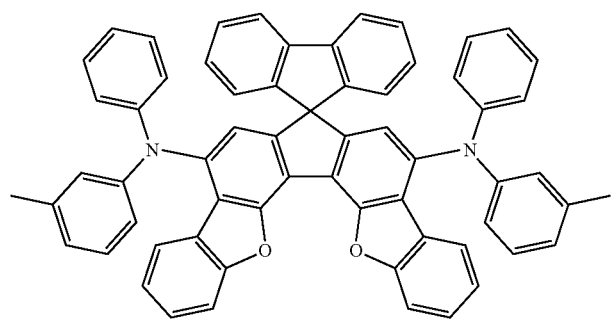

1243
1244
-continued
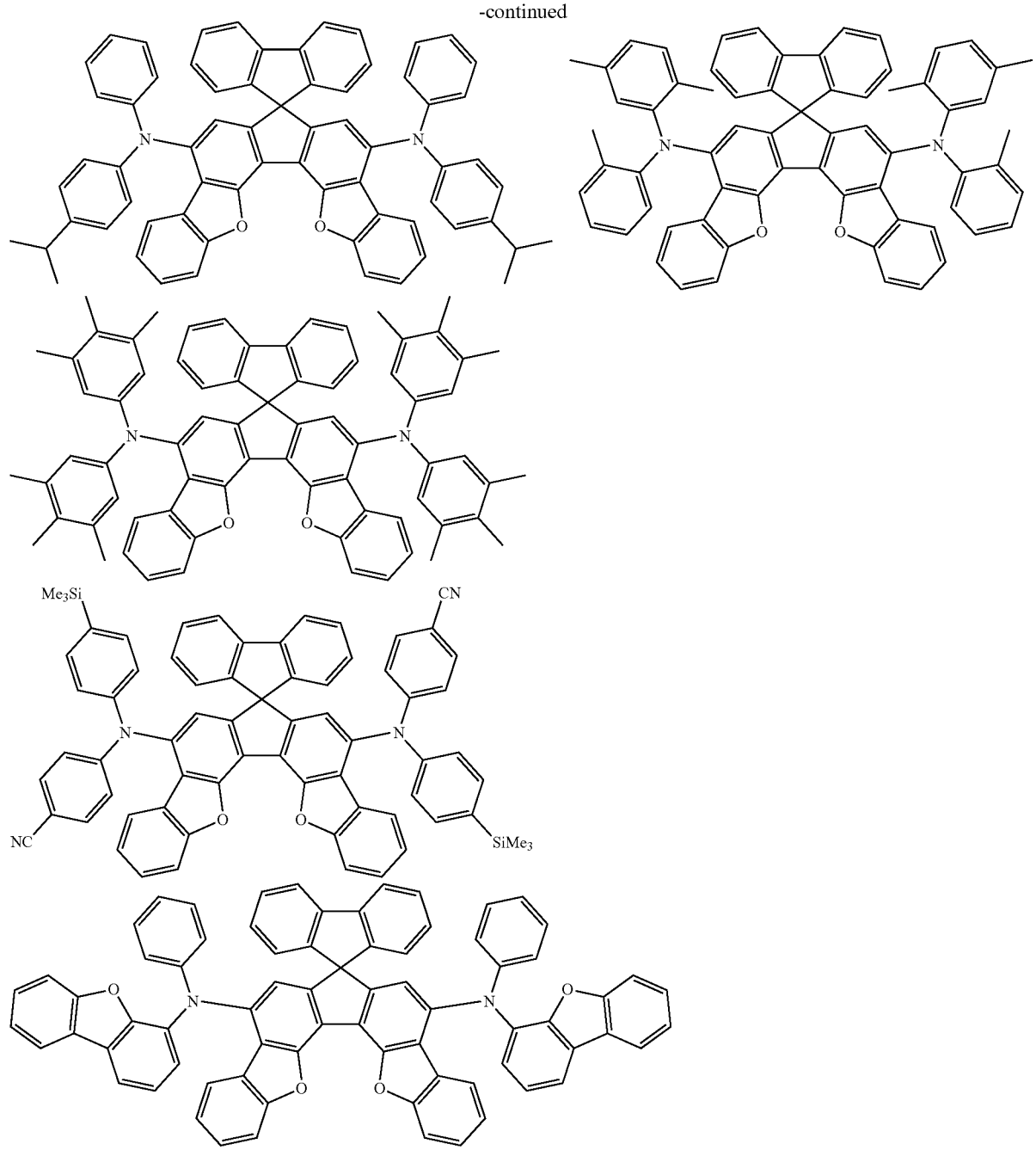
(Compound represented by formula (81))
The compound represented by the formula (81) which is explained below.
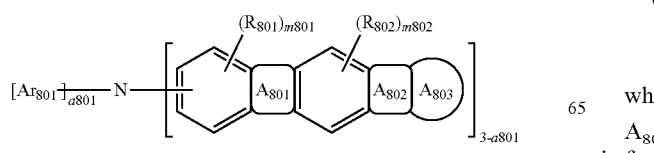
wherein, in the formula (81),
$A_{801}$ ring is a ring represented by the formula (82) which is fused to an adjacent ring at an arbitrary position;

$A_{802}$ ring is a ring represented by the formula (83) which is fused to an adjacent ring 1) at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m801 and m802 are independently an integer of 0 to 2; when these are 2, plural $R_{801}$s or $R_{802}$s may be the same or different;

a801 is an integer of 0 to 2; when a801 is 0 or 1, the structure in the parentheses indicated by "3-a801" may be the same or different from each other; when a801 is 2, $Ar_{801}$s may be the same or different from each other.

In one embodiment, $Ar_{801}$ is a substituted or unsubstituted aryl group having 6 to 50 ring carbon atoms.

In one embodiment, $A_{803}$ ring is a substituted or unsubstituted aromatic hydrocarbon ring having 6 to 50 ring carbon atoms, and it is a substituted or unsubstituted benzene ring, a substituted or unsubstituted naphthalene ring, or a substituted or unsubstituted anthracene ring, for example.

In one embodiment, $R_{803}$ and $R_{804}$ are independently a substituted or unsubstituted alkyl group having 1 to 50 carbon atoms.

In one embodiment, a801 is 1.

As specific example of the compound represented by the formula (81), the following compounds can be given, for example.

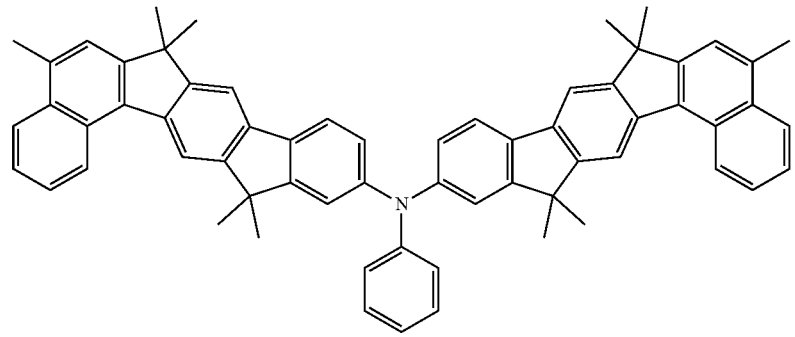

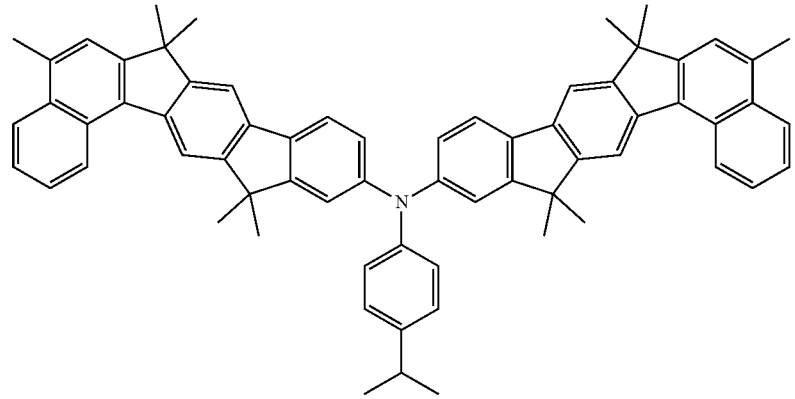

1247
-continued
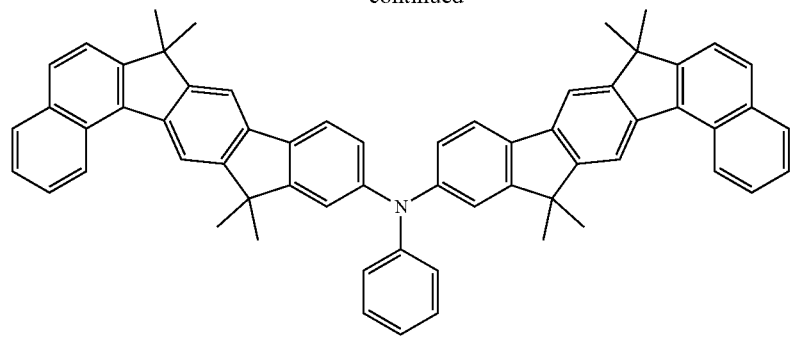
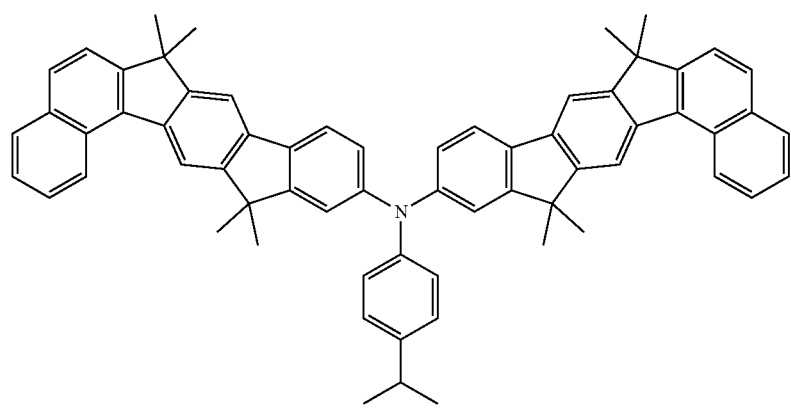
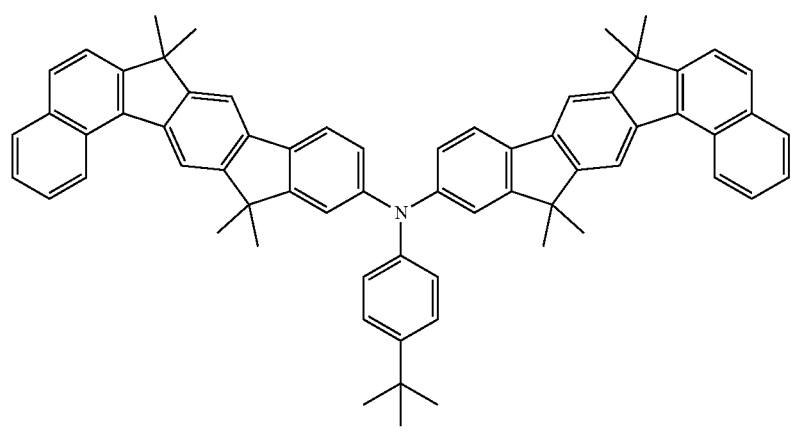
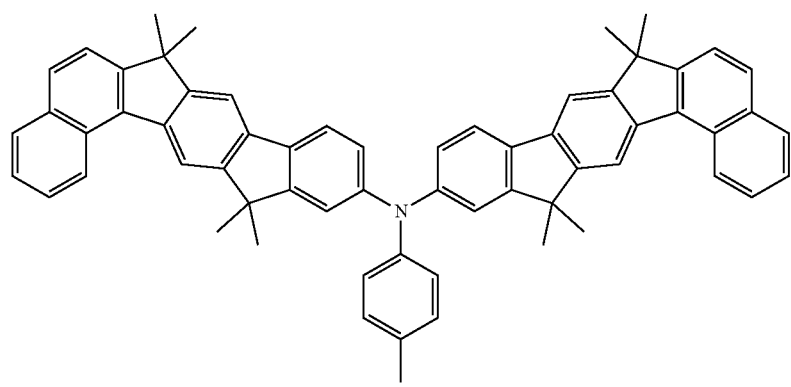
1248

-continued
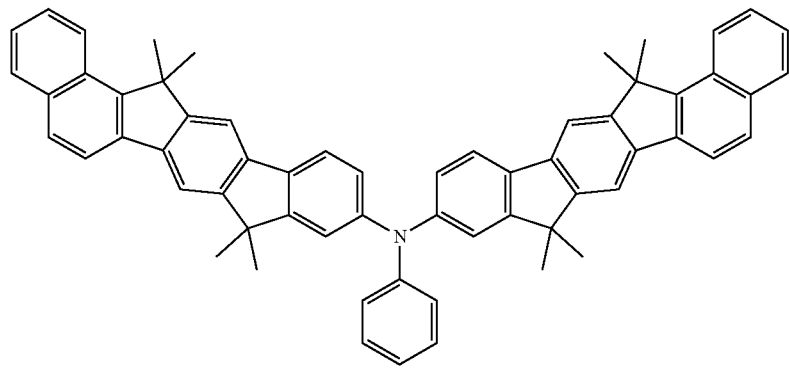
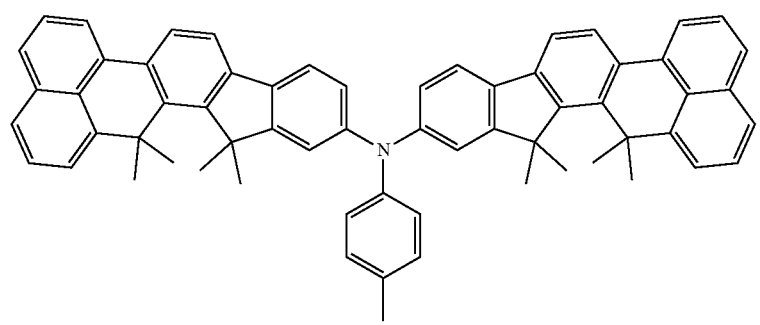
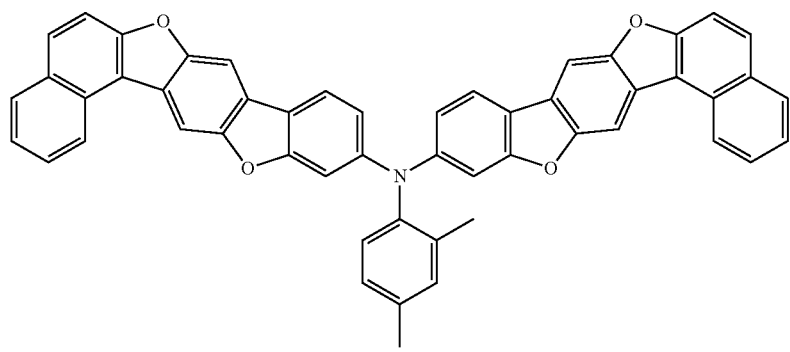
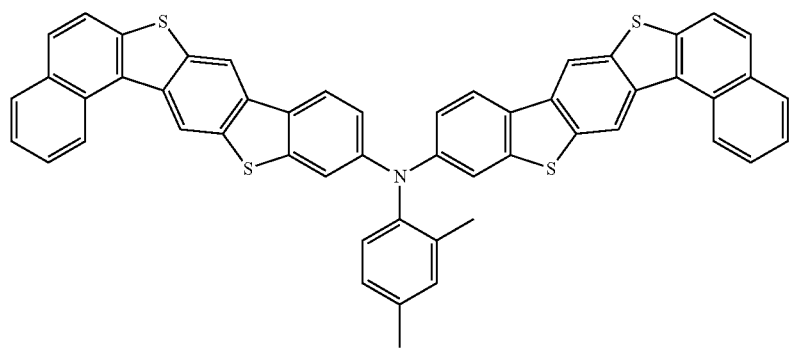

-continued

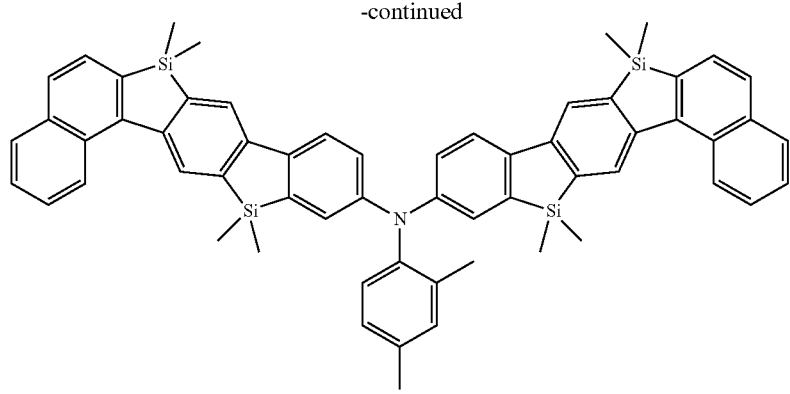

Specific examples of the above groups are as described in [Definition] of this specification.

In the organic EL device according to one aspect of the invention, known materials and device configurations may be applied as long as the device includes a cathode, an anode, and an emitting layer disposed between the cathode and the anode, and the emitting layer includes a compound represented by the following formula (1) and one or more compounds selected from the group consisting of compounds represented by formulas (11), (21), (31), (41), (51), (61), (71) and (81) as described above, and as long as the effect of the invention is not impaired.

In one embodiment, the emitting layer contains a compound represented by the formula (1A) and a compound represented by the formula (43D).

In one embodiment, the compound represented by the formula (1A) is one or more selected from the group consisting of the compound represented by the formulas BH-1 to BH-3, BH-5 to BH-13 and BH-15 to BH-17, and the compound represented by the formula (43D) is one or more selected from the group consisting of the compound represented by the formulas BD-9, BD-10, BD-11 and BD-12.

BH-1

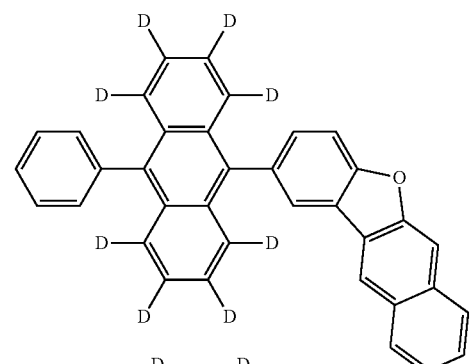

BH-2

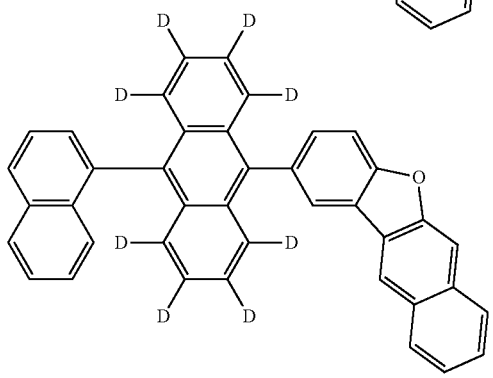

BH-3

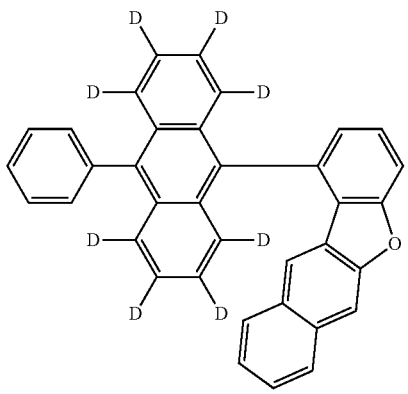

BH-5

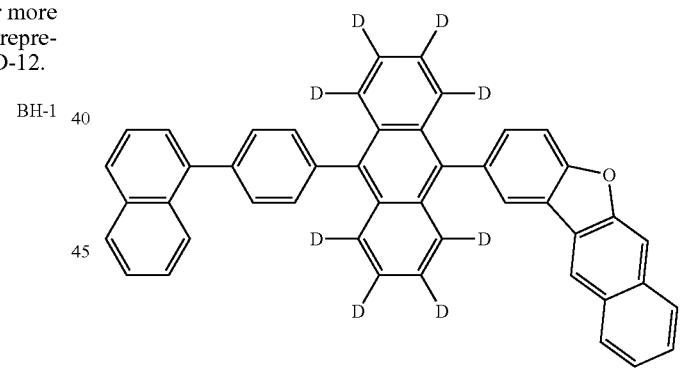

BH-6

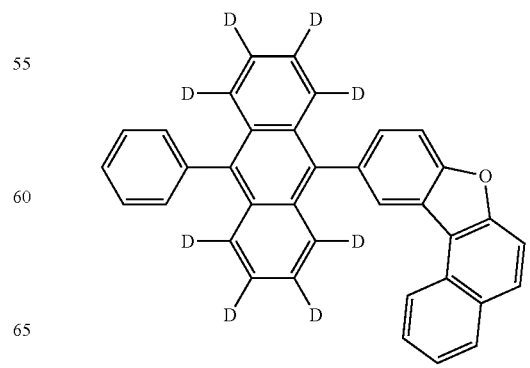

BH-7
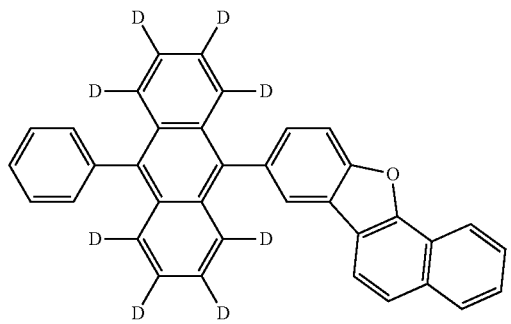
BH-8
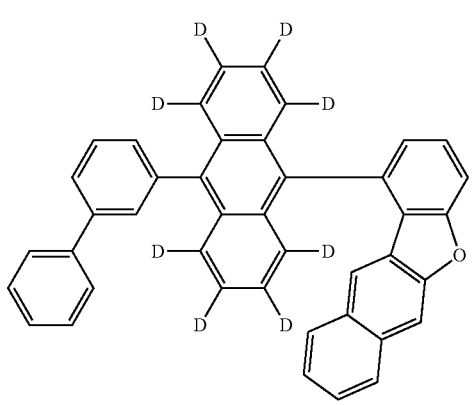
BH-9
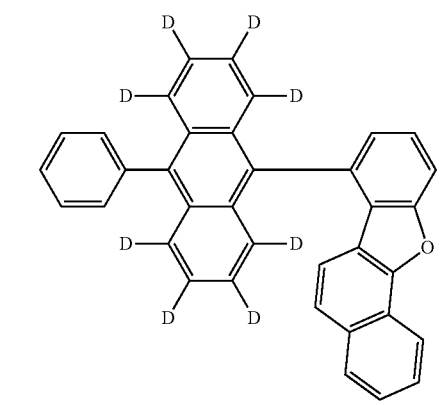
BH-10
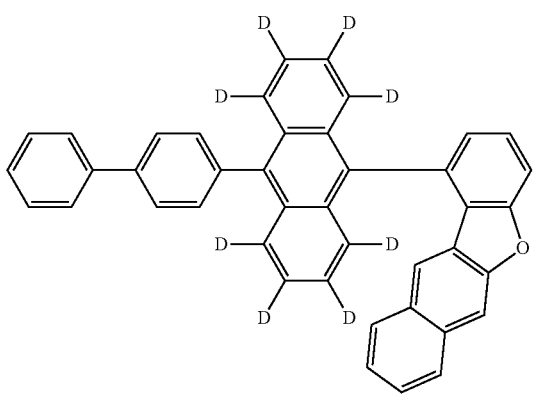
BH-11
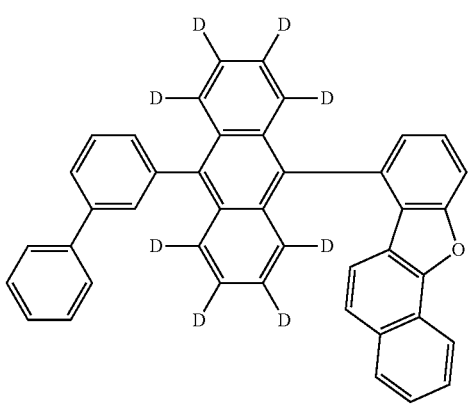
BH-12
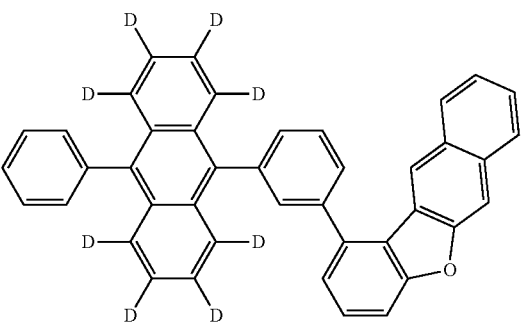
BH-13
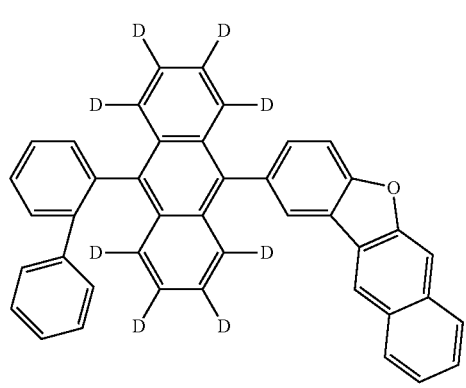
BH-15
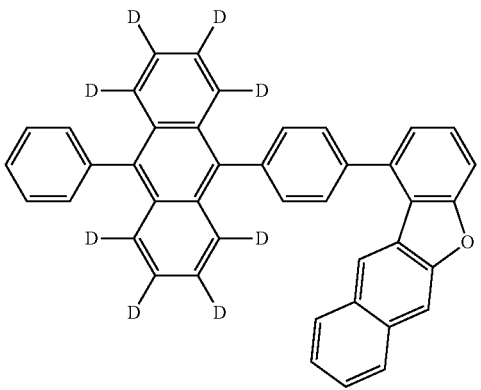

BH-16

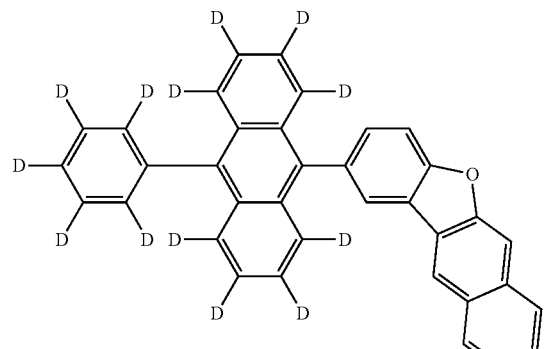

BH-17

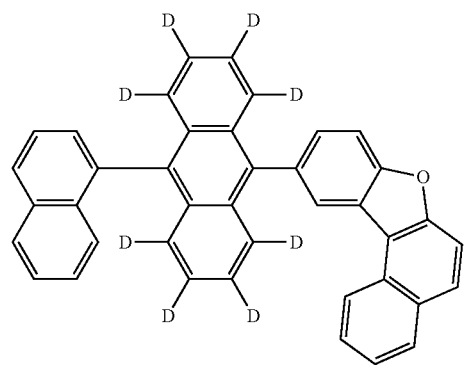

BD-9

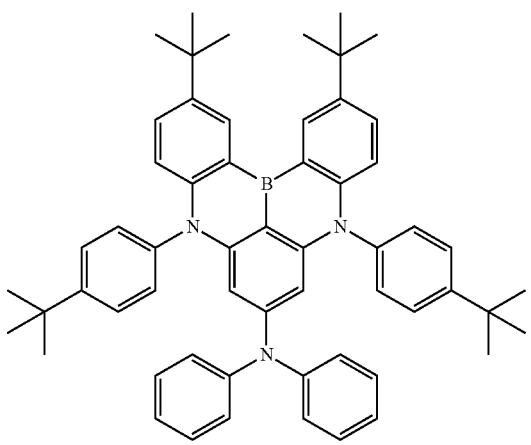

BD-10

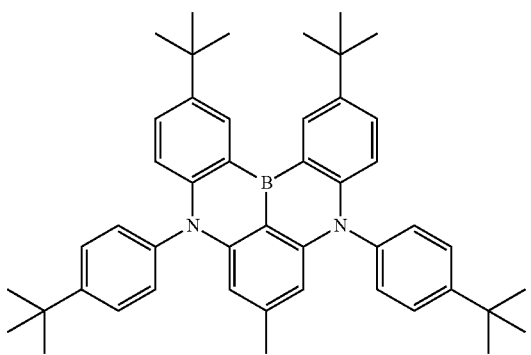

BD-11

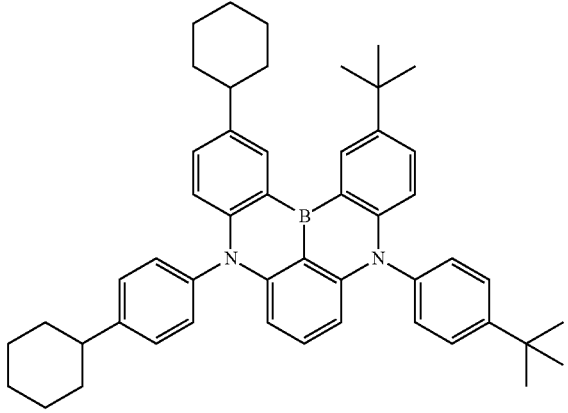

BD-12

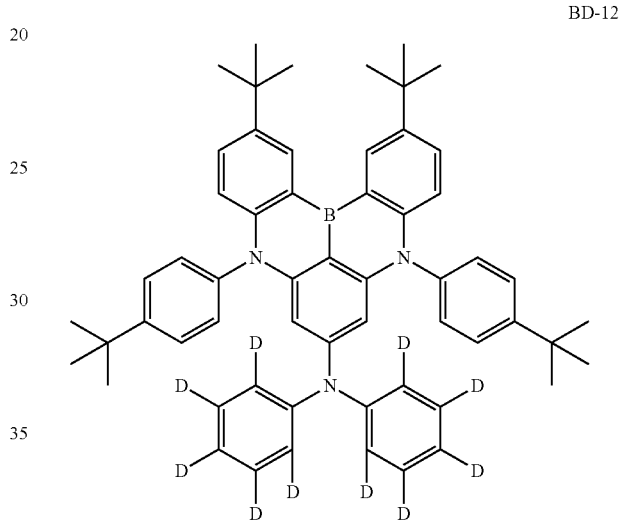

A content of the compound represented by the formula (1) in the emitting layer is preferably 80 mass % or more and 99 mass % or less based on the total mass of the emitting layer.

A content of the one or more compounds selected from the group consisting of compounds represented by formulas (11), (21), (31), (41), (51), (61), (71) and (81) is preferably 1 mass % or more and 20 mass % or less based on a total mass of the emitting layer.

One embodiment of the organic EL device preferably has the hole-transporting layer between the anode and the emitting layer.

One embodiment of the organic EL device preferably has the electron-transporting layer between the cathode and the emitting layer.

Specific examples of a typified device configuration of the organic EL device of the invention include structures such as
(1) an anode/an emitting layer/a cathode,
(2) an anode/a hole-injecting layer/an emitting layer/a cathode,
(3) an anode/an emitting layer/an electron-injecting-transporting layer/a cathode,
(4) an anode/a hole-injecting layer/an emitting layer/an electron-injecting-transporting layer/a cathode,
(5) an anode/an organic semiconductor layer/an emitting layer/a cathode,
(6) an anode/an organic semiconductor layer/an electron barrier layer/an emitting layer/a cathode, (7) an anode/an organic semiconductor layer/an emitting layer/an adhesion improving layer/a cathode,
(8) an anode/a hole-injecting-transporting layer/an emitting layer/an electron-injecting-transporting layer/a cathode,
(9) an anode/an insulating layer/an emitting layer/an insulating layer/a cathode,
(10) an anode/an inorganic semiconductor layer/an insulating layer/an emitting layer/an insulating layer/a cathode,
(11) an anode/an organic semiconductor layer/an insulating layer/an emitting layer/an insulating layer/a cathode,
(12) an anode/an insulating layer/a hole-injecting-transporting layer/an emitting layer/an insulating layer/a cathode, and
(13) an anode/an insulating layer/a hole-injecting-transporting layer/an emitting layer/an electron-injecting-transporting layer/a cathode.

Among the above-described structures, a configuration of (8) is preferably used, but the configuration is not limited thereto.

In this specification, the term "hole-injecting-transporting layer" herein means "at least one of the hole-injecting layer and the hole-transporting layer", and the term "electron-injecting-transporting layer" herein means "at least one of the electron-injecting layer and the electron-transporting layer".

Hereinbelow, an explanation will be made on elements and materials other than the above-mentioned compound constituting each layer that can be used in the organic EL device according to one aspect of the invention.
(Substrate)

The substrate is used as a supporting body of the emitting device. As the substrate, glass, quarts, plastic or the like can be used. Further, a flexible substrate may be used. The flexible substrate means a substrate that can be bent. For example, a plastic substrate made of polycarbonate or vinyl polychloride or the like can be given.
(Anode)

In an anode formed on a substrate, it is preferable to use a metal having a large work function (specifically, 4.0 eV or more), an alloy, an electric conductive compound, a mixture of these or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, or the like can be given. In addition, gold (Au), platinum (Pt) or a nitride of a metal material (e.g. titanium nitride) or the like can be given.
(Hole-Injecting Layer)

The hole-injecting layer is a layer containing a substance having a high hole-injecting property. As a substance having a high hole-injecting property, a substance selected from molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a polymer compound (oligomer, dendrimer, polymer, etc.) or the like can also be used
(Hole-Transporting Layer)

The hole-transporting layer is a layer containing a substance having a high hole-transporting property. For the hole-transporting layer, aromatic amine compounds, carbazole derivatives, anthracene derivatives and the like can be used. Polymer compounds such as poly (N-vinylcarbazole) (abbreviation: PVK) and poly(4-vinyltriphenylamine) (abbreviation: PVTPA) can also be used. However, any substance other than these may be used as long as it is a substance having a higher transporting property for holes than electrons. Note that the layer containing a substance having a high hole-transporting property is not limited to a single layer, but may be a stacked body of two or more layers made of the above substances.
(Guest Material of the Emitting Layer)

The emitting layer is a layer that comprises a substance having high luminous property, and various materials can be used. For example, as the substance having high luminous property, a fluorescent compound that emits fluorescent light or a phosphorescent compound that emits phosphorescent light can be used. The fluorescent compound is a compound capable of emitting light from a singlet excited state and the phosphorescent compound is a compound capable of emitting light from a triplet excited state.

As a blue fluorescent material that can be used for the emitting layer, pyrene derivatives, styrylamine derivatives, chrysene derivatives, fluoranthene derivatives, fluorene derivatives, diamine derivatives, triarylamine derivatives and the like can be used. An aromatic amine derivative or the like can be used as a green fluorescent light-emitting material that can be used in the emitting layer. As a red fluorescent material which can be used in emitting layer, a tetracene derivative, a diamine derivative or the like can be used.

Metal complexes such as iridium complexes, osmium complexes, platinum complexes and the like are used as the blue phosphorescent material that can be used in the emitting layer. An iridium complex or the like is used as a green phosphorescent material that can be used in the emitting layer. Metal complexes such as iridium complexes, platinum complexes, terbium complexes, europium complexes and the like are used as red phosphorescent materials that can be used in the emitting layer.
(Host Material of Emitting Layer)

The emitting layer may have a structure in which the substance having high luminescent property (guest material) described above is dispersed in another substance (host material). Various materials other than the compound represented by the formula (1) (for example, the compound represented by the formula (1A)) can be used as substances for dispersing substances with high luminescent properties, and it is preferable to use a material having a high lowest unoccupied molecular orbital level (LUMO level) and a low highest occupied molecular orbital level (HOMO level), rather than a material having a high luminous property.

As a substance (host material) for dispersing a substance having a high luminous property, 1) a metal complex such as an aluminum complex, a beryllium complex or a zinc complex, 2) a heterocyclic compound such as an oxadiazole derivative, a benzimidazole derivative, a phenanthroline derivative or the like, 3) a fused aromatic compound such as a carbazole derivative, an anthracene derivative, a phenanthrene derivative, a pyrene derivative or a chrysene derivative, and 4) an aromatic amine compound such as a triarylamine derivative or a fused polycyclic aromatic amine derivative are used.
(Electron-Transporting Layer)

The electron-transporting layer is a layer containing a substance having a high electron-transporting property. For the electron-transporting layer, 1) a metal complex such as an aluminum complex, a beryllium complex, or a zinc complex, 2) a heteroaromatic compound such as an imidazole derivative, a benzimidazole derivative, an azine derivative, a carbazole derivative or a phenanthroline derivative, and 3) a polymer compound can be used.
(Electron-Injecting Layer)

The electron-injection layer is a layer containing a substance having a high electron-injection property. For the electron-injection layer, alkali metals, alkaline earth metals or a compound thereof such as lithium ($L_1$), ytterbium (Yb), lithium fluoride (LiF), cesium fluoride (CsF), calcium fluoride ($CaF_2$), metal complex compound such as 8-quinolinolato lithium (Liq), lithium oxide (LiOx) or the like can be used.

(Cathode)

It is preferable to use a metal, an alloy, an electrically conductive compound, a mixture thereof, or the like having a small work function (specifically, 3.8 eV or less) for the cathode. Specific examples of such cathode material include elements belonging to Group 1 or Group 2 of the periodic table of elements, that is, alkali metals such as lithium ($L_1$) and cesium (Cs), alkaline earth metals such as magnesium (Mg), calcium (Ca), and strontium (Sr), an alloy containing these metals (for example, MgAg and AlLi), a rare earth metal such as europium (Eu) and ytterbium (Yb), and an alloy containing a rare earth metal.

In the organic EL device according to one aspect of the invention, the method for forming each layer is not particularly restricted. A conventionally known forming method such as a vacuum deposition method, a spin coating method or the like can be used. Each layer such as the emitting layer or the like can be formed by a vacuum deposition method, a molecular beam evaporation method (MBE method), or a known coating method such as a dipping method, a solution spin coating method, a casting method, a bar coating method, or the like, that uses a solution of a material forming each layer dissolved in a solvent.

In the organic EL device according to one aspect of the invention, the thickness of each layer is not particularly restricted. In general, in order to suppress occurrence of defects such as pinholes and to suppress the applied voltage and to improve luminous efficiency, the thickness is normally preferably in a range of several nm to 1 μm.

[Electronic Device]

The electronic device according to one aspect of the invention is characterized in that it is provided with the organic EL device according to one aspect of the invention.

Specific examples of the electronic device includes a display element such as an organic EL panel module; a display such as a TV, a mobile phone or a PC; and emitting devices such as lightings and lights for automobiles or the like.

EXAMPLES

Now, the invention will be explained in detail with reference to Examples and Comparative Examples. However, it should be understood that the invention be not restricted at all by these Examples.

Synthesis Example 1 [Synthesis of Compound BH-1]

Synthesis of Intermediate 1

Under argon atmosphere, 75 mL of toluene, 75 mL of dimethoxyethane, and 75 mL (150.0 mmol) of a 2M $Na_2CO_3$ aqueous solution were added to 13.3 g (50.0 mmol) of 9-bromoanthracene-d9, 6.4 g (52.5 mmol) of phenylboronic acid, and 1.2 g (1.00 mmol) of $Pd[PPh_3]_4$, and the mixture was refluxed and stirred with heat for 10 hours.

After completion of the reaction, the reaction solution was cooled to room temperature. The sample of the reaction mixture was transferred to a separation funnel and extracted with dichloromethane. The organic phase was dried over $MgSO_4$, followed by filtration and concentration. The concentrated residue was purified by silica gel column chromatography to obtain 10.9 g of white solid. The obtained compound was subjected to FD-MS analysis, and it was identified as Intermediate 1 below (yield: 83%).

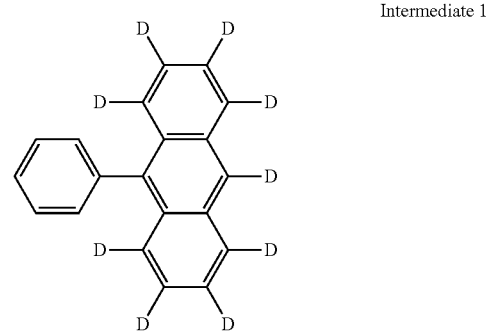 [SMILES: [2H]c1c([2H])c([2H])c2c(-c3ccccc3)c3c([2H])c([2H])c([2H])c([2H])c3c([2H])c2c1[2H]]

Intermediate 1

Synthesis of Intermediate 2

A solution of 5.3 g (20.0 mmol) of Intermediate 1 dissolved in 120 mL of dichloromethane was dropwise added at room temperature to a solution of 3.2 g (20.0 mmol) of bromine dissolved in 12 mL of dichloromethane, followed by stirring for one hour.

After completion of the reaction, the sample was transferred to a separation funnel, and washed with a 2M $Na_2S_2O_3$ aqueous solution. Subsequently, the organic phase was washed with 10% $Na_2CO_3$, and then with water, and the separated organic phase was dried over $MgSO_4$, followed by filtration and concentration.

The concentrated residue was suspended in 100 mL of methanol, and the precipitated crystals were collected to obtain 6.5 g of white solid. The obtained compound was subjected to FD-MS analysis, and was identified as Intermediate 2 below (yield: 95%).

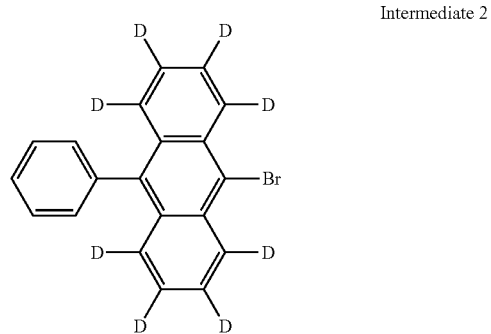 [SMILES: [2H]c1c([2H])c([2H])c2c(-c3ccccc3)c3c([2H])c([2H])c([2H])c([2H])c3c(Br)c2c1[2H]]

Intermediate 2

Synthesis of Compound BH-1

Under argon atmosphere, 7.5 mL of toluene, 7.5 mL of dimethoxyethane, and 7.5 mL (15.0 mmol) of a 2M $Na_2CO_3$ aqueous solution were added to 1.7 g (5.0 mmol) of Intermediate 2, 1.4 g (5.3 mmol) of benzo[b]naphtho[2,3-d]furan-2-boronic acid, and 0.1 g (0.1 mmol) of $Pd[PPh_3]_4$, and refluxed and stirred with heat for 10 hours.

After completion of the reaction, the reaction solution was cooled to room temperature, and the sample was transferred to a separation funnel and extracted with dichloromethane.

The organic phase was dried over MgSO₄, followed by filtration and concentration. The concentrated residue was purified by silica gel column chromatography to obtain 1.7 g of white solid. The obtained compound was subjected to FD-MS analysis, and was identified as Compound BH-1 below (yield: 70%).

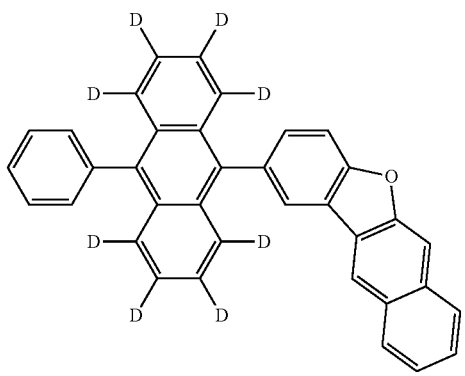

BH-1

Synthesis Example 2 [Synthesis of Compound BH-2]

Synthesis of Intermediate 3

Under argon atmosphere, 75 mL of toluene, 75 mL of dimethoxyethane, and 75 mL (150.0 mmol) of a 2M Na₂CO₃ aqueous solution were added to 13.3 g (50.0 mmol) of 9-bromoanthracene-d9, 9.0 g (52.5 mmol) of 1-naphthalene boronic acid, and 1.2 g (1.00 mmol) of Pd[PPh₃]₄, and the reaction mixture was refluxed and stirred with heat for 10 hours.

After completion of the reaction, the reaction solution was cooled to room temperature, and the sample was transferred to a separation funnel and extracted with dichloromethane. The organic phase was dried over MgSO₄, followed by filtration and concentration. The concentrated residue was purified by silica gel column chromatography to obtain 13.3 g of white solid. The obtained compound was subjected to FD-MS analysis, and identified as Intermediate 3 below (yield: 85%).

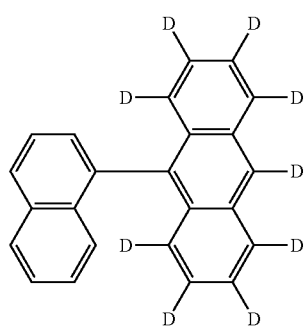

Intermediate 3

Synthesis of Intermediate 4

A solution of 6.3 g (20.0 mmol) of Intermediate 3 dissolved in 120 mL of dichloromethane was dropwise added at room temperature to a solution of 3.2 g (20.0 mmol) of bromine dissolved in 12 mL of dichloromethane, and stirred for one hour.

After completion of the reaction, the sample was transferred to a separation funnel, and washed with a 2M Na₂S₂O₃ aqueous solution. Subsequently, the organic phase was washed with 10% Na₂CO₃, and then, washed with water three times. The organic phase was dried over MgSO₄, followed by filtration and concentration.

The concentrated residue was suspended in 100 mL of methanol, and precipitated crystals were collected to obtain 7.5 g of white solid. The obtained compound was subjected to FD-MS analysis, and identified as Intermediate 4 below (yield: 96%).

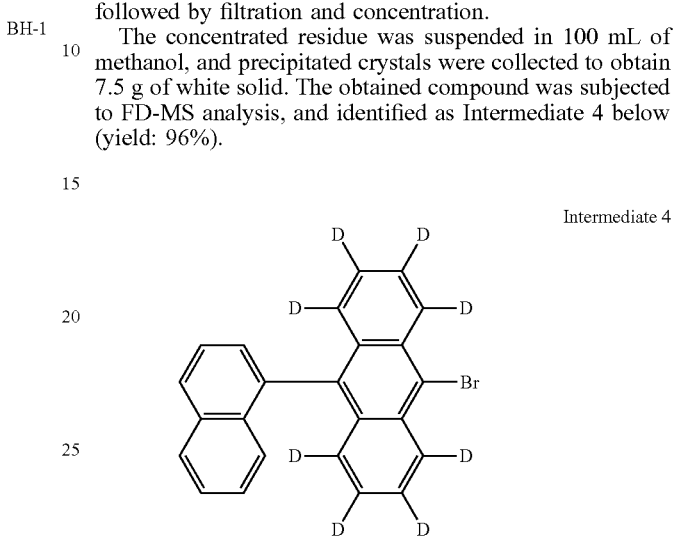

Intermediate 4

Synthesis of Compound BH-2

Under argon atmosphere, 7.5 mL of toluene, 7.5 mL of dimethoxyethane, and 7.5 mL (15.0 mmol) of a 2M Na₂CO₃ aqueous solution were added to 2.0 g (5.0 mmol) of Intermediate 4, 1.4 g (5.3 mmol) of benzo[b]naphtho[2,3-d]furan-2-boronic acid, and 0.1 g (0.1 mmol) of Pd[PPh₃]₄, and the reaction mixture was refluxed and stirred with heat for 10 hours.

After completion of the reaction, the reaction solution was cooled to room temperature, and the sample was transferred to a separation funnel and extracted with dichloromethane. The organic phase was dried over MgSO₄, followed by filtration and concentration. The concentrated residue was purified by silica gel column chromatography to obtain 1.9 g of white solid. The obtained compound was subjected to FD-MS analysis, and identified as Compound BH-2 below (yield: 73%).

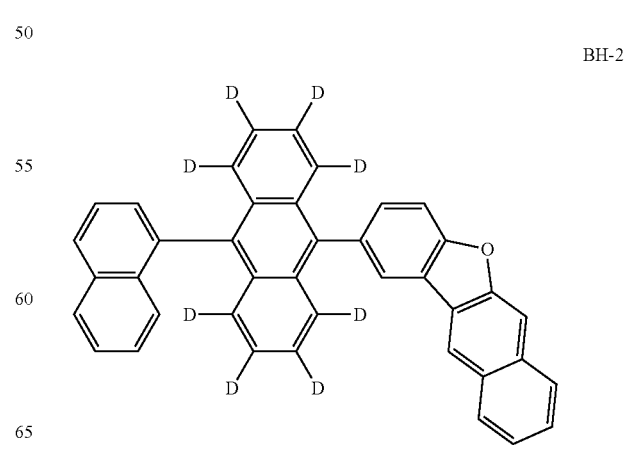

BH-2

Synthesis Example 3

Synthesis of Compound BH-3

The same reaction was conducted in the same manner as in Synthesis Example 1 except that 1.4 g (5.3 mmol) of benzo[b]naphtho[2,3-d]furan-1-boronic acid was used in place of benzo[b]naphtho[2,3-d]furan-2-boronic acid, to obtain 1.4 g of white crystals. The obtained compound was subjected to FD-MS analysis, and identified as Compound BH-3 below (yield: 57%).

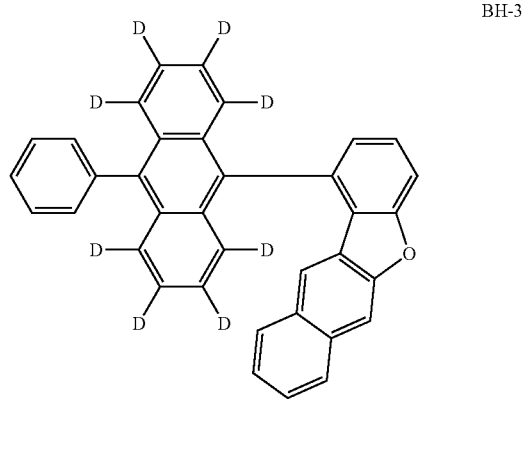 [SMILES: [2H]c1c([2H])c([2H])c2c(-c3cccc4oc5cc6ccccc6cc5c34)c3c([2H])c([2H])c([2H])c([2H])c3c(-c3ccccc3)c2c1[2H]]

BH-3

Synthesis Example 4

Synthesis of Compound BH-4

The same reaction was conducted in the same manner as in Synthesis Example 1 except that 1.4 g (5.3 mmol) of benzo[b]naphtho[2,3-d]furan-3-boronic acid was used in place of benzo[b]naphtho[2,3-d]furan-2-boronic acid, to obtain 1.8 g of white crystals. The obtained compound was subjected to FD-MS analysis, and identified as Compound BH-4 below (yield: 74%).

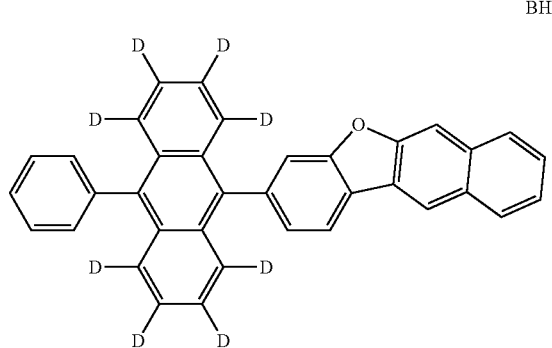

BH-4

Synthesis Example 5

Synthesis of Compound BH-5

Synthesis of Intermediate 5

Under argon atmosphere, 75 mL of toluene, 75 mL of dimethoxyethane, and 75 mL (150.0 mmol) of a 2M $Na_2CO_3$ aqueous solution were added to 13.3 g (50.0 mmol) of 9-bromoanthracene-d9, 13.0 g (52.5 mmol) of 4-(1-naphthyl)phenylboronic acid, and 1.2 g (1.00 mmol) of $Pd[PPh_3]_4$, and the reaction mixture was refluxed and stirred with heat for 10 hours.

After completion of the reaction, the reaction solution was cooled to room temperature, and the sample was transferred to a separation funnel and extracted with dichloromethane. The organic phase was dried over $MgSO_4$, followed by filtration and concentration. The concentrated residue was purified by silica gel column chromatography to obtain 15.6 g of white solid. The obtained compound was subjected to FD-MS analysis, and identified as Intermediate 5 below (yield: 80%).

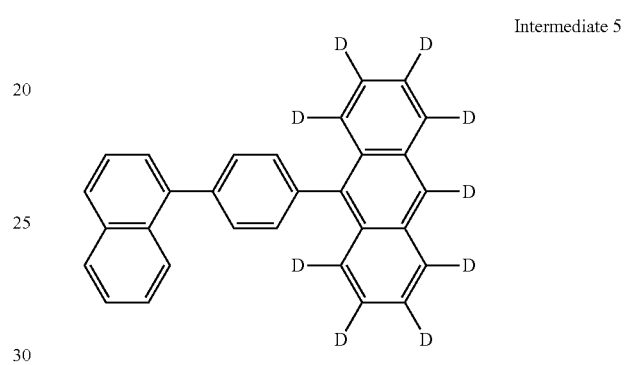

Intermediate 5

Synthesis of Intermediate 6

A solution of 7.8 g (20.0 mmol) of Intermediate 5 dissolved in 120 mL of dichloromethane was dropwise added at room temperature to a solution of 3.2 g (20.0 mmol) of bromine dissolved in 12 ml of dichloromethane, and the reaction mixture was stirred for one hour.

After completion of the reaction, the sample was transferred to a separation funnel, and washed with a 2M $Na_2S_2O_3$ aqueous solution. Subsequently, the organic phase was washed with 10% $Na_2CO_3$, and with water three times. The organic phase was dried over $MgSO_4$, followed by filtration and concentration.

The concentrated residue was suspended in 100 mL of methanol, and precipitated crystals were collected to obtain 8.6 g of white solid. The obtained compound was subjected to FD-MS analysis, and identified as Intermediate 6 below (yield: 92%).

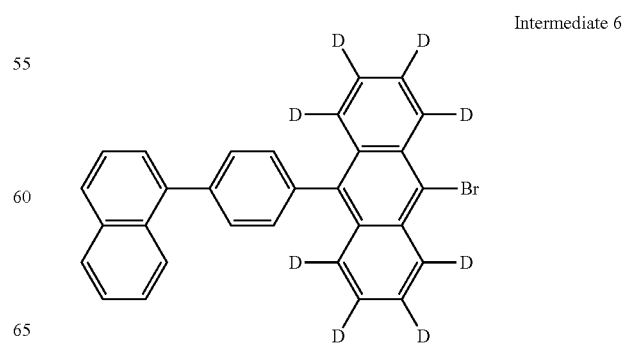

Intermediate 6

Synthesis of Compound BH-5

Under argon atmosphere, 7.5 mL of toluene, 7.5 mL of dimethoxyethane, and 7.5 mL (15.0 mmol) of a 2M $Na_2CO_3$ aqueous solution were added to 2.3 g (5.0 mmol) of Intermediate 6, 1.4 g (5.3 mmol) of benzo[b]naphtho[2,3-d]furan-2-boronic acid, and 0.1 g (0.1 mmol) of $Pd[PPh_3]_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 2.1 g of white solid. The obtained compound was subjected to FD-MS analysis, and identified as Compound BH-5 below (yield: 68%).

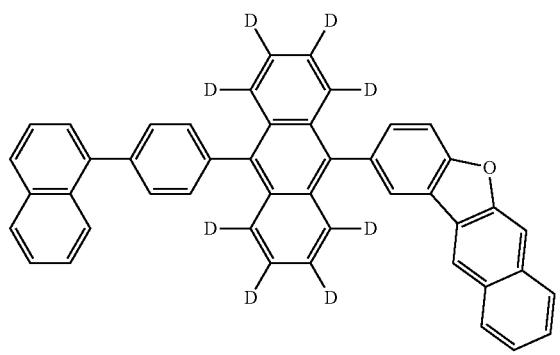

BH-5

Synthesis Example 6

Synthesis of Compound BH-6

The reaction was conducted in the same manner as in Synthesis Example 1 except that 1.4 g (5.3 mmol) of benzo[b]naphtho[1,2-d]furan-10-boronic acid was used in place of benzo[b]naphtho[2,3-d]furan-2-boronic acid, to obtain 1.7 g of white crystals. The obtained compound was subjected to FD-MS analysis, and identified as Compound BH-6 below (yield: 71%).

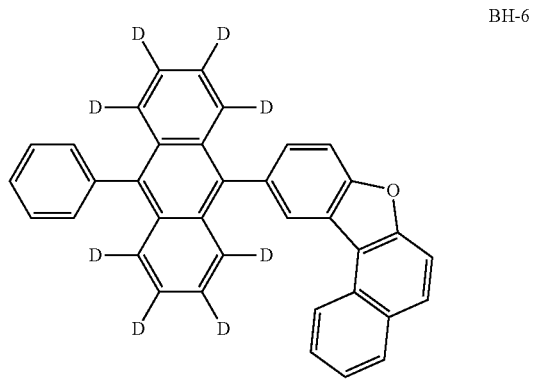 [SMILES: [2H]c1c([2H])c([2H])c2c(-c3ccc4oc5ccc6ccccc6c5c4c3)c3c([2H])c([2H])c([2H])c([2H])c3c(-c3ccccc3)c2c1[2H]]

BH-6

Synthesis Example 7

Synthesis of Compound BH-7

The reaction was conducted in the same manner as in Synthesis Example 1 except that 1.4 g (5.3 mmol) of benzo[b]naphtho[2,1-d]furan-8-boronic acid was used in place of benzo[b]naphtho[2,3-d]furan-2-boronic acid, to obtain 1.6 g of white crystals. The obtained compound was subjected to FD-MS analysis, and identified as Compound BH-7 below (yield: 65%).

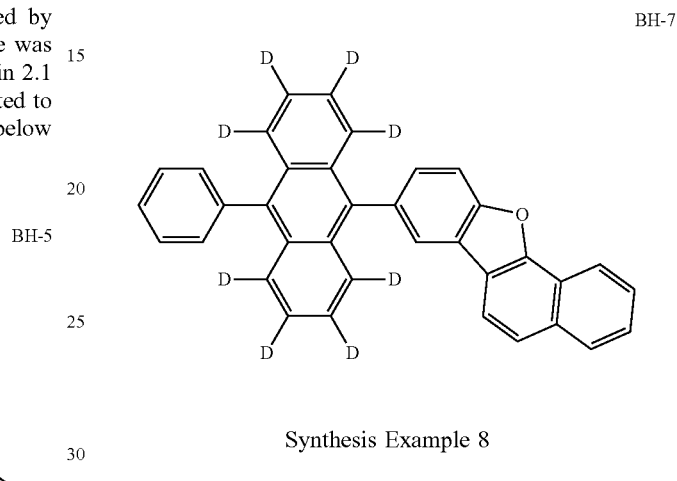

BH-7

Synthesis Example 8

Synthesis of Compound BH-8

Synthesis of Intermediate 7

Under argon atmosphere, 75 ml of toluene, 75 mL of dimethoxyethane, and 75 mL (150.0 mmol) of a 2M $Na_2CO_3$ aqueous solution were added to 13.3 g (50.0 mmol) of 9-bromoanthracene-d9, 10.4 g (52.5 mmol) of 3-biphenyl-boronic acid, and 1.2 g (1.00 mmol) of $Pd[PPh_3]_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 13.6 g of white solid. The obtained compound was subjected to FD-MS analysis, and identified as Intermediate 7 below (yield: 80%).

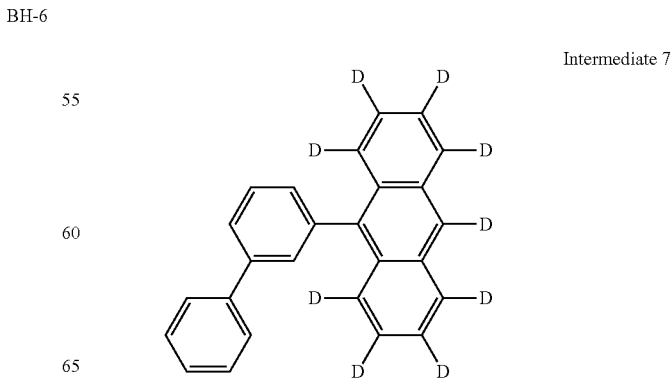

Intermediate 7

Synthesis of Intermediate 8

A solution of 6.8 g (20.0 mmol) of Intermediate 7 dissolved in 120 mL of dichloromethane was dropwise added to a solution of 3.2 g (20.0 mmol) of bromine dissolved in 12 mL of dichloromethane, and the reaction mixture was stirred for one hour.

After completion of the reaction, the sample was transferred to a separation funnel, and washed with a 2M $Na_2S_2O_3$ aqueous solution. Subsequently, the organic phase was washed with 10% $Na_2CO_3$, and then, with water three times. The organic phase was dried over $MgSO_4$, followed by filtration and concentration.

The concentrated residue was suspended in 100 mL of methanol, and precipitated crystals were collected to obtain 8.0 g of white solid. The obtained compound was subjected to FD-MS analysis, and identified as Intermediate 8 below (yield: 96%).

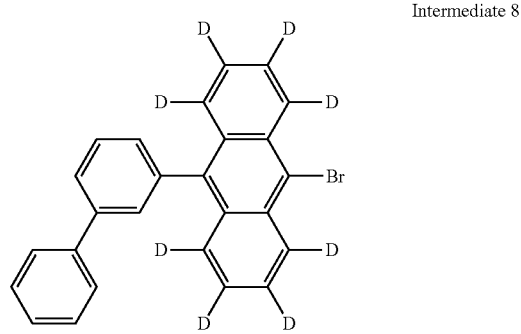 [SMILES: [2H]c1c([2H])c([2H])c2c(-c3cccc(-c4ccccc4)c3)c3c([2H])c([2H])c([2H])c([2H])c3c(Br)c2c1[2H]]

Intermediate 8

Synthesis of Compound BH-8

Under argon atmosphere, 7.5 mL of toluene, 7.5 mL of dimethoxyethane, and 7.5 mL (15.0 mmol) of a 2M $Na_2CO_3$ aqueous solution were added to 2.1 g (5.0 mmol) of Intermediate 8, 1.4 g (5.3 mmol) of benzo[b]naphtho[2,3-d]furan-1-boronic acid, and 0.1 g (0.1 mmol) of $Pd[PPh_3]_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 1.7 g of white solid. The obtained compound was subjected to FD-MS analysis, and identified as Compound BH-8 below (yield: 60%).

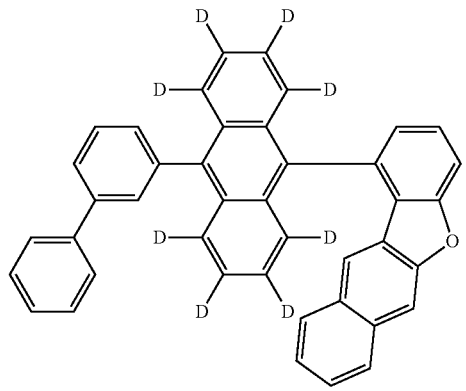

BH-8

Synthesis Example 9

Synthesis of Compound BH-9

The reaction was conducted in the same manner as in Synthesis Example 1 except that 1.4 g (5.3 mmol) of benzo[b]naphtho[2,1-d]furan-7-boronic acid was used in place of benzo[b]naphtho[2,3-d]furan-2-boronic acid, to obtain 1.6 g of white crystals. The obtained compound was subjected to FD-MS analysis, and identified as Compound BH-9 below (yield: 65%).

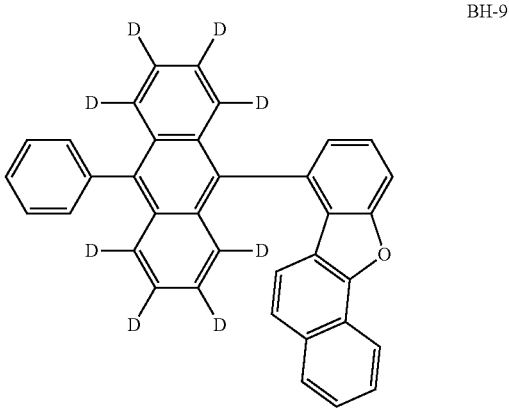 [SMILES: [2H]c1c([2H])c([2H])c2c(-c3cccc4oc5c6ccccc6ccc5c34)c3c([2H])c([2H])c([2H])c([2H])c3c(-c3ccccc3)c2c1[2H]]

BH-9

Synthesis Example 10

Synthesis of Compound BH-10

Synthesis of Intermediate 9

Under argon atmosphere, 75 ml of toluene, 75 mL of dimethoxyethane, and 75 mL (150.0 mmol) of a 2M $Na_2CO_3$ aqueous solution were added to 13.3 g (50.0 mmol) of 9-bromoanthracene-d9, 10.4 g (52.5 mmol) of 4-biphenylboronic acid, and 1.2 g (1.00 mmol) of $Pd[PPh_3]_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 14.1 g of white solid. The obtained compound was subjected to FD-MS analysis, and identified as Intermediate 9 below (yield: 83%).

Intermediate 9

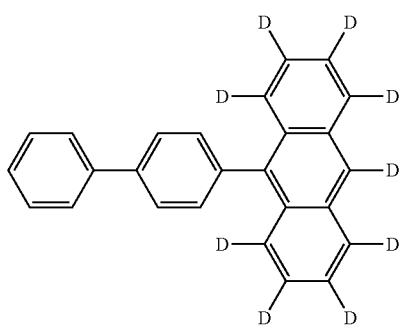

Synthesis of Intermediate 10

A solution of 6.8 g (20.0 mmol) of Intermediate 9 dissolved in 120 mL of dichloromethane was dropwise added to a solution of 3.2 g (20.0 mmol) of bromine dissolved in 12 mL of dichloromethane, and the reaction mixture was stirred for one hour.

After completion of the reaction, the sample was transferred to a separation funnel, and washed with a 2M $Na_2S_2O_3$ aqueous solution. Subsequently, the organic phase was washed with 10% $Na_2CO_3$, and then, with water three times. The organic phase was dried over $MgSO_4$, followed by filtration and concentration.

The concentrated residue was suspended in 100 mL of methanol, and precipitated crystals were collected to obtain 8.0 g of white solid. The obtained compound was subjected to FD-MS analysis, and identified as Intermediate 10 below (yield: 96%).

Intermediate 10

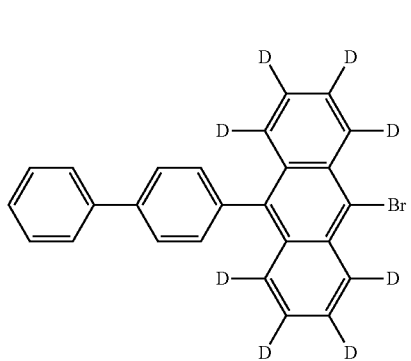

Synthesis of Compound BH-10

Under argon atmosphere, 7.5 mL of toluene, 7.5 mL of dimethoxyethane, and 7.5 mL (15.0 mmol) of a 2M $Na_2CO_3$ aqueous solution were added to 2.1 g (5.0 mmol) of Intermediate 10, 1.4 g (5.3 mmol) of benzo[b]naphtho[2,3-d]furan-1-boronic acid, and 0.1 g (0.1 mmol) of Pd[PPh$_3$]$_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 1.4 g of white solid. The obtained compound was subjected to FD-MS analysis, and identified as Compound BH-10 below (yield: 51%).

BH-10

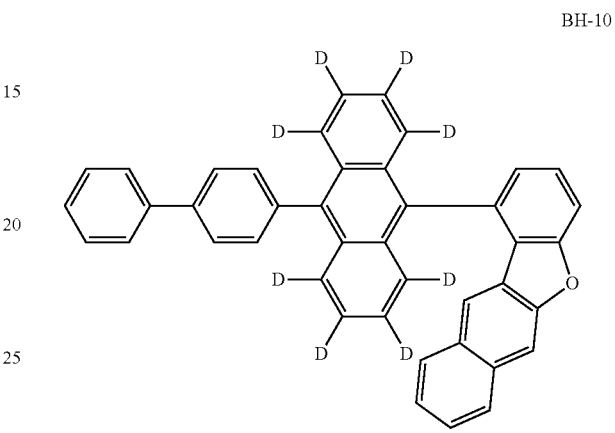

Synthesis Example 11

Synthesis of Compound BH-11

The reaction was conducted in the same manner as in Synthesis Example 8 except that 1.4 g (5.3 mmol) of benzo[b]naphtho[2, I-d]furan-7-boronic acid was used in place of benzo[b]naphtho[2,3-d]furan-1-boronic acid, to obtain 1.4 g of white crystals. The obtained compound was subjected to FD-MS analysis, and identified as Compound BH-11 below (yield: 52%).

BH-11

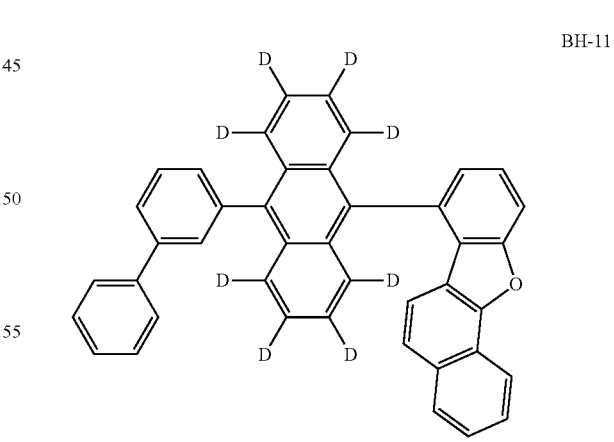

Synthesis Example 12

Synthesis of Compound BH-12

The reaction was conducted in the same manner as in Synthesis Example 1 except that 1.8 g (5.3 mmol) of 3-(benzo[b]naphtho[2,3-d]furan-1-yl)phenylboronic acid was used in place of benzo[b]naphtho[2,3-d]furan-2-boronic acid, to obtain 1.5 g of white crystals. The obtained compound was subjected to FD-MS analysis, and identified as Compound BH-12 below (yield: 53%).

BH-12

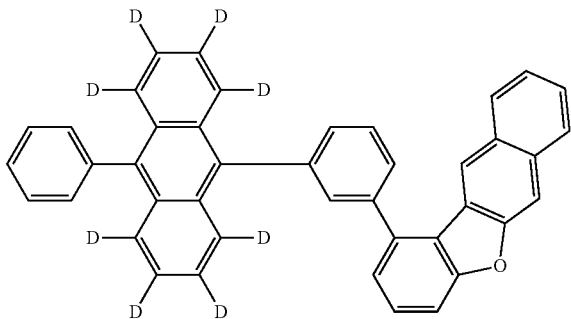

Synthesis Example 13

Synthesis of Compound BH-13

Synthesis of Intermediate 11

Under argon atmosphere, 75 ml of toluene, 75 mL of dimethoxyethane, and 75 mL (150.0 mmol) of a 2M Na₂CO₃ aqueous solution were added to 13.3 g (50.0 mmol) of 9-bromoanthracene-d9, 10.4 g (52.5 mmol) of 2-biphenylboronic acid, and 1.2 g (1.00 mmol) of Pd[PPh₃]₄, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over MgSO₄, followed by filtration and concentration. The concentrated residue was purified by silica gel column chromatography to obtain 10.9 g of white solid. The obtained compound was subjected to FD-MS analysis, and identified as Intermediate 11 below (yield: 64%).

Intermediate 11

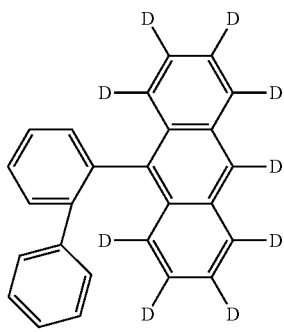

Synthesis of Intermediate 12

A solution of 6.8 g (20.0 mmol) of Intermediate 11 dissolved in 120 mL of dichloromethane was dropwise added to a solution of 3.2 g (20.0 mmol) of bromine dissolved in 12 mL of dichloromethane, and the reaction mixture was stirred for one hour.

After completion of the reaction, the sample was transferred to a separation funnel, and washed with a 2M Na₂S₂O₃ aqueous solution. Subsequently, the organic phase was washed with 10% Na₂CO₃, and then, with water three times. The organic phase was dried over MgSO₄, followed by filtration and concentration.

The concentrated residue was suspended in 100 mL of methanol, and precipitated crystals were collected to obtain 8.0 g of white solid. The obtained compound was subjected to FD-MS analysis, and identified as Intermediate 12 below (yield: 96%).

Intermediate 12

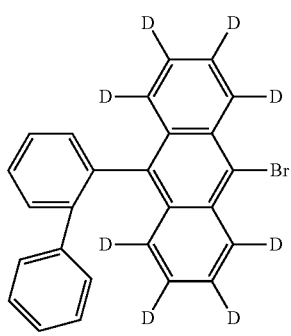

Synthesis of Compound BH-13

Under argon atmosphere, 7.5 mL of toluene, 7.5 mL of dimethoxyethane, and 7.5 mL (15.0 mmol) of a 2M Na₂CO₃ aqueous solution were added to 2.1 g (5.0 mmol) of Intermediate 12, 1.4 g (5.3 mmol) of benzo[b]naphtho[2,3-d]furan-2-boronic acid, and 0.1 g (0.1 mmol) of Pd[PPh₃]₄, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over MgSO₄, followed by filtration and concentration. The concentrated residue was purified by silica gel column chromatography to obtain 1.7 g of white solid. The obtained compound was subjected to FD-MS analysis, 3 and identified as Compound BH-13 below (yield: 60%).

BH-13

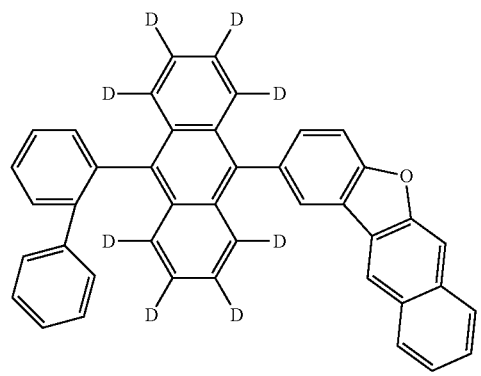

Synthesis Example 15

Synthesis of Compound BH-15

The reaction was conducted in the same manner as in Synthesis Example 1 except that 1.8 g (5.3 mmol) of 4-(benzo[b]naphtho[2,3-d]furan-1-yl)phenylboronic acid was used in place of benzo[b]naphtho[2,3-d]furan-2-boronic acid, to obtain 1.5 g of white crystals. The obtained compound was subjected to FD-MS analysis, and identified as Compound BH-below (yield: 55%).

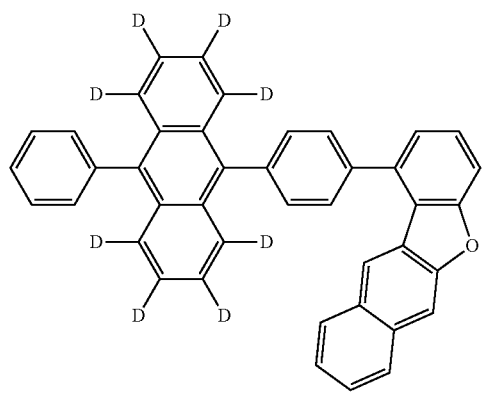

BH-15

Synthesis Example 16

Synthesis of Compound BH-16

Synthesis of Intermediate 13

Under argon atmosphere, 7.5 ml of toluene, 7.5 mL of dimethoxyethane, and 7.5 mL (15.0 mmol) of a 2M $Na_2CO_3$ aqueous solution were added to 1.33 g (5.00 mmol) of 9-bromoanthracene-d9, 0.67 g (5.25 mmol) of phenyl-d5-boronic acid, and 0.12 g (0.10 mmol) of $Pd[PPh_3]_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 1.07 g of white solid. The obtained compound was subjected to FD-MS analysis, and identified as Intermediate 13 below (yield: 80%).

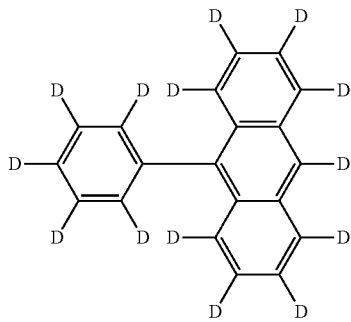

Intermediate 13

Synthesis of Intermediate 14

A solution of 1.07 g (4.0 mmol) of Intermediate 13 dissolved in 25 mL of dichloromethane was dropwise added to a solution of 0.64 g (4.0 mmol) of bromine dissolved in 3 mL of dichloromethane, and the reaction mixture was stirred for one hour.

After completion of the reaction, the sample was transferred to a separation funnel, and washed with a 2M $Na_2S_2O_3$ aqueous solution. Subsequently, the organic phase was washed with 10% $Na_2CO_3$, and then, with water three times. The organic phase was dried over $MgSO_4$, followed by filtration and concentration.

The concentrated residue was suspended in 100 mL of methanol, and precipitated crystals were collected to obtain 1.3 g of white solid. The obtained compound was subjected to FD-MS analysis, and identified as Intermediate 14 below (yield: 95%).

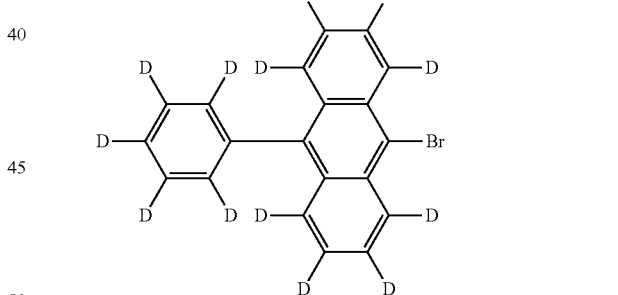

Intermediate 14

Synthesis of Compound BH-16

Under argon atmosphere, 5 mL of toluene, 5 mL of dimethoxyethane, and 5 mL (10.0 mmol) of a 2M $Na_2CO_3$ aqueous solution were added to 0.87 g (2.5 mmol) of Intermediate 14, 0.69 g (2.65 mmol) of benzo[b]naphtho[2,3-d]furan-2-boronic acid, and 0.06 g (0.05 mmol) of $Pd[PPh_3]_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 0.87 g of white solid. The obtained compound was subjected to FD-MS analysis, and identified as Compound BH-16 below (yield: 72%).

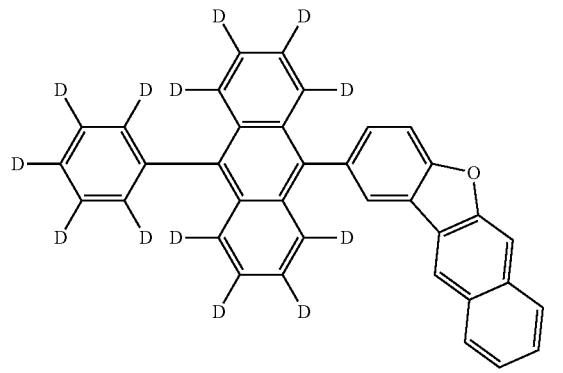

BH-16

Synthesis Example 17

Synthesis of Compound BH-17

The reaction was conducted in the same manner as in Synthesis Example 2 except that 1.4 g (5.3 mmol) of benzo[b]naphtho[1,2-d]furan-10-boronic acid was used in place of benzo[b]naphtho[2,3-d]furan-2-boronic acid, to obtain 1.5 g of white crystals. The obtained compound was subjected to FD-MS analysis, and identified as Compound BH-17 below (yield: 56%).

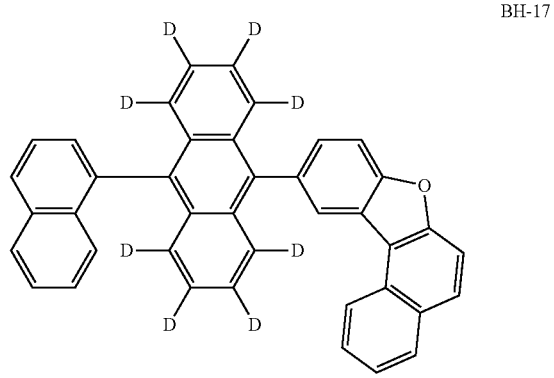 [SMILES: [2H]c1c([2H])c([2H])c2c(-c3cccc4ccccc34)c3c([2H])c([2H])c([2H])c([2H])c3c(-c3ccc4oc5ccc6ccccc6c5c4c3)c2c1[2H]]

BH-17

Example 1

(Fabrication of Organic EL Device)

A glass substrate of 25 mm by 75 mm by 1.1 mm thick with an ITO transparent electrode (anode) (manufactured by GEOMATEC Co., Ltd.) was subjected to ultrasonic cleaning with isopropyl alcohol for 5 minutes, and then subjected to UV-ozone cleaning for 30 minutes. The thickness of the ITO was 130 nm.

The cleaned glass substrate with a transparent electrode was mounted in a substrate holder of a vacuum vapor deposition apparatus. First, the compound HI was deposited on the surface where the transparent electrode was formed so as to cover the transparent electrode, thereby to form a 5 nm-thick HI film was formed. This HI film serves as a hole-injecting layer.

Subsequent to the formation of the HI film, the compound HT-1 was deposited, whereby a 80 nm-thick HT-1 film was formed on the HI film. This HT-1 film serves as a hole-transporting layer (first hole-transporting layer).

Subsequent to the formation of the HT-1 film, the compound HT-2 was deposited, whereby a 10 nm-thick HT-2 film was formed on the HT-1 film. This HT-2 film serves as an electron blocking layer (second hole-transporting layer).

On the HT-2 film, compound BH-1 (host material) and compound BD-1 (dopant material) were co-deposited such that the amount ratio of BD-1 (mass ratio) became 4 mass %, whereby a 25 nm-thick BH-1:BD-1 film was formed. The BH-1:BD-1 film serves as an emitting layer.

On the emitting layer, compound ET-1 was deposited, whereby a 10 nm-thick ET-1 film was formed. This ET-1 film serves as a hole barrier layer.

On the ET-1 film, compound ET-2 was deposited, whereby a 15 nm-thick ET-2 film was formed. This ET-2 film serves as an electron transporting layer. On this ET-2 film, LiF was deposited, whereby a 1 nm-thick LiF film. On this LiF film, metal Al was deposited, whereby a 80 nm-thick metal cathode was formed. By the above-mentioned procedures, an organic EL device was fabricated.

The resultant organic EL device has the following layer structure: ITO(130)/HI(5)/HT-1(80)/HT-2(10)/BH-1:BD-1 (25:4 mass %)/ET-1 (10)/ET-2(15)/LiF(1)/Al(80).

The numerical value in the parenthesis indicates the film thickness (unit: nm).

Materials used in Example 1 and the below-mentioned Examples and Comparative Examples are shown below.

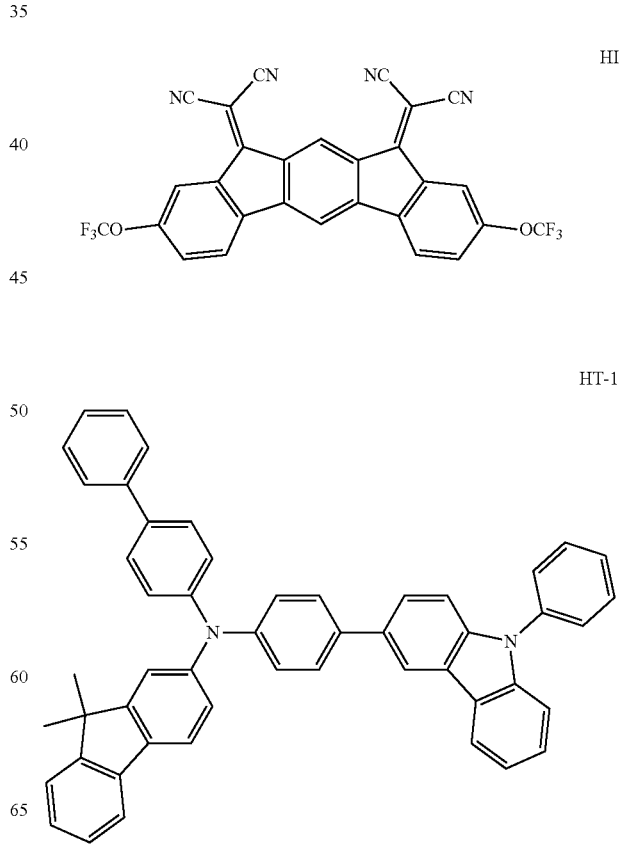

HT-2 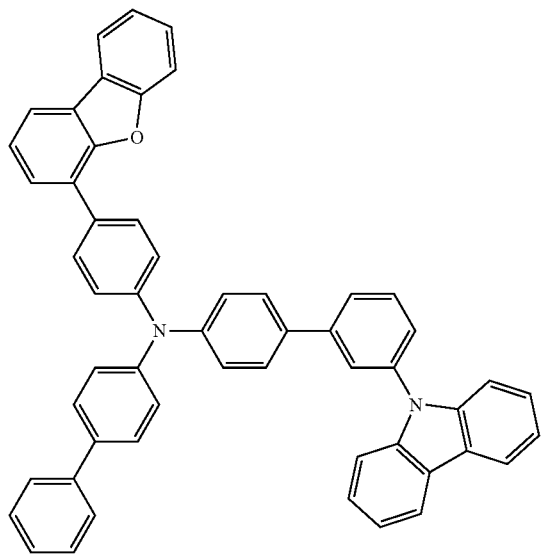
BH-1-a 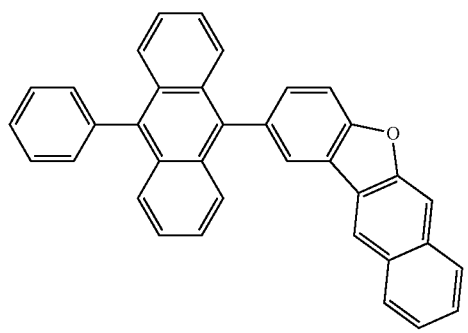
BH-2 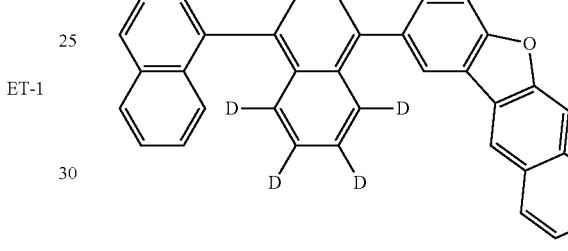
ET-1 
ET-2 
BH-2-a 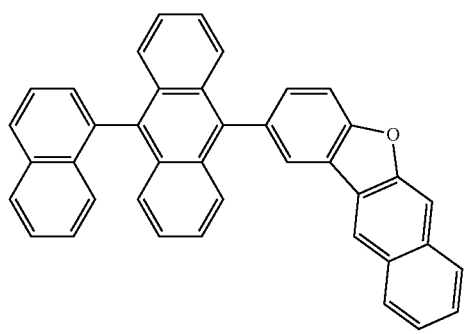
BH-1 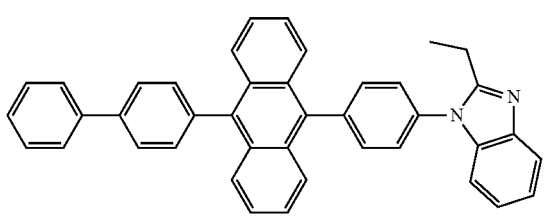
BH-3 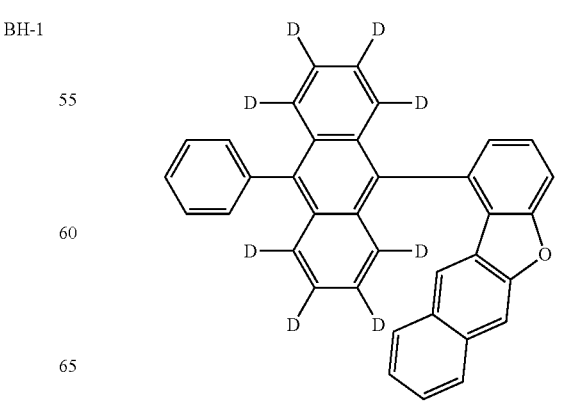

BH-3-a
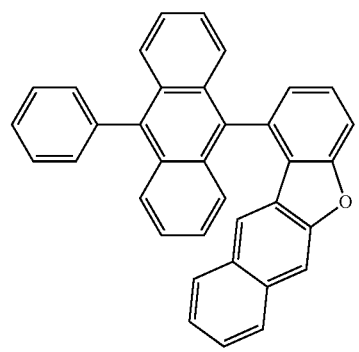
BH-4
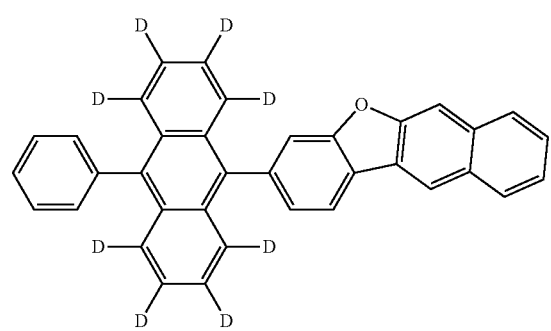
BH-4-a
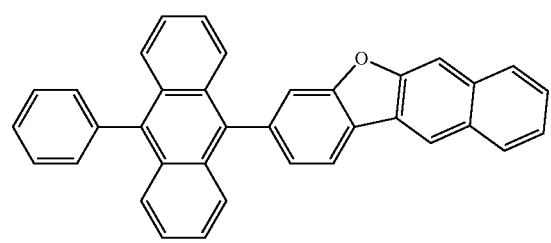
BH-5
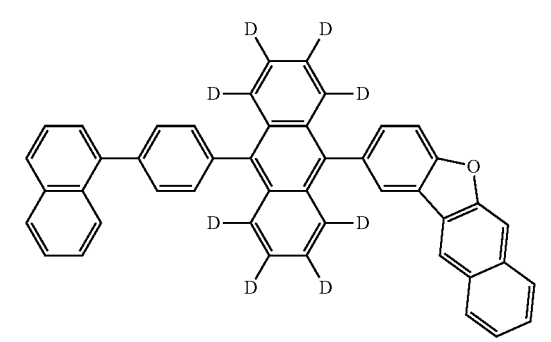
BH-5-a
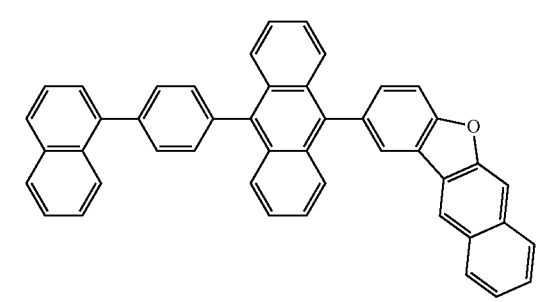
BH-6
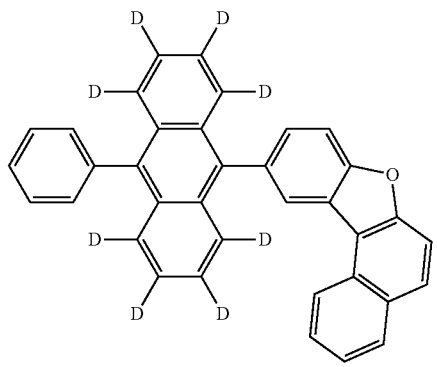
BH-6-a
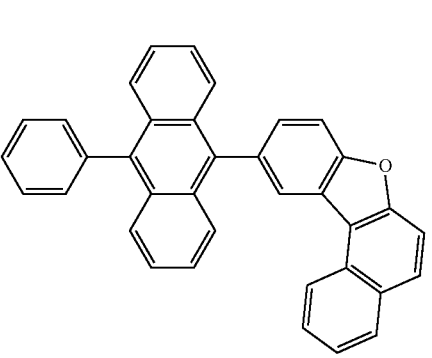
BH-7
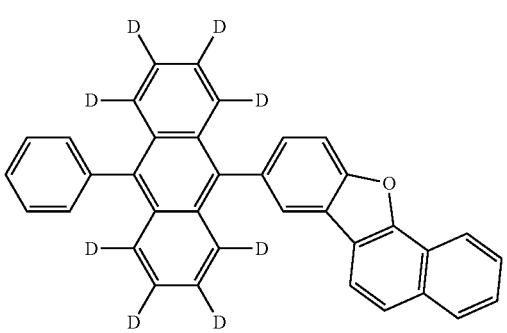
BH-7-a
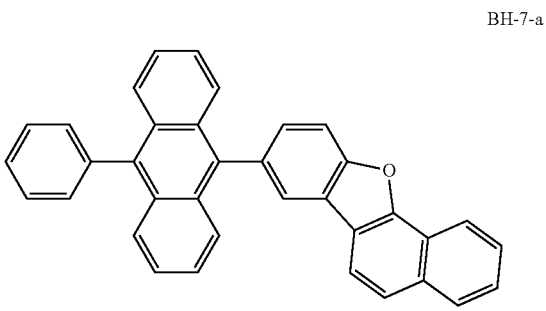

BH-8
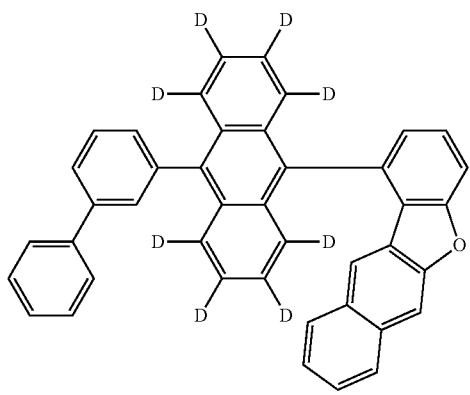
BH-8-a
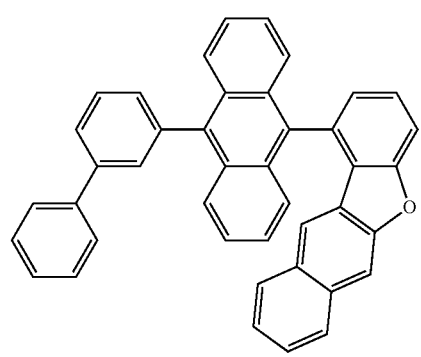
BH-9
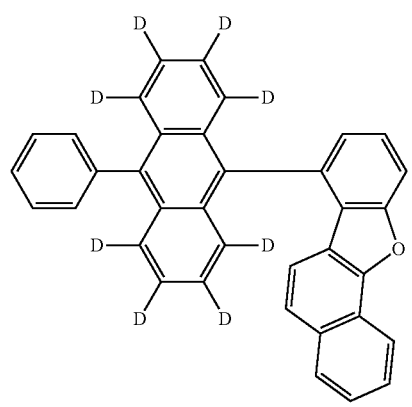
BH-9-a
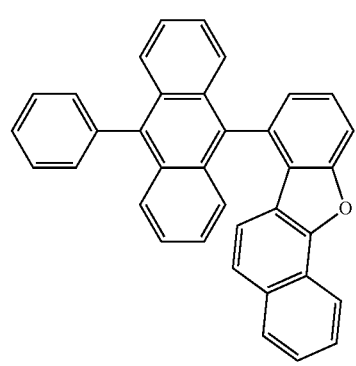
BH-10
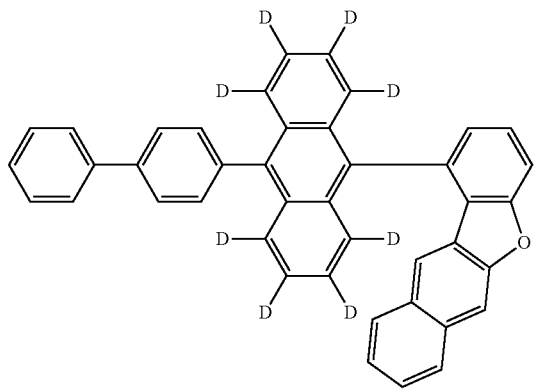
BH-10-a
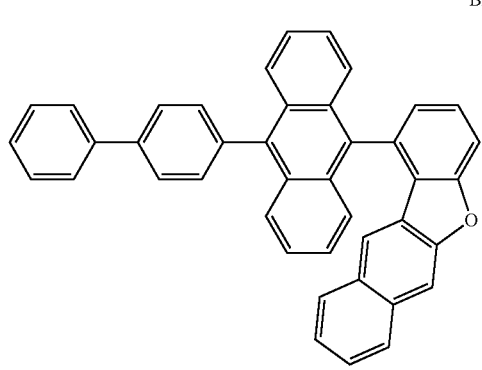
BH-11
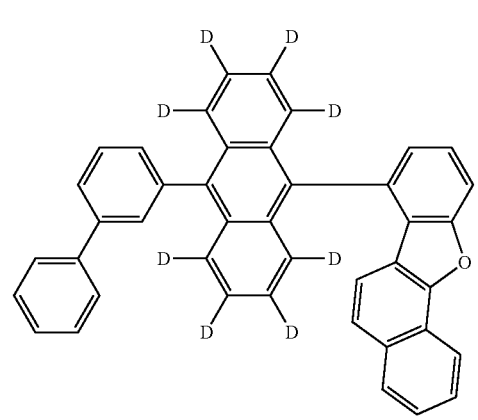
BH-11-a
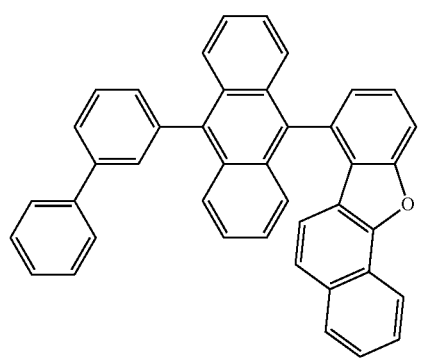

BH-12
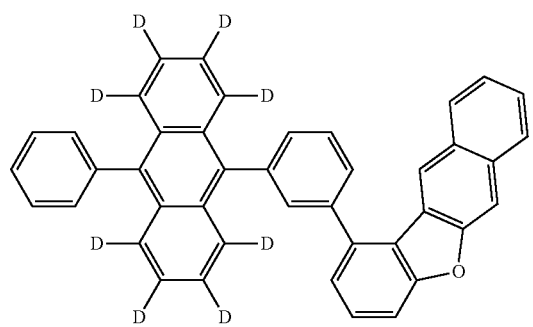
BH-12-a
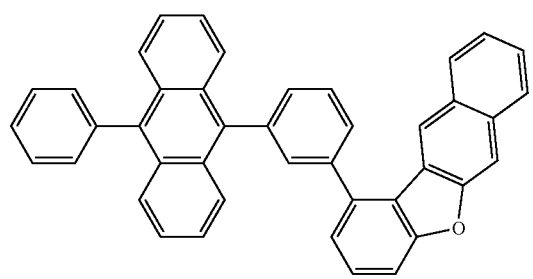
BH-13
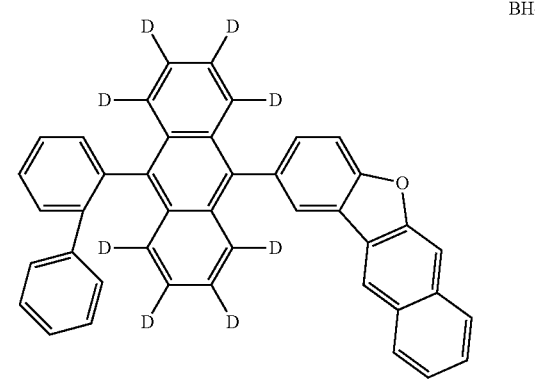
BH-13-a
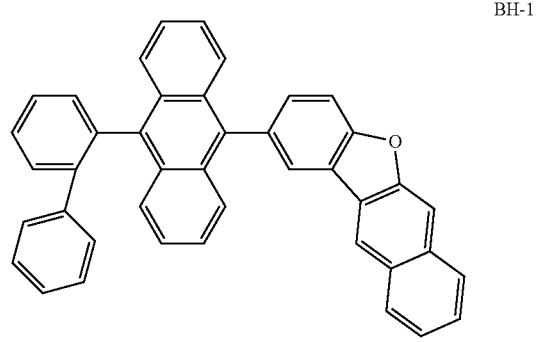
BH-15
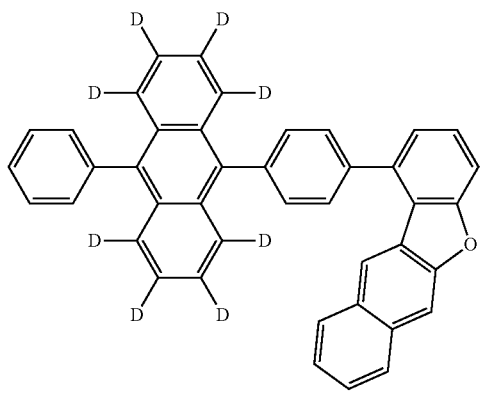
BH-15-a
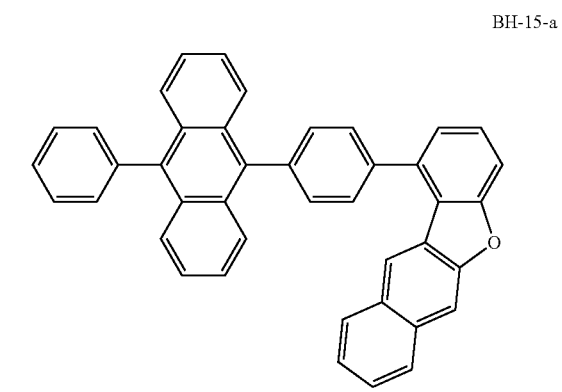
BH-16
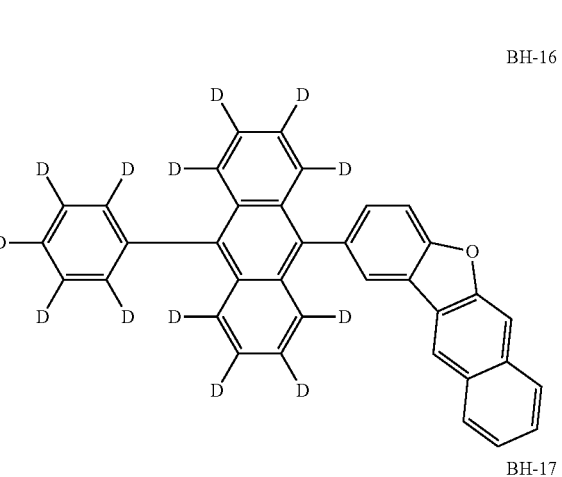
BH-17
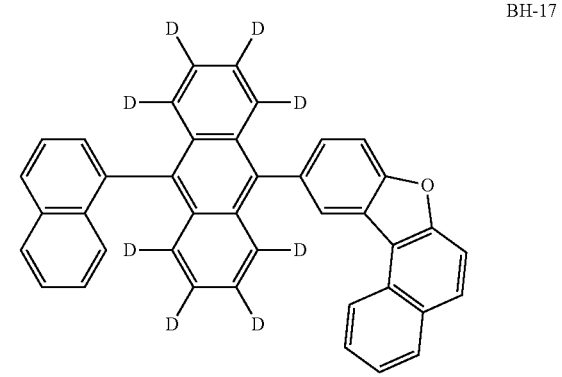

BH-17-a
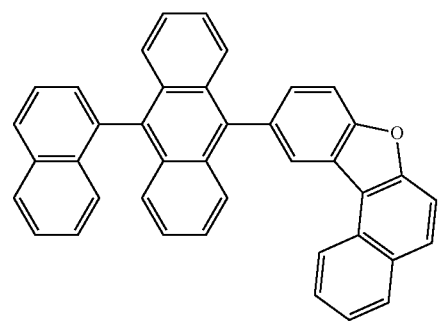
BD-5
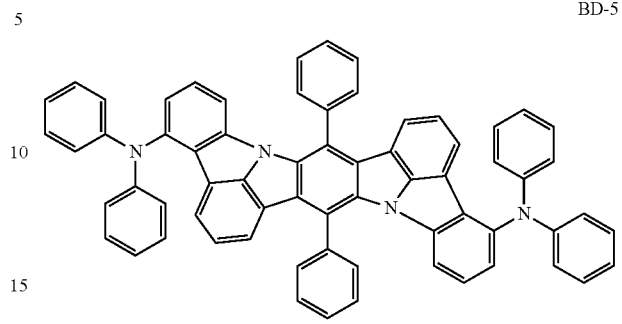
BD-1
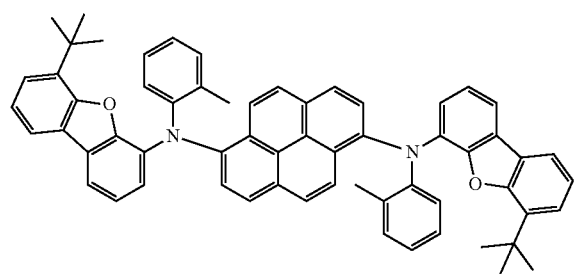
BD-6
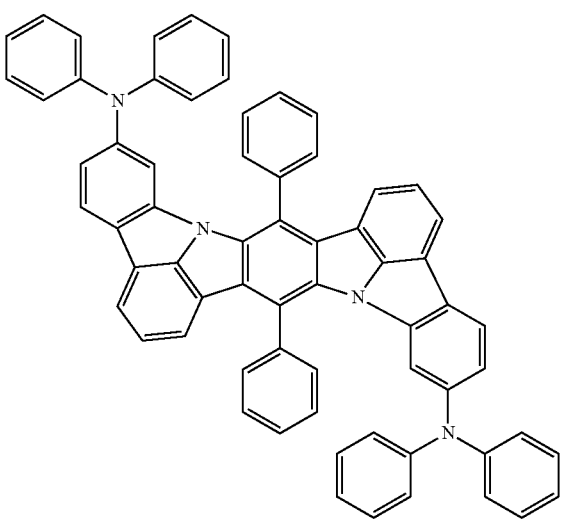
BD-2
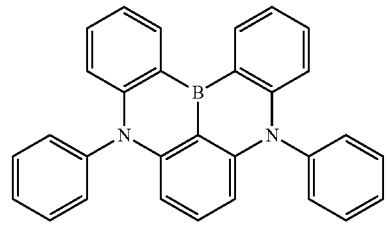
BD-3
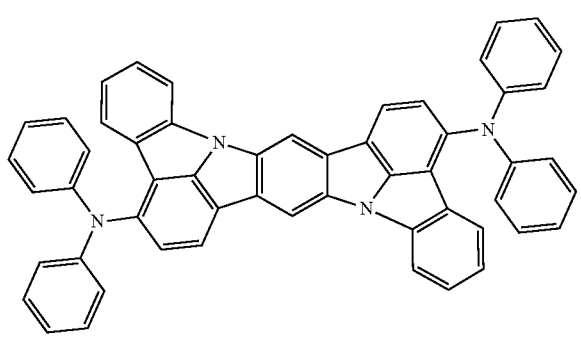
BD-7
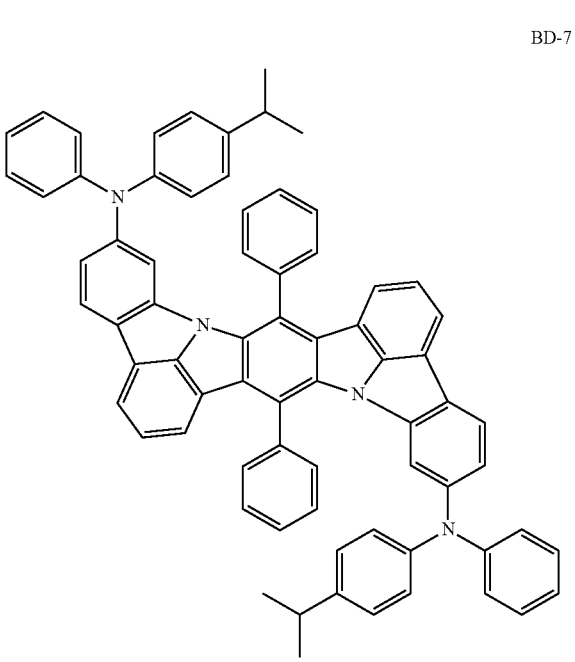
BD-4
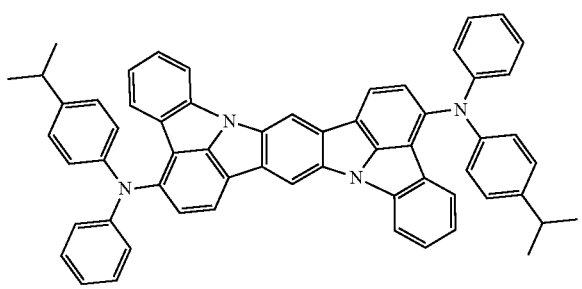

BD-8

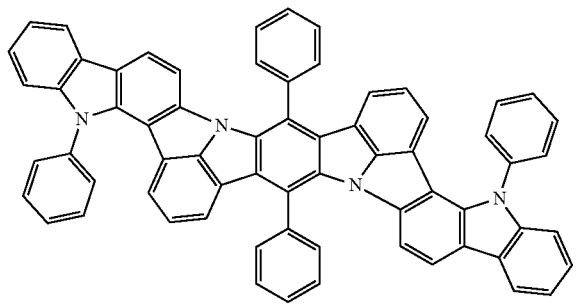

BD-9

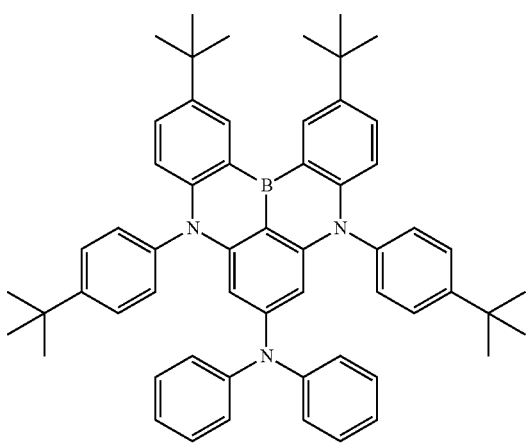

BD-10

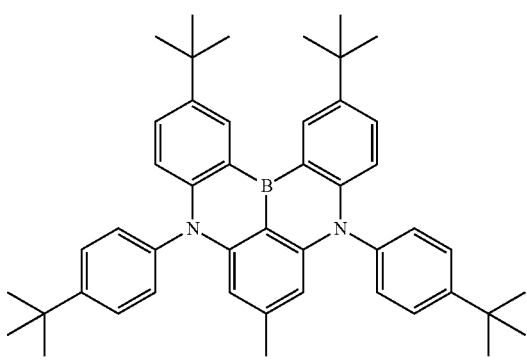

BD-11

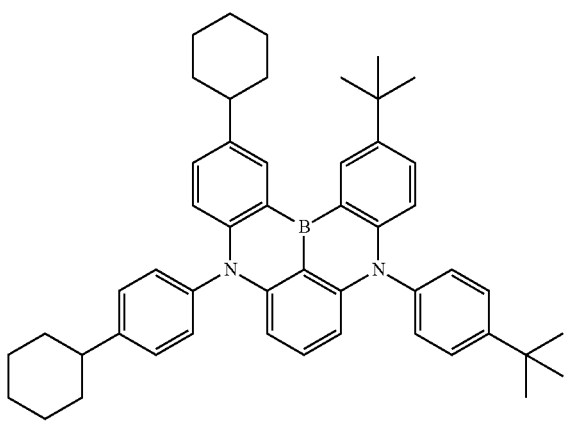

BD-12

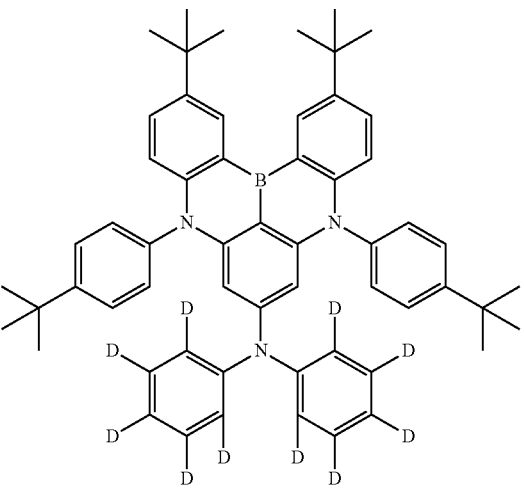

(Evaluation of Organic EL Device)

A voltage was applied to the resulting organic EL device such that the current density became 50 mA/cm$^2$, and the time taken until the luminance became 95% of the initial luminance (lifetime, LT95) were measured. The results are shown in Table 1.

Further, the CIE1931 chromaticity coordinates (CIEx and CIEy) of the resulting organic EL device at the time when a voltage was applied thereto such that the current density became 10 mA/cm$^2$, were determined from a spectral radiance spectrum measured by means of a spectral radiance meter CS-1000 (manufactured by Konica Minolta, Inc.). The results are shown in Table 1.

Comparative Example 1

The organic EL device was fabricated in the same manner as in Example 1 except that the compound indicated in the following table was used as the host material, and evaluated. The results are shown in Table 1.

TABLE 1

| | Emitting layer | | | Chromaticity | |
|---|---|---|---|---|---|
| | Host material | Dopant material | LT95(h) | CIEx | CIEy |
| Example 1 | BH-1 | BD-1 | 98 | 0.139 | 0.091 |
| Comparative Example 1 | BH-1-a | BD-1 | 60 | 0.139 | 0.091 |

Example 2 and Comparative Example 2

The organic EL device was fabricated in the same manner as in Example 1 except that the compound indicated in Table 2 was used as materials for the emitting layer, and evaluated. The results are shown in Table 2.

TABLE 2

| | Emitting layer | | | | |
|---|---|---|---|---|---|
| | Host material | Dopant material | LT95(h) | Chromaticity CIEx | CIEy |
| Example 2 | BH-1 | BD-2 | 33 | 0.137 | 0.068 |
| Comparative Example 2 | BH-1-a | BD-2 | 20 | 0.137 | 0.068 |

Example 3 and Comparative Example 3

The organic EL device was fabricated in the same manner as in Example 1 except that the compound indicated in Table 3 was used as materials for the emitting layer, and evaluated. The results are shown in Table 3.

TABLE 3

| | Emitting layer | | | | |
|---|---|---|---|---|---|
| | Host material | Dopant material | LT95(h) | Chromaticity CIEx | CIEy |
| Example 3 | BH-2 | BD-1 | 65 | 0.139 | 0.090 |
| Comparative Example 3 | BH-2-a | BD-1 | 40 | 0.139 | 0.090 |

Example 4 and Comparative Example 4

The organic EL device was fabricated in the same manner as in Example 1 except that the compound indicated in Table 4 was used as materials for the emitting layer, and evaluated. The results are shown in Table 4.

TABLE 4

| | Emitting layer | | | | |
|---|---|---|---|---|---|
| | Host material | Dopant material | LT95(h) | Chromaticity CIEx | CIEy |
| Example 4 | BH-2 | BD-2 | 23 | 0.137 | 0.067 |
| Comparative Example 4 | BH-2-a | BD-2 | 13 | 0.137 | 0.067 |

Example 5 and Comparative Example 5

The organic EL device was fabricated in the same manner as in Example 1 except that the compound indicated in Table 5 was used as materials for the emitting layer, and evaluated. The results are shown in Table 5.

TABLE 5

| | Emitting layer | | | | |
|---|---|---|---|---|---|
| | Host material | Dopant material | LT95(h) | Chromaticity CIEx | CIEy |
| Example 5 | BH-3 | BD-1 | 110 | 0.139 | 0.091 |
| Comparative Example 5 | BH-3-a | BD-1 | 69 | 0.139 | 0.091 |

Example 6 and Comparative Example 6

The organic EL device was fabricated in the same manner as in Example 1 except that the compound indicated in Table 6 was used as materials for the emitting layer, and evaluated. The results are shown in Table 6.

TABLE 6

| | Emitting layer | | | | |
|---|---|---|---|---|---|
| | Host material | Dopant material | LT95(h) | Chromaticity CIEx | CIEy |
| Example 6 | BH-3 | BD-2 | 40 | 0.137 | 0.068 |
| Comparative Example 6 | BH-3-a | BD-2 | 25 | 0.137 | 0.068 |

Example 7 and Comparative Example 7

The organic EL device was fabricated in the same manner as in Example 1 except that the compound indicated in Table 7 was used as materials for the emitting layer, and evaluated. The results are shown in Table 7.

TABLE 7

| | Emitting layer | | | | |
|---|---|---|---|---|---|
| | Host material | Dopant material | LT95(h) | Chromaticity CIEx | CIEy |
| Example 7 | BH-4 | BD-1 | 60 | 0.139 | 0.090 |
| Comparative Example 7 | BH-4-a | BD-1 | 35 | 0.139 | 0.090 |

Example 8 and Comparative Example 8

The organic EL device was fabricated in the same manner as in Example 1 except that the compound indicated in Table 8 was used as materials for the emitting layer, and evaluated. The results are shown in Table 8.

TABLE 8

| | Emitting layer | | | | |
|---|---|---|---|---|---|
| | Host material | Dopant material | LT95(h) | Chromaticity CIEx | CIEy |
| Example 8 | BH-4 | BD-2 | 23 | 0.137 | 0.067 |
| Comparative Example 8 | BH-4-a | BD-2 | 13 | 0.137 | 0.067 |

Example 11 and Comparative Example 11

The organic EL device was fabricated in the same manner as in Example 1 except that the compound indicated in the following table was used as materials for the emitting layer (host material and dopant material), and evaluated. The results are shown in Table 9.

TABLE 9

| | Emitting layer | | | | |
|---|---|---|---|---|---|
| | Host material | Dopant material | LT95(h) | Chromaticity CIEx | CIEy |
| Example 11 | BH-1 | BD-3 | 117 | 0.140 | 0.080 |
| Comparative Example 11 | BH-1-a | BD-3 | 73 | 0.140 | 0.080 |

Example 12 and Comparative Example 12

The organic EL device was fabricated in the same manner as in Example 1 except that the compound indicated in the following table was used as materials for the emitting layer (host material and dopant material), and evaluated. The results are shown in Table 10.

TABLE 10

| | Emitting layer | | | Chromaticity | |
|---|---|---|---|---|---|
| | Host material | Dopant material | LT95(h) | CIEx | CIEy |
| Example 12 | BH-2 | BD-3 | 74 | 0.140 | 0.080 |
| Comparative Example 12 | BH-2-a | BD-3 | 46 | 0.140 | 0.080 |

Example 13 and Comparative Example 13

The organic EL device was fabricated in the same manner as in Example 1 except that the compound indicated in the following table was used as materials for the emitting layer (host material and dopant material), and evaluated. The results are shown in Table 11.

TABLE 11

| | Emitting layer | | | Chromaticity | |
|---|---|---|---|---|---|
| | Host material | Dopant material | LT95(h) | CIEx | CIEy |
| Example 13 | BH-3 | BD-3 | 130 | 0.140 | 0.080 |
| Comparative Example 13 | BH-3-a | BD-3 | 82 | 0.140 | 0.081 |

Example 14 and Comparative Example 14

The organic EL device was fabricated in the same manner as in Example 1 except that the compound indicated in the following table was used as materials for the emitting layer (host material and dopant material), and evaluated. The results are shown in Table 12.

TABLE 12

| | Emitting layer | | | Chromaticity | |
|---|---|---|---|---|---|
| | Host material | Dopant material | LT95(h) | CIEx | CIEy |
| Example 14 | BH-4 | BD-3 | 74 | 0.140 | 0.080 |
| Comparative Example 14 | BH-4-a | BD-3 | 42 | 0.140 | 0.080 |

Example 15 and Comparative Example 15

The organic EL device was fabricated in the same manner as in Example 1 except that the compound indicated in the following table was used as materials for the emitting layer (host material and dopant material), and evaluated. The results are shown in Table 13.

TABLE 13

| | Emitting layer | | | Chromaticity | |
|---|---|---|---|---|---|
| | Host material | Dopant material | LT95(h) | CIEx | CIEy |
| Example 15 | BH-5 | BD-3 | 68 | 0.140 | 0.080 |
| Comparative Example 15 | BH-5-a | BD-3 | 49 | 0.140 | 0.080 |

Example 16 and Comparative Example 16

The organic EL device was fabricated in the same manner as in Example 1 except that the compound indicated in the following table was used as materials for the emitting layer (host material and dopant material), and evaluated. The results are shown in Table 14.

TABLE 14

| | Emitting layer | | | Chromaticity | |
|---|---|---|---|---|---|
| | Host material | Dopant material | LT95(h) | CIEx | CIEy |
| Example 16 | BH-6 | BD-3 | 141 | 0.140 | 0.080 |
| Comparative Example 16 | BH-6-a | BD-3 | 90 | 0.140 | 0.080 |

Example 17 and Comparative Example 17

The organic EL device was fabricated in the same manner as in Example 1 except that the compound indicated in the following table was used as materials for the emitting layer (host material and dopant material), and evaluated. The results are shown in Table 15.

TABLE 15

| | Emitting layer | | | Chromaticity | |
|---|---|---|---|---|---|
| | Host material | Dopant material | LT95(h) | CIEx | CIEy |
| Example 17 | BH-7 | BD-3 | 127 | 0.140 | 0.080 |
| Comparative Example 17 | BH-7-a | BD-3 | 68 | 0.140 | 0.080 |

Example 18 and Comparative Example 18

The organic EL device was fabricated in the same manner as in Example 1 except that the compound indicated in the following table was used as materials for the emitting layer (host material and dopant material), and evaluated. The results are shown in Table 16.

TABLE 16

| | Emitting layer | | | Chromaticity | |
|---|---|---|---|---|---|
| | Host material | Dopant material | LT95(h) | CIEx | CIEy |
| Example 18 | BH-8 | BD-3 | 126 | 0.140 | 0.080 |
| Comparative Example 18 | BH-8-a | BD-3 | 73 | 0.140 | 0.080 |

Example 19 and Comparative Example 19

The organic EL device was fabricated in the same manner as in Example 1 except that the compound indicated in the following table was used as materials for the emitting layer (host material and dopant material), and evaluated. The results are shown in Table 17.

TABLE 17

| | Emitting layer | | | | |
|---|---|---|---|---|---|
| | Host material | Dopant material | LT95(h) | Chromaticity CIEx | CIEy |
| Example 19 | BH-9 | BD-3 | 128 | 0.140 | 0.080 |
| Comparative Example 19 | BH-9-a | BD-3 | 76 | 0.140 | 0.080 |

Example 21 and Comparative Example 21

The organic EL device was fabricated in the same manner as in Example 1 except that the compound indicated in the following table was used as materials for the emitting layer (host material and dopant material), and evaluated. The results are shown in Table 18.

TABLE 18

| | Emitting layer | | | | |
|---|---|---|---|---|---|
| | Host material | Dopant material | LT95(h) | Chromaticity CIEx | CIEy |
| Example 21 | BH-1 | BD-4 | 137 | 0.135 | 0.098 |
| Comparative Example 21 | BH-1-a | BD-4 | 86 | 0.135 | 0.098 |

Example 22 and Comparative Example 22

The organic EL device was fabricated in the same manner as in Example 1 except that the compound indicated in the following table was used as materials for the emitting layer (host material and dopant material), and evaluated. The results are shown in Table 19.

TABLE 19

| | Emitting layer | | | | |
|---|---|---|---|---|---|
| | Host material | Dopant material | LT95(h) | Chromaticity CIEx | CIEy |
| Example 22 | BH-2 | BD-4 | 94 | 0.135 | 0.098 |
| Comparative Example 22 | BH-2-a | BD-4 | 58 | 0.135 | 0.098 |

Example 23 and Comparative Example 23

The organic EL device was fabricated in the same manner as in Example 1 except that the compound indicated in the following table was used as materials for the emitting layer (host material and dopant material), and evaluated. The results are shown in Table 20.

TABLE 20

| | Emitting layer | | | | |
|---|---|---|---|---|---|
| | Host material | Dopant material | LT95(h) | Chromaticity CIEx | CIEy |
| Example 23 | BH-3 | BD-4 | 152 | 0.135 | 0.098 |
| Comparative Example 23 | BH-3-a | BD-4 | 100 | 0.135 | 0.098 |

Example 24 and Comparative Example 24

The organic EL device was fabricated in the same manner as in Example 1 except that the compound indicated in the following table was used as materials for the emitting layer (host material and dopant material), and evaluated. The results are shown in Table 21.

TABLE 21

| | Emitting layer | | | | |
|---|---|---|---|---|---|
| | Host material | Dopant material | LT95(h) | Chromaticity CIEx | CIEy |
| Example 24 | BH-4 | BD-4 | 82 | 0.135 | 0.098 |
| Comparative Example 24 | BH-4-a | BD-4 | 53 | 0.135 | 0.098 |

Example 25 and Comparative Example 25

The organic EL device was fabricated in the same manner as in Example 1 except that the compound indicated in the following table was used as materials for the emitting layer (host material and dopant material), and evaluated. The results are shown in Table 22.

TABLE 22

| | Emitting layer | | | | |
|---|---|---|---|---|---|
| | Host material | Dopant material | LT95(h) | Chromaticity CIEx | CIEy |
| Example 25 | BH-5 | BD-4 | 77 | 0.135 | 0.098 |
| Comparative Example 25 | BH-5-a | BD-4 | 57 | 0.135 | 0.098 |

Example 26 and Comparative Example 26

The organic EL device was fabricated in the same manner as in Example 1 except that the compound indicated in the following table was used as materials for the emitting layer (host material and dopant material), and evaluated. The results are shown in Table 23.

TABLE 23

| | Emitting layer | | | | |
|---|---|---|---|---|---|
| | Host material | Dopant material | LT95(h) | Chromaticity CIEx | CIEy |
| Example 26 | BH-6 | BD-4 | 172 | 0.135 | 0.098 |
| Comparative Example 26 | BH-6-a | BD-4 | 100 | 0.135 | 0.098 |

Example 27 and Comparative Example 27

The organic EL device was fabricated in the same manner as in Example 1 except that the compound indicated in the following table was used as materials for the emitting layer (host material and dopant material), and evaluated. The results are shown in Table 24.

TABLE 24

| | Emitting layer | | | | |
|---|---|---|---|---|---|
| | Host material | Dopant material | LT95(h) | Chromaticity CIEx | CIEy |
| Example 27 | BH-7 | BD-4 | 142 | 0.135 | 0.099 |
| Comparative Example 27 | BH-7-a | BD-4 | 84 | 0.135 | 0.098 |

Example 28 and Comparative Example 28

The organic EL device was fabricated in the same manner as in Example 1 except that the compound indicated in the following table was used as materials for the emitting layer (host material and dopant material), and evaluated. The results are shown in Table 25.

TABLE 25

| | Emitting layer | | | | |
|---|---|---|---|---|---|
| | Host material | Dopant material | LT95(h) | Chromaticity CIEx | CIEy |
| Example 28 | BH-8 | BD-4 | 147 | 0.135 | 0.098 |
| Comparative Example 28 | BH-8-a | BD-4 | 85 | 0.135 | 0.098 |

Example 29 and Comparative Example 29

The organic EL device was fabricated in the same manner as in Example 1 except that the compound indicated in the following table was used as materials for the emitting layer (host material and dopant material), and evaluated. The results are shown in Table 26.

TABLE 26

| | Emitting layer | | | | |
|---|---|---|---|---|---|
| | Host material | Dopant material | LT95(h) | Chromaticity CIEx | CIEy |
| Example 29 | BH-9 | BD-4 | 150 | 0.135 | 0.098 |
| Comparative Example 29 | BH-9-a | BD-4 | 90 | 0.135 | 0.098 |

Example 31 and Comparative Example 31

The organic EL device was fabricated in the same manner as in Example 1 except that the compound indicated in the following table was used as materials for the emitting layer (host material and dopant material), and evaluated. The results are shown in Table 27.

TABLE 27

| | Emitting layer | | | | |
|---|---|---|---|---|---|
| | Host material | Dopant material | LT95(h) | Chromaticity CIEx | CIEy |
| Example 31 | BH-1 | BD-5 | 142 | 0.135 | 0.086 |
| Comparative Example 31 | BH-1-a | BD-5 | 86 | 0.135 | 0.086 |

Example 32 and Comparative Example 32

The organic EL device was fabricated in the same manner as in Example 1 except that the compound indicated in the following table was used as materials for the emitting layer (host material and dopant material), and evaluated. The results are shown in Table 28.

TABLE 28

| | Emitting layer | | | | |
|---|---|---|---|---|---|
| | Host material | Dopant material | LT95(h) | Chromaticity CIEx | CIEy |
| Example 32 | BH-2 | BD-5 | 92 | 0.135 | 0.086 |
| Comparative Example 32 | BH-2-a | BD-5 | 59 | 0.135 | 0.086 |

Example 33 and Comparative Example 33

The organic EL device was fabricated in the same manner as in Example 1 except that the compound indicated in the following table was used as materials for the emitting layer (host material and dopant material), and evaluated. The results are shown in Table 29.

TABLE 29

| | Emitting layer | | | | |
|---|---|---|---|---|---|
| | Host material | Dopant material | LT95(h) | Chromaticity CIEx | CIEy |
| Example 33 | BH-3 | BD-5 | 163 | 0.135 | 0.086 |
| Comparative Example 33 | BH-3-a | BD-5 | 99 | 0.135 | 0.086 |

Example 34 and Comparative Example 34

The organic EL device was fabricated in the same manner as in Example 1 except that the compound indicated in the following table was used as materials for the emitting layer (host material and dopant material), and evaluated. The results are shown in Table 30.

TABLE 30

| | Emitting layer | | | | |
|---|---|---|---|---|---|
| | Host material | Dopant material | LT95(h) | Chromaticity CIEx | CIEy |
| Example 34 | BH-4 | BD-5 | 83 | 0.135 | 0.086 |
| Comparative Example 34 | BH-4-a | BD-5 | 51 | 0.135 | 0.086 |

Example 35 and Comparative Example 35

The organic EL device was fabricated in the same manner as in Example 1 except that the compound indicated in the following table was used as materials for the emitting layer (host material and dopant material), and evaluated. The results are shown in Table 31.

TABLE 31

| | Emitting layer | | | | |
|---|---|---|---|---|---|
| | Host material | Dopant material | LT95(h) | Chromaticity CIEx | CIEy |
| Example 35 | BH-5 | BD-5 | 81 | 0.135 | 0.086 |
| Comparative Example 35 | BH-5-a | BD-5 | 56 | 0.135 | 0.086 | i

Example 36 and Comparative Example 36

The organic EL device was fabricated in the same manner as in Example 1 except that the compound indicated in the following table was used as materials for the emitting layer (host material and dopant material), and evaluated. The results are shown in Table 32.

TABLE 32

| | Emitting layer | | | | |
|---|---|---|---|---|---|
| | Host material | Dopant material | LT95(h) | Chromaticity CIEx | CIEy |
| Example 36 | BH-6 | BD-5 | 173 | 0.135 | 0.086 |
| Comparative Example 36 | BH-6-a | BD-5 | 97 | 0.135 | 0.086 |

Example 37 and Comparative Example 37

The organic EL device was fabricated in the same manner as in Example 1 except that the compound indicated in the following table was used as materials for the emitting layer (host material and dopant material), and evaluated. The results are shown in Table 33.

TABLE 33

| | Emitting layer | | | | |
|---|---|---|---|---|---|
| | Host material | Dopant material | LT95(h) | Chromaticity CIEx | CIEy |
| Example 37 | BH-7 | BD-5 | 142 | 0.135 | 0.085 |
| Comparative Example 37 | BH-7-a | BD-5 | 84 | 0.135 | 0.086 |

Example 38 and Comparative Example 38

The organic EL device was fabricated in the same manner as in Example 1 except that the compound indicated in the following table was used as materials for the emitting layer (host material and dopant material), and evaluated. The results are shown in Table 34.

TABLE 34

| | Emitting layer | | | | |
|---|---|---|---|---|---|
| | Host material | Dopant material | LT95(h) | Chromaticity CIEx | CIEy |
| Example 38 | BH-8 | BD-5 | 149 | 0.135 | 0.086 |
| Comparative Example 38 | BH-8-a | BD-5 | 94 | 0.135 | 0.086 |

Example 39 and Comparative Example 39

The organic EL device was fabricated in the same manner as in Example 1 except that the compound indicated in the following table was used as materials for the emitting layer (host material and dopant material), and evaluated. The results are shown in Table 35.

TABLE 35

| | Emitting layer | | | | |
|---|---|---|---|---|---|
| | Host material | Dopant material | LT95(h) | Chromaticity CIEx | CIEy |
| Example 39 | BH-9 | BD-5 | 152 | 0.135 | 0.086 |
| Comparative Example 39 | BH-9-a | BD-5 | 90 | 0.135 | 0.086 |

Example 41 and Comparative Example 41

The organic EL device was fabricated in the same manner as in Example 1 except that the compound indicated in the following table was used as materials for the emitting layer (host material and dopant material), and evaluated. The results are shown in Table 36.

TABLE 36

| | Emitting layer | | | | |
|---|---|---|---|---|---|
| | Host material | Dopant material | LT95(h) | Chromaticity CIEx | CIEy |
| Example 41 | BH-1 | BD-6 | 170 | 0.135 | 0.080 |
| Comparative Example 41 | BH-1-a | BD-6 | 101 | 0.135 | 0.080 |

Example 42 and Comparative Example 42

The organic EL device was fabricated in the same manner as in Example 1 except that the compound indicated in the following table was used as materials for the emitting layer (host material and dopant material), and evaluated. The results are shown in Table 37.

TABLE 37

| | Emitting layer | | | | |
|---|---|---|---|---|---|
| | Host material | Dopant material | LT95(h) | Chromaticity CIEx | CIEy |
| Example 42 | BH-2 | BD-6 | 121 | 0.135 | 0.080 |
| Comparative Example 42 | BH-2-a | BD-6 | 70 | 0.135 | 0.080 |

Example 43 and Comparative Example 43

The organic EL device was fabricated in the same manner as in Example 1 except that the compound indicated in the following table was used as materials for the emitting layer (host material and dopant material), and evaluated. The results are shown in Table 38.

TABLE 38

| | Emitting layer | | | | |
|---|---|---|---|---|---|
| | Host material | Dopant material | LT95(h) | Chromaticity CIEx | CIEy |
| Example 43 | BH-3 | BD-6 | 205 | 0.135 | 0.080 |
| Comparative Example 43 | BH-3-a | BD-6 | 123 | 0.135 | 0.080 |

Example 44 and Comparative Example 44

The organic EL device was fabricated in the same manner as in Example 1 except that the compound indicated in the following table was used as materials for the emitting layer (host material and dopant material), and evaluated. The results are shown in Table 39.

TABLE 39

| | Emitting layer | | | | |
|---|---|---|---|---|---|
| | Host material | Dopant material | LT95(h) | Chromaticity CIEx | CIEy |
| Example 44 | BH-4 | BD-6 | 108 | 0.135 | 0.080 |
| Comparative Example 44 | BH-4-a | BD-6 | 62 | 0.135 | 0.080 |

Example 45 and Comparative Example 45

The organic EL device was fabricated in the same manner as in Example 1 except that the compound indicated in the following table was used as materials for the emitting layer (host material and dopant material), and evaluated. The results are shown in Table 40.

TABLE 40

| | Emitting layer | | | | |
|---|---|---|---|---|---|
| | Host material | Dopant material | LT95(h) | Chromaticity CIEx | CIEy |
| Example 45 | BH-5 | BD-6 | 99 | 0.135 | 0.080 |
| Comparative Example 45 | BH-5-a | BD-6 | 71 | 0.135 | 0.080 |

Example 46 and Comparative Example 46

The organic EL device was fabricated in the same manner as in Example 1 except that the compound indicated in the following table was used as materials for the emitting layer (host material and dopant material), and evaluated. The results are shown in Table 41.

TABLE 41

| | Emitting layer | | | | |
|---|---|---|---|---|---|
| | Host material | Dopant material | LT95(h) | Chromaticity CIEx | CIEy |
| Example 46 | BH-6 | BD-6 | 214 | 0.135 | 0.081 |
| Comparative Example 46 | BH-6-a | BD-6 | 125 | 0.135 | 0.080 |

Example 47 and Comparative Example 47

The organic EL device was fabricated in the same manner as in Example 1 except that the compound indicated in the following table was used as materials for the emitting layer (host material and dopant material), and evaluated. The results are shown in Table 42.

TABLE 42

| | Emitting layer | | | | |
|---|---|---|---|---|---|
| | Host material | Dopant material | LT95(h) | Chromaticity CIEx | CIEy |
| Example 47 | BH-7 | BD-6 | 175 | 0.135 | 0.080 |
| Comparative Example 47 | BH-7-a | BD-6 | 106 | 0.135 | 0.080 |

Example 48 and Comparative Example 48

The organic EL device was fabricated in the same manner as in Example 1 except that the compound indicated in the following table was used as materials for the emitting layer (host material and dopant material), and evaluated. The results are shown in Table 43.

TABLE 43

| | Emitting layer | | | | |
|---|---|---|---|---|---|
| | Host material | Dopant material | LT95(h) | Chromaticity CIEx | CIEy |
| Example 48 | BH-8 | BD-6 | 183 | 0.135 | 0.081 |
| Comparative Example 48 | BH-8-a | BD-6 | 111 | 0.135 | 0.080 |

Example 49 and Comparative Example 49

The organic EL device was fabricated in the same manner as in Example 1 except that the compound indicated in the following table was used as materials for the emitting layer (host material and dopant material), and evaluated. The results are shown in Table 44.

TABLE 44

| | Emitting layer | | | | |
|---|---|---|---|---|---|
| | Host material | Dopant material | LT95(h) | Chromaticity CIEx | CIEy |
| Example 49 | BH-9 | BD-6 | 192 | 0.135 | 0.080 |
| Comparative Example 49 | BH-9-a | BD-6 | 115 | 0.135 | 0.080 |

Example 51 and Comparative Example 51

The organic EL device was fabricated in the same manner as in Example 1 except that the compound indicated in the following table was used as materials for the emitting layer (host material and dopant material), and evaluated. The results are shown in Table 45.

TABLE 45

| | Emitting layer | | | | |
|---|---|---|---|---|---|
| | Host material | Dopant material | LT95(h) | Chromaticity CIEx | CIEy |
| Example 51 | BH-1 | BD-7 | 210 | 0.136 | 0.090 |
| Comparative Example 51 | BH-1-a | BD-7 | 127 | 0.136 | 0.090 |

Example 52 and Comparative Example 52

The organic EL device was fabricated in the same manner as in Example 1 except that the compound indicated in the following table was used as materials for the emitting layer (host material and dopant material), and evaluated. The results are shown in Table 46.

TABLE 46

| | Emitting layer | | | | |
|---|---|---|---|---|---|
| | Host material | Dopant material | LT95(h) | Chromaticity CIEx | CIEy |
| Example 52 | BH-2 | BD-7 | 143 | 0.136 | 0.090 |
| Comparative Example 52 | BH-2-a | BD-7 | 80 | 0.136 | 0.090 |

Example 53 and Comparative Example 53

The organic EL device was fabricated in the same manner as in Example 1 except that the compound indicated in the following table was used as materials for the emitting layer (host material and dopant material), and evaluated. The results are shown in Table 47.

TABLE 47

| | Emitting layer | | | | |
|---|---|---|---|---|---|
| | Host material | Dopant material | LT95(h) | Chromaticity CIEx | CIEy |
| Example 53 | BH-3 | BD-7 | 236 | 0.136 | 0.090 |
| Comparative Example 53 | BH-3-a | BD-7 | 150 | 0.136 | 0.090 |

Example 54 and Comparative Example 54

The organic EL device was fabricated in the same manner as in Example 1 except that the compound indicated in the following table was used as materials for the emitting layer (host material and dopant material), and evaluated. The results are shown in Table 48.

TABLE 48

| | Emitting layer | | | | |
|---|---|---|---|---|---|
| | Host material | Dopant material | LT95(h) | Chromaticity CIEx | CIEy |
| Example 54 | BH-4 | BD-7 | 119 | 0.136 | 0.090 |
| Comparative Example 54 | BH-4-a | BD-7 | 74 | 0.136 | 0.090 |

Example 55 and Comparative Example 55

The organic EL device was fabricated in the same manner as in Example 1 except that the compound indicated in the following table was used as materials for the emitting layer (host material and dopant material), and evaluated. The results are shown in Table 49.

TABLE 49

| | Emitting layer | | | | |
|---|---|---|---|---|---|
| | Host material | Dopant material | LT95(h) | Chromaticity CIEx | CIEy |
| Example 55 | BH-5 | BD-7 | 121 | 0.136 | 0.090 |
| Comparative Example 55 | BH-5-a | BD-7 | 85 | 0.136 | 0.090 |

Example 56 and Comparative Example 56

The organic EL device was fabricated in the same manner as in Example 1 except that the compound indicated in the following table was used as materials for the emitting layer (host material and dopant material), and evaluated. The results are shown in Table 50.

TABLE 50

| | Emitting layer | | | | |
|---|---|---|---|---|---|
| | Host material | Dopant material | LT95(h) | Chromaticity CIEx | CIEy |
| Example 56 | BH-6 | BD-7 | 251 | 0.136 | 0.090 |
| Comparative Example 56 | BH-6-a | BD-7 | 137 | 0.136 | 0.090 |

Example 57 and Comparative Example 57

The organic EL device was fabricated in the same manner as in Example 1 except that the compound indicated in the following table was used as materials for the emitting layer (host material and dopant material), and evaluated. The results are shown in Table 51.

TABLE 51

| | Emitting layer | | | | |
|---|---|---|---|---|---|
| | Host material | Dopant material | LT95(h) | Chromaticity CIEx | CIEy |
| Example 57 | BH-7 | BD-7 | 210 | 0.136 | 0.090 |
| Comparative Example 57 | BH-7-a | BD-7 | 130 | 0.136 | 0.091 |

Example 58 and Comparative Example 58

The organic EL device was fabricated in the same manner as in Example 1 except that the compound indicated in the following table was used as materials for the emitting layer (host material and dopant material), and evaluated. The results are shown in Table 52.

TABLE 52

| | Emitting layer | | | Chromaticity | |
|---|---|---|---|---|---|
| | Host material | Dopant material | LT95(h) | CIEx | CIEy |
| Example 58 | BH-8 | BD-7 | 221 | 0.136 | 0.090 |
| Comparative Example 58 | BH-8-a | BD-7 | 135 | 0.136 | 0.090 |

Example 59 and Comparative Example 59

The organic EL device was fabricated in the same manner as in Example 1 except that the compound indicated in the following table was used as materials for the emitting layer (host material and dopant material), and evaluated. The results are shown in Table 53.

TABLE 53

| | Emitting layer | | | Chromaticity | |
|---|---|---|---|---|---|
| | Host material | Dopant material | LT95(h) | CIEx | CIEy |
| Example 59 | BH-9 | BD-7 | 225 | 0.136 | 0.090 |
| Comparative Example 59 | BH-9-a | BD-7 | 140 | 0.136 | 0.090 |

Example 61 and Comparative Example 61

The organic EL device was fabricated in the same manner as in Example 1 except that the compound indicated in the following table was used as materials for the emitting layer (host material and dopant material), and evaluated. The results are shown in Table 54.

TABLE 54

| | Emitting layer | | | Chromaticity | |
|---|---|---|---|---|---|
| | Host material | Dopant material | LT95(h) | CIEx | CIEy |
| Example 61 | BH-1 | BD-8 | 107 | 0.144 | 0.060 |
| Comparative Example 61 | BH-1-a | BD-8 | 66 | 0.144 | 0.061 |

Example 62 and Comparative Example 62

The organic EL device was fabricated in the same manner as in Example 1 except that the compound indicated in the following table was used as materials for the emitting layer (host material and dopant material), and evaluated. The results are shown in Table 55.

TABLE 55

| | Emitting layer | | | Chromaticity | |
|---|---|---|---|---|---|
| | Host material | Dopant material | LT95(h) | CIEx | CIEy |
| Example 62 | BH-2 | BD-8 | 68 | 0.144 | 0.061 |
| Comparative Example 62 | BH-2-a | BD-8 | 46 | 0.144 | 0.061 |

Example 63 and Comparative Example 63

The organic EL device was fabricated in the same manner as in Example 1 except that the compound indicated in the following table was used as materials for the emitting layer (host material and dopant material), and evaluated. The results are shown in Table 56.

TABLE 56

| | Emitting layer | | | Chromaticity | |
|---|---|---|---|---|---|
| | Host material | Dopant material | LT95(h) | CIEx | CIEy |
| Example 63 | BH-3 | BD-8 | 120 | 0.144 | 0.061 |
| Comparative Example 63 | BH-3-a | BD-8 | 76 | 0.144 | 0.061 |

Example 64 and Comparative Example 64

The organic EL device was fabricated in the same manner as in Example 1 except that the compound indicated in the following table was used as materials for the emitting layer (host material and dopant material), and evaluated. The results are shown in Table 57.

TABLE 57

| | Emitting layer | | | Chromaticity | |
|---|---|---|---|---|---|
| | Host material | Dopant material | LT95(h) | CIEx | CIEy |
| Example 64 | BH-4 | BD-8 | 69 | 0.144 | 0.061 |
| Comparative Example 64 | BH-4-a | BD-8 | 40 | 0.144 | 0.061 |

Example 65 and Comparative Example 65

The organic EL device was fabricated in the same manner as in Example 1 except that the compound indicated in the following table was used as materials for the emitting layer (host material and dopant material), and evaluated. The results are shown in Table 58.

TABLE 58

| | Emitting layer | | | Chromaticity | |
|---|---|---|---|---|---|
| | Host material | Dopant material | LT95(h) | CIEx | CIEy |
| Example 65 | BH-5 | BD-8 | 64 | 0.144 | 0.061 |
| Comparative Example 65 | BH-5-a | BD-8 | 49 | 0.144 | 0.061 |

Example 66 and Comparative Example 66

The organic EL device was fabricated in the same manner as in Example 1 except that the compound indicated in the following table was used as materials for the emitting layer (host material and dopant material), and evaluated. The results are shown in Table 59.

TABLE 59

| | Emitting layer | | | | |
|---|---|---|---|---|---|
| | Host material | Dopant material | LT95(h) | Chromaticity CIEx | CIEy |
| Example 66 | BH-6 | BD-8 | 137 | 0.144 | 0.061 |
| Comparative Example 66 | BH-6-a | BD-8 | 83 | 0.144 | 0.061 |

Example 67 and Comparative Example 67

The organic EL device was fabricated in the same manner as in Example 1 except that the compound indicated in the following table was used as materials for the emitting layer (host material and dopant material), and evaluated. The results are shown in Table 60.

TABLE 60

| | Emitting layer | | | | |
|---|---|---|---|---|---|
| | Host material | Dopant material | LT95(h) | Chromaticity CIEx | CIEy |
| Example 67 | BH-7 | BD-8 | 118 | 0.144 | 0.061 |
| Comparative Example 67 | BH-7-a | BD-8 | 66 | 0.144 | 0.061 |

Example 68 and Comparative Example 68

The organic EL device was fabricated in the same manner as in Example 1 except that the compound indicated in the following table was used as materials for the emitting layer (host material and dopant material), and evaluated. The results are shown in Table 61.

TABLE 61

| | Emitting layer | | | | |
|---|---|---|---|---|---|
| | Host material | Dopant material | LT95(h) | Chromaticity CIEx | CIEy |
| Example 68 | BH-8 | BD-8 | 119 | 0.144 | 0.061 |
| Comparative Example 68 | BH-8-a | BD-8 | 70 | 0.144 | 0.061 |

Example 69 and Comparative Example 69

The organic EL device was fabricated in the same manner as in Example 1 except that the compound indicated in the following table was used as materials for the emitting layer (host material and dopant material), and evaluated. The results are shown in Table 62.

TABLE 62

| | Emitting layer | | | | |
|---|---|---|---|---|---|
| | Host material | Dopant material | LT95(h) | Chromaticity CIEx | CIEy |
| Example 69 | BH-9 | BD-8 | 120 | 0.144 | 0.061 |
| Comparative Example 69 | BH-9-a | BD-8 | 75 | 0.144 | 0.061 |

Example 70 and Comparative Example 70

The organic EL device was fabricated in the same manner as in Example 1 except that the compound indicated in the following table was used as materials for the emitting layer (host material and dopant material), and evaluated. The results are shown in Table 63.

TABLE 63

| | Emitting layer | | | | |
|---|---|---|---|---|---|
| | Hosting material | Dopant material | LT95(h) | Chromaticity CIEx | CIEy |
| Example 70 | BH-1 | BD-9 | 96 | 0.141 | 0.056 |
| Comparative Example 70 | BH-1-a | BD-9 | 72 | 0.141 | 0.056 |

Example 71 and Comparative Example 71

The organic EL device was fabricated in the same manner as in Example 1 except that the compound indicated in the following table was used as materials for the emitting layer (host material and dopant material), and evaluated. The results are shown in Table 64.

TABLE 64

| | Emitting layer | | | | |
|---|---|---|---|---|---|
| | Hosting material | Dopant material | LT95(h) | Chromaticity CIEx | CIEy |
| Example 71 | BH-2 | BD-9 | 78 | 0.141 | 0.056 |
| Comparative Example 71 | BH-2-a | BD-9 | 50 | 0.141 | 0.056 |

Example 72 and Comparative Example 72

The organic EL device was fabricated in the same manner as in Example 1 except that the compound indicated in the following table was used as materials for the emitting layer (host material and dopant material), and evaluated. The results are shown in Table 65.

TABLE 65

| | Emitting layer | | | | |
|---|---|---|---|---|---|
| | Hosting material | Dopant material | LT95(h) | Chromaticity CIEx | CIEy |
| Example 72 | BH-3 | BD-9 | 112 | 0.141 | 0.056 |
| Comparative Example 72 | BH-3-a | BD-9 | 81 | 0.141 | 0.056 |

Example 73 and Comparative Example 73

The organic EL device was fabricated in the same manner as in Example 1 except that the compound indicated in the following table was used as materials for the emitting layer (host material and dopant material), and evaluated. The results are shown in Table 66.

TABLE 66

| | Emitting layer | | | | |
|---|---|---|---|---|---|
| | Hosting material | Dopant material | LT95(h) | Chromaticity CIEx | CIEy |
| Example 73 | BH-5 | BD-9 | 67 | 0.141 | 0.056 |
| Comparative Example 73 | BH-5-a | BD-9 | 51 | 0.141 | 0.056 |

Example 74 and Comparative Example 74

The organic EL device was fabricated in the same manner as in Example 1 except that the compound indicated in the following table was used as materials for the emitting layer (host material and dopant material), and evaluated. The results are shown in Table 67.

TABLE 67

| | Emitting layer | | | | |
|---|---|---|---|---|---|
| | Hosting material | Dopant material | LT95(h) | Chromaticity CIEx | CIEy |
| Example 74 | BH-6 | BD-9 | 130 | 0.141 | 0.056 |
| Comparative Example 74 | BH-6-a | BD-9 | 85 | 0.141 | 0.056 |

Example 75 and Comparative Example 75

The organic EL device was fabricated in the same manner as in Example 1 except that the compound indicated in the following table was used as materials for the emitting layer (host material and dopant material), and evaluated. The results are shown in Table 68.

TABLE 68

| | Emitting layer | | | | |
|---|---|---|---|---|---|
| | Hosting material | Dopant material | LT95(h) | Chromaticity CIEx | CIEy |
| Example 75 | BH-7 | BD-9 | 109 | 0.141 | 0.056 |
| Comparative Example 75 | BH-7-a | BD-9 | 73 | 0.141 | 0.056 |

Example 76 and Comparative Example 76

The organic EL device was fabricated in the same manner as in Example 1 except that the compound indicated in the following table was used as materials for the emitting layer (host material and dopant material), and evaluated. The results are shown in Table 69.

TABLE 69

| | Emitting layer | | | | |
|---|---|---|---|---|---|
| | Hosting material | Dopant material | LT95(h) | Chromaticity CIEx | CIEy |
| Example 76 | BH-8 | BD-9 | 113 | 0.141 | 0.057 |
| Comparative Example 76 | BH-8-a | BD-9 | 74 | 0.141 | 0.057 |

Example 77 and Comparative Example 77

The organic EL device was fabricated in the same manner as in Example 1 except that the compound indicated in the following table was used as materials for the emitting layer (host material and dopant material), and evaluated. The results are shown in Table 70.

TABLE 70

| | Emitting layer | | | | |
|---|---|---|---|---|---|
| | Hosting material | Dopant material | LT95(h) | Chromaticity CIEx | CIEy |
| Example 77 | BH-9 | BD-9 | 112 | 0.141 | 0.057 |
| Comparative Example 77 | BH-9-a | BD-9 | 79 | 0.141 | 0.057 |

Example 78 and Comparative Example 78

The organic EL device was fabricated in the same manner as in Example 1 except that the compound indicated in the following table was used as materials for the emitting layer (host material and dopant material), and evaluated. The results are shown in Table 71.

TABLE 71

| | Emitting layer | | | | |
|---|---|---|---|---|---|
| | Hosting material | Dopant material | LT95(h) | Chromaticity CIEx | CIEy |
| Example 78 | BH-10 | BD-9 | 107 | 0.141 | 0.057 |
| Comparative Example 78 | BH-10-a | BD-9 | 70 | 0.141 | 0.057 |

Example 79 and Comparative Example 79

The organic EL device was fabricated in the same manner as in Example 1 except that the compound indicated in the following table was used as materials for the emitting layer (host material and dopant material), and evaluated. The results are shown in Table 72.

TABLE 72

| | Emitting layer | | | | |
|---|---|---|---|---|---|
| | Hosting material | Dopant material | LT95(h) | Chromaticity CIEx | CIEy |
| Example 79 | BH-11 | BD-9 | 108 | 0.141 | 0.057 |
| Comparative Example 79 | BH-11-a | BD-9 | 78 | 0.141 | 0.057 |

Example 80 and Comparative Example 80

The organic EL device was fabricated in the same manner as in Example 1 except that the compound indicated in the following table was used as materials for the emitting layer (host material and dopant material), and evaluated. The results are shown in Table 73.

TABLE 73

|  | Emitting layer | | | Chromaticity | |
|---|---|---|---|---|---|
|  | Hosting material | Dopant material | LT95(h) | CIEx | CIEy |
| Example 80 | BH-12 | BD-9 | 111 | 0.141 | 0.056 |
| Comparative Example 80 | BH-12-a | BD-9 | 78 | 0.141 | 0.056 |

Example 81 and Comparative Example 81

The organic EL device was fabricated in the same manner as in Example 1 except that the compound indicated in the following table was used as materials for the emitting layer (host material and dopant material), and evaluated. The results are shown in Table 74.

TABLE 74

|  | Emitting layer | | | Chromaticity | |
|---|---|---|---|---|---|
|  | Hosting material | Dopant material | LT95(h) | CIEx | CIEy |
| Example 81 | BH-13 | BD-9 | 60 | 0.141 | 0.056 |
| Comparative Example 81 | BH-13-a | BD-9 | 40 | 0.141 | 0.056 |

Example 82 and Comparative Example 82

The organic EL device was fabricated in the same manner as in Example 1 except that the compound indicated in the following table was used as materials for the emitting layer (host material and dopant material), and evaluated. The results are shown in Table 75.

TABLE 75

|  | Emitting layer | | | Chromaticity | |
|---|---|---|---|---|---|
|  | Hosting material | Dopant material | LT95(h) | CIEx | CIEy |
| Example 82 | BH-15 | BD-9 | 67 | 0.141 | 0.056 |
| Comparative Example 82 | BH-15-a | BD-9 | 43 | 0.141 | 0.056 |

Example 83

The organic EL device was fabricated in the same manner as in Example 1 except that the compound indicated in the following table was used as materials for the emitting layer (host material and dopant material), and evaluated. The results are shown in Table 76.

TABLE 76

|  | Emitting layer | | | Chromaticity | |
|---|---|---|---|---|---|
|  | Hosting material | Dopant material | LT95(h) | CIEx | CIEy |
| Example 83 | BH-16 | BD-9 | 99 | 0.141 | 0.056 |

Example 84 and Comparative Example 84

The organic EL device was fabricated in the same manner as in Example 1 except that the compound indicated in the following table was used as materials for the emitting layer (host material and dopant material), and evaluated. The results are shown in Table 77.

TABLE 77

|  | Emitting layer | | | Chromaticity | |
|---|---|---|---|---|---|
|  | Hosting material | Dopant material | LT95(h) | CIEx | CIEy |
| Example 84 | BH-17 | BD-9 | 129 | 0.141 | 0.056 |
| Comparative Example 84 | BH-17-a | BD-9 | 88 | 0.141 | 0.056 |

Example 85 and Comparative Example 85

The organic EL device was fabricated in the same manner as in Example 1 except that the compound indicated in the following table was used as materials for the emitting layer (host material and dopant material), and evaluated. The results are shown in Table 78.

TABLE 78

|  | Emitting layer | | | Chromaticity | |
|---|---|---|---|---|---|
|  | Hosting material | Dopant material | LT95(h) | CIEx | CIEy |
| Example 85 | BH-1 | BD-10 | 172 | 0.133 | 0.078 |
| Comparative Example 85 | BH-1-a | BD-10 | 122 | 0.133 | 0.078 |

Example 86 and Comparative Example 86

The organic EL device was fabricated in the same manner as in Example 1 except that the compound indicated in the following table was used as materials for the emitting layer (host material and dopant material), and evaluated. The results are shown in Table 79.

TABLE 79

|  | Emitting layer | | | Chromaticity | |
|---|---|---|---|---|---|
|  | Hosting material | Dopant material | LT95(h) | CIEx | CIEy |
| Example 86 | BH-2 | BD-10 | 118 | 0.133 | 0.078 |
| Comparative Example 86 | BH-2-a | BD-10 | 82 | 0.133 | 0.078 |

Example 87 and Comparative Example 87

The organic EL device was fabricated in the same manner as in Example 1 except that the compound indicated in the following table was used as materials for the emitting layer (host material and dopant material), and evaluated. The results are shown in Table 80.

TABLE 80

| | Emitting layer | | | Chromaticity | |
|---|---|---|---|---|---|
| | Hosting material | Dopant material | LT95(h) | CIEx | CIEy |
| Example 87 | BH-3 | BD-10 | 199 | 0.133 | 0.078 |
| Comparative Example 87 | BH-3-a | BD-10 | 138 | 0.133 | 0.078 |

Example 88 and Comparative Example 88

The organic EL device was fabricated in the same manner as in Example 1 except that the compound indicated in the following table was used as materials for the emitting layer (host material and dopant material), and evaluated. The results are shown in Table 81.

TABLE 81

| | Emitting layer | | | Chromaticity | |
|---|---|---|---|---|---|
| | Hosting material | Dopant material | LT95(h) | CIEx | CIEy |
| Example 88 | BH-5 | BD-10 | 114 | 0.133 | 0.078 |
| Comparative Example 88 | BH-5-a | BD-10 | 80 | 0.133 | 0.078 |

Example 89 and Comparative Example 89

The organic EL device was fabricated in the same manner as in Example 1 except that the compound indicated in the following table was used as materials for the emitting layer (host material and dopant material), and evaluated. The results are shown in Table 82.

TABLE 82

| | Emitting layer | | | Chromaticity | |
|---|---|---|---|---|---|
| | Hosting material | Dopant material | LT95(h) | CIEx | CIEy |
| Example 89 | BH-6 | BD-10 | 220 | 0.133 | 0.078 |
| Comparative Example 89 | BH-6-a | BD-10 | 142 | 0.133 | 0.078 |

Example 90 and Comparative Example 90

The organic EL device was fabricated in the same manner as in Example 1 except that the compound indicated in the following table was used as materials for the emitting layer (host material and dopant material), and evaluated. The results are shown in Table 83.

TABLE 83

| | Emitting layer | | | Chromaticity | |
|---|---|---|---|---|---|
| | Hosting material | Dopant material | LT95(h) | CIEx | CIEy |
| Example 90 | BH-7 | BD-10 | 187 | 0.133 | 0.078 |
| Comparative Example 90 | BH-7-a | BD-10 | 124 | 0.133 | 0.078 |

Example 91 and Comparative Example 91

The organic EL device was fabricated in the same manner as in Example 1 except that the compound indicated in the following table was used as materials for the emitting layer (host material and dopant material), and evaluated. The results are shown in Table 84.

TABLE 84

| | Emitting layer | | | Chromaticity | |
|---|---|---|---|---|---|
| | Hosting material | Dopant material | LT95(h) | CIEx | CIEy |
| Example 91 | BH-8 | BD-10 | 189 | 0.133 | 0.079 |
| Comparative Example 91 | BH-8-a | BD-10 | 126 | 0.133 | 0.079 |

Example 92 and Comparative Example 92

The organic EL device was fabricated in the same manner as in Example 1 except that the compound indicated in the following table was used as materials for the emitting layer (host material and dopant material), and evaluated. The results are shown in Table 85.

TABLE 85

| | Emitting layer | | | Chromaticity | |
|---|---|---|---|---|---|
| | Hosting material | Dopant material | LT95(h) | CIEx | CIEy |
| Example 92 | BH-9 | BD-10 | 161 | 0.133 | 0.079 |
| Comparative Example 92 | BH-9-a | BD-10 | 131 | 0.133 | 0.079 |

Example 93 and Comparative Example 93

The organic EL device was fabricated in the same manner as in Example 1 except that the compound indicated in the following table was used as materials for the emitting layer (host material and dopant material), and evaluated. The results are shown in Table 86.

TABLE 86

| | Emitting layer | | | Chromaticity | |
|---|---|---|---|---|---|
| | Hosting material | Dopant material | LT95(h) | CIEx | CIEy |
| Example 93 | BH-10 | BD-10 | 166 | 0.133 | 0.079 |
| Comparative Example 93 | BH-10-a | BD-10 | 110 | 0.133 | 0.079 |

Example 94 and Comparative Example 94

The organic EL device was fabricated in the same manner as in Example 1 except that the compound indicated in the following table was used as materials for the emitting layer (host material and dopant material), and evaluated. The results are shown in Table 87.

TABLE 87

| | Emitting layer | | | | |
| --- | --- | --- | --- | --- | --- |
| | Hosting material | Dopant material | LT95(h) | Chromaticity | |
| | | | | CIEx | CIEy |
| Example 94 | BH-11 | BD-10 | 201 | 0.133 | 0.079 |
| Comparative Example 94 | BH-11-a | BD-10 | 131 | 0.133 | 0.079 |

Example 95 and Comparative Example 95

The organic EL device was fabricated in the same manner as in Example 1 except that the compound indicated in the following table was used as materials for the emitting layer (host material and dopant material), and evaluated. The results are shown in Table 88.

TABLE 88

| | Emitting layer | | | | |
| --- | --- | --- | --- | --- | --- |
| | Hosting material | Dopant material | LT95(h) | Chromaticity | |
| | | | | CIEx | CIEy |
| Example 95 | BH-12 | BD-10 | 198 | 0.133 | 0.078 |
| Comparative Example 95 | BH-12-a | BD-10 | 143 | 0.133 | 0.078 |

Example 96 and Comparative Example 96

The organic EL device was fabricated in the same manner as in Example 1 except that the compound indicated in the following table was used as materials for the emitting layer (host material and dopant material), and evaluated. The results are shown in Table 89.

TABLE 89

| | Emitting layer | | | | |
| --- | --- | --- | --- | --- | --- |
| | Hosting material | Dopant material | LT95(h) | Chromaticity | |
| | | | | CIEx | CIEy |
| Example 96 | BH-13 | BD-10 | 99 | 0.133 | 0.078 |
| Comparative Example 96 | BH-13-a | BD-10 | 67 | 0.133 | 0.078 |

Example 97 and Comparative Example 97

The organic EL device was fabricated in the same manner as in Example 1 except that the compound indicated in the following table was used as materials for the emitting layer (host material and dopant material), and evaluated. The results are shown in Table 90.

TABLE 90

| | Emitting layer | | | | |
| --- | --- | --- | --- | --- | --- |
| | Hosting material | Dopant material | LT95(h) | Chromaticity | |
| | | | | CIEx | CIEy |
| Example 97 | BH-15 | BD-10 | 116 | 0.133 | 0.078 |
| Comparative Example 97 | BH-15-a | BD-10 | 82 | 0.133 | 0.078 |

Example 98

The organic EL device was fabricated in the same manner as in Example 1 except that the compound indicated in the following table was used as materials for the emitting layer (host material and dopant material), and evaluated. The results are shown in Table 91.

TABLE 91

| | Emitting layer | | | | |
| --- | --- | --- | --- | --- | --- |
| | Hosting material | Dopant material | LT95(h) | Chromaticity | |
| | | | | CIEx | CIEy |
| Example 98 | BH-16 | BD-10 | 165 | 0.133 | 0.078 |

Example 99 and Comparative Example 99

The organic EL device was fabricated in the same manner as in Example 1 except that the compound indicated in the following table was used as materials for the emitting layer (host material and dopant material), and evaluated. The results are shown in Table 92.

TABLE 92

| | Emitting layer | | | | |
| --- | --- | --- | --- | --- | --- |
| | Hosting material | Dopant material | LT95(h) | Chromaticity | |
| | | | | CIEx | CIEy |
| Example 99 | BH-17 | BD-10 | 224 | 0.133 | 0.078 |
| Comparative Example 99 | BH-17-a | BD-10 | 144 | 0.133 | 0.078 |

Example 100 and Comparative Example 100

The organic EL device was fabricated in the same manner as in Example 1 except that the compound indicated in the following table was used as materials for the emitting layer (host material and dopant material), and evaluated. The results are shown in Table 93.

TABLE 93

| | Emitting layer | | LT95 | Chromaticity | |
| --- | --- | --- | --- | --- | --- |
| | Hosting material | Dopant material | (h) | CIEx | CIEy |
| Example 100 | BH-1 | BD-11 | 163 | 0.133 | 0.076 |
| Comparative Example 100 | BH-1-a | BD-11 | 315 | 0.133 | 0.076 |

Example 101 and Comparative Example 101

The organic EL device was fabricated in the same manner as in Example 1 except that the compound indicated in the following table was used as materials for the emitting layer (host material and dopant material), and evaluated. The results are shown in Table 94.

TABLE 94

| | Emitting layer | | LT95 | Chromaticity | |
|---|---|---|---|---|---|
| | Hosting material | Dopant material | (h) | CIEx | CIEy |
| Example 101 | BH-2 | BD-11 | 95 | 0.133 | 0.076 |
| Comparative Example 101 | BH-2-a | BD-11 | 77 | 0.133 | 0.076 |

Example 102 and Comparative Example 102

The organic EL device was fabricated in the same manner as in Example 1 except that the compound indicated in the following table was used as materials for the emitting layer (host material and dopant material), and evaluated. The results are shown in Table 95.

TABLE 95

| | Emitting layer | | LT95 | Chromaticity | |
|---|---|---|---|---|---|
| | Hosting material | Dopant material | (h) | CIEx | CIEy |
| Example 102 | BH-3 | BD-11 | 179 | 0.133 | 0.076 |
| Comparative Example 102 | BH-3-a | BD-11 | 135 | 0.133 | 0.076 |

Example 103 and Comparative Example 103

The organic EL device was fabricated in the same manner as in Example 1 except that the compound indicated in the following table was used as materials for the emitting layer (host material and dopant material), and evaluated. The results are shown in Table 96.

TABLE 96

| | Emitting layer | | LT95 | Chromaticity | |
|---|---|---|---|---|---|
| | Hosting material | Dopant material | (h) | CIEx | CIEy |
| Example 103 | BH-5 | BD-11 | 101 | 0.133 | 0.076 |
| Comparative Example 103 | BH-5-a | BD-11 | 77 | 0.133 | 0.076 |

Example 104 and Comparative Example 104

The organic EL device was fabricated in the same manner as in Example 1 except that the compound indicated in the following table was used as materials for the emitting layer (host material and dopant material), and evaluated. The results are shown in Table 97.

TABLE 97

| | Emitting layer | | LT95 | Chromaticity | |
|---|---|---|---|---|---|
| | Hosting material | Dopant material | (h) | CIEx | CIEy |
| Example 104 | BH-6 | BD-11 | 175 | 0.133 | 0.076 |
| Comparative Example 104 | BH-6-a | BD-11 | 133 | 0.133 | 0.076 |

Example 105 and Comparative Example 105

The organic EL device was fabricated in the same manner as in Example 1 except that the compound indicated in the following table was used as materials for the emitting layer (host material and dopant material), and evaluated. The results are shown in Table 98.

TABLE 98

| | Emitting layer | | LT95 | Chromaticity | |
|---|---|---|---|---|---|
| | Hosting material | Dopant material | (h) | CIEx | CIEy |
| Example 105 | BH-7 | BD-11 | 169 | 0.133 | 0.076 |
| Comparative Example 105 | BH-7-a | BD-11 | 117 | 0.133 | 0.076 |

Example 106 and Comparative Example 106

The organic EL device was fabricated in the same manner as in Example 1 except that the compound indicated in the following table was used as materials for the emitting layer (host material and dopant material), and evaluated. The results are shown in Table 99.

TABLE 99

| | Emitting layer | | LT95 | Chromaticity | |
|---|---|---|---|---|---|
| | Hosting material | Dopant material | (h) | CIEx | CIEy |
| Example 106 | BH-8 | BD-11 | 168 | 0.133 | 0.077 |
| Comparative Example 106 | BH-8-a | BD-11 | 125 | 0.133 | 0.077 |

Example 107 and Comparative Example 107

The organic EL device was fabricated in the same manner as in Example 1 except that the compound indicated in the following table was used as materials for the emitting layer (host material and dopant material), and evaluated. The results are shown in Table 100.

TABLE 100

| | Emitting layer | | LT95 | Chromaticity | |
|---|---|---|---|---|---|
| | Hosting material | Dopant material | (h) | CIEx | CIEy |
| Example 107 | BH-9 | BD-11 | 197 | 0.133 | 0.077 |
| Comparative Example 107 | BH-9-a | BD-11 | 127 | 0.133 | 0.077 |

Example 108 and Comparative Example 108

The organic EL device was fabricated in the same manner as in Example 1 except that the compound indicated in the following table was used as materials for the emitting layer (host material and dopant material), and evaluated. The results are shown in Table 101.

TABLE 101

| | Emitting layer | | LT95 | Chromaticity | |
|---|---|---|---|---|---|
| | Hosting material | Dopant material | (h) | CIEx | CIEy |
| Example 108 | BH-10 | BD-11 | 154 | 0.133 | 0.077 |
| Comparative Example 108 | BH-10-a | BD-11 | 105 | 0.133 | 0.077 |

Example 109 and Comparative Example 109

The organic EL device was fabricated in the same manner as in Example 1 except that the compound indicated in the following table was used as materials for the emitting layer (host material and dopant material), and evaluated. The results are shown in Table 102.

TABLE 102

| | Emitting layer | | LT95 | Chromaticity | |
|---|---|---|---|---|---|
| | Hosting material | Dopant material | (h) | CIEx | CIEy |
| Example 109 | BH-11 | BD-11 | 188 | 0.133 | 0.077 |
| Comparative Example 109 | BH-11-a | BD-11 | 127 | 0.133 | 0.077 |

Example 110 and Comparative Example 110

The organic EL device was fabricated in the same manner as in Example 1 except that the compound indicated in the following table was used as materials for the emitting layer (host material and dopant material), and evaluated. The results are shown in Table 103.

TABLE 103

| | Emitting layer | | LT95 | Chromaticity | |
|---|---|---|---|---|---|
| | Hosting material | Dopant material | (h) | CIEx | CIEy |
| Example 110 | BH-12 | BD-11 | 181 | 0.133 | 0.076 |
| Comparative Example 110 | BH-12-a | BD-11 | 125 | 0.133 | 0.076 |

Example 111 and Comparative Example 111

The organic EL device was fabricated in the same manner as in Example 1 except that the compound indicated in the following table was used as materials for the emitting layer (host material and dopant material), and evaluated. The results are shown in Table 104.

TABLE 104

| | Emitting layer | | LT95 | Chromaticity | |
|---|---|---|---|---|---|
| | Hosting material | Dopant material | (h) | CIEx | CIEy |
| Example 111 | BH-13 | BD-11 | 94 | 0.133 | 0.076 |
| Comparative Example 111 | BH-13-a | BD-11 | 62 | 0.133 | 0.076 |

Example 112 and Comparative Example 112

The organic EL device was fabricated in the same manner as in Example 1 except that the compound indicated in the following table was used as materials for the emitting layer (host material and dopant material), and evaluated. The results are shown in Table 105.

TABLE 105

| | Emitting layer | | LT95 | Chromaticity | |
|---|---|---|---|---|---|
| | Hosting material | Dopant material | (h) | CIEx | CIEy |
| Example 112 | BH-15 | BD-11 | 101 | 0.133 | 0.076 |
| Comparative Example 112 | BH-15-a | BD-11 | 68 | 0.133 | 0.076 |

Example 113

The organic EL device was fabricated in the same manner as in Example 1 except that the compound indicated in the following table was used as materials for the emitting layer (host material and dopant material), and evaluated. The results are shown in Table 106.

TABLE 106

| | Emitting layer | | LT95 | Chromaticity | |
|---|---|---|---|---|---|
| | Hosting material | Dopant material | (h) | CIEx | CIEy |
| Example 113 | BH-16 | BD-11 | 157 | 0.133 | 0.076 |

Example 114 and Comparative Example 114

The organic EL device was fabricated in the same manner as in Example 1 except that the compound indicated in the following table was used as materials for the emitting layer (host material and dopant material), and evaluated. The results are shown in Table 107.

TABLE 107

| | Emitting layer | | LT95 | Chromaticity | |
|---|---|---|---|---|---|
| | Hosting material | Dopant material | (h) | CIEx | CIEy |
| Example 114 | BH-17 | BD-11 | 211 | 0.133 | 0.076 |
| Comparative Example 114 | BH-17-a | BD-11 | 135 | 0.133 | 0.076 |

Example 115 and Comparative Example 115

The organic EL device was fabricated in the same manner as in Example 1 except that the compound indicated in the following table was used as materials for the emitting layer (host material and dopant material), and evaluated. The results are shown in Table 108.

TABLE 108

| | Emitting layer | | | Chromaticity | |
|---|---|---|---|---|---|
| | Hosting material | Dopant material | LT95(h) | CIEx | CIEy |
| Example 115 | BH-1 | BD-12 | 112 | 0.141 | 0.058 |
| Comparative Example 115 | BH-1-a | BD-12 | 85 | 0.141 | 0.058 |

Example 116 and Comparative Example 116

The organic EL device was fabricated in the same manner as in Example 1 except that the compound indicated in the following table was used as materials for the emitting layer (host material and dopant material), and evaluated. The results are shown in Table 109.

TABLE 109

| | Emitting layer | | | Chromaticity | |
|---|---|---|---|---|---|
| | Hosting material | Dopant material | LT95(h) | CIEx | CIEy |
| Example 116 | BH-2 | BD-12 | 88 | 0.141 | 0.058 |
| Comparative Example 116 | BH-2-a | BD-12 | 58 | 0.141 | 0.058 |

Example 117 and Comparative Example 117

The organic EL device was fabricated in the same manner as in Example 1 except that the compound indicated in the following table was used as materials for the emitting layer (host material and dopant material), and evaluated. The results are shown in Table 110.

TABLE 110

| | Emitting layer | | | Chromaticity | |
|---|---|---|---|---|---|
| | Hosting material | Dopant material | LT95(h) | CIEx | CIEy |
| Example 117 | BH-3 | BD-12 | 143 | 0.141 | 0.058 |
| Comparative Example 117 | BH-3-a | BD-12 | 100 | 0.141 | 0.058 |

Example 118 and Comparative Example 118

The organic EL device was fabricated in the same manner as in Example 1 except that the compound indicated in the following table was used as materials for the emitting layer (host material and dopant material), and evaluated. The results are shown in Table 111.

TABLE 111

| | Emitting layer | | | Chromaticity | |
|---|---|---|---|---|---|
| | Hosting material | Dopant material | LT95(h) | CIEx | CIEy |
| Example 118 | BH-5 | BD-12 | 80 | 0.141 | 0.058 |
| Comparative Example 118 | BH-5-a | BD-12 | 59 | 0.141 | 0.058 |

Example 119 and Comparative Example 119

The organic EL device was fabricated in the same manner as in Example 1 except that the compound indicated in the following table was used as materials for the emitting layer (host material and dopant material), and evaluated. The results are shown in Table 112.

TABLE 112

| | Emitting layer | | | Chromaticity | |
|---|---|---|---|---|---|
| | Hosting material | Dopant material | LT95(h) | CIEx | CIEy |
| Example 119 | BH-6 | BD-12 | 151 | 0.141 | 0.058 |
| Comparative Example 119 | BH-6-a | BD-12 | 100 | 0.141 | 0.058 |

Example 120 and Comparative Example 120

The organic EL device was fabricated in the same manner as in Example 1 except that the compound indicated in the following table was used as materials for the emitting layer (host material and dopant material), and evaluated. The results are shown in Table 113.

TABLE 113

| | Emitting layer | | | Chromaticity | |
|---|---|---|---|---|---|
| | Hosting material | Dopant material | LT95(h) | CIEx | CIEy |
| Example 120 | BH-7 | BD-12 | 138 | 0.141 | 0.058 |
| Comparative Example 120 | BH-7-a | BD-12 | 90 | 0.141 | 0.058 |

Example 121 and Comparative Example 121

The organic EL device was fabricated in the same manner as in Example 1 except that the compound indicated in the following table was used as materials for the emitting layer (host material and dopant material), and evaluated. The results are shown in Table 114.

TABLE 114

| | Emitting layer | | | Chromaticity | |
|---|---|---|---|---|---|
| | Hosting material | Dopant material | LT95(h) | CIEx | CIEy |
| Example 121 | BH-8 | BD-12 | 137 | 0.141 | 0.059 |
| Comparative Example 121 | BH-8-a | BD-12 | 90 | 0.141 | 0.059 |

Example 122 and Comparative Example 122

The organic EL device was fabricated in the same manner as in Example 1 except that the compound indicated in the following table was used as materials for the emitting layer (host material and dopant material), and evaluated. The results are shown in Table 115.

TABLE 115

| | Emitting layer | | | Chromaticity | |
|---|---|---|---|---|---|
| | Hosting material | Dopant material | LT95(h) | CIEx | CIEy |
| Example 122 | BH-9 | BD-12 | 125 | 0.141 | 0.059 |
| Comparative Example 122 | BH-9-a | BD-12 | 91 | 0.141 | 0.059 |

Example 123 and Comparative Example 123

The organic EL device was fabricated in the same manner as in Example 1 except that the compound indicated in the following table was used as materials for the emitting layer (host material and dopant material), and evaluated. The results are shown in Table 116.

TABLE 116

| | Emitting layer | | | Chromaticity | |
|---|---|---|---|---|---|
| | Hosting material | Dopant material | LT95(h) | CIEx | CIEy |
| Example 123 | BH-10 | BD-12 | 116 | 0.141 | 0.059 |
| Comparative Example 123 | BH-10-a | BD-12 | 80 | 0.141 | 0.059 |

Example 124 and Comparative Example 124

The organic EL device was fabricated in the same manner as in Example 1 except that the compound indicated in the following table was used as materials for the emitting layer (host material and dopant material), and evaluated. The results are shown in Table 117.

TABLE 117

| | Emitting layer | | | Chromaticity | |
|---|---|---|---|---|---|
| | Hosting material | Dopant material | LT95(h) | CIEx | CIEy |
| Example 124 | BH-11 | BD-12 | 128 | 0.141 | 0.059 |
| Comparative Example 124 | BH-11-a | BD-12 | 94 | 0.141 | 0.059 |

Example 125 and Comparative Example 125

The organic EL device was fabricated in the same manner as in Example 1 except that the compound indicated in the following table was used as materials for the emitting layer (host material and dopant material), and evaluated. The results are shown in Table 118.

TABLE 118

| | Emitting layer | | | Chromaticity | |
|---|---|---|---|---|---|
| | Hosting material | Dopant material | LT95(h) | CIEx | CIEy |
| Example 125 | BH-12 | BD-12 | 125 | 0.141 | 0.058 |
| Comparative Example 125 | BH-12-a | BD-12 | 90 | 0.141 | 0.058 |

Example 126 and Comparative Example 126

The organic EL device was fabricated in the same manner as in Example 1 except that the compound indicated in the following table was used as materials for the emitting layer (host material and dopant material), and evaluated. The results are shown in Table 119.

TABLE 119

| | Emitting layer | | | Chromaticity | |
|---|---|---|---|---|---|
| | Hosting material | Dopant material | LT95(h) | CIEx | CIEy |
| Example 126 | BH-13 | BD-12 | 73 | 0.141 | 0.058 |
| Comparative Example 126 | BH-13-a | BD-12 | 50 | 0.141 | 0.058 |

Example 127 and Comparative Example 127

The organic EL device was fabricated in the same manner as in Example 1 except that the compound indicated in the following table was used as materials for the emitting layer (host material and dopant material), and evaluated. The results are shown in Table 120.

TABLE 120

| | Emitting layer | | | Chromaticity | |
|---|---|---|---|---|---|
| | Hosting material | Dopant material | LT95(h) | CIEx | CIEy |
| Example 127 | BH-15 | BD-12 | 82 | 0.141 | 0.058 |
| Comparative Example 127 | BH-15-a | BD-12 | 52 | 0.141 | 0.058 |

Example 128

The organic EL device was fabricated in the same manner as in Example 1 except that the compound indicated in the following table was used as materials for the emitting layer (host material and dopant material), and evaluated. The results are shown in Table 121.

TABLE 121

| | Emitting layer | | | Chromaticity | |
|---|---|---|---|---|---|
| | Hosting material | Dopant material | LT95(h) | CIEx | CIEy |
| Example 128 | BH-16 | BD-12 | 122 | 0.141 | 0.058 |

Example 129 and Comparative Example 129

The organic EL device was fabricated in the same manner as in Example 1 except that the compound indicated in the following table was used as materials for the emitting layer (host material and dopant material), and evaluated. The results are shown in Table 122.

TABLE 122

| | Emitting layer | | | Chromaticity | |
|---|---|---|---|---|---|
| | Hosting material | Dopant material | LT95(h) | CIEx | CIEy |
| Example 129 | BH-17 | BD-12 | 155 | 0.141 | 0.058 |
| Comparative Example 129 | BH-17-a | BD-12 | 105 | 0.141 | 0.058 |

From the results shown in Tables 1 to 122, when the compound (host material) represented by the formula (1) (for example the compound represented by the formula (1A)) which has a deuterium atom at a particular position is used for the emitting layer in combination of a particular dopant material, it is understood that the lifetime of the organic EL device becomes longer than that of one which uses a compound (host material) which has no deuterium atom at the particular position in combination with the corresponding dopant material.

Several embodiments and/or examples of the present invention have been described in detail above. However, without substantially departing from novel teachings and effects of the present invention, the person skilled in the art can readily make a number of modifications to the embodiments and/or examples which are exemplifications of these teachings and effects. Thus, these modifications are included in the scope of the present invention.

The documents described in this specification and the contents of the application that serves as the basis of priority claim under Paris convention are incorporated herein by reference in its entirety.

The invention claimed is:

1. An organic electroluminescence device comprising:
a cathode,
an anode, and
an emitting layer disposed between the cathode and the anode, wherein
the emitting layer comprises a compound represented by the following formula (1A) and a compound represented by the following formula (43D):

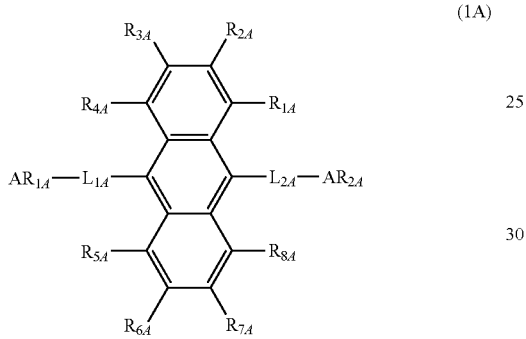
(1A)

wherein in the formula (1A),
$R_{1A}$ to $R_{8A}$ are independently a hydrogen atom, and at least one of $R_{1A}$ to $R_{8A}$ is a deuterium atom;
$L_{1A}$ and $L_{2A}$ are independently a single bond, an unsubstituted phenylene group, or an unsubstituted naphthylene group;
$Ar_{1A}$ is a substituted or unsubstituted phenyl group or a substituted or unsubstituted naphthyl group, and the substituent for $Ar_{1A}$ is a phenyl group;
$Ar_2A$ is a monovalent group represented by the following formula (2A), (3A) or (4A):

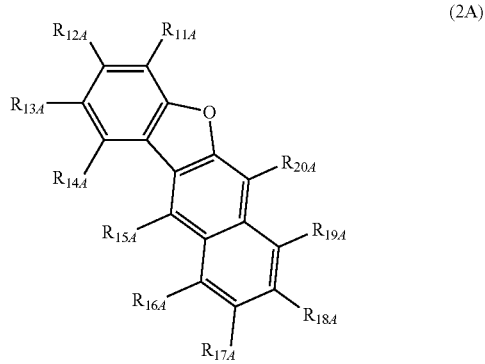
(2A)

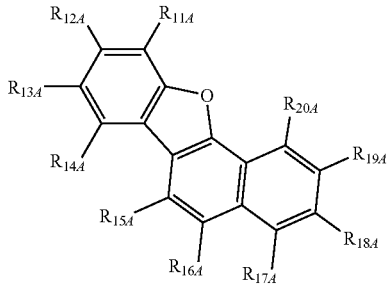
(3A)

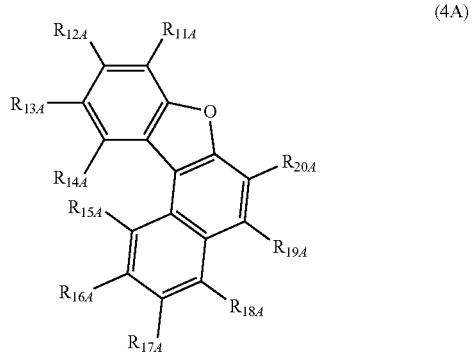
(4A)

wherein in the formulas (2A) to (4A),
any one of $R_{13A}$ to $R_{14A}$ is a single bond that binds to $L_{2A}$; and $R_{11A}$, $R_{12A}$, $R_{15A}$ to $R_{20A}$, as well as $R_{13A}$ to $R_{14A}$ that are not a single bond bonding to $L_{2A}$ are independently a hydrogen atom or an unsubstituted aryl group including 6 to 50 ring carbon atoms;

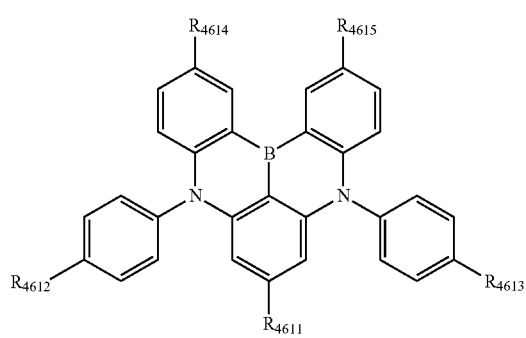
(43D)

wherein in the formula (43D),
$R_{4611}$ is a hydrogen atom, an unsubstituted alkyl group including 1 to 6 carbon atoms, an unsubstituted cycloalkyl group including 3 to 10 ring carbon atoms, —Si($R_{911}$)($R_{912}$)($R_{913}$), or —N($R_{914}$)($R_{915}$);
$R_{4612}$ to $R_{4615}$ are independently an unsubstituted alkyl group including 1 to 6 carbon atoms, an unsubstituted cycloalkyl group including 3 to 10 ring carbon atoms, or —Si($R_{911}$)($R_{912}$)($R_{913}$);
$R_{911}$ to $R_{913}$ are independently an unsubstituted alkyl group including 1 to 6 carbon atoms or an unsubstituted aryl group including 6 to 18 ring carbon atoms; and
$R_{914}$ to $R_{915}$ are independently an unsubstituted aryl group including 6 to 18 ring carbon atoms.

2. The organic electroluminescence device according to claim 1, wherein in the formula (1A), at least two of $R_{1A}$ to $R_{8A}$ are deuterium atoms.

3. The organic electroluminescence device according to claim 1, wherein in the formula (1A), $R_{1A}$ to $R_{8A}$ are all deuterium atoms.

4. The organic electroluminescence device according to claim 1, wherein in the formula (1A), at least one hydrogen atom contained in $Ar_{1A}$ is a deuterium atom.

5. The organic electroluminescence device according to claim 1, wherein in the formula (1A), $R_{11A}$, $R_{12A}$, $R_{15A}$ to $R_{20A}$, as well as $R_{13A}$ to $R_{14A}$ that are not a single bond bonding to $L_{2A}$ are hydrogen atoms.

6. The organic electroluminescence device according to claim 1, wherein in the formula (1A), at least one of $R_{11A}$, $R_{12A}$, $R_{15A}$ to $R_{20A}$, as well as $R_{13A}$ to $R_{14A}$ that are not a single bond bonding to $L_{2A}$ is a deuterium atoms.

7. The organic electroluminescence device according to claim 1, wherein in the emitting layer, based on the total of the compound represented by the formula (1A) and the compound having the same structure as the compound represented by the formula (1A) except that the compound represented by the formula (1A) contains only protium atoms as hydrogen atoms, the content ratio of the latter is 99 mol % or less.

8. The organic electroluminescence device according to claim 1, wherein in the formula (43D), $R_{4611}$ is a hydrogen atom, an unsubstituted alkyl group including 1 to 6 carbon atoms, or —N($R_{914}$)($R_{915}$).

9. The organic electroluminescence device according to claim 1, wherein in the formula (43D), $R_{4612}$ to $R_{4615}$ are independently an unsubstituted alkyl group including 1 to 6 carbon atoms, or an unsubstituted cycloalkyl group including 3 to 10 ring carbon atoms.

10. The organic electroluminescence device according to claim 1, wherein in the formula (43D), $R_{4611}$ is —N($R_{914}$)($R_{915}$), and $R_{4612}$ to $R_{4615}$ are independently an unsubstituted alkyl group including 1 to 6 carbon atoms.

11. The organic electroluminescence device according to claim 1, wherein in the formula (43D), $R_{4611}$ is an unsubstituted alkyl group including 1 to 6 carbon atoms, and $R_{4612}$ to $R_{4615}$ are independently an unsubstituted alkyl group including 1 to 6 carbon atoms.

12. The organic electroluminescence device according to claim 1, wherein in the formula (43D), $R_{4611}$ is a hydrogen atom, and $R_{4612}$ to $R_{4615}$ are independently an unsubstituted alkyl group including 1 to 6 carbon atoms, or an unsubstituted cycloalkyl group including 3 to 10 ring carbon atoms.

13. The organic electroluminescence device according to claim 1, wherein in the formula (43D), at least one of the hydrogen atoms included in one or more selected from the group consisting of $R_{914}$ and $R_{915}$ is a deuterium atom.

14. The organic electroluminescence device according to claim 1, wherein the compound represented by the formula (1A) is one or more selected from the group consisting of the compound represented by the formulas BH-1 to BH-3, BH-5 to BH-13 and BH-15 to BH-17, and the compound represented by the formula (43D) is one or more selected from the group consisting of the compound represented by the formulas BD-9, BD-10, BD-11 and BD-12.

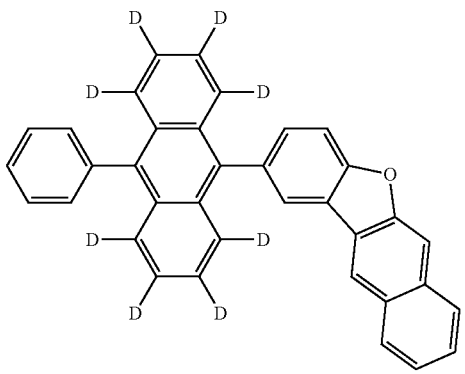

BH-1

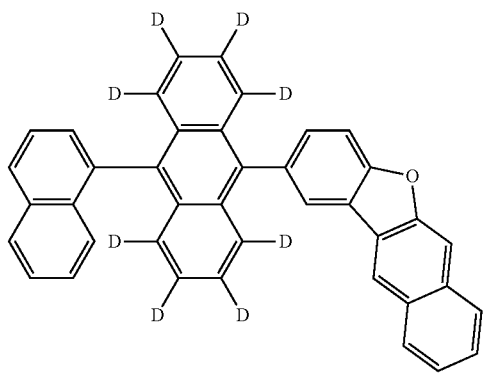

BH-2

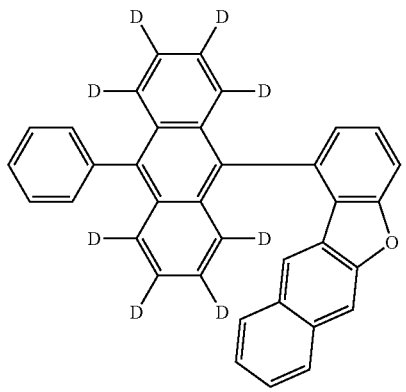

BH-3

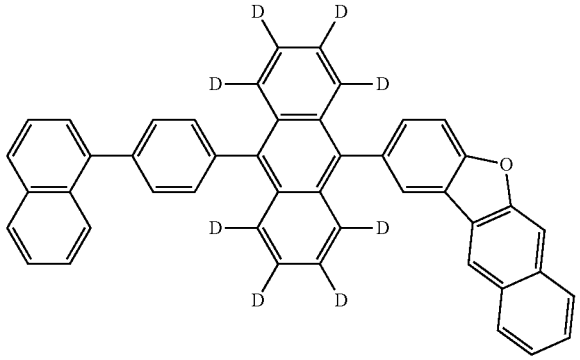

BH-5

BH-6
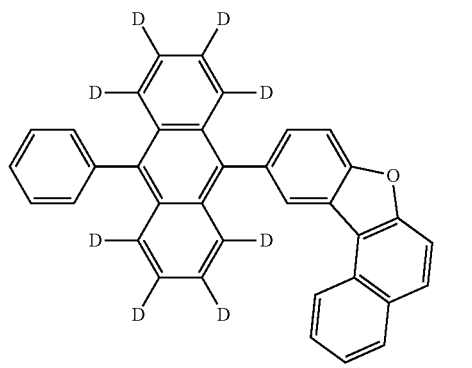
BH-7
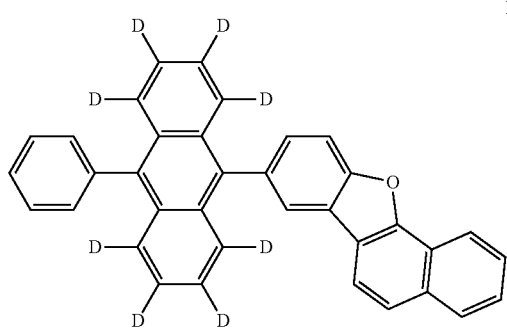
BH-8
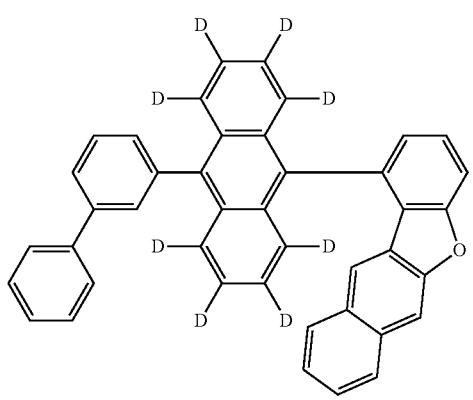
BH-9
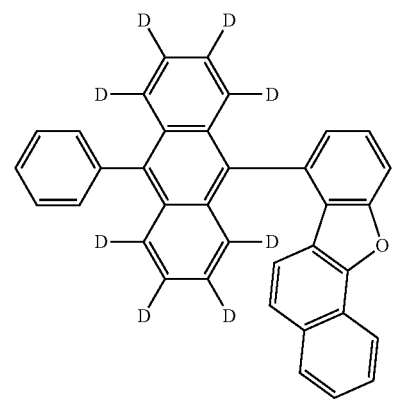
BH-10
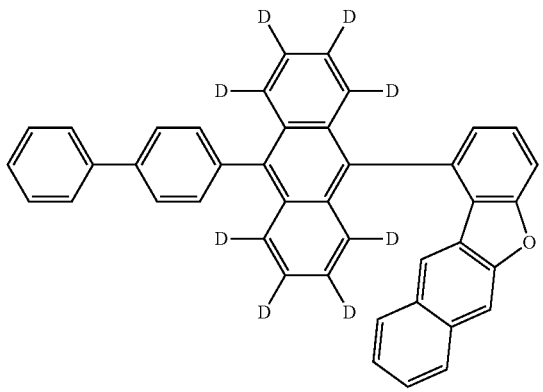
BH-11
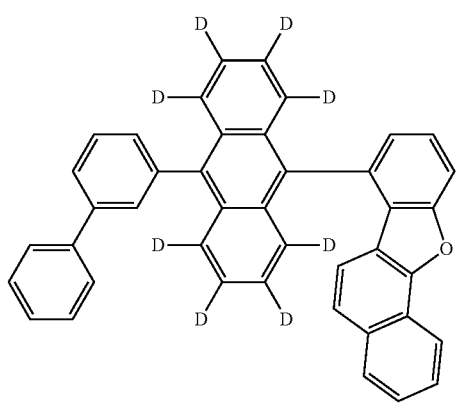
BH-12
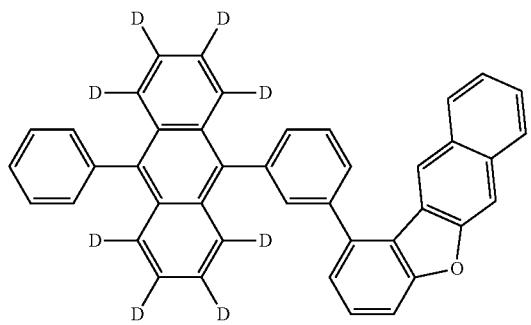
BH-13
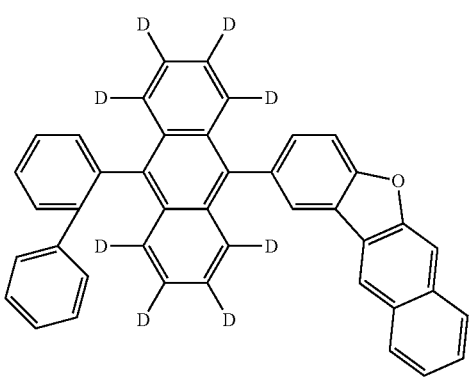

1329

-continued

BH-15

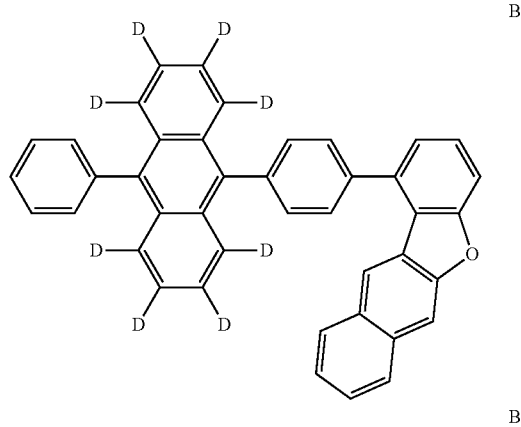

BH-16

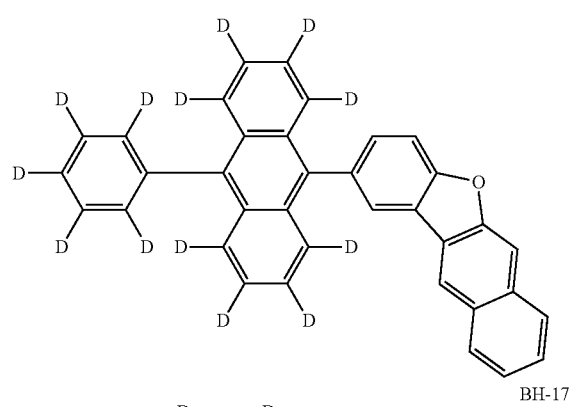

BH-17

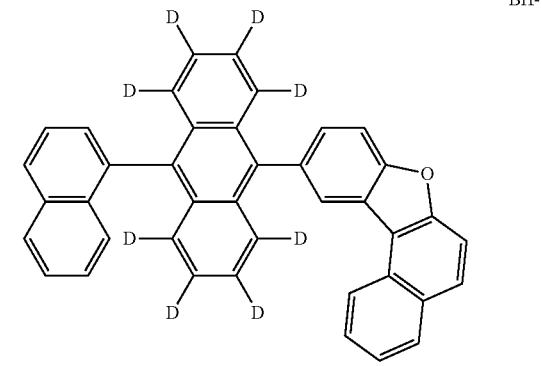

BD-9

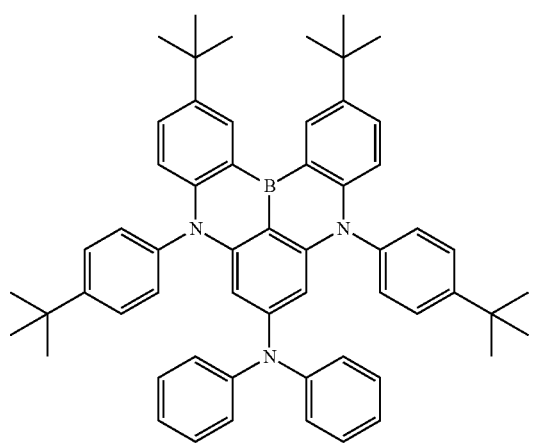

1330

-continued

BD-10

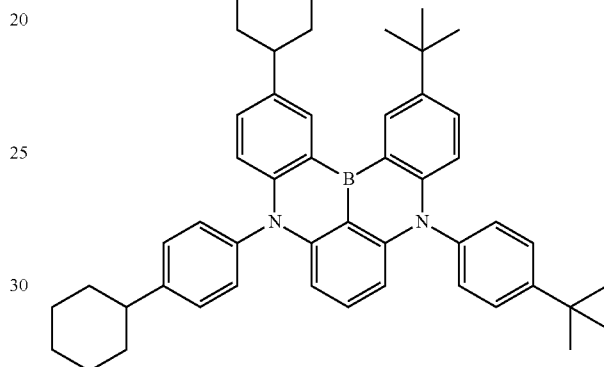

BD-11

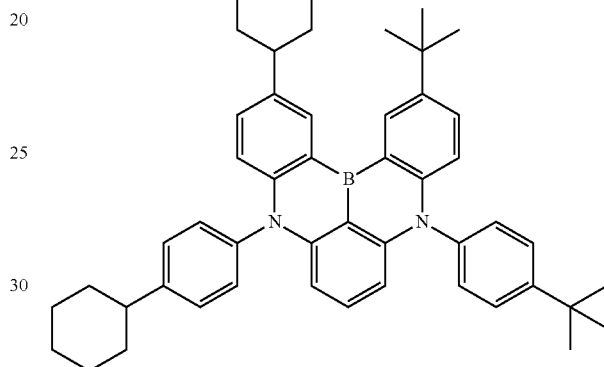

BD-12

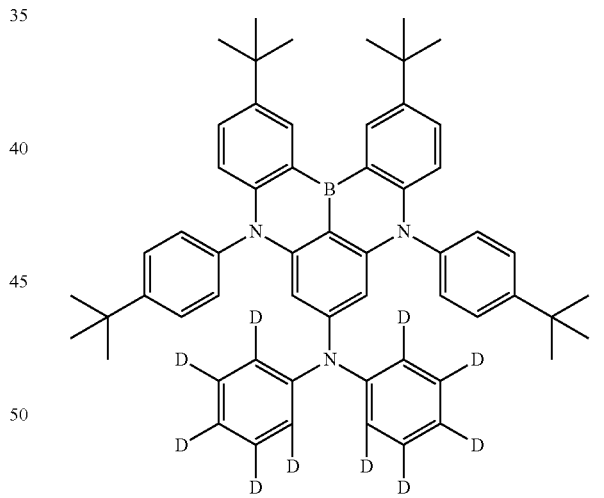

15. The organic electroluminescence device according to claim 1, which further comprises a hole-transporting layer between the anode and the emitting layer.

16. The organic electroluminescence device according to claim 1, which further comprises an electron-transporting layer between the cathode and the emitting layer.

17. An electronic apparatus wherein the organic electroluminescence device according to claim 1 is provided.

* * * * *